(12) United States Patent
Lin et al.

(10) Patent No.: US 12,421,254 B2
(45) Date of Patent: Sep. 23, 2025

(54) KRAS MODULATORS AND USES THEREOF

(71) Applicant: Quanta Therapeutics, Inc., South San Francisco, CA (US)

(72) Inventors: Hong Lin, Exton, PA (US); Juan Luengo, Phoenixville, PA (US); Audrey Hospital, North Wales, PA (US); Jin Zeng, Audubon, PA (US); Pei Gan, Claymont, DE (US)

(73) Assignee: QUANTA THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 18/892,208

(22) Filed: Sep. 20, 2024

(65) Prior Publication Data

US 2025/0051365 A1 Feb. 13, 2025

Related U.S. Application Data

(63) Continuation of application No. PCT/US2024/020319, filed on Mar. 15, 2024.

(60) Provisional application No. 63/490,475, filed on Mar. 15, 2023, provisional application No. 63/508,213, filed on Jun. 14, 2023.

(51) Int. Cl.
| | |
|---|---|
| *C07D 519/00* | (2006.01) |
| *A61K 31/53* | (2006.01) |
| *A61K 31/5377* | (2006.01) |
| *A61K 31/55* | (2006.01) |
| *A61K 31/551* | (2006.01) |
| *A61K 31/553* | (2006.01) |
| *A61K 31/554* | (2006.01) |
| *A61K 31/675* | (2006.01) |
| *C07D 487/04* | (2006.01) |
| *C07D 487/08* | (2006.01) |
| *C07D 495/10* | (2006.01) |
| *C07D 495/20* | (2006.01) |
| *C07F 9/6561* | (2006.01) |

(52) U.S. Cl.
CPC ............ *C07D 519/00* (2013.01); *A61K 31/53* (2013.01); *A61K 31/5377* (2013.01); *A61K 31/55* (2013.01); *A61K 31/551* (2013.01); *A61K 31/553* (2013.01); *A61K 31/554* (2013.01); *A61K 31/675* (2013.01); *C07D 487/04* (2013.01); *C07D 487/08* (2013.01); *C07D 495/10* (2013.01); *C07D 495/20* (2013.01); *C07F 9/6561* (2013.01)

(58) Field of Classification Search
CPC .. C07D 519/00; C07D 487/04; C07D 487/08; C07D 495/10; C07D 495/20; A61K 31/53; A61K 31/5377; A61K 31/55; A61K 31/551; A61K 31/553; A61K 31/675; C07F 9/6561
See application file for complete search history.

(56) References Cited

U.S. PATENT DOCUMENTS

| | | |
|---|---|---|
| 10,647,715 B2 | 5/2020 | Marx et al. |
| 10,822,312 B2 | 11/2020 | Li et al. |
| 11,267,812 B2 | 3/2022 | Fischer et al. |
| 11,312,724 B2 | 4/2022 | Li et al. |
| 11,912,723 B2 | 2/2024 | Lin et al. |
| 2005/0234108 A1 | 10/2005 | Himmelsbach et al. |
| 2011/0166135 A1 | 7/2011 | Morimoto et al. |
| 2013/0012485 A1 | 1/2013 | Bäschlin et al. |
| 2016/0136180 A1 | 5/2016 | Himmelsbach et al. |
| 2020/0331911 A1 | 10/2020 | Marx et al. |
| 2021/0380574 A1 | 12/2021 | Abbott et al. |
| 2022/0402916 A1 | 12/2022 | Hoover et al. |
| 2023/0135152 A1 | 5/2023 | Smrcina et al. |
| 2024/0199650 A1 | 6/2024 | Lin et al. |

FOREIGN PATENT DOCUMENTS

| | | |
|---|---|---|
| CN | 112409331 A | 2/2021 |
| CN | 113396147 A | 9/2021 |
| CN | 114685460 A | 7/2022 |
| JP | 2020111571 A | 7/2020 |
| WO | WO-2005003099 A2 | 1/2005 |
| WO | WO-2010064705 A1 | 6/2010 |
| WO | WO-2010120996 A1 | 10/2010 |
| WO | WO-2014172639 A1 | 10/2014 |
| WO | WO-2016081679 A1 | 5/2016 |
| WO | WO-2017087528 A1 | 5/2017 |
| WO | WO-2017201161 A1 | 11/2017 |
| WO | WO-2018212774 A1 | 11/2018 |
| WO | WO-2019013311 A1 | 1/2019 |
| WO | WO-2020028706 A1 | 2/2020 |
| WO | WO-2020146613 A1 | 7/2020 |
| WO | WO-2020236940 A1 | 11/2020 |
| WO | WO-2021041671 A1 | 3/2021 |

(Continued)

OTHER PUBLICATIONS

RN3056973-98-6 (Year: 2024).*

(Continued)

*Primary Examiner* — Jeffrey S Lundgren
*Assistant Examiner* — Ibrahim D Bori
(74) *Attorney, Agent, or Firm* — WILSON SONSINI GOODRICH & ROSATI

(57) ABSTRACT

Provided herein are KRAS modulating compounds, such as compounds of Formula (I), (I-A), (I-B), (I-C), (I-C*), (I-D), (I-E), (I-F), (I-G), (I-H), (I-I), (I-J), or pharmaceutically acceptable salts, solvates, stereoisomers, atom labelled, or tautomers of any one thereof. The compounds provided herein are useful for modulating KRAS G12D and/or other G12 mutants.

17 Claims, No Drawings
Specification includes a Sequence Listing.

(56) References Cited

FOREIGN PATENT DOCUMENTS

| | | |
|---|---|---|
| WO | WO-2021093758 A1 | 5/2021 |
| WO | WO-2021106231 A1 | 6/2021 |
| WO | WO-2021139748 A1 | 7/2021 |
| WO | WO-2022002102 A1 | 1/2022 |
| WO | WO-2022031678 A1 | 2/2022 |
| WO | WO-2022040469 A1 | 2/2022 |
| WO | WO-2022042630 A1 | 3/2022 |
| WO | WO-2022047260 A1 | 3/2022 |
| WO | WO-2022061251 A1 | 3/2022 |
| WO | WO-2022105857 A1 | 5/2022 |
| WO | WO-2022105859 A1 | 5/2022 |
| WO | WO-2022109487 A1 | 5/2022 |
| WO | WO-2022115439 A1 | 6/2022 |
| WO | WO-2022127827 A1 | 6/2022 |
| WO | WO-2022132200 A1 | 6/2022 |
| WO | WO-2022133038 A1 | 6/2022 |
| WO | WO-2022135470 A1 | 6/2022 |
| WO | WO-2022135546 A1 | 6/2022 |
| WO | WO-2022148422 A1 | 7/2022 |
| WO | WO-2022156761 A1 | 7/2022 |
| WO | WO-2022170999 A1 | 8/2022 |
| WO | WO-2022173870 A1 | 8/2022 |
| WO | WO-2022177917 A2 | 8/2022 |
| WO | WO-2022184178 A1 | 9/2022 |
| WO | WO-2022187527 A1 | 9/2022 |
| WO | WO-2022187528 A1 | 9/2022 |
| WO | WO-2022188729 A1 | 9/2022 |
| WO | WO-2022192790 A1 | 9/2022 |
| WO | WO-2022192794 A1 | 9/2022 |
| WO | WO-2022193982 A1 | 9/2022 |
| WO | WO-2022194066 A1 | 9/2022 |
| WO | WO-2022194191 A1 | 9/2022 |
| WO | WO-2022194192 A1 | 9/2022 |
| WO | WO-2022194245 A1 | 9/2022 |
| WO | WO-2022214102 A1 | 10/2022 |
| WO | WO-2022217118 A1 | 10/2022 |
| WO | WO-2022221386 A1 | 10/2022 |
| WO | WO-2022221739 A1 | 10/2022 |
| WO | WO-2022228543 A1 | 11/2022 |
| WO | WO-2022232331 A1 | 11/2022 |
| WO | WO-2022232332 A1 | 11/2022 |
| WO | WO-2022247760 A1 | 12/2022 |
| WO | WO-2022251576 A1 | 12/2022 |
| WO | WO-2022256459 A1 | 12/2022 |
| WO | WO-2022261210 A1 | 12/2022 |
| WO | WO-2022266069 A1 | 12/2022 |
| WO | WO-2022266249 A1 | 12/2022 |
| WO | WO-2022268051 A1 | 12/2022 |
| WO | WO-2022269508 A1 | 12/2022 |
| WO | WO-2022269525 A1 | 12/2022 |
| WO | WO-2022271658 A1 | 12/2022 |
| WO | WO-2022271823 A1 | 12/2022 |
| WO | WO-2022271923 A1 | 12/2022 |
| WO | WO-2023001123 A1 | 1/2023 |
| WO | WO-2023001141 A1 | 1/2023 |
| WO | WO-2023274324 A1 | 1/2023 |
| WO | WO-2023274383 A1 | 1/2023 |
| WO | WO-2023278600 A1 | 1/2023 |
| WO | WO-2023280026 A1 | 1/2023 |
| WO | WO-2023280136 A1 | 1/2023 |
| WO | WO-2023280280 A1 | 1/2023 |
| WO | WO-2023283213 A1 | 1/2023 |
| WO | WO-2023060362 A1 | 4/2023 |
| WO | WO-2023061294 A1 | 4/2023 |
| WO | WO-2023061463 A1 | 4/2023 |
| WO | WO-2023064857 A1 | 4/2023 |
| WO | WO-2023066371 A1 | 4/2023 |
| WO | WO-2023067546 A1 | 4/2023 |
| WO | WO-2023072188 A1 | 5/2023 |
| WO | WO-2023072297 A1 | 5/2023 |
| WO | WO-2023077441 A1 | 5/2023 |
| WO | WO-2023081476 A1 | 5/2023 |
| WO | WO-2023081840 A1 | 5/2023 |
| WO | WO-2023086383 A1 | 5/2023 |
| WO | WO-2023097227 A1 | 6/2023 |
| WO | WO-2023098425 A1 | 6/2023 |
| WO | WO-2023098426 A1 | 6/2023 |
| WO | WO-2023098832 A1 | 6/2023 |
| WO | WO-2023099592 A1 | 6/2023 |
| WO | WO-2023099608 A1 | 6/2023 |
| WO | WO-2023099612 A1 | 6/2023 |
| WO | WO-2023099620 A1 | 6/2023 |
| WO | WO-2023099623 A1 | 6/2023 |
| WO | WO-2023099624 A1 | 6/2023 |
| WO | WO-2023101928 A1 | 6/2023 |
| WO | WO-2023103523 A1 | 6/2023 |
| WO | WO-2023103906 A1 | 6/2023 |
| WO | WO-2023104018 A1 | 6/2023 |
| WO | WO-2023105491 A1 | 6/2023 |
| WO | WO-2023114733 A1 | 6/2023 |
| WO | WO-2023116934 A1 | 6/2023 |
| WO | WO-2023117681 A1 | 6/2023 |
| WO | WO-2023119677 A1 | 6/2023 |
| WO | WO-2023120742 A1 | 6/2023 |
| WO | WO-2023125627 A1 | 7/2023 |
| WO | WO-2023125989 A1 | 7/2023 |
| WO | WO-2023130012 A1 | 7/2023 |
| WO | WO-2023133181 A1 | 7/2023 |
| WO | WO-2023133183 A1 | 7/2023 |
| WO | WO-2023134465 A1 | 7/2023 |
| WO | WO-2023137223 A1 | 7/2023 |
| WO | WO-2023138524 A1 | 7/2023 |
| WO | WO-2023138589 A1 | 7/2023 |
| WO | WO-2023141570 A2 | 7/2023 |
| WO | WO-2023143312 A1 | 8/2023 |
| WO | WO-2023150284 A2 | 8/2023 |
| WO | WO-2023151621 A1 | 8/2023 |
| WO | WO-2023152255 A1 | 8/2023 |
| WO | WO-2023154766 | 8/2023 |
| WO | WO-2023230190 A1 | 11/2023 |
| WO | WO-2024192424 A1 | 9/2024 |
| WO | WO-2025016899 A1 | 1/2025 |

OTHER PUBLICATIONS

CAS Registry Substances: 2443964-06-3. SciFinder. Accessed Nov. 9, 2023. 2 pages.
CAS Registry Substances: 2443964-21-2. SciFinder. Accessed Nov. 9, 2023. 2 pages.
CAS Registry Substances: 2445825-88-5. SciFinder. Accessed Nov. 9, 2023. 2 pages.
CAS Registry Substances: 2445851-64-7. SciFinder. Accessed Nov. 9, 2023. 2 pages.
CAS Registry Substances: 2448474-02-8. SciFinder. Accessed Nov. 9, 2023. 2 pages.
CAS Registry Substances: 2448613-12-3. SciFinder. Accessed Nov. 9, 2023. 2 pages.
PCT/US2022/024111 International Search Report and Written Opinion dated Aug. 1, 2022.
PCT/US2022/031846 International Search Report and Written Opinion dated Oct. 5, 2022.
PCT/US2022/032680 International Search Report and Written Opinion dated Oct. 26, 2022.
PCT/US2022/081393 International Search Report and Written Opinion dated May 9, 2023.
PCT/US2023/062235 International Search Report and Written Opinion dated Aug. 17, 2023.
PCT/US2023/023445 International Search Report and Written Opinion dated Sep. 6, 2023.
PCT/US2024/020319 International Search Report and Written Opinion dated Jul. 8, 2024.
PUBCHEM-SID:325121534 Deposit Date: Jan. 25, 2017 (Jan. 25, 2017) pp. 1-7; p. 2.
U.S. Appl. No. 18/362,576 Notice of Allowance dated Dec. 6, 2023.
U.S. Appl. No. 18/362,576 Office Action dated Nov. 8, 2023.
U.S. Appl. No. 18/503,626 Corrected Notice of Allowability dated Oct. 3, 2024.

(56) References Cited

OTHER PUBLICATIONS

U.S. Appl. No. 18/503,626 Notice of Allowance dated Jun. 17, 2024.

* cited by examiner

KRAS MODULATORS AND USES THEREOF

CROSS-REFERENCE

This application is a continuation of International Patent Application No. PCT/US24/20319, filed on Mar. 15, 2024, which claims the benefit of U.S. Provisional Patent Applications Nos. 63/490,475 filed on Mar. 15, 2023; and 63/508,213 filed on Jun. 14, 2023; each of which is incorporated herein by reference in its entirety.

SEQUENCE LISTING

The instant application contains a Sequence Listing which has been submitted electronically in XML format and is hereby incorporated by reference in its entirety. Said XML copy, created on Jul. 23, 2025, is named 55172-730_301_SL.xml and is 11,239 bytes in size.

BACKGROUND

The small GTPase protein Kirsten Rat Sarcoma 2 Viral Oncogene Homolog (KRAS) is a member of the Ras family of cell signaling switches, regulating growth and survival of normal and cancerous cells (e.g., see Cully, M. and J. Downward, SnapShot: Ras Signaling. Cell, 2008. 133(7): p. 1292-1292 e1). KRAS mutations drive approximately 25% of human cancers by aberrant regulation of the mitogen-activated protein kinase (MAPK) signaling cascade and other effector pathways (e.g., see Stephen, A. G., et al., Dragging ras back in the ring. Cancer Cell, 2014. 25(3): p. 272-81). Though Ras has been recognized as a target in cancer for about 40 years, Ras-driven cancers remain among the most difficult to treat due to insensitivity to available targeted therapies. Ras, encoded by the three major genes KRAS, NRAS and HRAS, has the highest frequency of mutation of any oncogene. All oncogenic Ras mutations drive the switch to accumulate in the active GTP-bound state. The most common Ras mutation found across human tumor types is KRAS G12D (e.g., see The AACR Project GENIE Consortium. Cancer Discovery, 2017. 7(8): p. 818-831. Dataset Version 4). Activating mutations in codon 12 impair the small GTPases' ability to perform their role in hydrolyzing GTP. This regulatory impairment is fundamental for initiating and maintaining tumor progression.

Despite extensive efforts, small molecules have not been identified which block effector binding or restore GTPase activating protein (GAP) sensitivity, though some have been found which block interaction of Ras with the guanine nucleotide exchange factor (GEF), SOS, which activates Ras at the plasma membrane. KRAS G12C mutations, most common in lung adenocarcinoma, have been clinically shown to be susceptible to direct inhibition by covalent modification with small molecule inhibitors trapping the protein in the inactive GDP-bound state. KRAS G12D mutation confers a significantly slower intrinsic rate of GTP hydrolysis than G12C, resulting in more constitutive activation. Thus, pharmacological targeting the of inactive state is unlikely to achieve similar results against G12D, despite the existence of a similar binding pocket in the GDP-state. Additionally, a cysteine present at the site of the activating mutation yields itself to covalent chemistry, while aspartic acid does not provide typical medicinal chemistry approaches for selective covalent modification.

In order to potentially exploit the accumulation of KRAS G12D and other mutant variants in the GTP-bound state as a vulnerability to achieve selective inhibition of cancer cells while sparing normal Ras function, it is attractive for small molecule inhibitors to bind selectively to the GTP-state and stabilize a conformation that is incompetent for oncogenic signaling interactions with effector proteins. Furthermore, it has been shown that only constitutive activation of Raf, MEK and ERK kinases in the MAPK cascade downstream of Ras can bypass the requirement for Ras proteins in proliferative signaling (e.g., see Drosten, M., et al., Genetic analysis of Ras signalling pathways in cell proliferation, migration and survival. EMBO J, 2010. 29(6): p. 1091-104). As all evidence has indicated that MAPK signaling is essential for the growth effects of Ras in cancer, KRAS-mutant-selective inhibition in this pathway is considered the critical functional readout for potential clinical benefit of novel therapeutic approaches. Thus, there is a need to develop new inhibitors for KRAS-driven cancers that demonstrate inhibition of MAPK signals via a mechanism of action that is selective for binding to the active GTP-bound state over the inactive GDP-bound state.

SUMMARY OF THE INVENTION

In an aspect, the present disclosure provides a compound represented by Formula (I),

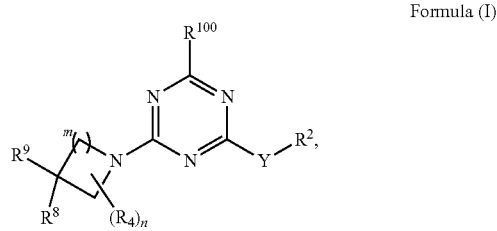

Formula (I)

or a pharmaceutically acceptable salt thereof wherein:
$R^{100}$ is selected from

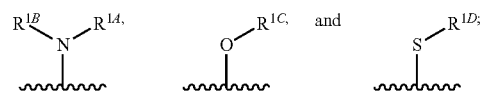

$R^{1A}$ is selected from $C_{1-6}$ alkyl, $C_3$-$C_{12}$ carbocycle, and 4- to 12-membered heterocycle, each of which is optionally substituted with one or more $R^{11}$, and wherein optionally two $R^{11}$ on the same atom of $R^{1A}$ come together to form a $C_3$-$C_6$ carbocycle or 3- to 8-membered heterocycle, wherein the $C_3$-$C_6$ carbocycle and 3- to 8-membered heterocycle are each optionally substituted with one or more $R^{11A}$;

$R^{1B}$ is selected from hydrogen, $C_{1-6}$ alkyl, $C_3$-$C_6$ carbocycle, 4- to 6-membered heterocycle, wherein the $C_{1-6}$ alkyl, $C_3$-$C_6$ carbocycle, and 4- to 6-membered heterocycle, are each optionally substituted with one or more $R^{10}$;

or $R^{1A}$ and $R^{1B}$ come together with the atom to which they are bound to form $R^1$, wherein $R^1$ is a 5- to 15-membered heterocycle, wherein the 5- to 15-membered heterocycle is optionally substituted with one or more substituents independently selected from halogen, —B(OR$^{20}$)$_2$, —N(R$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —C(=NR$^{20}$)N(R$^{20}$)$_2$, —C$_{1-6}$ alkyl(=NR$^{20}$OR$^{20}$), —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —C(O)R$^{20}$, —C(O)OR$^{20}$, —OC(O)R$^{20}$, —OC(O)N(R$^{20}$)$_2$, —NO$_2$, =O, =N(R$^{20}$), =NO(R$^{20}$), —CN, —NHCN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl-SO$_2$R$^{20}$, C$_{1-6}$ alkoxyalkyl, C$_{1-6}$ alkyl, C$_{2-6}$ alkenyl, C$_{2-6}$ alkynyl, C$_3$-C$_{12}$ carbocycle and 5- to 12-membered heterocycle, wherein the C$_3$-C$_{12}$ carbocycle and 5- to 12-membered heterocycle are each optionally substituted independently with one or more R$^{1*}$;

each R$^{1*}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =N(R$^{20}$), =NO(R$^{20}$), —CN, —NHCN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, and C$_3$-C$_{12}$ carbocycle;

R$^{1C}$ is selected from hydrogen, C$_{1-6}$ alkyl, C$_3$-C$_{12}$ carbocycle, and 4- to 12-membered heterocycle, each of which is optionally substituted with one or more R$^{12}$, and wherein optionally two R$^{12}$ on the same atom of R$^{1C}$ come together to form a C$_3$-C$_6$ carbocycle or 3- to 8-membered heterocycle, wherein the C$_3$-C$_6$ carbocycle and 3- to 8-membered heterocycle are each optionally substituted with one or more R$^{12A}$;

R$^{1D}$ is selected from hydrogen, C$_{1-6}$ alkyl, C$_3$-C$_{12}$ carbocycle, and 4- to 12-membered heterocycle, each of which is optionally substituted with one or more R$^{13}$, and wherein optionally two R$^{13}$ on the same atom of R$^{1D}$ come together to form a C$_3$-C$_6$ carbocycle or 3- to 8-membered heterocycle, wherein the C$_3$-C$_6$ carbocycle and 3- to 8-membered heterocycle are each optionally substituted with one or more R$^{13A}$;

Y is —O—;

R$^2$ is selected from heterocycle, -L-heterocycle, -L-N(R$^{20}$)$_2$, -L-OR$^{20}$, -L-aryl, -L-heteroaryl, -L-cycloalkyl, -L-NHC(=NH)NH$_2$, -L-C(O)N(R$^{20}$)$_2$, -L-C$_{1-6}$ haloalkyl, -L-NR$^{20}$C(O)-aryl, -L-COOH, -L-NR$^{20}$S(O)$_2$(R$^{20}$), -L-S(O)$_2$N(R$^{20}$)$_2$, -L-N(R$^{20}$)C(O)(OR$^{20}$), -L-OC(O)N(R$^{20}$)$_2$, and -L-C(=O)OC$_1$-C$_6$ alkyl, wherein the heterocycle, the heterocycle portion of -L-heterocycle, and the cycloalkyl portion of the -L-cycloalkyl are each optionally substituted with one or more R$^6$, and wherein the aryl portion of -L-NR$^{20}$C(O)-aryl, the aryl of the -L-aryl, and the heteroaryl of -L-heteroaryl are each optionally substituted with one or more R$^7$;

each L is independently selected from a C$_1$-C$_4$ alkylene optionally substituted with one or more substituents independently selected from halogen, hydroxy, C$_{1-6}$ alkoxy, C$_1$-C$_4$ hydroxyalkyl, C$_1$-C$_4$ alkyl, C$_3$-C$_6$ carbocycle, and 3- to 8-membered heterocycle, wherein the C$_3$-C$_6$ carbocycle and 3- to 8-membered heterocycle are each optionally substituted with one or more substituents independently selected from halogen, —OH, —NO$_2$, =O, =S, —CN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$haloalkyl; and wherein optionally two substituents on the same carbon atom of L come together to form a C$_3$-C$_6$ carbocycle or 3- to 8-membered heterocycle, wherein the C$_3$-C$_6$ carbocycle and 3- to 8-membered heterocycle are each optionally substituted with one or more substituents independently selected from halogen, —OH, —NO$_2$, =O, =S, —CN, C$_{1-6}$ alkyl-N(R$^{20}$)$_2$, C$_{1-6}$ aminoalkyl, C$_{1-6}$ alkoxy, C$_{1-6}$ hydroxyalkyl, and C$_{1-6}$ haloalkyl;

each R$^4$ is independently selected from halogen, —NO$_2$, —NH$_2$, —NH(C$_{1-6}$ alkyl), —N(C$_{1-6}$ alkyl)$_2$, =O, =S, —CN, C$_{1-6}$ alkyl, C$_{1-6}$ aminoalkyl, C$_{1-6}$ alkoxy, C$_{1-6}$ cyanoalkyl, C$_{1-6}$ hydroxyalkyl, and C$_{1-6}$haloalkyl;

n is selected from 0, 1, 2, 3, and 4;

m is selected from 1 and 2;

each R$^5$ is independently selected from hydrogen and C$_1$-C$_6$ alkyl;

each R$^6$ is independently selected from halogen, hydroxy, C$_1$-C$_3$ hydroxyalkyl, C$_1$-C$_3$ alkyl, oxo, C$_1$-C$_3$ haloalkyl, C$_1$-C$_3$ alkoxy, cyano, =CH$_2$, =NO—C$_1$-C$_3$ alkyl, C$_1$-C$_3$ aminoalkyl, —N(R$^5$)S(O)$_2$(R$^5$), -Q-phenyl, -Q-phenylSO$_2$F, —NHC(O)phenyl, —NHC(O)phenylSO$_2$F, C$_1$-C$_3$ alkyl substituted pyrazolyl, tert-butyldimethylsilyloxyCH$_2$—, —N(R$^5$)$_2$, (C$_1$-C$_3$ alkoxy)C$_1$-C$_3$ alkyl-, (C$_1$-C$_3$ alkyl)C(=O), oxo, (C$_1$-C$_3$ haloalkyl)C(=O)—, —SO$_2$F, (C$_1$-C$_3$ alkoxy)C$_1$-C$_3$ alkoxy, —CH$_2$OC(O)NCF$_3$(R$^5$), —CH$_2$O—C$_1$-C$_6$ alkyl, —CH$_2$OC(O)N(R$^5$)$_2$, —CH$_2$NHC(O)OC$_1$-C$_6$ alkyl, —CH$_2$NHC(O)N(R$^5$)$_2$, —CH$_2$NHC(O)C$_1$-C$_6$ alkyl, —CH$_2$(pyrazolyl), —CH$_2$NHSO$_2$C$_1$-C$_6$ alkyl, —CH$_2$OC(O)heterocycle, —OC(O)N(R$^5$)$_2$, —OC(O)NH(C$_1$-C$_3$ alkyl)O(C$_1$-C$_3$ alkyl), —OC(O)NH(C$_1$-C$_3$ alkyl)O(C$_1$-C$_3$ alkyl)phenyl(C$_1$-C$_3$ alkyl)N(CH$_3$)$_2$, —OC(O)NH(C$_1$-C$_3$ alkyl)O(C$_1$-C$_3$ alkyl)phenyl, —OC(O)heterocycle, —O—C$_1$-C$_3$ alkyl, —O—C$_1$-C$_6$ haloalkyl, —C$_1$-C$_3$ alkyl-O—C$_1$-C$_6$ haloalkyl, C$_{1-6}$ alkyl-N(R$^{20}$)$_2$, —SF$_5$, —C$_1$-C$_3$ alkyl-N$_3$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —(CH$_2$)$_{0-1}$S-heterocycle, —(CH$_2$)$_{0-1}$—O-heterocycle, —(CH$_2$)$_{0-1}$—O-phenyl, and —CH$_2$heterocycle, wherein the phenyl of —NHC(O)phenyl and —OC(O)NH(C$_1$-C$_3$ alkyl)(C$_1$-C$_3$ alkyl)phenyl are optionally substituted with one or more substituents selected from —C(O)H and OH, wherein the alkyl of —O—C$_1$-C$_3$ alkyl is optionally substituted with substituents selected from heterocycle, oxo and hydroxy;

wherein the alkyl of —CH$_2$O—C$_1$-C$_6$ alkyl is optionally substituted with one or more substituents selected from halogen and C$_3$-C$_6$ carbocycle;

wherein the heterocycle of —CH$_2$heterocycle is optionally substituted with oxo; and wherein the phenyl of —(CH$_2$)$_{0-1}$—O-phenyl is optionally substituted with one or more substituents selected from C$_{1-6}$ alkyl, C$_{1-6}$haloalkyl, SF$_5$, C$_{1-6}$ alkyl-OR$^{20}$, —OR$^{20}$;

wherein the heterocycle of —(CH$_2$)$_{0-1}$—O-heterocycle and —(CH$_2$)$_{0-1}$—S-heterocycle are each optionally substituted with one or more substituents selected from C$_{1-6}$ alkyl, C$_{1-6}$ haloalkyl, C$_{1-6}$ alkyl-OR$^{20}$, and —OR$^{20}$;

each Q is selected from a bond and O;

each R$^7$ is independently selected from halogen, hydroxy, HC(=O)—, C$_1$-C$_4$ alkyl, C$_1$-C$_4$ alkoxy, C$_1$-C$_4$ haloalkyl, C$_1$-C$_4$ hydroxyalkyl, and —N(R$^5$)$_2$;

R$^8$ is selected from 5- to 12-membered heterocycle, wherein the 5- to 12-membered heterocycle is optionally substituted with one or more substituents independently selected from halogen, —CN, —NO$_2$, =O, —N(R$^{20}$)$_2$, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —N($R^{20}$)C(O)$R^{20}$, —N($R^{20}$)C(O)N($R^{20}$)$_2$, —N($R^{20}$)C(O)O$R^{20}$, —C(O)$R^{20}$, C(O)O$R^{20}$, —OC(O)$R^{20}$, —OC(O)N($R^{20}$)$_2$, —C(O)N$R^{20}$—O$R^{20}$, $C_{1-6}$ alkyl-N($R^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle;

$R^9$ is selected from hydrogen, halogen, —CN, —$NO_2$, —N($R^{20}$)$_2$, —O$R^{20}$, —S$R^{20}$, $C_{1-6}$ alkyl-N($R^{20}$)$_2$, $C_{1-6}$ aminoalkyl, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, and $C_3$-$C_6$ carbocycle, wherein the $C_3$-$C_6$ carbocycle is optionally substituted with one or more halogen, —CN, —$NO_2$, —N($R^{20}$)$_2$, —O$R^{20}$, —S$R^{20}$, $C_{1-6}$ alkyl-N($R^{20}$)$_2$, $C_{1-6}$ aminoalkyl, $C_{1-6}$ alkoxyalkyl, $C_{1-6}$hydroxyalkyl, $C_{1-6}$ cyanoalkyl, $C_{1-6}$haloalkyl, $C_{1-6}$ alkyl, $C_{2-6}$ alkenyl, $C_{2-6}$ alkynyl; or $R^8$ and $R^9$ come together with the atoms to which they are bound to form B, wherein B is selected from a 7- to 15-membered heterocycle and $C_7$-$C_{15}$ carbocycle, wherein the 7- to 15-membered heterocycle and $C_7$-$C_{15}$ carbocycle are each optionally substituted with one or more substituents independently selected from halogen, —CN, —$NO_2$, =O, —N($R^{20}$)$_2$, —B(O$R^{20}$)$_2$, —O$R^{20}$, —S$R^{20}$, —S(O)$_2$($R^{20}$), —S(O)$_2$N($R^{20}$)$_2$, —N$R^{20}$S(O)$_2$$R^{20}$, —C(O)N($R^{20}$)$_2$, —C(O)N$R^{20}$O$R^{20}$, —N($R^{20}$)C(O)$R^{20}$, —N($R^{20}$)C(O)N($R^{20}$)$_2$, —N($R^{20}$)C(O)O$R^{20}$, —C(O)$R^{20}$, —C(O)O$R^{20}$, —OC(O)$R^{20}$, —OC(O)N($R^{20}$)$_2$, $C_{1-6}$ alkyl-N($R^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle;

each $R^{10}$ is independently selected from halogen, —B(O$R^{20}$)$_2$, —O$R^{20}$, —S$R^{20}$, —S(O)$_2$($R^{20}$), —S(O)$_2$N($R^{20}$)$_2$, —S(O)N($R^{20}$)$_2$, —S(O)$R^{20}$ (=N$R^{20}$), —N$R^{20}$S(O)$_2$$R^{20}$, —C(O)N($R^{20}$)$_2$, —N($R^{20}$)C(O)$R^{20}$, —N($R^{20}$)C(O)N($R^{20}$)$_2$, —N($R^{20}$)C(O)O$R^{20}$, —N($R^{20}$)$_2$, —C(O)$R^{20}$, —C(O)O$R^{20}$, —OC(O)$R^{20}$, —OC(O)N($R^{20}$)$_2$, —$NO_2$, =O, =NO($R^{20}$), —CN, —NHCN, $C_{1-6}$ alkyl-N($R^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle, wherein the $C_3$-$C_{12}$carbocycle and 5- to 12-membered heterocycle are each optionally substituted with one or more substituents independently selected from halogen, —OH, —CN, —$NO_2$, —$NH_2$, —NH($C_{1-6}$ alkyl), —N($C_{1-6}$ alkyl)$_2$, $C_{1-10}$ alkyl, —$C_{1-10}$ haloalkyl, —O—$C_{1-10}$ alkyl, oxo;

each $R^{11}$, $R^{12}$, and $R^{13}$ is independently selected from halogen, —B(O$R^{20}$)$_2$, —O$R^{20}$, —S$R^{20}$, —S(O)$_2$($R^{20}$), —S(O)$_2$N($R^{20}$)$_2$, —S(O)N($R^{20}$)$_2$, —S(O)$R^{20}$ (=N$R^{20}$), —N$R^{20}$S(O)$_2$$R^{20}$, —C(O)N($R^{20}$)$_2$, —N($R^{20}$)C(O)$R^{20}$, —N($R^{20}$)C(O)N($R^{20}$)$_2$, —N($R^{20}$)C(O)O$R^{20}$, —N($R^{20}$)$_2$, —C(O)$R^{20}$, —C(O)O$R^{20}$, —OC(O)$R^{20}$, —OC(O)N($R^{20}$)$_2$, —N$R^{20}$(C=NH)N($R^{20}$)$_2$, —$NO_2$, =O, =NO($R^{20}$), —CN, —NHCN, $C_{1-6}$ alkyl-N($R^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle, wherein the $C_3$-$C_{12}$ carbocycle and 5- to 12-membered heterocycle are each optionally substituted with one or more substituents independently selected from halogen, —OH, —CN, —$NO_2$, —N($R^{21}$)$_2$, —S$R^{21}$, —C(O)N($R^{21}$)$_2$, $C_{1-10}$ alkyl, —$C_{1-10}$ haloalkyl, —O—$C_{1-10}$ alkyl, —S(O)$_2$($R^{21}$), —P(O)(O$R^{21}$)$_2$, —OP(O)(O$R^{21}$)$_2$, —P(O)($R^{21}$)$_2$, and oxo;

each $R^{11A}$, $R^{12A}$, and $R^{13A}$ is independently selected from halogen, —B(O$R^{20}$)$_2$, —O$R^{20}$, —S$R^{20}$, —S(O)$_2$($R^{20}$), —S(O)$_2$N($R^{20}$)$_2$, —S(O)N($R^{20}$)$_2$, —S(O)$R^{20}$ (=N$R^{20}$), —N$R^{20}$S(O)$_2$$R^{20}$, —C(O)N($R^{20}$)$_2$, —N($R^{20}$)C(O)$R^{20}$, —N($R^{20}$)C(O)N($R^{20}$)$_2$, —N($R^{20}$)C(O)O$R^{20}$, —N($R^{20}$)$_2$, —C(O)$R^{20}$, —C(O)O$R^{20}$, —OC(O)$R^{20}$, —OC(O)N($R^{20}$)$_2$, —$NO_2$, =O, =NO($R^{20}$), —CN, —NHCN, $C_{1-6}$ alkyl-N($R^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, and $C_{2-6}$ alkynyl;

each $R^{20}$ is independently selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —$NO_2$, —$NH_2$, —NH($C_{1-6}$ alkyl), —N($C_{1-6}$ alkyl)$_2$, $C_{1-10}$ alkyl, $C_{1-10}$ haloalkyl, —O—$C_{1-10}$ alkyl, oxo, $C_{3-12}$ carbocycle, and 3- to 12-membered heterocycle; and each $R^{21}$ is independently selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —$NO_2$, —$NH_2$, —N($C_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle.

In some embodiments, for a compound or salt of Formula (I), wherein $R^{100}$ is selected from

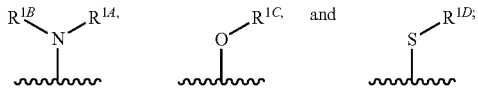

$R^{1A}$ is selected from $C_{1-6}$ alkyl, $C_3$-$C_{12}$ carbocycle, and 4- to 12-membered heterocycle, each of which is optionally substituted with one or more $R^{11}$, and wherein optionally two $R^{11}$ on the same atom of $R^{1A}$ come together to form a $C_3$-$C_6$ carbocycle or 3- to 8-membered heterocycle, wherein the $C_3$-$C_6$ carbocycle and 3- to 8-membered heterocycle are each optionally substituted with one or more $R^{11A}$.

$R^{1B}$ is selected from hydrogen, $C_{1-6}$ alkyl, $C_3$-$C_6$ carbocycle, wherein the $C_{1-6}$ alkyl and $C_3$-$C_6$ carbocycle are each optionally substituted with one or more $R^{10}$;

or $R^{1A}$ and $R^{1B}$ come together with the atom to which they are bound to form $R^1$, wherein $R^1$ is a 5- to 15-membered heterocycle, wherein the 5- to 15-membered heterocycle is optionally substituted with one or more substituents independently selected from halogen, —B(O$R^{20}$)$_2$, —N($R^{20}$)$_2$, —O$R^{20}$, —S$R^{20}$, —S(O)$_2$($R^{20}$), —S(O)$_2$N($R^{20}$)$_2$, —S(O)N($R^{20}$)$_2$, —S(O)$R^{20}$ (=N$R^{20}$), —N$R^{20}$S(O)$_2$$R^{20}$, —C(O)N($R^{20}$)$_2$, —C(=N$R^{20}$)N($R^{20}$)$_2$, —$C_{1-6}$ alkyl(=N$R^{20}$O$R^{20}$), —C(O)N$R^{20}$O$R^{20}$, —N($R^{20}$)C(O)$R^{20}$, —N($R^{20}$)C(O)N($R^{20}$)$_2$, —N($R^{20}$)C(O)O$R^{20}$, —C(O)$R^{20}$, —C(O)O$R^{20}$, —OC(O)$R^{20}$, —OC(O)N($R^{20}$)$_2$, —$NO_2$, =O, =N($R^{20}$), =NO($R^{20}$), —CN, —NHCN, $C_{1-6}$ alkyl-N($R^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl-SO$_2$$R^{20}$, $C_{1-6}$ alkoxyalkyl, $C_{1-6}$ alkyl, $C_{2-6}$ alkenyl, $C_{2-6}$ alkynyl, $C_3$-$C_{12}$ carbocycle and 5- to 12-membered heterocycle, wherein the $C_3$-$C_{12}$ carbocycle and 5- to 12-membered heterocycle are each optionally substituted independently with one or more $R^{1*}$;

each $R^{1*}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$ (=NR$^{20}$), —NR$^{20}$S(O)$_2$R$^{20}$, —C(O)N(R$^{20}$)$_2$, —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$^2$, =O, =N(R$^{20}$), =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, and $C_3$-$C_{12}$ carbocycle;

$R^{1C}$ is selected from hydrogen, $C_{1-6}$ alkyl, $C_3$-$C_{12}$ carbocycle, and 4- to 12-membered heterocycle, each of which is optionally substituted with one or more $R^{12}$, and wherein optionally two $R^{12}$ on the same atom of $R^{1C}$ come together to form a $C_3$-$C_6$ carbocycle or 3- to 8-membered heterocycle, wherein the $C_3$-$C_6$ carbocycle and 3- to 8-membered heterocycle are each optionally substituted with one or more $R^{12A}$;

$R^{1D}$ is selected from hydrogen, $C_{1-6}$ alkyl, $C_3$-$C_{12}$ carbocycle, and 4- to 12-membered heterocycle, each of which is optionally substituted with one or more $R^{13}$, and wherein optionally two $R^{13}$ on the same atom of $R^{1D}$ come together to form a $C_3$-$C_6$ carbocycle or 3- to 8-membered heterocycle, wherein the $C_3$-$C_6$ carbocycle and 3- to 8-membered heterocycle are each optionally substituted with one or more $R^{13A}$.

Y is —O—;

$R^2$ is selected from heterocycle, -L-heterocycle, -L-N(R$^{20}$)$_2$, -L-OR$^{20}$, -L-aryl, -L-heteroaryl, -L-cycloalkyl, -L-NHC(=NH)NH$_2$, -L-C(O)N(R$^{20}$)$_2$, -L-$C_1$-$C_6$ haloalkyl, -L-NR$^{20}$C(O)-aryl, -L-COOH, -L-NR$^{20}$S(O)$_2$(R$^{20}$), -L-S(O)$_2$N(R$^{20}$)$_2$, -L-N(R$^{20}$)C(O)(OR$^{20}$), -L-OC(O)N(R$^{20}$)$_2$, and -L-C(=O)OC$_1$-C$_6$ alkyl, wherein the heterocycle, the heterocycle portion of -L-heterocycle, and the cycloalkyl portion of the -L-cycloalkyl are each optionally substituted with one or more $R^6$, and wherein the aryl portion of -L-NR$^{20}$C(O)-aryl, the aryl of the -L-aryl, and the heteroaryl of -L-heteroaryl are each optionally substituted with one or more $R^7$;

each L is independently selected from a $C_1$-$C_4$ alkylene optionally substituted with one or more substituents independently selected from halogen, hydroxy, $C_{1-6}$ alkoxy, $C_1$-$C_4$ hydroxyalkyl, $C_1$-$C_4$ alkyl, $C_3$-$C_6$ carbocycle, and 3- to 8-membered heterocycle, wherein the $C_3$-$C_6$ carbocycle and 3- to 8-membered heterocycle are each optionally substituted with one or more substituents independently selected from halogen, —OH, —NO$_2$, =O, =S, —CN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ haloalkyl; and wherein optionally two substituents on the same carbon atom of L come together to form a $C_3$-$C_6$ carbocycle or 3- to 8-membered heterocycle, wherein the $C_3$-$C_6$ carbocycle and 3- to 8-membered heterocycle are each optionally substituted with one or more substituents independently selected from halogen, —OH, —NO$_2$, =O, =S, —CN, $C_{1-6}$ alkyl-N(R$^{20}$)$_2$, $C_{1-6}$ aminoalkyl, $C_{1-6}$ alkoxy, $C_{1-6}$ hydroxyalkyl, and $C_{1-6}$ haloalkyl;

each $R^4$ is independently selected from halogen, —NO$_2$, —NH$_2$, —NH($C_{1-6}$ alkyl), —N($C_{1-6}$ alkyl)$_2$, =O, =S, —CN, $C_{1-6}$ alkyl, $C_{1-6}$ aminoalkyl, $C_{1-6}$ alkoxy, $C_{1-6}$ cyanoalkyl, $C_{1-6}$ hydroxyalkyl, and $C_{1-6}$ haloalkyl;

n is selected from 0, 1, 2, 3, and 4;

m is selected from 1 and 2;

each $R^5$ is independently selected from hydrogen and $C_1$-$C_6$ alkyl;

each $R^6$ is independently selected from halogen, hydroxy, $C_1$-$C_3$ hydroxyalkyl, $C_1$-$C_3$ alkyl, oxo, $C_1$-$C_3$ haloalkyl, $C_1$-$C_3$ alkyl-N$_3$, $C_1$-$C_3$ alkoxy, cyano, =CH$_2$, =NO—$C_1$-$C_3$ alkyl, $C_1$-$C_3$ aminoalkyl, —N(R$^5$)S(O)$_2$(R$^5$), -Q-phenyl, -Q-phenylSO$_2$F, —NHC(O)phenyl, —NHC(O)phenylSO$_2$F, $C_1$-$C_3$ alkyl substituted pyrazolyl, tert-butyldimethylsilyloxyCH$_2$—, —N(R$^5$)$_2$, ($C_1$-$C_3$ alkoxy)$C_1$-$C_3$ alkyl-, ($C_1$-$C_3$ alkyl)C(=O), oxo, ($C_1$-$C_3$ haloalkyl)C(=O)—, —SO$_2$F, ($C_1$-$C_3$ alkoxy)$C_1$-$C_3$ alkoxy, —CH$_2$OC(O)N(R$^5$)$_2$, —CH$_2$NHC(O)OC$_1$-C$_6$ alkyl, —CH$_2$NHC(O)N(R$^5$)$_2$, —CH$_2$NHC(O)C$_1$-C$_6$ alkyl, —CH$_2$(pyrazolyl), —CH$_2$NHSO$_2$C$_1$-C$_6$ alkyl, —CH$_2$OC(O)heterocycle, —OC(O)N(R$^5$)$_2$, —OC(O)NH(C$_1$-C$_3$ alkyl)O(C$_1$-C$_3$ alkyl), —OC(O)NH(C$_1$-C$_3$ alkyl)O(C$_1$-C$_3$ alkyl)phenyl(C$_1$-C$_3$ alkyl)N(CH$_3$)$_2$, —OC(O)NH(C$_1$-C$_3$ alkyl)O(C$_1$-C$_3$ alkyl)phenyl, —OC(O)heterocycle, —O—$C_1$-$C_3$ alkyl, —S(O)$_2$(R$^{20}$), —S(O)$_2$N(R$^{20}$)$_2$, —S(O)N(R$^{20}$)$_2$, —S(O)R$^{20}$ (=NR$^{20}$), —NR$^{20}$S(O)$_2$R$^{20}$, and —CH$_2$heterocycle, wherein the phenyl of —NHC(O)phenyl and —OC(O)NH(C$_1$-C$_3$ alkyl)(C$_1$-C$_3$ alkyl)phenyl are optionally substituted with one or more substituents selected from —C(O)H and OH, and wherein the alkyl of —O—$C_1$-$C_3$ alkyl is optionally substituted with substituents selected from heterocycle, oxo and hydroxy; and wherein the heterocycle of —CH$_2$heterocyclyl is optionally substituted with oxo;

each Q is selected from a bond and O;

each $R^7$ is independently selected from halogen, hydroxy, HC(=O)—, $C_1$-$C_4$ alkyl, $C_1$-$C_4$ alkoxy, $C_1$-$C_4$ haloalkyl, $C_1$-$C_4$ hydroxyalkyl, and —N(R$^5$)$_2$;

$R^8$ is selected from 5- to 12-membered heterocycle, wherein the 5- to 12-membered heterocycle is optionally substituted with one or more substituents independently selected from halogen, —CN, —NO$_2$, =O, —N(R$^{20}$)$_2$, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$ (=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —C(O)R$^{20}$, C(O)OR$^{20}$, —OC(O)R$^{20}$, —OC(O)N(R$^{20}$)$_2$, —C(O)NR$^{20}$OR$^{20}$, $C_{1-6}$ alkyl-N(R$^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle;

$R^9$ is selected from hydrogen, halogen, —CN, —NO$_2$, —N(R$^{20}$)$_2$, —OR$^{20}$, —SR$^{20}$, $C_{1-6}$ alkyl-N(R$^{20}$)$_2$, $C_{1-6}$ aminoalkyl, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, and $C_3$-$C_6$ carbocycle, wherein the $C_3$-$C_6$ carbocycle is optionally substituted with one or more halogen, —CN, —NO$_2$, —N(R$^{20}$)$_2$, —OR$^{20}$, —SR$^{20}$, $C_{1-6}$ alkyl-N(R$^{20}$)$_2$, $C_{1-6}$ aminoalkyl, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl; or $R^8$ and $R^9$ come together with the atoms to which they are bound to form B, wherein B is selected from a 7- to 15-membered heterocycle and $C_7$-$C_{15}$ carbocycle, wherein the 7- to 15-membered heterocycle and $C_7$-$C_{15}$ carbocycle are each optionally substituted with one or more substituents independently selected from halogen, —CN, —NO$_2$, =O, —N(R$^{20}$)$_2$, —B(OR$^{20}$)$_2$, —OR$^{20}$, —SR$^{20}$, —S(O)$_2$(R$^{20}$), —S(O)$_2$N(R$^{20}$)$_2$, —NR$^{20}$S(O)$_2$R$^{20}$, —C(O)N(R$^{20}$)$_2$, —C(O)NR$^{20}$OR$^{20}$, —N($R^{20}$)C(O)$R^{20}$, —N($R^{20}$)C(O)N($R^{20}$)$_2$, —N($R^{20}$)C(O)O$R^{20}$, —C(O)$R^{20}$, —C(O)O$R^{20}$, —OC(O)$R^{20}$, —OC(O)N($R^{20}$)$_2$, $C_{1-6}$ alkyl-N($R^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle;

each $R^{10}$ is independently selected from halogen, —B(O$R^{20}$)$_2$, —O$R^{20}$, —S$R^{20}$, —S(O)$_2$($R^{20}$), —S(O)$_2$N($R^{20}$)$_2$, —S(O)N($R^{20}$)$_2$, —S(O)$R^{20}$ (=N$R^{20}$), —N$R^{20}$S(O)$_2$$R^{20}$, —C(O)N($R^{20}$)$_2$, —N($R^{20}$)C(O)$R^{20}$, —N($R^{20}$)C(O)N($R^{20}$)$_2$, —N($R^{20}$)C(O)O$R^{20}$, —N($R^{20}$)$_2$, —C(O)$R^{20}$, —C(O)O$R^{20}$, —OC(O)$R^{20}$, —OC(O)N($R^{20}$)$_2$, —NO$_2$, =O, =NO($R^{20}$), —CN, —NHCN, $C_{1-6}$ alkyl-N($R^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle, wherein the $C_3$-$C_{12}$ carbocycle and 5- to 12-membered heterocycle are each optionally substituted with one or more substituents independently selected from halogen, —OH, —CN, —NO$_2$, —NH$_2$, —NH($C_{1-6}$ alkyl), —N($C_{1-6}$ alkyl)$_2$, $C_{1-10}$ alkyl, —$C_{1-10}$ haloalkyl, —O—$C_{1-10}$ alkyl, oxo;

each $R^{11}$, $R^{12}$, and $R^{13}$ is independently selected from halogen, —B(O$R^{20}$)$_2$, —O$R^{20}$, —S$R^{20}$, —S(O)$_2$($R^{20}$), —S(O)$_2$N($R^{20}$)$_2$, —S(O)N($R^{20}$)$_2$, —S(O)$R^{20}$ (=N$R^{20}$), —N$R^{20}$S(O)$_2$$R^{20}$, —C(O)N($R^{20}$)$_2$, —N($R^{20}$)C(O)$R^{20}$, —N($R^{20}$)C(O)N($R^{20}$)$_2$, —N($R^{20}$)C(O)O$R^{20}$, —N($R^{20}$)$_2$, —C(O)$R^{20}$, —C(O)O$R^{20}$, —OC(O)$R^{20}$, —OC(O)N($R^{20}$)$_2$, —NO$_2$, =O, =NO($R^{20}$), —CN, —NHCN, $C_{1-6}$ alkyl-N($R^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle, wherein the $C_3$-$C_{12}$ carbocycle and 5- to 12-membered heterocycle are each optionally substituted with one or more substituents independently selected from halogen, —OH, —CN, —NO$_2$, —N($R^{21}$)$_2$, —S$R^{21}$, —C(O)N($R^{21}$)$_2$, $C_{1-10}$ alkyl, —$C_{1-10}$ haloalkyl, —O—$C_{1-10}$ alkyl, and oxo;

each $R^{11A}$, $R^{12A}$, and $R^{13A}$ is independently selected from halogen, —B(O$R^{20}$)$_2$, —O$R^{20}$, —S$R^{20}$, —S(O)$_2$($R^{20}$), —S(O)$_2$N($R^{20}$)$_2$, —S(O)N($R^{20}$)$_2$, —S(O)$R^{20}$ (=N$R^{20}$), —N$R^{20}$S(O)$_2$$R^{20}$, —C(O)N($R^{20}$)$_2$, —N($R^{20}$)C(O)$R^{20}$, —N($R^{20}$)C(O)N($R^{20}$)$_2$, —N($R^{20}$)C(O)O$R^{20}$, —N($R^{20}$)$_2$, —C(O)$R^{20}$, —C(O)O$R^{20}$, —OC(O)$R^{20}$, —OC(O)N($R^{20}$)$_2$, —NO$_2$, =O, =NO($R^{20}$), —CN, —NHCN, $C_{1-6}$ alkyl-N($R^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, and $C_{2-6}$ alkynyl;

each $R^{20}$ is independently selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —NO$_2$, —NH$_2$, —NH($C_{1-6}$ alkyl), —N($C_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle; and each $R^{21}$ is independently selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —NO$_2$, —NH$_2$, —N($C_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle.

In certain embodiments, the disclosure provides a pharmaceutical composition comprising a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), and a pharmaceutically acceptable excipient.

In certain embodiments, the disclosure provides a method of treating a disease or disorder, using a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J).

In certain embodiments, the disclosure provides a method of treating a disease or disorder, using a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), and a pharmaceutically acceptable excipient.

In certain embodiments, the disclosure provides a method of inhibiting KRas G12D and/or other G12 mutants, using a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J).

In certain embodiments, the disclosure provides a method of inhibiting KRas G12D and/or other G12 mutants, using a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), and a pharmaceutically acceptable excipient.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

The following description sets forth numerous exemplary configurations, methods, parameters, and the like. It should be recognized, however, that such description is not intended as a limitation on the scope of the present disclosure, but is instead provided as a description of exemplary embodiments.

In the following description, certain specific details are set forth in order to provide a thorough understanding of various embodiments of the disclosure. However, one skilled in the art will understand that the disclosure may be practiced without these details.

Definitions

Unless defined otherwise, all technical and scientific terms used herein have the same meaning as is commonly understood by one of skill in the art to which this invention belongs. All patents and publications referred to herein are incorporated by reference.

"Alkyl" refers to a straight or branched hydrocarbon chain radical consisting solely of carbon and hydrogen atoms, containing no unsaturation, and preferably having from one to fifteen carbon atoms (i.e., $C_1$-$C_{15}$ alkyl). In certain embodiments, an alkyl comprises one to thirteen carbon atoms (i.e., $C_1$-$C_{13}$ alkyl). In certain embodiments, an alkyl comprises one to eight carbon atoms (i.e., $C_1$-$C_8$ alkyl). In other embodiments, an alkyl comprises one to five carbon atoms (i.e., $C_1$-$C_5$ alkyl). In other embodiments, an alkyl comprises one to four carbon atoms (i.e., $C_1$-$C_4$ alkyl). In other embodiments, an alkyl comprises one to three carbon atoms (i.e., $C_1$-$C_3$ alkyl). In other embodiments, an alkyl comprises one to two carbon atoms (i.e., $C_1$-$C_2$ alkyl). In other embodiments, an alkyl comprises one carbon atom (i.e., $C_1$ alkyl). In other embodiments, an alkyl comprises five to fifteen carbon atoms (i.e., $C_5$-$C_{15}$ alkyl). In other embodiments, an alkyl comprises five to eight carbon atoms (i.e., $C_5$-$C_8$ alkyl). In other embodiments, an alkyl comprises two to five carbon atoms (i.e., $C_2$-$C_5$ alkyl). In other embodiments, an alkyl comprises three to five carbon atoms (i.e., $C_3$-$C_5$ alkyl). In certain embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond.

The term "$C_{x-y}$" or "$C_x$-$C_y$" when used in conjunction with a chemical moiety, such as alkyl, alkenyl, or alkynyl is meant to include groups that contain from x to y carbons in the chain. For example, the term "$C_{1-6}$alkyl" or "$C_1$-$C_6$alkyl" refers to substituted or unsubstituted saturated hydrocarbon groups, including straight-chain alkyl and branched-chain alkyl groups that contain from 1 to 6 carbons. The term —$C_{x-y}$alkylene- refers to a substituted or unsubstituted alkylene chain with from x to y carbons in the alkylene chain. For example —$C_{1-6}$alkylene- may be selected from methylene, ethylene, propylene, butylene, pentylene, and hexylene, any one of which is optionally substituted.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and preferably having from two to twelve carbon atoms (i.e., $C_2$-$C_{12}$ alkenyl). In certain embodiments, an alkenyl comprises two to eight carbon atoms (i.e., $C_2$-$C_8$ alkenyl). In certain embodiments, an alkenyl comprises two to six carbon atoms (i.e., $C_2$-$C_6$ alkenyl). In other embodiments, an alkenyl comprises two to four carbon atoms (i.e., $C_2$-$C_4$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like.

"Alkynyl" refers to a straight or branched hydrocarbon chain radical group consisting solely of carbon and hydrogen atoms, containing at least one carbon-carbon triple bond, and preferably having from two to twelve carbon atoms (i.e., $C_2$-$C_{12}$ alkynyl). In certain embodiments, an alkynyl comprises two to eight carbon atoms (i.e., $C_2$-$C_8$ alkynyl). In other embodiments, an alkynyl comprises two to six carbon atoms (i.e., $C_2$-$C_6$ alkynyl). In other embodiments, an alkynyl comprises two to four carbon atoms (i.e., $C_2$-$C_4$ alkynyl). The alkynyl is attached to the rest of the molecule by a single bond, for example, ethynyl, propynyl, butynyl, pentynyl, hexynyl, and the like.

The terms "$C_{x-y}$alkenyl" and "$C_{x-y}$alkynyl" refer to substituted or unsubstituted unsaturated aliphatic groups analogous in length and possible substitution to the alkyls described above, but that contain at least one double or triple bond, respectively. The term —$C_{x-y}$alkenylene-refers to a substituted or unsubstituted alkenylene chain with from x to y carbons in the alkenylene chain. For example, —$C_{2-6}$alkenylene- may be selected from ethenylene, propenylene, butenylene, pentenylene, and hexenylene, any one of which is optionally substituted. An alkenylene chain may have one double bond or more than one double bond in the alkenylene chain. The term —$C_{x-y}$alkynylene- refers to a substituted or unsubstituted alkynylene chain with from x to y carbons in the alkenylene chain. For example, —$C_{2-6}$alkenylene- may be selected from ethynylene, propynylene, butynylene, pentynylene, and hexynylene, any one of which is optionally substituted. An alkynylene chain may have one triple bond or more than one triple bond in the alkynylene chain.

"Alkylene" or "alkylene chain" refers to a straight or branched divalent hydrocarbon chain linking the rest of the molecule to a radical group, consisting solely of carbon and hydrogen, containing no unsaturation, and preferably having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group may be through any two carbons within the chain. In certain embodiments, an alkylene comprises one to ten carbon atoms (i.e., $C_1$-$C_8$ alkylene). In certain embodiments, an alkylene comprises one to eight carbon atoms (i.e., $C_1$-$C_8$ alkylene). In other embodiments, an alkylene comprises one to five carbon atoms (i.e., $C_1$-$C_5$ alkylene). In other embodiments, an alkylene comprises one to four carbon atoms (i.e., $C_1$-$C_4$ alkylene). In other embodiments, an alkylene comprises one to three carbon atoms (i.e., $C_1$-$C_3$ alkylene). In other embodiments, an alkylene comprises one to two carbon atoms (i.e., $C_1$-$C_2$ alkylene). In other embodiments, an alkylene comprises one carbon atom (i.e., $C_1$ alkylene). In other embodiments, an alkylene comprises five to eight carbon atoms (i.e., $C_5$-$C_8$ alkylene). In other embodiments, an alkylene comprises two to five carbon atoms (i.e., $C_2$-$C_5$ alkylene). In other embodiments, an alkylene comprises three to five carbon atoms (i.e., $C_3$-$C_5$ alkylene).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and preferably having from two to twelve carbon atoms. The alkenylene chain is attached to the rest of the molecule through a single bond and to the radical group through a single bond. The points of attachment of the alkenylene chain to the rest of the molecule and to the radical group may be through any two carbons within the chain. In certain embodiments, an alkenylene comprises two to ten carbon atoms (i.e., $C_2$-$C_{10}$ alkenylene). In certain embodiments, an alkenylene comprises two to eight carbon atoms (i.e., $C_2$-$C_8$ alkenylene). In other embodiments, an alkenylene comprises two to five carbon atoms (i.e., $C_2$-$C_5$ alkenylene). In other embodiments, an alkenylene comprises two to four carbon atoms (i.e., $C_2$-$C_4$ alkenylene). In other embodiments, an alkenylene comprises two to three carbon atoms (i.e., $C_2$-$C_3$ alkenylene). In other embodiments, an alkenylene comprises two carbon atom (i.e., $C_2$ alkenylene). In other embodiments, an alkenylene comprises five to eight carbon atoms (i.e., $C_5$-$C_8$ alkenylene). In other embodiments, an alkenylene comprises three to five carbon atoms (i.e., $C_3$-$C_5$ alkenylene).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and preferably having from two to twelve carbon atoms. The alkynylene chain is attached to the rest of the molecule through a single bond and to the radical group through a single bond. The points of attachment of the alkynylene chain to the rest of the molecule and to the radical group may be through any two carbons within the chain. In certain embodiments, an alkynylene comprises two to ten carbon atoms (i.e., $C_2$-$C_{10}$ alkynylene). In certain embodiments, an alkynylene comprises two to eight carbon atoms (i.e., $C_2$-$C_8$ alkynylene). In other embodiments, an alkynylene comprises two to five carbon atoms (i.e., $C_2$-$C_5$ alkynylene). In other embodiments, an alkynylene comprises two to four carbon atoms (i.e., $C_2$-$C_4$ alkynylene). In other embodiments, an alkynylene comprises two to three carbon atoms (i.e., $C_2$-$C_3$ alkynylene). In other embodiments, an alkynylene comprises two carbon atom (i.e., $C_2$ alkynylene). In other embodiments, an alkynylene comprises five to eight carbon atoms (i.e., $C_5$-$C_8$ alkynylene). In other embodiments, an alkynylene comprises three to five carbon atoms (i.e., $C_3$-$C_5$ alkynylene).

"Aryl" refers to a radical derived from an aromatic monocyclic or aromatic multicyclic hydrocarbon ring system by removing a hydrogen atom from a ring carbon atom. The aromatic monocyclic or aromatic multicyclic hydrocarbon ring system contains only hydrogen and carbon and from five to eighteen carbon atoms, where at least one of the rings in the ring system is aromatic, i.e., it contains a cyclic, delocalized (4n+2) π-electron system in accordance with the Hickel theory. The ring system from which aryl groups are derived include, but are not limited to, groups such as benzene, fluorene, indane, indene, tetralin and naphthalene.

"Aralkyl" refers to a radical of the formula —$R^c$-aryl where $R^c$ is an alkylene chain as defined above, for example, methylene, ethylene, and the like.

"Aralkenyl" refers to a radical of the formula —$R^d$-aryl where $R^d$ is an alkenylene chain as defined above. "Aralkynyl" refers to a radical of the formula —$R^e$-aryl, where $R^e$ is an alkynylene chain as defined above.

"Carbocycle" refers to a saturated, unsaturated or aromatic rings in which each atom of the ring is carbon. Carbocycle may include 3- to 10-membered monocyclic rings, 6- to 12-membered bicyclic rings, and 6- to 12-membered bridged rings. Each ring of a bicyclic carbocycle may be selected from saturated, unsaturated, and aromatic rings. An aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl. Bicyclic carbocycles may be fused, bridged or spiro-ring systems. In some cases, spiro-ring carbocycles have at least two molecular rings with only one common atom.

The term "unsaturated carbocycle" refers to carbocycles with at least one degree of unsaturation and excluding aromatic carbocycles. Examples of unsaturated carbocycles include cyclohexadiene, cyclohexene, and cyclopentene.

"Cycloalkyl" refers to a fully saturated monocyclic or polycyclic hydrocarbon radical consisting solely of carbon and hydrogen atoms, which includes fused or bridged ring systems, and preferably having from three to twelve carbon atoms. In certain embodiments, a cycloalkyl comprises three to ten carbon atoms. In other embodiments, a cycloalkyl comprises five to seven carbon atoms. The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and cyclooctyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like.

"Cycloalkenyl" refers to an unsaturated non-aromatic monocyclic or polycyclic hydrocarbon radical consisting solely of carbon and hydrogen atoms, which includes fused or bridged ring systems, preferably having from three to twelve carbon atoms and comprising at least one double bond. In certain embodiments, a cycloalkenyl comprises three to ten carbon atoms. In other embodiments, a cycloalkenyl comprises five to seven carbon atoms. The cycloalkenyl may be attached to the rest of the molecule by a single bond. Examples of monocyclic cycloalkenyls includes, e.g., cyclopentenyl, cyclohexenyl, cycloheptenyl, and cyclooctenyl.

"Cycloalkylalkyl" refers to a radical of the formula —$R^c$-cycloalkyl where $R^c$ is an alkylene chain as described above.

"Cycloalkylalkoxy" refers to a radical bonded through an oxygen atom of the formula —O—$R^c$-cycloalkyl where $R^c$ is an alkylene chain as described above.

"Halo" or "halogen" refers to halogen substituents such as bromo, chloro, fluoro and iodo substituents.

As used herein, the term "haloalkyl" or "haloalkane" refers to an alkyl radical, as defined above, that is substituted by one or more halogen radicals, for example, trifluoromethyl, dichloromethyl, bromomethyl, 2,2,2-trifluoroethyl, 1-fluoromethyl-2-fluoroethyl, and the like. In some embodiments, the alkyl part of the fluoroalkyl radical is optionally further substituted. Examples of halogen substituted alkanes ("haloalkanes") include halomethane (e.g., chloromethane, bromomethane, fluoromethane, iodomethane), di- and trihalomethane (e.g., trichloromethane, tribromomethane, trifluoromethane, triiodomethane), 1-haloethane, 2-haloethane, 1,2-dihaloethane, 1-halopropane, 2-halopropane, 3-halopropane, 1,2-dihalopropane, 1,3-dihalopropane, 2,3-dihalopropane, 1,2,3-trihalopropane, and any other suitable combinations of alkanes (or substituted alkanes) and halogens (e.g., Cl, Br, F, I, etc.). When an alkyl group is substituted with more than one halogen radicals, each halogen may be independently selected e.g., 1-chloro,2-fluoroethane.

"Fluoroalkyl" refers to an alkyl radical, as defined above, that is substituted by one or more fluoro radicals, for example, trifluoromethyl, difluoromethyl, fluoromethyl, 2,2,2-trifluoroethyl, 1-fluoromethyl-2-fluoroethyl, and the like.

"Aminoalkyl" refers to an alkyl radical, as defined above, that is substituted by one or more amine radicals, for example, propan-2-amine, butane-1,2-diamine, pentane-1,2,4-triamine and the like.

"Hydroxyalkyl" refers to an alkyl radical, as defined above, that is substituted by one or more hydroxy radicals, for example, propan-1-ol, butane-1,4-diol, pentane-1,2,4-triol, and the like.

"Alkoxyalkyl" refers to an alkyl radical, as defined above, that is substituted by one or more alkoxy radicals, for example, methoxymethane, 1,3-dimethoxybutane, 1-methoxypropane, 2-ethoxypentane, and the like.

"Cyanoalkyl" as used herein refers to an alkyl radical, as defined above, that is substituted by one or more cyano radicals, for example, acetonitrile, 2-ethyl-3-methylsuccinonitrile, butyronitrile, and the like.

"Heterocycle" refers to a saturated or unsaturated or aromatic ring comprising one or more heteroatoms. Exemplary heteroatoms include N, O, Si, P, B, Se, and S atoms. Heterocycles include 3- to 10-membered monocyclic rings, 6- to 12-membered bicyclic rings, and 6- to 12-membered bridged rings. Each ring of a bicyclic heterocycle may be selected from saturated, unsaturated, and aromatic rings. Bicyclic heterocycles may be fused, bridged or spiro-ring systems. In some cases, spiro-ring heterocycles have at least two molecular rings with only one common atom. The spiro-ring heterocycle includes at least one heteroatom.

"Heterocyclene" refers to a divalent heterocycle linking the rest of the molecule to a radical group.

"Heteroaryl" or "aromatic heterocycle" refers to a radical derived from a heteroaromatic ring radical that comprises one to eleven carbon atoms and at least one heteroatom wherein each heteroatom may be selected from N, O, and S. As used herein, the heteroaryl ring may be selected from monocyclic or bicyclic and fused or bridged ring systems rings wherein at least one of the rings in the ring system is aromatic, i.e., it contains a cyclic, delocalized (4n+2) π-electron system in accordance with the Hickel theory. The heteroatom(s) in the heteroaryl radical may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryls include, but are not limited to, pyridine, pyrimidine, oxazole, furan, pyran, thiophene, isoxazole, benzimidazole, benzthiazole, and imidazopyridine.

An "X-membered heteroaryl" refers to the number of endocylic atoms, i.e., X, in the ring. For example, a 5-membered heteroaryl ring or 5-membered aromatic heterocycle has 5 endocyclic atoms, e.g., triazole, oxazole, thiophene, etc.

The term "unsaturated heterocycle" refers to heterocycles with at least one degree of unsaturation and excluding aromatic heterocycles. Examples of unsaturated heterocycles include dihydropyrrole, dihydrofuran, oxazoline, pyrazoline, and dihydropyridine. Heterocycles may be optionally substituted by one or more substituents such as those substituents described herein.

The term "substituted" refers to moieties having substituents replacing a hydrogen on one or more carbons or substitutable heteroatoms, e.g., NH, of the structure. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group.

As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)OR$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, and heterocycle, any of which may be optionally substituted by alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O) OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain.

As used herein, the term "optional" or "optionally" means that the subsequently described event of circumstances may or may not occur, and that the description includes instances where the event or circumstance occurs and instances in which it does not. For example, "optionally substituted aryl" means that the aryl group may or may not be substituted and that the description includes both substituted aryl groups and aryl groups having no substitution.

As used herein, the term "electrophile" or "electrophilic moiety" is any moiety capable of reacting with a nucleophile (e.g., a moiety having a lone pair of electrons, a negative charge, a partial negative charge and/or an excess of electrons, for example an —SH group). Electrophiles typically are electron poor or comprise atoms which are electron poor. In certain embodiments, an electrophile contains a positive charge or partial positive charge, has a resonance structure which contains a positive charge or partial positive charge, or is a moiety in which delocalization or polarization of electrons results in one or more atoms which contains a positive charge or partial positive charge. In some embodiments, an electrophile comprises a conjugated double bond, for example an α,β-unsaturated carbonyl or α,β-unsaturated thiocarbonyl compound.

As used in the specification and claims, the singular form "a", "an" and "the" includes plural references unless the context clearly dictates otherwise.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the term "prevent" or "preventing" as related to a disease or disorder may refer to a compound that, in a statistical sample, reduces the occurrence of the disorder or condition in the treated sample relative to an untreated control sample, or delays the onset or reduces the severity of one or more symptoms of the disorder or condition relative to the untreated control sample.

The terms "treat," "treating" or "treatment," as used herein, may include alleviating, abating or ameliorating a disease or condition symptoms, preventing additional symptoms, ameliorating or preventing the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "G12 mutants", as used herein, refers to other oncogenic alleles of KRAS at amino acid position 12 (ie. G12X).

Compounds of the Disclosure

The following is a discussion of compounds and salts thereof that may be used in the methods of the disclosure.

In aspect, the present disclosure provides a compound of Formula (I):

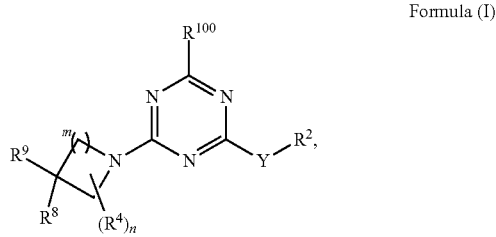

Formula (I)

or a pharmaceutically acceptable salt thereof wherein:
$R^{100}$ is selected from

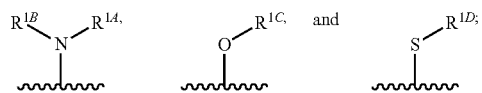

$R^{1A}$ is selected from $C_{1-6}$ alkyl, $C_3$-$C_{12}$ carbocycle, and 4- to 12-membered heterocycle, each of which is optionally substituted with one or more $R^{11}$, and wherein optionally two $R^{11}$ on the same atom of $R^{1A}$ come together to form a $C_3$-$C_6$ carbocycle or 3- to 8-membered heterocycle, wherein the $C_3$-$C_6$ carbocycle and 3- to 8-membered heterocycle are each optionally substituted with one or more $R^{11A}$;

$R^{1B}$ is selected from hydrogen, $C_{1-6}$ alkyl, $C_3$-$C_6$ carbocycle, 4- to 6-membered heterocycle, wherein the $C_{1-6}$ alkyl, $C_3$-$C_6$ carbocycle, and 4- to 6-membered heterocycle, are each optionally substituted with one or more $R^{10}$;

or $R^{1A}$ and $R^{1B}$ come together with the atom to which they are bound to form $R^1$, wherein $R^1$ is a 5- to 15-membered heterocycle, wherein the 5- to 15-membered heterocycle is optionally substituted with one or more substituents independently selected from halogen, —B(OR$^{20}$)$_2$, —N(R$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$ (=NR$^{20}$), —NR$^{20}$S(O)$_2$R$^{20}$, —C(O)N(R$^{20}$)$_2$, —C(=NR$^{20}$)N(R$^{20}$)$_2$, —C$_{1-6}$ alkyl(=NR$^{20}$OR$^{20}$), —C(O)NR$^{20}$OR$^{20}$, —N(R$^{20}$)C(O)R$^{20}$, —N(R$^{20}$)C(O)

N($R^{20}$)$_2$, —N($R^{20}$)C(O)O$R^{20}$, —C(O)$R^{20}$, —C(O)O$R^{20}$, —OC(O)$R^{20}$, —OC(O)N($R^{20}$)$_2$, —NO$_2$, =O, =N($R^{20}$), =NO($R^{20}$), —CN, —NHCN, $C_{1-6}$ alkyl-N($R^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl-SO$_2$$R^{20}$, $C_{1-6}$ alkoxyalkyl, $C_{1-6}$ alkyl, $C_{2-6}$ alkenyl, $C_{2-6}$ alkynyl, $C_3$-$C_{12}$ carbocycle and 5- to 12-membered heterocycle, wherein the $C_3$-$C_{12}$ carbocycle and 5- to 12-membered heterocycle are each optionally substituted independently with one or more $R^{1*}$;

each $R^{1*}$ is independently selected from halogen, —B(O$R^{20}$)$_2$, —O$R^{20}$, —S$R^{20}$, —S(O)$_2$($R^{20}$), —S(O)$_2$N($R^{20}$)$_2$, —S(O)N($R^{20}$)$_2$, —S(O)$R^{20}$ (=N$R^{20}$), —N$R^{20}$S(O)$_2$$R^{20}$, —C(O)N($R^{20}$)$_2$, —C(O)N$R^{20}$O$R^{20}$, —N($R^{20}$)C(O)$R^{20}$, —N($R^{20}$)C(O)N($R^{20}$)$_2$, —N($R^{20}$)C(O)O$R^{20}$, —N($R^{20}$)$_2$, —C(O)$R^{20}$, —C(O)O$R^{20}$, —OC(O)$R^{20}$, —OC(O)N($R^{20}$)$_2$, —NO$_2$, =O, =N($R^{20}$), =NO($R^{20}$), —CN, —NHCN, $C_{1-6}$ alkyl-N($R^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, and $C_3$-$C_{12}$ carbocycle;

$R^{1C}$ is selected from hydrogen, $C_{1-6}$ alkyl, $C_3$-$C_{12}$ carbocycle, and 4- to 12-membered heterocycle, each of which is optionally substituted with one or more $R^{12}$, and wherein optionally two $R^{12}$ on the same atom of $R^{1C}$ come together to form a $C_3$-$C_6$ carbocycle or 3- to 8-membered heterocycle, wherein the $C_3$-$C_6$ carbocycle and 3- to 8-membered heterocycle are each optionally substituted with one or more $R^{12A}$;

$R^{1D}$ is selected from hydrogen, $C_{1-6}$ alkyl, $C_3$-$C_{12}$ carbocycle, and 4- to 12-membered heterocycle, each of which is optionally substituted with one or more $R^{13}$, and wherein optionally two $R^{13}$ on the same atom of $R^D$ come together to form a $C_3$-$C_6$ carbocycle or 3- to 8-membered heterocycle, wherein the $C_3$-$C_6$ carbocycle and 3- to 8-membered heterocycle are each optionally substituted with one or more $R^{13A}$;

Y is —O—;

$R^2$ is selected from heterocycle, -L-heterocycle, -L-N($R^{20}$)$_2$, -L-O$R^{20}$, -L-aryl, -L-heteroaryl, -L-cycloalkyl, -L-NHC(=NH)NH$_2$, -L-C(O)N($R^{20}$)$_2$, -L-$C_1$-$C_6$ haloalkyl, -L-N$R^{20}$C(O)-aryl, -L-COOH, -L-N$R^{20}$S(O)$_2$($R^{20}$), -L-S(O)$_2$N($R^{20}$)$_2$, -L-N($R^{20}$)C(O)(O$R^{20}$), -L-OC(O)N($R^{20}$)$_2$, and -L-C(=O)O$C_1$-$C_6$ alkyl, wherein the heterocycle, the heterocycle portion of -L-heterocycle, and the cycloalkyl portion of the -L-cycloalkyl are each optionally substituted with one or more $R^6$, and wherein the aryl portion of -L-N$R^{20}$C(O)-aryl, the aryl of the -L-aryl, and the heteroaryl of -L-heteroaryl are each optionally substituted with one or more $R^7$;

each L is independently selected from a $C_1$-$C_4$ alkylene optionally substituted with one or more substituents independently selected from halogen, hydroxy, $C_{1-6}$ alkoxy, $C_1$-$C_4$ hydroxyalkyl, $C_1$-$C_4$ alkyl, $C_3$-$C_6$ carbocycle, and 3- to 8-membered heterocycle, wherein the $C_3$-$C_6$ carbocycle and 3- to 8-membered heterocycle are each optionally substituted with one or more substituents independently selected from halogen, —OH, —NO$_2$, =O, =S, —CN, $C_{1-6}$ alkyl-N($R^{20}$)$_2$, $C_{1-6}$ aminoalkyl, $C_{1-6}$ alkoxy, $C_{1-6}$ hydroxyalkyl, $C_{1-6}$ haloalkyl; and wherein optionally two substituents on the same carbon atom of L come together to form a $C_3$-$C_6$ carbocycle or 3- to 8-membered heterocycle, wherein the $C_3$-$C_6$ carbocycle and 3- to 8-membered heterocycle are each optionally substituted with one or more substituents independently selected from halogen, —OH, —NO$_2$, =O, =S, —CN, $C_{1-6}$ alkyl-N($R^{20}$)$_2$, $C_{1-6}$ aminoalkyl, $C_{1-6}$ alkoxy, $C_{1-6}$ hydroxyalkyl, and $C_{1-6}$ haloalkyl;

each $R^4$ is independently selected from halogen, —NO$_2$, —NH$_2$, —NH($C_{1-6}$ alkyl), —N($C_{1-6}$ alkyl)$_2$, =O, =S, —CN, $C_{1-6}$ alkyl, $C_{1-6}$ aminoalkyl, $C_{1-6}$ alkoxy, $C_{1-6}$ cyanoalkyl, $C_{1-6}$ hydroxyalkyl, and $C_{1-6}$haloalkyl;

n is selected from 0, 1, 2, 3, and 4;

m is selected from 1 and 2;

each $R^5$ is independently selected from hydrogen and $C_1$-$C_6$ alkyl;

each $R^6$ is independently selected from halogen, hydroxy, $C_1$-$C_3$ hydroxyalkyl, $C_1$-$C_3$ alkyl, oxo, $C_1$-$C_3$ haloalkyl, $C_1$-$C_3$ alkoxy, cyano, =CH$_2$, =NO—$C_1$-$C_3$ alkyl, $C_1$-$C_3$ aminoalkyl, —N($R^5$)S(O)$_2$($R^5$), -Q-phenyl, -Q-phenylSO$_2$F, —NHC(O)phenyl, —NHC(O)phenylSO$_2$F, $C_1$-$C_3$ alkyl substituted pyrazolyl, tert-butyldimethylsilyloxyCH$_2$—, —N($R^5$)$_2$, ($C_1$-$C_3$ alkoxy)$C_1$-$C_3$ alkyl-, ($C_1$-$C_3$ alkyl)C(=O), oxo, ($C_1$-$C_3$ haloalkyl)C(=O)—, —SO$_2$F, ($C_1$-$C_3$ alkoxy)$C_1$-$C_3$ alkoxy, —CH$_2$OC(O)NCF$_3$($R^5$), —CH$_2$O—$C_1$-$C_6$ alkyl, —CH$_2$OC(O)N($R^5$)$_2$, —CH$_2$NHC(O)O$C_1$-$C_6$ alkyl, —CH$_2$NHC(O)N($R^5$)$_2$, —CH$_2$NHC(O)$C_1$-$C_6$ alkyl, —CH$_2$(pyrazolyl), —CH$_2$NHSO$_2$$C_1$-$C_6$ alkyl, —CH$_2$OC(O)heterocycle, —OC(O)N($R^5$)$_2$, —OC(O)NH($C_1$-$C_3$ alkyl)O($C_1$-$C_3$ alkyl), —OC(O)NH($C_1$-$C_3$ alkyl)O($C_1$-$C_3$ alkyl)phenyl($C_1$-$C_3$ alkyl)N(CH$_3$)$_2$, —OC(O)NH($C_1$-$C_3$ alkyl)O($C_1$-$C_3$ alkyl)phenyl, —OC(O)heterocycle, —O—$C_1$-$C_3$ alkyl, —O—$C_1$-$C_6$ haloalkyl, —$C_1$-$C_3$ alkyl-O—$C_1$-$C_6$ haloalkyl, $C_{1-6}$ alkyl-N($R^{20}$)$_2$, —SF$_5$, —$C_1$-$C_3$ alkyl-N$_3$, —S(O)$_2$($R^{20}$), —S(O)$_2$N($R^{20}$)$_2$, —S(O)N($R^{20}$)$_2$, —S(O)$R^{20}$(=N$R^{20}$), —N$R^{20}$S(O)$_2$$R^{20}$, —(CH$_2$)$_{0-1}$S-heterocycle, —(CH$_2$)$_{0-1}$—O-heterocycle, —(CH$_2$)$_{0-1}$—O-phenyl, and —CH$_2$heterocycle, wherein the phenyl of —NHC(O)phenyl and —OC(O)NH($C_1$-$C_3$ alkyl)($C_1$-$C_3$ alkyl)phenyl are optionally substituted with one or more substituents selected from —C(O)H and OH, wherein the alkyl of —O—$C_1$-$C_3$ alkyl is optionally substituted with substituents selected from heterocycle, oxo and hydroxy;

wherein the alkyl of —CH$_2$O—$C_1$-$C_6$ alkyl is optionally substituted with one or more substituents selected from halogen and $C_3$-$C_6$ carbocycle;

wherein the heterocycle of —CH$_2$heterocycle is optionally substituted with oxo; and wherein the phenyl of —(CH$_2$)$_{0-1}$—O-phenyl is optionally substituted with one or more substituents selected from $C_{1-6}$ alkyl, $C_{1-6}$haloalkyl, SF$_5$, $C_{1-6}$ alkyl-O$R^{20}$, —O$R^{20}$;

wherein the heterocycle of —(CH$_2$)$_{0-1}$—O-heterocycle and —(CH$_2$)$_{0-1}$—S-heterocycle are each optionally substituted with one or more substituents selected from $C_{1-6}$ alkyl, $C_{1-6}$ haloalkyl, $C_{1-6}$ alkyl-O$R^{20}$, and —O$R^{20}$;

each Q is selected from a bond and O;

each $R^7$ is independently selected from halogen, hydroxy, HC(=O)—, $C_1$-$C_4$ alkyl, $C_1$-$C_4$ alkoxy, $C_1$-$C_4$ haloalkyl, $C_1$-$C_4$ hydroxyalkyl, and —N($R^5$)$_2$;

$R^8$ is selected from 5- to 12-membered heterocycle, wherein the 5- to 12-membered heterocycle is optionally substituted with one or more substituents independently selected from halogen, —CN, —NO$_2$, =O, —N($R^{20}$)$_2$, —B(O$R^{20}$)$_2$, —O$R^{20}$, —S$R^{20}$, —S(O)$_2$($R^{20}$), —S(O)$_2$N($R^{20}$)$_2$, —S(O)N($R^{20}$)$_2$, —S(O)$R^{20}$(=N$R^{20}$), —N$R^{20}$S(O)$_2$$R^{20}$, —C(O)N($R^{20}$)$_2$, —N($R^{20}$)C(O)$R^{20}$, —N($R^{20}$)C(O)N($R^{20}$)$_2$, —N($R^{20}$)C (O)OR$^{20}$, —C(O)R$^{20}$, C(O)OR$^{20}$, —OC(O)R$^{20}$, —OC(O)N(R$^{20}$)$_2$, —C(O)NR$^{20}$—OR$^{20}$, C$_{1-6}$ alkyl-N(R$^{20}$)$_2$, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, C$_3$-C$_{12}$ carbocycle and 5- to 12-membered heterocycle;

R$^9$ is selected from hydrogen, halogen, —CN, —NO$_2$, —N(R$^{20}$)$_2$, —OR$^{20}$, —SR$^{20}$, C$_{1-6}$ alkyl-N(R$^{20}$)$_2$, C$_{1-6}$ aminoalkyl, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, and C$_3$-C$_6$ carbocycle, wherein the C$_3$-C$_6$ carbocycle is optionally substituted with one or more halogen, —CN, —NO$_2$, —N(R$^{20}$)$_2$, —OR$^{20}$, —SR$^{20}$, C$_{1-6}$ alkyl-N(R$^{20}$)$_2$, C$_{1-6}$ aminoalkyl, C$_{1-6}$ alkoxyalkyl, C$_{1-6}$hydroxyalkyl, C$_{1-6}$ cyanoalkyl, C$_{1-6}$haloalkyl, C$_{1-6}$ alkyl, C$_{2-6}$ alkenyl, C$_{2-6}$ alkynyl; or R$^8$ and R$^9$ come together with the atoms to which they are bound to form B, wherein B is selected from a 7- to 15-membered heterocycle and C$_7$-C$_{15}$ carbocycle, wherein the 7- to 15-membered heterocycle and C$_7$-C$_{15}$ carbocycle are each optionally substituted with one or more substituents independently selected from halogen, —CN, —NO$_2$, =O, —N(R$^{20}$)$_2$, —B(OR$^{20}$)$_2$, —OR$^{20}$, —SR$^{20}$, —S(O)$_2$(R$^{20}$), —S(O)$_2$N(R$^{20}$)$_2$, —NR$^{20}$S(O)$_2$R$^{20}$, —C(O)N(R$^{20}$)$_2$, —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —C(O)R$^{20}$, —C(O)OR$^{20}$, —OC(O)R$^{20}$, —OC(O)N(R$^{20}$)$_2$, C$_{1-6}$ alkyl-N(R$^{20}$)$_2$, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, C$_3$-C$_{12}$ carbocycle and 5- to 12-membered heterocycle;

each R$^{10}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$ (=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =NO(R$^{20}$), —CN, —NHCN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, C$_3$-C$_{12}$carbocycle and 5- to 12-membered heterocycle, wherein the C$_3$-C$_{12}$carbocycle and 5- to 12-membered heterocycle are each optionally substituted with one or more substituents independently selected from halogen, —OH, —CN, —NO$_2$, —NH$_2$, —NH(C$_{1-6}$ alkyl), —N(C$_{1-6}$ alkyl)$_2$, C$_{1-10}$ alkyl, —C$_{1-10}$ haloalkyl, —O—C$_{1-10}$ alkyl, oxo;

each R$^{11}$, R$^{12}$, and R$^{13}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$ (=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NR$^{20}$(C=NH)N(R$^{20}$)$_2$, —NO$_2$, =O, =NO(R$^{20}$), —CN, —NHCN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, C$_3$-C$_{12}$ carbocycle and 5- to 12-membered heterocycle, wherein the C$_3$-C$_{12}$ carbocycle and 5- to 12-membered heterocycle are each optionally substituted with one or more substituents independently selected from halogen, —OH, —CN, —NO$_2$, —N(R$^{21}$)$_2$, —SR$^{21}$, —C(O)N(R$^{21}$)$_2$, C$_{1-10}$ alkyl, —C$_{1-10}$ haloalkyl, —O—C$_{1-10}$ alkyl, —S(O)$_2$(R$^{21}$), —P(O)(OR$^{21}$)$_2$, —OP(O)(OR$^{21}$)$_2$, —P(O)(R$^{21}$)$_2$, and oxo;

each R$^{11A}$, R$^{12A}$, and R$^{13A}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$ (=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =NO(R$^{20}$), —CN, —NHCN, C$_{1-6}$ alkyl-N(R$^{20}$)$_2$, C$_{1-6}$ aminoalkyl, C$_{1-6}$ alkoxy, C$_{1-6}$hydroxyalkyl, C$_{1-6}$ cyanoalkyl, C$_{1-6}$haloalkyl, C$_{1-6}$ alkyl, C$_{2-6}$ alkenyl, and C$_{2-6}$ alkynyl;

each R$^{20}$ is independently selected from hydrogen; and C$_{1-6}$ alkyl, C$_{2-6}$ alkenyl, C$_{2-6}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, —NH(C$_{1-6}$ alkyl), —N(C$_{1-6}$ alkyl)$_2$, C$_{1-10}$ alkyl, C$_{1-10}$ haloalkyl, —O—C$_{1-10}$ alkyl, oxo, C$_{3-12}$ carbocycle, and 3- to 12-membered heterocycle; and each R$^{21}$ is independently selected from hydrogen; and C$_{1-6}$ alkyl, C$_{2-6}$ alkenyl, C$_{2-6}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, C$_{1-10}$ alkyl, —C$_{1-10}$ haloalkyl, —O—C$_{1-10}$ alkyl, oxo, C$_{3-12}$ carbocycle, and 3- to 12-membered heterocycle.

In some embodiments, for a compound or salt of Formula (I), wherein
R$^{100}$ is selected from

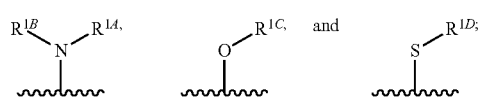

R$^{1A}$ is selected from C$_{1-6}$ alkyl, C$_3$-C$_{12}$ carbocycle, and 4- to 12-membered heterocycle, each of which is optionally substituted with one or more R$^{11}$, and wherein optionally two R$^{11}$ on the same atom of R$^{1A}$ come together to form a C$_3$-C$_6$ carbocycle or 3- to 8-membered heterocycle, wherein the C$_3$-C$_6$ carbocycle and 3- to 8-membered heterocycle are each optionally substituted with one or more R$^{11A}$.

R$^{1B}$ is selected from hydrogen, C$_{1-6}$ alkyl, C$_3$-C$_6$ carbocycle, wherein the C$_{1-6}$ alkyl and C$_3$-C$_6$ carbocycle are each optionally substituted with one or more R$^{10}$;

or R$^{1A}$ and R$^{1B}$ come together with the atom to which they are bound to form R$^1$, wherein R$^1$ is a 5- to 15-membered heterocycle, wherein the 5- to 15-membered heterocycle is optionally substituted with one or more substituents independently selected from halogen, —B(OR$^{20}$)$_2$, —N(R$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$ (=NR$^{20}$), —NR$^{20}$S(O)$_2$R$^{20}$, —C(O)N(R$^{20}$)$_2$, —C(=NR$^{20}$)N(R$^{20}$)$_2$, —C$_{1-6}$ alkyl(=NR$^{20}$OR$^{20}$), —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —C(O)R$^{20}$, —C(O)OR$^{20}$, —OC(O)R$^{20}$, —OC(O)N(R$^{20}$)$_2$, —NO$_2$, =O, =N(R$^{20}$), =NO(R$^{20}$), —CN, —NHCN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl- $SO_2R^{20}$, $C_{1-6}$ alkoxyalkyl, $C_{1-6}$ alkyl, $C_{2-6}$ alkenyl, $C_{2-6}$ alkynyl, $C_3$-$C_{12}$ carbocycle and 5- to 12-membered heterocycle, wherein the $C_3$-$C_{12}$ carbocycle and 5- to 12-membered heterocycle are each optionally substituted independently with one or more $R^{1*}$;

each $R^{1*}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =N(R$^{20}$), =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, and $C_3$-$C_{12}$ carbocycle;

$R^{1C}$ is selected from hydrogen, $C_{1-6}$ alkyl, $C_3$-$C_{12}$ carbocycle, and 4- to 12-membered heterocycle, each of which is optionally substituted with one or more $R^{12}$, and wherein optionally two $R^{12}$ on the same atom of $R^{1C}$ come together to form a $C_3$-$C_6$ carbocycle or 3- to 8-membered heterocycle, wherein the $C_3$-$C_6$ carbocycle and 3- to 8-membered heterocycle are each optionally substituted with one or more $R^{12A}$;

$R^{1D}$ is selected from hydrogen, $C_{1-6}$ alkyl, $C_3$-$C_{12}$ carbocycle, and 4- to 12-membered heterocycle, each of which is optionally substituted with one or more $R^{13}$, and wherein optionally two $R^{13}$ on the same atom of $R^{1D}$ come together to form a $C_3$-$C_6$ carbocycle or 3- to 8-membered heterocycle, wherein the $C_3$-$C_6$ carbocycle and 3- to 8-membered heterocycle are each optionally substituted with one or more $R^{13A}$;

Y is —O—;

$R^2$ is selected from heterocycle, -L-heterocycle, -L-N(R$^{20}$)$_2$, -L-OR$^{20}$, -L-aryl, -L-heteroaryl, -L-cycloalkyl, -L-NHC(=NH)NH$_2$, -L-C(O)N(R$^{20}$)$_2$, -L-$C_1$-$C_6$ haloalkyl, -L-NR$^{20}$C(O)-aryl, -L-COOH, -L-NR$^{20}$S(O)$_2$(R$^{20}$), -L-S(O)$_2$N(R$^{20}$)$_2$, -L-N(R$^{20}$)C(O)(OR$^{20}$), -L-OC(O)N(R$^{20}$)$_2$, and -L-C(=O)OC$_1$-$C_6$ alkyl, wherein the heterocycle, the heterocycle portion of -L-heterocycle, and the cycloalkyl portion of the -L-cycloalkyl are each optionally substituted with one or more $R^6$, and wherein the aryl portion of -L-NR$^{20}$C(O)-aryl, the aryl of the -L-aryl, and the heteroaryl of -L-heteroaryl are each optionally substituted with one or more $R^7$;

each L is independently selected from a $C_1$-$C_4$ alkylene optionally substituted with one or more substituents independently selected from halogen, hydroxy, $C_{1-6}$ alkoxy, $C_1$-$C_4$ hydroxyalkyl, $C_1$-$C_4$ alkyl, $C_3$-$C_6$ carbocycle, and 3- to 8-membered heterocycle, wherein the $C_3$-$C_6$ carbocycle and 3- to 8-membered heterocycle are each optionally substituted with one or more substituents independently selected from halogen, —OH, —NO$_2$, =O, =S, —CN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ haloalkyl; and wherein optionally two substituents on the same carbon atom of L come together to form a $C_3$-$C_6$ carbocycle or 3- to 8-membered heterocycle, wherein the $C_3$-$C_6$ carbocycle and 3- to 8-membered heterocycle are each optionally substituted with one or more substituents independently selected from halogen, —OH, —NO$_2$, =O, =S, —CN, $C_{1-6}$ alkyl-N(R$^{20}$)$_2$, $C_{1-6}$ aminoalkyl, $C_{1-6}$ alkoxy, $C_{1-6}$ hydroxyalkyl, and $C_{1-6}$ haloalkyl;

each $R^4$ is independently selected from halogen, —NO$_2$, —NH$_2$, —NH($C_{1-6}$ alkyl), —N($C_{1-6}$ alkyl)$_2$, =O, =S, —CN, $C_{1-6}$ alkyl, $C_{1-6}$ aminoalkyl, $C_{1-6}$ alkoxy, $C_{1-6}$ cyanoalkyl, $C_{1-6}$ hydroxyalkyl, and $C_{1-6}$ haloalkyl;

n is selected from 0, 1, 2, 3, and 4;

m is selected from 1 and 2;

each $R^5$ is independently selected from hydrogen and $C_1$-$C_6$ alkyl;

each $R^6$ is independently selected from halogen, hydroxy, $C_1$-$C_3$ hydroxyalkyl, $C_1$-$C_3$ alkyl, oxo, $C_1$-$C_3$ haloalkyl, $C_1$-$C_3$ alkoxy, cyano, =CH$_2$, =NO—$C_1$-$C_3$ alkyl, $C_1$-$C_3$ aminoalkyl, —N(R$^5$)S(O)$_2$(R$^5$), -Q-phenyl, -Q-phenylSO$_2$F, —NHC(O)phenyl, —NHC(O)phenylSO$_2$F, $C_1$-$C_3$ alkyl substituted pyrazolyl, tert-butyldimethylsilyloxyCH$_2$—, —N(R$^5$)$_2$, ($C_1$-$C_3$ alkoxy)$C_1$-$C_3$ alkyl-, ($C_1$-$C_3$ alkyl)C(=O), oxo, ($C_1$-$C_3$ haloalkyl)C(=O)—, —SO$_2$F, ($C_1$-$C_3$ alkoxy)$C_1$-$C_3$ alkoxy, —CH$_2$OC(O)N(R$^5$)$_2$, —CH$_2$NHC(O)OC$_1$-$C_6$ alkyl, —CH$_2$NHC(O)N(R$^5$)$_2$, —CH$_2$NHC(O)C$_1$-$C_6$ alkyl, —CH$_2$(pyrazolyl), —CH$_2$NHSO$_2$C$_1$-$C_6$ alkyl, —CH$_2$OC(O)heterocycle, —OC(O)N(R$^5$)$_2$, —OC(O)NH(C$_1$-$C_3$ alkyl)O(C$_1$-$C_3$ alkyl), —OC(O)NH(C$_1$-$C_3$ alkyl)O(C$_1$-$C_3$ alkyl)phenyl(C$_1$-$C_3$ alkyl)N(CH$_3$)$_2$, —OC(O)NH(C$_1$-$C_3$ alkyl)O(C$_1$-$C_3$ alkyl)phenyl, —OC(O)heterocycle, —O—$C_1$-$C_3$ alkyl, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, and —CH$_2$heterocycle, wherein the phenyl of —NHC(O)phenyl and —OC(O)NH(C$_1$-$C_3$ alkyl)(C$_1$-$C_3$ alkyl)phenyl are optionally substituted with one or more substituents selected from —C(O)H and OH, and wherein the alkyl of —O—$C_1$-$C_3$ alkyl is optionally substituted with substituents selected from heterocycle, oxo and hydroxy; and wherein the heterocycle of —CH$_2$heterocyclyl is optionally substituted with oxo;

each Q is selected from a bond and O;

each $R^7$ is independently selected from halogen, hydroxy, HC(=O)—, $C_1$-$C_4$ alkyl, $C_1$-$C_4$ alkoxy, $C_1$-$C_4$ haloalkyl, $C_1$-$C_4$ hydroxyalkyl, and —N(R$^5$)$_2$;

$R^8$ is selected from 5- to 12-membered heterocycle, wherein the 5- to 12-membered heterocycle is optionally substituted with one or more substituents independently selected from halogen, —CN, —NO$_2$, =O, —N(R$^{20}$)$_2$, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —C(O)R$^{20}$, C(O)OR$^{20}$, —OC(O)R$^{20}$, —OC(O)N(R$^{20}$)$_2$, —C(O)NR$^{20}$—OR$^{20}$, $C_{1-6}$ alkyl-N(R$^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle;

$R^9$ is selected from hydrogen, halogen, —CN, —NO$_2$, —N(R$^{20}$)$_2$, —OR$^{20}$, —SR$^{20}$, $C_{1-6}$ alkyl-N(R$^{20}$)$_2$, $C_{1-6}$ aminoalkyl, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, and $C_3$-$C_6$ carbocycle, wherein the $C_3$-$C_6$ carbocycle is optionally substituted with one or more halogen, —CN, —NO$_2$, —N(R$^{20}$)$_2$, —OR$^{20}$, —SR$^{20}$, $C_{1-6}$ alkyl-N(R$^{20}$)$_2$, $C_{1-6}$ aminoalkyl, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl; or $R^8$ and $R^9$ come together with the atoms to which they are bound to form B, wherein B is selected from a 7- to 15-membered heterocycle and $C_7$-$C_{15}$ carbocycle, wherein the 7- to 15-membered heterocycle and $C_7$-$C_{15}$ carbocycle are each optionally substituted with one or more substituents independently selected from halogen, —CN, —NO$_2$, =O, —N(R$^{20}$)$_2$, —B(OR$^{20}$)$_2$, —OR$^{20}$, —SR$^{20}$, —S(O)$_2$(R$^{20}$), —S(O)$_2$N(R$^{20}$)$_2$, —NR$^{20}$S(O)$_2$R$^{20}$, —C(O)N(R$^{20}$)$_2$, —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —C(O)R$^{20}$, —C(O)OR$^{20}$, —OC(O)R$^{20}$, —OC(O)N(R$^{20}$)$_2$, C$_{1-6}$ alkyl-N(R$^{20}$)$_2$, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, C$_3$-C$_{12}$ carbocycle and 5- to 12-membered heterocycle;

each R$^{10}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =NO(R$^{20}$), —CN, —NHCN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, C$_3$-C$_{12}$ carbocycle and 5- to 12-membered heterocycle, wherein the C$_3$-C$_{12}$ carbocycle and 5- to 12-membered heterocycle are each optionally substituted with one or more substituents independently selected from halogen, —OH, —CN, —NO$_2$, —NH$_2$, —NH(C$_{1-6}$ alkyl), —N(C$_{1-6}$ alkyl)$_2$, C$_{1-10}$ alkyl, —C$_{1-10}$ haloalkyl, —O—C$_{1-10}$ alkyl, oxo;

each R$^{11}$, R$^{12}$, and R$^{13}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =NO(R$^{20}$), —CN, —NHCN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, C$_3$-C$_{12}$ carbocycle and 5- to 12-membered heterocycle, wherein the C$_3$-C$_{12}$ carbocycle and 5- to 12-membered heterocycle are each optionally substituted with one or more substituents independently selected from halogen, —OH, —CN, —NO$_2$, —N(R$^{21}$)$_2$, —C(O)N(R$^{21}$)$_2$, C$_{1-10}$ alkyl, —C$_{1-10}$ haloalkyl, —O—C$_{1-10}$ alkyl, and oxo;

each R$^{11A}$, R$^{12A}$, and R$^{13A}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =NO(R$^{20}$), —CN, —NHCN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, C$_{2-6}$ alkenyl, and C$_{2-6}$ alkynyl;

each R$^{20}$ is independently selected from hydrogen; and C$_{1-6}$ alkyl, C$_{2-6}$ alkenyl, C$_{2-6}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, —NH(C$_{1-6}$ alkyl), —N(C$_{1-6}$ alkyl)$_2$, C$_{1-10}$ alkyl, —C$_{1-10}$ haloalkyl, —O—C$_{1-10}$ alkyl, oxo, C$_{3-12}$ carbocycle, and 3- to 12-membered heterocycle; and each R$^{21}$ is independently selected from hydrogen; and C$_{1-6}$ alkyl, C$_{2-6}$ alkenyl, C$_{2-6}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, C$_{1-10}$ alkyl, —C$_{1-10}$ haloalkyl, —O—C$_{1-10}$ alkyl, oxo, C$_{3-12}$ carbocycle, and 3- to 12-membered heterocycle.

In some embodiments, Formula (I) is represented by

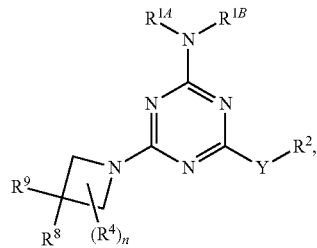

Formula (I-A)

or a pharmaceutically acceptable salt thereof.

In some embodiments, Formula (I) is represented by is represented by

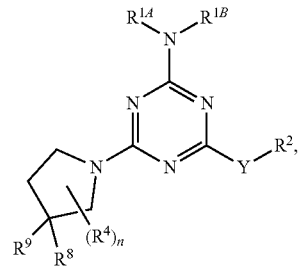

Formula (I-B)

or a pharmaceutically acceptable salt thereof.

In some embodiments, Formula (I) is represented by

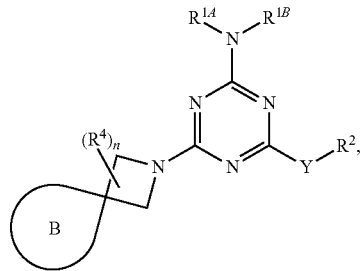

Formula (I-C)

or a pharmaceutically acceptable salt thereof.

In some embodiments, Formula (I) is represented by

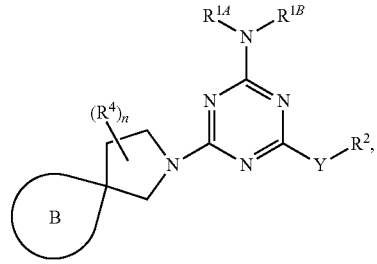

Formula (I-G)

or a pharmaceutically acceptable salt thereof.

In some embodiments, for a compound or salt of Formula (I), Formula (I-A), Formula (I-B), Formula (I-D), Formula (I-E), Formula (I-G), Formula (I-H), or Formula (I-J), $R^8$ and $R^9$ come together with the atoms to which they are bound to form B.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), B is selected from an optionally substituted 7- to 15-membered fused heterocycle and optionally substituted $C_7$-$C_{15}$ fused carbocycle. In some cases, and optionally substituted $C_7$-$C_{15}$ fused carbocycle. In some cases, B is an optionally substituted 7- to 15-membered fused heterocycle. In some cases, B is an optionally substituted unsaturated 7- to 15-membered fused heterocycle. In some cases, B is an optionally substituted 7- to 15-membered fused heteroaryl. In some cases, B is selected from an optionally substituted 7- to 15-membered fused heteroaryl and optionally substituted $C_7$-$C_{15}$ fused aryl. In some cases, B is an optionally substituted unsaturated $C_7$-$C_{15}$ fused carbocycle. In some cases, B is an optionally substituted 7- to 15-membered fused heterocycle, wherein the fused heterocycle is partially unsaturated. In some cases, B is an optionally substituted 7- to 15-membered fused heterocycle, wherein the fused heterocycle is partially saturated.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), B is selected from an optionally substituted 8- to 15-membered fused heterocycle and optionally substituted $C_8$-$C_{15}$ fused carbocycle. In some cases, and optionally substituted $C_8$-$C_{15}$ fused carbocycle. In some cases, B is an optionally substituted 8- to 15-membered fused heterocycle. In some cases, B is an optionally substituted unsaturated 8- to 15-membered fused heterocycle. In some cases, B is an optionally substituted unsaturated $C_8$-$C_{15}$ fused carbocycle. In some cases, B is an optionally substituted 8- to 15-membered fused heterocycle, wherein the fused heterocycle is partially unsaturated. In some cases, B is an optionally substituted 8- to 15-membered fused heterocycle, wherein the fused heterocycle is partially saturated.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), B is selected from an optionally substituted 8- to 15-membered fused heterocycle, wherein the fused heterocycle is formed by combining three rings (e.g., tricyclic). In some cases, B is selected from an optionally substituted 8- to 15-membered fused heterocycle, wherein the fused heterocycle is formed by combining two rings (e.g., bicyclic). In some cases, for B the optionally substituted 8- to 15-membered fused heterocycle and optionally substituted $C_8$-$C_{15}$ fused carbocycle are each independently bicyclic or tricyclic. In some cases, for B the optionally substituted 8- to 15-membered fused heterocycle is bicyclic. In some cases, for B the optionally substituted 8- to 15-membered fused heterocycle is tricyclic.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), the heterocycle or carbocycle of B is bicyclic. In some cases, the heterocycle or carbocycle of B is tricyclic. In some cases, the tricyclic heterocycle contains three interconnected rings of atoms.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), for B, the heterocycle and carbocycle are each independently selected from bicyclic and tricyclic. In some cases, for B, the heterocycle and carbocycle are each independently tricyclic. In some cases, for B, the heterocycle and carbocycle are each independently bicyclic.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), for B, the optionally substituted 8- to 15-membered fused heterocycle and optionally substituted $C_8$-$C_{15}$ fused carbocycle are selected from

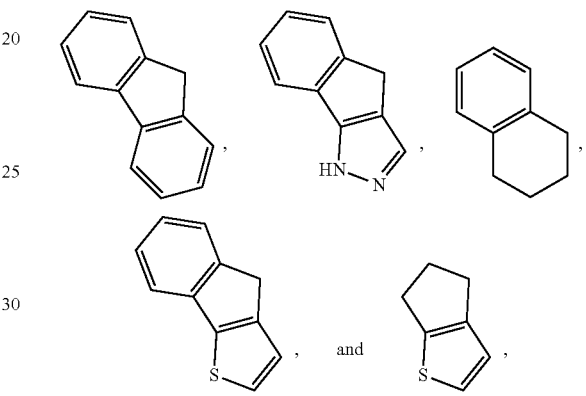

each of which is optionally substituted with one or more substituents. In some cases, for B, the optionally substituted 8- to 15-membered fused heterocycle and optionally substituted $C_8$-$C_{15}$ fused carbocycle are selected from,

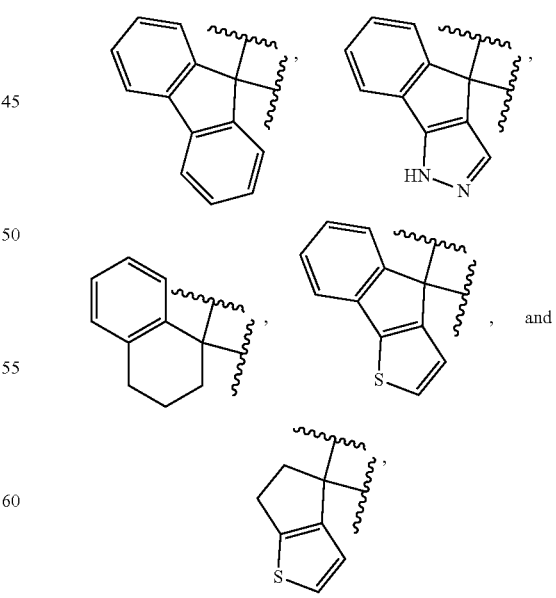

each of which is optionally substituted with one or more substituents. In some cases, B is selected from

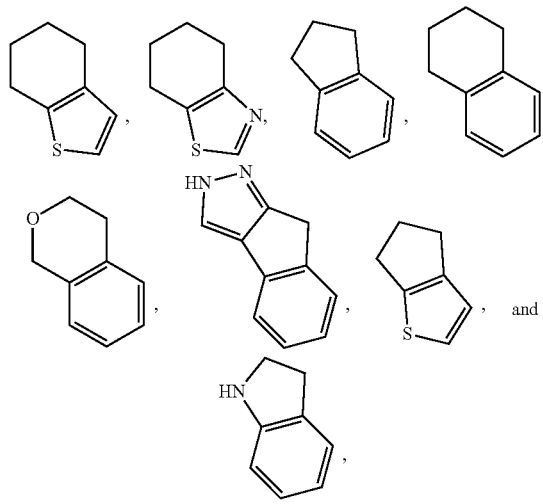

each of which is optionally substituted with one or more substituents. In some cases, B is selected from

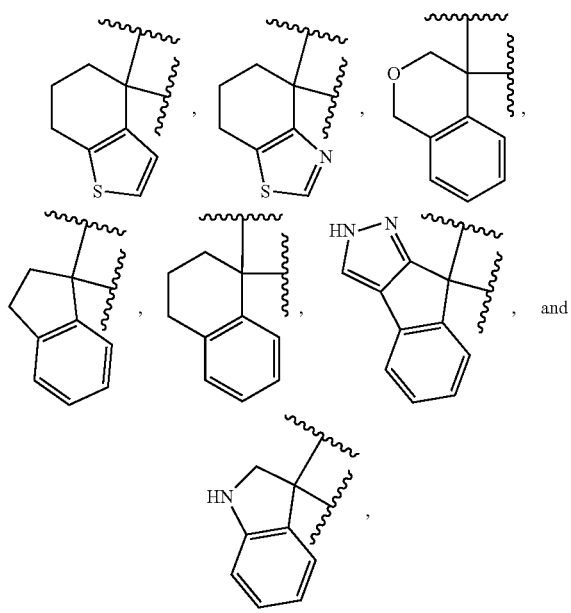

each of which is optionally substituted with one or more substituents. In some cases, B is selected from

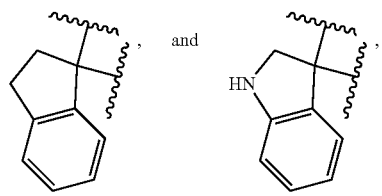 [SMILES: *C1(*)CCc2ccccc21 ; *C1(*)CNc2ccccc21]

each of which is optionally substituted with one or more substituents.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), B is selected from

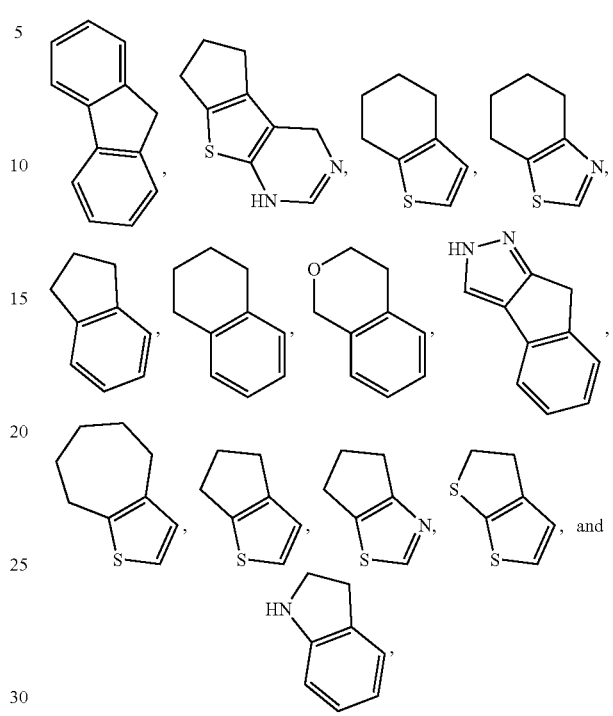

each of which is optionally substituted with one or more substituents. In some cases, B is selected from

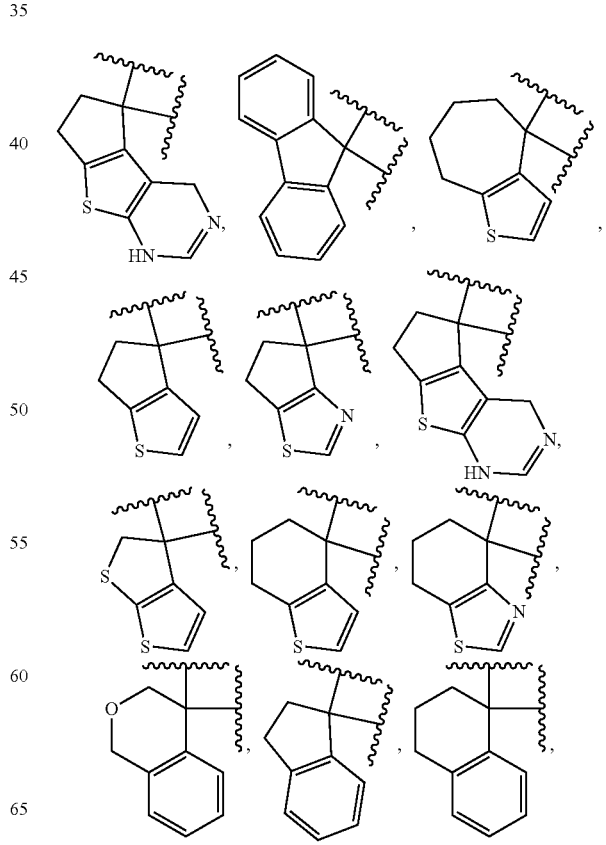

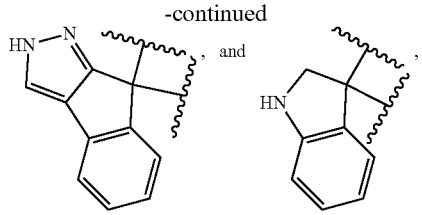

each of which is optionally substituted with one or more substituents. In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), B is an optionally substituted 8- to 15-membered fused heterocycle, wherein B contains at least one heteroatom selected from nitrogen, sulfur, and selenium. In some cases, B is an optionally substituted 8- to 15-membered fused heterocycle, wherein B contains at least one heteroatom selected from nitrogen, and selenium. In some cases, B is an optionally substituted 8- to 15-membered fused heterocycle, wherein B contains at least one heteroatom selected from selenium. In some cases, B is an optionally substituted 8- to 15-membered fused heterocycle, wherein B contains at least one heteroatom selected from sulfur and selenium. In some cases, B is an optionally substituted 8- to 10-membered fused heterocycle, wherein B contains at least one heteroatom selected from nitrogen, sulfur, and selenium. In some cases, B is an optionally substituted 8-membered fused heterocycle, wherein B contains at least one heteroatom selected from nitrogen, sulfur, and selenium.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), for B, the optional substituents of the heterocycle and carbocycle are each independently selected from halogen, —CN, —NO$_2$, =O, —N(R$^{20}$)$_2$, —B(OR$^{20}$)$_2$, —OR$^{20}$, —SR$^{20}$. C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, C$_3$-C$_{12}$ carbocycle and 5- to 12-membered heterocycle. In some cases, the optional substituents of the heterocycle and carbocycle are each independently selected from halogen, —CN, —NO$_2$, =O, —N(R$^{20}$)$_2$, —B(OR$^{20}$)$_2$, —OH, —SR$^{20}$, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkenyl, and C$_{2-6}$ alkynyl. In some cases, for B, the one or more optional substituents of the heterocycle and carbocycle are independently selected at each occurrence from halogen, oxo, —NH$_2$, C$_1$-C$_3$ alkyl, —B(OH)$_2$, —OH, —O—C$_1$-C$_3$ haloalkyl, —C(O)NH$_2$, —NH$_2$, =O, —CN, C$_{1-6}$ alkoxy, C$_{1-6}$ hydroxyalkyl, and C$_{2-6}$ alkynyl. In some cases, the optional substituents of the heterocycle and carbocycle are each independently selected from halogen, —CN, =O, —NH$_2$, —N(C$_{1-6}$ alkyl)H—N(C$_{1-6}$ alkyl)$_2$, —OH, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkenyl, and C$_{2-6}$ alkynyl. In some cases, the one or more optional substituents of the heterocycle and carbocycle are each independently selected from oxo, —NH$_2$, halogen, C$_1$-C$_3$ alkyl. In some cases, for B, the optionally substituted 8- to 15-membered fused heterocycle and optionally substituted C$_8$-C$_{15}$ fused carbocycle are selected from

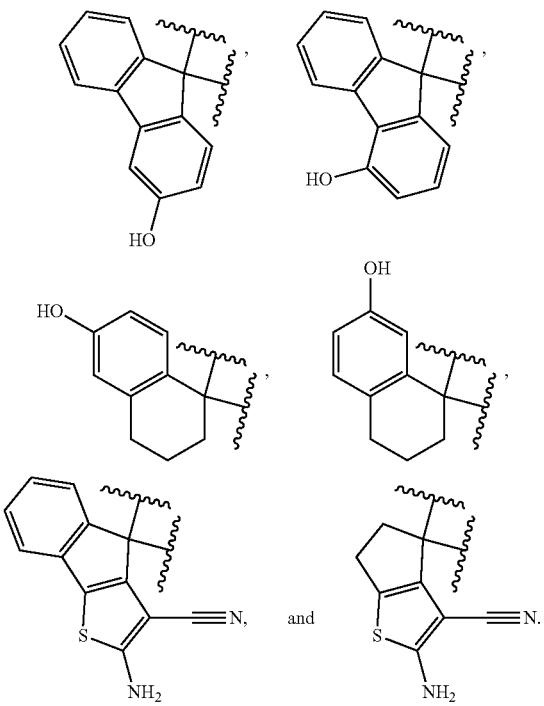

In some cases, B is selected from

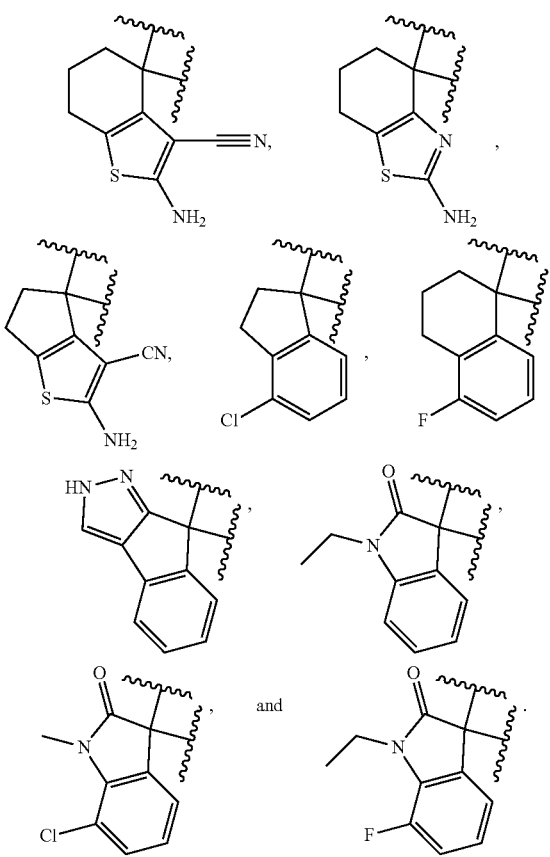

In some cases, B is selected from
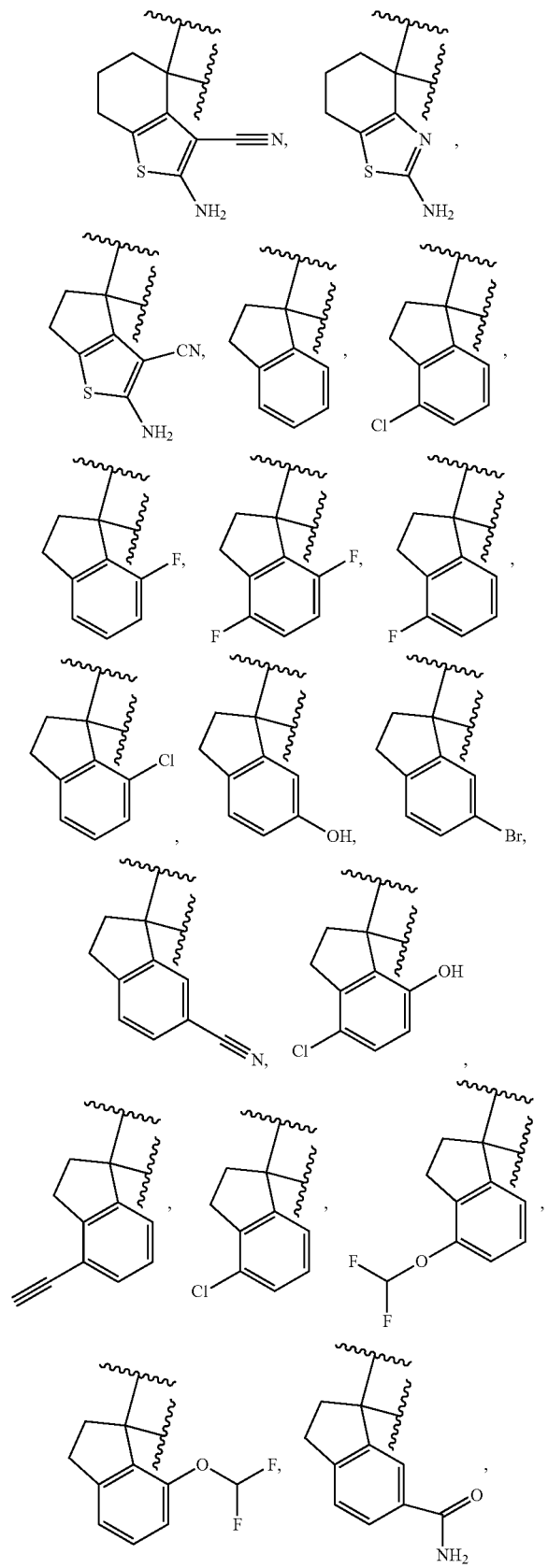
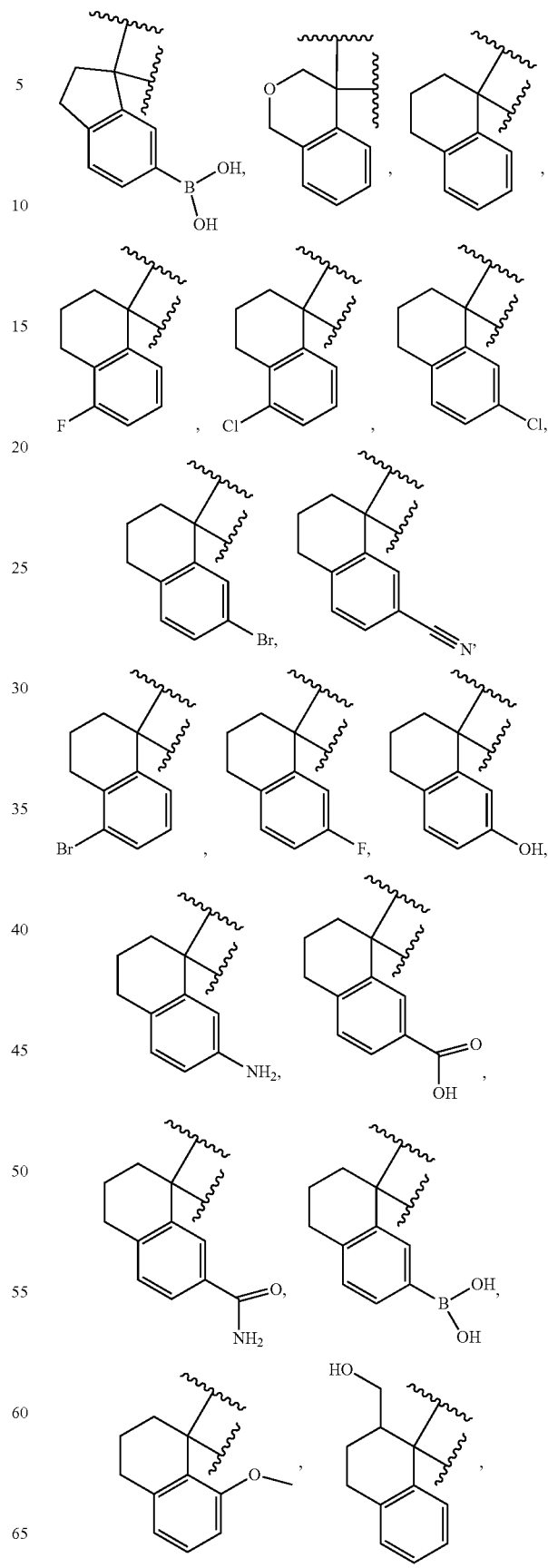

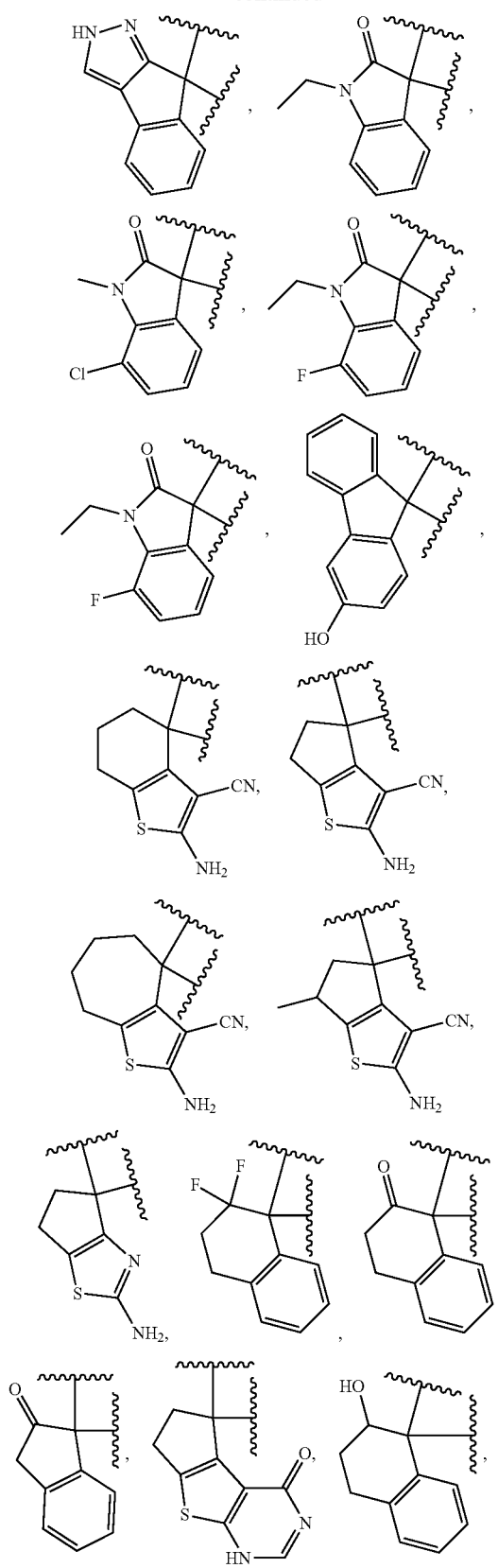
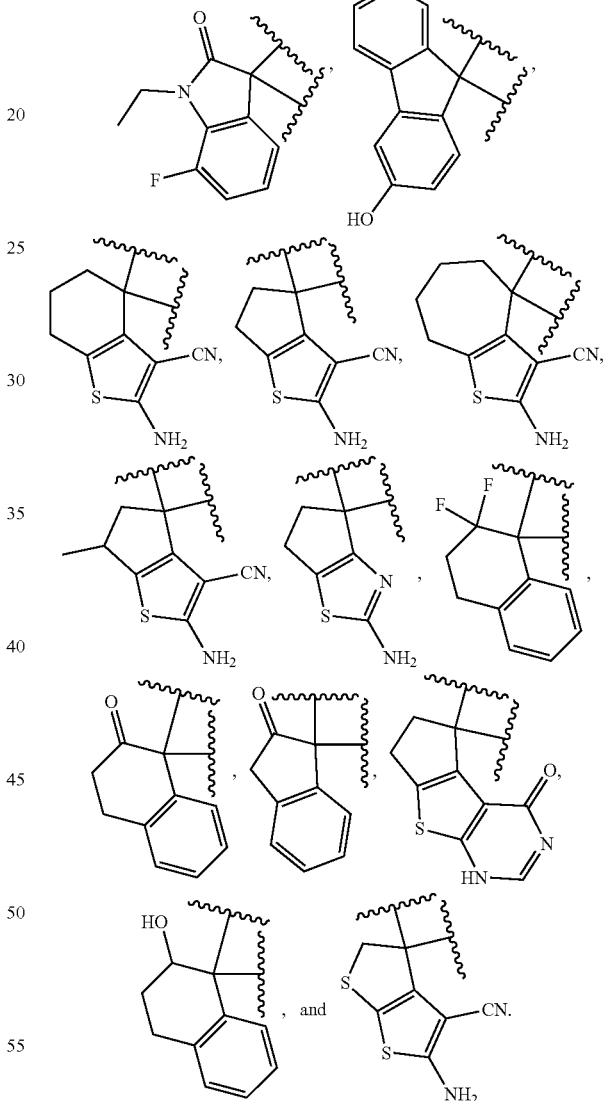

In some cases, B is selected from

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), B is selected from an optionally substituted 7- to 12-membered fused heterocycle and optionally substituted $C_{9-10}$ fused carbocycle. In some cases, the heterocycle of B has at least one sulfur atom. In some cases, the heterocycle of B has one or sulfur atoms. In some cases, the heterocycle of B has at least one nitrogen atom. In some cases, B is selected from

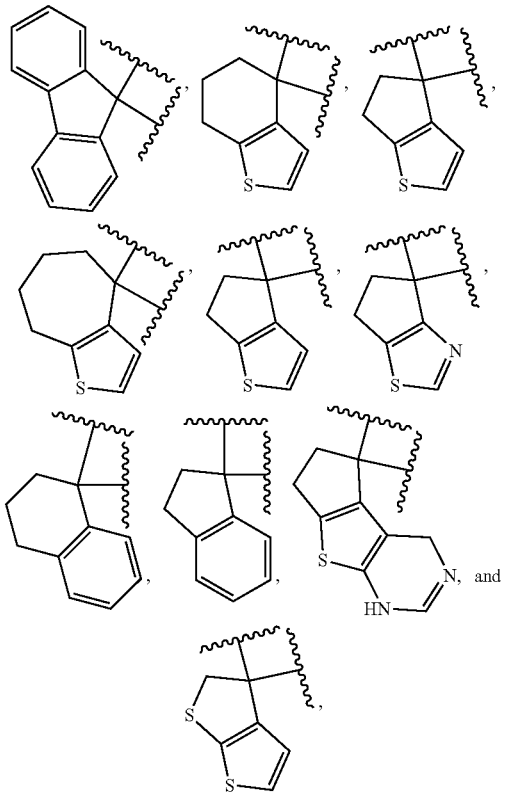

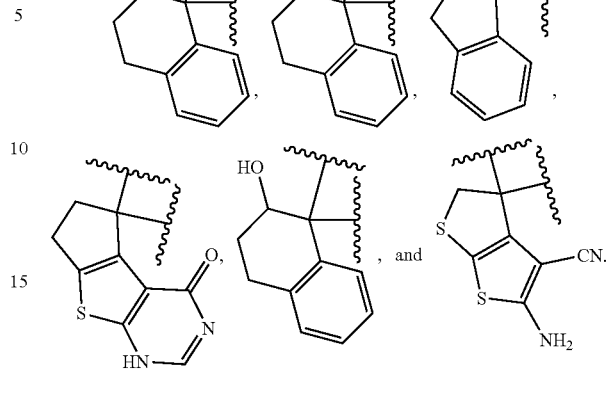

each of which is optionally substituted. In some cases, the one or more optional substituents of B are independently selected at each occurrence from halogen, $C_1$-$C_3$ alkyl, —B(OR$^{20}$)$_2$, —OR$^{20}$, —C(O)N(R$^{20}$)$_2$, —N(R$^{20}$)$_2$, =O, —CN, —NHCN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{2-6}$ alkenyl, and $C_{2-6}$ alkynyl. In some cases, the one or more optional substituents of B are independently selected at each occurrence from halogen, $C_1$-$C_3$ alkyl, —OH, —NH$_2$, =O, and —CN. In some cases, B is selected from

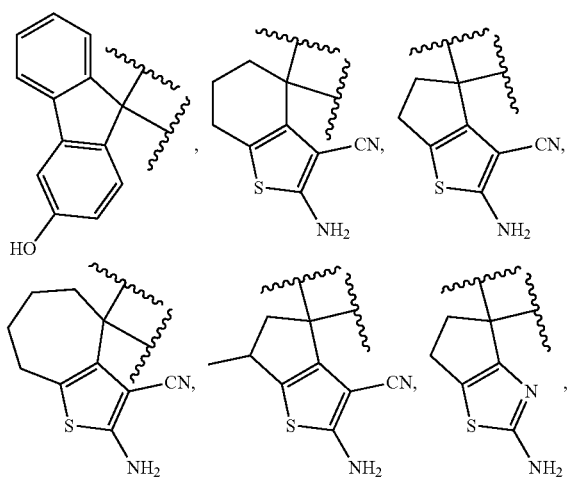

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), B is selected from an optionally substituted 8- to 10-membered fused heterocycle having at least one sulfur atom. In some cases, B is selected from

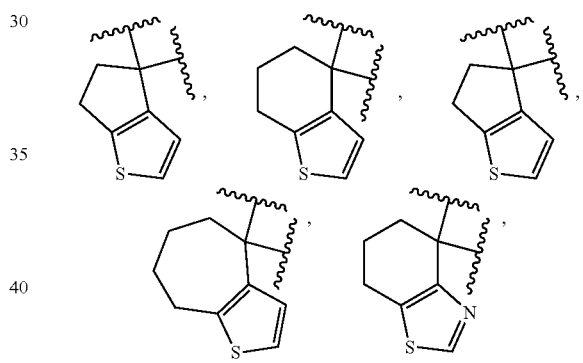

each of which is optionally substituted. In some cases, the one or more optional substituents of B are independently selected at each occurrence from halogen, $C_1$-$C_3$ alkyl, —OR$^{20}$, —C(O)N(R$^{20}$)$_2$, —N(R$^{20}$)$_2$, =O, —CN, —NHCN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{2-6}$ alkenyl, and $C_{2-6}$ alkynyl. In some cases, the one or more optional substituents of B are independently selected at each occurrence from halogen, $C_1$-$C_3$ alkyl, —NH$_2$, and —CN. In some cases, B is substituted. In some cases, B is substituted with at least one —NH$_2$. In some cases, B is selected from

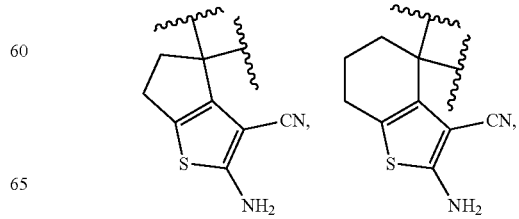

-continued

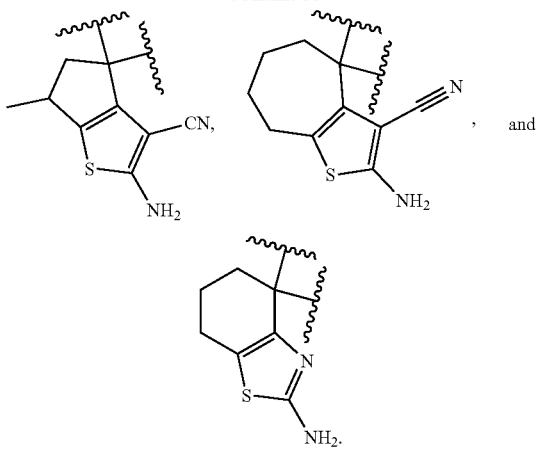

In some cases, B is substituted with at least one —NH₂ at least one —CN. In some cases, B is selected from

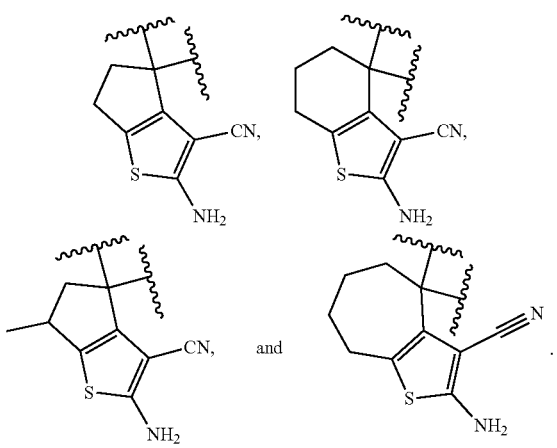

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), B is an optionally substituted 7- to 11-membered fused heterocycle. In some cases, B is an optionally substituted 8- to 10-membered fused heterocycle. In some cases, the heterocycle of B is an unsaturated heterocycle. In some cases, the heterocycle of B is a non-aromatic heterocycle. In some cases, B has at least one sulfur atom. In some cases, B has at two sulfur atoms. In some cases, B has at least one sulfur atom and at least one nitrogen atom. In some cases, B has at least one sulfur atom and at least one oxygen atom. In some cases, B has only 1 heteroatom. In some cases, B has at least 2 heteroatoms. In some cases, B is selected from

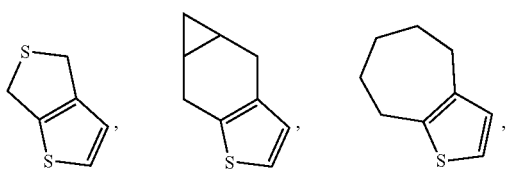

-continued

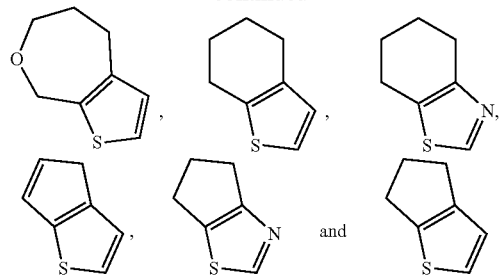

each of which is optionally substituted. In some cases B is selected from

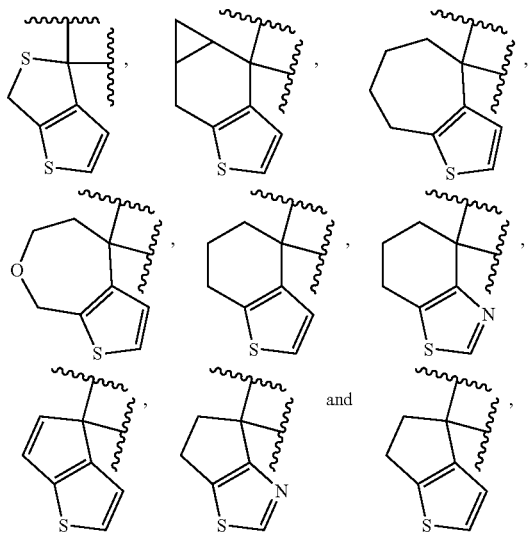

each of which is optionally substituted. In some cases, B is selected from

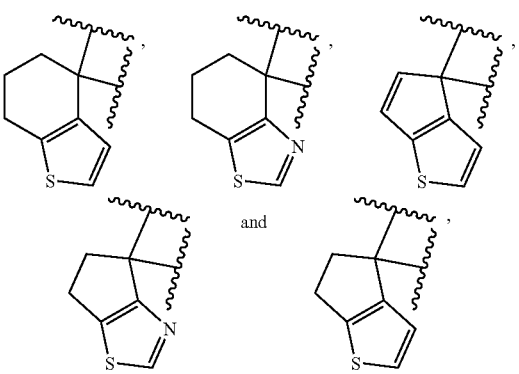

each of which is optionally substituted. In some cases, the one or more optional substituents of B, are independently selected at each occurrence from halogen, oxo, —NH₂, $C_1$-$C_3$ alkyl, —B(OH)₂, —OH, —O—$C_1$-$C_3$ haloalkyl, —C(O)NH₂, —NH₂, =O, —CN, $C_{1-6}$ alkoxy, $C_{1-6}$ hydroxyalkyl, and $C_{2-6}$ alkynyl. In some cases, the one or more optional substituents of B, are independently selected at each occurrence from halogen, $C_1$-$C_3$ alkyl, —NH₂, and —CN. In some cases, B is substituted with at least one substituent selected from halogen, $C_1$-$C_3$ alkyl, —NH₂, and —CN. In some cases, B is substituted with at least one substituent selected from halogen. In some cases, B is substituted with at least one substituent selected from —NH₂. In some cases, B is substituted with at least one substituent selected from CN. In some cases, B is substituted with at least one substituent. In some cases, B is selected from

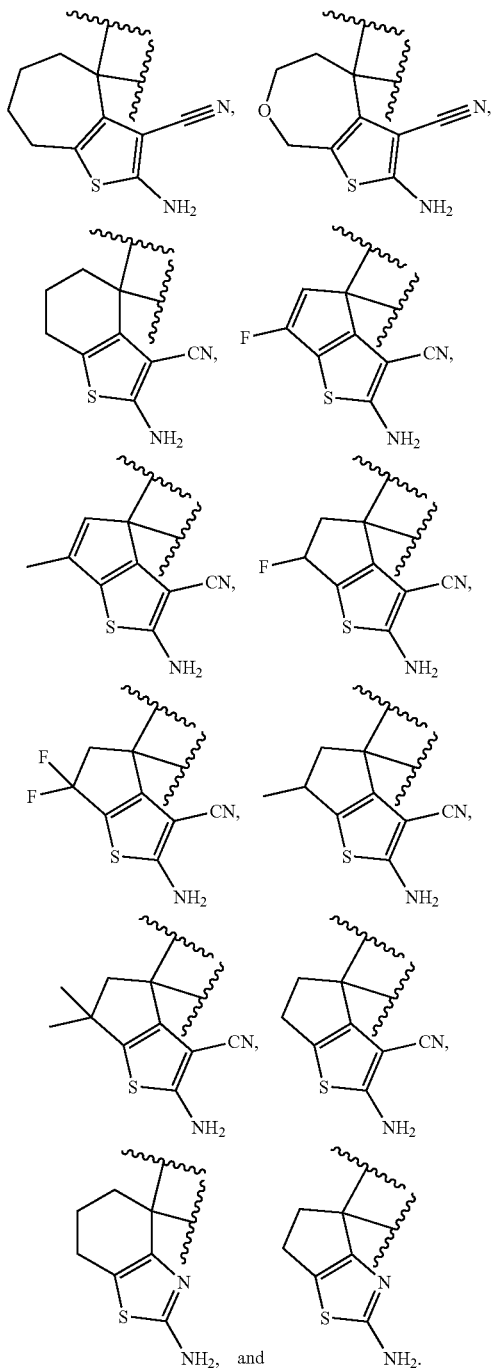

In some embodiments, for a compound or salt of Formula (I), Formula (I-A), Formula (I-B), Formula (I-D), Formula (I-E), Formula (I-H), or Formula (I-J), each $R^9$ is selected from hydrogen, halogen, —CN, —N(R²⁰)₂, —OR²⁰, $C_{1-6}$ aminoalkyl, $C_{1-6}$ alkoxyalkyl, $C_{1-6}$hydroxyalkyl, $C_{1-6}$ cyanoalkyl, $C_{1-6}$ haloalkyl, $C_{1-6}$ alkyl, and $C_3$-$C_6$ cycloalkyl, wherein the $C_3$-$C_6$ cycloalkyl is optionally substituted with one or more halogen, —CN, —NO₂, —N(R²⁰)₂, —OR²⁰, —SR²⁰, $C_{1-6}$ aminoalkyl, $C_{1-6}$ alkoxyalkyl, $C_{1-6}$ hydroxyalkyl, $C_{1-6}$ cyanoalkyl, $C_{1-6}$ haloalkyl, and $C_{1-6}$ alkyl. In some cases, each $R^9$ is selected from hydrogen, —CN, $C_{1-6}$ aminoalkyl, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, and $C_3$-$C_6$ cycloalkyl, wherein the $C_3$-$C_6$ cycloalkyl is optionally substituted with one or more halogen, —CN, —NO₂, —N(R²⁰)₂, —OR²⁰, —SR²⁰, $C_{1-6}$ aminoalkyl, $C_{1-6}$alkoxyalkyl, $C_{1-6}$hydroxyalkyl, $C_{1-6}$ cyanoalkyl, $C_{1-6}$haloalkyl, and $C_{1-6}$ alkyl. In some cases, each $R^9$ is selected from halogen, hydrogen, $C_{1-6}$ alkyl, and $C_3$-$C_6$ cycloalkyl. In some cases, each $R^9$ is selected from hydrogen, $C_{1-6}$ alkyl, and $C_3$-$C_6$ cycloalkyl. In some cases, each $R^9$ is selected from hydrogen, fluorine, methyl, and cyclopropyl. In some cases, each $R^9$ is selected from hydrogen, methyl, and cyclopropyl.

In some embodiments, for a compound or salt of Formula (I), Formula (I-A), Formula (I-B), Formula (I-D), Formula (I-E), Formula (I-H), or Formula (I-J), $R^8$ is selected from optionally substituted 5- to 6-membered heteroaryl. In some cases, $R^8$ is selected from optionally substituted 5-membered heteroaryl. In some cases, the heteroaryl of $R^8$ has at least heteroatom selected from oxygen, nitrogen, and sulfur. In some cases, the heteroaryl of $R^8$ contains only one sulfur atom. In some cases, the heteroaryl of $R^8$ has at least one sulfur atom. In some cases, the heteroaryl of $R^8$ has at most one sulfur atom. In some cases, the heteroaryl of $R^8$ has at least one oxygen atom. In some cases, the heteroaryl of $R^8$ has at least one nitrogen atom. In some cases, the heteroaryl of $R^8$ is

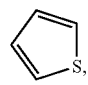

which is optionally substituted. In some cases, the heteroaryl of $R^8$ is

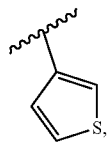

which is optionally substituted. In some cases, the heteroaryl of $R^8$ is

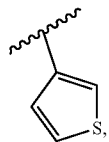

which is substituted. In some cases, the one or more optional substituents of $R^8$ are independently selected from halogen, $C_{1-6}$ alkyl, $C_{1-6}$ haloalkyl, —N(R²⁰)₂, and —CN. In some cases, the one or more optional substituents of $R^8$ are independently selected from halogen, —N(R²⁰)₂, and —CN. In some cases, the one or more optional substituents of $R^8$ are independently selected from halogen, —NH₂, and —CN. In some cases, the one or more substituents of $R^8$ are independently selected from halogen, —$NH_2$, and —CN. In some cases, the one or more optional substituents of $R^8$ are independently selected from chlorine, —$NH_2$, and —CN. In some cases, $R^8$ is selected from

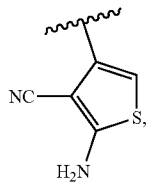 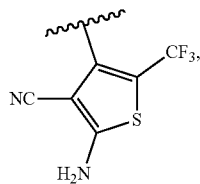

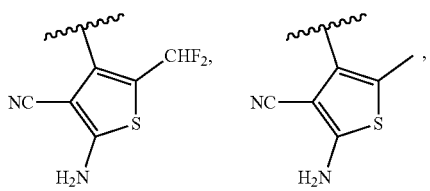

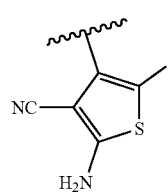 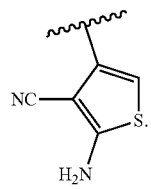

In some cases, $R^8$ is selected from

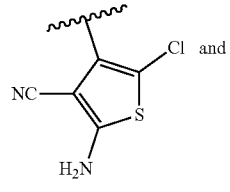 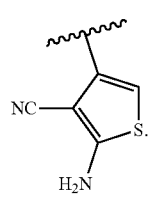

In some cases, $R^8$ is

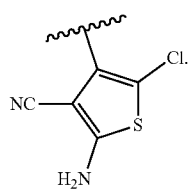 [SMILES: *c1c(Cl)sc(N)c1C#N]

In some cases, $R^8$ is

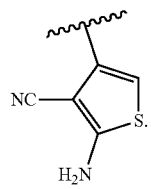

In some embodiments, for a compound or salt of Formula (I), Formula (I-A), Formula (I-B), Formula (I-D), Formula (I-E), Formula (I-H), or Formula (I-J), $R^8$ is selected from an optionally substituted 6- to 9-membered heteroaryl. In some cases, the $R^8$ is selected

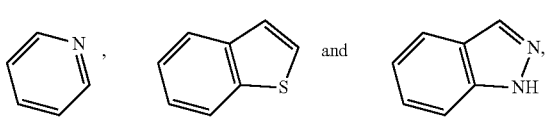 [SMILES: c1ccncc1 ; c1ccc2sccc2c1 ; c1ccc2[nH]ncc2c1]

each of which is optionally substituted. In some cases, the $R^8$ is selected

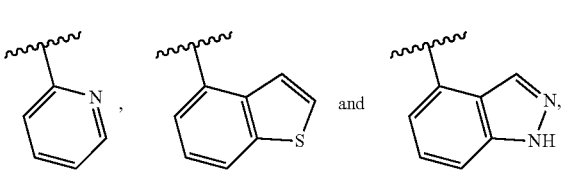 [SMILES: *c1ccccn1 ; *c1cccc2sccc12 ; *c1cccc2[nH]ncc12]

each of which is optionally substituted. In some cases, the one or more optional substituents of $R^8$ are independently selected from halogen, $C_{1-6}$ alkyl, $C_{1-6}$ haloalkyl, —$N(R^{20})_2$, and —CN. In some cases, the one or more optional substituents of $R^8$ are independently selected from halogen, $C_{2-6}$ alkyl, $C_{1-6}$ haloalkyl, —$N(R^{20})_2$, and —CN. In some cases, the one or more optional substituents of $R^8$ are independently selected from halogen, $C_{1-6}$ haloalkyl, —$N(R^{20})_2$, and —CN. In some cases, $R^8$ is selected from

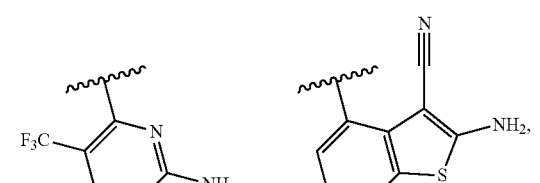

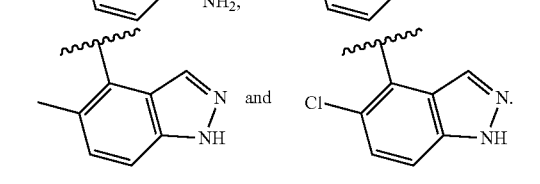

In some cases, the heteroaryl of $R^8$ has at least one sulfur atom. In some cases, the heteroaryl of $R^8$ is bicyclic. In some cases, the heteroaryl of $R^8$ is monocyclic. In some cases, $R^8$ is

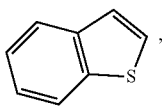, which is optionally substituted. In some cases, $R^8$ is

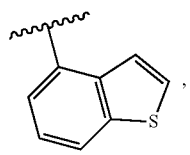, which is optionally substituted. In some cases, the one or more optional substituents of $R^8$ are independently selected from halogen, $C_{1-6}$ alkyl, $C_{1-6}$ haloalkyl, —$N(R^{20})_2$, and —CN. In some cases, $R^8$ is

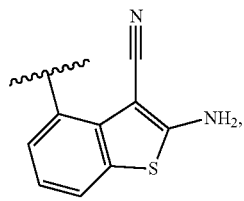 [SMILES: *c1cccc2sc(N)c(C#N)c12]

In some embodiments, for a compound or salt of Formula (I), Formula (I-A), Formula (I-B), Formula (I-D), Formula (I-E), Formula (I-H), or Formula (I-J), $R^8$ is selected from an optionally substituted 5- to 12-membered unsaturated heterocycle. In some cases, $R^8$ is selected from an optionally substituted 8- to 12-membered unsaturated bicyclic heterocycle. In some cases, $R^8$ is selected from an optionally substituted 9-membered unsaturated heterocycle. In some cases, the heterocycle of $R^8$ is a bicyclic heterocycle. In some cases, the bicyclic heterocycle has two rings. In some cases, one ring of the bicyclic heterocycle is an unsaturated carbocycle and the second ring is a heteroaryl. In some cases, the heterocycle of $R^8$ has at least one sulfur atom. In some cases, the heterocycle of $R^8$ is

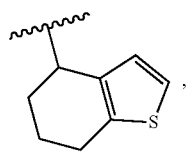 [SMILES: *C1CCCc2sccc21], which is optionally substituted. In some cases, the one or more optional substituents of $R^8$ are independently selected from halogen, —$N(R^{20})_2$, and —CN. In some cases, $R^8$ is

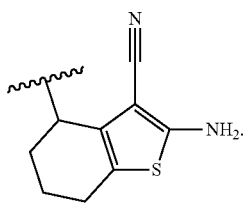 [SMILES: *C1CCCc2sc(N)c(C#N)c21]

is

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), n is selected from 0 and 1. In some cases, n is 1. In some cases, n is 0. In some cases, n is 3. In some cases, n is 2.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), each $R^4$ is independently selected from halogen, —$NO_2$, —$NH_2$, —$NH(C_{1-6}$ alkyl), —$N(C_{1-6}$ alkyl)$_2$, =O, —CN, $C_{1-6}$ alkyl, $C_{1-6}$ aminoalkyl, $C_{1-6}$ alkoxy, $C_{1-6}$ cyanoalkyl, $C_{1-6}$ hydroxyalkyl, and $C_{1-6}$ haloalkyl. In some cases, each $R^4$ is independently selected from =O.

In some embodiments, for a compound or salt of Formula (I), m is 1. In some cases, m is 2. In some cases, when $R^8$ and $R^9$ come together with the atoms to which they are bound to form B, m is 1. In some cases, when $R^8$ and $R^9$ come together with the atoms to which they are bound to form B, m is 2.

In some embodiments, for a compound or salt of Formula (I), $R^{100}$ is $R^1$.

In some embodiments, for a compound or salt of Formula (I), $R^{100}$ is selected from

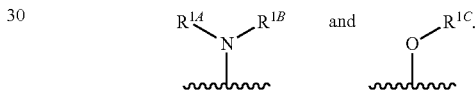

In some cases, $R^{100}$ is

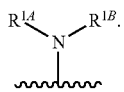

In some embodiments, for a compound or salt of Formula (I), $R^{100}$ is selected from

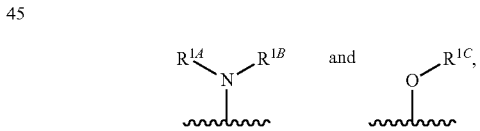

wherein $R^{1A}$ is selected from $C_{1-6}$ alkyl, wherein the $C_{1-6}$ alkyl is optionally substituted with one or more $R^{11}$, and wherein optionally two $R^{11}$ on the same atom of $R^{1A}$ come together to form a $C_3$-$C_6$ carbocycle, wherein the $C_3$-$C_6$ carbocycle is optionally substituted with one or more $R^{11A}$; or the $R^{1A}$ and $R^{1B}$ come together with the atom to which they are bound to form $R^1$, wherein $R^1$ is an optionally substituted 6- to 10-membered heterocycle; $R^{1B}$ is selected from hydrogen and $C_{1-6}$ alkyl; and $R^{1C}$ is selected from $C_{1-6}$ alkyl, wherein the $C_{1-6}$ alkyl is optionally substituted with one or more $R^{12}$, and wherein optionally two $R^{12}$ on the same atom of $R^{1C}$ come together to form a $C_3$-$C_6$ carbocycle, wherein the $C_3$-$C_6$ carbocycle is optionally substituted with one or more $R^{12A}$.

In some embodiments, for a compound or salt of Formula (I), $R^{100}$ is selected from:

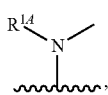

wherein $R^{1A}$ is selected from $C_{1-6}$ alkyl, wherein the $C_{1-6}$ alkyl is optionally substituted with one or more $R^{11}$, and wherein optionally two $R^{11}$ on the same atom of $R^{1A}$ come together to form an unsubstituted $C_3$ carbocycle;

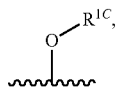

wherein $R^{1C}$ is selected from $C_{1-6}$ alkyl, wherein the $C_{1-6}$ alkyl is optionally substituted with one or more $R^{12}$, and wherein optionally two $R^{12}$ on the same atom of $R^{1C}$ come together to form an unsubstituted $C_3$ carbocycle; and

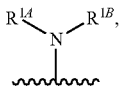

wherein $R^{1A}$ and $R^{1B}$ come together with the atom to which they are bound to form $R^1$, wherein $R^1$ is selected from

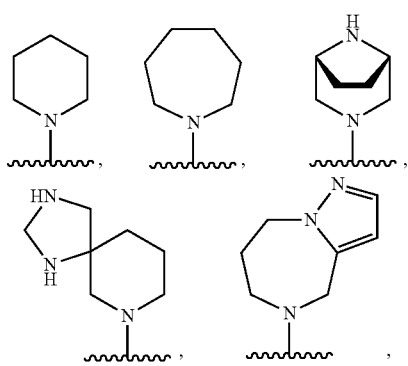

each of which is optionally substituted.

In some embodiments, for a compound or salt of Formula (I), each $R^{11}$ is selected from —CN, and wherein optionally two $R^{11}$ on the same atom of $R^{1A}$ come together to form an unsubstituted $C_3$ carbocycle; each $R^{12}$ is selected from —CN, and wherein optionally two $R^{12}$ on the same atom of $R^{1C}$ come together to form an unsubstituted $C_3$ carbocycle; and the one or more substituents of $R^1$ is independently selected from halogen, —OR$^{20}$, —CN, oxo, $C_{1-6}$ alkyl, $C_{1-6}$ hydroxyalkyl, and —C(O)N(R$^{20}$)$_2$.

In some embodiments, for a compound or salt of Formula (I), Formula (I-A), Formula (I-B), Formula (I-C), or Formula (I-G), each $R^{11}$ is selected from —CN, and wherein optionally two $R^{11}$ on the same atom of $R^{1A}$ come together to form an unsubstituted $C_3$ carbocycle.

In some embodiments, for a compound or salt of Formula (I), the one or more substituents of $R^1$ is independently selected from halogen, —OR$^{20}$, —CN, oxo, $C_{1-6}$ alkyl, $C_{1-6}$ hydroxyalkyl, and —C(O)N(R$^{20}$)$_2$. In some cases, the one or more substituents of $R^1$ is independently selected from halogen, —OH, —CN, oxo, $C_{1-6}$ alkyl, $C_{1-6}$ hydroxyalkyl, and —C(O)N(CH$_3$)$_2$.

In some embodiments, for a compound or salt of Formula (I), Formula (I-D), Formula (I-E), or Formula (I-F) each $R^{12}$ is selected from —CN, and wherein optionally two $R^{12}$ on the same atom of $R^{1C}$ come together to form an unsubstituted $C_3$ carbocycle.

In some embodiments, for a compound or salt of Formula (I), $R^{1A}$ is selected from

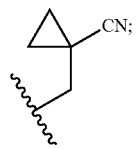

$R^{1C}$ is selected from

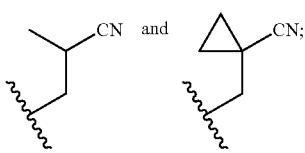

and the one or more substituents of $R^1$ is independently selected from halogen, —OH, —CN, oxo, $C_{1-6}$ alkyl, $C_{1-6}$ hydroxyalkyl, and —C(O)N(CH$_3$)$_2$.

In some embodiments, for a compound or salt of Formula (I), $R^{1A}$ is selected from

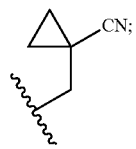

$R^{1C}$ is selected from

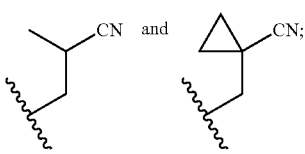

and the one or more substituents of $R^1$ is independently selected from halogen, —OH, —CN, oxo, $C_{1-6}$ alkyl, $C_{1-6}$ hydroxyalkyl, and —C(O)N(CH$_3$)$_2$.

In some embodiments, for a compound or salt of Formula (I), Formula (I-A), Formula (I-B), Formula (I-C), or Formula (I-G), $R^{1A}$ is selected from

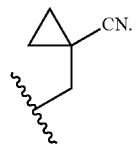

In some embodiments, for a compound or salt of Formula (I), Formula (I-D), Formula (I-E), or Formula (I-F), $R^{1C}$ is selected from

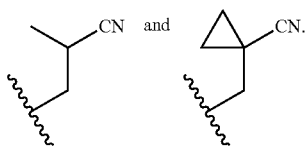

In some embodiments, for a compound or salt of Formula (I) $R^{100}$ is selected from

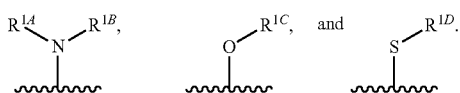

In some cases $R^{100}$ is selected from

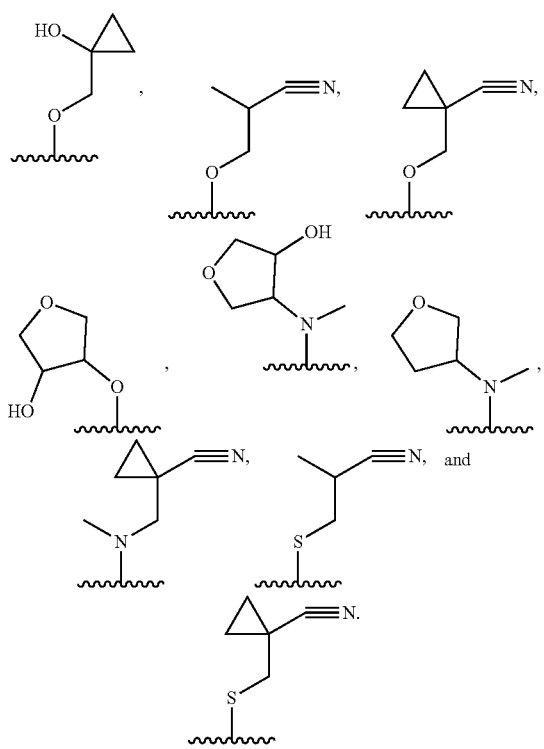

In some embodiments, for a compound or salt of Formula (I), $R^{100}$ is selected from

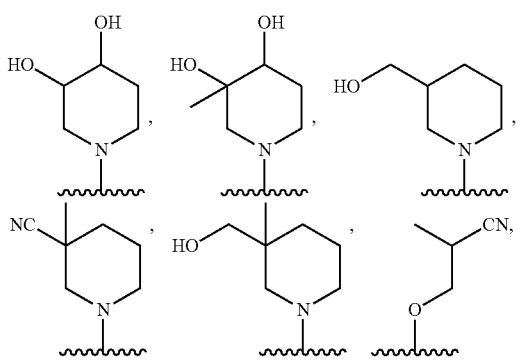

-continued

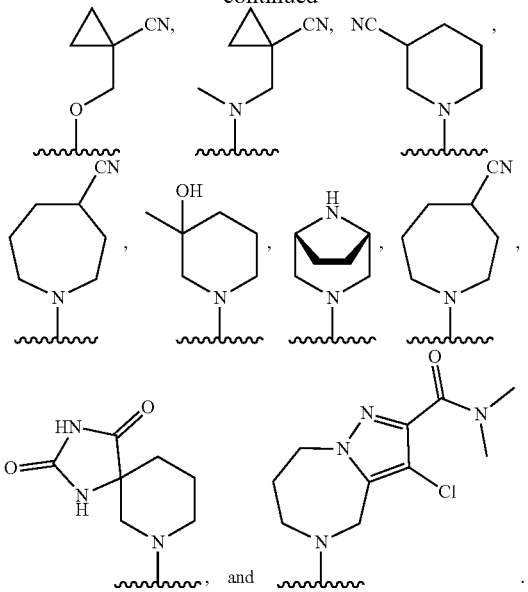

In some embodiments, for a compound or salt of Formula (I), $R^{100}$ is selected from

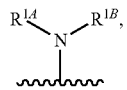

wherein $R^{1A}$ and $R^{1B}$ come together with the atom to which they are bound to form $R^1$.

In some embodiments, for a compound or salt of Formula (I), $R^{100}$ is selected from

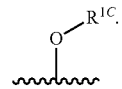

In some embodiments, for a compound or salt of Formula (I), $R^{100}$ is selected from:

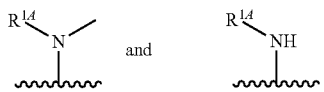

In some cases, $R^{1A}$ is selected from $C_{1-6}$ alkyl, $C_3$-$C_{12}$ carbocycle, and 4- to 12-membered heterocycle, each of which is optionally substituted with one or more $R^{11}$, and wherein optionally two $R^{11}$ on the same atom of $R^{1A}$ come together to form a $C_3$-$C_6$ carbocycle or 3- to 8-membered heterocycle, wherein the $C_3$-$C_6$ carbocycle and 3- to 8-membered heterocycle are each optionally substituted with one or more $R^{11A}$.

In some embodiments, for a compound or salt of Formula (I), Formula (I-A), Formula (I-B), Formula (I-C), or Formula (I-G), $R^{1B}$ is hydrogen. In some cases, $R^{1B}$ is selected from an optionally substituted $C_{1-6}$ alkyl. In some cases, $R^{1B}$ is selected from an optionally substituted $C_3$-$C_6$ carbocycle.

In some embodiments, for a compound or salt of Formula (I), Formula (I-A), Formula (I-B), Formula (I-C), or Formula (I-G), $R^{14}$ is selected from an optionally substituted $C_{1-6}$ alkyl. In some cases, $R^{11}$ is $-N(R^{20})_2$. In some cases, $R^{14}$ is selected

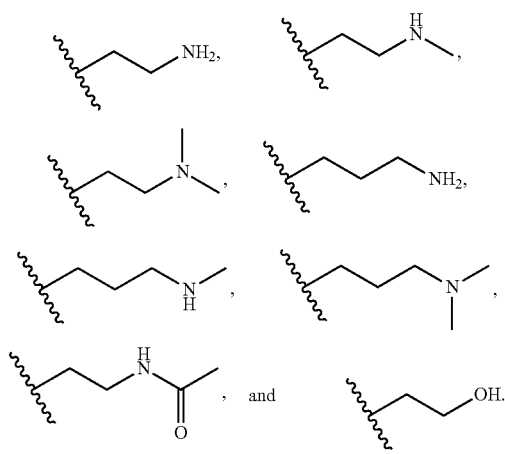

In some embodiments, for a compound or salt of Formula (I), Formula (I-A), Formula (I-B), Formula (I-C), or Formula (I-G), $R^{14}$ is $C_4$-$C_6$ carbocycle, wherein the $C_4$-$C_6$ carbocycle is optionally with one or more $R^{11}$. In some cases, each $R^{11}$ is selected from $-N(R^{20})_2$, wherein each $R^{20}$ is selected from hydrogen and optionally substituted $C_{1-6}$ alkyl. In some cases, $R^{14}$ is selected

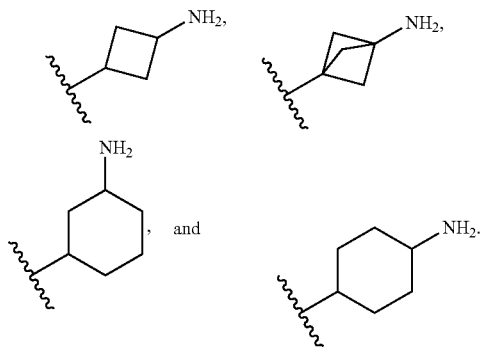

In some embodiments, for a compound or salt of Formula (I), Formula (I-A), Formula (I-B), Formula (I-C), or Formula (I-G), $R^{14}$ is selected from 4- to 12-membered heterocycle, wherein the 4- to 12-membered heterocycle is optionally with one or more $R^{11}$. In some cases, each $R^{11}$ is selected from halogen, $-N(R^{20})_2$, $-C(O)R^{20}$, $-C(O)N(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, and $C_{1-6}$ alkyl. In some cases, $R^{14}$ is selected from

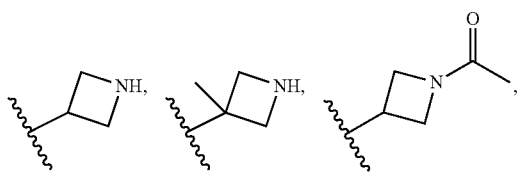

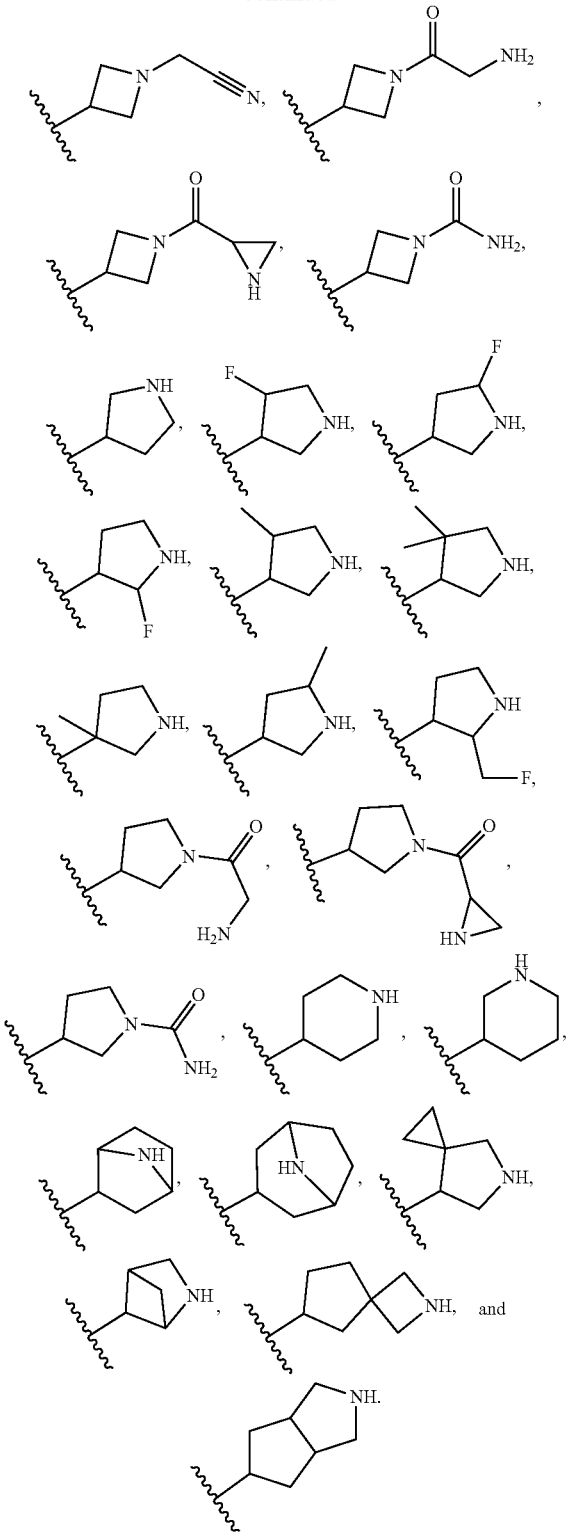

In some cases, $R^{14}$ is selected from 5- to 6-membered heterocycle, wherein the 5- to 6-membered heterocycle is optionally with one or more $R^{11}$. In some cases, the heterocycle has at least one oxygen atom. In some cases, the heterocycle has one oxygen atom. In some cases, $R^{14}$ is selected from

which is optionally substituted. In some cases, each $R^{11}$ is selected from —OH and $C_{1-6}$ hydroxyalkyl. In some cases, each $R^{11}$ is —OH. In some cases, $R^{1A}$ is selected from

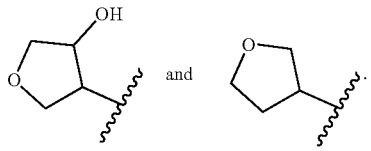 [SMILES: *C1COCC1O ; *C1CCOC1]

In some embodiments, for a compound or salt of Formula (I), Formula (I-A), Formula (I-B), Formula (I-C), or Formula (I-G), each $R^{11A}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, and $C_{2-6}$ alkynyl.

In some embodiments, for a compound or salt of Formula (I), Formula (I-A), Formula (I-B), Formula (I-C), or Formula (I-G), each $R^{11}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle. In some cases, each $R^{11}$ is independently selected from halogen, —OR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle. In some cases, each $R^{11}$ is independently selected from halogen, —OR$^{20}$, —N(R$^{20}$)$_2$, =O, =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle. In some cases, each $R^{11}$ is independently selected from halogen, —OR$^{20}$, —N(R$^{20}$)$_2$, —CN, —NHCN, $C_{1-6}$ aminoalkyl, $C_{1-6}$ alkoxy, $C_{1-6}$ hydroxyalkyl, $C_{1-6}$ cyanoalkyl, and $C_{1-6}$ haloalkyl.

In some embodiments, for a compound or salt of Formula (I), Formula (I-A), Formula (I-B), Formula (I-C), or Formula (I-G), $R^{1B}$ is selected from hydrogen, optionally substituted $C_{1-6}$ alkyl, and optionally substituted $C_3$-$C_6$ carbocycle. In some cases, $R^{1B}$ is hydrogen, $C_{1-6}$ alkyl, $C_{1-6}$ cyanoalkyl, $C_{1-6}$ hydroxyalkyl, and $C_3$-$C_6$ carbocycle. In some cases, $R^{1B}$ is hydrogen, methyl, ethyl, $C_2$ hydroxyalkyl, and cyclopropyl. In some cases, $R^{1B}$ is hydrogen. In some cases, $R^{1B}$ is selected from an optionally substituted $C_{1-6}$ alkyl. In some cases, $R^{1B}$ is selected from methyl and ethyl. In some cases, $R^{1B}$ is methyl. In some cases, $R^{1B}$ is selected from an optionally substituted $C_3$-$C_6$ carbocycle. In some cases, $R^{1B}$ is

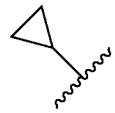 [SMILES: *C1CC1]

In some cases, $R^{1B}$ is selected from $C_{1-6}$ cyanoalkyl. In some cases, $R^{1B}$ is selected from $C_{1-6}$ hydroxyalkyl.

In some embodiments, for a compound or salt of Formula (I), Formula (I-A), Formula (I-B), Formula (I-C), or Formula (I-G), $R^{1A}$ is selected from an optionally substituted $C_{1-3}$ alkyl, and wherein optionally two $R^{11}$ on the same atom of $R^{1A}$ come together to form a $C_3$ carbocycle. In some cases, $R^{11}$ is selected from halogen, —N(R$^{20}$)$_2$, $C_3$ carbocycle, and 5- to 6-membered heterocycle, wherein the 5- to 6-membered heterocycle is optionally substituted with one or more substituents independently selected from halogen, —OH, —CN, —N(R$^{21}$)$_2$, $C_{1-10}$ alkyl, and —$C_{1-10}$ haloalkyl. In some cases, each $R^{21}$ is independently selected from hydrogen; and $C_{1-6}$ alkyl, wherein the $C_{1-6}$ alkyl is optionally substituted with one or more substituents independently selected from halogen, oxo, $C_{3-6}$ carbocycle, and 3- to 6-membered heterocycle.

In some embodiments, for a compound or salt of Formula (I), Formula (I-A), Formula (I-B), Formula (I-C), or Formula (I-G), $R^{11}$ is selected from

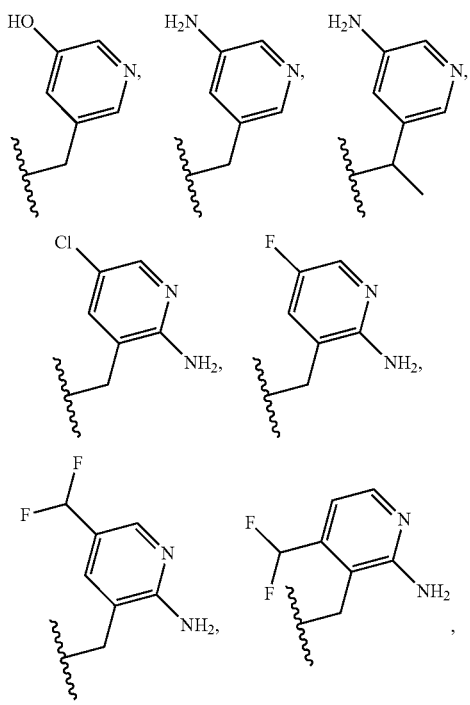

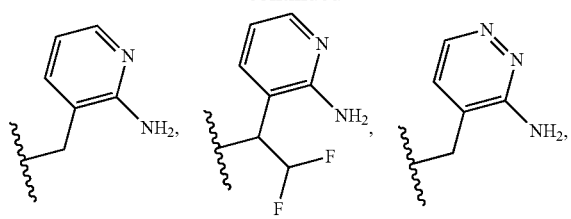
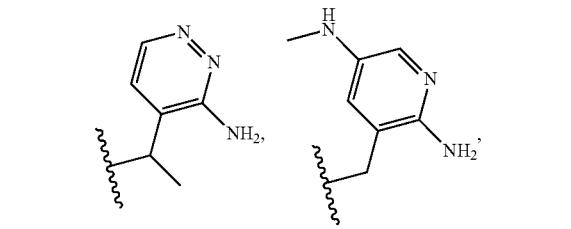
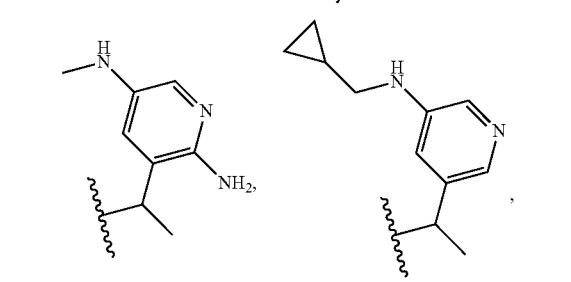
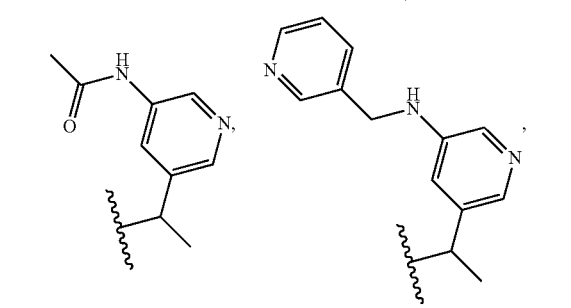
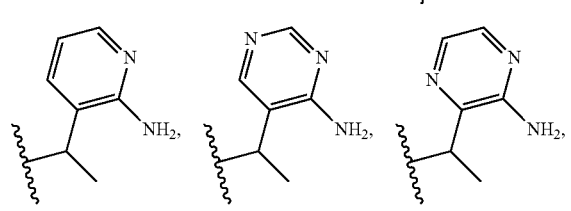
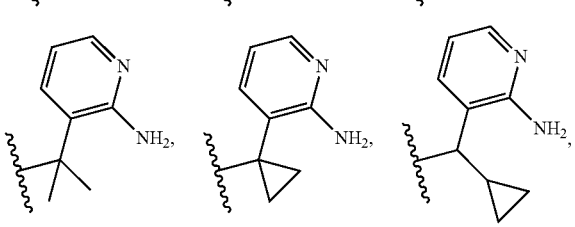
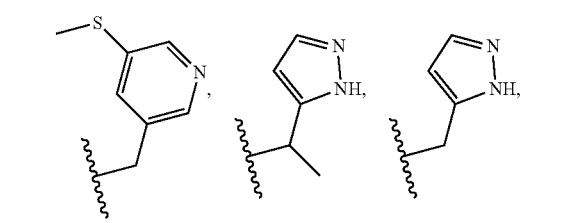
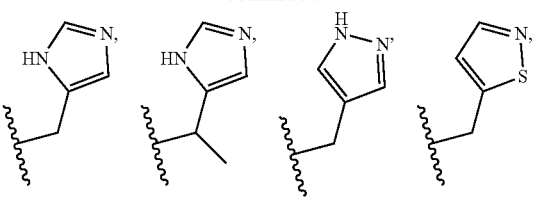
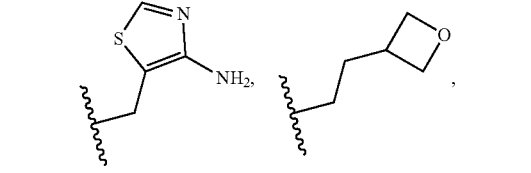
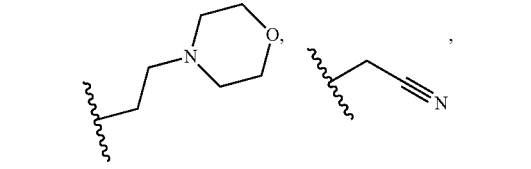
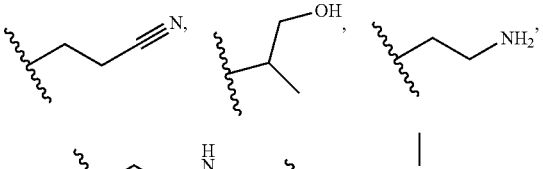
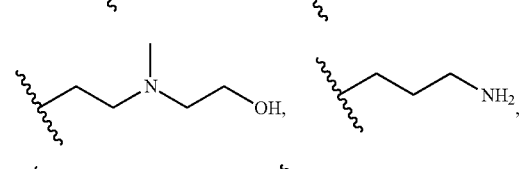
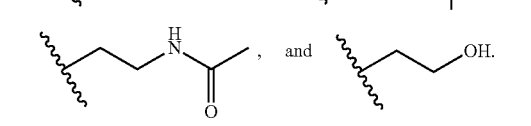
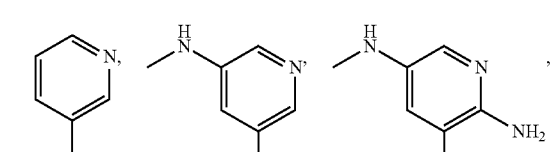
In some embodiments, for a compound or salt of Formula (I), $R^{100}$ is selected from
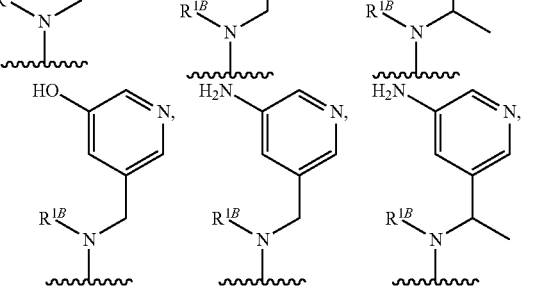

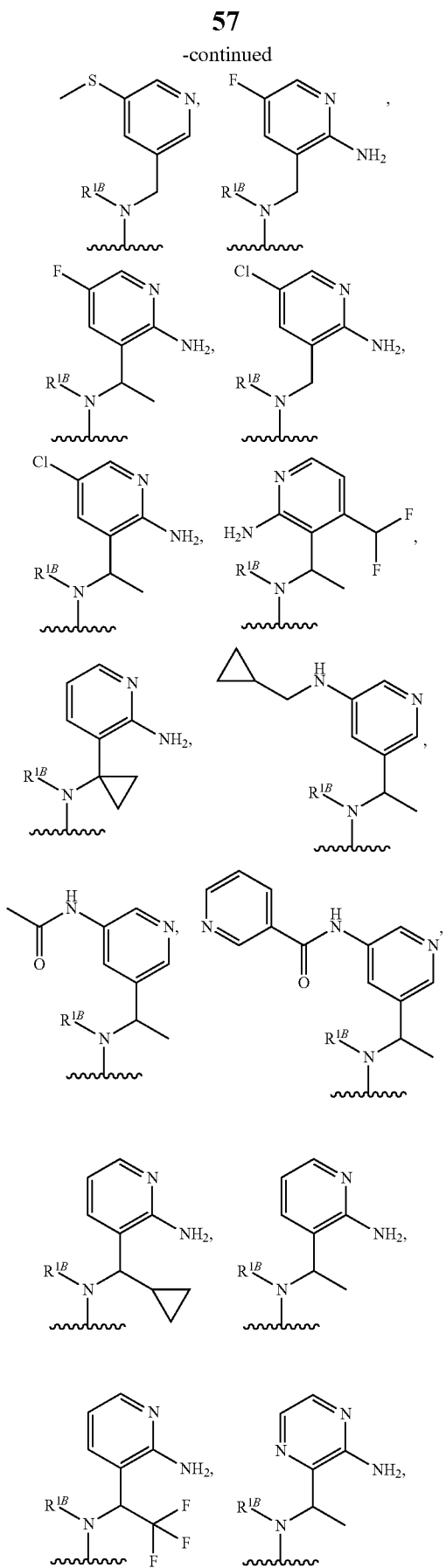
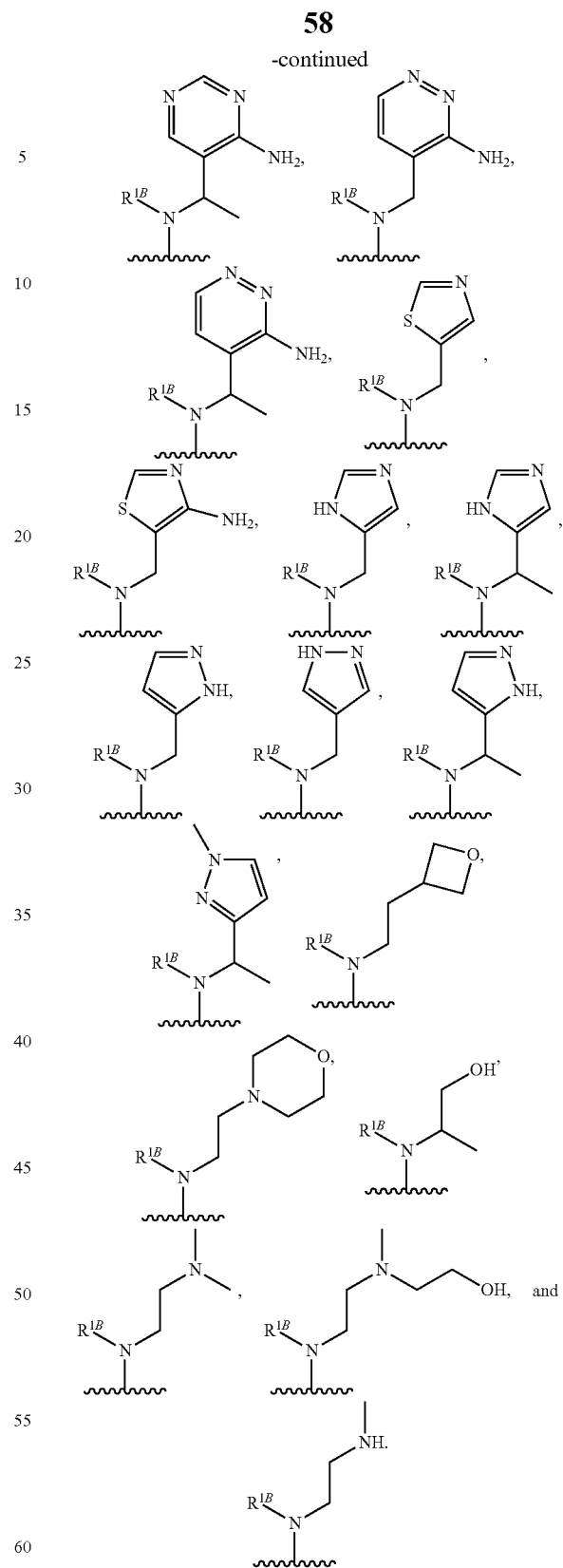
In some embodiments, for a compound or salt of Formula (I), Formula (I-A), Formula (I-B), Formula (I-C), or Formula (I-G), $R^{1A}$ is selected from an optionally substituted $C_{1-6}$ alkyl. In some cases, $R^{1A}$ is selected from an optionally substituted $C_{1-3}$ alkyl, and wherein optionally two $R^{11}$ on the same atom of $R^{14}$ come together to form a $C_3$ carbocycle. In some cases, $R^{14}$ is selected from an optionally substituted $C_{1-2}$ alkyl. In some cases, $R^{14}$ is selected from

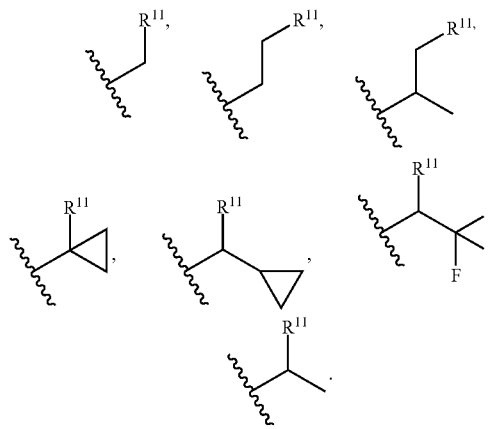

In some cases, $R^{14}$ is selected from

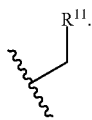

In some cases, $R^{14}$ is selected from

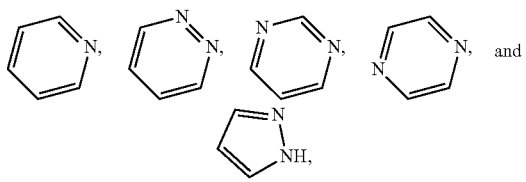

In some cases, $R^{11}$ is selected from an optionally substituted 5- to 12-membered heterocycle. In some cases, $R^{11}$ is selected from an optionally substituted 5- to 8-membered heterocycle. In some cases, $R^{11}$ is selected from an optionally substituted 5- to 6-membered heterocycle. In some cases, $R^{11}$ is selected from an optionally substituted 5- to 6-membered heteroaryl. In some cases, the heterocycle has at least one nitrogen atom. In some cases, the heterocycle has at least two nitrogen atoms. In some cases, the heteroaryl has at least one nitrogen atom. In some cases, the heteroaryl has at least two nitrogen atoms. In some cases, the heterocycle has only 1 nitrogen atom and no other heteroatoms. In some cases, the heterocycle has only 2 nitrogen atoms and no other heteroatoms. In some cases, $R^{11}$ is selected from

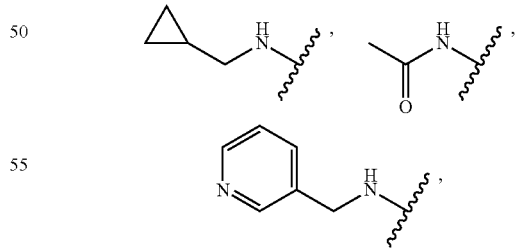

each of which is optionally substituted. In some cases, $R^{11}$ is selected from

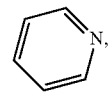

which is optionally substituted. In some cases, $R^{11}$ is selected from

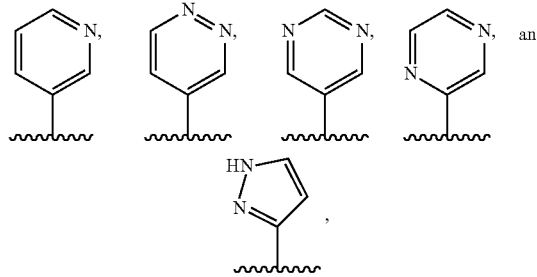

and each of which is optionally substituted. In some cases, $R^{11}$ is selected from

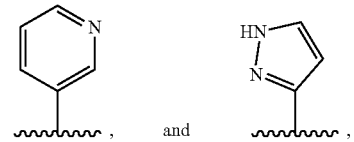 [SMILES: *c1cccnc1 ; *c1cc[nH]n1]

and each of which is optionally substituted. In some cases, the optional one or more substituents independently selected from halogen, —OH, —CN, —N($R^{21}$)$_2$, —C(O)N($R^{21}$)$_2$, $C_{1-10}$ alkyl, and —$C_{1-10}$ haloalkyl. In some cases, $R^{21}$ is independently selected from hydrogen; and $C_{1-6}$ alkyl, wherein the $C_{1-6}$ alkyl is optionally substituted with one or more substituents independently selected from halogen, oxo, $C_{3-6}$ carbocycle, and 3- to 6-membered heterocycle. In some cases, the optional one or more substituents of $R^{11}$ is selected from halogen, $C_{1-6}$ haloalkyl, —NH$_2$, —NH($C_{1-6}$ alkyl), —N($C_{1-6}$ alkyl)$_2$, and $C_{1-10}$ alkyl. In some cases, the optional one or more substituents of $R^{11}$ is selected from —NH$_2$, —NH($C_{1-6}$ alkyl), —N($C_{1-6}$ alkyl)$_2$, and $C_{1-10}$ alkyl. In some cases, the optional one or more substituents of $R^{11}$ is selected from —NH$_2$, and $C_{1-10}$ alkyl. In some cases, the optional one or more substituents of $R^{11}$ is selected from —NH$_2$. In some cases, $R^{11}$ is selected from

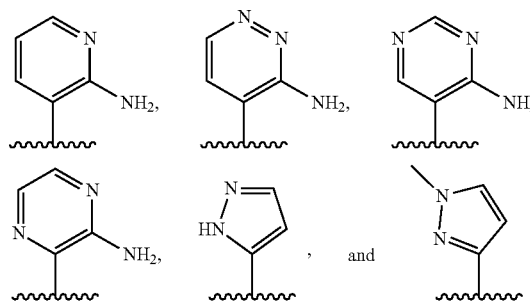
In some cases, $R^{1A}$ is selected from
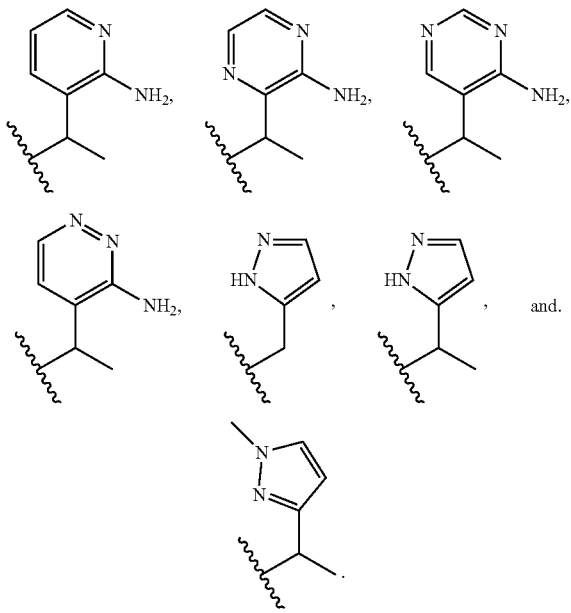
In some cases, $R^{1A}$ is selected from
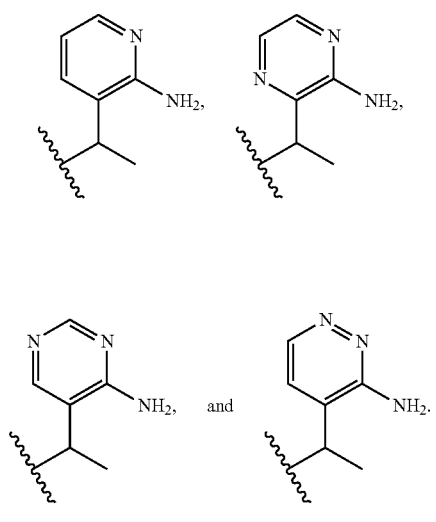
In some cases, $R^{1A}$ is
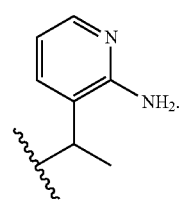 [SMILES: *C(C)c1cccnc1N]
In some embodiments, for a compound or salt of Formula (I), Formula (I-A), Formula (I-B), Formula (I-C), or Formula (I-G), $R^{100}$ is selected from
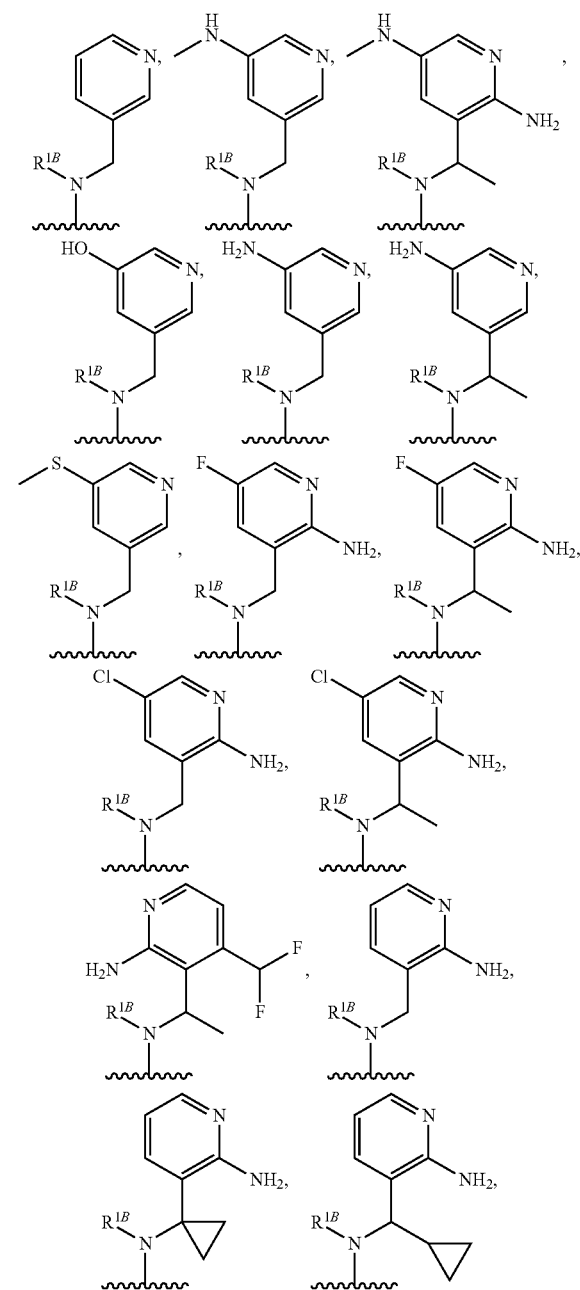

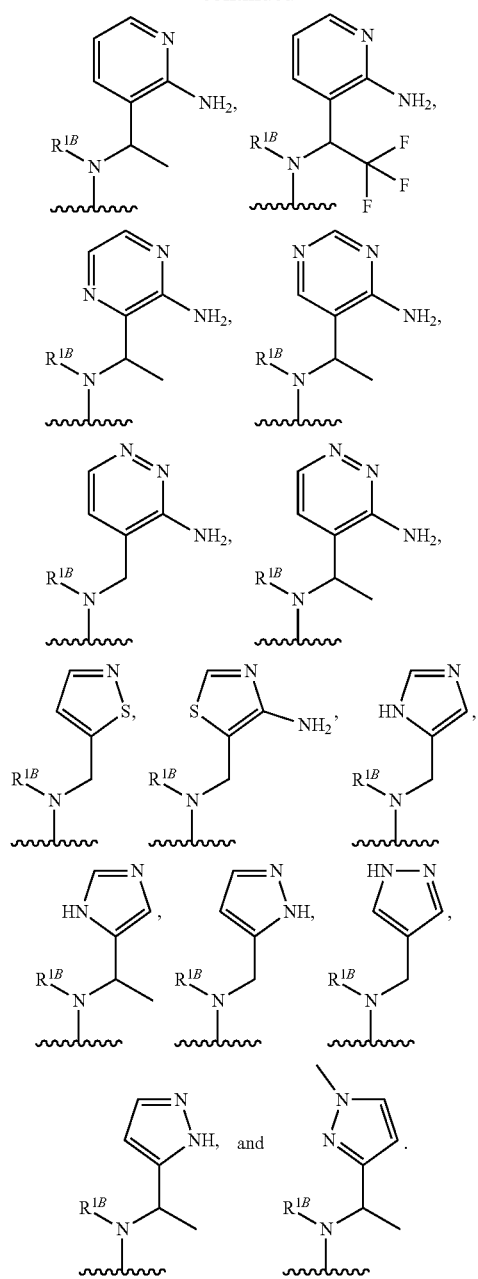
In some embodiments, for a compound or salt of Formula (I), $R^{100}$ is selected from
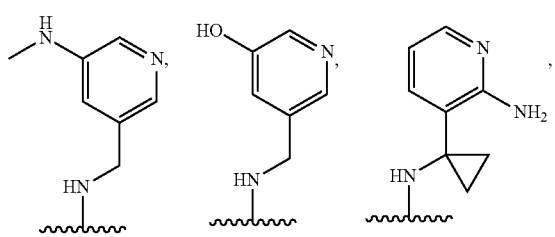
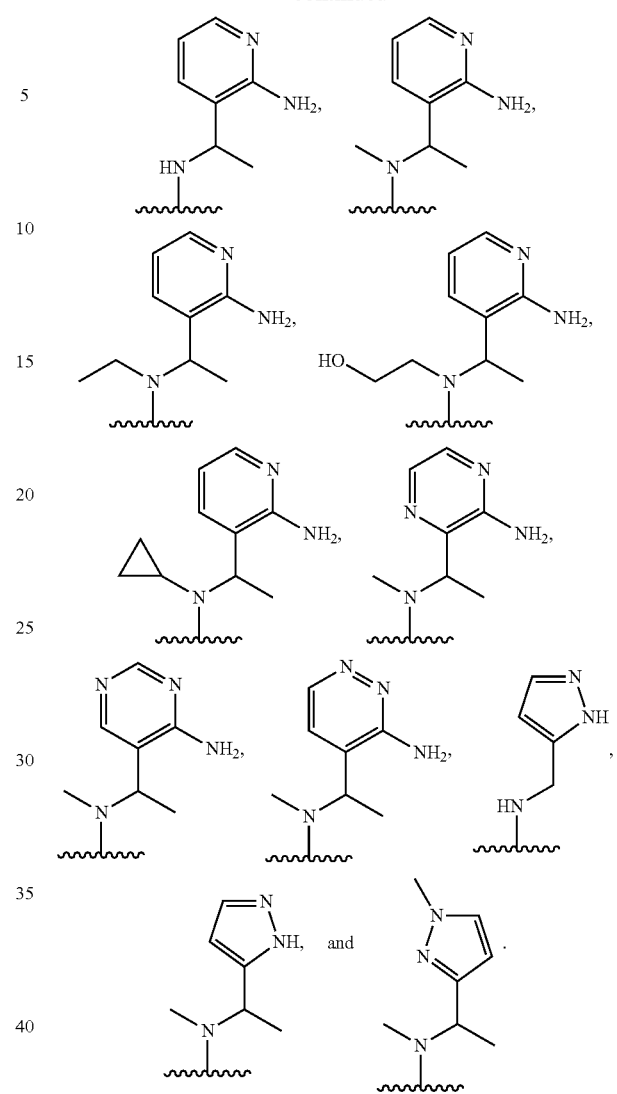
In some cases, $R^{100}$ is selected from In some cases, $R^{100}$ is selected from,
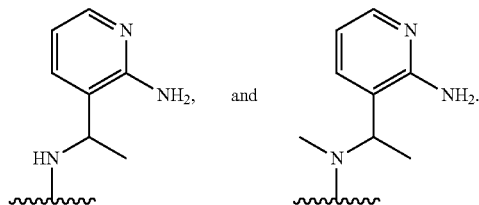 [SMILES: *NC(C)c1cccnc1N ; "and" ; *N(C)C(C)c1cccnc1N]
in some cases, $R^{100}$ is selected from
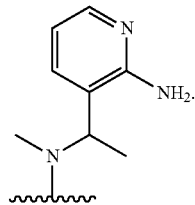 [SMILES: *N(C)C(C)c1cccnc1N]
In some embodiments, for a compound or salt of Formula (I), $R^{100}$ is selected from
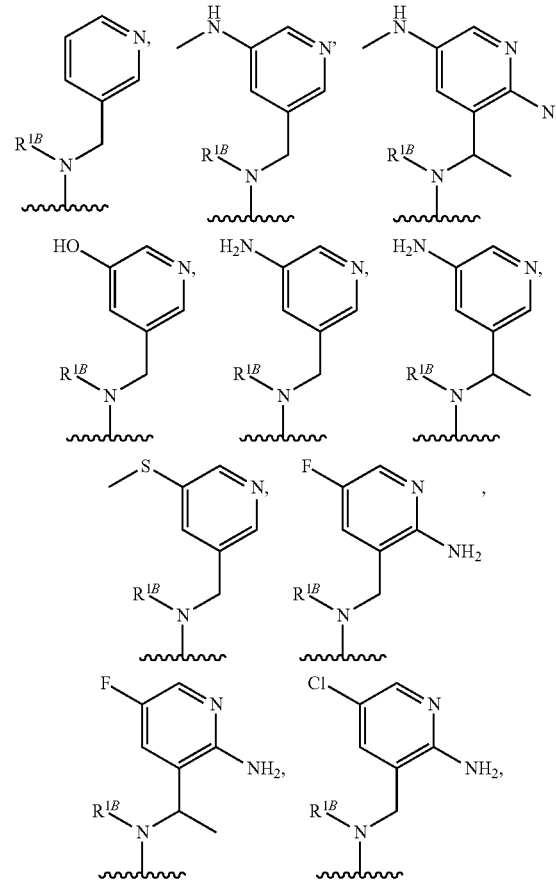
-continued
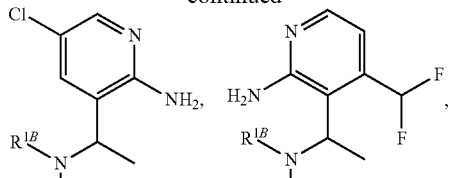
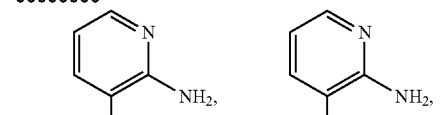
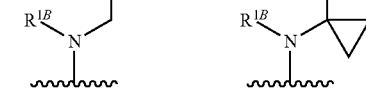
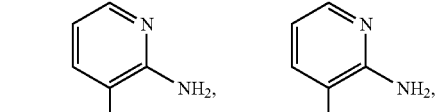
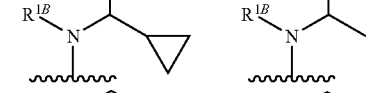
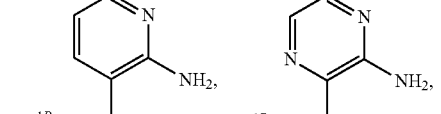
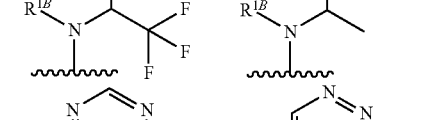
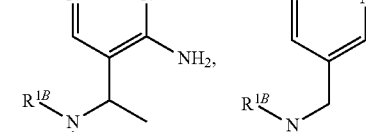

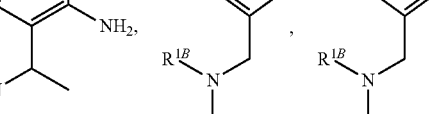

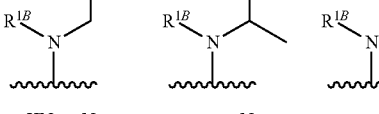
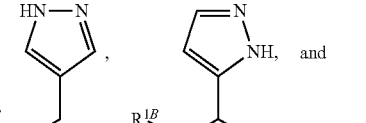
In some cases, $R^{1B}$ is selected from hydrogen, $C_{1-6}$ alkyl, $C_{1-6}$ hydroxyalkyl, and $C_{1-6}$ cyanoalkyl. In some cases, $R^{1B}$ is selected from hydrogen and $C_{1-6}$ alkyl. In some cases, $R^{1B}$ is selected from $C_{1-6}$ alkyl. In some cases, $R^{1B}$ is a cyclopropyl. In some cases, $R^{1B}$ is methyl. In some cases, $R^{1B}$ is ethyl. In some cases, $R^{100}$ is selected from

[chemical structures]

In some cases, $R^{100}$ is selected from

[chemical structures]

In some cases, $R^{100}$ is selected from

[chemical structures]

In some cases, $R^{100}$ is selected from

[chemical structures]

In some cases, $R^{100}$ is selected from

[chemical structures]

In some embodiments, for a compound or salt of Formula (I), Formula (I-A), Formula (I-B), and Formula (I-C), $R^{14}$ is selected from an $C_{1-3}$ alkyl, which is optionally substituted with one or more $R^{11}$, wherein each $R^{11}$ is selected from $C_3$-$C_6$ carbocycle, and 5- to 6-membered heterocycle, wherein the 5- to 6-membered heterocycle and $C_3$-$C_6$ carbocycle are each optionally substituted. In some cases, $R^{14}$ is selected from an $C_{1-3}$ alkyl, which is substituted with one or more $R^{11}$, wherein each $R^{11}$ is selected from phenyl, and 5- to 6-membered heterocycle, wherein the 5- to 6-membered heterocycle and phenyl are each optionally substituted. In some cases, $R^{11}$ is phenyl, which is optionally substituted. In some cases, $R^{11}$ is selected from a 5- to 6-membered heterocycle, which is optionally substituted. In some cases, $R^{11}$ is pyridine, which is optionally substituted. In some cases, $R^{14}$ is selected from,

[chemical structures] and [chemical structures]

In some cases, $R^{14}$ is

[chemical structure]

In some cases, the heterocycle is a heteroaryl. In some cases, the one or more substituents are independently selected from halogen, —P(O)(R$^{21}$)$_2$, —OH, —CN, —N(R$^{21}$)$_2$, —C(O)N(R$^{21}$)$_2$, C$_{1-10}$ alkyl, and —C$_{1-10}$ haloalkyl. In some cases, the one or more substituents are independently selected from —P(O)(R$^{21}$)$_2$, —N(R$^{21}$)$_2$, and C$_{1-10}$ alkyl. In some cases, the one or more substituents are independently selected from —P(O)(R$^{21}$)$_2$, and —N(R$^{21}$)$_2$. In some cases, the one or more substituents are independently selected from —P(O)(R$^{21}$)$_2$. In some cases, each R$^{21}$ is independently selected from hydrogen and C$_{1-6}$ alkyl. In some cases, each R$^{21}$ is independently selected from C$_{1-3}$ alkyl. In some cases, R$^{100}$ or

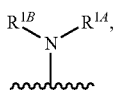

is selected from

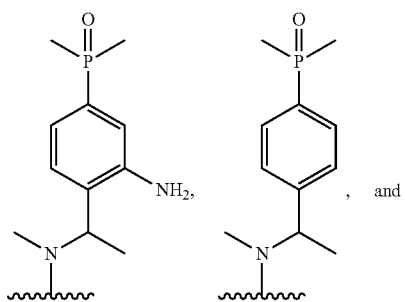

In some cases, R$^{100}$ is

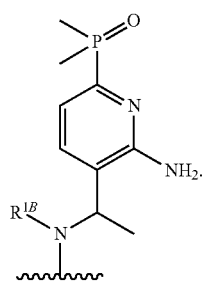

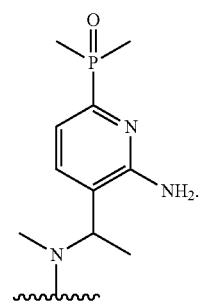 [SMILES: *N(C)C(C)c1ccc(P(C)(C)=O)nc1N]

In some cases, R$^{100}$ or

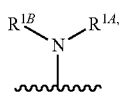

is selected from

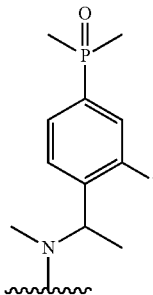 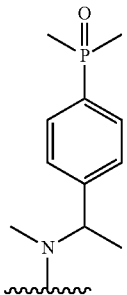

In some embodiments, for a compound or salt of Formula (I), R$^{100}$ is selected from

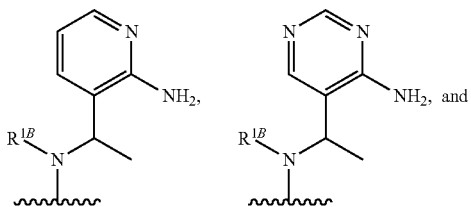

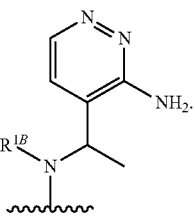

In some cases, R$^{100}$ is selected from

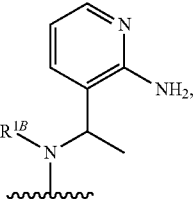

In some cases, R$^{1B}$ is selected from hydrogen and C$_{1-6}$ alkyl. In some cases, R$^{100}$ is selected from In some cases, R$^{100}$ is In some cases, $R^{100}$ is

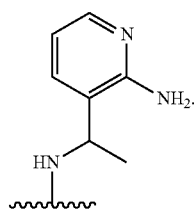 [SMILES: *NC(C)c1cccnc1N]

In some cases, $R^{100}$ is

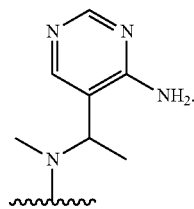 [SMILES: *N(C)C(C)c1cncnc1N]

In some cases, $R^{100}$ is

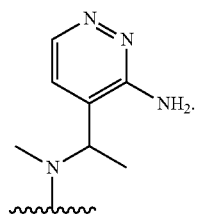 [SMILES: *N(C)C(C)c1ccnnc1N]

In some cases, $R^{100}$ is selected from

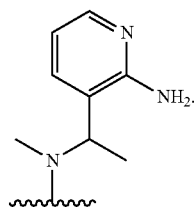 [SMILES: *N(C)C(C)c1cccnc1N]

In some cases, B is selected from an 8- to 10-membered heterocycle, wherein the 8- to 10-membered heterocycle is optionally substituted with one or more substituents independently selected from halogen, —CN, —NH$_2$, and C$_{1-6}$ alkyl. In some cases, B is selected from an 8-membered heterocycle, wherein the 8-membered heterocycle is substituted with one or more substituents independently selected from halogen, —CN, —NH$_2$, and C$_{1-6}$ alkyl. In some cases, the heterocycle of B has one sulfur atom and no other heteroatoms. In some cases, the heterocycle of B is an unsaturated heterocycle. In some cases, B is selected from

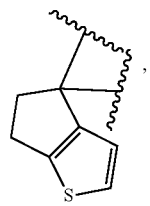 [SMILES: *C1(*)CCc2sccc21]

each of which is optionally substituted. In some cases, B is selected from

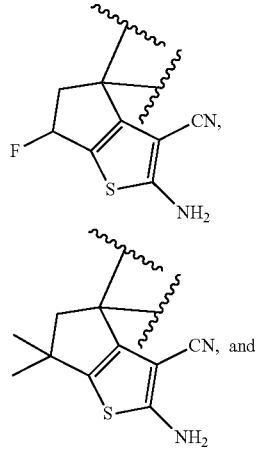

each of which is substituted with at least one substituent. In some cases, B is selected from

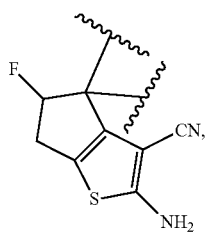 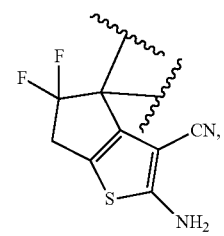

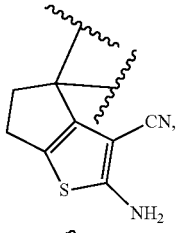 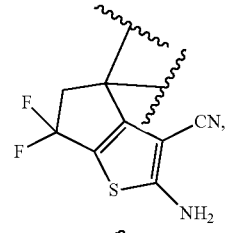

In some cases, B is

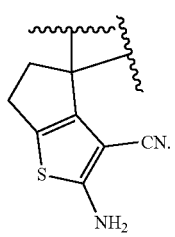 [SMILES: *C1(*)CCc2sc(N)c(C#N)c21]

In some cases, Y is O. In some cases, L is selected from $C_1$-$C_4$ alkylene. In some cases, L is selected from an unsubstituted $C_1$-$C_4$ alkylene. In some cases, L is selected from an unsubstituted $C_1$ alkylene. In some cases, two substituents on the same carbon atom of L come together to form a $C_3$-$C_6$ carbocycle or 3- to 8-membered heterocycle, wherein the $C_3$-$C_6$ carbocycle and 3- to 8-membered heterocycle are each optionally substituted with one or more substituents independently selected from halogen, —OH, —NO$_2$, =O, =S, —CN, $C_{1-6}$ aminoalkyl, $C_{1-6}$ alkoxy, $C_{1-6}$hydroxyalkyl, $C_{1-6}$haloalkyl. In some cases, two substituents on the same carbon atom of L come together to form a $C_3$-$C_6$ carbocycle or 3- to 8-membered heterocycle. In some cases, two substituents on the same carbon atom of L come together to form a $C_3$-$C_6$ carbocycle. In some cases, each L is selected from

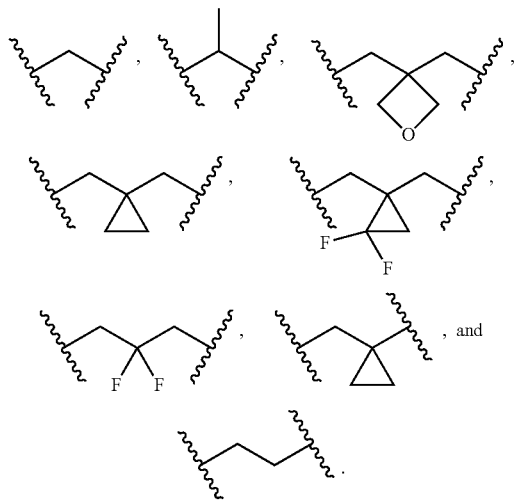

In some cases, $R^2$ is selected from optionally substituted -L-heterocycle. In some cases, $R^2$ is selected from optionally substituted -L-heterocycle, wherein the heterocycle is a saturated heterocycle. In some cases, the heterocycle is selected from

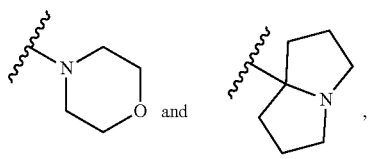

each of which is optionally substituted with one or more $R^6$. In some cases, each $R^6$ is independently selected from halogen, hydroxy, $C_1$-$C_3$ alkyl, $C_1$-$C_3$ haloalkyl, —N($R^5$)S(O)$_2$($R^5$), —OC(O)N($R^5$)$_2$, =CH$_2$, oxo, =NO—$C_1$-$C_3$ alkyl, —CH$_2$OC(O)heterocycle, —CH$_2$heterocycle, —CH$_2$OC(O)N($R^5$)$_2$, and —O—$C_1$-$C_3$ alkyl, wherein the alkyl of —O—$C_1$-$C_3$ alkyl is optionally substituted with substituents selected from heterocycle, oxo, and hydroxy. In some cases, each $R^6$ is independently selected from halogen, $C_1$-$C_3$ alkyl, and $C_1$-$C_3$ haloalkyl. In some cases, each $R^6$ is independently selected from halogen. In some cases, Y—$R^2$ is selected from

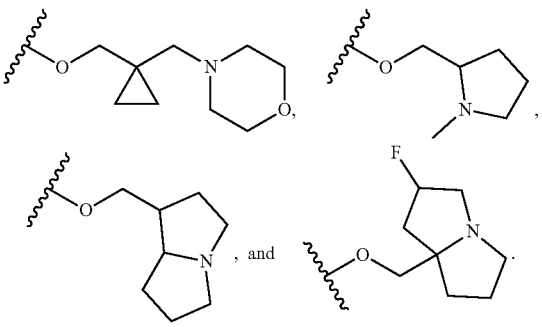

In some cases, Y—$R^2$ is

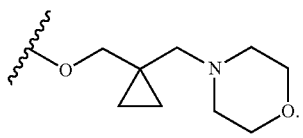 [SMILES: *OCC1(CN2CCOCC2)CC1]

In some cases, Y—$R^2$ is

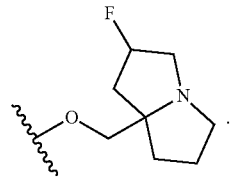 [SMILES: *OCC12CCCN1CC(F)C2]

In some embodiments, for a compound or salt of Formula (I), Formula (I-A), Formula (I-B), Formula (I-C), or Formula (I-G), for

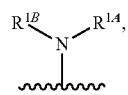

$R^{1A}$ is selected from $C_{1-6}$ alkyl, which is substituted with one $R^{11}$, wherein the one $R^{11}$ is selected from an optionally substituted 5- to 6-membered heteroaryl, wherein the 5- to 6-membered heteroaryl is optionally substituted;

$R^{1B}$ is selected from hydrogen, optionally substituted $C_{1-6}$ alkyl, and $C_3$-$C_6$ carbocycle.

or $R^{1A}$ and $R^{1B}$ come together with the atom to which they are bound to form $R^1$, wherein $R^1$ is selected from an optionally substituted 5- to 10-membered heterocycle. In some cases, for

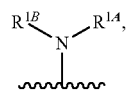

$R^{1A}$ is selected from $C_{1-6}$ alkyl, which is substituted with one $R^{11}$, wherein the one $R^{11}$ is selected from an optionally substituted 5- to 6-membered heteroaryl, wherein the 5- to 6-membered heteroaryl is optionally substituted with one or more substituents independently selected from halogen, —OH, —CN, —N(R$^{21}$)$_2$, C$_{1-10}$ alkyl, and —C$_{1-10}$ haloalkyl;

R$^{1B}$ is selected from hydrogen, C$_{1-6}$ alkyl, C$_{1-6}$ cyanoalkyl, C$_{1-6}$ hydroxyalkyl, and C$_3$-C$_6$ carbocycle.

or R$^{1A}$ and R$^{1B}$ come together with the atom to which they are bound to form R$^1$, wherein R$^1$ is selected from an optionally substituted 5- to 9-membered heterocycle, wherein the 5- to 9-membered heterocycle is optionally substituted with one or more substituents independently selected from —OH, —CN, oxo, —NHCN, C$_{1-6}$hydroxyalkyl, C$_{1-6}$ cyanoalkyl, C$_{1-6}$haloalkyl, and C$_{1-6}$ alkyl. In some cases, R$^1$ is selected from

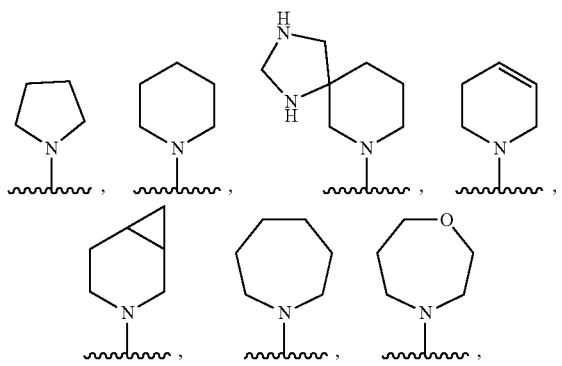

each of which is optionally substituted; and wherein R$^{1A}$ is selected from an C$_{1-3}$ alkyl substituted with an optionally substituted 6-membered heteroaryl (e.g., pyridine, pyrimidine). In some cases, R$^1$ is selected from

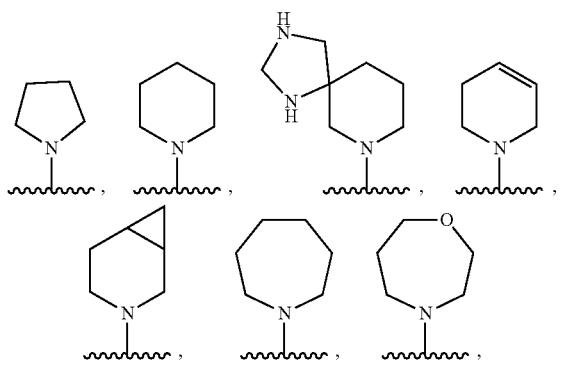

each of which is optionally substituted. In some cases, R$^1$ is selected from

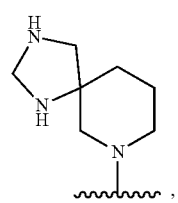

which is optionally substituted. In some cases, R$^1$ is selected from

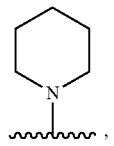

is optionally substituted. In some cases, R$^1$ is selected from

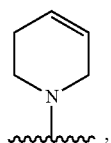

which is optionally substituted. In some cases, R$^1$ is selected from

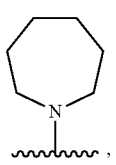

which is optionally substituted. In some cases, R$^1$ is selected from

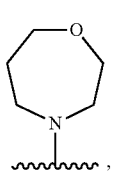 [SMILES: *N1CCCOCC1]

which is optionally substituted. In some cases, R$^1$ is selected from

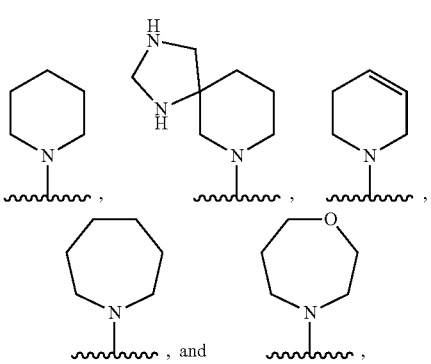

each of which is optionally substituted. In some cases, the optional one or more substituents of R$^1$ is independently selected from —OH, oxo, —CN, —NHCN, C$_{1-6}$ hydroxyalkyl, C$_{1-6}$ cyanoalkyl, C$_{1-6}$ haloalkyl, and C$_{1-6}$ alkyl.

In some embodiments, for a compound or salt of Formula (I), R$^{100}$ is selected from

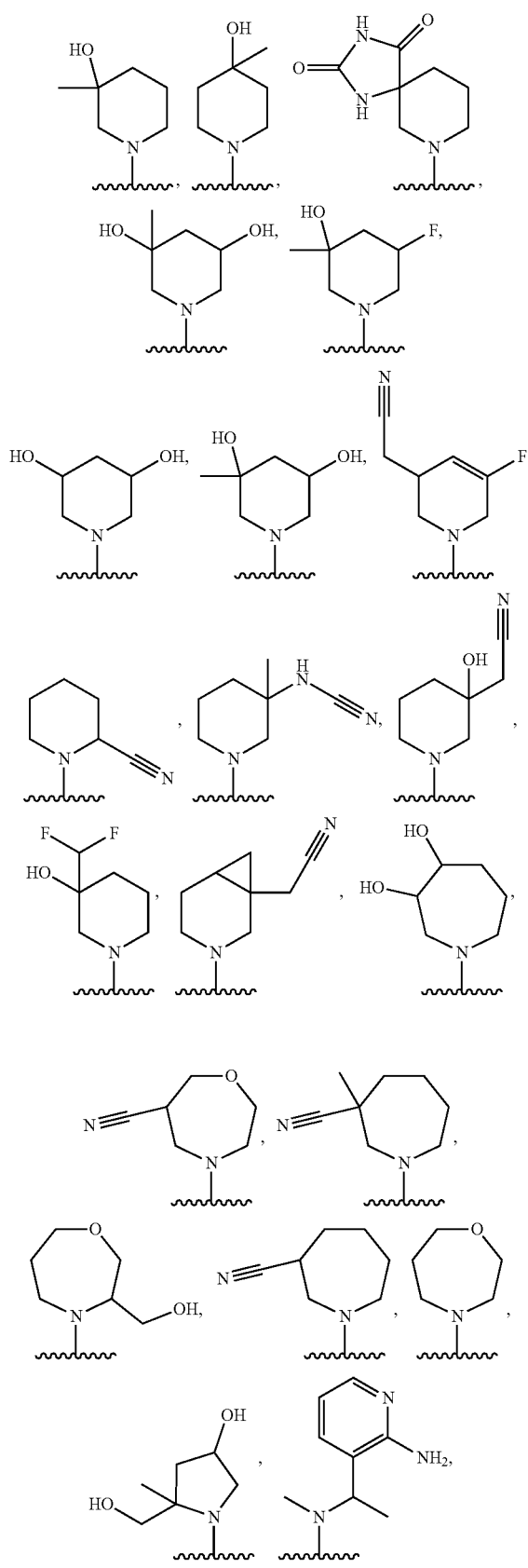
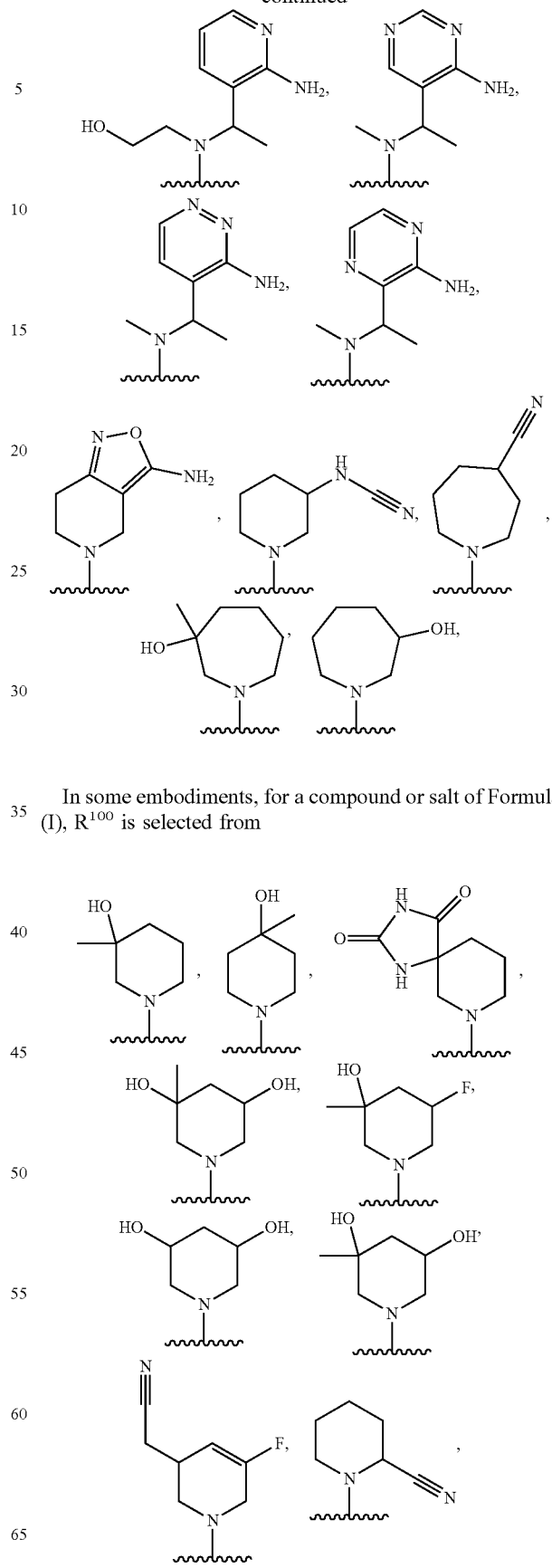
In some embodiments, for a compound or salt of Formula (I), $R^{100}$ is selected from -continued
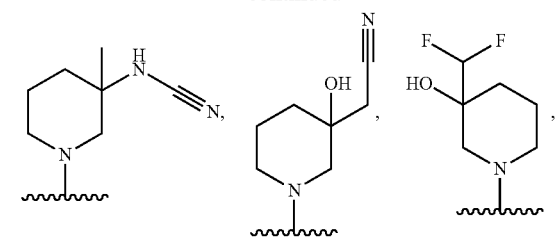
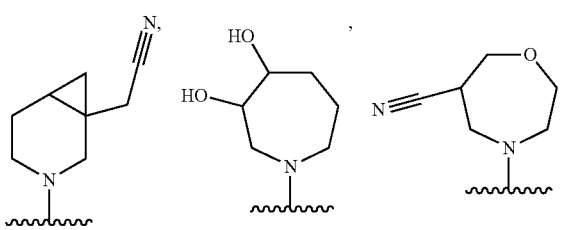
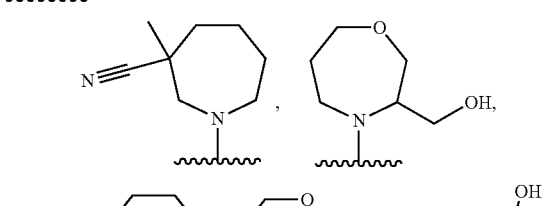
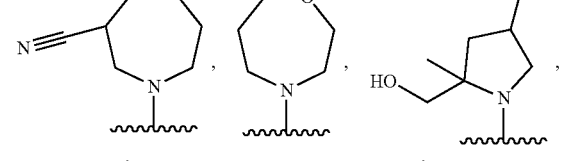
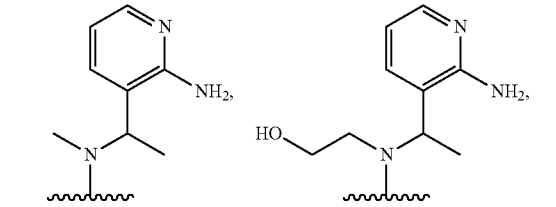
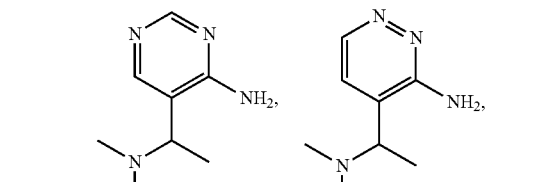
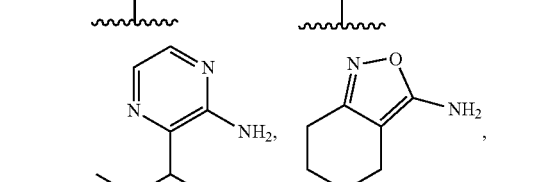
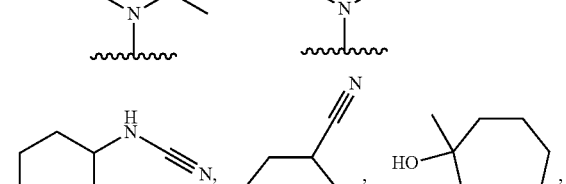
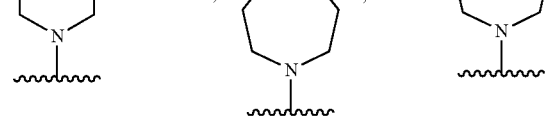
-continued
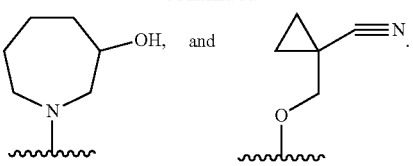
In some cases, R$^{100}$ is selected from
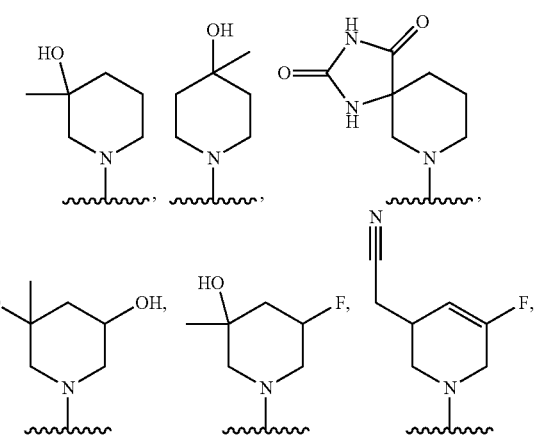
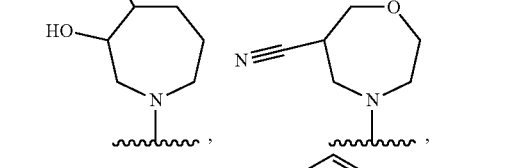
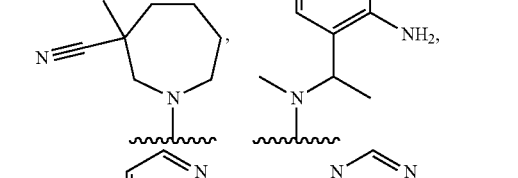
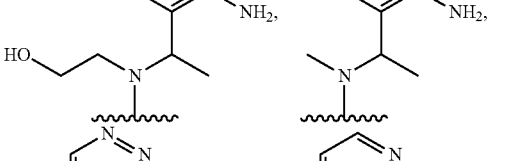
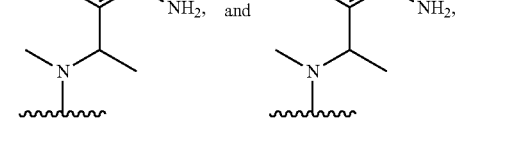
In some embodiments, for a compound or salt of Formula (I), R$^{100}$ is

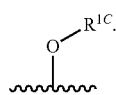

In some embodiments, Formula (I) is represented by

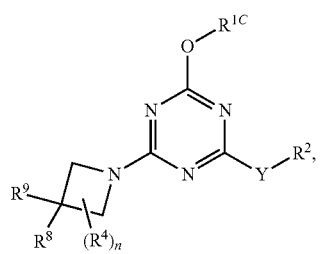

Formula (I-D)

or a pharmaceutically acceptable salt thereof.

In some embodiments, Formula (I) is represented by

Formula (I-E)

or a pharmaceutically acceptable salt thereof.

In some embodiments, Formula (I) is represented by

Formula (I-F)

or a pharmaceutically acceptable salt thereof.

In some embodiments, for a compound or salt of Formula (I), Formula (I-D), Formula (I-E), or Formula (I-F), $R^{1C}$ is selected from an optionally substituted $C_{1-6}$ alkyl. In some cases, $R^{1C}$ is selected from an optionally substituted $C_{1-6}$ alkyl, and wherein optionally two $R^{12}$ on the same atom of $R^{1C}$ come together to form an optionally substituted $C_3$-$C_6$ carbocycle.

In some embodiments, for a compound or salt of Formula (I), Formula (I-D), Formula (I-E), or Formula (I-F), each $R^{12}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle. In some cases, each $R^{12}$ is independently selected from halogen, —OR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle. In some cases, each $R^{12}$ is independently selected from halogen, —OR$^{20}$, —N(R$^{20}$)$_2$, =O, =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle. In some cases, each $R^{12}$ is independently selected from halogen, —OR$^{20}$, —N(R$^{20}$)$_2$, —CN, —NHCN, $C_{1-6}$ aminoalkyl, $C_{1-6}$ alkoxy, $C_{1-6}$ hydroxyalkyl, $C_{1-6}$ cyanoalkyl, and $C_{1-6}$ haloalkyl. In some cases, $R^{12}$ is selected from —OH and —CN, and wherein two $R^{12}$ on the same atom of $R^{1C}$ come together to form an unsubstituted $C_3$ carbocycle. In some cases, $R^{1C}$ is selected from

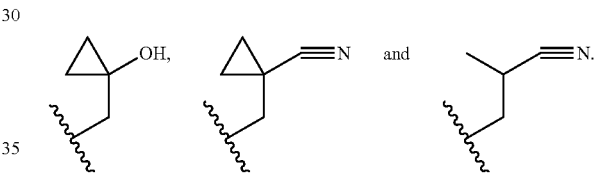

In some embodiments, for a compound or salt of Formula (I), Formula (I-D), Formula (I-E), or Formula (I-F), $R^{1C}$ is selected from an optionally substituted 5- to 6-membered heterocycle. In some cases, $R^{1C}$ is selected from an optionally substituted 5-membered heterocycle. In some cases, $R^{1C}$ is selected from an optionally substituted 5-membered heterocycle having at least one oxygen atom. In some cases, $R^{1C}$ is selected

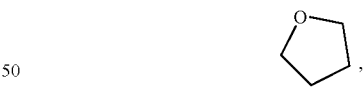

which is optionally substituted. In some cases, each $R^{12}$ is selected from halogen, —OR$^{20}$, $C_{1-6}$ hydroxyalkyl, $C_{1-6}$ cyanoalkyl, $C_{1-6}$ haloalkyl, and $C_{1-6}$ alkyl. In some cases, each $R^{12}$ is selected from —OH. In some cases, $R^{1C}$ is

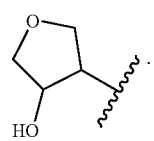 [SMILES: *C1COCC1O]

In some embodiments, for a compound or salt of Formula (I), Formula (I-D), Formula (I-E), or Formula (I-F), each $R^{12A}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =NO(R$^{20}$), —CN, —NHCN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, C$_{2-6}$ alkenyl, and C$_{2-6}$ alkynyl.

In some embodiments, for a compound or salt of Formula (I), Formula (I-D), Formula (I-E), or Formula (I-F), R$^{12}$ is —CN, and wherein two R$^{12}$ on the same atom of R$^{1C}$ come together to form an unsubstituted C$_3$ carbocycle.

In some embodiments, for a compound or salt of Formula (I), Formula (I-D), Formula (I-E), or Formula (I-F), R$^{1C}$ is selected from hydrogen, and optionally substituted C$_{1-6}$ alkyl. In some cases, R$^{1C}$ is selected from optionally substituted C$_{1-6}$ alkyl. In some cases, R$^{1C}$ is selected from hydrogen, and C$_{1-6}$ alkyl. In some cases, R$^{1C}$ is selected from hydrogen. In some cases, R$^{12}$ is selected from —OH and —CN, and wherein two R$^{12}$ on the same atom of R$^{1C}$ come together to form an unsubstituted C$_3$ carbocycle.

In some embodiments, for a compound or salt of Formula (I), Formula (I-D), Formula (I-E), or Formula (I-F), R$^{1C}$ is selected from

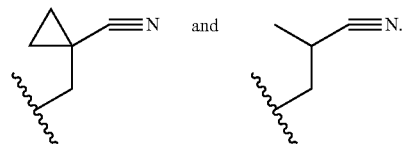

In some embodiments, for a compound or salt of Formula (I), R$^{100}$ is selected from

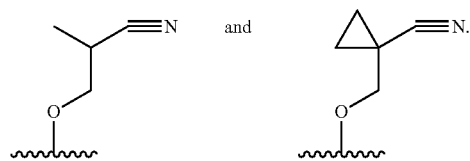

In some embodiments, for a compound or salt of Formula (I), R$^{100}$ is

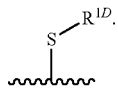

In some embodiments, Formula (I) is represented by

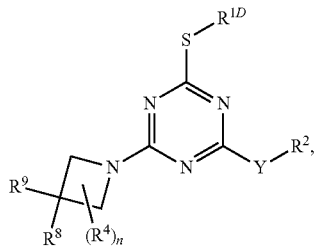

or a pharmaceutically acceptable salt thereof.

In some embodiments, Formula (I) is represented by

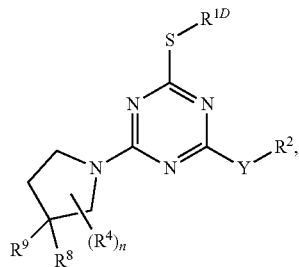

Formula (I-H)

or a pharmaceutically acceptable salt thereof.

In some embodiments, Formula (I) is represented by

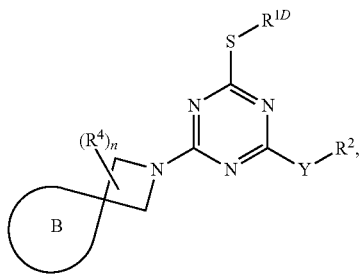

Formula (I-I)

or a pharmaceutically acceptable salt thereof.

In some embodiments, for a compound or salt of Formula (I), Formula (I-H), Formula (I-I), or Formula (I-J), wherein R$^{1D}$ is selected from an optionally substituted C$_{1-6}$ alkyl. In some cases, R$^{1D}$ is selected from an optionally substituted C$_{1-6}$ alkyl, and wherein optionally two R$^{13}$ on the same atom of R$^{1D}$ come together to form an optionally substituted C$_3$-C$_6$ carbocycle. In some cases, R$^{13}$ is selected from —OH and —CN, and wherein two R$^{13}$ on the same atom of R$^{1D}$ come together to form an unsubstituted C$_3$ carbocycle. In some cases, R$^{1D}$ is selected from

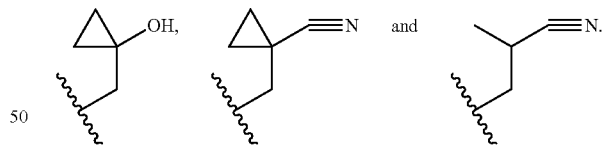

In some embodiments, for a compound or salt of Formula (I), Formula (I-H), Formula (I-I), or Formula (I-J), each R$^{13}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =NO(R$^{20}$), —CN, —NHCN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, C$_3$-C$_{12}$ carbocycle and 5- to 12-membered heterocycle. In some cases, each R$^{13}$ is independently selected from halogen, —OR$^{20}$, —S(O)$_2$(R$^{20}$), —S(O)$_2$N(R$^{20}$)$_2$, —S(O)N(R$^{20}$)$_2$, —S(O)R$^{20}$ (=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =NO(R$^{20}$), —CN, —NHCN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, C$_3$-C$_{12}$ carbocycle and 5- to 12-membered heterocycle. In some cases, each R$^{13}$ is independently selected from halogen, —OR$^{20}$, —N(R$^{20}$)$_2$, =O, =NO(R$^{20}$), —CN, —NHCN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, C$_3$-C$_{12}$ carbocycle and 5- to 12-membered heterocycle. In some cases, each R$^{13}$ is independently selected from halogen, —OR$^{20}$, —N(R$^{20}$)$_2$, —CN, —NHCN, C$_{1-6}$ aminoalkyl, C$_{1-6}$ alkoxy, C$_{1-6}$ hydroxyalkyl, C$_{1-6}$ cyanoalkyl, and C$_{1-6}$ haloalkyl.

In some embodiments, for a compound or salt of Formula (I), Formula (I-H), Formula (I-I), or Formula (I-J), each R$^{13A}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =NO(R$^{20}$), —CN, —NHCN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, C$_{2-6}$ alkenyl, and C$_{2-6}$ alkynyl.

In some embodiments, for a compound or salt of Formula (I), R$^{100}$ is selected from

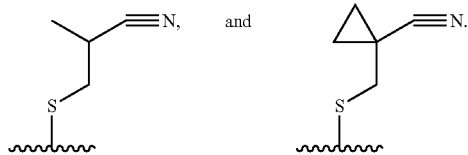

In some embodiments, for a compound or salt of Formula (I), Formula (I-A), Formula (I-B), Formula (I-C), or Formula (I-G), R$^{1A}$ and R$^{1B}$ come together with the atoms to which they are bound to form R$^1$.

In some embodiments, for a compound or salt of Formula (I), Formula (I-A), Formula (I-B), Formula (I-C), or Formula (I-G), R$^{1B}$ and R$^{1A}$ come together with the atoms to which they are bound to form R$^1$.

In some embodiments, for a compound or salt of Formula (I), Formula (I-A), Formula (I-B), Formula (I-C), or Formula (I-G), R$^1$ is a 5- to 12-membered heterocycle, wherein the 5- to 12-membered heterocycle is optionally substituted. In some cases, R$^{1B}$ and R$^{1A}$ come together with the atoms to which they are bound to form an optionally substituted 5- to 12-membered heterocycle, wherein the 5- to 12-membered heterocycle is optionally substituted. In some cases, R$^{1B}$ and R$^{1A}$ come together with the atoms to which they are bound to form a bridged heterocycle. In some cases, R$^{1B}$ and R$^{1A}$ come together with the atoms to which they are bound to form a spiro heterocycle. In some cases, R$^{1B}$ and R$^{1A}$ come together with the atoms to which they are bound to form a fused heterocycle. In some cases, R$^{1B}$ and R$^{1A}$ come together with the atoms to which they are bound to form a non-aromatic heterocycle. In some cases, R$^{1B}$ and R$^{1A}$ come together with the atoms to which they are bound to form a saturated heterocycle. Each heterocycle may be substituted as described elsewhere herein.

In some embodiments, for a compound or salt of Formula (I), Formula (I-A), Formula (I-B), Formula (I-C), or Formula (I-G), the heterocycle of R$^1$ is a 5- to 12-membered heterocycle, 6- to 12-membered heterocycle, 7- to 12-membered heterocycle, or 8- to 12-membered heterocycle. In some cases, the heterocycle of R$^1$ is a 5- to 11-membered heterocycle, 5- to 10-membered heterocycle, 5- to 9-membered heterocycle, or 5- to 8-membered heterocycle. In some cases, the heterocycle of R$^1$ is a 6- to 11-membered heterocycle, 6- to 10-membered heterocycle, 6- to 9-membered heterocycle, or 6- to 8-membered heterocycle. In some cases, the heterocycle of R$^1$ is a 7- to 11-membered heterocycle, 7- to 10-membered heterocycle, 7- to 9-membered heterocycle, or 7- to 8-membered heterocycle. In some cases, the heterocycle of R$^1$ is a 5- to 6-membered heterocycle or 5- to 9-membered heterocycle. In some cases, the heterocycle of R$^1$ is an 8- to 9-membered heterocycle. In some cases, the heterocycle of R$^1$ is saturated. The heterocycle is optionally substituted as described elsewhere herein.

In some embodiments, for a compound or salt of Formula (I), Formula (I-A), Formula (I-B), Formula (I-C), or Formula (I-G), R$^1$ is a 5- to 12-membered monocyclic heterocycle. In some cases, the heterocycle of R$^1$ is a 5- to 12-membered monocyclic heterocycle, 6- to 12-membered monocyclic heterocycle, 7- to 12-membered monocyclic heterocycle, or 8- to 12-membered monocyclic heterocycle. In some cases, the heterocycle of R$^1$ is a 5- to 11-membered monocyclic heterocycle, 5- to 10-membered monocyclic heterocycle, 5- to 9-membered monocyclic heterocycle, or 5- to 8-membered monocyclic heterocycle. In some cases, the heterocycle of R$^1$ is a 6- to 11-membered monocyclic heterocycle, 6- to 10-membered monocyclic heterocycle, 6- to 9-membered monocyclic heterocycle, or 6- to 8-membered monocyclic heterocycle. In some cases, the heterocycle of R$^1$ is a monocyclic 7- to 11-membered heterocycle, 7- to 10-membered monocyclic heterocycle, 7- to 9-membered monocyclic heterocycle, or 7- to 8-membered monocyclic heterocycle. In some cases, the heterocycle of R$^1$ is a 5- to 6-membered monocyclic heterocycle or 5- to 9-membered monocyclic heterocycle. In some cases, the heterocycle of R$^1$ is an 8- to 9-membered monocyclic heterocycle. In some cases, the heterocycle of R$^1$ is saturated. The monocyclic heterocycle is optionally substituted as described elsewhere herein.

In some embodiments, for a compound or salt of Formula (I), Formula (I-A), Formula (I-B), Formula (I-C), or Formula (I-G), R$^1$ is a bridged heterocycle. In some cases, the heterocycle of R$^1$ is a 5- to 12-membered bridged heterocycle, 6- to 12-membered bridged heterocycle, 7- to 12-membered bridged heterocycle, or 8- to 12-membered bridged heterocycle. In some cases, the heterocycle of R$^1$ is a 5- to 11-membered bridged heterocycle, 5- to 10-membered bridged heterocycle, 5- to 9-membered bridged heterocycle, or 5- to 8-membered bridged heterocycle. In some cases, the heterocycle of R$^1$ is a 6- to 11-membered bridged heterocycle, 6- to 10-membered bridged heterocycle, 6- to 9-membered bridged heterocycle, or 6- to 8-membered bridged heterocycle. In some cases, the heterocycle of R$^1$ is a bridged 7- to 11-membered heterocycle, 7-to 10-membered bridged heterocycle, 7- to 9-membered bridged heterocycle, or 7- to 8-membered bridged heterocycle. In some cases, the heterocycle of R$^1$ is a 5- to 6-membered bridged heterocycle or 5- to 9-membered bridged heterocycle. In some cases, the heterocycle of R$^1$ is an 8- to 9-membered bridged heterocycle. In some cases, the heterocycle of R$^1$ is saturated. In some cases, the bridged heterocycle is selected from

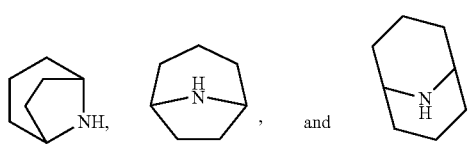

In some cases, the bridged heterocycle is selected from

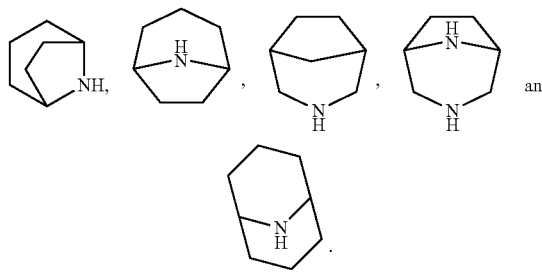

Each bridged heterocycle is optionally substituted as described elsewhere herein.

In some embodiments, for a compound or salt of Formula (I), Formula (I-A), Formula (I-B), Formula (I-C), or Formula (I-G), $R^1$ is a spiro heterocycle. The spiro heterocycle of $R^1$ is a 7- to 12-membered spiro heterocycle, 7- to 12-membered spiro heterocycle, or 8- to 12-membered spiro heterocycle. In some cases, the spiro heterocycle of $R^1$ is a 7- to 11-membered spiro heterocycle, 7- to 10-membered spiro heterocycle, 7- to 9-membered spiro heterocycle, or 7- to 8-membered spiro heterocycle. In some cases, the spiro heterocycle of $R^1$ is a 7- to 11-membered spiro heterocycle, 7- to 10-membered spiro heterocycle, 7- to 9-membered spiro heterocycle, or 7- to 8-membered spiro heterocycle. In some cases, the spiro heterocycle of $R^1$ is a 7- to 11-membered spiro heterocycle. In some cases, the spiro heterocycle of $R^1$ is a 7-membered spiro heterocycle. In some cases, the spiro heterocycle of $R^1$ is an 8-membered spiro heterocycle. In some cases, the spiro heterocycle of $R^1$ is a 9-membered spiro heterocycle. In some cases, the spiro heterocycle of $R^1$ is a 10-membered spiro heterocycle. In some cases, the spiro heterocycle of $R^1$ contains at most 1 nitrogen atom. In some cases, the spiro heterocycle of $R^1$ contains only 1 nitrogen atom. In some cases, the spiroheterocycle of $R^1$ contains at most 2 heteroatom atoms. In some cases, the spiro heterocycle of $R^1$ contains at least 2 heteroatom atoms. In some cases, the spiro heterocycle of $R^1$ contains at least 3 heteroatom atoms. In some cases, the heteroatom is selected from nitrogen, oxygen, and sulfur. In some cases, the spiroheterocycle of $R^1$ is bound to the Formula via the nitrogen atom. In some embodiments, the spiro heterocycle of $R^1$ is selected from

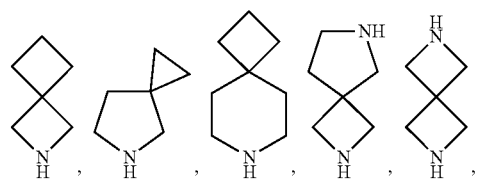

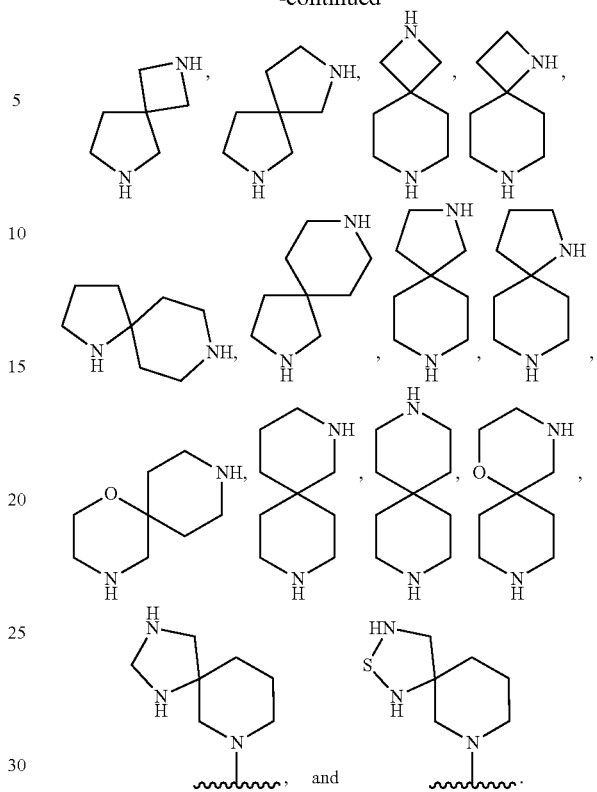

In some cases, the spiro heterocycle of $R^1$ is selected from

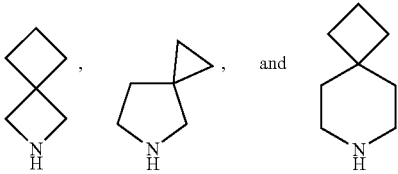

and H Each spiro heterocycle is optionally substituted as described elsewhere herein.

In some embodiments, for a compound or salt of Formula (I), Formula (I-A), Formula (I-B), Formula (I-C), or Formula (I-G), $R^1$ is a fused heterocycle. In some cases, the fused heterocycle of $R^1$ is a 6- to 12-membered fused heterocycle, 6- to 12-membered fused heterocycle, 7- to 12-membered fused heterocycle, or 8- to 12-membered fused heterocycle. In some cases, the fused heterocycle of $R^1$ is a 6- to 11-membered fused heterocycle, 6- to 10-membered fused heterocycle, 6- to 9-membered fused heterocycle, or 6- to 8-membered fused heterocycle. In some cases, the fused heterocycle of $R^1$ is a 7- to 11-membered fused heterocycle, 7- to 10-membered fused heterocycle, 7- to 9-membered fused heterocycle, or 7- to 8-membered fused heterocycle. In some cases, the fused heterocycle of $R^1$ is an 8- to 11-membered fused heterocycle. In some cases, the fused heterocycle of $R^1$ is a 6-membered fused heterocycle. In some cases, the fused heterocycle of $R^1$ is a 7-membered fused heterocycle. In some cases, the fused heterocycle of $R^1$ is a 10-membered fused heterocycle. In some cases, the fused heterocycle is selected from

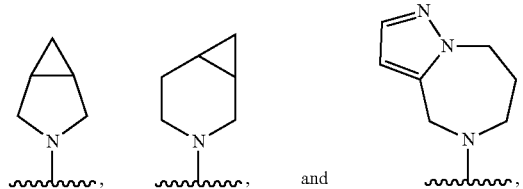 [SMILES: *N1CC2CC2C1 ; *N1CCC2CC2C1 ; *N1CCCn2nccc2C1]

Each fused heterocycle is optionally substituted as described elsewhere herein.

In some embodiments, for a compound or salt of Formula (I), Formula (I-A), Formula (I-B), Formula (I-C), or Formula (I-G), $R^1$ is selected from an optionally substituted 8- to 10-membered fused heterocycle. In some cases, the 8- to 10-membered fused heterocycle is a bicyclic heterocycle. In some cases, the 8- to 10-membered fused heterocycle is a saturated heterocycle. In some cases, the 8- to 10-membered fused heterocycle is an unsaturated heterocycle. In some cases, the 8- to 10-membered heterocycle is a non-aromatic heterocycle. In some cases, $R^1$ is selected from an optionally substituted 9-membered fused heterocycle. In some cases, $R^1$ is selected from an optionally substituted 10-membered fused heterocycle. In some cases, the 10-membered fused heterocycle is a bicyclic heterocycle. In some cases, the 10-membered fused heterocycle is a saturated heterocycle. In some cases, the 9-membered heterocycle is a non-aromatic heterocycle. In some cases, the 10-membered heterocycle is a non-aromatic heterocycle. In some cases, the fused heterocycle has one saturated ring and one aromatic ring. In some cases, the fused heterocycle has one saturated ring and one unsaturated ring. In some cases, the fused heterocycle has two saturated rings. In some cases, the 10-membered heterocycle contains at least 1 nitrogen atom. In some cases, the 10-membered heterocycle contains at least 2 nitrogen atoms. In some cases, the 10-membered heterocycle contains at least 3 nitrogen atoms. In some cases, the 9-membered heterocycle contains at least 1 nitrogen atom. In some cases, the 9-membered heterocycle contains at least 2 nitrogen atoms. In some cases, the 9-membered heterocycle contains at least 3 nitrogen atoms. In some cases, $R^1$ is selected from

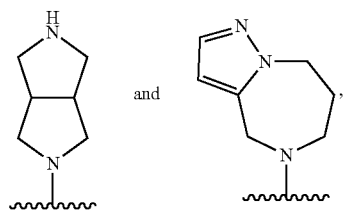 [SMILES: *N1CC2CNCC2C1 ; *N1CCCn2nccc2C1]

each of which is optionally substituted with one or more substituents. In some cases, $R^1$ is

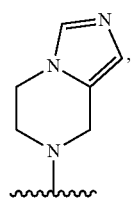

which is optionally substituted with one or more substituents. In some cases, $R^1$ is

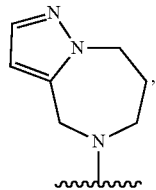 [SMILES: *N1CCCn2nccc2C1]

which is optionally substituted with one or more substituents. In some cases, the one or more optional substituents of $R^1$ are independently selected from halogen, —OH, —S(O)$_2$(R$^{20}$), —S(O)$_2$N(R$^{20}$)$_2$, —S(O)N(R$^{20}$)$_2$, —S(O)R$^{20}$(=NR$^{20}$), —C(=NR$^{20}$)N(R$^{20}$)$_2$, —C(O)N(R$^{20}$)$_2$, —C(O)NHOR$^{20}$, —N(R$^{20}$)$_2$, —C(O)R$^{20}$, —NO$_2$, =O, —CN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, C$_{2-6}$ alkynyl, and 5- to 12-membered heterocycle, wherein the 5- to 12-membered heterocycle are each optionally substituted independently with one or more $R^{1*}$. In some cases, the one or more optional substituents of $R^1$ are independently selected from halogen, —OH, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(O)NHOR$^{20}$, —N(R$^{20}$)$_2$, —C(O)R$^{20}$, —NO$_2$, =O, —CN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, and C$_{2-6}$ alkynyl. In some cases, the optional one or more substituents are independently selected from halogen, =O, —OH, —CN, —NHCN, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)R$^{20}$, —C(O)N(R$^{20}$)$_2$, —C(O)NR$^{20}$OR$^{20}$, C$_{1-6}$ alkyl-N(R$^{20}$)$_2$, C$_{1-6}$ aminoalkyl, C$_{1-6}$ hydroxyalkyl, C$_{1-6}$ cyanoalkyl, and C$_{1-6}$ alkyl. In some cases, the optional one or more substituents are independently selected from halogen, =O, C$_{1-6}$ alkyl-N(R$^{20}$)$_2$, —S(O)$_2$(R$^{20}$), —S(O)N(R$^{20}$)$_2$, —S(O)R$^{20}$(=NR$^{20}$), —C(O)R$^{20}$, —C(O)N(R$^{20}$)$_2$, and —C(O)NR$^{20}$OR$^{20}$. In some cases, the optional one or more substituents are independently selected from halogen, =O, —S(O)$_2$(R$^{20}$), —S(O)N(R$^{20}$)$_2$, —S(O)R$^{20}$(=NR$^{20}$), —C(O)R$^{20}$, —C(O)N(R$^{20}$)$_2$, and —C(O)NR$^{20}$OR$^{20}$. In some cases, the optional one or more substituents are independently selected from —C(O)R$^{20}$, —C(O)N(R$^{20}$)$_2$, and —C(O)NR$^{20}$OR$^{20}$. In some cases, the optional one or more substituents are independently selected from —S(O)$_2$(R$^{20}$), —S(O)$_2$N(R$^{20}$)$_2$, —S(O)N(R$^{20}$)$_2$, —S(O)R$^{20}$(=NR$^{20}$). In some cases, the optional one or more substituents are independently selected from —S(O)N(R$^{20}$)$_2$. In some cases, the optional one or more substituents are independently selected from S(O)$_2$(R$^{20}$). In some cases, the optional one or more substituents are independently selected from S(O)R$^{20}$(=NR$^{20}$). In some cases, the optional one or more substituents are independently selected from —C(O)R$^{20}$. In some cases, the optional one or more substituents are independently selected from —C(O)N(R$^{20}$)$_2$. In some cases, the optional one or more substituents are independently selected from —C(O)NR$^{20}$OR$^{20}$. In some cases, $R^1$ is selected from

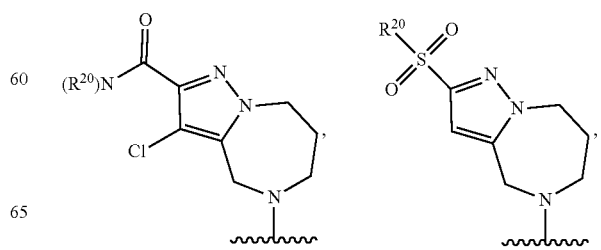

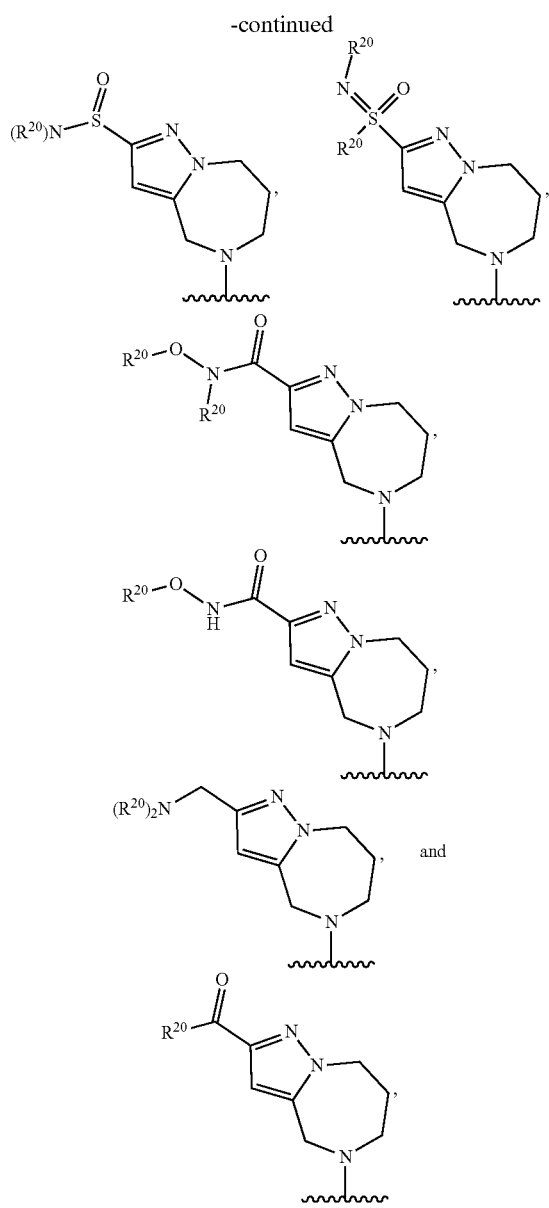

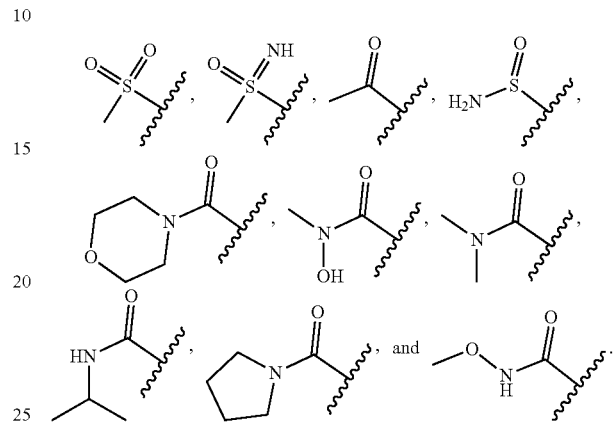

$R^{20}$ has at least one sulfur atom. In some cases, the heterocycle of $R^{20}$ has at least one oxygen atom. In some cases, the heterocycle of $R^{20}$ contains only 1 heteroatom. In some cases, the heterocycle of $R^{20}$ has at least two heteroatoms. In some cases, the heterocycle of $R^{20}$ contains only 2 heteroatoms. In some cases, the optional one or more substituents of $R^1$ are independently selected from halogen, —CN, $C_2$ alkenyl, In some cases, the optional one or more substituents of $R^1$ are independently selected from halogen,

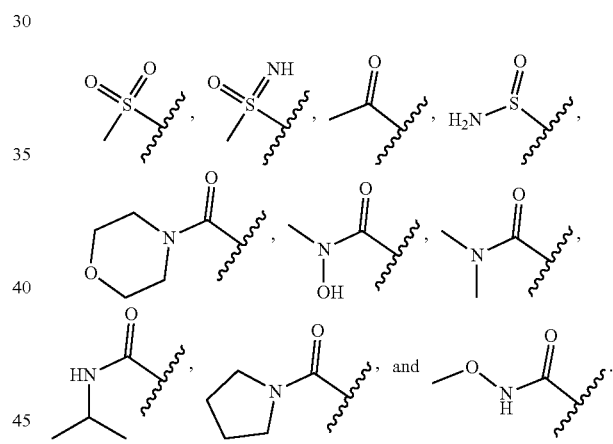

In some cases, the optional one or more substituents of $R^1$ are independently selected from

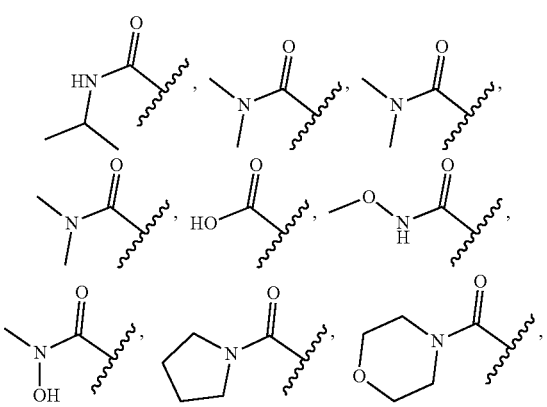

each of which is further optionally substituted. In some cases, the further one or more optional substituents are selected from halogen, —OH, =O, —CN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, and $C_{2-6}$ alkynyl. In some cases, the further one or more optional substituents are selected from halogen, —CN, $C_2$ alkenyl, and $C_{1-6}$ alkyl. In some cases, the further one or more optional substituents are selected from halogen, and $C_{1-6}$ alkyl. In some cases, the further one or more optional substituents are selected from halogen. In some cases, each $R^{20}$ is independently selected from hydrogen; and $C_{1-6}$ alkyl, $C_{3-12}$ carbocycle, and 3- to 12-membered heterocycle. In some cases, each $R^{20}$ is independently selected from hydrogen; and $C_{1-6}$ alkyl, and 3- to 12-membered heterocycle. In some cases, each $R^{20}$ is independently selected from hydrogen; and $C_{1-6}$ alkyl, and 3- to 12-membered saturated heterocycle. In some cases, each $R^{20}$ is independently selected from 5- to 6-membered saturated heterocycle. In some cases, the heterocycle of $R^{20}$ has at least one nitrogen atom. In some cases, the heterocycle of

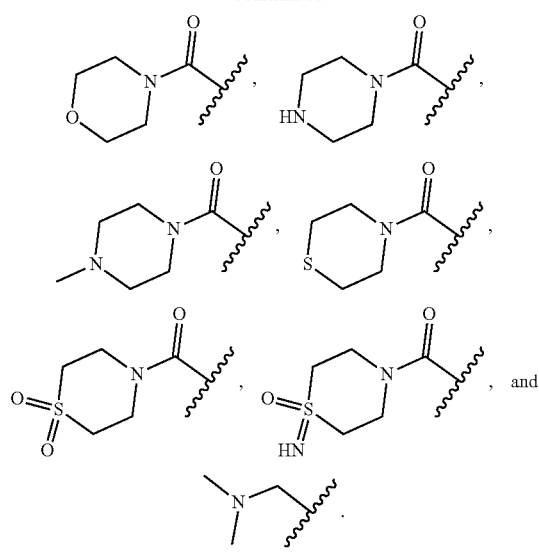
In some cases, the optional one or more substituents of $R^1$ are independently selected from halogen,
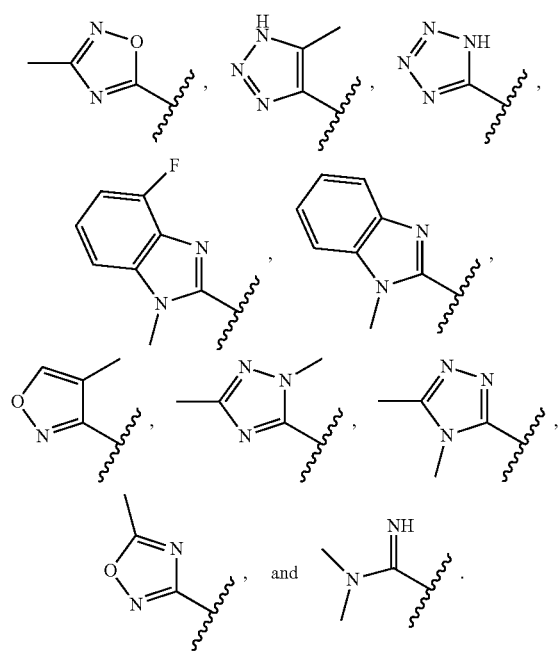
In some cases, $R^1$ is selected from
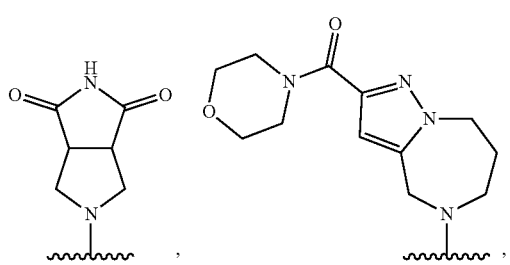
In some cases, $R^1$ is selected from
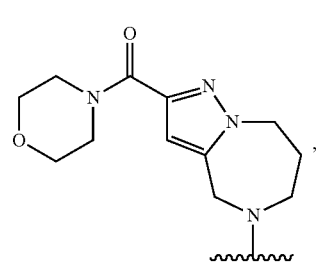

-continued
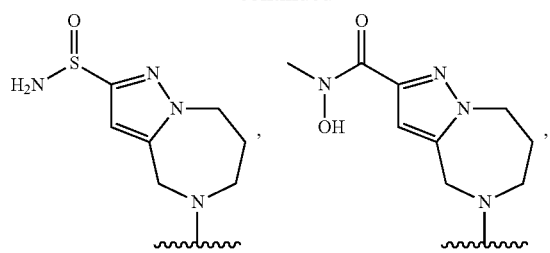
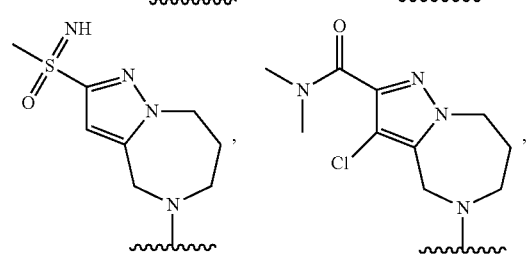
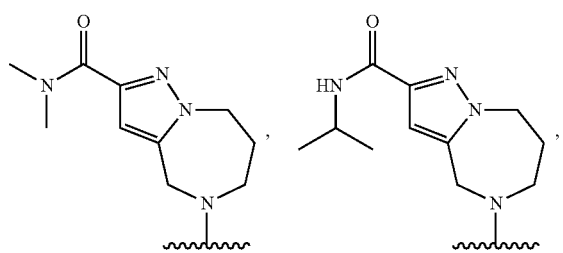
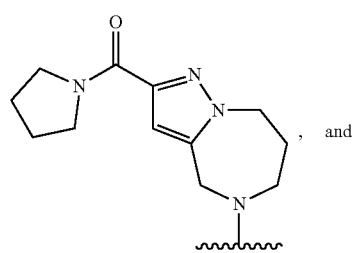
In some cases, R¹ is selected from
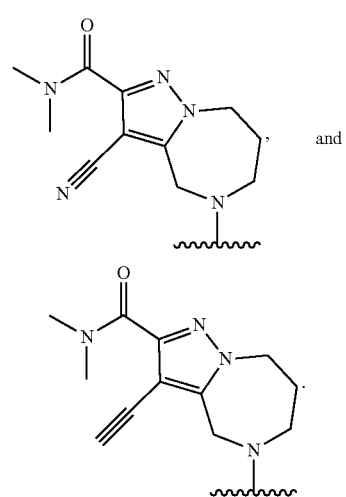
In some cases, R¹ is selected from
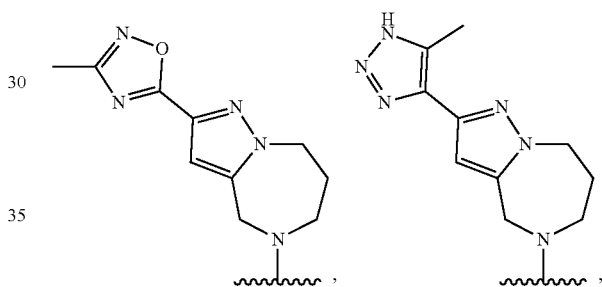
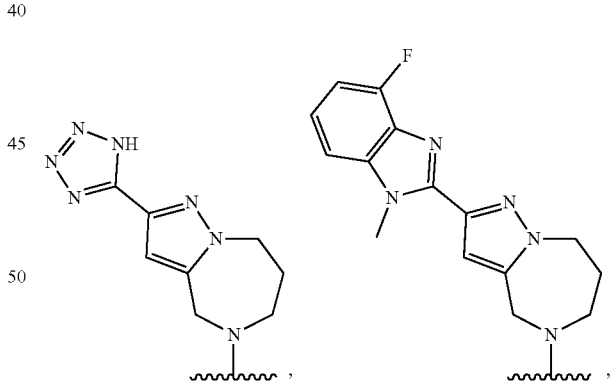
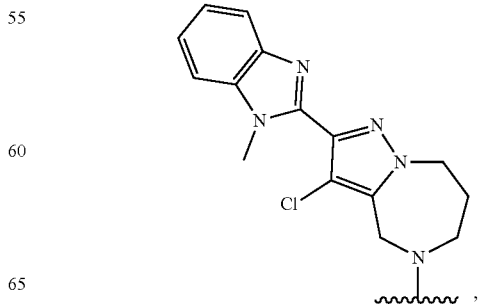

-continued

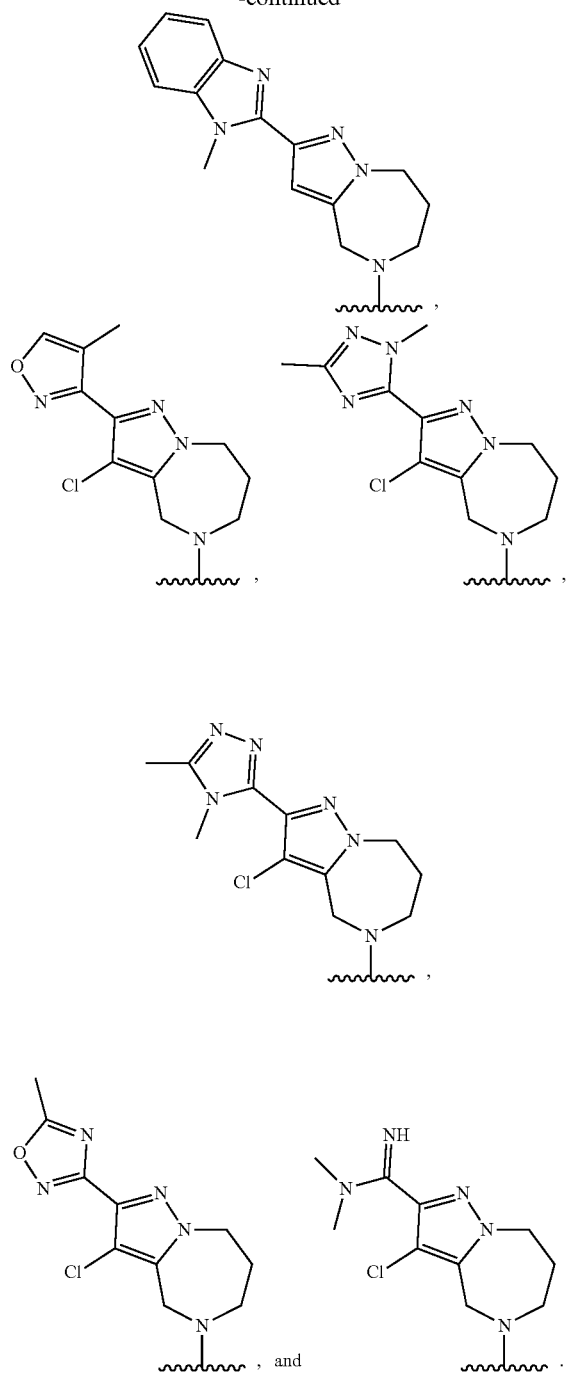

In some cases, the optional one or more substituents of R¹ are independently selected from halogen, and $C_{1-6}$ alkyl-N$(R^{20})_2$. In some cases, the optional one or more substituents of R¹ are independently selected from halogen, In some cases, R¹ is selected from

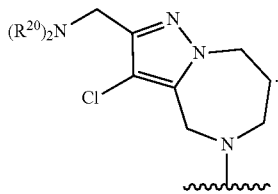

In some cases, each $R^{20}$ is independently selected from hydrogen, $C_{1-6}$ alkyl, and $C_{3-6}$ carbocycle. In some cases, R¹ is selected

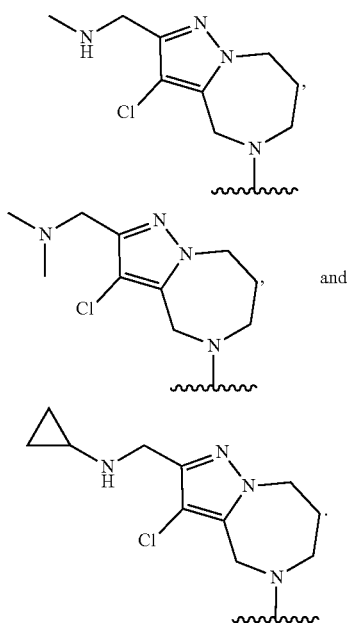

In some cases, R¹ is selected

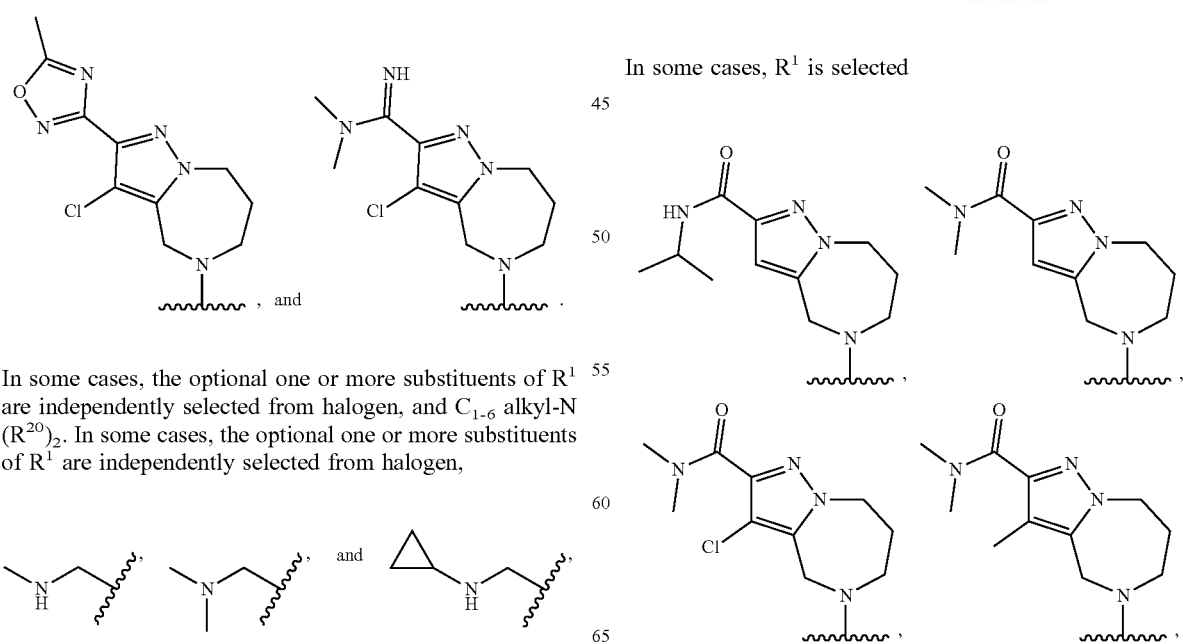

-continued

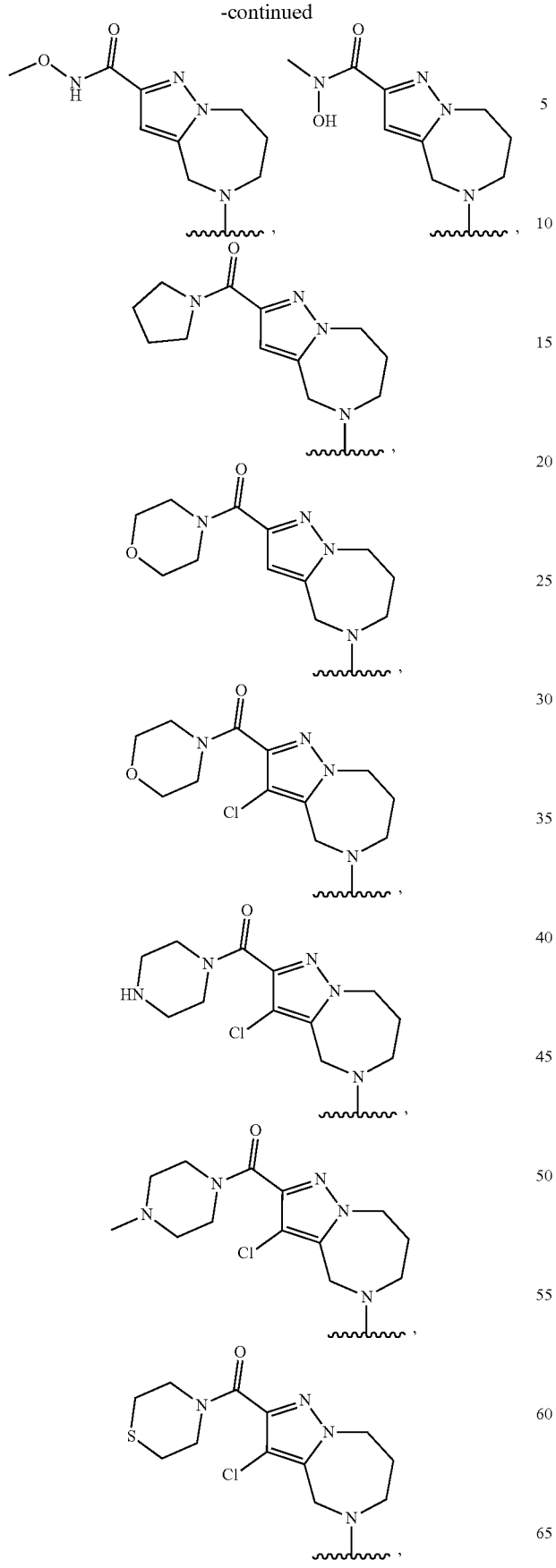

-continued

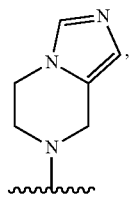

and

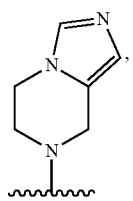

In some cases, $R^1$ is selected from which is optionally substituted with one more substituents independently selected from halogen, —OH, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(=NR$^{20}$)N(R$^{20}$)$_2$, —C(O)OR$^{20}$, —C(O)NHOR$^{20}$, —N(R$^{20}$)$_2$, —C(O)R$^{20}$, —NO$_2$, =O, —CN, C$_{1-6}$ alkyl-N(R$^{20}$)$_2$, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkynyl, 5- to 12-membered heterocycle, wherein the 5- to 12-membered heterocycle is optionally substituted with one or more substituents selected from halogen, —OR$^{20}$, and C$_{1-6}$ alkyl. In some cases, $R^1$ is selected from which is optionally substituted with one more substituents independently selected from halogen and C$_{1-6}$ alkyl. In some cases, $R^1$ is selected from

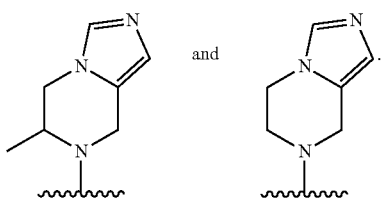 [SMILES: *N1Cc2cncn2CC1C ; *N1CCn2cncc2C1]

In some embodiments, for a compound or salt of Formula (I), Formula (I-A), Formula (I-B), Formula (I-C), or Formula (I-G), $R^1$ is selected from a

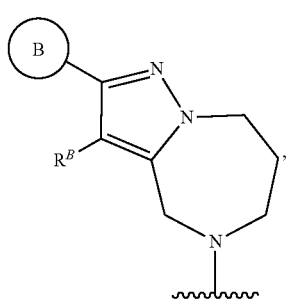

wherein Ⓑ is selected from a 5- to 12-membered heterocycle, wherein the 5- to 12-membered heterocycle is optionally substituted independently with one or more $R^{1*}$; and $R^B$ is selected from hydrogen, halogen, $C_{1-6}$ alkyl, $C_{1-6}$ haloalkyl, $C_{2-6}$ alkynyl, and —CN. In some cases, $R^B$ is selected from hydrogen, and halogen. In some cases, $R^B$ is chloride. In some cases, $R^B$ is hydrogen. In some cases, Ⓑ has at least 1, 2, 3, or 4 heteroatoms. In some cases, Ⓑ has at least 1, 2, 3, or 4 nitrogen atoms. In some cases, Ⓑ has at least 1 oxygen atom. In some cases, Ⓑ is a monocyclic heterocycle. In some cases, Ⓑ is a bicyclic heterocycle. In some cases, Ⓑ is selected from an optionally substituted 5-membered heterocycle. In some cases, Ⓑ is selected from an optionally substituted 9-membered heterocycle. In some cases, Ⓑ is selected from

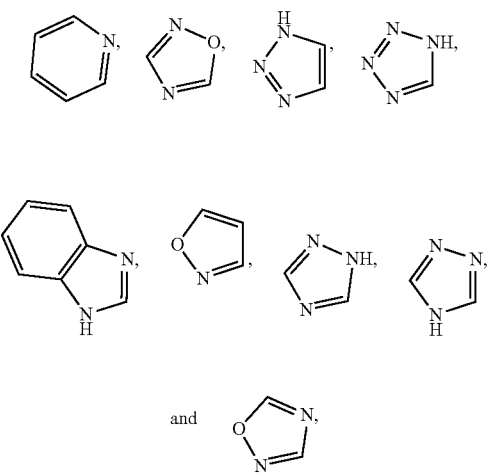

each of which is optionally substituted with one or more $R^{1*}$. In some cases, Ⓑ is selected from

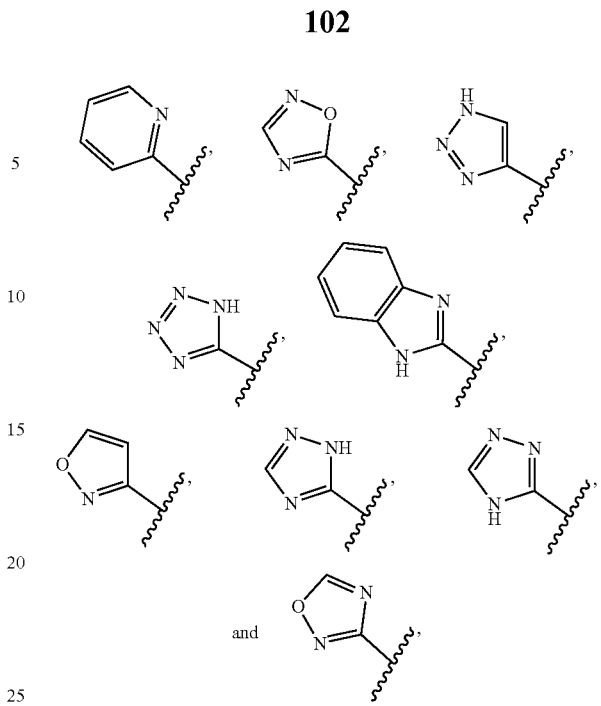

each of which is optionally substituted with one or more $R^{1*}$. In some cases, each $R^{1*}$ is independently selected from halogen, —$OR^{20}$, —$S(O)_2(R^{20})$, —$S(O)_2N(R^{20})_2$, —$S(O)N(R^{20})_2$, —$S(O)R^{20}$(=$NR^{20}$), —$NR^{20}S(O)_2R^{20}$, —$C(O)N(R^{20})_2$, —$C(O)NR^{20}OR^{20}$, —$N(R^{20})C(O)R^{20}$, —$N(R^{20})C(O)N(R^{20})_2$, —$N(R^{20})C(O)OR^{20}$, —$N(R^{20})_2$, —$C(O)R^{20}$, —$C(O)OR^{20}$, —$OC(O)R^{20}$, —$OC(O)N(R^{20})_2$, —$NO_2$, =O, =$N(R^{20})$, =$NO(R^{20})$, —CN, —NHCN, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, and $C_{1-6}$ alkyl. In some cases, each $R^{1*}$ is independently selected from halogen, $C_{1-6}$ alkyl-$N(R^{20})_2$, $C_{1-6}$ aminoalkyl, $C_{1-6}$ hydroxyalkyl, $C_{1-6}$ cyanoalkyl, $C_{1-6}$ haloalkyl, and $C_{1-6}$ alkyl. In some cases, each $R^{1*}$ is independently selected from halogen, and $C_{1-6}$ alkyl. In some cases, Ⓑ is selected from

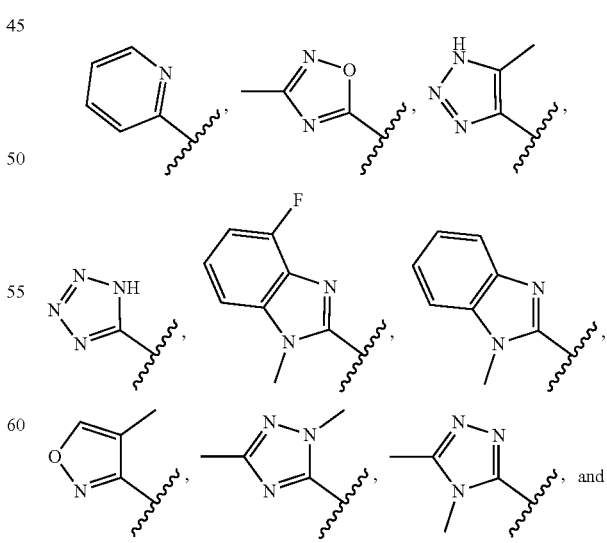

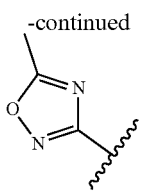

In some embodiments, for a compound or salt of Formula (I), Formula (I-A), Formula (I-B), Formula (I-C), or Formula (I-G), when $R^1$ is substituted with —C(O)$R^{20}$, $R^{20}$ is selected from a 5- to 12-membered heterocycle, which is optionally substituted. In some cases, $R^1$ is substituted with —C(O)$R^{20}$. In some cases, $R^{20}$ is selected from a 5- to 12-membered unsubstituted heterocycle. In some cases, $R^{20}$ is selected from a 5- to 6-membered heterocycle, which is optionally substituted. In some cases, the heterocycle has at least one nitrogen atom. In some cases, the heterocycle has at least one sulfur atom. In some cases, the heterocycle has at least one oxygen atom. In some cases, the heterocycle has two heteroatoms. In some cases, the heterocycle of $R^{20}$ is selected from

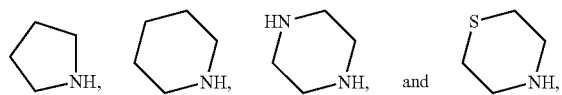 [SMILES: C1CCNC1 ; C1CCNCC1 ; C1CNCCN1 ; C1CSCCN1]

each of which is optionally substituted. In some cases, $R^{20}$ is selected from

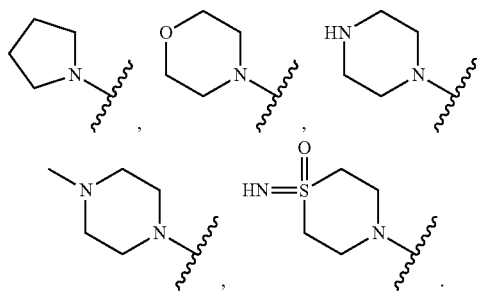

In some cases, the optional substituents are selected from $C_{1-10}$ alkyl, oxo, and =NH.

In some embodiments, for a compound or salt of Formula (I), Formula (I-A), Formula (I-B), Formula (I-C), or Formula (I-G), each $R^{20}$ is independently selected from hydrogen; and $C_{1-6}$ alkyl, $C_{3-12}$ carbocycle, and 3- to 12-membered heterocycle, each of which is optionally substituted with one or more substituents independently selected from halogen, —OH, —CN, —NO$_2$, —NH$_2$, —N($C_{1-6}$ alkyl)$_2$, $C_{1-10}$ alkyl, —$C_{1-10}$ haloalkyl, —O—$C_{1-10}$ alkyl, oxo, and =NH. In some cases, each $R^{20}$ is independently selected from hydrogen; and unsubstituted $C_{1-6}$ alkyl, and 3- to 12-membered heterocycle which is optionally substituted with one or more substituents independently selected from halogen, —OH, —CN, —NO$_2$, —NH$_2$, —N($C_{1-6}$ alkyl)$_2$, $C_{1-10}$ alkyl, —$C_{1-10}$ haloalkyl, —O—$C_{1-10}$ alkyl, oxo, and =NH.

In some embodiments, for a compound or salt of Formula (I), Formula (I-A), Formula (I-B), Formula (I-C), or Formula (I-G), $R^1$ is selected from 5- to 12-membered heterocycle, wherein the 5- to 12-membered heterocycle is optionally substituted with one or more substituents. In some cases, the one or more optional substituents are independently selected from halogen, —CN, —NO$_2$, =O, —N($R^{20}$)$_2$, —B(O$R^{20}$)$_2$, —O$R^{20}$, —S$R^{20}$, —S(O)$_2$($R^{20}$), —S(O)$_2$N($R^{20}$)$_2$, —N$R^{20}$S(O)$_2$$R^{20}$, —C(O)N($R^{20}$)$_2$, —N($R^{20}$)C(O)$R^{20}$, —N($R^{20}$)C(O)N($R^{20}$)$_2$, —N($R^{20}$)C(O)O$R^{20}$, —C(O)$R^{20}$, C(O)O$R^{20}$, —OC(O)$R^{20}$, —OC(O)N($R^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, and $C_{2-6}$ alkynyl. In some cases, the one or more optional substituents are independently selected from halogen, —OH, —N($R^{20}$)$_2$, —NO$_2$, =O, —CN, $C_{1-6}$ aminoalkyl, $C_{1-6}$ alkoxy, $C_{1-6}$ hydroxyalkyl, and $C_{1-6}$ haloalkyl. In some cases, the one or more optional substituents are independently selected from halogen, —OH, —N($R^{20}$)$_2$, —NO$_2$, $C_{1-6}$ aminoalkyl, $C_{1-6}$ alkoxy, $C_{1-6}$ hydroxyalkyl, and $C_{1-6}$ haloalkyl. In some cases, $R^{20}$ is selected from hydrogen and $C_{1-3}$ alkyl.

In some embodiments, for a compound or salt of Formula (I), Formula (I-A), Formula (I-B), Formula (I-C), or Formula (I-G), $R^1$ is selected from a saturated 5- to 12-membered heterocycle, which is optionally substituted with one or more substituents. In some cases, the 5- to 12-membered heterocycle of $R^1$ is bridged. In some cases, the 5- to 12-membered heterocycle of $R^1$ is not bridged. In some cases, the 5- to 12-membered heterocycle is selected from

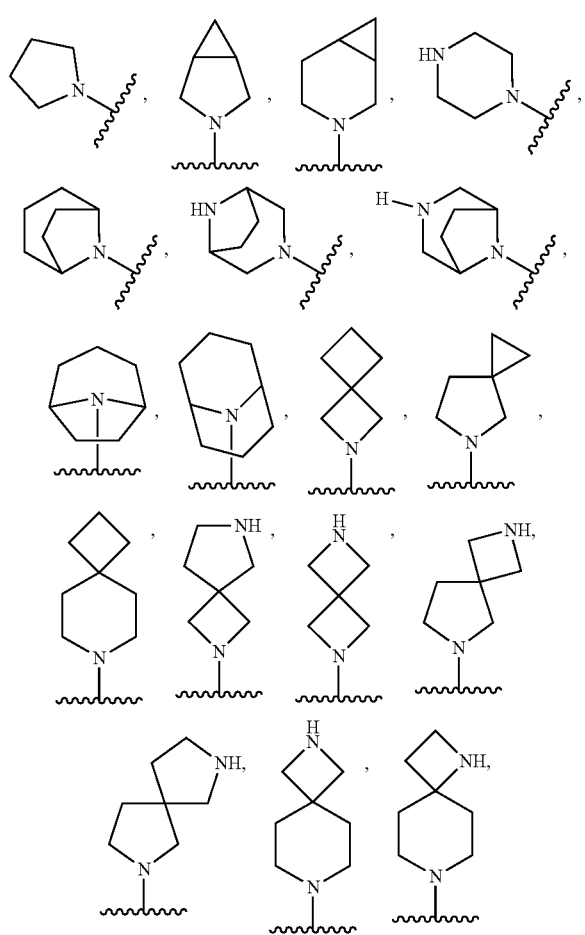

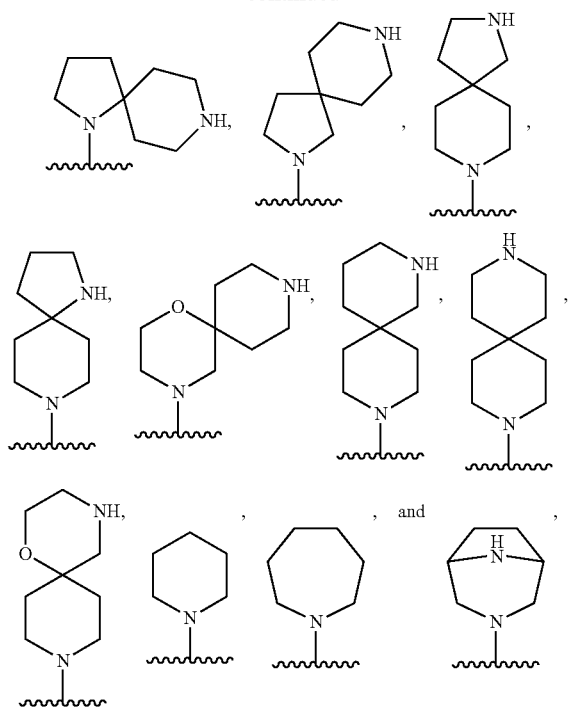
each of which is optionally substituted with one or more substituents.
In some embodiments, for a compound or salt of Formula (I), Formula (I-A), Formula (I-B), Formula (I-C), or Formula (I-G), $R^1$ is selected from
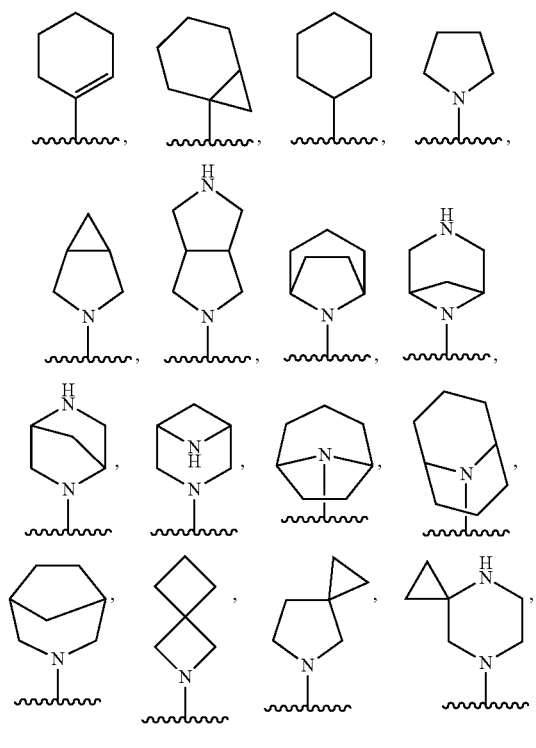
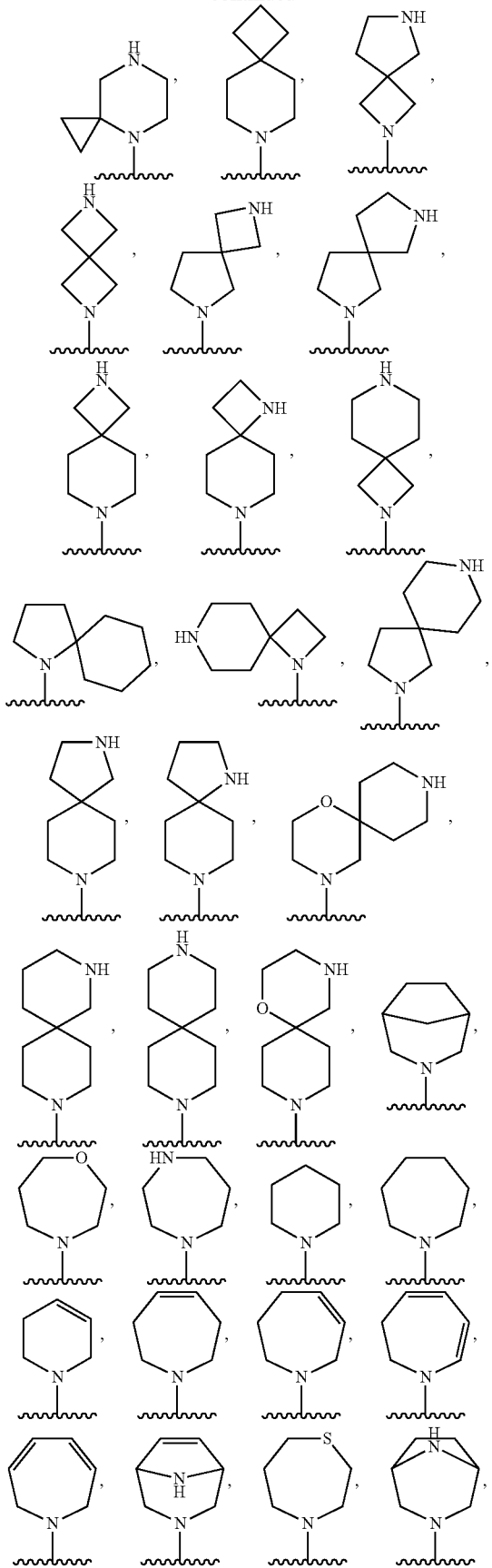

107

-continued

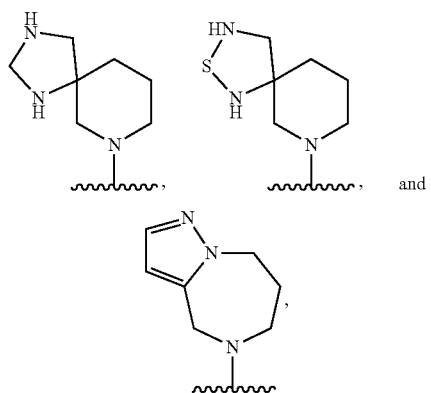

each of which is optionally substituted with one or more substituents. In some cases, the one or more of the optional substituents are independently selected from halogen, —OH, —N(R$^{20}$)$_2$, —B(OH)$_2$, —C(O)N(R$^{20}$)$_2$, —NHCN, —NO$_2$, C$_{1-6}$ alkoxy, =O, —CN, C$_{1-6}$ alkyl, C$_{2-6}$ alkenyl, C$_{1-6}$ alkyl-N(R$^{20}$)$_2$, C$_{1-6}$ aminoalkyl, C$_{1-6}$ hydroxyalkyl, and C$_{1-6}$ haloalkyl. In some cases, R$^1$ is selected from

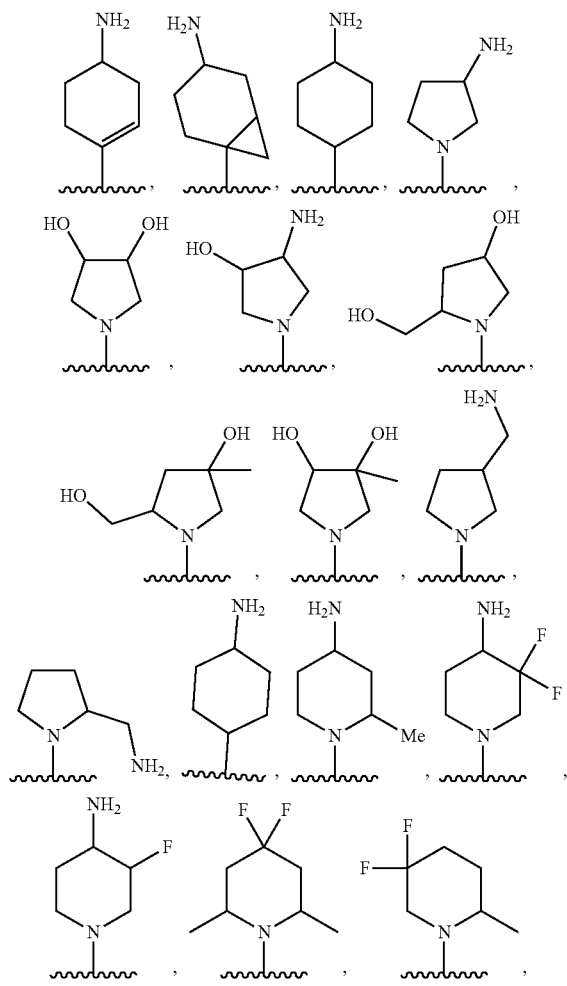

108

-continued

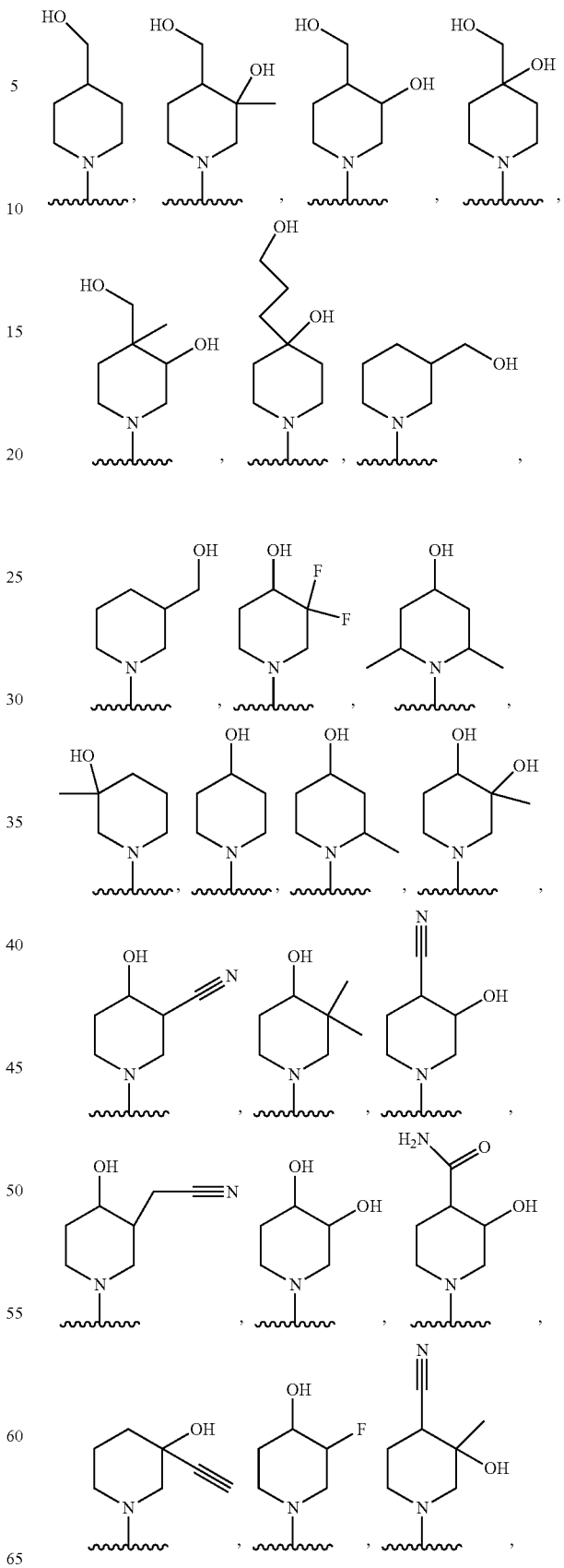

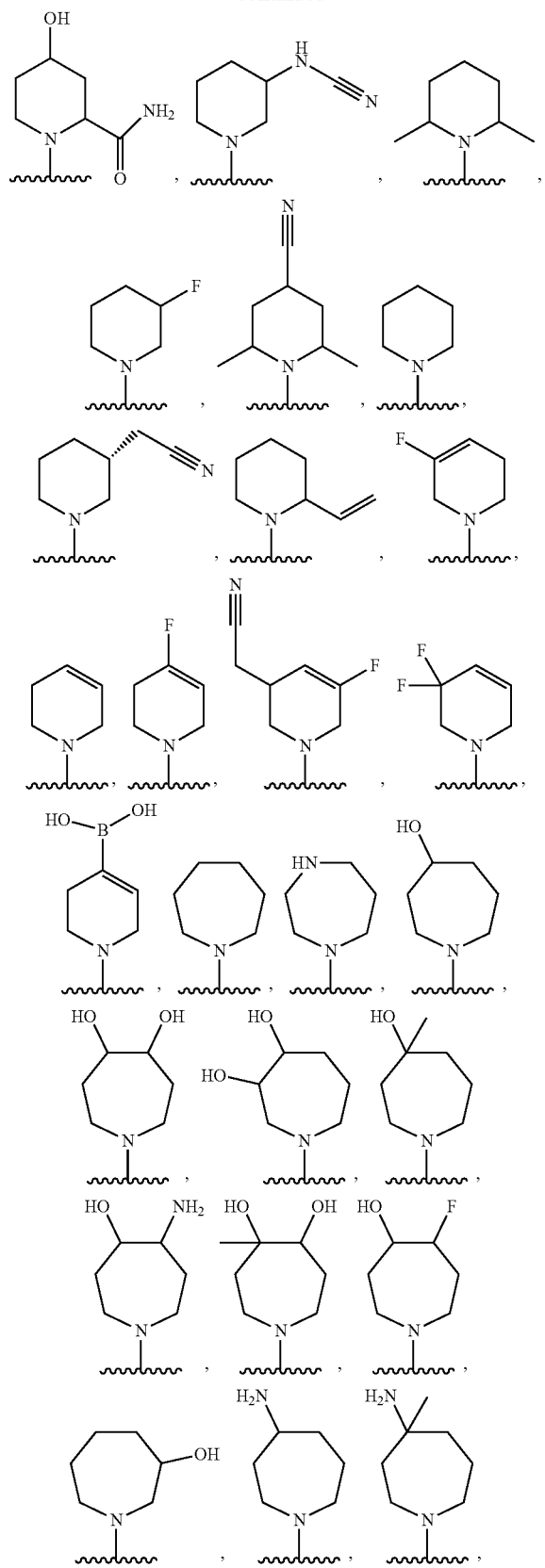
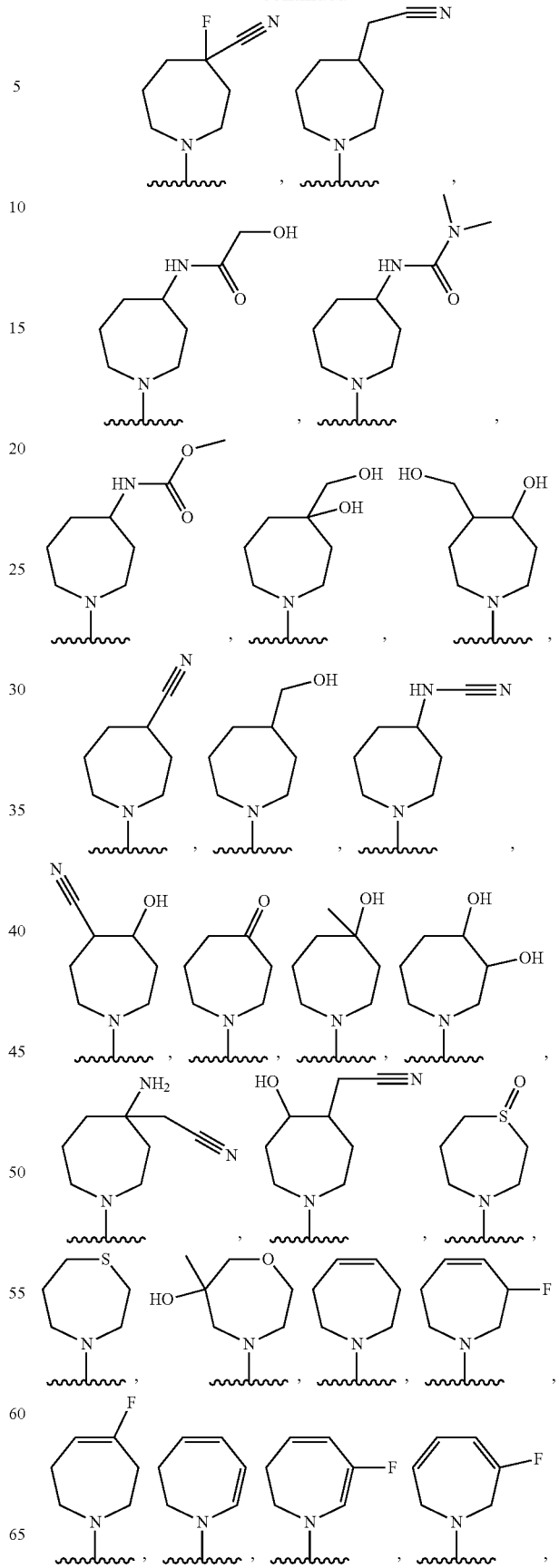

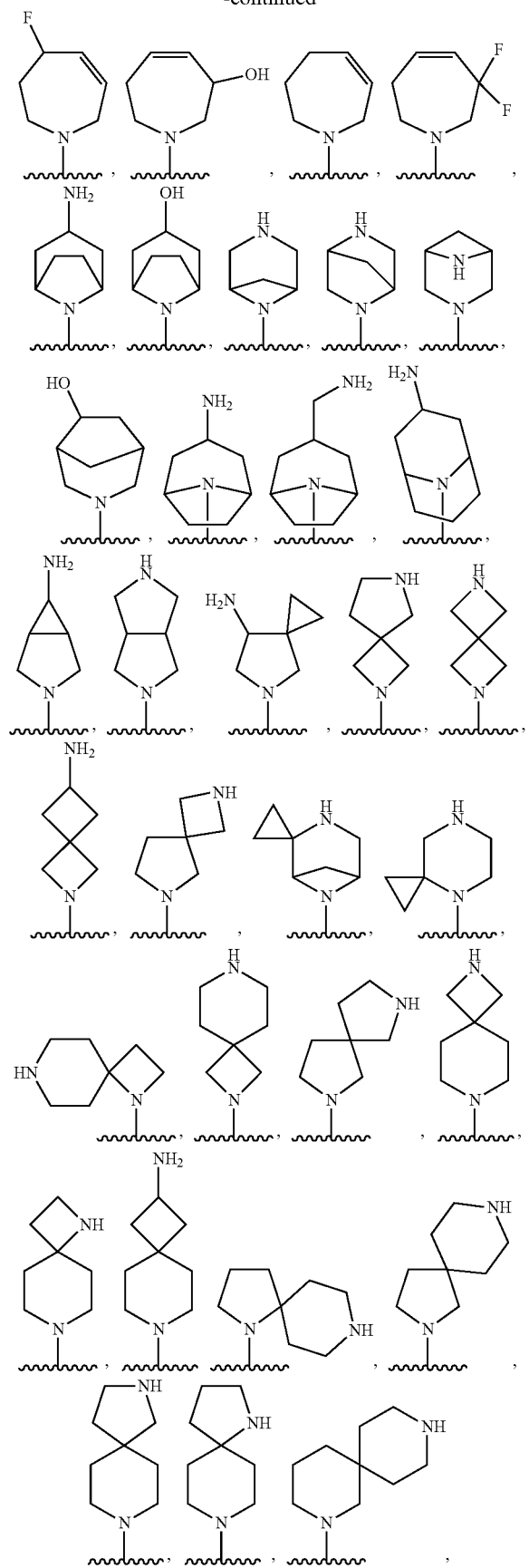
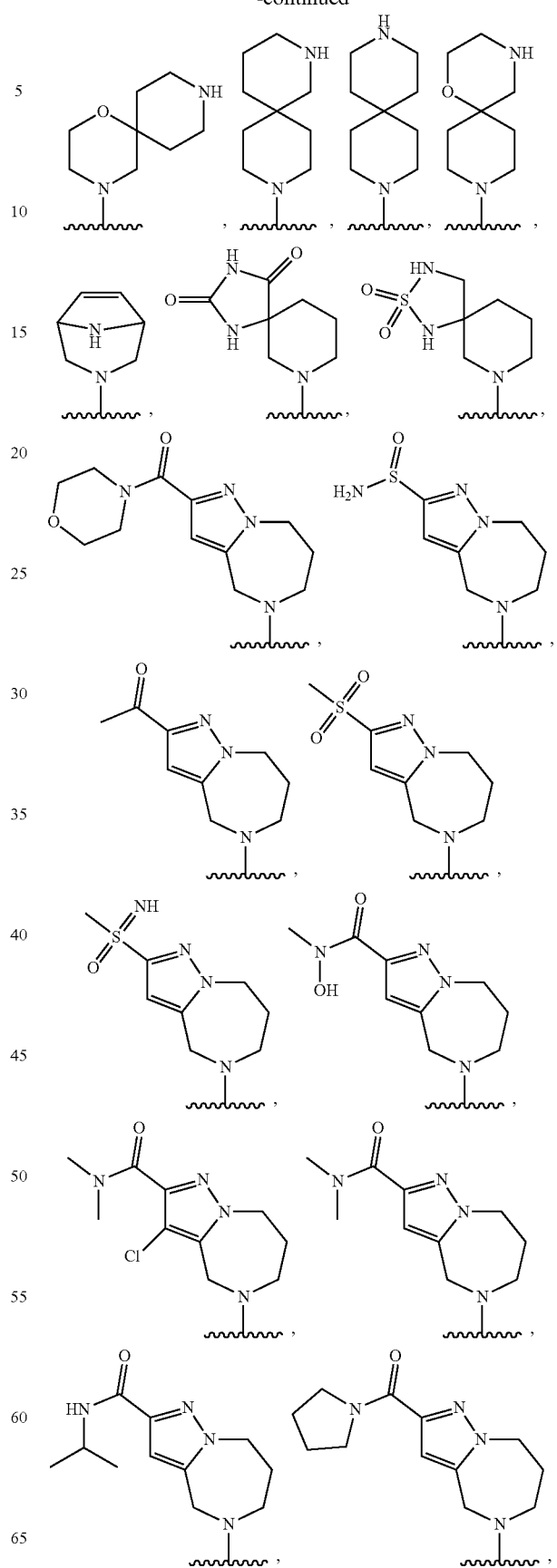

-continued

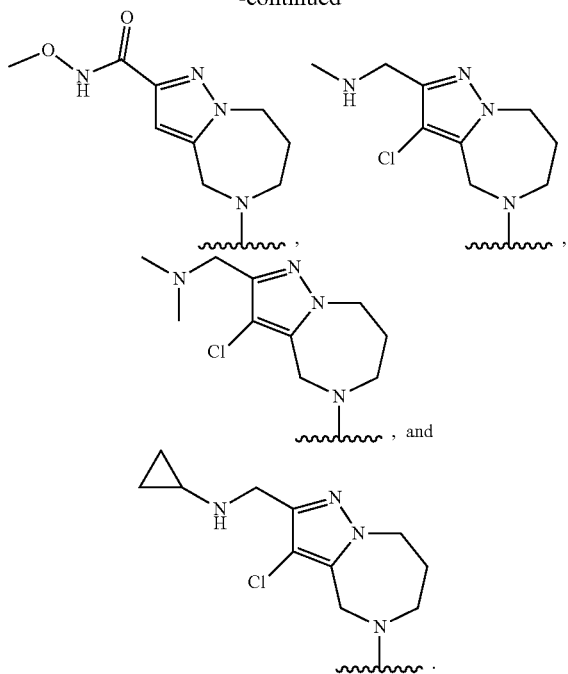

In some embodiments, for a compound or salt of Formula (I), Formula (I-A), Formula (I-B), Formula (I-C), or Formula (I-G), $R^1$ is selected from an optionally substituted 5- to 12-membered unsaturated heterocycle, wherein the heterocycle has as most one nitrogen atom. In some cases, the 5- to 12-membered unsaturated heterocycle has at least one nitrogen atom. In some cases, the 5- to 12-membered unsaturated heterocycle has at most one nitrogen atom.

In some embodiments, for a compound or salt of Formula (I), Formula (I-A), Formula (I-B), Formula (I-C), or Formula (I-G), the heterocycle of $R^1$ contains only 1 nitrogen atom and optionally one or more heteroatoms selected from oxygen, and sulfur. In some cases, the heterocycle is a fused heterocycle or a bridged heterocycle. In some cases, the heterocycle is a monocyclic heterocycle or a bridged heterocycle. In some cases, the heterocycle is a monocyclic heterocycle. In some cases, the heterocycle is a bridged heterocycle. In some cases, the heterocycle is selected from

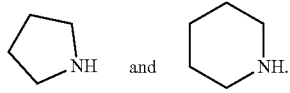 [SMILES: C1CCNC1 ; C1CCNCC1]

The heterocycle is optionally substituted as described elsewhere herein.

In some embodiments, for a compound or salt of Formula (I), Formula (I-A), Formula (I-B), Formula (I-C), or Formula (I-G), the heterocycle of $R^1$ has at most 1 nitrogen atom. In some cases, the heterocycle of $R^1$ has only 1 nitrogen atom and optionally one or more other heteroatoms selected from oxygen and sulfur. In some cases, the heterocycle of $R^1$ has only 1 nitrogen atom and no other heteroatoms.

In some embodiments, for a compound or salt of Formula (I), Formula (I-A), Formula (I-B), Formula (I-C), or Formula (I-G), $R^1$ is selected from an optionally substituted 5- to 12-membered saturated heterocycle, wherein the heterocycle has as most one nitrogen atom. In some cases, the 5- to 12-membered unsaturated heterocycle has at least one nitrogen atom. In some cases, the 5- to 12-membered unsaturated heterocycle has only one nitrogen atom and 0-2 other heteroatoms selected from nitrogen, oxygen, and sulfur. In some cases, the 5- to 12-membered unsaturated heterocycle has only one nitrogen atom and no further heteroatoms. In some cases, the 5- to 12-membered unsaturated heterocycle has three nitrogen atoms and no further heteroatoms.

In some embodiments, for a compound or salt of Formula (I), Formula (I-A), Formula (I-B), Formula (I-C), or Formula (I-G), $R^1$ is selected from an optionally substituted 5- to 12-membered unsaturated heterocycle, wherein the heterocycle has as most one nitrogen atom. In some cases, the 5- to 12-membered unsaturated heterocycle has at least one nitrogen atom. In some cases, the 5- to 12-membered unsaturated heterocycle has only one nitrogen atom and no further heteroatoms.

In some embodiments, for a compound or salt of Formula (I), Formula (I-A), Formula (I-B), Formula (I-C), or Formula (I-G), $R^1$ is selected from 6- to 9-membered heterocycle. In some cases, $R^1$ is selected from 6- to 7-membered heterocycle. In some cases, $R^1$ is selected from 7-membered heterocycle. In some cases, $R^1$ is selected from 6-membered heterocycle. In some cases, the 6- to 7-membered heterocycle contains only 1 nitrogen atom and optionally one or more additional heteroatoms selected from oxygen, and sulfur. In some cases, the optionally one or more additional heteroatoms are selected from sulfur. In some cases, the optionally one or more additional heteroatoms are selected from oxygen. In some cases, the 6- to 7-membered heterocycle contains only 1 nitrogen atom and no further additional heteroatoms. In some cases, the 6- to 7-membered heterocycle is a non-aromatic 6- to 7-membered heterocycle. In some cases, $R^1$ is selected from

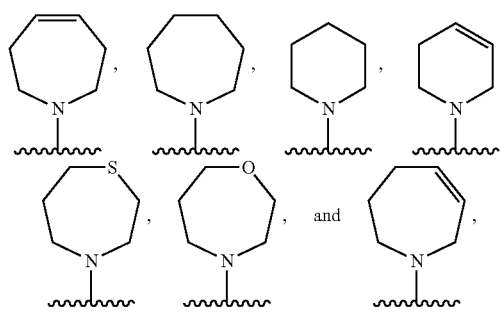

each of which is optionally substituted. In some cases, $R^1$ is selected from

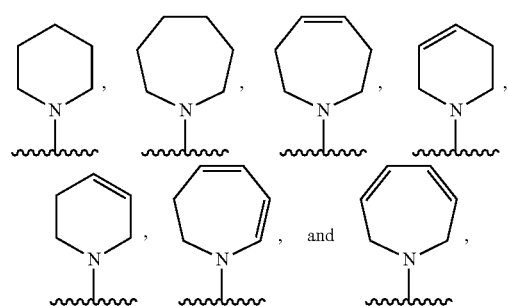

each of which is substituted. In some cases, the substituents of $R^1$ are each selected from one or more halogen, —$OR^{20}$, —$SR^{20}$, —$N(R^{20})_2$, —NHCN, —$NO_2$, =O, —CN, $C_{1-6}$ haloalkyl, —$C(O)N(R^{20})_2$, $C_{1-6}$ aminoalkyl, $C_{1-6}$ hydroxyalkyl, $C_{1-6}$ cyanoalkyl, $C_{1-6}$ alkyl, $C_{2-6}$ alkenyl, and $C_{2-6}$ alkynyl. In some cases, the substituents of $R^1$ are each selected from one or more halogen, —$OR^{20}$, —$N(R^{20})_2$, —NHCN, =O, —CN, —$C(O)N(R^{20})_2$, $C_{1-6}$ aminoalkyl, $C_{1-6}$ hydroxyalkyl, $C_{1-6}$ cyanoalkyl, $C_{1-6}$ alkyl, and $C_{2-6}$ alkynyl. In some cases, the substituents of $R^1$ are each selected from one or more halogen, —OH, —NHCN, =O, —CN, $C_{2-6}$ alkynyl, and $C_{1-6}$ alkyl. In some cases, $R^1$ is selected from

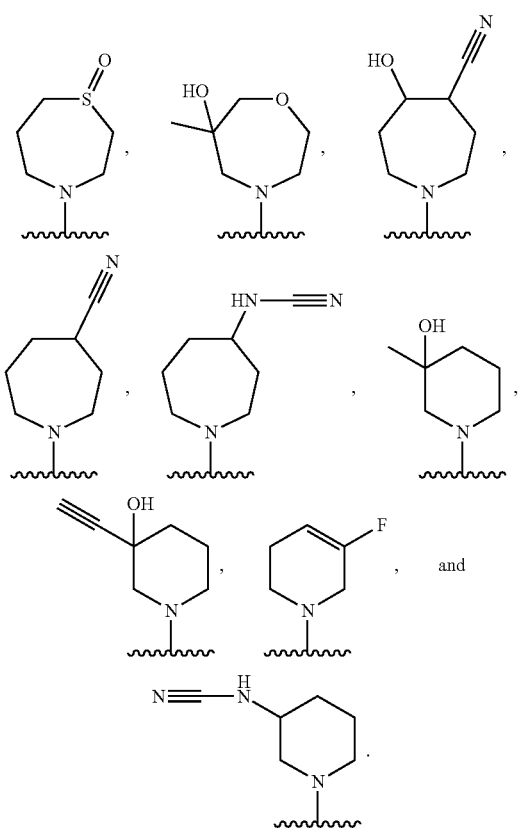

In some cases, $R^1$ is selected from

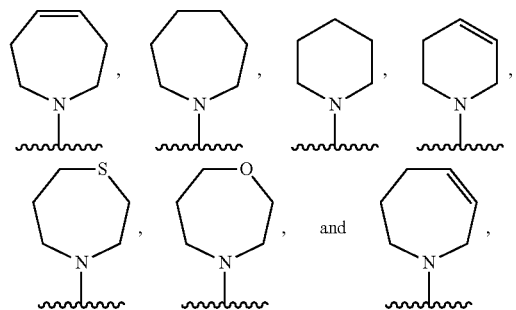

each of which is optionally substituted. In some cases, $R^1$ is selected from

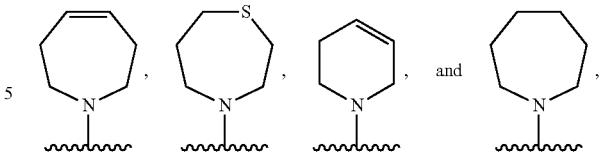

each of which is optionally substituted. In some cases, $R^1$ is selected from

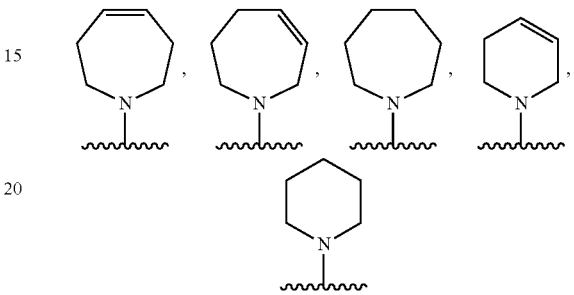

each of which is optionally substituted. In some cases, the one or more optional substituents of $R^1$ are each independently selected from fluorine, —OH, —$C(O)NH_2$, —NH—$C(O)$—($C_{1-6}$ alkoxy), —NH—$C(O)$—($C_{1-6}$ hydroxyalkyl), —$NH_2$, —NH(CN), =O, —CN, $C_{1-6}$ hydroxyalkyl, $C_{1-6}$ cyanoalkyl, $C_{1-6}$ alkyl, and $C_{2-6}$ alkynyl. In some cases, the one or more optional substituents of $R^1$ are each independently selected from halogen, —OH, —CN, $C_{1-6}$ cyanoalkyl, $C_{1-6}$ alkyl, and $C_{2-6}$ alkynyl. In some cases, the one or more optional substituents of $R^1$ are each independently selected from halogen, —OH, and —CN. In some cases, the one or more optional substituents of $R^1$ are each independently selected from fluorine, —OH, —CN, $C_{1-6}$ cyanoalkyl, $C_{1-6}$ alkyl, oxo, and $C_{2-6}$ alkynyl. In some cases, the one or more optional substituents of $R^1$ are each independently selected from fluorine, —OH, —CN, $C_{1-6}$ cyanoalkyl, $C_{1-6}$ alkyl, and $C_{2-6}$ alkynyl. In some cases, $R^1$ is selected from

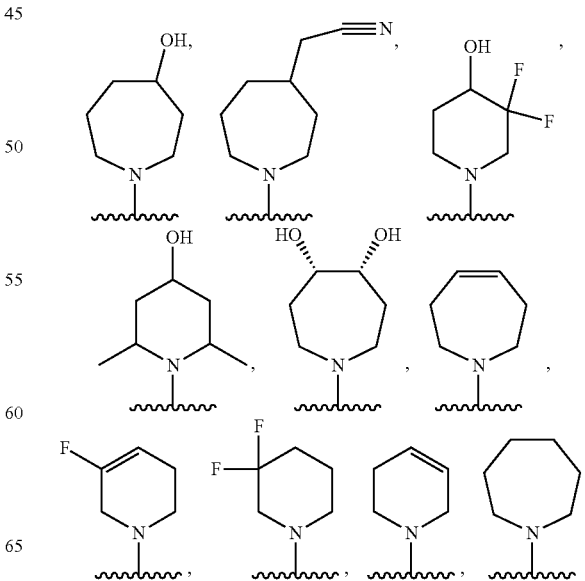

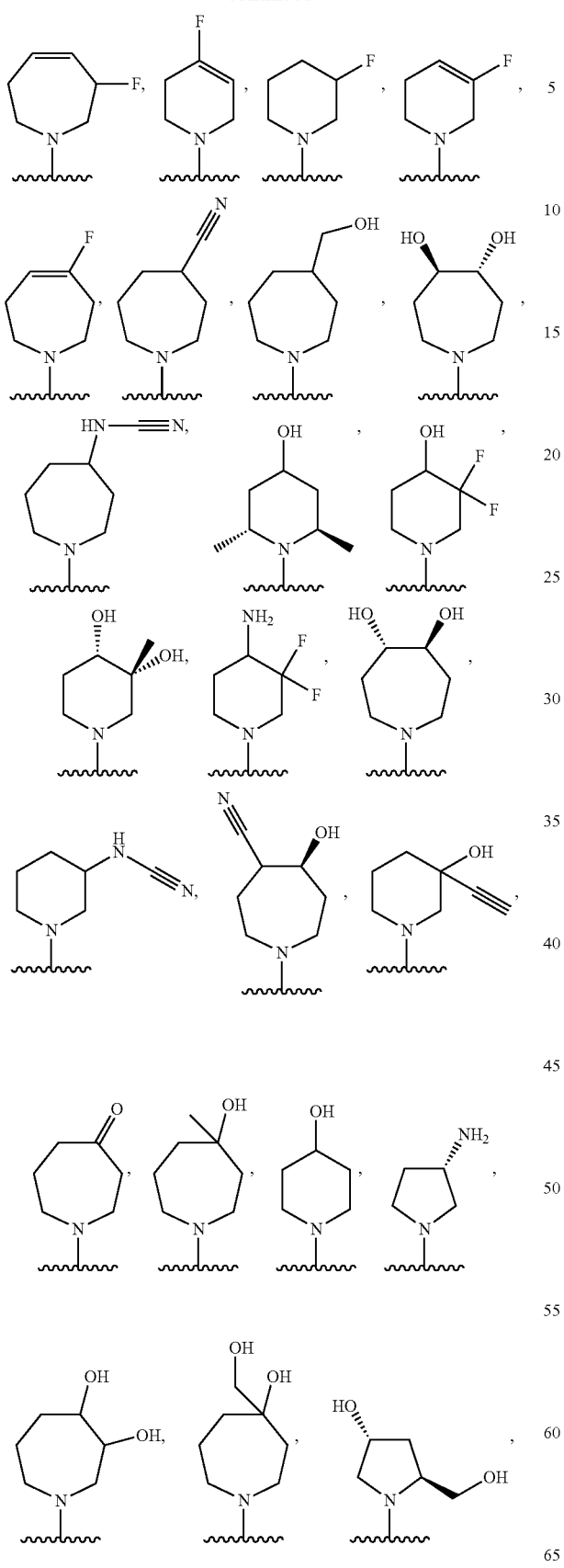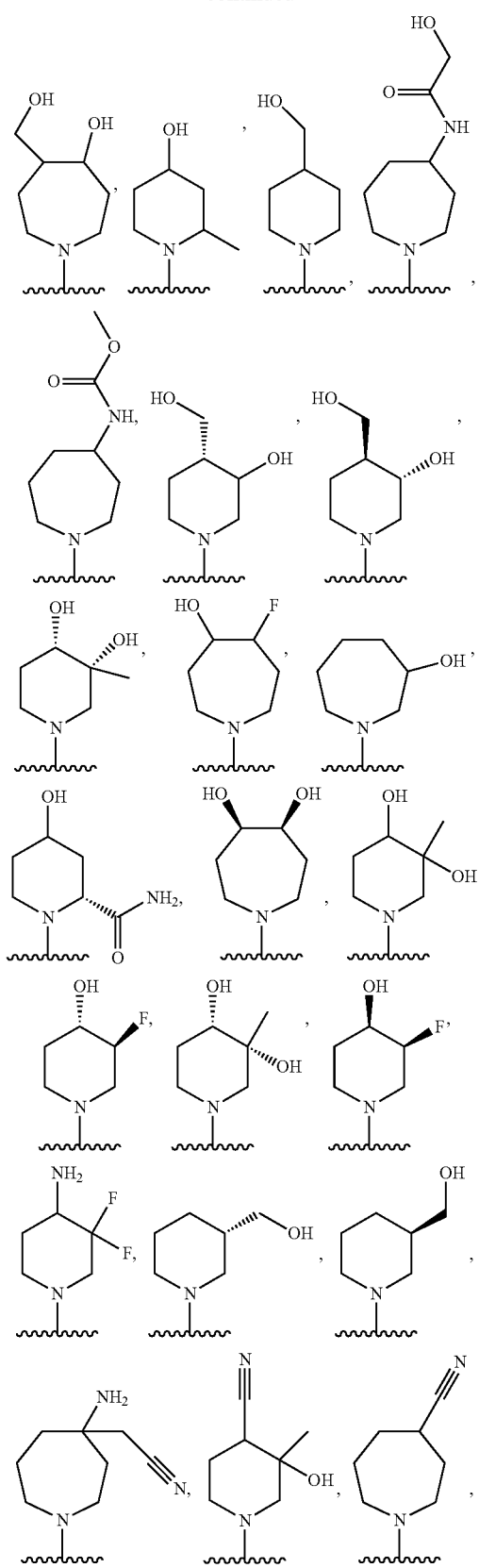

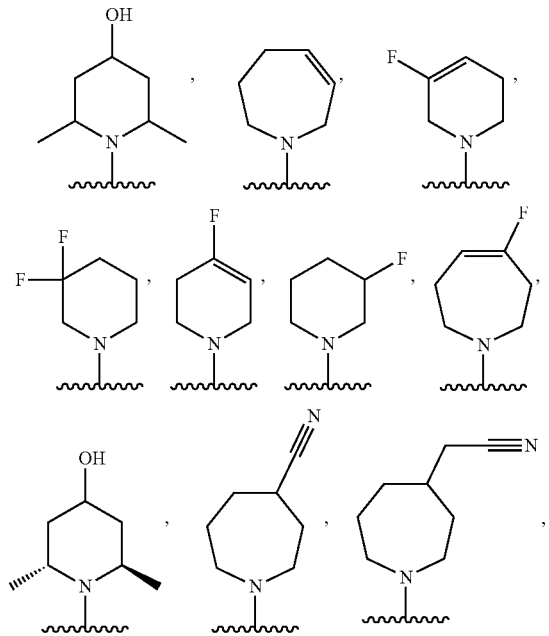
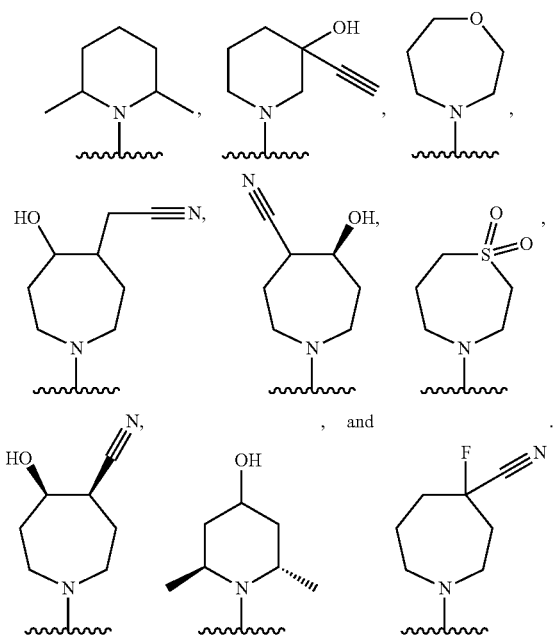
In some cases, R[1] is selected from
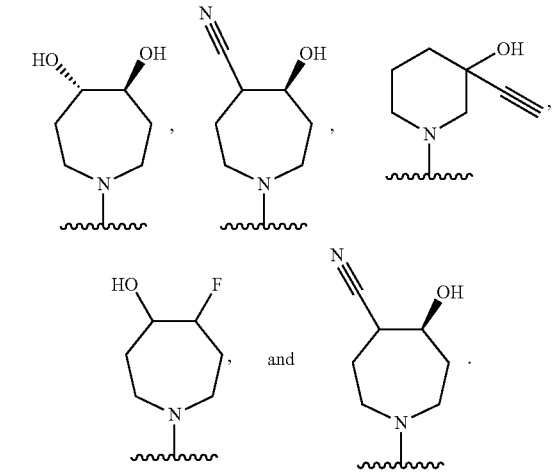
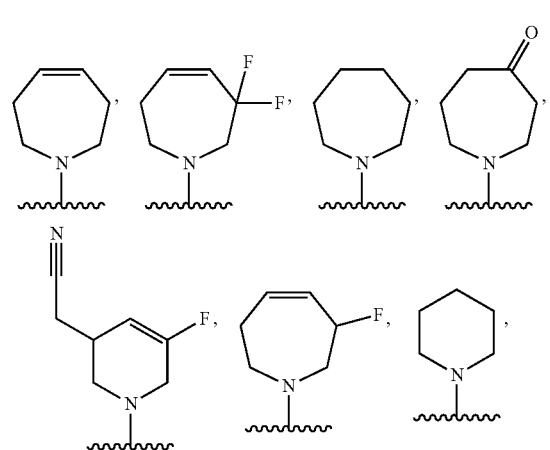
In some cases, R[1] is selected from
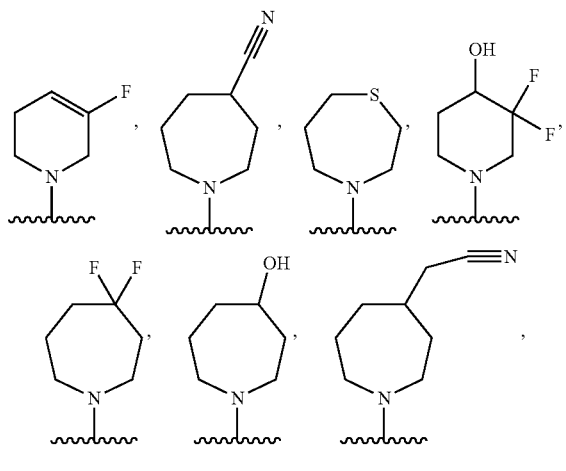
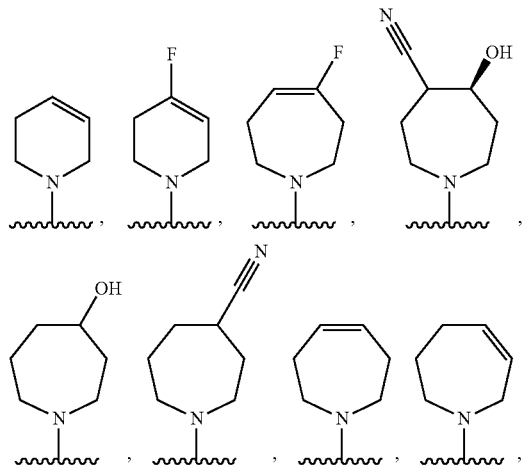

-continued
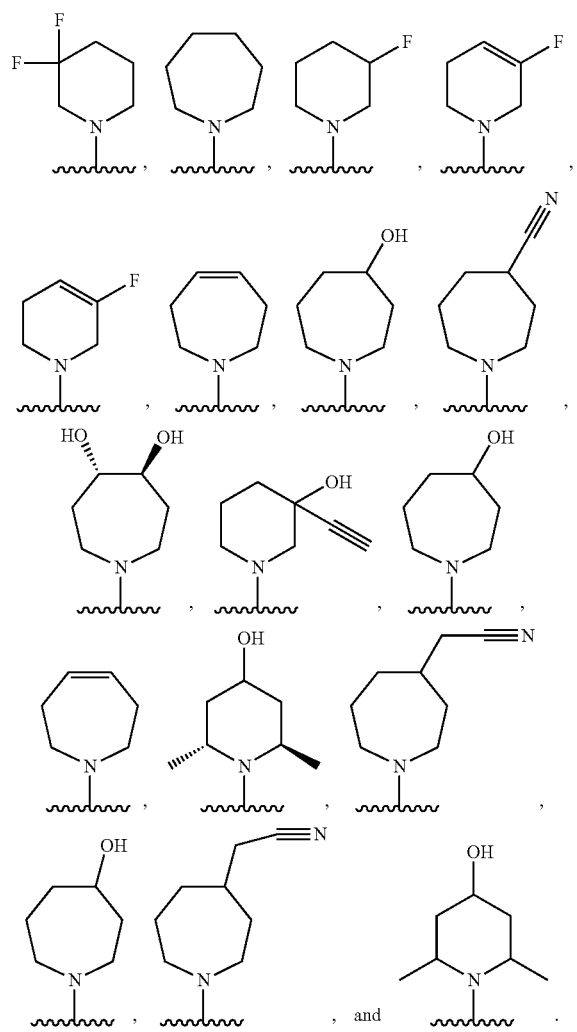
In some cases, $R^1$ is selected from
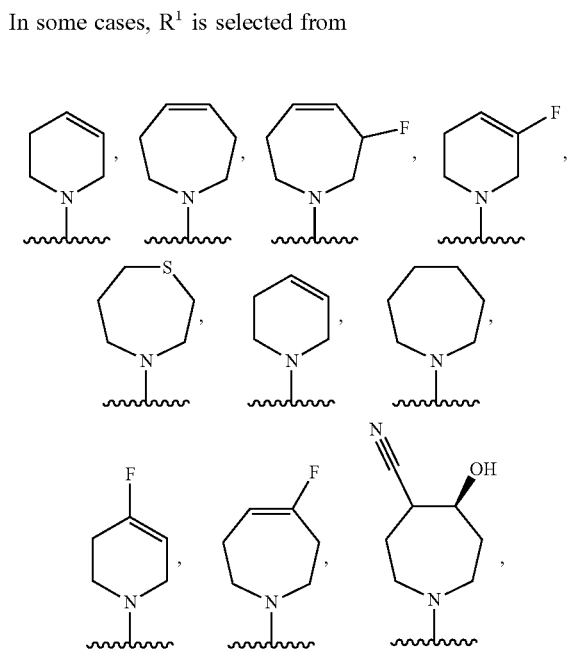
-continued
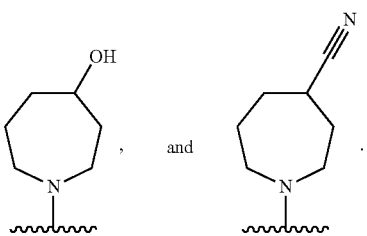
In some cases, $R^1$ is selected from
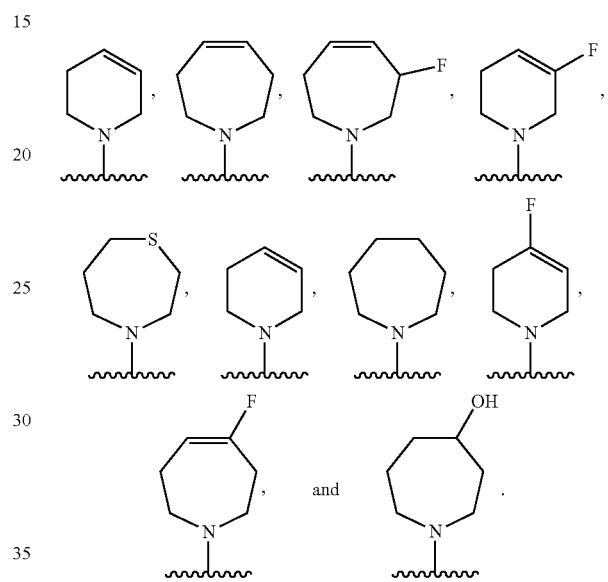
In some embodiments, for a compound or salt of Formula (I), Formula (I-A), Formula (I-B), Formula (I-C), or Formula (I-G), $R^1$ is selected from
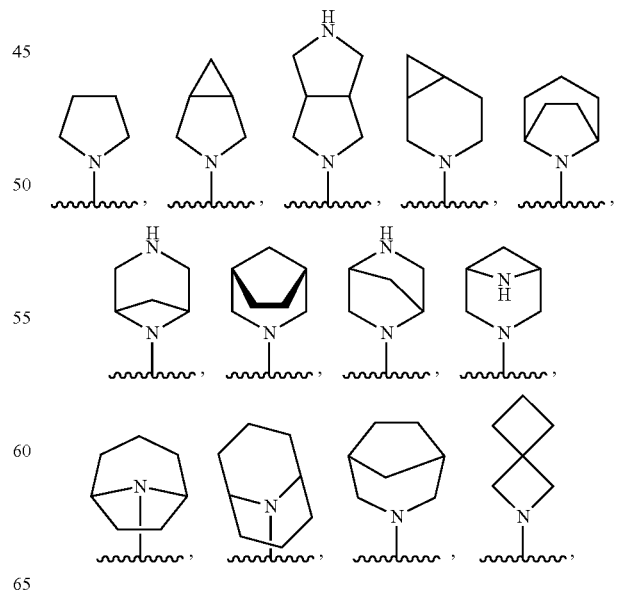

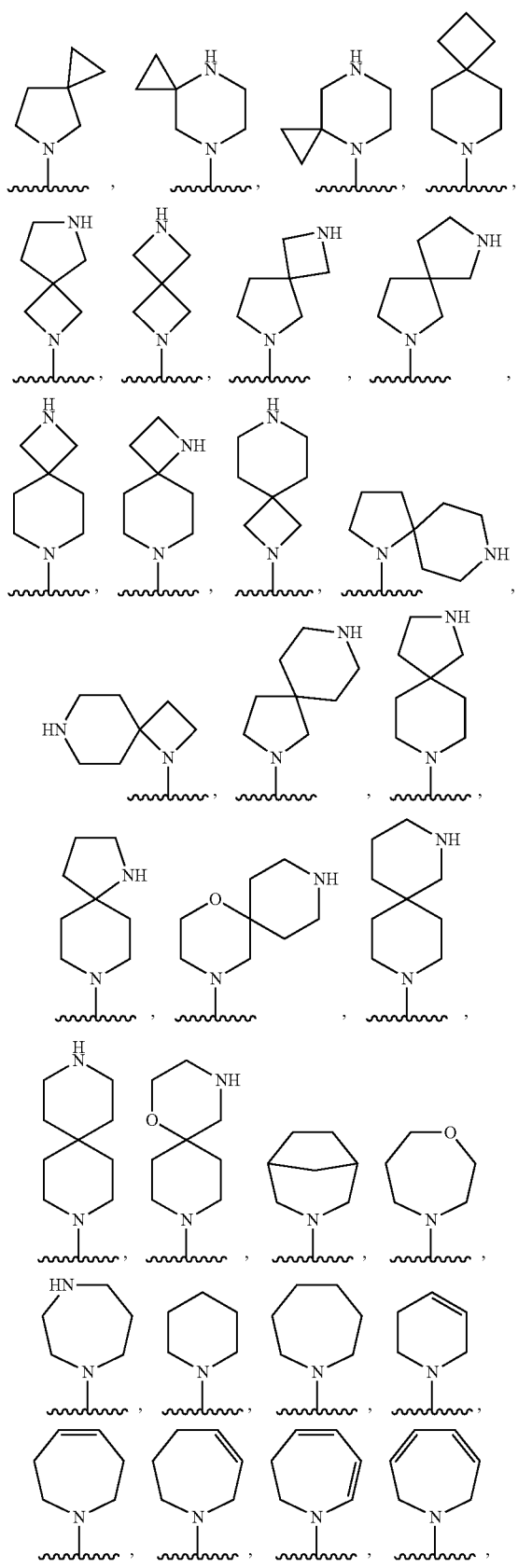
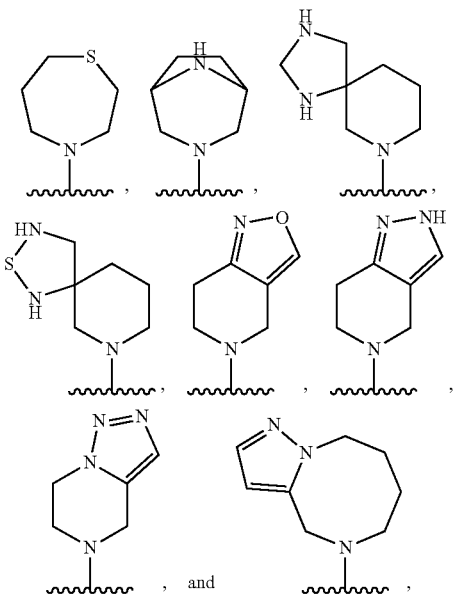
each of which is optionally substituted with one or more substituents. In some cases, the one or more of the optional substituents are independently selected from halogen, —OH, —N(R$^{20}$)$_2$, —B(OH)$_2$, —C(O)N(R$^{20}$)$_2$, —NHCN, —NO$_2$, C$_{1-6}$ alkoxy, =O, —CN, C$_{1-6}$ alkyl, C$_{2-6}$ alkenyl, C$_{1-6}$ aminoalkyl, C$_{1-6}$ cyanoalkyl, C$_{1-6}$ hydroxyalkyl, and C$_{1-6}$ haloalkyl. In some cases, R$^1$ is selected from
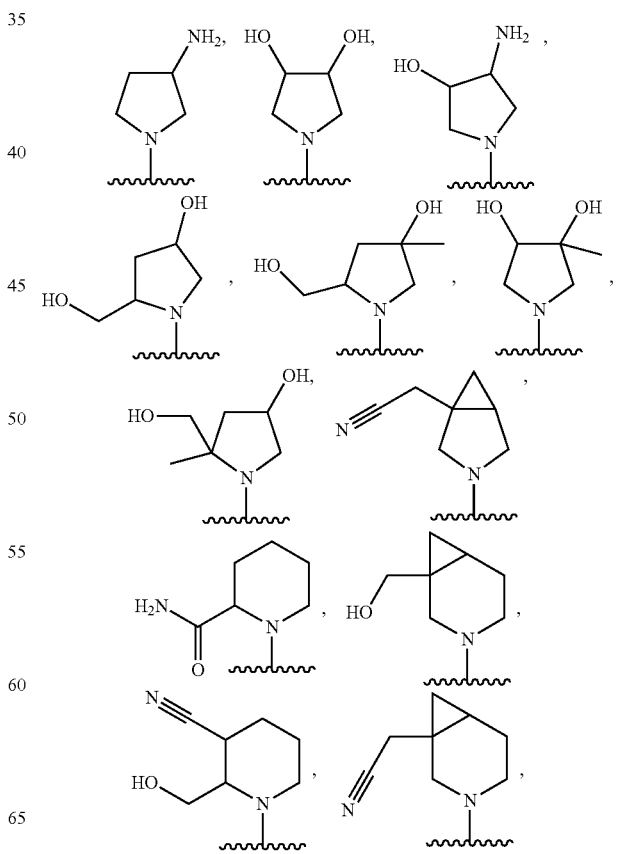

-continued
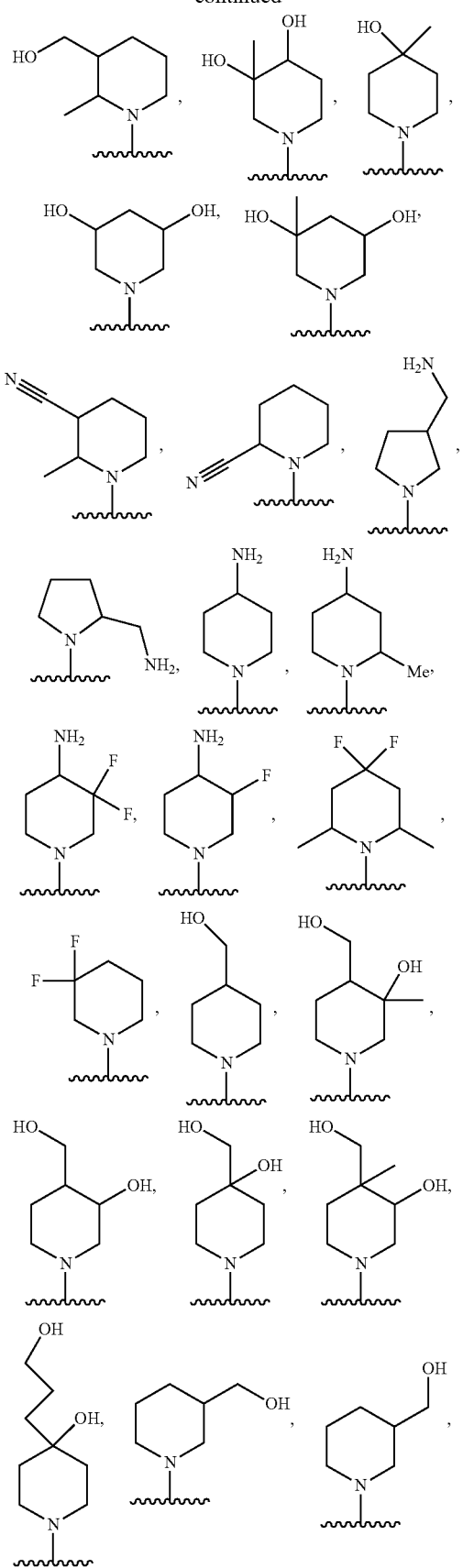
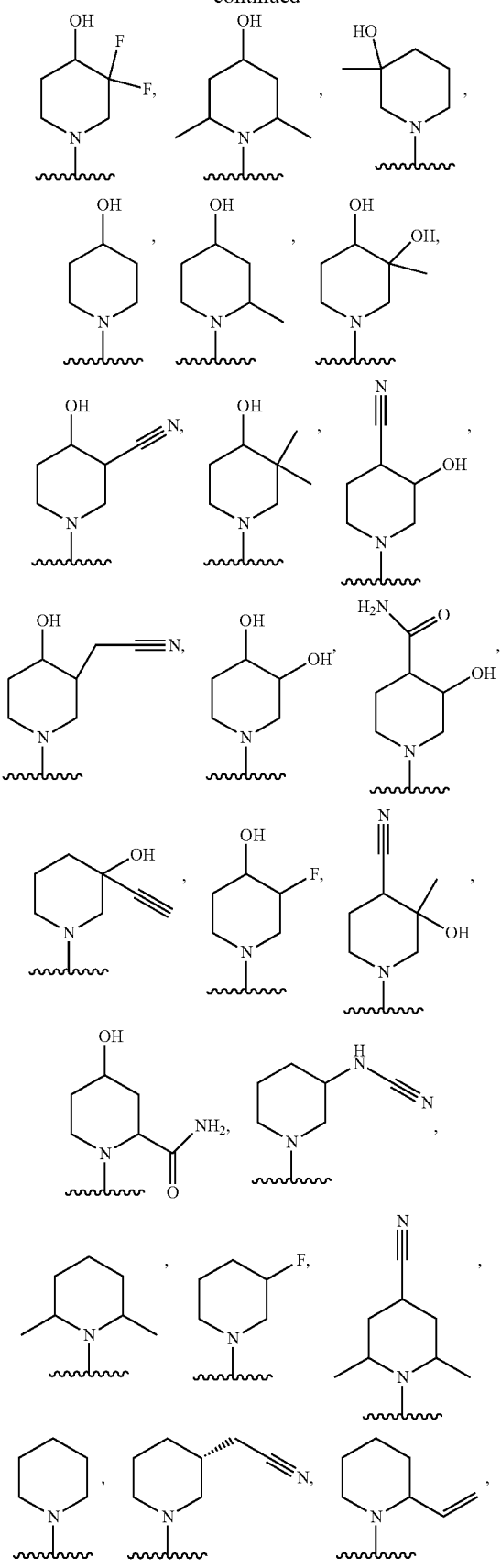

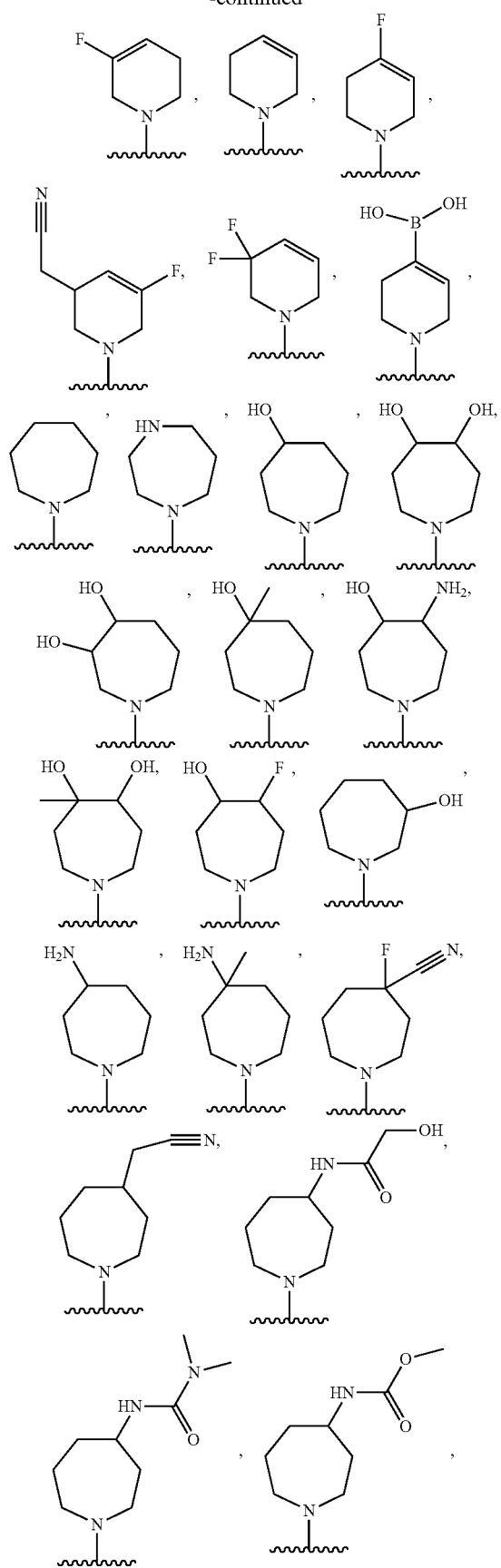
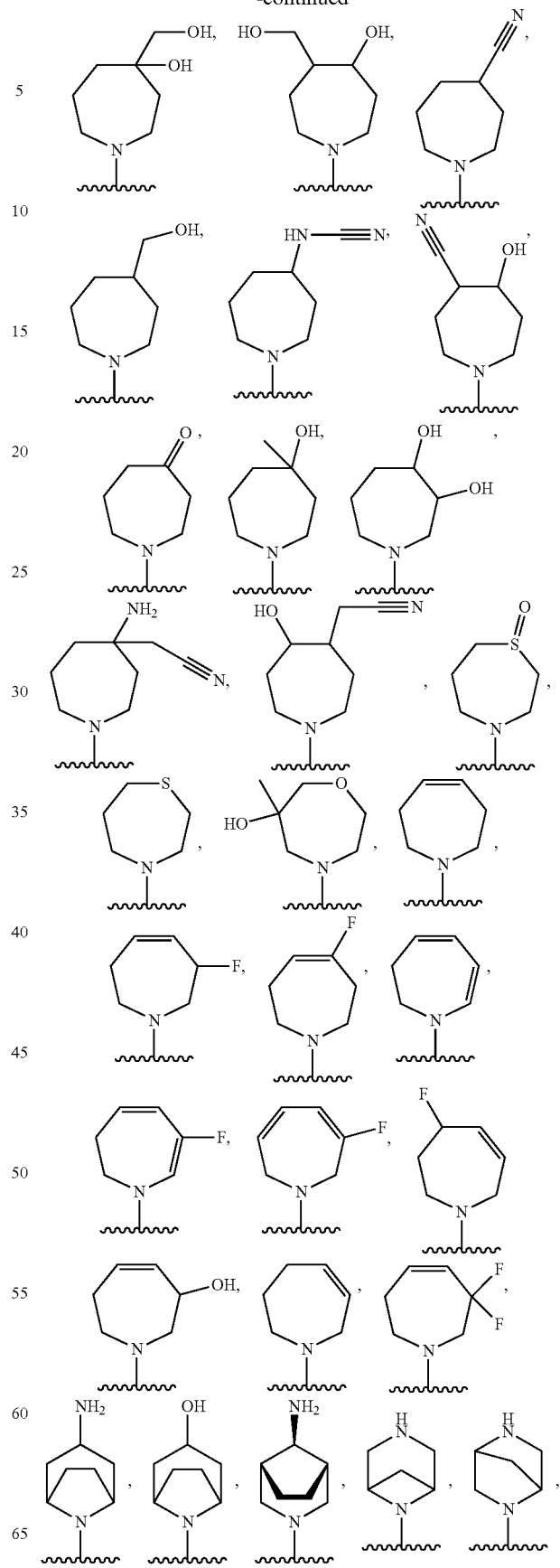

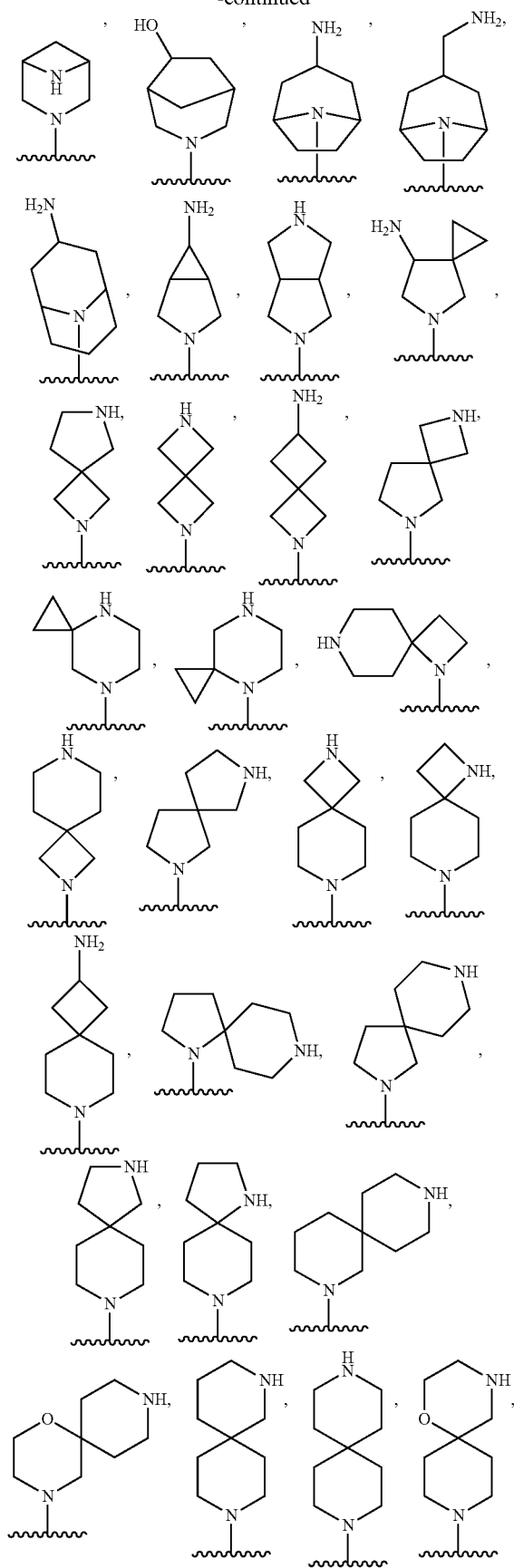
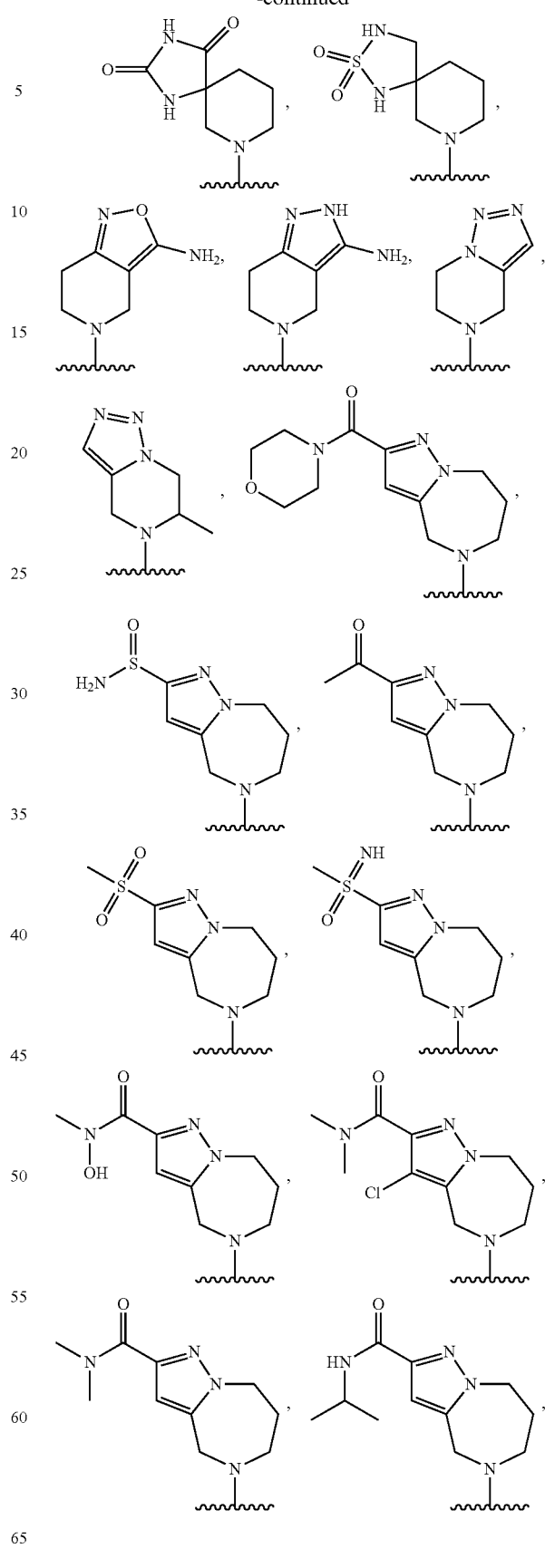

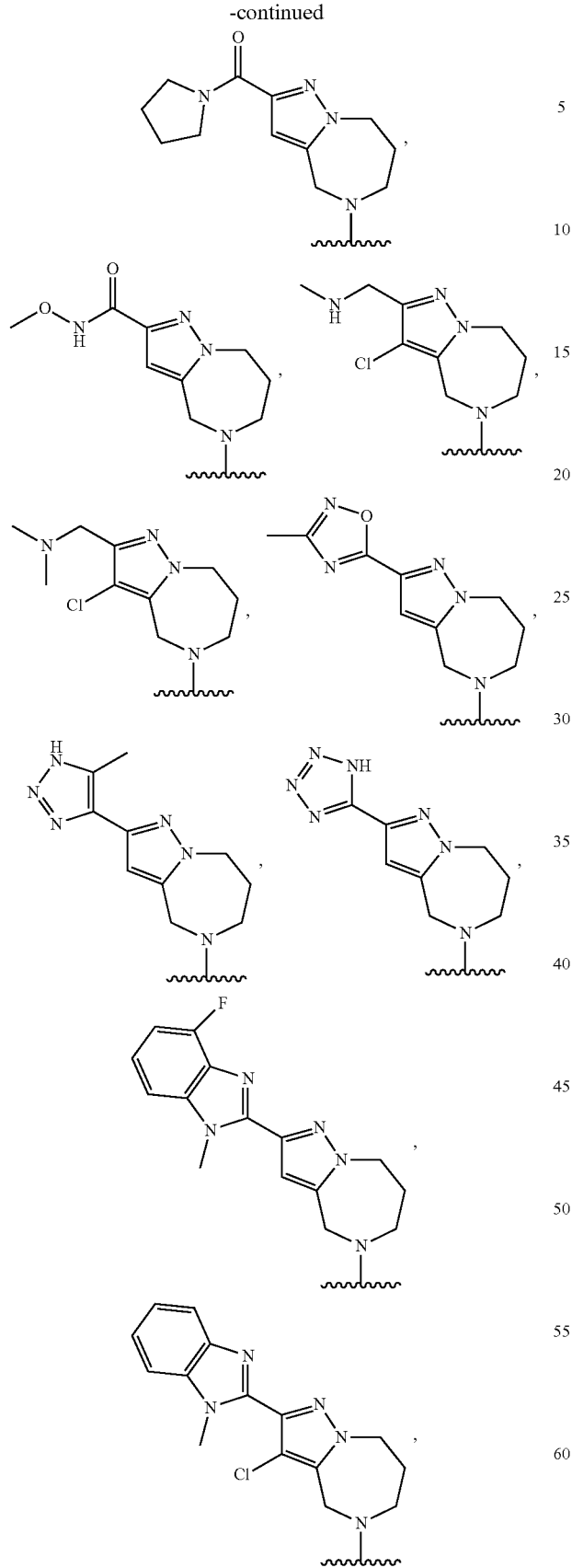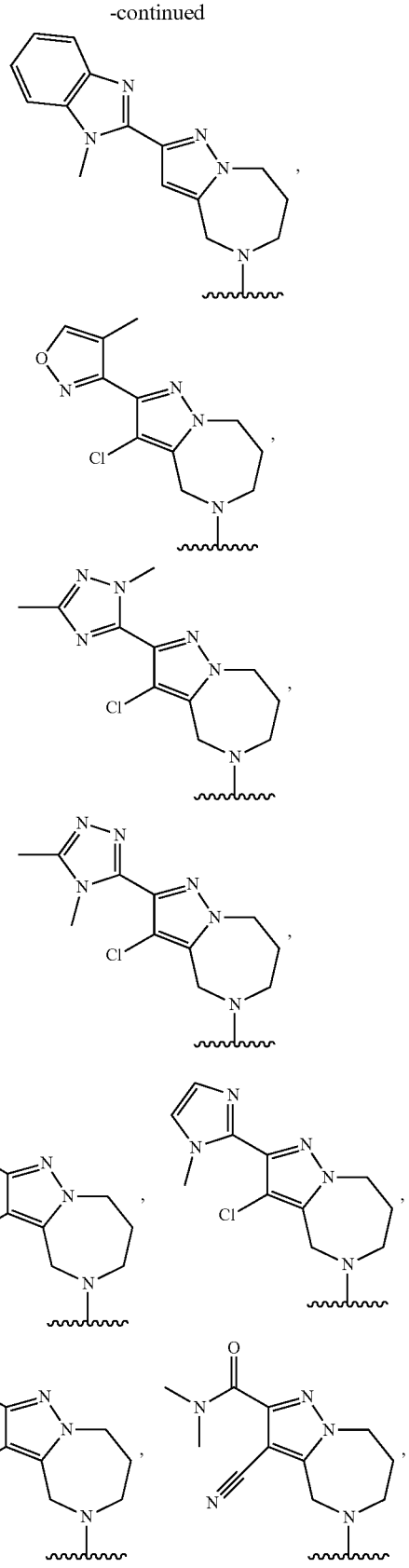

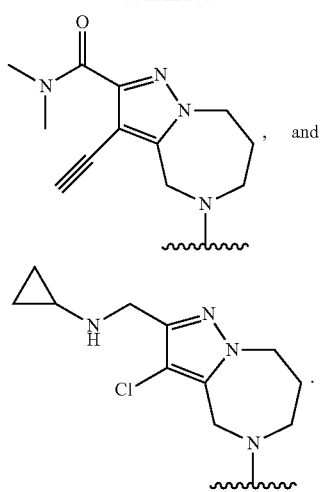, and

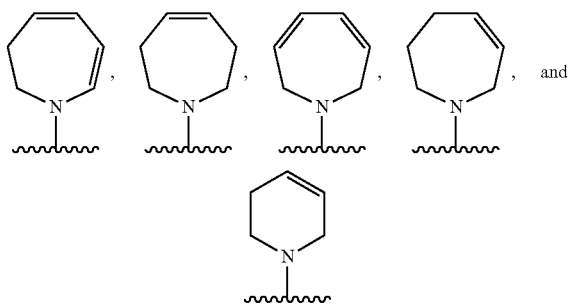

In some embodiments, for a compound or salt of Formula (I), Formula (I-A), Formula (I-B), Formula (I-C), or Formula (I-G), $R^1$ is selected from an optionally substituted unsaturated 6- to 8-membered heterocycle. In some cases, $R^1$ is selected from an optionally substituted unsaturated 6-membered heterocycle. In some cases, $R^1$ is selected from an optionally substituted unsaturated 7-membered heterocycle. In some cases, the heterocycle has 1 or 2 double bonds. In some cases, the heterocycle has only 1 double bond. In some cases, the heterocycle has only 2 double bonds. In some cases, $R^1$ is selected from

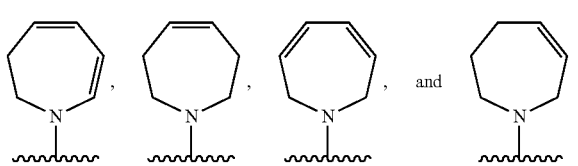

wherein each is optionally substituted with one or more substituents independently selected from halogen, —OH, —NH$_2$, —NO$_2$, C$_{1-6}$ aminoalkyl, C$_{1-6}$ alkoxy, C$_{1-6}$ haloalkyl, and C$_{1-6}$ alkyl. In some cases, $R^1$ is selected from

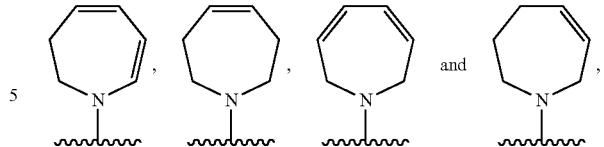

wherein each is optionally substituted with one or more substituents independently selected from halogen, —OH, —NH$_2$, —NO$_2$, C$_{1-6}$ aminoalkyl, C$_{1-6}$ alkoxy, C$_{1-6}$ hydroxyalkyl, C$_{1-6}$ haloalkyl, and C$_{1-6}$ alkyl. In some cases, $R^1$ is selected from

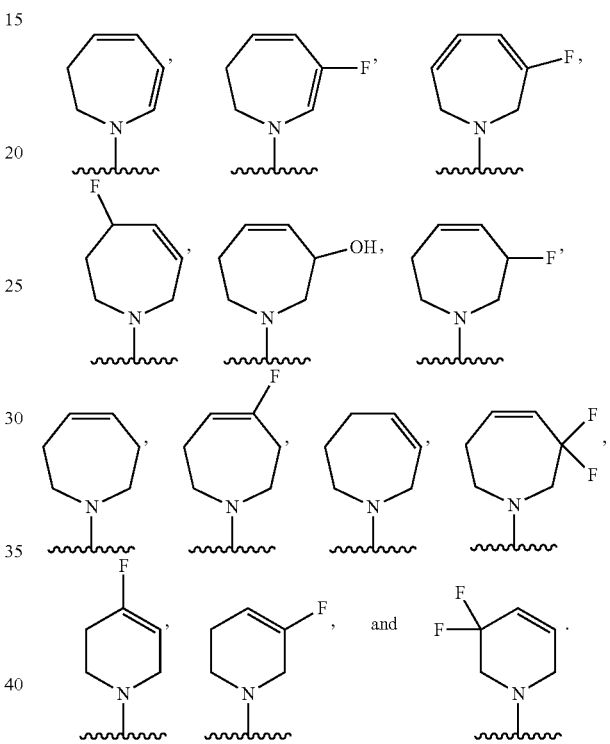

In some cases, $R^1$ is selected from

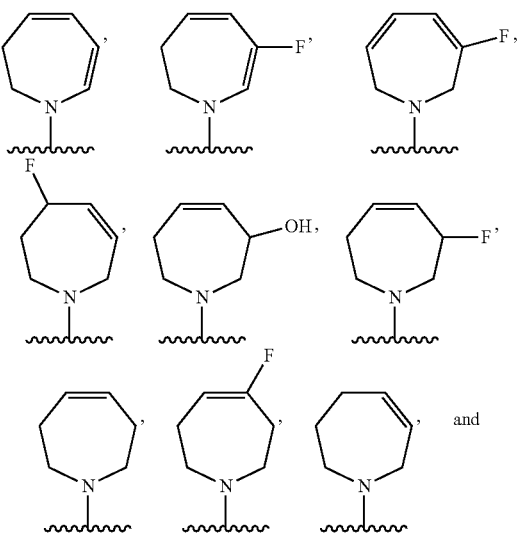

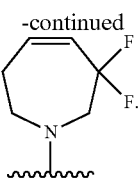

In some cases, R[1] is selected from

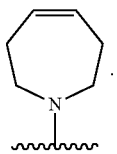 [SMILES: *N1CCC=CCC1]

In some cases, R[1] is

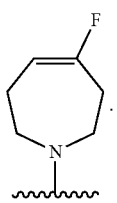 [SMILES: *N1CCC=C(F)CC1]

In some cases, R[1] is selected from

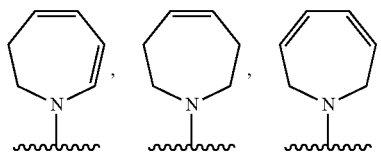 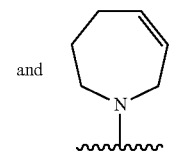

wherein each is substituted with one or more substituents independently selected from halogen.

In some embodiments, for a compound or salt of Formula (I), Formula (I-A), Formula (I-B), Formula (I-C), or Formula (I-G), R[1] is selected from an unsaturated 6- to 7-membered heterocycle, wherein the unsaturated 6- to 7-membered heterocycle is substituted with one or more substituents selected from halogen. In some cases, the unsaturated 6- to 7-membered heterocycle is substituted with at least one halogen. In some cases, the unsaturated 6- to 7-membered heterocycle is substituted with at only one halogen. In some cases, the unsaturated 7-membered heterocycle is substituted with one fluorine. In some cases, R[1] is selected from an unsaturated 6-membered heterocycle, substituted with at least one halogen. In some cases, R[1] is selected from an unsaturated 7-membered heterocycle, substituted with at least one halogen. In some cases, R[1] is selected from

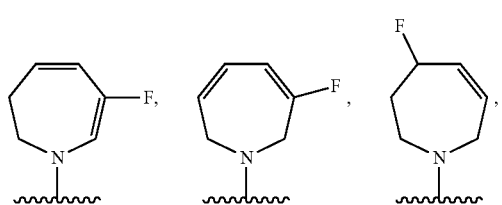

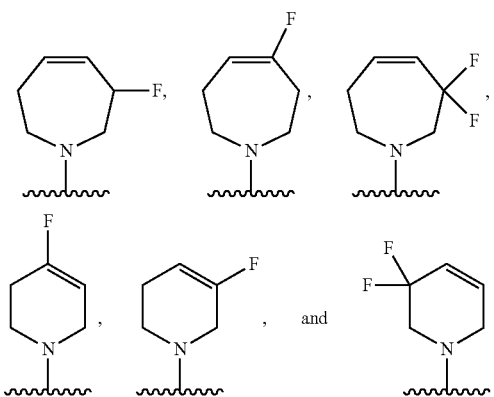

In some cases, R[1] is selected from

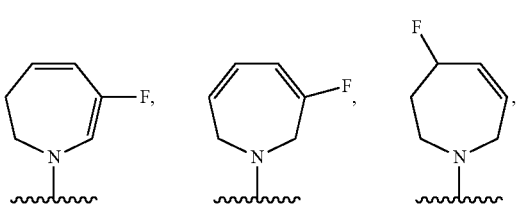

In some cases, R[1] is selected

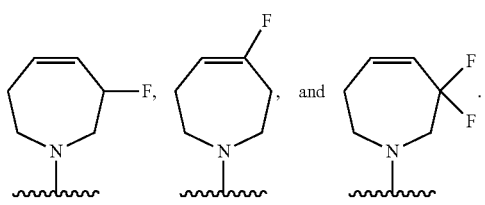

In some cases, R[1] is selected from

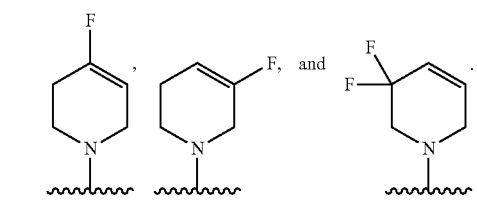

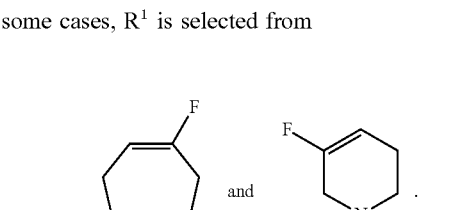

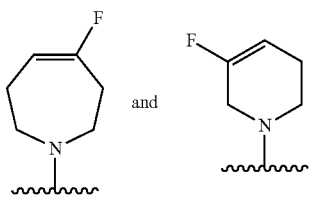

In some cases, $R^1$ is

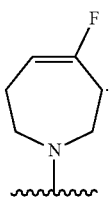

In some cases, $R^1$ is

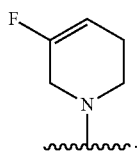

In some cases, $R^1$ is

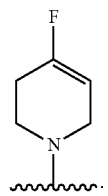 [SMILES: *N1CC=C(F)CC1]

In some embodiments, for a compound or salt of Formula (I), Formula (I-A), Formula (I-B), Formula (I-C), or Formula (I-G), $R^1$ is selected from an optionally substituted unsaturated 6- to 8-membered heterocycle. In some cases, $R^1$ is selected from an optionally substituted unsaturated 7-membered heterocycle. In some cases, $R^1$ is selected from

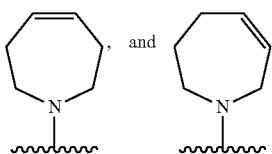 [SMILES: *N1CCC=CCC1 ; *N1CC=CCCC1]

wherein each is optionally substituted with one or more substituents independently selected from halogen, —OH, —NH$_2$, —NO$_2$, C$_{1-6}$ aminoalkyl, C$_{1-6}$alkoxy, C$_{1-6}$hydroxyalkyl, C$_{1-6}$haloalkyl, and C$_{1-6}$ alkyl. In some cases, $R^1$ is selected from

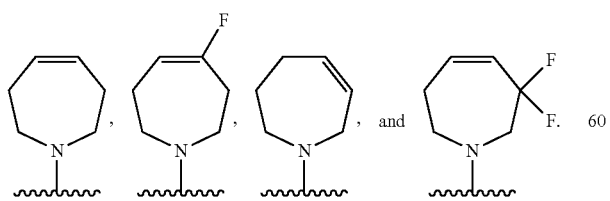

In some embodiments, for a compound or salt of Formula (I), Formula (I-A), Formula (I-B), Formula (I-C), or Formula (I-G), $R^1$ is selected from an optionally substituted 6-membered heterocycle. In some cases, the 6-membered heterocycle contains only 1 nitrogen atom. In some cases, the 6-membered heterocycle of $R^1$ is bound to the respective Formula via the only 1 nitrogen atom. In some cases, $R^1$ is selected from

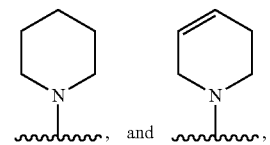

any of which is optionally substituted. In some cases, the one or more optional substituents of $R^1$ are each independently selected from halogen, —OR$^{20}$, —N(R$^{20}$)$_2$, =O, —CN, C$_{1-6}$ hydroxyalkyl, C$_{1-6}$ cyanoalkyl, C$_{1-6}$ alkyl, and C$_{2-6}$ alkynyl. In some cases, the one or more optional substituents of $R^1$ are each independently selected from fluorine, —OH, —NH$_2$, —NH(CN), =O, —CN, C$_{1-6}$ hydroxyalkyl, C$_{1-6}$ cyanoalkyl, C$_{1-6}$ alkyl, and C$_{2-6}$ alkynyl. In some cases, the one or more optional substituents of $R^1$ are each independently selected from fluorine, —OH, —NH$_2$, —NH(CN), =O, —CN, C$_{1-6}$ hydroxyalkyl, C$_{1-6}$ alkyl, and C$_{2-6}$ alkynyl. In some cases, the 6-membered heterocycle is a partially unsaturated 6-membered heterocycle or a saturated 6-membered heterocycle. In some cases, the 6-membered heterocycle is partially unsaturated. In some cases, the 6-membered heterocycle is a saturated 6-membered heterocycle. In some cases, the 6-membered heterocycle is a monocyclic 6-membered heterocycle. In some cases, the 6-membered heterocycle is not a bridged heterocycle. In some cases $R^1$ is selected from

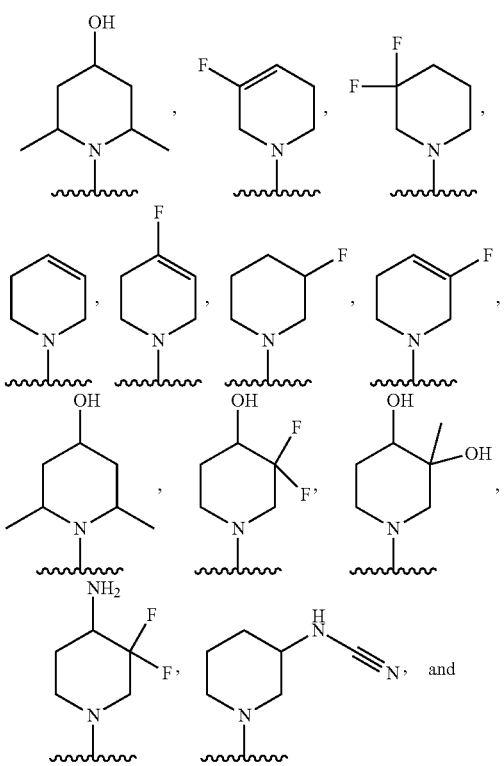

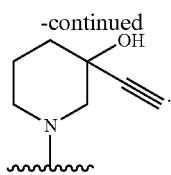

In some embodiments, for a compound or salt of Formula (I), Formula (I-A), Formula (I-B), Formula (I-C), or Formula (I-G), $R^1$ is selected from an optionally substituted 6-membered unsaturated heterocycle and 6-membered saturated heterocycle. In some cases, $R^1$ is selected from

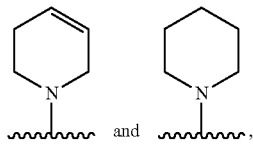 [SMILES: *N1CC=CCC1 ; *N1CCCCC1]

wherein each is optionally substituted with one or more substituents independently selected from halogen, —OH, —NH$_2$, —NO$_2$, C$_{1-6}$ aminoalkyl, C$_{1-6}$ cyanoalkyl, C$_{1-6}$ alkoxy, C$_{1-6}$ hydroxyalkyl, C$_{1-6}$ haloalkyl, and C$_{1-6}$ alkyl. In some cases, $R^1$ is selected from

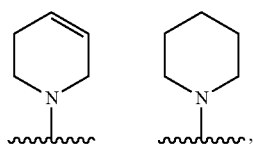 [SMILES: *N1CC=CCC1 ; *N1CCCCC1]

and wherein each is optionally substituted with one or more substituents independently selected from halogen, and C$_{1-6}$ haloalkyl. In some cases, $R^1$ is selected from

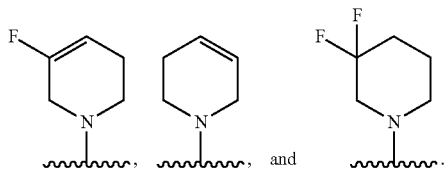

In some cases, $R^1$ is selected from

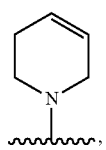

which is optionally substituted with one or more substituents independently selected from halogen, C$_{1-6}$ cyanoalkyl, and C$_{1-6}$ haloalkyl. In some cases, $R^1$ is

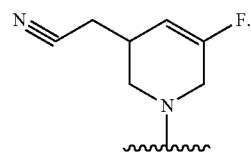 [SMILES: *N1CC(F)=CC(CC#N)C1]

In some embodiments, for a compound or salt of Formula (I), Formula (I-A), Formula (I-B), Formula (I-C), or Formula (I-G), $R^1$ is selected from

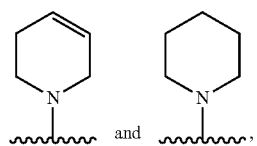 [SMILES: *N1CC=CCC1 ; *N1CCCCC1]

wherein each is optionally substituted two substituents independently selected from halogen, —OH, —NH$_2$, —NO$_2$, C$_{1-6}$ aminoalkyl, C$_{1-6}$ alkoxy, C$_{1-6}$ hydroxyalkyl, C$_{1-6}$ haloalkyl, and C$_{1-6}$ alkyl. In some cases, $R^1$ is selected from

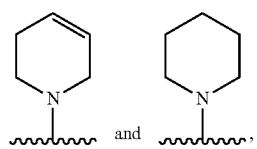 [SMILES: *N1CC=CCC1 ; *N1CCCCC1]

wherein each is optionally substituted with two substituents independently selected from halogen, and C$_{1-6}$ haloalkyl. In some cases, $R^1$ is

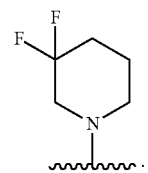

In some embodiments, for a compound or salt of Formula (I), Formula (I-A), Formula (I-B), Formula (I-C), or Formula (I-G), $R^1$ is selected from an optionally substituted 6- to 10-membered heterocycle. In some cases, the 6- to 10-membered heterocycle contains 0-2 additional heteroatoms selected from nitrogen, oxygen, and sulfur. In some cases, the 6- to 10-membered heterocycle contains at least 1 nitrogen atom. In some cases, $R^1$ is selected from

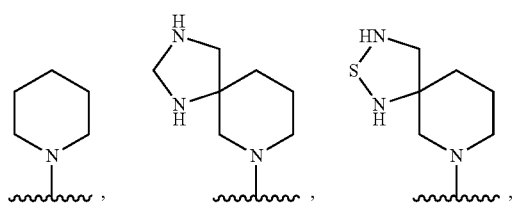

-continued

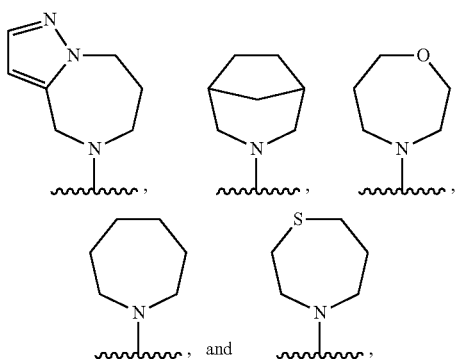

each of which is optionally substituted with one or more substituents independently selected from halogen, =O, —OH, —CN, —NHCN, —C(O)N($R^{20}$)$_2$, $C_{1-6}$ aminoalkyl, $C_{1-6}$ hydroxyalkyl, $C_{1-6}$ cyanoalkyl, and $C_{1-6}$ alkyl. In some cases, each $R^{20}$ is independently selected from hydrogen; and $C_{1-6}$ alkyl, $C_{3-12}$ carbocycle, and 3- to 12-membered heterocycle, each of which is optionally substituted with one or more substituents independently selected from halogen, —OH, —CN, —NO$_2$, —NH$_2$, —N($C_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle. In some cases, $R^1$ is selected from

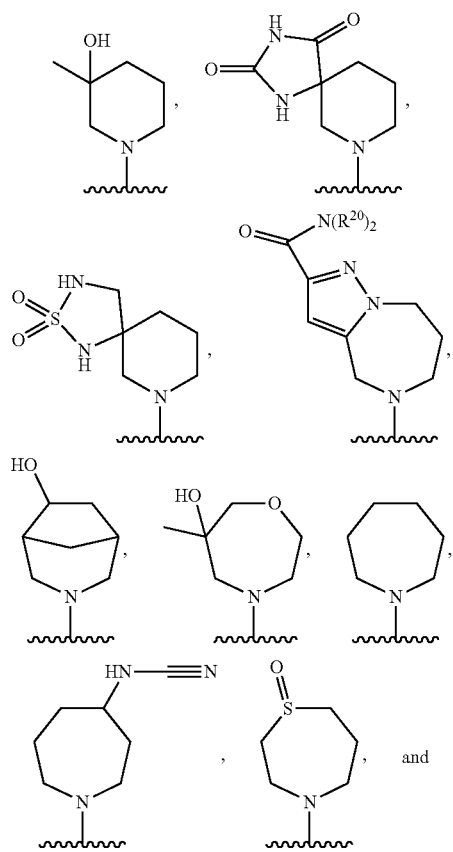

-continued

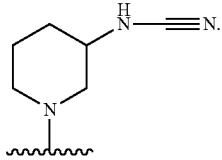

In some embodiments, for a compound or salt of Formula (I), Formula (I-A), Formula (I-B), Formula (I-C), or Formula (I-G), $R^1$ is selected from 6- to 7-membered heterocycle. In some cases, $R^1$ is selected from 7-membered heterocycle. In some cases, $R^1$ is selected from 6-membered heterocycle. In some cases, the 6- to 7-membered heterocycle contains only 1 nitrogen atom and optionally one or more additional heteroatoms selected from oxygen, and sulfur. In some cases, the optionally one or more additional heteroatoms are selected from sulfur. In some cases, the optionally one or more additional heteroatoms are selected from oxygen. In some cases, the 6- to 7-membered heterocycle contains only 1 nitrogen atom and no further additional heteroatoms. In some cases, the 6- to 7-membered heterocycle is a non-aromatic 6- to 7-membered heterocycle. In some cases, the 6- to 7-membered heterocycle of $R^1$ is bound to the respective Formula via the only 1 nitrogen atom. In some cases, $R^1$ is selected from

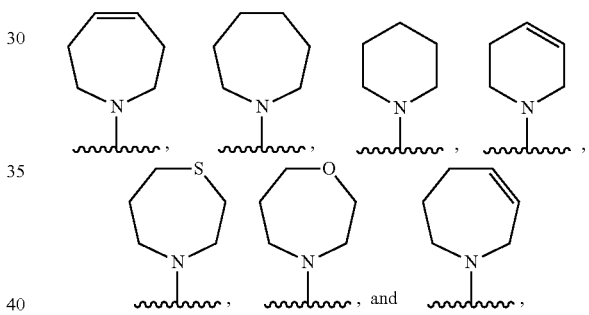

each of which is substituted. In some cases, $R^1$ is selected from

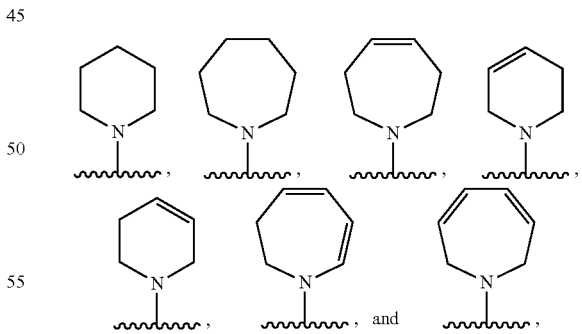

each of which is substituted. In some cases, the substituents of $R^1$ are each selected from one or more halogen, —OR$^{20}$, —SR$^{20}$, —N($R^{20}$)$_2$, —NHCN, —NO$_2$, =O, —CN, $C_{1-6}$ fluoroalkyl, and $C_{2-6}$ alkynyl; and further optionally substituted with one or more substituents independently selected from —C(O)N($R^{20}$)$_2$, $C_{1-6}$ aminoalkyl, $C_{1-6}$ hydroxyalkyl, $C_{1-6}$ cyanoalkyl, $C_{1-6}$ alkyl, and $C_{2-6}$ alkenyl. In some cases, the substituents of $R^1$ are each selected from one or more halogen, —OR$^{20}$, —N($R^{20}$)$_2$, —NHCN, =O, —CN, and $C_{2-6}$ alkynyl; and further optionally substituted with one or more substituents independently selected from —C(O)N($R^{20}$)$_2$, $C_{1-6}$ aminoalkyl, $C_{1-6}$ hydroxyalkyl, $C_{1-6}$ cyanoalkyl, and $C_{1-6}$ alkyl. In some cases, the substituents of $R^1$ are each selected from one or more halogen, —OH, —NHCN, =O, —CN, and $C_{2-6}$ alkynyl; and further optionally substituted with one or more substituents independently selected from $C_{1-6}$ alkyl. In some cases, $R^1$ is selected from

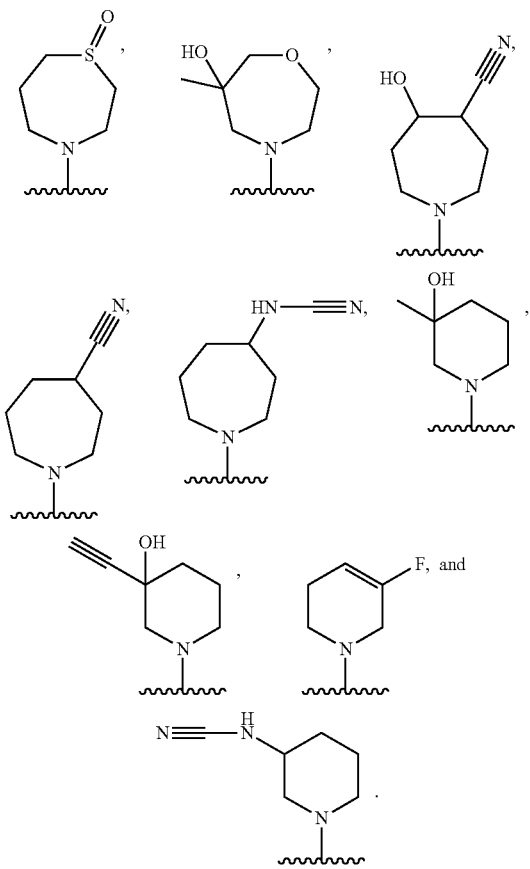

In some cases, $R^1$ is selected from

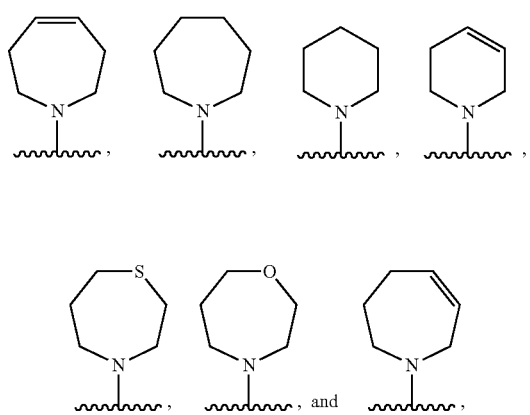

each of which is optionally substituted. In some cases, $R^1$ is selected from

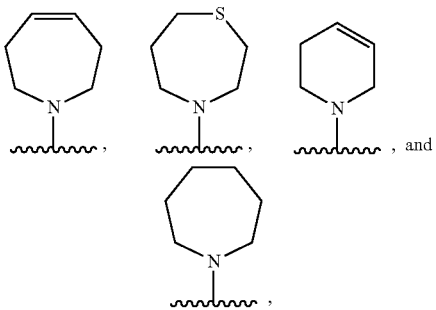

each of which is optionally substituted. In some cases, $R^1$ is selected from

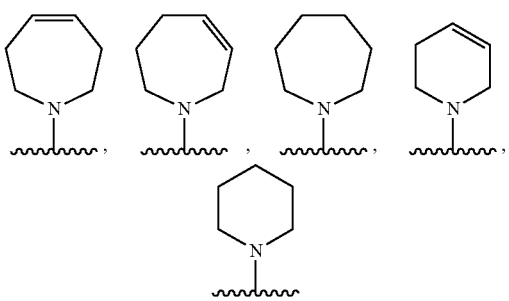

each of which is optionally substituted. In some cases, the one or more optional substituents of $R^1$ are each independently selected from fluorine, —OH, —C(O)NH$_2$, —NH—C(O)—($C_{1-6}$ alkoxy), —NH—C(O)—($C_{1-6}$ hydroxyalkyl), —NH$_2$, —NH(CN), =O, —CN, $C_{1-6}$ hydroxyalkyl, $C_{1-6}$ cyanoalkyl, $C_{1-6}$ alkyl, and $C_{2-6}$ alkynyl. In some cases, the one or more optional substituents of $R^1$ are each independently selected from halogen, —OH, —CN, $C_{1-6}$ cyanoalkyl, $C_{1-6}$ alkyl, and $C_{2-6}$ alkynyl. In some cases, the one or more optional substituents of $R^1$ are each independently selected from halogen, —OH, and —CN. In some cases, the one or more optional substituents of $R^1$ are each independently selected from fluorine, —OH, —CN, $C_{1-6}$ cyanoalkyl, $C_{1-6}$ alkyl, oxo, and $C_{2-6}$ alkynyl. In some cases, the one or more optional substituents of $R^1$ are each independently selected from fluorine, —OH, —CN, $C_{1-6}$ cyanoalkyl, $C_{1-6}$ alkyl, and $C_{2-6}$ alkynyl. In some cases, $R^1$ is selected from

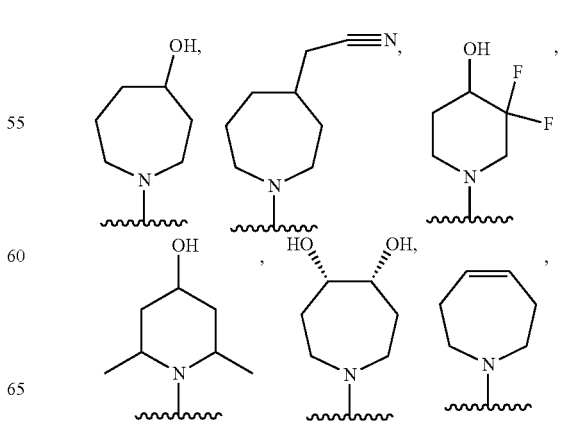

-continued
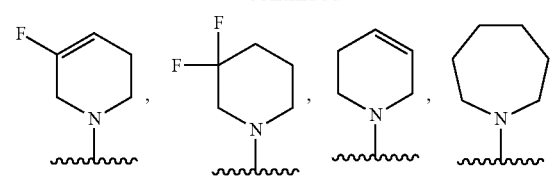
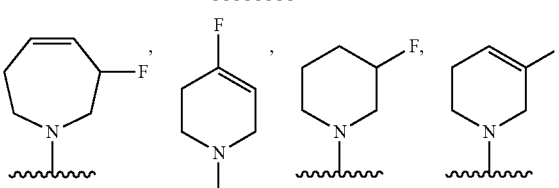
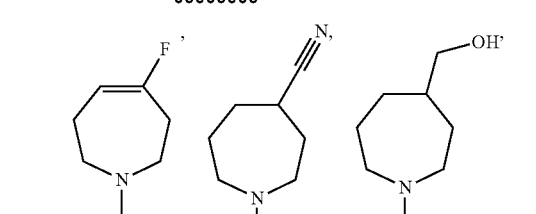
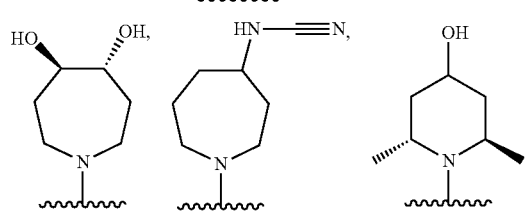
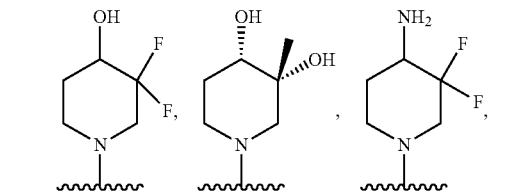
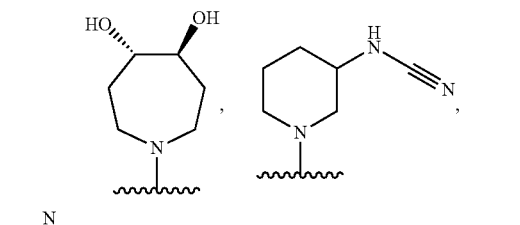
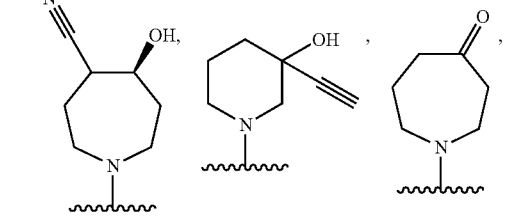
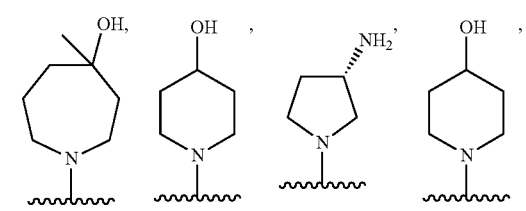
-continued
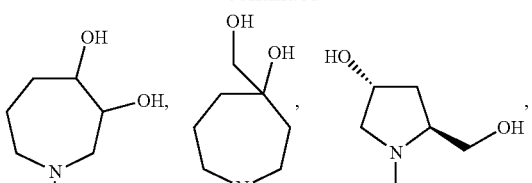
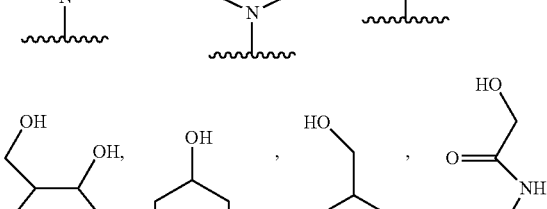
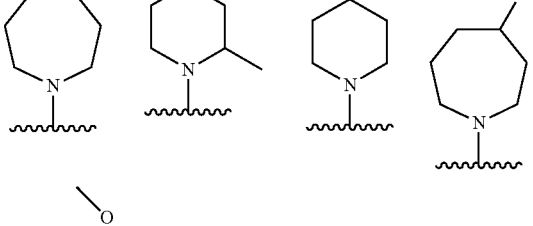
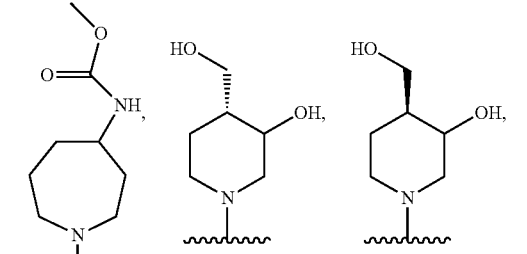
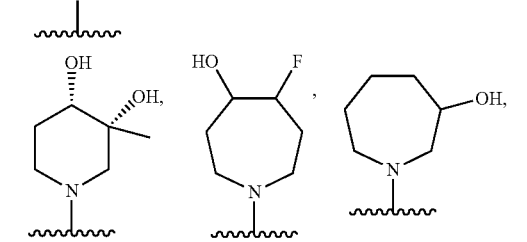
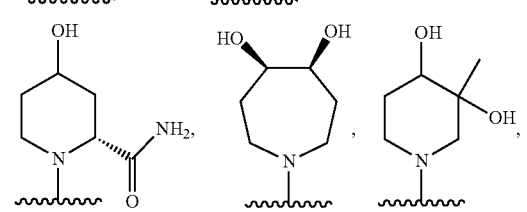
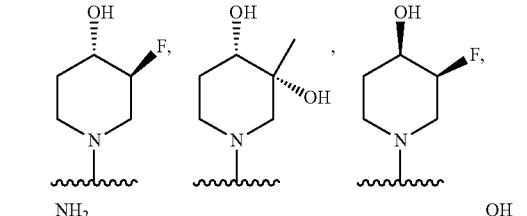
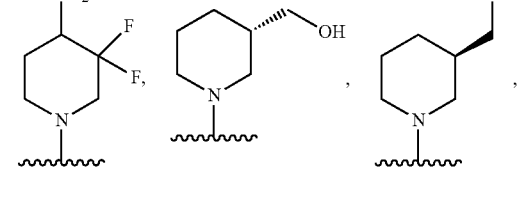

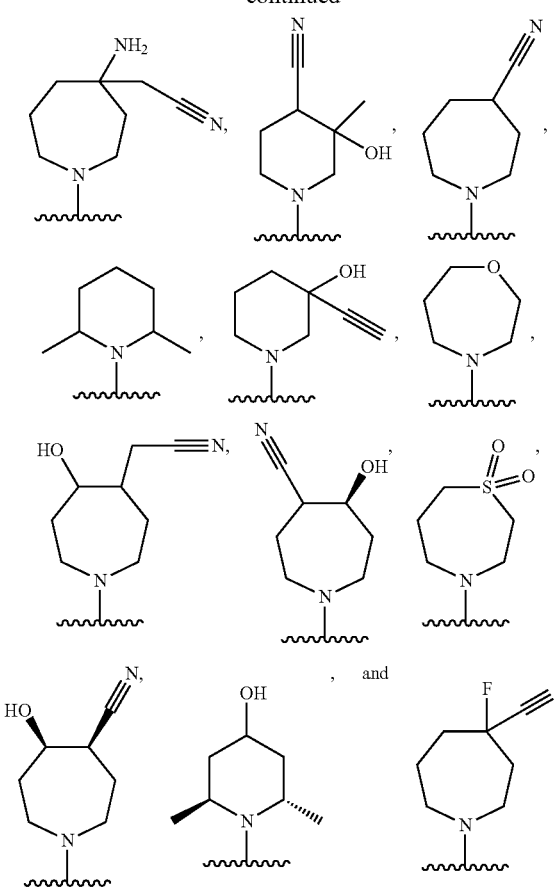
In some cases, R¹ is selected from
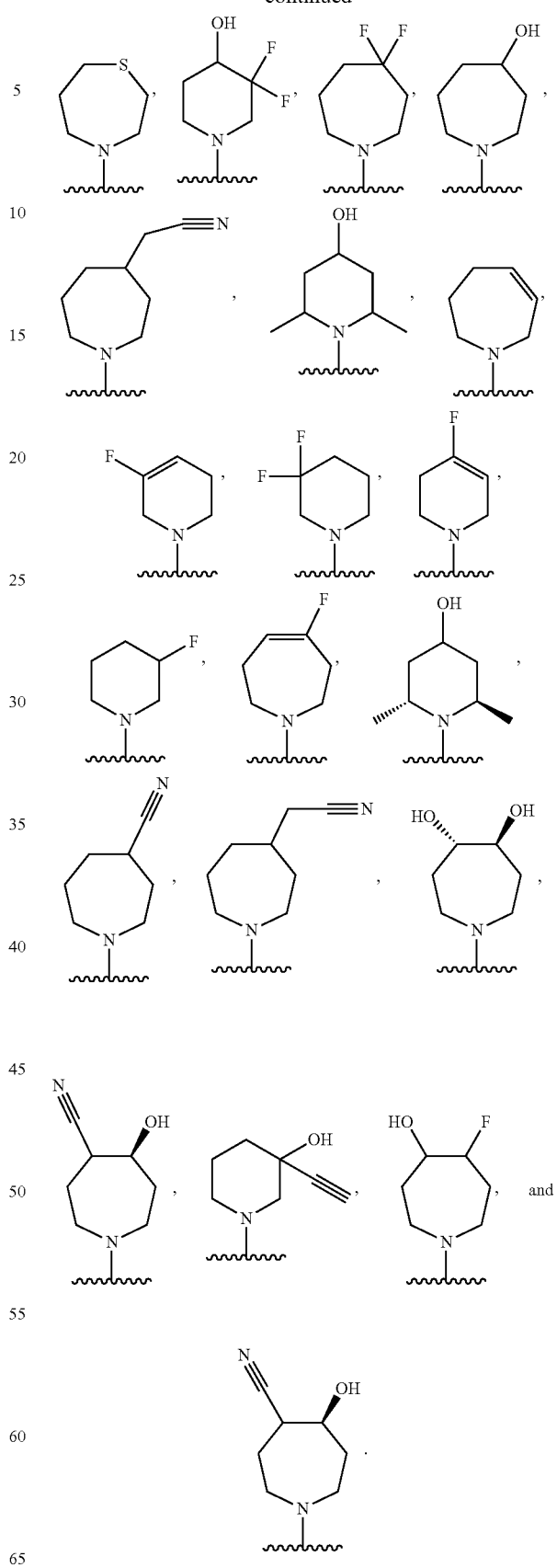

149

In some cases, R¹ is selected from

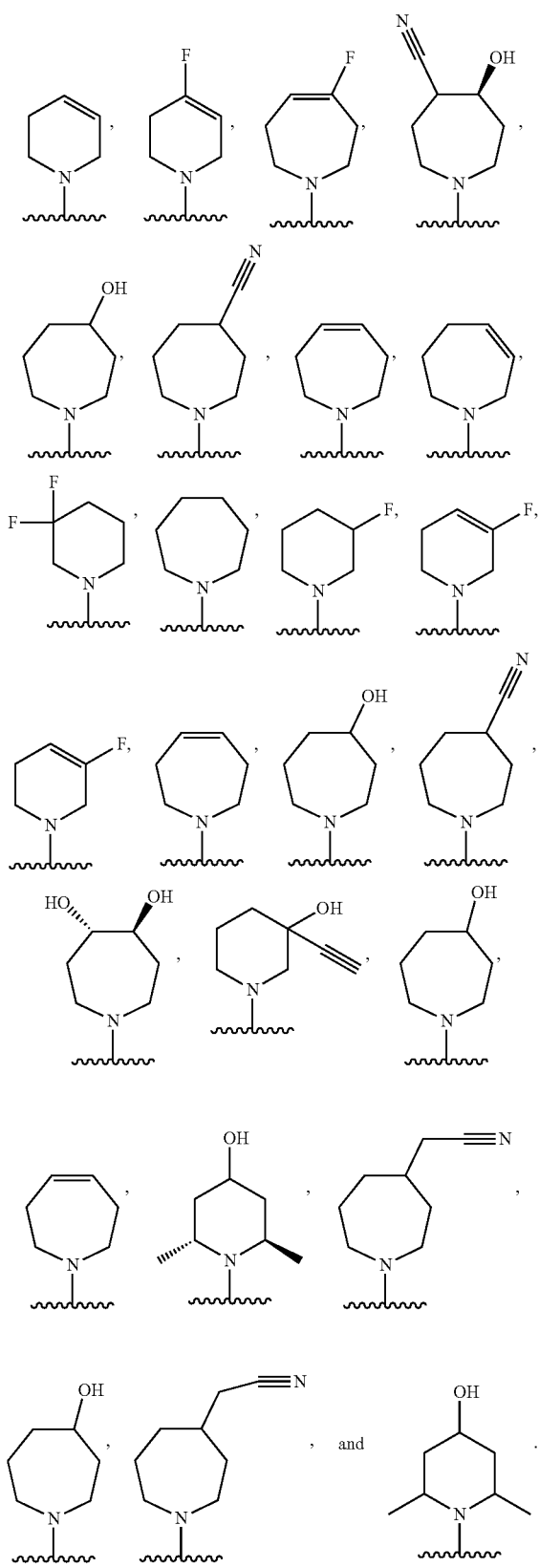

150

In some cases, R¹ is selected from

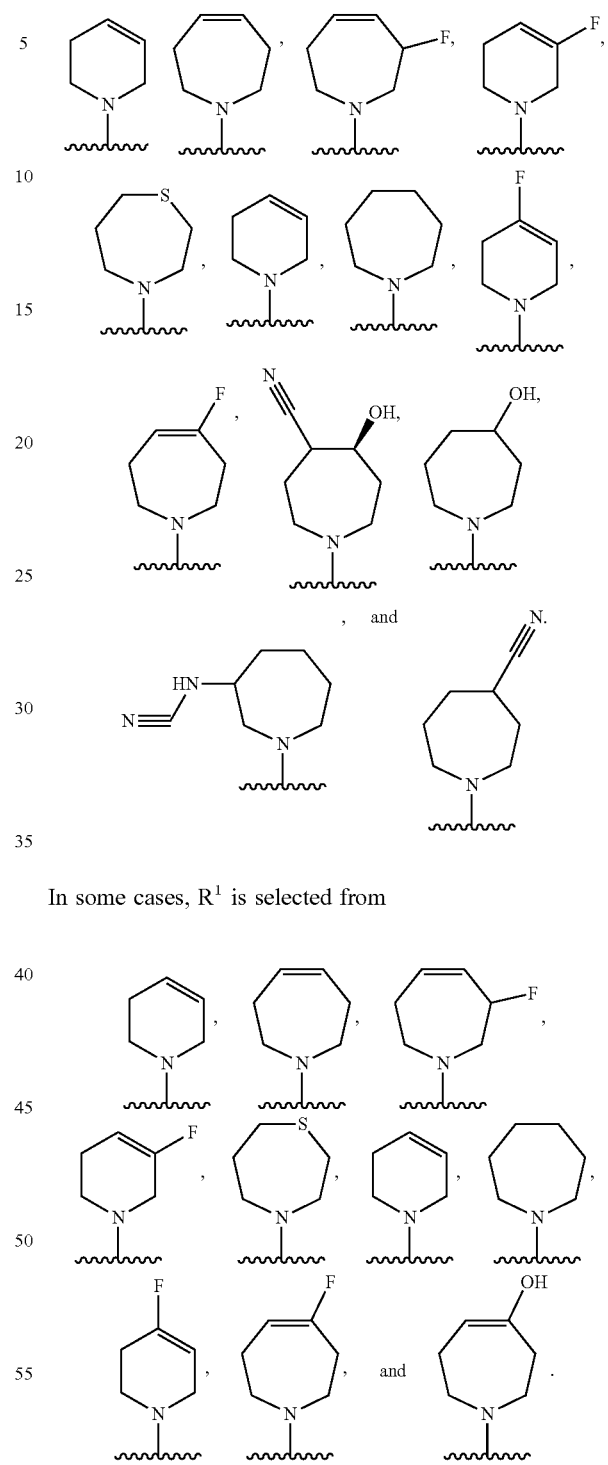

In some embodiments, for a compound or salt of Formula (I), Formula (I-A), Formula (I-B), Formula (I-C), or Formula (I-G), the 5- to 12-membered heterocycle of R¹ is unsaturated and a bridged heterocycle. In some cases, R¹ is selected from an optionally substituted 7- to 8-membered unsaturated and bridged heterocycle. In some cases, R¹ is selected from

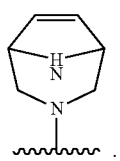

In some embodiments, for a compound or salt of Formula (I), Formula (I-A), Formula (I-B), Formula (I-C), or Formula (I-G), $R^1$ is selected from 5- to 10-membered heterocycle, 7-, 8-, 10-, 11-membered spiro heterocycle, and 6-, 9-, 10-, 11-, and 12-membered fused heterocycle, and wherein each are optionally substituted with one or more substituents independently selected from halogen, $-N(R^{20})_2$, $C_{1-6}$ alkyl, $-OR^{20}$, $-N(R^{20})C(O)N(R^{20})_2$, $-B(OR^{20})_2$, $C_{1-6}$ cyanoalkyl, $-N(R^{20})C(O)N(R^{20})_2$, =O, $C_{1-6}$ hydroxyalkyl, halogen, $-N(R^{20})C(O)R^{20}$, $-N(R^{20})S(O)_2(R^{20})$, and $C_{1-6}$ aminoalkyl. In some cases, $R^1$ is selected from

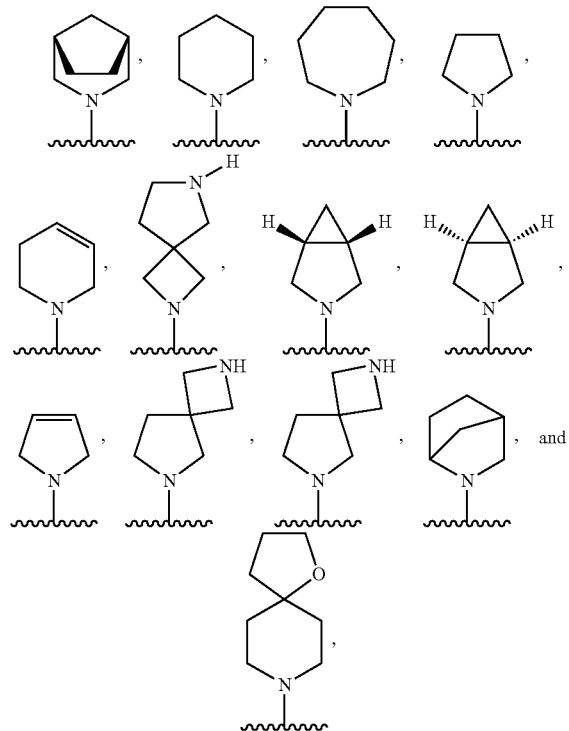

wherein each is optionally substituted with one or more substituents independently selected from halogen, $-N(R^{20})_2$, $C_{1-6}$ alkyl, $-OR^{20}$, $-N(R^{20})C(O)N(R^{20})_2$, $-B(OR^{20})_2$, $C_{1-6}$ cyanoalkyl, $-N(R^{20})C(O)N(R^{20})_2$, =O, $C_{1-6}$ hydroxyalkyl, halogen, $-N(R^{20})C(O)R^{20}$, $-N(R^{20})S(O)_2(R^{20})$, and $C_{1-6}$ aminoalkyl. In some cases, $R^1$ is selected from

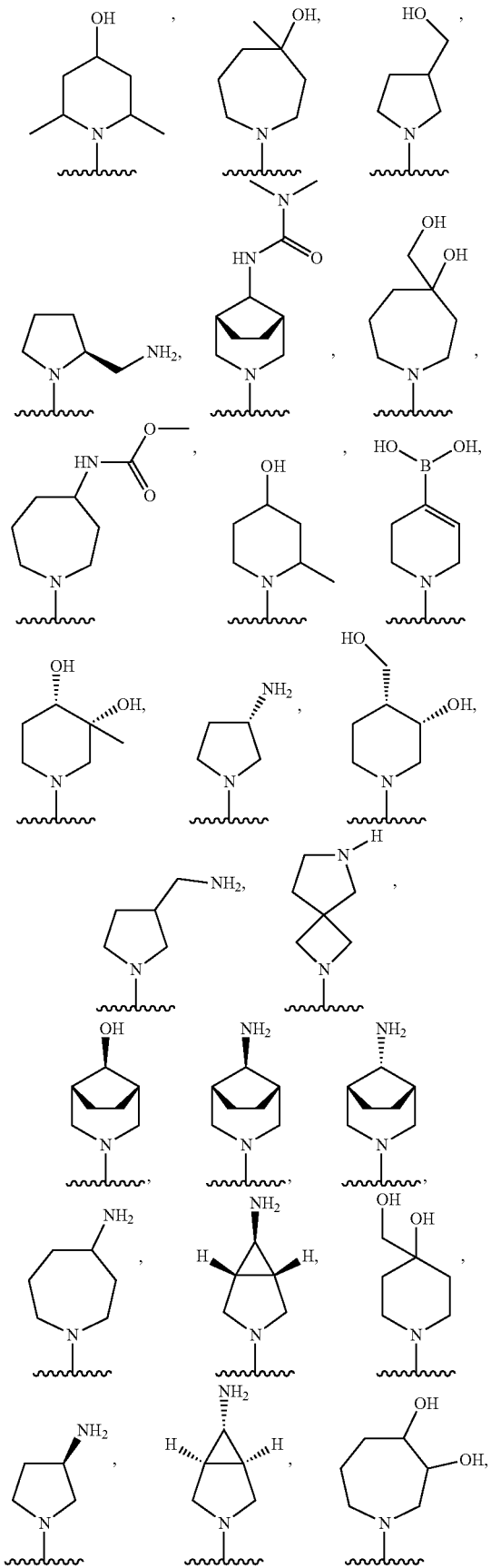

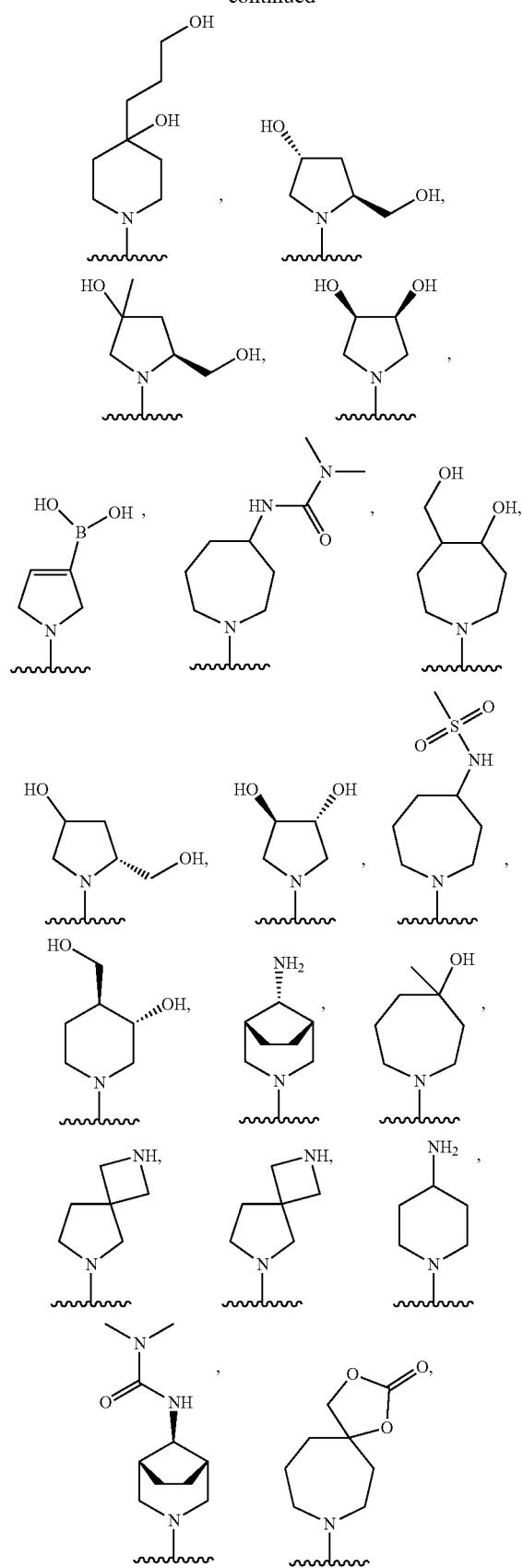

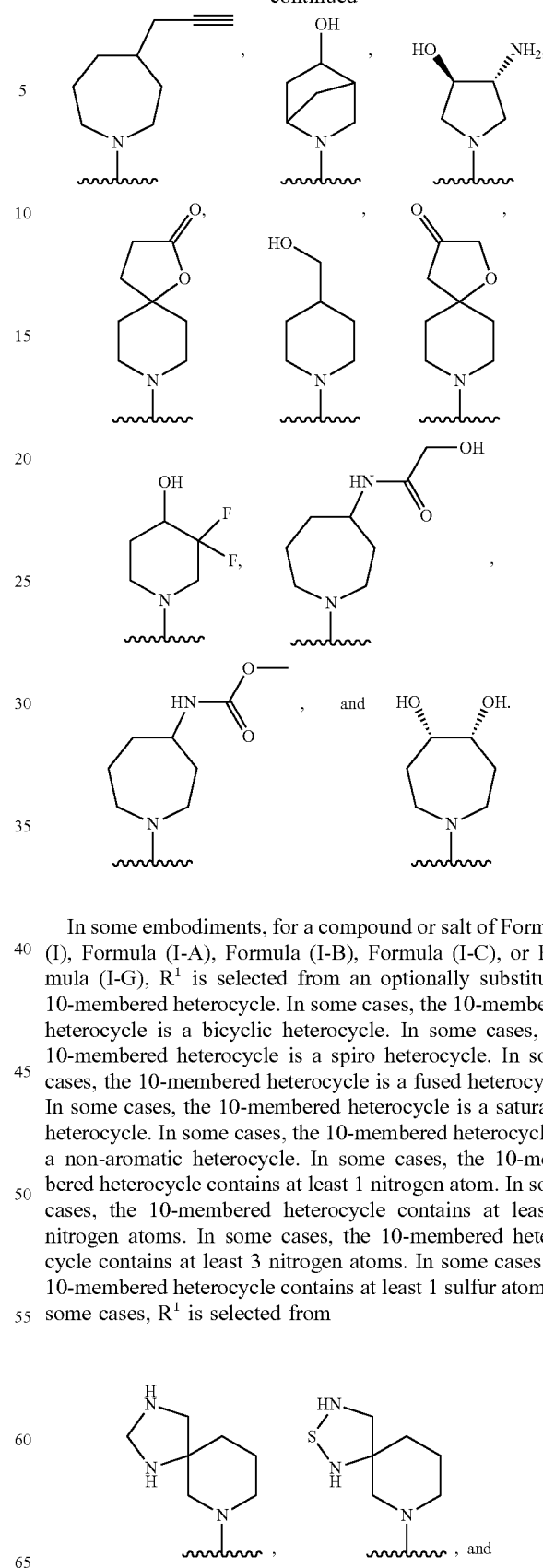

In some embodiments, for a compound or salt of Formula (I), Formula (I-A), Formula (I-B), Formula (I-C), or Formula (I-G), $R^1$ is selected from an optionally substituted 10-membered heterocycle. In some cases, the 10-membered heterocycle is a bicyclic heterocycle. In some cases, the 10-membered heterocycle is a spiro heterocycle. In some cases, the 10-membered heterocycle is a fused heterocycle. In some cases, the 10-membered heterocycle is a saturated heterocycle. In some cases, the 10-membered heterocycle is a non-aromatic heterocycle. In some cases, the 10-membered heterocycle contains at least 1 nitrogen atom. In some cases, the 10-membered heterocycle contains at least 2 nitrogen atoms. In some cases, the 10-membered heterocycle contains at least 3 nitrogen atoms. In some cases the 10-membered heterocycle contains at least 1 sulfur atom. In some cases, $R^1$ is selected from

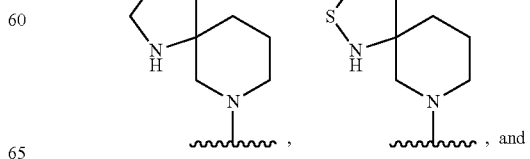

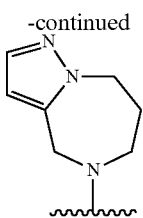

each of which is optionally substituted with one or more substituents independently selected from halogen, =O, —OH, —CN, —NHCN, —C(O)N($R^{20}$)$_2$, $C_{1-6}$ aminoalkyl, $C_{1-6}$ hydroxyalkyl, $C_{1-6}$ cyanoalkyl, and $C_{1-6}$ alkyl. In some cases, $R^1$ is selected from

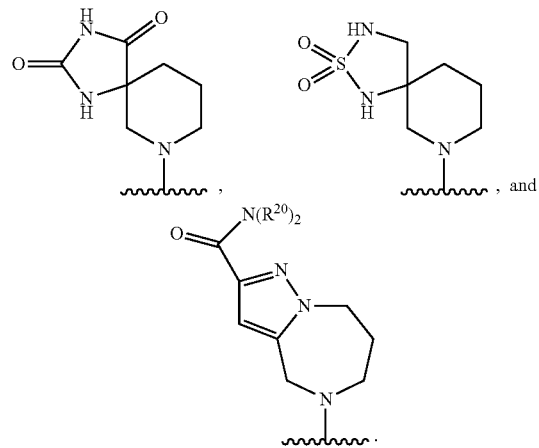

In some cases, $R^1$ is selected from

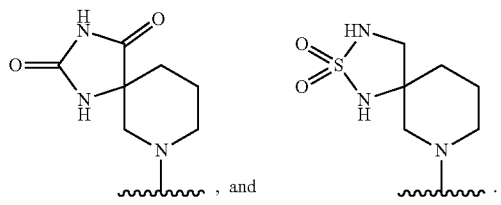 [SMILES: *N1CCCC2(C1)NC(=O)NC2=O ; *N1CCCC2(CNS(=O)(=O)N2)C1]

In some cases, $R^1$ is selected from

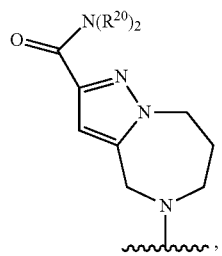

which is optionally substituted with one or more substituents independently selected from halogen, —O$R^{20}$, —S$R^{20}$, —N($R^{20}$)$_2$, —NO$_2$, =O, —CN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, and $C_{2-6}$ alkynyl.

In some embodiments, for a compound or salt of Formula (I), Formula (I-A), Formula (I-B), Formula (I-C), or Formula (I-G), $R^1$ is selected from an optionally substituted unsaturated 9- to 11-membered heterocycle. In some cases, $R^1$ is selected from an optionally substituted unsaturated 10-membered heterocycle. In some cases, $R^1$ is selected from an optionally substituted unsaturated 10-membered fused heterocycle. In some cases, $R^1$ is

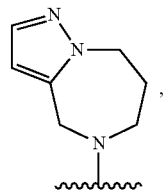 [SMILES: *N1CCCn2nccc2C1]

which is optionally substituted. In some cases, the one or more optional substituents are selected from halogen, —OH, —C(O)N($R^{20}$)$_2$, —N($R^{20}$)$_2$, —C(O)$R^{20}$, —NO$_2$, =O, —CN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, and $C_{2-6}$ alkynyl. In some cases, $R^1$ is

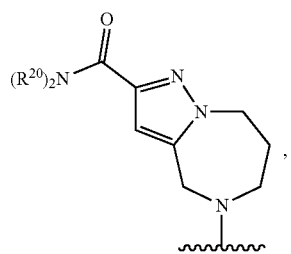

optionally substituted with one or more substituents selected from —N($R^{20}$)$_2$, —C(O)$R^{20}$, —NO$_2$, =O, —CN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, and $C_{2-6}$ alkynyl. In some cases, each $R^{20}$ is independently selected from hydrogen; and $C_{1-6}$ alkyl, and $C_{3-12}$ carbocycle, and each of which is optionally substituted with one or more substituents independently selected from halogen, —OH, —CN, —NO$_2$, —NH$_2$, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-12}$ carbocycle, and 3- to 12-membered heterocycle.

In some embodiments, for a compound or salt of Formula (I), Formula (I-A), Formula (I-B), Formula (I-C), or Formula (I-G), $R^1$ is selected from a 7- to 11-membered spiro heterocycle. In some cases, $R^1$ is selected from a 10-membered spiro heterocycle. In some cases, the spiro heterocycle has at least 3 nitrogen atoms. In some cases, the spiro heterocycle has at least 1 sulfur atom. In some cases, $R^1$ is selected from

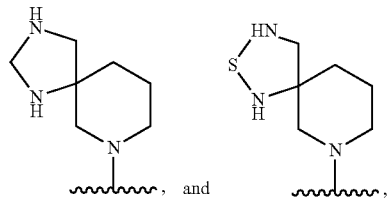 [SMILES: *N1CCCC2(CNCN2)C1 ; *N1CCCC2(CNSN2)C1]

each of which is optionally substituted. In some cases, the one or more optional substituents are independently selected from halogen, —OH, —N(R$^{20}$)$_2$, —NO$_2$, =O, —CN, —NHCN, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, C$_{2-6}$ alkenyl, and C$_{2-6}$ alknyl. In some cases, R$^1$ is selected from

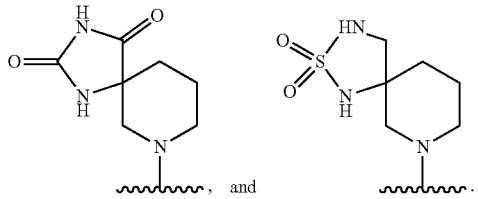 [SMILES: *N1CCCC2(C1)NC(=O)NC2=O ; *N1CCCC2(CNS(=O)(=O)N2)C1]

In some cases, R$^1$ is

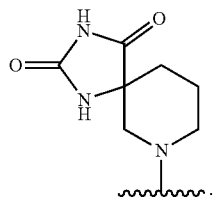 [SMILES: *N1CCCC2(C1)NC(=O)NC2=O]

In some cases, R$^1$ is

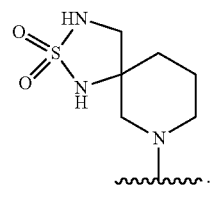

In some embodiments, for a compound or salt of Formula (I), Formula (I-A), Formula (I-B), Formula (I-C), or Formula (I-G), R$^1$ is selected from an optionally substituted 8- to 10-membered fused heterocycle. In some cases, the 8- to 10-membered fused heterocycle is a bicyclic heterocycle. In some cases, the 8- to 10-membered fused heterocycle is a saturated heterocycle. In some cases, the 8- to 10-membered fused heterocycle is an unsaturated heterocycle. In some cases, the 8- to 10-membered heterocycle is a non-aromatic heterocycle. In some cases, R$^1$ is selected from an optionally substituted 10-membered fused heterocycle. In some cases, the 10-membered fused heterocycle is a bicyclic heterocycle. In some cases, the 10-membered fused heterocycle is a saturated heterocycle. In some cases, the 10-membered heterocycle is a non-aromatic heterocycle. In some cases, the fused heterocycle has one saturated ring and one aromatic ring. In some cases, the fused heterocycle has one saturated ring and one unsaturated ring. In some cases, the fused heterocycle has two saturated rings. In some cases, the 10-membered heterocycle contains at least 1 nitrogen atom. In some cases, the 10-membered heterocycle contains at least 2 nitrogen atoms. In some cases, the 10-membered heterocycle contains at least 3 nitrogen atoms. In some cases, R$^1$ is selected from

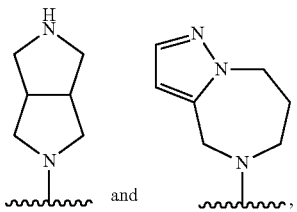 [SMILES: *N1CC2CNCC2C1 ; *N1CCCn2nccc2C1]

each of which is optionally substituted with one or more substituents. In some cases, R$^1$ is

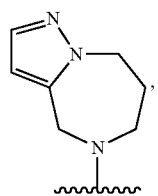

which is optionally substituted with one or more substituents. In some cases, the one or more optional substituents of R$^1$ are independently selected from halogen, —OH, —S(O)$_2$(R$^{20}$), —S(O)$_2$N(R$^{20}$)$_2$, —S(O)N(R$^{20}$)$_2$, —S(O)R$^{20}$ (=NR$^{20}$), —C(O)N(R$^{20}$)$_2$, —C(O)NHOR$^{20}$, —N(R$^{20}$)$_2$, —C(O)R$^{20}$, —NO$_2$, =O, —CN, C$_{1-6}$ alkyl-N(R$^{20}$)$_2$, C$_{1-6}$ aminoalkyl, C$_{1-6}$alkoxy, C$_{1-6}$hydroxyalkyl, C$_{1-6}$ cyanoalkyl, C$_{1-6}$haloalkyl, C$_{1-6}$alkyl, and C$_{2-6}$ alkynyl. In some cases, the optional one or more substituents are independently selected from halogen, =O, —OH, —CN, —NHCN, —S(O)$_2$(R$^{20}$), —S(O)$_2$N(R$^{20}$)$_2$, —S(O)N(R$^{20}$)$_2$, —S(O)R$^{20}$ (=NR$^{20}$), —C(O)R$^{20}$, —C(O)N(R$^{20}$)$_2$, —C(O)NR$^{20}$OR$^{20}$, C$_{1-6}$ alkyl-N(R$^{20}$)$_2$, C$_{1-6}$ aminoalkyl, C$_{1-6}$ hydroxyalkyl, C$_{1-6}$ cyanoalkyl, and C$_{1-6}$ alkyl. In some cases, the optional one or more substituents are independently selected from halogen, =O, C$_{1-6}$ alkyl-N(R$^{20}$)$_2$, —S(O)$_2$(R$^{20}$), —S(O)N(R$^{20}$)$_2$, —S(O)R$^{20}$(=NR$^{20}$), —C(O)R$^{20}$, —C(O)N(R$^{20}$)$_2$, and —C(O)NR$^{20}$OR$^{20}$. In some cases, the optional one or more substituents are independently selected from halogen, =O, —S(O)$_2$(R$^{20}$), —S(O)N(R$^{20}$)$_2$, —S(O)R$^{20}$(=NR$^{20}$), —C(O)R$^{20}$, —C(O)N(R$^{20}$)$_2$, and —C(O)NR$^{20}$OR$^{20}$. In some cases, R$^1$ is selected from

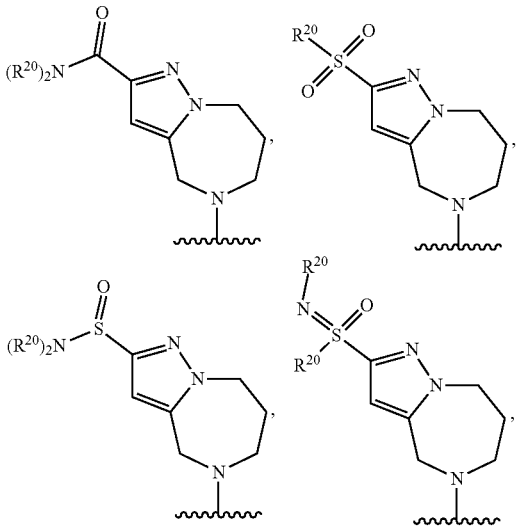

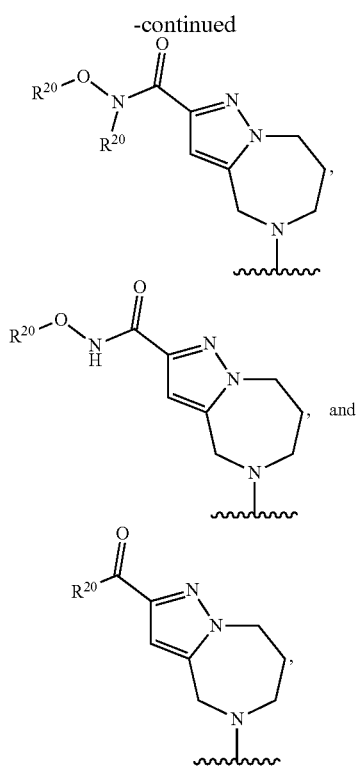

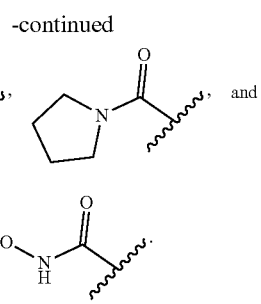

each of which is optionally substituted. In some cases, the optional one or more substituents are independently selected from —C(O)R$^{20}$, —C(O)N(R$^{20}$)$_2$, and —C(O)NR$^{20}$OR$^{20}$. In some cases, the optional one or more substituents are independently selected from —S(O)$_2$(R$^{20}$), —S(O)$_2$N(R$^{20}$)$_2$, —S(O)N(R$^{20}$)$_2$, —S(O)R$^{20}$(=NR$^{20}$). In some cases, the optional one or more substituents are independently selected from —S(O)N(R$^{20}$)$_2$. In some cases, the optional one or more substituents are independently selected from S(O)$_2$(R$^{20}$). In some cases, the optional one or more substituents are independently selected from S(O)R$^{20}$ (=NR$^{20}$). In some cases, the optional one or more substituents are independently selected from —C(O)R$^{20}$. In some cases, the optional one or more substituents are independently selected from —C(O)N(R$^{20}$)$_2$. In some cases, the optional one or more substituents are independently selected from —C(O)NR$^{20}$OR$^{20}$. In some cases, each R$^{20}$ is independently selected from hydrogen; and C$_{1-6}$ alkyl, C$_{3-12}$ carbocycle, and 3- to 12-membered heterocycle. In some cases, each R$^{20}$ is independently selected from hydrogen; and C$_{1-6}$ alkyl, and 3- to 12-membered heterocycle. In some cases, each R$^{20}$ is independently selected from hydrogen; and C$_{1-6}$ alkyl, and 3- to 12-membered saturated heterocycle. In some cases, the optional one or more substituents of R$^1$ are independently selected from halogen,

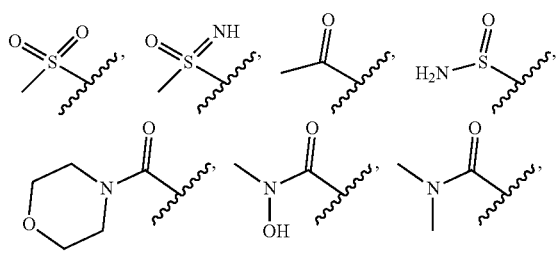

In some cases, R$^1$ is selected from

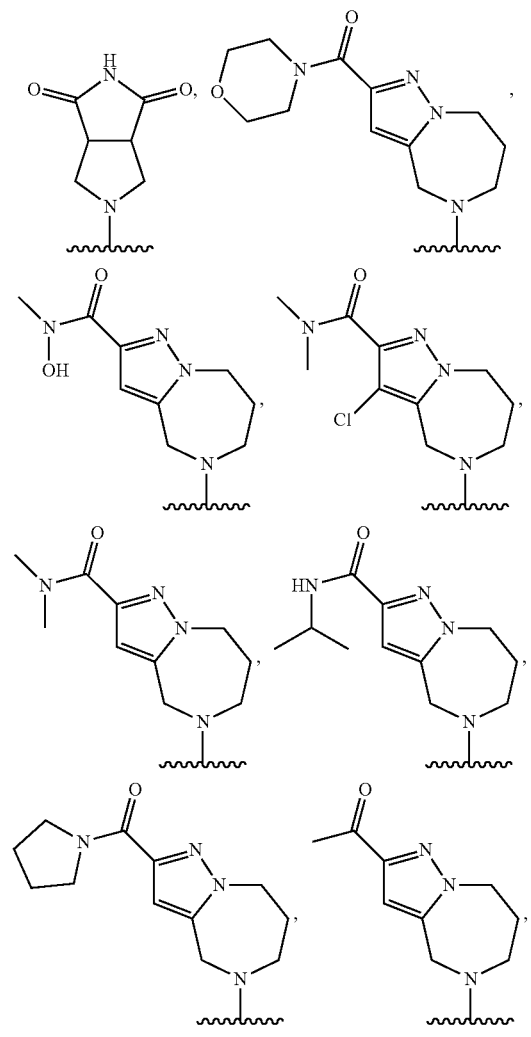

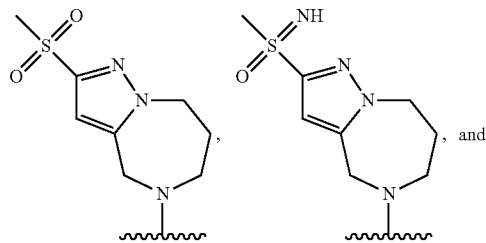

-continued

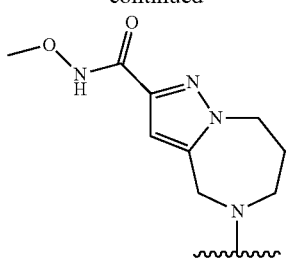

In some cases, R¹ is selected from

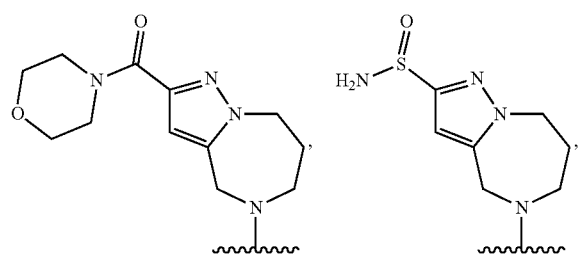

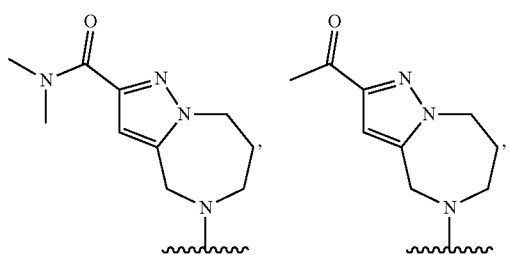

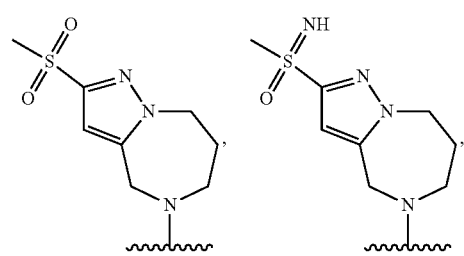

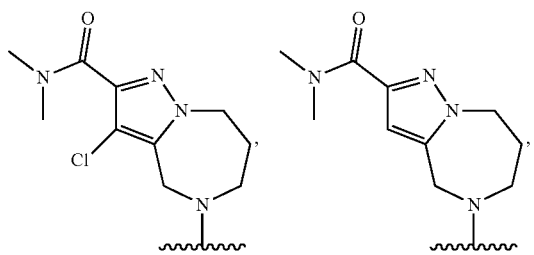

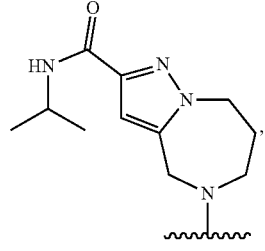

-continued

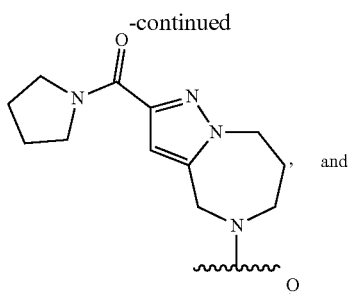, and

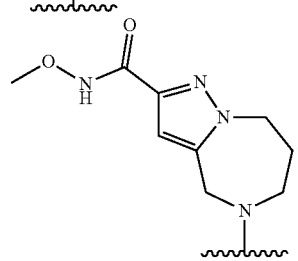

In some cases, the optional one or more substituents of R¹ are independently selected from halogen, and $C_{1-6}$ alkyl-N$(R^{20})_2$. In some cases, the optional one or more substituents of R¹ are independently selected from halogen,

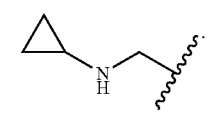

In some cases, R¹ is selected from

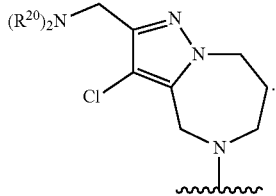

In some cases, each $R^{20}$ is independently selected from hydrogen, $C_{1-6}$ alkyl, and $C_{3-6}$ carbocycle. In some cases, R¹ is selected

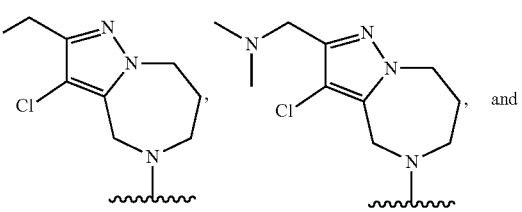

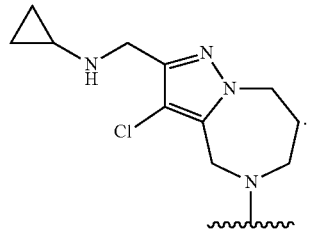

In some embodiments, for a compound or salt of Formula (I), Formula (I-A), Formula (I-B), Formula (I-C), or Formula (I-G), $R^1$ is selected from an optionally substituted 8- to 10-membered fused heterocycle. In some cases, the 8- to 10-membered fused heterocycle is a bicyclic heterocycle. In some cases, the 8- to 10-membered fused heterocycle is a saturated heterocycle. In some cases, the 8- to 10-membered fused heterocycle is an unsaturated heterocycle. In some cases, the 8- to 10-membered heterocycle is a non-aromatic heterocycle. In some cases, $R^1$ is selected from an optionally substituted 10-membered fused heterocycle. In some cases, the 10-membered fused heterocycle is a bicyclic heterocycle. In some cases, the 10-membered fused heterocycle is a saturated heterocycle. In some cases, the 10-membered heterocycle is a non-aromatic heterocycle. In some cases, the fused heterocycle has one saturated ring and one aromatic ring. In some cases, the fused heterocycle has one saturated ring and one unsaturated ring. In some cases, the fused heterocycle has two saturated rings. In some cases, the 10-membered heterocycle contains at least 1 nitrogen atom. In some cases, the 10-membered heterocycle contains at least 2 nitrogen atoms. In some cases, the 10-membered heterocycle contains at least 3 nitrogen atoms. In some cases, $R^1$ is selected from

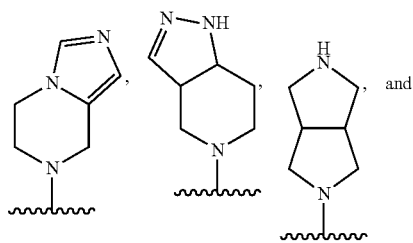

each of which is optionally substituted with one or more substituents. In some cases, $R^1$ is selected from

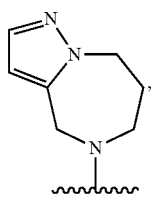 [SMILES: *N1CCCn2nccc2C1]

each of which is optionally substituted with one or more substituents. In some cases, $R^1$ is

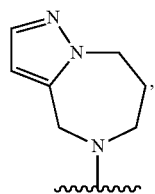

which is optionally substituted with one or more substituents. In some cases, the one or more optional substituents of $R^1$ are independently selected from halogen, —OH, —S(O)$_2$(R$^{20}$), —S(O)$_2$N(R$^{20}$)$_2$, —S(O)N(R$^{20}$)$_2$, —S(O)R$^{20}$ (=NR$^{20}$), —C(O)N(R$^{20}$)$_2$, —C(O)NHOR$^{20}$, —N(R$^{20}$)$_2$, —C(O)R$^{20}$, —NO$_2$, =O, —CN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, and C$_{2-6}$ alkynyl. In some cases, the optional one or more substituents are independently selected from halogen, =O, —OH, —CN, —NHCN, —S(O)$_2$(R$^{20}$), —S(O)$_2$N(R$^{20}$)$_2$, —S(O)N(R$^{20}$)$_2$, —S(O)R$^{20}$ (=NR$^{20}$), —C(O)R$^{20}$, —C(O)N(R$^{20}$)$_2$, —C(O)NR$^{20}$OR$^{20}$, C$_{1-6}$ alkyl-N(R$^{20}$)$_2$, C$_{1-6}$ aminoalkyl, C$_{1-6}$ hydroxyalkyl, C$_{1-6}$ cyanoalkyl, and C$_{1-6}$ alkyl. In some cases, the optional one or more substituents are independently selected from halogen, =O, C$_{1-6}$ alkyl-N(R$^{20}$)$_2$, —S(O)$_2$(R$^{20}$), —S(O)N(R$^{20}$)$_2$, —S(O)R$^{20}$(=NR$^{20}$), —C(O)R$^{20}$, —C(O)N(R$^{20}$)$_2$, and —C(O)NR$^{20}$OR$^{20}$. In some cases, the optional one or more substituents are independently selected from halogen, =O, —S(O)$_2$(R$^{20}$), —S(O)N(R$^{20}$)$_2$, —S(O)R$^{20}$(=NR$^{20}$), —C(O)R$^{20}$, —C(O)N(R$^{20}$)$_2$, and —C(O)NR$^{20}$OR$^{20}$. In some cases, the optional one or more substituents are independently selected from —C(O)R$^{20}$, —C(O)N(R$^{20}$)$_2$, and —C(O)NR$^{20}$OR$^{20}$. In some cases, the optional one or more substituents are independently selected from —S(O)$_2$(R$^{20}$), —S(O)$_2$N(R$^{20}$)$_2$, —S(O)N(R$^{20}$)$_2$, —S(O)R$^{20}$(=NR$^{20}$). In some cases, the optional one or more substituents are independently selected from —S(O)N(R$^{20}$)$_2$. In some cases, the optional one or more substituents are independently selected from S(O)$_2$(R$^{20}$). In some cases, the optional one or more substituents are independently selected from S(O)R$^{20}$(=NR$^{20}$). In some cases, the optional one or more substituents are independently selected from —C(O)R$^{20}$. In some cases, the optional one or more substituents are independently selected from —C(O)N(R$^{20}$)$_2$. In some cases, the optional one or more substituents are independently selected from —C(O)NR$^{20}$OR$^{20}$. In some cases, $R^1$ is selected from

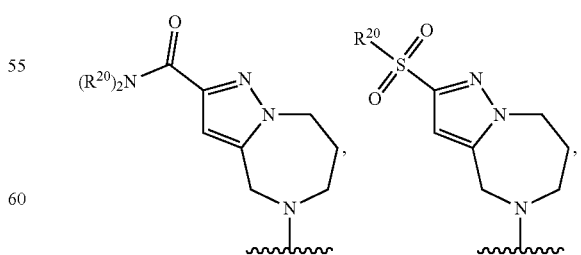

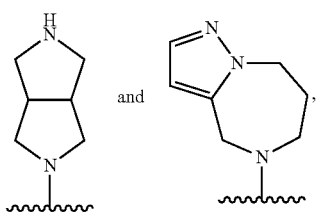

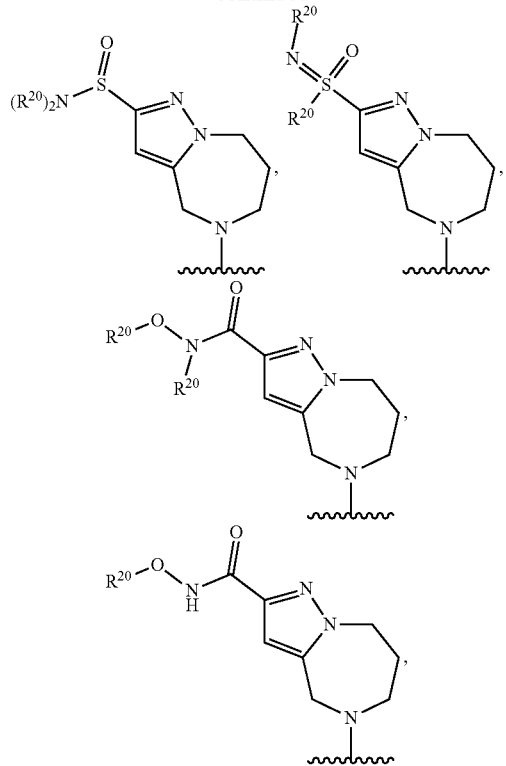

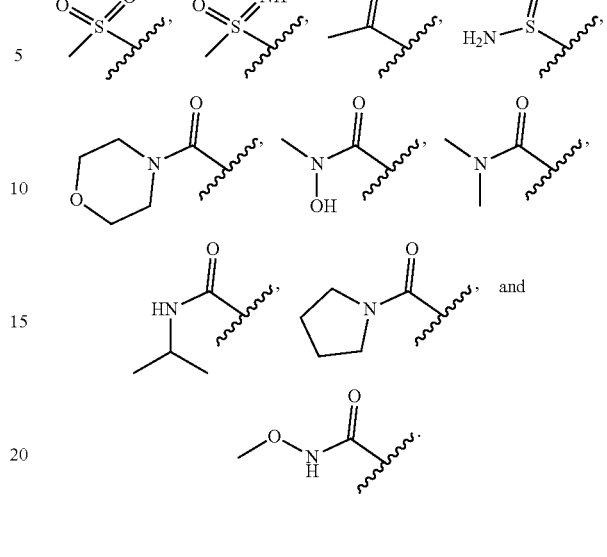

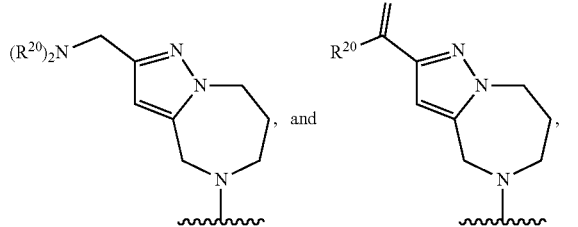

each of which is further optionally substituted. In some cases, the further one or more optional substituents are selected from halogen, —OH, =O, —CN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, and $C_{2-6}$ alkynyl. In some cases, the further one or more optional substituents are selected from halogen and $C_{1-6}$ alkyl. In some cases, the further one or more optional substituents are selected from halogen. In some cases, each $R^{20}$ is independently selected from hydrogen; and $C_{1-6}$ alkyl, $C_{3-12}$ carbocycle, and 3- to 12-membered heterocycle. In some cases, each $R^{20}$ is independently selected from hydrogen; and $C_{1-6}$ alkyl, and 3- to 12-membered heterocycle. In some cases, each $R^{20}$ is independently selected from hydrogen; and $C_{1-6}$ alkyl, and 3- to 12-membered saturated heterocycle. In some cases, each $R^{20}$ is independently selected from 5- to 6-membered saturated heterocycle. In some cases, the heterocycle of $R^{20}$ has at least one nitrogen atom. In some cases, the heterocycle of $R^{20}$ has at least one sulfur atom. In some cases, the heterocycle of $R^{20}$ has at least one oxygen atom. In some cases, the heterocycle of $R^{20}$ contains only 1 heteroatom. In some cases, the heterocycle of $R^{20}$ has at least two heteroatoms. In some cases, the heterocycle of $R^{20}$ contains only 2 heteroatoms. In some cases, the optional one or more substituents of $R^1$ are independently selected from halogen, In some cases, the optional one or more substituents of $R^1$ are independently selected from

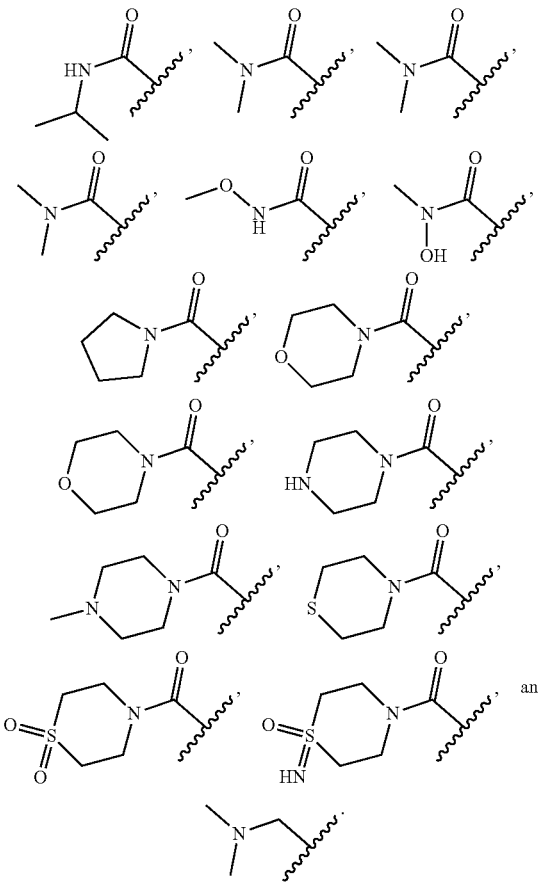

In some cases, R¹ is selected from
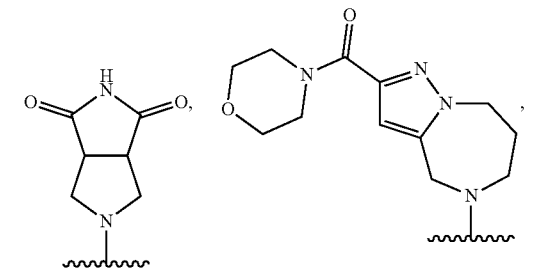
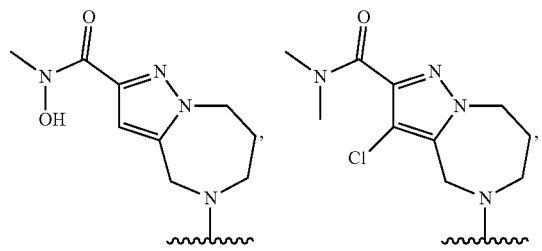
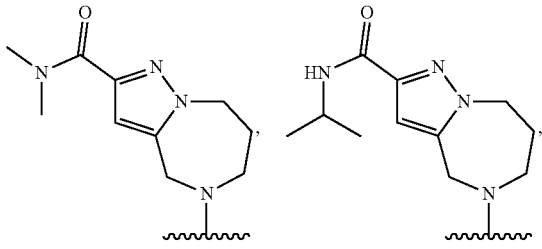
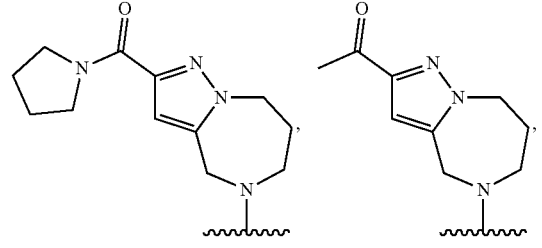
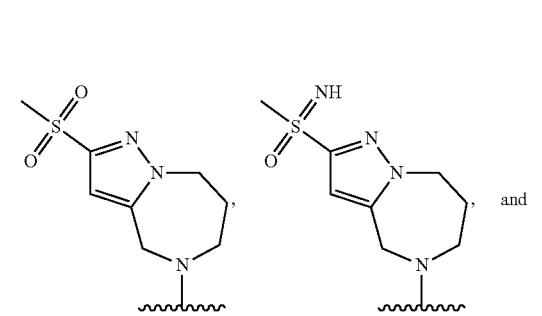
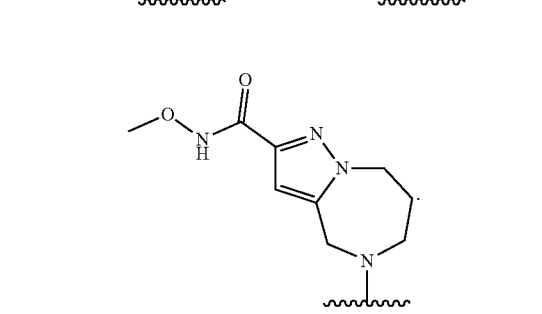
In some cases, R¹ is selected from
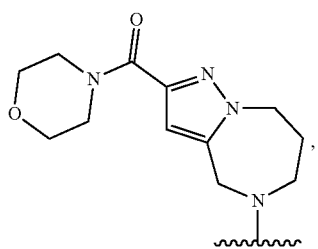
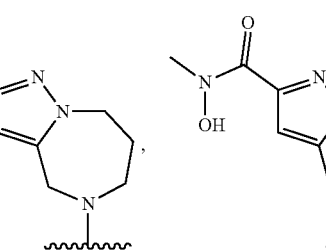
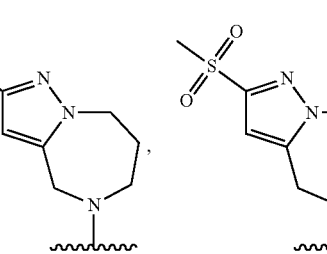
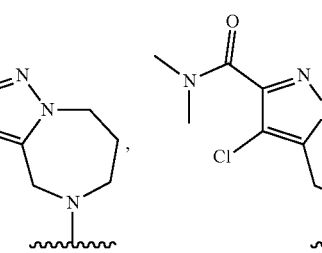
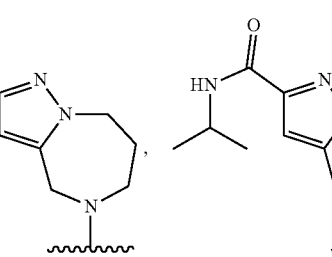
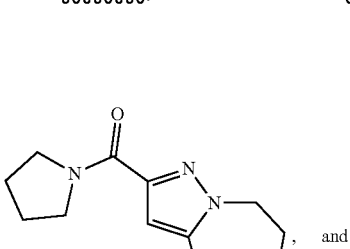

-continued

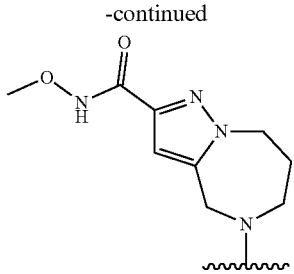

In some cases, the optional one or more substituents of R¹ are independently selected from halogen, and $C_{1-6}$ alkyl-N $(R^{20})_2$. In some cases, the optional one or more substituents of R¹ are independently selected from halogen,

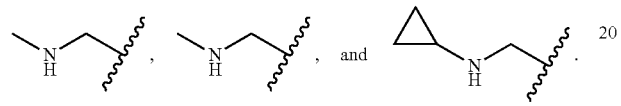

In some cases, R¹ is selected from

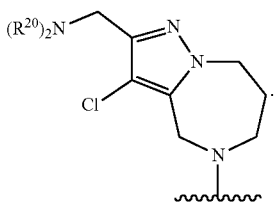

In some cases, each $R^{20}$ is independently selected from hydrogen, $C_{1-6}$ alkyl, and $C_{3-6}$ carbocycle. In some cases, R¹ is selected

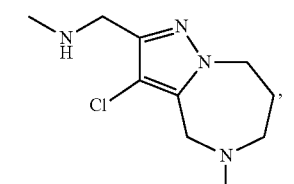

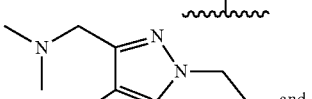, and

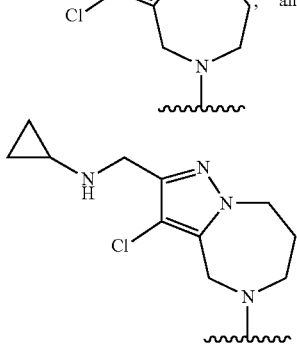

In some cases, R¹ is selected

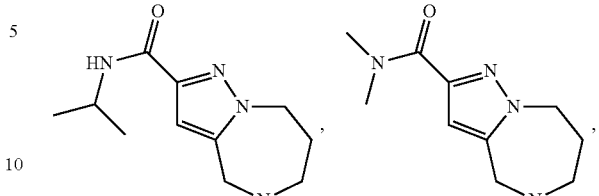

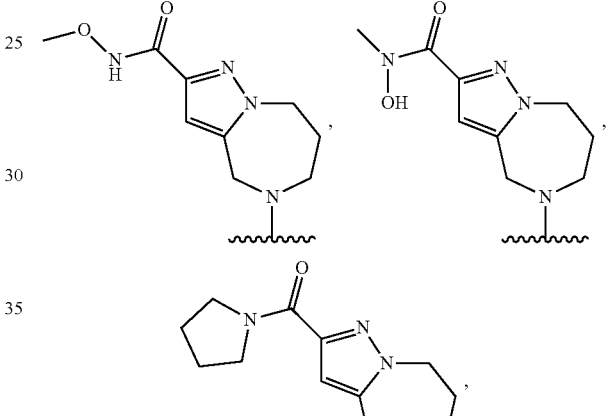

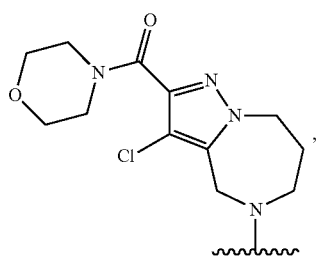

-continued

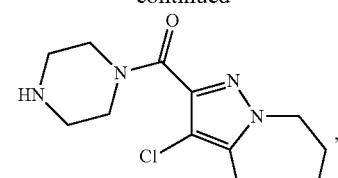

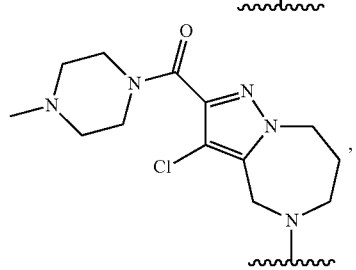

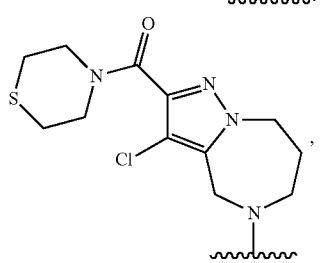

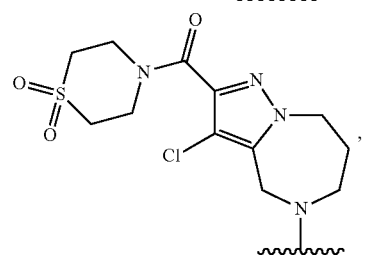

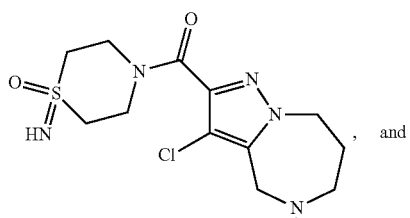, and

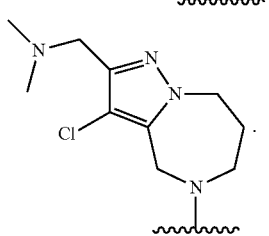.

In some embodiments, for a compound or salt of Formula (I), Formula (I-A), Formula (I-B), Formula (I-C), or Formula (I-G), when $R^1$ is substituted with —C(O)$R^{20}$, $R^{20}$ is selected from a 5- to 12-membered heterocycle.

In some embodiments, for a compound or salt of Formula (I), Formula (I-A), Formula (I-B), Formula (I-C), or Formula (I-G), $R^1$ is

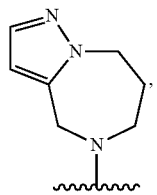 [SMILES: *N1CCCn2nccc2C1], and the one or more optional substituents of $R^1$ are independently selected from halogen, —OH, —S(O)$_2$($R^{20}$), —S(O)$_2$N($R^{20}$)$_2$, —S(O)N($R^{20}$)$_2$, —S(O)$R^{20}$(=N$R^{20}$), —C(O)N($R^{20}$)$_2$, —C(=N$R^{20}$)N($R^{20}$)$_2$, —C(O)NHO$R^{20}$, —N($R^{20}$)$_2$, —C(O)$R^{20}$, —NO$_2$, =O, —CN, $C_{1-6}$ alkyl-N($R^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkynyl, and optionally substituted 5- to 12-membered heterocycle. In some cases, the one or more optional substituents of $R^1$ are independently selected from halogen, —OH, —S(O)$_2$($R^{20}$), —S(O)$_2$N($R^{20}$)$_2$, —S(O)N($R^{20}$)$_2$, —S(O)$R^{20}$(=N$R^{20}$), —C(O)N($R^{20}$)$_2$, —C(=N$R^{20}$)N($R^{20}$)$_2$, —C(O)NHO$R^{20}$, —N($R^{20}$)$_2$, —C(O)$R^{20}$, —NO$_2$, =O, —CN, $C_{1-6}$ alkyl-N($R^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkynyl, and optionally substituted 5- to 12-membered heterocycle. In some cases, the one or more optional substituents of $R^1$ are independently selected from halogen, —CN, $C_{2-6}$ alkynyl, —C(=N$R^{20}$)N($R^{20}$)$_2$, and optionally substituted 5- to 12-membered heterocycle. In some cases, the one or more optional substituents of $R^1$ are independently selected from halogen, —C(=N$R^{20}$)N($R^{20}$)$_2$, and optionally substituted 5- to 12-membered heterocycle. In some cases, the one or more optional substituents of $R^1$ are independently selected from —C(=N$R^{20}$)N($R^{20}$)$_2$, and optionally substituted 5- to 12-membered heterocycle. In some cases, the one or more optional substituents of $R^1$ are independently selected from optionally substituted 5- to 12-membered heterocycle. In some cases, the one or more optional substituents of $R^1$ are independently selected from a 5-membered heterocycle and 9-membered heterocycle, each of which is optionally substituted independently with one or more $R^{1*}$. In some cases, $R^1$ is substituted with at least one halogen atom and optionally substituted with one or more substituents are independently selected from —CN, $C_{2-6}$ alkynyl, —C(=N$R^{20}$)N($R^{20}$)$_2$, and 5- to 12-membered heterocycle, wherein the 5- to 12-membered heterocycle is optionally substituted independently with one or more $R^{1*}$. In some cases, the heterocycle has at least one nitrogen atom. In some cases, the heterocycle has at least oxygen atom. In some cases, the heterocycle has at least one nitrogen atom and at least one oxygen atom. In some cases, heterocycle has at least two heteroatoms. In some cases, the heterocycle has at least three heteroatoms. In some cases, the heterocycle has at least four heteroatoms. In some cases, the heterocycle of the one or more optional substituents of $R^1$ is selected from

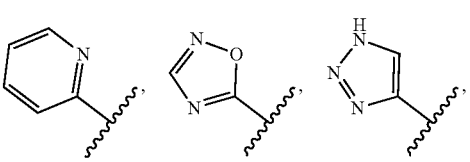

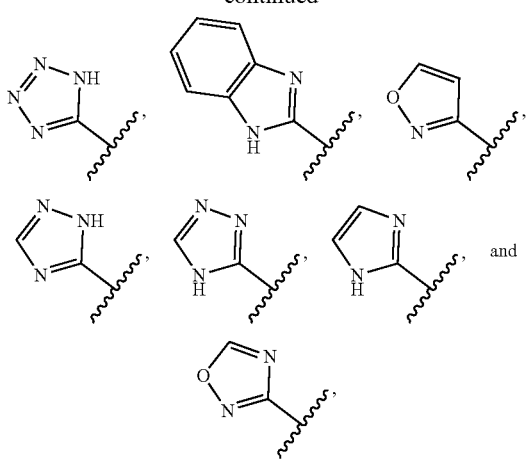

each of which is optionally substituted with one or more $R^{1*}$. In some cases, the heterocycle of the one or more optional substituents of $R^1$ is selected from

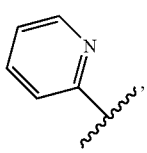

which is optionally substituted with one or more $R^{1*}$. In some cases, each $R^{1*}$ is independently selected from halogen, —$OR^{20}$, —$S(O)_2(R^{20})$, —$S(O)_2N(R^{20})_2$, —$S(O)N(R^{20})_2$, —$S(O)R^{20}(=NR^{20})$, —$NR^{20}S(O)_2R^{20}$, —$C(O)N(R^{20})_2$, —$C(O)NR^{20}OR^{20}$, —$N(R^{20})C(O)R^{20}$, —$N(R^{20})C(O)N(R^{20})_2$, —$N(R^{20})C(O)OR^{20}$, —$N(R^{20})_2$, —$C(O)R^{20}$, —$C(O)OR^{20}$, —$OC(O)R^{20}$, —$OC(O)N(R^{20})_2$, —$NO_2$, =O, =$N(R^{20})$, =$NO(R^{20})$, —CN, —NHCN, $C_{1-6}$ alkyl-N$(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, and $C_{1-6}$ alkyl. In some cases, each $R^{1*}$ is independently selected from halogen, —$OR^{20}$, —$S(O)_2(R^{20})$, —$S(O)_2N(R^{20})_2$, —$S(O)N(R^{20})_2$, —$S(O)R^{20}(=NR^{20})$, —$NR^{20}S(O)_2R^{20}$, —$C(O)N(R^{20})_2$, —$C(O)NR^{20}OR^{20}$, —$N(R^{20})C(O)R^{20}$, —$N(R^{20})C(O)N(R^{20})_2$, —$N(R^{20})C(O)OR^{20}$, —$N(R^{20})_2$, —$C(O)R^{20}$, —$C(O)OR^{20}$, —$OC(O)R^{20}$, —$OC(O)N(R^{20})_2$, —$NO_2$, =O, =$N(R^{20})$, =$NO(R^{20})$, —CN, —NHCN, $C_{1-6}$ alkyl-N$(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, and $C_{1-6}$ alkyl. In some cases, each $R^{1*}$ is independently selected from halogen, $C_{1-6}$ alkyl-N$(R^{20})_2$, $C_{1-6}$ aminoalkyl, $C_{1-6}$ hydroxy alkyl, $C_{1-6}$ cyanoalkyl, $C_{1-6}$ haloalkyl, and $C_{1-6}$ alkyl. In some cases, each $R^{1*}$ is independently selected from halogen, $C_{1-6}$ haloalkyl, and $C_{1-6}$ alkyl. In some cases, each $R^{1*}$ is independently selected from halogen, and $C_{1-6}$ alkyl. In some cases, each $R^{1*}$ is independently selected from halogen. In some cases, each $R^{1*}$ is independently selected from $C_{1-6}$ alkyl. In some cases, each $R^{1*}$ is independently selected from —$OR^{20}$. In some cases, each $R^{1*}$ is independently selected from —OH. In some cases, each $R^{1*}$ is independently selected from —OMe. In some cases, the heterocycle of the one or more optional substituents of $R^1$ is selected from

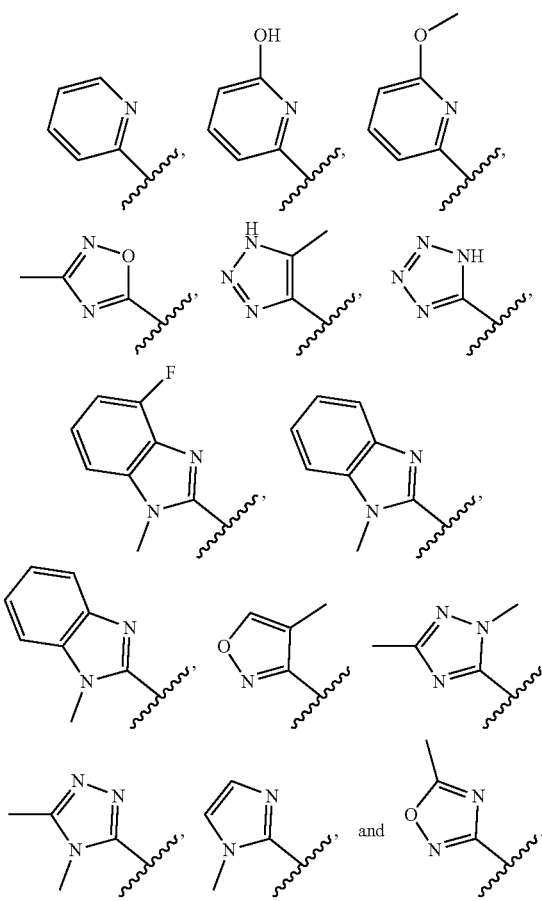

In some embodiments, for a compound or salt of Formula (I), Formula (I-A), Formula (I-B), Formula (I-C), or Formula (I-G), the one or more optional substituents of $R^1$ are independently selected from —C(=$NR^{20}$)N$(R^{20})_2$, and optionally substituted 5- to 12-membered heterocycle. In some cases, the one or more optional substituents of $R^1$ are independently selected from optionally substituted 5- to 12-membered heterocycle. In some cases, the heterocycle is selected from

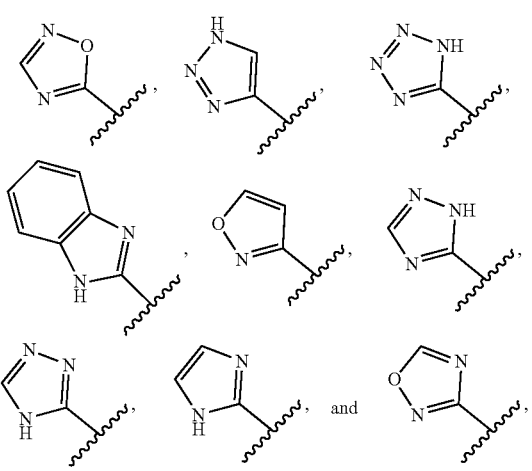

each of which is optionally substituted with one or more $R^{1*}$. In some cases, the one or more optional substituents of $R^1$ is selected from

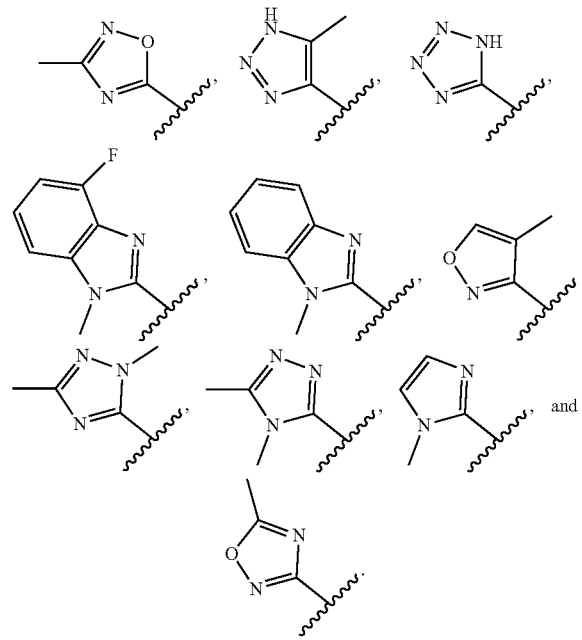

In some embodiments, for a compound or salt of Formula (I), Formula (I-A), Formula (I-B), Formula (I-C), or Formula (I-G), each $R^{1*}$ is independently selected from halogen, $-OR^{20}$, $-S(O)_2(R^{20})$, $-S(O)_2N(R^{20})_2$, $-S(O)N(R^{20})_2$, $-S(O)R^{20}(=NR^{20})$, $-NR^{20}S(O)_2R^{20}$, $-C(O)N(R^{20})_2$, $-C(O)NR^{20}OR^{20}$, $-N(R^{20})C(O)R^{20}$, $-N(R^{20})C(O)N(R^{20})_2$, $-N(R^{20})C(O)OR^{20}$, $-N(R^{20})_2$, $-C(O)R^{20}$, $-C(O)OR^{20}$, $-OC(O)R^{20}$, $-OC(O)N(R^{20})_2$, $-NO_2$, $=O$, $=N(R^{20})$, $=NO(R^{20})$, $-CN$, $-NHCN$, $C_{1-6}$ alkyl-N $(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, and $C_{1-6}$ alkyl. In some cases, each $R^{1*}$ is independently selected from halogen, $-OR^{20}$, $-S(O)_2(R^{20})$, $-S(O)_2N(R^{20})_2$, $-S(O)N(R^{20})_2$, $-S(O)R^{20}(=NR^{20})$, $-NR^{20}S(O)_2R^{20}$, $-C(O)N(R^{20})_2$, $-C(O)NR^{20}OR^{20}$, $-N(R^{20})C(O)R^{20}$, $-N(R^{20})C(O)N(R^{20})_2$, $-N(R^{20})C(O)OR^{20}$, $-N(R^{20})_2$, $-C(O)R^{20}$, $-C(O)OR^{20}$, $-OC(O)R^{20}$, $-OC(O)N(R^{20})_2$, $-NO_2$, $=O$, $=N(R^{20})$, $=NO(R^{20})$, $-CN$, $-NHCN$, $C_{1-6}$ alkyl-N $(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, and $C_{1-6}$ alkyl. In some cases, each $R^{1*}$ is independently selected from halogen, $C_{1-6}$ alkyl-N$(R^{20})_2$, $C_{1-6}$ aminoalkyl, $C_{1-6}$ hydroxyalkyl, $C_{1-6}$ cyanoalkyl, $C_{1-6}$ haloalkyl, and $C_{1-6}$ alkyl. In some cases, each $R^{1*}$ is independently selected from halogen, $C_{1-6}$ haloalkyl, and $C_{1-6}$ alkyl. In some cases, each $R^{1*}$ is independently selected from halogen, and $C_{1-6}$ alkyl. In some cases, each $R^{1*}$ is independently selected from halogen. In some cases, each $R^{1*}$ is independently selected from $C_{1-6}$ alkyl.

In some embodiments, for a compound or salt of Formula (I), Formula (I-A), Formula (I-B), Formula (I-C), or Formula (I-G), $R^1$ is selected from 5- to 15-membered heterocycle (preferably 8- to 10-membered heterocycle or preferably 10-membered heterocycle), each of which are optionally substituted with one or more substituents independently selected from halogen, oxo, $-C(O)N(R^{20})_2$, $-C(O)NR^{20}OR^{20}$, $-N(R^{20})_2$, $-C(O)R^{20}$, $-C(O)OR^{20}$, $-SO_2R^{20}$, $-NHCN$, $C_{1-6}$ cyanoalkyl, $C_{1-6}$ alkyl, $C_{1-6}$ alkyl-N$(R^{20})_2$, $C_{2-6}$ alkynyl, and 5- to 12-membered heterocycle (preferably 5- to 9-membered heterocycle), wherein the 5- to 12-membered heterocycle are each optionally substituted independently with one or more $R^{1*}$; each $R^{1*}$ is independently selected from halogen, $C_{1-6}$ haloalkyl, and $C_{1-6}$ alkyl. In some cases, the 8- to 10-membered heterocycle is bicyclic. In some cases, the 10-membered heterocycle is substituted. In some cases, $R^1$ is selected

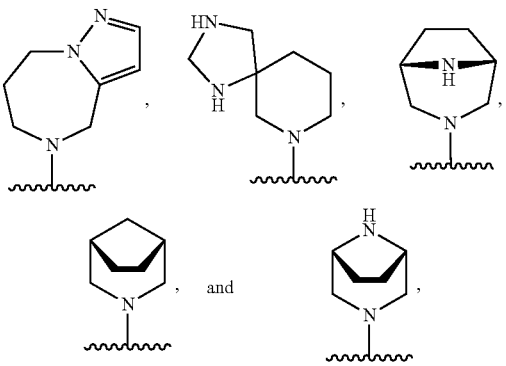

each of which is optionally substituted. In some cases, $R^1$ is selected

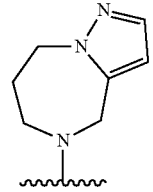

which is optionally substituted. In some cases, $R^1$ is selected

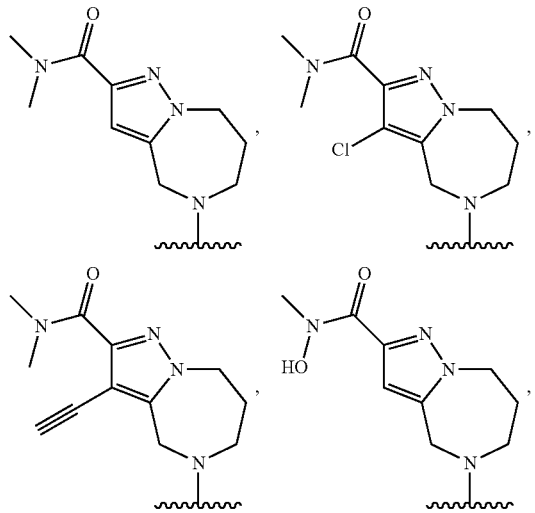

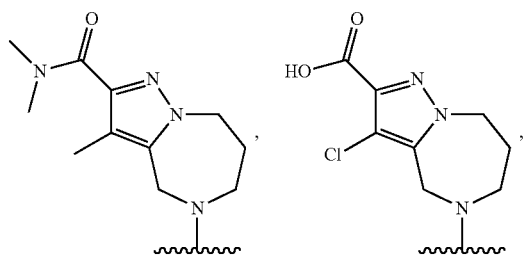
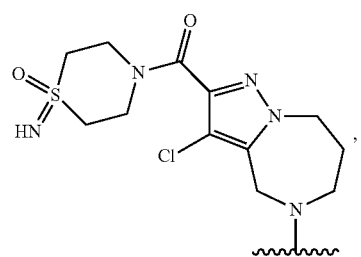

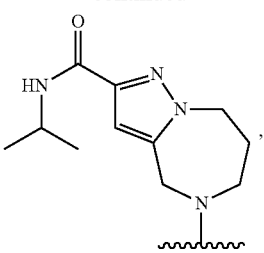,

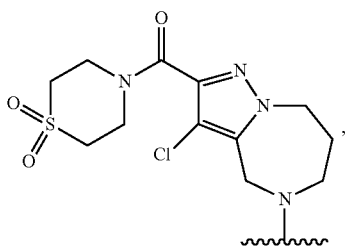,

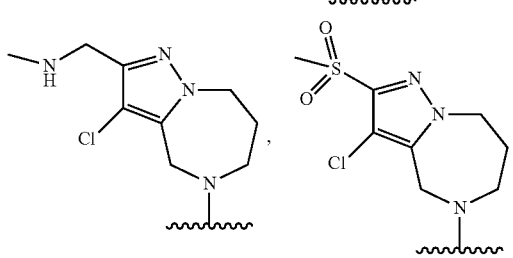,

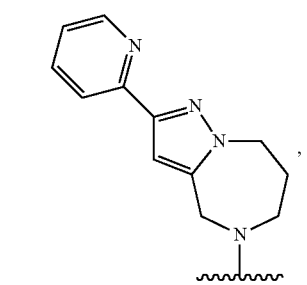,

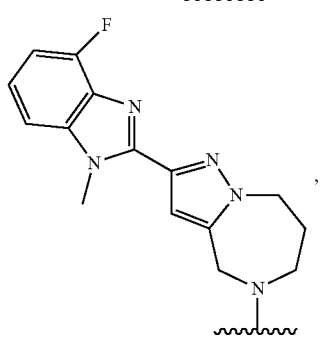,

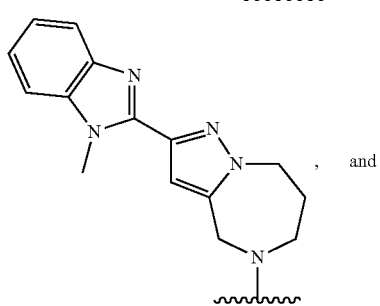 and

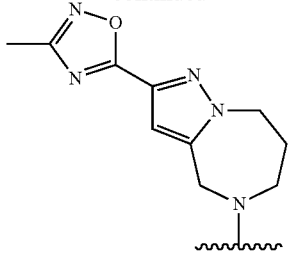

In some cases, $R^1$ is selected

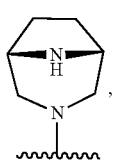, , and

In some cases, $R^1$ is

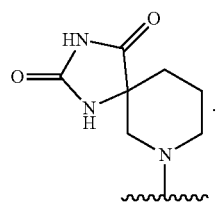 [SMILES: *N1CCCC2(C1)NC(=O)NC2=O].

In some embodiments, for a compound or salt of Formula (I), Formula (I-A), Formula (I-B), Formula (I-C), or Formula (I-G), $R^1$ is selected from 5- to 15-membered heterocycle (preferably 8- to 10-membered heterocycle or preferably 10-membered heterocycle or preferably 8-membered heterocycle), each of which are optionally substituted with one or more substituents independently selected from halogen, —C(O)N($R^{20}$)$_2$, —C(O)N$R^{20}$O$R^{20}$, —N($R^{20}$)$_2$, —C(O)$R^{20}$, —C(O)O$R^{20}$, —NHCN, $C_{1-6}$ cyanoalkyl, $C_{1-6}$ alkyl, $C_{2-6}$ alkynyl, and 5- to 12-membered heterocycle (preferably 5- to 6-membered heterocycle), wherein the 5- to 12-membered heterocycle are each optionally substituted independently with one or more $R^{1*}$; each $R^{1*}$ is independently selected from halogen, $C_{1-6}$ haloalkyl, and $C_{1-6}$ alkyl. In some cases, the 8- to 10-membered heterocycle is bicyclic. In some cases, the 10-membered heterocycle is substituted. In some cases, $R^1$ is selected

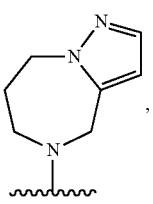, 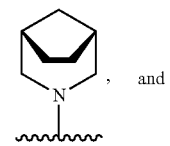 and 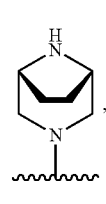, each of which is optionally substituted. In some cases R¹ is selected
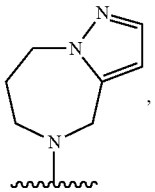 [SMILES: *N1CCCn2nccc2C1]
which is optionally substituted. In some cases, R¹ is selected
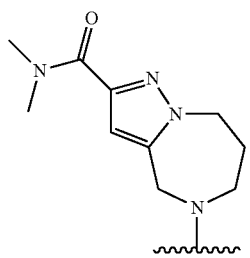 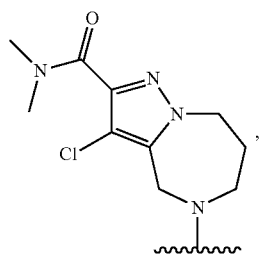
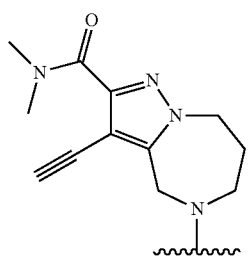 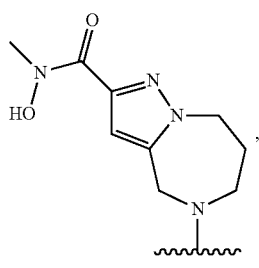
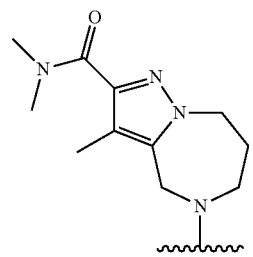 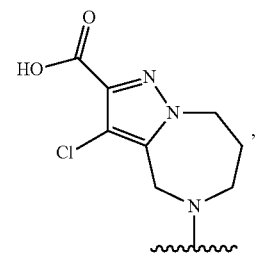
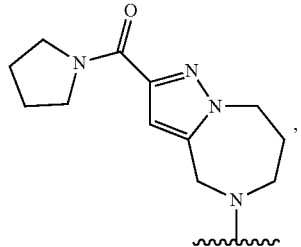
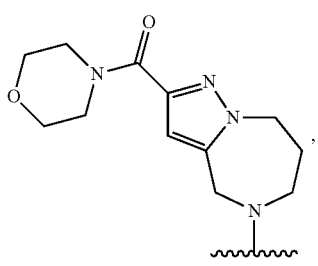
-continued
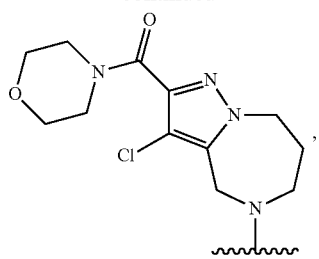
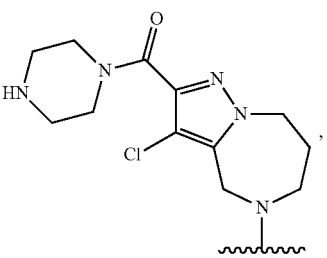
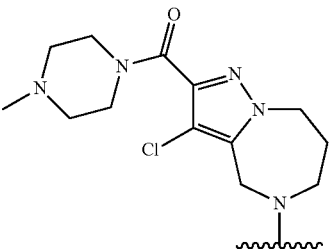
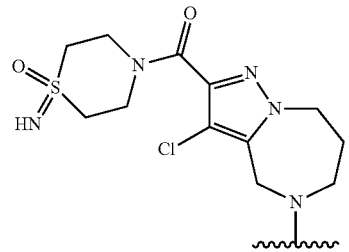
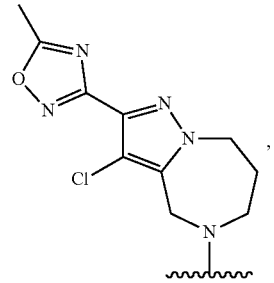 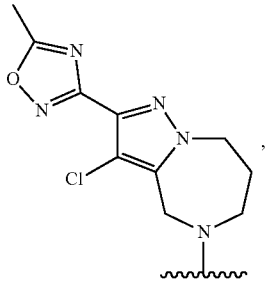
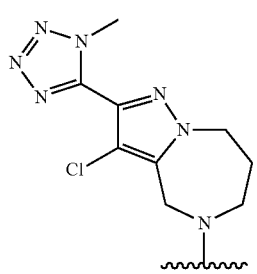 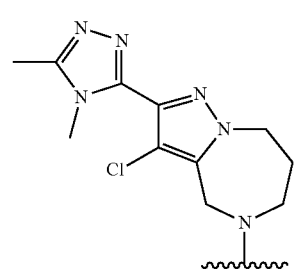

-continued

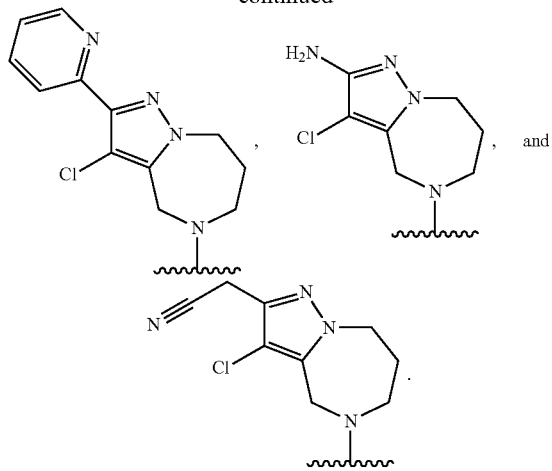

In some cases, $R^1$ is selected

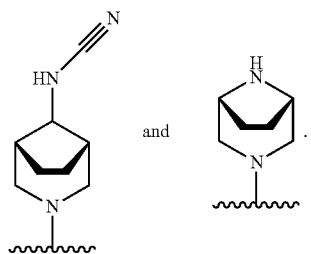

In some embodiments, for a compound or salt of Formula (I), Formula (I-A), Formula (I-B), Formula (I-C), or Formula (I-G), $R^1$ is selected from an optionally substituted 7- to 10-membered spiro heterocycle and optionally substituted 7- to 10-membered fused heterocycle. In some cases, the heterocycle of $R^1$ has at least one nitrogen atom. In some cases, the at least one nitrogen at of the heterocycle of $R^1$ is bound to Formula (I). In some cases, $R^1$ is selected from an optionally substituted 10-membered spiro heterocycle and optionally substituted 10-membered fused heterocycle. In some cases, the optional one or more substituents of $R^1$ are independently selected from halogen, —OH, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(=NR$^{20}$)N(R$^{20}$)$_2$, —C(O)OR$^{20}$, —C(O)NHOR$^{20}$, —N(R$^{20}$)$_2$, —C(O)R$^{20}$, —NO$_2$, =O, —CN, C$_{1-6}$ alkyl-N(R$^{20}$)$_2$, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkynyl, 5- to 12-membered heterocycle, wherein the 5- to 12-membered heterocycle is optionally substituted with one or more substituents selected from halogen, and C$_{1-6}$ alkyl. In some cases, $R^1$ is selected from

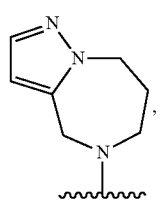 [SMILES: *N1CCCn2nccc2C1]

which is substituted with one or more substituents independently selected from halogen, —OH, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(=NR$^{20}$)N(R$^{20}$)$_2$, —C(O)OR$^{20}$, —C(O)NHOR$^{20}$, —N(R$^{20}$)$_2$, —C(O)R$^{20}$, —NO$_2$, =O, —CN, C$_{1-6}$ alkyl-N(R$^{20}$)$_2$, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkynyl, 5- to 12-membered heterocycle, wherein the 5- to 12-membered heterocycle is optionally substituted with one or more substituents selected from halogen, and C$_{1-6}$ alkyl. In some cases, $R^1$ is selected from

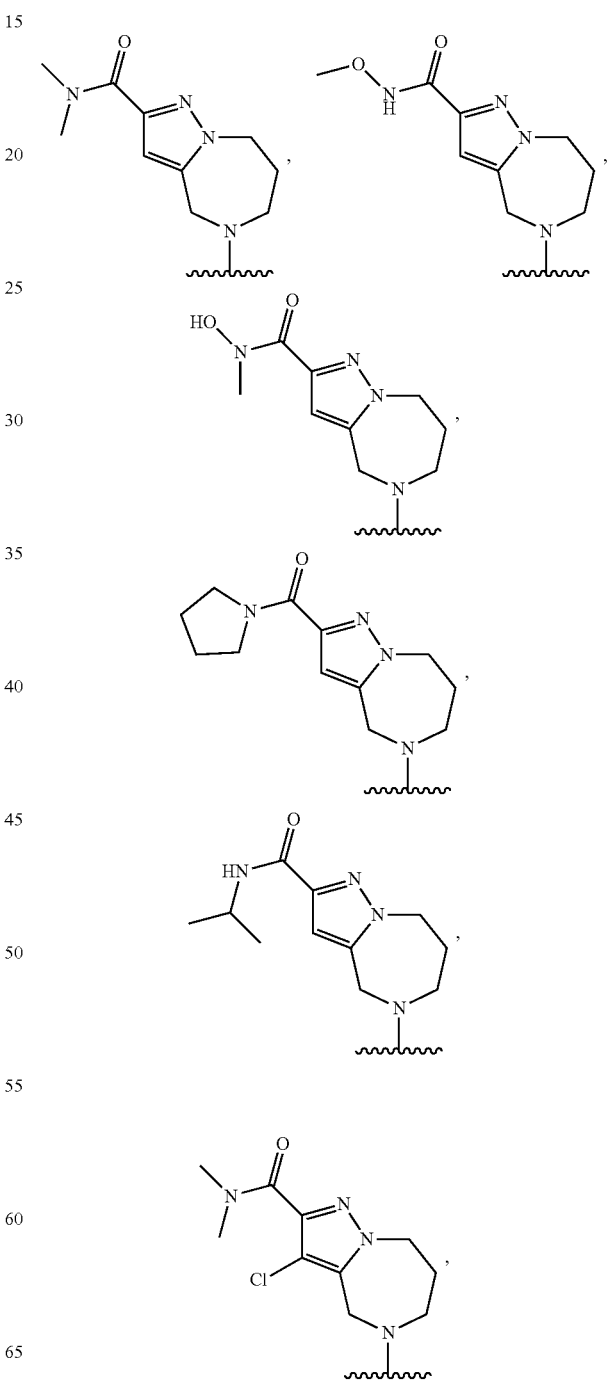

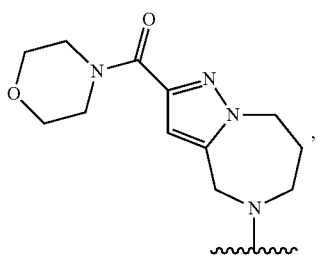
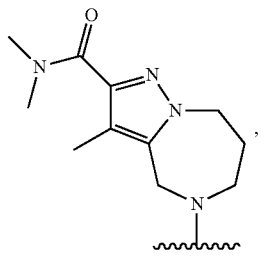
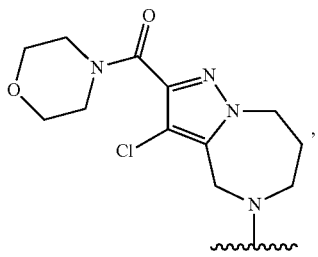
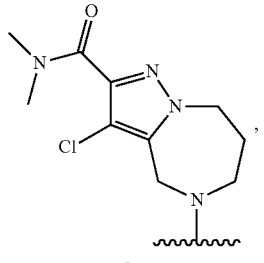
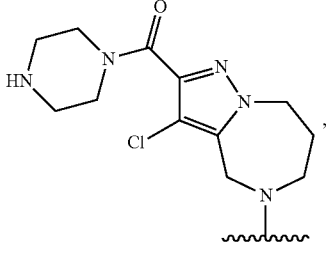
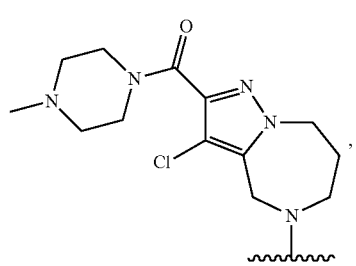
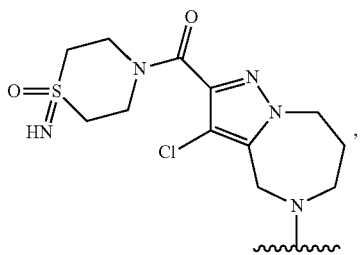
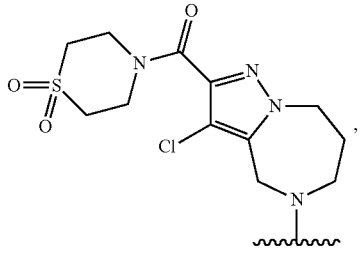
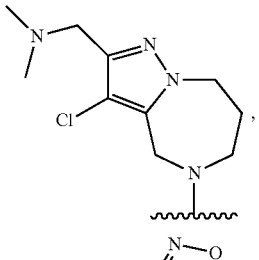
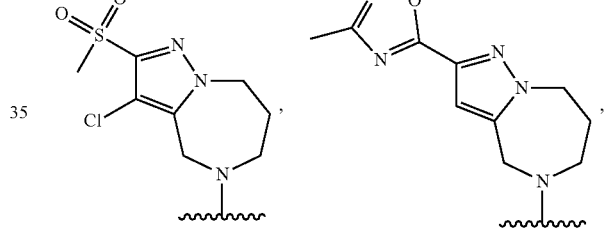
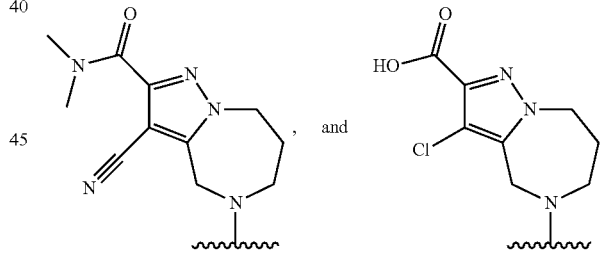, and
In some cases, R[1] is selected
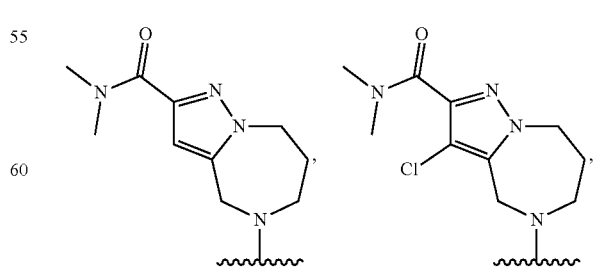

187
-continued

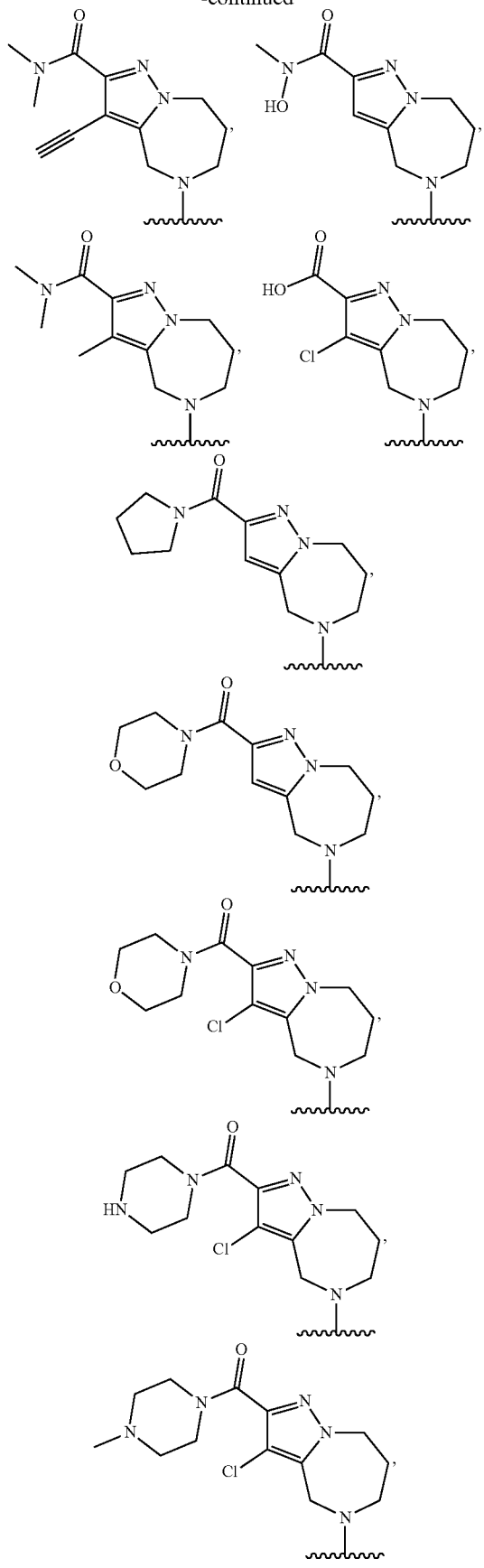

188
-continued

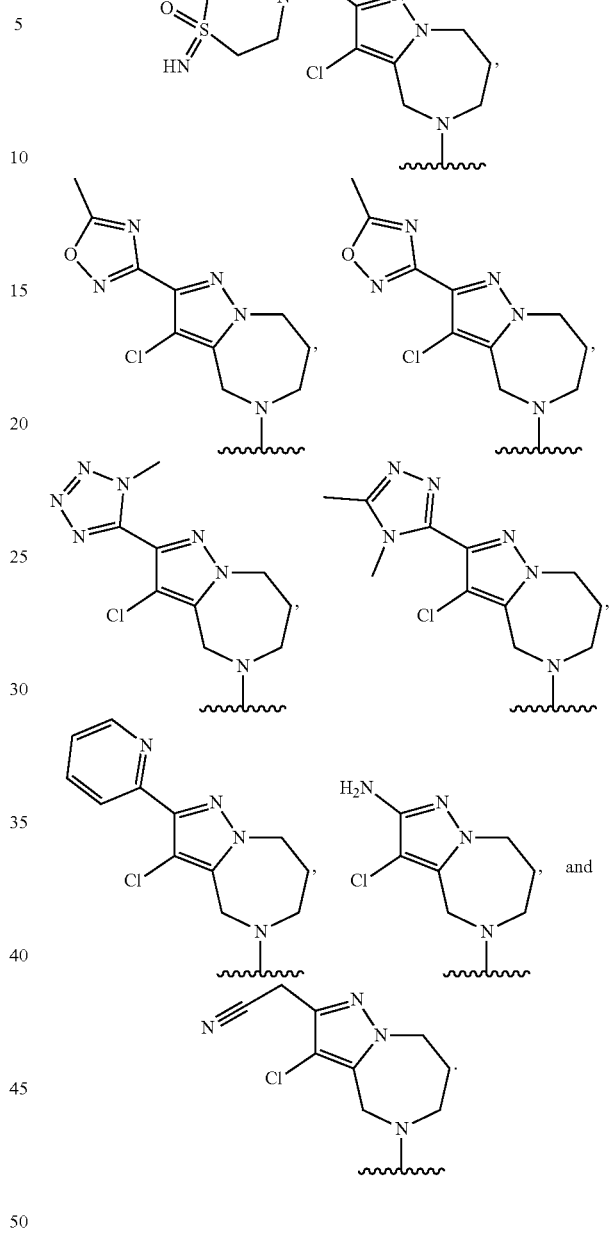

In some embodiments, for a compound or salt of Formula (I), Formula (I-A), Formula (I-B), Formula (I-C), or Formula (I-G), $R^1$ is selected from an optionally substituted 6- to 11-membered heterocycle, wherein the 6- to 11-membered heterocycle has at least one nitrogen atom. In some cases, the one or more optional substituents of $R^1$ is selected from halogen, —$OR^{20}$, —$C(O)N(R^{20})_2$, —$C(O)R^{20}$, —$S(O)_2R^{20}$, =O, —$C_{1-6}$ alkyl(=$NR^{20}OR^{20}$), =$NO(R^{20})$, —CN, —NHCN, $C_{1-6}$ alkyl, and 5- to 12-membered heterocycle, wherein the 5- to 12-membered heterocycle is optionally substituted independently with one or more $R^{1*}$; and wherein each $R^{1*}$ is independently selected from halogen, and $C_{1-6}$ alkyl. In some embodiments, $R^1$ is selected from

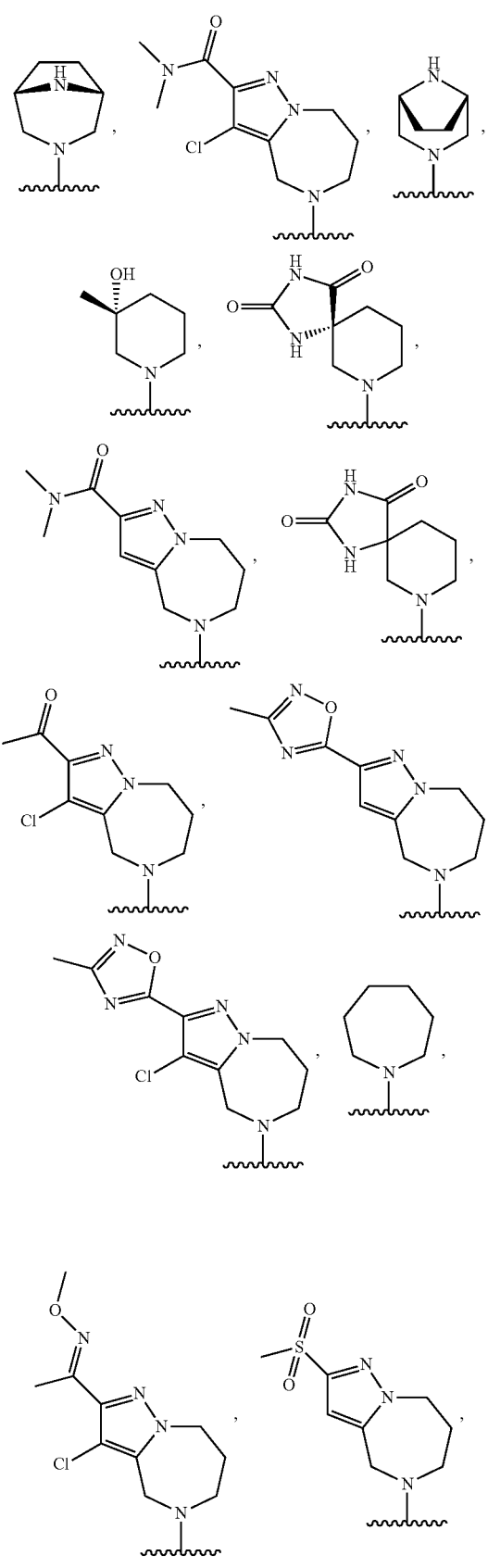
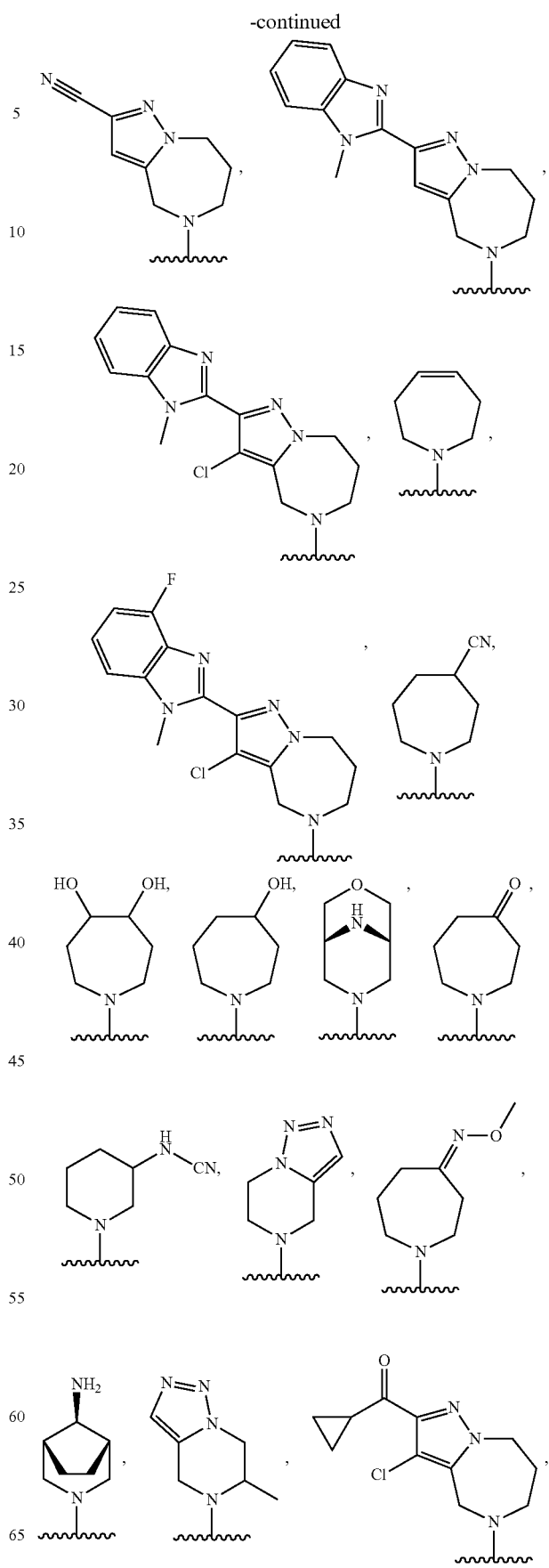

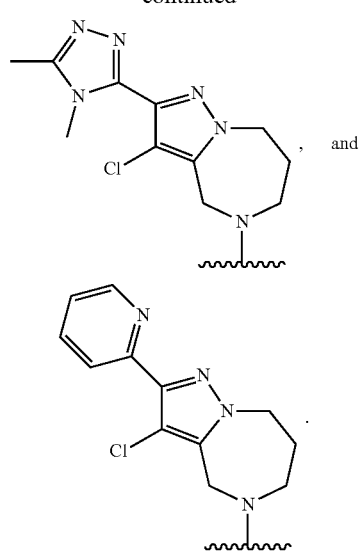
In some cases, $R^1$ is selected from hydrogen,
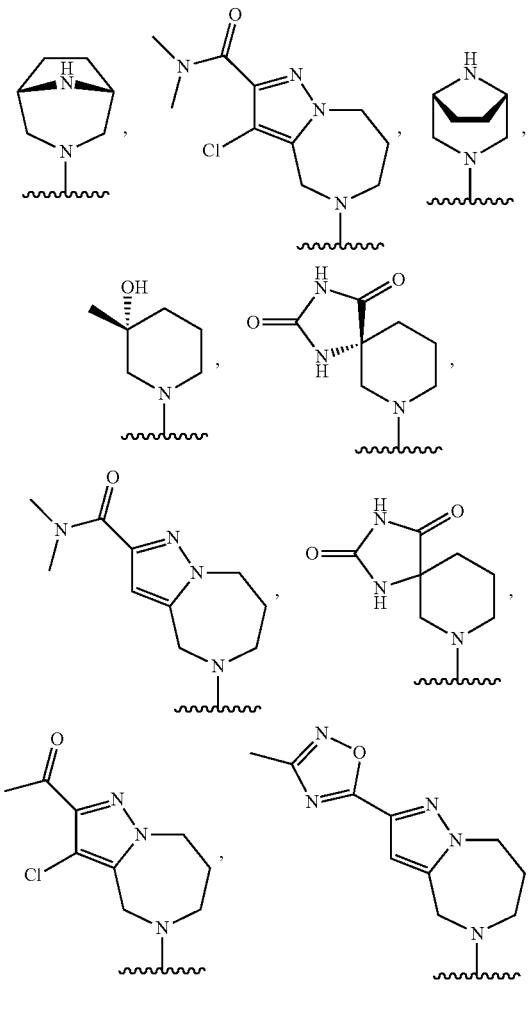
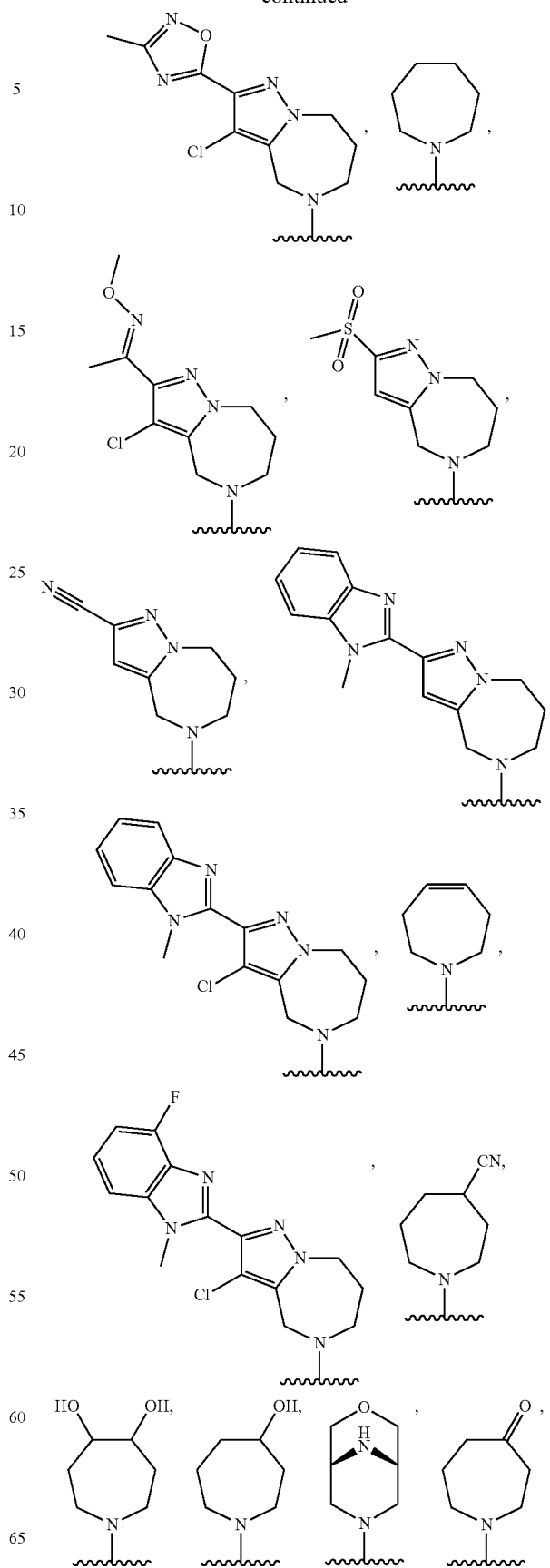

-continued
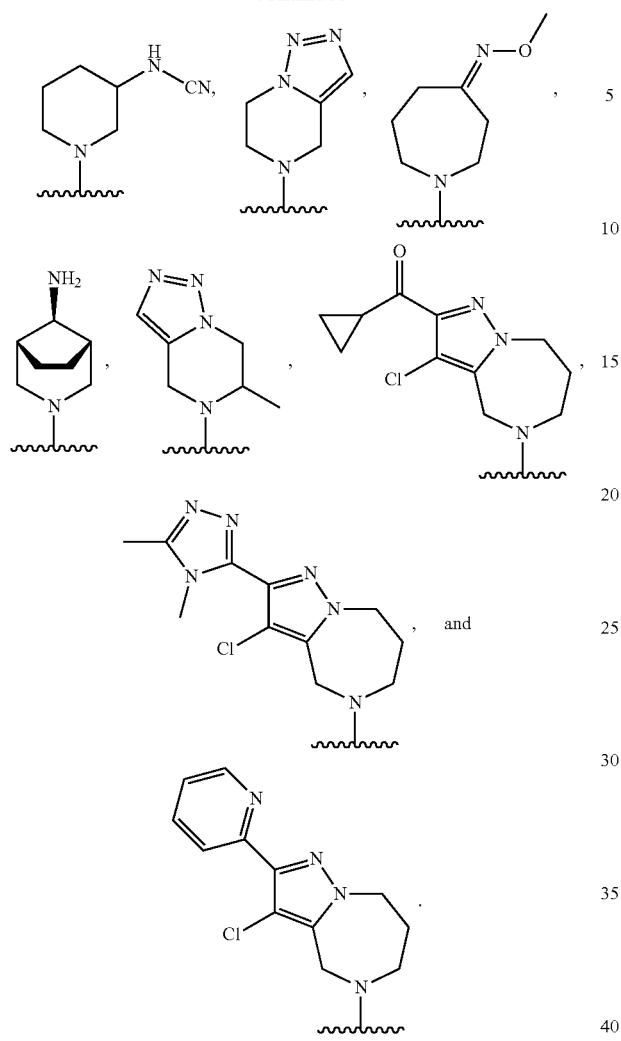
In some cases, R[1] is selected from hydrogen,
-continued
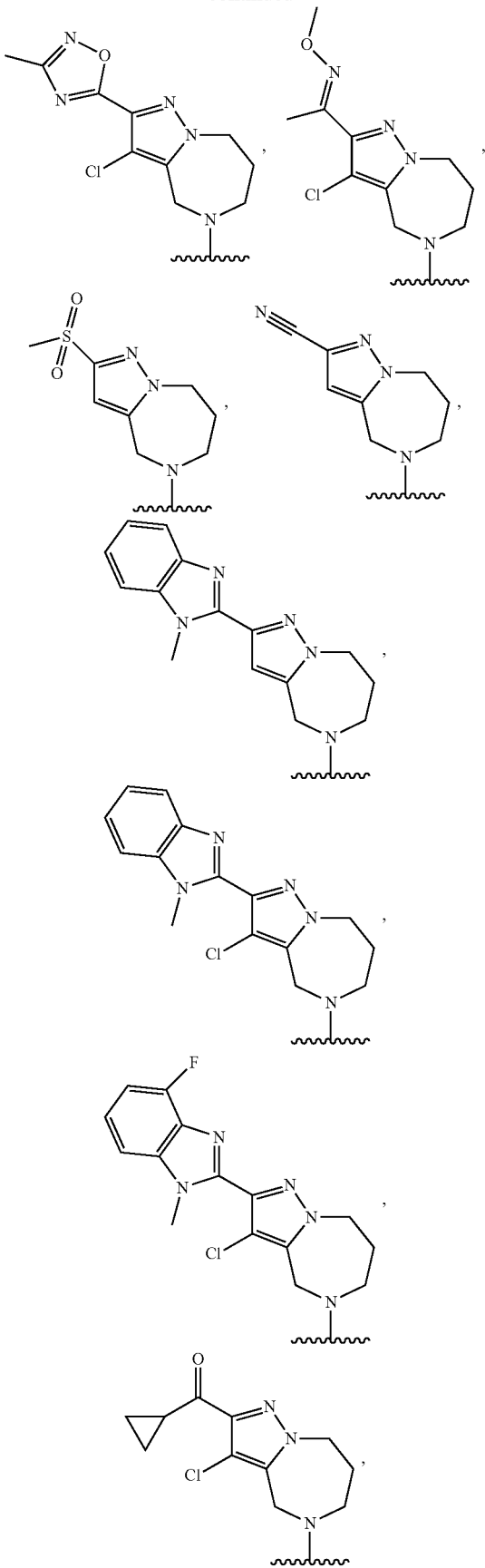

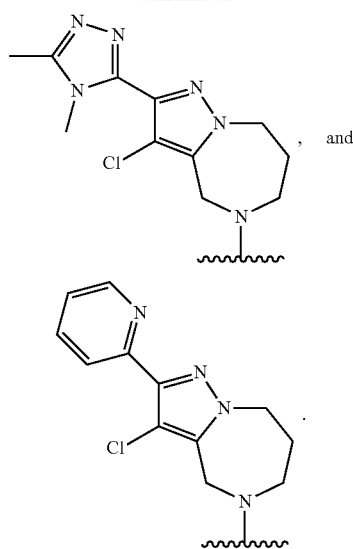

In some embodiments, for a compound or salt of Formula (I), Formula (I-A), Formula (I-B), Formula (I-C), or Formula (I-G), $R^1$ is selected from hydrogen and optionally substituted 5- to 15-membered heterocycle. In some cases, $R^1$ is selected from

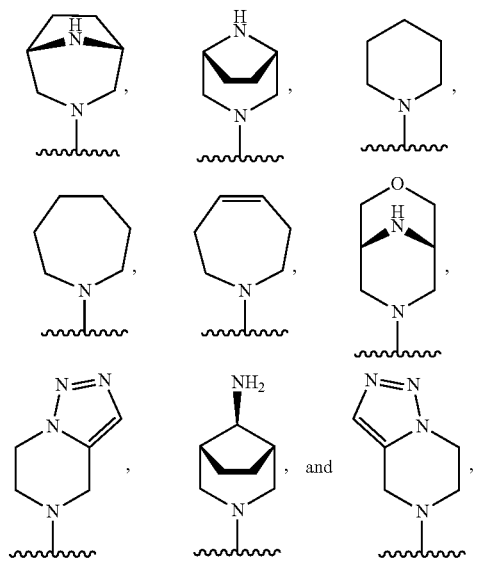

each of which is optionally substituted. In some cases, the optional one or more substituents of $R^1$ is selected from —OH, =NO($R^{20}$), —NHCN, and $C_{1-6}$ alkyl. In some cases, $R^1$ is selected from hydrogen,

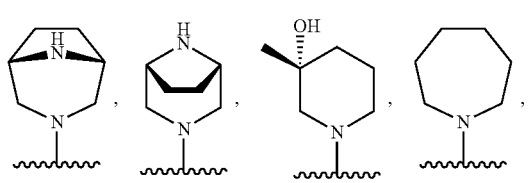

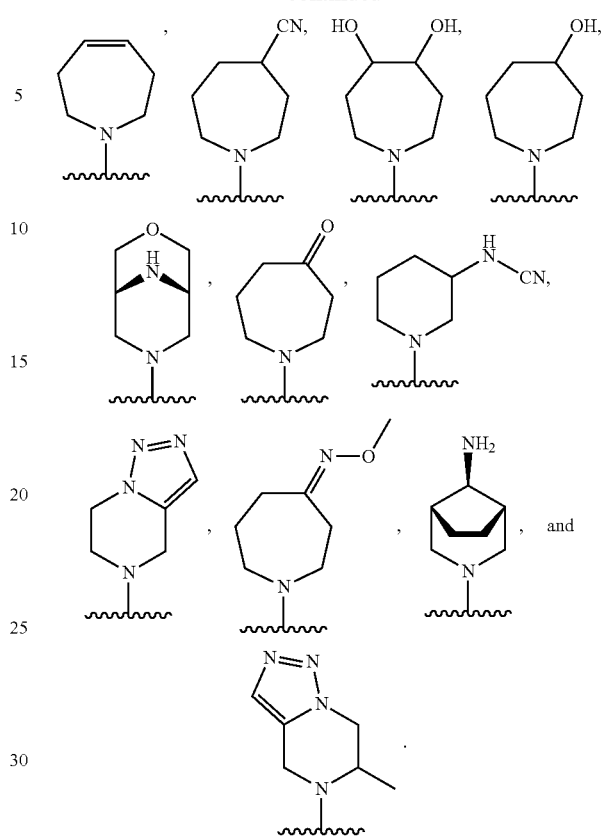

In some embodiments, for a compound or salt of Formula (I), Formula (I-A), Formula (I-B), Formula (I-C), or Formula (I-G), $R^1$ is

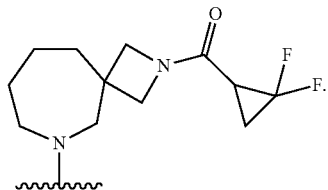 [SMILES: *N1CCCCC2(C1)CN(C(=O)C1CC1(F)F)C2]

In some embodiments, for a compound or salt of Formula (I), Formula (I-A), Formula (I-B), Formula (I-C), or Formula (I-G), $R^1$ is selected from hydrogen and optionally substituted 7- to 10-membered heterocycle. In some cases, $R^1$ is selected from hydrogen

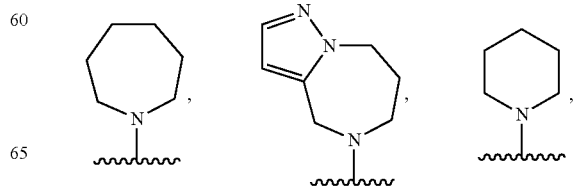

-continued

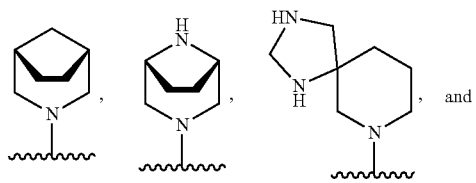, and

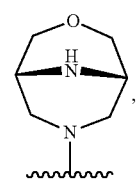

each of which is optionally substituted. In some cases, the optional one or more substituents of $R^1$ are independently selected from halogen, $-NH_2$, $-S(O)_2(R^{20})$, $-C(O)R^{20}$, $-C(O)N(R^{20})_2$, $=O,=NO(R^{20})$, $-CN$, $-NHCN$, $C_{1-6}$ alkyl, and 5- to 12-membered heterocycle, wherein the 5- to 12-membered heterocycle is optionally substituted independently with one or more $R^{1*}$; and wherein each $R^{1*}$ is independently selected from halogen, and $C_{1-6}$ alkyl. In some cases, $R^1$ is selected from hydrogen,

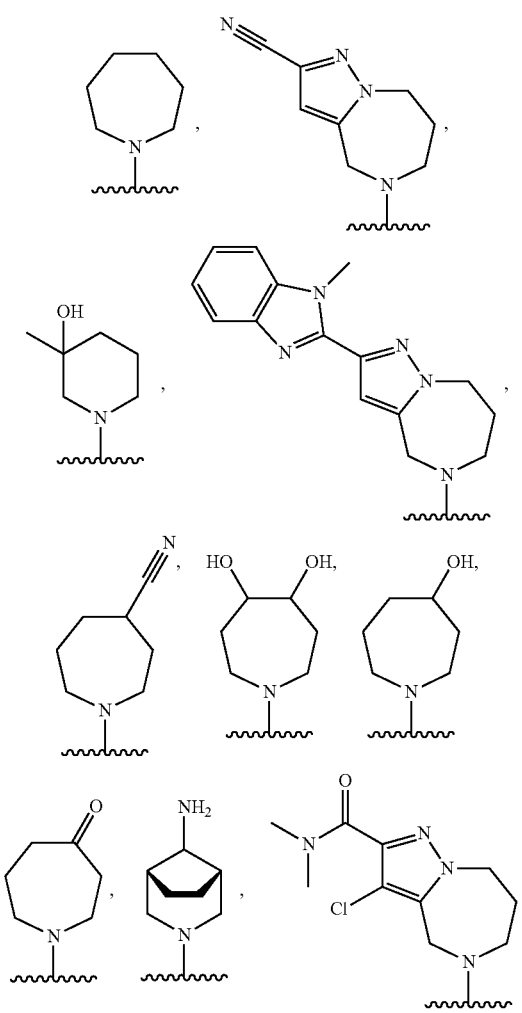

-continued

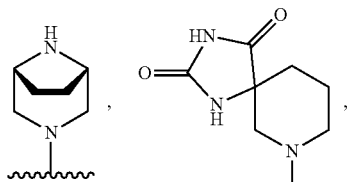

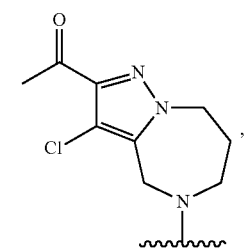

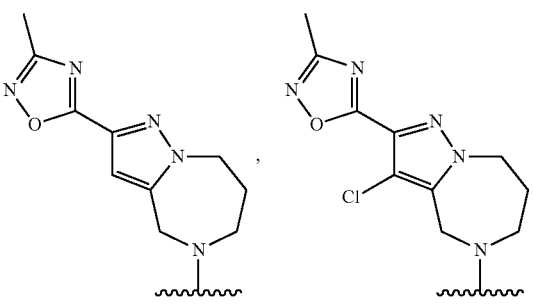

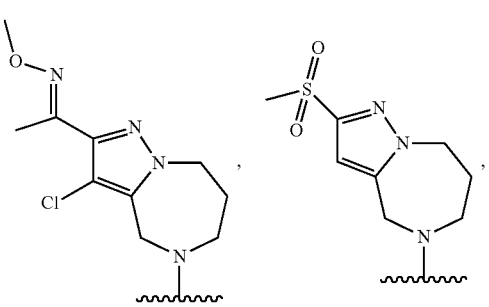

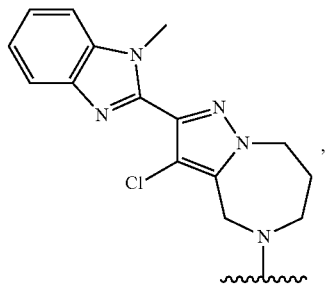

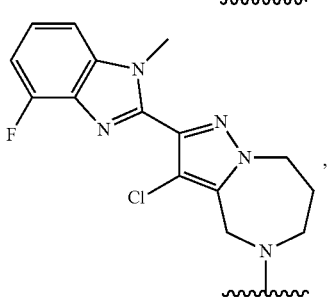

-continued

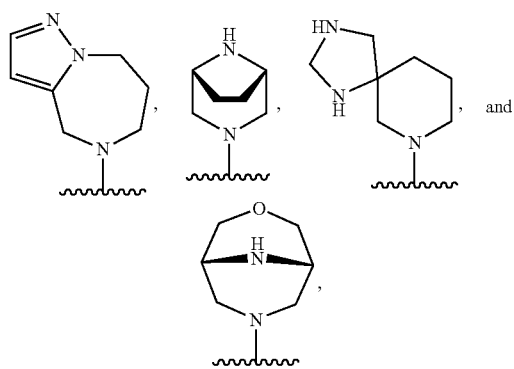

In some embodiments, for a compound or salt of Formula (I), Formula (I-A), Formula (I-B), Formula (I-C), or Formula (I-G), $R^1$ is selected from an optionally substituted 8- to 10-membered heterocycle. In some cases, the heterocycle is bicyclic. In some cases, the heterocycle has at least one nitrogen atom. In some cases, the heterocycle has at least two nitrogen atoms. In some cases,

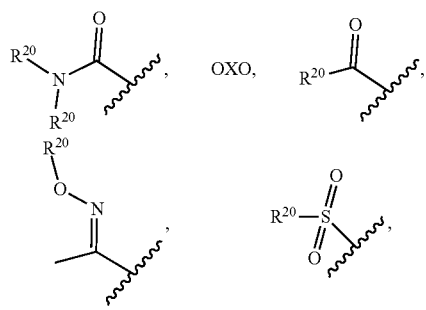

and each of which is optionally substituted. In some cases, the optional one or more substituents of $R^1$ are independently selected from halogen,

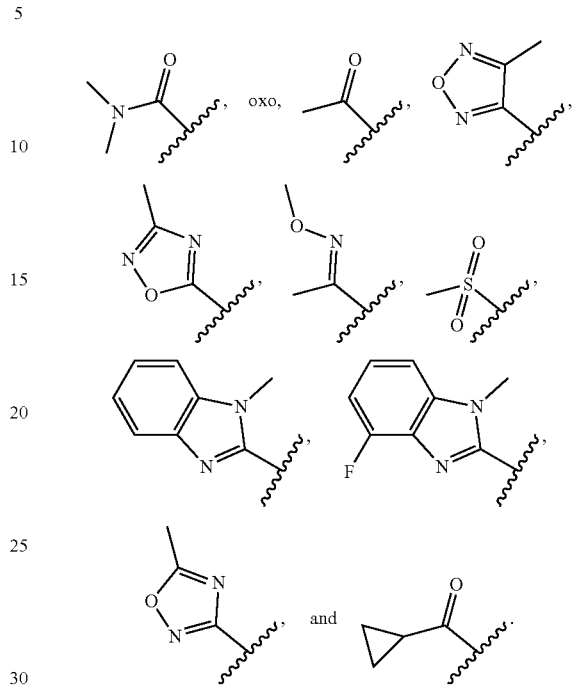

and 5- to 9-membered heteroaryl, wherein the 5- to 9-membered heteroaryl is substituted with at least one $R^{1*}$, wherein the $R^{1*}$ is selected from halogen, and $C_{1-6}$ alkyl. In some cases, the optional one or more substituents of $R^1$ are independently selected from chlorine,

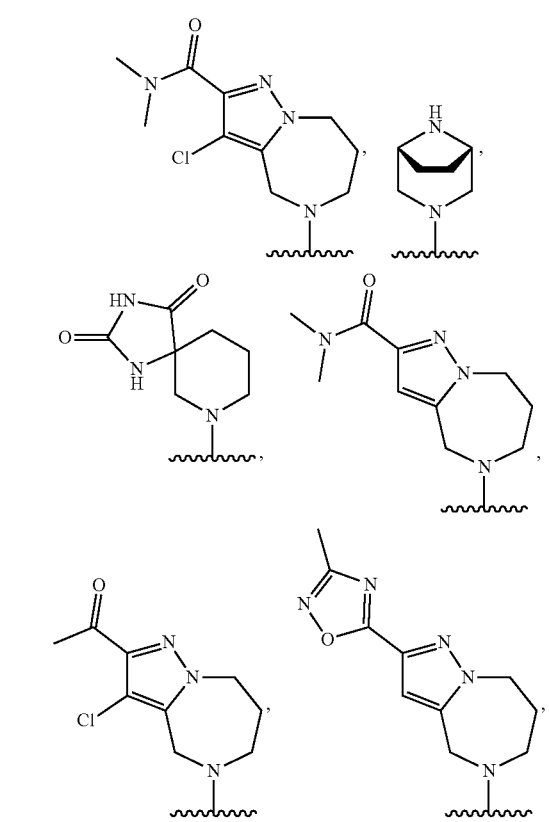

In some cases, $R^1$ is selected from

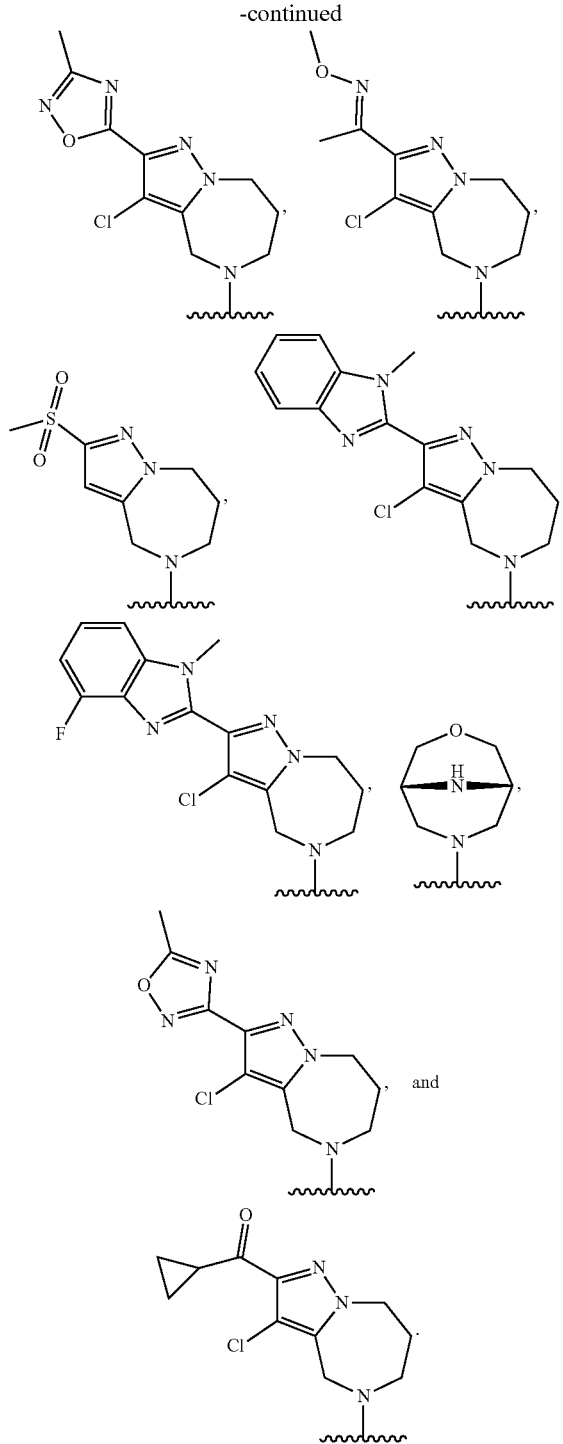

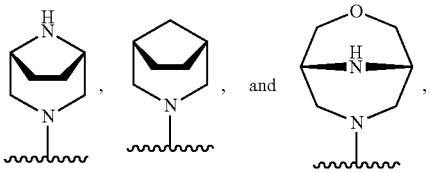

each of which is optionally substituted. In some cases, the one or more substituents of R are selected from halogen, $C_{1-6}$ alkyl, $-N(R^{20})_2$, and $C_{1-6}$ aminoalkyl. In some cases, $R^1$ is selected

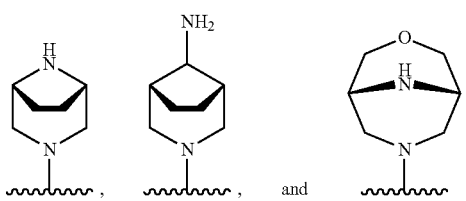

In some embodiments, for a compound or salt of Formula (I), Formula (I-A), Formula (I-B), Formula (I-C), or Formula (I-G), $R^1$ is selected from an optionally substituted bridged 8-membered heterocycle, wherein the heterocycle contains heteroatoms selected from nitrogen. In some cases, the one or more substituents of $R^1$ are selected from $C_{1-6}$ alkyl, $-N(R^{20})_2$, and $C_{1-6}$ aminoalkyl. In some cases, the heterocycle of $R^1$ is selected from

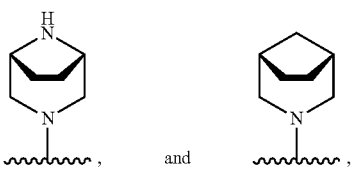

each of which is optionally substituted. In some cases, $R^1$ is selected

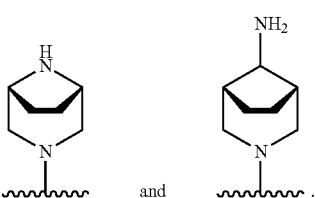

In some cases, $R^1$ is

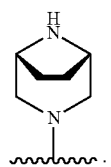

In some embodiments, for a compound or salt of Formula (I), Formula (I-A), Formula (I-B), Formula (I-C), or Formula (I-G), $R^1$ is selected from an optionally substituted bridged 8- to 9-membered heterocycle. In some cases, the heterocycle of $R^1$ is selected from In some cases, $R^1$ is

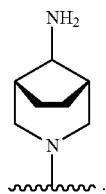

In some embodiments, for a compound or salt of Formula (I), Formula (I-A), Formula (I-B), Formula (I-C), or Formula (I-G), $R^1$ is an optionally substituted 12- to 15-membered heterocycle. In some cases, $R^1$ is an optionally substituted 12-membered heterocycle. In some cases, $R^1$ is an optionally substituted 13-membered heterocycle. In some cases, $R^1$ is an optionally substituted 14-membered heterocycle. In some cases, $R^1$ is an optionally substituted 15-membered heterocycle. In some cases, the heterocycle of $R^1$ is tricyclic. In some cases, the heterocycle of $R^1$ contains a fused heterocycle. In some cases, the heterocycle of $R^1$ contains a spiro-heterocycle. In some cases, the heterocycle of $R^1$ contains a fused and spiro-heterocycle. In some cases, the heterocycle of $R^1$ is an unsaturated heterocycle. In some cases, the heterocycle of $R^1$ is a non-aromatic heterocycle. In some cases, the heterocycle of $R^1$ has at least one double bond. In some cases, the heterocycle of $R^1$ has at least two double bonds. In some cases, the heterocycle of $R^1$ has at least 2 heteroatoms. In some cases, the heterocycle of $R^1$ has at least 3 heteroatoms. In some cases, the heterocycle of $R^1$ has at least 4 heteroatoms. In some cases, the heterocycle of $R^1$ has at least 5 heteroatoms. In some cases, the heterocycle of $R^1$ has at least 6 heteroatoms. In some cases, the heterocycle of $R^1$ has at least 7 heteroatoms. In some cases, the heteroatoms are selected from oxygen, nitrogen, and sulfur. In some cases, the heterocycle of $R^1$ has at least 3, 4, or 5 nitrogen atoms, and at least 1 sulfur atom. In some cases, the heterocycle of $R^1$ has at least 3, 4, or 5 nitrogen atoms, and at least 1 oxygen atom. In some cases, the heterocycle of $R^1$ has at least 3, 4, or 5 nitrogen atoms. In some cases, the heterocycle of $R^1$ has at least 3, 4, or 5 nitrogen atoms and no other heteroatoms. In some cases, the heteroatoms are selected from nitrogen and sulfur. In some cases, the heteroatoms are selected from nitrogen and oxygen. In some cases, $R^1$ is selected from

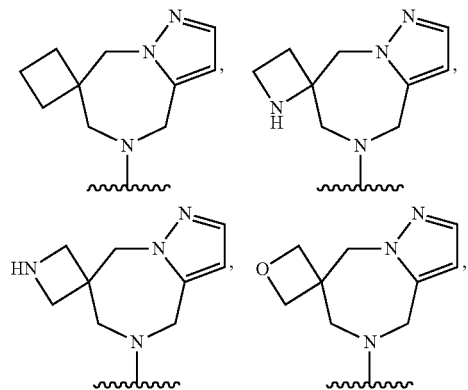

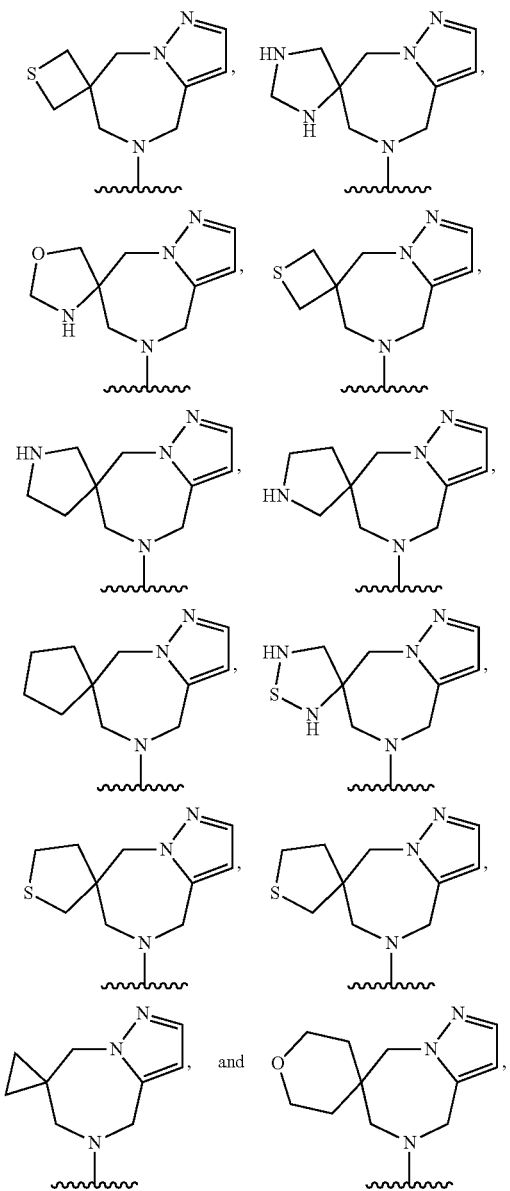

each of which is optionally substituted with one or more substituents. In some cases, $R^1$ is selected from

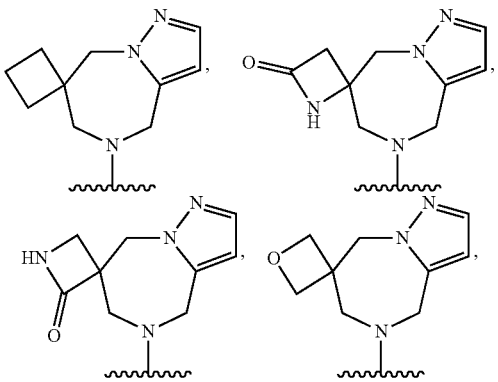

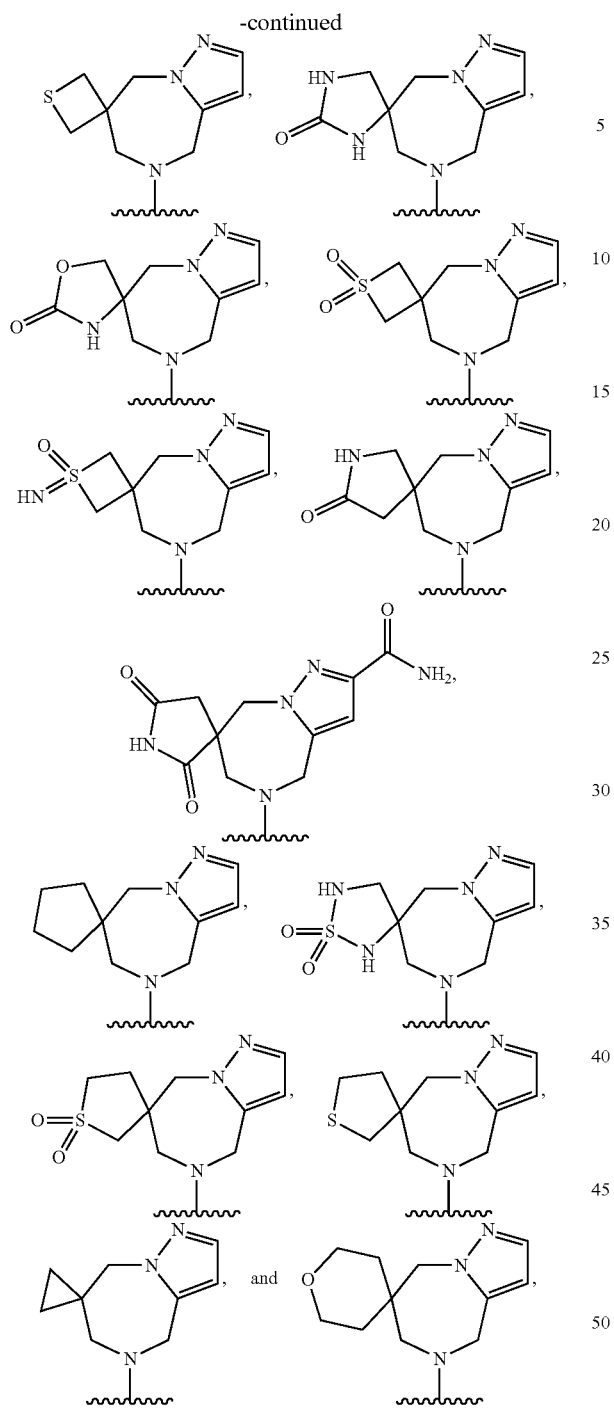

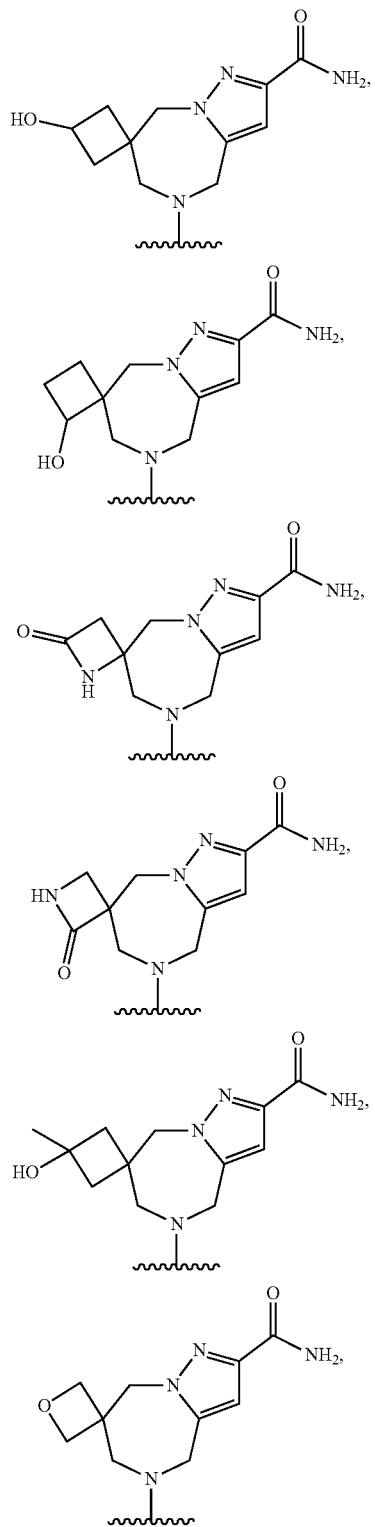

each of which is optionally substituted with one or more substituents. In some cases, the optional one or more substituents of $R^1$ are independently selected from halogen, —OH, —NHCN, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(O)NHOR$^{20}$, —N(R$^{20}$)$_2$, —C(O)R$^{20}$, —NO$_2$, =O, =NH, —CN, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, and C$_{2-6}$ alkynyl. In some cases, the optional one or more substituents of $R^1$ are independently selected from halogen, —OH, —NHCN, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(O)NHOR$^{20}$, —N(R$^{20}$)$_2$, —C(O)R$^{20}$, —NO$_2$, =O, —CN, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, and C$_{2-6}$ alkynyl. In some cases, the optional one or more substituents of $R^1$ are independently selected from halogen, —OH, C$_{1-6}$ alkyl, and —C(O)N(R$^{20}$)$_2$. In some cases, $R^1$ is selected from

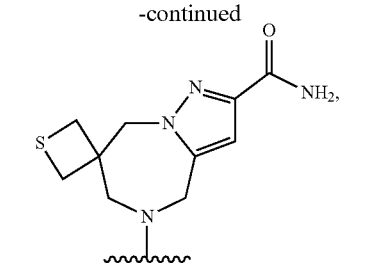
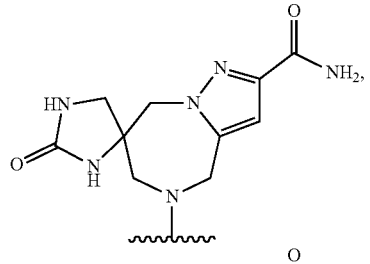
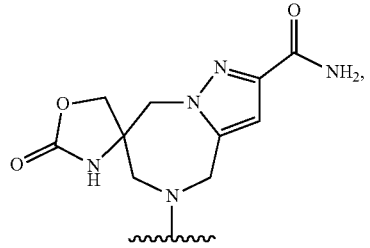
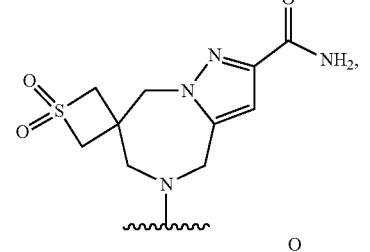

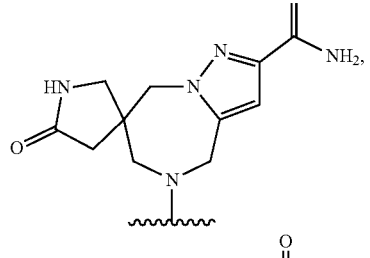
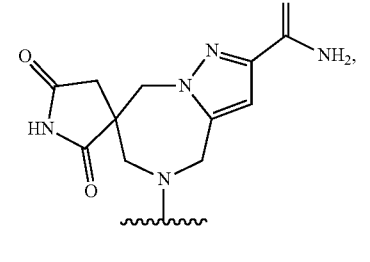
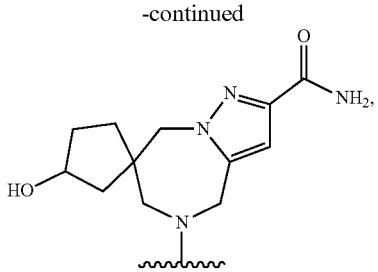
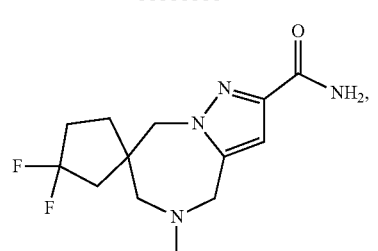
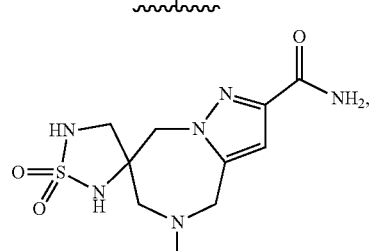
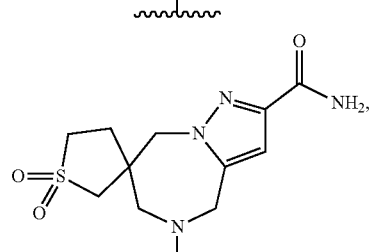
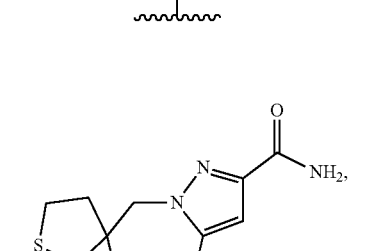
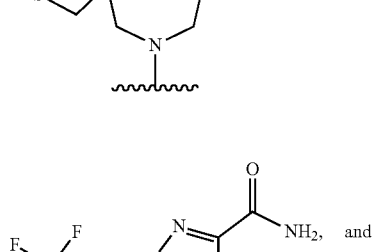
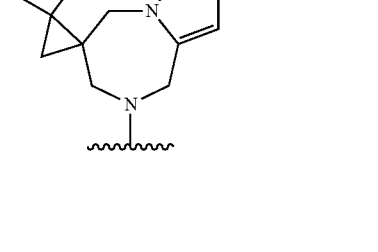

-continued

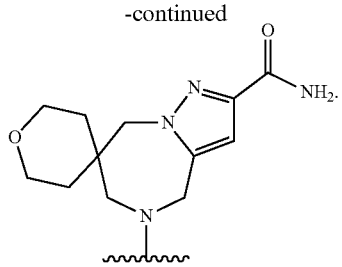

In some embodiments, for a compound or salt of Formula (I), Formula (I-A), Formula (I-B), Formula (I-C), or Formula (I-G), $R^1$ is an optionally substituted 12- to 15-membered heterocycle. In some cases, $R^1$ is

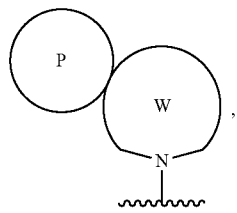

wherein Ring W is an optionally substituted heterocycle and Ring P is an optionally substituted carbocycle or optionally substituted heterocycle, wherein Ring P forms a spirocycle with Ring W. In some cases, Ring W is an optionally substituted fused heterocycle. In some cases, Ring P and Ring W combine to form a heterocycle having at least 12 atoms and most 15 atoms. In some cases, Ring P and Ring W have in total at least 12 atoms and most 15 atoms. In some cases, Ring W is an optionally substituted 10-membered fused heterocycle. In some cases, $R^1$ is

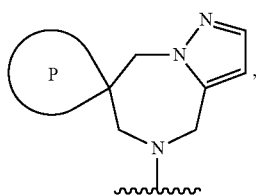

wherein Ring P is an optionally substituted carbocycle or optionally substituted heterocycle. In some cases, $R^1$ is

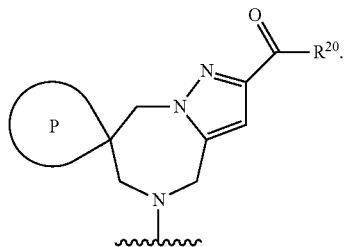

In some cases, Ring P is an optionally substituted carbocycle. In some cases, Ring P is an optionally substituted heterocycle. In some cases, Ring P forms an optionally substituted $C_3$-$C_6$ carbocycle or optionally substituted 4- to 6-membered heterocycle. In some cases, Ring P forms an optionally substituted $C_3$ carbocycle. In some cases, Ring P forms an optionally substituted $C_4$ carbocycle. In some cases, Ring P forms an optionally substituted $C_5$ carbocycle. In some cases, Ring P forms an optionally substituted 4-membered heterocycle. In some cases, Ring P forms an optionally substituted 5-membered heterocycle. In some cases, Ring P forms an optionally substituted 5-membered heterocycle. In some cases, Ring P has at least 1, 2, or 3 heteroatoms. In some cases, the heteroatoms are selected from oxygen, nitrogen, and sulfur. In some cases, Ring P has 1 sulfur atom. In some cases, Ring P has 1 nitrogen atom. In some cases, Ring P has 1 oxygen atom. In some cases, the one or more optional substituents of Ring P are independently selected from halogen, —OH, —NHCN, =O, =NR$^{20}$, —CN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, and $C_{2-6}$ alkynyl. In some cases, the one or more optional substituents of Ring P are independently selected from halogen, —OH, =O, =NH, —CN, and $C_{1-6}$ alkyl. In some cases, the one or more optional substituents of Ring W are independently selected from halogen, —OH, —NHCN, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(O)NHOR$^{20}$, —N(R$^{20}$)$_2$, —C(O)R$^{20}$, —NO$_2$, —CN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, and $C_{2-6}$ alkynyl. In some cases, the one or more optional substituents of Ring W are independently selected from halogen, —S(O)$_2$(R$^{20}$), —S(O)$_2$N(R$^{20}$)$_2$, —S(O)N(R$^{20}$)$_2$, —S(O)R$^{20}$ (=NR$^{20}$), —C(O)N(R$^{20}$)$_2$, —C(O)NHOR$^{20}$, —N(R$^{20}$)$_2$, —C(O)R$^{20}$, and $C_{1-6}$ alkyl. In some cases, the one or more optional substituents of Ring W are independently selected from —C(O)R$^{20}$. In some cases, Ring P is substituted. In some cases, Ring W is substituted.

In some embodiments, for a compound or salt of Formula (I), Formula (I-A), Formula (I-B), Formula (I-C), or Formula (I-G), $R^1$ is selected from an optionally substituted saturated 6- to 7-membered heterocycle. In some cases, $R^1$ is selected from an optionally substituted saturated 6-membered heterocycle. In some cases, $R^1$ is selected from

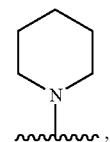 [SMILES: *N1CCCCC1]

Which is optionally substituted. In some cases, the optional one or more substituents are independently selected from halogen, —CN, —NHCN, $C_{1-6}$ cyanoalkyl, and $C_{1-6}$ alkyl. In some cases, the optional one or more substituents are independently selected from —CN, —NHCN, $C_{1-6}$ cyanoalkyl, and $C_{1-6}$ alkyl. In some cases, the optional one or more substituents are independently selected from —CN, —NHCN, $C_{1-6}$ cyanoalkyl, and $C_{1-6}$ alkyl. In some cases, the optional one or more substituents are independently selected from —NHCN, and $C_{1-6}$ alkyl. In some cases, $R^1$ is selected from

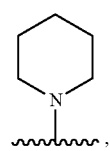

which is substituted with one or more substituents selected from —NHCN, and $C_{1-6}$ alkyl. In some cases, $R^1$ is selected from

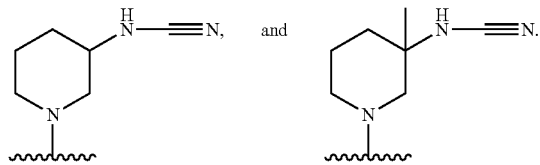 [SMILES: *N1CCCC(NC#N)C1 ; "and" ; *N1CCCC(C)(NC#N)C1]

In some embodiments, for a compound or salt of Formula (I), Formula (I-A), Formula (I-B), Formula (I-C), or Formula (I-G), $R^1$ is a bridged heterocycle. In some cases, $R^1$ is selected from an 7- to 10-membered bridged heterocycle. In some cases, $R^1$ is selected from an 8-membered bridged heterocycle. In some cases, the bridged heterocycle of $R^1$ has at most 1 nitrogen atom. In some cases, the bridged heterocycle of $R^1$ has at most 2 nitrogen atoms. In some cases, the bridged heterocycle of $R^1$ has at least 2 nitrogen atom. In some cases, $R^1$ is selected from

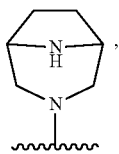 [SMILES: *N1CC2CCC(C1)N2]

which is optionally substituted. In some cases, $R^1$ is

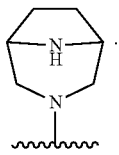

In some embodiments, for a compound or salt of Formula (I), Formula (I-A), Formula (I-B), Formula (I-C), or Formula (I-G), the optional substituents of $R^1$ are independently selected from one or more halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, and $C_{2-6}$ alkynyl. In some cases, the optional substituents of $R^1$ are independently selected from one or more halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =NO(R$^{20}$), —CN, —NHCN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, and $C_{2-6}$ alkynyl.

In some embodiments, for a compound or salt of Formula (I), Formula (I-A), Formula (I-B), Formula (I-C), or Formula (I-G), the optional substituents of $R^1$ are independently selected from one or more halogen, —B(OR$^{20}$)$_2$, —OH, —O—$C_{1-6}$ alkyl, —SR$^{20}$, —N(R$^{20}$)$_2$, —NO$_2$, =O, =NO(R$^{20}$), —CN, —NHCN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, and $C_{1-6}$ alkyl. In some cases, the optional substituents of $R^1$ are independently selected from one or more halogen, —B(OR$^{20}$)$_2$, —OH, —SR$^{20}$, —N(R$^{20}$)$_2$, —NO$_2$, =O, =NO(R$^{20}$), $C_{1-6}$ alkoxyalkyl, $C_{1-6}$ aminoalkyl, $C_{1-6}$ alkoxy, $C_{1-6}$ hydroxyalkyl, $C_{1-6}$ haloalkyl, and $C_{1-6}$ alkyl. In some cases, the optional substituents of $R^1$ are independently selected from one or more halogen, —OH, —NH$_2$, and $C_{1-6}$ alkoxy. In some cases, the optional substituents of $R^1$ are independently selected from one or more halogen, —OH, and $C_{1-6}$ alkoxy. In some cases, the optional substituents of $R^1$ are independently selected from one or more halogen, and —OH. In some cases, the optional substituents of $R^1$ are independently selected from one or more —OH. In some cases, the optional substituents of $R^1$ are independently selected from one or more $C_{1-6}$ alkyl, $C_{1-6}$ hydroxyalkyl and —OH. In some cases, the optional substituents of $R^1$ are independently selected from one or more $C_{1-6}$ hydroxyalkyl and —OH. In some cases, $R^1$ is substituted with at least one substituent independently selected from $C_{1-6}$ hydroxyalkyl and —OH. In some cases, $R^1$ is substituted with at least one substituent independently selected from —OH.

In some embodiments, for a compound or salt of Formula (I), Formula (I-A), Formula (I-B), Formula (I-C), or Formula (I-G), the heterocycle of $R^1$ is substituted with one or more substituents. In some cases, the substituents of $R^1$ are independently selected from one or more halogen, —B(OR$^{20}$)$_2$, —OH, —O—$C_{1-6}$ alkyl, —SR$^{20}$, —N(R$^{20}$)$_2$, —NO$_2$, =O, =NO(R$^{20}$), —CN, —NHCN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, and $C_{1-6}$ alkyl. In some cases, the substituents of $R^1$ are independently selected from one or more halogen, —B(OR$^{20}$)$_2$, —OH, —SR$^{20}$, —N(R$^{20}$)$_2$, —NO$_2$, =NO(R$^{20}$), $C_{1-6}$ aminoalkyl, $C_{1-6}$ alkoxy, $C_{1-6}$ hydroxyalkyl, $C_{1-6}$ haloalkyl, and $C_{1-6}$ alkyl. In some cases, the substituents of $R^1$ are independently selected from one or more halogen, —OH, —NH$_2$, and $C_{1-6}$ alkoxy. In some cases, the substituents of $R^1$ are independently selected from one or more halogen, —OH, and $C_{1-6}$ alkoxy. In some cases, the optional substituents of $R^1$ are independently selected from one or more halogen, and —OH.

In some embodiments, for a compound or salt of Formula (I), Formula (I-A), Formula (I-B), Formula (I-C), or Formula (I-G), the heterocycle of $R^1$ is substituted with one or more substituents. In some cases, the heterocycle of $R^1$ is substituted with one or more substituents selected from halogen, —B(OR$^{20}$)$_2$, —OR$^{20}$, —SR$^{20}$, —S(O)$_2$(R$^{20}$), —S(O)$_2$N(R$^{20}$)$_2$, —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —NO$_2$, =O, =NO(R$^{20}$), —CN, —NHCN, $C_{1-6}$ alkoxyalkyl, $C_{2-6}$ alkenyl, and $C_{2-6}$ alkynyl; and further optionally substituted with one or more substituents independently selected from $C_{1-6}$ alkoxyalkyl, $C_{1-6}$ aminoalkyl, $C_{1-6}$ hydroxyalkyl, $C_{1-6}$ cyanoalkyl, $C_{1-6}$ haloalkyl, and $C_{1-6}$ alkyl. In some cases, the substituents of $R^1$ are each selected from one or more halogen, —OR$^{20}$, —SR$^{20}$, —N(R$^{20}$)$_2$, —NHCN, —NO$_2$, =O, —CN, $C_{1-6}$ fluoroalkyl, and $C_{2-6}$ alkynyl; and further optionally substituted with one or more substituents independently selected from —C(O)N(R$^{20}$)$_2$, $C_{1-6}$ aminoalkyl, $C_{1-6}$ hydroxyalkyl, $C_{1-6}$ cyanoalkyl, $C_{1-6}$ alkyl, and $C_{2-6}$ alkenyl. In some cases, the substituents of $R^1$ are each selected from one or more halogen, —OR$^{20}$, —N(R$^{20}$)$_2$, —NHCN, =O, —CN, and $C_{2-6}$ alkynyl; and further optionally substituted with one or more substituents independently selected from —C(O)N(R$^{20}$)$_2$, C$_{1-6}$ aminoalkyl, C$_{1-6}$ hydroxyalkyl, C$_{1-6}$ cyanoalkyl, and C$_{1-6}$ alkyl. In some cases, the substituents of R$^1$ are each selected from one or more halogen, —OH, —NHCN, =O, —CN, and C$_{2-6}$ alkynyl; and further optionally substituted with one or more substituents independently selected from C$_{1-6}$ alkyl. In some cases, the substituents of R$^1$ are each selected from one or more halogen, NH$_2$, —OH, and =O.

In some embodiments, for a compound or salt of Formula (I), R$^{100}$ is different than Y—R$^2$. In some cases,

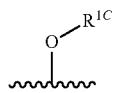

is different than Y—R$^2$.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), L is selected from C$_1$-C$_4$ alkylene. In some cases, L is selected from C$_1$-C$_2$ alkylene. In some cases, L is selected from C$_1$ alkylene.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), L is selected from unsubstituted C$_1$-C$_4$ alkylene. In some cases, L is selected from unsubstituted C$_1$-C$_2$ alkylene. In some cases, L is selected from unsubstituted C alkylene. In some cases, L is selected from methylene and ethylene. In some cases, L is methylene.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), R$^2$ is selected from optionally substituted -L-heterocycle, optionally substituted -L-heteroaryl, optionally substituted -L-aryl, -L-N(R$^5$)$_2$, and -L-O—R$^5$. In some cases, R$^2$ is selected from optionally substituted -L-5- to 12-membered heterocycle, optionally substituted -L-5- to 12-membered heteroaryl, optionally substituted -L-C$_6$-C$_{12}$aryl, -L-N(R$^5$)$_2$, and -L-O—R$^5$. In some cases, R$^2$ is selected from optionally substituted -L-heterocycle, optionally substituted -L-heteroaryl, and -L-N(R$^5$)$_2$. In some cases, R$^2$ is selected from optionally substituted -L-5- to 12-membered heterocycle, optionally substituted -L-5-to-12-membered heteroaryl, and -L-N(R$^5$)$_2$. In some cases, R$^2$ is selected from optionally substituted -L-heterocycle and -L-N(R$^5$)$_2$. In some cases, R$^2$ is selected from optionally substituted -L-5- to 12-membered heterocycle and -L-N(R$^5$)$_2$. In some cases, R$^2$ is selected from optionally substituted -L-5- to 12-membered heterocycle. In some cases, R$^2$ is selected from optionally substituted -L-5- to 12-membered saturated heterocycle. In some cases, R$^2$ is selected from optionally substituted -L-heterocycle. In some cases, the heterocycle is selected from pyrrolidine, hexahydro-1H-pyrrolizine, pyrazolidine, imidazolidine, tetrahydrofuran, piperidine, piperazine, morpholine, azocane, and azonane. In some cases, the heterocycle is selected from cyclic sulfonamide. In some cases, the heterocycle is selected from pyrrolidine, hexahydro-1H-pyrrolizine, pyrazolidine, imidazolidine, piperidine, piperazine, azocane, and azonane. In some cases, the heteroaryl is selected from pyrrole, pyrazole, furan, thiohene, oxazole, isoxazole, isothiazole, thiazole, pyridine, pyrazine, and triazine. In some cases, the heteroaryl or heterocycle has at most 1 nitrogen atom. In some cases, the heteroaryl or heterocycle has at least 1 nitrogen atom. In some cases, the heteroaryl or heterocycle has 1 nitrogen atom.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), L is selected from C$_1$-C$_4$ alkylene. In some cases, L is selected from an unsubstituted C$_1$-C$_4$ alkylene. In some cases, L is selected from an unsubstituted C$_1$ alkylene. In some cases, two substituents on the same carbon atom of L come together to form a C$_3$-C$_6$ carbocycle or 3- to 8-membered heterocycle, wherein the C$_3$-C$_6$ carbocycle and 3- to 8-membered heterocycle are each optionally substituted with one or more substituents independently selected from halogen, —OH, —NO$_2$, =O, =S, —CN, C$_{1-6}$ aminoalkyl, C$_{1-6}$ alkoxy, C$_{1-6}$ hydroxyalkyl, C$_{1-6}$ haloalkyl. In some cases, two substituents on the same carbon atom of L come together to form a C$_3$-C$_6$ carbocycle or 3- to 8-membered heterocycle. In some cases, two substituents on the same carbon atom of L come together to form a C$_3$-C$_6$ carbocycle.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), L is selected from C$_1$-C$_4$ alkylene. In some cases, L is selected from unsubstituted C$_1$-C$_4$ alkylene. In some cases, each L is independently selected from a C$_1$-C$_4$ alkylene optionally substituted; and wherein optionally two substituents on the same carbon atom of L come together to form a C$_3$-C$_6$ carbocycle or 3- to 8-membered heterocycle wherein the C$_3$-C$_6$ carbocycle and 3- to 8-membered heterocycle are each optionally substituted with one or more substituents selected from halogen, —OH, —NO$_2$, =O, =S, —CN, C$_{1-6}$ aminoalkyl, C$_{1-6}$ alkoxy, C$_{1-6}$ hydroxyalkyl, C$_{1-6}$ haloalkyl. In some cases, the optional substituents of L are selected from C$_1$-C$_4$ hydroxyalkyl, C$_1$-C$_4$ alkyl, C$_3$-C$_6$ carbocycle; and wherein optionally two substituents on the same carbon atom of L come together to form a C$_3$-C$_6$ carbocycle or 3- to 8-membered heterocycle wherein the C$_3$-C$_6$ carbocycle and 3- to 8-membered heterocycle are optionally substituted with one or more substituents selected from halogen and C$_{1-6}$ haloalkyl. In some cases, L is selected from

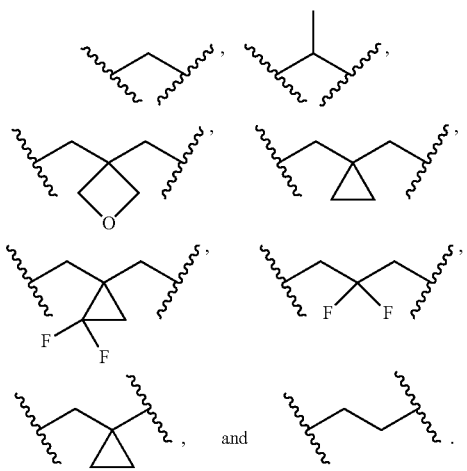

In some cases, L is selected from

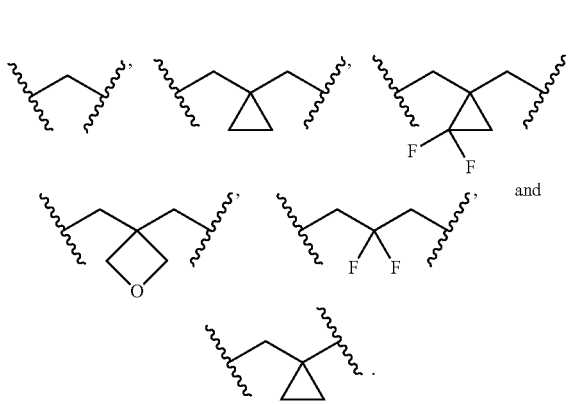

In some cases, each L is independently selected from a substituted $C_1$-$C_4$ alkylene, and wherein two substituents on the same carbon atom of L come together to form a $C_3$-$C_6$ carbocycle 3- to 5-membered heterocycle. In some cases, each L is independently selected from a substituted $C_{2-3}$ alkylene, and wherein two substituents on the same carbon atom of L come together to form a $C_3$ carbocycle or 4-membered heterocycle, wherein the $C_3$ carbocycle is optionally substituted with one or more substituents selected from halogen. In some cases, each L is independently selected from

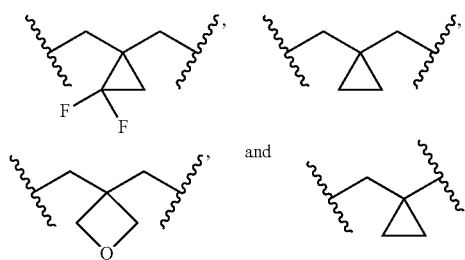

In some cases, each L is independently selected from

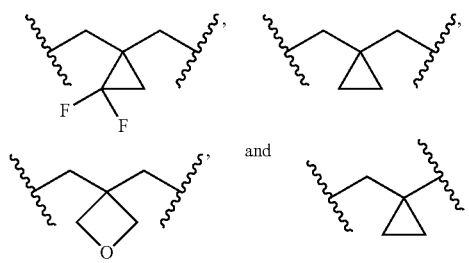

In some cases, each L is independently selected from a $C_1$-$C_4$ alkylene optionally substituted with one or more substituents independently selected from halogen and $C_1$-$C_4$ alkyl. In some cases, L is selected from

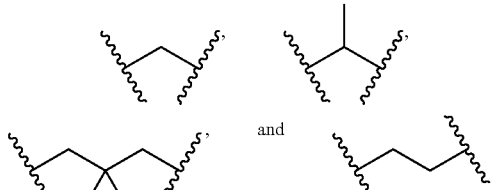

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), each L is independently selected from an unsubstituted $C_1$-$C_4$ alkylene. In some cases, L is selected from

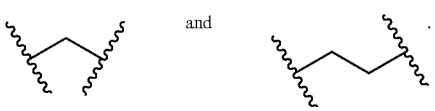

In some cases, L is selected from

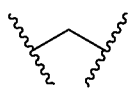

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), $R^2$ is selected from heterocycle, $C_1$-$C_6$ alkyl, -L-heterocycle, -L-N($R^{20}$)$_2$, -L-O$R^{20}$, -L-aryl, -L-heteroaryl, -L-cycloalkyl, -L-N($R^{20}$)$_2$, -L-NHC(=NH)NH$_2$, -L-C(O)N($R^{20}$)$_2$, -L-$C_1$-$C_6$ haloalkyl, -L-O$R^{20}$, -L-N$R^{20}$C(O)-aryl, -L-COOH, -L-N$R^{20}$S(O)$_2$($R^{20}$), -L-S(O)$_2$N($R^{20}$)$_2$, -L-N($R^{20}$)C(O)(O$R^{20}$), -L-OC(O)N($R^{20}$)$_2$, and -L-C(=O)O$C_1$-$C_6$ alkyl, wherein the heterocycle, the heterocycle portion of -L-heterocycle, and the cycloalkyl portion of the -L-cycloalkyl are each optionally substituted with one or more $R^6$, and wherein the aryl portion of -L-N$R^{20}$C(O)-aryl, the aryl portion of -L-N$R^{20}$C(O)-aryl, the aryl of the -L-aryl, and the heteroaryl of -L-heteroaryl are each optionally substituted with one or more $R^7$.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), $R^2$ is selected from heterocycle, -L-heterocycle, -L-aryl, -L-heteroaryl, and -L-N($R^{20}$)$_2$, wherein the heterocycle, the heterocycle portion of -L-heterocycle, are each optionally substituted with one or more $R^6$, and wherein the aryl of the -L-aryl, and the heteroaryl of -L-heteroaryl are each optionally substituted with one or more $R^7$.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), $R^2$ is selected from heterocycle, -L-heterocycle, -L-N($R^{20}$)$_2$, -L-O$R^{20}$, -L-aryl, -L-heteroaryl, -L-cycloalkyl, -L-NHC(=NH)NH$_2$, -L-C(O)N($R^{20}$)$_2$, -L-$C_1$-$C_6$ haloalkyl, -L-N$R^{20}$C(O)-aryl, -L-COOH, -L-N$R^{20}$S(O)$_2$($R^{20}$), -L-S(O)$_2$N($R^{20}$)$_2$, -L-N($R^{20}$)C(O)

(OR$^{20}$), -L-OC(O)N(R$^{20}$)$_2$, and -L-C(=O)OC$_1$-C$_6$ alkyl, wherein the heterocycle, the heterocycle portion of -L-heterocycle, and the cycloalkyl portion of the -L-cycloalkyl are each optionally substituted with one or more R$^6$, and wherein the aryl portion of -L-NR$^{20}$C(O)-aryl, the aryl of the -L-aryl, and the heteroaryl of -L-heteroaryl are each optionally substituted with one or more R$^7$; and wherein the heterocycle, the heterocycle portion of -L-heterocycle, and the heteroaryl of -L-heteroaryl each have at least one heteroatom selected from nitrogen, oxygen, silicon, and sulfur.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), R$^2$ is -L-heterocycle, wherein the heterocycle portion is optionally substituted. In some cases, R$^2$ is -L-heterocycle, wherein the heterocycle portion is a bicyclic heterocycle. In some cases, R$^2$ is -L-heterocycle, wherein the heterocycle portion is a monocyclic heterocycle. In some cases, R$^2$ is -L-heterocycle, wherein the heterocycle portion is a saturated heterocycle. In some cases, R$^2$ is selected from a -L-5- to 10-membered heterocycle. In some cases, R$^2$ is selected from a —(C$_1$-C$_2$ alkylene)-5- to 10-membered heterocycle. In some cases, R$^2$ is selected from a -L-5- to 8-membered heterocycle. In some cases, R$^2$ is selected from a -L-5- to 8-membered saturated heterocycle. In some cases, R$^2$ is a -L-5-membered heterocycle. In some cases, R$^2$ is a -L-8-membered heterocycle. In some cases, the heterocycle contains at least 1 nitrogen atom. In some cases, the heterocycle contains at most 1 nitrogen atom. In some cases, the heterocycle contains 1 nitrogen atom. In some cases, the bicyclic heterocycle contains at least 1 nitrogen atom. In some cases, the heterocycle has a silicon atom. In some cases, the bicyclic heterocycle contains at most 1 nitrogen atom. In some cases, the bicyclic heterocycle contains 1 nitrogen atom. In some cases, Y—R$^2$ is selected from

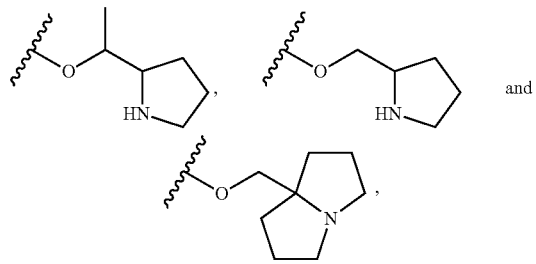

wherein the heterocycle portion is optionally substituted. In some cases, Y—R$^2$ is selected from

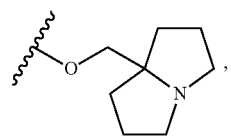 [SMILES: *OCC12CCCN1CCC2]

wherein the heterocycle portion is optionally substituted. In some cases, the heterocycle portion is optionally substituted with one or more substituents selected from halogen, hydroxy, C$_1$-C$_3$ hydroxyalkyl, C$_1$-C$_3$ alkyl, C$_1$-C$_3$ haloalkyl, C$_1$-C$_3$ alkoxy, —CN, and C$_1$-C$_3$ aminoalkyl. In some cases, the heterocycle portion is optionally substituted with one or more substituents selected from halogen, hydroxy, —CN, C$_1$-C$_3$ hydroxyalkyl, C$_1$-C$_3$ alkyl, C$_1$-C$_3$ haloalkyl, C$_1$-C$_3$ alkoxy, and C$_1$-C$_3$ aminoalkyl. In some cases, the heterocycle portion is optionally substituted with one or more substituents selected from C$_1$-C$_3$ alkyl and halogen. In some cases, Y—R$^2$ is selected from

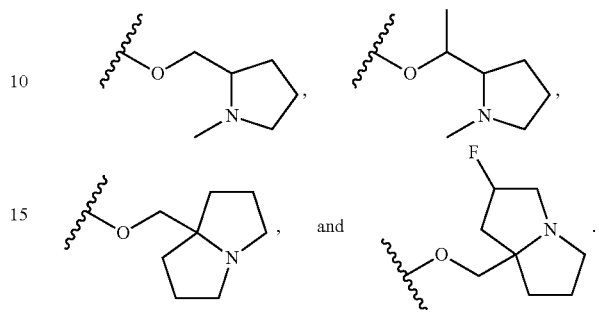

In some cases, Y—R$^2$ is selected from

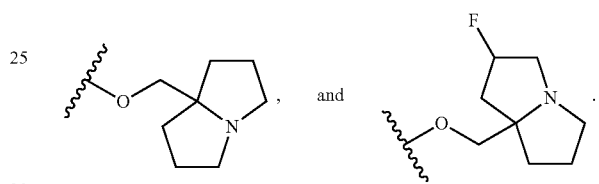

In some cases, Y—R$^2$ is selected from

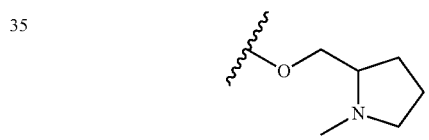

In some cases, Y—R$^2$ is

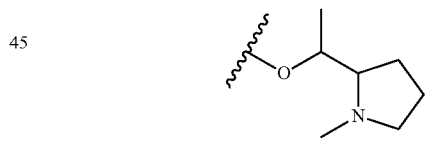

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), R$^2$ is selected from optionally substituted -L-heterocycle. In some cases, the heterocycle is a monocyclic heterocycle. In some cases, the heterocycle has only 1 nitrogen atom. In some cases, the heterocycle has only 1 nitrogen atom and no other heteroatoms. In some cases, Y—R$^2$ is selected from

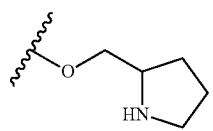

which is optionally substituted with one or more $R^6$. In some cases, each $R^6$ is independently selected from halogen, $C_1$-$C_3$ hydroxyalkyl, $C_1$-$C_3$ alkyl, $C_1$-$C_3$ haloalkyl, ($C_1$-$C_3$ alkoxy)$C_1$-$C_3$ alkyl-, and $C_{1-6}$ alkyl-N($R^{20}$)$_2$. In some cases, Y—$R^2$ is selected from

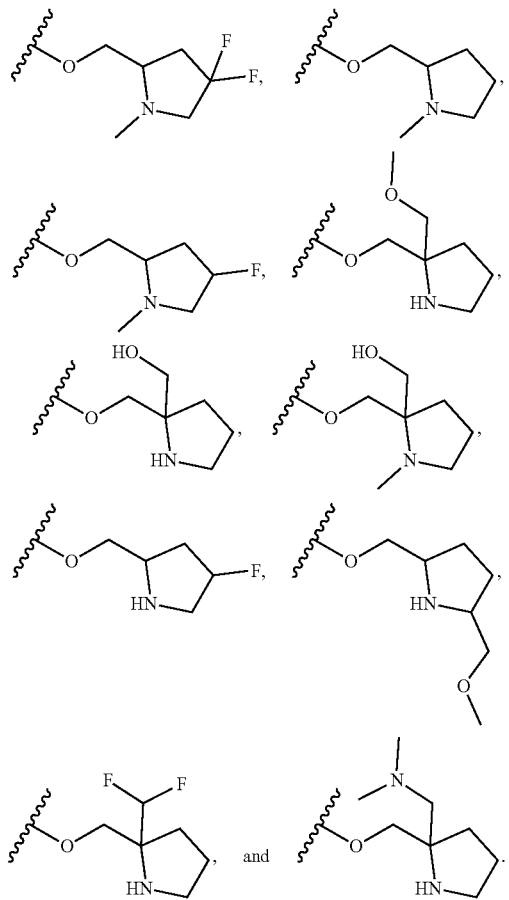

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), $R^2$ is selected from optionally substituted -L-heterocycle. In some cases, the heterocycle is a bicyclic heterocycle. In some cases, the heterocycle is a monocyclic heterocycle. In some cases, the heterocycle has only 1 nitrogen atom. In some cases, the heterocycle has only 1 nitrogen atom and no other heteroatoms. In some cases, Y—$R^2$ is selected from

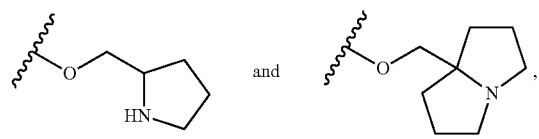 [SMILES: *OCC1CCCN1 ; *OCC12CCCN1CCC2]

wherein the heterocycle portion is optionally substituted. In some cases, Y—$R^2$ is selected from

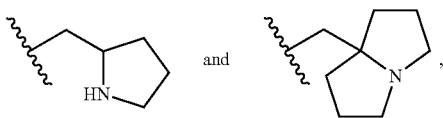 [SMILES: *CC1CCCN1 ; *CC12CCCN1CCC2]

wherein the heterocycle portion is optionally substituted. In some cases, Y—$R^2$ is selected from

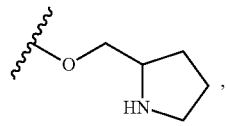 [SMILES: *OCC1CCCN1]

wherein the heterocycle portion is optionally substituted. In some cases, Y—$R^2$ is selected from

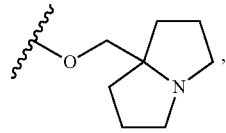 [SMILES: *OCC12CCCN1CCC2]

wherein the heterocycle portion is optionally substituted. In some cases, the heterocycle is optionally substituted with one or more substituent selected from halogen, hydroxy, $C_1$-$C_3$ alkyl, —N($R^5$)S(O)$_2$($R^5$), —OC(O)N($R^5$)$_2$, oxo, =CH$_2$, =NO—$C_1$-$C_3$ alkyl, —CH$_2$OC(O)heterocycle, —CH$_2$heterocycle, —CH$_2$OC(O)N($R^5$)$_2$, and —O—$C_1$-$C_3$ alkyl, wherein the alkyl of —O—$C_1$-$C_3$ alkyl is optionally substituted with substituents selected from heterocycle, oxo, and hydroxy. In some cases, Y—$R^2$ is selected from

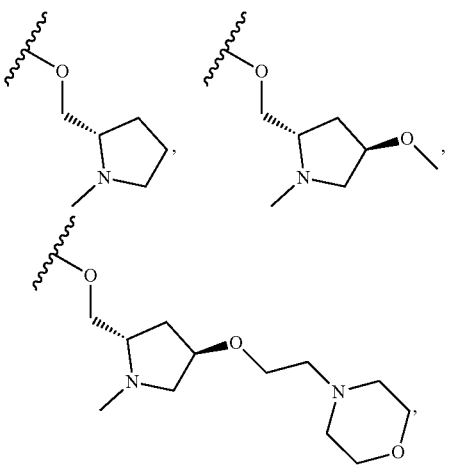

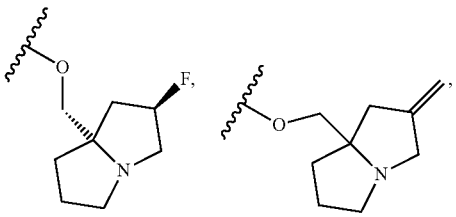

221
-continued
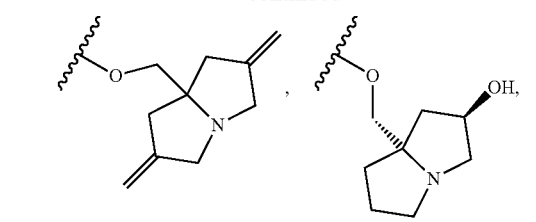
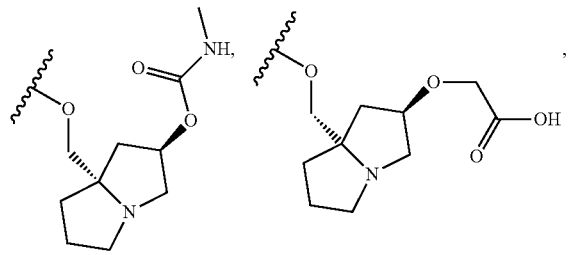
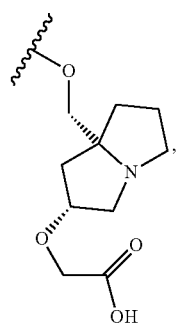
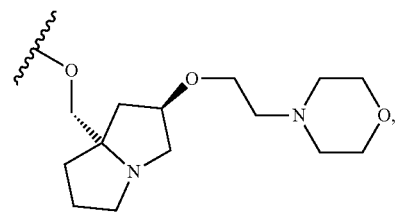
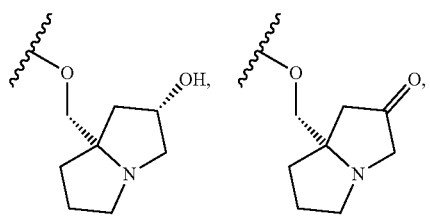
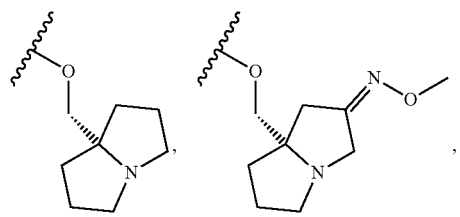
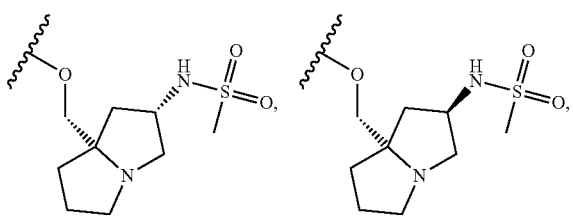
222
-continued
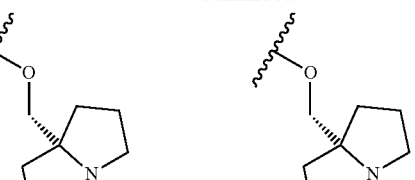
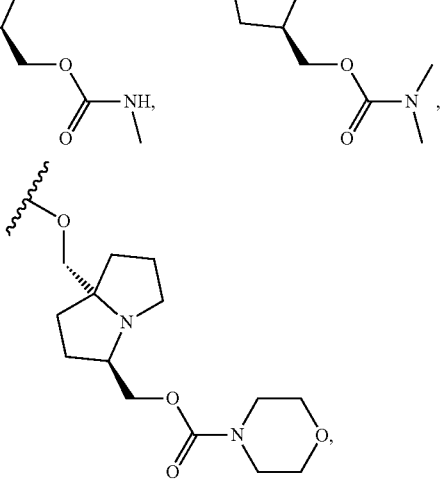
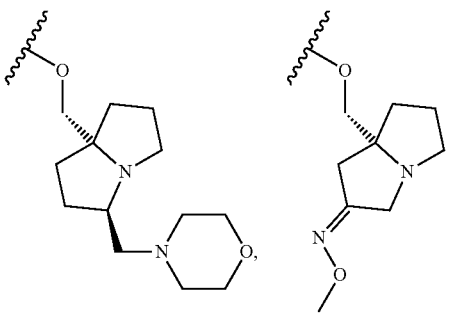
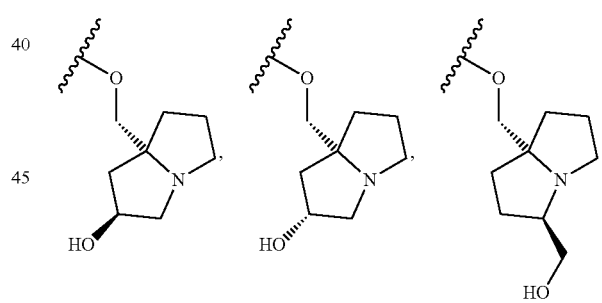
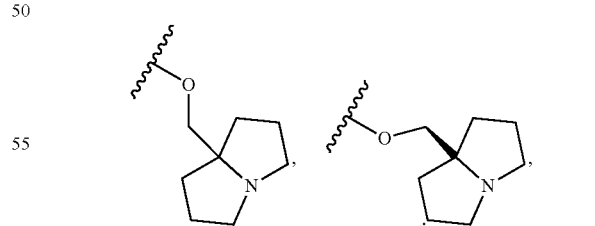
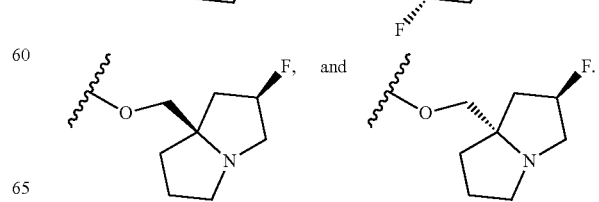

In some cases, Y—R² is selected from
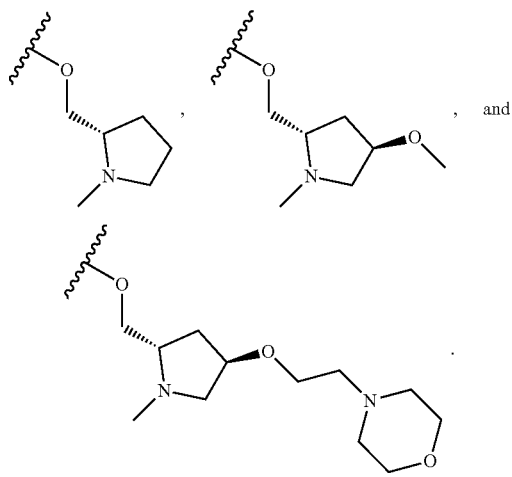
In some cases, Y—R² is selected from
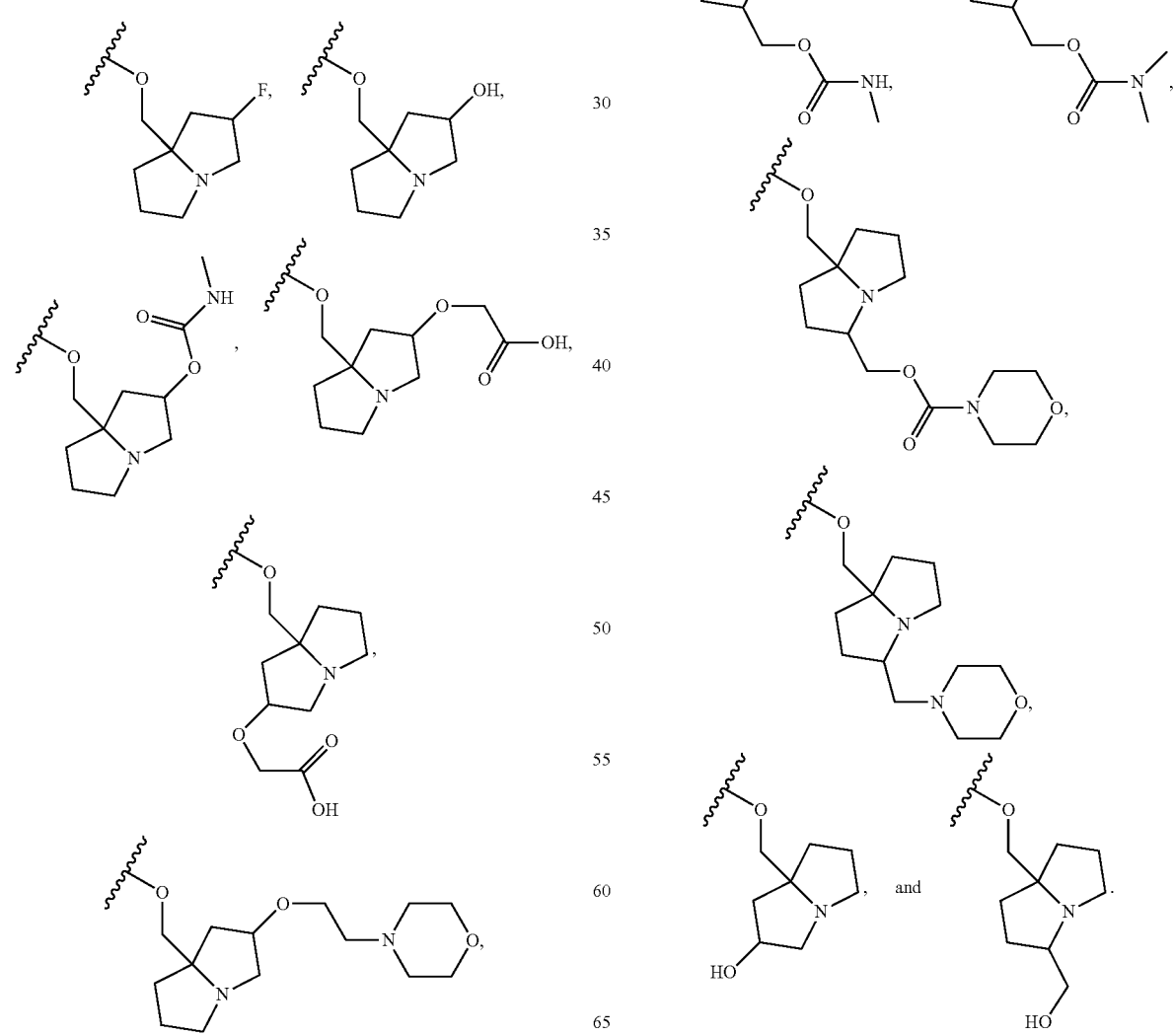

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), R² is -L-heteroaryl, wherein the heteroaryl portion is optionally substituted with one or more R⁷. In some cases, the heteroaryl has at least one nitrogen atom. In some cases, the heteroaryl has two nitrogen atoms. In some cases, the heteroaryl is

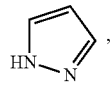, which is optionally substituted. In some cases, the heteroaryl is

, which is optionally substituted. In some cases, the heteroaryl is

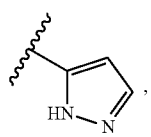 [SMILES: *c1ccn[nH]1], which is optionally substituted. In some cases, Y—R² is selected from

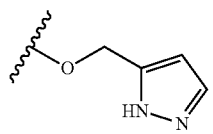 and 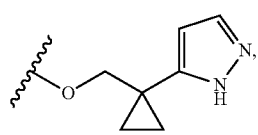, wherein the heteroaryl portion is optionally substituted with one or more R⁷. In some cases, each R⁷ is independently selected from $C_1$-$C_4$ alkyl, halogen, and $C_1$-$C_4$ haloalkyl. In some cases, Y—R² is selected from

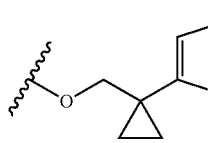 and 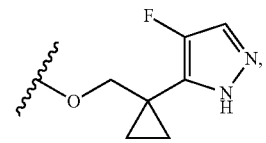,

In some cases, Y—R² is selected from

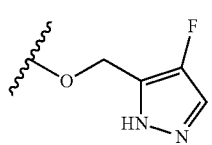 and 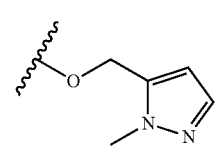.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), R² is -L-aryl, optionally substituted with one or more R⁷. In some cases, wherein Y—R² is selected from

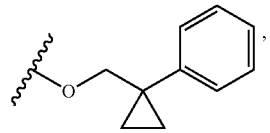 [SMILES: *OCC1(c2ccccc2)CC1], wherein the heterocycle portion is optionally substituted with one or more R⁷. In some cases, Y—R² is selected from

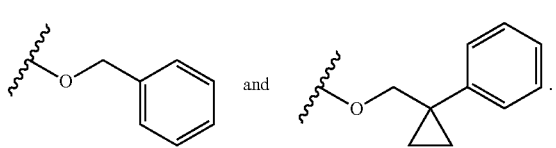 [SMILES: *OCc1ccccc1 ; *OCC1(c2ccccc2)CC1] and 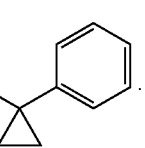.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), R² is -L-N(R²⁰)₂. In some cases, Y—R² is selected from

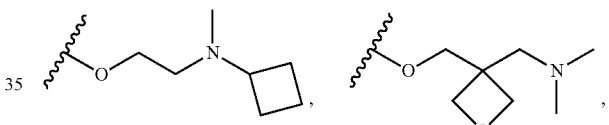

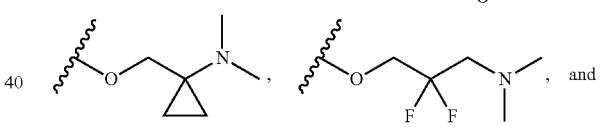, and

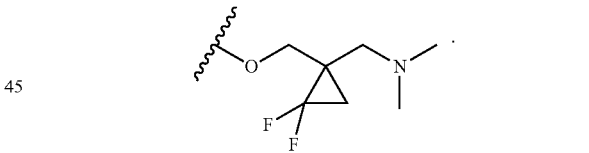.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), R² is heterocycle, optionally substituted with one or more R⁶. In some cases, the heterocycle of R⁶ is

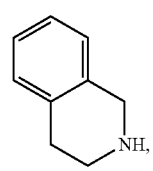

which is optionally substituted. In some cases, the heterocycle of R⁶ is

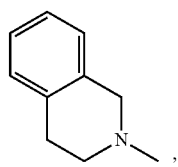

In some cases, Y—R² is

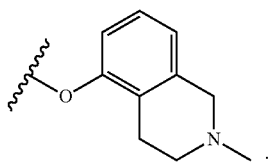 [SMILES: *Oc1cccc2c1CCN(C)C2]

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), Y—R² is selected from

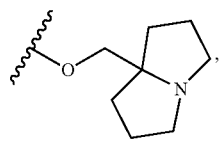 [SMILES: *OCC12CCCN1CCC2]

wherein the heterocycle portion is optionally substituted, where the optional one or more substituents are selected from halogen, hydroxy, C₁-C₃ alkyl, —N(R⁵)S(O)₂(R⁵), —OC(O)N(R⁵)₂, =CH₂, oxo, =NO—C₁-C₃ alkyl, —CH₂OC(O)heterocycle, —CH₂heterocycle, —CH₂OC(O)N(R⁵)₂, —(CH₂)₀₋₁—O-heterocycle, and —O—C₁-C₃ alkyl, wherein the alkyl of —O—C₁-C₃ alkyl is optionally substituted with substituents selected from heterocycle, oxo, and hydroxy, and wherein the heterocycle of —(CH₂)₀₋₁—O-heterocycle is optionally substituted with one or more substituents selected from C₁₋₆ alkyl, C₁₋₆ haloalkyl, C₁₋₆ alkyl-OR²⁰, and —OR²⁰. In some cases, the optional one or more substituents are selected from:

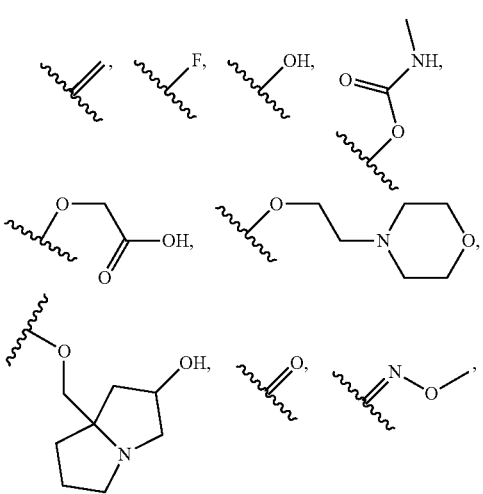

-continued

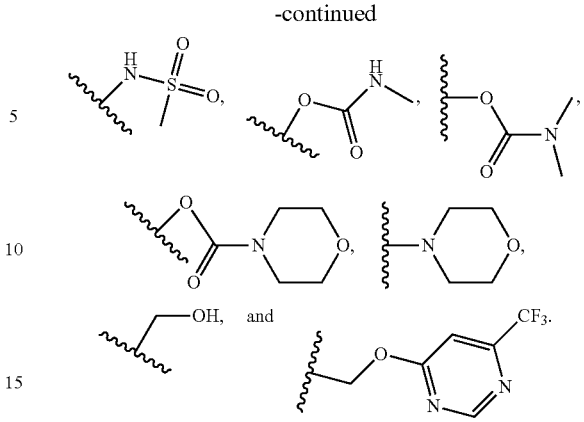

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), Y—R² is selected from

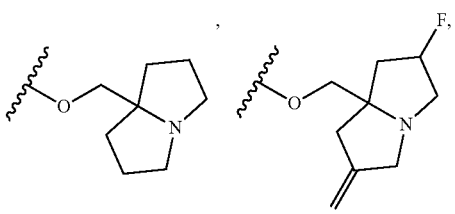

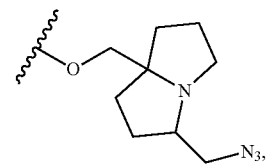

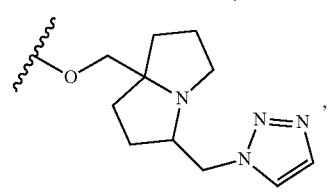

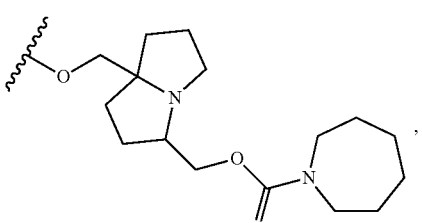

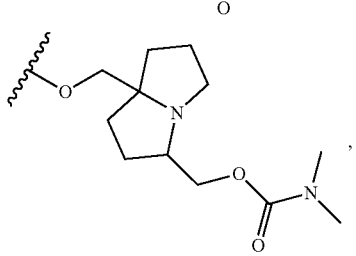

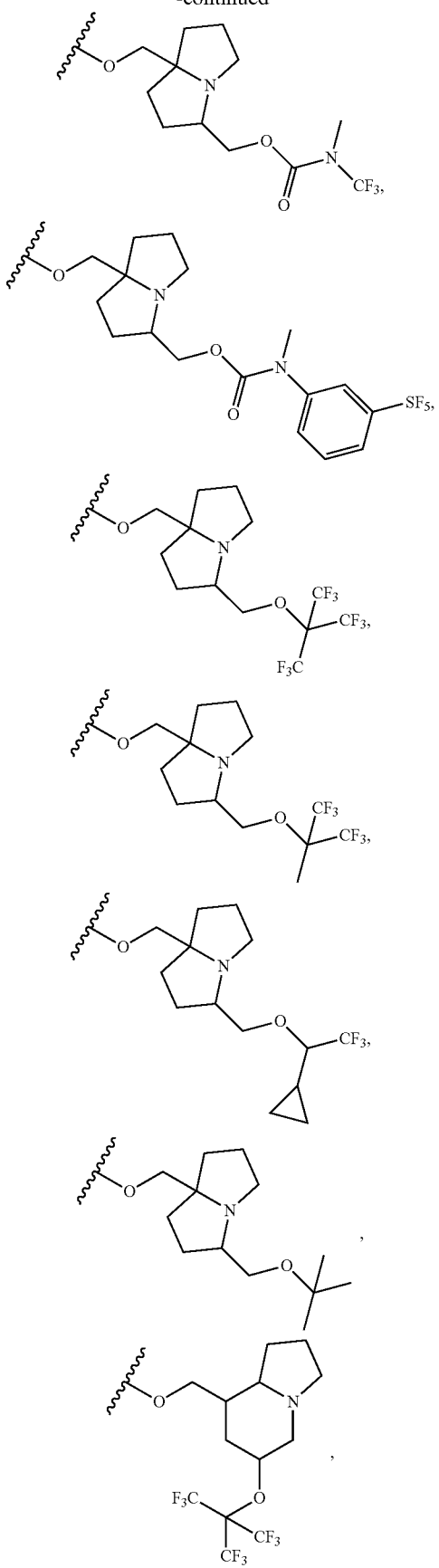
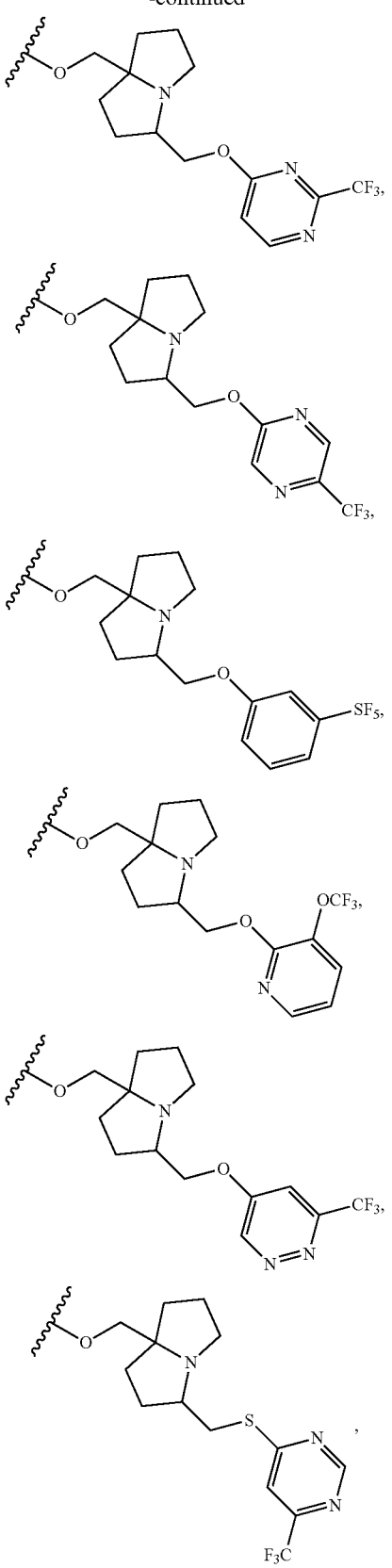

-continued

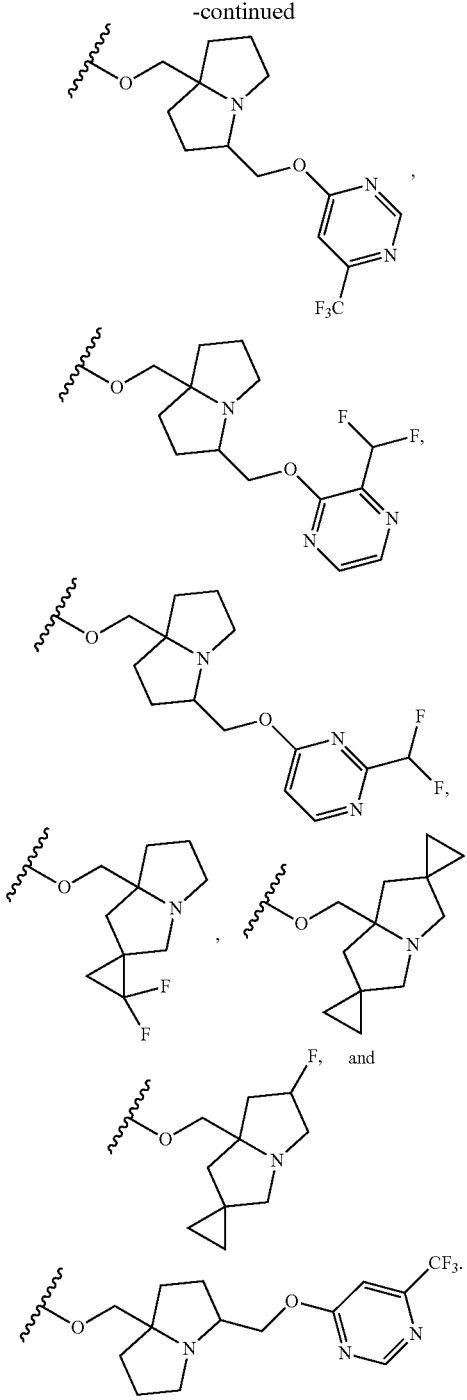

In some cases, Y—R² is selected from

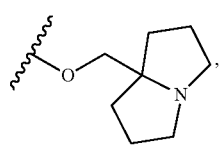 [SMILES: *OCC12CCCN1CCC2]

wherein the heterocycle portion is optionally substituted with one or more R⁶. In some cases, each R⁶ is selected from —(CH₂)₀₋₁S-heterocycle, and —(CH₂)₀₋₁—O-heterocycle, wherein the heterocycle of —(CH₂)₀₋₁—O-heterocycle and —(CH₂)₀₋₁—S-heterocycle are each optionally substituted with one or more substituents selected from $C_{1-6}$ alkyl, $C_{1-6}$ haloalkyl, $C_{1-6}$ alkyl-OR²⁰, and —OR²⁰. In some cases, each R⁶ is selected from —CH₂—S-heterocycle, and —CH₂—O-heterocycle, wherein the heterocycle of —CH₂—O-heterocycle and —CH₂—S-heterocycle are each optionally substituted with one or more substituents selected from $C_{1-6}$ alkyl, $C_{1-6}$ haloalkyl, $C_{1-6}$ alkyl-OR²⁰, and —OR²⁰. In some cases, each R²⁰ is independently selected from hydrogen; and $C_{1-6}$ alkyl, each of which is optionally substituted with one or more substituents independently selected from halogen. In some cases, each R²⁰ is independently selected from $C_{1-6}$ alkyl, each of which is optionally substituted with one or more substituents independently selected from halogen. In some cases, the heterocycle has one or two nitrogen atoms. In some cases, the heterocycle is a heteroaryl. In some cases, the heterocycle is selected from:

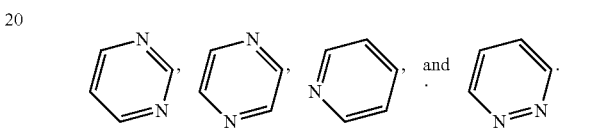

In some cases, each R⁶ is selected from —CH₂—S-heterocycle, and —CH₂—O-heterocycle, wherein the heterocycle of —CH₂—O-heterocycle and —CH₂—S-heterocycle are each optionally substituted with one or more substituents selected from

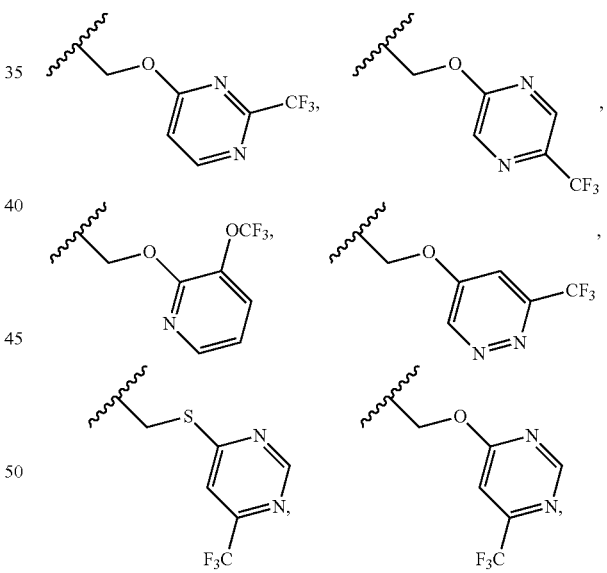

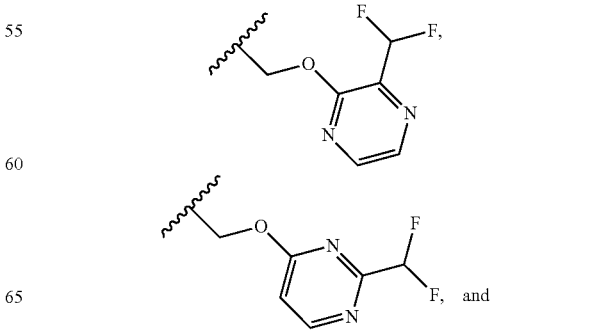

-continued

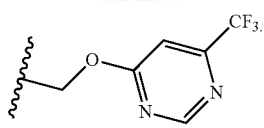

In some cases, Y—R$^2$ is selected from

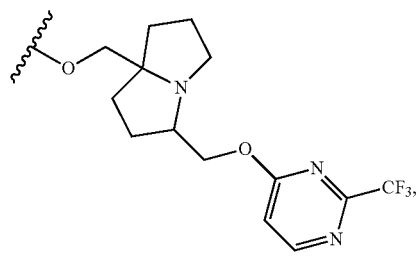

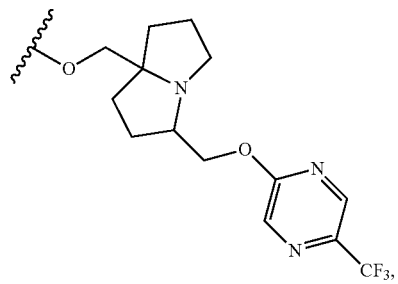

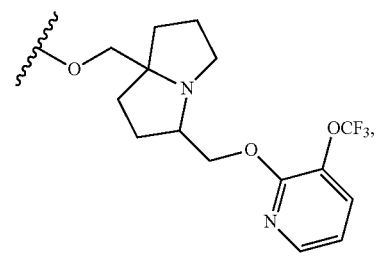

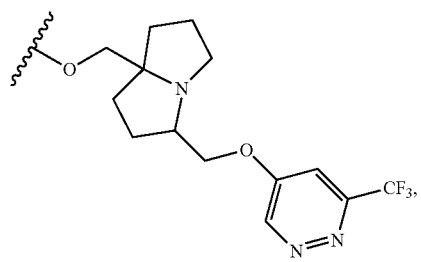

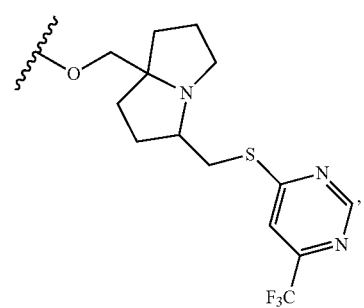

-continued

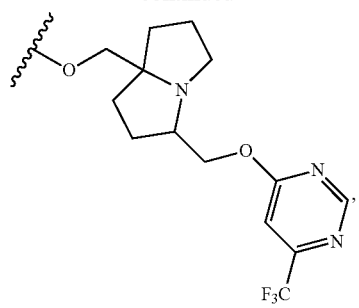

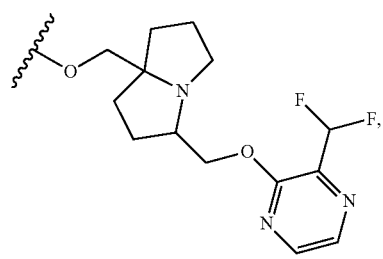

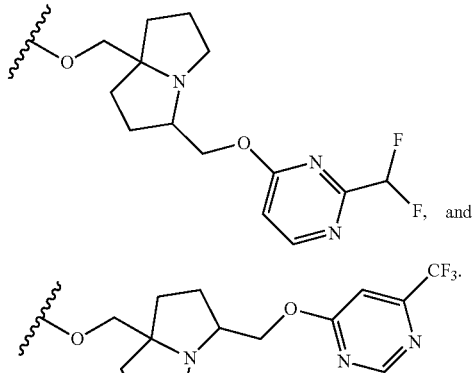

In some cases, Y—R$^2$ is selected from

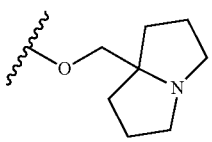 and 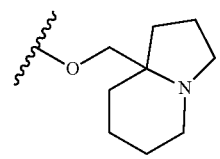

(preferably 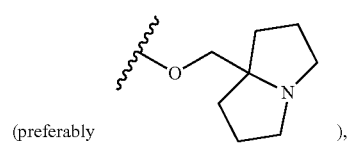 ), wherein the heterocycle portion is optionally substituted with one or more R$^6$. In some cases, R$^6$ is selected from —CH$_2$O—C$_1$-C$_6$ alkyl, wherein the alkyl of —CH$_2$O—C$_1$-C$_6$ alkyl is optionally substituted with one or more substituents selected from halogen and C$_3$-C$_6$ carbocycle.

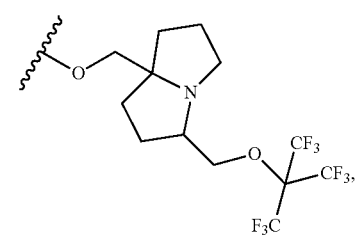
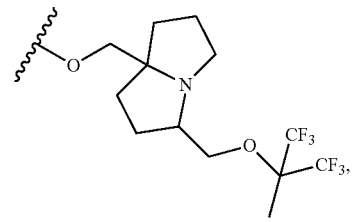
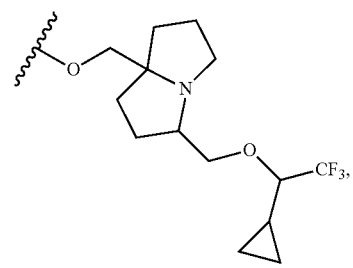
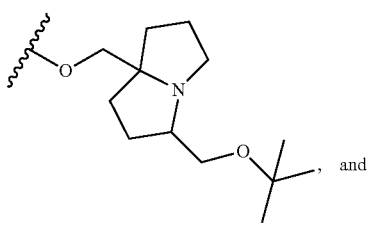
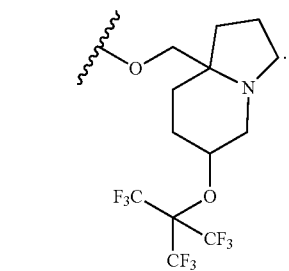

In some cases, Y—R² is selected from

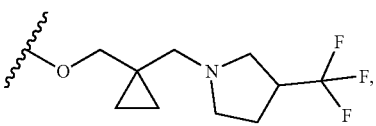
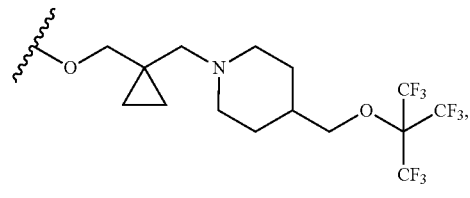

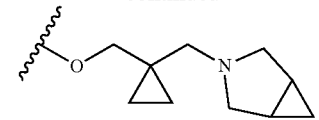
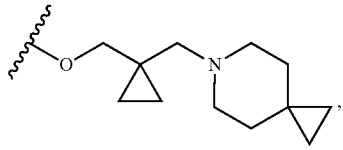
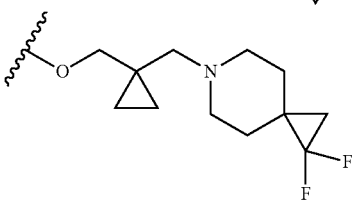
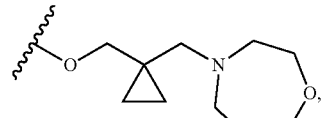
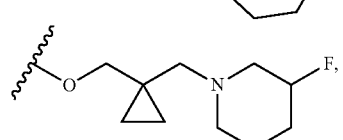
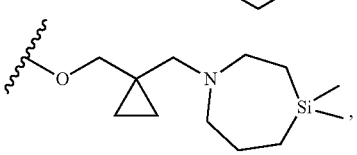
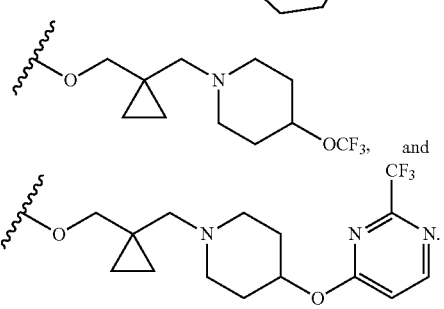

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), R² is selected from heterocycle, -L-heterocycle, wherein the heterocycle, and the heterocycle portion of -L-heterocycle, are each optionally substituted with one or more R⁶; -L-aryl, and -L-heteroaryl, wherein the aryl of the -L-aryl, and the heteroaryl of -L-heteroaryl are each optionally substituted with one or more R⁷ and -L-N(R²⁰)₂. In some cases the heterocycle of R is selected from

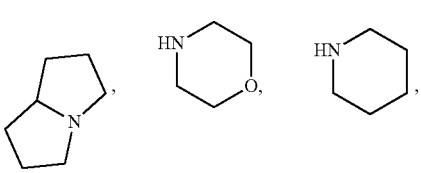

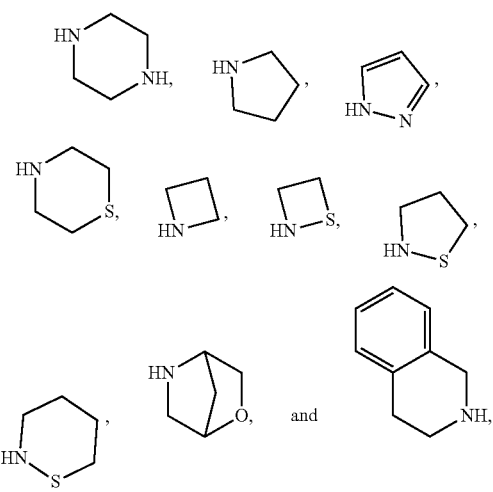

wherein the heterocycle of R² is optionally substituted with one or more R⁶; wherein the aryl and heteroaryl of R² is selected from

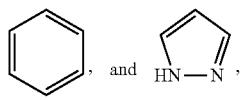 [SMILES: c1ccccc1 ; c1cn[nH]c1]

wherein the aryl and the heteroaryl are each optionally substituted with one or more R⁷; and

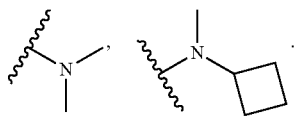

In some cases, the heterocycle of R² is selected from

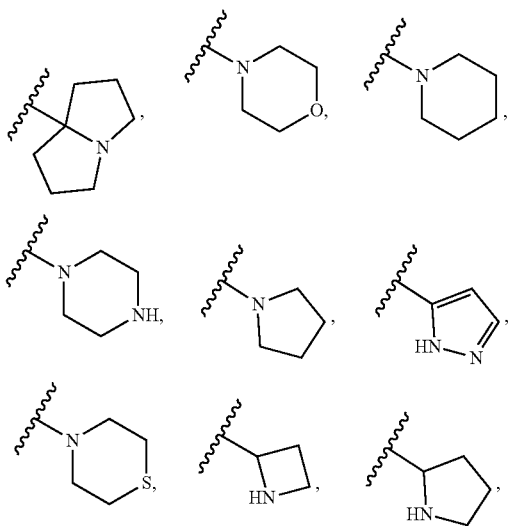

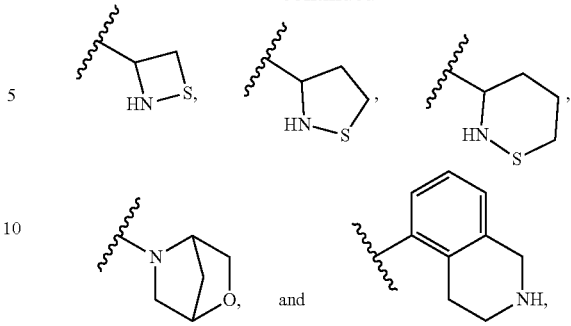

wherein the heterocycle is optionally substituted with one or more R⁶; wherein the aryl and heteroaryl of R² is selected from

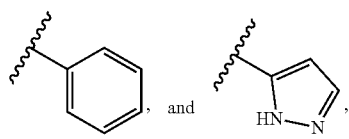 [SMILES: *c1ccccc1 ; *c1ccn[nH]1]

wherein the aryl and the heteroaryl are each optionally substituted with one or more R⁷; and

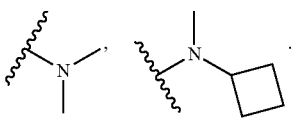

In some cases, each R⁶ is independently selected from halogen, hydroxy, $C_1$-$C_3$ alkyl, $C_1$-$C_3$ haloalkyl, —N(R⁵)S(O)₂(R⁵), —OC(O)N(R⁵)₂, =CH₂, oxo, =NO—$C_1$-$C_3$ alkyl, —CH₂OC(O)heterocycle, —CH₂heterocycle, —CH₂OC(O)N(R⁵)₂, and —O—$C_1$-$C_3$ alkyl, wherein the alkyl of —O—$C_1$-$C_3$ alkyl is optionally substituted with substituents selected from heterocycle, oxo, and hydroxy; and wherein each R⁷ is selected from $C_1$-$C_3$ alkyl, halogen and $C_1$-$C_3$ haloalkyl. In some cases, the heterocycle of R², the aryl and heteroaryl of R², and —N(R²⁰)₂ of R² is selected from

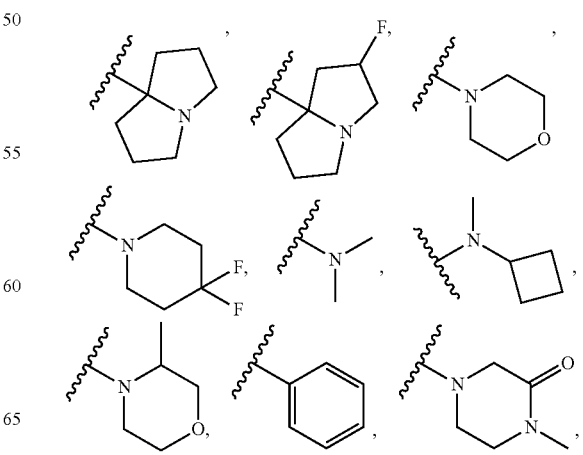

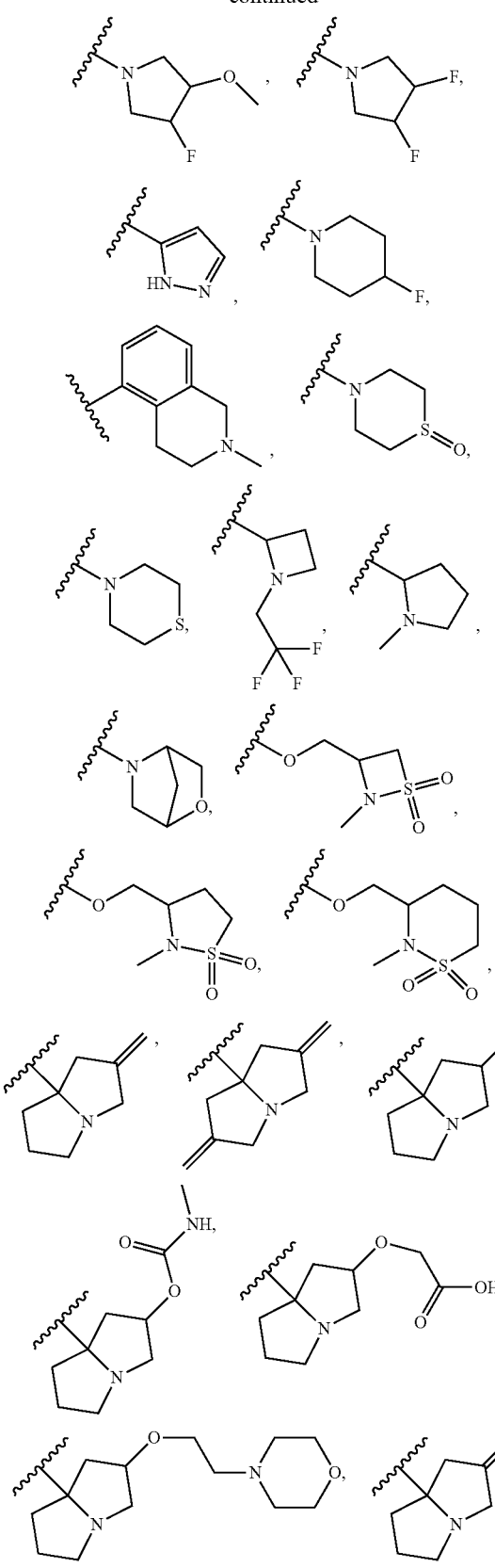
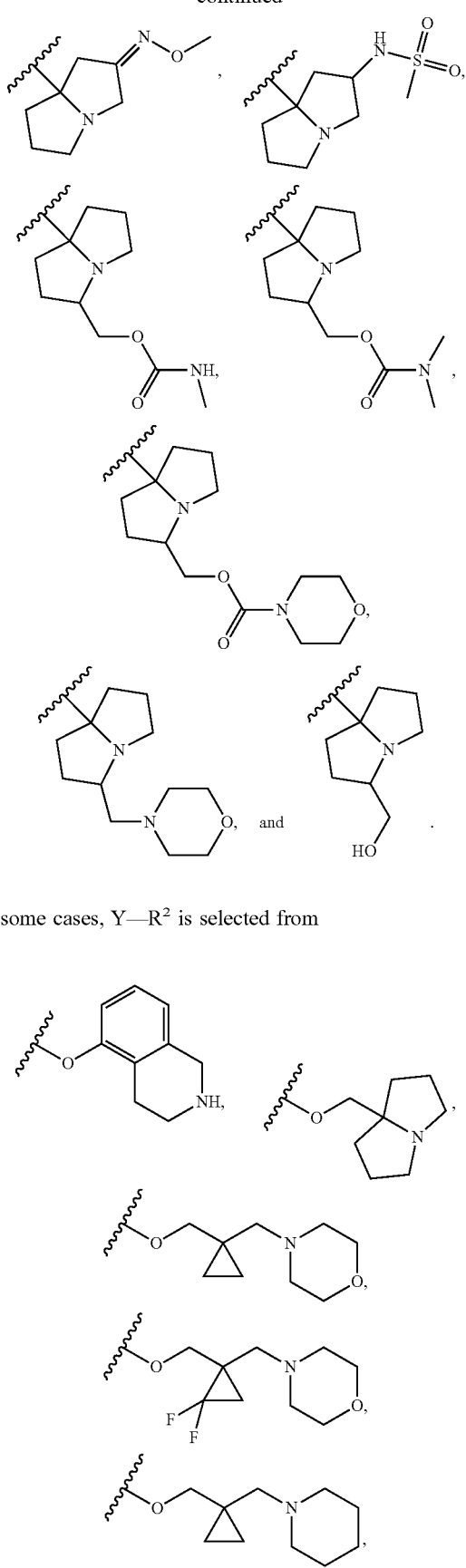
In some cases, Y—R² is selected from

-continued
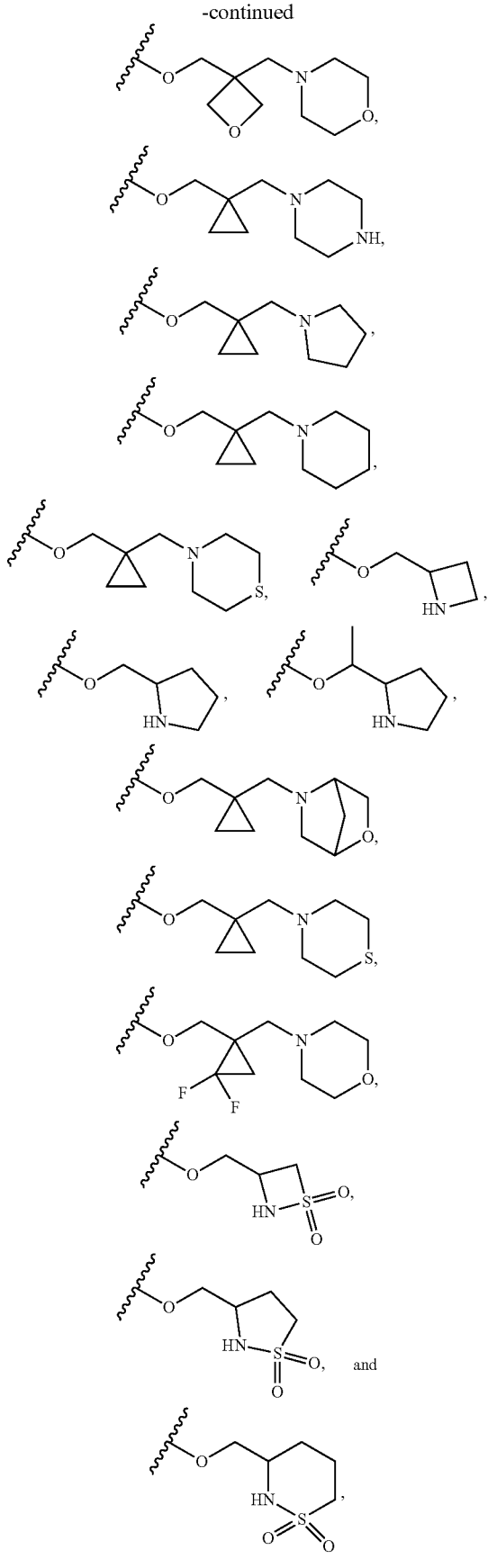
wherein the heterocycle, and the heterocycle portion of -L-heterocycle, are each optionally substituted with one or more $R^6$;
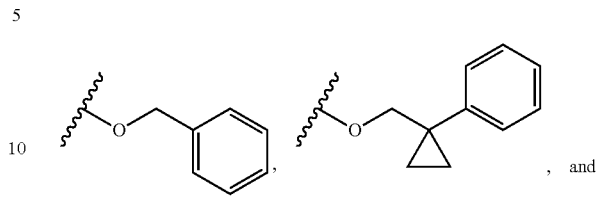
wherein the aryl of the -L-aryl, and the heteroaryl of -L-heteroaryl are each optionally substituted with one or more $R^7$; and
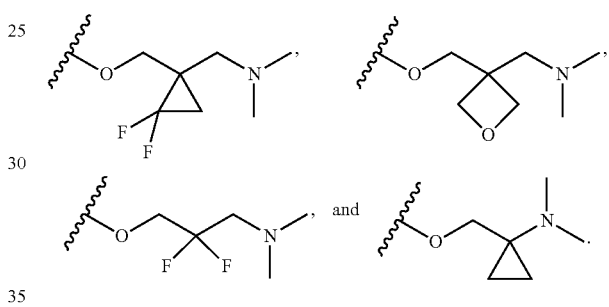
In some cases, $Y-R^2$ is selected from
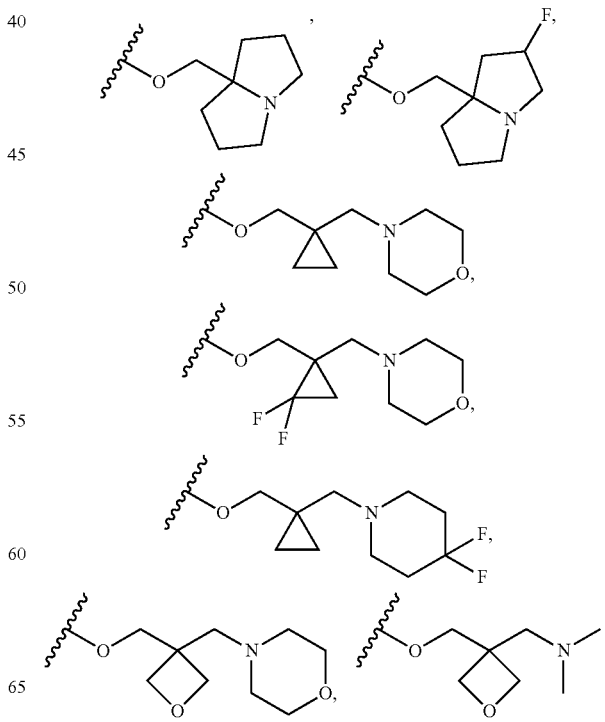

243
-continued
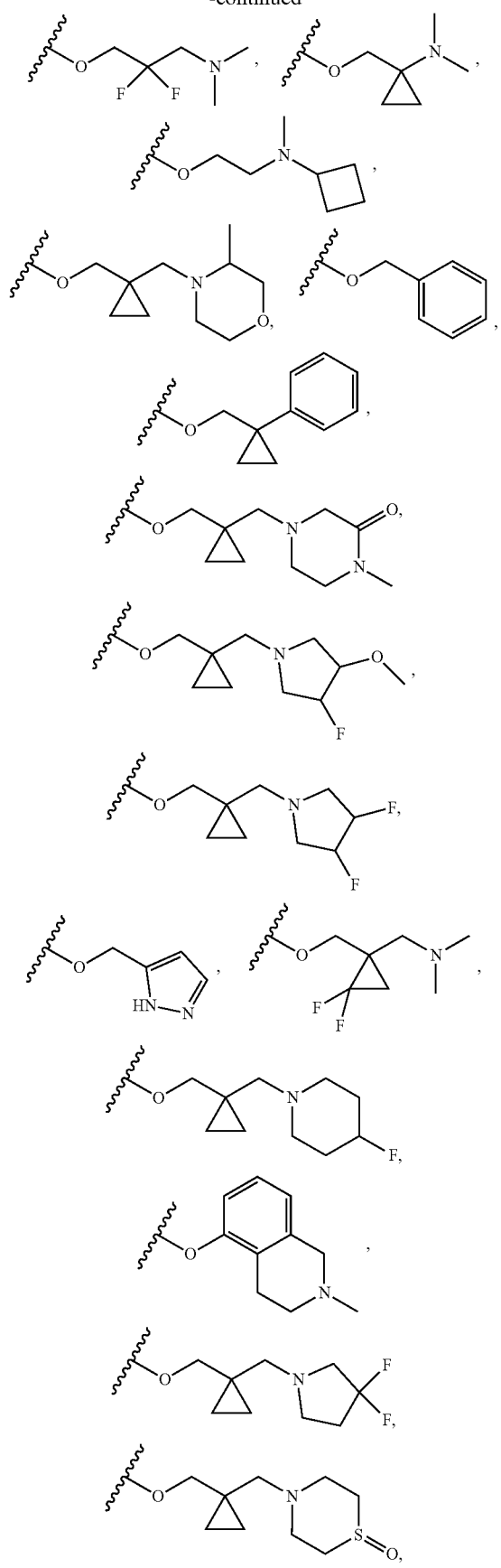
244
-continued
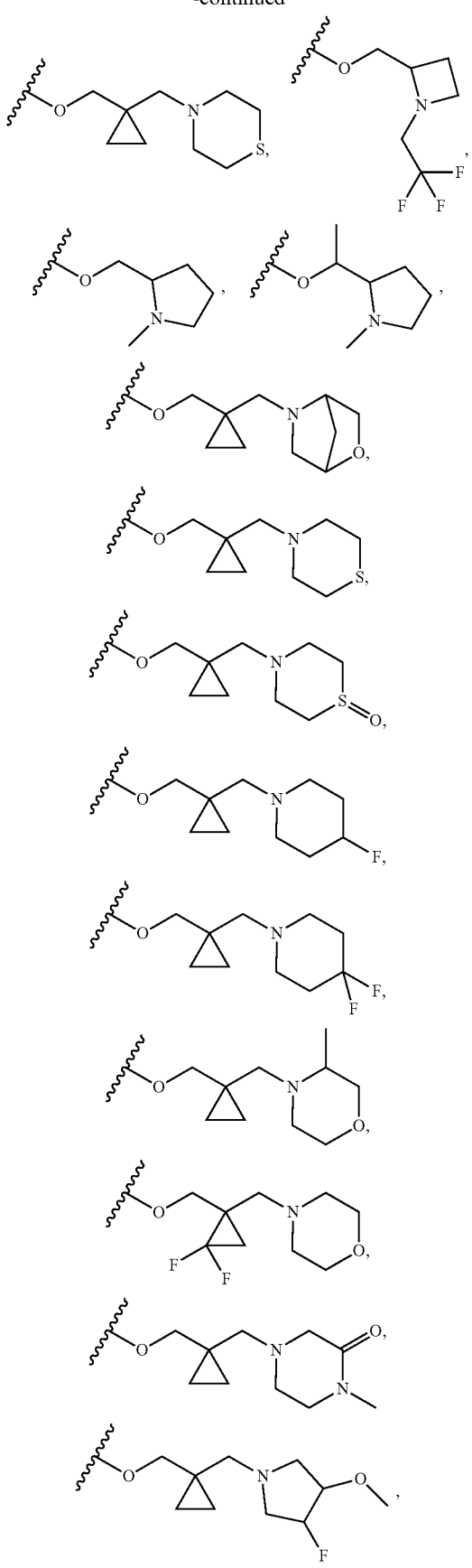

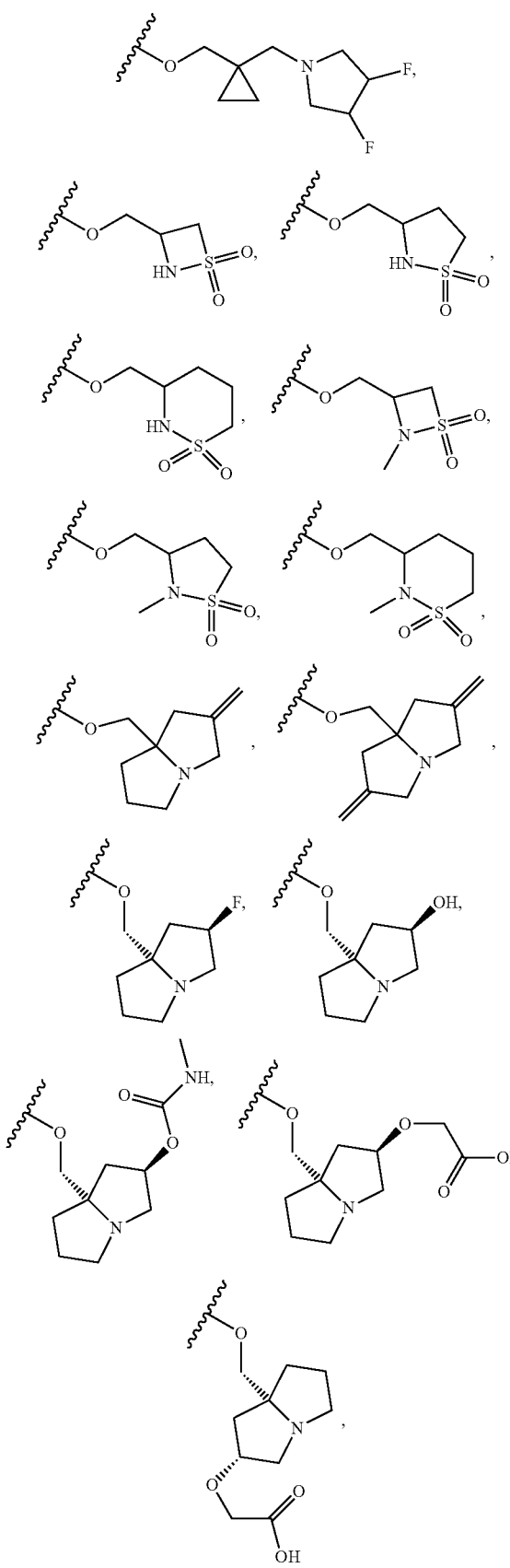
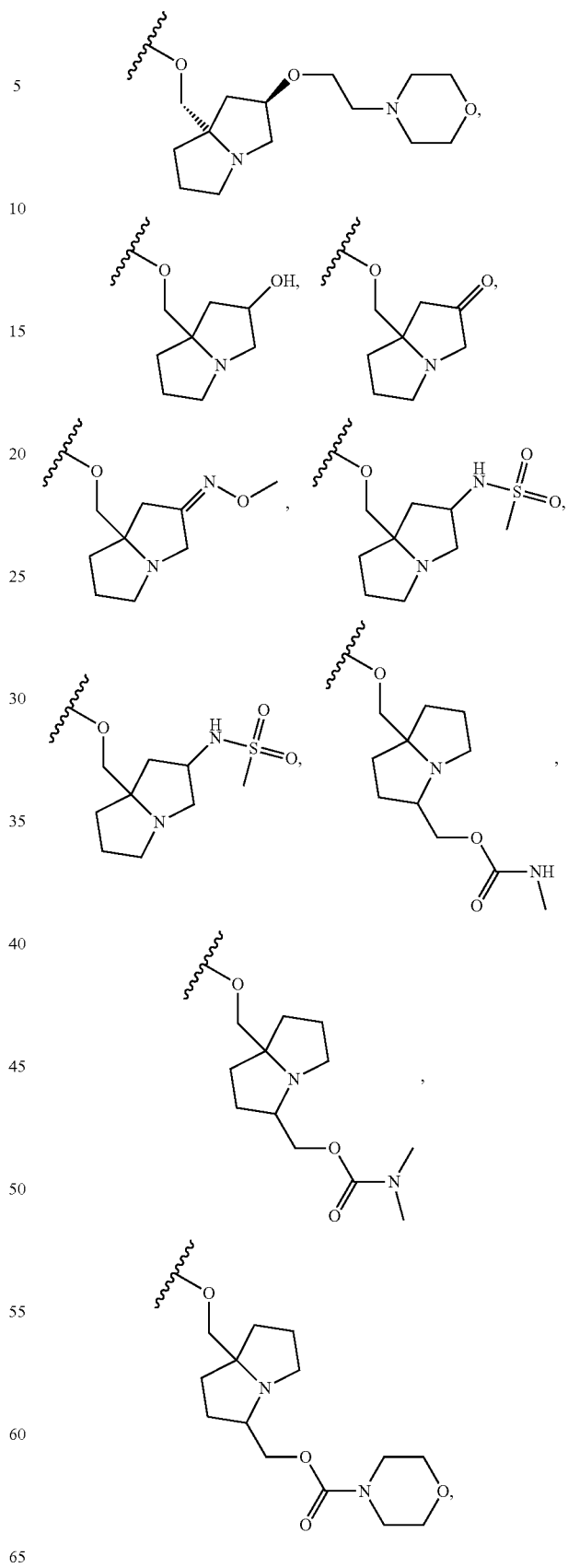

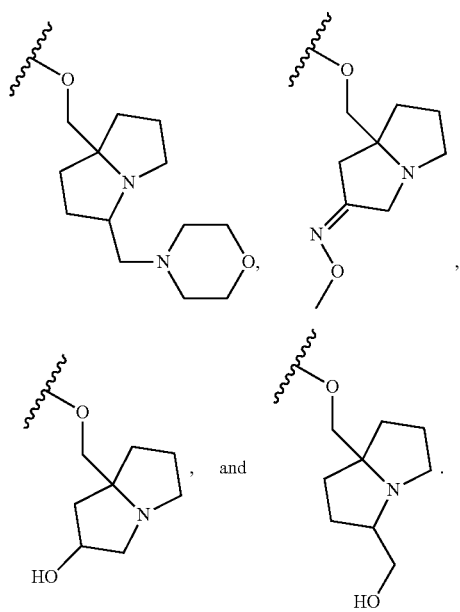

In some cases, Y—R² is selected from

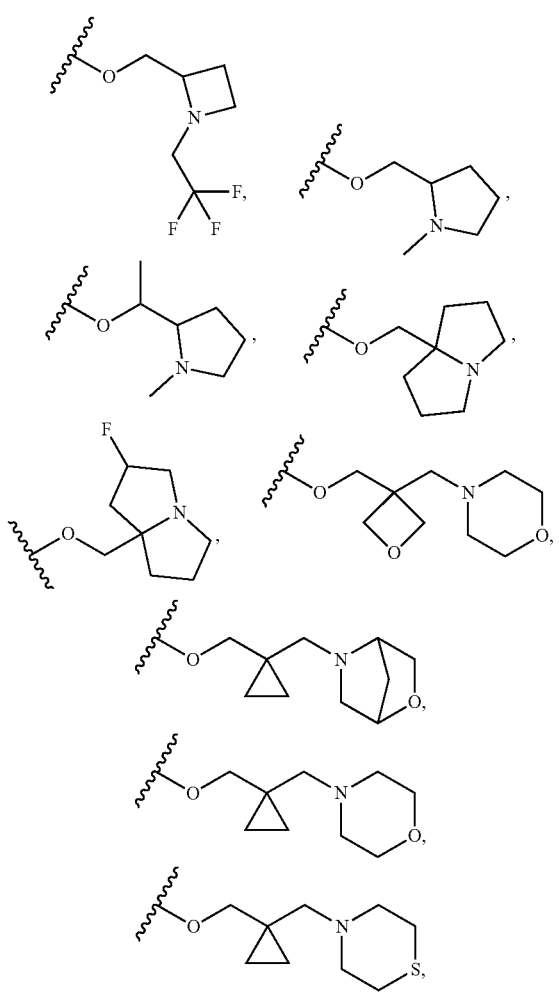

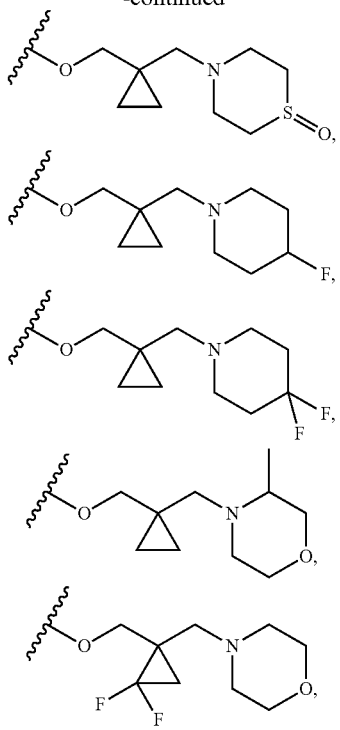

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), L is independently selected from a $C_1$-$C_4$ alkylene optionally substituted with one or more substituents independently selected from hydroxy, $C_1$-$C_4$ hydroxyalkyl and $C_1$-$C_4$ alkyl. In some cases, L is independently selected from a $C_1$-$C_4$ alkylene optionally substituted with one or more substituents independently selected from $C_1$-$C_4$ alkyl. In some cases, L is selected from $C_1$-$C_4$ alkylene. In some cases, L is selected from $C_1$-$C_2$ alkylene. In some cases, L is

In some cases, L is

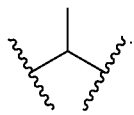

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), each L is independently selected from an optionally substituted $C_1$-$C_4$ alkylene; and wherein optionally two substituents on the same carbon atom of L come together to form a $C_3$-$C_6$ carbocycle, wherein the $C_3$-$C_6$ carbocycle is optionally substituted with one or more substituents selected from halogen, —OH, —NO$_2$, =O, =S, —CN, $C_{1-6}$ aminoalkyl, $C_{1-6}$ alkoxy, $C_{1-6}$ hydroxyalkyl, $C_{1-6}$ haloalkyl. In some cases, the optional substituents of L are selected from $C_1$-$C_4$ hydroxyalkyl, $C_1$-$C_4$ alkyl, $C_3$-$C_6$ carbocycle; and wherein optionally two substituents on the same carbon atom of L come together to form a $C_3$-$C_6$ carbocycle or 3- to 8-membered heterocycle wherein the $C_3$-$C_6$ carbocycle and 3- to 8-membered heterocycle are optionally substituted with one or more substituents selected from halogen and $C_{1-6}$ haloalkyl.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), each L is independently selected from a substituted $C_1$-$C_4$ alkylene, wherein two substituents on the same carbon atom of L come together to form a $C_3$-$C_6$ carbocycle. In some cases, the $C_3$-$C_6$ carbocycle is optionally substituted with one or more substituents selected from halogen, —OH, —NO$_2$, =O, =S, —CN, $C_{1-6}$ aminoalkyl, $C_{1-6}$ alkoxy, $C_{1-6}$ hydroxyalkyl, $C_{1-6}$ haloalkyl.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), each L is independently selected from a substituted $C_1$-$C_4$ alkylene, and two substituents on the same carbon atom of L come together to form a $C_3$-$C_6$ carbocycle. In some cases, each L is independently selected from a substituted $C_3$ alkylene, and wherein two substituents on the same carbon atom of L come together to form a $C_3$ carbocycle. In some cases, each L is independently selected from

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), $R^2$ is selected from -L-heterocycle, wherein the heterocycle portion of -L-heterocycle is optionally substituted with one or more $R^6$. In some cases, the heterocycle is a saturated heterocycle. In some cases, the heterocycle has at least one nitrogen atom and at least one sulfur atom. In some cases, the heterocycle has at least one nitrogen atom. In some cases, the heterocycle has at least one sulfur atom.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), $R^2$ is selected from

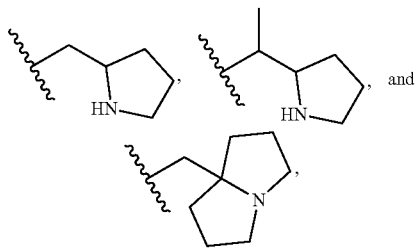

wherein the heterocycle portion is optionally substituted with one or more $R^6$.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), Y—$R^2$ is selected from

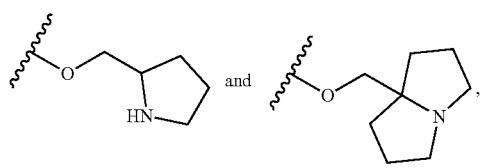 [SMILES: *OCC1CCCN1 ; *OCC12CCCN1CCC2]

wherein the heterocycle portion is optionally substituted with one or more $R^6$.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), Y—$R^2$ is selected from

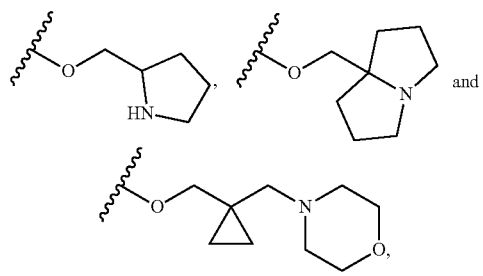

wherein the heterocycle portion is optionally substituted with one or more $R^6$.

In some embodiments, for a compound or salt of Formula (I), Formula (I-A), Formula (I-B) Formula (I-C), Formula (I-D), Formula (I-E), Formula (I-F), Formula (I-G), Formula (I-H), Formula (I-I), or Formula (I-J), Y—$R^2$ is selected from

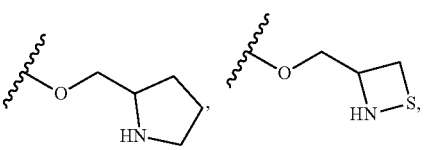

-continued

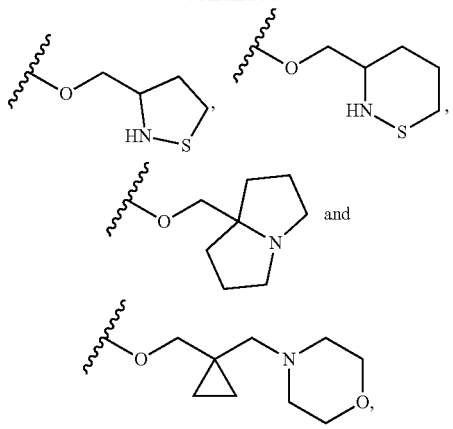

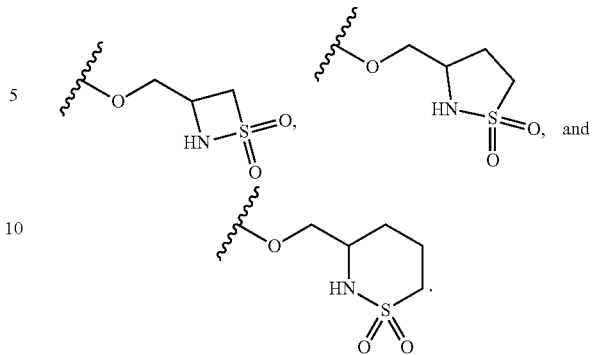

In some cases, Y—R² is selected from

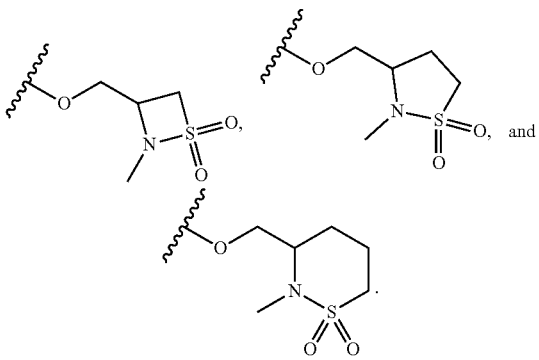

wherein the heterocycle portion is optionally substituted with one or more R⁶.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), R² is selected from -L-saturated heterocycle, wherein the saturated heterocycle portion of the -L-saturated heterocycle is optionally substituted with one or more R⁶, and contains one nitrogen atom and one sulfur atom. In some cases, Y—R² is selected from

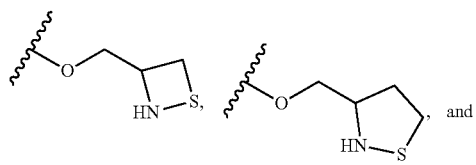

wherein the heterocycle portion is optionally substituted with one or more R⁶. In some cases, Y—R² is selected from

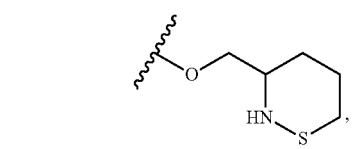

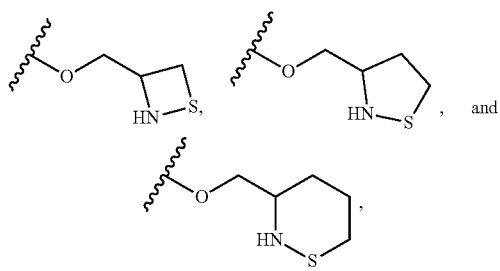

wherein the heterocycle portion is optionally substituted with one or more substituents selected from C₁-C₃ alkyl and oxo. In some cases, Y—R² is selected from In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), each R⁶ is independently selected from halogen, —OH, C₁-C₃ hydroxyalkyl, C₁-C₃ alkyl, C₁-C₃ haloalkyl, C₁-C₃ alkoxy, —CN, C₁-C₃ aminoalkyl, -Q-phenyl, -Q-phenylSO₂F, —NHC(O)phenyl, —NHC(O)phenylSO₂F, C₁-C₃ alkyl substituted pyrazolyl, —N(R⁵)₂, (C₁-C₃ alkoxy)C₁-C₃ alkyl-, (C₁-C₃ alkyl)C(═O), oxo, (C₁-C₃ haloalkyl)C(═O)—, —SO₂F, (C₁-C₃ alkoxy)C₁-C₃ alkoxy, —CH₂OC(O)N(R⁵)₂, —CH₂NHC(O)OC₁-C₆ alkyl, —CH₂NHC(O)N(R⁵)₂, —CH₂NHC(O)C₁-C₆ alkyl, —CH₂(pyrazolyl), —CH₂NHSO₂C₁-C₆ alkyl, —CH₂OC(O)heterocycle, —OC(O)N(R⁵)₂, —OC(O)NH(C₁-C₃ alkyl)O(C₁-C₃ alkyl), —OC(O)NH(C₁-C₃ alkyl)O(C₁-C₃ alkyl)phenyl(C₁-C₃ alkyl)N(CH₃)₂, —OC(O)NH(C₁-C₃ alkyl)O(C₁-C₃ alkyl)phenyl, —OC(O)heterocycle, and —CH₂heterocycle, wherein the phenyl of —NHC(O)phenyl and —OC(O)NH(C₁-C₃ alkyl)(C₁-C₃ alkyl)phenyl are each optionally substituted with —C(O)H and OH, and wherein the heterocycle of —CH₂heterocyclyl is optionally substituted with oxo.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), each R⁶ is independently selected from halogen, —OH, C₁-C₃ hydroxyalkyl, C₁-C₃ alkyl, C₁-C₃ haloalkyl, C₁-C₃ alkoxy, —CN, and C₁-C₃ aminoalkyl.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), each R⁶ is independently selected from halogen, —OH, $C_1$-$C_3$ hydroxyalkyl, $C_1$-$C_3$ alkyl, $C_1$-$C_3$ aminoalkyl, $C_1$-$C_3$ haloalkyl, $C_1$-$C_3$ alkoxy, —N($R^5$)$_2$, and oxo. In some cases, each $R^6$ is independently selected from —OH, $C_1$-$C_3$ hydroxyalkyl, $C_1$-$C_3$ alkyl, $C_1$-$C_3$ aminoalkyl, $C_1$-$C_3$ alkoxy, and —N($R^5$)$_2$. In some cases, each $R^6$ is independently selected from $C_1$-$C_3$ alkyl, $C_1$-$C_3$ alkoxy, and —N($R^5$)$_2$. In some cases, each $R^6$ is independently selected from halogen, hydroxy, $C_1$-$C_3$ alkyl, $C_1$-$C_3$ haloalkyl, —N($R^5$)S(O)$_2$($R^5$), —OC(O)N($R^5$)$_2$, =$CH_2$, oxo, =NO—$C_1$-$C_3$ alkyl, —$CH_2$OC(O)heterocycle, —$CH_2$heterocycle, —$CH_2$OC(O) N($R^5$)$_2$, and —O—$C_1$-$C_3$ alkyl, wherein the alkyl of —O—$C_1$-$C_3$ alkyl is optionally substituted with substituents selected from heterocycle, oxo, and hydroxy; and wherein each $R^7$ is selected from $C_1$-$C_3$ alkyl, halogen and $C_1$-$C_3$ haloalkyl.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), $R^6$ is selected from halogen, —OH, $C_1$-$C_3$ hydroxyalkyl, $C_1$-$C_3$ alkyl, $C_1$-$C_3$ haloalkyl, $C_1$-$C_3$ alkoxy, —CN, and $C_1$-$C_3$ aminoalkyl. In some cases, $R^6$ is selected from halogen and $C_1$-$C_3$ alkyl. In some cases, $R^6$ is halogen. In some cases, $R^6$ is $C_1$-$C_3$ alkyl. In some cases, $R^6$ is selected from halogen and $C_1$-$C_3$ alkyl. In some cases, $R^6$ is selected from methyl and fluorine.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), $R^2$ is selected from

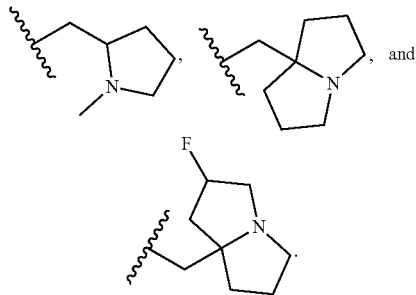

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), Y—$R^2$ is selected from

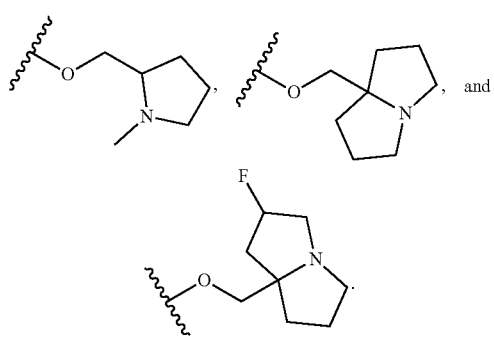

In some embodiments, for a compound or salt of Formula (I), Formula (I-A), Formula (I-B), Formula (I-C), Formula (I-D), Formula (I-E), Formula (I-F), Formula (I-G), Formula I-H Formula (I-I), or Formula (I-J), Y—$R^2$ is selected from

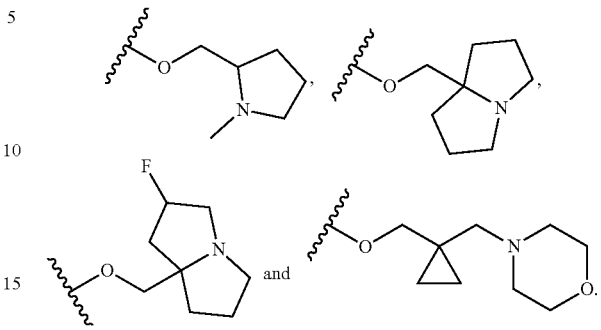

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), Y—$R^2$ is

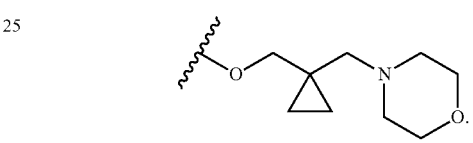

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), L is selected from unsubstituted $C_1$-$C_4$ alkylene.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), Y—$R^2$ is selected from

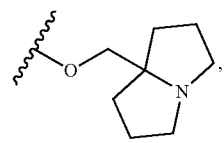 [SMILES: *OCC12CCCN1CCC2]

wherein the heterocycle portion is optionally substituted with one or more $R^6$.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), $R^6$ of $R^2$ is independently selected at each occurrence from halogen, hydroxy, $C_1$-$C_3$ hydroxyalkyl, $C_1$-$C_3$ alkyl, $C_1$-$C_3$ haloalkyl, $C_1$-$C_3$ alkoxy, cyano, and $C_1$-$C_3$ aminoalkyl.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), $R^6$ of $R^2$ is independently selected at each occurrence from $C_1$-$C_3$ alkyl and halogen.

In some embodiments, for a compound or salt of Formula (I), Formula (I-A), Formula (I-B), Formula (I-C), Formula (I-D), Formula (I-E), Formula (I-F), Formula (I-G), Formula (I-H), Formula (I-I), or Formula (I-J), Y—R² is selected from

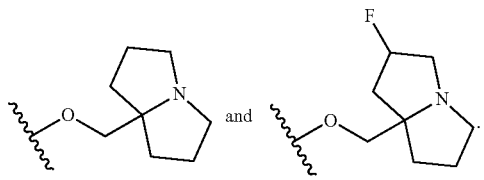 [SMILES: *OCC12CCCN1CCC2 ; *OCC12CCCN1CC(F)C2]

In some embodiments, for a compound or salt of Formula (I), Formula (I-A), Formula (I-B), Formula (I-C), or Formula (I-G), the heterocycle of $R^1$ is substituted with at least one halogen. In some cases, the heterocycle of $R^1$ is substituted with at least one substituent selected from —S(O)$_2$(R$^{20}$), —S(O)$_2$N(R$^{20}$)$_2$, —S(O)N(R$^{20}$)$_2$, —S(O)R$^{20}$ (=NR$^{20}$), —C(O)N(R$^{20}$)$_2$, and —C(O)NHOR$^{20}$. In some cases, the heterocycle of $R^1$ is substituted with at least one $C_{1-6}$ alkyl-N(R$^{20}$)$_2$.

In some embodiments, Formula (I) is represented by Formula (I-C*).

In an aspect, the present disclosure provides a compound of Formula (I-C*):

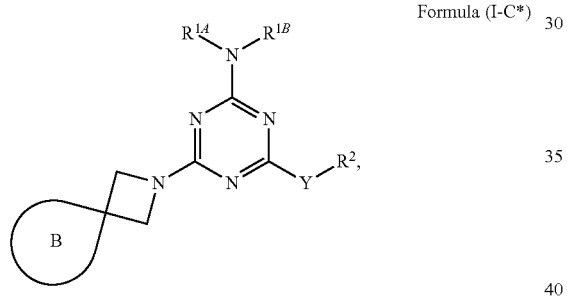

Formula (I-C*)

or a pharmaceutically acceptable salt thereof wherein:
$R^{1A}$ is selected from $C_{1-6}$ alkyl, $C_3$-$C_{12}$ carbocycle, and 4- to 12-membered heterocycle, each of which is optionally substituted with one or more $R^{11}$, and wherein optionally two $R^{11}$ on the same atom of $R^{1A}$ come together to form a $C_3$-$C_6$ carbocycle or 3- to 8-membered heterocycle, wherein the $C_3$-$C_6$ carbocycle and 3- to 8-membered heterocycle are each optionally substituted with one or more $R^{11A}$;
$R^{1B}$ is selected from hydrogen, $C_{1-6}$ alkyl, $C_3$-$C_6$ carbocycle, 4- to 6-membered heterocycle, wherein the $C_{1-6}$ alkyl, $C_3$-$C_6$ carbocycle, and 4- to 6-membered heterocycle, are each optionally substituted with one or more $R^{10}$;
or $R^{1A}$ and $R^{1B}$ come together with the atom to which they are bound to form $R^1$, wherein $R^1$ is a 5- to 15-membered heterocycle, wherein the 5- to 15-membered heterocycle is optionally substituted with one or more substituents independently selected from halogen, —B(OR$^{20}$)$_2$, —N(R$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$ (=NR$^{20}$), —NR$^{20}$S(O)$_2$R$^{20}$, —C(O)N(R$^{20}$)$_2$, —C(=NR$^{20}$)N(R$^{20}$)$_2$, —C$_{1-6}$ alkyl(=NR$^{20}$OR$^{20}$), —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =N(R$^{20}$), =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl-SO$_2$R$^{20}$, $C_{1-6}$ alkoxyalkyl, $C_{1-6}$ alkyl, $C_{2-6}$ alkenyl, $C_{2-6}$ alkynyl, $C_3$-$C_{12}$ carbocycle and 5- to 12-membered heterocycle, wherein the $C_3$-$C_{12}$ carbocycle and 5- to 12-membered heterocycle are each optionally substituted independently with one or more $R^{1*}$;

each $R^{1*}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$ (=NR$^{20}$), —NR$^{20}$S(O)$_2$R$^{20}$, —C(O)N(R$^{20}$)$_2$, —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =N(R$^{20}$), =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, and $C_3$-$C_{12}$ carbocycle;

Y is —O—;

$R^2$ is selected from heterocycle, -L-heterocycle, -L-N(R$^{20}$)$_2$, -L-OR$^{20}$, -L-aryl, -L-heteroaryl, -L-cycloalkyl, -L-NHC(=NH)NH$_2$, -L-C(O)N(R$^{20}$)$_2$, -L-C$_1$-C$_6$ haloalkyl, -L-NR$^{20}$C(O)-aryl, -L-COOH, -L-NR$^{20}$S(O)$_2$(R$^{20}$), -L-S(O)$_2$N(R$^{20}$)$_2$, -L-N(R$^{20}$)C(O)(OR$^{20}$), -L-OC(O)N(R$^{20}$)$_2$, and -L-C(=O)OC$_1$-C$_6$ alkyl, wherein the heterocycle, the heterocycle portion of -L-heterocycle, and the cycloalkyl portion of the -L-cycloalkyl are each optionally substituted with one or more $R^6$, and wherein the aryl portion of -L-NR$^{20}$C(O)-aryl, the aryl of the -L-aryl, and the heteroaryl of -L-heteroaryl are each optionally substituted with one or more $R^7$;

each L is independently selected from a $C_1$-$C_4$ alkylene optionally substituted with one or more substituents independently selected from halogen, hydroxy, $C_{1-6}$ alkoxy, $C_1$-$C_4$ hydroxyalkyl, $C_1$-$C_4$ alkyl, $C_3$-$C_6$ carbocycle, and 3- to 8-membered heterocycle, wherein the $C_3$-$C_6$ carbocycle and 3- to 8-membered heterocycle are each optionally substituted with one or more substituents independently selected from halogen, —OH, —NO$_2$, =O, =S, —CN, $C_{1-6}$ alkyl-N(R$^{20}$)$_2$, $C_{1-6}$ aminoalkyl, $C_{1-6}$ alkoxy, $C_{1-6}$hydroxyalkyl, $C_{1-6}$haloalkyl; and wherein optionally two substituents on the same carbon atom of L come together to form a $C_3$-$C_6$ carbocycle or 3- to 8-membered heterocycle, wherein the $C_3$-$C_6$ carbocycle and 3- to 8-membered heterocycle are each optionally substituted with one or more substituents independently selected from halogen, —OH, —NO$_2$, =O, =S, —CN, $C_{1-6}$ alkyl-N(R$^{20}$)$_2$, $C_{1-6}$ aminoalkyl, $C_{1-6}$ alkoxy, $C_{1-6}$ hydroxyalkyl, and $C_{1-6}$ haloalkyl;

each $R^5$ is independently selected from hydrogen and $C_1$-$C_6$ alkyl;

each $R^6$ is independently selected from halogen, hydroxy, $C_1$-$C_3$ hydroxyalkyl, $C_1$-$C_3$ alkyl, oxo, $C_1$-$C_3$ haloalkyl, $C_1$-$C_3$ alkyl-N$_3$, $C_1$-$C_3$ alkoxy, cyano, =CH$_2$, =NO—$C_1$-$C_3$ alkyl, $C_1$-$C_3$ aminoalkyl, —N(R$^5$)S(O)$_2$(R$^5$), -Q-phenyl, -Q-phenylSO$_2$F, —NHC(O)phenyl, —NHC(O)phenylSO$_2$F, $C_1$-$C_3$ alkyl substituted pyrazolyl, tert-butyldimethylsilyloxyCH$_2$—, —N(R$^5$)$_2$, ($C_1$-$C_3$ alkoxy)$C_1$-$C_3$ alkyl-, ($C_1$-$C_3$ alkyl)C(=O), oxo, ($C_1$-$C_3$ haloalkyl)C(=O)—, —SO$_2$F, ($C_1$-$C_3$ alkoxy)$C_1$-$C_3$ alkoxy, —CH$_2$OC(O)NCF$_3$(R$^5$), —CH$_2$O—$C_1$-$C_6$ alkyl, —CH$_2$OC(O)N(R$^5$)$_2$, —CH$_2$NHC(O)OC$_1$-$C_6$ alkyl, —CH$_2$NHC(O)N(R$^5$)$_2$, —CH$_2$NHC(O)C$_1$-$C_6$ alkyl, —CH$_2$(pyrazolyl), —CH$_2$NHSO$_2$C$_1$-$C_6$ alkyl, —CH$_2$OC(O)heterocycle, —OC(O)N(R$^5$)$_2$, —OC(O)

NH($C_1$-$C_3$ alkyl)O($C_1$-$C_3$ alkyl), —OC(O)NH($C_1$-$C_3$ alkyl)O($C_1$-$C_3$ alkyl)phenyl($C_1$-$C_3$ alkyl)N(CH$_3$)$_2$, —OC(O)NH($C_1$-$C_3$ alkyl)O($C_1$-$C_3$ alkyl)phenyl, —OC(O)heterocycle, —O—$C_1$-$C_3$ alkyl, —O—$C_1$-$C_6$ haloalkyl, —$C_1$-$C_3$ alkyl-O—$C_1$-$C_6$ haloalkyl, $C_{1-6}$ alkyl-N($R^{20}$)$_2$, —SF$_5$, —$C_1$-$C_3$ alkyl-N$_3$, —S(O)$_2$($R^{20}$), —S(O)$_2$N($R^{20}$)$_2$, —S(O)N($R^{20}$)$_2$, —S(O)$R^{20}$(=N$R^{20}$), —N$R^{20}$S(O)$_2$$R^{20}$, —(CH$_2$)$_{0-1}$S-heterocycle, —(CH$_2$)$_{0-1}$—O-heterocycle, —(CH$_2$)$_{0-1}$—O-phenyl, and —CH$_2$heterocycle,
wherein the phenyl of —NHC(O)phenyl and —OC(O)NH($C_1$-$C_3$ alkyl)($C_1$-$C_3$ alkyl)phenyl are optionally substituted with one or more substituents selected from —C(O)H and OH,
wherein the alkyl of —O—$C_1$-$C_3$ alkyl is optionally substituted with substituents selected from heterocycle, oxo and hydroxy;
wherein the alkyl of —CH$_2$O—$C_1$-$C_6$ alkyl is optionally substituted with one or more substituents selected from halogen and $C_3$-$C_6$ carbocycle;
wherein the heterocycle of —CH$_2$heterocycle is optionally substituted with oxo; and
wherein the phenyl of —(CH$_2$)$_{0-1}$—O-phenyl is optionally substituted with one or more substituents selected from $C_{1-6}$ alkyl, $C_{1-6}$haloalkyl, SF$_5$, $C_{1-6}$ alkyl-O$R^{20}$, —O$R^{20}$;
wherein the heterocycle of —(CH$_2$)$_{0-1}$—O-heterocycle and —(CH$_2$)$_{0-1}$—S-heterocycle are each optionally substituted with one or more substituents selected from $C_{1-6}$ alkyl, $C_{1-6}$haloalkyl, $C_{1-6}$alkyl-O$R^{20}$, and —O$R^{20}$;
each Q is selected from a bond and O;
each $R^7$ is independently selected from halogen, hydroxy, HC(=O)—, $C_1$-$C_4$ alkyl, $C_1$-$C_4$ alkoxy, $C_1$-$C_4$ haloalkyl, $C_1$-$C_4$ hydroxyalkyl, and —N($R^5$)$_2$;
B is selected from a 7- to 15-membered heterocycle and $C_7$-$C_{15}$ carbocycle, wherein the 7- to 15-membered heterocycle and $C_7$-$C_{15}$ carbocycle are each optionally substituted with one or more substituents independently selected from halogen, —CN, —NO$_2$, =O, —N($R^{20}$)$_2$, —B(O$R^{20}$)$_2$, —O$R^{20}$, —S$R^{20}$, —S(O)$_2$($R^{20}$), —S(O)$_2$N($R^{20}$)$_2$, —N$R^{20}$S(O)$_2$$R^{20}$, —C(O)N($R^{20}$)$_2$, —C(O)N$R^{20}$O$R^{20}$, —N($R^{20}$)C(O)$R^{20}$, —N($R^{20}$)C(O)N($R^{20}$)$_2$, —N($R^{20}$)C(O)O$R^{20}$, —C(O)$R^{20}$, —C(O)O$R^{20}$, —OC(O)$R^{20}$, —OC(O)N($R^{20}$)$_2$, $C_{1-6}$ alkyl-N($R^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle;
each $R^{10}$ is independently selected from halogen, —B(O$R^{20}$)$_2$, —O$R^{20}$, —S$R^{20}$, —S(O)$_2$($R^{20}$), —S(O)$_2$N($R^{20}$)$_2$, —S(O)N($R^{20}$)$_2$, —S(O)$R^{20}$(=N$R^{20}$), —N$R^{20}$S(O)$_2$$R^{20}$, —C(O)N($R^{20}$)$_2$, —N($R^{20}$)C(O)$R^{20}$, —N($R^{20}$)C(O)N($R^{20}$)$_2$, —N($R^{20}$)C(O)O$R^{20}$, —N($R^{20}$)$_2$, —C(O)$R^{20}$, —C(O)O$R^{20}$, —OC(O)$R^{20}$, —OC(O)N($R^{20}$)$_2$, —NO$_2$, =O, =NO($R^{20}$), —CN, —NHCN, $C_{1-6}$ alkyl-N($R^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle, wherein the $C_3$-$C_{12}$ carbocycle and 5- to 12-membered heterocycle are each optionally substituted with one or more substituents independently selected from halogen, —OH, —CN, —NO$_2$, —NH$_2$, —NH($C_{1-6}$ alkyl), —N($C_{1-6}$ alkyl)$_2$, $C_{1-10}$ alkyl, $C_{1-10}$ haloalkyl, —O—$C_{1-10}$ alkyl, oxo;

each $R^{11}$ is independently selected from halogen, —B(O$R^{20}$)$_2$, —O$R^{20}$, —S$R^{20}$, —S(O)$_2$($R^{20}$), —S(O)$_2$N($R^{20}$)$_2$, —S(O)N($R^{20}$)$_2$, —S(O)$R^{20}$(=N$R^{20}$), —N$R^{20}$S(O)$_2$$R^{20}$, —C(O)N($R^{20}$)$_2$, —N($R^{20}$)C(O)$R^{20}$, —N($R^{20}$)C(O)N($R^{20}$)$_2$, —N($R^{20}$)C(O)O$R^{20}$, —N($R^{20}$)$_2$, —C(O)$R^{20}$, —C(O)O$R^{20}$, —OC(O)$R^{20}$, —OC(O)N($R^{20}$)$_2$, —N$R^{20}$(C=NH)N($R^{20}$)$_2$, —NO$_2$, =O, =NO($R^{20}$), —CN, —NHCN, $C_{1-6}$ alkyl-N($R^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle, wherein the $C_3$-$C_{12}$ carbocycle and 5- to 12-membered heterocycle are each optionally substituted with one or more substituents independently selected from halogen, —OH, —CN, —NO$_2$, —N($R^{21}$)$_2$, —S$R^{21}$, —C(O)N($R^{21}$)$_2$, $C_{1-10}$ alkyl, —$C_{1-10}$ haloalkyl, —O—$C_{1-10}$ alkyl, —S(O)$_2$($R^{21}$), —P(O)(O$R^{21}$)$_2$, —OP(O)(O$R^{21}$)$_2$, —P(O)($R^{21}$)$_2$, and oxo;
each $R^{11A}$ is independently selected from halogen, —B(O$R^{20}$)$_2$, —O$R^{20}$, —S$R^{20}$, —S(O)$_2$($R^{20}$), —S(O)$_2$N($R^{20}$)$_2$, —S(O)N($R^{20}$)$_2$, —S(O)$R^{20}$(=N$R^{20}$), —N$R^{20}$S(O)$_2$$R^{20}$, —C(O)N($R^{20}$)$_2$, —N($R^{20}$)C(O)$R^{20}$, —N($R^{20}$)C(O)N($R^{20}$)$_2$, —N($R^{20}$)C(O)O$R^{20}$, —N($R^{20}$)$_2$, —C(O)$R^{20}$, —C(O)O$R^{20}$, —OC(O)$R^{20}$, —OC(O)N($R^{20}$)$_2$, —NO$_2$, =O, =NO($R^{20}$), —CN, —NHCN, $C_{1-6}$ alkyl-N($R^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, and $C_{2-6}$ alkynyl;
each $R^{20}$ is independently selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —NO$_2$, —NH$_2$, —NH($C_{1-6}$ alkyl), —N($C_{1-6}$ alkyl)$_2$, $C_{1-10}$ alkyl, $C_{1-10}$ haloalkyl, —O—$C_{1-10}$ alkyl, oxo, $C_{3-12}$ carbocycle, and 3- to 12-membered heterocycle; and
each $R^{21}$ is independently selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —NO$_2$, —NH$_2$, —N($C_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle.

In some embodiments, for a compound or salt of Formula (I) or Formula (I-C*), $R^{1A}$ is selected from $C_{1-3}$ alkyl, $C_3$-$C_9$ carbocycle, and 4- to 8-membered heterocycle, each of which is optionally substituted with one or more $R^{11}$, and wherein optionally two $R^{11}$ on the same atom of $R^{1A}$ come together to form a $C_3$-$C_6$ carbocycle or 3- to 8-membered heterocycle, wherein the $C_3$-$C_6$ carbocycle and 3- to 8-membered heterocycle are each optionally substituted with one or more $R^{11A}$;
$R^{1B}$ is selected from hydrogen, $C_{1-3}$ alkyl, $C_3$-$C_5$ carbocycle, 4- to 6-membered heterocycle, wherein the $C_{1-6}$ alkyl, $C_3$-$C_6$ carbocycle, and 4- to 6-membered heterocycle, are each optionally substituted with one or more $R^{10}$;
or $R^{1A}$ and $R^{1B}$ come together with the atom to which they are bound to form $R^1$, wherein $R^1$ is a 5- to 9-membered heterocycle, wherein the 5- to 9-membered heterocycle is optionally substituted with one or more substituents independently selected from halogen, —B(O$R^{20}$)$_2$, —N($R^{20}$)$_2$, —O$R^{20}$, —S$R^{20}$, —N($R^{20}$)C(O)$R^{20}$, —N($R^{20}$)C(O)O$R^{20}$, —C(O)$R^{20}$, —C(O)O$R^{20}$, —OC(O)$R^{20}$, —OC(O)N($R^{20}$)$_2$, —NO$_2$, =O, =N($R^{20}$), =NO($R^{20}$), —CN, —NHCN, $C_{1-6}$ alkyl-N($R^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkoxyalkyl, $C_{1-6}$ alkyl, $C_{2-6}$ alkenyl, $C_{2-6}$ alkynyl, $C_3$-$C_6$ carbocycle and 5- to 7-membered heterocycle, wherein the $C_3$-$C_6$ carbocycle and 5- to 7-membered heterocycle are each optionally substituted independently with one or more $R^{1*}$; each $R^{1*}$ is independently selected from halogen, —B(OR$^{20}$)$_2$, —OR$^{20}$, —SR$^{20}$, —C(O)N(R$^{20}$)$_2$, —C(O)NR$^{20}$OR$^{20}$, —N(R$^{20}$)C(O)R$^{20}$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =N(R$^{20}$), =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, and $C_3$-$C_6$ carbocycle;

B is selected from a 7- to 9-membered heterocycle, wherein the 7- to 9-membered heterocycle is optionally substituted with one or more substituents independently selected from —CN, —NH$_2$, and $C_{1-6}$ alkyl;

Y is —O—;

$R^2$ is selected from -L-heterocycle, and -L-N(CH$_3$)$_2$, wherein the heterocycle portion of -L-heterocycle, is optionally substituted with one or more $R^6$.

each L is independently selected from a $C_1$-$C_4$ alkylene optionally substituted with one or more substituents independently selected from $C_1$-$C_4$ alkyl; and wherein optionally two substituents on the same carbon atom of L come together to form a $C_3$-$C_4$ carbocycle or 4-membered heterocycle, wherein the $C_3$-$C_4$ carbocycle and 4-membered heterocycle are each optionally substituted with one or more substituents independently selected from halogen;

each $R^6$ is independently selected from halogen, $C_1$-$C_3$ hydroxyalkyl, $C_1$-$C_3$ alkyl, oxo, $C_1$-$C_3$ haloalkyl, =CH$_2$, ($C_1$-$C_3$ alkoxy)$C_1$-$C_3$ alkyl-, and —CH$_2$—O-heterocycle,
wherein the heterocycle of —CH$_2$—O-heterocycle is optionally substituted with one or more substituents selected from $C_{1-6}$ alkyl, $C_{1-6}$ haloalkyl, $C_{1-6}$ alkyl-OR$^{20}$, and —OR$^{20}$;

each $R^{10}$ is independently selected from halogen, —B(OR$^{20}$)$_2$, —OR$^{20}$, —SR$^{20}$, —C(O)N(R$^{20}$)$_2$, —N(R$^{20}$)C(O)R$^{20}$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_6$ carbocycle and 5- to 7-membered heterocycle, wherein the $C_3$-$C_6$ carbocycle and 5- to 7-membered heterocycle are each optionally substituted with one or more substituents independently selected from halogen, —OH, —CN, —NO$_2$, —NH$_2$, —NH($C_{1-6}$ alkyl), —N($C_{1-6}$ alkyl)$_2$, $C_{1-5}$ alkyl, —$C_{1-5}$ haloalkyl, —O—$C_{1-5}$ alkyl, oxo;

each $R^{11}$ is independently selected from halogen, —B(OR$^{20}$)$_2$, —OR$^{20}$, —SR$^{20}$, —C(O)N(R$^{20}$)$_2$, —N(R$^{20}$)C(O)R$^{20}$, —N(R$^{20}$)C(O)OR$^{20}$, —N(R$^{20}$)$_2$, —C(O)R$^{20}$, —C(O)OR$^{20}$, —OC(O)R$^{20}$, —NO$_2$, =O, =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_6$ carbocycle and 5- to 9-membered heterocycle, wherein the $C_3$-$C_6$ carbocycle and 5- to 9-membered heterocycle are each optionally substituted with one or more substituents independently selected from halogen, —OH, —CN, —NO$_2$, —N(R$^{21}$)$_2$, —SR$^{21}$, —C(O)N(R$^{21}$)$_2$, $C_{1-5}$ alkyl, —$C_{1-5}$ haloalkyl, —O—$C_{1-5}$ alkyl, —S(O)$_2$(R$^{21}$), —P(O)(OR$^{21}$)$_2$, —OP(O)(OR$^{21}$)$_2$, —P(O)(R$^{21}$)$_2$, and oxo;

each $R^{11A}$ is independently selected from halogen, —B(OR$^{20}$)$_2$, —OR$^{20}$, —SR$^{20}$, —C(O)N(R$^{20}$)$_2$, —N(R$^{20}$)C(O)R$^{20}$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, and $C_{2-6}$ alkynyl.

In some embodiments, for a compound or salt of Formula (I) or Formula (I-C*),

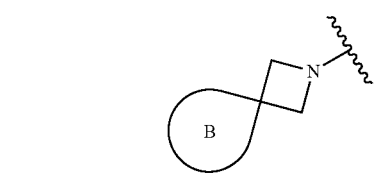

is represented by

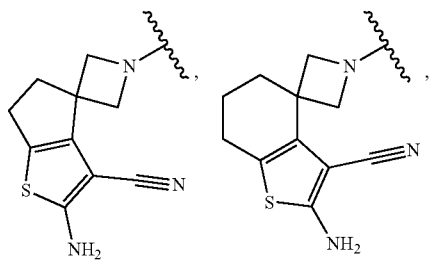

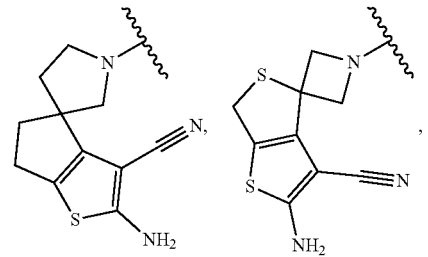

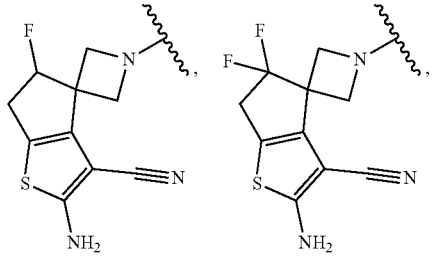

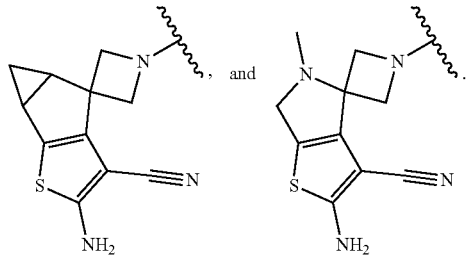

In some cases,
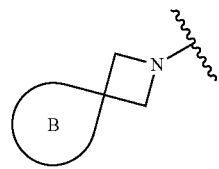
is represented by
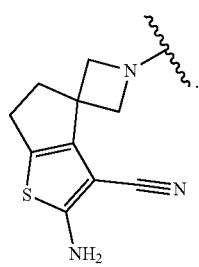
In some cases,
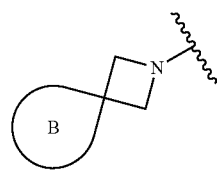
is represented by
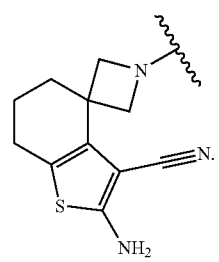 [SMILES: *N1CC2(CCCc3sc(N)c(C#N)c32)C1]
In some cases,
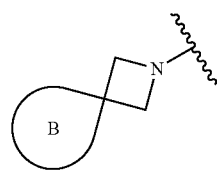
is represented by
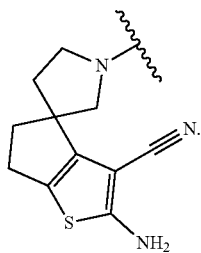 [SMILES: *N1CCC2(CCc3sc(N)c(C#N)c32)C1]
In some cases,
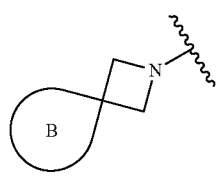
is represented by
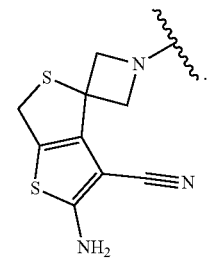 [SMILES: *N1CC2(C1)SCc1sc(N)c(C#N)c12]
In some cases,
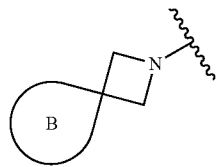
is represented by
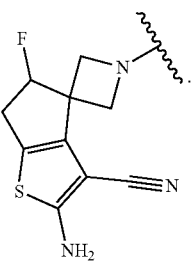 [SMILES: *N1CC2(C1)c1c(sc(N)c1C#N)CC2F]

In some cases,
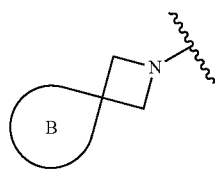
is represented by
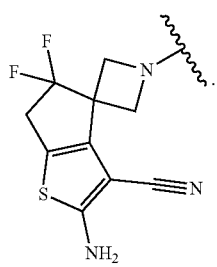 [SMILES: *N1CC2(C1)c1c(sc(N)c1C#N)CC2(F)F]
In some cases,
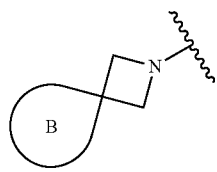
is represented by
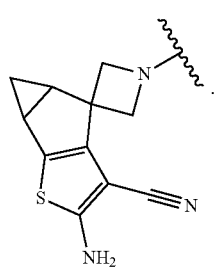 [SMILES: *N1CC2(C1)c1c(sc(N)c1C#N)C1CC12]
In some cases,
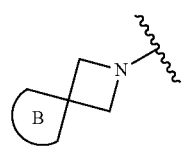
is represented by
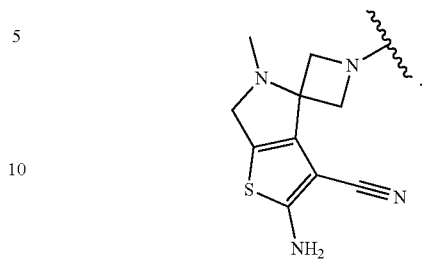
In some cases, Y—R² is selected from:
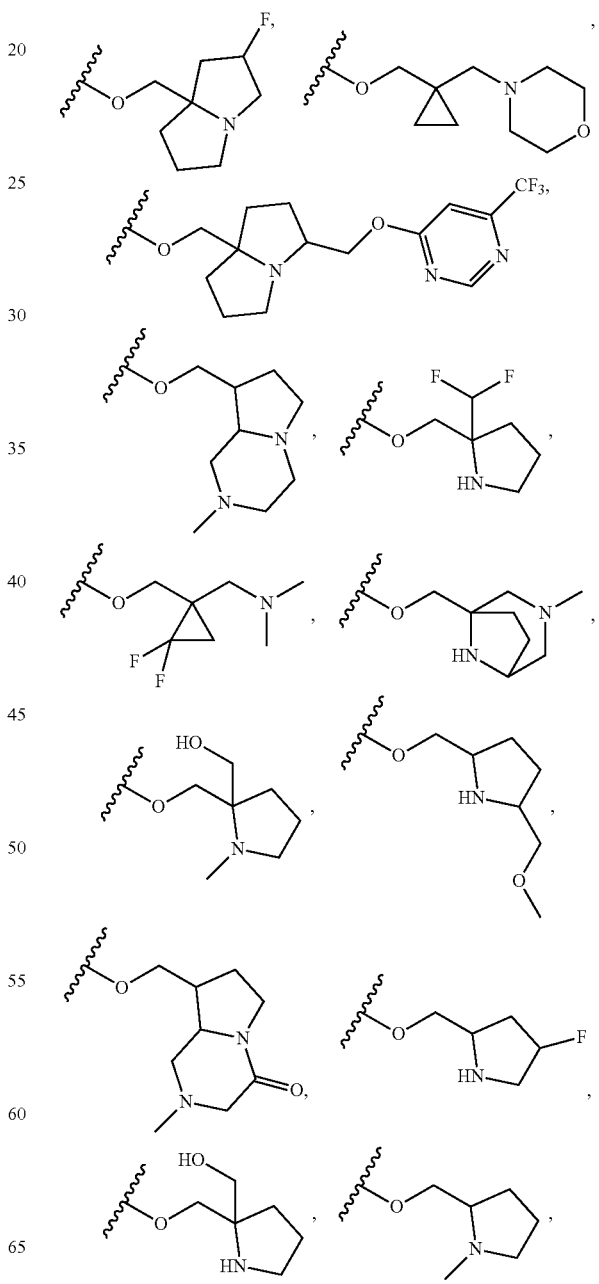

-continued
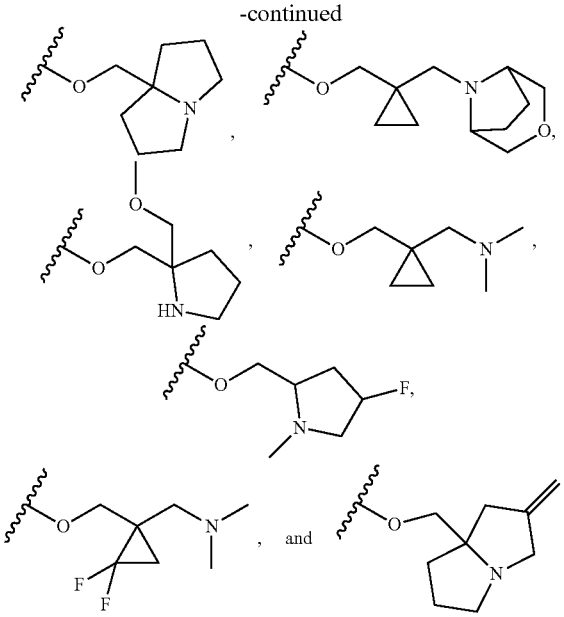
In some cases, Y—R² is:
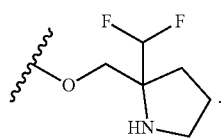 [SMILES: *OCC1(C(F)F)CCCN1]
In some cases, Y—R² is:
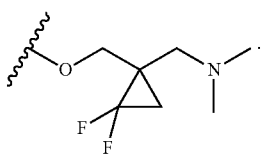 [SMILES: *OCC1(CN(C)C)CC1(F)F]
In some cases, Y—R² is:
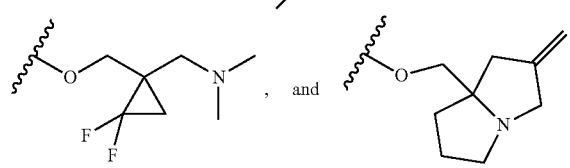
In some cases, Y—R² is:
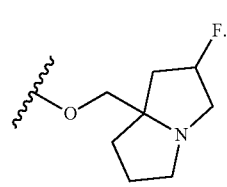
In some cases, Y—R² is:
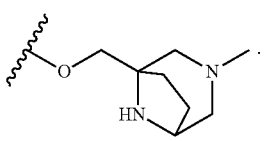 [SMILES: *OCC12CCC(CN(C)C1)N2]
In some cases, Y—R² is:
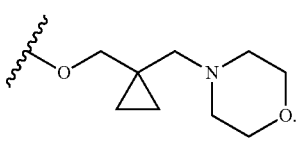
In some cases, Y—R² is:
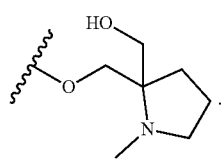 [SMILES: *OCC1(CO)CCCN1C]
In some cases, Y—R² is:
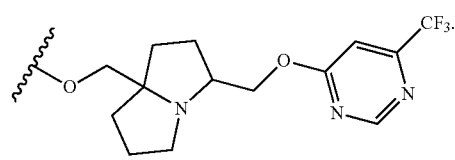
In some cases, Y—R² is:
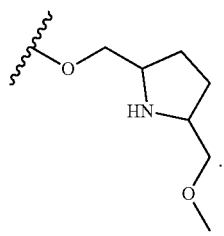 [SMILES: *OCC1CCC(COC)N1]
In some cases, Y—R² is:
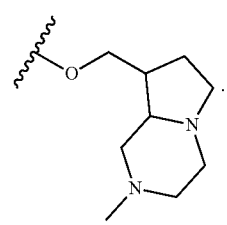
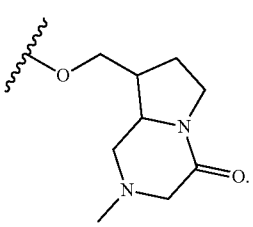 [SMILES: *OCC1CCN2C(=O)CN(C)CC12]

In some cases, Y—R² is:
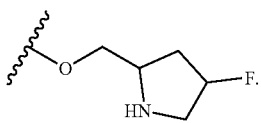 [SMILES: *OCC1CC(F)CN1]
In some cases, Y—R² is:
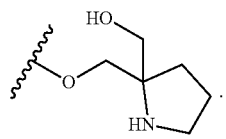 [SMILES: *OCC1(CO)CCCN1]
In some cases, Y—R² is:
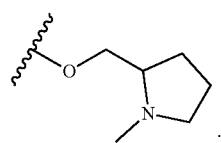 [SMILES: *OCC1CCCN1C]
In some cases, Y—R² is:
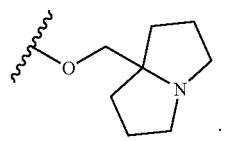 [SMILES: *OCC12CCCN1CCC2]
In some cases, Y—R² is:
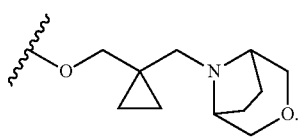 [SMILES: *OCC1(CN2C3CCC2COC3)CC1]
In some cases, Y—R² is:
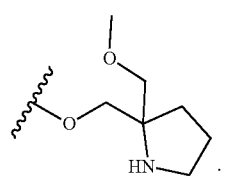 [SMILES: *OCC1(COC)CCCN1]
In some cases, Y—R² is:
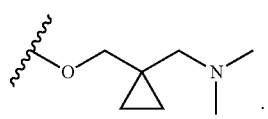 [SMILES: *OCC1(CN(C)C)CC1]
In some cases, Y—R² is:
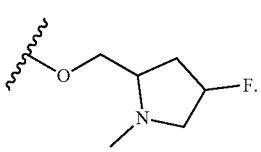 [SMILES: *OCC1CC(F)CN1C]
In some cases, Y—R² is:
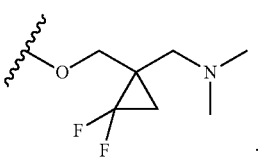 [SMILES: *OCC1(CN(C)C)CC1(F)F]
In some cases, Y—R² is:
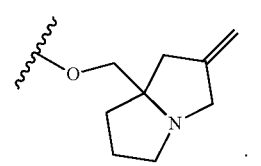 [SMILES: *OCC12CCCN1CC(=C)C2]
In some cases,
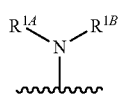
is selected from
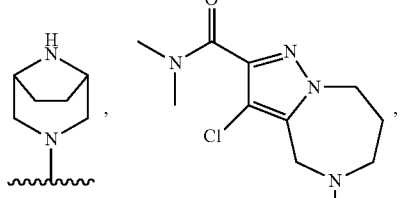
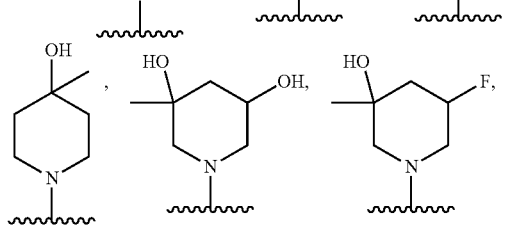

269
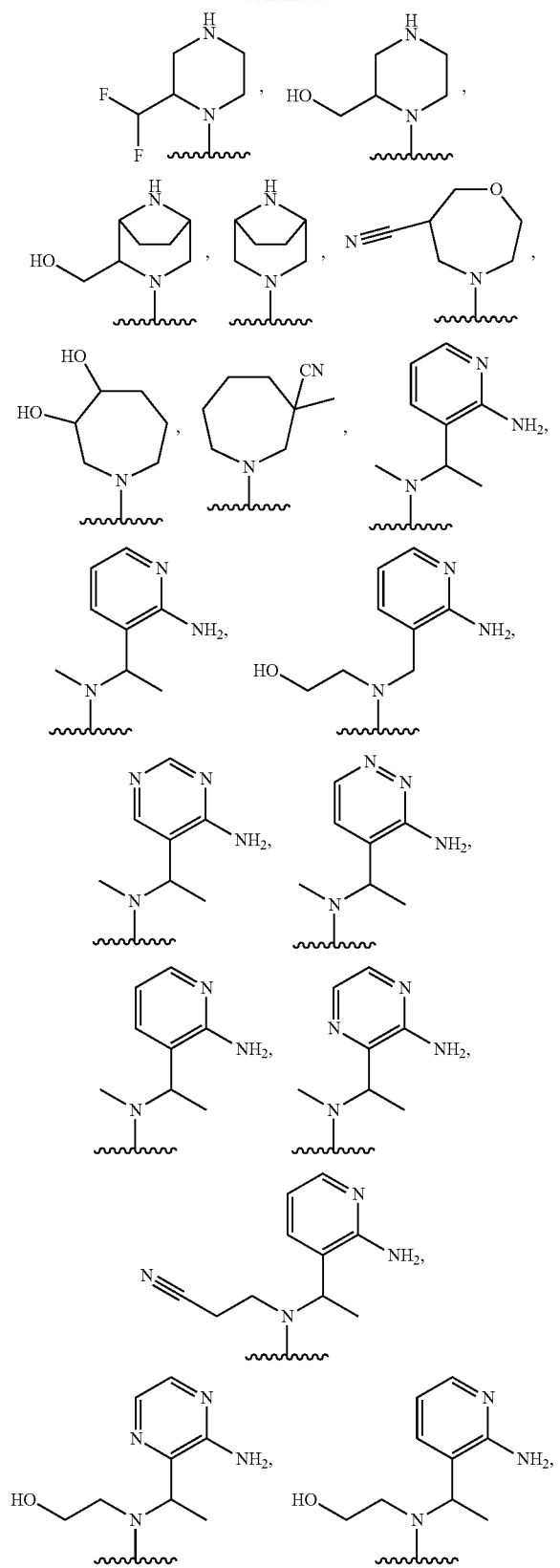
270
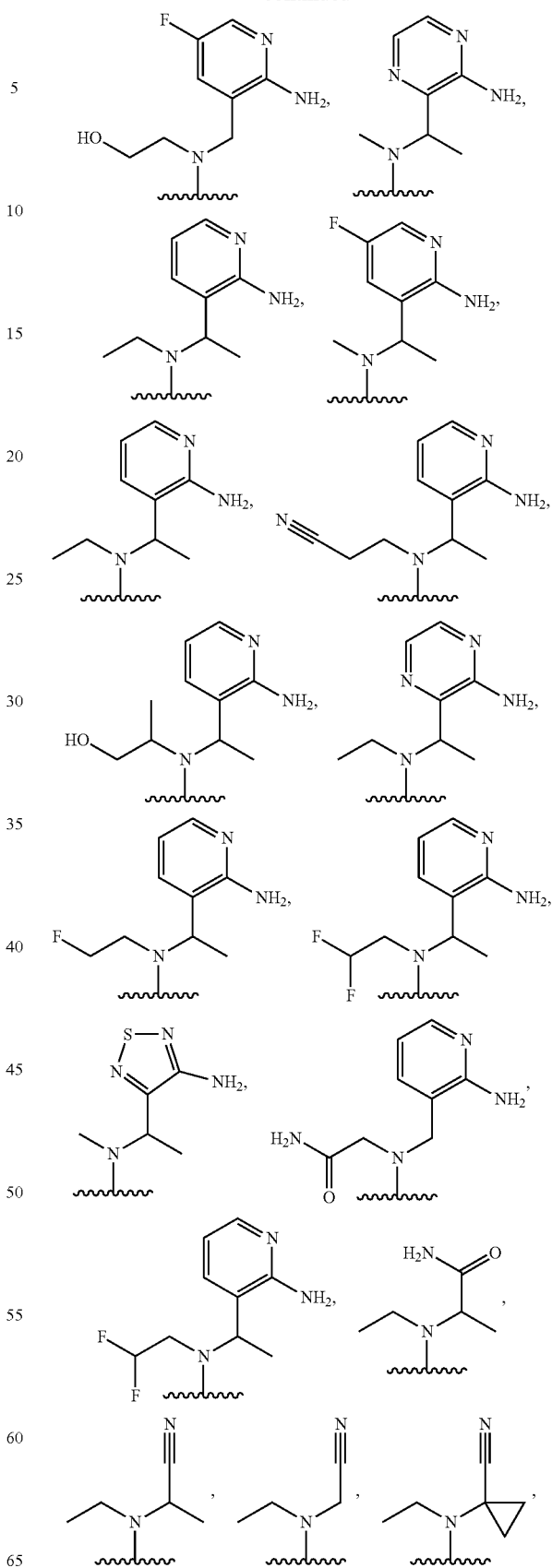

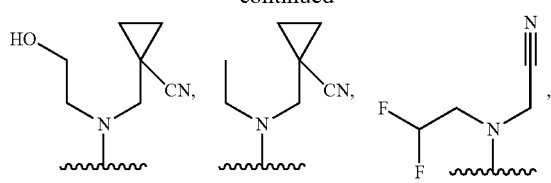
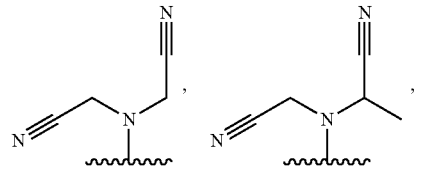
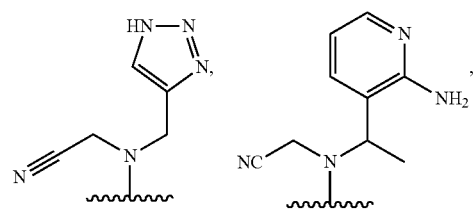
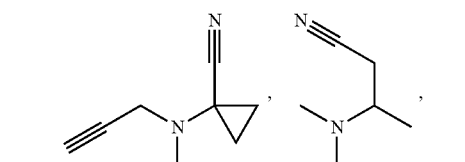
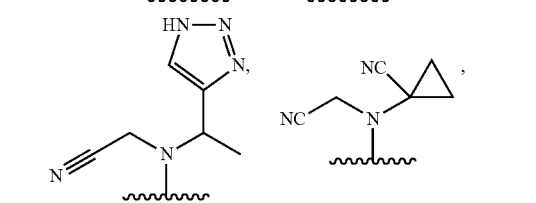
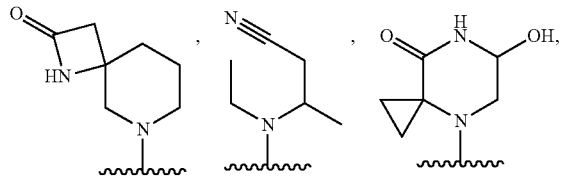
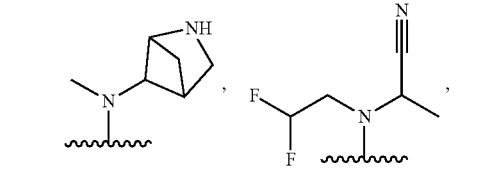
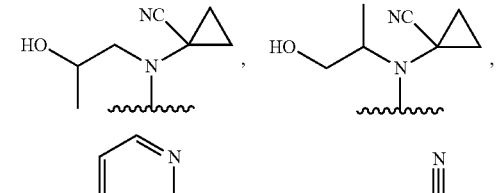
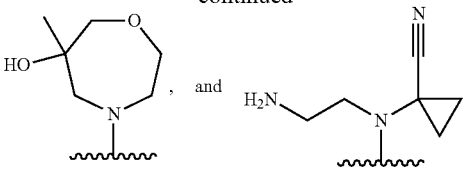
In some cases,
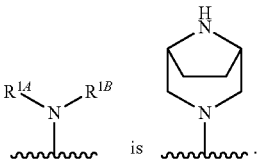 is 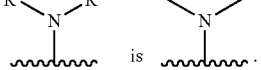.
In some cases,
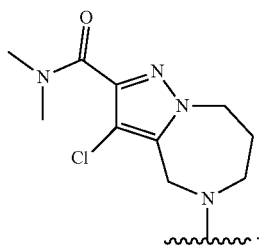
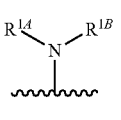 is 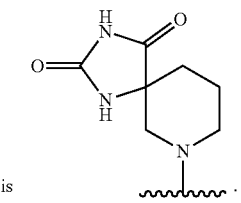.
In some cases,
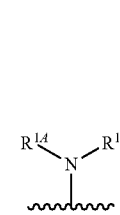 is 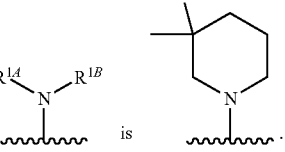.
In some cases,
 is 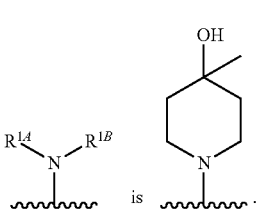.
In some cases, In some cases,
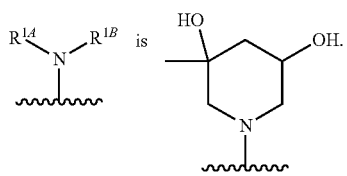
In some cases,
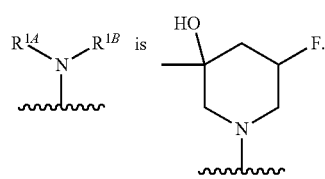
In some cases,
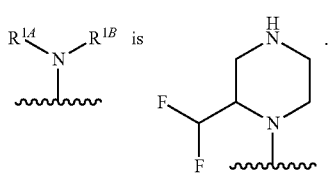
In some cases,
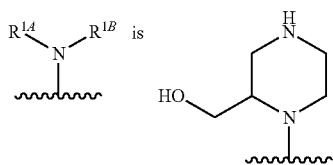
In some cases,
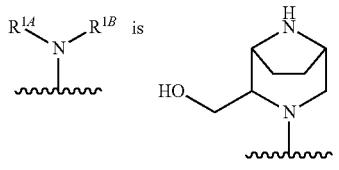
In some cases,
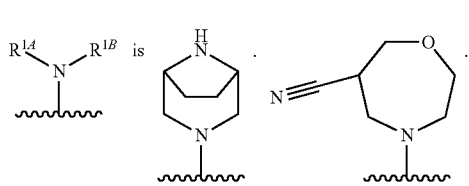
In some cases,
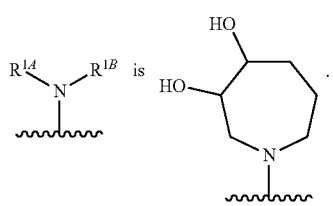
In some cases,
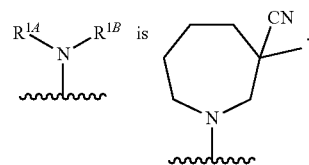
In some cases,
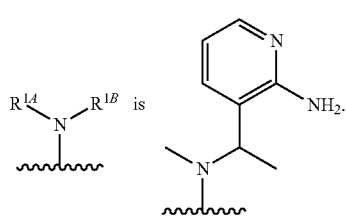
In some cases,
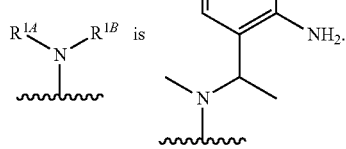
In some cases,
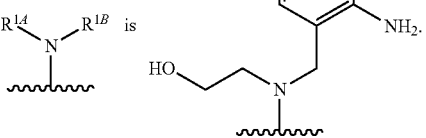

In some cases 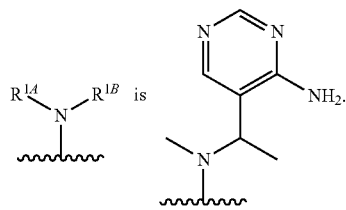 is 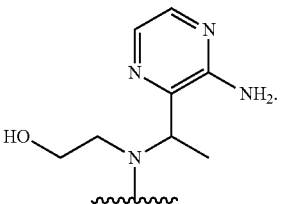
In some cases, 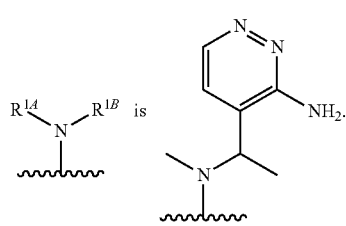 is 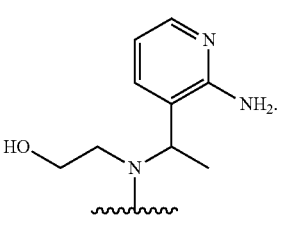
In some cases 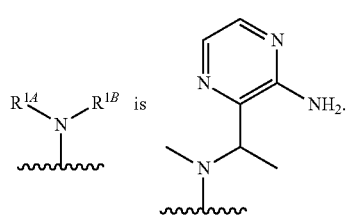 is 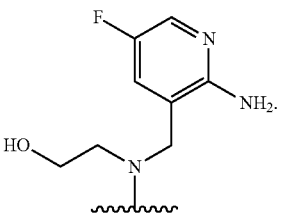
In some cases, 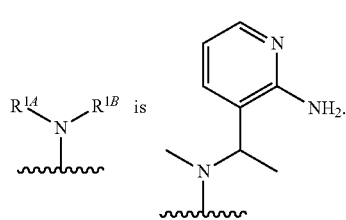 is 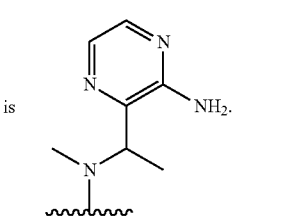
In some cases, 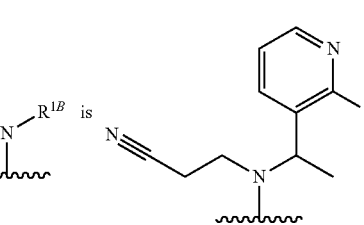 is
In some cases, 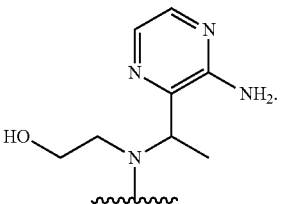 is 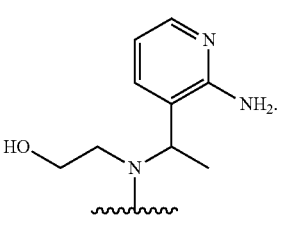
In some cases, is 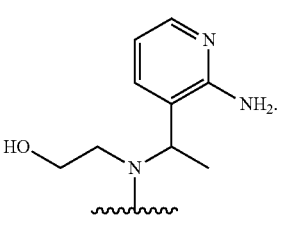
In some cases, is 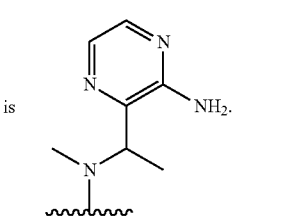
In some cases, is 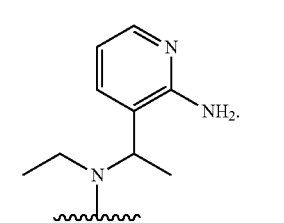
In some cases, In some cases, 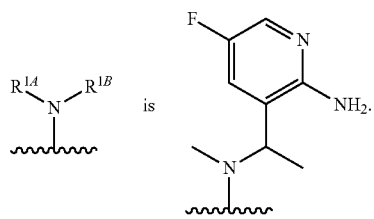
In some cases, 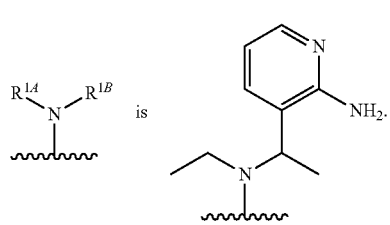
In some cases, 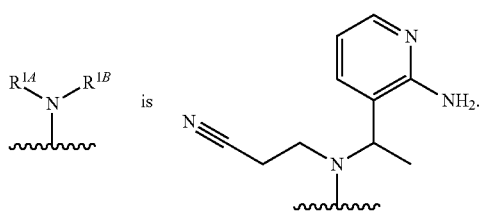
In some cases, 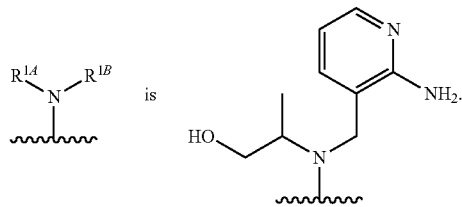
In some cases, 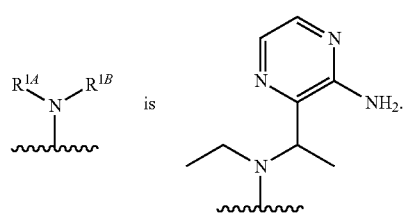
In some cases, 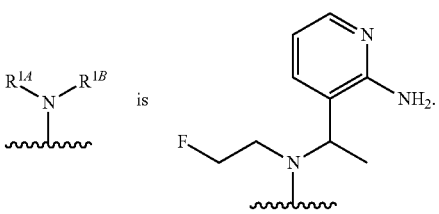
In some cases, 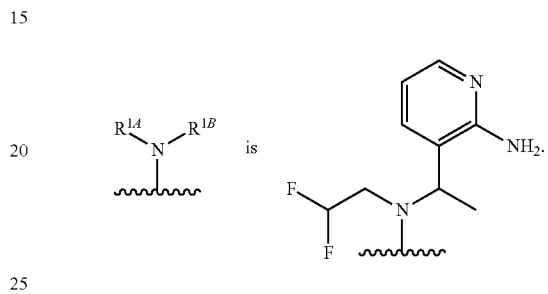
In some cases, 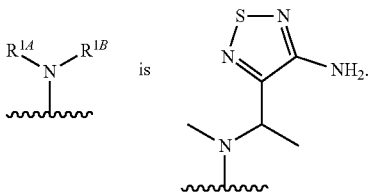
In some cases, 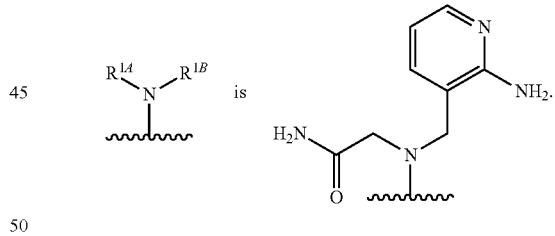
In some cases, 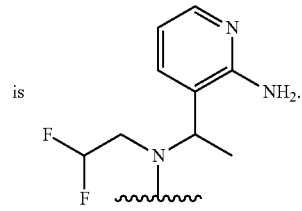

In some cases,
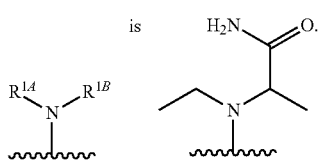
In some cases,
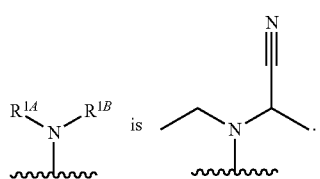
In some cases,
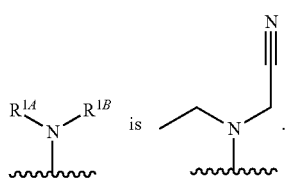
In some cases,
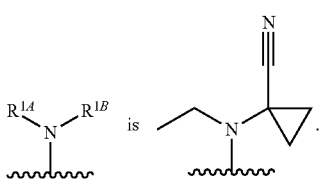
In some cases,
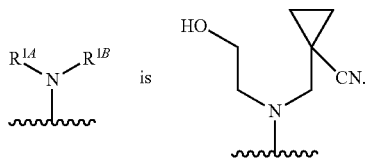
In some cases,
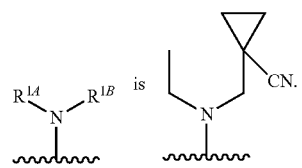
In some cases,
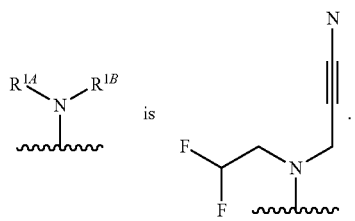
In some cases,
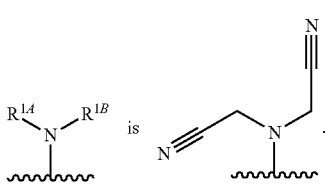
In some cases,
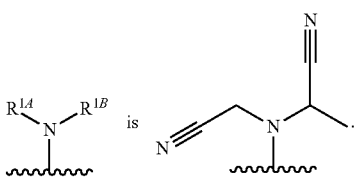
In some cases,
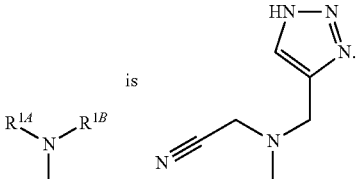
In some cases,
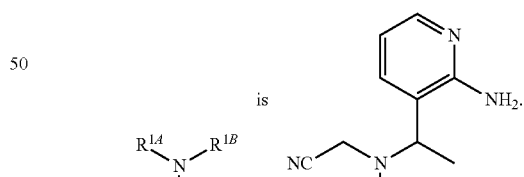
In some cases,
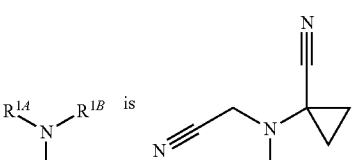

In some cases,
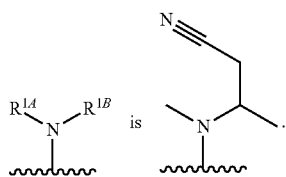
In some cases,
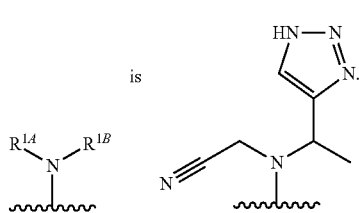
In some cases
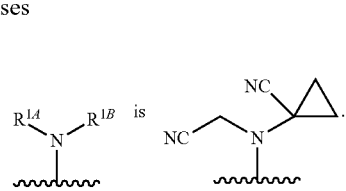
In some cases,
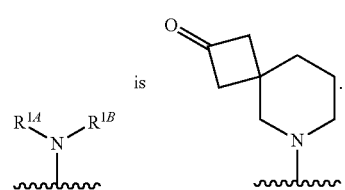
In some cases,
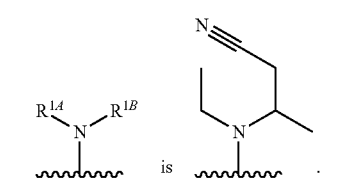
In some cases,
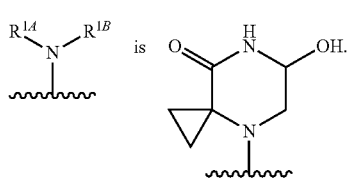
in some cases,
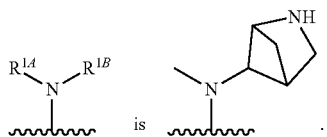
In some cases,
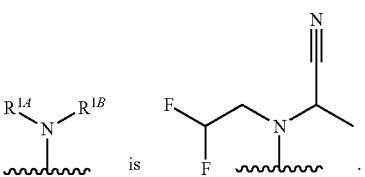
In some cases,
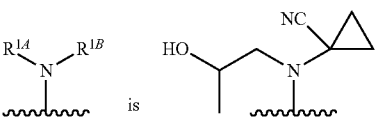
In some cases,
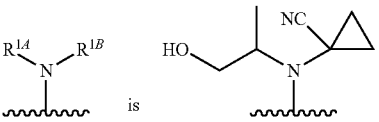
In some cases,
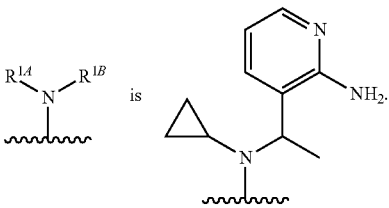
In some cases,
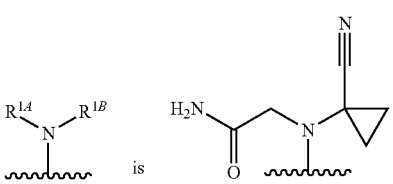

In some cases,

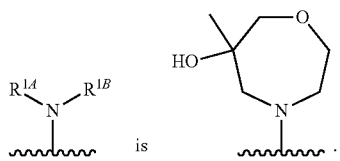

is

In some cases,

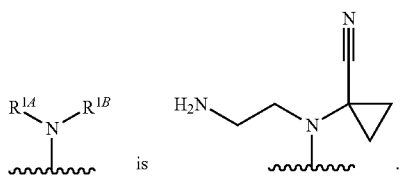

is

In some embodiments, for a compound or salt of Formula (I), Formula (I-A), Formula (I-B), Formula (I-C), Formula (I-C*), Formula (I-D), Formula (I-E), Formula (I-F), Formula (I-G), Formula (I-H), Formula (I-I), Formula (I-J), wherein the compound is not a Michael acceptor.

In some embodiments, for a compound or salt of Formula (I), Formula (I-A), Formula (I-B), Formula (I-C), Formula (I-C*), Formula (I-D), Formula (I-E), Formula (I-F), Formula (I-G), Formula (I-H), Formula (I-I), Formula (I-J), the compound or salt does not include an electrophilic substituent.

In some embodiments, for a compound or salt of Formula (I), Formula (I-A), Formula (I-B), Formula (I-C), Formula (I-C*), Formula (I-D), Formula (I-E), Formula (I-F), Formula (I-G), Formula (I-H), Formula (I-I), Formula (I-J), the compound or salt does include an electrophilic moiety.

In some embodiments, for a compound or salt of Formula (I), Formula (I-A), Formula (I-B), Formula (I-C), Formula (I-C*), Formula (I-D), Formula (I-E), Formula (I-F), Formula (I-G), Formula (I-H), Formula (I-I), Formula (I-J), the compound or salt does not include an electrophilic moiety.

In some embodiments, for a compound or salt of Formula (I), Formula (I-A), Formula (I-B), Formula (I-C), Formula (I-C*), Formula (I-D), Formula (I-E), Formula (I-F), Formula (I-G), Formula (I-H), Formula (I-I), Formula (I-J), the compound or salt does not form a covalent bond with any of the KRAS G12D and/or other G12 mutants.

In some embodiments, for a compound or salt of Formula (I), Formula (I-A), Formula (I-B), Formula (I-C), Formula (I-C*), Formula (I-D), Formula (I-E), Formula (I-F), Formula (I-G), Formula (I-H), Formula (I-I), Formula (I-J), the compound or salt does form a covalent bond with any of the KRAS G12D and/or other G12 mutants.

In some embodiments, for a compound or salt of Formula (I), Formula (I-A), Formula (I-B), Formula (I-C), Formula (I-C*), Formula (I-D), Formula (I-E), Formula (I-F), Formula (I-G), Formula (I-H), Formula (I-I), Formula (I-J), the compound or salt is not a covalent modifier of KRAS G12D and/or other G12 mutants.

In some embodiments, for a compound or salt of Formula (I), Formula (I-A), Formula (I-B), Formula (I-C), Formula (I-C*), Formula (I-D), Formula (I-E), Formula (I-F), Formula (I-G), Formula (I-H), Formula (I-I), Formula (I-J), the compound or salt is a covalent modifier of KRAS G12D and/or other G12 mutants.

In some embodiments, for a compound or salt of Formula (I), Formula (I-A), Formula (I-B), Formula (I-C), Formula (I-C*), Formula (I-D), Formula (I-E), Formula (I-F), Formula (I-G), Formula (I-H), Formula (I-I), Formula (I-J), the compound or salt is capable of reacting with a cysteine.

In some embodiments, for a compound or salt of Formula (I), Formula (I-A), Formula (I-B), Formula (I-C), Formula (I-C*), Formula (I-D), Formula (I-E), Formula (I-F), Formula (I-G), Formula (I-H), Formula (I-I), Formula (I-J), the compound or salt is not a covalent inhibitor for KRAS G12D and/or other G12 mutants.

Included in the present disclosure are salts, particularly pharmaceutically acceptable salts, of the compounds described herein. The compounds of the present invention that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, compounds described herein are intended to include all Z-, E- and tautomeric forms as well.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

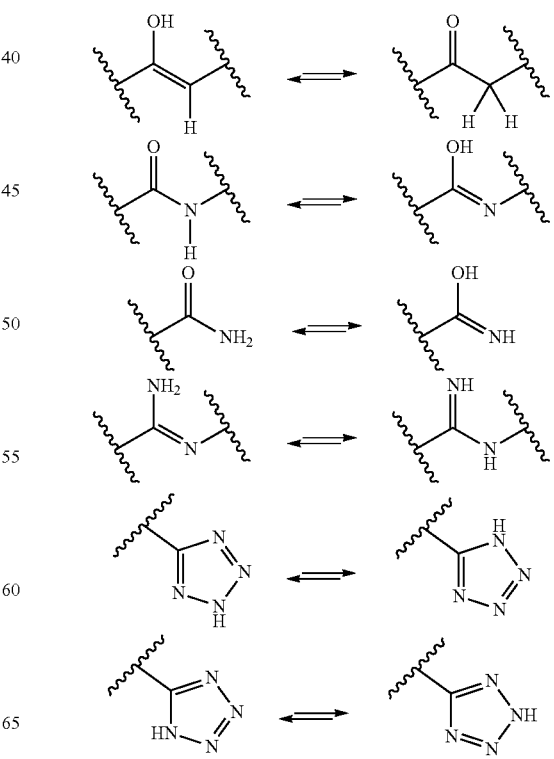

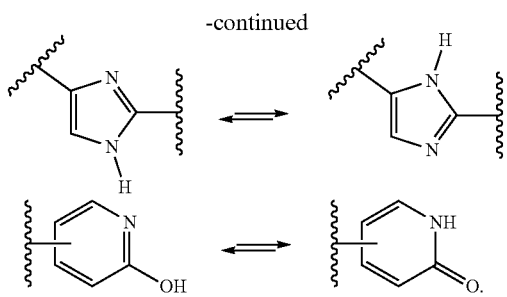

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, compounds described herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$ $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, and $^{125}I$ are all contemplated. All isotopic variations of the compounds of the present invention, whether radioactive or not, are encompassed within the scope of the present invention.

In certain embodiments, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Compounds of the present invention also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

The compounds described herein may in some cases exist as diastereomers, enantiomers, or other stereoisomeric forms. Where absolute stereochemistry is not specified, the compounds presented herein include all diastereomeric, enantiomeric, and epimeric forms as well as the appropriate mixtures thereof. Separation of stereoisomers may be performed by chromatography or by forming diastereomers and separating by recrystallization, or chromatography, or any combination thereof (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

The methods and compositions described herein include the use of amorphous forms as well as crystalline forms (also known as polymorphs). The compounds described herein may be in the form of pharmaceutically acceptable salts. As well, in some embodiments, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In certain embodiments, compounds or salts of the compounds may be prodrugs, e.g., wherein a hydroxyl in the parent compound is presented as an ester or a carbonate, or carboxylic acid present in the parent compound is presented as an ester. The term "prodrug" is intended to encompass compounds which, under physiologic conditions, are converted into pharmaceutical agents of the present disclosure. One method for making a prodrug is to include one or more selected moieties which are hydrolyzed under physiologic conditions to reveal the desired molecule. In other embodiments, the prodrug is converted by an enzymatic activity of the host animal such as specific target cells in the host animal. For example, esters or carbonates (e.g., esters or carbonates of alcohols or carboxylic acids and esters of phosphonic acids) are preferred prodrugs of the present disclosure.

Prodrug forms of the herein described compounds, wherein the prodrug is metabolized in vivo to produce a compound as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. Prodrugs may help enhance the cell permeability of a compound relative to the parent drug. The prodrug may also have improved solubility in pharmaceutical compositions over the parent drug. Prodrugs may be designed as reversible drug derivatives, for use as modifiers to enhance drug transport to site-specific tissues or to increase drug residence inside of a cell.

In some embodiments, the design of a prodrug increases the lipophilicity of the pharmaceutical agent. In some embodiments, the design of a prodrug increases the effective water solubility. See, e.g., Fedorak et al., *Am. J Physiol.*, 269:G210-218 (1995); McLoed et al., *Gastroenterol*, 106: 405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103 (1988); Sinkula et al., *J. Pharm. Sci.,* 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein for such disclosure). According to another embodiment, the present disclosure provides methods of producing the above-defined compounds. The compounds may be synthesized using conventional techniques. Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis,* 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

Pharmaceutical Formulations

Provided herein, in certain embodiments, are compositions comprising a therapeutically effective amount of any compound or salt of any one of Formula (I), Formula (I-A), Formula (I-B), Formula (I-C), Formula (I-C*), Formula (I-D), Formula (I-E), Formula (I-F), or Formula (I-G) (also referred to herein as "a pharmaceutical agent").

Pharmaceutical compositions may be formulated using one or more physiologically acceptable carriers including excipients and auxiliaries which facilitate processing of the pharmaceutical agent into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa., Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

The compositions and methods of the present disclosure may be utilized to treat an individual in need thereof. In certain embodiments, the individual is a mammal such as a human, or a non-human mammal. When administered to an animal, such as a human, the composition or the pharmaceutical agent, is preferably administered as a pharmaceutical composition comprising, for example, a pharmaceutical agent and a pharmaceutically acceptable carrier or excipient. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration, e.g., routes, such as injection or implantation, that circumvent transport or diffusion through an epithelial barrier, the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule, granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable excipient can contain physiologically acceptable agents that act, for example, to stabilize, increase solubility or to increase the absorption of a compound such as a pharmaceutical agent. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable excipient, including a physiologically acceptable agent, depends, for example, on the route of administration of the composition. The preparation or pharmaceutical composition can be a self emulsifying drug delivery system or a self microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

A pharmaceutical composition (preparation) can be administered to a subject by any of a number of routes of administration including, for example, orally, for example, drenches as in aqueous or non-aqueous solutions or suspensions, tablets, capsules, including sprinkle capsules and gelatin capsules, boluses, powders, granules, pastes for application to the tongue; absorption through the oral mucosa, e.g., sublingually; anally, rectally or vaginally, for example, as a pessary, cream or foam; parenterally, including intramuscularly, intravenously, subcutaneously or intrathecally as, for example, a sterile solution or suspension; nasally; intraperitoneally; subcutaneously; transdermally, for example, as a patch applied to the skin; and topically, for example, as a cream, ointment or spray applied to the skin, or as an eye drop. The compound may also be formulated for inhalation. In certain embodiments, a compound may be simply dissolved or suspended in sterile water.

A pharmaceutical composition may be a sterile aqueous or non-aqueous solution, suspension or emulsion, e.g., a microemulsion. The excipients described herein are examples and are in no way limiting. An effective amount or therapeutically effective amount refers to an amount of the one or more pharmaceutical agents administered to a subject, either as a single dose or as part of a series of doses, which is effective to produce a desired therapeutic effect.

Subjects may generally be monitored for therapeutic effectiveness using assays and methods suitable for the condition being treated, which assays will be familiar to those having ordinary skill in the art and are described herein. Pharmacokinetics of a pharmaceutical agent, or one or more metabolites thereof, that is administered to a subject may be monitored by determining the level of the pharmaceutical agent or metabolite in a biological fluid, for example, in the blood, blood fraction, e.g., serum, and/or in the urine, and/or other biological sample or biological tissue from the subject. Any method practiced in the art and described herein to detect the agent may be used to measure the level of the pharmaceutical agent or metabolite during a treatment course.

The dose of a pharmaceutical agent described herein for treating a disease or disorder may depend upon the subject's condition, that is, stage of the disease, severity of symptoms caused by the disease, general health status, as well as age, gender, and weight, and other factors apparent to a person skilled in the medical art. Pharmaceutical compositions may be administered in a manner appropriate to the disease to be treated as determined by persons skilled in the medical arts. In addition to the factors described herein and above related to use of pharmaceutical agent for treating a disease or disorder, suitable duration and frequency of administration of the pharmaceutical agent may also be determined or adjusted by such factors as the condition of the patient, the type and severity of the patient's disease, the particular form of the active ingredient, and the method of administration. Optimal doses of an agent may generally be determined using experimental models and/or clinical trials. The optimal dose may depend upon the body mass, weight, or blood volume of the subject. The use of the minimum dose that is sufficient to provide effective therapy is usually preferred. Design and execution of pre-clinical and clinical studies for a pharmaceutical agent, including when administered for prophylactic benefit, described herein are well within the skill of a person skilled in the relevant art. When two or more pharmaceutical agents are administered to treat a disease or disorder, the optimal dose of each pharmaceutical agent may be different, such as less than when either agent is administered alone as a single agent therapy. In certain particular embodiments, two pharmaceutical agents in combination may act synergistically or additively, and either agent may be used in a lesser amount than if administered alone. An amount of a pharmaceutical agent that may be administered per day may be, for example, between about 0.01 mg/kg and 100 mg/kg, e.g., between about 0.1 to 1 mg/kg, between about 1 to 10 mg/kg, between about 10-50 mg/kg, between about 50-100 mg/kg body weight. In other embodiments, the amount of a pharmaceutical agent that may be administered per day is between about 0.01 mg/kg and 1000 mg/kg, between about 100-500 mg/kg, or between about 500-1000 mg/kg body weight. The optimal dose, per day or per course of treatment, may be different for the disease or disorder to be treated and may also vary with the administrative route and therapeutic regimen.

Pharmaceutical compositions comprising a pharmaceutical agent can be formulated in a manner appropriate for the delivery method by using techniques routinely practiced in the art. The composition may be in the form of a solid, e.g., tablet, capsule, semi-solid, e.g., gel, liquid, or gas, e.g., aerosol. In other embodiments, the pharmaceutical composition is administered as a bolus infusion.

Pharmaceutical acceptable excipients are well known in the pharmaceutical art and described, for example, in Rowe et al., Handbook of Pharmaceutical Excipients: A Comprehensive Guide to Uses, Properties, and Safety, 5$^{th}$ Ed., 2006, and in *Remington: The Science and Practice of Pharmacy* (Gennaro, 21$^{st}$ Ed. Mack Pub. Co., Easton, PA (2005)). Exemplary pharmaceutically acceptable excipients include sterile saline and phosphate buffered saline at physiological pH. Preservatives, stabilizers, dyes, buffers, and the like may be provided in the pharmaceutical composition. In addition, antioxidants and suspending agents may also be used. In general, the type of excipient is selected based on the mode of administration, as well as the chemical composition of the active ingredient(s). Alternatively, compositions described herein may be formulated as a lyophilizate. A composition described herein may be lyophilized or otherwise formulated as a lyophilized product using one or more appropriate excipient solutions for solubilizing and/or diluting the pharmaceutical agent(s) of the composition upon administration. In other embodiments, the pharmaceutical agent may be encapsulated within liposomes using technology known and practiced in the art. In certain particular embodiments, a pharmaceutical agent is not formulated within liposomes for application to a stent that is used for treating highly, though not totally, occluded arteries. Pharmaceutical compositions may be formulated for any appropriate manner of administration described herein and in the art.

A pharmaceutical composition, e.g., for oral administration or for injection, infusion, subcutaneous delivery, intramuscular delivery, intraperitoneal delivery or other method, may be in the form of a liquid. A liquid pharmaceutical composition may include, for example, one or more of the following: a sterile diluent such as water, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral composition can be enclosed in ampoules, disposable syringes or multiple dose vials made of glass or plastic. The use of physiological saline is preferred, and an injectable pharmaceutical composition is preferably sterile. In another embodiment, for treatment of an ophthalmological condition or disease, a liquid pharmaceutical composition may be applied to the eye in the form of eye drops. A liquid pharmaceutical composition may be delivered orally.

For oral formulations, at least one of the pharmaceutical agents described herein can be used alone or in combination with appropriate additives to make tablets, powders, granules or capsules, and if desired, with diluents, buffering agents, moistening agents, preservatives, coloring agents, and flavoring agents. The pharmaceutical agents may be formulated with a buffering agent to provide for protection of the compound from low pH of the gastric environment and/or an enteric coating. A pharmaceutical agent included in a pharmaceutical composition may be formulated for oral delivery with a flavoring agent, e.g., in a liquid, solid or semi-solid formulation and/or with an enteric coating.

A pharmaceutical composition comprising any one of the pharmaceutical agents described herein may be formulated for sustained or slow release, also called timed release or controlled release. Such compositions may generally be prepared using well known technology and administered by, for example, oral, rectal, intradermal, or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of pharmaceutical agent contained within a sustained release formulation depends upon the site of implantation, the rate and expected duration of release, and the nature of the condition, disease or disorder to be treated or prevented.

In certain embodiments, the pharmaceutical compositions comprising a pharmaceutical agent are formulated for transdermal, intradermal, or topical administration. The compositions can be administered using a syringe, bandage, transdermal patch, insert, or syringe-like applicator, as a powder/talc or other solid, liquid, spray, aerosol, ointment, foam, cream, gel, paste. This preferably is in the form of a controlled release formulation or sustained release formulation administered topically or injected directly into the skin adjacent to or within the area to be treated, e.g., intradermally or subcutaneously. The active compositions can also be delivered via iontophoresis. Preservatives can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetypyridinium chloride, chlorobutanol, phenol, phenylethyl alcohol, thimerosal, and combinations thereof.

Pharmaceutical compositions comprising a pharmaceutical agent can be formulated as emulsions for topical application. An emulsion contains one liquid distributed in the body of a second liquid. The emulsion may be an oil-in-water emulsion or a water-in-oil emulsion. Either or both of the oil phase and the aqueous phase may contain one or more surfactants, emulsifiers, emulsion stabilizers, buffers, and other excipients. The oil phase may contain other oily pharmaceutically approved excipients. Suitable surfactants include, but are not limited to, anionic surfactants, non-ionic surfactants, cationic surfactants, and amphoteric surfactants. Compositions for topical application may also include at least one suitable suspending agent, antioxidant, chelating agent, emollient, or humectant.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays may be delivered from pressurized packs, for example, via a specially shaped closure. Oil-in-water emulsions can also be used in the compositions, patches, bandages and articles. These systems are semisolid emulsions, micro-emulsions, or foam emulsion systems.

In some embodiments, the pharmaceutical agent described herein can be formulated as in inhalant. Inhaled methods can deliver medication directly to the airway. The pharmaceutical agent can be formulated as aerosols, microspheres, liposomes, or nanoparticles. The pharmaceutical agent can be formulated with solvents, gases, nitrates, or any combinations thereof. Compositions described herein are optionally formulated for delivery as a liquid aerosol or inhalable dry powder. Liquid aerosol formulations are optionally nebulized predominantly into particle sizes that can be delivered to the terminal and respiratory bronchioles. Liquid aerosol and inhalable dry powder formulations are preferably delivered throughout the endobronchial tree to the terminal bronchioles and eventually to the parenchymal tissue.

Aerosolized formulations described herein are optionally delivered using an aerosol forming device, such as a jet, vibrating porous plate or ultrasonic nebulizer, preferably selected to allow the formation of aerosol particles having with a mass medium average diameter predominantly between 1 to 5μ. Further, the formulation preferably has balanced osmolarity ionic strength and chloride concentration, and the smallest aerosolizable volume able to deliver effective dose of the pharmaceutical agent. Additionally, the aerosolized formulation preferably does not impair negatively the functionality of the airways and does not cause undesirable side effects.

Aerosolization devices suitable for administration of aerosol formulations described herein include, for example, jet, vibrating porous plate, ultrasonic nebulizers and energized dry powder inhalers, that are able to nebulize the formulation into aerosol particle size predominantly in the size range from 1-5. Predominantly in this application means that at least 70% but preferably more than 90% of all generated aerosol particles are within 1-5 μrange. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb™ and AeroDose™ vibrating porous plate nebulizers (AeroGen, Inc., Sunnyvale, California), Sidestream® nebulizers (Medic-Aid Ltd., West Sussex, England), Pari LC® and Pari LC Star® jet nebulizers (Pari Respiratory Equipment, Inc., Richmond, Virginia), and Aerosonic™ (DeVilbiss Medizinische Produkte (Deutschland) GmbH, Heiden, Germany) and UltraAire® (Omron Healthcare, Inc., Vernon Hills, Illinois) ultrasonic nebulizers.

In some embodiments, the pharmaceutical agent(s) can be formulated with oleaginous bases or ointments to form a semisolid composition with a desired shape. In addition to the pharmaceutical agent, these semisolid compositions can contain dissolved and/or suspended bactericidal agents, preservatives and/or a buffer system. A petrolatum component that may be included may be any paraffin ranging in viscosity from mineral oil that incorporates isobutylene, colloidal silica, or stearate salts to paraffin waxes. Absorption bases can be used with an oleaginous system. Additives may include cholesterol, lanolin (lanolin derivatives, beeswax, fatty alcohols, wool wax alcohols, low HLB (hydrophobel-lipophobe balance) emulsifiers, and assorted ionic and non-ionic surfactants, singularly or in combination.

Controlled or sustained release transdermal or topical formulations can be achieved by the addition of time-release additives, such as polymeric structures, matrices, that are available in the art. For example, the compositions may be administered through use of hot-melt extrusion articles, such as bioadhesive hot-melt extruded film. The formulation can comprise a cross-linked polycarboxylic acid polymer formulation. A cross-linking agent may be present in an amount that provides adequate adhesion to allow the system to remain attached to target epithelial or endothelial cell surfaces for a sufficient time to allow the desired release of the compound.

An insert, transdermal patch, bandage or article can comprise a mixture or coating of polymers that provide release of the pharmaceutical agents at a constant rate over a prolonged period of time. In some embodiments, the article, transdermal patch or insert comprises water-soluble pore forming agents, such as polyethylene glycol (PEG) that can be mixed with water insoluble polymers to increase the durability of the insert and to prolong the release of the active ingredients.

Transdermal devices (inserts, patches, bandages) may also comprise a water insoluble polymer. Rate controlling polymers may be useful for administration to sites where pH change can be used to effect release. These rate controlling polymers can be applied using a continuous coating film during the process of spraying and drying with the active compound. In one embodiment, the coating formulation is used to coat pellets comprising the active ingredients that are compressed to form a solid, biodegradable insert.

A polymer formulation can also be utilized to provide controlled or sustained release. Bioadhesive polymers described in the art may be used. By way of example, a sustained-release gel and the compound may be incorporated in a polymeric matrix, such as a hydrophobic polymer matrix. Examples of a polymeric matrix include a microparticle. The microparticles can be microspheres, and the core may be of a different material than the polymeric shell. Alternatively, the polymer may be cast as a thin slab or film, a powder produced by grinding or other standard techniques, or a gel such as a hydrogel. The polymer can also be in the form of a coating or part of a bandage, stent, catheter, vascular graft, or other device to facilitate delivery of the pharmaceutical agent. The matrices can be formed by solvent evaporation, spray drying, solvent extraction and other methods known to those skilled in the art.

Kits with unit doses of one or more of the agents described herein, usually in oral or injectable doses, are provided. Such kits may include a container containing the unit dose, an informational package insert describing the use and attendant benefits of the drugs in treating disease, and optionally an appliance or device for delivery of the composition.

Methods of Treatment

In an aspect, the present disclosure provides compounds that inhibit KRas G12 mutants. In some cases, the method may inhibit KRas G12 mutants activity in a cell. In some cases, inhibiting KRas G12 mutants activity in a cell may include contacting the cell in which inhibition of KRas G12 mutants activity is desired with an effective amount of a compound of Formula (I), Formula (I-A), Formula (I-B), Formula (I-C), Formula (I-C*), Formula (I-D), Formula (I-E), Formula (I-F), Formula (I-G), Formula (I-H), Formula (I-I), or Formula (I-J), or pharmaceutical compositions containing any one of the Formulas thereof or a pharmaceutically acceptable salt thereof. In some cases, the contacting is in vitro. In some cases, the contacting is in vivo. As used herein, the term "contacting" refers to the bringing together of indicated moieties in an in vitro system or an in vivo system. For example, "contacting" a KRas G12D and/or other G12 mutants with a compound provided herein includes the administration of a compound provided herein to an individual or patient, such as a human, having KRas G12D and/or other G12 mutants, as well as, for example, introducing a compound provided herein into a sample containing a cellular or purified preparation containing the KRas G12D and/or other G12 mutants. In some cases, a cell in which inhibition of KRas G12D and/or other G12 mutants activity is desired is contacted with an effective amount of a compound of Formula (I), Formula (I-A), Formula (I-B), or pharmaceutically acceptable salt thereof to negatively modulate the activity of KRas G12D and/or other G12 mutants. In some cases, by negatively modulating the activity of KRas G12D and/or other G12 mutants, the methods described herein are designed to inhibit undesired cellular proliferation resulting from enhanced KRas G12D and/or other G12 mutants activity within the cell. The cells may be contacted in a single dose or multiple doses in accordance with a particular treatment regimen to effect the desired negative modulation of KRas G12D and/or other G12 mutants. The ability of compounds to bind KRas G12D and/or other G12 mutants may be monitored in vitro using well known methods.

In some embodiments, the inhibitory activity of exemplary compounds in cells may be monitored, for example, by measuring the inhibition of KRas G12D and/or other G12 mutants activity of the amount of phosphorylated ERK.

In another aspect, methods of treating cancer in a patient in need thereof, comprising administering to said patient a therapeutically effective amount of a compound of Formula (I), Formula (I-A), Formula (I-B), Formula (I-C), Formula (I-C*), Formula (I-D), Formula (I-E), Formula (I-F), Formula (I-G), Formula (I-H), Formula (I-I), or Formula (I-J), or a pharmaceutically acceptable salt of any one thereof, or a pharmaceutical composition comprising the compound or pharmaceutically acceptable salt thereof are provided. The compositions and methods provided herein may be used for the treatment of a KRas G12D and/or other G12 mutants-associated cancer in a patient in need thereof, comprising administering to the patient a therapeutically effective amount of a compound of Formula (I), Formula (I-A), Formula (I-B), Formula (I-C), Formula (I-D), Formula (I-E), Formula (I-F), Formula (I-G), Formula (I-H), Formula (I-I), or Formula (I-J), or a pharmaceutically acceptable salt of any one thereof, or a pharmaceutical composition comprising the compound or pharmaceutically acceptable salt of any one thereof are provided. In some cases, the KRas G12D and/or other G12 mutants associated cancer is lung cancer. The compositions and methods provided herein may be used for the treatment of a wide variety of cancers including tumors such as lung, prostate, breast, brain, skin, cervical carcinomas, testicular carcinomas, etc. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In some cases, the cancer is non-small cell lung cancer, small cell lung cancer, colorectal cancer, rectal cancer or pancreatic cancer. In some cases, the cancer is non-small cell lung cancer. In some cases, the concentration and route of administration to the patient will vary depending on the cancer to be treated. The compounds, pharmaceutically acceptable salts thereof and pharmaceutical compositions comprising such compounds and salts also may be co-administered with other anti-neoplastic compounds, e.g., chemotherapy, or used in combination with other treatments, such as radiation or surgical intervention, either as an adjuvant prior to surgery or post-operatively.

Also provided herein is a compound of Formula (I), Formula (I-A), Formula (I-B), Formula (I-C), Formula (I-C*), Formula (I-D), Formula (I-E), Formula (I-F), Formula (I-G), Formula (I-H), Formula (I-I), or Formula (I-J), or a pharmaceutically acceptable salt thereof, or a pharmaceutical composition thereof as defined herein for use in therapy.

Also provided herein is a compound of Formula (I), Formula (I-A), Formula (I-B), Formula (I-C), Formula (I-C*), Formula (I-D), Formula (I-E), Formula (I-F), Formula (I-G), Formula (I-H), Formula (I-I), or Formula (I-J), or a pharmaceutically acceptable salt of any one thereof, or a pharmaceutical composition thereof as defined herein for use in the treatment of cancer.

Also provided herein is a compound of Formula (I), Formula (I-A), Formula (I-B), Formula (I-C), Formula (I-C*), Formula (I-D), Formula (I-E), Formula (I-F), Formula (I-G), Formula (I-H), Formula (I-I), or Formula (I-J), or a pharmaceutically acceptable salt of any one thereof, or a pharmaceutical composition of any one thereof for use in the inhibition of KRas G12D and/or other G12 mutants.

Also provided herein is a compound of Formula (I), Formula (I-A), Formula (I-B), Formula (I-C), Formula (I-C*), Formula (I-D), Formula (I-E), Formula (I-F), Formula (I-G), Formula (I-H), Formula (I-I), or Formula (I-J), or a pharmaceutically acceptable salt of any one thereof, or a pharmaceutical composition of any one thereof as defined herein, for use in the treatment of a KRas G12D and/or other G12 mutants-associated disease or disorder.

Also provided herein is the use of a compound of Formula (I), Formula (I-A), Formula (I-B), Formula (I-C), Formula (I-C*), Formula (I-D), Formula (I-E), Formula (I-F), Formula (I-G), Formula (I-H), Formula (I-I), or Formula (I-J), or a pharmaceutically acceptable salt of any one thereof, in the manufacture of a medicament for the treatment of cancer.

Also provided herein is a use of a compound of Formula (I), Formula (I-A), Formula (I-B), Formula (I-C), Formula (I-C*), Formula (I-D), Formula (I-E), Formula (I-F), Formula (I-G), Formula (I-H), Formula (I-I), or Formula (I-J), or a pharmaceutically acceptable salt of any one thereof, in the manufacture of a medicament for the inhibition of activity of KRas G12D and/or other G12 mutants.

Also provided herein is the use of a compound of Formula (I), Formula (I-A), Formula (I-B), Formula (I-C), Formula (I-C*), Formula (I-D), Formula (I-E), Formula (I-F), Formula (I-G), Formula (I-H), Formula (I-I), or Formula (I-J), or a pharmaceutically acceptable salt of any one thereof, in the manufacture of a medicament for the treatment of a KRas G12D and/or other G12 mutants-associated disease or disorder.

In another aspect, the present disclosure provides a method for treating cancer in a patient in need thereof, the method comprising (a) determining that cancer is associated with a KRas G12D mutation and/or other G12 mutants (e.g., a KRas G12D and/or other G12 mutants-associated cancer) (e.g., as determined using a regulatory agency-approved, e.g., FDA-approved, assay or kit); and (b) administering to the patient a therapeutically effective amount of a compound of Formula (I), Formula (I-A), Formula (I-B), Formula (I-C), Formula (I-C*), Formula (I-D), Formula (I-E), Formula (I-F), Formula (I-G), Formula (I-H), Formula (I-I), or Formula (I-J), or a pharmaceutically acceptable salt of any one thereof, or a pharmaceutical composition of any one thereof.

The compounds described herein can be used in the preparation of medicaments for the prevention or treatment of diseases or conditions. In addition, a method for treating any of the diseases or conditions described herein in a subject in need of such treatment, involves administration of pharmaceutical compositions containing at least one compound described herein, or a pharmaceutically acceptable salt, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion, the administration of the compounds may be administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.02- about 5000 mg per day, in some embodiments, about 1- about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

In certain embodiments, the invention provides a method of treating or preventing a disease, state, or condition in a patient in need thereof comprising administering to the patient an effective amount of a compound of any one of embodiments of the invention or a pharmaceutically acceptable salt thereof. The disease, state or condition may be selected from a group as described elsewhere herein.

Bifunctional Compounds

In some embodiments, compounds herein can adopt to selectively eliminate an over activated KRas signaling which is induced by KRas mutations by directly binding with the mutated KRas protein, either by stabilizing its GDP bound form (the inactive form) or by blocking the interaction between GTP bound form and its downstream target protein. In some embodiments, another way is to hijack the protein degradation mechanism in a cell and leverage E3 ligases' (like VHL, CRBN or IAPs) substrate specificity through a bi-functional molecule called Proteolysis targeting chimera (PROTAC) (Winter G E, Buckley D L, Paulk J, Roberts J M, Souza A, Dhe-Paganon S, Bradner J E. DRUG DEVELOPMENT. Phthalimide conjugation as a strategy for in vivo target protein degradation. Science. 2015 Jun. 19; 348 (6241): 1376-81), which can bind with both mutated KRas protein and E3 ligase, create interactions between those two proteins and induce KRas degradation.

Disclosed herein is a bifunctional compound composed of a target protein (i.e., KRAS G12D)-binding moiety and an E3 ubiquitin ligase-binding moiety, which may induce proteasome-mediated degradation of selected proteins. In some embodiments, the bifunctional compound comprises a target protein (i.e., KRAS G12D)-binding moiety and an E3 ubiquitin ligase-binding moiety known in the art. In some embodiments, disclosed herein is the use of the compound disclosed herein in the preparation of degrading a target protein compound by using chemical modification of the compound disclosed herein. In some cases, the target protein-binding moiety is derived from a compound of Formula (I), Formula (I-A), Formula (I-B), Formula (I-C), Formula (I-C*), Formula (I-D), Formula (I-E), Formula (I-F), Formula (I-G), Formula (I-H), Formula (I-I), or Formula (I-J).

Preparation of Compounds

The compounds of the present disclosure can generally be prepared in a number of ways well known to those skilled in the art of organic synthesis. By way of example, compounds of the present disclosure can be synthesized using the methods described herein, together with synthetic methods known in the art of synthetic organic chemistry, or variations thereof as appreciated by those skilled in the art. The compounds of the present disclosure may be prepared as described in the schemes and examples described elsewhere herein.

The following examples further illustrate the invention but, of course, should not be construed as in any way limiting its scope.

EXAMPLES

The following synthetic schemes are provided for purposes of illustration, not limitation. The following examples illustrate the various methods of making compounds described herein. It is understood that one skilled in the art may be able to make these compounds by similar methods or by combining other methods known to one skilled in the art. It is also understood that one skilled in the art would be able to make, in a similar manner as described below by using the appropriate starting materials and modifying the synthetic route as needed. In general, starting materials and reagents can be obtained from commercial vendors or synthesized according to sources known to those skilled in the art or prepared as described herein.

INTERMEDIATES

Intermediate 1. Preparation of 2-aminospiro[5,6-dihydrocyclopenta[b]thiophene-4,3'-azetidine]-3-carbonitrile

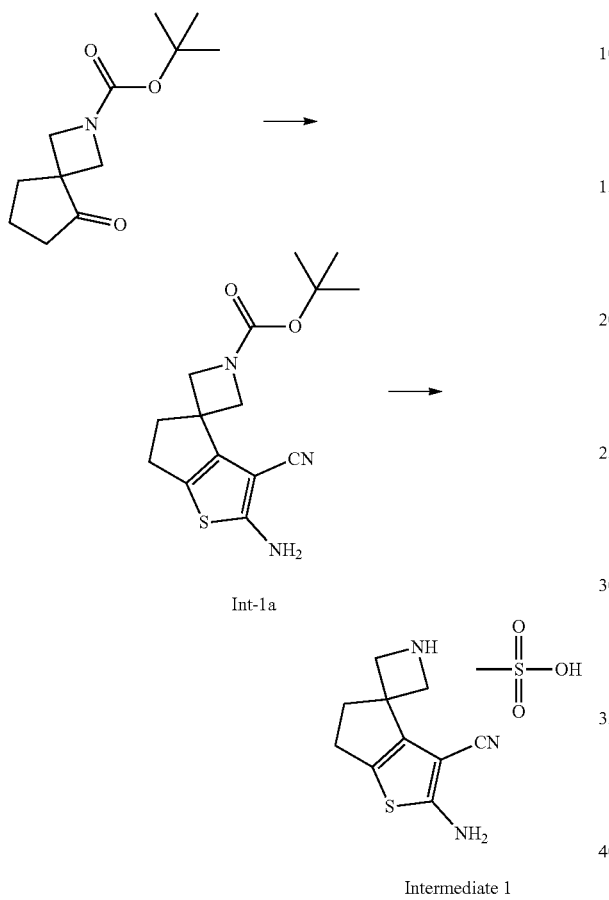

Int-1a

Intermediate 1

Step 1. Synthesis of tert-butyl 2-amino-3-cyano-spiro[5,6-dihydrocyclopenta[b]thiophene-4,3'-azetidine]-1'-carboxylate (Int-1a). To a solution of propanedinitrile (1407.5 mg, 21.31 mmol) and tert-butyl 5-oxo-2-azaspiro[3.4]octane-2-carboxylate (3200 mg, 14.2 mmol) in Ethanol (30 mL) was added sulfur (726.14 mg, 21.31 mmol) and NH₄OAc (1657.7 mg, 21.31 mmol) at 25° C. under N2. The reaction was heated at 60° C. for 16 h. Then the mixture was cooled down and filtered to afford a crude solution. The crude product was triturated with EtOAc and filtered to afford tert-butyl 2-amino-3-cyano-spiro[5,6-dihydrocyclopenta[b]thiophene-4,3'-azetidine]-1'-carboxylate (Int-1a, 3.80 g, 12.4 mmol, 87.60% yield) as white solid. LCMS calculated for $C_{15}H_{20}N_3O_2S$ (M+H)$^+$ m/z=306.1, found: 306.1. $^1$H NMR (400 MHz, CD$_3$OD) δ 4.19 (s, 2H), 3.95 (d, J=8.1 Hz, 2H), 2.76-2.69 (m, 2H), 2.69-2.61 (m, 2H), 1.45 (s, 9H).

Step 2. Synthesis of 2-aminospiro[5,6-dihydrocyclopenta[b]thiophene-4,3'-azetidine]-3-carbonitrile (Intermediate 1). To a solution of tert-butyl 2-amino-3-cyano-spiro[5,6-dihydrocyclopenta[b]thiophene-4,3'-azetidine]-1'-carboxylate (Int-1a, 7 g, 22.92 mmol) in IPA (140 mL) was added MsOH (5231.92 mg, 54.44 mmol) at 25° C. under N₂. Then the reaction was heated at 60° C. for 16 h. Then the mixture was cooled down and filtered. The solid was washed with MTBE (30 mL×2) to give the crude product 2-aminospiro[5,6-dihydrocyclopenta[b]thiophene-4,3'-azetidine]-3-carbonitrile; methanesulfonic acid (Intermediate 1, 6800 mg, 22.6 mmol, 98.44% yield). LCMS calculated for $C_{10}H_{12}N_3S$ (M+H)$^+$ m/z=206.2, found: 206.1.

Intermediate 2. Preparation of 2-amino-5-chloro-4-pyrrolidin-3-yl-thiophene-3-carbonitrile

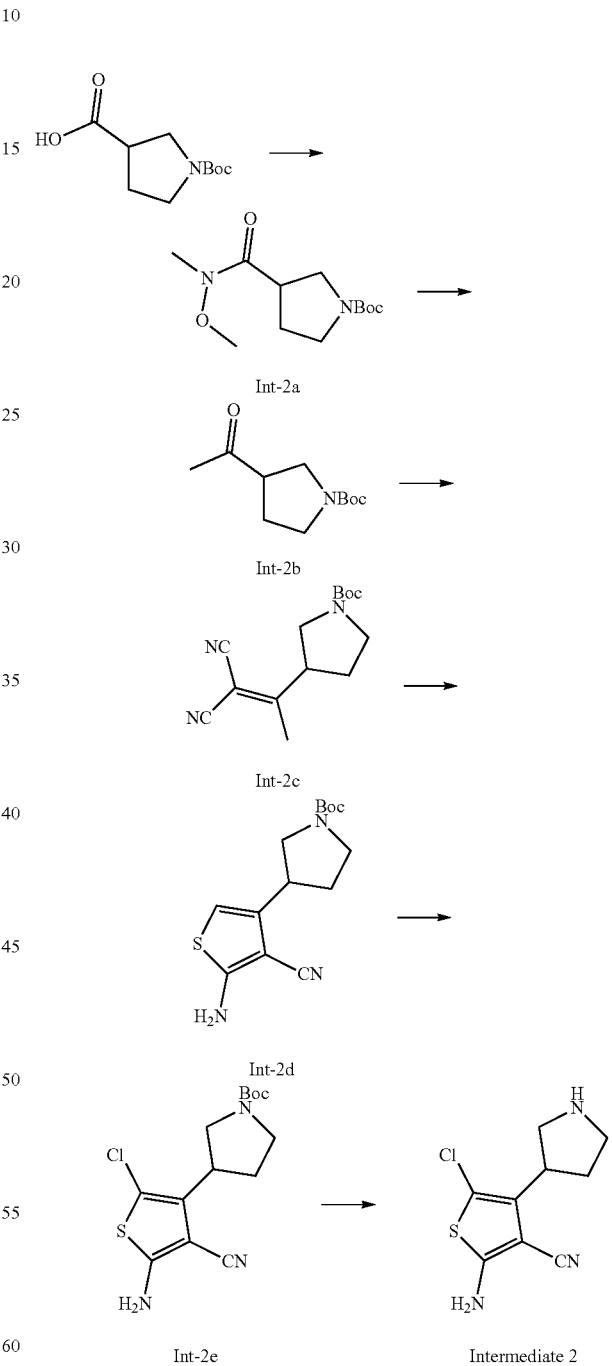

Step 1. Preparation of tert-butyl 3-[methoxy(methyl)carbamoyl]pyrrolidine-1-carboxylate (Int-2a). To a solution of 1-tert-butoxycarbonylpyrrolidine-3-carboxylic acid (25 g, 116.14 mmol) in THF (250 mL) was added N,O-Dimethylhydroxylamine Hydrochloride (14.73 g, 150.99 mmol) and DIEA (101.15 mL, 580.72 mmol), followed by the addition of HATU (66.24 g, 174.22 mmol). The reaction was stirred for 16 h at room temperature. The mixture was quenched with sat. NH$_4$Cl (100 mL) and extracted with EtOAc (200 mL×3). The combined organic layers were dried over Na$_2$SO$_4$ and concentrated under vacuum to give the crude product. The crude product was purified by silica gel chromatography (eluted with EtOAc in petroleum ether from 10% to 25%) to give the final product tert-butyl 3-[methoxy(methyl)carbamoyl]
pyrrolidine-1-carboxylate (Int-2a, 26 g, 100.65 mmol, 86.66% yield) as yellow oil.

Step 2. Preparation of tert-butyl 3-acetylpyrrolidine-1-carboxylate (Int-2b). A solution of tert-butyl 3-[methoxy(methyl)carbamoyl]pyrrolidine-1-carboxylate (Int-2a, 26 g, 100.65 mmol) in THF (360 mL) was added chloro(methyl)magnesium (100.65 mL, 301.96 mmol) at −78° C. The mixture was stirred at 25° C. for 16 h. The reaction mixture was quenched with sat. NH$_4$Cl (200 mL) and extracted with EtOAc (200 mL×2). The combined organic layers were dried over Na$_2$SO$_4$ and concentrated under vacuum. The residue was purified by column chromatography (10%-30% EtOAc/heptane) to afford tert-butyl 3-acetylpyrrolidine-1-carboxylate (Int-2b, 19.00 g, 89.1 mmol, 88.51% yield) as colorless oil.

Step 3. Preparation of tert-butyl 3-(2,2-dicyano-1-methyl-vinyl)pyrrolidine-1-carboxylate (Int-2c). To a solution of propanedinitrile (0.89 mL, 14.07 mmol) and tert-butyl 3-acetylpyrrolidine-1-carboxylate (Int-2b, 2000 mg, 9.38 mmol) in o-Xylene (20 mL) was added AcOH (0.11 mL, 1.88 mmol) and NH$_4$OAc (289.21 mg, 3.75 mmol) at 25° C. The reaction was heated at 110° C. for 16 h. The mixture was cooled down and was extracted with EtOAc (100 ml), dried over Na$_2$SO$_4$, concentrated. The crude product was purified by column chromatography (eluted with EtOAc in petroleum ether from 10% to 90%) to give the final product tert-butyl 3-(2,2-dicyano-1-methyl-vinyl)pyrrolidine-1-carboxylate (Int-2c, 2.17 g, 8.30 mmol, 88.55% yield) as yellow oil.

Step 4. Preparation of tert-butyl 3-(5-amino-4-cyano-3-thienyl)pyrrolidine-1-carboxylate (Int-2d). To a solution of tert-butyl 3-(2,2-dicyano-1-methyl-vinyl)pyrrolidine-1-carboxylate (Int-2c, 2.17 g, 8.3 mmol) in THF (18 mL) and Water (6 mL) was added Sulfur (0.27 g, 8.3 mmol) and NaHCO$_3$ (1.09 g, 10.8 mmol) at 25° C. The reaction was heated at 35° C. for 2 h. The mixture was quenched with water (50 mL) and extracted with EtOAc (50 mL×2), dried over Na$_2$SO$_4$, concentrated. The crude product was purified by column chromatography to afford tert-butyl 3-(5-amino-4-cyano-3-thienyl)pyrrolidine-1-carboxylate (Int-2d, 1.00 g, 3.41 mmol, 41.05% yield) was obtained as off-white solid. LCMS calculated for C$_{14}$H$_{20}$N$_3$O$_2$S (M+H)$^+$ m/z=294.2, found: 294.2.

Step 5. Preparation of tert-butyl 3-(5-amino-2-chloro-4-cyano-3-thienyl)pyrrolidine-1-cyano-3-thienyl)pyrrolidine-1-carboxylate (Int-2e). A solution of tert-butyl 3-(5-amino-4-cyano-3-thienyl)pyrrolidine-1-carboxylate (Int-2d, 2.5 g, 8.52 mmol) in CH$_3$CN (25 mL) was stirred at 25° C. for 2 h. The mixture was filtered to afford a crude product. The crude product was triturated in CH$_3$CN (15 mL) and filtered to give tert-butyl 3-(5-amino-2-chloro-4-cyano-3-thienyl)pyrrolidine-1-carboxylate (Int-2e, 1900 mg, 5.80 mmol, 68.01% yield) as yellow solid. LCMS calculated for C$_{14}$H$_{18}$ClNaN$_3$O$_2$S (M+Na)$^+$ m/z=350.2, found: 350.1.

Step 6. Preparation of 2-amino-5-chloro-4-pyrrolidin-3-yl-thiophene-3-carbonitrile (Int-2). A solution of trifluoroacetic acid (0.63 mL, 8.16 mmol) and tert-butyl 3-(5-amino-2-chloro-4-cyano-3-thienyl)pyrrolidine-1-carboxylate (Int-2e, 100 mg, 0.31 mmol) in DCM (2 mL) was stirred at 25° C. for 1 h. The solvent was removed to give 2-amino-5-chloro-4-pyrrolidin-3-yl-thiophene-3-carbonitrile (Intermediate 2, 69 mg, 0.303 mmol, 99.34% yield). LCMS calculated for C$_9$H$_{11}$ClN$_3$S (M+H)$^+$ m/z=228.0, found: 228.0.

Intermediate 3. Synthesis of 3-chloro-N,N-dimethyl-5,6,7,8-tetrahydro-4H-pyrazolo[1,5-a][1,4]diazepine-2-carboxamide

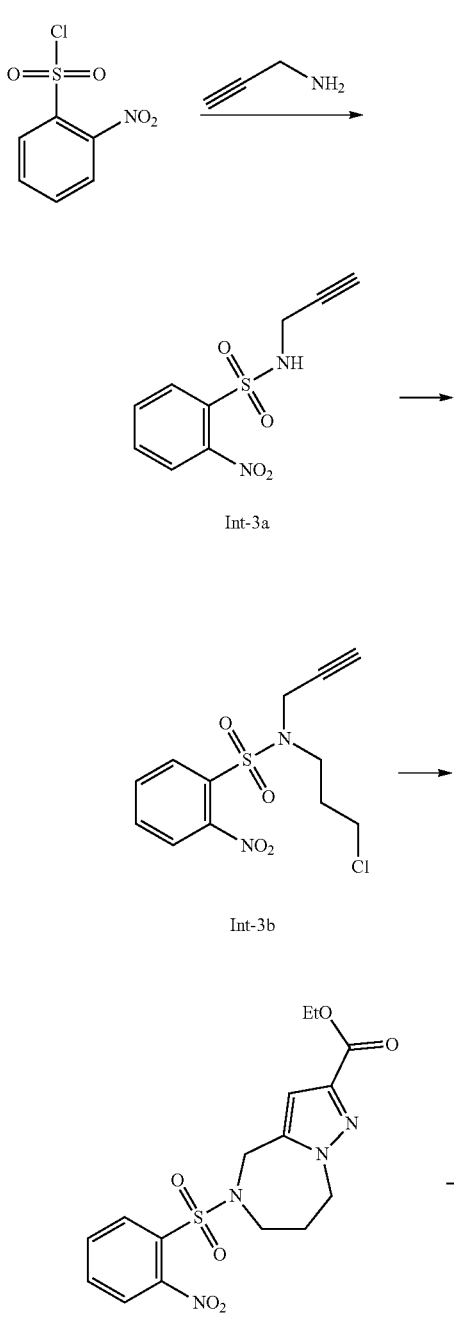

Int-3a

Int-3b

Int-3c

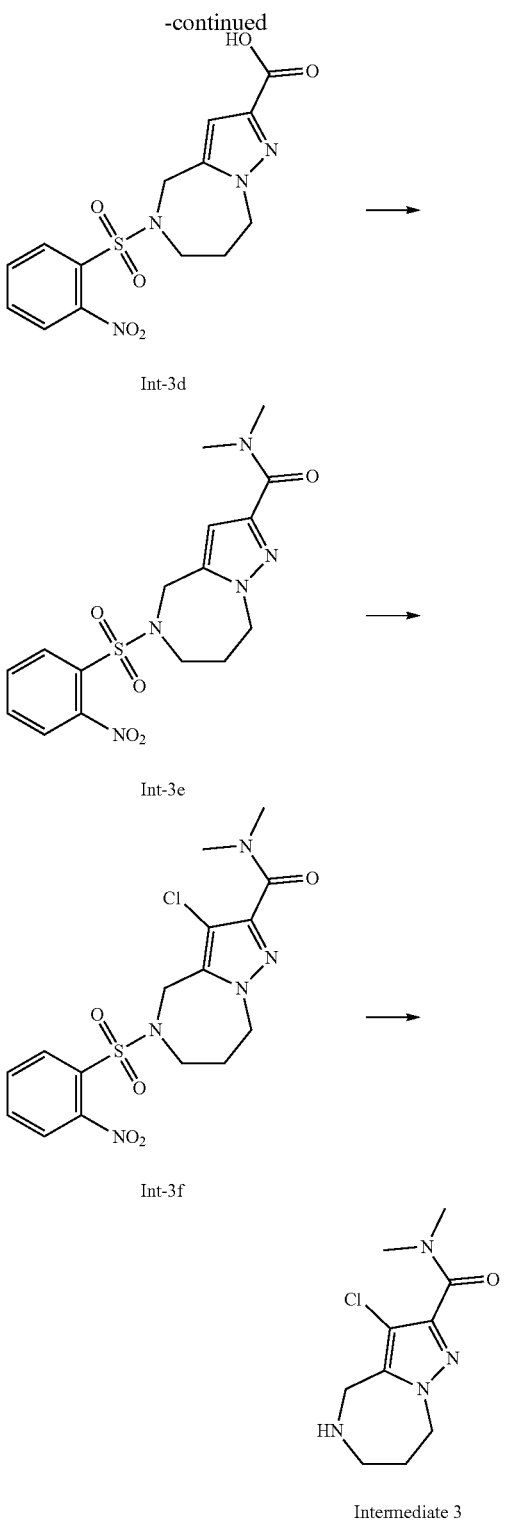

Int-3d

Int-3e

Int-3f

Intermediate 3

Step 1. Synthesis of 2-nitro-prop-2-ynyl-benzenesulfonamide (Int-3a). A solution of prop-2-yl-1-amine (1.87 mL, 29.1 mmol) and N,N-diisopropylethylamine (10.15 mL, 58.3 mmol) in DCM (100 mL) was cooled to 0° C. followed by the portion addition of 2-nitrobenzenesulfonyl chloride (6.46 g, 29.15 mmol). The mixture was warmed to RT and was stirred for 1 hr at RT. The mixture was washed with water and brine, dried over $Na_2SO_4$, and concentrated. The crude product was purified by flash chromatography to afford 2-nitro-prop-2-ynyl-benzenesulfonamide (Int-3a, 5.98 g, 24.9 mmol, 85.4% yield) as a yellow solid. LCMS calculated for $C_9H_9N_2O_4S$ (M+H)$^+$ m/z=241.0, found: 241.0.

Step 2. Synthesis of (3-chloropropyl)-2-nitro-prop-2-ynyl-benzenesulfonamide (Int-3b). To a solution of 2-nitro-prop-2-ynyl-benzenesulfonamide (Int-3a, 1.0 g, 4.16 mmol) and cesium carbonate (6.764 g, 20.81 mmol) in acetone (30 mL) was added 1-bromo-3-chloro-propane (6.05 mL, 61.19 mmol) dropwise. The reaction mixture was stirred at rt for 2 hrs. The mixture was filtered and concentrated. Then the mixture was diluted with EtOAc, washed with water and brine, dried over $Na_2SO_4$, concentrated. The crude product was purified by flash chromatography to give 3-chloropropyl)-2-nitro-prop-2-ynyl-benzenesulfonamide (Int-3b, 2.43 g, 7.67 mmol, 92.1% yield) as a yellow oil. LCMS calculated for $C_{12}H_{14}ClN_2O_4S$ (M+H)$^+$ m/z=317.0, found: 317.0.

Step 3. Synthesis of ethyl 5-(2-nitrophenyl)sulfonyl-4,6,7,8-tetrahydropyrazolo[1,5-a][1,4]diazepine-2-carboxylate (Int-3c). To a solution of (3-chloropropyl)-2-nitro-prop-2-ynyl-benzenesulfonamide (Int-3b, 10.0 g, 31.6 mmol) and ethyl 2-diazoacetate (5.4 g, 47.3 mmol) in chlorobenzene (80 mL) was added N,N-diisopropylethylamine (5.5 mL, 31.57 mmol). The reaction was heated at 140° C. for 1.5 hours, followed by the addition of cesium carbonate (12.3 g, 37.9 mmol). The reaction was heated at 140° C. for another 30 min. The solvent was removed, and the residue was extracted with EtOAc, washed with brine, dried over $Na_2SO_4$, concentrated. The crude product was purified by flash chromatography to afford ethyl 5-(2-nitrophenyl)sulfonyl-4,6,7,8-tetrahydropyrazolo[1,5-a][1,4]diazepine-2-carboxylate (Int-3c, 5.80 g, 14.7 mmol, 46.6% yield) as a yellow solid. LCMS calculated for $C_{16}H_{19}N_4O_6S$ (M+H)$^+$ m/z=395.1, found: 395.0.

Step 4. Synthesis of 5-(2-nitrophenyl)sulfonyl-4,6,7,8-tetrahydropyrazolo[1,5-a][1,4]diazepine-2-carboxylic acid (Int-3d). To a solution of ethyl 5-(2-nitrophenyl)sulfonyl-4,6,7,8-tetrahydropyrazolo[1,5-a][1,4]diazepine-2-carboxylate (Int-3c, 12.6 g, 31.95 mmol) in THF (100 mL) and methanol (25 mL) was added 1M LiOH (128 mL, 128 mmol) at 25° C. The mixture was heated at 55° C. for 2 h. The mixture was acidified with 1N HCl to pH=6 and the crude product was triturated by water and filtered to give 5-(2-nitrophenyl)sulfonyl-4,6,7,8-tetrahydropyrazolo[1,5-a][1,4]diazepine-2-carboxylic acid (Int-3d, 11.5 g, 31.1 mmol, 97.3% yield) as yellow solid. LCMS calculated for $C_{14}H_{15}N_4O_6S$ (M+H)$^+$ m/z=367.1, found: 367.0.

Step 5. Synthesis of N,N-dimethyl-5-(2-nitrophenyl)sulfonyl-4,6,7,8-tetrahydropyrazolo[1,5-a][1,4]diazepine-2-carboxamide (Int-3e). To a solution of 5-(2-nitrophenyl)sulfonyl-4,6,7,8-tetrahydropyrazolo[1,5-a][1,4]diazepine-2-carboxylic acid (Int-3d, 9.6 mg, 26.2 mmol), DIEA (18.3 mL, 104.8 mmol) and HATU (14.95 g, 39.3 mmol) in DMF (90 mL) was added 2M methylmethanamine in THF (20 mL, 39.3 mmol) at 30° C. The reaction was stirred at 30° C. for 2 h. The mixture was diluted with DCM (300×2 mL), washed with water (400 mL) and brine (400×2 mL), dried over $Na_2SO_4$ and concentrated to afford a crude product N,N-dimethyl-5-(2-nitrophenyl)sulfonyl-4,6,7,8-tetrahydropyrazolo[1,5-a][1,4]diazepine-2-carboxamide (Int-3e, 10.1 g, 24.4 mmol, 93.1% yield) as yellow oil. LCMS calculated for $C_{16}H_{20}N_5O_5S$ (M+H)$^+$ m/z=394.1, found: 394.2.

Step 6. Synthesis of 3-chloro-N,N-dimethyl-5-(2-nitrophenyl)sulfonyl-4,6,7,8-tetrahydropyrazolo[1,5-a][1,4]diazepine-2-carboxamide (Int-3f). To a solution of N,N-dimethyl-5-(2-nitrophenyl)sulfonyl-4,6,7,8-tetrahydropyrazolo

[1,5-a][1,4]diazepine-2-carboxamide (Int-1e, 10 g, 25.67 mmol) in DMF (100 mL) was added Chlorosuccinimide (3.428 g, 25.67 mmol) at 0° C. under argon. The mixture was heated at 45° C. for 1 h. The mixture was concentrated to afford a crude product. The crude product was triturated in water and filtered to afford 3-chloro-N,N-dimethyl-5-(2-nitrophenyl)sulfonyl-4,6,7,8-tetrahydropyrazolo[1,5-a][1,4]diazepine-2-carboxamide (Int-3f, 10.2 g, 23.4 mmol, 91.0% yield) as crude yellow solid. LCMS calculated for $C_{16}H_{17}ClN_5O_5S$ (M+H)⁺ m/z=428.1, found: 428.0.

Step 7. Synthesis of 3-chloro-N,N-dimethyl-5,6,7,8-tetrahydro-4H-pyrazolo[1,5-a][1,4]diazepine-2-carboxamide (Intermediate 3). To a solution of 3-chloro-N,N-dimethyl-5-(2-nitrophenyl)sulfonyl-4,6,7,8-tetrahydropyrazolo[1,5-a][1,4]diazepine-2-carboxamide (Int-1f, 10.2 g, 23.84 mmol), 4-methoxybenzenethiol (8.8 mL, 71.52 mmol) and $Cs_2CO_3$ (31067.73 mg, 95.36 mmol) in acetonitrile (100 mL). The mixture was stirred at 25° C. for 2 h. The mixture was concentrated, and the crude product was purified by column chromatography to afford 3-chloro-N,N-dimethyl-5,6,7,8-tetrahydro-4H-pyrazolo[1,5-a][1,4]diazepine-2-carboxamide (Intermediate 3, 3.2 g, 13.2 mmol, 55.3% yield) as yellow solid. LCMS calculated for $C_{10}H_{16}ClN_4O$ (M+H)⁺ m/z=243.1, found: 243.0

Intermediate 4. Synthesis of 2-amino-5,6-dihydrospiro[cyclopenta[b]thiophene-4,3'-pyrrolidine]-3-carbonitrile

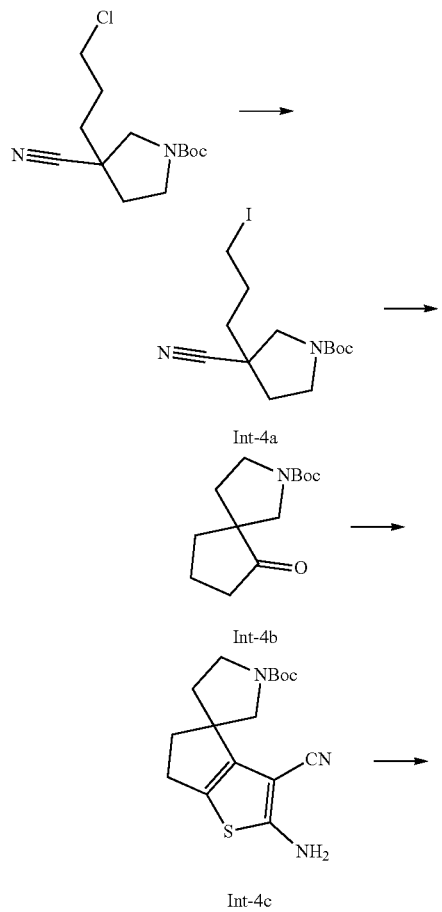

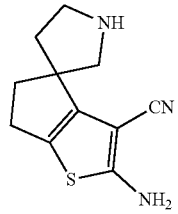

Intermediate 4

Step 1. Preparation of tert-butyl 3-cyano-3-(3-iodopropyl)pyrrolidine-1-carboxylate (Int-4a). To a solution of tert-butyl 3-(3-chloropropyl)-3-cyano-pyrrolidine-1-carboxylate (CN 112574085A, 1.1 g, 4.03 mmol) in Methyl ethyl ketone (10 mL) were added NaI (2605.93 mg, 20.16 mmol). The mixture was heated at 100° C. for 16 h. The mixture was extracted with EtOAc (40 mL), dried over $Na_2SO_4$, and concentrated. The crude product was purified by column chromatography to afford tert-butyl 3-cyano-3-(3-iodopropyl)pyrrolidine-1-carboxylate (Int-4a, 700 mg, 1.92 mmol, 47.66% yield) as colorless oil.

Step 2. Preparation of tert-butyl 9-oxo-2-azaspiro[4.4]nonane-2-carboxylate (Int-4b). 1.6M butyllithium in hexane (6.68 mL, 10.71 mmol) was added to THF (13 mL) at −68° C. The solution was stirred at −68° C. for 10 min, followed by the addition of a solution of tert-butyl 3-cyano-3-(3-iodopropyl)pyrrolidine-1-carboxylate (Int-4a, 1.3 g, 3.57 mmol) in THF (13 mL). The reaction was stirred at −68° C. for 3 h. The mixture was quenched with acetic acid (2 mL) at −40° C., extracted with tert-Butyl methyl ether (5×2 mL) and water (10 mL). The solution was washed with $NaHCO_3$ (10 mL), $Na_2S_2O_3$ (20% 10 mL) and brine (10 mL), dried over $Na_2SO_4$, and concentrated. The crude product was purified by flash chromatography (eluted with EtOAc in PE from 0% to 20%) to give tert-butyl 9-oxo-2-azaspiro[4.4]nonane-2-carboxylate (Int-4b, 0.60 g, 2.51 mmol, 70.24% yield) as colorless oil.

Step 3. Preparation of tert-butyl 2-amino-3-cyano-spiro[5,6-dihydrocyclopenta[b]thiophene-4,3'-pyrrolidine]-1'-carboxylate (Int-4c). To a solution of propanedinitrile (82.81 mg, 1.25 mmol) and tert-butyl 9-oxo-2-azaspiro[4.4]nonane-2-carboxylate (Int-4b, 200 mg, 0.84 mmol) in DMF (1.5 mL) was added L-Proline (96.22 mg, 0.84 mmol) and Sulfur (42.72 mg, 1.25 mmol) at 25° C. under $N_2$. The mixture was heated at 60° C. for 10 h. Then the mixture was cooled down and filtered to afford a crude solution. The crude product was purified by Prep-HPLC (eluted with $CH_3CN$ in $H_2O$ from 0% to 65%) to afford tert-butyl 2-amino-3-cyano-spiro[5,6-dihydrocyclopenta[b]thiophene-4,3'-pyrrolidine]-1'-carboxylate (Int-4c, 60 mg, 0.188 mmol, 22.48% yield) as yellow solid. LCMS calculated for $C_{16}H_{21}NaN_3O_2S$ (M+Na)⁺ m/z=342.1, found: 342.1.

Step 4. Preparation of 2-aminospiro[5,6-dihydrocyclopenta[b]thiophene-4,3'-pyrrolidine]-3-carbonitrile (Intermediate 4). A solution of tert-butyl 2-amino-3-cyano-spiro[5,6-dihydrocyclopenta[b]thiophene-4,3'-pyrrolidine]-1'-carboxylate (Int-4c, 50 mg, 0.16 mmol) in DCM (5 mL) was added TFA (1 mL, 13.07 mmol). Then the mixture was stirred at 25° C. for 1 h. The mixture was filtered to afford a crude solution. The crude product 2-aminospiro[5,6-dihydrocyclopenta[b]thiophene-4,3'-pyrrolidine]-3-carbonitrile; 2,2,2-trifluoroacetic acid (Intermediate 4, 35 mg, 0.105 mmol, 67.079% yield) was obtained as yellow solid. LCMS calculated for $C_{11}H_{14}N_3S$ (M+H)⁺ m/z=220.1, found: 220.1.

Intermediate 5. Synthesis of (3S,5R)-3-methylpiperidine-3,5-diol

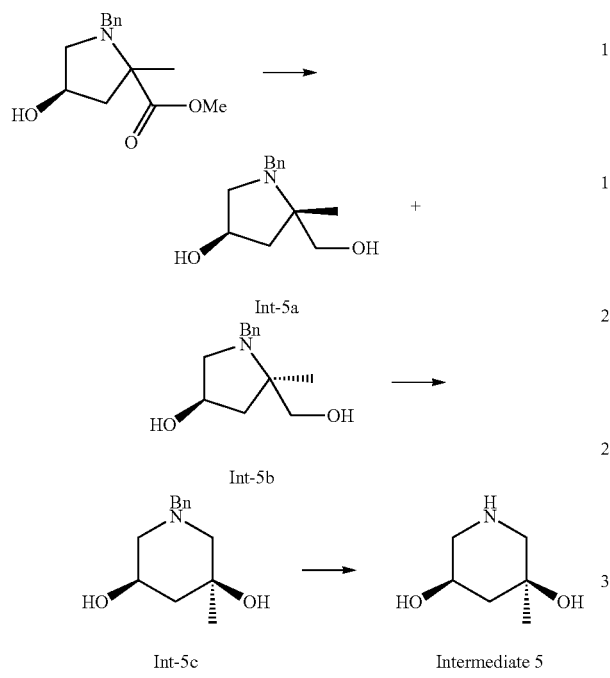

Step 1. Preparation of (3R,5R)-1-benzyl-5-(hydroxymethyl)-5-methyl-pyrrolidin-3-ol (Int-5b). A solution of methyl (4R)-1-benzoyl-4-hydroxy-2-methyl-pyrrolidine-2-carboxylate (3.5 g, 13.29 mmol) in THF (30 mL) was added dropwise to a suspension of LiAlH4 in THF (19 mL, 47.5 mmol) at 0° C. The reaction mixture was kept at 0° C. for 15 min, then was heated to 70° C. for 3 h. The reaction was cooled to 0° C. Water (0.02 mL), 3.75M NaOH solution (0.2 mL) and water (0.6 mL) were successively added. The reaction mixture was filtered through Celite, and the residue was washed with THF. The organic solvent was removed in vacuo. The residue was purified by Prep-HPLC with mobile phase: $H_2O$ (0.1% $NH_4HCO_3$)/MeCN to afford (3R,5S)-1-benzyl-5-(hydroxymethyl)-5-methyl-pyrrolidin-3-ol (Int-5a, 23 mg, 0.104 mmol, 9.12% yield), and (3R,5R)-1-benzyl-5-(hydroxymethyl)-5-methyl-pyrrolidin-3-ol (Int-5b, 145 mg, 0.655 mmol, 57.50% yield) as a colorless oil. LCMS calculated for $C_{13}H_{20}NO_2$ (M+H)⁺ m/z=222.15; found: 222.6.

Step 2. Synthesis of (3S,5R)-1-benzyl-3-methyl-piperidine-3,5-diol (Int-5c). To a solution of (3R,5R)-1-benzyl-5-(hydroxymethyl)-5-methyl-pyrrolidin-3-ol (Int-5b, 200 mg, 0.9 mmol) in THF (5 mL) was added trifluoroacetic anhydride (0.31 mL, 2.26 mmol) dropwise at RT. The mixture was stirred at 0° C. for 1.5 hrs. Then the reaction was cooled to −70° C. and TEA (1 mL, 7.23 mmol) was added dropwise. The reaction was stirred at −70° C. for 0.5 hour and then heated at 70° C. for 24 h. NaOH (8.68 mL, 21.69 mmol) was added, and the reaction was stirred at RT for 1 hour, and then concentrated. The residue was extracted with EtOAc. The organic layer was washed with brine, dried over $Na_2SO_4$ and concentrated. The residue was purified by column chromatography to give (3S,5R)-1-benzyl-3-methyl-piperidine-3,5-diol (Int-5c 163 mg, 0.737 mmol, 81.50% yield) as a yellow oil. LCMS calculated for $C_{13}H_{20}NO_2$ (M+H)⁺ m/z=222.15; found: 222.6.

Step 3. Synthesis of (3S,5R)-3-methylpiperidine-3,5-diol (Intermediate 5). The mixture of (3S,5R)-1-benzyl-3-methyl-piperidine-3,5-diol (Int-5c, 160 mg, 0.72 mmol) and Pd/C (70 mg, 0.06 mmol) in Ethanol (3 mL) was stirred at 30° C. for 16 h under $H_2$. The mixture was filtrated, and the solvent was removed in vacuo to give the (3S,5R)-3-methylpiperidine-3,5-diol as crude (Intermediate 5, 72 mg). LCMS calculated for $C_6H_{14}NO_2$ (M+H)⁺ m/z=132.1; found: 132.4.

Intermediate 6. Synthesis of 2-aminospiro[6H-thieno[2,3-c]thiophene-4,3'-azetidine]-3-carbonitrile; methanesulfonic acid

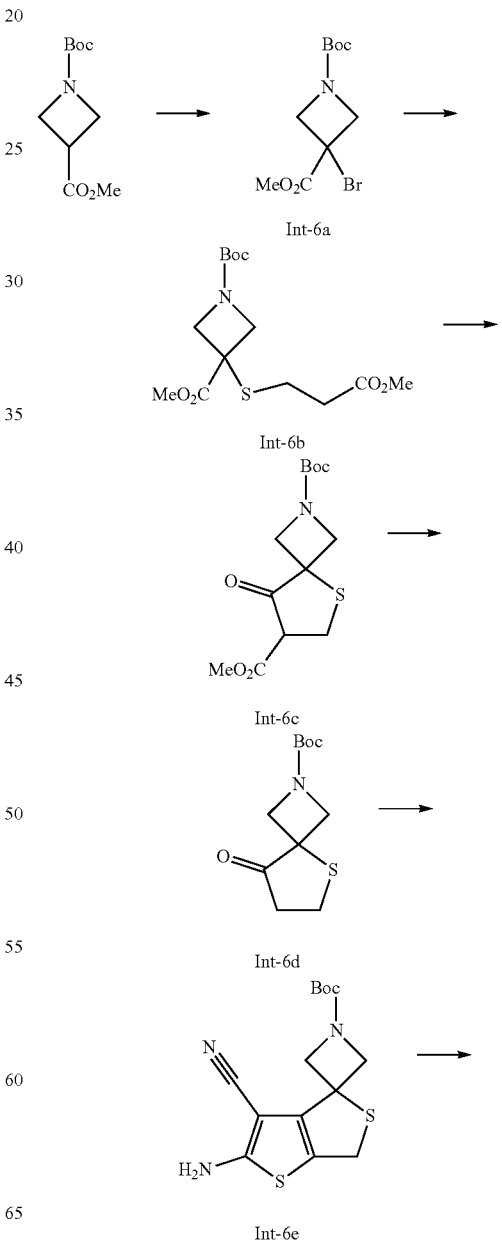

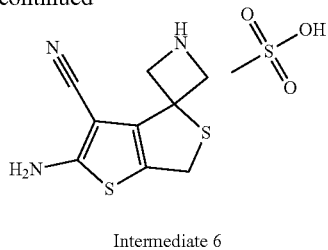

Intermediate 6

Step 1. Preparation of O1-tert-butyl O3-methyl 3-bromoazetidine-1,3-dicarboxylate (Int-6a). To a solution of [bis(trimethylsilyl)amino]lithium (2798.55 mg, 16.72 mmol) in THF (60 mL) was added dropwise O1-tert-butyl O3-methyl azetidine-1,3-dicarboxylate (3 g, 13.94 mmol) in THF (30 mL) at −70° C. under $N_2$. The mixture was stirred at RT for 15 min, followed by the dropwise addition of a solution of carbon tetrabromide (6933.03 mg, 20.91 mmol) in THF (30 mL). The resulting mixture was stirred at RT for 16 h. The reaction mixture was quenched with aq. $NH_4Cl$, and wash with aq. $NaHCO_3$, brine, concentrated. The residue was purified by column chromatography (0%-25% EtOAc/PE) to afford O1-tert-butyl O3-methyl 3-bromoazetidine-1,3-dicarboxylate (Int-6a, 2.30 g, 7.82 mmol, 56.10% yield) as a yellow oil. LCMS calculated for $C_{10}H_{17}BrNO_4$ $(M+H)^+$ m/z=295.0; found: 239.8 (M-tBu). $^1H$ NMR (400 MHz, $CDCl_3$) δ=4.65 (dd, J=10.3, 1.3 Hz, 2H), 4.30 (dd, J=10.3, 1.3 Hz, 2H), 3.85 (s, 3H), 1.45 (s, 9H).

Step 2. Preparation of O1-tert-butyl O3-methyl 3-(3-methoxy-3-oxo-propyl)sulfanylazetidine-1,3-dicarboxylate (Int-6b). To a solution of O1-tert-butyl O3-methyl 3-bromoazetidine-1,3-dicarboxylate (Int-6a, 1.5 g, 5.1 mmol) in DMF (16 mL) was added methyl 3-sulfanylpropanoate (1348.2 mg, 11.22 mmol) and $K_2CO_3$ (2819.27 mg, 20.4 mmol) at 20° C. under $N_2$. The mixture was stirred at RT overnight. Then the reaction mixture was quenched with water, extracted with EtOAc, wash with water and brine, concentrated. The residue was purified by column chromatography (0%-25% EtOAc in PE) to afford O1-tert-butyl O3-methyl 3-(3-methoxy-3-oxo-propyl)sulfanylazetidine-1,3-dicarboxylate (Int-6b, 1.60 g, 4.80 mmol, 94.11% yield) as a colorless oil. LCMS calculated for $C_{14}H_{24}NO_6S$ $(M+H)^+$ m/z=334.13; found: 233.9 (M-Boc).

Step 3. Preparation of O2-tert-butyl O7-methyl 8-oxo-5-thia-2-azaspiro[3.4]octane-2,7-dicarboxylate (Int-6c). To a solution of O1-tert-butyl O3-methyl 3-(3-methoxy-3-oxo-propyl)sulfanylazetidine-1,3-dicarboxylate (Int-6b, 200 mg, 3.6 mmol) in THF (20 mL) was added t-BuONa (691.78 mg, 7.2 mmol) by portions at 0° C. under $N_2$. The mixture was stirred at 0° C. for 2 h. The reaction mixture was diluted with water and adjusted pH to 5-6 by acetic acid. The mixture was extracted with EtOAc, wash with brine and dried over $Na_2SO_4$, concentrated. The residue was purified by flash chromatography (10%-30% EtOAc/PE) to afford O2-tert-butyl O7-methyl 8-oxo-5-thia-2-azaspiro[3.4]octane-2,7-dicarboxylate (Int-6c, 800 mg, 2.65 mmol, 73.75% yield) as light red oil. LCMS calculated for $C_{13}H_{20}NO_5S$ $(M+H)^+$ m/z=302.36; found: 246.1 (M-tBu). $^1H$ NMR (400 MHz, $CDCl_3$) δ=11.02 (s, 1H), 4.47 (d, J=9.9 Hz, 2H), 4.03 (d, J=9.8, 2H), 3.82 (s, 3H), 3.72 (s, 2H), 1.45 (s, 9H).

Step 4. Preparation of tert-butyl 8-oxo-5-thia-2-azaspiro[3.4]octane-2-carboxylate (Int-6d). To a solution of O2-tert-butyl O7-methyl 8-oxo-5-thia-2-azaspiro[3.4]octane-2,7-dicarboxylate (Int-6c, 800 mg, 2.65 mmol) in DMSO (12 mL) was added LiCl (225.06 mg, 5.31 mmol) and water (1.2 mL) at rt under $N_2$. then the mixture was heated at 160° C. for 1.5 h, The reaction mixture was diluted with water, extracted with EtOAc, washed with brine dried $Na_2SO_4$ and concentrated. The residue was purified by column chromatography (0%-30% EtOAc in PE) to afford tert-butyl 8-oxo-5-thia-2-azaspiro[3.4]octane-2-carboxylate (Int-6d, 480 mg, 1.97 mmol, 74.31% yield) as a colorless oil. LCMS calculated for $C_{11}H_{18}NO_3S$ $(M+H)^+$ m/z=244.32; found: 187.9 (M-tBu). $^1H$ NMR (400 MHz, $CDCl_3$) δ=4.27 (d, J=9.1, 2H), 3.93 (d, J=9.3, 2H), 2.97 (t, J=7.1, 2H), 2.70 (t, J=7.1, 2H), 1.44 (s, 9H).

Step 5. Preparation of tert-butyl 2-amino-3-cyano-spiro[6H-thieno[2,3-c]thiophene-4,3'-azetidine]-1'-carboxylate (Int-6e). A solution of tert-butyl 8-oxo-5-thia-2-azaspiro [3.4]octane-2-carboxylate (480 mg, 1.97 mmol), Sulfur (94.93 mg, 2.96 mmol), ammonium acetate (228.08 mg, 2.96 mmol) in Ethanol (7 mL) was added to propanedinitrile (195.48 mg, 2.96 mmol) at RT. Then the mixture was stirred at 60° C. for 1.5 h, then diluted with water and extracted with EtOAc. The combined extracts were dried, filtered, and concentrated. The crude product was purified by chromatography (20-30% EtOAc in PE) to afford tert-butyl 2-amino-3-cyano-spiro[6H-thieno[2,3-c]thiophene-4,3'-azetidine]-1'-carboxylate (Int-6e, 250 mg, 0.773 mmol, 39.18% yield) as yellow solid, the chromatographic column was washed with MeOH, and concentrated, the residue was wash with IPA, and filtered to afford an additional tert-butyl 2-amino-3-cyano-spiro[6H-thieno[2,3-c]thiophene-4,3'-azetidine]-1'-carboxylate, (Int-6e, 360 mg, 1.11 mmol, 56.42% yield) as yellow solid. LCMS calculated for $C_{14}H_{18}N_3O_2S_2$ $(M+H)^+$ m/z=324.08; found: 268.0 (M-tBu), 224.0 (M-Boc).

Step 6. Preparation of 2-aminospiro[6H-thieno[2,3-c]thiophene-4,3'-azetidine]-3-carbonitrile; methanesulfonic acid (Intermediate 6). A solution of tert-butyl 2-amino-3-cyano-spiro[6H-thieno[2,3-c]thiophene-4,3'-azetidine]-1'-carboxylate (Int-6e, 250 mg, 0.77 mmol) in IPA (2.5 mL) was added methanesulfonic acid (0.1 mL, 1.54 mmol) at RT. The mixture was heated at 60° C. for 8 h. The reaction was cooled down and was filtered. The solid was wash with IPA (2 mL×3) and was dried over in vacuum to afford 2-aminospiro[6H-thieno[2,3-c]thiophene-4,3'-azetidine]-3-carbonitrile; methanesulfonic acid (Intermediate 6,210 mg, 0.657 mmol, 85% yield) as grey solid. LCMS calculated for $C_9H_{10}N_3S_2$ $(M+H)^+$ m/z=224.31; found: 224.2.

Intermediate 7. Synthesis of 2-aminospiro[4a,5,5a,6-tetrahydrocyclopropa[f]benzothiophene-4,3'-azetidine]-3-carbonitrile

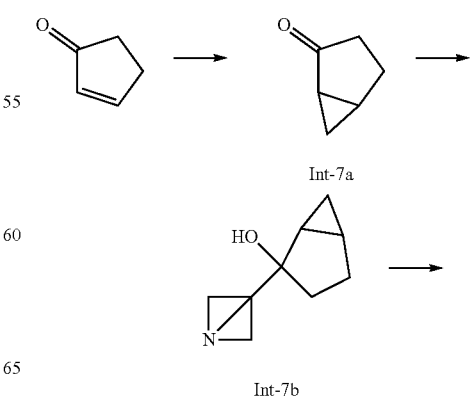

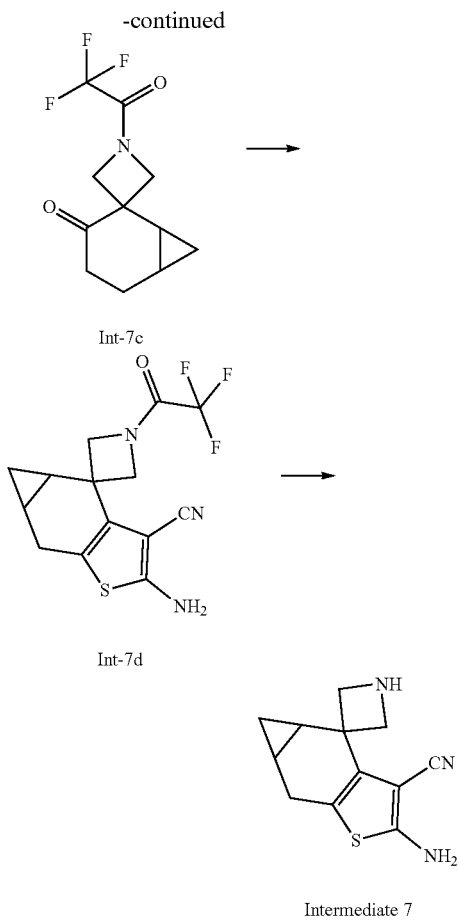

Step 1. Preparation of bicyclo[3.1.0]hexan-2-one (Int-7a). NaH (4872.11 mg, 121.8 mmol) in DMSO (50 mL) was added BLAH methane; iodide (26805.12 mg, 121.8 mmol) at 25° C. The mixture was stirred at 25° C. for 1 h, followed by the addition of cyclopent-2-en-1-one (10.2 mL, 121.8 mmol). The mixture was stirred at 25° C. for 30 mins, then it was heated at 50° C. for 2 h. The mixture was extracted with MTBE (100 ml), the organic phase was concentrated. The residue was purified by column chromatography (100% DCM) to give product bicyclo[3.1.0]hexan-2-one (2000 mg, 20.805 mmol, 17.08% yield) as a colorless oil. LCMS calculated for $C_6H_9O$ (M+H)$^+$ m/z=97.07, found: 97.2.

Step 2. Preparation of 2-(1-azabicyclo[1.1.0]butan-3-yl)bicyclo[3.1.0]hexan-2-ol (Int-7b). PhLi (3386.32 mg, 40.29 mmol) was added to a solution of 2,3-dibromopropan-1-amine; hydrobromide (4000 mg, 13.43 mmol) in THF (80 mL) at −78° C. The mixture was stirred at −78° C. for 2 h. The reaction was stirred at RT for 10 min before it was cooled down to −78° C. TMDEA (3901.82 mg, 33.58 mmol) was added followed by the dropwise addition of s-BuLi (6703.94 mg, 33.58 mmol). The resulting solution was stirred for 1 hour at −78° C., followed by the dropwise addition of bicyclo[3.1.0]hexan-2-one (Int-7a, 1291.16 mg, 13.43 mmol). The reaction was stirred for 1 hour at −78° C. Then the mixture was diluted with EtOAC (40 mL), washed with water (200 mL), dried over $Na_2SO_4$, concentrated to give the crude product 2-(1-azabicyclo[1.1.0]butan-3-yl)bicyclo[3.1.0]hexan-2-ol (Int-7b, 3500 mg) as yellow oil.

Step 3. Preparation of 1-(2,2,2-trifluoroacetyl)spiro[azetidine-3,2'-norcarane]-3'-one (Int-7c). A solution of 2-(1-azabicyclo[1.1.0]butan-3-yl)bicyclo[3.1.0]hexan-2-ol (Int-7b, 3500 mg, 23.15 mmol) in DCM (66 mL) was added TFAA (6.44 mL, 46.29 mmol) at −78° C. Then the mixture was stirred at −78° C. for 1 h. The solution was added EtOAc (20 ml), washed with aqueous $NaHCO_3$ until PH=7, the organic phase was concentrated. The residue was purified by silica gel chromatography (17%-50% EtOAc in PE). The product 1-(2,2,2-trifluoroacetyl)spiro[azetidine-3,2'-norcarane]-3'-one (Int-7c, 1000 mg, 4.045 mmol, 17.48% yield) was obtained as a brown oil. LCMS calculated for $C_{11}H_{13}F_3NO_2$ (M+H)$^+$ m/z=248.09, found: 248.1.

Step 4. Preparation of 2-amino-1'-(2,2,2-trifluoroacetyl) spiro[4a,5,5a,6-tetrahydrocyclopropa[f]benzothiophene-4,3'-azetidine]-3-carbonitrile (Int-7d). To a solution of 1-(2,2,2-trifluoroacetyl)spiro[azetidine-3,2'-norcarane]-3'-one (Int-7c, 180 mg, 0.73 mmol) in Ethanol (2 mL) was added $NH_4OAc$ (84.97 mg, 1.09 mmol), propanedinitrile (72.15 mg, 1.09 mmol) and S8 (34.95 mg, 1.09 mmol) at 25° C. The reaction stirred at 55° C. for 16 h.

The solvent was removed and the residue was purified by prep-HPLC (5%-95% $CH_3CN$ in $H_2O$) to give the product of 2-amino-1'-(2,2,2-trifluoroacetyl)spiro[4a,5,5a,6-tetrahydrocyclopropa[f]benzothiophene-4,3'-azetidine]-3-carbonitrile (Int-7d, 100 mg, 0.306 mmol, 41.96% yield) was obtained as a yellow solid. LCMS calculated for $C_{14}H_{13}F_3N_3OS$ (M+H)$^+$ m/z=328.07, found: 328.0.

Step 5. Preparation of 2-aminospiro[4a,5,5a,6-tetrahydrocyclopropa[f]benzothiophene-4,3'-azetidine]-3-carbonitrile (Intermediate 7). To a solution of 2-amino-1'-(2,2,2-trifluoroacetyl)spiro[4a,5,5a,6-tetrahydrocyclopropa[f]benzothiophene-4,3'-azetidine]-3-carbonitrile (Int-7d, 80 mg, 0.24 mmol) in Methanol (5 mL) was added $K_2CO_3$ (67.56 mg, 0.49 mmol) at 25° C. The reaction was heated at 80° C. for 1 h. The solvent was removed and the residue was purified by column chromatography (0%-20% MeOH in DCM) to give 2-aminospiro[4a,5,5a,6-tetrahydrocyclopropa[f]benzothiophene-4,3'-azetidine]-3-carbonitrile (Intermediate 7, 52 mg, 0.225 mmol, 91.98% yield) as a yellow solid. LCMS calculated for $C_{12}H_{14}N_3S$ (M+H)$^+$ m/z=232.09, found: 232.1.

Intermediate 8. Synthesis of 2-aminospiro[6,7-dihydro-5H-benzothiophene-4,3'-pyrrolidine]-3-carbonitrile; hydrochloride

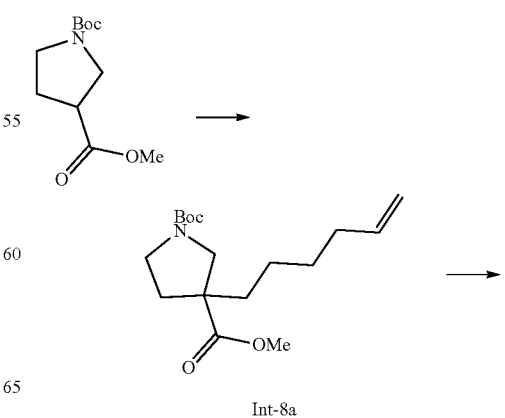

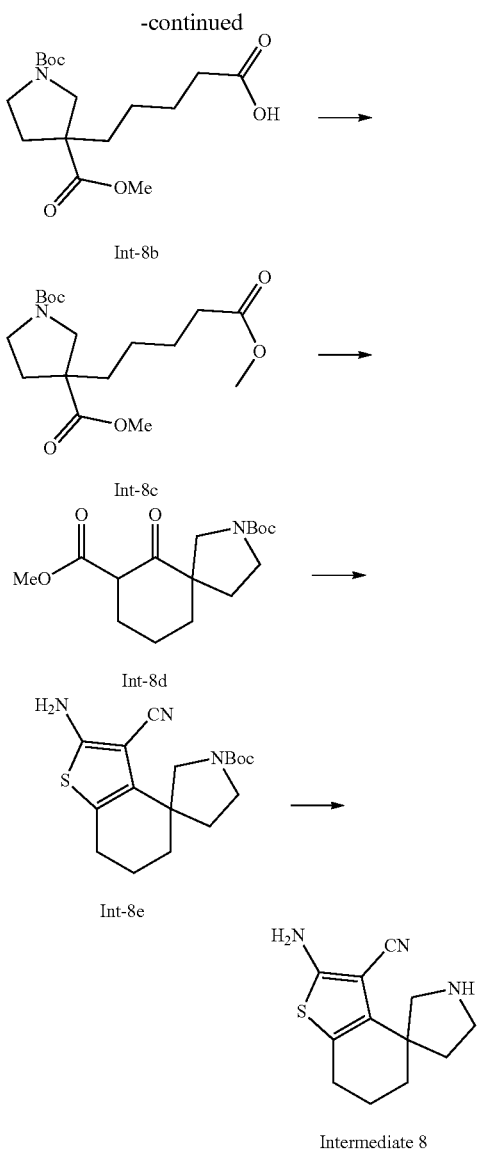

To a solution of O1-tert-butyl O3-methyl 3-hex-5-enylpyrrolidine-1,3-dicarboxylate (Int-8a, 12 g, 38.53 mmol) in EtOAc (60 mL), MeCN (60 mL) and water (108 mL) was added RuCl3 (799.26 mg, 3.85 mmol). Then the mixture was cooled to 0° C., and NaIO$_4$ (32967.44 mg, 154.13 mmol) was added at 0° C. The resulting mixture was stirred at 0° C. for 1.5 h. The reaction mixture was filtered, and then diluted with EtOAc. The organic layer was washed with brine, dried over Na$_2$SO$_4$, concentrated to afford crude 5-(1-tert-butoxycarbonyl-3-methoxycarbonyl-pyrrolidin-3-yl)pentanoic acid (Int-8b, 11 g) as a brown oil. LCMS calculated for $C_{16}H_{28}NO_6$ (M+H)$^+$ m/z=330.29; found: 230.2 (M-Boc).

Step 3. Preparation of O1-tert-butyl O3-methyl 3-(5-methoxy-5-oxo-pentyl)pyrrolidine-1,3-dicarboxylate (Int-8c). To a solution of 5-(1-tert-butoxycarbonyl-3-methoxycarbonyl-pyrrolidin-3-yl)pentanoic acid (Int-8b, 12 g, 36.43 mmol) in DMF (120 mL) were added K$_2$CO$_3$ (7.55 g, 54.65 mmol) and methyl iodide (3.42 mL, 54.65 mmol) at 0° C. Then the mixture was stirred at RT for 40 h. The reaction mixture was quenched with ice water, and then extracted with EtOAc. The organic layer was washed with water and brine, dried over Na$_2$SO$_4$, concentrated and purified by flash column chromatography (0%-40% EtOAc in PE) to afford O1-tert-butyl O3-methyl 3-(5-methoxy-5-oxo-pentyl)pyrrolidine-1,3-dicarboxylate (Int-8c, 9 g, 26.21 mmol, 71.94% yield) as a colorless oil. LCMS calculated for $C_{17}H_{30}NO_6$ (M+H)$^+$ m/z=344.21; found: 244.2 (M-Boc). $^1$H NMR (400 MHz, CDCl$_3$) δ=3.81 (d, J=11.2, 1H), 3.71 (s, 3H), 3.66 (s, 3H), 3.46-3.28 (m, 2H), 3.16 (d, J=11.2, 1H), 2.38-2.26 (m, 3H), 1.81-1.55 (m, 5H), 1.46 (s, 9H), 1.34-1.15 (m, 2H).

Step 4. Preparation of O2-tert-butyl O7-methyl 6-oxo-2-azaspiro[4.5]decane-2,7-dicarboxylate (Int-8d). To a solution of O1-tert-butyl O3-methyl 3-(5-methoxy-5-oxo-pentyl)pyrrolidine-1,3-dicarboxylate (Int-8c, 500 mg, 1.46 mmol) in THF (5 mL) was added [bis(trimethylsilyl)amino] potassium (2.18 mL, 2.18 mmol) at −70° C. dropwise. Then the mixture was stirred at −70° C. for 1.5 h. The reaction mixture was quenched with NH$_4$Cl aqueous, and then extracted with EtOAc (60 mL×3). The organic layer was washed with water (50 mL×3) and brine (50 mL), dried over Na$_2$SO$_4$, concentrated and to afford crude O2-tert-butyl O7-methyl 6-oxo-2-azaspiro[4.5]decane-2,7-dicarboxylate (Int-8d, 510 mg) as a colorless oil. LCMS calculated for $C_{16}H_{26}NO_5$ (M+H)$^+$ m/z=312.18; found: 256.2 (M-tBu), 334.3 (M+Na)+.

Step 5. Preparation of tert-butyl 6-oxo-2-azaspiro[4.5]decane-2-carboxylate (Int-8e)

To the solution of O2-tert-butyl O7-methyl 6-oxo-2-azaspiro[4.5]decane-2,7-dicarboxylate (Int-8d, 16.5 g, 52.99 mmol) in Methanol (120 mL), 50% aqueous KOH (129.41 g, 1153.2 mmol) solution (120 mL) was added. The resulting mixture was refluxed for 2 h. The reaction mixture was evaporated, diluted with EtOAc (30 mL), washed with brine (2×20 mL), dried over anhydrous Na$_2$SO$_4$, filtered, and concentrated in vacuo. The residue was purified by column chromatography (PE:EtOAc=3:1) to afford tert-butyl 6-oxo-2-azaspiro[4.5]decane-2-carboxylate (Int-8e, 7.00 g, 27.6 mmol, 52.14% yield) as colorless oil. LCMS calculated for $C_{14}H_{24}NO_3$ (M+H)$^+$ m/z=254.34; found: 198.2 (M-tBu), 276.3 (M+Na)+. $^1$H NMR (400 MHz, CDCl$_3$) δ=3.75 (d, J=11.2, 1H), 3.49-3.27 (m, 2H), 3.17 (d, J=11.1, 1H), 2.54-2.38 (m, 2H), 2.37-2.23 (m, 1H), 1.97-1.65 (m, 7H), 1.45 (s, 9H).

Step 6. Preparation of tert-butyl 2-amino-3-cyano-spiro [6,7-dihydro-5H-benzothiophene-4,3'-pyrrolidine]-1'-carboxylate (8f). A solution of tert-butyl 6-oxo-2-azaspiro[4.5]

decane-2-carboxylate (Int-8e 1 g, 3.95 mmol), Sulfur (379.88 mg, 11.84 mmol), NH₄OAc (460.65 mg, 5.92 mmol) in Ethanol (12 mL) was added to propanedinitrile (391.13 mg, 5.92 mmol) at RT. Then the mixture was stirred at 55° C. for 16 h. Diluted with water and extracted with EtOAc. The combined extracts were dried, filtered and concentrated and the crude product was purified by chromatography (20-30% EtOAc in hexane) to afford tert-butyl 2-amino-3-cyano-spiro[6,7-dihydro-5H-benzothiophene-4,3'-pyrrolidine]-1'-carboxylate (Int-8f, 1.00 g, 3.00 mmol, 75.98% yield) as light-yellow solid. LCMS calculated for $C_{17}H_{24}N_3O_2S$ (M+H)⁺ m/z=334.45; found: 278.1 (M-tBu), 234.0 (M-Boc). ¹H NMR (400 MHz, DMSO) δ=7.01 (s, 2H), 3.57-3.40 (m, 2H), 3.39-3.32 (m, 1H), 3.24 (t, J=11.6, 1H), 2.48-2.30 (m, 3H), 1.81-1.53 (m, 5H), 1.40 (d, J=6.0, 9H).

Step 7. Preparation of 2-aminospiro[6,7-dihydro-5H-benzothiophene-4,3'-pyrrolidine]-3-carbonitrile; hydrochloride (Intermediate 8). To a solution of tert-butyl 2-amino-3-cyano-spiro[6,7-dihydro-5H-benzothiophene-4,3'-pyrrolidine]-1'-carboxylate (Int-8f 1 g, 3 mmol) in DCM (15 mL) was HCL/dioxane (3 mL, 12 mmol) portion wise at 18° C. under N₂. Then the mixture was stirred at 18° C. for 16 h. Then concentrated to afford crude 2-aminospiro[6,7-dihydro-5H-benzothiophene-4,3'-pyrrolidine]-3-carbonitrile; hydrochloride (Intermediate 8, 870 mg) as a solid. LCMS calculated for $C_{12}H_{16}N_3S$ (M+H)⁺ m/z=234.33; found: 234.1. ¹H NMR (400 MHz, DMSO) δ=9.54 (d, J=90.1, 2H), 7.11 (s, 1H), 3.48-3.34 (m, 2H), 3.30-3.11 (m, 2H), 2.47-2.36 (m, 3H), 1.99-1.84 (m, 2H), 1.79-1.53 (m, 3H).

Intermediate 9. Synthesis of 2-amino-5-fluoro-spiro[5,6-dihydrocyclopenta[b]thiophene-4,3'-azetidine]-3-carbonitrile; hydrochloride

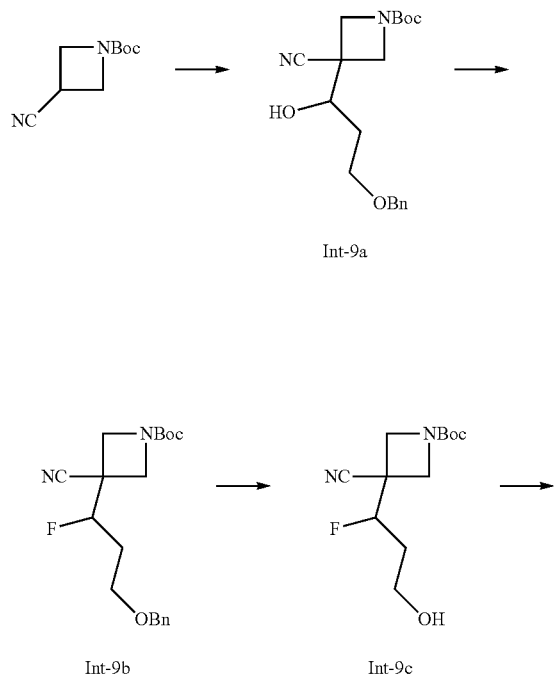

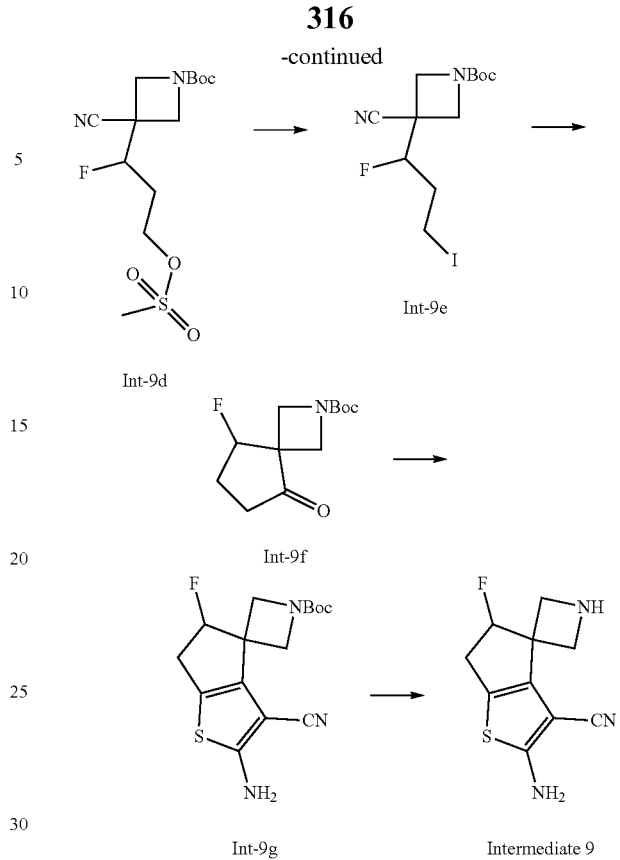

Step 1. Preparation of tert-butyl 3-(3-benzyloxy-1-hydroxy-propyl)-3-cyano-azetidine-1-carboxylate (Int-9a). To a solution of tert-butyl 3-cyanoazetidine-1-carboxylate (500 mg, 2.74 mmol) in THF (5 mL) was added LDA (1.92 mL, 3.84 mmol) portion wise at −70° C. under N₂. Then the mixture was stirred at −70° C. for 1 h, and 3-benzyloxy-propanal (630.78 mg, 3.84 mmol) was added at −70° C. The resulting mixture was stirred at −70° C. for 30 min and warmed to RT for 1 h. The reaction mixture was quenched with saturated NH₄Cl solution, and then extracted with EtOAc. The organic layer was washed with water and brine, dried over Na₂SO4, concentrated and purified by flash column chromatography (0%-40% EtOAc in PE) to afford tert-butyl 3-(3-benzyloxy-1-hydroxy-propyl)-3-cyano-azetidine-1-carboxylate (Int-9a, 450 mg, 1.299 mmol, 47.34% yield) as a colorless oil. LCMS calculated for $C_{19}H_{27}N_2O_4$ (M+H)⁺ m/z=347.20; found: 247.3 (M-Boc), 291.2 (M-tBu).

Step 2. Preparation of tert-butyl 3-(3-benzyloxy-1-fluoro-propyl)-3-cyano-azetidine-1-carboxylate (Int-9b). To a solution of tert-butyl 3-(3-benzyloxy-1-hydroxy-propyl)-3-cyano-azetidine-1-carboxylate (100 mg, 0.29 mmol) in DCM (2 mL) was added diethylaminosulfur Trifluoride (0.08 mL, 0.58 mmol) portion wise at −70° C. under N₂. Then the mixture was stirred at −70° C. for 30 min, then warmed to RT for 4 h. The reaction mixture was quenched with ice water, and then extracted with EtOAc. The organic layer was washed with water and brine, dried over Na₂SO₄, concentrated and purified by flash column chromatography (0%-40% EtOAc in PE) to afford tert-butyl 3-(3-benzyloxy-1-fluoro-propyl)-3-cyano-azetidine-1-carboxylate (72 mg, 0.2067 mmol, 71.589% yield) as a colorless oil. LCMS calculated for $C_{19}H_{26}FN_2O_3$(M+H)⁺ m/z=349.19; found: 249.3 (M-Boc).

Step 3. Preparation of tert-butyl 3-cyano-3-(1-fluoro-3-hydroxy-propyl)azetidine-1-carboxylate (Int-9c). The mixture of tert-butyl 3-(3-benzyloxy-1-fluoro-propyl)-3-cyano-azetidine-1-carboxylate (2000 mg, 5.74 mmol), 2,3-Dichloro-5,6-dicyano-1,4-benzoquinone (5212.25 mg, 22.96 mmol) in DCM (20 mL) and Water (3 mL) was stirred at 45° C. for 20 h. The resulting mixture was filtered. The filtrate was treated with saturated NaHCO$_3$, extracted with DCM. The organic layer was washed with brine, dried over Na$_2$SO$_4$, concentrated and purified by flash column chromatography (0%-60% EtOAc in PE) to afford tert-butyl 3-cyano-3-(1-fluoro-3-hydroxy-propyl)azetidine-1-carboxylate (Int-9c, 1090 mg, 4.220 mmol, 73.52% yield) as a brown oil. LCMS calculated for C$_{12}$H$_{20}$FN$_2$O$_3$(M+H)$^+$ m/z=259.15; found: 203.2 (M-tBu).

Step 4. Preparation of tert-butyl 3-cyano-3-(1-fluoro-3-methylsulfonyloxy-propyl)azetidine-1-carboxylate (Int-9d). To a solution of tert-butyl 3-cyano-3-(1-fluoro-3-hydroxy-propyl)azetidine-1-carboxylate (Int-9c, 100 mg, 0.39 mmol) in DCM (2 mL) were added nethanesulfonyl chloride (0.05 mL, 0.58 mmol) and triethylamine (0.11 mL, 0.77 mmol) at 0° C. Then the mixture was stirred at RT for 1 h. The resulting mixture was quenched with water, and then extracted with EtOAc. The organic layer was washed with brine, dried over Na$_2$SO$_4$, concentrated to afford tert-butyl 3-cyano-3-(1-fluoro-3-methylsulfonyloxy-propyl)azetidine-1-carboxylate (Int-9d, 130 mg, 0.387 mmol, 99.82% yield) as a green oil. LCMS calculated for C$_{13}$H$_{22}$FN$_2$O$_5$S (M+H)$^+$ m/z=337.13; found: 281.0 (M-tBu)

Step 5. Preparation of tert-butyl 3-cyano-3-(1-fluoro-3-iodo-propyl)azetidine-1-carboxylate (Int-9e). The mixture of tert-butyl 3-cyano-3-(1-fluoro-3-methylsulfonyloxy-propyl)azetidine-1-carboxylate (130 mg, 0.39 mmol) and NaI (173.78 mg, 1.16 mmol) in Acetone (2 mL) was stirred at RT overnight. The reaction mixture was stirred at 60° C. for 5 h. The mixture was cooled to RT and the solvent was removed under reduced pressure. The mixture was diluted with water, extracted with EtOAc, washed with brine, dried over Na$_2$SO$_4$, concentrated and purified by flash column chromatography (0%-70% EtOAc/PE) to afford tert-butyl 3-cyano-3-(1-fluoro-3-iodo-propyl)azetidine-1-carboxylate (103 mg, 0.280 mmol, 72.386% yield) as a colorless oil. LCMS calculated for C$_{12}$H$_{19}$FIN$_2$O$_2$ (M+H)$^+$ m/z=369.05; found: 313.0 (M-tBu).

Step 6. Preparation of tert-butyl 5-fluoro-8-oxo-2-azaspiro[3.4]octane-2-carboxylate (Int-9f). To a solution of tert-butyl 3-cyano-3-(1-fluoro-3-iodo-propyl)azetidine-1-carboxylate (1450 mg, 3.94 mmol) in THF (15 mL) was added butyllithium (504.56 mg, 7.88 mmol) at −78° C. under N$_2$. Then the mixture was stirred at −78° C. for 30 min. HOAc (0.68 mL, 11.81 mmol) was added drop wise at −70° C. The resulting mixture was diluted with EtOAc and water was added. The organic layer was washed with brine, dried over Na$_2$SO$_4$, concentrated and purified by flash column chromatography (0%-70% EtOAc/PE) to afford tert-butyl 5-fluoro-8-oxo-2-azaspiro[3.4]octane-2-carboxylate (655 mg, 2.693 mmol, 68.37% yield). LCMS calculated for C$_{12}$H$_{19}$FNO$_3$ (M+H)$^+$ m/z=244.14; found: 188.0 (M-tBu).

Step 7. Preparation of tert-butyl 2-amino-3-cyano-5-fluoro-spiro[5,6-dihydrocyclopenta[b]thiophene-4,3'-azetidine]-1'-carboxylate (Int-9g). To a solution of tert-butyl 5-fluoro-8-oxo-2-azaspiro[3.4]octane-2-carboxylate (600 mg, 2.47 mmol), Sulfur (118.68 mg, 3.7 mmol), NH$_4$OAc (287.83 mg, 3.7 mmol) in Ethanol (12 mL) was added propanedinitrile (244.4 mg, 3.7 mmol) at RT. Then the mixture was stirred at 30° C. for 3 h. Diluted with water and extracted with EtOAc. The combined extracts were dried, filtered and concentrated and the crude product was purified by flash column chromatography (0% to 50% EtOAc/PE) to afford tert-butyl 2-amino-3-cyano-5-fluoro-spiro[5,6-dihydrocyclopenta[b]thiophene-4,3'-azetidine]-1'-carboxylate (407 mg, 1.26 mmol, 51.03% yield) as light yellow solid. LCMS calculated for C$_{15}$H$_{19}$FN$_3$O$_2$S (M+H)$^+$ m/z=324.12; found: 224.0 (M-Boc), 268.0 (M-tBu).

Step 8. Preparation of 2-amino-5-fluoro-spiro[5,6-dihydrocyclopenta[b]thiophene-4,3'-azetidine]-3-carbonitrile; hydrochloride (Intermediate 9). To a solution of tert-butyl 2-amino-3-cyano-5-fluoro-spiro[5,6-dihydrocyclopenta[b]thiophene-4,3'-azetidine]-1'-carboxylate (360 mg, 1.11 mmol) in DCM (15 mL) was added HCl in Dioxane (3 mL, 12 mmol). Then the mixture was stirred at rt overnight. The resulting mixture was diluted with DCM, concentrated to afford 2-amino-5-fluoro-spiro[5,6-dihydrocyclopenta[b]thiophene-4,3'-azetidine]-3-carbonitrile; hydrochloride (Intermediate 9, 322 mg, 1.1034 mmol, 99.117% yield) as a brown solid. LCMS calculated for C$_{10}$H$_{11}$FN$_3$S (M+H)$^+$ m/z=224.07; found: 224.2.

Intermediate 10. Synthesis of 3-[1-(methylamino)ethyl]pyridin-2-amine

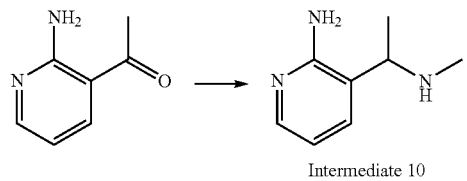

Intermediate 10

To a stirred solution of 1-(2-amino-3-pyridyl)ethanone (1985.56 mg, 14.58 mmol) in THF (30 mL). Methylamine in CH$_3$OH (3019.79 mg, 29.17 mmol) was added at 0° C. followed by the drop wise addition of titanium(IV)isopropoxide (12.95 mL, 43.75 mmol). The reaction mixture was stirred overnight at room temperature. The reaction mixture was concentrated, added Methanol (45 mL), and cooled to 0° C. NaBH$_4$ (1079.19 mg, 29.17 mmol) was added and was stirred for 3 h at room temperature. The reaction was quenched with ice, filtered and solids were washed thoroughly with methanol. The filtrate was evaporated to dryness under reduced pressure and the residue was purified by automated flash chromatography using 20% MeOH in DCM to obtain 3-[1-(methylamino)ethyl]pyridin-2-amine (Intermediate 10, 1500 mg, 9.92 mmol, 68.021% yield) as white solid. LCMS calculated for C$_8$H$_{14}$N$_3$(M+H)$^+$ m/z=152.12; found: 152.2.

Chiral Synthesis of Intermediate 10A.

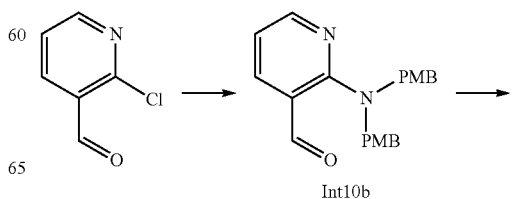

Int10b

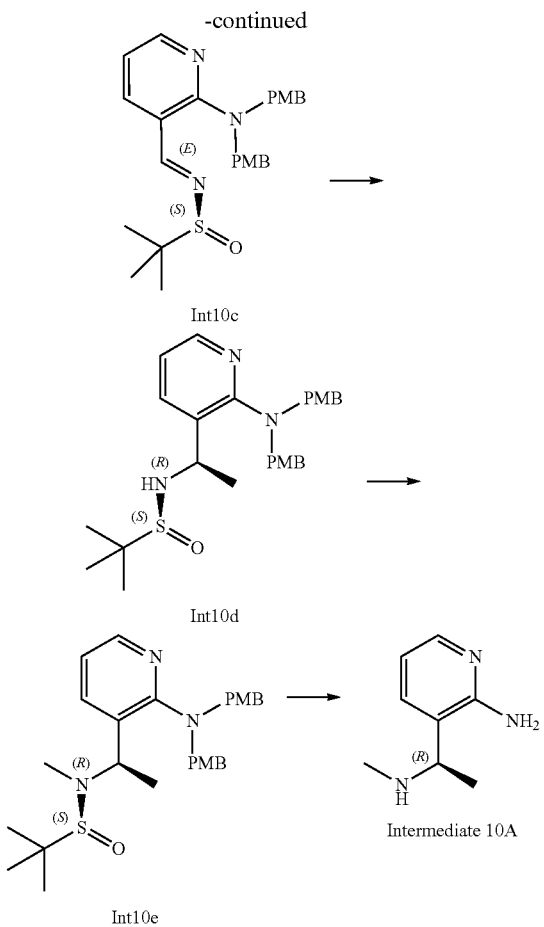

Step 1. Synthesis of 2-(bis(4-methoxybenzyl)amino)nicotinaldehyde (Int10b)

The mixture of 2-chloropyridine-3-carbaldehyde (23.0 g, 162.48 mmol), 1-(4-methoxyphenyl)-N-[(4-methoxyphenyl)methyl]methanamine (50171.72 mg, 194.97 mmol) and Potassium carbonate (44843.18 mg, 324.95 mmol) in 1,4-Dioxane (320 mL)/Water (210 mL) was heated to 110° C. for 6 days. The reaction mixture was cooled to rt and extracted with EtOAc (100 mL×3). The organic layer was washed with saturated brine (50 ml), dried (MgSO$_4$) and concentrated in vacuo to dryness. The crude product was then purified by using FC (eluting 9-20% EtOAc in PE). The desired fractions were concentrated to dryness in vacuo to afford 2-[bis[(4-methoxyphenyl)methyl]amino]pyridine-3-carbaldehyde (47.90 g, 132 mmol, 81.34% yield) as yellow oil. LCMS calculated for C$_{22}$H$_{23}$N$_2$O$_3$ (M+H)$^+$ m/z=363.4; found: 363.3.

Step 2. Synthesis of (S,E)-N-((2-(bis(4-methoxybenzyl)amino)pyridin-3-yl)methylene)-2-methylpropane-2-sulfinamide (Int10c)

To the solution of (S)-2-methylpropane-2-sulfinamide (32037.3 mg, 264.33 mmol) and 2-[bis[(4-methoxyphenyl)methyl]amino]pyridine-3-carbaldehyde (47.9 g, 132.17 mmol) in THF (300 mL) was added Titanium(IV) ethanolate (60297.27 mg, 264.33 mmol) at rt under N$_2$. The mixture was stirred at 20° C. overnight. TLC showed the reaction was completed. Ice water, celite and MgSO$_4$ was added to the reaction, filtered and purified using FC (eluant with EtOAc in PE 0 to 30%) to give the product (NE,S)—N-[[2-[bis[(4-methoxyphenyl)methyl]amino]-3-pyridyl]methylene]-2-methyl-propane-2-sulfinamide, 61.00 g, 131 mmol, 99.13% yield as a yellow oil. LCMS calculated for C$_{26}$H$_{32}$N$_3$O$_3$S (M+H)$^+$ m/z=466.6; found: 466.2.

Step 3. Synthesis of (S)—N—((R)-1-(2-(bis(4-methoxybenzyl)amino)pyridin-3-yl)ethyl)-2-methyl-propane-2-sulfinamide (Int10d)

To the mixture of (NE,S)—N-[[2-[bis[(4-methoxyphenyl)methyl]amino]-3-pyridyl]methylene]-2-methyl-propane-2-sulfinamide (61.0 g, 131.01 mmol) in DCM (500 mL) was added Bromo(methyl)magnesium in THF (87.34 mL, 3M 262.02 mmol) at −70° C. dropwise under N$_2$. The mixture was stirred at −40° C. for 4 h and then allowed to warm to rt and stirred for 16 h. It was quenched by the addition of NH$_4$Cl solution and extracted with EtOAc. The organic layer was washed with saturated brine followed by the drying over Na$_2$SO$_4$. The solvent was removed in vacuo and the residue was purified using FC (eluant with EtOAc in PE 0 to 60%) to give the product (S)—N-[(1R)-1-[2-[bis[(4-methoxyphenyl)methyl]amino]-3-pyridyl]ethyl]-2-methyl-propane-2-sulfinamide, 45.70 g, 92.4 mmol, 70.54% yield. LCMS calculated for C$_{27}$H$_{36}$N$_3$O$_3$S (M+H)$^+$ m/z=482.2; found: 482.2.

Step 4. Synthesis of (S)—N—((R)-1-(2-(bis(4-methoxybenzyl)amino)pyridin-3-yl)ethyl)-N,2-dimethylpropane-2-sulfinamide (Int10e)

To the mixture of (S)—N-[(1R)-1-[2-[bis[(4-methoxyphenyl)methyl]amino]-3-pyridyl]ethyl]-2-methyl-propane-2-sulfinamide (46.92 g, 94.88 mmol) in DMF (500 mL) was added NaH (60%, 7590.57 mg, 189.76 mmol) at 0° C. under N$_2$. The mixture was stirred at the same temperature for 1 h and then MeI (11.82 mL, 189.76 mmol) was added. The whole mixture was stirred at 0° C. for 1 h. The reaction was quenched by the addition of H$_2$O and then extracted with EtOAc (300 mL*3). The organic layer was washed with H$_2$O, followed by saturated brine. It was then dried over Na$_2$SO$_4$ and concentrated in vacuo to give the crude product. It was purified using FC (eluant with EtOAc in PE 0 to 60%) to give the product (S)—N-[(1R)-1-[2-[bis[(4-methoxyphenyl)methyl]amino]-3-pyridyl]ethyl]-N,2-dimethyl-propane-2-sulfinamide (43.80 g, 88.4 mmol, 93.13% yield) as a color-less oil. LCMS calculated for C$_{28}$H$_{38}$N$_3$O$_3$S (M+H)$^+$ m/z=496.68; found: 496.2.

Step 5. Synthesis of (R)-3-(1-(methylamino)ethyl)pyridin-2-amine (Intermediate 10A)

To the mixture of (S)—N-[(1R)-1-[2-[bis[(4-methoxyphenyl)methyl]amino]-3-pyridyl]ethyl]-N,2-dimethyl-propane-2-sulfinamide (43.8 g, 88.36 mmol) in TFA (120 mL, 1568.15 mmol) was added Trifluoromethanesulfonic acid (1800.92 mg, 12.0 mmol) at rt under N$_2$. The mixture was stirred at 35° C. for 24 h. TFA was removed in vacuo, aq Na$_2$CO$_3$ was added to the mixture to adjust the pH to 9-10. It was extracted with DCM/MeOH (10/1, 200 mL*3). The combined extracts were dried over Na$_2$SO$_4$ and concentrated in vacuo to give the crude product. It was purified using FC (eluant with MeOH in DCM 0 to 10%, 0.1% NH$_4$OH) to give the product 3-[(1R)-1-(methylamino)ethyl]pyridin-2- amine (11.10 g, 73.4 mmol, 83.07% yield) as a red solid. LCMS calculated for $C_8H_{14}N_3(M+H)^+$ m/z=152.12; found: 152.0.

Intermediate 11. 2-amino-5,5-difluoro-spiro[6H-cyclopenta[b]thiophene-4,3'-azetidine]-3-carbonitrile

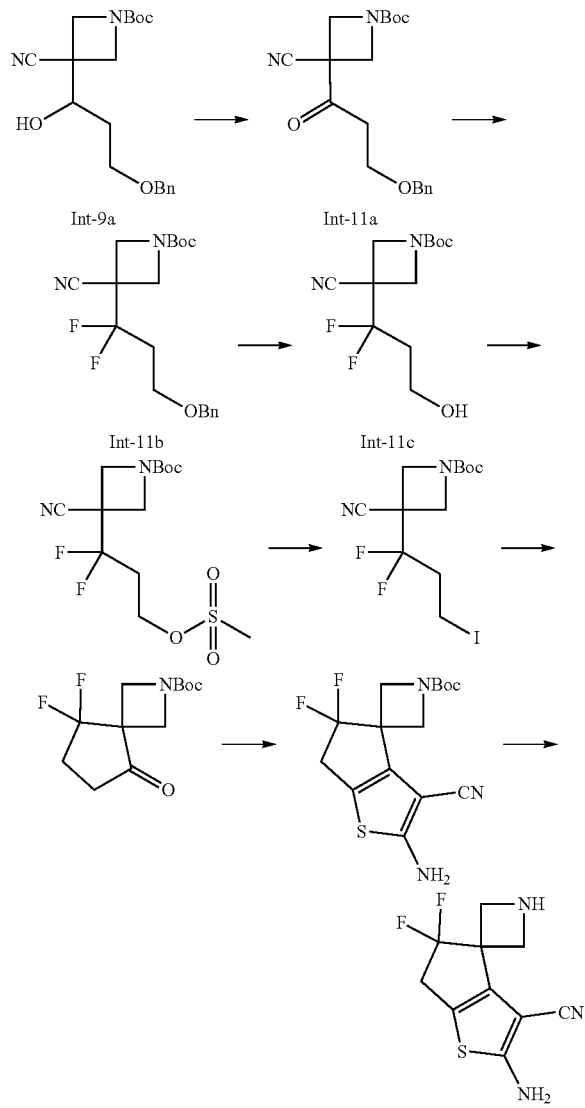

Step 1. Preparation of tert-butyl 3-(3-benzyloxypropanoyl)-3-cyano-azetidine-1-carboxylate (Int-11a)

To a solution of tert-butyl 3-(3-benzyloxy-1-hydroxy-propyl)-3-cyano-azetidine-1-carboxylate (Int-9a, 5000 mg, 14.43 mmol) in DCM (50 mL) was added DMP (9182.64 mg, 21.65 mmol) at 0° C. Then the mixture was stirred at RT for 3 h. The reaction mixture was diluted with ice water, and then extracted with DCM. The organic layer was washed with brine, dried over $Na_2SO_4$, concentrated and purified by flash column chromatography (0%-35% EtOAc/PE) to afford tert-butyl 3-(3-benzyloxypropanoyl)-3-cyano-azetidine-1-carboxylate (4000 mg, 11.61 mmol, 80.47% yield) as a colorless oil. LCMS calculated for $C_{19}H_{25}N_2O_4$ $(M+H)^+$ m/z=345.18; found: 245.2 (M-Boc).

Step 2. Preparation of tert-butyl 3-(3-benzyloxy-1,1-difluoro-propyl)-3-cyano-azetidine-1-carboxylate (Int-11b)

To a solution of tert-butyl 3-(3-benzyloxypropanoyl)-3-cyano-azetidine-1-carboxylate (Int-11a, 4000 mg, 11.61 mmol) in DCM (35 mL) was added Diethylaminosulfur Trifluoride (10.74 mL, 81.3 mmol) portion wise at −70° C. under $N_2$. Then the mixture was stirred at −70° C. for 10 min, then warmed to RT for 16 h. The reaction mixture was quenched with $NaHCO_3$ aqueous at 0° C., and then extracted with EtOAc. The organic layer was washed with brine, dried over $Na_2SO_4$, concentrated and purified by flash column chromatography (0%-30% EtOAc/PE) to afford tert-butyl 3-(3-benzyloxy-1,1-difluoro-propyl)-3-cyano-azetidine-1-carboxylate (Int-11b, 1820 mg, 4.97 mmol, 42.77% yield). LCMS calculated for C19H25F2N2O3 $(M+H)+$ m/z=367.19; found: 267.2 (M-Boc).

Step 3. Preparation of tert-butyl 3-cyano-3-(1,1-difluoro-3-hydroxy-propyl)azetidine-1-carboxylate (Int-11c)

The mixture of tert-butyl 3-(3-benzyloxy-1,1-difluoro-propyl)-3-cyano-azetidine-1-carboxylate (Int-11b, 1700 mg, 4.64 mmol), 2,3-Dichloro-5,6-Dicyano-1,4-Benzoquinone (5266.1 mg, 23.2 mmol) in DCM (15 mL) and Water (2 mL) was stirred at 50° C. for 20 h. The resulting mixture was filtered. The filtrate was treated with saturated $NaHCO_3$, extracted with DCM. The organic layer was washed with brine, dried over $Na_2SO_4$, concentrated and purified by flash column chromatography (0%-50% EtOAc/PE) to afford tert-butyl 3-cyano-3-(1,1-difluoro-3-hydroxy-propyl)azetidine-1-carboxylate (Int-11c, 630 mg, 2.280 mmol, 49.15% yield) as a light-brown oil. LCMS calculated for $C_{12}H_{19}F_2N_2O_3(M+H)^+$ m/z=277.14; found: 221.2 (M-tBu).

Step 4. Preparation of tert-butyl 3-cyano-3-(1,1-difluoro-3-methylsulfonyloxy-propyl)azetidine-1-carboxylate (Int-11d)

To a solution of tert-butyl 3-cyano-3-(1,1-difluoro-3-hydroxy-propyl)azetidine-1-carboxylate (Int-11c, 820 mg, 2.97 mmol) in DCM (1.5 mL) were added methanesulfonyl chloride (0.35 mL, 4.45 mmol) and DIEA (1150.75 mg, 8.9 mmol) at 0° C. Then the mixture was stirred at RT for 1 h. The resulting mixture was quenched with water, and then extracted with EtOAc. The organic layer was washed with brine, dried over $Na_2SO_4$, concentrated to afford tert-butyl 3-cyano-3-(1,1-difluoro-3-methylsulfonyloxy-propyl)azetidine-1-carboxylate (Int-11d, 1050 mg, 2.96 mmol, 99.83% yield) as a colorless oil. LCMS calculated for $C_{13}H_{21}F_2N_2O_5S$ $(M+H)^+$ m/z=355.12; found: 255.2 (M-Boc).

Step 5. Preparation of tert-butyl 3-cyano-3-(1,1-difluoro-3-iodo-propyl)azetidine-1-carboxylate (Int-11e)

The mixture of tert-butyl 3-cyano-3-(1,1-difluoro-3-methylsulfonyloxy-propyl)azetidine-1-carboxylate (Int-11d, 1050 mg, 2.96 mmol) and NaI (2220.62 mg, 14.82 mmol) in Acetone (12 mL) was stirred at 60° C. for 20 h. The mixture was cooled to room temperature and the solvent was removed under reduced pressure. The mixture was diluted with water, extracted with EtOAc, washed with brine, dried over Na$_2$SO$_4$, concentrated and purified by flash column chromatography (0%-70% EtOAc/PE) to afford tert-butyl 3-cyano-3-(1,1-difluoro-3-iodo-propyl)azetidine-1-carboxylate (Int-11e, 1000 mg, 2.59 mmol, 87.39% yield) as a light yellow oil. LCMS calculated for C$_{12}$H$_{18}$F$_2$IN$_2$O$_2$ (M+H)$^+$ m/z=387.04; found: 331.0 (M-tBu)

Step 6. Preparation of tert-butyl 8,8-difluoro-5-oxo-2-azaspiro[3.4]octane-2-carboxylate (Int-11f)

To a solution of tert-butyl 3-cyano-3-(1,1-difluoro-3-iodo-propyl)azetidine-1-carboxylate (Int-11e, 200 mg, 0.52 mmol) in THF (3 mL) was added butyllithium (66.35 mg, 1.04 mmol) at −70° C. under N$_2$. Then the mixture was stirred at −70° C. for 1.5 h. HOAc (0.09 mL, 1.55 mmol) was added dropwise at −70° C. The resulting mixture was diluted with EtOAc and water was added. The organic layer was washed with brine, dried over Na$_2$SO$_4$, concentrated and purified by flash column chromatography (0%-60% EtOAc/PE) to afford tert-butyl 8,8-difluoro-5-oxo-2-azaspiro[3.4]octane-2-carboxylate (Int-11f, 125 mg, 0.478 mmol, 92.38% yield) as a colorless oil. LCMS calculated for C$_{12}$H$_{18}$F$_2$NO$_3$ (M+H)$^+$ m/z=262.13; found: 206.2 (M-tBu).

Step 7. Preparation of tert-butyl 2-amino-3-cyano-5,5-difluoro-spiro[6H-cyclopenta[b]thiophene-4,3'-azetidine]-1'-carboxylate (Int-11g)

To a solution of tert-butyl 8,8-difluoro-5-oxo-2-azaspiro[3.4]octane-2-carboxylate (Int-11f, 460 mg, 1.76 mmol), Sulfur (112.96 mg, 3.52 mmol), NH$_4$OAc (205.47 mg, 2.64 mmol) in Ethanol (7 mL) was added propanedinitrile (174.46 mg, 2.64 mmol) at RT. Then the mixture was stirred at 40° C. for 3 h. Diluted with water and extracted with EtOAc. The combined extracts were dried, filtered and concentrated and the crude product was purified by flash column chromatography (0%-50% EtOAc/PE) to afford tert-butyl 2-amino-3-cyano-5,5-difluoro-spiro[6H-cyclopenta[b]thiophene-4,3'-azetidine]-1'-carboxylate, (Int-11g, 70 mg, 0.205 mmol, 11.65% yield) as light yellow solid. LCMS calculated for C$_{15}$H$_{18}$F$_2$N$_3$O$_2$S (M+H)$^+$ m/z=342.11; found: 286.1 (M-tBu), 364.2 (M+Na)$^+$ Step 8. Preparation of 2-amino-5,5-difluoro-spiro[6H-cyclopenta[b]thiophene-4,3'-azetidine]-3-carbonitrile (Intermediate 11)

To a solution of tert-butyl 2-amino-3-cyano-5,5-difluoro-spiro[6H-cyclopenta[b]thiophene-4,3'-azetidine]-1'-carboxylate (Int-11g, 20 mg, 0.06 mmol) in 1,4-Dioxane (0.5 mL) was added HCl in Dioxane (0.5 mL, 2 mmol). Then the mixture was stirred at RT for 1 h. The resulting mixture was concentrated to afford crude 2-amino-5,5-difluoro-spiro[6H-cyclopenta[b]thiophene-4,3'-azetidine]-3-carbonitrile (13 mg, 0.054 mmol, 91.97% yield) as a colorless oil. LCMS calculated for C$_{10}$H$_{10}$F$_2$N$_3$S (M+H)$^+$ m/z=242.06; found: 242.1.

Intermediate 12. Synthesis of 2-[(2-amino-3-pyridyl)methylamino]ethanol

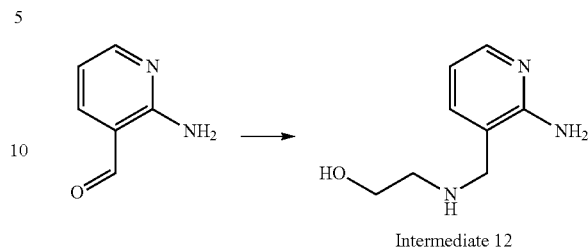

Intermediate 12

A solution of 2-aminopyridine-3-carbaldehyde (1000 mg, 8.19 mmol) and Ethanolamine (0.5 mL, 8.19 mmol) in Toluene (10 mL) was stirred at 130° C. for 10 h. The solvent was concentrated under vacuum. The mixture was dissolved in Methanol (15 mL), NaBH$_4$ (619.55 mg, 16.38 mmol) was added and stirred at 0° C. for 2 h. The reaction was quenched with water, filtrated and concentrated. The residue was purified by Prep-HPLC on a C18 column (5 uM, 50×150 mm) with mobile phase: H$_2$O (0.1% NH$_4$HCO$_3$)/ACN at flow rate: 40 mL/min to afford 2-[(2-amino-3-pyridyl)methylamino]ethanol (Intermediate 12, mol, 58.43% yield) as a yellow oil. LCMS calculated for C$_8$H$_{14}$N$_3$O (M+H)$^+$ m/z=168.1; found: 168.2.

Intermediate 13. Synthesis of 3-[1-(2-amino-3-pyridyl)ethylamino]propanenitrile

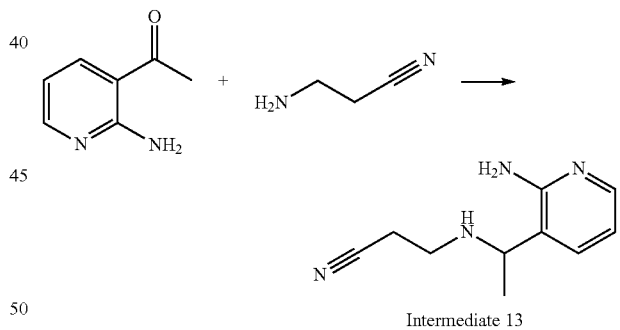

Intermediate 13

A solution of 1-(2-amino-3-pyridyl)ethanone (1000 mg, 7.34 mmol), 3-aminopropanenitrile (1029.6 mg, 14.69 mmol) and Titanium ethoxide (10437.75 mg, 36.72 mmol) in Methanol (10 mL) was stirred at 90° C. for 16 h in a closed environment. Then added NaBH$_4$ (555.71 mg, 14.69 mmol) to the mixture in batches at 0° C. and stirred at RT for 2 h. The solvent was concentrated under vacuum. The reaction was quenched with water, filtrated, concentrated and purified by flash column chromatography (silica gel, eluting with PE/EA) and concentrated to afford 3-[1-(2-amino-3-pyridyl)ethylamino]propanenitrile, (Intermediate 13, 860 mg, 4.52 mmol, 61.55% yield as a colorless oil. LCMS calculated for C$_{10}$H$_{15}$N$_4$(M+H)$^+$ m/z=191.3, found: 191.1.

Intermediate 14. Synthesis of 3-(1-aminoethyl)pyridin-2-amine

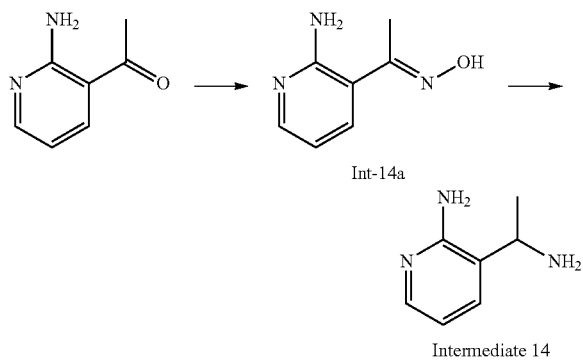

Step 1. Preparation of 1-(2-amino-3-pyridyl)ethanone oxime (Int-14a). To a solution of 1-(2-amino-3-pyridyl)ethanone (1000 mg, 7.34 mmol) in pyridine (18 mL) was added hydroxylamine hydrochloride (765.59 mg, 11.02 mmol). The mixture was stirred at 80° C. for 2 h. Then reaction mixture was concentrated under reduced pressure to give the crude of 1-(2-amino-3-pyridyl)ethanone oxime (1110 mg, 7.34 mmol, 99.97% yield) as a yellow solid for next step without further purification. LCMS calculated for $C_7H_{10}N_3O$ $(M+H)^+$ m/z=152.2; found: 152.2.

Step 2. Preparation of 3-(1-aminoethyl)pyridin-2-amine (Intermediate 14). To a mixture of 1-(2-amino-3-pyridyl)ethanone oxime (996 mg, 6.59 mmol) and zinc (1723.05 mg, 26.35 mmol) at RT was slowly added conc. hydrochloric acid (16.8 mL, 201.6 mmol) with vigorous stirring. The mixture was heated at 90° C. overnight. The reaction mixture was concentrated under reduced pressure to remove solvent. The residue was diluted with water (20 mL), then basified with 2N NaOH at room temperature to pH=9-10, and then extracted with EtOAc (20 mL*3). The combined organic layers were washed with brine (20 mL), dried over $Na_2SO_4$, filtered and concentrated. The residue was purified by Prep-HPLC on a C18 column (5 uM, 50×150 mm) with mobile phase: $H_2O$ (0.1% $NH_4HCO_3$)/ACN at flow rate: 40 mL/min to afford 3-(1-aminoethyl)pyridin-2-amine (276 mg, 2.01 mmol, 30.54% yield) as a white solid. LCMS calculated for $C_7H_{12}N_3(M+H)^+$ m/z=138.1, found: 138.2.

Intermediate 15. Synthesis of 3-[(1R)-1-(2,2-difluoroethylamino)ethyl]pyridin-2-amine

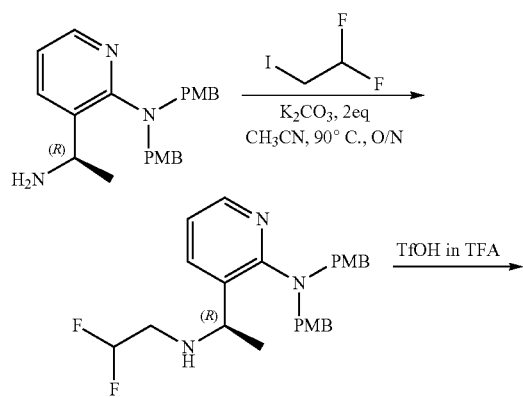

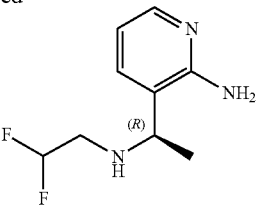

Step 1. Synthesis of (R)-3-(1-((2,2-difluoroethyl)amino)ethyl)-N,N-bis(4-methoxybenzyl)pyridin-2-amine. The mixture of 3-[(1R)-1-aminoethyl]-N,N-bis[(4-methoxyphenyl)methyl]pyridin-2-amine (1800 mg, 4.77 mmol), 1,1-difluoro-2-iodo-ethane (915.27 mg, 4.77 mmol) and $K_2CO_3$ (1.32 g, 9.54 mmol) in MeCN (10 mL) was stirred at 90° C. under $N_2$ for 16 h. The reaction was concentrated to dryness and the residue was diluted with EtOAc (30 mL) and washed with water (2×10 mL) followed by saturated brine (10 mL). The organic layer was dried ($MgSO_4$) and concentration to dryness. The residue was then purified using FCC (eluting with MeOH in DCM 0 to 2%). The desired fractions were concentrated to dryness to afford the product 3-[(1R)-1-(2,2-difluoroethylamino)ethyl]-N,N-bis[(4-methoxyphenyl)methyl]pyridin-2-amine (1.36 g, 3.08 mmol, 61.20% yield) as yellow oil. LCMS: calculated for $C_{25}H_{30}F_2N_3O_2$ $(M+H)^+$ m/z=442.5; found: 442.5.

Step 2. Synthesis of (R)-3-(1-((2,2-difluoroethyl)amino)ethyl)pyridin-2-amine. To the mixture of 3-[(1R)-1-(2,2-difluoroethylamino)ethyl]-N,N-bis[(4-methoxyphenyl)methyl]pyridin-2-amine (1.36 g, 3.08 mmol) in TFA (3.0 mL, 39.2 mmol) was added TfOH (0.3 mL, 3.39 mmol) at rt under $N_2$. The mixture was stirred at 35° C. for 2 h. TFA was removed in vavuo. The residue was basified using aq $NaHCO_3$ and $Na_2CO_3$, and then extracted with EtOAc (2×30 mL). The combined extracts were dried ($Na_2SO_4$) and concentrated in vacuo to give the residue. It was purified using FCC (eluant with MeOH in DCM 0 to 5%). The desired fractions were concentrated to dryness to afford the product 3-[(1R)-1-(2,2-difluoroethylamino)ethyl]pyridin-2-amine (479 mg, 2.38 mmol, 77.28% yield) as a yellow oil. LCMS: calculated for $C_9H_{14}F_2N_3$ $(M+H)^+$ m/z=202.2; found: 202.8.

Intermediate 16. Synthesis of 8-aminospiro[9-thiatricyclo[4.3.0.0²,⁴]nona-1(6),7-diene-5,3'-azetidine]-7-carbonitrile; methanesulfonic acid & 2-aminospiro[6,7-dihydro-5H-benzothiophene-4,3'-azetidine]-3-carbonitrile; methanesulfonic acid

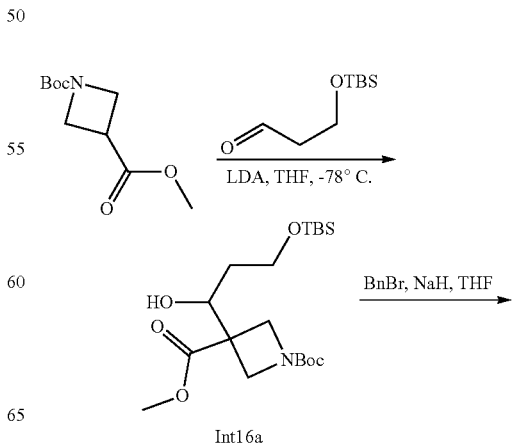

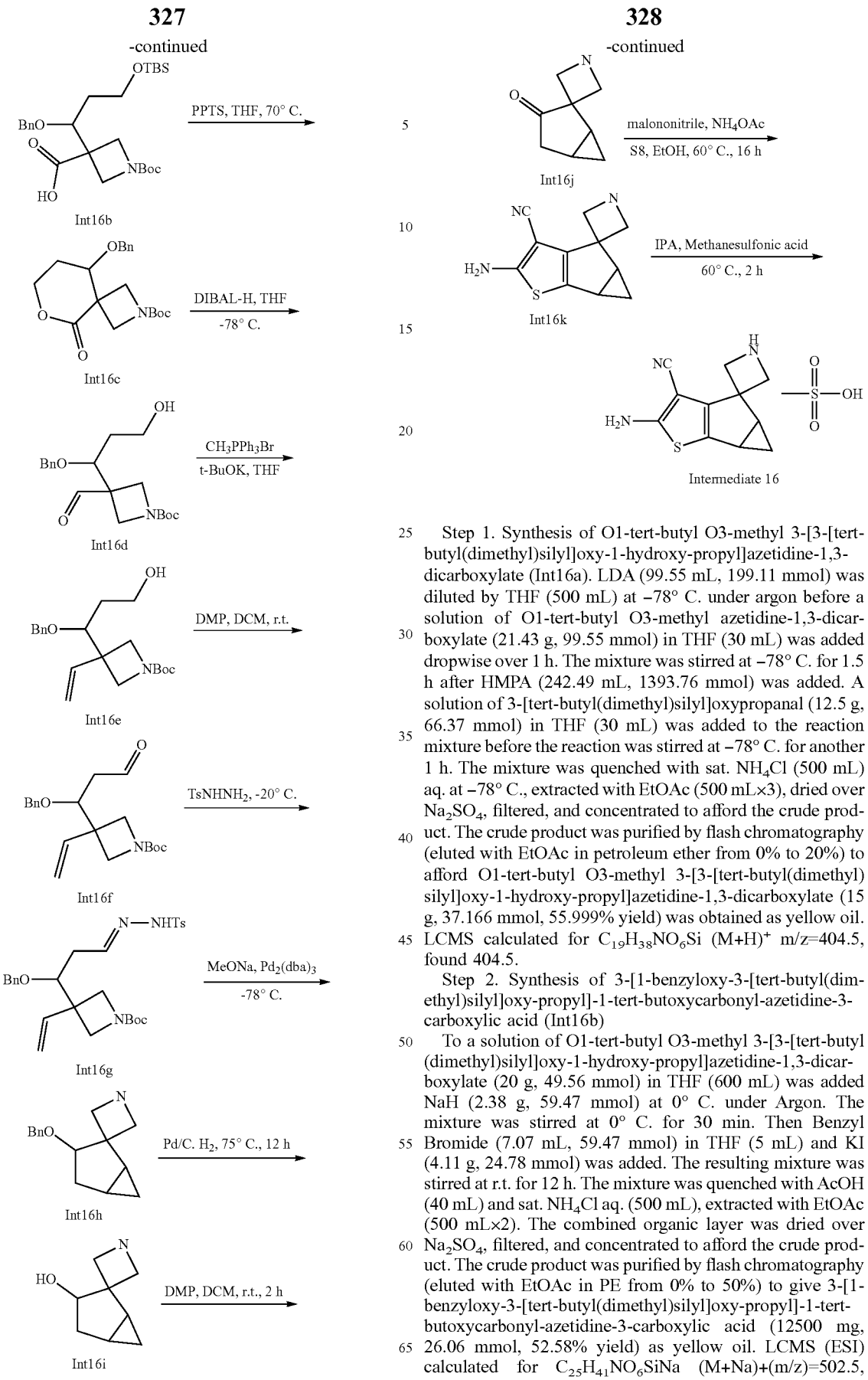

Step 1. Synthesis of O1-tert-butyl O3-methyl 3-[3-[tert-butyl(dimethyl)silyl]oxy-1-hydroxy-propyl]azetidine-1,3-dicarboxylate (Int16a). LDA (99.55 mL, 199.11 mmol) was diluted by THF (500 mL) at −78° C. under argon before a solution of O1-tert-butyl O3-methyl azetidine-1,3-dicarboxylate (21.43 g, 99.55 mmol) in THF (30 mL) was added dropwise over 1 h. The mixture was stirred at −78° C. for 1.5 h after HMPA (242.49 mL, 1393.76 mmol) was added. A solution of 3-[tert-butyl(dimethyl)silyl]oxypropanal (12.5 g, 66.37 mmol) in THF (30 mL) was added to the reaction mixture before the reaction was stirred at −78° C. for another 1 h. The mixture was quenched with sat. NH$_4$Cl (500 mL) aq. at −78° C., extracted with EtOAc (500 mL×3), dried over Na$_2$SO$_4$, filtered, and concentrated to afford the crude product. The crude product was purified by flash chromatography (eluted with EtOAc in petroleum ether from 0% to 20%) to afford O1-tert-butyl O3-methyl 3-[3-[tert-butyl(dimethyl)silyl]oxy-1-hydroxy-propyl]azetidine-1,3-dicarboxylate (15 g, 37.166 mmol, 55.999% yield) was obtained as yellow oil. LCMS calculated for C$_{19}$H$_{38}$NO$_6$Si (M+H)$^+$ m/z=404.5, found 404.5.

Step 2. Synthesis of 3-[1-benzyloxy-3-[tert-butyl(dimethyl)silyl]oxy-propyl]-1-tert-butoxycarbonyl-azetidine-3-carboxylic acid (Int16b)

To a solution of O1-tert-butyl O3-methyl 3-[3-[tert-butyl(dimethyl)silyl]oxy-1-hydroxy-propyl]azetidine-1,3-dicarboxylate (20 g, 49.56 mmol) in THF (600 mL) was added NaH (2.38 g, 59.47 mmol) at 0° C. under Argon. The mixture was stirred at 0° C. for 30 min. Then Benzyl Bromide (7.07 mL, 59.47 mmol) in THF (5 mL) and KI (4.11 g, 24.78 mmol) was added. The resulting mixture was stirred at r.t. for 12 h. The mixture was quenched with AcOH (40 mL) and sat. NH$_4$Cl aq. (500 mL), extracted with EtOAc (500 mL×2). The combined organic layer was dried over Na$_2$SO$_4$, filtered, and concentrated to afford the crude product. The crude product was purified by flash chromatography (eluted with EtOAc in PE from 0% to 50%) to give 3-[1-benzyloxy-3-[tert-butyl(dimethyl)silyl]oxy-propyl]-1-tert-butoxycarbonyl-azetidine-3-carboxylic acid (12500 mg, 26.06 mmol, 52.58% yield) as yellow oil. LCMS (ESI) calculated for C$_{25}$H$_{41}$NO$_6$SiNa (M+Na)+(m/z)=502.5, found: 502.5.

Step 3. Synthesis of tert-butyl 9-benzyloxy-5-oxo-6-oxa-2-azaspiro[3.5]nonane-2-carboxylate (Int16c). To a solution of 3-[1-benzyloxy-3-[tert-butyl(dimethyl)silyl]oxy-propyl]-1-tert-butoxycarbonyl-azetidine-3-carboxylic acid (20 g, 41.69 mmol) in THF (600 mL) was added PPTS (5.24 g, 20.85 mmol) at r.t. under Ar. The resulting mixture was stirred at 70° C. for 16 h. Upon cocomplete, the mixture was cooled down to r.t., and quenched with $H_2O$ (600 mL), extracted with EtOAc (500 mL×3). The combined organic layer was washed with brine (300 mL), dried over $Na_2SO_4$, filtered, and concentrated to afford the crude product. The crude product was purified by silica gel chromatography (eluted with EtOAc in PE from 0% to 50%) to give tert-butyl 9-benzyloxy-5-oxo-6-oxa-2-azaspiro[3.5]nonane-2-carboxylate (13 g, 37.42 mmol, 89.75% yield) as yellow oil. LCMS (ESI) calculated for $C_{19}H_{26}NO_5$ $(M+H)^+$ m/z=348.2, found: 348.2.

Step 4. Synthesis of tert-butyl 3-(1-benzyloxy-3-hydroxy-propyl)-3-formyl-azetidine-1-carboxylate (Int16d). To a solution of tert-butyl 9-benzyloxy-5-oxo-6-oxa-2-azaspiro[3.5]nonane-2-carboxylate (23 g, 66.2 mmol) in DCM (800 mL) was added DIBAL-H in hexane (99.31 mL, 99.31 mmol) at −78° C. under Ar. The resulting mixture was stirred at −78° C. for 3 h. Upon completion, the mixture was warmed to r.t., and quenched with sat. $NH_4Cl$ aq. (1 L), extracted with EtOAc (800 mL×2). The combined organic layer was dried over $Na_2SO_4$, filtered, and concentrated to afford tert-butyl 3-(1-benzyloxy-3-hydroxy-propyl)-3-formyl-azetidine-1-carboxylate (20 g, 57.24 mmol) as yellow oil. The crude product was used directly for the next step. LCMS (ESI) calculated for $C_{19}H_{28}NO_5$ $(M+H)^+$ m/z=350.3, found: 350.3.

Step 5. Synthesis of tert-butyl 3-(1-benzyloxy-3-hydroxy-propyl)-3-vinyl-azetidine-1-carboxylate (Int16e). To a solution of Methyltriphenylphosphonium Bromide (40.89 g, 114.47 mmol) in THF (600 mL) was added t-BuOK in THF (114.47 mL, 114.47 mmol) at 0° C. under Ar. The resulting mixture was stirred at r.t. for 0.5 h. Then tert-butyl 3-(1-benzyloxy-3-hydroxy-propyl)-3-formyl-azetidine-1-carboxylate (20 g, 57.24 mmol) was added. The mixture was stirred for another 1 h. Upon completion, the mixture was quenched with sat. $NH_4Cl$ aq. (1000 mL), extracted with EtOAc (800 mL×2). The combined organic layer was dried over $Na_2SO_4$, filtered, and concentrated to afford the crude product. The crude product was purified by silica gel chromatography (eluted with EtOAc in petroleum ether from 0% to 50%) to give tert-butyl 3-(1-benzyloxy-3-hydroxy-propyl)-3-vinyl-azetidine-1-carboxylate (9.8 g, 28.20 mmol, 49.27% yield) as yellow oil. LCMS (ESI) calculated for $C_{20}H_{30}NO_4$ $(M+H)^+$ m/z=348.3, found: 348.3.

Step 6. Synthesis of tert-butyl 3-(1-benzyloxy-3-oxo-propyl)-3-vinyl-azetidine-1-carboxylate (Int16f). To a solution of tert-butyl 3-(1-benzyloxy-3-hydroxy-propyl)-3-vinyl-azetidine-1-carboxylate (11 g, 31.66 mmol) in DCM (350 mL) was added DMP (26.86 g, 63.32 mmol). The resulting mixture was stirred at r.t. for 6 h. Then, the reaction mixture was diluted with $CH_2Cl_2$ (500 mL) and added 1.3 M NaOH (200 mL). After the mixture was stirred for 10 min, the organic layer was separated, and washed with water (200 mL) and brine (200 mL), dried over $Na_2SO_4$ and concentrated. The crude product was purified by flash chromatography (Mobile phase A: 0.1% $NH_4HCO_3$ in $H_2O$, mobile phase B: ACN; Gradient from 5 to 95%) to give tert-butyl 3-(1-benzyloxy-3-oxo-propyl)-3-vinyl-azetidine-1-carboxylate (6.4 g, 18.52 mmol, 58.52% yield) as yellow oil. LCMS (ESI) calculated for $C_{20}H_{28}NO_4$ $(M+H)^+$ m/z=346.4, found: 346.4.

Step 7. Synthesis of tert-butyl 3-[(3E)-1-benzyloxy-3-(p-tolylsulfonylhydrazono)propyl]-3-vinyl-azetidine-1-carboxylate (Int16g). To a solution of tert-butyl 3-(1-benzyloxy-3-oxo-propyl)-3-vinyl-azetidine-1-carboxylate (2 g, 5.79 mmol) in THF (60 mL) was added $TsNHNH_2$ (1.62 g, 8.68 mmol). The resulting mixture was stirred at −20° C. for 0.2 h. The mixture was quenched with $H_2O$ (50 mL), extracted with EtOAc (50 mL×3). The combined organic layer was washed with brine (50 mL), dried over $Na_2SO_4$, filtered, and concentrated. The crude product was purified by silica gel chromatography (eluted with EtOAc in petroleum ether from 0% to 50%) to give tert-butyl 3-[(3E)-1-benzyloxy-3-(p-tolylsulfonylhydrazono)propyl]-3-vinyl-azetidine-1-carboxylate (2.3 g, 4.48 mmol, 77.34% yield) as yellow oil. LCMS (ESI) calculated for $C_{27}H_{36}N_3O_5S$ $(M+H)^+$ m/z=514.2, found: 514.2.

Step 8. Synthesis of tert-butyl 3'-benzyloxyspiro[azetidine-3,2'-bicyclo[3.1.0]hexane]-1-carboxylate (Int16h). To a solution of tert-butyl 3-[(3E)-1-benzyloxy-3-(p-tolylsulfonylhydrazono)propyl]-3-vinyl-azetidine-1-carboxylate (2 g, 3.89 mmol) and MeONa (420 mg, 7.79 mmol) in DMF (60 mL) was added $Pd_2(dba)_3$ (1.07 g, 1.17 mmol) under Ar. The resulting mixture was stirred at 80° C. for 12 h. Upon completion, the mixture was cooled down to r.t., and quenched with $H_2O$ (100 mL), extracted with EtOAc (100 mL×3). The combined organic layer was washed with brine (100 mL), dried over $Na_2SO_4$, filtered, and concentrated. The crude product was purified by silica gel chromatography (eluted with EtOAc in petroleum ether from 0% to 20%) to give tert-butyl 3'-benzyloxyspiro[azetidine-3,2'-bicyclo[3.1.0]hexane]-1-carboxylate (600 mg, 1.82 mmol, 46.77% yield) as yellow solid. LCMS calculated for $C_{20}H_{28}NO_3$ $(M+H)^+$ m/z=330.1; found: 230.1 (M-Boc).

Step 9. Synthesis of tert-butyl 3'-hydroxyspiro[azetidine-3,2'-bicyclo[3.1.0]hexane]-1-carboxylate & tert-butyl 5-hydroxy-2-azaspiro[3.5]nonane-2-carboxylate (Int16i)

To a solution of tert-butyl 3'-benzyloxyspiro[azetidine-3,2'-bicyclo[3.1.0]hexane]-1-carboxylate (300 mg, 0.91 mmol) in Methanol (10 mL) was added Pd/C (150 mg, 1.41 mmol). The resulting mixture was stirred at 75° C. under atmosphere of $H_2$ (3 MPa) for 12 h. Upon completion, the mixture was cooled down to r.t. The mixture was filtered over celite and concentrated to give a crude mixture of tert-butyl 3'-hydroxyspiro[azetidine-3,2'-bicyclo[3.1.0]hexane]-1-carboxylate and tert-butyl 5-hydroxy-2-azaspiro[3.5]nonane-2-carboxylate (280 mg, 1.17 mmol) as yellow oil. The crude product was used directly for the next step. LCMS calculated for $C_{13}H_{22}NO_3$ $(M+H)^+$ m/z=239.2; found: 184.1 (M-tBu).

Step 10. Synthesis of tert-butyl 3'-oxospiro[azetidine-3,2'-bicyclo[3.1.0]hexane]-1-carboxylate & tert-butyl 5-oxo-2-azaspiro[3.5]nonane-2-carboxylate (Int16j)

To a solution of tert-butyl 3'-hydroxyspiro[azetidine-3,2'-bicyclo[3.1.0]hexane]-1-carboxylate and tert-butyl 5-hydroxy-2-azaspiro[3.5]nonane-2-carboxylate (280 mg, 1.17 mmol) and in DCM (3 mL) was added DMP (744.35 mg, 1.75 mmol). The reaction mixture was stirred at r.t. for 2 h. The reaction mixture was diluted with $CH_2Cl_2$ (10 mL) and the resulting mixture was added to 1.3 M NaOH (10 mL). After the mixture was stirred for 10 min, the organic layer was separated, washed with water (10 mL) and brine (10 mL). The organic layer was then dried over $Na_2SO_4$ and concentrated. The crude product was purified by flash chromatography (Mobile phase A: 0.1% NH4HCO3 in $H_2O$, mobile phase B: ACN; Gradient from 5 to 95%) to give a mixture of tert-butyl 3'-oxospiro[azetidine-3,2'-bicyclo [3.1.0]hexane]-1-carboxylate and tert-butyl 5-oxo-2-azaspiro[3.5]nonane-2-carboxylate (70 mg, 0.2950 mmol, 25.213% yield) as yellow oil. LCMS calculated for $C_{13}H_{20}NO_3$ $(M+H)^+$ m/z=237.1; found: 182.0 (M-tBu).

Step 11. Synthesis of tert-butyl 8-amino-7-cyano-spiro[9-thiatricyclo[4.3.0.02,4]nona-1(6),7-diene-5, 3'-azetidine]-1'-carboxylate & tert-butyl 2-amino-3-cyano-spiro[6,7-dihydro-5H-benzothiophene-4,3'-azetidine]-1'-carboxylate (Int16k)

To a solution of tert-butyl 3'-oxospiro[azetidine-3,2'-bicyclo[3.1.0]hexane]-1-carboxylate and tert-butyl 5-oxo-2-azaspiro[3.5]nonane-2-carboxylate (80 mg, 0.34 mmol), S (21.62 mg, 0.67 mmol) and Malononitrile (44.54 mg, 0.67 mmol) in Ethanol (3 mL) was added Ammonium acetate (51.92 mg, 0.67 mmol) under Ar. The resulting mixture was stirred at 60° C. for 12 h. Upon completion, the mixture was cooled down to r.t. The mixture was quenched with $H_2O$ (10 mL), extracted with EtOAc (10 mL×3), The combined organic layers were washed with brine (10 mL), dried over $Na_2SO_4$, filtered, and concentrated to afford the crude product. The crude product was purified by flash chromatography (Mobile phase A: 0.1% NH4HCO3 in $H_2O$, mobile phase B: ACN; Gradient from 5 to 95%.) to give a mixture of tert-butyl 8-amino-7-cyano-spiro[9-thiatricyclo[4.3.0.02,4] nona-1(6),7-diene-5,3'-azetidine]-1'-carboxylate and tert-butyl 2-amino-3-cyano-spiro[6,7-dihydro-5H-benzothiophene-4,3'-azetidine]-1'-carboxylate (60 mg, 0.0851 mmol, 25.232% yield) as yellow oil. LCMS calculated for $C_{16}H_{20}N_3O_2S$ $(M-H)^-$ m/z=316.1; found: 316.1.

Step 12. Synthesis of 8-aminospiro[9-thiatricyclo [4.3.0.02,4]nona-1(6),7-diene-5,3'-azetidine]-7-carbonitrile; methanesulfonic acid & 2-aminospiro[6,7-dihydro-5H-benzothiophene-4,3'-azetidine]-3-carbonitrile; methanesulfonic acid (Intermediate 16)

To a solution of tert-butyl 8-amino-7-cyano-spiro[9-thiatricyclo[4.3.0.02,4]nona-1(6),7-diene-5,3'-azetidine]-1'-carboxylate and tert-butyl 2-amino-3-cyano-spiro[6,7-dihydro-5H-benzothiophene-4,3'-azetidine]-1'-carboxylate (50 mg, 0.16 mmol) in IPA (1 mL) was added Methanesulfonic acid (45.42 mg, 0.47 mmol). The reaction mixture was stirred at 60° C. for 3 h. Upon completion, the mixture was cooled down to r.t. The mixture was concentrated to afford a crude mixture of 8-aminospiro[9-thiatricyclo [4.3.0.02,4]nona-1(6),7-diene-5,3'-azetidine]-7-carbonitrile; methanesulfonic acid & 2-aminospiro[6,7-dihydro-5H-benzothiophene-4,3'-azetidine]-3-carbonitrile; methanesulfonic acid (59 mg, 0.1883 mmol) as yellow oil. The crude product was used directly for the next step. LCMS (ESI): m/z calculated for $C_{11}H_{11}N_3S+H$: 218.1, found: 218.1.

Intermediate 17. Synthesis of (3R,5R)-5-fluoro-3-methylpiperidin-3-ol

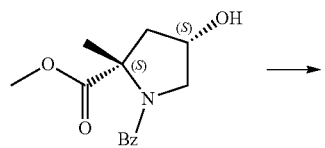

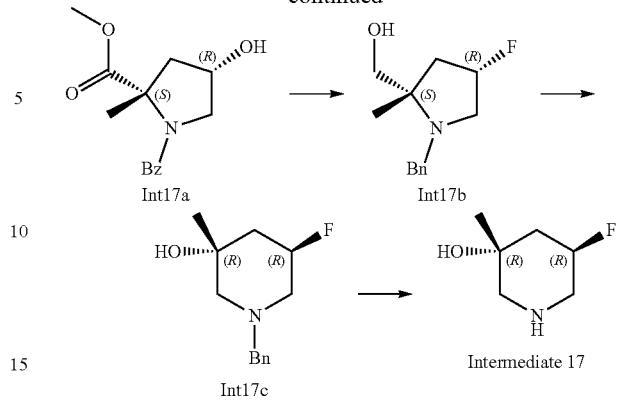

Step 1. Synthesis of methyl (2S,4R)-1-benzoyl-4-fluoro-2-methyl-pyrrolidine-2-carboxylate (Int17a). To a solution of methyl (2S,4S)-1-benzoyl-4-hydroxy-2-methyl-pyrrolidine-2-carboxylate (1 g, 3.8 mmol) in DCM (12 mL) was added DAST (1.51 mL, 11.39 mmol) portion wise at −70° C. under $N_2$. Then the mixture was stirred at −70° C. for 3 h, then warmed to rt for 3 h. The reaction mixture was quenched with aq. NaHCO3, and then extracted with DCM (50 mL*2). The combined extracts were washed with water and saturated brine, dried ($Na_2SO_4$) and concentrated in vacuo to give the crude product. It was purified using FC (silica gel, eluting with EtOAc in PE, 0 to 25%) to afford methyl (2S,4R)-1-benzoyl-4-fluoro-2-methyl-pyrrolidine-2-carboxylate (280 mg, 1.056 mmol, 27.79% yield) as a colorless oil. LCMS calculated for $C_{14}H_{17}FNO_3$ $(M+H)^+$ m/z=266.12; found: 266.1.

Step 2. Synthesis of [(2S,4R)-1-benzyl-4-fluoro-2-methyl-pyrrolidin-2-yl]methanol (Int17b). To a solution of LiAlH4 in THF (5.01 mL, 5.01 mmol, 1M), a solution of methyl (2S,4R)-1-benzoyl-4-fluoro-2-methyl-pyrrolidine-2-carboxylate (380 mg, 1.43 mmol) in THF (7 mL) was added dropwise at 0° C. After stirring for 15 min, the reaction mixture was heated to 70° C. for 3 h. The reaction was quenched by the addition of Water (0.05 mL) followed by MgSO4. The mixture was filtered and the filtrate was concentrated in vacuo to afford an oil, which was purified using FC (silica gel, eluent with EtOAc in PE 0 to 30%) followed by pre-HPLC (C18, eluent with MeCN in 0.1% NH4HCO3/ $H_2O$) to afford the title product [(2S,4R)-1-benzyl-4-fluoro-2-methyl-pyrrolidin-2-yl]methanol (193 mg, 0.778 mmol, 54.31% yield) as a colorless oil.

LCMS calculated for $C_{13}H_{19}FNO$ $(M+H)^+$ m/z=224.15; found: 224.4.

Step 3. Synthesis of (3R,5R)-1-benzyl-5-fluoro-3-methyl-piperidin-3-ol (Int17c). To a solution of [(2S,4R)-1-benzyl-4-fluoro-2-methyl-pyrrolidin-2-yl]methanol (193 mg, 0.78 mmol) in THF (5 mL) was added TFAA (0.27 mL, 1.94 mmol) dropwise at 0° C. The mixture was stirred for 1.5 hrs and then cooled to −70° C. TEA (0.86 mL, 6.22 mmol) was added dropwise. The whole mixture was stirred at −70° C. for 0.5 hour and then 70° C. for 16 h. NaOH (3.11 mL, 7.78 mmol, 2.5 M) was added and stirred at room temperature for 1 hour. The residue was extracted with EtOAc (10 mL). The organic layers were separated and washed with saturated brine, dried ($Na_2SO_4$) and then concentrated in vacuo to give the crude product. It was purified using FC (silica gel Eluent with EtOAc in DCM, 0 to 3%) to give (3R,5R)-1-benzyl-5-fluoro-3-methyl-piperidin-3-ol (56 mg, 0.251 mmol, 32.24% yield) as colorless oil. LCMS calculated for C₁₃H₁₉FNO (M+H)⁺=224.15; found: 224.0.

Step 4. Synthesis of (3R,5R)-5-fluoro-3-methyl-piperidin-3-ol (Intermediate 17). The mixture of (3R,5R)-1-benzyl-5-fluoro-3-methyl-piperidin-3-ol (26 mg, 0.12 mmol), Pd(OH)₂/C (5 mg, 0.04 mmol) and Pd/C (5 mg, 0.004 mmol) in Ethanol (1.5 mL) was stirred at RT for 16 h under H₂. The mixture was filtrated, and the solvent was removed in vacuo to give the title product (3R,5R)-5-fluoro-3-methyl-piperidin-3-ol (15.19 mg, 0.1141 mmol, 100% yield) as a colorless oil. LCMS calculated for C₆H₁₃FNO (M+H)⁺ m/z=134.1; found: 134.0.

Intermediate 18. Synthesis of (3R,5S)-5-fluoro-3-methylpiperidin-3-ol

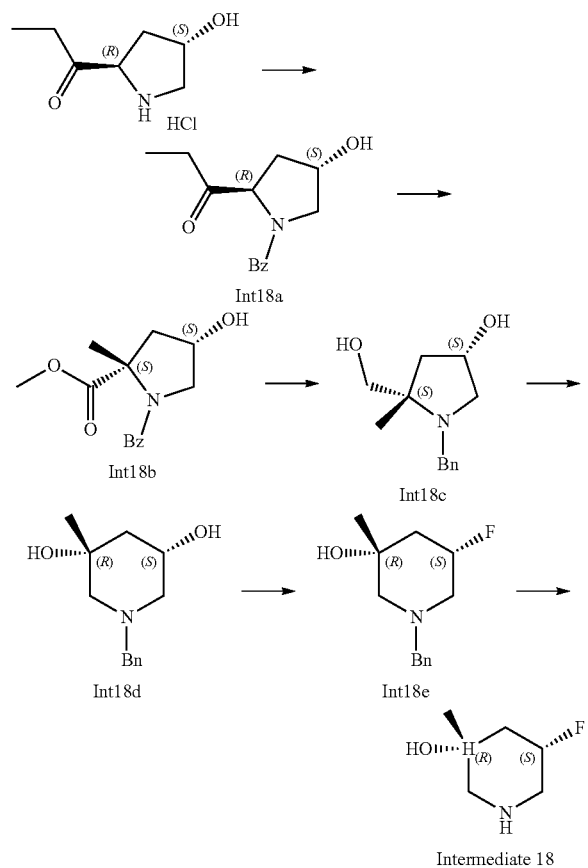

Intermediate 18

Step 1. Synthesis of Methyl (2R,4S)-1-benzoyl-4-hydroxy-pyrrolidine-2-carboxylate (Int18a)

To a solution of methyl (2R,4S)-4-hydroxypyrrolidine-2-carboxylate; hydrochloride (10 g, 55.06 mmol) in THF (20 mL) and Water (20 mL), NaHCO₃ (9.71 g, 115.63 mmol) was slowly added, and the mixture was cooled to 0° C. A solution of Benzoyl Chloride (7.03 mL, 60.57 mmol) in THF (18 mL) was added dropwise and the mixture was stirred at RT for 1.5 h. The solvent was removed under vacuum, the residue was diluted with CHCl₃ (100 mL) and washed with saturated brine. The organic layer was separated and dried (Na₂SO₄, filtered and concentrated under reduced pressure to give the crude product. It was purified using FC (silica gel, eluent with MeOH in DCM, 0% to 5%) to afford the title product methyl (2R,4S)-1-benzoyl-4-hydroxy-pyrrolidine-2-carboxylate (13.76 g, 52.4 mmol, 95.25% yield) as a white solid.

LCMS calculated for C₁₃H₁₆NO₄ (M+H)⁺ m/z=250.11; found: 250.1

Step 2. Synthesis of Methyl (2S,4S)-1-benzoyl-4-hydroxy-2-methyl-pyrrolidine-2-carboxylate (Int18b)

To a stirred solution of LDA (57.71 mL, 115.42 mmol, 2M) in THF (100 mL), a solution of methyl (2R,4S)-1-benzoyl-4-hydroxy-pyrrolidine-2-carboxylate (13.7 g, 54.96 mmol) in THF (170 mL) was added dropwise −78° C. under N2. After stirring for 30 min at −78° C., Methyl Iodide (4.64 mL, 74.18 mmol) was added. It was allowed to warm to −30° C. and stirred for 2 h. The reaction was quenched with water (100 mL) and extracted with CH₂Cl₂ (200 mL*2). The combined extracts were washed with saturated brine and then dried (MgSO₄) and filtered. The solvent was removed in vacuo to afford an oil, which was purified using FC (silica gel, eluent with MeOH in DCM, 0% to 2%) to give the title product methyl (2S,4S)-1-benzoyl-4-hydroxy-2-methyl-pyrrolidine-2-carboxylate (7.67 g, 29.1 mmol, 53.00% yield) as a yellow oil.

LCMS calculated for C₁₄H₁₈NO₄ (M+H)⁺ m/z=264.13; found: 264.1

Step 3. Synthesis of (3S,5S)-1-benzyl-5-(hydroxymethyl)-5-methyl-pyrrolidin-3-ol (Int18c)

To a suspension of LiAlH₄ in THF (54.29 mL, 54.29 mmol) at 0° C., a solution of methyl (2S,4S)-1-benzoyl-4-hydroxy-2-methyl-pyrrolidine-2-carboxylate (4 g, 15.19 mmol) in THF (30 mL) was added dropwise. After 15 min at 0° C., the reaction mixture was heated to 70° C. for 3 h. The reaction was quenched by the addition of water (0.05 mL) at 0° C. And then MgSO₄ was added and the mixture was stirred for 10 min. Filtered and the filtrate was concentrated in vacuo to afford an oil, which was purified using FC (silica gel, eluent with MeOH in DCM, 0% to 5%) to afford the title product (3S,5S)-1-benzyl-5-(hydroxymethyl)-5-methyl-pyrrolidin-3-ol (3.16 g, 13.3 mmol, 87.41% yield) as a colorless oil. LCMS calculated for C₁₃H₂₀NO₂ (M+H)⁺ m/z=222.15; found: 222.2

Step 4. Synthesis of (3R,5S)-1-benzyl-3-methyl-piperidine-3,5-diol (Int18d)

To a solution of (3S,5S)-1-benzyl-5-(hydroxymethyl)-5-methyl-pyrrolidin-3-ol (3.16 g, 14.28 mmol) in THF (40 mL) was added TFAA (4.96 mL, 35.7 mmol) dropwise at 0° C. under N2. The mixture was stirred for 1.5 h and then cooled to −70° C., TEA (15.85 mL, 114.23 mmol) was added dropwise. The reaction was stirred at −70° C. for 0.5 hour and then heated to 70° C. for 24 h. NaOH (19.99 mL, 49.99 mmol, 2.5 M) was added and the whole mixture was stirred at room temperature for 1 hour. The residue was extracted with EtOAc (50 mL*2). The combined extracts were washed with saturated brine and then dried over Na₂SO₄. The solvent was removed in vacuo and the residue was purified using FC (silica gel, eluent with MeOH in DCM, 0 to 2%) to give the title product (3R,5S)-1-benzyl-3-methyl-piperidine-3,5-diol (1.29 g, 5.83 mmol, 40.82% yield) as a yellow oil. LCMS calculated for C₁₃H₁₉NO₂ (M+H)⁺ m/z=222.15; found: 222.2.

Step 5. Synthesis of (3R,5S)-1-benzyl-5-fluoro-3-methyl-piperidin-3-ol (Int18e)

To a solution of (3R,5S)-1-benzyl-3-methyl-piperidine-3,5-diol (590 mg, 2.67 mmol) in Toluene (8 mL) was added pyridine-2-sulfonyl fluoride (515.56 mg, 3.2 mmol) at 0° C. After stirring for 5 min, DBU (0.8 mL, 5.33 mmol) was added. The whole mixture was stirred at rt for 16 h. The mixture was diluted with DCM, washed with saturated brine and then dried ($Na_2SO_4$). The solvent was removed in vacuo and the residue was purified using FC (silica gel, eluting with EtOAc in PE 0% to 20%) to afford the title product (3R,5S)-1-benzyl-5-fluoro-3-methyl-piperidin-3-ol (64 mg, 0.2866 mmol, 10.751% yield) as a colorless oil.

LCMS calculated for $C_{13}H_{19}FNO$ $(M+H)^+$ m/z=224.15; found: 224.2.

Step 6. Synthesis of (3R,5S)-5-fluoro-3-methyl-piperidin-3-ol (Intermediate 18)

The mixture of (3R,5S)-1-benzyl-5-fluoro-3-methyl-piperidin-3-ol (54 mg, 0.24 mmol), $Pd(OH)_2/C$ (11 mg, 0.08 mmol) and Pd/C (11 mg, 0.01 mmol) in Ethanol (3 mL) was stirred at RT for 16 h under $H_2$. The mixture was filtrated, and the solvent was removed in vacuo to give the (3R,5S)-5-fluoro-3-methyl-piperidin-3-ol (22 mg, 0.1652 mmol, 68.316% yield). LCMS calculated for $C_6H_{13}FNO$ $(M+H)^+$ m/z=134.1; found: 134.0.

Intermediate 19. Synthesis of 2-amino-5-methyl-spiro[6H-thieno[2,3-c]pyrrole-4,3'-azetidine]-3-carbonitrile

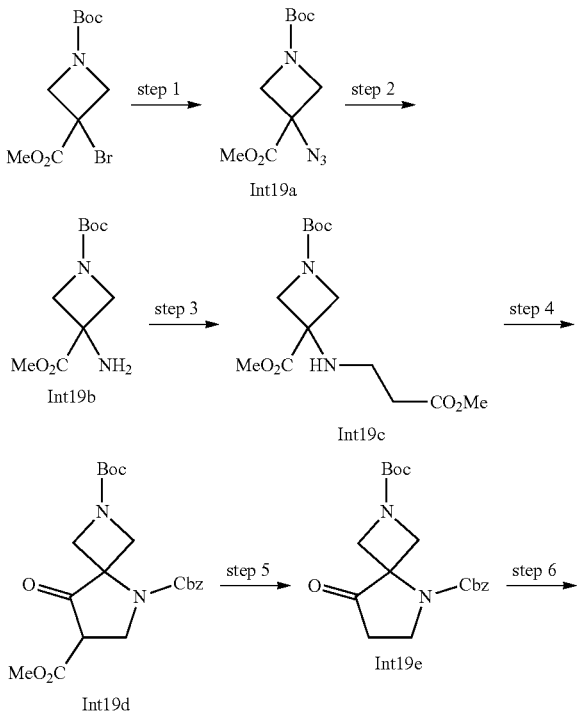

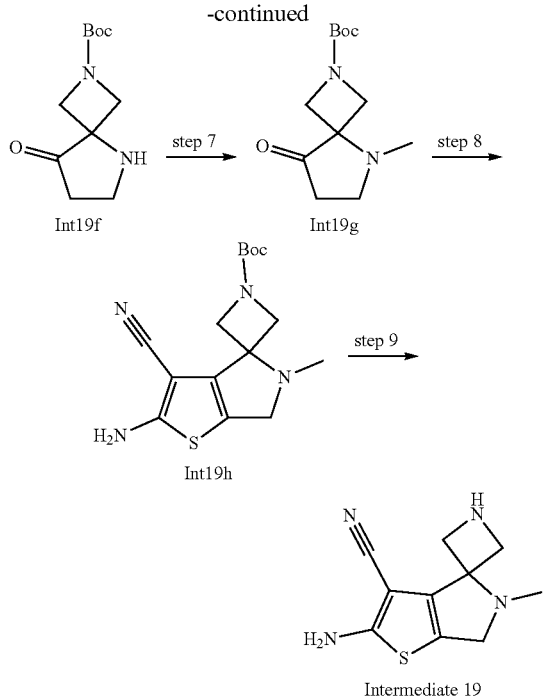

Step 1. Synthesis of 1-(tert-butyl) 3-methyl 3-azidoazetidine-1,3-dicarboxylate (Int19a). The mixture of 1-(tert-butyl) 3-methyl 3-bromoazetidine-1,3-dicarboxylate (2.00 g, 6.80 mmol) and azidosodium (1.33 g, 20.4 mmol) in anhydrous DMSO (20.0 mL) was stirred at 50° C. for 18 h under $N_2$. The reaction mixture was cooled to r.t and diluted with EtOAc (200 mL). It was washed with saturated aqueous $NaHCO_3$ (150 mL) followed by saturated brine (2*150 mL), dried ($Na_2SO_4$) and concentrated in vacuo to dryness to afford 1-(tert-butyl) 3-methyl 3-azidoazetidine-1,3-dicarboxylate (1.67 g, 6.52 mmol, 95.8% yield) as a yellow oil. LCMS calculated for $C_{10}H_{17}N_4O_4(M+H)^+$ m/z=256.1; found: 201.1 (M-tBu).

Step 2. Synthesis of 1-(tert-butyl) 3-methyl 3-aminoazetidine-1,3-dicarboxylate (Int19b). The mixture of 1-(tert-butyl) 3-methyl 3-azidoazetidine-1,3-dicarboxylate (1.66 g, 6.48 mmol) and 10% Pd/C (55% wt, 300 mg) in Ethanol (20.0 mL) was stirred at r.t under $H_2$ atmosphere overnight. The mixture was filtrated through Celite and the filtrate was concentrated in vacuo to get 1-(tert-butyl) 3-methyl 3-aminoazetidine-1,3-dicarboxylate (1.43 g, 6.21 mmol, 95.9% yield) as a colorless. LCMS calculated for $C_{10}H_{18}N_2O_4$ (M+H)+ m/z=231.1; found: 231.1.

Step 3. Synthesis of 1-(tert-butyl) 3-methyl 3-((3-methoxy-3-oxopropyl)amino)azetidine-1,3-dicarboxylate (Int19c). The mixture of 1-(tert-butyl) 3-methyl 3-aminoazetidine-1,3-dicarboxylate (1.30 g, 5.65 mmol), Methyl Acrylate (3.58 mL, 39.5 mmol), $Et_3N$ (2.36 mL, 16.9 mmol) and CuO (0.09 g, 1.13 mmol) in MeOH (10 mL) was stirred at 85° C. for 8 h under $N_2$. It was cooled to r.t and filtered. The filtrate was concentrated in vacuo to give the residue. It was purified using FCC (silica gel, eluting with EtOAc in pet.ether 0 to 50%) to afford 1-(tert-butyl) 3-methyl 3-((3-methoxy-3-oxopropyl)amino)azetidine-1,3-dicarboxylate (1.48 g, 4.68 mmol, 82.9% yield) as a light yellow oil. LCMS calculated for $C_{14}H_{25}N_2O_6$ $(M+H)^+$ m/z=317.2; found: 317.2.

Step 4. Synthesis of 5-benzyl 2-(tert-butyl) 7-methyl 8-oxo-2,5-diazaspiro[3.4]octane-2,5,7-tricarboxylate (Int19d). To a solution of 1-(tert-butyl) 3-methyl 3-((3-methoxy-3-oxopropyl)amino)azetidine-1,3-dicarboxylate (5.50 g, 17.4 mmol) in THF (80 mL) was added t-BuONa (3.34 g, 34.8 mmol) in five batches at 0° C. under $N_2$. Then the mixture was stirred at same temperature for 2 h. Upon SM was consumed, Benzyl Chloroformate (4.96 mL, 34.8 mmol), DIEA (7.57 mL, 43.5 mmol) and DMAP (0.53 g, 4.35 mmol) was added and the whole mixture was stirred at r.t overnight. The reaction mixture was diluted with $H_2O$ (100 mL) and extracted with EtOAc (100 mL*3). The combined organic layer was washed with water (100 mL) followed by saturated brine (100 mL), dried ($Na_2SO_4$) and concentrated in vacuo to give the residue. It was purified using FCC (silica gel, eluting with EtOAc in 0 to 50%) to afford 5-benzyl 2-(tert-butyl) 7-methyl 8-oxo-2,5-diazaspiro [3.4]octane-2,5,7-tricarboxylate (7.20 g, 12.9 mmol, 74.2% yield) as a light red oil. LCMS calculated for $C_{21}H_{27}N_2O_7$ $(M+H)^+$ m/z=419.2; found (M-Boc): 319.2.

Step 5. Synthesis of 5-benzyl 2-(tert-butyl) 8-oxo-2,5-diazaspiro[3.4]octane-2,5-dicarboxylate (Int19e). The mixture of 5-benzyl 2-(tert-butyl) 7-methyl 8-oxo-2,5-diazaspiro[3.4]octane-2,5,7-tricarboxylate (7.20 g, 12.9 mmol) and LiCl (1.09 g, 25.8 mmol) in DMSO (115 mL) and Water (11.5 mL) was stirred at 160° C. for 1.5 h under $N_2$. It was cooled to r.t and diluted with water (500 mL). It was extracted with EtOAc (200 mL*2). The combined extracts was wash with water (200 mL*3) followed by saturated brine (100 mL), dried ($Na_2SO_4$) and concentrated in vacuo to give the residue. It was purified using FCC (silica gel, eluting with EtOAc in PE 0 to 50) to afford 5-benzyl 2-(tert-butyl) 8-oxo-2,5-diazaspiro[3.4]octane-2,5-dicarboxylate (2.74 g, 7.60 mmol, 58.9% yield) as a colorless oil. LCMS calculated for $C_{19}H_{25}N_2O_5$ $(M+H)^+$ m/z=361.2; found: 261.1 ((M-Boc)).

Step 6. Synthesis of tert-butyl 8-oxo-2,5-diazaspiro[3.4] octane-2-carboxylate (Int19f). The mixture of 5-benzyl 2-(tert-butyl) 8-oxo-2,5-diazaspiro[3.4]octane-2,5-dicarboxylate (2.00 g, 5.55 mmol) and 10% Pd/C (55% wt, 250 mg) in Methanol (40 mL) was stirred at room temperature overnight under $H_2$. The mixture was filtered through Celite and the filtrate was concentrated in vacuo to afford crude of tert-butyl 8-oxo-2,5-diazaspiro[3.4]octane-2-carboxylate (1.20 g, 5.30 mmol, 95.6% yield) as a yellow solid. LCMS calculated for $C_{11}H_{19}N_2O_3$ $(M+H)^+$ m/z=227.1; found: 127.0 ((M-Boc))/171.0 ((M-tBu)).

Step 7. Synthesis of tert-butyl 5-methyl-8-oxo-2,5-diazaspiro[3.4]octane-2-carboxylate (Int19g). The mixture of tert-butyl 8-oxo-2,5-diazaspiro[3.4]octane-2-carboxylate (60.0 mg, 0.27 mmol), Methyl Iodide (0.05 mL, 0.80 mmol) and DIEA (0.12 mL, 0.66 mmol) in THF (2 mL) was stirred at 60° C. for 16 h under $N_2$. The mixture was cooled to r.t and diluted with water (10 mL), extracted with EtOAc (10 m). The extracts was washed with saturated brine (10 mL), dried ($Na_2SO_4$) and concentrated in vacuo to give the residue. It was purified using (silica gel, eluting with MeOH in DCM 0 to 3%) to afford tert-butyl 5-methyl-8-oxo-2,5-diazaspiro[3.4]octane-2-carboxylate (35.0 mg, 0.146 mmol, 54.9% yield) as a yellow oil. LCMS calculated for $C_{12}H_{21}N_2O_3$ $(M+H)^+$ m/z=241.2; found: 141.2 (MW-100)/185.2 (MW-56).

Step 8. Synthesis of tert-butyl 2-amino-3-cyano-5-methyl-spiro[6H-thieno[2,3-c]pyrrole-4,3'-azetidine]-1'-carboxylate (Int19h). The mixture of tert-butyl 5-methyl-8-oxo-2,5-diazaspiro[3.4]octane-2-carboxylate (158 mg, 0.66 mmol) Sulfur (31.6 mg, 0.99 mmol), ammonium acetate (76.0 mg, 0.99 mmol) and malononitrile (65.1 mg, 0.99 mmol) in Ethanol (4 mL) was stirred at 55° C. for 1 h under $N_2$. It was cooled to r.t and diluted with water, extracted with EtOAc (20 mL). The extracts was wash with saturated brine dried ($Na_2SO_4$) and concentrated under reduce pressure to give the residue. It was purified using FCC (silica gel, eluting with MeOH in DCM 0 to 3%) to afford tert-butyl 2-amino-3-cyano-5-methyl-spiro[6H-thieno[2,3-c]pyrrole-4,3'-azetidine]-1'-carboxylate (150 mg, 0.47 mmol, 71.2% yield) as brown solid. LCMS calculated for $C_{15}H_{21}N_4O_2S$ $(M+H)^+$ m/z=321.1; found: 221.1 ((M-Boc))/265.1 ((M-tBu)).

Step 9. Synthesis of 2-amino-5-methyl-spiro[6H-thieno [2,3-c]pyrrole-4,3'-azetidine]-3-carbonitrile (Intermediate 19). To the solution of tert-butyl 2-amino-3-cyano-5-methyl-spiro[6H-thieno[2,3-c]pyrrole-4,3'-azetidine]-1'-carboxylate (150 mg, 0.47 mmol) in IPA (1.5 mL) was added MsOH (0.09 mL, 1.40 mmol) at room temperature. Then the mixture was stirred at 60° C. for 8 h under $N_2$. The solid was collected by filtration and wash with IPA (3*2 mL). It was dried in vacuo to afford 2-amino-5-methyl-spiro[6H-thieno [2,3-c]pyrrole-4,3'-azetidine]-3-carbonitrile; methanesulfonic acid (155 mg, 0.38 mmol, 80.2% yield) as grey solid. LCMS calculated for $C_{10}H_{13}N_4S$ $(M+H)^+$ m/z=221.1; found: 221.0

Intermediate 20. Synthesis of 2'-amino-6'H-spiro [azetidine-3,4'-selenopheno[2,3-c]thiophene]-3'-carbonitrile hydrochloride

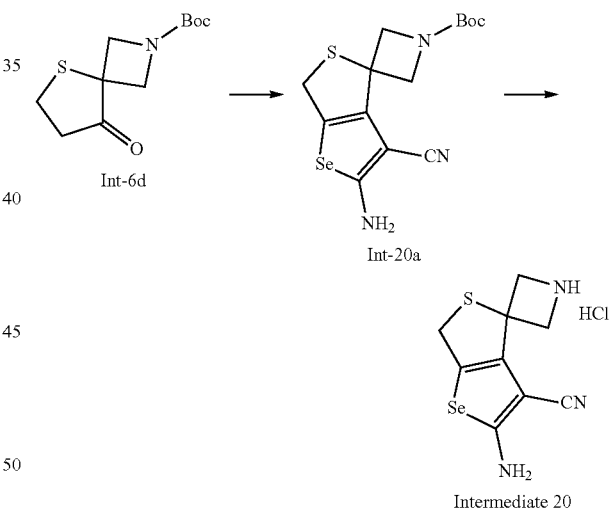

Intermediate 20

Step 1. Synthesis of tert-butyl 2'-amino-3'-cyano-6'H-spiro[azetidine-3,4'-selenopheno[2,3-c]thiophene]-1-carboxylate (Int-20a). To the solution of tert-butyl 8-oxo-5-thia-2-azaspiro[3.4]octane-2-carboxylate (50 mg, 0.21 mmol) in DMF (1.00 mL) were added propanedinitrile (17.65 mg, 0.27 mmol), selenium (21.09 mg, 0.27 mmol, 200 mesh) and Morpholine (0.25 mL, 2.88 mmol) at rt then the whole mixture was heated to 80° C. and stirred for 16 h. The mixture was cooled to r.t and diluted with EA and water. The combined extracts were wash with saturated brine and dried over Na2SO4. The solvent was removed in vacuo and the residue was purified by FC (silica gel, eluted with PE/EA 0% to 100%) to afford the crude material. It was then added into EtOH (1.5 mL) and stirred for 10 min, the solid was collected by filtration and dried in vacuum to afford tert-butyl 2-amino-3-cyano-spiro[6H-selenopheno[2,3-c]thiophene-4,3'-azetidine]-1'-carboxylate (30 mg, 0.0810 mmol, 39.42% yield) as light yellow solid. LCMS calculated for $C_{14}H_{18}N_3O_2SeS$ $(M+H)^+$ m/z=372.03; found: 316.0 (M-tBu).

Step 2. Synthesis of 2'-amino-6'H-spiro[azetidine-3,4'-selenopheno[2,3-c]thiophene]-3'-carbonitrile hydrochloride (Intermediate 20). To the solution of tert-butyl 2-amino-3-cyano-spiro[6H-selenopheno[2,3-c]thiophene-4,3'-azetidine]-1'-carboxylate (50.00 mg, 0.13 mmol) in DCM (2 mL) was added HCl/dioxane (1.00 mL, 4.0 mmol) at RT and the whole mixture was stirred for 3 h at 20° C., LCMS showed SM was consumed and the solvent was removed by nitrogen gas to afford crude 2-aminospiro[6H-selenopheno[2,3-c]thiophene-4,3'-azetidine]-3-carbonitrile; hydrochloride (40 mg, 0.130 mmol, 96.61% yield) as yellow solid, which was used directly in the next reaction without further purification. LCMS calculated for $C_9H_{10}N_3SeS$ $(M+H)^+$ m/z=272.0; found: 272.0.

Example 1. Exemplary synthesis of 2-amino-1'-[4-(3,8-diazabicyclo[3.2.1]octan-3-yl)-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile (Compound 1)

Step 1. Preparation of tert-butyl (1R,5S)-3-(4,6-dichloro-1,3,5-triazin-2-yl)-3,8-diazabicyclo[3.2.1]octane-8-carboxylate (1a). To a solution of tert-butyl (1R,5S)-3,8-diazabicyclo[3.2.1]octane-8-carboxylate (1.15 g, 5.42 mmol) and 2,4,6-trichloro-1,3,5-triazine (1.0 g, 5.42 mmol) in DCM (10 mL) was added DIEA (1.89 mL, 10.85 mmol) at 0° C. The mixture was stirred at 0° C. for 1 h. The mixture was diluted with EtOAc (40 mL), washed with H₂O (2×30 mL) and brine (30 mL), dried over Na₂SO₄, concentrated. The crude product was purified by silica gel chromatography (PE:EtOAc=50:1 to 15:1) to afford tert-butyl (1R,5S)-3-(4,6-dichloro-1,3,5-triazin-2-yl)-3,8-diazabicyclo[3.2.1]octane-8-carboxylate (1a, 1.85 g, 5.136 mmol, 94.70% yield) as white solid. LCMS calcd for $C_{14}H_{20}Cl_2N_5O_2$ $(M+H)^+$ m/z=360.1, found: 360.2.

Step 2. Preparation of tert-butyl 3-[4-chloro-6-[[(2R,8S)-2-fluoro-1,2,3,5,6,7-hexahydropyrrolizin-8-yl]methoxy]-1,3,5-triazin-2-yl]-3,8-diazabicyclo[3.2.1]octane-8-carboxylate (1b). To a solution of [(2R,8S)-2-fluoro-1,2,3,5,6,7-hexahydropyrrolizin-8-yl]methanol (22.1 mg, 0.14 mmol) in THF (2 mL) was added NaH (11.1 mg, 0.28 mmol) at 25° C. The mixture was stirred at 25° C. for 5 min, followed by the addition of tert-butyl 3-(4,6-dichloro-1,3,5-triazin-2-yl)-3,8-diazabicyclo[3.2.1]octane-8-carboxylate (1a, 50 mg, 0.14 mmol). The reaction was stirred at 25° C. for 10 min, extracted with EtOAc (3×10 mL), dried over Na₂SO₄, concentrated to provide crude product tert-butyl 3-[4-chloro-6-[[(2R,8S)-2-fluoro-1,2,3,5,6,7-hexahydropyrrolizin-8-yl]methoxy]-1,3,5-triazin-2-yl]-3,8-diazabicyclo[3.2.1]octane-8-carboxylate (1b, 65 mg, 0.135 mmol) as a white solid. LCMS calcd for $C_{22}H_{33}ClFN_6O_3$ $(M+H)^+$ m/z=483.2, found: 483.3.

Step 3. Preparation of tert-butyl 3-[4-(2-amino-3-cyano-spiro[5,6-dihydrocyclopenta[b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-3,8-diazabicyclo[3.2.1]octane-8-carboxylate (1c). The solution of tert-butyl 3-[4-chloro-6-[[(2R,8S)-2-fluoro-1,2,3,5,6,7-hexahydropyrrolizin-8-yl]methoxy]-1,3,5-triazin-2-yl]-3,8-diazabicyclo[3.2.1]octane-8-carboxylate (1b, 60 mg, 0.12 mmol), DIEA (0.02 mL, 0.12 mmol) and 2-aminospiro[5,6-dihydrocyclopenta[b]thiophene-4,3'-azetidine]-3-carbonitrile (Int-1, 25.5 mg, 0.12 mmol) in Dioxane (5 mL) was stirred at 25° C. for 2 h under argon. The mixture was diluted with EtOAc (35 mL), washed with H₂O (2×10 mL) and brine (10 mL), dried over Na₂SO₄, and concentrated to give crude product tert-butyl 3-[4-(2-amino-3-cyano-spiro[5,6-dihydrocyclopenta[b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-3,8-diazabicyclo[3.2.1]octane-8-carboxylate (1c, 70 mg, 0.107 mmol, 86.45% yield). LCMS calcd for $C_{32}H_{43}FN_9O_3S$ $(M+H)^+$ m/z=652.3 found: 652.2.

Step 4. Preparation of 2-amino-1'-[4-(3,8-diazabicyclo[3.2.1]octan-3-yl)-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile (Compound 1). The mixture of tert-butyl 3-[4-(2-amino-3-cyano-spiro[5,6-dihydrocyclopenta[b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-3,8-diazabicyclo[3.2.1]octane-8-carboxylate (1c, 70 mg, 0.11 mmol) in DCM (3 mL) was add TFA (0.5 mL, 6.53 mmol) was stirred at 25° C. for 2 h under argon. The mixture was concentrated to afford a crude product. The crude product was purified by Prep-HPLC (eluted with CH₃CN in H₂O (0.1% TFA) from 5.0% to 95%) to give the titled compound 2-amino-1'-[4-(3,8-diazabicyclo[3.2.1]octan-3-yl)-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile as a TFA salt (1, 49.41 mg, 0.055 mmol, 51.22% yield). LCMS calcd for $C_{27}H_{35}FN_9OS$ $(M+H)^+$ m/z=552.3 found: 552.2. $^1H$ NMR (400 MHz, CD₃OD) δ 5.55 (d, J=51.7 Hz, 1H), 4.78-4.63 (m, 2H), 4.59-4.43 (m, 2H), 4.41-4.30 (m, 2H), 4.24-4.09 (m, 4H), 4.06-3.79 (m, 3H), 3.53-3.38 (m, 1H), 3.33-3.27 (m, 4H), 2.86-2.69 (m, 4H), 2.67-2.46 (m, 2H), 2.42-2.24 (m, 3H), 2.23-1.79 (m, 5H)

Compound 2. 2-amino-1'-[4-[[1-(morpholinomethyl)cyclopropyl]methoxy]-6-[(1R,5S)-3,8-diazabicyclo[3.2.1]octan-3-yl]-1,3,5-triazin-2-yl]spiro[5,6-dihydrocyclopenta[b]thiophene-4,3'-azetidine]-3-carbonitrile

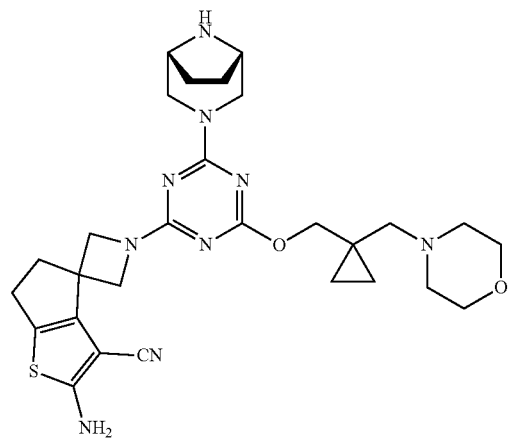

Compound 2 was prepared similarly to that of Ex. 1 as a TFA salt. LCMS calcd for C$_{28}$H$_{38}$N$_9$O$_2$S (M+H)$^+$ m/z=564.3, found: 564.2. $^1$H NMR (400 MHz, CD$_3$OD) δ 4.78-4.55 (m, 2H), 4.42-4.24 (m, 4H), 4.22-3.98 (m, 6H), 3.94-3.48 (m, 4H), 3.29-2.92 (m, 6H), 2.80-2.70 (m, 4H), 2.14-1.85 (m, 4H), 0.99-0.89 (m, 2H), 0.87-0.76 (m, 2H).

Compound 3. 2-amino-1'-[4-[(1R,5S)-3,8-diazabicyclo[3.2.1]octan-3-yl]-6-[[1-(morpholinomethyl)cyclopropyl]methoxy]-1,3,5-triazin-2-yl]spiro[6,7-dihydro-5H-benzothiophene-4,3'-azetidine]-3-carbonitrile

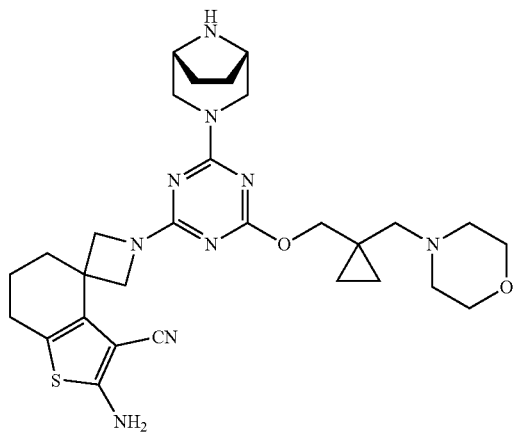

Compound 3 was prepared similarly to that of Ex. 1 as a TFA salt. LCMS calcd for C$_{29}$H$_{40}$N$_9$O$_2$S (M+H)$^+$ m/z=578.3, found: 578.2. $^1$H NMR (DMSO-d6, 400 MHz) δ 7.06 (s, 2H), 4.42 (d, J=12.0 Hz, 2H), 4.30-4.25 (m, 2H), 4.14 (q, J=12.0 Hz, 2H), 3.96 (m, 2H), 3.84-3.82 (m, 2H), 3.55 (t, J=4.0 Hz, 4H), 3.15 (d, J=16.0 Hz, 2H), 2.43 (t, J=4.0 Hz, 2H), 2.36 (m, 3H), 2.29-2.20 (m, 2H), 2.03-1.97 (m, 4H), 1.85 (m, 2H), 1.70-1.64 (m, 4H), 0.56 (s, 2H), 0.36 (s, 2H).

Compound 4. 2-amino-5-chloro-4-[1-[4-[[1-(morpholinomethyl)cyclopropyl]methoxy]-6-[(1R,5S)-3,8-diazabicyclo[3.2.1]octan-3-yl]-1,3,5-triazin-2-yl]pyrrolidin-3-yl]thiophene-3-carbonitrile

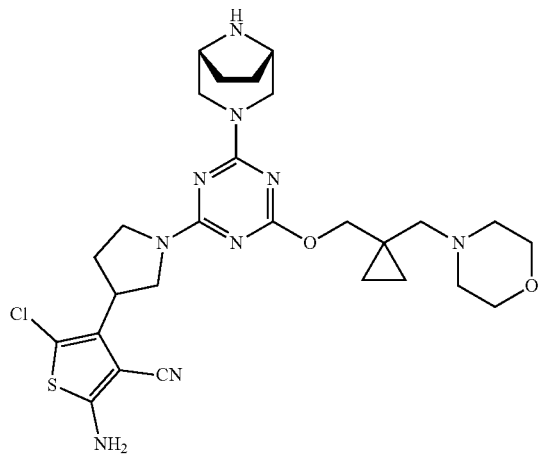

Compound 4 was prepared similarly to that of Ex. 1 using Int-2 instead of Int-1. LCMS calcd for C$_{27}$H$_{37}$ClN$_9$O$_2$S (M+H)$^+$ m/z=586.2, found: 586.2. $^1$H NMR (400 MHz, CD$_3$OD) δ 4.48 (d, J=77.4 Hz, 2H), 4.27 (s, 2H), 3.87 (d, J=14.4 Hz, 2H), 3.67 (t, J=9.8 Hz, 6H), 3.52 (d, J=33.9 Hz, 3H), 3.04 (d, J=13.1 Hz, 2H), 2.43 (d, J=38.1 Hz, 7H), 2.20 (s, 1H), 1.86-1.62 (m, 4H), 0.64 (s, 2H), 0.43 (d, J=4.7 Hz, 2H).

Compound 5. 5-[4-(2-amino-3-cyano-spiro[5,6-dihydrocyclopenta[b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-3-chloro-N,N-dimethyl-4,6,7,8-tetrahydropyrazolo[1,5-a][1,4]diazepine-2-carboxamide

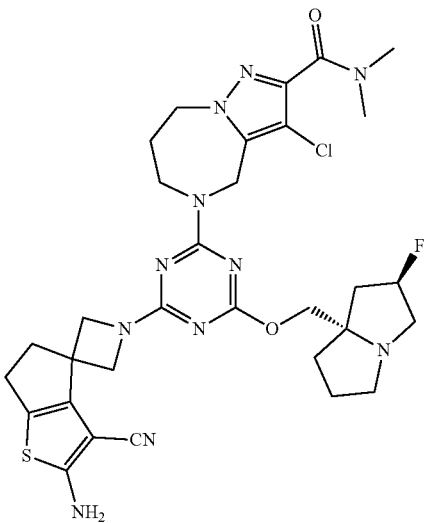 [SMILES: CN(C)C(=O)c1nn2c(c1Cl)CN(c1nc(OC[C@@]34CCCN3C[C@H](F)C4)nc(N3CC4(CCc5sc(N)c(C#N)c54)C3)n1)CCC2]

Compound 5 was prepared similarly to that of Ex. 1 using Intermediate 3 instead of tert-butyl (1R,5S)-3,8-diazabicyclo[3.2.1]octane-8-carboxylate. LCMS calcd for C$_{31}$H$_{38}$ClFN$_{11}$O$_2$S (M+H)$^+$ m/z=682.3, found: 682.4. $^1$H NMR (400 MHz, CD$_3$OD) δ 5.26 (d, J=54.4 Hz, 1H), 5.01-4.92 (m, 2H), 4.64-3.98 (m, 10H), 3.25-3.11 (m, 3H), 3.07 (s, 6H), 3.01-2.92 (m, 1H), 2.79-2.67 (m, 4H), 2.26-1.79 (m, 8H).

343

Compound 6. 2-amino-1'-[4-[[1-(morpholinomethyl)cyclopropyl]methoxy]-6-[(5R)-2,4-dioxo-1,3,9-triazaspiro[4.5]decan-9-yl]-1,3,5-triazin-2-yl]spiro[6,7-dihydro-5H-benzothiophene-4,3'-azetidine]-3-carbonitrile

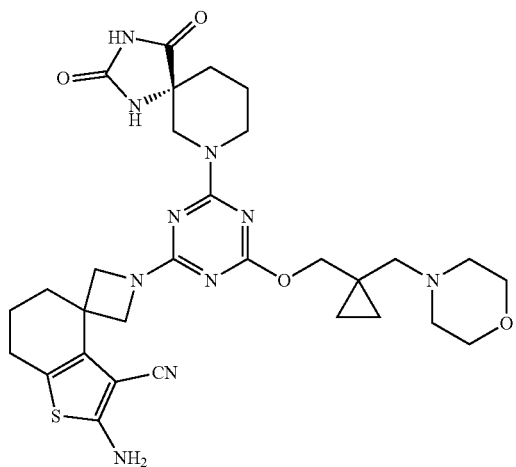 [SMILES: N#Cc1c(N)sc2c1C1(CCC2)CN(c2nc(OCC3(CN4CCOCC4)CC3)nc(N3CCC[C@]4(C3)NC(=O)NC4=O)n2)C1]

Compound 6 was prepared similarly to that of Ex. 1 as a TFA salt. LCMS calcd for $C_{30}H_{39}N_{10}O_4S$ (M+H)$^+$ m/z=635.3 found: 635.5. $^1$H NMR (400 MHz, CD$_3$OD) δ 4.76-4.23 (m, 5H), 4.17-3.52 (m, 8H), 3.21-3.01 (m, 2H), 2.59-2.40 (m, 1H), 2.26-1.97 (m, 4H), 1.95-1.66 (m, 4H), 1.41-1.25 (m, 6H), 0.97-0.89 (m, 2H), 0.84 (dt, J=20.2, 12.1 Hz, 2H)

Example 2. Exemplary Synthesis of 2-amino-1'-[4-(2,4-dioxo-1,3,9-triazaspiro[4.5]decan-9-yl)-6-[[1-(morpholinomethyl)cyclopropyl]methoxy]-1,3,5-triazin-2-yl]spiro[5,6-dihydrocyclopenta[b]thiophene-4,3'-azetidine]-3-carbonitrile (Compound 7)

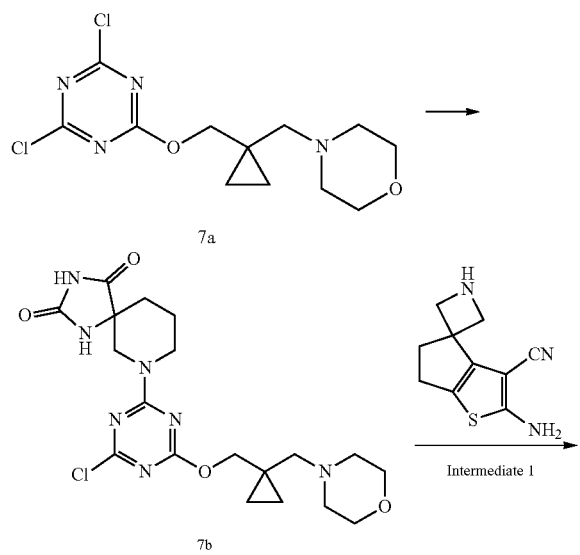

344

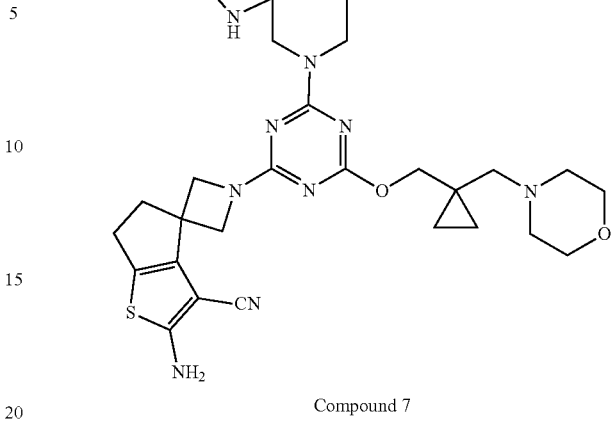

Compound 7

Step 1. Synthesis of 4-[[1-[(4,6-dichloro-1,3,5-triazin-2-yl)oxymethyl]cyclopropyl]methyl]morpholine (7a). A solution of 2,4,6-trichloro-1,3,5-triazine (50 mg, 0.27 mmol) in Acetone (5 mL) was added [1-(morpholinomethyl)cyclopropyl]methanol (85.43 mg, 0.5 mmol) in NMP (5 mL) at 0° C. The mixture was stirred at 15° C. for 4 h. The reaction mixture was used directly for the next step. 4-[[1-[(4,6-dichloro-1,3,5-triazin-2-yl)oxymethyl]cyclopropyl]methyl]morpholine (7a, 86 mg). LCMS calcd for $C_{12}H_{17}Cl_2N_4O_2$ (M+H)$^+$ m/z=319.1, found: 319.0.

Step 2. Synthesis of 9-[4-chloro-6-[[1-(morpholinomethyl)cyclopropyl]methoxy]-1,3,5-triazin-2-yl]-1,3,9-triazaspiro[4.5]decane-2,4-dione (7b). A solution of 4-[[1-[(4,6-dichloro-1,3,5-triazin-2-yl)oxymethyl]cyclopropyl]methyl]morpholine (7a, 86.54 mg, 0.27 mmol) in Acetone (5 mL) and NMP (5 mL) was added 1,3,9-triazaspiro[4.5]decane-2,4-dione (45.87 mg, 0.27 mmol) at 15° C. The mixture was stirred at 50° C. for 16 h. The reaction mixture was used directly for the next step. 9-[4-chloro-6-[[1-(morpholinomethyl)cyclopropyl]methoxy]-1,3,5-triazin-2-yl]-1,3,9-triazaspiro[4.5]decane-2,4-dione (7b, 122 mg). LCMS calcd for $C_{19}H_{27}ClN_7O_4$ (M+H)$^+$ m/z=452.2, found: 452.1.

Step 3. Synthesis of 2-amino-1'-[4-(2,4-dioxo-1,3,9-triazaspiro[4.5]decan-9-yl)-6-[[1-(morpholinomethyl)cyclopropyl]methoxy]-1,3,5-triazin-2-yl]spiro[5,6-dihydrocyclopenta[b]thiophene-4,3'-azetidine]-3-carbonitrile (Compound 7). A solution of crude 9-[4-chloro-6-[[1-(morpholinomethyl)cyclopropyl]methoxy]-1,3,5-triazin-2-yl]-1,3,9-triazaspiro[4.5]decane-2,4-dione (122.53 mg, 0.27 mmol) in Acetone (5 mL) and NMP (5 mL) was added a solution of 2-aminospiro[5,6-dihydrocyclopenta[b]thiophene-4,3'-azetidine]-3-carbonitrile; methanesulfonic acid (98.06 mg, 0.33 mmol) and DIEA (140.17 mg, 1.08 mmol) in NMP (1 mL) at 50° C. The mixture was stirred at 80° C. for 1 h. The reaction was concentrated in vacuum to give the residue and was added water (30 mL). The solution was extracted with EtOAc (30 mL×3). The combined organic layers were washed with brine (20 mL×3), dried over Na$_2$SO$_4$, concentrated. The crude product was purified by flash chromatography (eluted with CH$_3$CN in H$_2$O (0.1% NH$_4$HCO$_3$) from 5.0% to 95%) to give 91% purity product. The product was purified again by flash chromatography (eluted with CH$_3$CN in H$_2$O (0.1% TFA) from 5.0% to 95%). 2-amino-1'-[4-(2,4-dioxo-1,3,9-triazaspiro[4.5]decan-9-yl)-6-[[1-(morpholinomethyl)cyclopropyl]methoxy]-

1,3,5-triazin-2-yl]spiro[5,6-dihydrocyclopenta[b]thiophene-4,3'-azetidine]-3-carbonitrile (Compound 7, 5.52 mg, 0.0073 mmol, 2.71% yield) was obtained as yellow solid. LCMS calcd for $C_{29}H_{37}N_{10}O_4S$ (M+H)+ m/z=621.3, found: 621.1. ¹H NMR (400 MHz, CD₃OD) δ 4.67-4.41 (m, 2H), 4.32 (s, 4H), 4.18 (s, 2H), 4.04 (s, 2H), 3.86 (s, 2H), 3.67 (s, 2H), 3.44 (d, J=13.4 Hz, 1H), 3.22-3.02 (m, 3H), 2.83-2.61 (m, 5H), 2.08 (dd, J=16.9, 7.9 Hz, 1H), 1.97-1.59 (m, 4H), 0.94 (s, 2H), 0.83 (s, 2H).

Compound 8. 2-amino-1'-[4-(4-cyanoazepan-1-yl)-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

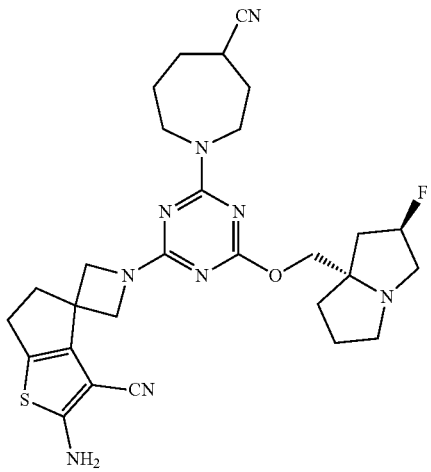 [SMILES: N#Cc1c(N)sc2c1C1(CC2)CN(c2nc(OC[C@@]34CCCN3C[C@H](F)C4)nc(N3CCCC(C#N)CC3)n2)C1]

Compound 8 was prepared similarly to that of Ex. 1 as a TFA salt. LCMS calcd for $C_{28}H_{35}FN_9OS$ (M+H)+ m/z=564.3, found: 564.8. ¹H NMR (400 MHz, CD₃OD) δ 5.55 (d, J=51.4 Hz, 1H), 4.60-4.47 (m, 2H), 4.39-4.35 (m, 2H), 4.19 (d, J=9.4 Hz, 2H), 4.02-3.78 (m, 7H), 3.44 (td, J=10.8, 5.7 Hz, 1H), 3.03 (s, 1H), 2.84-2.48 (m, 6H), 2.41-1.75 (m, 10H)

Compound 9. 2-amino-1'-[4-[(1R,5S)-3,8-diazabicyclo[3.2.1]octan-3-yl]-6-[[1-(morpholinomethyl)cyclopropyl]methoxy]-1,3,5-triazin-2-yl]spiro[5,6-dihydrocyclopenta[b]thiophene-4,3'-pyrrolidine]-3-carbonitrile

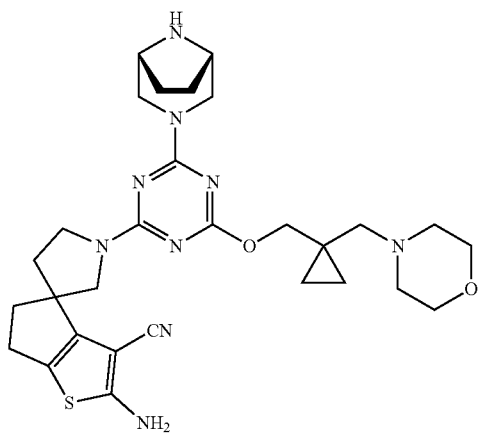

Compound 9 was prepared similarly to that of Ex. 1 as a TFA salt using Int-4. LCMS calcd for $C_{29}H_{40}N_9O_2S$ (M+H)+ m/z=578.3, found: 578.2. ¹H NMR (400 MHz, CD₃OD) δ 5.09-4.90 (m, 2H), 4.82-4.58 (m, 2H), 4.40-4.25 (m, 2H), 4.20-3.96 (m, 4H), 3.93-3.49 (m, 8H), 3.39-3.32 (m, 1H), 3.28-3.07 (m, 3H), 2.89-2.70 (m, 2H), 2.44-2.26 (m, 3H), 2.15-1.83 (m, 5H), 0.97-0.75 (m, 4H).

Compound 10. 2-amino-1'-[4-[[(2R,8S)-2-fluoro-1,2,3,5,6,7-hexahydropyrrolizin-8-yl]methoxy]-6-[(3R)-3-hydroxy-3-methyl-1-piperidyl]-1,3,5-triazin-2-yl]spiro[5,6-dihydrocyclopenta[b]thiophene-4,3'-azetidine]-3-carbonitrile

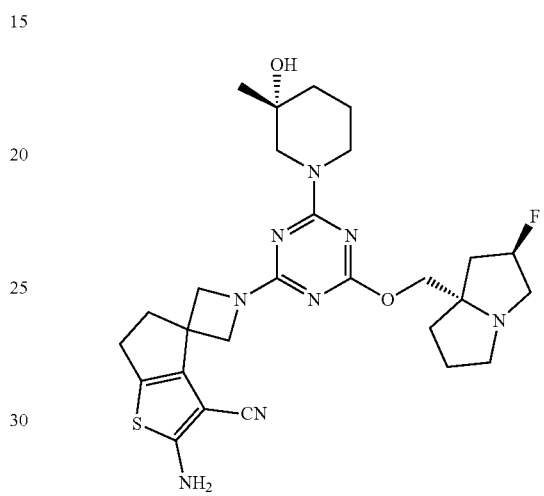

Compound 10 was prepared similarly to that of Ex. 1 as a TFA salt. LCMS calcd for $C_{27}H_{36}FN_8O_2S$ (M+H)+ m/z=555.3, found: 555.8. ¹H NMR (400 MHz, CD₃OD) δ 5.54 (d, J=51.8 Hz, 1H), 4.54 (m, 2H), 4.28 (m, 4H), 4.04-3.71 (m, 5H), 3.62-3.35 (m, 3H), 2.79-2.48 (m, 6H), 2.41-2.04 (m, 4H), 1.90-1.48 (m, 4H), 1.21 (s, 3H).

Compound 11. 2-amino-1'-[4-[[(2R,8S)-2-fluoro-1,2,3,5,6,7-hexahydropyrrolizin-8-yl]methoxy]-6-[(3R)-3-hydroxy-3-methyl-1-piperidyl]-1,3,5-triazin-2-yl]spiro[5,6-dihydrocyclopenta[b]thiophene-4,3'-pyrrolidine]-3-carbonitrile

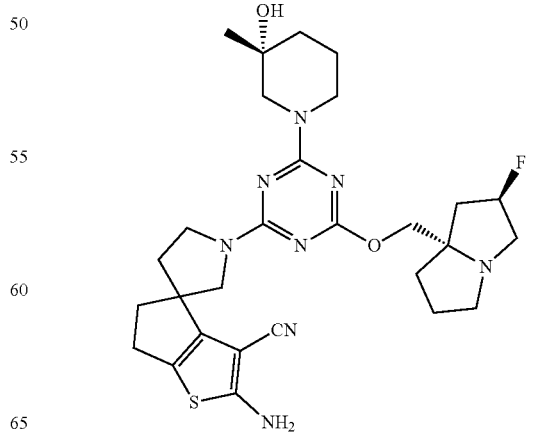

Compound 11 was prepared similarly to that of Ex. 1 as a TFA salt using Int-4. LCMS calcd for $C_{28}H_{38}FN_8O_2S$ (M+H)$^+$ m/z=569.3, found: 569.3. $^1$H NMR (400 MHz, CD$_3$OD) δ 5.54 (d, J=52.0 Hz, 1H), 4.54 (s, 2H), 4.32-3.78 (m, 6H), 3.78-3.34 (m, 6H), 2.93-2.47 (m, 4H), 2.47-2.22 (m, 6H), 2.21-1.49 (m, 6H), 1.21 (d, J=5.3 Hz, 3H).

Compound 12. 2-amino-1'-[4-(4-cyanoazepan-1-yl)-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-pyrrolidine]-3-carbonitrile

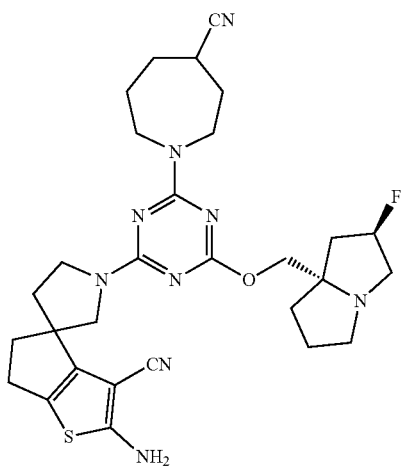 [SMILES: N#Cc1c(N)sc2c1C1(CC2)CCN(c2nc(OC[C@@]34CCCN3C[C@H](F)C4)nc(N3CCCC(C#N)CC3)n2)C1]

Compound 12 was prepared similarly to that of Ex. 1 as a TFA salt using Int-4. LCMS calculated for $C_{29}H_{37}FN_9OS$ (M+H)$^+$ m/z=578.3, found: 578.2. $^1$H NMR (400 MHz, CD$_3$OD) δ: 5.54 (d, J=51.6 Hz, 1H), 4.64-4.47 (m, 2H), 4.06-3.60 (m, 11H), 3.48-3.40 (m, 1H), 3.05-3.03 (m, 1H), 2.85-2.78 (s, 2H), 2.74-2.67 (m, 2H), 2.39-2.27 (m, 6H), 2.15-1.89 (m, 8H).

Compound 13. 2-amino-1'-[4-(3-cyano-1-piperidyl)-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

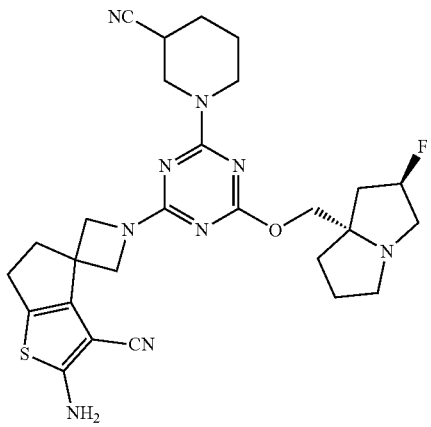 [SMILES: N#Cc1c(N)sc2c1C1(CC2)CN(c2nc(OC[C@@]34CCCN3C[C@H](F)C4)nc(N3CCCC(C#N)C3)n2)C1]

Compound 13 was prepared similarly to that of Ex. 1 as a formate salt. LCMS calcd for $C_{27}H_{33}FN_9OS$ (M+H)$^+$ m/z=550.2, found: 550.6. $^1$H NMR (400 MHz, CD$_3$OD) δ 5.43 (d, J=52.7 Hz, 1H), 4.51-4.24 (m, 4H), 4.24-3.80 (m, 5H), 3.79-3.42 (m, 4H), 3.29-3.21 (m, 1H), 2.95 (s, 1H), 2.86-2.64 (m, 4H), 2.57-1.89 (m, 8H), 1.88-1.47 (m, 2H).

Compound 14. 2-amino-1'-[4-[(1-cyanocyclopropyl)methyl-methyl-amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-pyrrolidine]-3-carbonitrile

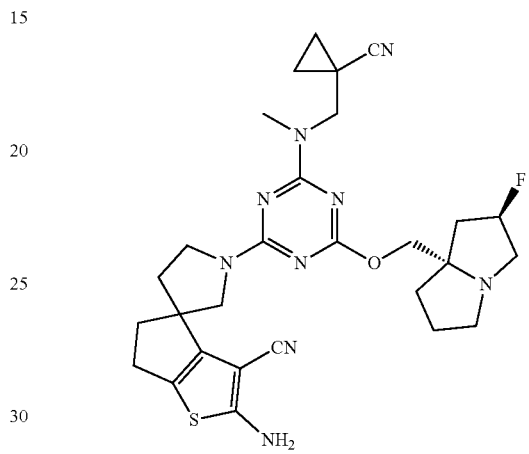

Compound 14 was prepared similarly to that of Ex. 1 as a TFA salt. LCMS calcd for $C_{28}H_{35}FN_9OS$ (M+H)$^+$ m/z=564.3, found: 564.2. $^1$H NMR (400 MHz, CD$_3$OD) δ 5.55 (d, J=50.8 Hz, 1H), 4.68-4.45 (m, 2H), 4.16-3.53 (m, 9H), 3.50-3.38 (m, 1H), 3.28 (s, 3H), 2.85-2.47 (m, 4H), 2.47-1.93 (m, 8H), 1.33-1.13 (m, 4H).

Compound 15. 2-amino-1'-[4-[(1-cyanocyclopropyl)methyl-methyl-amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

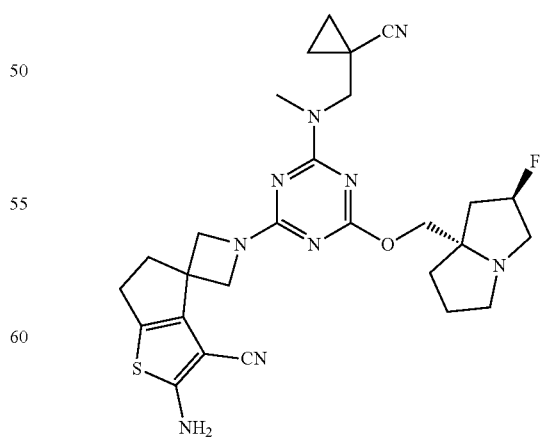

Compound 15 was prepared similarly to that of Ex. 1 as a TFA salt. LCMS calcd for $C_{27}H_{33}FN_9OS$ (M+H)$^+$ m/z=550.2, found: 550.2. ¹H NMR (400 MHz, CD₃OD) δ 5.55 (d, J=51.6 Hz, 1H), 4.64-4.47 (m, 2H), 4.42-4.32 (m, 2H), 4.27-3.77 (m, 6H), 3.67-3.37 (m, 2H), 3.25 (s, 3H), 2.83-2.47 (m, 6H), 2.43-2.23 (m, 3H), 2.18-2.06 (m, 1H), 1.34-1.12 (m, 4H).

Example 3. Exemplary Synthesis of 2-amino-1'-[4-[(1-cyanocyclopropyl)methoxy]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile (Compound 16)

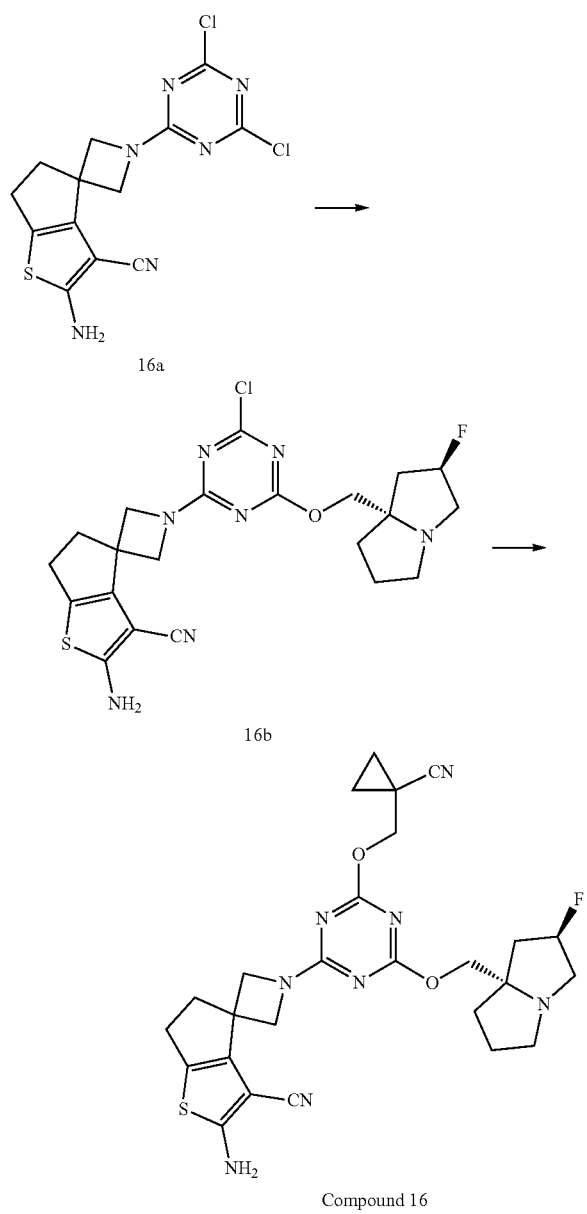

Step 1. Synthesis of 2-amino-1'-(4,6-dichloro-1,3,5-triazin-2-yl)spiro[5,6-dihydrocyclopenta[b]thiophene-4,3'-azetidine]-3-carbonitrile (16a). To a solution of 2-aminospiro[5,6-dihydrocyclopenta[b]thiophene-4,3'-azetidine]-3-carbonitrile; methanesulfonic acid (200 mg, 0.66 mmol) and DIEA (0.35 mL, 1.99 mmol) in DCM (3 mL) at −60° C. was added 2-aminospiro[5,6-dihydrocyclopenta[b]thiophene-4,3'-azetidine]-3-carbonitrile methanesulfonic acid (200 mg, 0.66 mmol) in DCM which was filtrated. The reaction was stirred at −60° C. for 30 min. The reaction was washed with brine (50 mL×2) and dried over Na₂SO₄, the organic layer was filtrated and concentrated under vacuum. Then, MeCN (2 mL×5) was added to the crude, filtration afford a light-yellow solid. The crude was purified by pre-HPLC (ACN/FA-H₂O) to get 2-amino-1'-(4,6-dichloro-1,3,5-triazin-2-yl)spiro[5,6-dihydrocyclopenta[b]thiophene-4,3'-azetidine]-3-carbonitrile (80 mg, 0.2265 mmol, 34.13% yield) and 2-amino-1'-(4,6-dichloro-1,3,5-triazin-2-yl)spiro[5,6-dihydrocyclopenta[b]thiophene-4,3'-azetidine]-3-carbonitrile (16a, 30 mg, 0.0849 mmol, 12.7% yield). LCMS calculated for C₁₃H₁₁Cl₂N₆S (m/z)=353.0; found: 353.0.

Step 2. Synthesis of 2-amino-1'-[4-chloro-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile (16b). To a solution of [(2R,8S)-2-fluoro-1,2,3,5,6,7-hexahydropyrrolizin-8-yl]methanol (27.04 mg, 0.17 mmol) and 2-amino-1'-(4,6-dichloro-1,3,5-triazin-2-yl)spiro[5,6-dihydrocyclopenta[b]thiophene-4,3'-azetidine]-3-carbonitrile (16a, 30 mg, 0.08 mmol) in THF (2 mL) was added K₂CO₃ (35.16 mg, 0.25 mmol). The mixture was stirred at 20° C. for 48 h. Water was added, the mixture was extracted by DCM, concentrated to get a crude. The crude was purified by flash (DCM/MeOH=10/1) to get 2-amino-1'-[4-chloro-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile (16b, 27 mg, 0.0567 mmol, 66.791% yield). LCMS calculated for C₂₁H₂₄ClFN₇OS (m/z)=476.1; found: 475.9

Step 3. Synthesis of 2-amino-1'-[4-[(1-cyanocyclopropyl)methoxy]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile (Compound 16). To a solution of 2-amino-1'-[4-chloro-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile (16b, 27 mg, 0.06 mmol) and 1-(hydroxymethyl)cyclopropanecarbonitrile (16.53 mg, 0.17 mmol) in THF (3 mL) was added LiHMDS (0.28 mL, 0.28 mmol) and KI (0.73 mg, 0.01 mmol) at 0° C. under N₂. The mixture was stirred at rt for 16 h. Water was added into the mixture, extracted with EtOAc, dried, filtered and concentrated under vacuum. The crude product was purified by pre-HPLC (ACN/H₂O—NH₄HCO₃) to afford 2-amino-1'-[4-[(1-cyanocyclopropyl)methoxy]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile (Compound 16, 8.9 mg, 0.017 mmol, 29.24% yield) as a white solid. LCMS calculated for C₂₆H₃₀FN₈O₂S (M+H)⁺ m/z=537.2; found: 537.0. ¹H NMR (400 MHz, CD₃OD) δ 5.26 (d, J=54.0 Hz, 1H), 4.07-4.45 (m, 8H), 3.10-3.24 (m, 3H), 2.92-3.02 (m, 1H), 2.67-2.80 (m, 4H), 1.80-2.27 (m, 6H), 1.32-1.42 (m, 2H), 1.19-1.26 (m, 2H).

Compound 17. 2-amino-1'-[4-(2-cyanopropoxy)-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

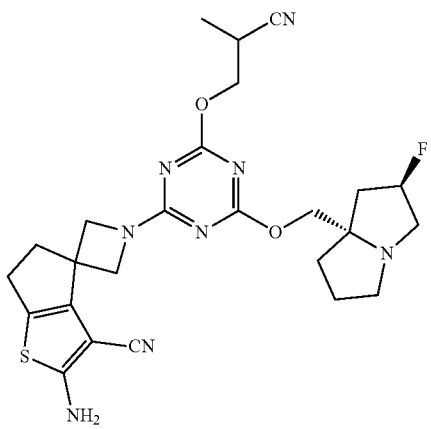 [SMILES: CC(C#N)COc1nc(OC[C@@]23CCCN2C[C@H](F)C3)nc(N2CC3(CCc4sc(N)c(C#N)c43)C2)n1]

Compound 17 was prepared similarly to that of Ex. 3. LCMS calculated for $C_{25}H_{30}FN_8O_2S$ (M+H)$^+$ m/z=525.2; found: 525.0. $^1$H NMR (400 MHz, CD$_3$OD) δ 5.26 (d, J=54.0 Hz, 1H), 4.34-4.50 (m, 4H), 4.06-4.26 (m, 4H), 3.11-3.28 (m, 4H), 2.93-3.02 (m, 1H), 2.67-2.81 (m, 4H), 1.78-2.29 (m, 6H), 1.35-1.43 (m, 3H).

Compound 18. 2-amino-1'-[4-[[(2R)-2-fluoro-1,2,3,5,6,7-hexahydropyrrolizin-8-yl]methoxy]-6-[3-(hydroxymethyl)-3-methyl-1-piperidyl]-1,3,5-triazin-2-yl]spiro[5,6-dihydrocyclopenta[b]thiophene-4,3'-azetidine]-3-carbonitrile

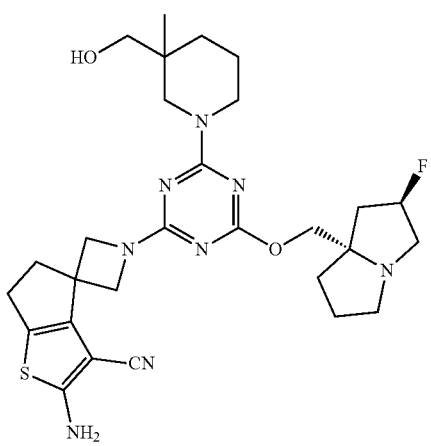 [SMILES: CC1(CO)CCCN(c2nc(OC[C@@]34CCCN3C[C@H](F)C4)nc(N3CC4(CCc5sc(N)c(C#N)c54)C3)n2)C1]

Compound 18 was prepared similarly to that of Ex. 1 as a TFA salt. LCMS calcd for $C_{28}H_{38}FN_8O_2S$ (M+H)$^+$ m/z=569.3; found: 569.6. $^1$H NMR (400 MHz, CD$_3$OD) δ 5.55 (d, J=51.7 Hz, 1H), 4.70-4.45 (m, 2H), 4.44-4.31 (m, 2H), 4.20 (m, 2H), 4.09-3.67 (m, 5H), 3.62 (s, 2H), 3.54-3.33 (m, 2H), 3.30-3.25 (m, 1H), 2.84-2.67 (m, 4H), 2.68-2.45 (m, 2H), 2.42-2.06 (m, 4H), 1.63 (s, 3H), 1.47-1.35 (m, 1H), 0.92 (s, 3H)

Compound 19. 2-amino-1'-[4-(3-cyano-3-methyl-1-piperidyl)-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

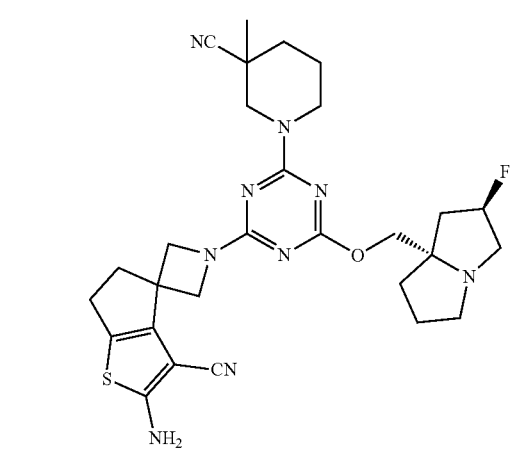 [SMILES: CC1(C#N)CCCN(c2nc(OC[C@@]34CCCN3C[C@H](F)C4)nc(N3CC4(CCc5sc(N)c(C#N)c54)C3)n2)C1]

Compound 19 was prepared similarly to that of Ex. 1 as a formate salt. LCMS calcd for $C_{28}H_{35}FN_9OS$ (M+H)$^+$ m/z=564.3, found: 564.2. $^1$H NMR (400 MHz, CD$_3$OD) δ 8.50 (s, 1H), 5.40 (d, J=52.4 Hz, 1H), 4.68 (s, 1H), 4.32 (m, 4H), 4.16 (s, 3H), 3.71-3.43 (m, 4H), 3.20 (m, 1H), 2.95 (s, 2H), 2.81-2.64 (m, 4H), 2.51-2.31 (m, 2H), 2.23 (m, 1H), 2.19-2.05 (m, 3H), 2.03-1.90 (m, 1H), 1.76 (s, 2H), 1.69-1.57 (m, 1H), 1.38 (s, 3H).

Compound 20. 2-amino-1'-[4-[[(2R,8S)-2-fluoro-1,2,3,5,6,7-hexahydropyrrolizin-8-yl]methoxy]-6-[(3R)-3-(hydroxymethyl)-1-piperidyl]-1,3,5-triazin-2-yl]spiro[5,6-dihydrocyclopenta[b]thiophene-4,3'-azetidine]-3-carbonitrile

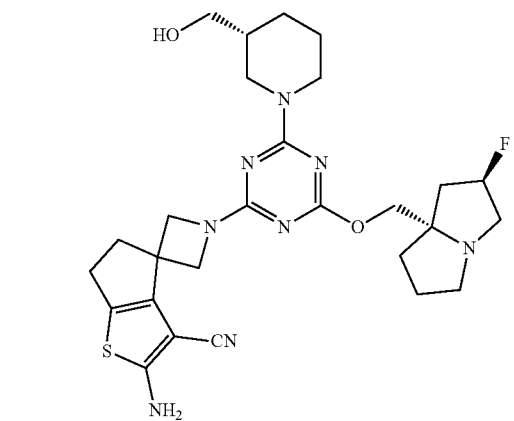 [SMILES: N#Cc1c(N)sc2c1C1(CC2)CN(c2nc(OC[C@@]34CCCN3C[C@H](F)C4)nc(N3CCC[C@@H](CO)C3)n2)C1]

Compound 20 was prepared similarly to that of Ex. 1 as a TFA salt. LCMS calcd for $C_{27}H_{36}FN_8O_2S$ (M+H)$^+$ m/z=555.2; found: 555.2. $^1$H NMR (400 MHz, CD$_3$OD) δ 5.55 (d, J=51.9 Hz, 1H), 4.74-4.44 (m, 4H), 4.43-4.29 (m, 2H), 4.19 (d, J=9.4 Hz, 2H), 4.06-3.77 (m, 3H), 3.53-3.34 (m, 3H), 3.05 (t, J=11.0 Hz, 1H), 2.93-2.81 (m, 1H), 2.81-2.64 (m, 4H), 2.64-2.06 (m, 6H), 1.95-1.71 (m, 2H), 1.72-1.63 (m, 1H), 1.59-1.41 (m, 1H), 1.35-1.22 (m, 1H).

Compound 21. 2-amino-1'-[4-[(3S,4R)-3,4-dihydroxy-3-methyl-1-piperidyl]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

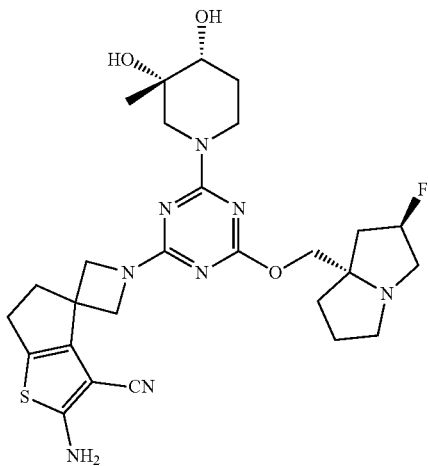 [SMILES: C[C@]1(O)CN(c2nc(OC[C@@]34CCCN3C[C@H](F)C4)nc(N3CC4(CCc5sc(N)c(C#N)c54)C3)n2)CC[C@H]1O]

Compound 21 was prepared similarly to that of Ex. 3 as a cis-diol mixture of diastereomers, TFA salt. LCMS calculated for $C_{27}H_{36}FN_8O_3S$ (M+H)$^+$ m/z=571.3; found: 571.0. $^1$H NMR (400 MHz, CD$_3$OD) δ 5.26 (d, J=54.8 Hz, 1H), 4.28-4.41 (m, 2H), 3.98-4.25 (m, 6H), 3.32-3.55 (m, 3H), 3.14-3.26 (m, 3H), 2.92-3.03 (m, 1H), 2.64-2.81 (m, 4H), 1.70-2.30 (m, 8H), 1.20 (s, 3H).

Compound 22. 2-amino-1'-[4-[rac-(3S,4R)-3,4-dihydroxy-1-piperidyl]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

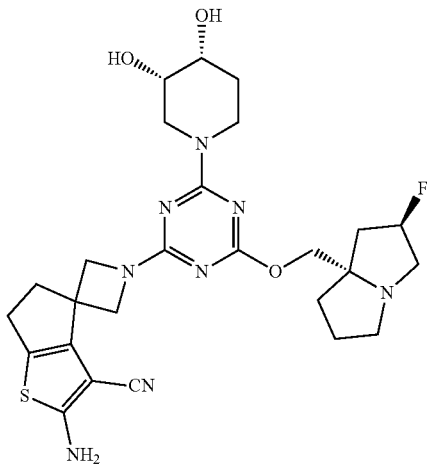 [SMILES: N#Cc1c(N)sc2c1C1(CC2)CN(c2nc(OC[C@@]34CCCN3C[C@H](F)C4)nc(N3CC[C@@H](O)[C@@H](O)C3)n2)C1]

Compound 22 was prepared similarly to that of Ex. 3 as a cis-diol mixture of diastereomers. LCMS calculated for $C_{26}H_{34}FN_8O_3S$ (M+H)$^+$ m/z=557.2; found: 557.4. $^1$H NMR (400 MHz, CD$_3$OD) δ 5.26 (d, J=54.4 Hz, 1H), 4.27-4.40 (m, 2H), 3.99-4.20 (m, 4H), 3.62-3.95 (m, 6H), 3.10-3.27 (m, 3H), 2.90-3.04 (m, 1H), 2.63-2.81 (m, 4H), 1.59-2.32 (m, 8H).

Compound 23. 2-amino-1'-[4-[[(2R,8S)-2-fluoro-1,2,3,5,6,7-hexahydropyrrolizin-8-yl]methoxy]-6-[(3R)-3-hydroxy-1-piperidyl]-1,3,5-triazin-2-yl]spiro[5,6-dihydrocyclopenta[b]thiophene-4,3'-azetidine]-3-carbonitrile

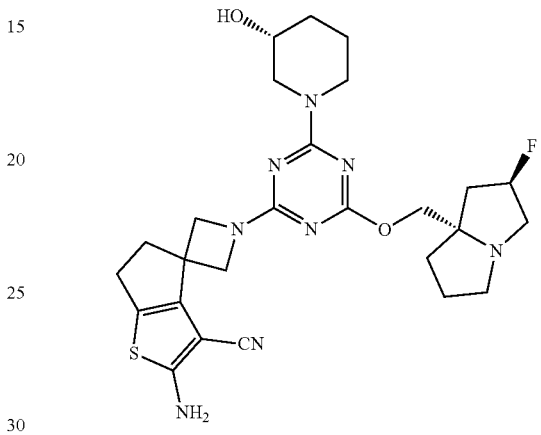

Compound 23 was prepared similarly to that of Ex. 1 as a TFA salt. LCMS calcd for $C_{26}H_{33}FN_8O_2S$ (M+H)$^+$ m/z=541.66, found: 541.5. $^1$H NMR (400 MHz, CD$_3$OD) δ 5.45 (d, J=51.3 Hz, 1H), 4.43 (m, 2H), 4.26 (m, 2H), 4.07 (m, 2H), 3.81 (m, 3H), 3.52 (m, 2H), 3.37 (m, 2H), 2.71-2.56 (m, 4H), 2.46 (m, 2H), 2.29-1.86 (m, 6H), 1.71 (m, 1H), 1.49 (m, 3H).

Compound 24. 2-amino-1'-[4-[[(2R,8S)-2-fluoro-1,2,3,5,6,7-hexahydropyrrolizin-8-yl]methoxy]-6-[rac-(2R,3R)-3-(hydroxymethyl)-2-methyl-1-piperidyl]-1,3,5-triazin-2-yl]spiro[5,6-dihydrocyclopenta[b]thiophene-4,3'-azetidine]-3-carbonitrile

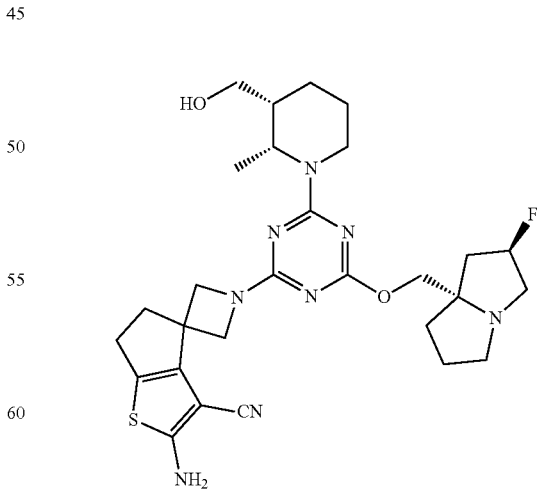

Compound 24 was prepared similarly to that of Ex. 1. LCMS calcd for $C_{28}H_{38}FN_8O_2S$ (M+H)$^+$ m/z=569.2; found: 569.6. $^1$H NMR (400 MHz, CD$_3$OD) δ 5.36-5.12 (m, 2H), 4.71-4.59 (m, 1H), 4.38-4.28 (m, 2H), 4.20-3.98 (m, 4H), 3.46-3.38 (m, 2H), 3.31-3.10 (m, 3H), 3.03-2.83 (m, 2H), 2.80-2.65 (m, 4H), 2.34-2.02 (m, 2H), 2.00-1.57 (m, 6H), 1.50-1.25 (m, 2H), 1.07 (d, J=7.2 Hz, 3H).

Compound 25. 2-amino-1'-[4-[3-(cyanomethyl)-5-fluoro-3,6-dihydro-2H-pyridin-1-yl]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

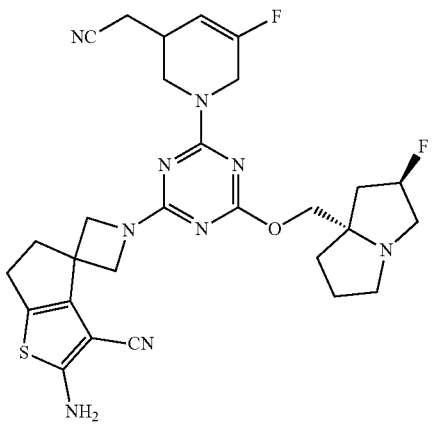 [SMILES: N#CCC1C=C(F)CN(c2nc(OC[C@@]34CCCN3C[C@H](F)C4)nc(N3CC4(CCc5sc(N)c(C#N)c54)C3)n2)C1]

Compound 25 was prepared similarly to that of Ex. 3. LCMS calculated for C$_{28}$H$_{32}$F$_2$N$_9$OS (M+H)$^+$ m/z=580.23; found: 580.4. $^1$H NMR (400 MHz, CD$_3$OD) δ 5.44 (dd, J=16.0, 4.8 Hz, 1H), 5.26 (d, J=54.4 Hz, 1H), 3.96-4.59 (m, 9H), 3.52-3.72 (m, 1H), 3.08-3.28 (m, 3H), 2.89-3.04 (m, 1H), 2.64-2.83 (m, 5H), 2.41-2.61 (m, 2H), 1.77-2.30 (m, 6H).

Compound 26. 2-amino-1'-[4-[(3R,5R)-3,5-dihydroxy-1-piperidyl]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

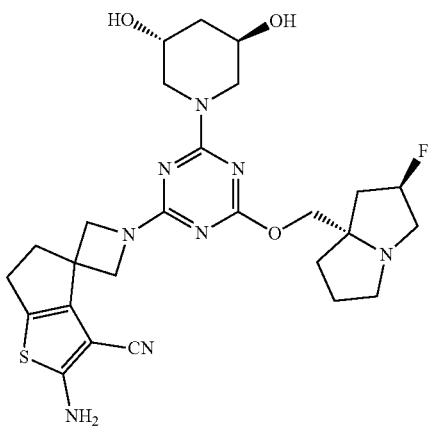 [SMILES: N#Cc1c(N)sc2c1C1(CC2)CN(c2nc(OC[C@@]34CCCN3C[C@H](F)C4)nc(N3C[C@H](O)C[C@@H](O)C3)n2)C1]

Compound 26 was prepared similarly to that of Ex. 3. LCMS calculated for C$_{26}$H$_{34}$FN$_8$O$_3$S (M+H)$^+$ m/z=557.24; found: 557.8. $^1$H NMR (400 MHz, CD$_3$OD) δ 5.26 (d, J=53.2 Hz, 1H), 4.27-4.42 (m, 2H), 3.54-4.20 (m, 10H), 3.13-3.28 (m, 3H), 2.91-3.03 (m, 1H), 2.67-2.81 (m, 4H), 1.76-2.29 (m, 8H).

Compound 27. 2-amino-1'-[4-(2-cyanopropylsulfanyl)-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

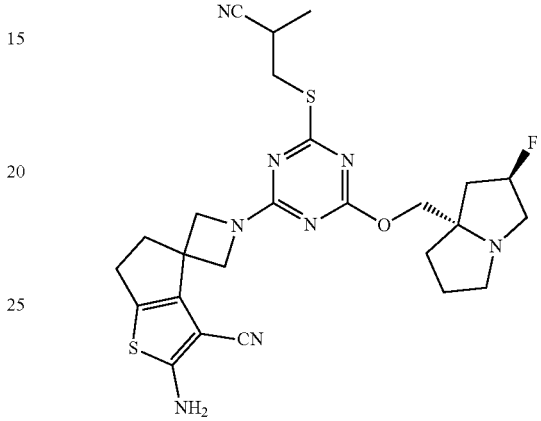

Compound 27 was prepared similarly to that of Ex. 3 as a formate salt. LCMS calculated for C$_{25}$H$_{30}$FN$_8$OS$_2$ (M+H)$^+$ m/z=541.19; found: 541.2. $^1$H NMR (400 MHz, CD$_3$OD) δ 5.34 (d, J=52.4 Hz, 1H), 4.15-4.48 (m, 6H), 3.21-3.46 (m, 6H), 3.05-3.16 (m, 1H), 2.68-2.83 (m, 4H), 1.86-2.41 (m, 6H), 1.35-1.47 (m, 3H).

Compound 28. 2-amino-1'-[4-[[(2R,8S)-2-fluoro-1,2,3,5,6,7-hexahydropyrrolizin-8-yl]methoxy]-6-[rac-(3R,4S)-4-hydroxytetrahydrofuran-3-yl]oxy-1,3,5-triazin-2-yl]spiro[5,6-dihydrocyclopenta[b]thiophene-4,3'-azetidine]-3-carbonitrile

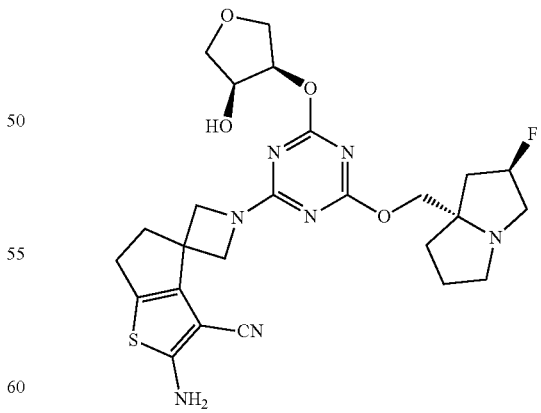

Compound 28 was prepared similarly to that of Ex. 1 as a TFA salt. LCMS calcd for C$_{25}$H$_{31}$N$_7$O$_4$S (M+H)$^+$ m/z=544.2, found: 544.1. $^1$H NMR (400 MHz, CD$_3$OD) δ 5.65-5.36 (m, 2H), 4.64-4.47 (m, 3H), 4.45-4.35 (m, 2H), 4.32-4.21 (m, 2H), 4.17-4.08 (m, 1H), 4.03-3.82 (m, 5H), 3.78-3.66 (m, 1H), 3.54-3.38 (m, 1H), 2.86-2.71 (m, 4H), 2.70-2.48 (m, 2H), 2.44-2.23 (m, 3H), 2.20-2.05 (m, 1H).

Compound 29. 2-amino-1'-[4-[rac-(2R,3R)-3-cyano-2-methyl-1-piperidyl]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

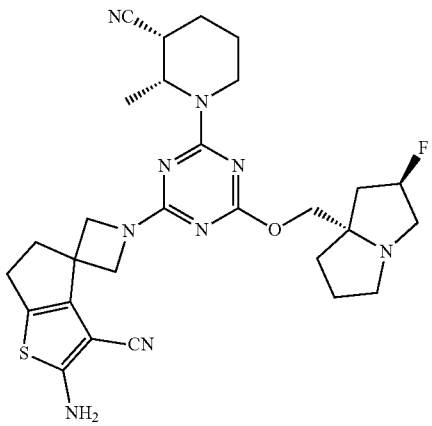 [SMILES: C[C@@H]1[C@H](C#N)CCCN1c1nc(OC[C@@]23CCCN2C[C@H](F)C3)nc(N2CC3(CCc4sc(N)c(C#N)c43)C2)n1]

Compound 29 was prepared similarly to that of Ex. 1 as a TFA salt. LCMS calcd for $C_{28}H_{35}FN_9OS$ $(M+H)^+$ m/z=564.2, found: 564.2. $^1H$ NMR (400 MHz, $CD_3OD$) δ 5.55 (d, J=52.0 Hz, 1H), 5.38-5.29 (m, 1H), 4.70-4.32 (m, 5H), 4.23-4.13 (m, 2H), 4.06-3.78 (m, 3H), 3.50-3.38 (m, 1H), 3.04-2.93 (m, 2H), 2.83-2.46 (m, 6H), 2.41-2.22 (m, 3H), 2.20-1.96 (m, 3H), 1.83-1.73 (m, 1H), 1.55-1.33 (m, 4H).

Compound 30. 2-amino-1'-[4-[[(2R,8S)-2-fluoro-1,2,3,5,6,7-hexahydropyrrolizin-8-yl]methoxy]-6-[(3R)-3-hydroxy-3-methyl-1-piperidyl]-1,3,5-triazin-2-yl]spiro[6,7-dihydro-5H-benzothiophene-4,3'-azetidine]-3-carbonitrile

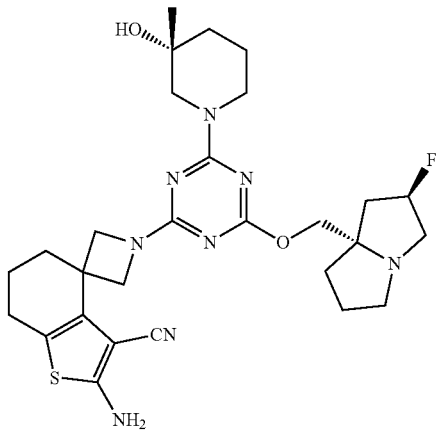 [SMILES: C[C@@]1(O)CCCN(c2nc(OC[C@@]34CCCN3C[C@H](F)C4)nc(N3CC4(CCCc5sc(N)c(C#N)c54)C3)n2)C1]

Compound 30 was prepare similarly to that of Ex. 1 as a formate salt. LCMS calcd for $C_{28}H_{38}FN_{10}O_2S$ $(M+H)^+$ m/z=569.2, found: 569.2. $^1H$ NMR (400 MHz, $CD_3OD$) δ 8.47 (s, 1H), 5.46 (d, J=51.5 Hz, 1H), 4.44 (m, 2H), 4.40 (m, 3H), 4.00-3.36 (m, 9H), 2.63-2.35 (m, 4H), 2.33-2.14 (m, 3H), 2.09 (m, 3H), 1.88-1.73 (m, 3H), 1.68 (s, 2H), 1.55 (s, 1H), 1.20 (s, 3H).

Compound 31. 2-amino-1'-[4-(3-amino-6,7-dihydro-4H-isoxazolo[4,3-c]pyridin-5-yl)-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

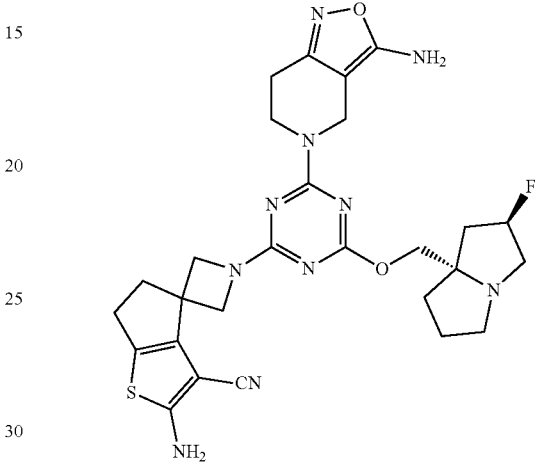

Compound 31 was prepared similarly to that of Ex. 3 as a TFA salt. LCMS for $C_{28}H_{32}FN_{10}O_2S$ $(M+H)^+$ m/z=579.68, found: 579.4. $^1H$ NMR (400 MHz, $CD_3OD$) δ 5.56 (d, J=51.7 Hz, 1H), 4.59-4.37 (m, 4H), 4.38 (m, 2H), 4.25-3.78 (m, 7H), 3.45 (m, 1H), 2.88-2.46 (m, 8H), 2.45-2.25 (m, 3H), 2.14 (s, 1H).

Compound 32. 2-amino-1'-[4-[(1-cyanocyclopropyl)methylsulfanyl]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

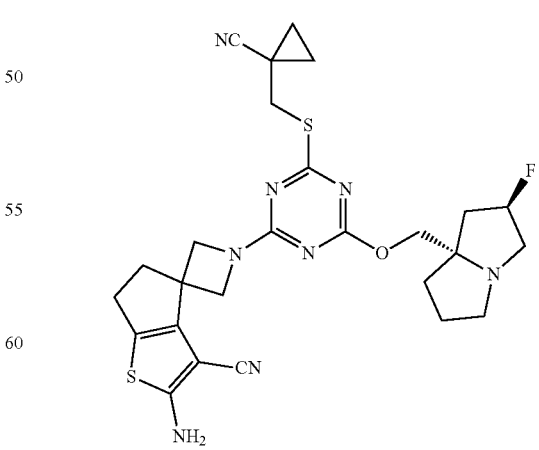

Compound 32 was prepared similarly to that of Ex. 3. LCMS calculated for $C_{26}H_{30}FN_8OS_2$ $(M+H)^+$ m/z=553.19;

found: 553.2. $^1$H NMR (400 MHz, CD$_3$OD) δ 5.26 (d, J=53.6 Hz, 1H), 4.35-4.46 (m, 2H), 4.06-4.30 (m, 4H), 3.44 (m, 2H), 3.11-3.25 (m, 3H), 2.93-3.04 (m, 1H), 2.67-2.84 (m, 4H), 1.77-2.30 (m, 6H), 1.15-1.37 (m, 4H).

Compound 33. [1-[4-(2-amino-3-cyano-spiro[5,6-dihydrocyclopenta[b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-3-piperidyl]cyanamide

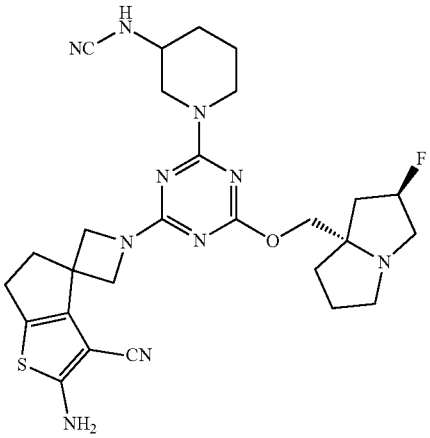 [SMILES: N#CNC1CCCN(c2nc(OC[C@@]34CCCN3C[C@H](F)C4)nc(N3CC4(CCc5sc(N)c(C#N)c54)C3)n2)C1]

Compound 33 was prepared similarly to that of Ex. 1. LCMS calcd for C$_{27}$H$_{34}$FN$_{10}$OS (M+H)$^+$ m/z=565.2, found: 565.2. $^1$H NMR (400 MHz, CD$_3$OD) δ 5.25 (d, J=54.8 Hz, 1H), 4.51-3.96 (m, 8H), 3.66-3.33 (m, 2H), 3.22-3.10 (m, 3H), 3.00-2.91 (m, 1H), 2.76-2.65 (m, 4H), 2.36-2.10 (m, 2H), 2.10-1.71 (m, 6H), 1.70-1.45 (m, 2H).

Compound 34. 2-amino-1'-[4-[[1-[(dimethylamino)methyl]-2,2-difluoro-cyclopropyl]methoxy]-6-[(3R)-3-hydroxy-3-methyl-1-piperidyl]-1,3,5-triazin-2-yl]spiro[5,6-dihydrocyclopenta[b]thiophene-4,3'-azetidine]-3-carbonitrile

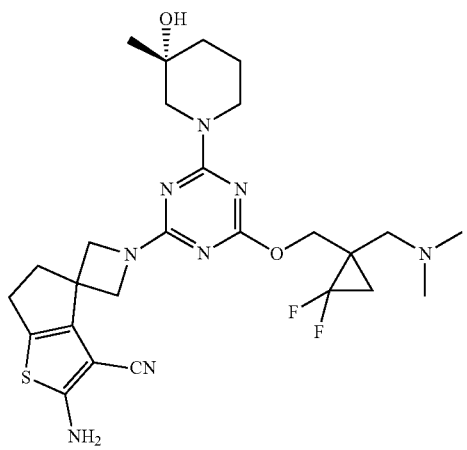 [SMILES: CN(C)CC1(COc2nc(N3CC4(CCc5sc(N)c(C#N)c54)C3)nc(N3CCC[C@@](C)(O)C3)n2)CC1(F)F]

Compound 34 was prepared similarly to that of Ex. 1 as a TFA salt. LCMS calcd for C$_{26}$H$_{35}$F$_2$N$_8$O$_2$S (M+H)$^+$ m/z=561.3, found: 561.4. $^1$H NMR (400 MHz, CD$_3$OD) δ 4.66 (m, 1H), 4.49 (m, 1H), 4.38 (m, 2H), 4.21 (d, J=8.8 Hz, 2H), 3.91 (s, 2H), 3.70 (m, 1H), 3.53 (s, 1H), 3.42 (m, 2H), 2.99 (s, 6H), 2.75 (m, 4H), 1.95 (s, 1H), 1.80 (s, 2H), 1.68 (m, 2H), 1.57 (s, 1H), 1.20 (s, 3H).

Compound 35. 2-amino-1'-[4-(3-amino-2,4,6,7-tetrahydropyrazolo[4,3-c]pyridin-5-yl)-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

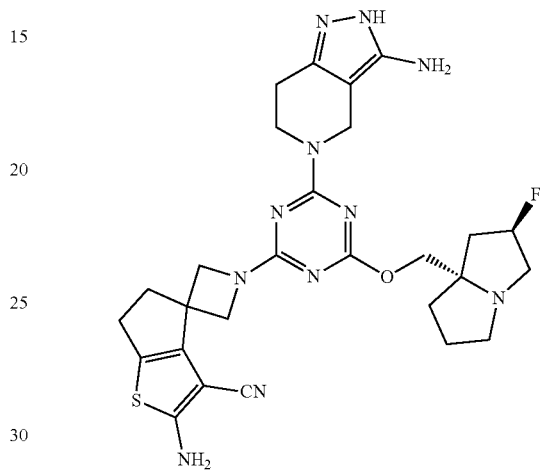

Compound 35 was prepared similarly to that of Ex. 3 as a TFA salt. LCMS calculated for C$_{27}$H$_{33}$FN$_{11}$OS (M+H)$^+$ m/z=578.26, found: 578.2. $^1$H NMR (400 MHz, CD$_3$OD) δ 5.35 (d, J=51.6 Hz, 1H), 4.69-4.49 (m, 4H), 4.39-4.36 (m, 2H), 4.20-4.12 (m, 4H), 4.05-3.82 (m, 3H), 3.48-3.41 (m, 1H), 2.78-2.73 (m, 6H), 2.67-2.49 (m, 2H), 2.37-2.27 (m, 3H), 2.19-2.09 (m, 1H).

Compound 36. 2-amino-1'-[4-[[(2R,8S)-2-fluoro-1,2,3,5,6,7-hexahydropyrrolizin-8-yl]methoxy]-6-[methyl(tetrahydrofuran-3-yl)amino]-1,3,5-triazin-2-yl]spiro[5,6-dihydrocyclopenta[b]thiophene-4,3'-azetidine]-3-carbonitrile

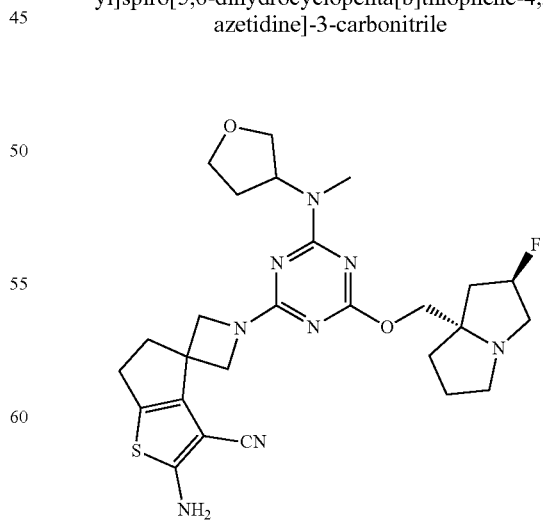

Compound 36 was prepared similarly to that of Ex. 3 as a TFA salt. LCMS calcd for C$_{26}$H$_{34}$F$_7$N$_8$O$_2$S (M+H)$^+$ m/z=541.2, found: 541.2. ¹H NMR (400 MHz, CD₃OD) δ 5.54 (d, J=56 Hz, 2H), 4.58-4.46 (m, 2H), 4.36 (d, J=8 Hz, 2H), 4.17 (d, J=12 Hz, 2H), 4.08-3.68 (m, 7H), 3.47-3.40 (m, 1H), 3.07 (s, 3H), 2.79-2.65 (m, 6H), 2.37-2.25 (m, 4H), 2.15-1.95 (m, 2H).

Compound 37. 2-amino-1'-[4-[(3R)-3-hydroxy-3-methyl-1-piperidyl]-6-[[1-(morpholinomethyl)cyclopropyl]methoxy]-1,3,5-triazin-2-yl]spiro[5,6-dihydrocyclopenta[b]thiophene-4,3'-azetidine]-3-carbonitrile

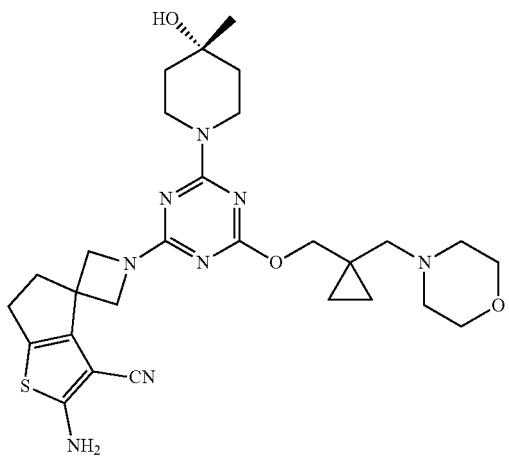

Compound 37 was prepared similarly to that of Ex. 1 as a TFA salt. LCMS calcd for C₂₈H₃₉N₈O₃S (M+H)⁺ m/z=567.2, found: 567.2. ¹H NMR (400 MHz, CD₃OD) δ 4.39-4.37 (m, 4H), 4.23-4.21 (m, 2H), 4.09-3.65 (m, 6H), 3.60-3.29 (m, 5H), 3.27-3.00 (m, 3H), 2.79-2.72 (m, 4H), 1.84-1.54 (m, 4H), 1.2 (s, 3H), 0.96 (s, 2H), 0.85 (s, 2H).

Compound 38. 2-amino-1'-[4-[(1-cyanocyclopropyl)methoxy]-6-[[1-(morpholinomethyl)cyclopropyl]methoxy]-1,3,5-triazin-2-yl]spiro[5,6-dihydrocyclopenta[b]thiophene-4,3'-azetidine]-3-carbonitrile

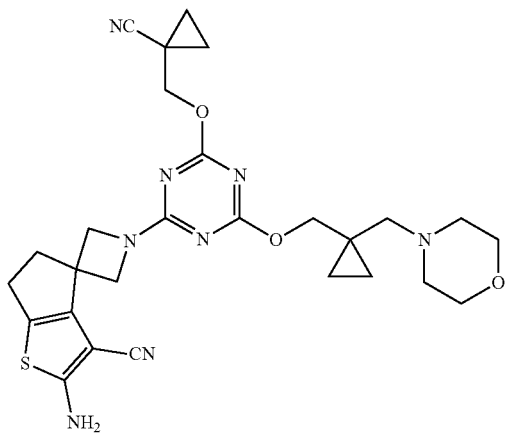 [SMILES: N#Cc1c(N)sc2c1C1(CC2)CN(c2nc(OCC3(C#N)CC3)nc(OCC3(CN4CCOCC4)CC3)n2)C1]

Compound 38 was prepared similarly to that of Ex. 1. LCMS calculated for C₂₇H₃₃N₈O₃S (M+H)⁺ m/z=549.23; found: 549.3. ¹H NMR (400 MHz, CD₃OD) δ 4.16-4.45 (m, 8H), 3.60-3.71 (m, 4H), 2.67-2.82 (m, 4H), 2.28-2.55 (m, 6H), 1.32-1.40 (m, 2H), 1.17-1.27 (m, 2H), 0.61-0.70 (m, 2H), 0.41-0.50 (m, 1H).

Compound 39. 2-amino-1'-[4-(4-cyanoazepan-1-yl)-6-[[(2R,8S)-2-fluoro-1,2,3,5,6,7-hexahydropyrrolizin-8-yl]methoxy]-1,3,5-triazin-2-yl]spiro[6,7-dihydro-5H-benzothiophene-4,3'-azetidine]-3-carbonitrile

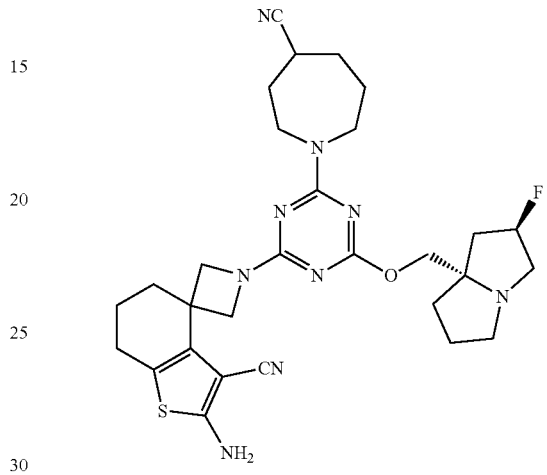

Compound 39 was prepared similarly to that of Ex. 1 as a TFA salt. LCMS calculated for C₂₉H₃₇FN₉OS (M+H)⁺ m/z=578.28, found: 578.2. ¹H NMR (400 MHz, CD₃OD) δ: 5.55 (d, J=52 Hz, 1H), 4.60-4.40 (m, 4H), 4.04-3.71 (m, 9H), 3.48-3.40 (m, 1H), 3.02-2.93 (m, 1H), 2.72-2.49 (m, 4H), 2.42-2.26 (m, 3H), 2.23-1.99 (m, 6H), 1.98-1.78 (m, 5H).

Compound 40. 1-[4-(2-amino-3-cyano-spiro[5,6-dihydrocyclopenta[b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]piperidine-2-carboxamide

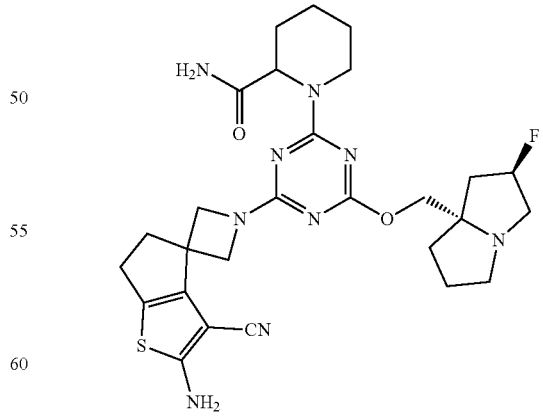

Compound 40 was prepared similarly to that of Ex. 1. LCMS calcd for C₂₇H₃₅FN₉O₂S (M+H)⁺ m/z=568.25, found: 569.2. ¹H NMR (400 MHz, CD₃OD) δ 5.45 (d, J=46.9 Hz, 1H), 4.75-3.98 (m, 8H), 3.92-3.53 (m, 4H), 3.27-3.06 (m, 2H), 2.83-2.57 (m, 4H), 2.46-2.00 (m, 6H), 1.72-1.60 (m, 2H), 1.59-1.28 (m, 3H).

Compound 41. 2-amino-1'-[4-[[(2R,8S)-2-fluoro-1,2,3,5,6,7-hexahydropyrrolizin-8-yl]methoxy]-6-[1-(hydroxymethyl)-3-azabicyclo[4.1.0]heptan-3-yl]-1,3,5-triazin-2-yl]spiro[5,6-dihydrocyclopenta[b]thiophene-4,3'-azetidine]-3-carbonitrile

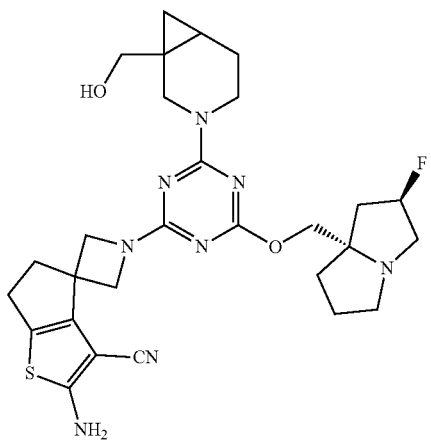 [SMILES: N#Cc1c(N)sc2c1C1(CC2)CN(c2nc(OC[C@@]34CCCN3C[C@H](F)C4)nc(N3CCC4CC4(CO)C3)n2)C1]

Compound 41 was prepared similarly to that of Ex. 1. LCMS calcd for C$_{28}$H$_{36}$FN$_8$O$_2$S (M+H)$^+$ m/z=567.2, found: 567.2. $^1$H NMR (400 MHz, CD$_3$OD) δ 5.44-5.24 (m, 1H), 4.40-4.22 (m, 4H), 4.14-4.09 (m, 2H), 3.88-3.72 (m, 2H), 3.49-3.35 (m, 4H), 3.28-3.20 (m, 1H), 3.15-3.03 (m, 1H), 2.80-2.74 (m, 2H), 2.73-2.68 (m, 2H), 2.46-2.23 (m, 2H), 2.21-2.11 (m, 1H), 2.10-1.96 (m, 3H), 1.95-1.82 (m, 1H), 1.80-1.66 (m, 1H), 1.38-1.26 (m, 1H), 1.09-0.97 (m, 1H), 0.67-0.55 (m, 1H), 0.44-0.24 (m, 1H).

Compound 42. 2-amino-1'-[4-[1-(cyanomethyl)-3-azabicyclo[3.1.0]hexan-3-yl]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

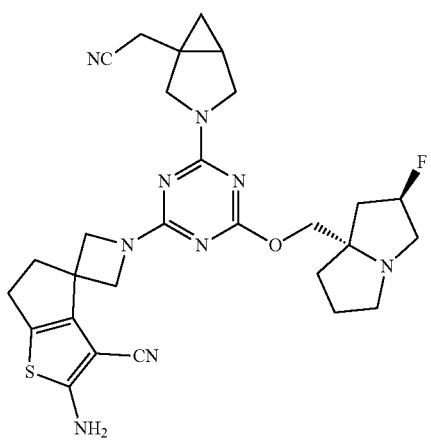 [SMILES: N#CCC12CC1CN(c1nc(OC[C@@]34CCCN3C[C@H](F)C4)nc(N3CC4(CCc5sc(N)c(C#N)c54)C3)n1)C2]

Compound 42 was prepared similarly to that of Ex. 1. LCMS calcd for C$_{28}$H$_{33}$FN$_9$OS (M+H)$^+$ m/z=562.3, found:

562.3. $^1$H NMR (400 MHz, CD$_3$OD) δ 5.27 (d, J=53.6 Hz, 1H), 4.09-3.84 (m, 8H), 3.58-3.38 (m, 2H), 3.30-3.09 (m, 3H), 3.04-2.92 (m, 1H), 2.87-2.41 (m, 6H), 2.32-1.78 (m, 6H), 1.67-1.60 (m, 1H), 0.98-0.90 (m, 1H), 0.56-0.46 (m, 1H).

Compound 43. 2-amino-1'-[4-[1-(cyanomethyl)-3-azabicyclo[4.1.0]heptan-3-yl]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

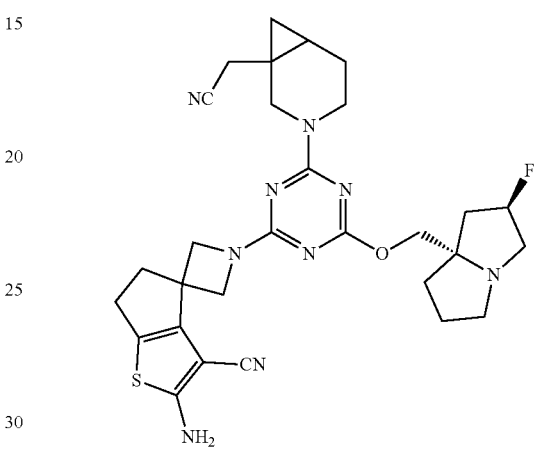

Compound 43 was prepared similarly to that of Ex. 1 as a TFA salt. LCMS calcd for C$_{29}$H$_{35}$FN$_9$OS (M+H)$^+$ m/z=576.3, found: 576.3. $^1$H NMR (400 MHz, CD$_3$OD) δ 5.66-5.42 (m, 1H), 4.62-4.29 (m, 5H), 4.24-4.11 (m, 2H), 4.06-3.65 (m, 5H), 3.50-3.37 (m, 1H), 3.28-3.18 (m, 1H), 2.86-2.46 (m, 8H), 2.43-2.05 (m, 5H), 1.85-1.65 (m, 1H), 1.21-1.08 (m, 1H), 0.81-0.67 (m, 1H), 0.53-0.36 (m, 1H).

Compound 44. 2-amino-1'-[4-(2-cyano-1-piperidyl)-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

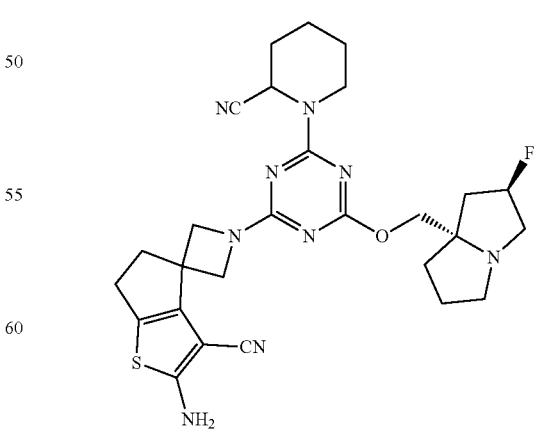

Compound 44 was prepared similarly to that of Ex. 1. LCMS calcd for C$_{27}$H$_{33}$FN$_9$OS (M+H)+ m/z=550.2, found:

550.2. $^1$H NMR (400 MHz, CD$_3$OD) δ: 6.02 (s, 1H), 5.27 (d, J=52 Hz, 1H), 4.75 (d, J=12.8 Hz, 1H), 4.39-4.37 (m, 2H), 4.19-4.17 (m, 4H), 3.24-3.15 (m, 3H), 3.00-2.95 (m, 2H), 2.77-2.75 (m, 4H), 2.22-1.78 (m, 10H), 1.50-1.30 (m, 2H).

Compound 45. 2-amino-1'-[4-(2,4-dioxo-1,3,9-triazaspiro[4.5]decan-9-yl)-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

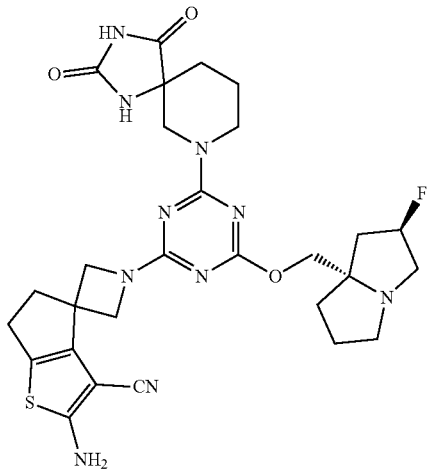 [SMILES: N#Cc1c(N)sc2c1C1(CC2)CN(c2nc(OC[C@@]34CCCN3C[C@H](F)C4)nc(N3CCCC4(C3)NC(=O)NC4=O)n2)C1]

Compound 45 was prepared similarly to that of Ex. 3. LCMS calculated for C$_{28}$H$_{34}$FN$_{10}$O$_3$S (M+H)$^+$ m/z=609.25, found: 609.2. $^1$H NMR (400 MHz, CD$_3$OD) δ: 5.26 (d, J=54.8 Hz, 1H), 4.65-4.53 (m, 2H), 4.38-4.30 (m, 2H), 4.20-3.96 (m, 4H), 3.40-3.33 (m, 1H), 3.24-3.09 (m, 4H), 3.03-2.94 (m, 1H), 2.76-2.70 (m, 4H), 2.27-1.64 (m, 10H).

Compound 46. 2-amino-1'-[4-[(3S,5R)-3,5-dihydroxy-3-methyl-1-piperidyl]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

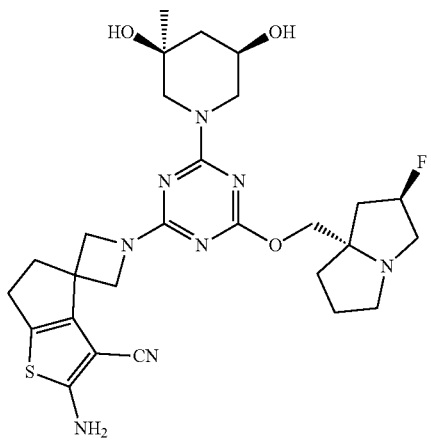 [SMILES: C[C@]1(O)C[C@@H](O)CN(c2nc(OC[C@@]34CCCN3C[C@H](F)C4)nc(N3CC4(CCc5sc(N)c(C#N)c54)C3)n2)C1]

Compound 46 was prepared similarly to that of Ex. 3. LCMS calculated for C$_{27}$H$_{36}$FN$_8$O$_3$S (M+H)$^+$ m/z=571.26; found: 572.0. $^1$H NMR (400 MHz, CD$_3$OD) δ 5.27 (d, J=54.3 Hz, 1H), 4.35 (s, 2H), 4.13 (s, 5H), 3.92 (d, 1H), 3.78 (s, 1H), 3.52-3.37 (m, 2H), 3.27-3.09 (m, 3H), 3.05-2.94 (m, 1H), 2.81-2.66 (m, 4H), 2.37-1.78 (m, 7H), 1.67 (dd, J=12.6, 8.4 Hz, 1H), 1.16 (s, 3H).

Compound 47. 2-amino-1'-[4-[(3R,5R)-3,5-dihydroxy-3-methyl-1-piperidyl]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

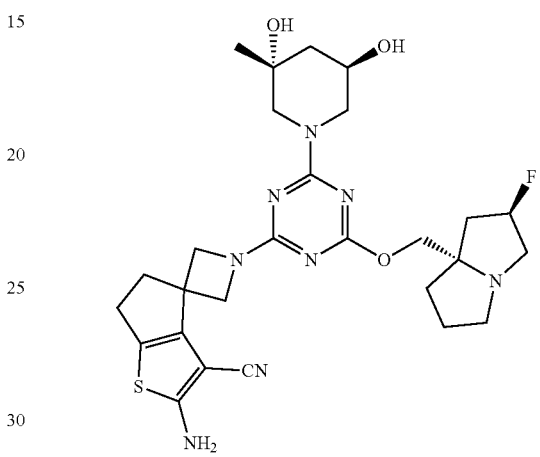

Compound 47 was prepared similarly to that of Ex. 3 with Intermediate 5. LCMS calculated for C$_{27}$H$_{36}$FN$_8$O$_3$S (M+H)$^+$ m/z=571.25; found: 571.3. $^1$H NMR (400 MHz, CD$_3$OD) δ 5.27 (d, J=55.2 Hz, 1H), 4.45-4.65 (m, 2H), 4.27-4.40 (m, 2H), 4.01-4.20 (m, 4H), 3.82-3.97 (m, 1H), 3.13-3.27 (m, 3H), 2.93-3.03 (m, 1H), 2.66-2.84 (m, 5H), 2.48-2.61 (m, 1H), 1.79-2.31 (m, 7H), 1.37-1.50 (m, 1H), 1.26 (s, 3H).

Compound 48. 2-amino-1'-[4-(3-hydroxy-3-methylazepan-1-yl)-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

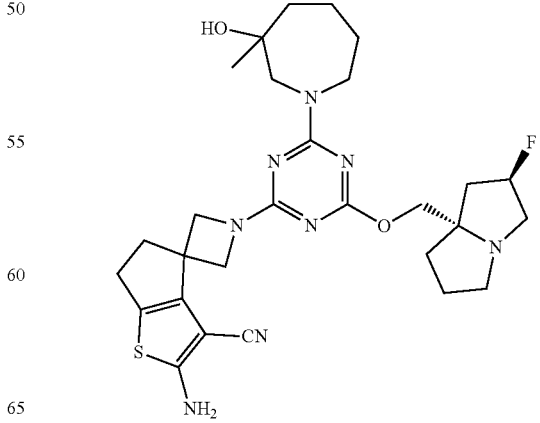

Compound 48 was prepared similarly to that of Ex. 1. LCMS calcd for $C_{28}H_{38}FN_8O_2S$ (M+H)$^+$ m/z=569.2, found: 569.2. $^1$H NMR (400 MHz, CD$_3$OD) δ: 5.25 (d, J=54.4 Hz, 1H), 4.36-3.98 (m, 8H), 3.48-3.12 (m, 1H), 3.47-3.12 (m, 4H), 2.99-2.93 (m, 1H), 2.78-2.68 (m, 4H), 2.23-2.08 (m, 3H), 2.05-1.25 (m, 9H), 1.2 (s, 3H).

Compound 49. 2-amino-1'-[4-[[(2R,8S)-2-fluoro-1,2,3,5,6,7-hexahydropyrrolizin-8-yl]methoxy]-6-[(3R)-3-hydroxy-3-methyl-1-piperidyl]-1,3,5-triazin-2-yl]spiro[6H-thieno[2,3-c]thiophene-4,3'-azetidine]-3-carbonitrile

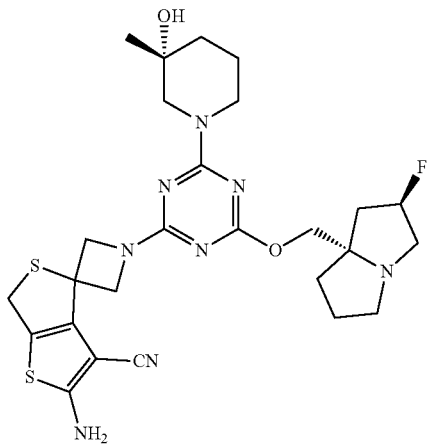

Compound 49 was prepared similarly to that of Ex. 1 with intermediate 6 as a TFA salt. LCMS calculated for $C_{26}H_{34}FN_8O_2S_2$ (M+H)$^+$ m/z=573.3, found: 573.3. $^1$H NMR (400 MHz, CD$_3$OD) δ 5.54 (d, J=51.6 Hz, 1H), 4.72-4.33 (m, 6H), 4.20-3.76 (m, 7H), 3.67-3.37 (m, 3H), 2.75-2.46 (m, 2H), 2.40-2.22 (m, 3H), 2.20-2.06 (m, 1H), 1.83-1.48 (m, 4H), 1.20 (s, 3H).

Compound 50. 2-amino-1'-[4-(3-hydroxyazepan-1-yl)-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

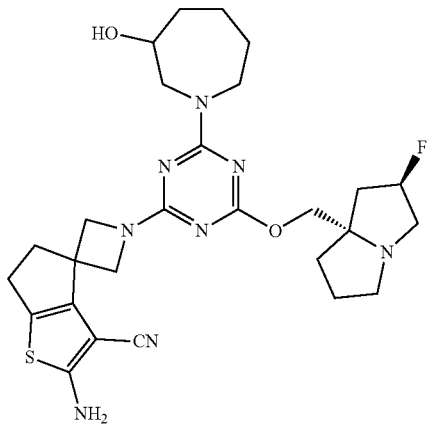 [SMILES: N#Cc1c(N)sc2c1C1(CC2)CN(c2nc(OC[C@@]34CCCN3C[C@H](F)C4)nc(N3CCCCC(O)C3)n2)C1]

Compound 50 was prepared similarly to that of Ex. 1 as a TFA salt. LCMS calcd for $C_{27}H_{36}FN_8O_2S$ (M+H)$^+$ m/z=555.1, found: 555.1. $^1$H NMR (400 MHz, CD$_3$OD) δ: 5.55 (d, J=56 Hz, 1H), 4.60-4.48 (m, 2H), 4.07-3.59 (m, 2H), 4.23-3.98 (m, 3H), 3.97-3.81 (m, 5H), 3.55-3.43 (m, 3H), 2.79-2.67 (m, 4H), 2.58-2.53 (m, 2H), 2.49-2.29 (m, 3H), 2.28 (s, 1H), 2.14-1.81 (m, 4H), 1.71-1.58 (m, 2H).

Compound 51. 2-amino-1'-[4-[[(2R,8S)-2-fluoro-1,2,3,5,6,7-hexahydropyrrolizin-8-yl]methoxy]-6-[(3R)-3-hydroxy-3-methyl-1-piperidyl]-1,3,5-triazin-2-yl]spiro[4a,5,5a,6-tetrahydrocyclopropa[f]benzothiophene-4,3'-azetidine]-3-carbonitrile

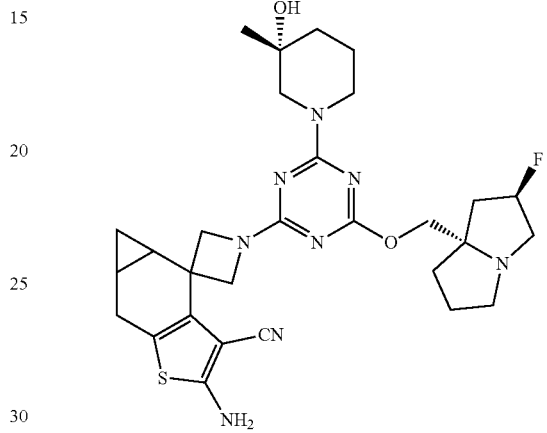

Compound 51 was prepared similarly to that of Ex. 1 with Intermediate 7 as a TFA salt. LCMS calculated for $C_{29}H_{38}FN_8O_2S$ (M+H)$^+$ m/z=581.3, found: 581.3. $^1$H NMR (400 MHz, CD$_3$OD) δ: 5.54 (d, J=51.6 Hz, 1H), 4.78-4.71 (m, 1H), 4.56-4.46 (m, 2H), 4.21-4.20 (m, 3H), 4.00-3.80 (m, 5H), 3.61-3.40 (m, 3H), 2.90-2.80 (m, 2H), 2.71-2.49 (m, 2H), 2.41-2.26 (m, 3H), 2.15-2.12 (m, 1H), 1.81-1.48 (m, 6H), 1.20 (s, 3H), 0.789-0.737 (m, 1H), 0.20-0.15 (m, 1H).

Compound 52. [1-[4-(2-amino-3-cyano-spiro[5,6-dihydrocyclopenta[b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-3-methyl-3-piperidyl]cyanamide

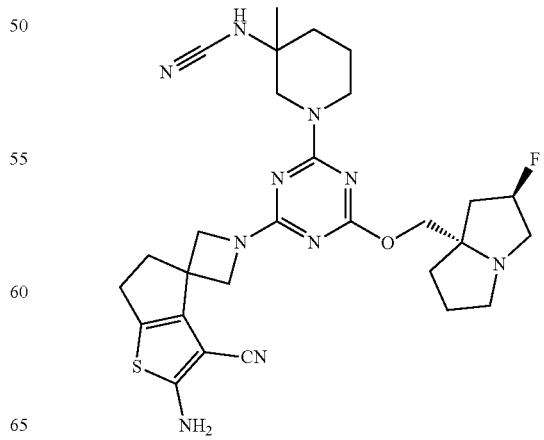

Compound 52 was prepared similarly to that of Ex. 1 as a TFA salt. LCMS calculated for $C_{28}H_{36}FN_{10}OS$ (M+H)$^+$ m/z=579.3, found: 579.3. $^1$H NMR (400 MHz, CD$_3$OD) δ 5.55 (d, J=51.6 Hz, 1H), 5.17-4.98 (m, 2H), 4.70-4.17 (m, 10H), 3.99 (s, 3H), 3.98-3.79 (m, 3H), 3.51-3.35 (m, 1H), 2.82-2.44 (m, 6H), 2.40-2.22 (m, 8H), 2.17-2.04 (m, 1H).

Compound 53. 2-amino-1'-[4-[[(2R,8S)-2-fluoro-1,2,3,5,6,7-hexahydropyrrolizin-8-yl]methoxy]-6-[[rac-(3S,4S)-4-hydroxytetrahydrofuran-3-yl]-methyl-amino]-1,3,5-triazin-2-yl]spiro[5,6-dihydrocyclopenta[b]thiophene-4,3'-azetidine]-3-carbonitrile

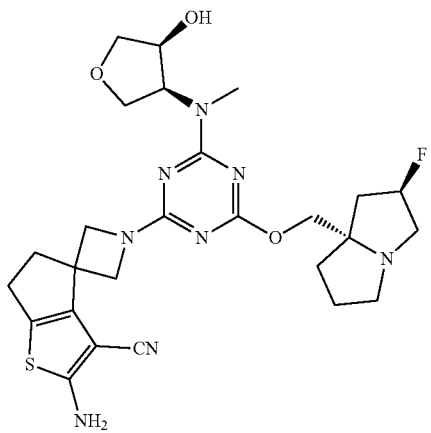 [SMILES: CN(c1nc(OC[C@@]23CCCN2C[C@H](F)C3)nc(N2CC3(CCc4sc(N)c(C#N)c43)C2)n1)[C@H]1COC[C@H]1O]

Compound 53 was prepared similarly to that of Ex. 1 as a formate salt. LCMS calcd for $C_{26}H_{34}FN_8O_3S$ (M+H)$^+$ m/z=557.1, found: 557.3. $^1$H NMR (400 MHz, CD$_3$OD) δ 5.55 (d, J=51.7 Hz, 1H), 5.14-5.01 (m, 2H), 4.64-4.28 (m, 4H), 4.23-4.02 (m, 3H), 4.00-3.79 (m, 4H), 3.79-3.57 (m, 2H), 3.49-3.37 (m, 1H), 3.20 (s, 3H), 2.84-2.69 (m, 4H), 2.59-2.51 (m, 1H), 2.43-2.23 (m, 3H), 2.23-2.08 (m, 1H).

Compound 54. 2-amino-1'-[4-[(1-cyanocyclopropyl)methoxy]-6-[[(2R,8S)-2-fluoro-1,2,3,5,6,7-hexahydropyrrolizin-8-yl]methoxy]-1,3,5-triazin-2-yl]spiro[6,7-dihydro-5H-benzothiophene-4,3'-azetidine]-3-carbonitrile

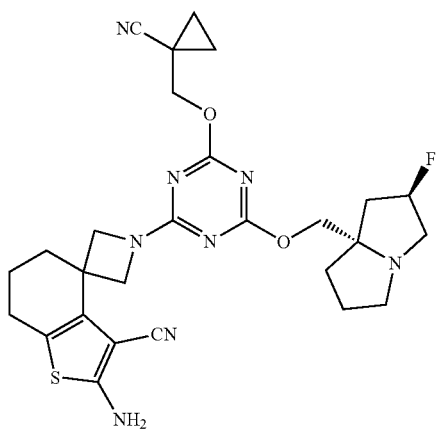 [SMILES: N#Cc1c(N)sc2c1C1(CCC2)CN(c2nc(OCC3(C#N)CC3)nc(OC[C@@]34CCCN3C[C@H](F)C4)n2)C1]

Compound 54 was prepared similarly to that of Ex. 3. LCMS calculated for $C_{27}H_{32}FN_8O_2S$ (M+H)$^+$ m/z=551.23; found: 551.3. $^1$H NMR (400 MHz, CD$_3$OD) δ 5.26 (d, J=54.0 Hz, 1H), 4.31-4.50 (m, 4H), 4.06-4.25 (m, 2H), 3.94-4.04 (m, 2H), 3.11-3.26 (m, 3H), 2.93-3.02 (m, 1H), 2.43-2.58 (m, 2H), 1.76-2.29 (m, 10H), 1.30-1.39 (m, 2H), 1.17-1.27 (m, 2H).

Compound 55. 2-amino-1'-[4-[(3R)-3-hydroxy-3-methyl-1-piperidyl]-6-[(6-methylene-2,3,5,7-tetrahydro-1H-pyrrolizin-8-yl)methoxy]-1,3,5-triazin-2-yl]spiro[5,6-dihydrocyclopenta[b]thiophene-4,3'-azetidine]-3-carbonitrile

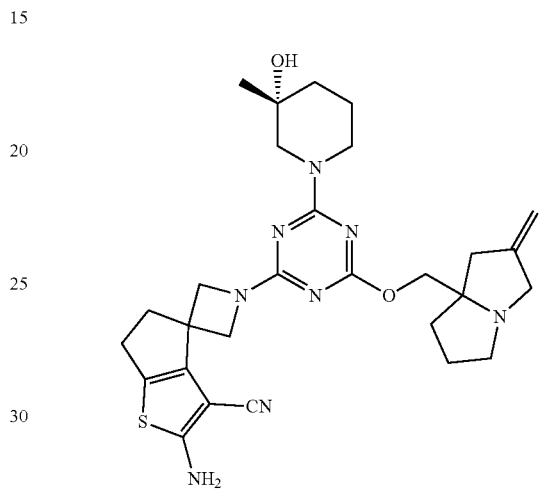

Compound 55 was prepared similarly to that of Ex. 3. LCMS calculated for $C_{28}H_{37}N_8O_2S$ (M+H)$^+$ m/z=549.27; found: 549.3. $^1$H NMR (400 MHz, CD$_3$OD) δ 4.98 (s, 2H), 4.26-4.39 (m, 2H), 4.00-4.21 (m, 4H), 3.50-3.96 (m, 5H), 3.32-3.36 (m, 1H), 3.08-3.18 (m, 1H), 2.62-2.85 (m, 6H), 2.43 (d, J=15.6 Hz, 1H), 1.49-2.15 (m, 8H), 1.18 (s, 3H).

Compound 56. 2-amino-1'-[4-(3-cyano-1-piperidyl)-6-[[1-(morpholinomethyl)cyclopropyl]methoxy]-1,3,5-triazin-2-yl]spiro[5,6-dihydrocyclopenta[b]thiophene-4,3'-azetidine]-3-carbonitrile

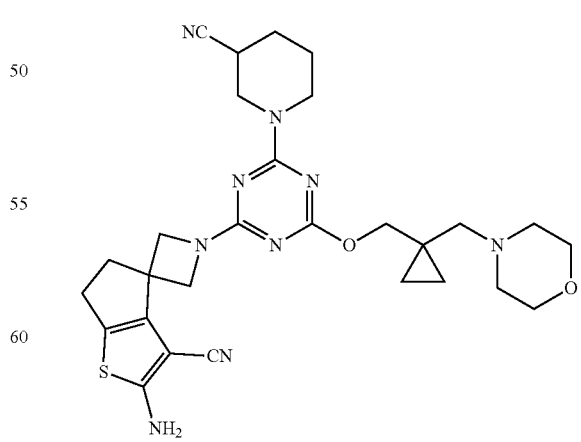

Compound 56 was prepared similarly to that of Ex. 1 as a TFA salt. LCMS calcd for $C_{28}H_{36}N_9O_2S$ (M+H)$^+$ m/z=562.3, found: 562.6. ¹H NMR (400 MHz, CD₃OD) δ 4.51-4.28 (m, 4H), 4.31-3.95 (m, 6H), 3.96-3.49 (m, 6H), 3.40-3.31 (m, 2H), 3.25-3.04 (m, 2H), 3.04-2.90 (m, 1H), 2.85-2.63 (m, 4H), 2.16-1.87 (m, 2H), 1.06-0.91 (m, 2H), 0.90-0.74 (m, 4H).

Compound 57. 2-amino-1'-[4-(3-cyano-3-methyl-1-piperidyl)-6-[[1-(morpholinomethyl)cyclopropyl]methoxy]-1,3,5-triazin-2-yl]spiro[5,6-dihydrocyclopenta[b]thiophene-4,3'-azetidine]-3-carbonitrile

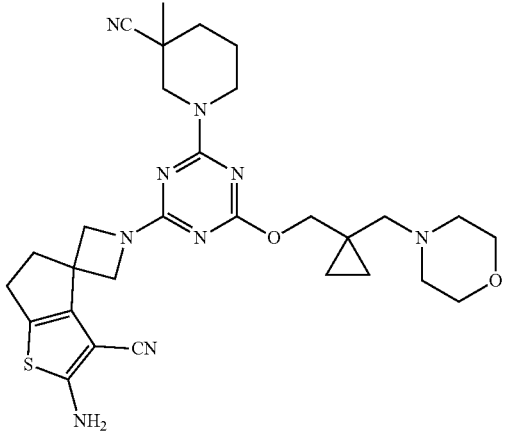 [SMILES: CC1(C#N)CCCN(c2nc(OCC3(CN4CCOCC4)CC3)nc(N3CC4(CCc5sc(N)c(C#N)c54)C3)n2)C1]

Compound 57 was prepared similarly to that of Ex. 1 as a TFA salt. LCMS calcd for C₂₉H₃₈N₉O₂S (M+H)⁺ m/z=576.2, found: 576.3. ¹H NMR (400 MHz, CD₃OD) δ 4.82-4.59 (m, 2H), 4.44-4.27 (m, 4H), 4.25-4.15 (m, 2H), 4.11-3.98 (m, 2H), 3.94-3.80 (m, 2H), 3.77-3.62 (m, 2H), 3.22-3.06 (m, 2H), 3.02-2.88 (m, 2H), 2.81-2.68 (m, 4H), 2.25-1.57 (m, 5H), 1.43-1.31 (m, 4H), 0.97-0.80 (m, 4H).

Compound 58. 2-amino-1'-[4-[[(2R,8S)-2-fluoro-1,2,3,5,6,7-hexahydropyrrolizin-8-yl]methoxy]-6-[(2R,4R)-4-hydroxy-2-(hydroxymethyl)-2-methyl-pyrrolidin-1-yl]-1,3,5-triazin-2-yl]spiro[5,6-dihydrocyclopenta[b]thiophene-4,3'-azetidine]-3-carbonitrile

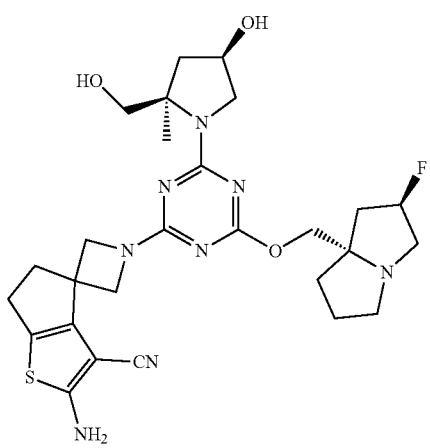 [SMILES: C[C@]1(CO)C[C@@H](O)CN1c1nc(OC[C@@]23CCCN2C[C@H](F)C3)nc(N2CC3(CCc4sc(N)c(C#N)c43)C2)n1]

Compound 58 was prepared similarly to that of Ex. 3. LCMS calculated for C₂₇H₃₆FN₈O₃S (M+H)⁺ m/z=571.26; found: 571.3. 1H NMR (400 MHz, CD₃OD) δ 5.27 (d, J=52.8 Hz, 1H), 3.97-4.40 (m, 8H), 3.52-3.89 (m, 3H), 3.08-3.25 (m, 3H), 2.90-3.06 (m, 1H), 2.63-2.82 (m, 4H), 1.76-2.35 (m, 8H), 1.48 (d, J=7.6 Hz, 3H).

Compound 59. 2-amino-1'-[4-[[(2R,8S)-2-fluoro-1,2,3,5,6,7-hexahydropyrrolizin-8-yl]methoxy]-6-[(2S,4R)-4-hydroxy-2-(hydroxymethyl)-2-methyl-pyrrolidin-1-yl]-1,3,5-triazin-2-yl]spiro[5,6-dihydrocyclopenta[b]thiophene-4,3'-azetidine]-3-carbonitrile

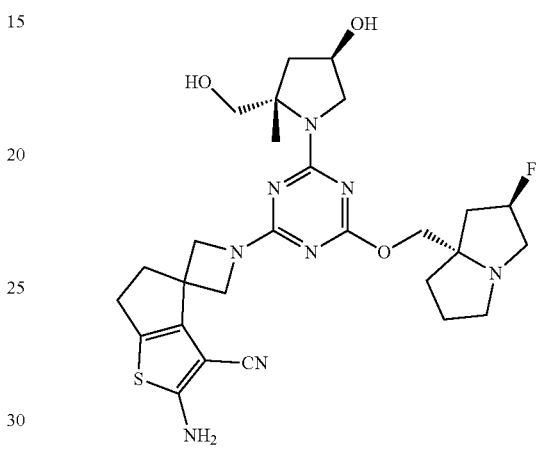

Compound 59 was prepared similarly to that of Ex. 3. LCMS calculated for C₂₇H₃₆FN₈O₃S (M+H)⁺ m/z=571.26; found: 571.9. ¹H NMR (400 MHz, CD₃OD) δ 5.55 (d, J=50.8 Hz, 1H), 4.55-4.28 (m, 5H), 4.13 (dd, J=27.4, 8.8 Hz, 3H), 4.05-3.66 (m, 5H), 3.59-3.50 (m, 1H), 3.44 (s, 1H), 2.82-2.46 (m, 6H), 2.32 (d, J=5.7 Hz, 4H), 2.11 (s, 1H), 1.88 (d, J=12.7 Hz, 1H), 1.61 (d, J=7.7 Hz, 3H).

Compound 60. 2-amino-1'-[4-[[(2R,8S)-2-fluoro-1,2,3,5,6,7-hexahydropyrrolizin-8-yl]methoxy]-6-[(3R)-3-hydroxy-3-methyl-1-piperidyl]-1,3,5-triazin-2-yl]spiro[6,7-dihydro-5H-benzothiophene-4,3'-pyrrolidine]-3-carbonitrile

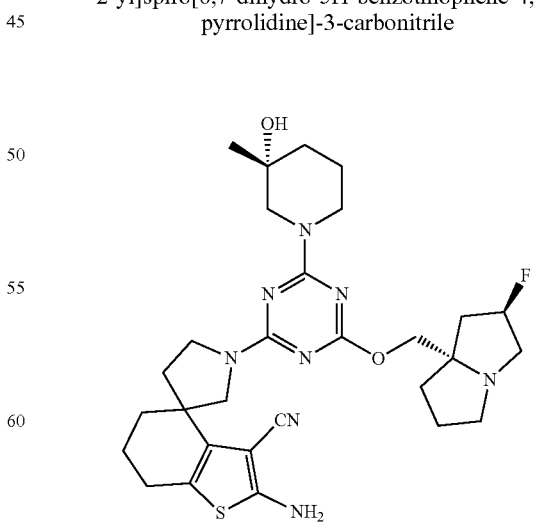

Compound 60 was prepared similarly to that of Ex. 3 with Intermediate 8. LCMS calculated for C₂₉H₄₀FN₈O₂S (M+H)⁺ m/z=583.3; found: 583.2. ¹H NMR (400 MHz, CD₃OD) δ 5.26 (d, J=52.4 Hz, 1H), 4.58 (s, 2H), 4.12-4.22 (m, 1H), 4.01-4.11 (m, 1H), 3.73-3.87 (m, 3H), 3.56-3.68 (m, 3H), 3.11-3.28 (m, 3H), 2.92-3.03 (m, 1H), 2.61-2.73 (m, 1H), 2.46-2.55 (m, 2H), 2.05-2.32 (m, 3H), 1.48-2.01 (m, 12H), 1.19 (d, J=4.8 Hz, 3H).

Compound 61. 2-amino-5-fluoro-1'-[4-[(3R)-3-hydroxy-3-methyl-1-piperidyl]-6-[[1-(morpholinomethyl)cyclopropyl]methoxy]-1,3,5-triazin-2-yl]spiro[5,6-dihydrocyclopenta[b]thiophene-4,3'-azetidine]-3-carbonitrile

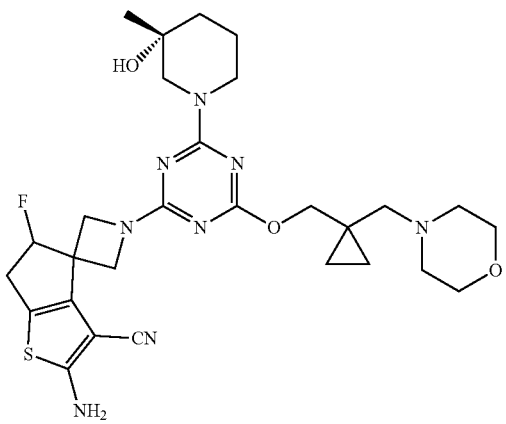 [SMILES: C[C@@]1(O)CCCN(c2nc(OCC3(CN4CCOCC4)CC3)nc(N3CC4(C3)c3c(sc(N)c3C#N)CC4F)n2)C1]

Compound 61 was prepared similarly to that of Ex. 2. LCMS calculated for C₂₈H₃₈FN₈O₃S (M+H)⁺ m/z=585.28; found: 585.3. ¹H NMR (400 MHz, CD₃OD) δ 5.55 (d, J=52.4 Hz, 1H), 4.50 (m, 1H), 4.08-4.36 (m, 5H), 3.78-3.91 (m, 1H), 3.56-3.76 (m, 7H), 3.19 (m, 1H), 2.88 (m, 1H), 2.24-2.58 (m, 6H), 1.48-1.85 (m, 4H), 1.19 (s, 3H), 0.64 (m, 2H), 0.44 (m, 2H).

Compound 62. 2-amino-1'-[4-[rac-(3S,4S)-3,4-dihydroxy-3-methyl-1-piperidyl]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

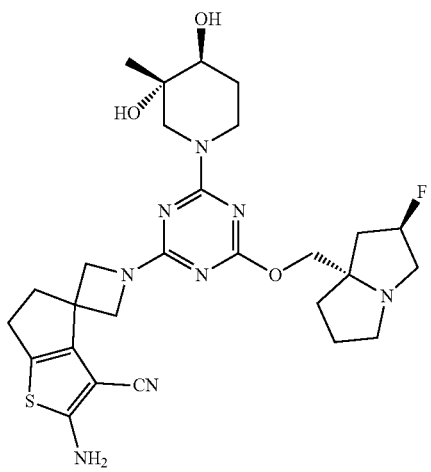 [SMILES: C[C@]1(O)CN(c2nc(OC[C@@]34CCCN3C[C@H](F)C4)nc(N3CC4(CCc5sc(N)c(C#N)c54)C3)n2)CC[C@@H]1O]

Compound 62 was prepared similarly to that of Ex. 1 as a formate salt. LCMS calcd for C₂₇H₃₆FN₈O₃S (M+H)+ m/z=571.3, found: 571.4. ¹H NMR (400 MHz, CD₃OD) δ 8.47 (s, 1H), 5.46 (d, J=52.4 Hz, 1H), 4.51-4.28 (m, 4H), 4.22-3.83 (m, 4H), 3.80-3.39 (m, 6H), 2.87-2.66 (m, 4H), 2.46 (m, 2H), 2.20 (m, 3H), 2.00 (m, 2H), 1.51 (s, 1H), 1.14 (s, 3H).

Compound 63. 2-amino-1'-[4-[rac-(2R,3S)-3-cyano-2-(hydroxymethyl)-1-piperidyl]-6-[[(2R,8S)-2-fluoro-1,2,3,5,6,7-hexahydropyrrolizin-8-yl]methoxy]-1,3,5-triazin-2-yl]spiro[3a,5-dihydrocyclopenta[b]thiophene-4,3'-azetidine]-3-carbonitrile

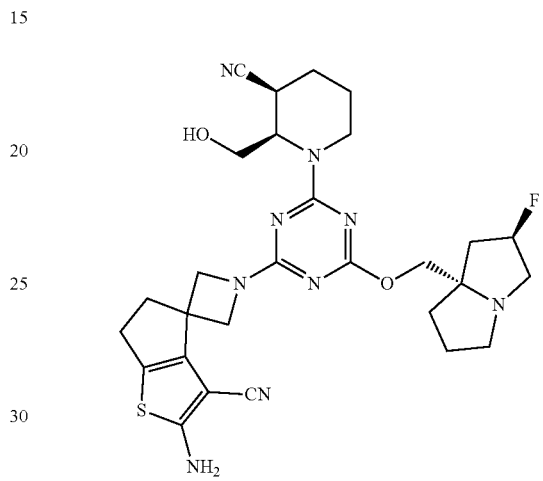

Compound 63 was prepared similarly to that of Ex. 1. LCMS calcd for C₂₈H₃₅FN₉O₂S (M+H)⁺ m/z=580 found: 580.1. ¹H NMR (400 MHz, CD₃OD) δ 8.56-8.49 (m, 1H), 5.44-5.39 (m, 1H), 4.66-4.51 (m, 4H), 4.40-4.24 (m, 2H), 4.20-4.12 (m, 2H), 4.10-3.91 (m, 1H), 3.53-3.35 (m, 4H), 3.17-2.98 (m, 3H), 2.81-2.74 (m, 2H), 2.74-2.67 (m, 2H), 2.23-2.14 (m, 2H), 2.12-1.89 (m, 6H), 1.82-1.71 (m, 1H), 1.68-1.57 (m, 1H), 0.93-0.86 (m, 1H).

Compound 64. 2-amino-1'-[4-[(3R)-3-hydroxy-3-methyl-1-piperidyl]-6-[[1-(morpholinomethyl)cyclopropyl]methoxy]-1,3,5-triazin-2-yl]spiro[6,7-dihydro-5H-benzothiophene-4,3'-pyrrolidine]-3-carbonitrile

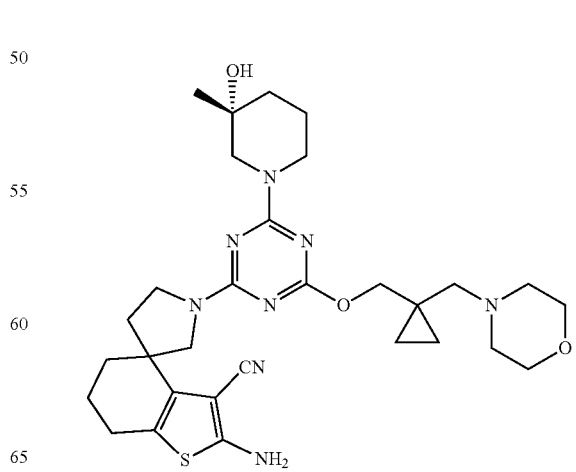

Compound 64 was prepared similarly to that of Ex. 1 with Intermediate 8. LCMS calculated for $C_{30}H_{43}N_8O_3S$ (M+H)+ m/z=595.3; found: 595.3. $^1$H NMR (400 MHz, CD$_3$OD) δ 4.20-4.35 (m, 2H), 3.74-3.91 (m, 3H), 3.74-3.53 (m, 9H), 2.67 (dd, J=22.4, 10.0 Hz, 1H), 2.30-2.58 (m, 8H), 1.74-1.92 (m, 5H), 1.62-1.74 (m, 3H), 1.49-1.59 (m, 1H), 1.19 (d, J=4.0 Hz, 3H), 0.64 (d, J=3.2 Hz, 2H), 0.43 (d, J=6.4 Hz, 2H).

Compound 65. 2-amino-1'-[4-[3-(cyanomethyl)-5-fluoro-3,6-dihydro-2H-pyridin-1-yl]-6-[[1-(morpholinomethyl)cyclopropyl]methoxy]-1,3,5-triazin-2-yl]spiro[5,6-dihydrocyclopenta[b]thiophene-4,3'-azetidine]-3-carbonitrile

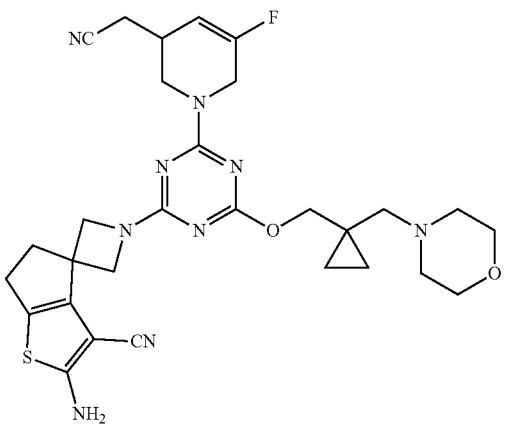 [SMILES: N#CCC1C=C(F)CN(c2nc(OCC3(CN4CCOCC4)CC3)nc(N3CC4(CCc5sc(N)c(C#N)c54)C3)n2)C1]

Compound 65 was prepared similarly to that of Ex. 3. LCMS calculated for $C_{29}H_{35}FN_9O_2S$ (M+H)+ m/z=592.3; found: 592.2. $^1$H NMR (400 MHz, CD$_3$OD) δ 5.43 (dd, J=16.0, 4.8 Hz, 1H), 3.98-4.68 (m, 10H), 3.65-3.70 (m, 4H), 2.67-2.82 (m, 5H), 2.26-2.61 (m, 8H), 0.60-0.71 (m, 2H), 0.40-0.50 (m, 2H).

Compound 66. 2-amino-1'-[4-[[(2R,8S)-2-fluoro-1,2,3,5,6,7-hexahydropyrrolizin-8-yl]methoxy]-6-[(2S,4S)-4-hydroxy-2-(hydroxymethyl)-2-methyl-pyrrolidin-1-yl]-1,3,5-triazin-2-yl]spiro[5,6-dihydrocyclopenta[b]thiophene-4,3'-azetidine]-3-carbonitrile

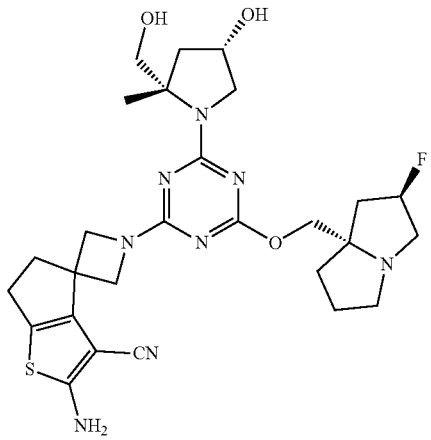 [SMILES: C[C@@]1(CO)C[C@H](O)CN1c1nc(OC[C@@]23CCCN2C[C@H](F)C3)nc(N2CC3(CCc4sc(N)c(C#N)c43)C2)n1]

Compound 66 was prepared similarly to that of Ex. 3. LCMS calculated for $C_{27}H_{36}FN_8O_3S$ (M+H)+ m/z=571.26; found: 571.3. $^1$H NMR (400 MHz, CD$_3$OD) δ 5.27 (d, J=54.0 Hz, 1H), 4.00-4.38 (m, 8H), 3.55-3.88 (m, 3H), 3.13-3.26 (m, 3H), 2.92-3.05 (m, 1H), 2.65-2.82 (m, 4H), 2.03-2.31 (m, 5H), 1.78-2.01 (m, 3H), 1.48 (d, J=8.0 Hz, 3H).

Compound 67. 2-amino-1'-[4-[(3R,5S)-3,5-dihydroxy-3-methyl-1-piperidyl]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

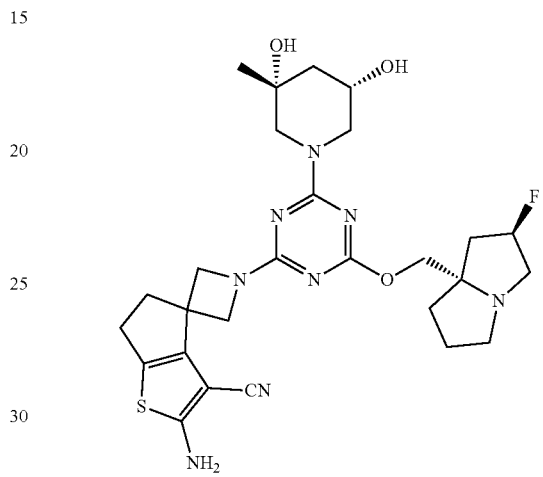

Compound 67 was prepared similarly to that of Ex. 3. LCMS calculated for $C_{27}H_{36}FN_8O_3S$ (M+H)+ m/z=571.26; found: 571.3. H NMR (400 MHz, CD$_3$OD) δ 5.26 (d, J=54.4 Hz, 1H), 4.27-4.40 (m, 2H), 3.72-4.23 (m, 7H), 3.34-3.46 (m, 2H), 3.11-3.26 (m, 3H), 2.92-3.04 (m, 1H), 2.66-2.82 (m, 4H), 1.78-2.33 (m, 7H), 1.67 (dd, J=12.8, 8.4 Hz, 1H), 1.16 (s, 3H).

Compound 68. (5S)-2-amino-5-fluoro-1'-[4-[(3R)-3-hydroxy-3-methyl-1-piperidyl]-6-[[1-(morpholinomethyl)cyclopropyl]methoxy]-1,3,5-triazin-2-yl]spiro[5,6-dihydrocyclopenta[b]thiophene-4,3'-azetidine]-3-carbonitrile

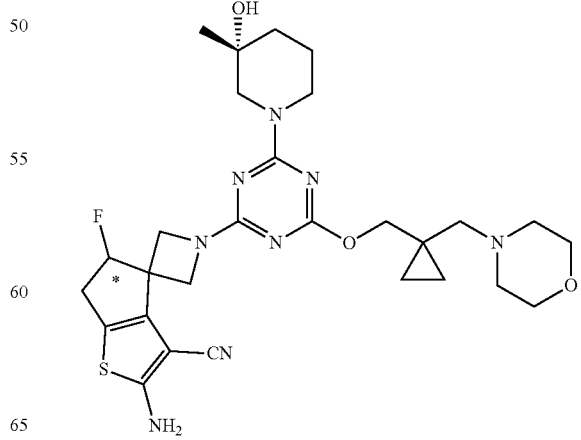

Compound 68 was prepared similarly to that of Ex. 1 with unsigned enantiomer of Intermediate 9. LCMS calculated for $C_{28}H_{38}FN_8O_3S$ (M+H)+ m/z=585.28; found: 585.3. $^1$H NMR (400 MHz, CD$_3$OD) δ 5.56 (m, 1H), 4.50 (d, J=9.6 Hz, 1H), 4.13-4.32 (m, 5H), 3.80-3.90 (m, 1H), 3.59-3.78 (m, 7H), 3.12-3.26 (m, 1H), 2.88 (m, 1H), 2.32-2.56 (m, 6H), 1.48-1.85 (m, 4H), 1.19 (s, 3H), 0.64 (t, J=5.0 Hz, 2H), 0.44 (t, J=5.2 Hz, 2H).

Compound 69. 2-amino-1'-[4-[[(2R,8S)-2-fluoro-1,2,3,5,6,7-hexahydropyrrolizin-8-yl]methoxy]-6-[(3R)-3-(hydroxymethyl)-1,4-oxazepan-4-yl]-1,3,5-triazin-2-yl]spiro[5,6-dihydrocyclopenta[b]thiophene-4,3'-azetidine]-3-carbonitrile

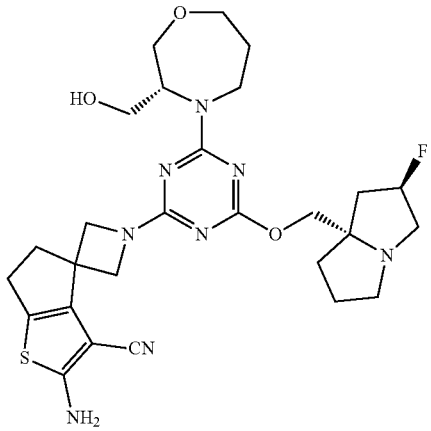 [SMILES: N#Cc1c(N)sc2c1C1(CC2)CN(c2nc(OC[C@@]34CCCN3C[C@H](F)C4)nc(N3CCCOC[C@H]3CO)n2)C1]

Compound 69 was prepared similarly to that of Ex. 1. LCMS calculated for $C_{27}H_{36}FN_8O_3S$ (M+H)$^+$ m/z=571.25; found: 571.2. $^1$H NMR (400 MHz, CD$_3$OD) δ 5.29 (d, J=54.3 Hz, 1H), 4.78-4.70 (m, 1H), 4.60-4.44 (m, 1H), 4.33 (m, 2H), 4.24-4.17 (m, 1H), 4.16-4.06 (m, 4H), 4.00-3.90 (m, 1H), 3.84-3.69 (m, 2H), 3.65 (m, 2H), 3.55 (m, 1H), 3.40 (m, 1H), 3.23 (m, 1H), 3.08-2.98 (m, 1H), 2.80-2.68 (m, 4H), 2.65 (s, 3H), 2.33-2.17 (m, 2H), 2.11 (m, 1H), 1.96 (m, 2H), 1.86 (s, 2H), 1.67 (m, 1H).

Compound 70. (5R)-2-amino-5-fluoro-1'-[4-[(3R)-3-hydroxy-3-methyl-1-piperidyl]-6-[[1-(morpholinomethyl)cyclopropyl]methoxy]-1,3,5-triazin-2-yl]spiro[5,6-dihydrocyclopenta[b]thiophene-4,3'-azetidine]-3-carbonitrile

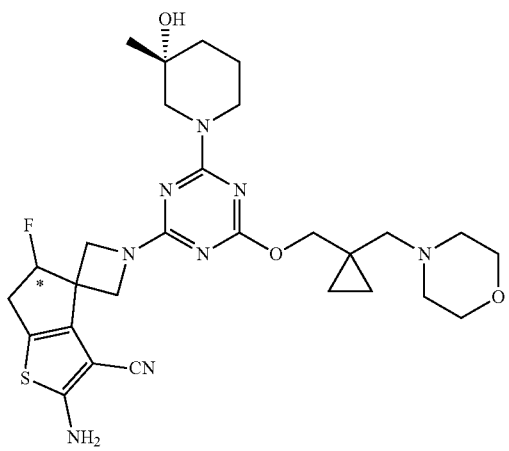

Compound 70 was prepared similarly to that of Ex. 1 with unsigned enantiomer of Intermediate 9. LCMS calculated for $C_{28}H_{38}FN_8O_3S$ (M+H)+ m/z=585.28; found: 585.3. $^1$H NMR (400 MHz, CD$_3$OD) δ 4.78-5.28 (m, 1H), 4.49 (d, J=9.6 Hz, 1H), 4.14-4.32 (m, 5H), 3.59-3.89 (m, 8H), 3.19-3.31 (m, 1H), 2.87-2.93 (m, 1H), 2.34-2.55 (m, 6H), 1.49-1.86 (m, 4H), 1.19 (s, 3H), 0.65 (t, J=5.1 Hz, 2H), 0.44 (t, J=5.1 Hz, 2H).

Compound 71. 2-amino-5-fluoro-1'-[4-[[(2R,8S)-2-fluoro-1,2,3,5,6,7-hexahydropyrrolizin-8-yl]methoxy]-6-[(3R)-3-hydroxy-3-methyl-1-piperidyl]-1,3,5-triazin-2-yl]spiro[5,6-dihydrocyclopenta[b]thiophene-4,3'-azetidine]-3-carbonitrile

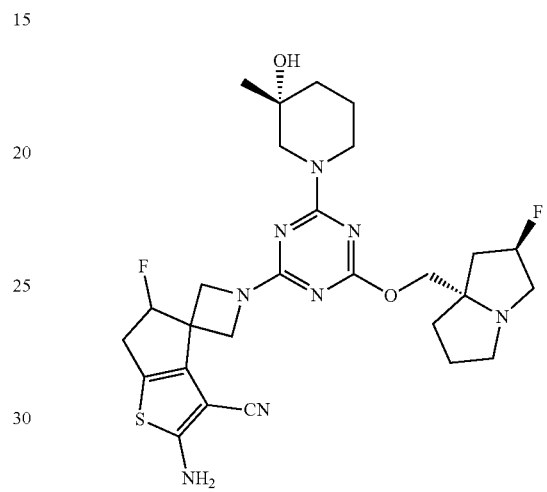

Compound 71 was prepared similarly to that of Ex. 1. LCMS calculated for $C_{27}H_{35}F_2N_8O_2S$ (M+H)+ m/z=573.26; found: 573.1. $^1$H NMR (400 MHz, CD$_3$OD) δ 5.20-5.61 (m, 1H), 5.27 (d, J=54.4 Hz, 1H), 4.50 (d, J=9.6 Hz, 1H), 4.01-4.33 (m, 5H), 3.71-3.98 (m, 2H), 3.49-3.68 (m, 2H), 3.09-3.26 (m, 4H), 2.79-3.04 (m, 2H), 1.49-2.33 (m, 10H), 1.19 (s, 3H).

Compound 72. 2-amino-1'-[4-[[(2R,8S)-2-fluoro-1,2,3,5,6,7-hexahydropyrrolizin-8-yl]methoxy]-6-[(2R,4S)-4-hydroxy-2-(hydroxymethyl)-2-methylpyrrolidin-1-yl]-1,3,5-triazin-2-yl]spiro[5,6-dihydrocyclopenta[b]thiophene-4,3'-azetidine]-3-carbonitrile

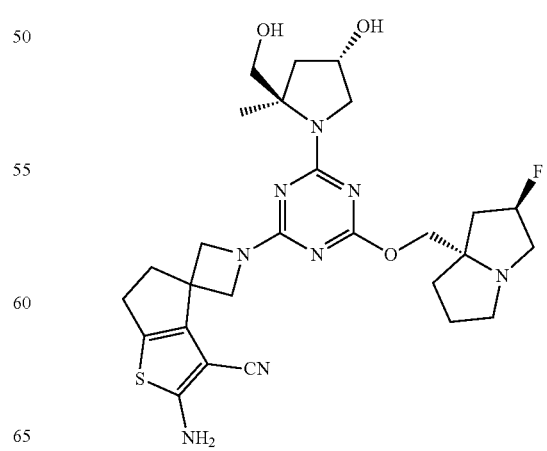

Compound 72 was prepared similarly to that of Ex. 1. LCMS calculated for $C_{27}H_{35}FN_8O_3S$ (M+H)+ m/z=571.26; found: 571.2. $^1$H NMR (400 MHz, CD$_3$OD) δ 5.26 (d, J=55.2 Hz, 1H), 4.41-3.95 (m, 8H), 3.84-3.66 (m, 2H), 3.57-3.49 (m, 1H), 3.17 (m, 3H), 2.98 (s, 1H), 2.74 (m, 4H), 2.43-1.78 (m, 8H), 1.65-1.54 (m, 3H).

Compound 73. 2-amino-1'-[4-[(3R)-3-hydroxy-3-methyl-1-piperidyl]-6-[[1-(morpholinomethyl)cyclopropyl]methoxy]-1,3,5-triazin-2-yl]spiro[6H-thieno[2,3-c]thiophene-4,3'-azetidine]-3-carbonitrile

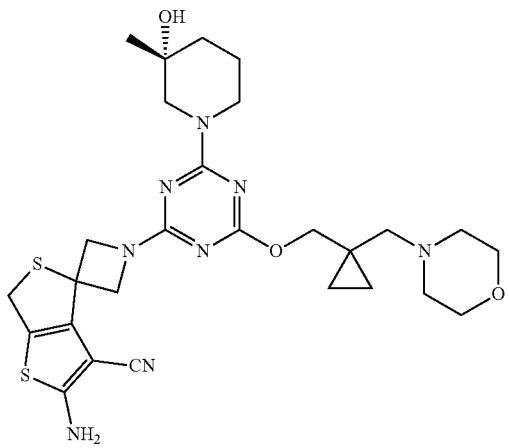 [SMILES: C[C@@]1(O)CCCN(c2nc(OCC3(CN4CCOCC4)CC3)nc(N3CC4(C3)SCc3sc(N)c(C#N)c34)n2)C1]

Compound 73 was prepared similarly to that of Ex. 1 as a TFA salt. LCMS calculated for $C_{27}H_{37}N_8O_3S_2$ (M+H) m/z=585.24, found: 585.1. $^1$H NMR (400 MHz, CD$_3$OD) δ: 4.67-4.5 (m, 2H), 4.43-4.24 (m, 4H), 4.12-3.81 (m, 8H), 3.73-3.44 (m, 5H), 3.23-3.08 (m, 3H), 1.82-1.74 (m, 1H), 1.73-1.62 (m, 2H), 1.56-1.53 (m, 1H), 1.19 (s, 3H), 0.95 (s, 2H), 0.83 (s, 2H).

Compound 74. 2-amino-1'-[4-(3-cyanoazepan-1-yl)-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

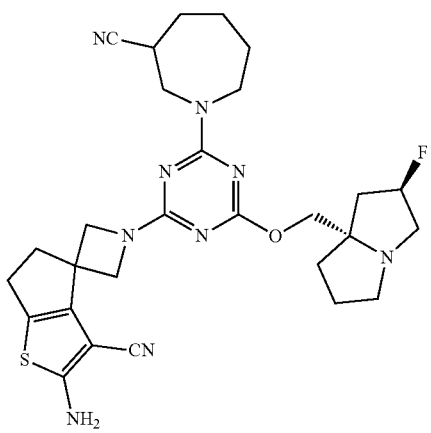 [SMILES: N#Cc1c(N)sc2c1C1(CC2)CN(c2nc(OC[C@@]34CCCN3C[C@H](F)C4)nc(N3CCCCC(C#N)C3)n2)C1]

Compound 74 was prepared similarly to that of Ex. 1. LCMS calcd for $C_{28}H_{35}FN_9OS$ (M+H)+ m/z=564.1, found: 564.3. $^1$H NMR (400 MHz, CD$_3$OD) δ: 5.25 (d, 1H), 4.40-3.81 (m, 9H), 3.81-3.44 (m, 1H), 3.29-3.13 (m, 4H), 2.99-2.93 (m, 1H), 2.77-2.70 (m, 4H), 2.24-2.07 (m, 3H), 1.97-1.81 (m, 8H), 1.53-1.29 (m, 1H).

Compound 75. 2-amino-1'-[4-[(3S,5S)-3,5-dihydroxy-3-methyl-1-piperidyl]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

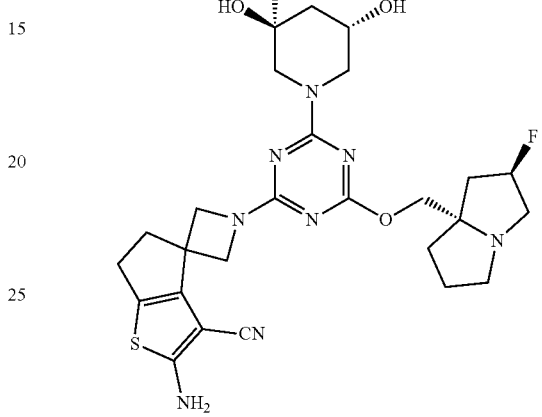

Compound 75 was prepared similarly to that of Ex. 1. LCMS calculated for $C_{27}H_{36}FN_9O_3S$ (M+H)+ m/z=571.26; found: 571.1. $^1$H NMR (400 MHz, CD$_3$OD) δ 5.26 (d, J=53.8 Hz, 1H), 4.65-4.47 (m, 2H), 4.34 (d, J=7.8 Hz, 2H), 4.23-3.84 (m, 5H), 3.25-3.10 (m, 3H), 3.03-2.93 (m, 1H), 2.87-2.66 (m, 5H), 2.56 (m, 1H), 2.32-1.79 (m, 7H), 1.48-1.37 (m, 1H), 1.27 (m, 3H).

Compound 76. 2-amino-1'-[4-[[(2R,8S)-2-fluoro-1,2,3,5,6,7-hexahydropyrrolizin-8-yl]methoxy]-6-[(1-hydroxycyclopropyl)methoxy]-1,3,5-triazin-2-yl]spiro[5,6-dihydrocyclopenta[b]thiophene-4,3'-azetidine]-3-carbonitrile

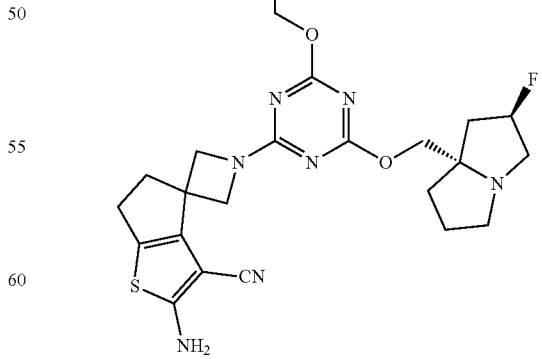

Compound 76 was prepared similarly to that of Ex. 1. LCMS calculated for $C_{25}H_{31}FN_7O_3S$ (M+H)+ m/z=528.21, found: 528.3. $^1$H NMR (400 MHz, CD$_3$OD) δ 5.26 (d, J=54.0 Hz, 1H), 4.33-4.44 (m, 4H), 4.05-4.24 (m, 4H), 3.11-3.24 (m, 3H), 2.93-3.03 (m, 1H), 2.67-2.82 (m, 4H), 1.78-2.29 (m, 6H), 0.68-0.83 (m, 4H).

Compound 77. 2-amino-1'-[4-[rac-(3S,4S)-4-hydroxytetrahydrofuran-3-yl]oxy-6-[[1-(morpholinomethyl)cyclopropyl]methoxy]-1,3,5-triazin-2-yl]spiro[5,6-dihydrocyclopenta[b]thiophene-4,3'-azetidine]-3-carbonitrile; 2,2,2-trifluoroacetic acid

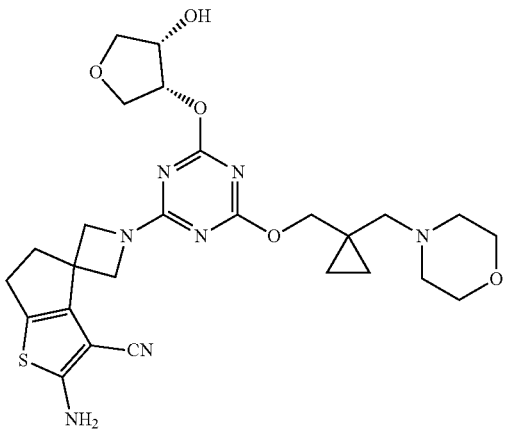 [SMILES: N#Cc1c(N)sc2c1C1(CC2)CN(c2nc(OCC3(CN4CCOCC4)CC3)nc(O[C@@H]3COC[C@@H]3O)n2)C1]

Compound 77 was prepared similarly to that of Ex. 1 as a TFA salt. LCMS calcd for $C_{26}H_{34}N_7O_5S$ (M+H)$^+$ m/z=556.2, found: 556.6. $^1$H NMR (400 MHz, CD$_3$OD) δ 5.47-5.38 (m, 1H), 4.68-4.45 (m, 1H), 4.46-4.17 (m, 6H), 4.18-4.01 (m, 3H), 4.02-3.82 (m, 4H), 3.78-3.65 (m, 3H), 3.29-3.24 (m, 2H), 3.21-3.06 (m, 2H), 2.90-2.58 (m, 4H), 1.01-0.91 (m, 2H), 0.88-0.74 (m, 2H).

Compound 78. 2-amino-1'-[4-[[(2R,8S)-2-fluoro-1,2,3,5,6,7-hexahydropyrrolizin-8-yl]methoxy]-6-tetrahydrofuran-3-yloxy-1,3,5-triazin-2-yl]spiro[5,6-dihydrocyclopenta[b]thiophene-4,3'-azetidine]-3-carbonitrile; formic acid

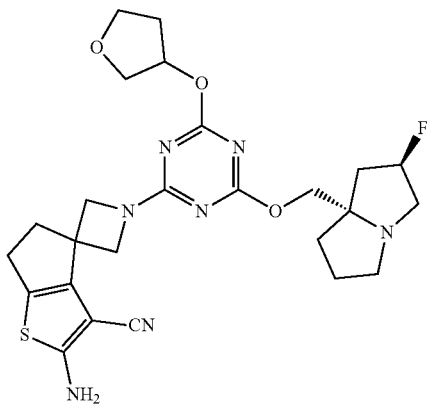 [SMILES: N#Cc1c(N)sc2c1C1(CC2)CN(c2nc(OC[C@@]34CCCN3C[C@H](F)C4)nc(OC3CCOC3)n2)C1]

Compound 78 was prepared similarly to that of Ex. 1 as a formate salt. LCMS calcd for $C_{25}H_{31}FN_7O_3S$ (M+H)+ m/z=528.2, found: 528.2. $^1$H NMR (400 MHz, CD$_3$OD) δ 5.56 (dd, J=6.0, 4.4 Hz, 1H), 5.44 (d, J=51.6 Hz, 1H), 4.50-4.28 (m, 4H), 4.24 (d, J=9.8 Hz, 2H), 4.05-3.78 (m, 4H), 3.61 (dd, J=22.0, 8.4 Hz, 3H), 3.25 (dd, J=10.4, 5.6 Hz, 1H), 2.83-2.68 (m, 4H), 2.55-2.32 (m, 2H), 2.32-1.94 (m, 6H).

Compound 79. 2-amino-1'-[4-[3-(cyanomethyl)-3-hydroxy-1-piperidyl]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile; 2,2,2-trifluoroacetic acid

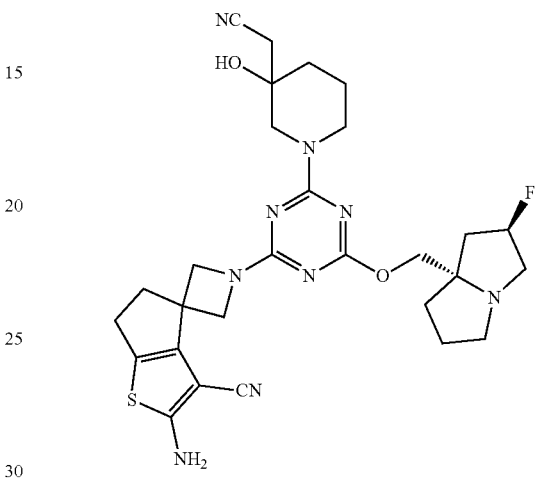

Compound 79 was prepared similarly to that of Ex. 1 as a TFA salt. LCMS calcd for $C_{28}H_{35}FN_9O_2S$ (M+H)+ m/z=580.2, found: 580.3. $^1$H NMR (400 MHz, CD$_3$OD) δ 5.54 (d, J=51.2 Hz, 1H), 4.64-4.43 (m, 2H), 4.36 (m, 2H), 4.18 (m, 2H), 4.12-3.95 (m, 2H), 3.95-3.75 (m, 3H), 3.62 (s, 2H), 3.47-3.38 (m, 1H), 2.85-2.61 (m, 6H), 2.52 (m, 2H), 2.30 (m, 3H), 2.14 (s, 1H), 1.96-1.71 (m, 3H), 1.55 (s, 1H).

Compound 80. 2-amino-1'-[4-[[(2R,8S)-2-fluoro-1,2,3,5,6,7-hexahydropyrrolizin-8-yl]methoxy]-6-[rac-(3R,4R)-4-hydroxytetrahydrofuran-3-yl]oxy-1,3,5-triazin-2-yl]spiro[5,6-dihydrocyclopenta[b]thiophene-4,3'-azetidine]-3-carbonitrile; 2,2,2-trifluoroacetic acid

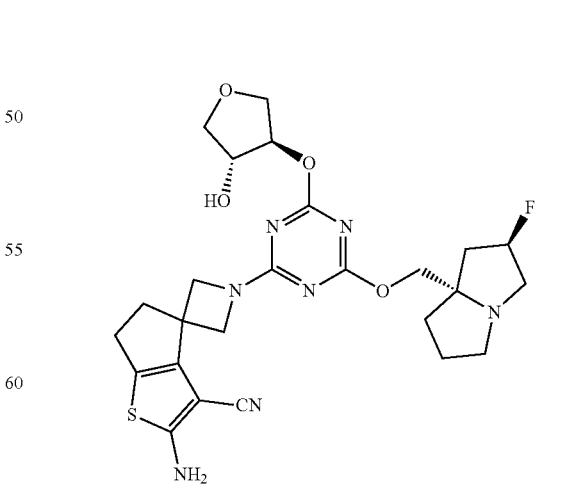

Compound 80 was prepared similarly to that of Ex. 1 as a TFA salt. LCMS m/z calcd for $C_{25}H_{31}FN_7O_4S$ (M+H)$^+$ m/z: 544.6, found: 544.5. ¹H NMR (400 MHz, CD₃OD) δ 5.55 (d, J=52.9 Hz, 1H), 5.33-5.26 (m, 1H), 4.63-4.45 (m, 2H), 4.43-4.36 (m, 3H), 4.31-4.23 (m, 2H), 4.22-4.15 (m, 1H), 4.04-3.95 (m, 1H), 3.93-3.82 (m, 4H), 3.78-3.71 (m, 1H), 3.49-3.40 (m, 1H), 2.82-2.70 (m, 4H), 2.66-2.51 (m, 2H), 2.39-2.25 (m, 3H), 2.22-2.12 (m, 1H).

Compound 81. 2-amino-1'-[4-[(3S,4R)-3,4-dihydroxyazepan-1-yl]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile; 2,2,2-trifluoroacetic acid

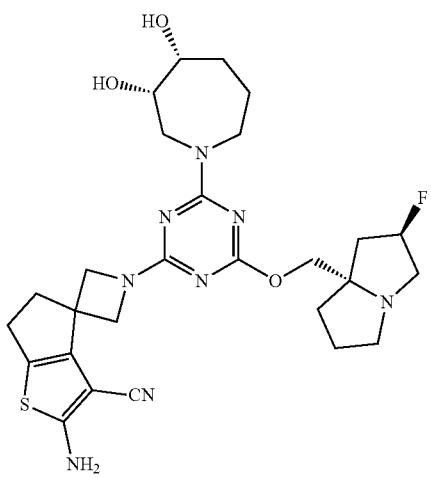 [SMILES: N#Cc1c(N)sc2c1C1(CC2)CN(c2nc(OC[C@@]34CCCN3C[C@H](F)C4)nc(N3CCC[C@@H](O)[C@@H](O)C3)n2)C1]

Compound 81 was prepared similarly to that of Ex. 1 as a TFA salt. LCMS calculated for C₂₇H₃₆FN₈O₃S (M+H)⁺ m/z=571.3, found: 571.3. ¹H NMR (400 MHz, CD₃OD) δ 5.55 (d, J=52.0 Hz, 1H), 4.67-4.32 (m, 4H), 4.24-3.76 (m, 9H), 3.65-3.40 (m, 3H), 2.81-2.46 (m, 6H), 2.43-2.23 (m, 3H), 2.20-1.91 (m, 3H), 1.83-1.68 (m, 1H), 1.52-1.41 (m, 1H).

Compound 82. 2'-amino-1-(4-(5-fluoro-3-hydroxy-3-methylpiperidin-1-yl)-6-(((2R,7aS)-2-fluorotetrahydro-1H-pyrrolizin-7a(5H)-yl)methoxy)-1,3,5-triazin-2-yl)-5',6'-dihydrospiro[azetidine-3,4'-cyclopenta[b]thiophene]-3'-carbonitrile

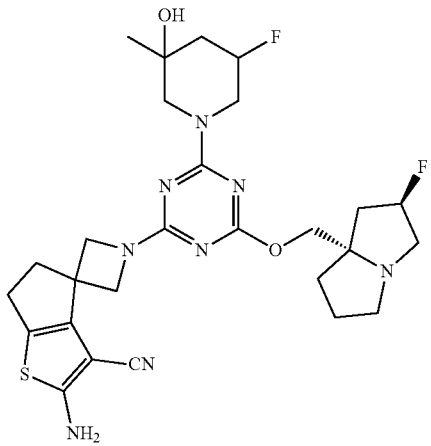 [SMILES: CC1(O)CC(F)CN(c2nc(OC[C@@]34CCCN3C[C@H](F)C4)nc(N3CC4(CCc5sc(N)c(C#N)c54)C3)n2)C1]

Compound 82 was prepared similarly to that of Ex. 1. LCMS calculated for C₂₇H₃₅F₂N₈O₂S (M+H)⁺ m/z=573.26; found: 573.3. ¹H NMR (400 MHz, CD₃OD) δ 5.27 (d, J=54.8 Hz, 1H), 4.59-4.78 (m, 1H), 4.29-4.41 (s, 2H), 4.06-4.20 (m, 4H), 3.67-3.94 (m, 2H), 3.50-3.64 (m, 1H), 3.14-3.35 (m, 4H), 2.93-3.04 (m, 1H), 2.64-2.81 (m, 4H), 1.79-2.34 (m, 8H), 1.17 (s, 3H).

Example 4. 2-amino-1'-[4-[1-(2-amino-3-pyridyl)ethyl-methyl-amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile (Compound 83)

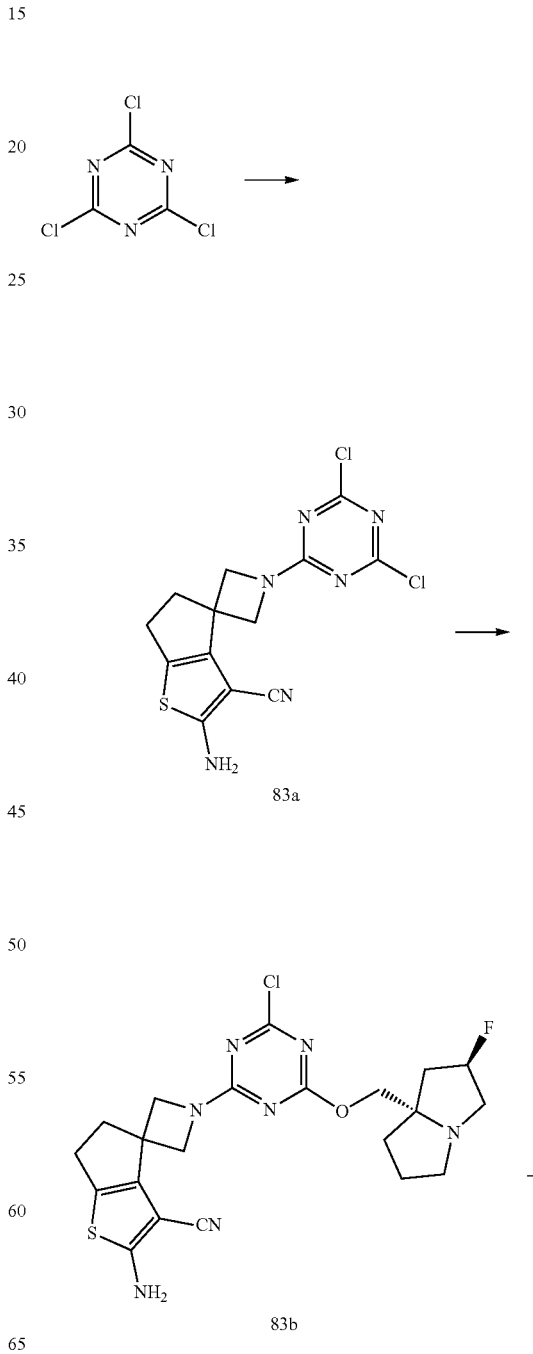

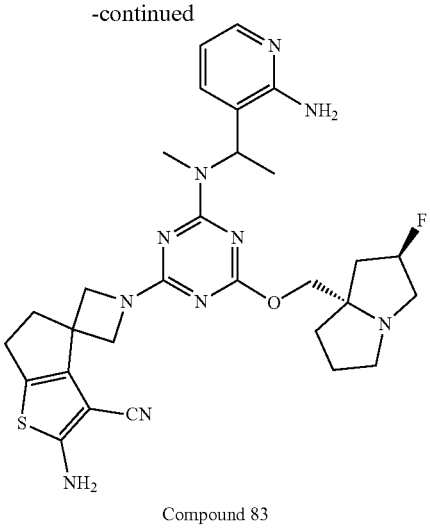

Compound 83

Step 1. Preparation of 2-amino-1'-(4,6-dichloro-1,3,5-triazin-2-yl)spiro[5,6-dihydrocyclopenta[b]thiophene-4,3'-azetidine]-3-carbonitrile (83a)

To a solution of 2-aminospiro[5,6-dihydrocyclopenta[b]thiophene-4,3'-azetidine]-3-carbonitrile; methanesulfonic acid (Intermediate 1, 1000 mg, 3.32 mmol) and DIEA (1.73 mL, 9.95 mmol) in DCM (18 mL) at −60° C. was added 2,4,6-trichloro-1,3,5-triazine (734.24 mg, 3.98 mmol) in DCM which was filtrated. The reaction was stirred at −60° C. for 30 min. The reaction was washed with brine (50 mL*2) and dried over $Na_2SO_4$, the organic layer was filtrated and concentrated. Then the crude was dissolved in DMSO and purified by pre-HPLC (ACN/Formic Acid-$H_2O$) to get 2-amino-1'-(4,6-dichloro-1,3,5-triazin-2-yl)spiro[5,6-dihydrocyclopenta[b]thiophene-4,3'-azetidine]-3-carbonitrile (83a, 353 mg, 0.9993 mmol, 30.12% yield) as a yellow solid.

LCMS calculated for $C_{13}H_{11}Cl_2N_6S$ $(M+H)^+$ (m/z)=353.02; found: 353.0

Step 2. Preparation of 2-amino-1'-[4-chloro-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile (83b).

To a solution of [(2R,8S)-2-fluoro-1,2,3,5,6,7-hexahydropyrrolizin-8-yl]methanol (315.49 mg, 1.98 mmol) and 2-amino-1'-(4,6-dichloro-1,3,5-triazin-2-yl)spiro[5,6-dihydrocyclopenta[b]thiophene-4,3'-azetidine]-3-carbonitrile (83a, 350 mg, 0.99 mmol) in THF (5 mL) was added $K_2CO_3$ (410.21 mg, 2.97 mmol). The mixture was stirred at 20° C. for 48 h. Water was added, the mixture was extracted by DCM, concentrated to get a crude. The crude was washed by ACN to get 2-amino-1'-[4-chloro-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile (83b, 730 mg, 0.690 mmol, 69.65% yield). LCMS calculated for $C_{21}H_{24}ClFN_7OS$ (M+H)+ m/z=476.14; found: 476.0

Step 3. Preparation of 2-amino-1'-[4-[1-(2-amino-3-pyridyl)ethyl-methyl-amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile (Compound 83)

To a solution of 2-amino-1'-[4-chloro-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile (83b, 132.21 mg, 0.28 mmol) and 3-[1-(methylamino)ethyl]pyridin-2-amine (Intermediate 11, 60 mg, 0.4 mmol) in DMSO (4 mL) was added DIPEA (153.85 mg, 1.19 mmol). The mixture was stirred at 20° C. for 5 days. The mixture was purified with pre-HPLC by a C18 column (ACN, $NH_4HCO_3$/water) to get 2-amino-1'-[4-[1-(2-amino-3-pyridyl)ethyl-methyl-amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile (Compound 83, 80 mg, 0.1322 mmol, 33.304% yield) as a white solid. LCMS calculated for $C_{29}H_{36}FN_{10}OS$ $(M+H)^+$ m/z=591.28; found: 591.3. $^1H$ NMR (400 MHz, DMSO-d) δ 7.89 (dd, J=4.8, 1.6 Hz, 1H), 7.49-7.63 (m, 1H), 7.22 (s, 2H), 6.54-6.64 (m, 1H), 5.60-6.06 (m, 3H), 5.24 (d, J=53.6 Hz, 1H), 3.76-4.36 (m, 6H), 2.92-3.13 (m, 3H), 2.58-2.87 (m, 8H), 1.64-2.13 (m, 6H), 1.45 (d, J=6.8 Hz, 3H).

Compound 84. 2-amino-1'-[4-[[(2R,8S)-2-fluoro-1,2,3,5,6,7-hexahydropyrrolizin-8-yl]methoxy]-6-(1H-pyrazol-5-ylmethylamino)-1,3,5-triazin-2-yl]spiro[5,6-dihydrocyclopenta[b]thiophene-4,3'-azetidine]-3-carbonitrile

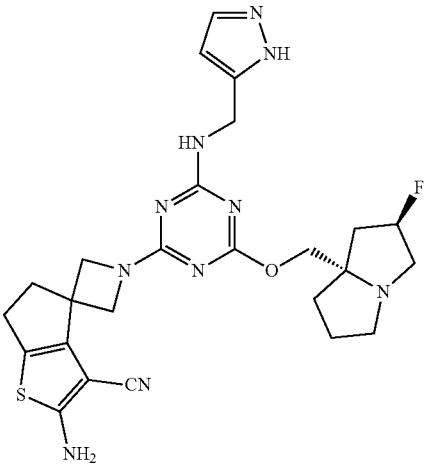 [SMILES: N#Cc1c(N)sc2c1C1(CC2)CN(c2nc(NCc3ccn[nH]3)nc(OC[C@@]34CCCN3C[C@H](F)C4)n2)C1]

Compound 84 was prepared similarly to that of Ex. 4. LCMS calcd for $C_{25}H_{30}FN_{10}OS$ $(M+H)^+$ m/z=537.1, found: 537.3. $^1H$ NMR (400 MHz, $CD_3OD$) δ 7.56 (s, 1H), 6.25 (s, 1H), 5.26 (d, J=55.6 Hz, 1H), 4.58 (s, 2H), 4.35 (s, 2H), 4.14 (s, 4H), 3.18 (m, 3H), 2.97 (s, 1H), 2.84-2.58 (m, 4H), 2.09 (m, 6H).

Compound 85. 2-amino-1'-[4-[3-hydroxy-3-(hydroxymethyl)-1-piperidyl]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

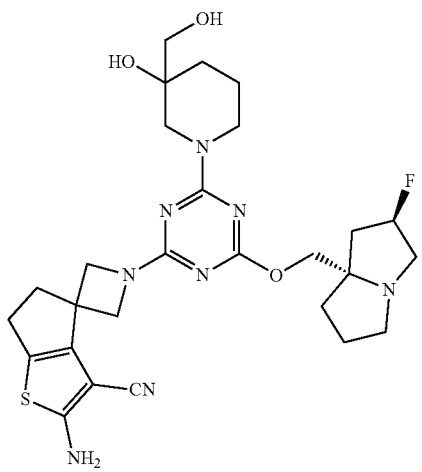 [SMILES: N#Cc1c(N)sc2c1C1(CC2)CN(c2nc(OC[C@@]34CCCN3C[C@H](F)C4)nc(N3CCCC(O)(CO)C3)n2)C1]

Compound 85 was prepared similarly to that of Ex. 1. LCMS calcd for $C_{27}H_{36}FN_8O_3S$ (M+H)$^+$ m/z=571.1, found: 571.2. $^1$H NMR (400 MHz, CD$_3$OD) δ: 5.60-5.47 (d, J=51.6, 1H), 4.57-4.52 (m, 2H), 4.47-4.44 (m, 2H), 4.38-4.35 (m, 3H), 4.19-3.80 (m, 5H), 3.48-3.40 (in, 5H), 2.79-2.66 (m, 4H), 2.58-2.52 (m, 1H), 2.38-2.27 (m, 3H), 2.15-2.12 (m, 1H), 1.78-1.59 (d, 2H), 1.56-1.28 (m, 2H).

Compound 86. 2-amino-1'-[4-(3-cyanoazepan-1-yl)-6-[[1-(morpholinomethyl)cyclopropyl]methoxy]-1,3,5-triazin-2-yl]spiro[5,6-dihydrocyclopenta[b]thiophene-4,3'-azetidine]-3-carbonitrile

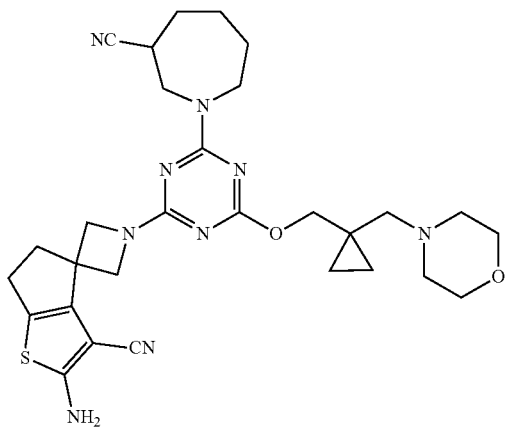 [SMILES: N#Cc1c(N)sc2c1C1(CC2)CN(c2nc(OCC3(CN4CCOCC4)CC3)nc(N3CCCCC(C#N)C3)n2)C1]

Compound 86 was prepared similarly to that of Ex. 1 as a TFA salt. LCMS calcd for $C_{29}H_{38}N_9O_2S$ (M+H)$^+$ m/z=576.3, found: 576.3. $^1$H NMR (400 MHz, CD$_3$OD) δ 4.57-4.11 (m, 7H), 4.14-3.45 (m, 10H), 3.43-3.32 (m, 1H), 3.29-3.09 (m, 3H), 2.87-2.62 (m, 4H), 2.09-1.70 (m, 5H), 1.67-1.49 (m, 1H), 1.08-0.69 (m, 4H).

Compound 87. 2-amino-1'-[4-[3-(difluoromethyl)-3-hydroxy-1-piperidyl]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

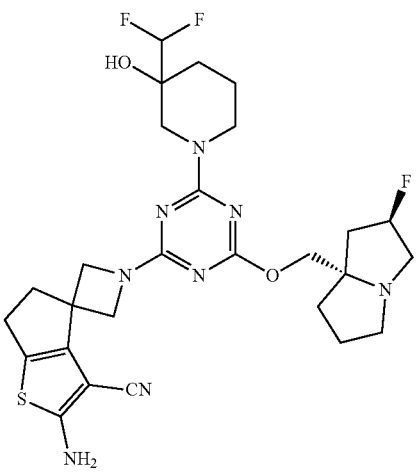 [SMILES: N#Cc1c(N)sc2c1C1(CC2)CN(c2nc(OC[C@@]34CCCN3C[C@H](F)C4)nc(N3CCCC(O)(C(F)F)C3)n2)C1]

Compound 87 was prepared similarly to that of Ex. 1 as a TFA salt. LCMS m/z calcd for $C_{27}H_{34}F_3N_8O_2S$ (M+H)$^+$ m/z: 591.3, found: 591.6. $^1$H NMR (400 MHz, CD$_3$OD) δ 5.86-5.42 (m, 2H), 4.66-4.30 (m, 6H), 4.25-4.13 (m, 2H), 4.02-3.79 (m, 3H), 3.51-3.39 (m, 1H), 2.79-2.68 (m, 4H), 2.60-2.44 (m, 2H), 2.40-2.03 (m, 5H), 1.92-1.55 (m, 5H).

Compound 88. 2-amino-1'-[4-[1-(2-amino-3-pyridyl)ethylamino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

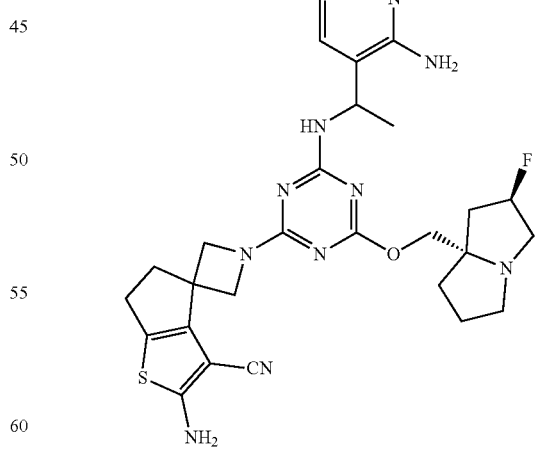

Compound 88 was prepared similarly to that of Ex. 4. LCMS calculated for $C_{28}H_{34}FN_{10}OS$ (M+H)$^+$ m/z=577.3; found: 577.1. $^1$H NMR (400 MHz, DMSO) δ 7.71-8.04 (m, 2H), 7.31-7.47 (m, 1H), 7.21 (s, 2H), 6.45-6.59 (m, 1H), 5.75-5.95 (m, 2H), 5.26 (d, J=52.6 Hz, 1H), 4.95-5.09 (m, 1H), 3.81-4.27 (m, 6H), 2.80-3.14 (m, 4H), 2.60-2.74 (m, 4H), 1.70-2.08 (m, 6H), 1.31-1.42 (m, 3H).

Compound 89. 2-amino-1'-[4-[[(2R,8S)-2-fluoro-1,2,3,5,6,7-hexahydropyrrolizin-8-yl]methoxy]-6-(1,4-oxazepan-4-yl)-1,3,5-triazin-2-yl]spiro[5,6-dihydrocyclopenta[b]thiophene-4,3'-azetidine]-3-carbonitrile

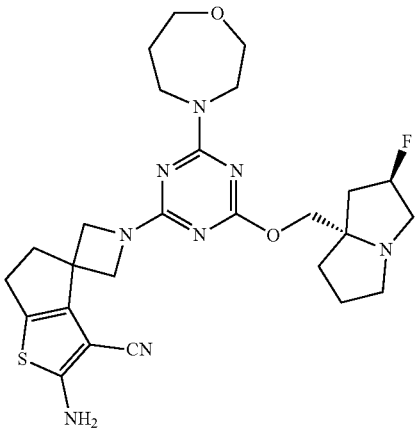 [SMILES: N#Cc1c(N)sc2c1C1(CC2)CN(c2nc(OC[C@@]34CCCN3C[C@H](F)C4)nc(N3CCCOCC3)n2)C1]

Compound 89 was prepared similarly to that of Ex. 1. LCMS calculated for $C_{26}H_{34}FN_8O_2S$ (M+H)$^+$ m/z=541.2; found: 541.1. $^1$H NMR (400 MHz, DMSO) δ 7.20 (s, 2H), 5.26 (d, J=54.0 Hz, 1H), 4.03-4.21 (m, 4H), 3.81-4.02 (m, 2H), 3.64-3.81 (m, 6H), 3.60 (t, J=5.6 Hz, 2H), 2.78-3.14 (m, 4H), 2.61-2.70 (m, 4H), 1.91-2.13 (m, 3H), 1.67-1.88 (m, 5H).

Compound 90. 2-amino-1'-[4-[[(2R,8S)-2-fluoro-1,2,3,5,6,7-hexahydropyrrolizin-8-yl]methoxy]-6-[[rac-(3R,4S)-4-hydroxytetrahydrofuran-3-yl]-methyl-amino]-1,3,5-triazin-2-yl]spiro[5,6-dihydrocyclopenta[b]thiophene-4,3'-azetidine]-3-carbonitrile

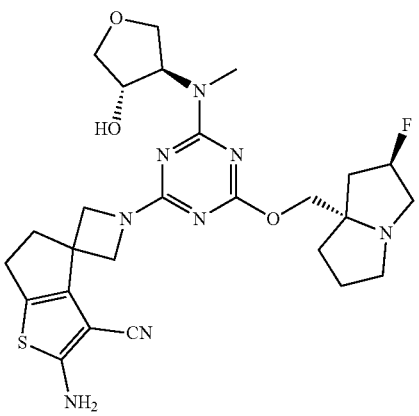 [SMILES: CN(c1nc(OC[C@@]23CCCN2C[C@H](F)C3)nc(N2CC3(CCc4sc(N)c(C#N)c43)C2)n1)[C@@H]1COC[C@H]1O]

Compound 90 was prepared similarly to that of Ex. 1 as a TFA salt. LCMS calcd for $C_{26}H_{34}FN_8O_3S$ (M+H)$^+$ m/z=557.3, found: 557.3. $^1$H NMR (400 MHz, CD$_3$OD) δ 5.55 (d, J=51.6 Hz, 1H), 5.08 (s, 1H), 4.55 (s, 2H), 4.44 (s, 1H), 4.37 (m, 2H), 4.18 (s, 2H), 4.12-4.03 (m, 2H), 4.02-3.76 (m, 4H), 3.64 (m, 1H), 3.49-3.39 (m, 1H), 3.11 (s, 3H), 2.81-2.68 (m, 4H), 2.68-2.46 (m, 2H), 2.33 (m, 3H), 2.14 (s, 1H).

Compounds 91A and 91B. (6*)-4-[4-(2-amino-3-cyano-spiro[5,6-dihydrocyclopenta[b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-1,4-oxazepane-6-carbonitrile

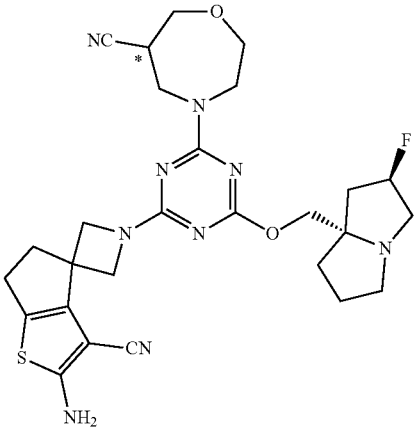 [SMILES: N#Cc1c(N)sc2c1C1(CC2)CN(c2nc(OC[C@@]34CCCN3C[C@H](F)C4)nc(N3CCOCC(C#N)C3)n2)C1]

Compound 91 was prepared similarly to that of Ex. 1 and was purified with pre-HPLC by a C18 column (ACN, NH$_4$HCO$_3$/water) to get the faster eluting P1 (91A, 6.2 mg, 0.00931 mmol, 8.90% yield) and the slower eluting P2 (91B, 9.3 mg, 0.0144 mmol, 13.78% yield) as white solid.

P1. LCMS calculated for $C_{27}H_{33}FN_9O_2S$ (M+H)$^+$ m/z=566.6; found: 566.6.

1H NMR (400 MHz, CD$_3$OD) δ 5.26 (d, J=54.4 Hz, 1H), 3.57-4.48 (m, 14H), 3.35-3.52 (m, 1H), 3.08-3.27 (m, 3H), 2.93-3.03 (m, 1H), 2.63-2.83 (m, 4H), 1.76-2.33 (m, 6H).

P2. LCMS calculated for $C_{27}H_{33}FN_9O_2S$ (M+H)$^+$ m/z=566.6; found: 566.6.

1H NMR (400 MHz, CD$_3$OD) δ 6.00 (d, J=36.8 Hz, 2H), 5.26 (d, J=53.3 Hz, 1H), 4.49-4.74 (m, 2H), 4.02-4.48 (m, 7H), 3.57-3.89 (m, 4H), 3.11-3.28 (m, 3H), 2.93-3.05 (m, 1H), 2.64-2.83 (m, 4H), 1.77-2.33 (m, 6H).

Compound 92. 2-amino-1'-[4-[[(2R,8S)-2-fluoro-1,2,3,5,6,7-hexahydropyrrolizin-8-yl]methoxy]-6-[[rac-(1R,2S)-2-hydroxycyclopentyl]-methyl-amino]-1,3,5-triazin-2-yl]spiro[5,6-dihydrocyclopenta[b]thiophene-4,3'-azetidine]-3-carbonitrile

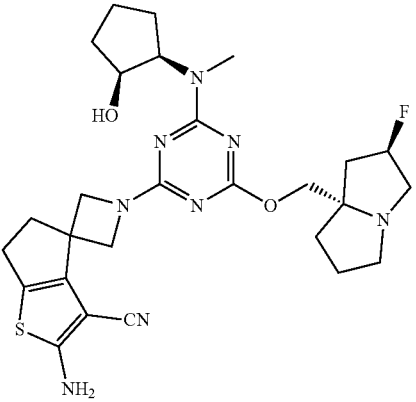 [SMILES: CN(c1nc(OC[C@@]23CCCN2C[C@H](F)C3)nc(N2CC3(CCc4sc(N)c(C#N)c43)C2)n1)[C@@H]1CCC[C@@H]1O]

Compound 92 was prepared similarly to that of Ex. 1 as TFA salt. LCMS calculated for $C_{27}H_{36}FN_8O_2S$ (M+H)$^+$ m/z=555.3, found: 555.3. $^1$H NMR (400 MHz, CD$_3$OD) δ 5.64-5.45 (m, 1H), 4.67-4.54 (m, 2H), 4.49 (d, J=10.4 Hz, 1H), 4.35 (s, 3H), 4.18 (d, J=9.6 Hz, 2H), 4.07-3.79 (m, 3H), 3.44 (m, 1H), 3.20 (s, 3H), 2.81-2.68 (m, 4H), 2.67-2.47 (m, 2H), 2.32 (m, 3H), 2.21-1.71 (m, 6H), 1.69-1.50 (m, 2H).

Compound 93. 2'-amino-1-(4-(5-fluoro-3-hydroxy-3-methylpiperidin-1-yl)-6-((1-(morpholinomethyl)cyclopropyl)methoxy)-1,3,5-triazin-2-yl)-5',6'-dihydrospiro[azetidine-3,4'-cyclopenta[b]thiophene]-3'-carbonitrile

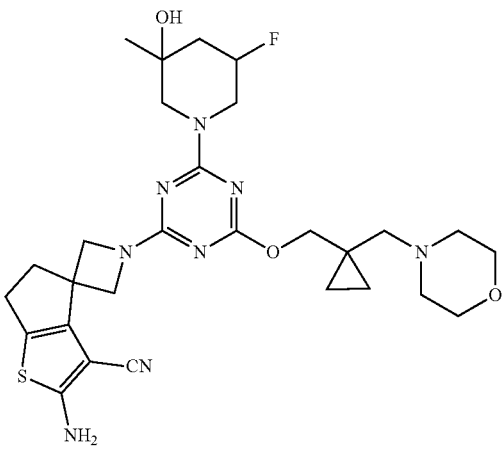 [SMILES: CC1(O)CC(F)CN(c2nc(OCC3(CN4CCOCC4)CC3)nc(N3CC4(CCc5sc(N)c(C#N)c54)C3)n2)C1]

Compound 93 was prepared similarly to that of Ex. 1. LCMS calculated for $C_{28}H_{38}FN_8O_3S$ (M+H)$^+$ m/z=585.28; found: 585.3. $^1$H NMR (400 MHz, CD$_3$OD) δ 4.58-4.76 (m, 1H), 4.18-4.44 (m, 5H), 4.05-4.16 (m, 2H), 3.83-4.01 (m, 1H), 3.46-3.78 (m, 6H) 2.64-2.83 (m, 4H), 2.25-2.58 (m, 6H), 1.81-2.17 (m, 2H), 1.18 (s, 3H), 0.58-0.73 (m, 2H), 0.37-0.51 (m, 2H).

Compound 94. 2-amino-1'-[4-[[rac-(3R,4R)-4-hydroxytetrahydrofuran-3-yl]-methyl-amino]-6-[[1-(morpholinomethyl)cyclopropyl]methoxy]-1,3,5-triazin-2-yl]spiro[5,6-dihydrocyclopenta[b]thiophene-4,3'-azetidine]-3-carbonitrile

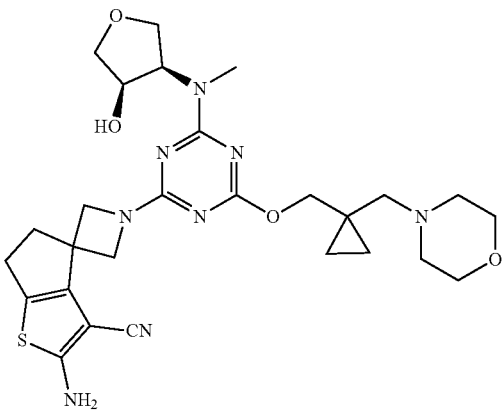 [SMILES: CN(c1nc(OCC2(CN3CCOCC3)CC2)nc(N2CC3(CCc4sc(N)c(C#N)c43)C2)n1)[C@@H]1COC[C@@H]1O]

Compound 94 was prepared similarly to that of Ex. 1 as a TFA salt. LCMS for $C_{27}H_{37}N_8O_4S$ (M+H)$^+$ m/z=569.3, found: 569.5. $^1$H NMR (400 MHz, CD$_3$OD) δ 5.07 (s, 1H), 4.82 (s, 2H), 4.55 (s, 1H), 4.40-4.20 (m, 6H), 4.12-3.60 (m, 9H), 3.27 (s, 2H), 3.19-3.10 (m, 4H), 2.75-2.72 (m, 4H), 0.95-0.85 (m, 4H).

Compound 95. 2-amino-1'-[4-[3-hydroxy-3-(hydroxymethyl)-1-piperidyl]-6-[[1-(morpholinomethyl)cyclopropyl]methoxy]-1,3,5-triazin-2-yl]spiro[5,6-dihydrocyclopenta[b]thiophene-4,3'-azetidine]-3-carbonitrile

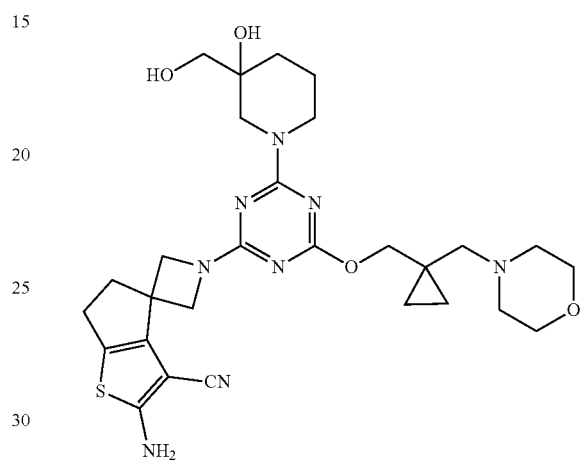

Compound 95 was prepared similarly to that of Ex. 1 as a TFA salt. LCMS calcd for $C_{28}H_{39}N_8O_4S$ (M+H)$^+$ m/z=583.7, found: 583.2. $^1$H NMR (400 MHz, CD$_3$OD) δ: 4.37-4.31 (m, 4H), 4.29-3.66 (m, 10H), 3.64-3.32 (m, 6H), 3.25-3.12 (m, 2H), 2.79-2.69 (m, 4H), 1.81-1.78 (m, 2H), 1.62-1.54 (m, 2H), 0.96-0.95 (m, 2H), 0.85-0.83 (m, 2H).

Compound 96. 2-amino-1'-[4-(4-cyano-3-hydroxy-azepan-1-yl)-6-[[rac-(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

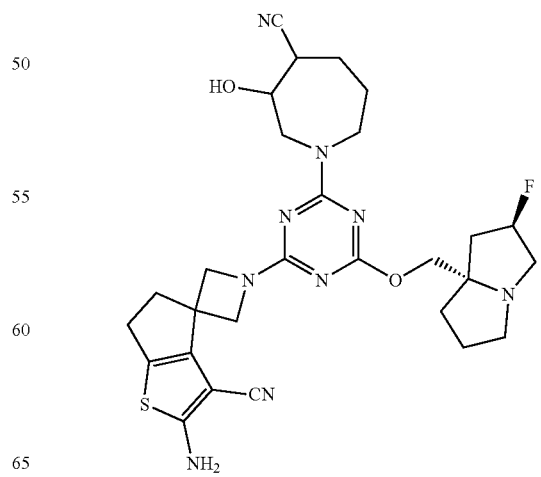

Compound 96 was prepared similarly to that of Ex. 1. LCMS for $C_{28}H_{35}FN_9O_2S$ (M+H)$^+$ m/z=580.3, found: 580.4. $^1$H NMR (400 MHz, CD$_3$OD) δ 5.55 (d, J=53.8 Hz, 1H), 4.64-4.30 (m, 4H), 4.24-4.17 (m, 3H), 4.13-3.80 (m, 5H), 3.64-3.45 (m, 3H), 2.90-2.47 (m, 7H), 2.44-1.61 (m, 8H).

Compound 97. 2-amino-1'-[4-[1-(2-amino-3-pyridyl)ethyl-methyl-amino]-6-[[1-(morpholinomethyl)cyclopropyl]methoxy]-1,3,5-triazin-2-yl]spiro[5,6-dihydrocyclopenta[b]thiophene-4,3'-azetidine]-3-carbonitrile

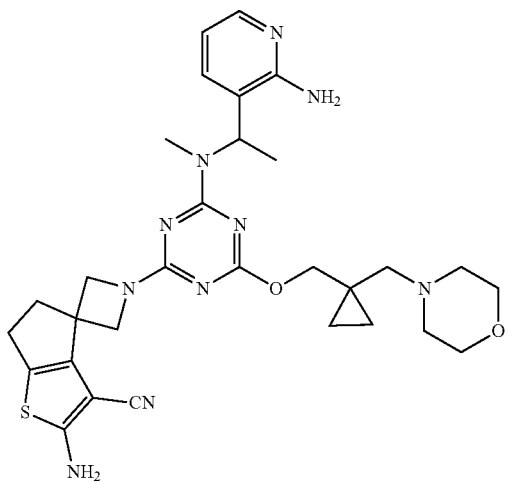 [SMILES: CC(c1cccnc1N)N(C)c1nc(OCC2(CN3CCOCC3)CC2)nc(N2CC3(CCc4sc(N)c(C#N)c43)C2)n1]

Compound 97 was prepared similarly to that of Ex. 1. LCMS calculated for $C_{30}H_{39}N_{10}O_2S$ (M+H)$^+$ m/z=603.30; found: 603.3. $^1$H NMR (400 MHz, CD$_3$OD) δ 7.86 (s, 1H), 7.65 (dd, J=7.6, 1.2 Hz, 1H), 6.53-6.76 (m, 1H), 5.86-6.17 (m, 1H), 4.05-4.52 (m, 6H), 3.65 (s, 4H), 2.63-2.87 (m, 7H), 2.25-2.59 (m, 6H), 1.54 (d, J=6.8 Hz, 3H), 0.64 (s, 2H), 0.44 (s, 2H).

Compound 98. 2-amino-5,5-difluoro-1'-[4-[(3R)-3-hydroxy-3-methyl-1-piperidyl]-6-[[1-(morpholinomethyl)cyclopropyl]methoxy]-1,3,5-triazin-2-yl]spiro[6H-cyclopenta[b]thiophene-4,3'-azetidine]-3-carbonitrile

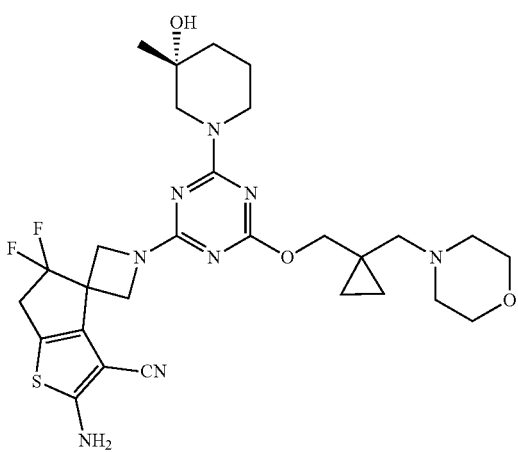 [SMILES: C[C@@]1(O)CCCN(c2nc(OCC3(CN4CCOCC4)CC3)nc(N3CC4(C3)c3c(sc(N)c3C#N)CC4(F)F)n2)C1]

Compound 98 was prepared similarly to that of Ex. 1. LCMS calculated for $C_{28}H_{37}F_2N_8O_3S$ (M+H)$^+$ m/z=603.27; found: 603.3. $^1$H NMR (400 MHz, CD$_3$OD) δ 4.47 (d, J=9.6 Hz, 2H), 4.12-4.33 (m, 4H), 3.81-3.91 (m, 1H), 3.56-3.77 (m, 7H), 3.20-3.32 (m, 2H), 2.29-2.57 (m, 6H), 1.50-1.85 (m, 4H), 1.20 (s, 3H), 0.65 (t, J=5.2 Hz, 2H), 0.44 (t, 5.2 Hz, 2H).

Compound 99. 2-amino-1'-[4-(3,5-dihydro-2H-pyrido[3,2-f][1,4]thiazepin-4-yl)-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

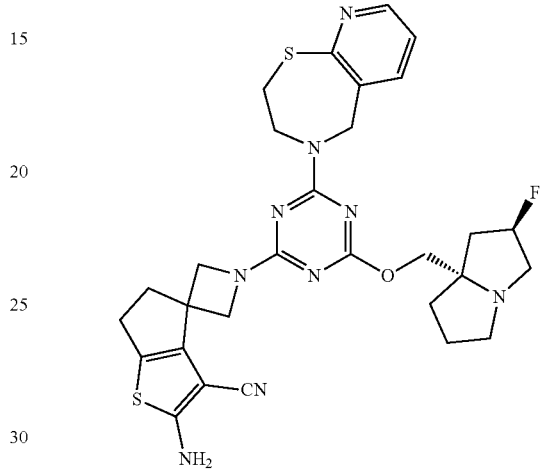

Compound 99 was prepared similarly to that of Ex. 1. LCMS calculated for $C_{29}H_{33}FN_9OS_2$ (M+H)$^+$ m/z=606.22; found: 606.3. $^1$H NMR (400 MHz, CD$_3$OD) δ 8.21-8.26 (m, 1H), 7.90-8.01 (m, 1H), 7.25 (dd, J=7.6, 4.9 Hz, 1H), 5.14-5.36 (m, 1H), 4.86-4.90 (m, 2H), 4.22-4.49 (m, 4H), 3.95-4.21 (m, 4H), 2.89-3.26 (m, 6H), 2.62-2.81 (m, 4H), 1.73-2.27 (m, 6H).

Compound 100A and 100B. 2-amino-1'-[4-[[(1*)-1-(2-amino-3-pyridyl)ethyl]-methyl-amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

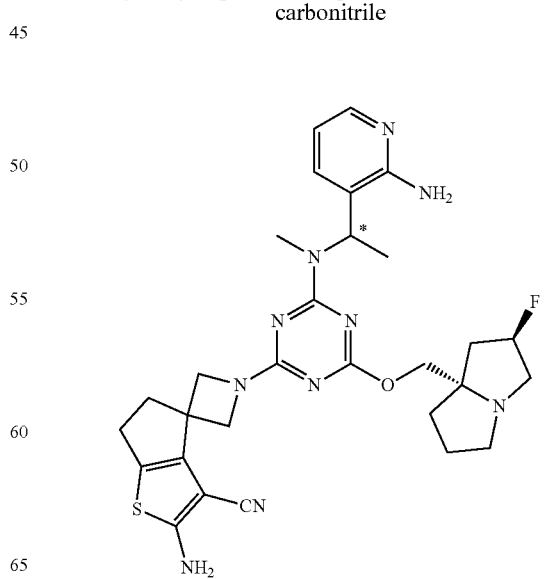

Compound 83 was purified on an DAICELCHIRALCEL®AS (250*25 mm 10 um) column on a Waters SFC 150 system (Mobile Phase A: Supercritical $CO_2$, Mobile Phase B: MeOH[0.2% $NH_3$ (7M in MeOH)]); A:B: 75:25; Flow: 100 ml/min) to give faster eluting P1 (100A) and slower eluting P2 (100B).

Compound 101. 2-amino-1'-[4-[3-(cyanomethyl)-3-hydroxy-1-piperidyl]-6-[[1-(morpholinomethyl)cyclopropyl]methoxy]-1,3,5-triazin-2-yl]spiro[5,6-dihydrocyclopenta[b]thiophene-4,3'-azetidine]-3-carbonitrile

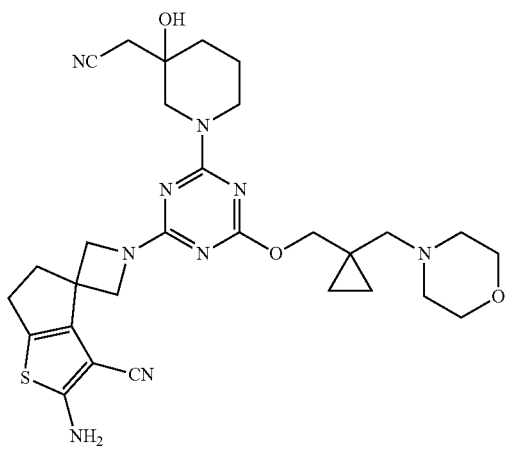 [SMILES: N#CCC1(O)CCCN(c2nc(OCC3(CN4CCOCC4)CC3)nc(N3CC4(CCc5sc(N)c(C#N)c54)C3)n2)C1]

Compound 101 was prepared similarly to that of Ex. 1 as a TFA salt. LCMS calcd for $C_{29}H_{38}N_9O_3S$ $(M+H)^+$ m/z=592.73, found: 592.3. $^1$H NMR (400 MHz, $CD_3OD$) δ 4.38 (d, J=8.8 Hz, 4H), 4.22 (d, J=9.7 Hz, 2H), 4.11-3.83 (m, 6H), 3.79-3.55 (m, 4H), 3.14 (t, J=17.0 Hz, 2H), 2.80-2.58 (m, 6H), 2.23-1.59 (m, 4H), 1.62-1.48 (m, 1H), 1.50-1.16 (m, 1H), 0.95 (s, 2H), 0.85 (s, 2H).

Compound 102. 2-amino-1'-[4-[1-(3-aminopyrazin-2-yl)ethyl-methyl-amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

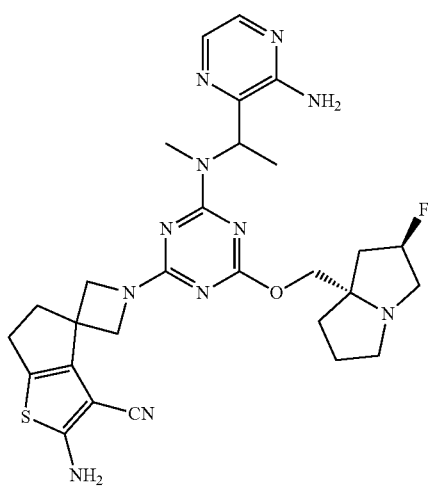

Compound 102 was prepared similarly to that of Ex. 4. LCMS calculated for $C_{28}H_{35}FN_{11}OS$ $(M+H)^+$ m/z=592.28; found: 592.3. $^1$H NMR (400 MHz, DMSO) δ 7.89 (d, J=2.4 Hz, 1H), 7.76 (d, J=1.2 Hz, 1H), 7.22 (s, 2H), 6.19-6.48 (m, 2H), 5.87-5.97 (m, 1H), 5.24 (d, J=53.6 Hz, 1H), 3.79-4.36 (m, 6H), 2.95-3.12 (m, 3H), 2.60-2.85 (m, 8H), 1.69-2.10 (m, 6H), 1.47 (d, J=6.8 Hz, 3H).

Compound 103. 2-amino-1'-[4-[[(2R,8S)-2-fluoro-1,2,3,5,6,7-hexahydropyrrolizin-8-yl]methoxy]-6-[[rac-(3R,4R)-4-hydroxytetrahydrofuran-3-yl]amino]-1,3,5-triazin-2-yl]spiro[5,6-dihydrocyclopenta[b]thiophene-4,3'-azetidine]-3-carbonitrile

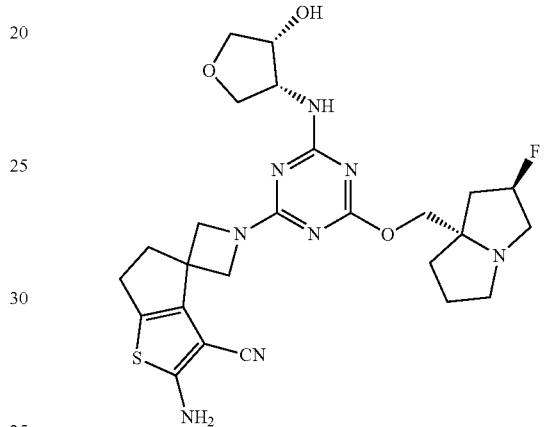

Compound 103 was prepared similarly to that of Ex. 1 as a TFA salt. LCMS m/z calcd for $C_{25}H_{32}FN_8O_3S$ (M+H)+: 543.3, found: 543.3. $^1$H NMR (400 MHz, $CD_3OD$) δ 5.55 (d, J=53.7 Hz, 1H), 4.62-4.29 (m, 6H), 4.25-4.15 (m, 2H), 4.11-3.82 (m, 5H), 3.80-3.65 (m, 1H), 3.64-3.51 (m, 1H), 3.51-3.36 (m, 1H), 2.80-2.65 (m, 4H), 2.60-2.43 (m, 2H), 2.43-2.19 (m, 3H), 2.21-2.04 (m, 1H).

Example 5. Synthesis of 2-amino-1'-[4-[[1-[(dimethylamino)methyl]-2,2-difluoro-cyclopropyl]methoxy]-6-[(3R)-3-hydroxy-3-methyl-1-piperidyl]-1,3,5-triazin-2-yl]spiro[6H-thieno[2,3-c]thiophene-4,3'-azetidine]-3-carbonitrile (Compound 104)

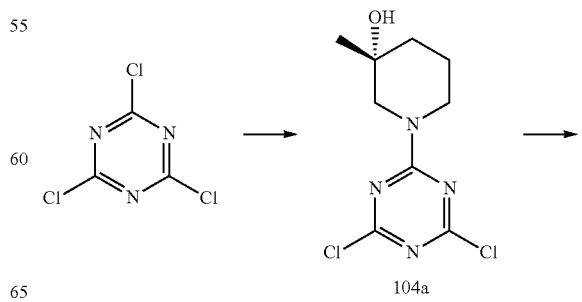

104a

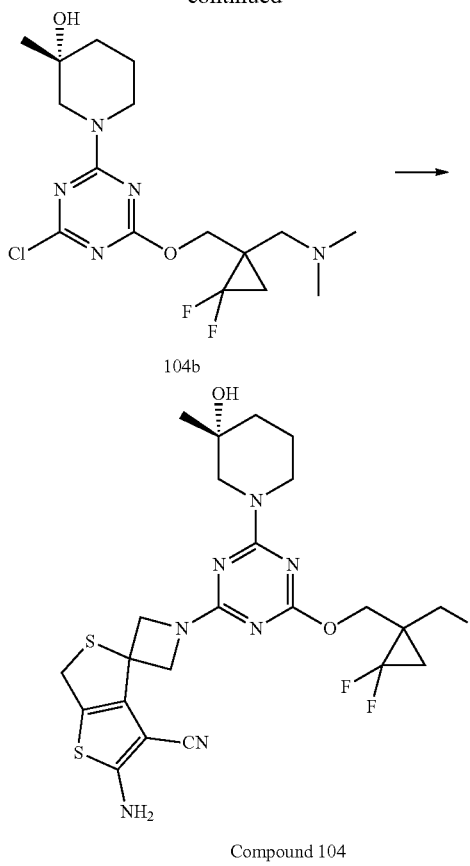

Compound 104

Step 1. Preparation of (3R)-1-(4,6-dichloro-1,3,5-triazin-2-yl)-3-methyl-piperidin-3-ol (104a). To a solution of 2,4,6-trichloro-1,3,5-triazine (150 mg, 0.81 mmol) in DCM (2 mL) was added DIEA (0.43 mL, 2.44 mmol) and (3R)-3-methylpiperidin-3-ol; hydrochloride (123.34 mg, 0.81 mmol) at 0° C. for 1 h. The reaction was concentrated. The residue was purified by silica gel chromatography (eluing with EtOAc in petroleum ether from 0% to 50%) to afford (3R)-1-(4,6-dichloro-1,3,5-triazin-2-yl)-3-methyl-piperidin-3-ol (200 mg, 0.7601 mmol, 93.448% yield) was obtained as a white solid. LCMS calculated for $C_9H_{13}Cl_2N_4O$ (M+H)$^+$ m/z=263.1, found: 263.2.

Step 2. Preparation of (3R)-1-[4-chloro-6-[[1-[(dimethyl-amino)methyl]-2,2-difluoro-cyclopropyl]methoxy]-1,3,5-triazin-2-yl]-3-methyl-piperidin-3-ol (104b). To a solution [1-[(dimethylamino)methyl]-2,2-difluoro-cyclopropyl]methanol (106.72 mg, 0.65 mmol) in THF (2 mL) was added NaH (38.77 mg, 0.97 mmol) at 0° C. Then the reaction was stirred for 15 min 25° C. (3R)-1-(4,6-dichloro-1,3,5-triazin-2-yl)-3-methyl-piperidin-3-ol (170 mg, 0.65 mmol) was added and stirred for 1 h at 25° C. The mixture was diluted with acetic acid solution, extracted with EtOAc (50 mL×3) and washed with brine (15 ml), dried over $Na_2SO_4$, concentrated. The crude product was purified by flash chromatography (eluted with EtOAc in petroleum ether from 10% to 100%) to afford (3R)-1-[4-chloro-6-[[1-[(dimethylamino)methyl]-2,2-difluoro-cyclopropyl]methoxy]-1,3,5-triazin-2-yl]-3-methyl-piperidin-3-ol (164 mg, 0.4185 mmol, 64.78% yield) was obtained as white oil. LCMS calcd for $C_{16}H_{25}ClF_2N_5O_2$ (M+H)+ m/z=392.8, found: 392.1.

Step 3. Preparation of 2-amino-1'-[4-[[1-[(dimethyl-amino)methyl]-2,2-difluoro-cyclopropyl]methoxy]-6-[(3R)-3-hydroxy-3-methyl-1-piperidyl]-1,3,5-triazin-2-yl]spiro[6H-thieno[2,3-c]thiophene-4,3'-azetidine]-3-carbonitrile (Compound 104)

To a solution of (3R)-1-[4-chloro-6-[[1-[(dimethylamino)methyl]-2,2-difluoro-cyclopropyl]methoxy]-1,3,5-triazin-2-yl]-3-methyl-piperidin-3-ol (104b, 35 mg, 0.09 mmol) in 1,4-Dioxane (1 mL) was added DIEA (34.63 mg, 0.27 mmol) and 2-aminospiro[6H-thieno[2,3-c]thiophene-4,3'-azetidine]-3-carbonitrile; methanesulfonic acid (Intermediate 1, 31.38 mg, 0.1 mmol) at 25° C. Then the mixture was stirred at 80° C. for 1 h. The mixture was concentrated to afford a crude product. The crude product was purified by Prep-HPLC (eluted with $CH_3CN$ in $H_2O$ (0.1% TFA) from 5.0% to 95%). 2-amino-1'-[4-[[1-[(dimethylamino)methyl]-2,2-difluoro-cyclopropyl]methoxy]-6-[(3R)-3-hydroxy-3-methyl-1-piperidyl]-1,3,5-triazin-2-yl]spiro[6H-thieno[2,3-c]thiophene-4,3'-azetidine]-3-carbonitrile (Compound 104, 44 mg, 0.0539 mmol, 60.36% yield) was obtained as white solid. LCMS calcd for $C_{25}H_{33}F_2N_8O_2S_2$ (M+H)$^+$ m/z=579.3 found 579.2. $^1$H NMR (400 MHz, $CD_3OD$) δ 4.77-4.30 (m, 6H), 4.06 (s, 2H), 4.03-3.34 (m, 6H), 2.99 (s, 6H), 2.02-1.88 (m, 1H), 1.87-1.73 (m, 2H), 1.73-1.61 (m, 2H), 1.61-1.49 (m, 1H), 1.20 (s, 3H).

Compound 105. 2-amino-1'-[4-[methyl(1H-pyrazol-5-ylmethyl)amino]-6-[[rac-(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

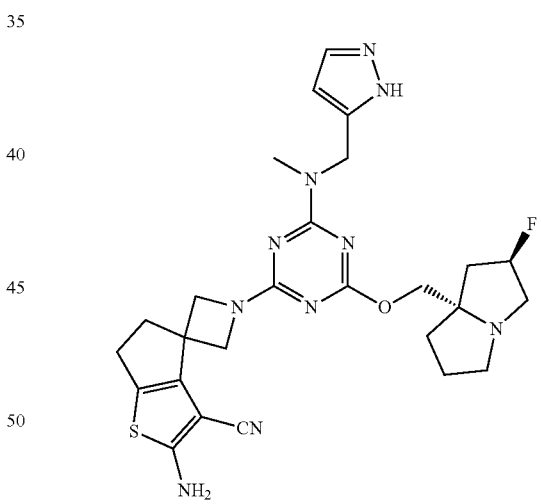

Compound 105 was prepared similarly to that of Ex. 4 as a TFA salt. LCMS calcd for $C_{26}H_{32}FN_{10}OS$ (M+H)$^+$ m/z=551.2, found: 551.2. $^1$H NMR (400 MHz, $CD_3OD$) δ 7.59 (s, 1H), 6.26 (d, J=17.8 Hz, 1H), 5.69-5.37 (m, 1H), 4.95-4.87 (m, 2H), 4.65-4.44 (m, 2H), 4.45-4.29 (m, 2H), 4.25-4.15 (m, 2H), 4.09-3.75 (m, 3H), 3.53-3.36 (m, 1H), 3.12 (s, 3H), 2.86-2.68 (m, 4H), 2.68-2.44 (m, 2H), 2.42-2.01 (m, 4H).

Compound 106. 2-amino-1'-[4-[3-(difluoromethyl)-3-hydroxy-1-piperidyl]-6-[[1-(morpholinomethyl)cyclopropyl]methoxy]-1,3,5-triazin-2-yl]spiro[5,6-dihydrocyclopenta[b]thiophene-4,3'-azetidine]-3-carbonitrile

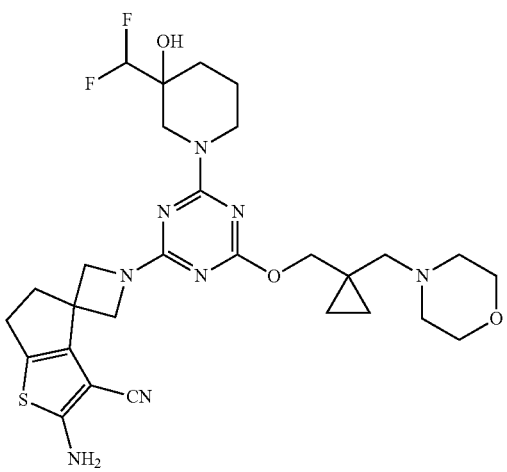 [SMILES: N#Cc1c(N)sc2c1C1(CC2)CN(c2nc(OCC3(CN4CCOCC4)CC3)nc(N3CCCC(O)(C(F)F)C3)n2)C1]

Compound 106 was prepared similarly to that of Ex. 1 as a TFA salt. LCMS calcd for $C_{28}H_{37}F_2N_8O_3S$ (M+H)$^+$ m/z=603.3, found: 603.3. $^1$H NMR (400 MHz, CD$_3$OD) δ 5.87-5.51 (m, 1H), 4.53-4.13 (m, 8H), 4.09-3.58 (m, 6H), 3.46-3.33 (m, 2H), 3.28-3.00 (m, 4H), 2.83-2.66 (m, 4H), 1.91-1.54 (m, 4H), 0.98-0.76 (m, 4H).

Compound 107. 2-amino-1'-[4-[(2-amino-3-pyridyl)methyl-(2-hydroxyethyl)amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

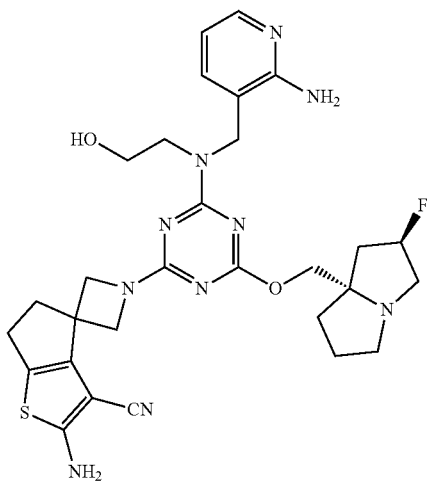 [SMILES: N#Cc1c(N)sc2c1C1(CC2)CN(c2nc(OC[C@@]34CCCN3C[C@H](F)C4)nc(N(CCO)Cc3cccnc3N)n2)C1]

Compound 107 was prepared similarly to that of Ex. 4. LCMS calculated for $C_{29}H_{36}FN_{10}O_2S$ (M+H)$^+$ m/z=607.3; found: 607.3. $^1$H NMR (400 MHz, CD$_3$OD) δ 7.86 (m, 1H), 7.45 (m, 1H), 6.62 (m, 1H), 5.25 (d, J=54.0 Hz, 1H), 4.52-4.69 (m, 2H), 4.26-4.48 (m, 2H), 4.00-4.24 (m, 4H), 3.46-3.78 (m, 4H), 3.05-3.25 (m, 3H), 2.87-3.04 (m, 1H), 2.66-2.83 (m, 4H), 2.01-2.33 (m, 3H), 1.72-2.00 (m, 3H).

Compound 108. 2-amino-1'-[4-[1-(4-aminopyrimidin-5-yl)ethyl-methyl-amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

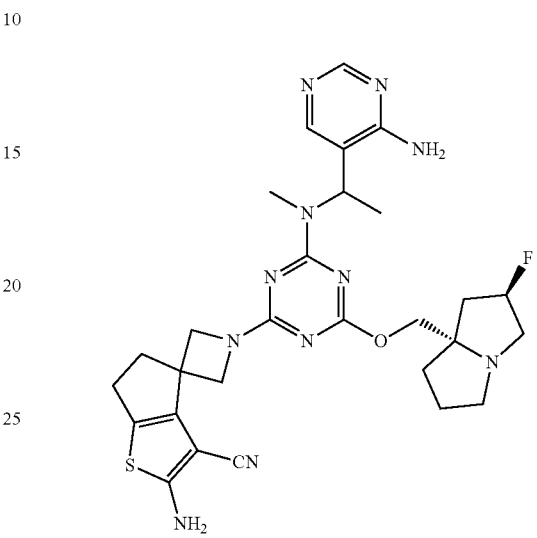

Compound 108 was prepared similarly to that of Ex. 4. LCMS calculated for $C_{28}H_{35}FN_{11}OS$ (M+H)$^+$ m/z=592.28; found: 592.2. $^1$H NMR (400 MHz, DMSO) δ 8.33 (s, 1H), 8.20-8.29 (m, 1H), 7.22 (s, 2H), 6.53-7.03 (m, 2H), 5.80 (d, J=7.2 Hz, 1H), 5.25 (d, J=55.2 Hz, 1H), 3.82-4.33 (m, 6H), 2.94-3.11 (m, 3H), 2.58-2.84 (m, 8H), 1.68-2.09 (m, 6H), 1.49 (d, J=6.8 Hz, 3H).

Compound 109. 2-amino-1'-[4-[1-(3-aminopyridazin-4-yl)ethyl-methyl-amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

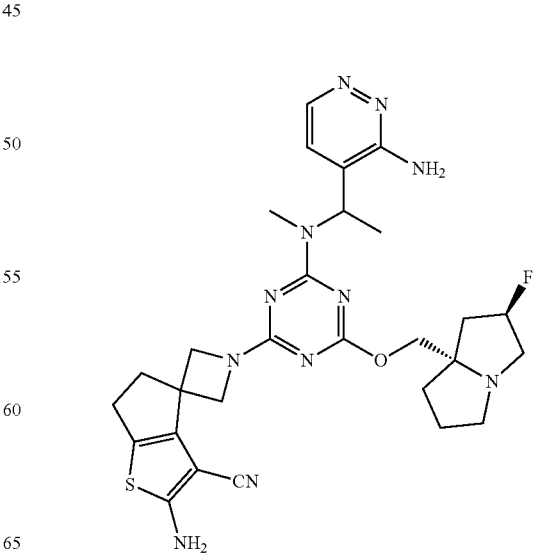

Compound 109 was prepared similarly to that of Ex. 4. LCMS calculated for $C_{28}H_{35}FN_{11}OS$ (M+H)$^+$ m/z=592.28; found: 592.3. $^1$H NMR (400 MHz, DMSO) δ 8.47 (d, J=4.8 Hz, 1H), 7.01-7.51 (m, 3H), 6.02-6.51 (m, 2H), 5.77 (d, J=5.7 Hz, 1H), 5.25 (d, J=53.4 Hz, 1H), 3.80-4.31 (m, 6H), 3.07 (s, 3H), 2.61-2.83 (m, 8H), 1.69-2.12 (m, 6H), 1.47 (d, J=6.8 Hz, 3H).

Compound 110. 2-amino-1'-[4-[1-(2-amino-3-pyridyl)ethyl-(2-hydroxyethyl)amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

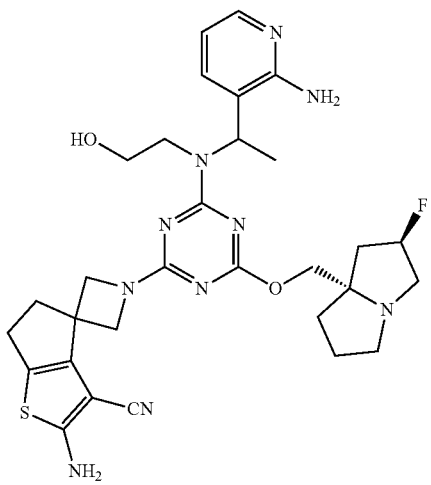 [SMILES: CC(c1cccnc1N)N(CCO)c1nc(OC[C@@]23CCCN2C[C@H](F)C3)nc(N2CC3(CCc4sc(N)c(C#N)c43)C2)n1]

Compound 110 was prepared similarly to that of Ex. 4. LCMS calculated for $C_{30}H_{38}FN_{10}O_2S$ (M+H)$^+$ m/z=621.29; found: 621.2. $^1$H NMR (400 MHz, DMSO) δ 7.90 (d, J=4.2 Hz, 1H), 7.50-7.64 (m, 1H), 7.21 (s, 2H), 6.55-6.67 (m, 1H), 5.73-5.90 (m, 2H), 5.52-5.70 (m, 1H), 5.27 (d, J=54.0 Hz, 1H), 4.45-4.63 (m, 1H), 3.89-4.30 (m, 7H), 3.01-3.19 (m, 3H), 2.79-2.95 (m, 2H), 2.64-2.72 (m, 5H), 1.70-2.13 (m, 7H), 1.46 (d, J=6.8 Hz, 3H).

Compound 111. 2-amino-1'-[4-(3-cyano-3-methyl-azepan-1-yl)-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

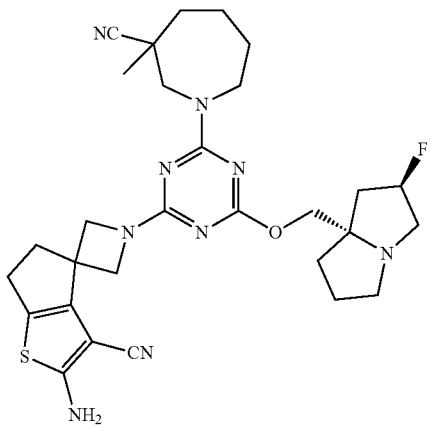 [SMILES: CC1(C#N)CCCCN(c2nc(OC[C@@]34CCCN3C[C@H](F)C4)nc(N3CC4(CCc5sc(N)c(C#N)c54)C3)n2)C1]

Compound 111 was prepared similarly to that of Ex. 1 as a TFA salt. LCMS m/z calcd for $C_{29}H_{37}FN_9OS$ (M+H)+: 578.3, found: 578.3. $^1$H NMR (400 MHz, CD$_3$OD) δ 5.54 (d, J=51.8 Hz, 1H), 4.77-4.31 (m, 5H), 4.27-4.04 (m, 2H), 4.04-3.76 (m, 3H), 3.51-3.32 (m, 2H), 3.23-3.08 (m, 1H), 2.80-2.62 (m, 4H), 2.59-2.24 (m, 5H), 2.19-1.53 (m, 8H), 1.42 (s, 3H).

Compound 112. 2-amino-1'-[4-[1-(2-amino-3-pyridyl)ethyl-methyl-amino]-6-[[(2S)-5-oxopyrrolidin-2-yl]methoxy]-1,3,5-triazin-2-yl]spiro[5,6-dihydrocyclopenta[b]thiophene-4,3'-azetidine]-3-carbonitrile

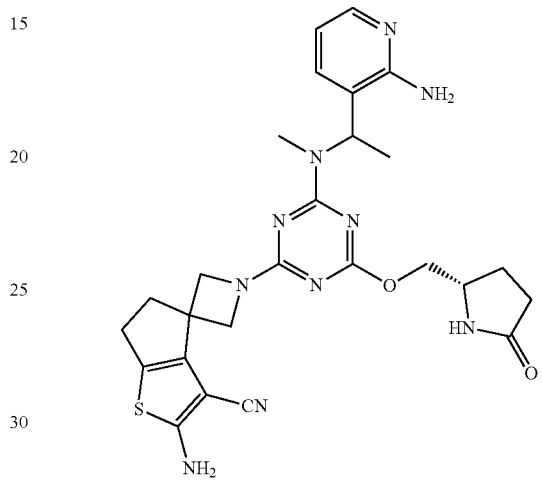

Compound 112 was prepared similarly to that of Ex. 4. LCMS calculated for $C_{26}H_{31}N_{10}O_2S$ (M+H)$^+$ m/z=547.23; found: 546.8. $^1$H NMR (400 MHz, DMSO-d6) δ 7.86-7.92 (m, 1H), 7.76-7.86 (m, 1H), 7.50-7.62 (m, 1H), 7.22 (s, 2H), 6.55-6.69 (m, 1H), 5.68-6.03 (m, 3H), 4.03-4.34 (m, 6H), 3.77-3.91 (m, 1H), 2.63-2.73 (m, 7H), 2.04-2.26 (m, 3H), 1.72-1.88 (m, 1H), 1.37-1.53 (m, 3H).

Compound 113. 2-amino-5,5-dioxo-1'-[4-[[rac-(2R,8S)-2-fluoro-1,2,3,5,6,7-hexahydropyrrolizin-8-yl]methoxy]-6-[rac-(3R)-3-hydroxy-3-methyl-1-piperidyl]-1,3,5-triazin-2-yl]spiro[6H-thieno[3,4-b]thiophene-4,3'-azetidine]-3-carbonitrile

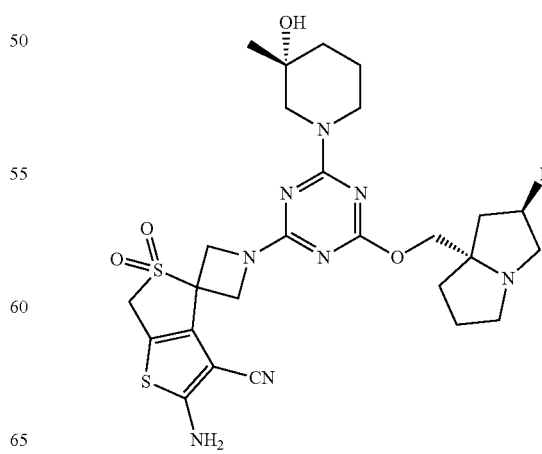

Compound 113 was prepared similarly to that of Ex. 5 as a TFA salt. LCMS calcd for $C_{26}H_{34}FN_8O_4S_2$ (M+H)+ m/z=605.2, found=605.6. $^1$H NMR (400 MHz, CD$_3$OD) δ 5.55 (d, J=51.6 Hz, 1H), 4.73 (d, J=10.6 Hz, 2H), 4.55-4.43 (m, 4H), 4.32 (s, 2H), 4.24-3.78 (m, 5H), 3.69-3.36 (m, 3H), 2.72-2.74 (m, 2H), 2.43-2.04 (m, 4H), 1.81-1.57 (m, 4H), 1.21 (s, 3H).

Compound 114. 2-amino-5,5-difluoro-1'-[4-[[(2R,8S)-2-fluoro-1,2,3,5,6,7-hexahydropyrrolizin-8-yl]methoxy]-6-[(3R)-3-hydroxy-3-methyl-1-piperidyl]-1,3,5-triazin-2-yl]spiro[6H-cyclopenta[b]thiophene-4,3'-azetidine]-3-carbonitrile

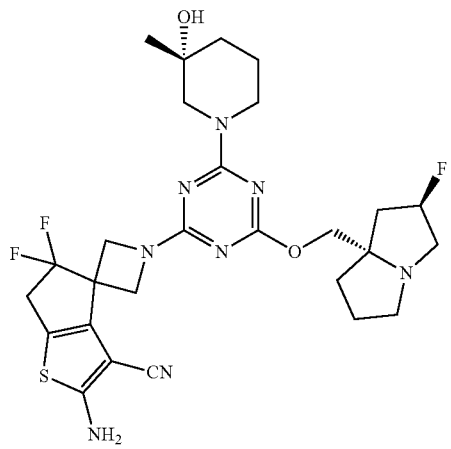 [SMILES: C[C@@]1(O)CCCN(c2nc(OC[C@@]34CCCN3C[C@H](F)C4)nc(N3CC4(C3)c3c(sc(N)c3C#N)CC4(F)F)n2)C1]

Compound 114 was prepared similarly to that of Ex. 5. LCMS calculated for $C_{27}H_{34}F_3N_8O_2S$ (M+H)+ m/z=591.6; found: 591.3. $^1$H NMR (400 MHz, CD$_3$OD) δ 5.16-5.38 (m, 1H), 4.42-4.67 (m, 4H), 4.02-4.27 (m, 4H), 3.73-3.98 (m, 2H), 3.58 (s, 2H), 3.15-3.29 (m, 4H), 2.94-3.04 (m, 1H), 1.48-2.37 (m, 10H), 1.19 (s, 3H).

Example 6. Exemplary synthesis of 2-amino-1'-[4-[1-(2-amino-3-pyridyl)ethyl-methyl-amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile (Compound 115)

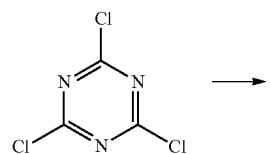

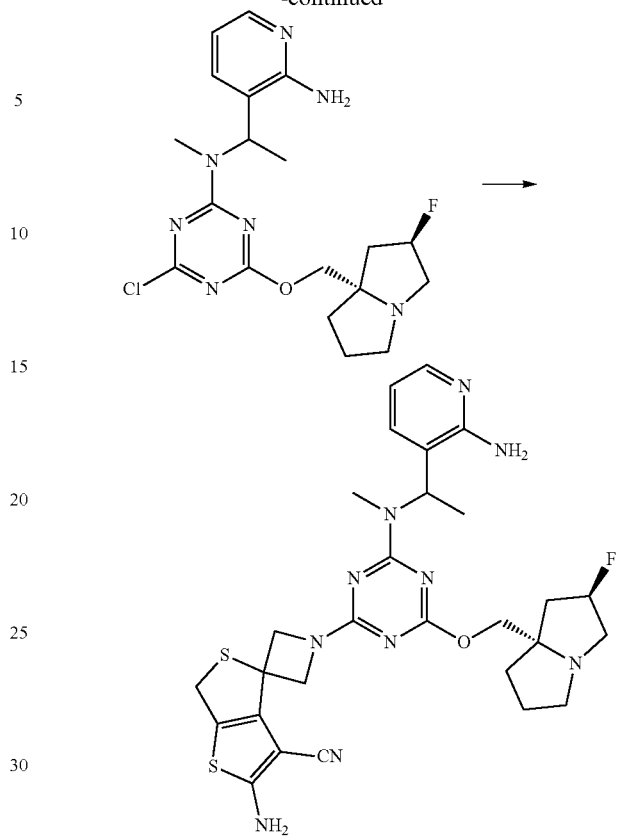

Step 1. Synthesis of N-[1-(2-amino-3-pyridyl)ethyl]-4-chloro-6-[[(2R,8S)-2-fluoro-1,2,3,5,6,7-hexahydropyrrolizin-8-yl]methoxy]-N-methyl-1,3,5-triazin-2-amine To a solution of 2,4,6-trichloro-1,3,5-triazine (243.91 mg, 1.32 mmol) and DIEA (0.69 mL, 3.97 mmol) in THF (5 mL) at −60° C. was added 3-[1-(methylamino)ethyl]pyridin-2-amine (200 mg, 1.32 mmol). The reaction was stirred at −60° C. for 1 h. Then [(2R,8S)-2-fluoro-1,2,3,5,6,7-hexahydropyrrolizin-8-yl]methanol (631.7 mg, 3.97 mmol) was added at rt. The reaction was stirred at RT for 16 h. The reaction was extracted with DCM and dried over Na$_2$SO$_4$, the organic layer was filtrated and concentrated in vacuo. Then the crude was purified by column chromatography (DCM:MeOH=0% to 4%) to get N-[1-(2-amino-3-pyridyl)ethyl]-4-chloro-6-[[(2R,8S)-2-fluoro-1,2,3,5,6,7-hexahydropyrrolizin-8-yl]methoxy]-N-methyl-1,3,5-triazin-2-amine (297 mg, 0.704 mmol, 53.22% yield) as a white solid. LCMS calculated for $C_{19}H_{26}ClFN_7O$ (M+H)+ m/z=422.19, 424.19; found: 421.9, 423.8. $^1$H NMR (400 MHz, DMSO-d6) δ 7.94 (dd, J=4.9, 1.5 Hz, 1H), 7.57 (t, J=8.0 Hz, 1H), 6.68-6.59 (m, 1H), 5.79-5.68 (m, 1H), 5.58-5.51 (m, 1H), 5.39-5.16 (m, 1H), 4.28-3.93 (m, 2H), 2.96 (d, J=103.6 Hz, 4H), 2.18-1.67 (m, 7H), 1.50 (d, J=6.7 Hz, 3H).

Step 2. Synthesis of 2-amino-1'-[4-[1-(2-amino-3-pyridyl)ethyl-methyl-amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile To a solution of 2-aminospiro[6H-thieno[2,3-c]thiophene-4,3'-azetidine]-3-carbonitrile; hydrochloride (24. mg, 0.09 mmol) and N-[1-(2-amino-3-pyridyl)ethyl]-4-chloro-6-[[(2R,8S)-2-fluoro-1,2,3,5,6,7-hexahydropyrrolizin-8-yl]methoxy]-N-methyl-1,3,5-triazin-2-amine (40.93 mg, 0.1 mmol) in DMSO (1.2 mL) was added DIEA (35.82 mg, 0.28 mmol) at 25° C. Then the mixture was stirred at 30° C. overnight. The reaction mixture was directly purified by Prep-HPLC on a C18 column (5 uM, 50×150 mm) with mobile phase: H$_2$O (0.1% NH$_4$HCO$_3$)/MeOH at flow rate: 50 mL/min to afford 2-amino-1'-[4-[1-(2-amino-3-pyridyl)ethyl-methyl-amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile, 33 mg, 0.0542 mmol, 58.68% yield as a creamy-white solid.

LCMS calculated for C$_{28}$H$_{34}$FN$_{10}$OS$_2$ (M+H)$^+$ m/z=609.23; found: 609.2. $^1$H NMR (400 MHz, CD$_3$OD) δ=7.86 (d, J=4.7 Hz, 1H), 7.65 (d, J=6.6 Hz, 1H), 6.69 (dd, J=7.4, 5.2 Hz, 1H), 6.07 (s, 1H), 5.26 (d, J=54.7 Hz, 1H), 4.55-4.82 (m, 2H), 4.31-4.47 (m, 2H), 3.99-4.24 (m, 4H), 3.09-3.28 (m, 3H), 2.91-3.04 (m, 1H), 2.75 (s, 3H), 1.75-2.35 (m, 6H), 1.53 (d, J=6.9 Hz, 3H).

Compound 116A and 116B. 2-amino-1'-[4-[[(1*)-1-(3-aminopyrazin-2-yl)ethyl]-methyl-amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

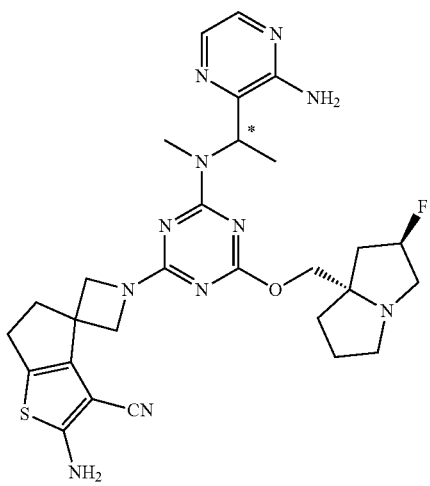 [SMILES: CC(c1nccnc1N)N(C)c1nc(OC[C@@]23CCCN2C[C@H](F)C3)nc(N2CC3(CCc4sc(N)c(C#N)c43)C2)n1]

Compounds 102 was purified on an DAICELCHIRALCEL®AS (250*25 mm 10 um) column on a Waters SFC 150 system (Mobile Phase A: Supercritical CO$_2$, Mobile Phase B: MeOH[0.2% NH$_3$ (7M in MeOH)]; A/B: 80/20; Flow: 100 ml/min) to give faster eluting P1 (compound 116A), and slower eluting P2 (compound 116B).

P1: $^1$H NMR (400 MHz, CD$_3$OD) δ 7.82 (dd, J=19.6, 2.8 Hz, 2H), 6.19-6.00 (m, 1H), 5.26 (d, J=54.0 Hz, 1H), 4.50-4.05 (m, 6H), 3.26-3.14 (m, 3H), 3.03-2.92 (m, 1H), 2.87-2.70 (m, 6H), 2.29-2.04 (m, 3H), 2.00-1.80 (m, 3H), 1.56 (d, J=6.8 Hz, 3H).

P2: $^1$H NMR (400 MHz, CD$_3$OD) δ 7.82 (dd, J=20.0, 2.4 Hz, 2H), 6.18-6.02 (m, 1H), 5.27 (d, J=54.8 Hz, 1H), 4.48-4.06 (m, 6H), 3.25-3.14 (m, 3H), 3.01-2.94 (m, 1H), 2.85-2.68 (m, 7H), 2.28-2.14 (m, 2H), 2.12-2.04 (m, 1H), 1.99-1.79 (m, 3H), 1.56 (d, J=6.8 Hz, 3H).

Compound 117. 2-amino-1'-[4-[1-(2-amino-3-pyridyl)ethyl-methyl-amino]-6-[2-(1-methylimidazol-2-yl)ethoxy]-1,3,5-triazin-2-yl]spiro[5,6-dihydrocyclopenta[b]thiophene-4,3'-azetidine]-3-carbonitrile

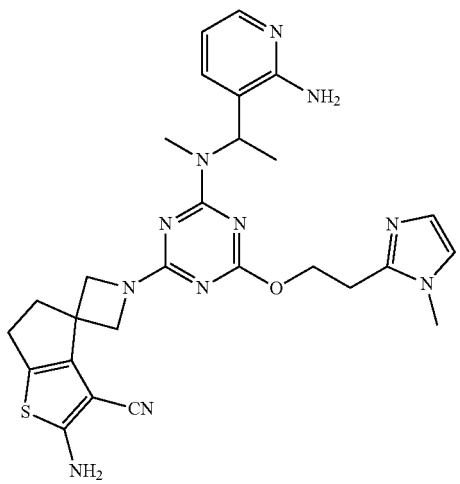 [SMILES: CC(c1cccnc1N)N(C)c1nc(OCCc2nccn2C)nc(N2CC3(CCc4sc(N)c(C#N)c43)C2)n1]

Compound 117 was prepared similarly to that of Ex. 4. LCMS calculated for C$_{27}$H$_{32}$N$_{11}$OS (M+H)$^+$ m/z=558.24; found: 558.4. $^1$H NMR (400 MHz, DMSO) δ 7.83-7.93 (m, 1H), 7.54-7.62 (m, 1H), 7.13-7.37 (m, 2H), 7.02 (br, 1H), 6.73-6.80 (m, 1H), 6.49-6.62 (m, 1H), 5.65-6.18 (m, 3H), 4.50-4.54 (m, 2H), 4.05-4.32 (m, 4H), 3.58 (s, 6H), 3.00-3.18 (m, 2H), 2.65-2.72 (m, 4H), 2.54 (s, 3H), 1.25-1.51 (m, 3H).

Compound 118. 2-amino-1'-[4-[1-(2-amino-3-pyridyl)ethyl-(2-cyanoethyl)amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

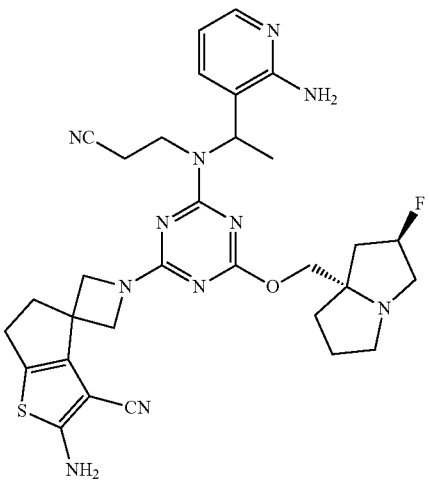 [SMILES: CC(c1cccnc1N)N(CCC#N)c1nc(OC[C@@]23CCCN2C[C@H](F)C3)nc(N2CC3(CCc4sc(N)c(C#N)c43)C2)n1]

Compound 118 was prepared similarly to that of Ex. 4 with Intermediate 13. LCMS calculated for C$_{31}$H$_{37}$FN$_{11}$OS (M+H)⁺ m/z=630.29; found: 629.8. ¹H NMR (400 MHz, CD₃OD) δ 7.90 (s, 1H), 7.60-7.82 (m, 1H), 6.73 (dd, J=7.2, 5.2 Hz, 1H), 5.88-6.19 (m, 1H), 5.27 (d, J=54.4 Hz, 1H), 4.05-4.52 (m, 6H), 3.64-3.82 (m, 1H), 3.36-3.45 (m, 1H), 3.09-3.26 (m, 3H), 2.93-3.05 (m, 1H), 2.55-2.83 (m, 5H), 2.03-2.35 (m, 4H), 1.77-2.02 (m, 3H), 1.56 (d, J=6.8 Hz, 3H).

Compound 119. 2-amino-1'-[4-[[(2R,8S)-2-fluoro-1,2,3,5,6,7-hexahydropyrrolizin-8-yl]methoxy]-6-[methyl-[1-(1-methylpyrazol-3-yl)ethyl]amino]-1,3,5-triazin-2-yl]spiro[5,6-dihydrocyclopenta[b]thiophene-4,3'-azetidine]-3-carbonitrile

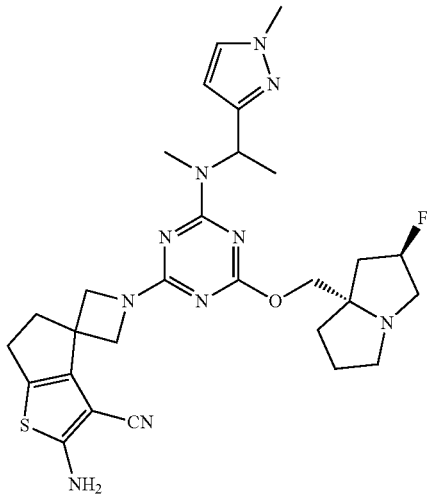 [SMILES: CC(c1ccn(C)n1)N(C)c1nc(OC[C@@]23CCCN2C[C@H](F)C3)nc(N2CC3(CCc4sc(N)c(C#N)c43)C2)n1]

Compound 119 was prepared similarly to that of Ex. 4 as TFA salt. LCMS calcd for C₂₈H₃₆FN₁₀OS (M+H)⁺ m/z=579.3, found: 579.3. ¹H NMR (400 MHz, CD₃OD) δ 7.52 (s, 1H), 6.18 (s, 1H), 5.54 (d, J=51.8 Hz, 1H), 5.49 (s, 3H), 4.63-4.14 (m, 5H), 4.04-3.87 (m, 2H), 3.85 (s, 3H), 3.52-3.36 (m, 1H), 2.88 (s, 3H), 2.80-2.62 (m, 4H), 2.63-1.96 (m, 6H), 1.53 (d, J=7.0 Hz, 3H).

Compound 120A & 120B 2-amino-1'-[4-[[(1*)-1-(2-amino-3-pyridyl)ethyl]-methyl-amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

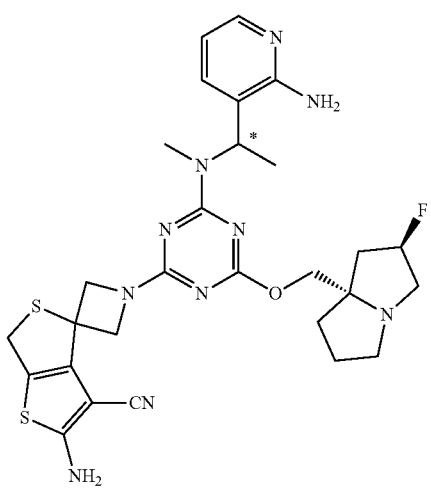 [SMILES: CC(c1cccnc1N)N(C)c1nc(OC[C@@]23CCCN2C[C@H](F)C3)nc(N2CC3(C2)SCc2sc(N)c(C#N)c23)n1]

Compound 115 was purified on a DAICELCHIRALCEL®AS (250*25 mm 10 um) column on a Waters SFC 150 system (Mobile Phase A: Supercritical CO₂, Mobile Phase B: MeOH[0.2% NH₃ (7M in MeOH)]; A:B: 70/30; Flow: 100 ml/min) to give faster eluting P1 (compound 120A), and slower eluting P2 (compound 120B). P1: ¹H NMR (400 MHz, CD₃OD) δ 7.86 (d, J=4.6 Hz, 1H), 7.65 (d, J=6.8 Hz, 1H), 6.69 (dd, J=7.4, 5.2 Hz, 1H), 6.06 (br s, 1H), 5.27 (d, J=54.2 Hz, 1H), 4.72-4.79 (m, 1H), 4.62-4.70 (m, 1H), 4.30-4.47 (m, 2H), 3.99-4.28 (m, 4H), 3.14-3.28 (m, 3H), 2.93-3.04 (m, 1H), 2.75 (s, 3H), 1.80-2.35 (m, 6H), 1.53 (d, J=6.9 Hz, 3H). P2: ¹H NMR (400 MHz, CD₃OD) δ=7.86 (d, J=4.6 Hz, 1H), 7.65 (d, J=6.6 Hz, 1H), 6.69 (dd, J=7.4, 5.2 Hz, 1H), 6.07 (br s, 1H), 5.27 (d, J=55.2 Hz, 1H), 4.73-4.79 (m, 1H), 4.62-4.71 (m, 1H), 4.30-4.47 (m, 2H), 3.96-4.24 (m, 4H), 3.10-3.28 (m, 3H), 2.91-3.04 (m, 1H), 2.75 (s, 3H), 1.79-2.33 (m, 6H), 1.53 (d, J=6.9 Hz, 3H).

Compound 121. 2'-amino-1-(4-((1-(2-aminophenyl)ethyl)(methyl)amino)-6-(((2R,7aS)-2-fluorotetrahydro-1H-pyrrolizin-7a(5H)-yl)methoxy)-1,3,5-triazin-2-yl)-5',6'-dihydrospiro[azetidine-3,4'-cyclopenta[b]thiophene]-3'-carbonitrile

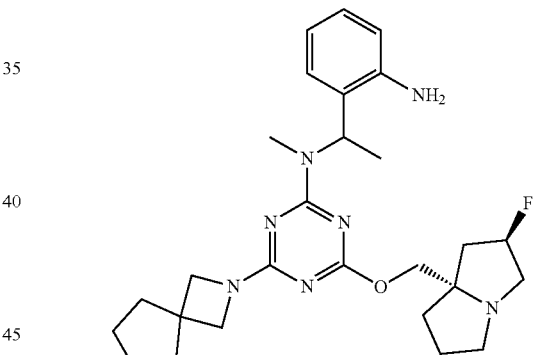

Compound 121 was prepared similarly to that of Ex. 4. LCMS calculated for C₃₀H₃₇FN₉OS (M+H)⁺ m/z=590.7; found: 590.2. ¹H NMR (400 MHz, d6-DMSO) δ 7.21 (s, 3H), 7.00 (t, J=7.5 Hz, 1H), 6.68-6.52 (m, 2H), 6.01-5.83 (m, 1H), 5.39-4.89 (m, 3H), 4.33-3.79 (m, 6H), 3.13-2.62 (m, 11H), 2.14-1.65 (m, 6H), 1.45 (d, J=6.5 Hz, 3H).

409

Compound 122A &122B. 2-amino-1'-[4-[[(1*)-1-(2-amino-3-pyridyl)ethyl]-(2-hydroxyethyl)amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

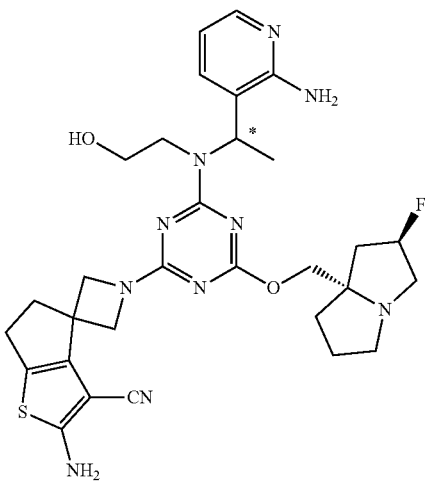 [SMILES: CC(c1cccnc1N)N(CCO)c1nc(OC[C@@]23CCCN2C[C@H](F)C3)nc(N2CC3(CCc4sc(N)c(C#N)c43)C2)n1]

Compound 110 was purified on a DAICELCHIRALCEL®AS (250*25 mm 10 um) column on a Waters SFC 150 system (Mobile Phase A: Supercritical $CO_2$, Mobile Phase B: MeOH[0.2% $NH_3$ (7M in MeOH)]; A:B: 50/50; Flow: 100 ml/min) to give faster eluting P1 (compound 122A), and slower eluting P2 (compound 122B). Compound 110 was purified on a DAICELCHIRALCEL®AS (250*25 mm 10 um) column on a Waters SFC 150 system (Mobile Phase A: Supercritical $CO_2$, Mobile Phase B: MeOH[0.2% $NH_3$ (7M in MeOH)]; A:B: 50/50; Flow: 100 ml/min) to give faster eluting P1 (compound 122A), and slower eluting P2 (compound 122B). P1: LCMS calculated for $C_{30}H_{38}FN_{10}O_2S$ $(M+H)^+$ m/z=621.29; found: 620.8.

$^1$H NMR (400 MHz, $CD_3OD$) δ=7.98-7.78 (m, 1H), 7.68 (d, J=7.2 Hz, 1H), 6.76-6.60 (m, 1H), 6.14-5.90 (m, 1H), 5.27 (d, J=54.0 Hz, 1H), 4.46-4.05 (m, 6H), 3.60-3.50 (m, 2H), 3.27-3.08 (m, 5H), 3.04-2.95 (m, 1H), 2.81-2.68 (m, 4H), 2.07-1.79 (m, 6H), 1.54 (d, J=6.8 Hz, 3H).

P2: LCMS calculated for $C_{30}H_{38}FN_{10}O_2S$ $(M+H)^+$ m/z=621.29; found: 620.8.

$^1$H NMR (400 MHz, $CD_3OD$) δ=7.88 (s, 1H), 7.68 (d, J=7.2 Hz, 1H), 6.75-6.60 (m, 1H), 6.12-5.91 (m, 1H), 5.27 (d, J=54.8 Hz, 1H), 4.51-4.04 (m, 6H), 3.60-3.43 (m, 2H), 3.26-2.92 (m, 6H), 2.80-2.67 (m, 4H), 2.34-1.77 (m, 6H), 1.54 (d, J=6.8 Hz, 3H).

410

Compound 123. 2-amino-1'-[4-[[(2R,8S)-2-fluoro-1,2,3,5,6,7-hexahydropyrrolizin-8-yl]methoxy]-6-[(3R,5R)-5-fluoro-3-hydroxy-3-methyl-1-piperidyl]-1,3,5-triazin-2-yl]spiro[6H-thieno[3,4-b]thiophene-4,3'-azetidine]-3-carbonitrile

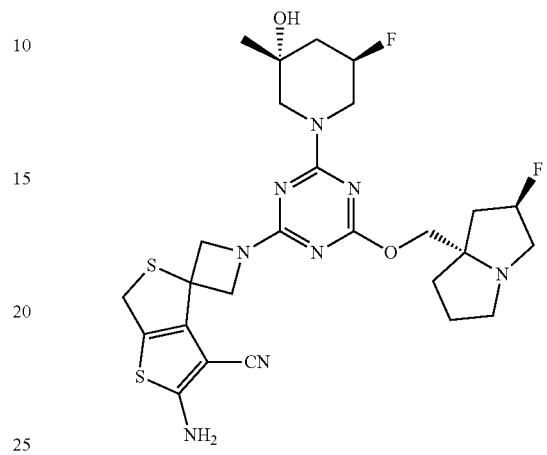

Compound 123 was prepared similarly to that of Ex. 5. LCMS calculated for $C_{26}H_{33}F_2N_8O_2S_2$ $(M+H)^+$ m/z=591.22; found: 590.8. $^1$H NMR (400 MHz, d6-DMSO) δ 7.40 (s, 2H), 5.95-5.82 (m, 1H), 5.25 (d, J=55.7 Hz, 1H), 4.76 (t, J=41.3 Hz, 2H), 4.54 (d, J=10.1 Hz, 2H), 4.26 (d, J=10.0 Hz, 2H), 4.02 (d, J=23.1 Hz, 3H), 3.95-3.49 (m, 4H), 3.16-2.76 (m, 4H), 2.14-1.65 (m, 8H), 1.15 (s, 3H).

Compound 124. 2-amino-1'-[4-[1-(3-aminopyrazin-2-yl)ethyl-(2-hydroxyethyl)amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

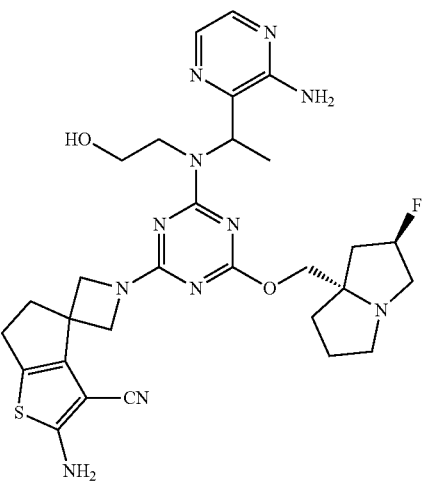 [SMILES: CC(c1nccnc1N)N(CCO)c1nc(OC[C@@]23CCCN2C[C@H](F)C3)nc(N2CC3(CCc4sc(N)c(C#N)c43)C2)n1]

Compound 124 was prepared similarly to that of Ex. 4. LCMS calculated for $C_{29}H_{37}FN_{11}O_2S$ $(M+H)^+$ m/z=622.3; found: 622.5. $^1$H NMR (400 MHz, d6-DMSO) δ=7.89 (d, J=2.4 Hz, 1H), 7.74 (d, J=5.8 Hz, 1H), 7.28-7.14 (m, 2H), 6.41-6.08 (m, 2H), 5.92-5.84 (m, 1H), 5.27 (d, J=54.0 Hz, 1H), 4.76-4.58 (m, 1H), 4.30-3.85 (m, 6H), 3.52-3.37 (m, 2H), 3.28-2.95 (m, 5H), 2.85-2.82 (m, 1H), 2.71-2.63 (m, 4H), 2.12-1.70 (m, 6H), 1.48 (d, J=6.8 Hz, 3H).

Compound 125. 2-amino-1'-[4-[[(2R,8S)-2-fluoro-1,2,3,5,6,7-hexahydropyrrolizin-8-yl]methoxy]-6-[methyl-[i-(2-methylpyrazol-3-yl)ethyl]amino]-1,3,5-triazin-2-yl]spiro[5,6-dihydrocyclopenta[b]thiophene-4,3'-azetidine]-3-carbonitrile

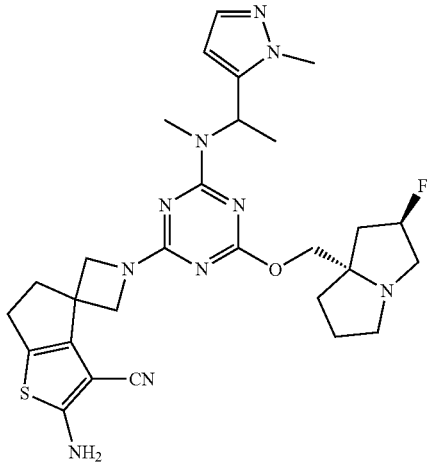 [SMILES: CC(c1ccnn1C)N(C)c1nc(OC[C@@]23CCCN2C[C@H](F)C3)nc(N2CC3(CCc4sc(N)c(C#N)c43)C2)n1]

Compound 125 was prepared similarly to that of Ex. 4. LCMS calculated for $C_{28}H_{36}FN_{10}OS$ (M+H)+ m/z=579.2, found: 579.2. $^1$H NMR (400 MHz, CD$_3$OD) δ 7.45-7.37 (m, 1H), 6.42-6.39 (m, 1H), 6.38-6.20 (m, 1H), 5.27 (d, J=55.6 Hz, 1H), 4.48-4.29 (m, 2H), 4.24-4.04 (m, 4H), 3.73-3.68 (m, 2H), 3.68-3.65 (m, 1H), 3.25-3.17 (m, 2H), 3.17-3.12 (m, 1H), 3.04-2.92 (m, 1H), 2.76 (s, 6H), 2.73-2.63 (m, 1H), 2.34-2.00 (m, 4H), 2.01-1.89 (m, 2H), 1.88-1.78 (m, 1H), 1.70-1.55 (m, 1H), 1.54 (s, 3H).

Compound 126. 2-amino-5-oxo-1'-[4-[[(2R,8S)-2-fluoro-1,2,3,5,6,7-hexahydropyrrolizin-8-yl]methoxy]-6-[(3R)-3-hydroxy-3-methyl-1-piperidyl]-1,3,5-triazin-2-yl]spiro[6H-thieno[3,4-b]thiophene-4,3'-azetidine]-3-carbonitrile

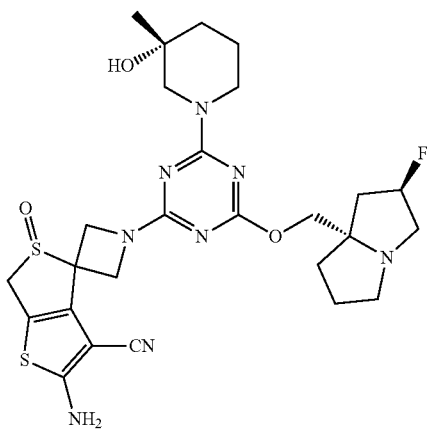 [SMILES: C[C@@]1(O)CCCN(c2nc(OC[C@@]34CCCN3C[C@H](F)C4)nc(N3CC4(C3)c3c(sc(N)c3C#N)CS4=O)n2)C1]

Compound 126 was prepared similarly to that of Ex. 5. LCMS calculated for $C_{26}H_{34}FN_8O_3S_2$ (M+H)+ m/z=589.2, found=589.3. $^1$H NMR (400 MHz, CD$_3$OD) δ 5.41 (d, J=51.7 Hz, 1H), 4.85-4.81 (m, 1H), 4.70-4.47 (m, 3H), 4.46-4.20 (m, 3H), 4.06-3.88 (m, 2H), 3.80-3.40 (m, 6H), 3.22 (dd, J=15.9, 9.8 Hz, 1H), 2.62-1.93 (m, 6H), 1.87-1.47 (m, 4H), 1.20 (s, 3H).

Compound 127. 2-amino-1'-[4-[1-(4-chloro-1H-pyrazol-5-yl)ethyl-methyl-amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

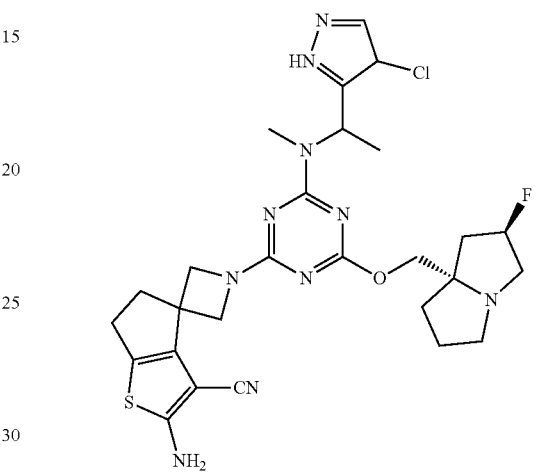

Compound 127 was prepared similarly to that of Ex. 4 as a HCl salt. LCMS calculated for $C_{27}H_{33}ClFN_{10}OS$ (M+H)+ m/z=599.2, found: 599.2. $^1$H NMR (400 MHz, CD$_3$OD) δ 7.85-7.57 (m, 1H), 6.35-6.07 (m, 1H), 5.75-5.41 (m, 1H), 4.81-4.64 (m, 2H), 4.60-4.35 (m, 4H), 4.18-3.68 (m, 3H), 3.55-3.39 (m, 1H), 3.11-2.93 (m, 3H), 2.89-2.15 (m, 10H), 1.85-1.47 (m, 3H).

Compound 128. 2-amino-1'-[4-[1-(2-amino-3-pyridyl)ethyl-methyl-amino]-6-[[1-(morpholinomethyl)cyclopropyl]methoxy]-1,3,5-triazin-2-yl]spiro[6H-thieno[3,4-b]thiophene-4,3'-azetidine]-3-carbonitrile

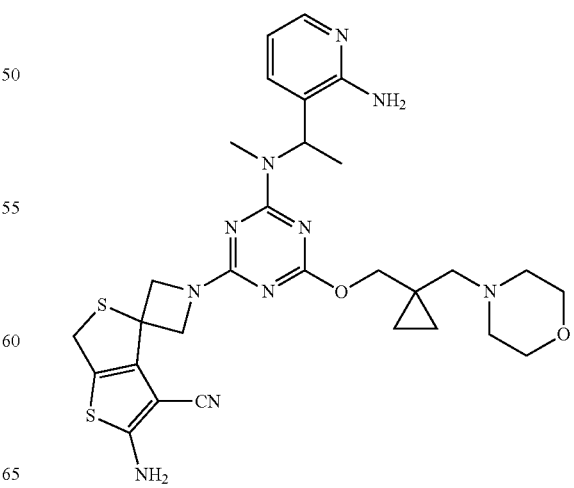

Compound 128 was prepared similarly to that of Ex. 4. LCMS calculated for $C_{29}H_{37}N_{10}O_2S_2$ (M+H)$^+$ m/z=621.3; found: 621.2. $^1$H NMR (400 MHz, d6-DMSO) δ=7.89 (d, J=4.4 Hz, 1H), 7.60-7.50 (m, 1H), 7.45-7.35 (m, 2H), 6.64-6.55 (m, 1H), 5.96-5.59 (m, 3H), 4.69-4.46 (m, 2H), 4.37-4.02 (m, 6H), 3.55 (br, 4H), 2.69 (s, 3H), 2.43-2.21 (m, 6H), 1.45 (d, J=6.8 Hz, 3H), 0.59-0.59 (m, 2H), 0.40-0.39 (m, 2H).

Compound 129. 2-amino-1'-[4-[methyl-[1-(1H-pyrazol-5-yl)ethyl]amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

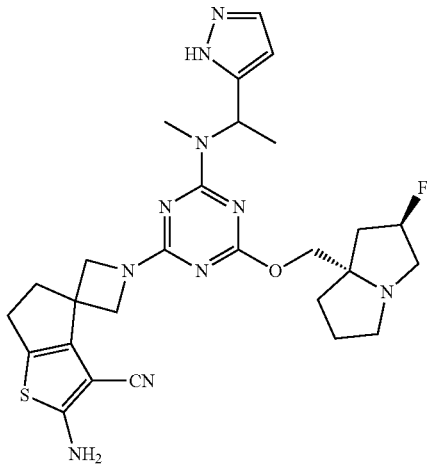 [SMILES: CC(c1ccn[nH]1)N(C)c1nc(OC[C@@]23CCCN2C[C@H](F)C3)nc(N2CC3(CCc4sc(N)c(C#N)c43)C2)n1]

Compound 129 was prepared similarly to that of Ex. 4 as a hydrochloride salt. LCMS calculated for $C_{27}H_{34}FN_{10}OS$ (M+H)$^+$ m/z=565.3, found: 565.3. $^1$H NMR (400 MHz, CD$_3$OD) δ 8.07 (s, 1H), 6.69 (s, 1H), 6.42-6.13 (m, 1H), 5.59 (d, J=51.8 Hz, 1H), 4.85-4.64 (m, 2H), 4.63-4.29 (m, 4H), 4.11-3.82 (m, 3H), 3.53-3.41 (m, 1H), 3.20-3.01 (m, 3H), 2.86-2.55 (m, 6H), 2.54-2.12 (m, 4H), 1.73 (d, J=6.8 Hz, 3H).

Compound 130. 2-amino-1'-[4-[[(2R,8S)-2-fluoro-1,2,3,5,6,7-hexahydropyrrolizin-8-yl]methoxy]-6-(2-oxo-1,8-diazaspiro[3.5]nonan-8-yl)-1,3,5-triazin-2-yl]spiro[5,6-dihydrocyclopenta[b]thiophene-4,3'-azetidine]-3-carbonitrile

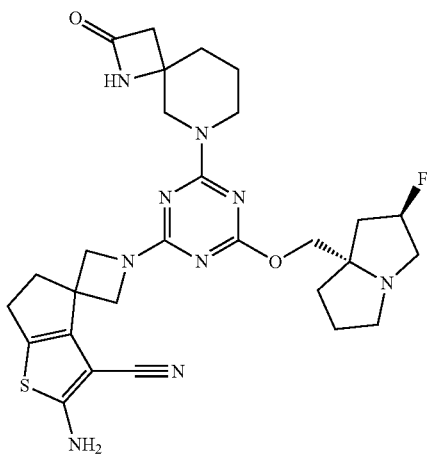 [SMILES: N#Cc1c(N)sc2c1C1(CC2)CN(c2nc(OC[C@@]34CCCN3C[C@H](F)C4)nc(N3CCCC4(CC(=O)N4)C3)n2)C1]

Compound 130 was prepared similarly to that of Ex. 1 as a hydrochloride salt. LCMS calculated for $C_{28}H_{35}FN_9O_2S$ (M+H)$^+$ m/z: 580.2, found: 580.2. $^1$H NMR (400 MHz, CD$_3$OD) δ 5.57 (d, J=51.1 Hz, 1H), 4.80-4.58 (m, 3H), 4.52-4.32 (m, 4H), 4.21-3.65 (m, 7H), 3.50-3.40 (m, 1H), 2.90-2.74 (m, 4H), 2.72-2.48 (m, 4H), 2.28 (dt, J=23.2, 22.4 Hz, 4H), 2.07-1.85 (m, 2H), 1.86-1.64 (m, 2H).

Compound 131. 2-amino-1'-[4-[[(2R,8S)-2-fluoro-1,2,3,5,6,7-hexahydropyrrolizin-8-yl]methoxy]-6-[2-hydroxyethyl(1H-pyrazol-5-ylmethyl)amino]-1,3,5-triazin-2-yl]spiro[5,6-dihydrocyclopenta[b]thiophene-4,3'-azetidine]-3-carbonitrile

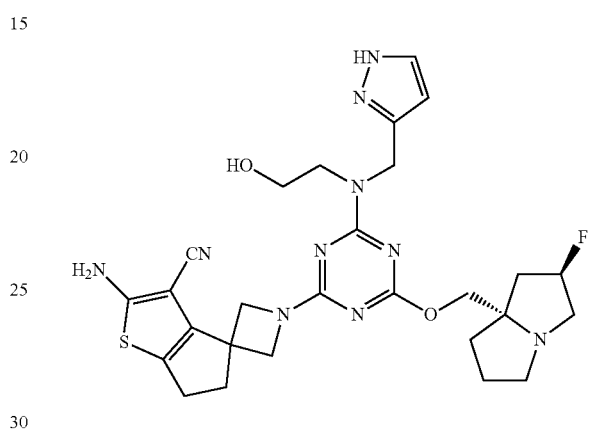

Compound 131 was prepared similarly to that of Ex. 4 as a hydrochloride salt. LCMS calculated for $C_{27}H_{34}FN_{10}O_2S$ (M+H)$^+$ m/z=581.2, found: 581.5. $^1$H NMR (400 MHz, CD$_3$OD) δ 8.15 (s, 1H), 6.79 (d, J=10.5 Hz, 1H), 5.60 (d, J=51.9 Hz, 1H), 5.28-5.10 (m, 2H), 4.86-4.75 (m, 2H), 4.55-4.47 (m, 3H), 4.35 (s, 1H), 4.19-3.78 (m, 7H), 3.47 (s, 1H), 2.91-2.54 (m, 6H), 2.35-2.22 (m, 4H).

Compound 132. 2'-amino-1-(4-((1-(3-amino-6-chloropyridazin-4-yl)ethyl)(methyl)amino)-6-(((2R,7aS)-2-fluorotetrahydro-1H-pyrrolizin-7a(5H)-yl)methoxy)-1,3,5-triazin-2-yl)-5',6'-dihydrospiro[azetidine-3,4'-cyclopenta[b]thiophene]-3'-carbonitrile

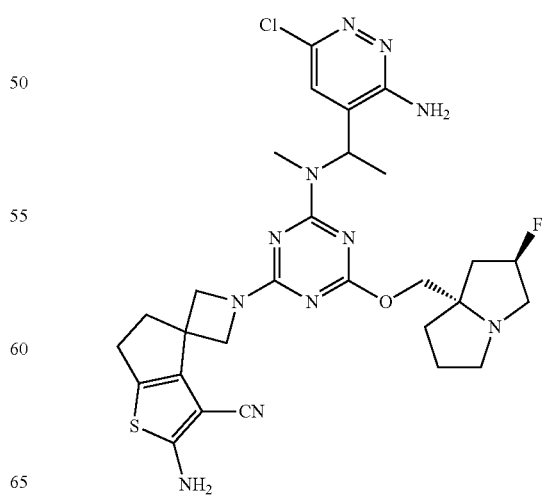

Compound 132 was prepared similarly to that of Ex. 4. LCMS calculated for $C_{28}H_{34}ClFN_{11}OS$ (M+H)$^+$ m/z=626.6; found: 626.2. $^1$H NMR (400 MHz, d6-DMSO) δ 7.56-7.38 (m, 1H), 7.21 (s, 2H), 6.73-6.41 (m, 2H), 5.80-5.65 (m, 1H), 5.25 (d, J=54.0 Hz, 1H), 4.30-3.80 (m, 6H), 3.12-2.92 (m, 3H), 2.81-2.79 (m, 4H), 2.74-2.61 (m, 4H), 2.10-1.69 (m, 6H), 1.48 (d, J=6.8 Hz, 3H).

Compound 133. 2-amino-1'-[4-[(2-amino-5-fluoro-3-pyridyl)methyl-(2-hydroxyethyl)amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

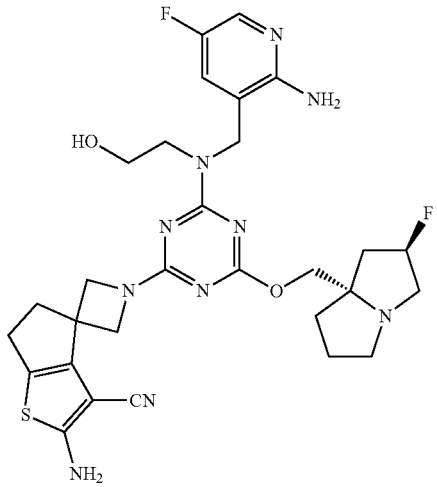 [SMILES: N#Cc1c(N)sc2c1C1(CC2)CN(c2nc(OC[C@@]34CCCN3C[C@H](F)C4)nc(N(CCO)Cc3cc(F)cnc3N)n2)C1]

Compound 133 was prepared similarly to that of Ex. 4. LCMS calculated for $C_{29}H_{35}F_2N_{10}O_2S$ (M+H)$^+$ m/z=625.2, found: 625.6. $^1$H NMR (400 MHz, CD$_3$OD) δ 7.82-7.72 (m, 1H), 7.45-7.16 (m, 1H), 5.38-5.18 (m, 1H), 4.63-4.56 (m, 2H), 4.43-4.23 (m, 2H), 4.22-3.97 (m, 4H), 3.79-3.51 (m, 4H), 3.19-3.08 (m, 2H), 3.04-2.88 (m, 1H), 2.82-2.60 (m, 4H), 2.22-2.12 (m, 2H), 2.04-1.78 (m, 4H), 1.64-1.54 (m, 1H).

Compound 134. 2-amino-1'-[4-[1-(3-aminopyrazin-2-yl)ethyl-methyl-amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

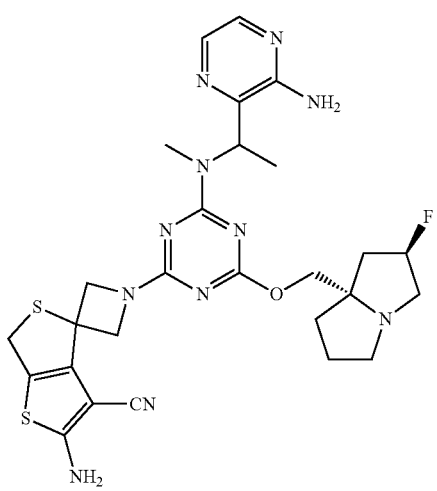 [SMILES: CC(c1nccnc1N)N(C)c1nc(OC[C@@]23CCCN2C[C@H](F)C3)nc(N2CC3(C2)SCc2sc(N)c(C#N)c23)n1]

Compound 134 was prepared similarly to that of Ex. 4. LCMS calculated for $C_{27}H_{33}FN_{11}OS_2$ (M+H)$^+$ m/z=610.3; found: 610.3. $^1$H NMR (400 MHz, CD$_3$OD) δ=7.85 (d, J=2.8 Hz, 1H), 7.80 (d, J=2.8 Hz, 1H), 6.12-6.08 (m, 1H), 5.26 (d, J=54.0 Hz, 1H), 4.78-4.57 (m, 2H), 4.49-4.31 (m, 2H), 4.27-3.97 (m, 4H), 3.27-3.11 (m, 3H), 3.03-2.93 (m, 1H), 2.83-2.80 (m, 3H), 2.32-1.76 (m, 6H), 1.56 (d, J=6.8 Hz, 3H).

Compound 135. 5-[[[4-(2-amino-3-cyano-spiro[5,6-dihydrocyclopenta[b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-methyl-amino]methyl]-1-methyl-pyrazole-3-carboxamide

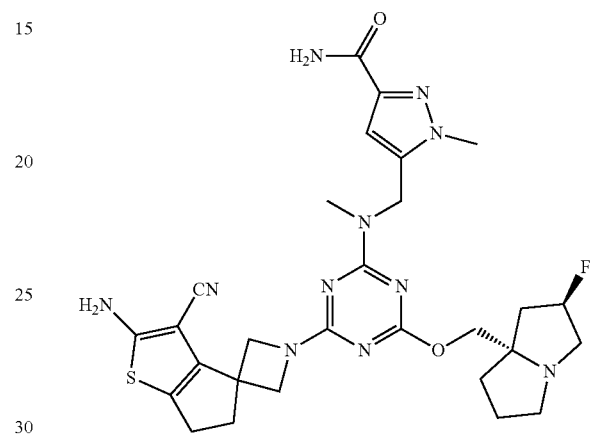

Compound 135 was prepared similarly to that of Ex. 4 as a hydrochloride salt. LCMS calculated for $C_{28}H_{35}FN_{11}O_2S$ (M+H)$^+$ m/z=608.2, found: 608.6. $^1$H NMR (400 MHz, CD$_3$OD) δ 6.79 (s, 1H), 5.58 (d, J=51.6 Hz, 1H), 5.16-5.02 (m, 2H), 4.80-4.64 (m, 2H), 4.57-4.34 (m, 4H), 4.04-3.81 (m, 6H), 3.52-3.39 (m, 1H), 3.28-3.21 (m, 3H), 2.86-2.74 (m, 4H), 2.65-2.16 (m, 6H).

Compound 136. 2-amino-1'-[4-[[(2R,8S)-2-fluoro-1,2,3,5,6,7-hexahydropyrrolizin-8-yl]methoxy]-6-[2-hydroxyethyl-[(2-oxo-1H-pyridin-3-yl)methyl]amino]-1,3,5-triazin-2-yl]spiro[5,6-dihydrocyclopenta[b]thiophene-4,3'-azetidine]-3-carbonitrile

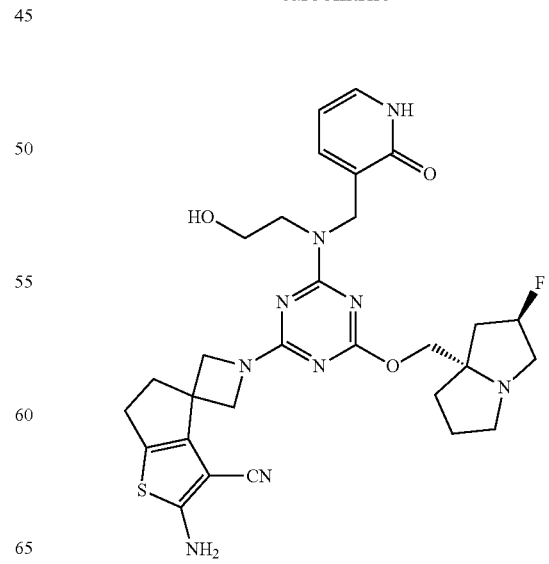

Compound 136 was prepared similarly to that of Ex. 4. LCMS calculated for $C_{29}H_{35}FN_9O_3S$ (M+H)+ m/z=608.2, found: 608.2. $^1$H NMR (400 MHz, $CD_3OD$) δ 7.48-7.27 (m, 2H), 6.40-6.31 (m, 1H), 5.36-5.10 (m, 1H), 4.79-4.60 (m, 2H), 4.45-4.18 (m, 2H), 4.18-3.92 (m, 4H), 3.85-3.65 (m, 4H), 3.26-2.87 (m, 4H), 2.80-2.65 (m, 4H), 2.31-2.08 (m, 2H), 2.06-1.53 (m, 4H).

Compound 137. 2-amino-1'-[4-[[(2R,8S)-2-fluoro-1,2,3,5,6,7-hexahydropyrrolizin-8-yl]methoxy]-6-[2-hydroxyethyl(1H-pyrazol-4-ylmethyl)amino]-1,3,5-triazin-2-yl]spiro[5,6-dihydrocyclopenta[b]thiophene-4,3'-azetidine]-3-carbonitrile

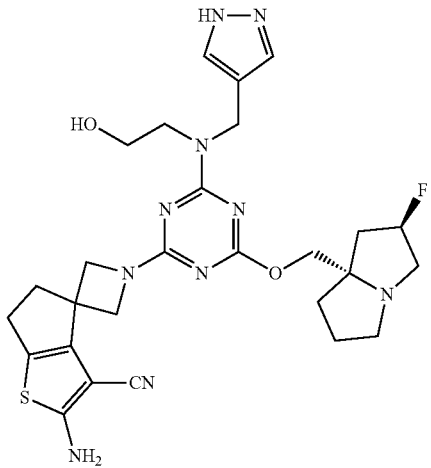 [SMILES: N#Cc1c(N)sc2c1C1(CC2)CN(c2nc(OC[C@@]34CCCN3C[C@H](F)C4)nc(N(CCO)Cc3cn[nH]c3)n2)C1]

Compound 137 was prepared similarly to that of Ex. 4. LCMS calculated for $C_{27}H_{34}FN_{10}O_2S$ (M+H)+=581.3, found: 581.3. $^1$H NMR (400 MHz, $CD_3OD$) δ 7.74-7.46 (m, 2H), 5.25 (d, J=54.4 Hz, 1H), 4.85-4.54 (m, 2H), 4.50-4.28 (m, 2H), 4.27-3.99 (m, 4H), 3.79-3.52 (m, 4H), 3.24-3.06 (m, 3H), 3.03-2.91 (m, 1H), 2.82-2.61 (m, 4H), 2.32-2.11 (m, 2H), 2.11-1.69 (m, 4H).

Compound 138. 2-amino-1'-[4-[[(2R,8S)-2-fluoro-1,2,3,5,6,7-hexahydropyrrolizin-8-yl]methoxy]-6-[1-(2-hydroxy-3-pyridyl)ethyl-methyl-amino]-1,3,5-triazin-2-yl]spiro[5,6-dihydrocyclopenta[b]thiophene-4,3'-azetidine]-3-carbonitrile

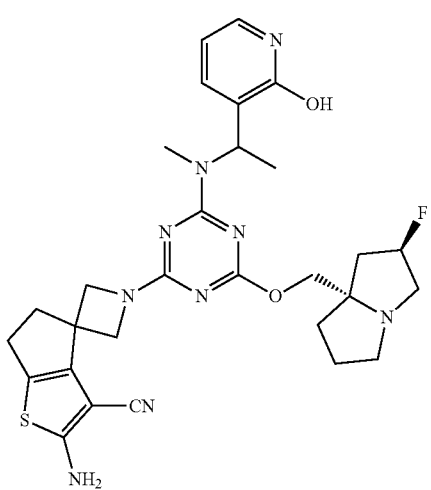 [SMILES: CC(c1cccnc1O)N(C)c1nc(OC[C@@]23CCCN2C[C@H](F)C3)nc(N2CC3(CCc4sc(N)c(C#N)c43)C2)n1]

Compound 138 was prepared similarly to that of Ex. 4 as a hydrochloride salt. LCMS calculated for $C_{29}H_{35}FN_9O_2S$ (M+H)+ m/z=592.3, found: 592.3. $^1$H NMR (400 MHz, d6-DMSO) 7.40 (d, J=8.0 Hz, 1H), 7.32 (s, 1H), 6.19 (s, 1H), 5.78-5.41 (m, 2H), 4.59-4.34 (m, 3H), 4.30-4.02 (m, 6H), 3.25 (s, 1H), 3.03-2.95 (m, 1H), 2.95-2.87 (m, 3H), 2.77-2.64 (m, 5H), 2.42-2.31 (m, 1H), 2.30-1.91 (m, 5H), 1.48-1.40 (m, 3H).

Example 7. Exemplary synthesis of 2-amino-1'-[4-[[(1*)-1-(2-amino-3-pyridyl)ethyl]-ethyl-amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile Compound 139A and Compound 139B

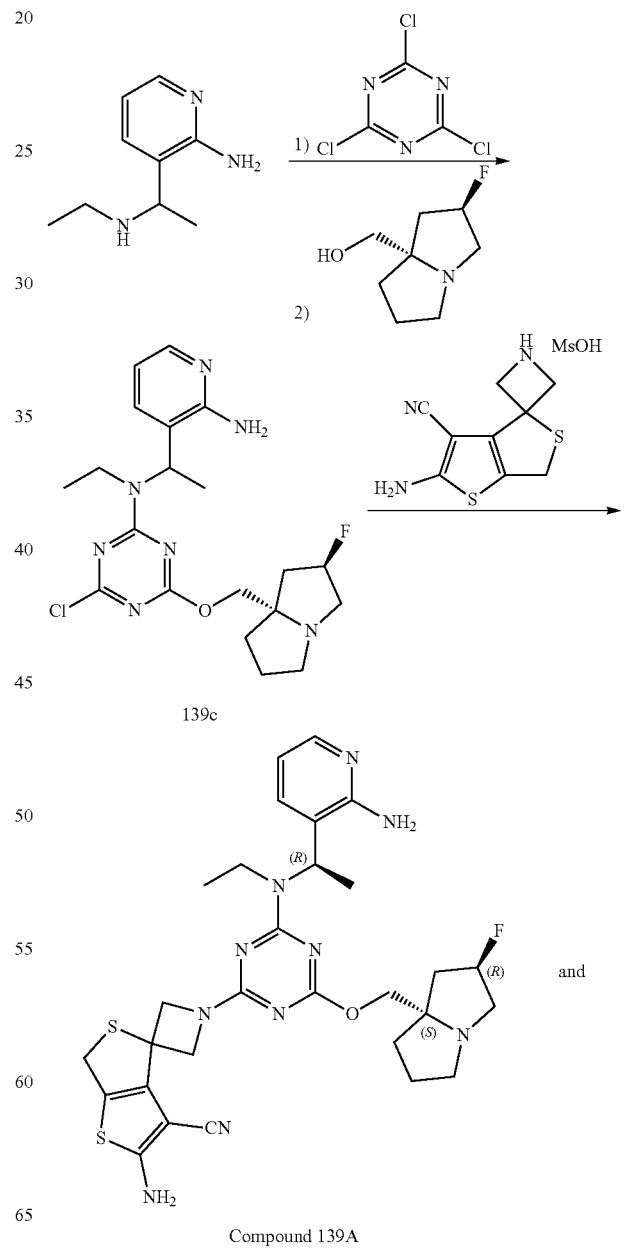

Compound 139A

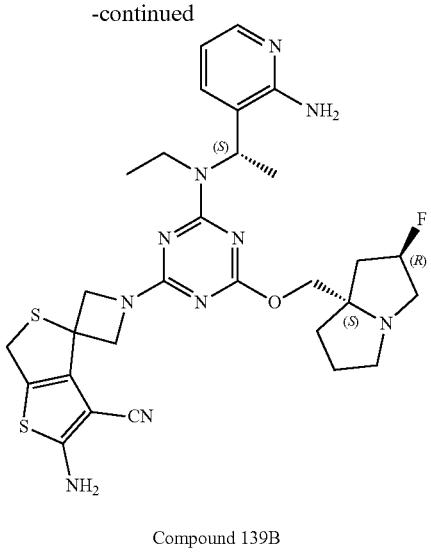

Compound 139B

Step 1. Synthesis of N-[1-(2-amino-3-pyridyl)ethyl]-4-chloro-N-ethyl-6-[[(2R,8S)-2-fluoro-1,2,3,5,6,7-hexahydropyrrolizin-8-yl]methoxy]-1,3,5-triazin-2-amine (139c)

To a solution of 3-[1-(ethylamino)ethyl]pyridin-2-amine (178 mg, 1.08 mmol, 1 eq) in THF (2 mL) was added 2,4,6-trichloro-1,3,5-triazine (220 mg, 1.20 mmol, 1.11 eq) and DIPEA (464 mg, 3.59 mmol, 3.33 eq) at −78° C. under $N_2$, and stirred at the same temperature for 2 h. [(2R,8S)-2-fluoro-1,2,3,5,6,7-hexahydropyrrolizin-8-yl]methanol (285 mg, 1.80 mmol, 1.67 eq) was added and the mixture was allowed to warm to r.t and stirred overnight. It was quenched with $NH_4Cl$ aqueous solution, and extracted with EtOAc (20 mL×3). The combined organic phase were washed with water and brine, dried ($Na_2SO_4$) and concentrated in vacuo to give the residue. It was purified using reverse phase FCC (C18, MeCN in aqueous 0.1% $NH_4HCO_3$) to afford N-[1-(2-amino-3-pyridyl)ethyl]-4-chloro-N-ethyl-6-[[(2R,8S)-2-fluoro-1,2,3,5,6,7-hexahydropyrrolizin-8-yl]methoxy]-1,3,5-triazin-2-amine (94.0 mg, 0.216 mmol, 20.0% yield) as an oil. LCMS calculated for $C_{20}H_{28}ClFN_7O$ (M+H)$^+$ m/z=436.2; found: 436.4/438.4

Step 2. Synthesis of 2-amino-1'-[4-[[(1*)-1-(2-amino-3-pyridyl)ethyl]-ethyl-amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile To the solution of N-[1-(2-amino-3-pyridyl)ethyl]-4-chloro-N-ethyl-6-[[(2R,8S)-2-fluoro-1,2,3,5,6,7-hexahydropyrrolizin-8-yl]methoxy]-1,3,5-triazin-2-amine (94.0 mg, 0.216 mmol, 1 eq) in DMSO (2.5 mL) was added 2-aminospiro[6H-thieno[2,3-c]thiophene-4,3'-azetidine]-3-carbonitrile; methanesulfonic acid (82.7 mg, 0.259 mmol, 1.2 eq) followed by DIPEA (83.6 mg, 0.647 mmol, 3 eq). The mixture was stirred at 30° C. for 2 h. Then the mixture was filtered and the filtrate was purified using reverse phase FCC (C18, MeCN in aqueous 0.1% $NH_4HCO_3$) to afford 2-amino-1'-[4-[1-(2-amino-3-pyridyl)ethyl-ethyl-amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile (70.0 mg, 0.111 mmol, 51.4% yield) as a white solid. The racemic mixture was purified on a Daicel IC (250×25 mm 10 um) column on a Waters SFC 150 system (Mobile Phase A: Supercritical $CO_2$, Mobile Phase B: EtOH[0.5% $NH_3$ (7M in MeOH)]; A:B: 45/55; Flow: 100 ml/min) to give faster eluting P1 and slower eluting P2.

P1: LCMS calculated for $C_{29}H_{36}FN_{10}OS_2$ (M+H)$^+$ m/z=623.3; found: 623.2. $^1$H NMR (400 MHz, $CD_3OD$) δ 7.82-7.90 (m, 1H), 7.68 (d, J=7.6 Hz, 1H), 6.64-6.74 (m, 1H), 5.91-6.17 (m, 1H), 5.26 (d, J=54.4 Hz, 1H), 4.54-4.68 (m, 2H), 4.34-4.46 (m, 2H), 4.02-4.21 (m, 4H), 3.40-3.46 (m, 2H), 3.14-3.21 (m, 3H), 2.92-3.02 (m, 1H), 2.03-2.26 (m, 3H), 1.79-2.01 (m, 3H), 1.54 (d, J=6.8 Hz, 3H), 0.84 (t, J=6.8 Hz, 3H).

P2: LCMS calculated for $C_{29}H_{36}FN_{10}OS_2$ (M+H)$^+$ m/z=623.3; found: 623.2. $^1$H NMR (400 MHz, $CD_3OD$) δ 7.82-7.90 (m, 1H), 7.67 (d, J=7.2 Hz, 1H), 6.64-6.74 (m, 1H), 5.92-6.15 (m, 1H), 5.26 (d, J=54.4 Hz, 1H), 4.61-4.79 (m, 2H), 4.33-4.47 (m, 2H), 4.01-4.25 (m, 4H), 3.35-3.60 (m, 2H), 3.11-3.20 (m, 3H), 2.91-3.02 (m, 1H), 2.02-2.31 (m, 3H), 1.76-2.00 (m, 3H), 1.53 (d, J=6.8 Hz, 3H), 0.83 (t, J=6.8 Hz, 3H).

Compound 140. 2-amino-1'-[4-[1-(3-chloro-1H-pyrazol-4-yl)ethyl-methyl-amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

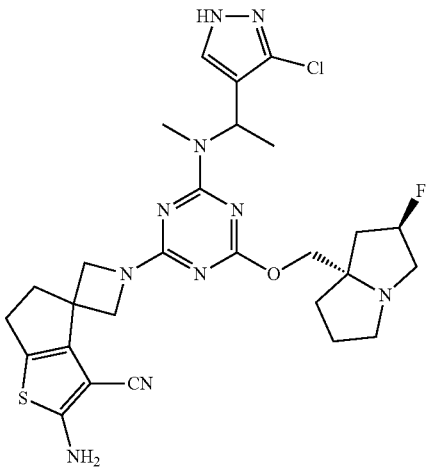 [SMILES: CC(c1c[nH]nc1Cl)N(C)c1nc(OC[C@@]23CCCN2C[C@H](F)C3)nc(N2CC3(CCc4sc(N)c(C#N)c43)C2)n1]

Compound 140 was prepared similarly to that of Ex. 4 as a hydrochloride salt. LCMS calculated for $C_{27}H_{33}ClFN_{10}OS$ (M+H)$^+$ m/z=599.2, found: 599.1. $^1$H NMR (400 MHz, $CD_3OD$) δ 7.86 (s, 1H), 6.10 (s, 1H), 5.57 (m, 1H), 4.74 (m, 1H), 4.51 (m, 3H), 3.90 (m, 3H), 3.65 (s, 1H), 3.48 (s, 1H), 2.94 (d, J=14.8 Hz, 3H), 2.79 (s, 4H), 2.61 (m, 2H), 2.26 (m, 4H), 1.58 (d, J=6.8 Hz, 3H).

Compound 141. 2-amino-1'-[4-[(2-amino-3-pyridyl)
methyl-(2-hydroxypropyl)amino]-6-[[(2R,8S)-2-
fluoro-1,2,3,5,6,7-hexahydropyrrolizin-8-yl]
methoxy]-1,3,5-triazin-2-yl]spiro[5,6-
dihydrocyclopenta[b]thiophene-4,3'-azetidine]-3-
carbonitrile

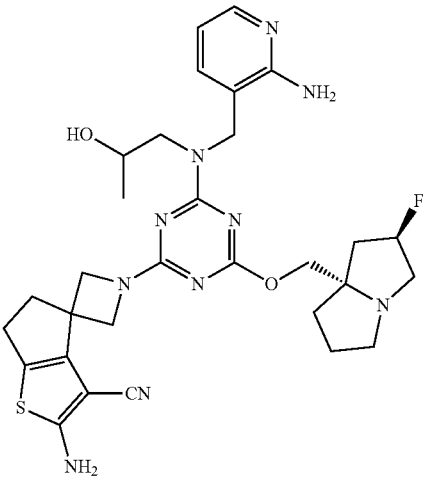 [SMILES: CC(O)CN(Cc1cccnc1N)c1nc(OC[C@@]23CCCN2C[C@H](F)C3)nc(N2CC3(CCc4sc(N)c(C#N)c43)C2)n1]

Compound 141 was prepared similarly to that of Ex. 4 as a formate salt. LCMS calculated for $C_{30}H_{38}FN_{10}O_2S$ (M+H)$^+$ m/z=621.2, found: 621.5. $^1$H NMR (400 MHz, CD$_3$OD) δ 8.42 (s, 2H), 7.86 (d, J=4.8 Hz, 1H), 7.59-7.35 (m, 1H), 6.65 (t, J=5.9 Hz, 1H), 5.45 (d, J=53.0 Hz, 1H), 5.21-4.89 (m, 2H), 4.80-4.50 (m, 1H), 4.50-4.25 (m, 4H), 4.24-4.06 (m, 3H), 3.82-3.34 (m, 5H), 2.85-2.65 (m, 4H), 2.62-2.33 (m, 2H), 2.32-1.95 (m, 4H), 1.12 (d, J=6.3 Hz, 3H).

Compound 142. 2-amino-1'-[4-[[(1R)-1-(2-amino-5-
fluoro-4-pyridyl)ethyl]-methyl-amino]-6-[[(2R,8S)-
2-fluoro-1,2,3,5,6,7-hexahydropyrrolizin-8-yl]
methoxy]-1,3,5-triazin-2-yl]spiro[5,6-
dihydrocyclopenta[b]thiophene-4,3'-azetidine]-3-
carbonitrile

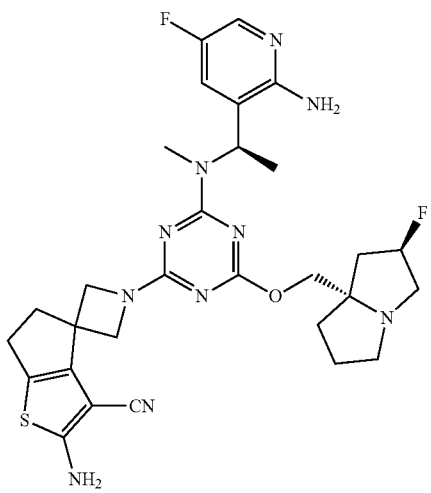 [SMILES: C[C@H](c1cc(F)cnc1N)N(C)c1nc(OC[C@@]23CCCN2C[C@H](F)C3)nc(N2CC3(CCc4sc(N)c(C#N)c43)C2)n1]

Compound 142 was prepared similarly to that of Ex. 4 as a hydrochloride salt. LCMS calculated for $C_{29}H_{35}F_2N_{10}OS$ (M+H)$^+$ m/z=609.3, found: 609.6. $^1$H NMR (400 MHz, CD$_3$OD) δ 7.95 (d, J=4.0 Hz, 1H), 7.21-6.95 (m, 1H), 6.14-5.73 (m, 1H), 5.68-5.46 (m, 1H), 4.83-4.60 (m, 2H), 4.38 (d, J=57.9 Hz, 4H), 4.11-3.80 (m, 3H), 3.51-3.40 (m, 1H), 3.37-3.32 (m, 2H), 3.25-3.07 (m, 1H), 2.77 (s, 3H), 2.73-2.52 (m, 3H), 2.45-2.14 (m, 4H), 1.71 (d, J=6.8 Hz, 3H).

Compound 143. 2-amino-1'-[4-[[(2R,8S)-2-fluoro-1,
2,3,5,6,7-hexahydropyrrolizin-8-yl]methoxy]-6-
[(3R,5S)-5-fluoro-3-hydroxy-3-methyl-1-piperidyl]-
1,3,5-triazin-2-yl]spiro[6H-thieno[3,4-b]thiophene-4,
3'-azetidine]-3-carbonitrile

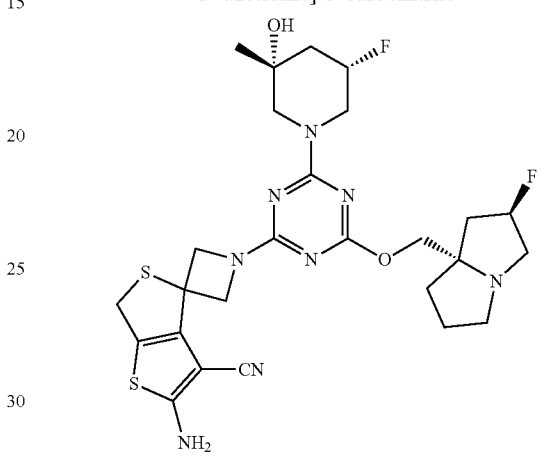

Compound 143 was prepared similarly to that of Ex. 5. LCMS calculated for $C_{26}H_{33}F_2N_8O_2S_2$ (M+H)$^+$ m/z=591.22; found: 591.2. $^1$H NMR (400 MHz, CD$_3$OD) δ 5.27 (d, J=53.9 Hz, 1H), 4.55-4.77 (m, 3H), 3.53-4.13 (m, 10H), 3.20-3.29 (m, 3H), 3.00 (s, 1H), 1.76-2.33 (m, 8H), 1.17 (s, 3H).

Compound 144. 2-amino-1'-[4-[1-(2-amino-3-
pyridyl)ethyl-ethyl-amino]-6-[[(2R,8S)-2-fluoro-1,2,
3,5,6,7-hexahydropyrrolizin-8-yl]methoxy]-1,3,5-
triazin-2-yl]spiro[6H-thieno[3,4-b]thiophene-4,3'-
azetidine]-3-carbonitrile

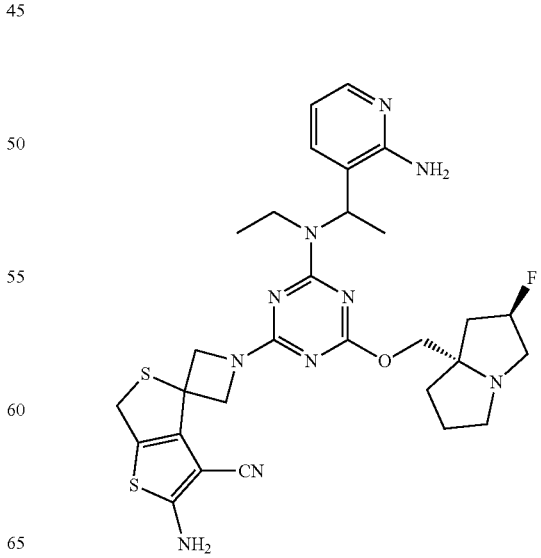

Compound 144 was prepared similarly to that of Ex. 4. LCMS calculated for $C_{29}H_{36}FN_{10}OS_2$ (M+H)$^+$ m/z=623.3; found: 623.5. $^1$H NMR (400 MHz, CD$_3$OD) δ 7.90-7.82 (m, 1H), 7.67 (d, J=7.2 Hz, 1H), 6.75-6.64 (m, 1H), 6.12-5.93 (m, 1H), 5.25 (d, J=54.4 Hz, 1H), 4.78-4.59 (m, 2H), 4.46-4.30 (m, 2H), 4.23-4.00 (m, 4H), 3.53-3.40 (m, 2H), 3.22-3.16 (m, 2H), 3.14-3.10 (m, 1H), 3.03-2.91 (m, 1H), 2.33-2.03 (m, 3H), 2.00-1.75 (m, 3H), 1.53 (d, J=6.8 Hz, 3H), 0.84 (t, J=4.8 Hz, 3H).

Compound 145. 2-amino-1'-[4-[[(2R,8S)-2-fluoro-1,2,3,5,6,7-hexahydropyrrolizin-8-yl]methoxy]-6-[(1R,5S)-8-(3-oxobutanoyl)-3,8-diazabicyclo[3.2.1]octan-3-yl]-1,3,5-triazin-2-yl]spiro[6H-thieno[3,4-b]thiophene-4,3'-azetidine]-3-carbonitrile

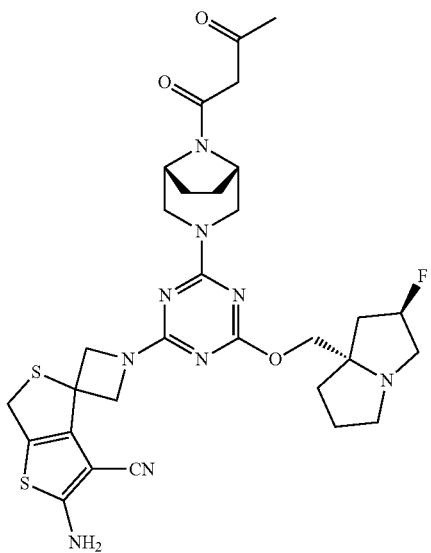 [SMILES: CC(=O)CC(=O)N1[C@@H]2CC[C@H]1CN(c1nc(OC[C@@]34CCCN3C[C@H](F)C4)nc(N3CC4(C3)SCc3sc(N)c(C#N)c34)n1)C2]

Compound 145 was prepared similarly to that of Ex. 1. LCMS calculated for $C_{30}H_{37}FN_9O_3S_2$ (M+H)$^+$ m/z=654.2; found: 654.0. $^1$H NMR (400 MHz, CD$_3$OD) δ=5.27 (d, J=54.4 Hz, 1H), 4.73-4.48 (m, 7H), 4.36-4.33 (m, 2H), 4.30-4.12 (m, 2H), 4.10-3.99 (m, 3H), 3.27-2.95 (m, 6H), 2.25 (s, 3H), 2.23-1.62 (m, 10H).

Compound 146. 4-[4-(2-amino-3-cyano-spiro[6H-thieno[3,4-b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-1,4-oxazepane-6-carbonitrile

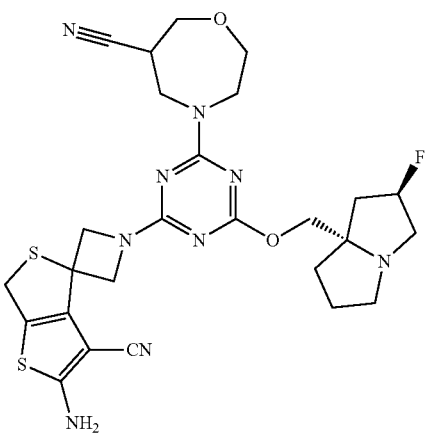 [SMILES: N#Cc1c(N)sc2c1C1(CN(c3nc(OC[C@@]45CCCN4C[C@H](F)C5)nc(N4CCOCC(C#N)C4)n3)C1)SC2]

Compound 146 was prepared similarly to that of Ex. 1. LCMS calculated for $C_{26}H_{31}FN_9O_2S_2$ (M+H)$^+$ m/z=584.19; found: 584.2. $^1$H NMR (400 MHz, CD$_3$OD) δ 5.26 (d, J=53.6 Hz, 1H), 4.92-5.07 (m, 1H), 4.61-4.73 (m, 2H), 4.32-4.47 (m, 3H), 4.01-4.22 (m, 4H), 3.85-3.97 (m, 2H), 3.62-3.72 (m, 1H), 3.44-3.56 (m, 1H), 3.10-3.25 (m, 4H), 2.80-3.03 (m, 3H), 1.80-2.28 (m, 6H).

Compound 147. 2-amino-1'-[4-[[(2R,8S)-2-fluoro-1,2,3,5,6,7-hexahydropyrrolizin-8-yl]methoxy]-6-[isothiazol-4-ylmethyl(methyl)amino]-1,3,5-triazin-2-yl]spiro[5,6-dihydrocyclopenta[b]thiophene-4,3'-azetidine]-3-carbonitrile

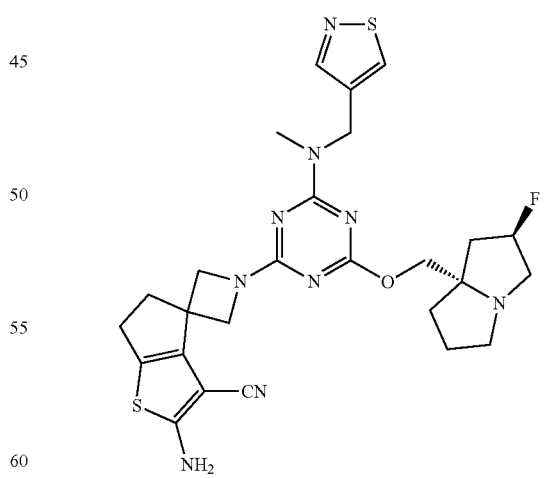

Compound 147 was prepared similarly to that of Ex. 4 as a hydrochloride salt. LCMS calculated for $C_{26}H_{31}FN_9OS_2$ (M+H)$^+$ m/z=568.2, found: 568.5. $^1$H NMR (400 MHz, d6-DMSO) δ 8.92 (s, 1H), 8.56 (s, 1H), 7.44-6.68 (m, 2H), 5.54 (d, J=52.8 Hz, 1H), 4.85 (s, 2H), 4.55-4.42 (m, 2H), 4.19 (dd, J=55.1, 9.1 Hz, 4H), 3.90-3.59 (m, 3H), 3.39-3.29 (m, 1H), 3.10 (s, 3H), 2.77-2.63 (m, 4H), 2.37-2.09 (m, 4H), 2.07-1.96 (m, 2H).

Compound 148. (R)-2'-amino-1-(4-((1-(2-amino-pyridin-3-yl)ethyl)(2-cyanoethyl)amino)-6-((1-(morpholinomethyl)cyclopropyl)methoxy)-1,3,5-triazin-2-yl)-6'H-spiro[azetidine-3,4'-thieno[3,4-b]thiophene]-3'-carbonitrile

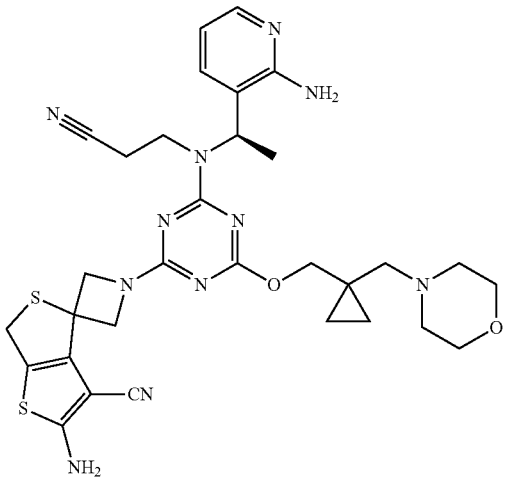 [SMILES: C[C@H](c1cccnc1N)N(CCC#N)c1nc(OCC2(CN3CCOCC3)CC2)nc(N2CC3(C2)SCc2sc(N)c(C#N)c23)n1]

Compound 148 was prepared similarly to that of Ex. 4. LCMS calculated for $C_{31}H_{38}N_{11}O_2S_2$ (M+H)$^+$ m/z=660.5; found: 660.3. $^1$H NMR (400 MHz, CD$_3$OD) δ 7.91 (d, J=4.6 Hz, 1H), 7.73 (d, J=7.2 Hz, 1H), 6.74 (dd, J=7.4, 5.1 Hz, 1H), 6.18-5.87 (m, 1H), 4.79-4.61 (m, 2H), 4.46-4.24 (m, 4H), 4.12-4.00 (m, 2H), 3.78-3.60 (m, 5H), 3.47-3.36 (m, 1H), 2.78-2.69 (m, 1H), 2.57-2.32 (m, 6H), 2.30-2.01 (m, 1H), 1.57 (d, J=6.9 Hz, 3H), 0.66 (s, 2H), 0.46 (s, 2H).

Compound 149. 2-amino-1'-[4-[(2-amino-3-pyridyl)methyl-(2-hydroxy-1-methyl-ethyl)amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

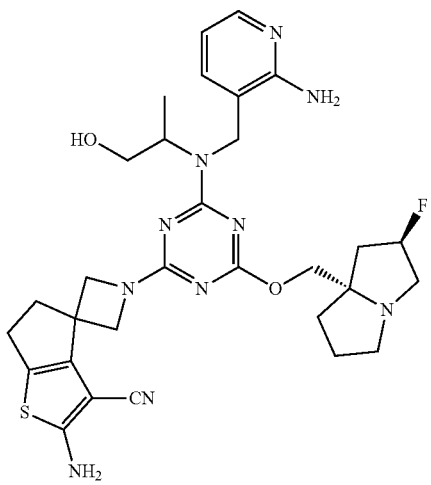 [SMILES: CC(CO)N(Cc1cccnc1N)c1nc(OC[C@@]23CCCN2C[C@H](F)C3)nc(N2CC3(CCc4sc(N)c(C#N)c43)C2)n1]

Compound 149 was prepared similarly to that of Ex. 4 as a hydrochloride salt. LCMS calculated for $C_{30}H_{38}FN_{10}O_2S$ (M+H)$^+$ m/z=621.2, found: 621.4. $^1$H NMR (400 MHz, CD$_3$OD) δ 8.04-7.75 (m, 2H), 7.08-6.83 (m, 1H), 5.67-5.44 (m, 1H), 5.12-4.98 (m, 1H), 4.83-4.64 (m, 4H), 4.64-4.27 (m, 3H), 4.17-3.61 (m, 6H), 3.52-3.35 (m, 1H), 2.87-1.98 (m, 10H), 1.25 (d, J=6.6 Hz, 3H).

Compound 150. 2-amino-1'-[4-[[(2R,8S)-2-fluoro-1,2,3,5,6,7-hexahydropyrrolizin-8-yl]methoxy]-6-[1-(3-hydroxypyrazin-2-yl)ethyl-methyl-amino]-1,3,5-triazin-2-yl]spiro[5,6-dihydrocyclopenta[b]thiophene-4,3'-azetidine]-3-carbonitrile

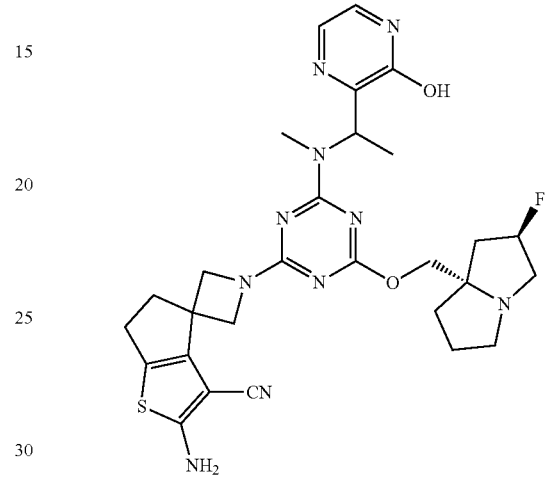

Compound 150 was prepared similarly to that of Ex. 4 as a formate salt. LCMS calculated for $C_{28}H_{34}FN_{10}O_2S$ (M+H)$^+$ m/z=593.3, found: 593.2. $^1$H NMR (400 MHz, CD$_3$OD) δ 7.46-7.14 (m, 2H), 6.21-5.78 (m, 1H), 5.33 (m, 1H), 4.41-3.92 (m, 6H), 3.70-3.35 (m, 3H), 3.26-3.18 (m, 1H), 3.11 (s, 3H), 2.85-2.60 (m, 4H), 2.42-1.82 (m, 6H), 1.52 (d, J=6.2 Hz, 3H).

Compound 151. 2-amino-1'-[4-[(3-chloro-1H-pyrazol-4-yl)methyl-(2-hydroxyethyl)amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

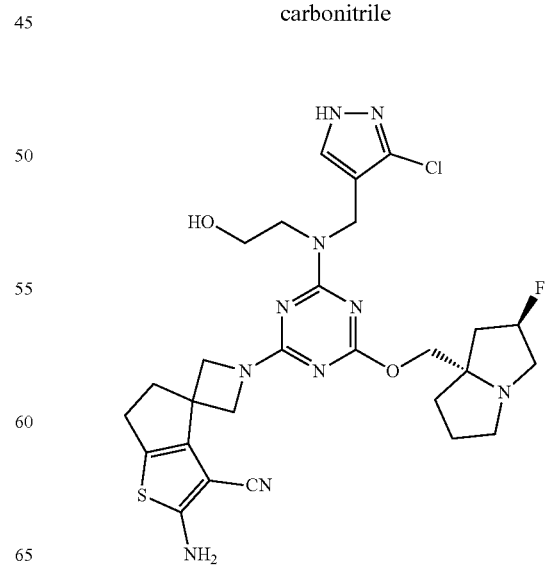

Compound 151 was prepared similarly to that of Ex. 4 as a hydrochloride salt. LCMS calculated for $C_{27}H_{33}ClFN_{10}O_2S$ (M+H)$^+$ m/z=615.2, found: 615.2. $^1$H NMR (400 MHz, CD$_3$OD) δ 7.82 (d, J=8.8 Hz, 1H), 5.57 (m, 1H), 4.76 (d, J=15.6 Hz, 2H), 4.49 (m, 4H), 4.09-3.60 (m, 8H), 3.45 (s, 1H), 2.78 (s, 4H), 2.73-2.07 (m, 7H).

Compound 152. 2-amino-1'-[4-[[(2R,8S)-2-fluoro-1,2,3,5,6,7-hexahydropyrrolizin-8-yl]methoxy]-6-[methyl(thiazol-5-ylmethyl)amino]-1,3,5-triazin-2-yl]spiro[5,6-dihydrocyclopenta[b]thiophene-4,3'-azetidine]-3-carbonitrile

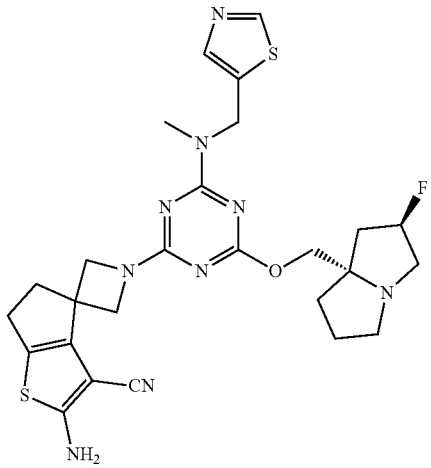 [SMILES: CN(Cc1cncs1)c1nc(OC[C@@]23CCCN2C[C@H](F)C3)nc(N2CC3(CCc4sc(N)c(C#N)c43)C2)n1]

Compound 152 was prepared similarly to that of Ex. 4 as a hydrochloride salt. LCMS calculated for $C_{26}H_{31}FN_9OS_2$ (M+H)$^+$ m/z=568.2, found: 568.3. $^1$H NMR (400 MHz, CD$_3$OD) δ 9.54 (d, J=21.2 Hz, 1H), 8.23 (d, J=18.0 Hz, 1H), 5.56 (d, J=52.0 Hz, 1H), 5.17 (d, J=12.0 Hz, 2H), 5.03 (d, J=14.8 Hz, 1H), 4.97-4.88 (m, 2H), 4.72 (d, J=21.6 Hz, 1H), 4.67-4.57 (m, 1H), 4.48 (s, 3H), 4.07-3.81 (m, 3H), 3.53-3.42 (m, 1H), 3.26 (s, 1H), 2.79 (s, 4H), 2.69-2.52 (m, 2H), 2.36 (d, J=32.0 Hz, 3H), 2.17 (s, 1H).

Compound 153. 2-amino-1'-[4-[[1-[(dimethylamino)methyl]-2,2-difluoro-cyclopropyl]methoxy]-6-[(3R,5S)-5-fluoro-3-hydroxy-3-methyl-1-piperidyl]-1,3,5-triazin-2-yl]spiro[6H-thieno[3,4-b]thiophene-4,3'-azetidine]-3-carbonitrile

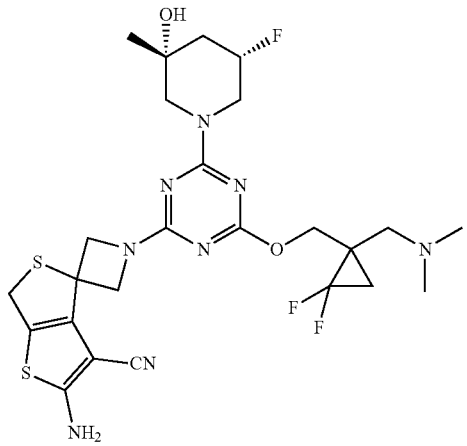 [SMILES: CN(C)CC1(COc2nc(N3CC4(C3)SCc3sc(N)c(C#N)c34)nc(N3C[C@@H](F)C[C@@](C)(O)C3)n2)CC1(F)F]

Compound 153 was prepared similarly to that of Ex. 5. LCMS calculated for $C_{25}H_{32}F_3N_8O_2S_2$ (M+H)$^+$ m/z=597.20; found: 597.2. $^1$H NMR (400 MHz, CD$_3$OD) δ 4.57-4.75 (m, 3H), 4.30-4.53 (m, 4H), 4.12-4.27 (m, 1H), 4.05 (s, 2H), 3.68-3.93 (m, 2H), 3.50-3.65 (m, 1H), 2.74-2.90 (m, 1H), 2.35-2.45 (m, 1H), 2.27 (s, 6H), 1.99-2.12 (m, 1H), 1.85-1.95 (m, 1H), 1.57-1.68 (m, 1H), 1.28-1.39 (m, 1H), 1.18 (s, 3H).

Compound 154. 2-amino-1'-[4-[(2-amino-4-fluoro-3-pyridyl)methyl-(2-hydroxyethyl)amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

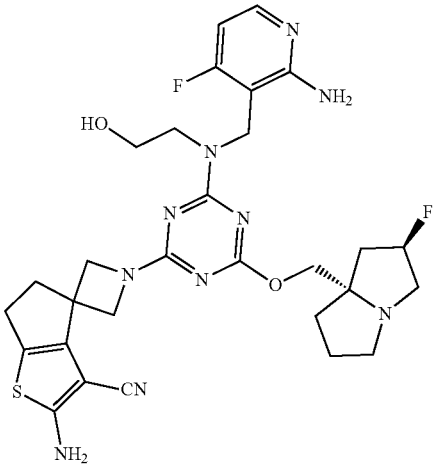 [SMILES: N#Cc1c(N)sc2c1C1(CC2)CN(c2nc(OC[C@@]34CCCN3C[C@H](F)C4)nc(N(CCO)Cc3c(F)ccnc3N)n2)C1]

Compound 154 was prepared similarly to that of Ex. 4 as a hydrochloride salt. LCMS calculated for $C_{29}H_{35}F_2N_{10}O_2S$ (M+H)$^+$ m/z=625.3, found: 625.3. $^1$H NMR (400 MHz, CD$_3$OD) δ 8.22-7.88 (m, 1H), 6.99-6.85 (m, 1H), 5.58 (d, J=51.6 Hz, 1H), 5.13-5.00 (m, 2H), 4.87-4.68 (m, 2H), 4.60-4.43 (m, 4H), 4.17-3.70 (m, 7H), 3.51-3.37 (m, 1H), 2.79 (s, 4H), 2.70-2.53 (m, 2H), 2.52-2.13 (m, 4H).

Compound 155. 2-amino-1'-[4-[[(2R,8S)-2-fluoro-1,2,3,5,6,7-hexahydropyrrolizin-8-yl]methoxy]-6-[1-(4-hydroxypyrimidin-5-yl)ethyl-methyl-amino]-1,3,5-triazin-2-yl]spiro[5,6-dihydrocyclopenta[b]thiophene-4,3'-azetidine]-3-carbonitrile

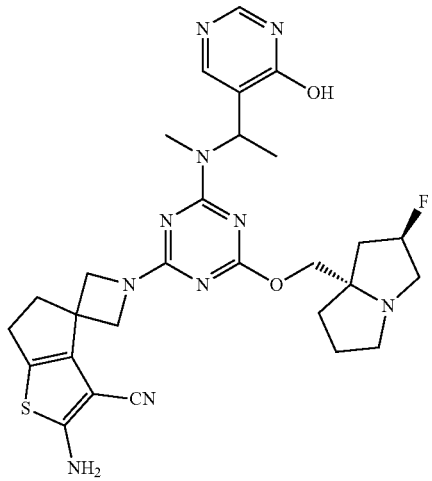 [SMILES: CC(c1cncnc1O)N(C)c1nc(OC[C@@]23CCCN2C[C@H](F)C3)nc(N2CC3(CCc4sc(N)c(C#N)c43)C2)n1]

Compound 155 was prepared similarly to that of Ex. 4. As a hydrochloride salt. LCMS calculated for $C_{28}H_{34}FN_{10}O_2S$ (M+H)⁺ m/z=593.2, found: 593.2. ¹H NMR (400 MHz, CD₃OD) δ 9.19-8.99 (m, 1H), 8.26-7.99 (m, 1H), 5.94 (s, 1H), 5.57 (d, J=51.1 Hz, 2H), 4.74 (s, 2H), 4.44 (d, J=17.0 Hz, 4H), 4.13-3.73 (m, 3H), 3.46 (s, 1H), 3.25 (s, 1H), 3.13 (s, 1H), 2.83-2.71 (m, 4H), 2.70-2.51 (m, 2H), 2.33 (s, 4H), 1.73-1.56 (m, 3H).

Example 8. Synthesis of 2'-amino-1-(4-((1-(4-amino-1,2,5-oxadiazol-3-yl)ethyl)(methyl)amino)-6-(((2R,7aS)-2-fluorotetrahydro-TH-pyrrolizin-7a(5H)-yl)methoxy)-1,3,5-triazin-2-yl)-5',6'-dihydrospiro[azetidine-3,4'-cyclopenta[b]thiophene]-3'-carbonitrile

Compound 156

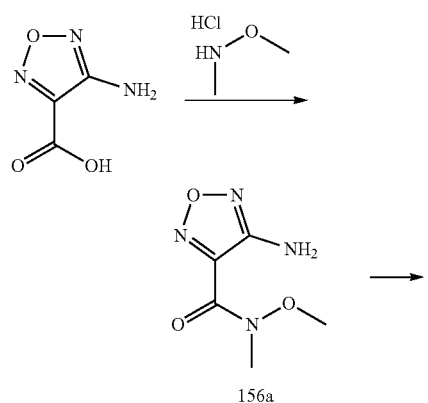

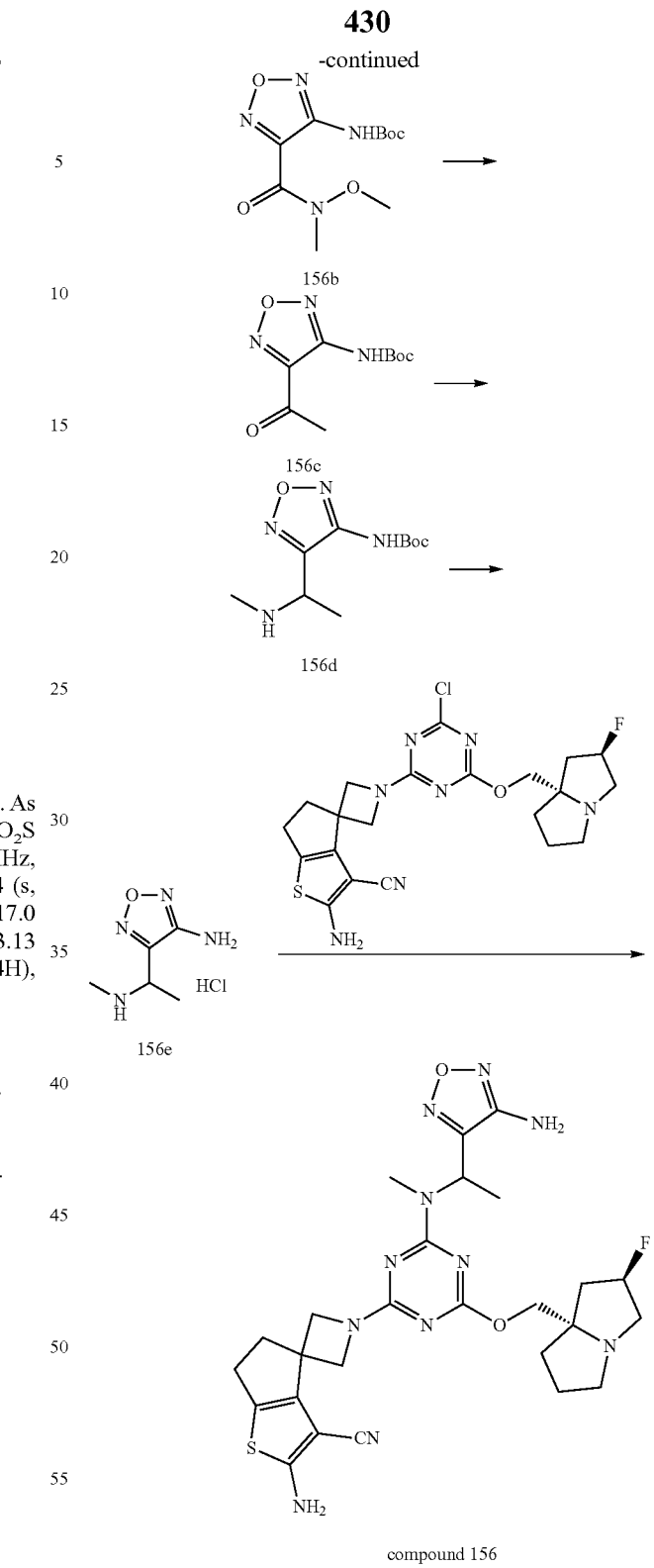

Step 1. Preparation of 4-amino-N-methoxy-N-methyl-1,2,5-oxadiazole-3-carboxamide (156a). To the solution of N,O-Dimethylhydroxylamine Hydrochloride (906.86 mg, 9.3 mmol) and 4-amino-1,2,5-oxadiazole-3-carboxylic acid (1 g, 7.75 mmol) in DMF (20 mL) was added HATU (2.88 mL, 11.62 mmol) and DIEA (4.01 g, 30.99 mmol) at r.t. The mixture was stirred at 25° C. for 16 h. Upon completion, the mixture was diluted with water (20 mL), and then extracted with EtOAc (50 mL). The organic phase was washed with brine (30 mL), dried over Na$_2$SO$_4$, filtered and concentrated. The crude product was purified by silica gel chromatography (eluted with EtOAc in petroleum ether from 10% to 80%). 4-amino-N-methoxy-N-methyl-1,2,5-oxadiazole-3-carboxamide (550 mg, 3.20 mmol, 41.24% yield) was obtained as yellow solid. LCMS calculated for C$_5$H$_9$N$_4$O$_3$(M+H)$^+$ m/z=173.3, found: 173.3.

Step 2. Preparation of tert-butyl (4-(methoxy(methyl) carbamoyl)-1,2,5-oxadiazol-3-yl)carbamate (156b). To a solution of 4-amino-N-methoxy-N-methyl-1,2,5-oxadiazole-3-carboxamide (500 mg, 2.9 mmol) and (Boc)$_2$O (1267.86 mg, 5.81 mmol) in MeCN (10 mL) was added DMAP (70.97 mg, 0.58 mmol) at 25° C. The mixture was stirred at 80° C. for 2 h. Upon completion, the reaction was cooled down to r.t., diluted with water (20 mL), and then extracted with EtOAc (50 mL). The organic phase was washed with brine (30 mL), dried over Na$_2$SO$_4$, filtered and concentrated. The crude product was purified by silica gel chromatography (eluted with EtOAc in petroleum ether from 0% to 40%). Tert-butyl N-[4-[methoxy(methyl)carbamoyl]-1,2,5-oxadiazol-3-yl]carbamate (370 mg, 1.36 mmol, 46.79% yield) was obtained as yellow solid. LCMS calculated for C$_{10}$H$_{16}$N$_4$O$_5$Na (M+Na)$^+$ m/z=295.1, found: 295.1.

Step 3. Preparation of tert-butyl (4-acetyl-1,2,5-oxadiazol-3-yl)carbamate (156c). To a solution of tert-butyl N-[4-[methoxy(methyl)carbamoyl]-1,2,5-oxadiazol-3-yl]carbamate (320 mg, 1.18 mmol) in THF (10 mL) was added 1 M CH$_3$MgBr in THF (5.88 mL, 5.88 mmol) at 0° C. The mixture was warmed to 25° C. and stirred for 16 h. The mixture was quenched with NH$_4$Cl solution at 0° C., diluted with DCM (50 mL), washed with H$_2$O (2×20 mL) and brine (20 mL). The organic phase was dried over Na$_2$SO$_4$, filtered and concentrated. The crude product was purified by silica gel chromatography (eluted with EtOAc in petroleum ether from 10% to 30%). Tert-butyl N-(4-acetyl-1,2,5-oxadiazol-3-yl)carbamate (210 mg, 0.9242 mmol, 78.633% yield) was obtained as yellow oil. LCMS calculated for C$_9$H$_{13}$N$_3$O$_4$Na (M+Na)$^+$ m/z=250.2, found: 250.2.

Step 4. Preparation of tert-butyl (4-(1-(methylamino) ethyl)-1,2,5-oxadiazol-3-yl)carbamate (156d) To the solution of tert-butyl N-(4-acetyl-1,2,5-oxadiazol-3-yl)carbamate (150 mg, 0.66 mmol) and methylamine in MeOH (41.01 mg, 1.32 mmol, 5 mL) was added titanium tetraisopropanolate (375.26 mg, 1.32 mmol) at 25° C. The mixture was stirred at 80° C. for 16 h. Upon completion, the reaction was cooled down to r.t. Then the mixture was added NaBH$_4$ (49.95 mg, 1.32 mmol) at r.t. The mixture was stirred at r.t. for 1 h. The mixture was filtered over celite and concentrated to afford a crude product. The crude product was purified by Prep-HPLC (eluted with CH$_3$CN in H$_2$O from 5% to 95%). Tert-butyl N-[4-[1-(methylamino)ethyl]-1,2,5-oxadiazol-3-yl]carbamate (100 mg, 0.413 mmol, 62.52% yield) was obtained as white solid. LCMS calculated for C$_{10}$H$_{19}$N$_4$O$_3$ (M+H)$^+$ m/z=243.2, found: 243.2.

Step 5. Preparation of 4-(1-(methylamino)ethyl)-1,2,5-oxadiazol-3-amine hydrochloride (156e). To the solution of tert-butyl N-[4-[1-(methylamino)ethyl]-1,2,5-oxadiazol-3-yl]carbamate (80 mg, 0.33 mmol) in methanol (1 mL) was added 4 M HCl in MeOH (2 mL, 0.33 mmol) at 25° C. The mixture was stirred at 25° C. for 1 h. The mixture was concentrated to afford a crude product. The crude product was used in the next step without further purification. 4-[1-(methylamino)ethyl]-1,2,5-oxadiazol-3-amine hydrochloride (59 mg, 0.330 mmol) was obtained as yellow oil. LCMS calculated for C$_5$H$_{11}$N$_4$O (M+H)$^+$ m/z=143.3, found: 143.3.

Step 6. Preparation of 2'-amino-1-(4-((1-(4-amino-1,2,5-oxadiazol-3-yl)ethyl)(methyl)amino)-6-(((2R,7aS)-2-fluorotetrahydro-1H-pyrrolizin-7a(5H)-yl)methoxy)-1,3,5-triazin-2-yl)-5',6'-dihydrospiro[azetidine-3,4'-cyclopenta[b]thiophene]-3'-carbonitrile (Compound 156). To the solution of 4-[1-(methylamino)ethyl]-1,2,5-oxadiazol-3-amine hydrochloride (33.77 mg, 0.19 mmol) and 2-amino-1'-[4-chloro-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile (30 mg, 0.06 mmol) in 1,4-Dioxane (2 mL) was added DIEA (32.58 mg, 0.25 mmol) at 25° C. The mixture was heated to 100° C. and stirred for 16 h. Upon completion, the reaction was cooled down to r.t. The mixture was concentrated to afford a crude product. The crude product was purified by Prep-HPLC (Mobile phase A was 0.1% NH$_4$HCO$_3$ in H$_2$O, mobile phase B 0.1% NH$_4$HCO$_3$ was ACN; Gradient from 5% to 95%). 2-amino-1'-[4-[1-(4-amino-1,2,5-oxadiazol-3-yl)ethyl-methyl-amino]-6-[[(2R,8S)-2-fluoro-1,2,3,5,6,7-hexahydropyrrolizin-8-yl]methoxy]-1,3,5-triazin-2-yl]spiro [5,6-dihydrocyclopenta[b]thiophene-4,3'-azetidine]-3-carbonitrile (7.8 mg, 0.0128 mmol, 20.33% yield) was obtained as white solid. LCMS calculated for C$_{26}$H$_{33}$FN$_{11}$O$_2$S (M+H)$^+$ m/z=582.2, found: 582.3. $^1$H NMR (400 MHz, CD$_3$OD) δ 6.24-6.06 (m, 1H), 5.26 (d, J=54.0 Hz, 1H), 4.46-4.26 (m, 2H), 4.24-4.02 (m, 4H), 3.30-3.10 (m, 3H), 3.02-2.84 (m, 4H), 2.81-2.68 (m, 4H), 2.32-1.76 (m, 6H), 1.64 (d, J=7.2 Hz, 3H).

Compound 157, amino-1'-[4-[1-(3-amino-1-methyl-pyrazol-4-yl)ethyl-methyl-amino]-6-[[(2R,8S)-2-fluoro-1,2,3,5,6,7-hexahydropyrrolizin-8-yl] methoxy]-1,3,5-triazin-2-yl]spiro[5,6-dihydrocyclopenta[b]thiophene-4,3'-azetidine]-3-carbonitrile

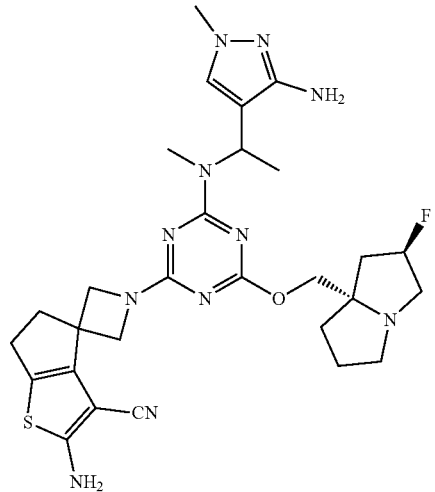 [SMILES: CC(c1cn(C)nc1N)N(C)c1nc(OC[C@@]23CCCN2C[C@H](F)C3)nc(N2CC3(CCc4sc(N)c(C#N)c43)C2)n1]

Compound 157 was prepared similarly to that of Ex. 7. LCMS calculated for C$_{28}$H$_{37}$FN$_{11}$OS (M+H)$^+$ m/z=594.3, found: 594.3. $^1$H NMR (400 MHz, CD$_3$OD) δ 7.39 (s, 1H), 6.11-5.88 (m, 1H), 5.26 (d, J=53.9 Hz, 1H), 4.59-4.25 (m, 2H), 4.24-3.94 (m, 4H), 3.65 (s, 3H), 3.18 (d, J=23.6 Hz, 3H), 2.97 (dd, J=13.7, 7.3 Hz, 1H), 2.83 (s, 3H), 2.74 (d, J=8.7 Hz, 4H), 2.37-2.02 (m, 3H), 2.02-1.71 (m, 3H), 1.45 (d, J=6.8 Hz, 3H).

Compound 158. 2-amino-1'-[4-[[(2R,8S)-2-fluoro-1,2,3,5,6,7-hexahydropyrrolizin-8-yl]methoxy]-6-[1-isothiazol-5-ylethyl(methyl)amino]-1,3,5-triazin-2-yl]spiro[5,6-dihydrocyclopenta[b]thiophene-4,3'-azetidine]-3-carbonitrile

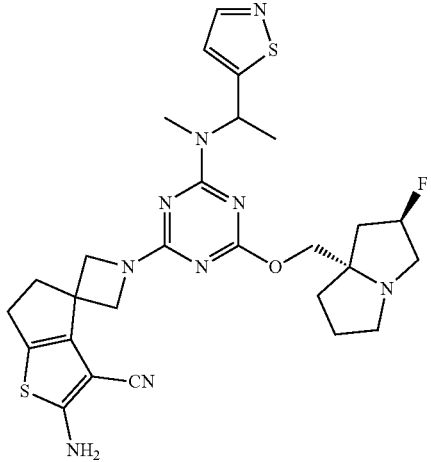 [SMILES: CC(c1ccns1)N(C)c1nc(OC[C@@]23CCCN2C[C@H](F)C3)nc(N2CC3(CCc4sc(N)c(C#N)c43)C2)n1]

Compound 158 was prepared similarly to that of Ex. 7. LCMS calculated for $C_{27}H_{33}FN_9OS_2$ (M+H)$^+$ m/z=582.22, found: 582.1. $^1$H NMR (400 MHz, CD$_3$OD) δ 8.39 (s, 1H), 7.24 (s, 1H), 6.42 (q, J=6.9 Hz, 1H), 5.25 (d, J=55.3 Hz, 1H), 4.36 (d, J=8.9 Hz, 2H), 4.15 (d, J=9.3 Hz, 4H), 4.09-4.01 (m, 1H), 3.22-3.09 (m, 3H), 2.95 (s, 4H), 2.73 (dd, J=11.2, 4.3 Hz, 4H), 2.28-1.76 (m, 6H), 1.69 (d, J=7.1 Hz, 3H).

Compound 159. 2-amino-1'-[4-[(1R,5S)-8-(2,2-dihydroxy-3-oxo-butanoyl)-3,8-diazabicyclo[3.2.1]octan-3-yl]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

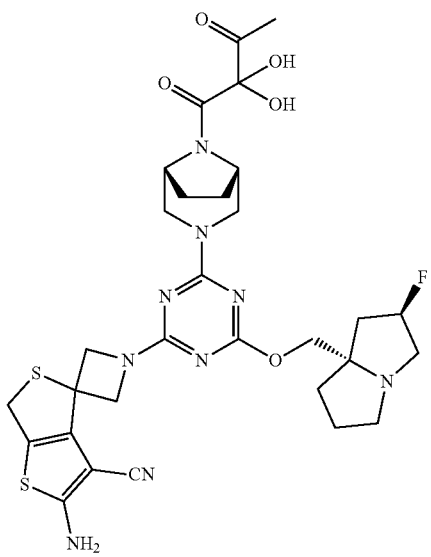 [SMILES: CC(=O)C(O)(O)C(=O)N1[C@@H]2CC[C@H]1CN(c1nc(OC[C@@]34CCCN3C[C@H](F)C4)nc(N3CC4(C3)SCc3sc(N)c(C#N)c34)n1)C2]

Compound 159 was prepared similarly to that of Ex. 1. LCMS calculated for $C_{30}H_{37}FN_9O_5S_2$ (M+H)$^+$ m/z=686.2; found: 686.2. $^1$H NMR (400 MHz, d6-DMSO) δ=7.40 (s, 2H), 5.24 (d, J=54.4 Hz, 1H), 4.79-4.19 (m, 8H), 4.05 (s, 2H), 4.02-3.64 (m, 3H), 3.23-2.87 (m, 6H), 2.83-2.75 (m, 1H), 2.36-1.41 (m, 13H).

Compound 160. 2-amino-1'-[4-[cyclopropyl(methyl)amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

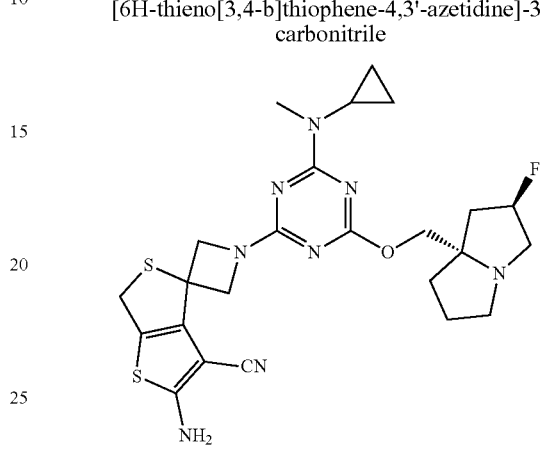

Compound 160 was prepared similarly to that of Ex. 1. LCMS calculated for $C_{24}H_{30}FN_8OS_2$ (M+H)$^+$ m/z=529.19; found: 529.2. $^1$H NMR (400 MHz, CD$_3$OD) δ 5.26 (d, J=53.4 Hz, 1H), 4.72-4.60 (m, 2H), 4.39-4.29 (m, 2H), 4.22-4.14 (m, 1H), 4.12-4.01 (m, 3H), 3.26-3.11 (m, 3H), 3.08 (s, 3H), 3.01-2.93 (m, 1H), 2.81-2.72 (m, 1H), 2.30-2.04 (m, 3H), 2.02-1.77 (m, 3H), 0.91-0.77 (m, 2H), 0.75-0.62 (m, 2H).

Compound 161. 2-amino-1'-[4-[[(2R,8S)-2-fluoro-1,2,3,5,6,7-hexahydropyrrolizin-8-yl]methoxy]-6-[(1R,5S)-8-[(2Z)-2-methoxyimino-3-oxo-butanoyl]-3,8-diazabicyclo[3.2.1]octan-3-yl]-1,3,5-triazin-2-yl]spiro[6H-thieno[3,4-b]thiophene-4,3'-azetidine]-3-carbonitrile

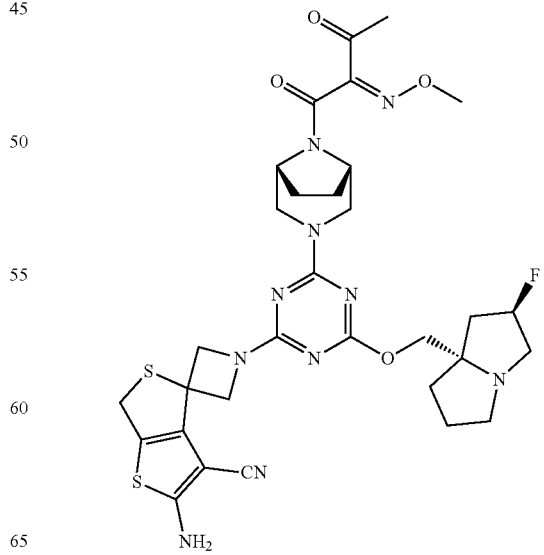

Compound 161 was prepared similarly to that of Ex. 1. LCMS calculated for $C_{31}H_{38}FN_{10}O_4S_2$ (M+H)$^+$ m/z=697.2; found: 697.2. $^1$H NMR (400 MHz, CD$_3$OD) δ=5.26 (d, J=54.0 Hz, 1H), 4.76-4.61 (m, 5H), 4.35 (d, J=10.0 Hz, 2H), 4.12-4.05 (m, 7H), 3.86 (s, 1H), 3.25-2.90 (m, 6H), 2.43 (s, 3H), 2.29-1.69 (m, 10H).

Compound 162. 2-amino-1'-[4-[1-(2-amino-6-fluoro-3-pyridyl)ethyl-methyl-amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

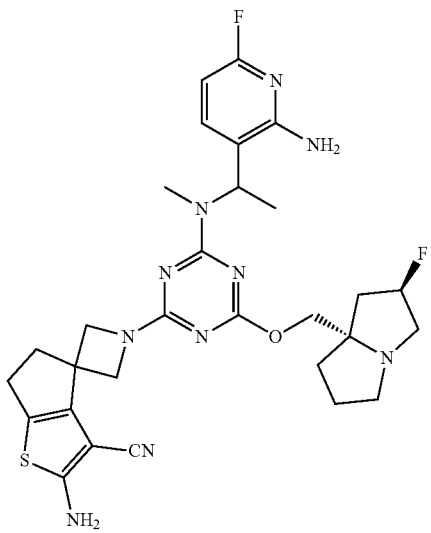 [SMILES: CC(c1ccc(F)nc1N)N(C)c1nc(OC[C@@]23CCCN2C[C@H](F)C3)nc(N2CC3(CCc4sc(N)c(C#N)c43)C2)n1]

Compound 162 was prepared similarly to that of Ex. 4. LCMS calculated for $C_{29}H_{35}F_2N_{10}OS$ (M+H)$^+$ m/z=609.3; found: 609.3. $^1$H NMR (400 MHz, CD$_3$OD) δ 7.70 (t, J=8.0 Hz, 1H), 6.20 (d, J=6.2 Hz, 1H), 6.10-5.90 (m, 1H), 5.26 (d, J=53.4 Hz, 1H), 4.51-3.98 (m, 6H), 3.17 (d, J=22.6 Hz, 3H), 2.97 (d, J=5.3 Hz, 1H), 2.76 (s, 7H), 2.30-1.84 (m, 6H), 1.52 (d, J=6.8 Hz, 3H).

Compound 163. 2-amino-1'-[4-[[(1R)-1-(2-amino-3-pyridyl)ethyl]-methyl-amino]-6-[[(2R,8S)-2-fluoro-1,2,3,5,6,7-hexahydropyrrolizin-8-yl]methoxy]-1,3,5-triazin-2-yl]spiro[6,7-dihydro-5H-benzothiophene-4,3'-azetidine]-3-carbonitrile

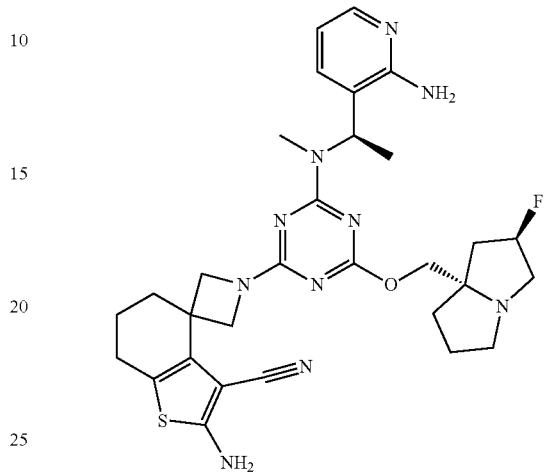

Compound 163 was prepared similarly to that of Ex. 4. LCMS calculated for $C_{30}H_{38}FN_{10}OS$ (M+H)$^+$ m/z=605.2, found: 605.3. $^1$H NMR (400 MHz, CD$_3$OD) δ: 7.85-7.82 (m, 1H), 7.65-7.61 (m, 1H), 6.69-6.64 (m, 1H), 6.12-5.97 (m, 1H), 5.25 (m, 1H), 4.54-4.29 (m, 2H), 4.20-4.15 (m, 1H), 4.14-3.89 (m, 3H), 3.21-3.13 (m, 3H), 2.99-2.94 (m, 1H), 2.76-2.74 (m, 3H), 2.51-2.49 (m, 2H), 2.31-1.73 (m, 10H), 1.53 (d, J=6.8, 3H).

Compound 164. 2-amino-1'-[4-[[(2R,8S)-2-fluoro-1,2,3,5,6,7-hexahydropyrrolizin-8-yl]methoxy]-6-(1H-pyrazol-4-yloxy)-1,3,5-triazin-2-yl]spiro[6H-thieno[3,4-b]thiophene-4,3'-azetidine]-3-carbonitrile

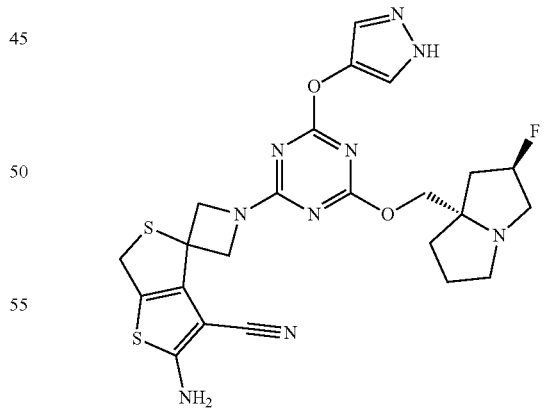

Compound 164 was prepared similarly to that of Ex. 3. LCMS calculated for $C_{23}H_{25}FN_9O_2S_2$ (M+H)$^+$ m/z=542.16; found: 542.2. $^1$H NMR (400 MHz, d6-DMSO) δ 12.74 (s, 1H), 7.85 (s, 1H), 7.55 (s, 1H), 7.42 (s, 2H), 5.24 (d, J=54.0 Hz, 1H), 4.59 (dd, J=10.4, 7.2 Hz, 2H), 4.38 (dd, J=10.4, 3.6 Hz, 2H), 4.05 (s, 2H), 3.87-4.05 (m, 2H), 2.90-3.11 (m, 3H), 2.73-2.86 (m, 1H), 1.61-2.09 (m, 6H).

Compound 165. 2-amino-1'-[4-[[(2R,8S)-2-fluoro-1,2,3,5,6,7-hexahydropyrrolizin-8-yl]methoxy]-6-(1H-pyrazol-3-yloxy)-1,3,5-triazin-2-yl]spiro[6H-thieno[3,4-b]thiophene-4,3'-azetidine]-3-carbonitrile

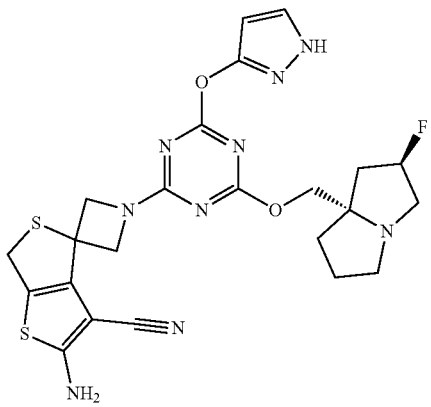 [SMILES: N#Cc1c(N)sc2c1C1(CN(c3nc(OC[C@@]45CCCN4C[C@H](F)C5)nc(Oc4cc[nH]n4)n3)C1)SC2]

Compound 165 was prepared similarly to that of Ex. 3. LCMS calculated for $C_{23}H_{25}FN_9O_2S_2$ (M+H)$^+$ m/z=542.15; found: 542.2. $^1$H NMR (400 MHz, d6-DMSO) δ 12.46 (s, 1H), 7.68 (s, 1H), 7.42 (s, 2H), 6.10 (s, 1H), 5.12-5.31 (m, 1H), 4.26-4.65 (m, 4H), 4.05 (s, 2H), 3.83-4.01 (m, 2H), 2.74-3.09 (m, 4H), 1.64-2.06 (m, 6H).

Compound 166. 2-amino-1'-[4-[(4-amino-1,2,5-thiadiazol-3-yl)methyl-methyl-amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

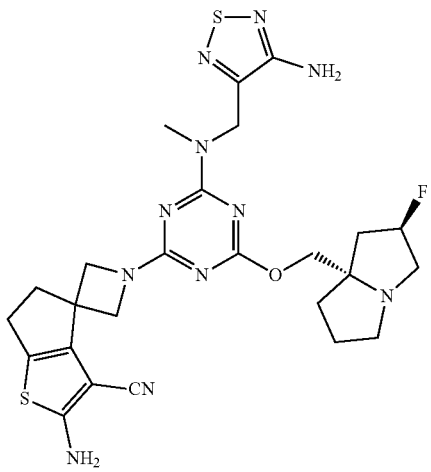 [SMILES: CN(Cc1nsnc1N)c1nc(OC[C@@]23CCCN2C[C@H](F)C3)nc(N2CC3(CCc4sc(N)c(C#N)c43)C2)n1]

Compound 166 was prepared similarly to that of Ex. 7 as a formate salt. LCMS calculated for $C_{25}H_{31}FN_{11}OS_2$ (M+H)$^+$ m/z=584.2, found: 584.2. $^1$H NMR (400 MHz, CD$_3$OD) δ 5.49-5.24 (m, 1H), 4.86 (m, 2H), 4.53-4.08 (m, 6H), 3.59-3.36 (m, 3H), 3.13 (m, 4H), 2.74 (d, J=9.2 Hz, 4H), 2.46-1.83 (m, 6H).

Compound 167. 1-(4-((1R,5S)-3,8-diazabicyclo[3.2.1]octan-3-yl)-6-((1-(morpholinomethyl)cyclopropyl)methoxy)-1,3,5-triazin-2-yl)-2'-amino-6'H-spiro[azetidine-3,4'-thieno[3,4-b]thiophene]-3'-carbonitrile Compound 167 was prepared similarly to that of Ex. 1. LCMS calculated for $C_{27}H_{36}N_9O_2S_2$ (M+H)$^+$ m/z=582.2; found (M/2+H)$^+$: 292.0. $^1$H NMR (400 MHz, CD$_3$OD) δ 4.64 (d, J=10.0 Hz, 2H), 4.51-4.20 (m, 6H), 4.05 (s, 2H), 3.66 (t, J=4.6 Hz, 4H), 3.56 (s, 2H), 3.06-3.02 (m, 2H), 2.57-2.31 (m, 6H), 1.85-1.65 (m, 4H), 0.66-0.58 (m, 2H), 0.47-0.39 (m, 2H).

Compound 168A and compound 168B. 2-amino-1'-[4-[[(1*)-1-(3-aminopyrazin-2-yl)ethyl]-ethyl-amino]-6-[[(2R,8S)-2-fluoro-1,2,3,5,6,7-hexahydro-pyrrolizin-8-yl]methoxy]-1,3,5-triazin-2-yl]spiro[6H-thieno[3,4-b]thiophene-4,3'-azetidine]-3-carbonitrile Racemic mixture was prepared similarly to that of Ex. 4, then separated on a Daicel OJ-3 (250*25 mm 10 um) column on a Waters SFC 150 system (Mobile Phase A: Supercritical CO$_2$, Mobile Phase B: MeOH[0.2% NH$_3$ (7M in MeOH)];

A:B: 80/20; Flow: 3 ml/min) to give faster eluting P1 (compound 168A), and slower eluting P2 (compound 168B)

P1: LCMS calculated for $C_{28}H_{35}FN_{11}OS_2$ (M+H)$^+$ m/z=624.2; found: 624.6. $^1$H NMR (400 MHz, d6-DMSO) δ=7.90 (d, J=2.4 Hz, 1H), 7.76 (d, J=2.4 Hz, 1H), 7.40 (s, 2H), 6.33-6.02 (m, 2H), 5.95-5.93 (m, 1H), 5.23 (d, J=54.0 Hz, 1H), 4.68-4.47 (m, 2H), 4.42-4.21 (m, 2H), 4.11-3.80 (m, 4H), 3.50-3.37 (m, 1H), 3.27-3.15 (m, 1H), 3.12-2.91 (m, 3H), 2.86-2.74 (m, 1H), 2.12-1.90 (m, 3H), 1.86-1.65 (m, 3H), 1.48 (d, J=6.8 Hz, 3H), 0.87-0.72 (m, 3H).

P2: LCMS calculated for $C_{28}H_{35}FN_{11}OS_2$ (M+H)$^+$ m/z=624.2; found: 624.6

$^1$H NMR (400 MHz, d6-DMSO) δ=7.91 (d, J=2.4 Hz, 1H), 7.76 (d, J=2.4 Hz, 1H), 7.40 (s, 2H), 6.33-6.01 (m, 2H), 5.94 (d, J=6.4 Hz, 1H), 5.24 (d, J=54.0 Hz, 1H), 4.68-4.49 (m, 2H), 4.41-4.21 (m, 2H), 4.13-3.82 (m, 4H), 3.51-3.36 (m, 1H), 3.26-3.14 (m, 1H), 3.11-2.93 (m, 3H), 2.85-2.74 (m, 1H), 2.10-1.89 (m, 3H), 1.86-1.66 (m, 3H), 1.48 (d, J=6.8 Hz, 3H), 0.85-0.73 (m, 3H).

Compound 169. 2-amino-1'-[4-[[(2R,8S)-2-fluoro-1,2,3,5,6,7-hexahydropyrrolizin-8-yl]methoxy]-6-pyridazin-4-yloxy-1,3,5-triazin-2-yl]spiro[6H-thieno[2,3-c]thiophene-4,3'-azetidine]-3-carbonitrile

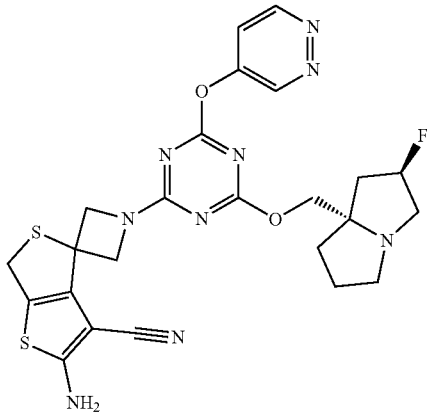 [SMILES: N#Cc1c(N)sc2c1C1(CN(c3nc(OC[C@@]45CCCN4C[C@H](F)C5)nc(Oc4ccnnc4)n3)C1)SC2]

Compound 169 was prepared similarly to that of Ex. 3. LCMS calculated for $C_{24}H_{25}FN_9O_2S_2$ (M+H)$^+$ m/z=554.2, found: 554.2. $^1$H NMR (400 MHz, CDCl$_3$) δ 9.23-9.15 (m, 1H), 8.05-7.98 (m, 1H), 6.57-6.48 (m, 1H), 5.38-5.10 (m, 3H), 4.88-4.77 (m, 2H), 4.65-4.44 (m, 3H), 3.47-3.37 (m, 2H), 3.50-3.38 (m, 1H), 3.22-3.10 (m, 1H), 2.52-2.28 (m, 3H), 2.18-2.09 (m, 2H), 2.06-1.96 (m, 1H), 1.40-1.26 (m, 3H).

Compound 170. -amino-1'-[4-[1-(4-amino-1,2,5-thiadiazol-3-yl)ethyl-methyl-amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

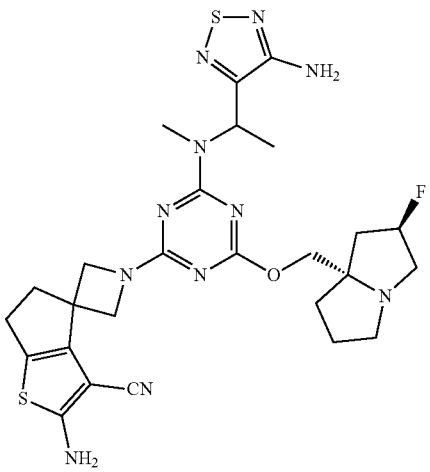

Compound 170 was prepared similarly to that of Ex. 7 as a formate salt. LCMS calculated for $C_{26}H_{33}FN_{11}OS_2$ (M+H)$^+$ m/z=598.2, found: 598.5. $^1$H NMR (400 MHz, CD$_3$OD) δ 6.32-6.00 (m, 1H), 5.47-5.23 (m, 1H), 4.67-4.54 (m, 5H), 4.48-4.11 (m, 5H), 3.09-2.99 (m, 1H), 2.98-2.68 (m, 6H), 2.44-1.79 (m, 6H), 1.64 (d, J=6.9 Hz, 3H).

Compound 171. 2-amino-1'-[4-[1-(4-amino-1,2,5-oxadiazol-3-yl)ethyl-ethyl-amino]-6-[[(2R,8S)-2-fluoro-1,2,3,5,6,7-hexahydropyrrolizin-8-yl]methoxy]-1,3,5-triazin-2-yl]spiro[6H-thieno[2,3-c]thiophene-4,3'-azetidine]-3-carbonitrile

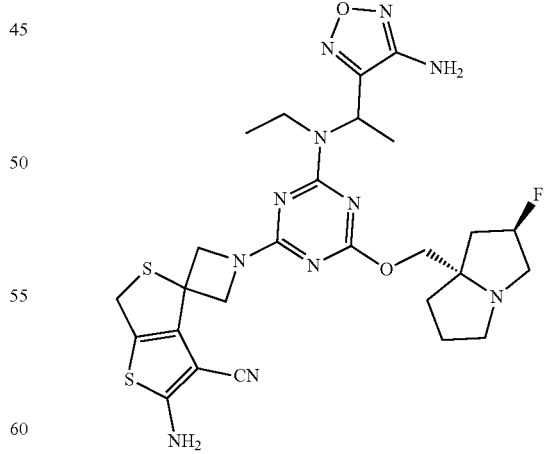

Compound 171 was prepared similarly to that of Ex. 7. LCMS calculated for LCMS calculated for $C_{26}H_{33}FN_{11}O_2S_2$ (M+H)$^+$ m/z=614.2, found: 614.2. $^1$H NMR (400 MHz, CD$_3$OD) δ 6.14 (m, 1H), 5.27 (m, 1H), 4.64 (m, 2H), 4.39 (s, 2H), 4.17 (s, 1H), 4.05 (s, 3H), 3.44

(s, 2H), 3.25-3.11 (m, 3H), 2.98 (m, 1H), 2.35-2.03 (m, 3H), 2.01-1.75 (m, 3H), 1.67 (m, 3H), 1.09 (s, 3H).

Compound 172. 2-amino-4-[1-[4-[[(1R)-1-(2-amino-3-pyridyl)ethyl]-methyl-amino]-6-[[(2R,8S)-2-fluoro-1,2,3,5,6,7-hexahydropyrrolizin-8-yl]methoxy]-1,3,5-triazin-2-yl]-3-methyl-azetidin-3-yl]thiophene-3-carbonitrile

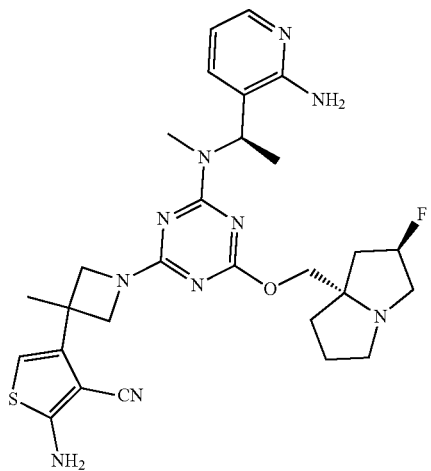 [SMILES: C[C@H](c1cccnc1N)N(C)c1nc(OC[C@@]23CCCN2C[C@H](F)C3)nc(N2CC(C)(c3csc(N)c3C#N)C2)n1]

Compound 172 was prepared similarly to that of Ex. 4. LCMS calculated for $C_{28}H_{36}FN_{10}OS$ (M+H)$^+$ m/z=579.3, found: 579.3. $^1$H NMR (400 MHz, CD$_3$OD) δ 7.86 (d, J=4.4 Hz, 1H), 7.65 (d, J=7.2 Hz, 1H), 6.69 (dd, J=7.2, 5.4 Hz, 1H), 6.16 (s, 1H), 6.04 (s, 1H), 5.27 (dd, J=34.8, 30.0 Hz, 1H), 4.58 (s, 1H), 4.34 (d, J=8.4 Hz, 1H), 4.21-3.94 (m, 4H), 3.20 (dd, J=28.8, 19.6 Hz, 3H), 2.97 (d, J=5.6 Hz, 1H), 2.76 (s, 3H), 2.21-1.82 (m, 6H), 1.69 (s, 3H), 1.53 (d, J=6.8 Hz, 3H).

Compound 173. 2-amino-1'-[4-[[(1R)-1-(2-amino-3-pyridyl)ethyl]-ethyl-amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-azetidine]-3-carbonitrile

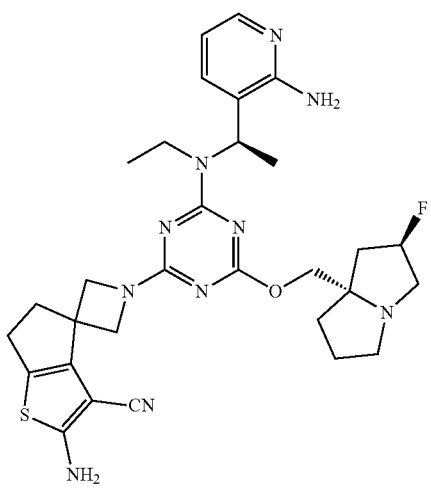 [SMILES: CCN(c1nc(OC[C@@]23CCCN2C[C@H](F)C3)nc(N2CC3(CCc4sc(N)c(C#N)c43)C2)n1)[C@H](C)c1cccnc1N]

Compound 173 was prepared similarly to that of Ex. 4. LCMS calculated for $C_{30}H_{38}FN_{10}OS$ (M+H)$^+$ m/z=605.30; found: 605.3. $^1$H NMR (400 MHz, CD$_3$OD) δ=7.86 (s, 1H), 7.68 (d, J=7.4 Hz, 1H), 6.74-6.61 (m, 1H), 6.08-6.05 (m, 1H), 5.25 (d, J=54.4 Hz, 1H), 4.52-3.99 (m, 6H), 3.54-3.41 (m, 1H), 3.24-3.09 (m, 4H), 3.02-2.90 (m, 1H), 2.84-2.65 (m, 4H), 2.32-1.77 (m, 6H), 1.54 (d, J=6.8 Hz, 3H), 0.84 (t, J=6.8 Hz, 3H).

Compound 174. 2-amino-1'-[4-[1-(4-amino-1,2,5-thiadiazol-3-yl)ethyl-methyl-amino]-6-[[(2R,8S)-2-fluoro-1,2,3,5,6,7-hexahydropyrrolizin-8-yl]methoxy]-1,3,5-triazin-2-yl]spiro[6H-thieno[2,3-c]thiophene-4,3'-azetidine]-3-carbonitrile

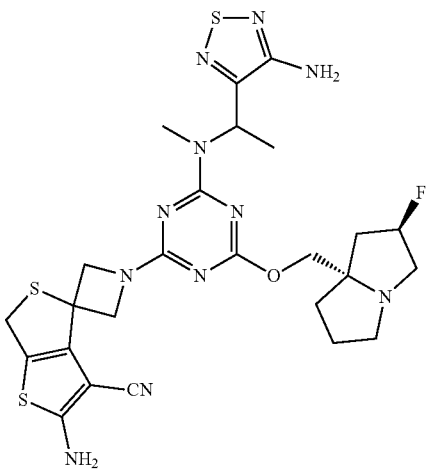 [SMILES: CC(c1nsnc1N)N(C)c1nc(OC[C@@]23CCCN2C[C@H](F)C3)nc(N2CC3(C2)SCc2sc(N)c(C#N)c23)n1]

Compound 174 was prepared similarly to that of Ex. 7. LCMS calculated for $C_{25}H_{31}FN_{11}OS_3$ (M+H)$^+$ m/z=616.2, found: 616.2. $^1$H NMR (400 MHz, CD$_3$OD) δ 6.25-5.99 (m, 1H), 5.26 (d, J=53.4 Hz, 1H), 4.80-4.56 (m, 2H), 4.49-4.30 (m, 2H), 4.25-3.94 (m, 4H), 3.25-3.08 (m, 3H), 3.02-2.94 (m, 1H), 2.91-2.78 (m, 3H), 2.33-1.80 (m, 6H), 1.64 (d, J=6.8 Hz, 3H).

Example 9. Exemplary synthesis of (*)-2-amino-1'-(4-(((R)-1-(2-aminopyridin-3-yl)ethyl)(methyl)amino)-6-(((2R,7aS)-2-fluorotetrahydro-1H-pyrrolizin-7a(5H)-yl)methoxy)-1,3,5-triazin-2-yl)-2'-oxo-6,7-dihydro-5H-spiro[benzo[b]thiophene-4,3'-pyrrolidine]-3-carbonitrile (Compound 175A&B)

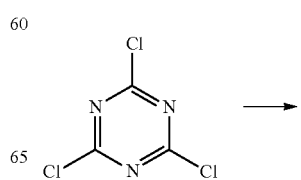

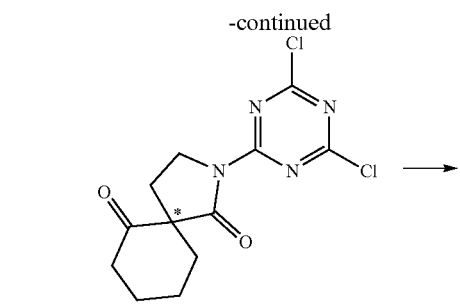

175a

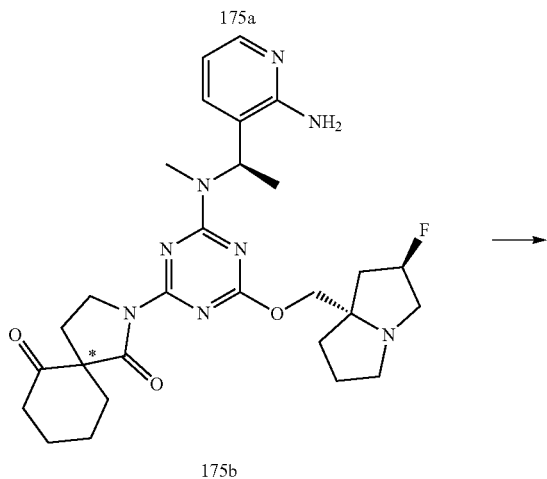

175b

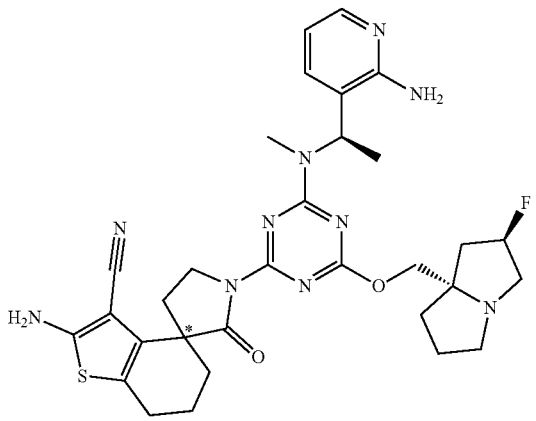

Compound 175A&B

Step 1. Preparation of 2-(4,6-dichloro-1,3,5-triazin-2-yl)-2-azaspiro[4.5]decane-1,6-dione (175a)

To the mixture of 2-azaspiro[4.5]decane-1,6-dione (200 mg, 1.2 mmol) in THF (5 mL) was added LiHMDS (1.8 mL, 1.79 mmol) at −70° C. under $N_2$. After stirring for 1 h, the mixture was added to the solution of 2,4,6-trichloro-1,3,5-triazine (264.67 mg, 1.44 mmol) in THF (5 mL) at −70° C. under $N_2$. The whole mixture was stirred at −70° C. for 1 h. It was quenched by the addition of aqueous $NH_4Cl$ solution and extracted with EA (20 mL×2). The combined extracts were washed with saturated brine and dried ($Na_2SO_4$). The solvent was removed in vacuo and the residue was purified using FC (silica gel, eluent with EtOAc in PE=0 to 30%) to give the product 2-(4,6-dichloro-1,3,5-triazin-2-yl)-2-azaspiro[4.5]decane-1,6-dione (40 mg, 0.116 mmol, 9.66% yield) as a yellow solid.

LCMS calculated for $C_{12}H_{13}Cl_2N_4O_2$ (M+H)$^+$ m/z=315.03; found: 315.1.

Step 2. Preparation 2-(4-(((R)-1-(2-aminopyridin-3-yl)ethyl)(methyl)amino)-6-(((2R,7aS)-2-fluorotetra-hydro-1H-pyrrolizin-7a(5H)-yl)methoxy)-1,3,5-tri-azin-2-yl)-2-azaspiro[4.5]decane-1,6-dione (175b)

To a solution of 2-(4,6-dichloro-1,3,5-triazin-2-yl)-2-azaspiro[4.5]decane-1,6-dione (40 mg, 0.13 mmol) and [(2R,8S)-2-fluoro-1,2,3,5,6,7-hexahydropyrrolizin-8-yl]methanol (20.21 mg, 0.13 mmol) in DMSO (1.5 mL) were added DIPEA (49.2 mg, 0.38 mmol) at 15° C. under $N_2$. The mixture was stirred at same temperature for 0.5 h, then 3-[(1R)-1-(methylamino) ethyl]pyridin-2-amine (28.79 mg, 0.19 mmol) was added in one portion and stirred for 1 h. The reaction mixture was partitioned between $H_2O$ (5 mL) and EtOAc (15 mL). The aqueous layer was extracted with EtOAc (2×20 mL), and the combined organic layers were washed with brine, dried ($Na_2SO_4$) and concentrated under reduced pressure. The crude residue was purified using FC (silica gel, Eluent with EtOAc in PE, 0 to 20%) to afford the title product 2-[4-[[(1R)-1-(2-amino-3-pyridyl)ethyl]-methyl-amino]-6-[[(2R,8S)-2-fluoro-1,2,3,5,6,7-hexahydro-pyrrolizin-8-yl]methoxy]-1,3,5-triazin-2-yl]-2-azaspiro[4.5] decane-1,6-dione (40 mg, 0.0651 mmol, 51.32% yield) as a yellow solid. LCMS calculated for $C_{28}H_{38}FN_8O_3$(M+H)$^+$ m/z=553.3; found: 553.3.

Step 3. Preparation of (*)-2-amino-1'-(4-(((R)-1-(2-aminopyridin-3-yl)ethyl)(methyl)amino)-6-(((2R,7aS)-2-fluorotetrahydro-1H-pyrrolizin-7a(5H)-yl)methoxy)-1,3,5-triazin-2-yl)-2'-oxo-6,7-dihydro-5H-spiro[benzo[b]thiophene-4,3'-pyrrolidine]-3-carbonitrile (compound 175A & 175B)

The mixture of 2-[4-[[(1R)-1-(2-amino-3-pyridyl)ethyl]-methyl-amino]-6-[[(2R,8S)-2-fluoro-1,2,3,5,6,7-hexahydro-pyrrolizin-8-yl]methoxy]-1,3,5-triazin-2-yl]-2-azaspiro[4.5] decane-1,6-dione (40 mg, 0.07 mmol), propanedinitrile (7.17 mg, 0.11 mmol), Sulfur (3.48 mg, 0.11 mmol) and ammonium acetate (8.37 mg, 0.11 mmol) in Ethanol (1.5 mL) was stirred at 45° C. for 4 h under N2. It was diluted with water (10 mL) and extracted with EtOAc (3×30 mL). The combined organic phases were washed with water and brine, dried ($Na_2SO_4$) and concentrated in vacuo. The crude residue was purified using prep-TLC (silica gel, eluent with DCM/MeOH=10/1) and then prep-HPLC (C18, MeCN in NH4HCO3 0.1% water) to afford faster eluting P1 compound (3.3 mg, 0.00496 mmol, 6.85% yield), and slower eluting P2 (2.8 mg, 0.00371 mmol, 5.12% yield) as a yellow solid. LCMS calculated for $C_{31}H_{38}FN_{10}O_2S$ (M+H)$^+$ m/z=633.28; found: 633.5

P1: $^1$H NMR (400 MHz, CD$_3$OD) δ 7.94-7.81 (m, 1H), 7.68 (d, J=7.5 Hz, 1H), 6.75-6.62 (m, 1H), 6.21-5.89 (m, 1H), 5.41-5.17 (m, 1H), 4.28-3.81 (m, 4H), 3.26-2.93 (m, 4H), 2.75-2.54 (m, 3H), 2.56 (s, 2H), 2.47-1.77 (m, 12H), 1.56 (d, J=6.9 Hz, 3H).

P2: $^1$H NMR (400 MHz, CD$_3$OD) δ7.94-7.81 (m, 1H), 7.68 (d, J=7.5 Hz, 1H), 6.75-6.62 (m, 1H), 6.21-5.89 (m, 1H), 5.41-5.17 (m, 1H), 4.28-3.81 (m, 4H), 3.26-2.93 (m, 4H), 2.75-2.54 (m, 3H), 2.56 (s, 2H), 2.47-1.77 (m, 12H), 1.56 (d, J=6.9 Hz, 3H).

LCMS calculated for $C_{31}H_{38}FN_{10}O_2S$ (M+H)+ m/z=633.28; found: 633.5

Compound 176. 2-amino-1'-[4-[[(1R)-1-(2-amino-3-pyridyl)ethyl]-ethyl-amino]-6-[[(2S)-4,4-difluoro-1-methyl-pyrrolidin-2-yl]methoxy]-1,3,5-triazin-2-yl]spiro[6H-thieno[3,4-b]thiophene-4,3'-azetidine]-3-carbonitrile

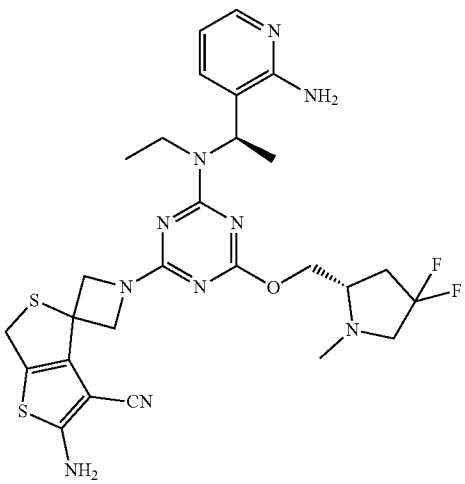 [SMILES: CCN(c1nc(OC[C@@H]2CC(F)(F)CN2C)nc(N2CC3(C2)SCc2sc(N)c(C#N)c23)n1)[C@H](C)c1cccnc1N]

Compound 176 was prepared similarly to that of Ex. 4. LCMS calculated for $C_{27}H_{33}F_2N_{10}OS_2$ (M+H)$^+$ m/z=615.2; found: 615.2. $^1$H NMR (400 MHz, CD$_3$OD) δ=7.87 (d, J=4.0 Hz, 1H), 7.68 (d, J=6.4 Hz, 1H), 6.76-6.64 (m, 1H), 6.15-5.90 (m, 1H), 4.78-4.64 (m, 2H), 4.48-4.27 (m, 4H), 4.14-3.99 (m, 2H), 3.57-3.32 (m, 2H), 3.20-3.17 (m, 1H), 3.06-2.93 (m, 1H), 2.79-2.62 (m, 1H), 2.56-2.46 (m, 1H), 2.44 (s, 3H), 2.33-2.10 (m, 1H), 1.54 (d, J=6.8 Hz, 3H), 0.84 (t, J=6.8 Hz, 3H).

Compound 177. 2-amino-1'-[4-[[(1R)-1-(2-amino-3-pyridyl)ethyl]-ethyl-amino]-6-[2-(dimethylamino)propoxy]-1,3,5-triazin-2-yl]spiro[6H-thieno[3,4-b]thiophene-4,3'-azetidine]-3-carbonitrile

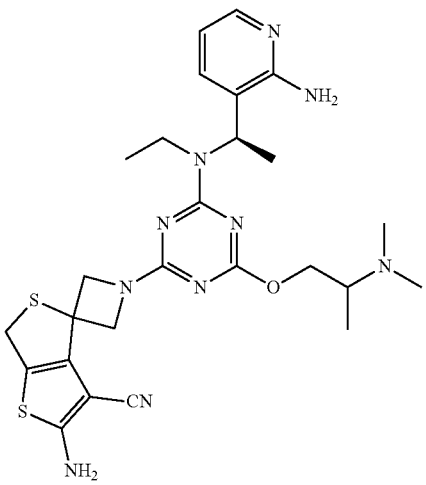 [SMILES: CCN(c1nc(OCC(C)N(C)C)nc(N2CC3(C2)SCc2sc(N)c(C#N)c23)n1)[C@H](C)c1cccnc1N]

Compound 177 was prepared similarly to that of Ex. 4. LCMS calculated for $C_{26}H_{35}N_{10}OS_2$ (M+H)$^+$ m/z=567.2; found: 567.4. $^1$H NMR (400 MHz, CD$_3$OD) δ 7.87 (d, J=3.6 Hz, 1H), 7.68 (d, J=6.8 Hz, 1H), 6.69 (dd, J=6.8, 3.6 Hz, 1H), 6.09-5.96 (m, 1H), 4.77-4.62 (m, 2H), 4.49-4.21 (m, 4H), 4.11-4.02 (m, 2H), 3.53-3.44 (m, 1H), 3.20-3.12 (m, 1H), 3.08-3.00 (m, 1H), 2.37 (s, 6H), 1.54 (d, J=7.2 Hz, 3H), 1.16-1.15 (m, 3H), 0.86-0.83 (m, 3H).

Compound 178. 2-amino-1'-[4-[[(1R)-1-(2-amino-3-pyridyl)ethyl]-ethyl-amino]-6-[2-(1-piperidyl)ethoxy]-1,3,5-triazin-2-yl]spiro[6H-thieno[3,4-b]thiophene-4,3'-azetidine]-3-carbonitrile

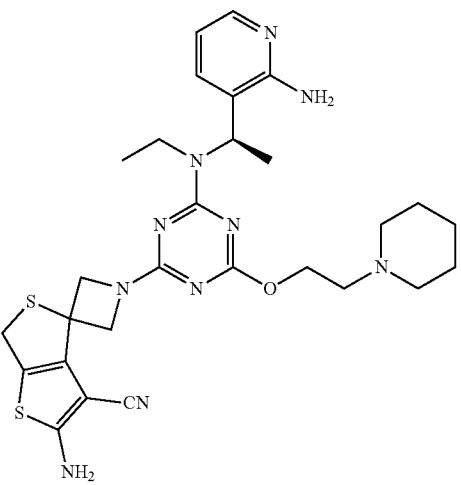 [SMILES: CCN(c1nc(OCCN2CCCCC2)nc(N2CC3(C2)SCc2sc(N)c(C#N)c23)n1)[C@H](C)c1cccnc1N]

Compound 178 was prepared similarly to that of Ex. 4. LCMS calculated for $C_{28}H_{37}N_{10}OS_2$ (M+H)$^+$ m/z=593.2; found: 593.2. $^1$H NMR (400 MHz, CD$_3$OD) δ=7.87 (d, J=4.0 Hz, 1H), 7.68 (d, J=6.8 Hz, 1H), 6.74-6.65 (m, 1H), 6.16-5.93 (m, 1H), 4.79-4.60 (m, 2H), 4.58-4.28 (m, 4H), 4.13-3.99 (m, 2H), 3.55-3.40 (m, 1H), 3.22-3.09 (m, 1H), 2.76 (br, 2H), 2.56 (br, 4H), 1.67-1.57 (m, 4H), 1.54 (d, J=6.8 Hz, 3H), 1.51-1.42 (m, 2H), 0.84 (t, J=6.8 Hz, 3H).

Compound 179. 2-amino-1'-[4-[(2-amino-4-fluoro-3-pyridyl)methyl-methyl-amino]-6-[[(2R,8S)-2-fluoro-1,2,3,5,6,7-hexahydropyrrolizin-8-yl]methoxy]-1,3,5-triazin-2-yl]spiro[6H-thieno[2,3-c]thiophene-4,3'-azetidine]-3-carbonitrile

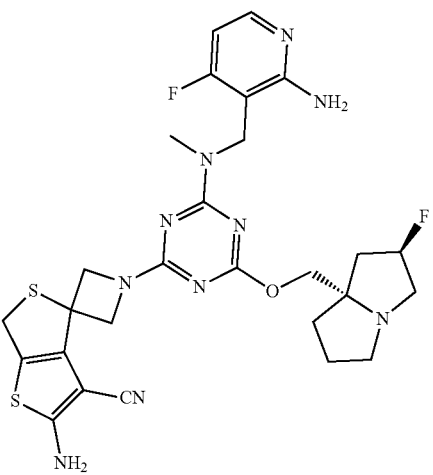 [SMILES: CN(Cc1c(F)ccnc1N)c1nc(OC[C@@]23CCCN2C[C@H](F)C3)nc(N2CC3(C2)SCc2sc(N)c(C#N)c23)n1]

Compound 179 was prepared similarly to that of Ex. 4. LCMS calculated for $C_{27}H_{31}F_2N_{10}OS_2$ (M+H)$^+$ m/z=613.0, found: 613.0. $^1$H NMR (400 MHz, CD$_3$OD) δ 7.92-7.80 (m, 1H), 6.55-6.37 (m, 1H), 5.39-5.13 (m, 1H), 4.99-4.89 (m, 1H), 4.80-4.59 (m, 3H), 4.48-4.32 (m, 2H), 4.26-4.13 (m, 1H), 4.14-4.00 (m, 3H), 3.27-3.20 (m, 2H), 3.17 (s, 1H), 3.03 (s, 3H), 3.01-2.95 (m, 1H), 2.33-2.06 (m, 3H), 2.05-1.77 (m, 3H).

Compound 180. 2'-amino-1-(4-(((R)-1-(2-amino-pyridin-3-yl)ethyl)(2-fluoroethyl)amino)-6-(((2R,7aS)-2-fluorotetrahydro-1H-pyrrolizin-7a(5H)-yl)methoxy)-1,3,5-triazin-2-yl)-6'H-spiro[azetidine-3,4'-thieno[3,4-b]thiophene]-3'-carbonitrile

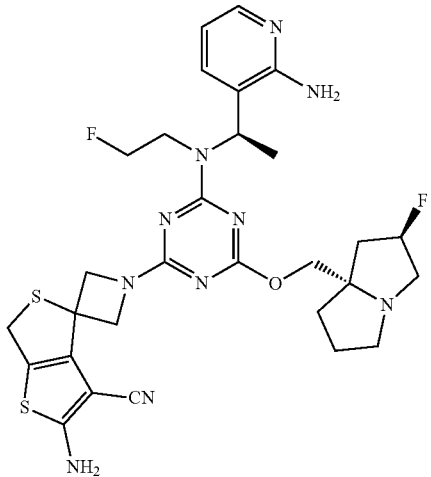 [SMILES: C[C@H](c1cccnc1N)N(CCF)c1nc(OC[C@@]23CCCN2C[C@H](F)C3)nc(N2CC3(C2)SCc2sc(N)c(C#N)c23)n1]

Compound 180 was prepared similarly to that of Ex. 4. LCMS calculated for $C_{29}H_{35}F_2N_{10}OS_2$ (M+H)$^+$ m/z=641.8; found: 641.2. $^1$H NMR (400 MHz, d6-DMSO) δ 7.90 (d, J=3.8 Hz, 1H), 7.57 (d, J=7.0 Hz, 1H), 7.41 (s, 2H), 6.60 (s, 1H), 5.89-5.46 (m, 3H), 5.24 (d, J=53.5 Hz, 1H), 4.67-3.83 (m, 10H), 3.66-3.46 (m, 1H), 3.17-2.72 (m, 5H), 2.10-1.66 (m, 6H), 1.46 (d, J=6.6 Hz, 3H).

Compound 181. 2-amino-1'-[4-[[(1R)-1-(2-amino-3-pyridyl)ethyl]-methyl-amino]-6-[[1-(dimethylamino)cyclopropyl]methoxy]-1,3,5-triazin-2-yl]spiro[6H-thieno[2,3-c]thiophene-4,3'-azetidine]-3-carbonitrile

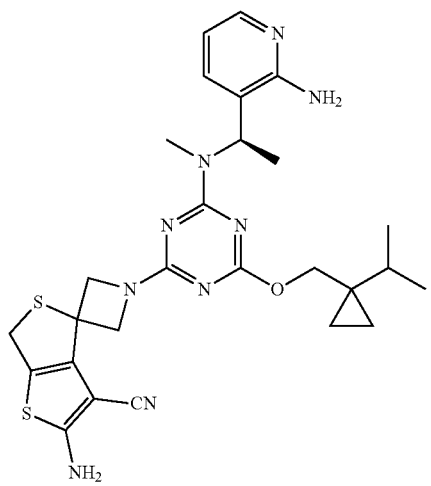 [SMILES: CC(C)C1(COc2nc(N3CC4(C3)SCc3sc(N)c(C#N)c34)nc(N(C)[C@H](C)c3cccnc3N)n2)CC1]

Compound 181 was prepared similarly to that of Ex. 4. LCMS calculated for $C_{26}H_{33}N_{10}OS_2$ (M+H)+ m/z=565.2, found: 565.1. $^1$H NMR (400 MHz, CD$_3$OD) δ 7.86 (d, J=4.4 Hz, 1H), 7.65 (d, J=7.2 Hz, 1H), 6.78-6.61 (m, 1H), 6.07 (s, 1H), 4.72-4.59 (m, 2H), 4.45 (dd, J=30.8, 8.8 Hz, 4H), 4.14-3.97 (m, 2H), 2.76 (d, J=3.6 Hz, 3H), 2.46 (s, 6H), 1.54 (d, J=6.8 Hz, 3H), 0.75 (d, J=20.8 Hz, 4H).

Compound 182. 2-amino-1'-[4-[(2-amino-4-hydroxy-3-pyridyl)methyl-methyl-amino]-6-[[(2R,8S)-2-fluoro-1,2,3,5,6,7-hexahydropyrrolizin-8-yl]methoxy]-1,3,5-triazin-2-yl]spiro[6H-thieno[2,3-c]thiophene-4,3'-azetidine]-3-carbonitrile

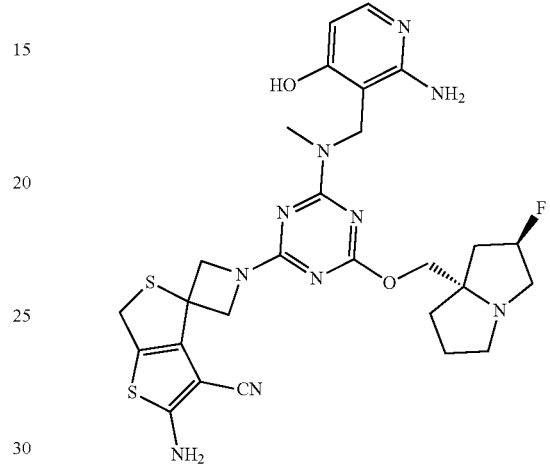

Compound 182 was prepared similarly to that of Ex. 4. LCMS calculated for $C_{27}H_{32}FN_{10}O_2S_2$ (M+H)$^+$ m/z=611.1, found: 611.1. $^1$H NMR (400 MHz, CD$_3$OD) δ 7.50-7.16 (m, 2H), 6.04 (d, J=7.3 Hz, 1H), 5.39-5.12 (m, 1H), 4.71-4.64 (m, 3H), 4.39 (dd, J=23.9, 9.9 Hz, 2H), 4.27-4.13 (m, 1H), 4.12-4.00 (m, 3H), 3.25-3.17 (m, 2H), 3.14 (s, 1H), 3.05 (s, 3H), 3.01-2.92 (m, 1H), 2.27-2.04 (m, 3H), 2.03-1.78 (m, 3H).

Compound 183. 2-amino-1'-[4-[[(1R)-1-(2-amino-3-pyridyl)ethyl]-(2,2-difluoroethyl)amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

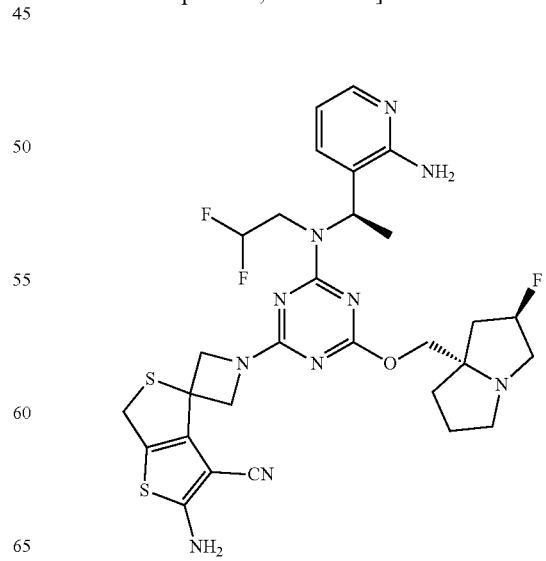

Compound 183 was prepared similarly to that of Ex. 4. LCMS calculated for $C_{29}H_{34}F_3N_{10}OS_2$ (M+H)$^+$ m/z=659.7; found: 659.3. $^1$H NMR (400 MHz, CD$_3$OD) δ 7.87 (d, J=4.9 Hz, 1H), 7.66 (d, J=7.0 Hz, 1H), 6.70 (dd, J=7.4, 5.2 Hz, 1H), 5.78-6.22 (m, 2H), 5.25 (d, J=54.1 Hz, 1H), 4.57-4.83 (m, 2H), 4.30-4.48 (m, 2H), 3.98-4.25 (m, 4H), 3.38-3.76 (m, 2H), 3.09-3.27 (m, 3H), 2.97 (s, 1H), 1.71-2.34 (m, 6H), 1.54 (d, J=6.8 Hz, 3H).

Compound 184A & 184B. 2-amino-1'-[4-[[(1*)-1-(4-amino-1,2,5-thiadiazol-3-yl)ethyl]-methyl-amino]-6-[[(2R,8S)-2-fluoro-1,2,3,5,6,7-hexahydro-pyrrolizin-8-yl]methoxy]-1,3,5-triazin-2-yl]spiro[6H-thieno[2,3-c]thiophene-4,3'-azetidine]-3-carbonitrile

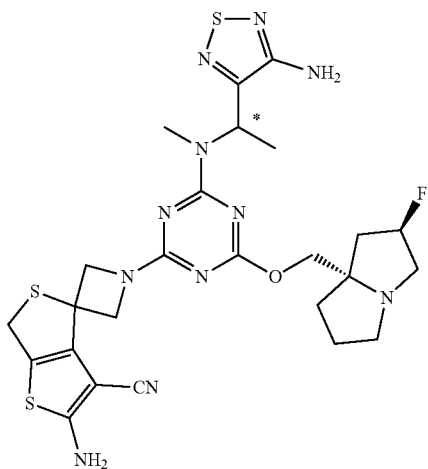 [SMILES: CC(c1nsnc1N)N(C)c1nc(OC[C@@]23CCCN2C[C@H](F)C3)nc(N2CC3(C2)SCc2sc(N)c(C#N)c23)n1]

Compound 174 was purified on a DAICELCHIRALPAK®AD (250*25 mm 10 um) column on a Waters SFC 150 system (Mobile Phase A: Supercritical CO2, Mobile Phase B: IPA[0.1% NH$_3$ (7M in MeOH)]; A:B: 50/50; Flow: 120 ml/min) to give faster eluting P1, and slower eluting P2.

P1: LCMS calculated for $C_{25}H_{31}FN_{11}OS_3$ (M+H)$^+$ m/z=616.2, found: 616.1. $^1$H NMR (400 MHz, CD$_3$OD) δ 6.25-5.99 (m, 1H), 5.26 (d, J=53.4 Hz, 1H), 4.80-4.56 (m, 2H), 4.49-4.30 (m, 2H), 4.25-3.94 (m, 4H), 3.25-3.08 (m, 3H), 3.02-2.94 (m, 1H), 2.91-2.78 (m, 3H), 2.33-1.80 (m, 6H), 1.64 (d, J=6.8 Hz, 3H).

P2: LCMS calculated for $C_{25}H_{31}FN_{11}OS_3$ (M+H)$^+$ m/z=616.2, found: 616.1. $^1$H NMR (400 MHz, CD$_3$OD) δ 6.25-5.99 (m, 1H), 5.26 (d, J=53.4 Hz, 1H), 4.80-4.56 (m, 2H), 4.49-4.30 (m, 2H), 4.25-3.94 (m, 4H), 3.25-3.08 (m, 3H), 3.02-2.94 (m, 1H), 2.91-2.78 (m, 3H), 2.33-1.80 (m, 6H), 1.64 (d, J=6.8 Hz, 3H).

Compound 185. (R)-2'-amino-1-(4-(2-(hydroxymethyl)piperazin-1-yl)-6-((1-(morpholinomethyl)cyclopropyl)methoxy)-1,3,5-triazin-2-yl)-6'H-spiro[azetidine-3,4'-thieno[3,4-b]thiophene]-3'-carbonitrile

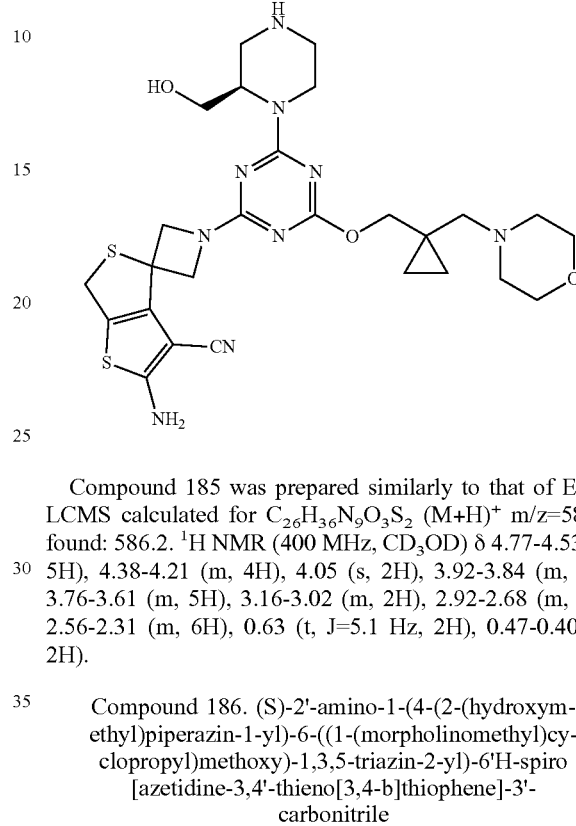

Compound 185 was prepared similarly to that of Ex. 1. LCMS calculated for $C_{26}H_{36}N_9O_3S_2$ (M+H)$^+$ m/z=586.7; found: 586.2. $^1$H NMR (400 MHz, CD$_3$OD) δ 4.77-4.53 (m, 5H), 4.38-4.21 (m, 4H), 4.05 (s, 2H), 3.92-3.84 (m, 1H), 3.76-3.61 (m, 5H), 3.16-3.02 (m, 2H), 2.92-2.68 (m, 2H), 2.56-2.31 (m, 6H), 0.63 (t, J=5.1 Hz, 2H), 0.47-0.40 (m, 2H).

Compound 186. (S)-2'-amino-1-(4-(2-(hydroxymethyl)piperazin-1-yl)-6-((1-(morpholinomethyl)cyclopropyl)methoxy)-1,3,5-triazin-2-yl)-6'H-spiro[azetidine-3,4'-thieno[3,4-b]thiophene]-3'-carbonitrile

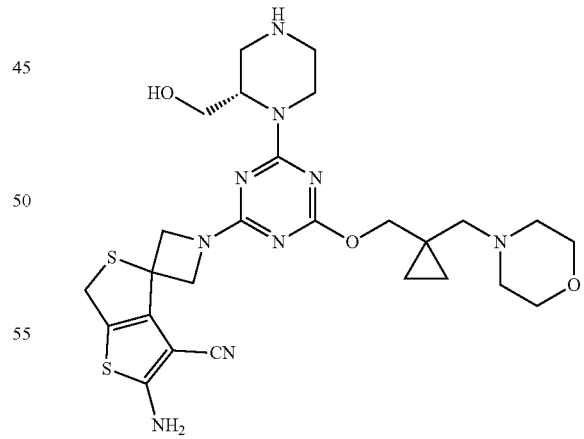

Compound 186 was prepared similarly to that of Ex. 1. LCMS calculated for $C_{26}H_{36}N_9O_3S_2$ (M+H)$^+$ m/z=586.7; found: 586.2. $^1$H NMR (400 MHz, CD$_3$OD) δ 4.76-4.48 (m, 5H), 4.41-4.20 (m, 4H), 4.05 (s, 2H), 3.92-3.83 (m, 1H), 3.74-3.62 (m, 5H), 3.18-2.97 (m, 2H), 2.83-2.64 (m, 2H), 2.54-2.30 (m, 6H), 0.63 (t, J=5.1 Hz, 2H), 0.46-0.41 (m, 2H).

Compound 187. 2-[[4-(2-amino-3-cyano-spiro[6H-thieno[3,4-b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-[(2-amino-3-pyridyl)methyl]amino]acetic acid

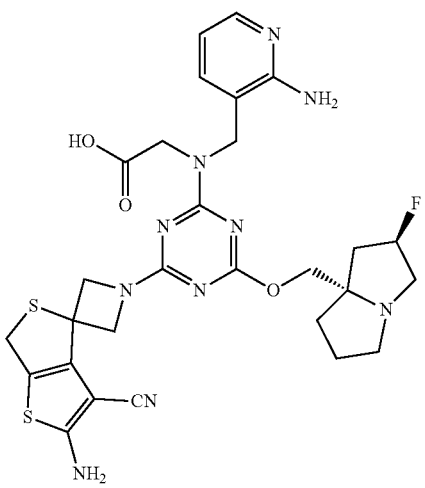 [SMILES: N#Cc1c(N)sc2c1C1(CN(c3nc(OC[C@@]45CCCN4C[C@H](F)C5)nc(N(CC(=O)O)Cc4cccnc4N)n3)C1)SC2]

Compound 187 was prepared similarly to that of Ex. 4. LCMS calculated for C$_{28}$H$_{32}$FN$_{10}$O$_3$S$_2$ (M+H)$^+$ m/z=639.2; found: 639.3. $^1$H NMR (400 MHz, d6-DMSO) δ=7.88-7.84 (m, 1H), 7.45-7.25 (m, 3H), 6.54-6.44 (m, 1H), 6.01-5.96 (m, 2H), 5.24 (d, J=54.4 Hz, 1H), 4.67-4.46 (m, 4H), 4.33-3.83 (m, 8H), 3.07-2.93 (m, 3H), 2.83-2.74 (m, 1H), 2.06-1.66 (m, 6H).

Compound 188. 2'-amino-1-(4-((1R,5S)-2-(hydroxymethyl)-3,8-diazabicyclo[3.2.1]octan-3-yl)-6-((1-(morpholinomethyl)cyclopropyl)methoxy)-1,3,5-triazin-2-yl)-6'H-spiro[azetidine-3,4'-thieno[3,4-b]thiophene]-3'-carbonitrile

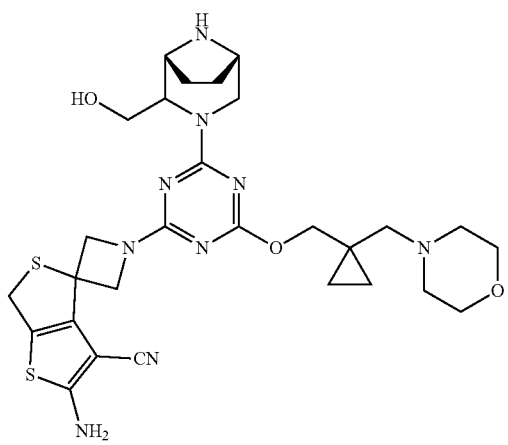 [SMILES: N#Cc1c(N)sc2c1C1(CN(c3nc(OCC4(CN5CCOCC5)CC4)nc(N4C[C@@H]5CC[C@@H](N5)C4CO)n3)C1)SC2]

Compound 188 was prepared similarly to that of Ex. 1. LCMS calculated for C$_{28}$H$_{38}$N$_9$O$_3$S$_2$ (M+H)$^+$ m/z=612.7; found: 612.3. $^1$H NMR (400 MHz, d6-DMSO) δ 7.41 (br, 2H), 4.54-4.53 (m, 2H), 4.27-4.24 (m, 2H), 4.20-4.10 (m, 2H), 4.05 (s, 2H), 3.95-3.91 (m, 2H), 3.76-3.52 (m, 9H), 2.39-2.30 (m, 4H), 2.26-2.19 (m, 2H), 2.02-1.91 (m, 1H), 1.82-1.70 (m, 1H), 1.65-1.51 (m, 2H), 0.61-0.50 (m, 2H), 0.45-0.33 (m, 2H).

Compound 189. 2-amino-1'-[4-[[(2R,8S)-2-fluoro-1,2,3,5,6,7-hexahydropyrrolizin-8-yl]methoxy]-6-(2-oxo-3,5-dihydro-1H-pyrido[2,3-e][1,4]diazepin-4-yl)-1,3,5-triazin-2-yl]spiro[6H-thieno[3,4-b]thiophene-4,3'-azetidine]-3-carbonitrile

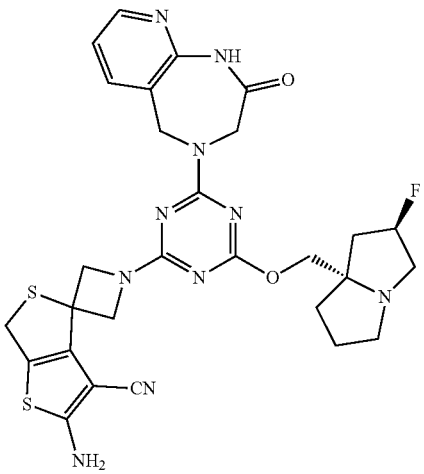 [SMILES: N#Cc1c(N)sc2c1C1(CN(c3nc(OC[C@@]45CCCN4C[C@H](F)C5)nc(N4CC(=O)Nc5ncccc5C4)n3)C1)SC2]

Compound 189 was prepared similarly to that of Ex. 1. LCMS calculated for C$_{28}$H$_{30}$FN$_{10}$O$_2$S$_2$ (M+H)$^+$ m/z=621.2; found: 621.2. $^1$H NMR (400 MHz, d6-DMSO) δ=10.16-10.12 (m, 1H), 8.22-8.15 (m, 1H), 7.74 (d, J=6.0 Hz, 1H), 7.40 (s, 2H), 7.08-7.00 (m, 1H), 5.23 (d, J=53.6 Hz, 1H), 4.88-4.48 (m, 6H), 4.28-4.19 (m, 2H), 4.08-3.81 (m, 4H), 3.09-2.93 (m, 3H), 2.84-2.73 (m, 1H), 2.05-1.67 (m, 6H).

Compound 190. (S)-2'-amino-1-(4-(2-(difluoromethyl)piperazin-1-yl)-6-((1-(morpholinomethyl)cyclopropyl)methoxy)-1,3,5-triazin-2-yl)-6'H-spiro[azetidine-3,4'-thieno[3,4-b]thiophene]-3'-carbonitrile

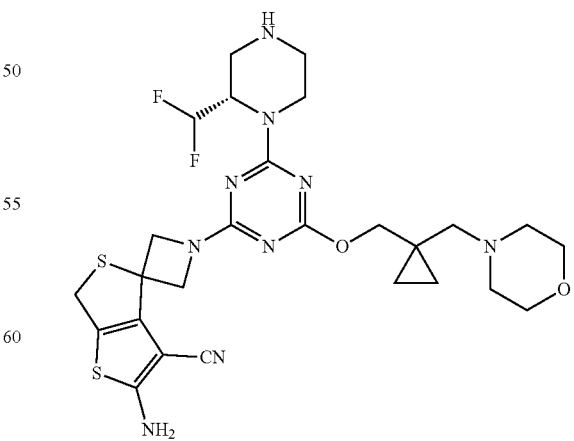

Compound 190 was prepared similarly to that of Ex. 1. LCMS calculated for C$_{26}$H$_{34}$F$_2$N$_9$O$_2$S$_2$ (M+H)$^+$ m/z=606.7;

found (M/2+H)+: 304.5. ¹H NMR (400 MHz, CD₃OD) δ 6.24 (td, J=56.2, 4.8 Hz, 1H), 4.95-4.90 (m, 1H), 4.70-4.53 (m, 4H), 4.41-4.17 (m, 4H), 4.05 (s, 2H), 3.66 (t, J=4.6 Hz, 4H), 3.17-2.98 (m, 2H), 2.94-2.83 (m, 1H), 2.78-2.64 (m, 1H), 2.56-2.29 (m, 6H), 0.64 (s, 2H), 0.50-0.39 (m, 2H).

Compound 191. 2-amino-4-[1-[4-[[(1R)-1-(2-amino-3-pyridyl)ethyl]-methyl-amino]-6-[[(2R,8S)-2-fluoro-1,2,3,5,6,7-hexahydropyrrolizin-8-yl]methoxy]-1,3,5-triazin-2-yl]pyrrolidin-3-yl]-5-chloro-thiophene-3-carbonitrile

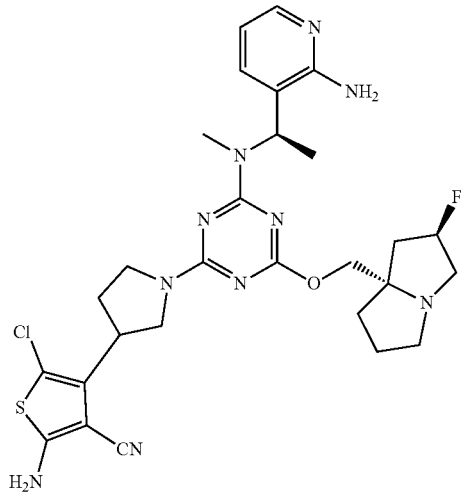 [SMILES: C[C@H](c1cccnc1N)N(C)c1nc(OC[C@@]23CCCN2C[C@H](F)C3)nc(N2CCC(c3c(Cl)sc(N)c3C#N)C2)n1]

Compound 191 was prepared similarly to that of Ex. 4 as a formate salt. LCMS calculated for C₂₈H₃₆ClFN₁₀OS (M+H)⁺ m/z=613.1, found: 613.3. ¹H NMR (400 MHz, CD₃OD) δ 7.87 (s, 1H), 7.68 (s, 1H), 6.72 (s, 1H), 6.10 (s, 1H), 5.47 (d, J=54.5 Hz, 1H), 4.43 (m, 2H), 3.72 (m, 8H), 3.32 (s, 1H), 2.78 (s, 3H), 2.33 (m, 8H), 1.54 (d, J=6.4 Hz, 3H).

Compound 192. 2-amino-1'-[4-[1-(4-amino-1H-pyrazol-3-yl)ethyl-methyl-amino]-6-[[(2R,8S)-2-fluoro-1,2,3,5,6,7-hexahydropyrrolizin-8-yl]methoxy]-1,3,5-triazin-2-yl]spiro[6H-thieno[2,3-c]thiophene-4,3'-azetidine]-3-carbonitrile

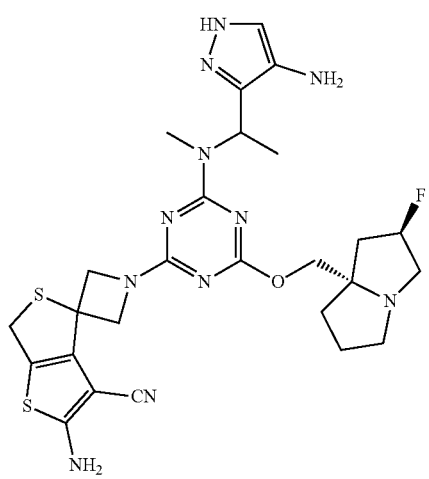 [SMILES: CC(c1n[nH]cc1N)N(C)c1nc(OC[C@@]23CCCN2C[C@H](F)C3)nc(N2CC3(C2)SCc2sc(N)c(C#N)c23)n1]

Compound 192 was prepared similarly to that of Ex. 7. LCMS calculated for C₂₆H₃₃FN₁₁OS₂ (M+H)⁺ m/z=598.2, found: 598.2. ¹H NMR (400 MHz, CDCl₃) δ: 7.16 (s, 1H), 6.26-6.16 (m, 1H), 5.26 (d, J=60.4 Hz, 1H), 4.76-4.61 (m, 2H), 4.42-4.31 (m, 2H), 4.19-4.05 (m, 4H), 3.18-2.85 (m, 4H), 2.5 (s, 3H), 2.26-2.11 (m, 3H), 1.97-1.85 (m, 3H), 156 (d, J=7.2, 3H).

Compound 193. (R)-2'-amino-1-(4-(2-(difluoromethyl)piperazin-1-yl)-6-((1-(morpholinomethyl)cyclopropyl)methoxy)-1,3,5-triazin-2-yl)-6'H-spiro[azetidine-3,4'-thieno[3,4-b]thiophene]-3'-carbonitrile

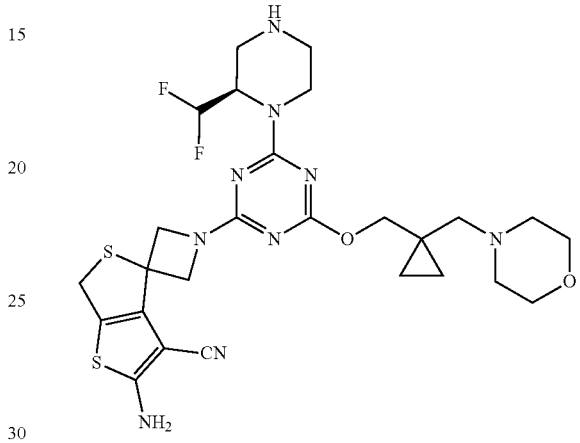

Compound 193 was prepared similarly to that of Ex. 1. LCMS calculated for C₂₆H₃₄F₂N₉O₂S₂ (M+H)⁺ m/z=606.7; found (M+2H)²⁺: 304.4. ¹H NMR (400 MHz, CD₃OD) δ 6.24 (td, J=56.2, 4.8 Hz, 1H), 5.07-4.91 (m, 1H), 4.66-4.60 (m, 4H), 4.41-4.20 (m, 4H), 4.05 (s, 2H), 3.66 (t, J=4.6 Hz, 4H), 3.17-2.97 (m, 2H), 2.94-2.82 (m, 1H), 2.75-2.63 (m, 1H), 2.54-2.30 (m, 6H), 0.68-0.59 (m, 2H), 0.49-0.37 (m, 2H).

Compound 194. 2-[[4-(2-amino-3-cyano-spiro[6H-thieno[3,4-b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-[(2-amino-3-pyridyl)methyl]amino]acetamide

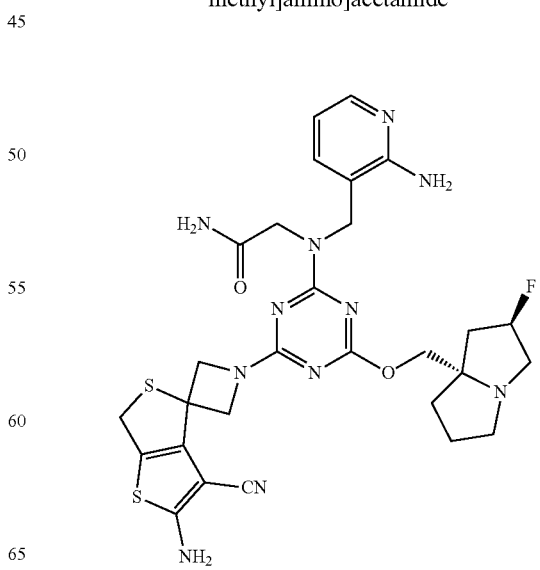

Compound 194 was prepared similarly to that of Ex. 4. LCMS calculated for $C_{28}H_{33}FN_{11}O_2S_2$ (M+H)+ m/z=638.2; found: 638.3. H NMR (400 MHz, d6-DMSO) δ=7.91-7.84 (m, 1H), 7.47-7.17 (m, 4H), 7.02 (s, 1H), 6.55-6.47 (m, 1H), 5.97 (d, J=17.2 Hz, 2H), 5.24 (d, J=53.6 Hz, 1H), 4.73-4.41 (m, 4H), 4.34-4.21 (m, 2H), 4.10-3.76 (m, 6H), 3.11-2.90 (m, 3H), 2.84-2.73 (m, 1H), 2.08-1.63 (m, 6H).

Compound 195. 2-amino-1'-[4-[methyl-[(1R)-1-(2-amino-3-pyridyl)ethyl]amino]-6-[[(2R,8S)-2-fluoro-1,2,3,5,6,7-hexahydropyrrolizin-8-yl]methoxy]-1,3,5-triazin-2-yl]spiro[5,6-dihydrocyclopenta[b]thiophene-4,3'-pyrrolidine]-3-carbonitrile

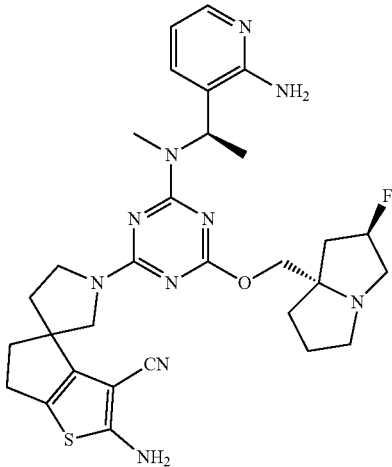 [SMILES: C[C@H](c1cccnc1N)N(C)c1nc(OC[C@@]23CCCN2C[C@H](F)C3)nc(N2CCC3(CCc4sc(N)c(C#N)c43)C2)n1]

Compound 195 was prepared similarly to that of Ex. 4. LCMS calculated for $C_{30}H_{38}FN_{10}OS$ (M+H)+ m/z=605.3, found: 605.3. ¹H NMR (400 MHz, CD₃OD) δ 7.89-7.82 (m, 1H), 7.68-7.60 (m, 1H), 6.73-6.63 (m, 1H), 6.04 (s, 1H), 5.27 (d, J=53.2 Hz, 1H), 4.30-4.04 (m, 2H), 3.95-3.80 (s, 1H), 3.79-3.51 (m, 3H), 3.27-3.10 (m, 3H), 3.06-2.92 (m, 1H), 2.84-2.76 (m, 2H), 2.75 (s, 3H), 2.48-2.21 (m, 4H), 2.21-2.05 (m, 2H), 2.05-1.76 (m, 4H), 1.53 (t, J=6.0 Hz, 3H).

Compound 196. 2'-amino-1-(4-(((R)-1-(2-amino-pyridin-3-yl)ethyl)(2,2-difluoroethyl)amino)-6-(((S)-1-methylpyrrolidin-2-yl)methoxy)-1,3,5-triazin-2-yl)-6'H-spiro[azetidine-3,4'-thieno[3,4-b]thiophene]-3'-carbonitrile

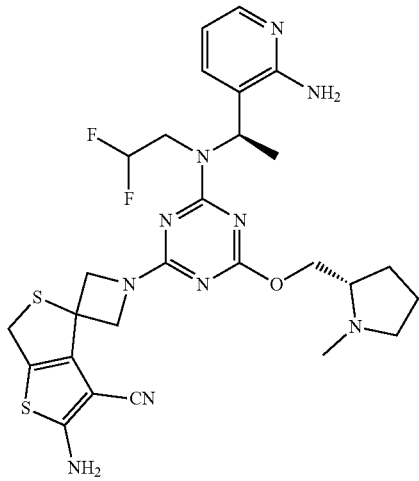 [SMILES: C[C@H](c1cccnc1N)N(CC(F)F)c1nc(OC[C@@H]2CCCN2C)nc(N2CC3(C2)SCc2sc(N)c(C#N)c23)n1]

Compound 196 was prepared similarly to that of Ex. 4. LCMS calculated for $C_{27}H_{33}F_2N_{10}OS_2$ (M+H)+ m/z=615.7; found: 615.4. ¹H NMR (400 MHz, CD₃OD) δ 7.88 (d, J=4.9 Hz, 1H), 7.66 (d, J=7.4 Hz, 1H), 6.71 (dd, J=7.4, 5.2 Hz, 1H), 6.31-5.76 (m, 2H), 4.82-4.73 (m, 1H), 4.70-4.62 (m, 1H), 4.49-4.23 (m, 4H), 4.13-3.98 (m, 2H), 3.72-3.40 (m, 2H), 3.15-3.05 (m, 1H), 2.88-2.74 (m, 1H), 2.50 (s, 3H), 2.45-2.32 (m, 1H), 2.16-2.04 (m, 1H), 1.87-1.63 (m, 3H), 1.54 (d, J=6.9 Hz, 3H).

Compound 197. 2'-amino-1-(4-(((R)-1-(2-amino-pyridin-3-yl)ethyl)(2,2-difluoroethyl)amino)-6-(((2S,4R)-4-fluoro-1-methylpyrrolidin-2-yl)methoxy)-1,3,5-triazin-2-yl)-6'H-spiro[azetidine-3,4'-thieno[3,4-b]thiophene]-3'-carbonitrile

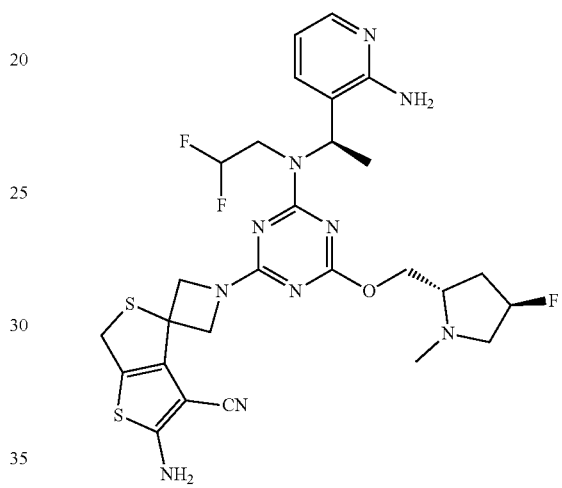

Compound 197 was prepared similarly to that of Ex. 4. LCMS calculated for $C_{27}H_{32}F_3N_{10}OS_2$ (M+H)+ m/z=633.7; found: 633.2. ¹H NMR (400 MHz, CD₃OD) δ 7.88 (d, J=4.9 Hz, 1H), 7.66 (d, J=7.4 Hz, 1H), 6.71 (dd, J=7.3, 5.2 Hz, 1H), 6.26-5.82 (m, 2H), 5.14 (d, J=55.2 Hz, 1H), 4.80-4.63 (m, 2H), 4.50-4.28 (m, 4H), 4.13-3.99 (m, 2H), 3.72-3.41 (m, 3H), 3.15-3.01 (m, 1H), 2.70-2.46 (m, 4H), 2.35-2.18 (m, 1H), 2.06-1.82 (m, 1H), 1.54 (d, J=6.9 Hz, 3H).

Compound 198. 2-amino-1'-[4-[[(1R)-1-(2-amino-3-pyridyl)ethyl]-ethyl-amino]-6-[[1-[(dimethylamino)methyl]-2,2-difluoro-cyclopropyl]methoxy]-1,3,5-triazin-2-yl]spiro[6H-thieno[3,4-b]thiophene-4,3'-azetidine]-3-carbonitrile Compound 198 was prepared similarly to that of Ex. 4. LCMS calculated for $C_{28}H_{35}F_2N_{10}OS_2$ (M+H)+ m/z=629.23; found: 629.3. ¹H NMR (400 MHz, CD₃OD) δ 7.87 (s, 1H), 7.68 (d, J=6.8 Hz, 1H), 6.76-6.63 (m, 1H), 6.14-5.89 (m, 1H), 4.80-4.59 (m, 2H), 4.52-4.28 (m, 4H), 4.15-3.96 (m, 2H), 3.58-3.40 (m, 1H), 3.21-3.05 (m, 1H), 2.89-2.71 (m, 1H), 2.43-2.32 (m, 1H), 2.30-2.15 (m, 6H), 1.70-1.48 (m, 4H), 1.43-1.29 (m, 1H), 0.84 (t, J=6.8 Hz, 3H).

Compound 199. 2-[[4-(2-amino-3-cyano-spiro[6H-thieno[3,4-b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-[(1R)-1-(2-amino-3-pyridyl)ethyl]amino]acetamide

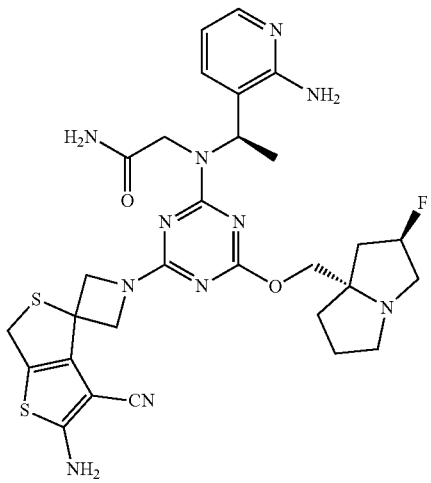 [SMILES: C[C@H](c1cccnc1N)N(CC(N)=O)c1nc(OC[C@@]23CCCN2C[C@H](F)C3)nc(N2CC3(C2)SCc2sc(N)c(C#N)c23)n1]

Compound 199 was prepared similarly to that of Ex. 4. LCMS calculated for C$_{29}$H$_{35}$FN$_{11}$O$_2$S$_2$ (M+H)$^+$ m/z=652.2; found: 652.3. $^1$H NMR (400 MHz, d6-DMSO) δ=7.88 (dd, J=4.8, 1.6 Hz, 1H), 7.59-7.49 (m, 1H), 7.42 (s, 2H), 7.13-6.78 (m, 2H), 6.63-6.55 (m, 1H), 5.92-5.57 (m, 3H), 5.25 (dd, J=54.8, 12.0 Hz, 1H), 4.67-4.41 (m, 2H), 4.40-4.15 (m, 2H), 4.11-3.43 (m, 6H), 3.16-2.92 (m, 3H), 2.87-2.74 (m, 1H), 2.13-1.65 (m, 6H), 1.45 (d, J=6.4 Hz, 3H).

Compound 200. 2'-amino-1-(4-(((2R,7aS)-2-fluoro-tetrahydro-1H-pyrrolizin-7a(5H)-yl)methoxy)-6-((1S,5S)-1-(hydroxymethyl)-3-oxa-8-azabicyclo[3.2.1]octan-8-yl)-1,3,5-triazin-2-yl)-6'H-spiro[azetidine-3,4'-thieno[3,4-b]thiophene]-3'-carbonitrile

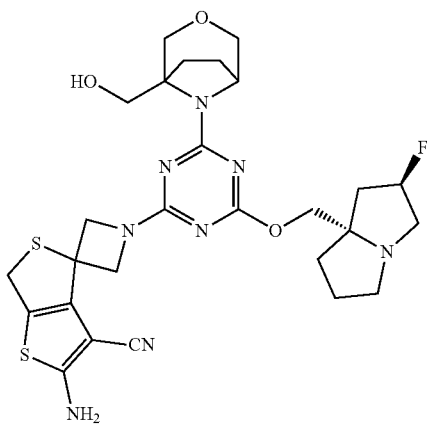 [SMILES: N#Cc1c(N)sc2c1C1(CN(c3nc(OC[C@@]45CCCN4C[C@H](F)C5)nc(N4C5CCC4(CO)COC5)n3)C1)SC2]

Compound 200 was prepared similarly to that of Ex. 1. LCMS calculated for C$_{27}$H$_{34}$FN$_8$O$_3$S$_2$ (M+H)$^+$ m/z=601.22; found: 601.3. $^1$H NMR (400 MHz, CD$_3$OD) δ 5.26 (d, J=54.4 Hz, 1H), 4.56-4.70 (m, 2H), 4.30-4.44 (m, 2H), 3.98-4.22 (m, 4H), 3.77-3.95 (m, 3H), 3.54-3.70 (m, 3H), 3.40 (s, 1H), 3.10-3.24 (m, 3H), 2.92-3.02 (m, 1H), 1.73-2.30 (m, 10H).

Example 10. Exemplary synthesis of 2-amino-1'-[4-[[(1R)-1-(2-amino-3-pyridyl)ethyl]-ethyl-amino]-6-[[(2R,8S)-2-fluoro-1,2,3,5,6,7-hexahydropyrrolizin-8-yl]methoxy]-1,3,5-triazin-2-yl]-2'-oxo-spiro[5,6-dihydrocyclopenta[b]thiophene-4,3'-azetidine]-3-carbonitrile (Compound 201)

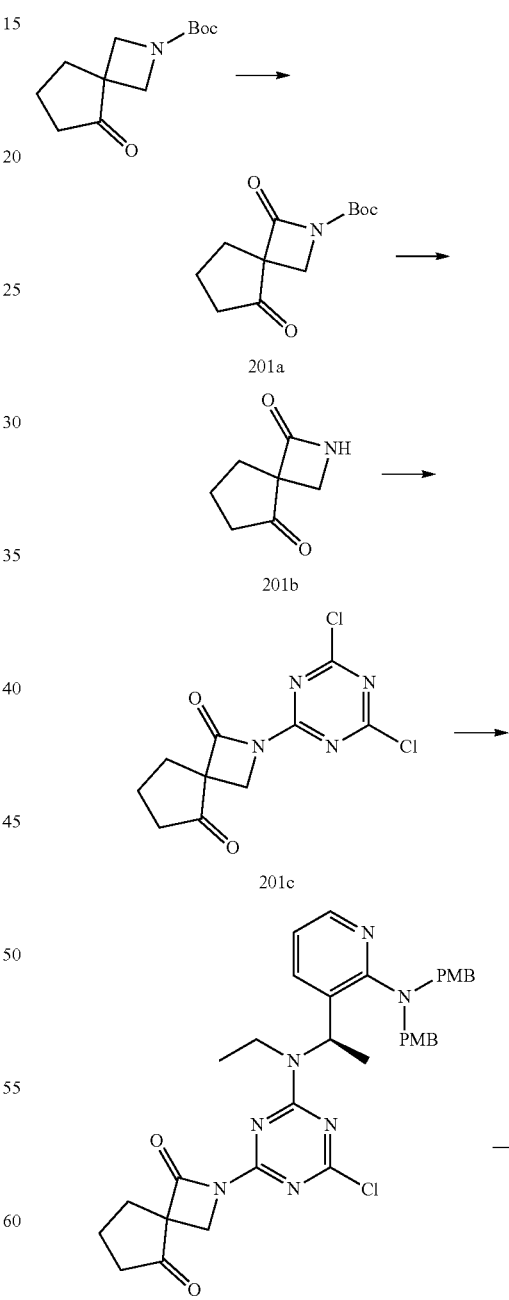

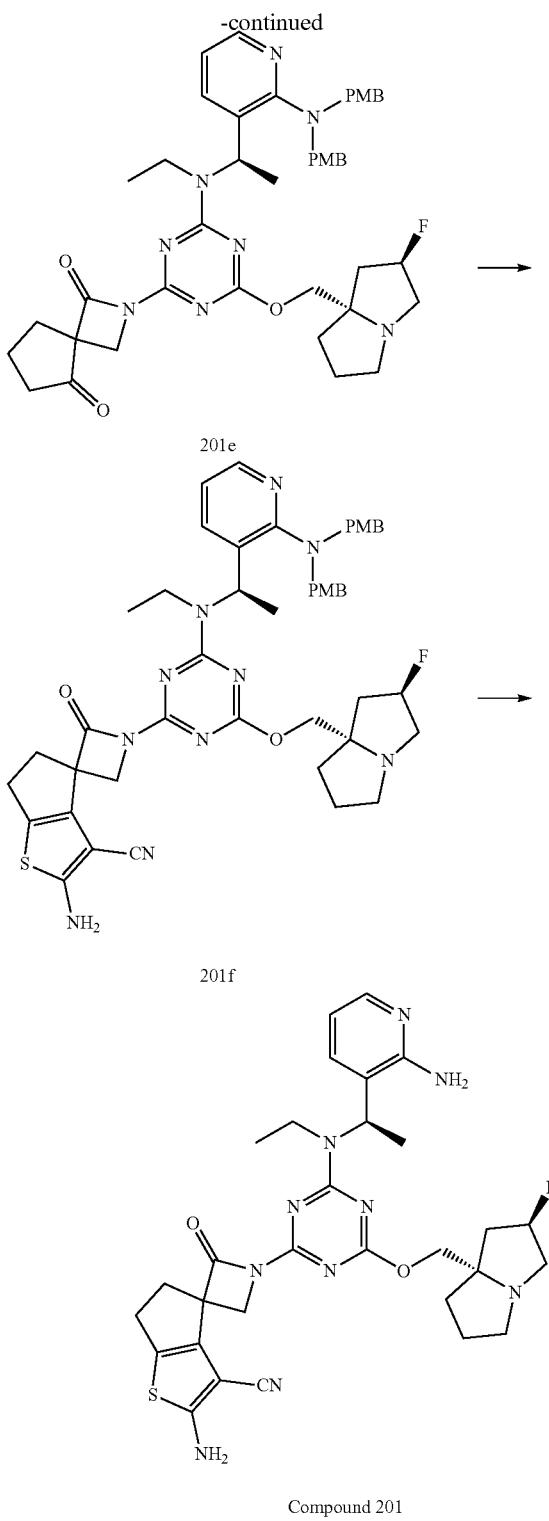

Compound 201

Step 1. Synthesis of tert-butyl 3,5-dioxo-2-azaspiro[3.4]octane-2-carboxylate (201a). A solution of tert-butyl 5-oxo-2-azaspiro[3.4]octane-2-carboxylate (2.0 g, 8.88 mmol), Ruthenium (III) chloride (80.00 mg, 0.39 mmol) and sodium periodate (7.59 g, 35.51 mmol) in MeCN (20 mL), CCl₄ (2 mL) and Water (25 mL) was stirred at 25° C. for 36 h. Then the reaction was diluted with water and extracted with EtOAc (100 mL×2). The organic layer was washed with water and saturated brine, dried over Na₂SO₄ and concentrated in vacuo to afford tert-butyl 3,5-dioxo-2-azaspiro[3.4]octane-2-carboxylate (1.79 g, 7.48 mmol, 84.27% yield). LCMS calculated for $C_{12}H_{18}NO_4$ $(M+H)^+$ m/z=240.12; found: 184.1 (M+H-Boc)$^+$ Step 2. Synthesis of 2-azaspiro[3.4]octane-3,5-dione (201b)

To a solution of tert-butyl 3,5-dioxo-2-azaspiro[3.4]octane-2-carboxylate (0.6 g, 2.51 mmol) in DCM (7.5 mL) was added TFA (1.5 mL, 19.47 mmol) portion wise at 0° C. The reaction was stirred at room temperature for 2 h. Then the mixture was diluted with DCM, neutralized with NaHCO₃ solution, extracted with EtOAc. The organic layer was washed with saturated brine, dried over Na₂SO₄ and concentrated in vacuo to give the crude product. The crude product was purified by flash chromatography to afford 2-azaspiro[3.4]octane-3,5-dione (236.00 mg, 1.70 mmol, 67.63% yield) as a colorless oil. LCMS calculated for $C_7H_{10}NO_2$ $(M+H)^+$ m/z=140.07; found: 140.2

Step 3. Synthesis of 2-(4,6-dichloro-1,3,5-triazin-2-yl)-2-azaspiro[3.4]octane-3,5-dione (201c). To a solution of 2-azaspiro[3.4]octane-3,5-dione (220.00 mg, 1.58 mmol) in THF (5 mL) was added LiHMDS (2.37 mL, 2.37 mmol) at −70° C. under N₂. The reaction was stirred for 0.5 h followed by the addition of 2,4,6-trichloro-1,3,5-triazine (874.62 mg, 4.74 mmol). The reaction was stirred for another 4 h. The mixture was quenched with aq. NH₄Cl and was extracted with EtOAc (20 mL×3). The combined extracts were washed with water and saturated brine, dried over Na₂SO₄ and concentrated in vacuo to give the crude product. The crude product was purified by flash chromatography to afford the title product 2-(4,6-dichloro-1,3,5-triazin-2-yl)-2-azaspiro[3.4]octane-3,5-dione (79.00 mg, 0.28 mmol, 17.40% yield) as a colorless oil. LCMS calculated for $C_{10}H_9Cl_2N_4O_2$ $(M+H)^+$ m/z=287.01; found: 287.1.

Step 4. Synthesis of 2-[4-[[(1R)-1-[2-[bis[(4-methoxyphenyl)methyl]amino]-3-pyridyl]ethyl]-ethyl-amino]-6-chloro-1,3,5-triazin-2-yl]-2-azaspiro[3.4]octane-3,5-dione (201d). To a solution of 2-(4,6-dichloro-1,3,5-triazin-2-yl)-2-azaspiro[3.4]octane-3,5-dione (79.00 mg, 0.28 mmol) in THF (1.5 mL) were added 3-[(1R)-1-(ethylamino)ethyl]-N,N-bis[(4-methoxyphenyl)methyl]pyridin-2-amine (122.75 mg, 0.30 mmol) followed by DIEA (0.19 mL, 1.10 mmol) at 0° C. under N₂. The mixture was stirred at 0° C. for 3 h. Then the mixture was diluted with water (10 mL) and extracted with EtOAc (10 mL×2). The combined extracts were washed with saturated brine, dried over Na₂SO₄ and concentrated in vacuo to give the crude product. The crude product was purified by flash chromatography to afford the title product 2-[4-[[(1R)-1-[2-[bis[(4-methoxyphenyl)methyl]amino]-3-pyridyl]ethyl]-ethyl-amino]-6-chloro-1,3,5-triazin-2-yl]-2-azaspiro[3.4]octane-3,5-dione (77.00 mg, 0.12 mmol, 42.65% yield) as a light yellow oil. LCMS calculated for $C_{35}H_{39}ClN_7O_4$$(M+H)^+$ m/z=656.28; found: 656.5.

Step 5. Synthesis of 2-[4-[[(1R)-1-[2-[bis[(4-methoxyphenyl)methyl]amino]-3-pyridyl]ethyl]-ethyl-amino]-6-[[(2R,8S)-2-fluoro-1,2,3,5,6,7-hexahydropyrrolizin-8-yl]methoxy]-1,3,5-triazin-2-yl]-2-azaspiro[3.4]octane-3,5-dione (201e)

The mixture of 2-[4-[[(1R)-1-[2-[bis[(4-methoxyphenyl)methyl]amino]-3-pyridyl]ethyl]-ethyl-amino]-6-chloro-1,3,5-triazin-2-yl]-2-azaspiro[3.4]octane-3,5-dione (77.00 mg, 0.12 mmol), [(2R,8S)-2-fluoro-1,2,3,5,6,7-hexahydropyrrolizin-8-yl]methanol (37.36 mg, 0.23 mmol) and DIEA (0.06 mL, 0.35 mmol) in 1,4-Dioxane (1.5 mL) was heated at 60° C. for 16 h and then 70° C. for 3 h under $N_2$. The mixture was diluted with water (10 mL) and then extracted with EtOAc (10 mL×2). The combined extracts were washed with saturated brine, dried over $Na_2SO_4$ and concentrated in vacuo. The residue was purified by flash chromatography to afford the title product 2-[4-[[(1R)-1-[2-[bis[(4-methoxyphenyl)methyl]amino]-3-pyridyl]ethyl]-ethyl-amino]-6-[[(2R,8S)-2-fluoro-1,2,3,5,6,7-hexahydropyrrolizin-8-yl]methoxy]-1,3,5-triazin-2-yl]-2-azaspiro[3.4]octane-3,5-dione (28.00 mg, 0.04 mmol, 30.63% yield) as a white solid. LCMS calculated for $C_{43}H_{52}FN_8O_5$ $(M+H)^+$ m/z=779.41; found: 779.5.

Step 6. Synthesis of 2-amino-1'-[4-[[(1R)-1-[2-[bis[(4-methoxyphenyl)methyl]amino]-3-pyridyl]ethyl]-ethyl-amino]-6-[[(2R,8S)-2-fluoro-1,2,3,5,6,7-hexahydropyrrolizin-8-yl]methoxy]-1,3,5-triazin-2-yl]-2'-oxo-spiro[5,6-dihydrocyclopenta[b]thiophene-4,3'-azetidine]-3-carbonitrile (201f). The mixture of 2-[4-[[(1R)-1-[2-[bis[(4-methoxyphenyl)methyl]amino]-3-pyridyl]ethyl]-ethyl-amino]-6-[[(2R,8S)-2-fluoro-1,2,3,5,6,7-hexahydropyrrolizin-8-yl]methoxy]-1,3,5-triazin-2-yl]-2-azaspiro[3.4]octane-3,5-dione (28.00 mg, 0.04 mmol), propanedinitrile (7.12 mg, 0.11 mmol), sulfur (3.46 mg, 0.11 mmol) and ammonium acetate (8.31 mg, 0.11 mmol) in Ethanol (1 mL) was heated at 45° C. for 2 h under $N_2$. Then the mixture was diluted with water (10 mL) and extracted with EtOAc (10 mL×2). The combined extracts were washed with saturated brine, dried over $Na_2SO_4$ and concentrated in vacuo. The residue was purified by flash chromatography to afford the title product 2-amino-1'-[4-[[(1R)-1-[2-[bis[(4-methoxyphenyl)methyl]amino]-3-pyridyl]ethyl]-ethyl-amino]-6-[[(2R,8S)-2-fluoro-1,2,3,5,6,7-hexahydropyrrolizin-8-yl]methoxy]-1,3,5-triazin-2-yl]-2'-oxo-spiro[5,6-dihydrocyclopenta[b]thiophene-4,3'-azetidine]-3-carbonitrile (29.00 mg, 0.03 mmol, 82.64% yield) as a light yellow solid. LCMS calculated for $C_{46}H_{52}FN_{10}O_4S$ $(M+H)^+$ m/z=859.39; found: $(M+H)^+$ m/2=430.2

Step 7. Synthesis of 2-amino-1'-[4-[[(1R)-1-(2-amino-3-pyridyl)ethyl]-ethyl-amino]-6-[[(2R,8S)-2-fluoro-1,2,3,5,6,7-hexahydropyrrolizin-8-yl]methoxy]-1,3,5-triazin-2-yl]-2'-oxo-spiro[5,6-dihydrocyclopenta[b]thiophene-4,3'-azetidine]-3-carbonitrile (Compound 201). To a solution of 2-amino-1'-[4-[[(1R)-1-[2-[bis[(4-methoxyphenyl)methyl]amino]-3-pyridyl]ethyl]-ethyl-amino]-6-[[(2R,8S)-2-fluoro-1,2,3,5,6,7-hexahydropyrrolizin-8-yl]methoxy]-1,3,5-triazin-2-yl]-2'-oxo-spiro[5,6-dihydrocyclopenta[b]thiophene-4,3'-azetidine]-3-carbonitrile (29.00 mg, 0.03 mmol) in TFA (1 mL) was added methanesulfonic acid (0.03 mL, 0.46 mmol) at 0° C. The reaction was stirred at 0° C. for 30 min and then at room temperature for 0.5 h. The mixture was diluted with EtOAc (5 mL) and neutralized with aqueous $NaHCO_3$. The organic layer was separated and then washed with water and saturated brine, dried over $Na_2SO_4$ and concentrated in vacuo. The residue was purified by prep-HPLC (water and 0.1% $NH_4HCO_3$ in $CH_3CN$ from 10% to 95%) to afford the title product 2-amino-1'-[4-[[(1R)-1-(2-amino-3-pyridyl)ethyl]-ethyl-amino]-6-[[(2R,8S)-2-fluoro-1,2,3,5,6,7-hexahydropyrrolizin-8-yl]methoxy]-1,3,5-triazin-2-yl]-2'-oxo-spiro[5,6-dihydrocyclopenta[b]thiophene-4,3'-azetidine]-3-carbonitrile (5.78 mg, 0.01 mmol, 31.45% yield) as a white solid. LCMS calculated for $C_{30}H_{36}FN_{10}O_2S$ $(M+H)^+$ m/z=619.27; found: 619.3. $^1H$ NMR (400 MHz, $CD_3OD$) δ=7.94-7.81 (m, 1H), 7.79-7.60 (m, 1H), 6.80-6.61 (m, 1H), 6.18-5.91 (m, 1H), 5.27 (d, J=55.2 Hz, 1H), 4.30-3.92 (m, 4H), 3.57-3.45 (m, 1H), 3.28-3.09 (m, 4H), 3.07-2.84 (m, 4H), 2.80-2.66 (m, 1H), 2.34-2.06 (m, 3H), 2.03-1.79 (m, 3H), 1.63-1.51 (m, 3H), 0.93-0.77 (m, 3H).

Compound 202. 2-amino-1'-[4-[[(1R)-1-(2-amino-3-pyridyl)ethyl]-ethyl-amino]-6-[[2-(methoxymethyl)pyrrolidin-2-yl]methoxy]-1,3,5-triazin-2-yl]spiro[6H-thieno[3,4-b]thiophene-4,3'-azetidine]-3-carbonitrile

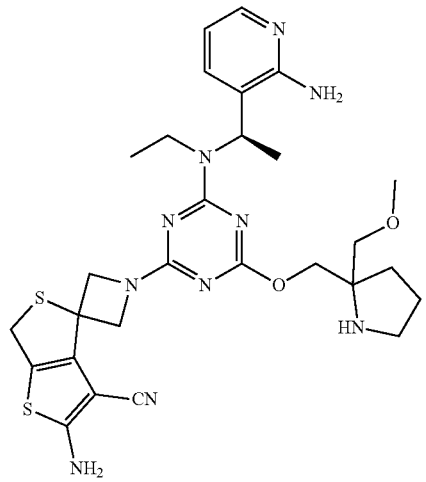 [SMILES: CCN(c1nc(OCC2(COC)CCCN2)nc(N2CC3(C2)SCc2sc(N)c(C#N)c23)n1)[C@H](C)c1cccnc1N]

Compound 202 was prepared similarly to that of Ex. 4. LCMS calculated for $C_{28}H_{37}N_{10}O_2S_2$ $(M+H)^+$ m/z=609.3; found: 609.3. $^1H$ NMR (400 MHz, $CD_3OD$) δ 7.91-7.84 (m, 1H), 7.72-7.66 (m, 1H), 6.74-6.64 (m, 1H), 6.12-5.94 (m, 1H), 4.82-4.60 (m, 2H), 4.51-4.19 (m, 4H), 4.14-3.99 (m, 2H), 3.52-3.38 (m, 3H), 3.34 (s, 3H), 3.23-3.08 (m, 1H), 3.04-2.91 (m, 2H), 1.93-1.66 (m, 4H), 1.54 (d, J=6.8 Hz, 3H), 0.84 (t, J=6.8 Hz, 3H).

Compound 203. 2-amino-1'-[4-[[(1R)-1-(2-amino-3-pyridyl)ethyl]-ethyl-amino]-6-[[1-(3-oxa-8-azabicyclo[3.2.1]octan-8-ylmethyl)cyclopropyl]methoxy]-1,3,5-triazin-2-yl]spiro[6H-thieno[3,4-b]thiophene-4,3'-azetidine]-3-carbonitrile

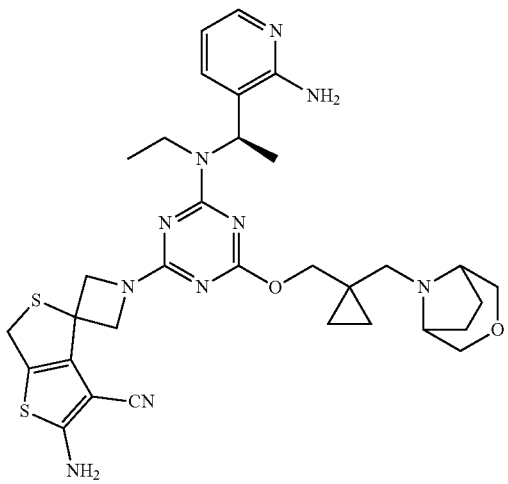 [SMILES: CCN(c1nc(OCC2(CN3C4CCC3COC4)CC2)nc(N2CC3(C2)SCc2sc(N)c(C#N)c23)n1)[C@H](C)c1cccnc1N]

Compound 203 was prepared similarly to that of Ex. 4. LCMS calculated for $C_{32}H_{41}N_{10}O_2S_2$ (M+H)⁺ m/z=661.1; found: 661.3. ¹H NMR (400 MHz, CD₃OD) δ 7.87 (s, 1H), 7.68 (d, J=7.5 Hz, 1H), 6.76-6.53 (m, 1H), 6.07 (s, 1H), 4.70 (m, J=43.1 Hz, 2H), 4.40 (m, 4H), 4.05 (m, 2H), 3.66 (d, J=8.6 Hz, 2H), 3.45 (m, J=9.5 Hz, 3H), 3.13 (d, J=3.4 Hz, 3H), 2.39 (s, 2H), 1.86 (m, J=43.5, 11.9 Hz, 4H), 1.54 (d, J=6.9 Hz, 3H), 0.86 (dd, J=15.4, 8.6 Hz, 3H), 0.59 (s, 2H), 0.47 (s, 2H).

Compound 204. 1-(4-((3-oxa-8-azabicyclo[3.2.1]octan-1-yl)methoxy)-6-(((R)-1-(2-aminopyridin-3-yl)ethyl)(ethyl)amino)-1,3,5-triazin-2-yl)-2'-amino-6'H-spiro[azetidine-3,4'-thieno[3,4-b]thiophene]-3'-carbonitrile

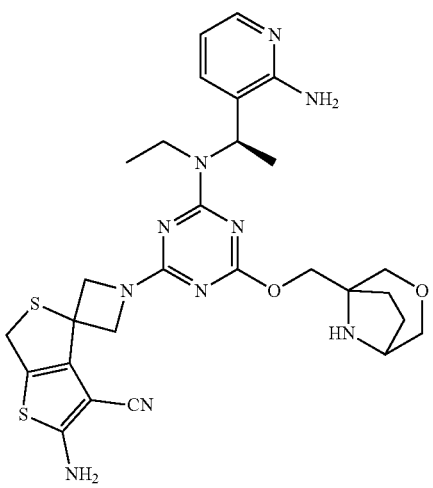 [SMILES: CCN(c1nc(OCC23CCC(COC2)N3)nc(N2CC3(C2)SCc2sc(N)c(C#N)c23)n1)[C@H](C)c1cccnc1N]

Compound 204 was prepared similarly to that of Ex. 4. LCMS calculated for $C_{28}H_{35}N_{10}O_2S_2$ (M+H)⁺ m/z=607.77; found: 607.4. ¹H NMR (400 MHz, CD₃OD) δ=7.96-7.83 (m, 1H), 7.77-7.65 (m, 1H), 6.69 (dd, J=7.0 Hz, 5.4 Hz, 1H), 6.15-5.91 (m, 1H), 4.81-4.58 (m, 2H), 4.49-4.20 (m, 4H), 4.15-3.98 (m, 2H), 3.75-3.54 (m, 4H), 3.53-3.35 (m, 2H), 3.24-3.06 (m, 1H), 2.13-1.87 (m, 3H), 1.78-1.62 (m, 1H), 1.54 (d, J=6.8 Hz, 3H), 0.84 (t, J=6.8 Hz, 3H).

Compound 205. 2-amino-1'-[4-[1-[2-(difluoromethyl)-3-pyridyl]ethyl-methyl-amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

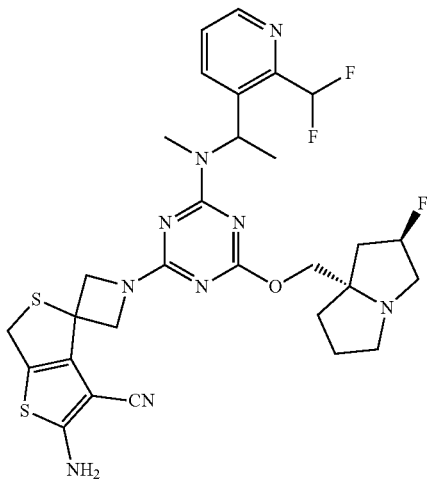 [SMILES: CC(c1cccnc1C(F)F)N(C)c1nc(OC[C@@]23CCCN2C[C@H](F)C3)nc(N2CC3(C2)SCc2sc(N)c(C#N)c23)n1]

Compound 205 was prepared similarly to that of Ex. 4. LCMS calculated for $C_{29}H_{33}F_3N_9OS_2$ (M+H)⁺ m/z=644.2; found: 644.2. ¹H NMR (400 MHz, CD₃OD) δ=8.57 (d, J=4.0 Hz, 1H), 8.08 (d, J=8.0 Hz, 1H), 7.59 (dd, J=8.0, 4.8 Hz, 1H), 7.09 (t, J=53.6 Hz, 1H), 6.40-6.26 (m, 1H), 5.26 (d, J=53.8 Hz, 1H), 4.72-4.62 (m, 2H), 4.40-4.28 (m, 2H), 4.21-4.10 (m, 1H), 4.10-4.05 (m, 3H), 3.28-3.12 (m, 3H), 3.01-2.93 (m, 1H), 2.90 (s, 3H), 2.30-1.79 (m, 6H), 1.59 (d, J=6.8 Hz, 3H).

Compound 206. (R)-2'-amino-1-(4-((1-(2-amino-pyridin-3-yl)ethyl)(ethyl)amino)-6-((tetrahydro-1H-pyrrolizin-7a(5H)-yl)methoxy)-1,3,5-triazin-2-yl)-6'H-spiro[azetidine-3,4'-thieno[3,4-b]thiophene]-3'-carbonitrile

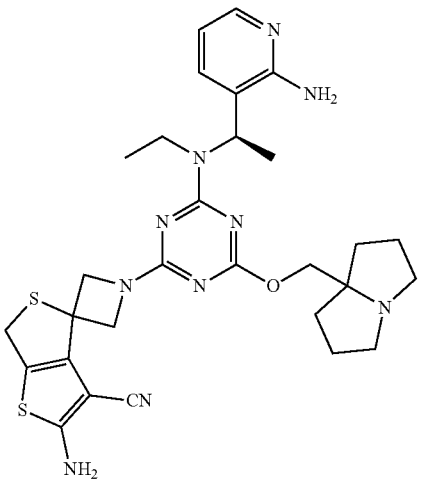 [SMILES: CCN(c1nc(OCC23CCCN2CCC3)nc(N2CC3(C2)SCc2sc(N)c(C#N)c23)n1)[C@H](C)c1cccnc1N]

Compound 206 was prepared similarly to that of Ex. 4 as a formate salt. LCMS calculated for $C_{29}H_{37}N_{10}OS_2$ (M+H)⁺ m/z=605.26; found: 605.5. ¹H NMR (400 MHz, d6-DMSO) δ 7.90 (d, J=4.8 Hz, 1H), 7.58 (d, J=7.9 Hz, 1H), 7.42 (br, 2H), 6.60 (s, 1H), 5.93-5.52 (m, 3H), 4.57-4.55 (m, 2H), 4.35-4.28 (m, 2H), 4.17-3.99 (m, 4H), 3.07-3.00 (m, 4H), 2.72-2.67 (m, 2H), 1.98-1.63 (m, 8H), 1.46 (d, J=6.5 Hz, 3H), 0.78 (d, 3H).

Compound 207. 2-amino-1'-[4-[[(1R)-1-(2-amino-3-pyridyl)ethyl]-ethyl-amino]-6-[[(2S)-1-methylpyrrolidin-2-yl]methoxy]-1,3,5-triazin-2-yl]spiro[6H-thieno[3,4-b]thiophene-4,3'-azetidine]-3-carbonitrile

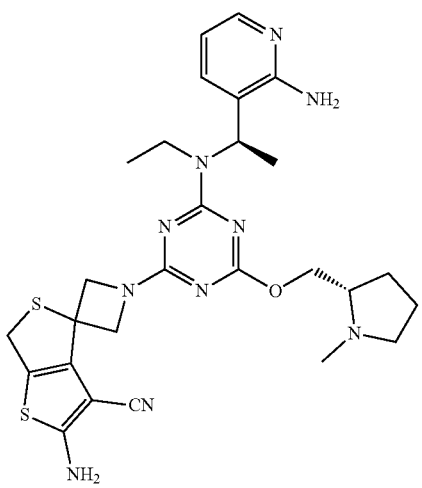 [SMILES: CCN(c1nc(OC[C@@H]2CCCN2C)nc(N2CC3(C2)SCc2sc(N)c(C#N)c23)n1)[C@H](C)c1cccnc1N]

Compound 207 was prepared similarly to that of Ex. 4. LCMS calculated for $C_{27}H_{35}N_{10}OS_2$ (M+H)$^+$ m/z=579.2, found: 579.2. $^1$H NMR (400 MHz, CD$_3$OD) δ 7.93-7.78 (m, 1H), 7.75-7.52 (m, 1H), 6.78-6.66 (m, 1H), 6.13-5.89 (m, 1H), 4.83-4.57 (m, 2H), 4.50-4.23 (m, 4H), 4.06-4.01 (m, 1H), 3.52-3.42 (m, 1H), 3.20-3.04 (m, 2H), 2.82-2.72 (m, 1H), 2.52-2.44 (m, 3H), 2.40-2.29 (m, 1H), 2.19-2.00 (m, 2H), 1.84-1.76 (m, 2H), 1.74-1.62 (m, 1H), 1.58-1.51 (m, 3H), 0.86-0.79 (m, 3H).

Compound 208. 2-amino-1'-[4-[[(1R)-1-(2-amino-3-pyridyl)ethyl]-ethyl-amino]-6-[[2-(hydroxymethyl)pyrrolidin-2-yl]methoxy]-1,3,5-triazin-2-yl]spiro[6H-thieno[3,4-b]thiophene-4,3'-azetidine]-3-carbonitrile

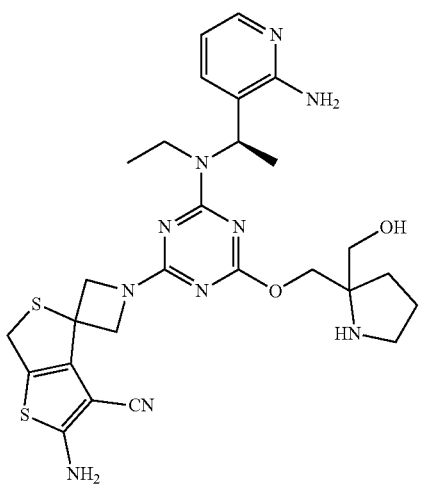 [SMILES: CCN(c1nc(OCC2(CO)CCCN2)nc(N2CC3(C2)SCc2sc(N)c(C#N)c23)n1)[C@H](C)c1cccnc1N]

Compound 208 was prepared similarly to that of Ex. 4. LCMS calculated for $C_{27}H_{35}N_{10}O_2S_2$ (M+H)+ m/z=595.2; found: 595.2. $^1$H NMR (400 MHz, CD$_3$OD) δ 7.91-7.82 (m, 1H), 7.68 (d, J=7.2 Hz, 1H), 6.73-6.65 (m, 1H), 6.14-5.94 (m, 1H), 4.80-4.55 (m, 2H), 4.46-4.25 (m, 4H), 4.13-4.00 (m, 2H), 3.71-3.57 (m, 2H), 3.51-3.43 (m, 1H), 3.23-3.11 (m, 1H), 3.03-2.85 (m, 2H), 1.86-1.72 (m, 4H), 1.54 (d, J=6.8 Hz, 3H), 0.84 (t, J=6.4 Hz, 3H).

Compound 209. 2-amino-1'-[4-[[(1R)-1-(2-amino-3-pyridyl)ethyl]-ethyl-amino]-6-[[(2S,4R)-4-fluoropyrrolidin-2-yl]methoxy]-1,3,5-triazin-2-yl]spiro[6H-thieno[3,4-b]thiophene-4,3'-azetidine]-3-carbonitrile

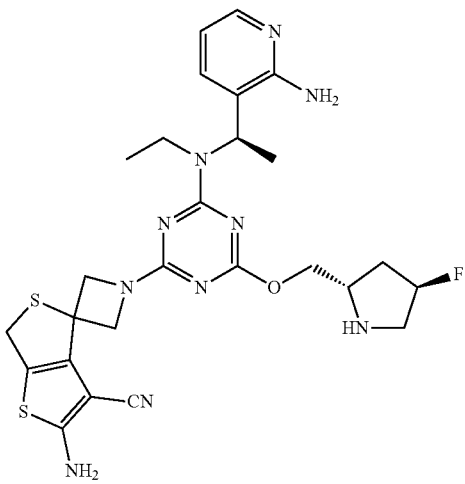 [SMILES: CCN(c1nc(OC[C@@H]2C[C@@H](F)CN2)nc(N2CC3(C2)SCc2sc(N)c(C#N)c23)n1)[C@H](C)c1cccnc1N]

Compound 209 was prepared similarly to that of Ex. 4. LCMS calculated for $C_{26}H_{32}FN_{10}OS_2$ (M+H)$^+$ m/z=583.2, found: 583.2. $^1$H NMR (400 MHz, CD$_3$OD) δ 7.90-7.84 (m, 1H), 7.71-7.65 (m, 1H), 6.72-6.66 (m, 1H), 6.10-5.95 (m, 1H), 5.33-5.12 (m, 1H), 4.69-4.58 (m, 1H), 4.48-4.25 (m, 4H), 4.11-4.00 (m, 2H), 3.77-3.69 (m, 1H), 3.53-3.40 (m, 1H), 3.23-3.12 (m, 2H), 3.09 (s, 1H), 2.28-2.13 (m, 1H), 1.92-1.71 (m, 1H), 1.54 (d, J=6.9 Hz, 3H), 1.43-1.23 (m, 1H), 0.83 (t, J=6.8 Hz, 3H).

Compound 210. 1'-[4-[[(6SR,8aSR)-2-methyl-1-oxo-3,4,6,7,8,8a-hexahydropyrrolo[1,2-a]pyrazin-6-yl]methoxy]-6-[[(1R)-1-(2-amino-3-pyridyl) ethyl]-ethyl-amino]-1,3,5-triazin-2-yl]-2-amino-spiro[6H-thieno[3,4-b]thiophene-4,3'-azetidine]-3-carbonitrile Compound 210 was prepared similarly to that of Ex. 4. LCMS calculated for $C_{30}H_{38}N_{11}O_2S_2$ (M+H)$^+$ m/z=648.27; found: 648.3. $^1$H NMR (400 MHz, CD$_3$OD) δ=7.95-7.78 (m, 1H), 7.69 (d, J=7.6 Hz, 1H), 6.78-6.56 (m, 1H), 6.16-5.85 (m, 1H), 4.78-4.59 (m, 2H), 4.45-4.24 (m, 4H), 4.12-4.00 (m, 2H), 3.80-3.58 (m, 2H), 3.45 (dd, J=18.4, 3.6 Hz, 2H), 3.28-3.10 (m, 4H), 2.95 (s, 3H), 2.24-1.92 (m, 3H), 1.72-1.59 (m, 1H), 1.54 (d, J=6.8 Hz, 3H), 0.92-0.76 (m, 3H).

Compound 211. 2-amino-1'-[4-[[(1R)-1-(2-amino-3-pyridyl)ethyl]-(2,2-difluoroethyl)amino]-6-[[(2SR,5SR)-5-(methoxymethyl)pyrrolidin-2-yl]methoxy]-1,3,5-triazin-2-yl]spiro[6H-thieno[3,4-b]thiophene-4,3'-azetidine]-3-carbonitrile

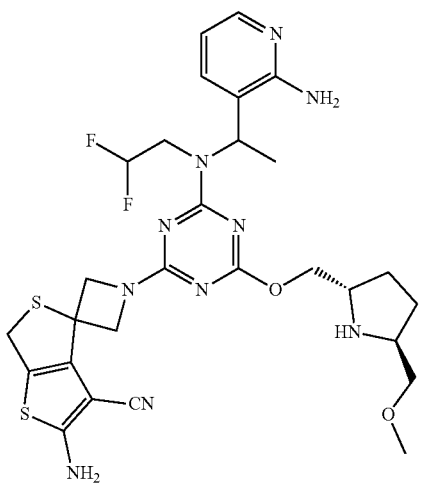 [SMILES: COC[C@@H]1CC[C@@H](COc2nc(N3CC4(C3)SCc3sc(N)c(C#N)c34)nc(N(CC(F)F)C(C)c3cccnc3N)n2)N1]

Compound 211 was prepared similarly to that of Ex. 4. LCMS calculated for $C_{28}H_{35}F_2N_{10}O_2S_2$ (M+H)$^+$ m/z=645.2; found: 645.3. $^1$H NMR (400 MHz, CD$_3$OD) δ=7.88 (d, J=4.8 Hz, 1H), 7.66 (d, J=7.2 Hz, 1H), 6.70 (dd, J=7.2, 5.2 Hz, 1H), 6.25-5.76 (m, 2H), 4.81-4.60 (m, 2H), 4.48-4.17 (m, 4H), 4.05 (s, 2H), 3.80-3.32 (m, 9H), 2.10-1.91 (m, 2H), 1.71-1.46 (m, 5H).

Compound 212. 8-amino-1'-[4-[[(1R)-1-(2-amino-3-pyridyl)ethyl]-ethyl-amino]-6-[[(2R,8S)-2-fluoro-1,2,3,5,6,7-hexahydropyrrolizin-8-yl]methoxy]-1,3,5-triazin-2-yl]spiro[9-thiatricyclo[4.3.0.0.2,4]nona-1(6),7-diene-5,3'-azetidine]-7-carbonitrile

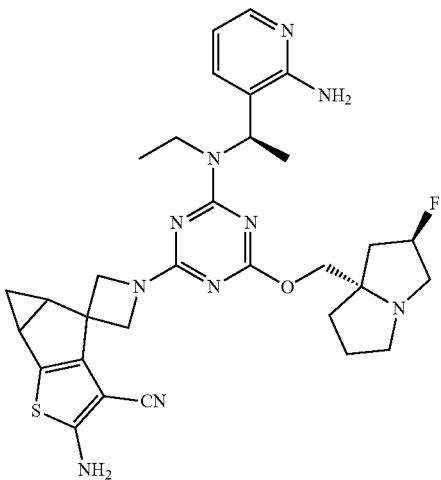 [SMILES: CCN(c1nc(OC[C@@]23CCCN2C[C@H](F)C3)nc(N2CC3(C2)c2c(sc(N)c2C#N)C2CC23)n1)[C@H](C)c1cccnc1N]

Compound 212 was prepared similarly to that of Ex. 4. LCMS calculated for $C_{31}H_{38}FN_{10}OS$ (M+H)$^+$ m/z=617.3, found: 617.3. $^1$H NMR (400 MHz, d6-DMSO) δ 7.90 (d, J=4.4 Hz, 1H), 7.62-7.55 (m, 1H), 7.23-7.07 (m, 2H), 6.64-6.56 (m, 1H), 6.04-5.75 (m, 2H), 5.74-5.64 (m, 1H), 5.36-5.13 (m, 1H), 4.31-4.03 (m, 5H), 4.02-3.91 (m, 2H), 3.10-3.01 (m, 3H), 3.00-2.94 (m, 1H), 2.84-2.75 (m, 1H), 2.38-2.29 (m, 2H), 2.12-2.05 (m, 1H), 2.03-1.90 (m, 2H), 1.86-1.79 (m, 1H), 1.77-1.65 (m, 2H), 1.51-1.42 (m, 3H), 1.01 (br, 1H), 0.82-0.74 (m, 3H), 0.22 (br, 1H).

Compound 213. 2-amino-1'-[4-[[(1R)-1-(2-amino-3-pyridyl)ethyl]-ethyl-amino]-6-[[2-(hydroxymethyl)-1-methyl-pyrrolidin-2-yl]methoxy]-1,3,5-triazin-2-yl]spiro[6H-thieno[3,4-b]thiophene-4,3'-azetidine]-3-carbonitrile

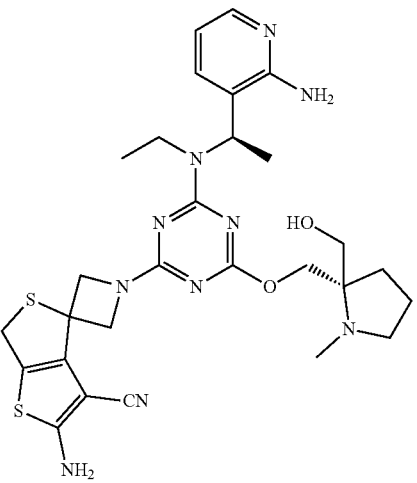 [SMILES: CCN(c1nc(OC[C@]2(CO)CCCN2C)nc(N2CC3(C2)SCc2sc(N)c(C#N)c23)n1)[C@H](C)c1cccnc1N]

Compound 213 was prepared similarly to that of Ex. 4. LCMS calculated for $C_{28}H_{37}N_{10}O_2S_2$ (M+H)$^+$ m/z=609.7; found: 609.3. $^1$H NMR (400 MHz, CD$_3$OD) δ 7.87 (d, J=2.7 Hz, 1H), 7.68 (d, J=7.1 Hz, 1H), 6.76-6.62 (m, 1H), 6.14-5.91 (m, 1H), 4.80-4.72 (m, 1H), 4.69-4.61 (m, 1H), 4.46-4.27 (m, 4H), 4.14-3.98 (m, 2H), 3.75-3.41 (m, 3H), 3.25-3.09 (m, 1H), 2.89 (s, 2H), 2.52 (s, 3H), 1.98-1.73 (m, 4H), 1.54 (d, J=6.9 Hz, 3H), 0.85 (t, J=6.4 Hz, 3H).

Compound 214. 2'-amino-1-(4-(((R)-1-(2-amino-pyridin-3-yl)ethyl)(ethyl)amino)-6-(((1S,5R)-3-methyl-3,8-diazabicyclo[3.2.1]octan-1-yl)methoxy)-1,3,5-triazin-2-yl)-6'H-spiro[azetidine-3,4'-thieno[3,4-b]thiophene]-3'-carbonitrile

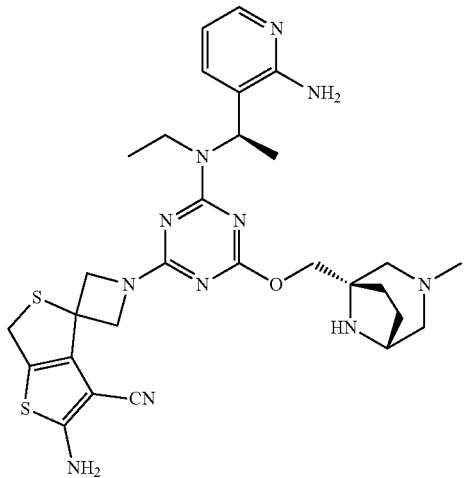 [SMILES: CCN(c1nc(OC[C@@]23CC[C@H](CN(C)C2)N3)nc(N2CC3(C2)SCc2sc(N)c(C#N)c23)n1)[C@H](C)c1cccnc1N]

Compound 214 was prepared similarly to that of Ex. 4. LCMS calculated for $C_{29}H_{38}N_{11}OS_2$ (M+H)$^+$ m/z=620.27;

found: 620.3. ¹H NMR (400 MHz, CD₃OD) δ=7.93-7.82 (m, 1H), 7.73-7.64 (m, 1H), 6.77-6.64 (m, 1H), 6.18-5.91 (m, 1H), 4.82-4.58 (m, 2H), 4.47-4.26 (m, 4H), 4.14-3.98 (m, 2H), 3.50-3.48 (m, 2H), 3.22-3.08 (m, 1H), 2.86-2.76 (m, 1H), 2.76-2.67 (m, 1H), 2.26 (s, 3H), 2.23-2.12 (m, 2H), 2.02-1.83 (m, 3H), 1.74-1.59 (m, 1H), 1.54 (d, J=6.8 Hz, 3H), 0.84 (t, J=6.4 Hz, 3H).

Compound 215. 2-[[4-(2-amino-3-cyano-spiro[6H-thieno[3,4-b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-methyl-amino]-N-carbamimidoyl-acetamide

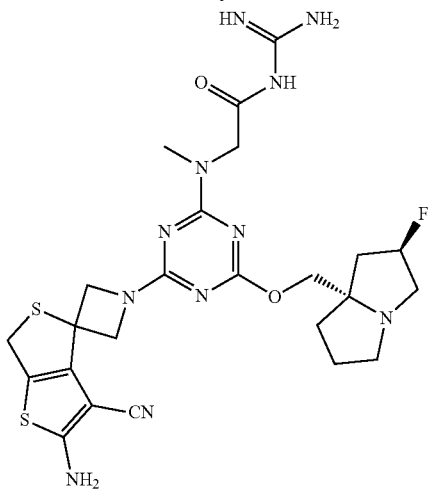

Compound 215 was prepared similarly to that of Ex. 4 as a hydrochloride salt. LCMS calculated for C₂₄H₃₁FN₁₁O₂S₂ (M+H)+ m/z=588.2, found: 588.2. ¹H NMR (400 MHz, CD₃OD) δ 5.59 (d, J=33.6 Hz, 1H), 4.86-4.43 (m, 9H), 4.12-3.80 (m, 5H), 3.51-3.41 (m, 1H), 3.36 (s, 2H), 2.77-2.10 (m, 6H).

Compound 216. 1'-[4-[[(6SR,8aRS)-2-methyl-3,4,6,7,8,8a-hexahydro-1H-pyrrolo[1,2-a]pyrazin-6-yl]methoxy]-6-[[(1R)-1-(2-amino-3-pyridyl)ethyl]-ethyl-amino]-1,3,5-triazin-2-yl]-2-amino-spiro[6H-thieno[3,4-b]thiophene-4,3'-azetidine]-3-carbonitrile

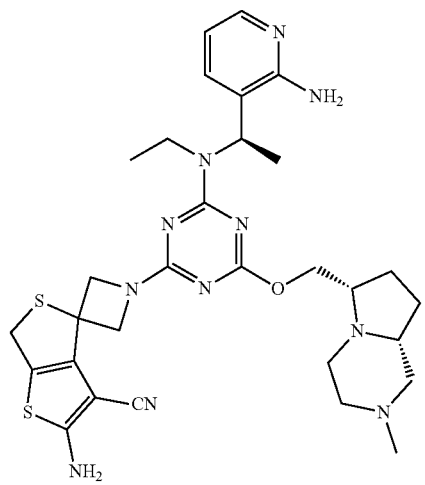 [SMILES: CCN(c1nc(OC[C@@H]2CC[C@@H]3CN(C)CCN32)nc(N2CC3(C2)SCc2sc(N)c(C#N)c23)n1)[C@H](C)c1cccnc1N]

Compound 216 was prepared similarly to that of Ex. 4. LCMS calculated for C₃₀H₄₀N₁₁OS₂ (M+H)+ m/z=634.1, found: 634.0. ¹H NMR (400 MHz, CD₃OD) δ 7.86 (s, 1H), 7.77-7.61 (m, 1H), 6.79-6.60 (m, 1H), 6.20-5.94 (m, 1H), 4.70-4.55 (m, 2H), 4.45-4.31 (m, 4H), 4.13-3.98 (m, 2H), 3.67-3.43 (m, 2H), 3.20-3.09 (m, 2H), 3.07-2.96 (m, 1H), 2.95-2.85 (m, 1H), 2.83-2.74 (m, 1H), 2.43-2.38 (m, 3H), 2.36-2.32 (m, 2H), 2.23-2.14 (m, 1H), 2.10-1.97 (m, 2H), 1.86-1.72 (m, 1H), 1.67-1.58 (m, 2H), 1.57-1.52 (m, 3H), 1.38-1.32 (m, 3H), 1.31-1.27 (m, 3H).

Compound 217. 2-amino-1'-[4-[(2-amino-3-pyridyl)methyl-(oxetan-3-yl)amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

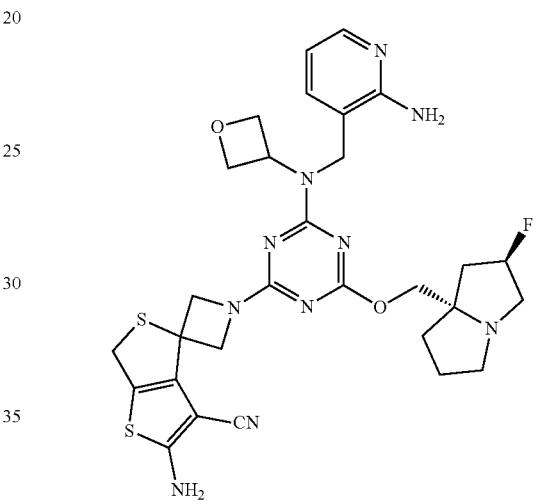

Compound 217 was prepared similarly to that of Ex. 4. LCMS calculated for C₂₉H₃₄FN₁₀O₂S₂ (M+H)+ m/z=637.2, found: 637.2. ¹H NMR (400 MHz, CD₃OD) δ 8.19-8.10 (m, 1H), 7.92 (d, J=5.4 Hz, 1H), 6.99 (t, J=6.8 Hz, 1H), 5.62-5.46 (m, 1H), 5.36-5.03 (m, 4H), 4.78-4.67 (m, 2H), 4.66-4.59 (m, 2H), 4.47-4.34 (m, 2H), 4.09 (s, 2H), 3.95-3.59 (m, 6H), 3.50-3.38 (m, 1H), 2.73-2.46 (m, 2H), 2.44-2.24 (m, 3H), 2.21-2.06 (m, 1H).

Compound 218. 2'-amino-1-(4-(((R)-1-(2-amino-pyridin-3-yl)ethyl)(ethyl)amino)-6-((3,8-dimethyl-3,8-diazabicyclo[3.2.1]octan-1-yl)methoxy)-1,3,5-triazin-2-yl)-6'H-spiro[azetidine-3,4'-thieno[3,4-b]thiophene]-3'-carbonitrile

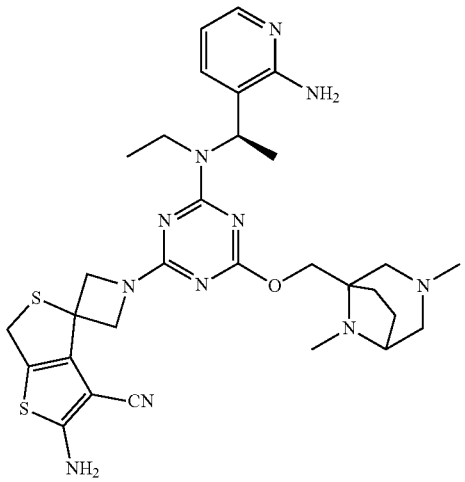 [SMILES: CCN(c1nc(OCC23CCC(CN(C)C2)N3C)nc(N2CC3(C2)SCc2sc(N)c(C#N)c23)n1)[C@H](C)c1cccnc1N]

Compound 218 was prepared similarly to that of Ex. 4. LCMS calculated for $C_{30}H_{40}N_{11}OS_2$ (M+H)⁺ m/z=643.84; found: 634.2. ¹H NMR (400 MHz, CD₃OD) δ=7.94-7.81 (m, 1H), 7.72-7.63 (m, 1H), 6.69 (dd, J=7.2 Hz, 5.2 Hz, 1H), 6.17-5.90 (m, 1H), 4.81-4.58 (m, 2H), 4.52-4.24 (m, 4H), 4.14-3.98 (m, 2H), 3.57-3.39 (m, 1H), 3.26-3.09 (m, 2H), 2.75-2.61 (m, 1H), 2.60-2.31 (m, 6H), 2.26 (s, 3H), 2.14-1.92 (m, 2H), 1.92-1.71 (m, 2H), 1.54 (d, J=6.8 Hz, 3H), 0.84 (t, J=6.8 Hz, 3H).

Compound 219. 1'-[4-[[(6SR,8aSR)-2-methyl-3,4,6,7,8,8a-hexahydro-1H-pyrrolo[1,2-a]pyrazin-6-yl]methoxy]-6-[[(1R)-1-(2-amino-3-pyridyl)ethyl]-ethyl-amino]-1,3,5-triazin-2-yl]-2-amino-spiro[6H-thieno[3,4-b]thiophene-4,3'-azetidine]-3-carbonitrile

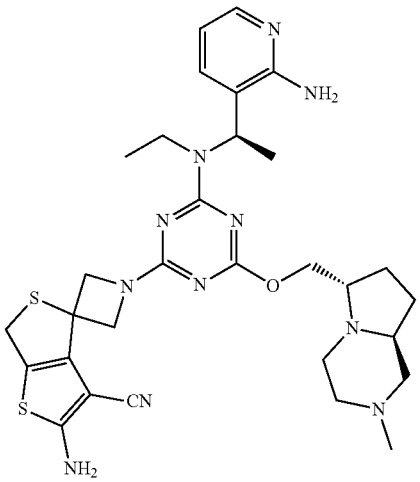 [SMILES: CCN(c1nc(OC[C@@H]2CC[C@H]3CN(C)CCN23)nc(N2CC3(C2)SCc2sc(N)c(C#N)c23)n1)[C@H](C)c1cccnc1N]

Compound 219 was prepared similarly to that of Ex. 4. LCMS calculated for $C_{30}H_{40}N_{11}OS_2$ (M+H)⁺ m/z=634.29; found: 634.3. ¹H NMR (400 MHz, CD₃OD) δ=7.87 (d, J=3.6 Hz, 1H), 7.68 (d, J=7.2 Hz, 1H), 6.73-6.64 (m, 1H), 6.14-5.91 (m, 1H), 4.79-4.58 (m, 2H), 4.47-4.31 (m, 3H), 4.26-4.17 (m, 1H), 3.64-3.40 (m, 2H), 3.24-3.08 (m, 3H), 3.06-2.94 (m, 1H), 2.78-2.73 (m, 2H), 2.43-2.27 (m, 4H), 2.22-2.10 (m, 1H), 2.07-1.90 (m, 2H), 1.76-1.31 (m, 7H), 0.88-0.78 (m, 3H).

Compound 220. 2-amino-1'-[4-[[(1R)-1-(2-amino-3-pyridyl)ethyl]-(2,2-difluoroethyl)amino]-6-[[1-[(dimethylamino)methyl]-2,2-difluoro-cyclopropyl]methoxy]-1,3,5-triazin-2-yl]spiro[6H-thieno[3,4-b]thiophene-4,3'-azetidine]-3-carbonitrile

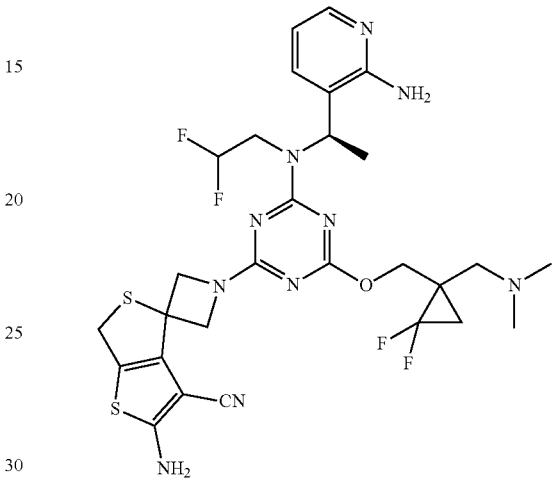

Compound 220 was prepared similarly to that of Ex. 4. LCMS calculated for $C_{28}H_{33}F_4N_{10}OS_2$ (M+H)⁺ m/z=665.21; found: 665.2. ¹H NMR (400 MHz, CD₃OD) δ 7.88-7.87 (m, 1H), 7.66 (d, J=7.6 Hz, 1H), 6.71 (dd, J=7.2, 5.2 Hz, 1H), 6.26-5.84 (m, 2H), 4.80-4.32 (m, 6H), 4.14-3.96 (m, 2H), 3.72-3.39 (m, 2H), 2.88-2.66 (m, 1H), 2.54-2.32 (m, 1H), 2.31-2.16 (m, 6H), 1.71-1.47 (m, 4H), 1.42-1.26 (m, 1H).

Compound 221. 2-amino-1'-[4-[[(1R)-1-(2-amino-3-pyridyl)ethyl]-ethyl-amino]-6-[[(2S)-2-(difluoromethyl)pyrrolidin-2-yl]methoxy]-1,3,5-triazin-2-yl]spiro[6H-thieno[3,4-b]thiophene-4,3'-azetidine]-3-carbonitrile

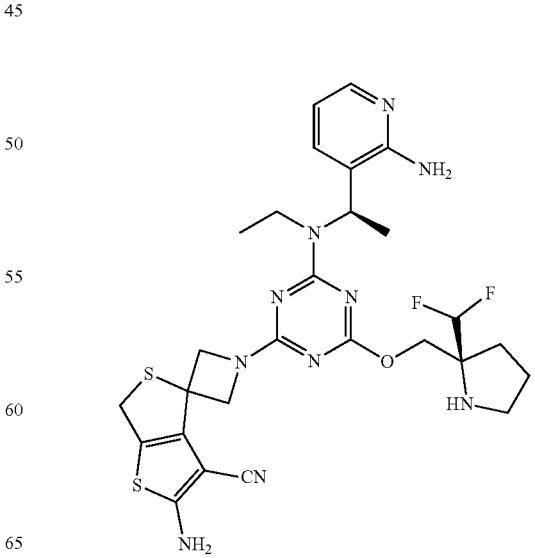

Compound 221 was prepared similarly to that of Ex. 4. LCMS calculated for $C_{27}H_{33}F_2N_{10}OS_2$ (M+H)+ m/z=615.2; found: 615.4. $^1$H NMR (400 MHz, CD$_3$OD) δ 7.91-7.83 (m, 1H), 7.68 (d, J=7.6 Hz, 1H), 6.74-6.65 (m, 1H), 6.13-5.74 (m, 2H), 4.80-4.59 (m, 2H), 4.49-4.27 (m, 4H), 4.14-3.98 (m, 2H), 3.53-3.42 (m, 1H), 3.16-2.84 (m, 3H), 2.06-1.94 (m, 1H), 1.91-1.71 (m, 3H), 1.54 (d, J=6.8 Hz, 3H), 0.83 (t, J=6.8 Hz, 3H).

Compound 222. 2-amino-1'-[4-[[(1R)-1-(2-amino-3-pyridyl)ethyl]-ethyl-amino]-6-[[1-(methoxymethyl)cyclopentyl]methoxy]-1,3,5-triazin-2-yl]spiro[6H-thieno[3,4-b]thiophene-4,3'-azetidine]-3-carbonitrile

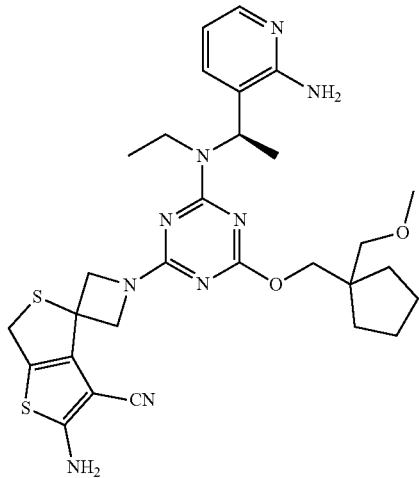 [SMILES: CCN(c1nc(OCC2(COC)CCCC2)nc(N2CC3(C2)SCc2sc(N)c(C#N)c23)n1)[C@H](C)c1cccnc1N]

Compound 222 was prepared similarly to that of Ex. 4. LCMS calculated for $C_{29}H_{38}N_9O_2S_2$ (M+H)+ m/z=608.26; found: 608.4. $^1$H NMR (400 MHz, CD$_3$OD) δ=7.86 (d, J=4.4 Hz, 1H), 7.68 (dd, J=7.2, 0.8 Hz, 1H), 6.69 (dd, J=6.8, 5.2 Hz, 1H), 6.15-5.91 (m, 1H), 4.86-4.56 (m, 4H), 4.47-4.29 (m, 2H), 4.27-4.00 (m, 4H), 3.54-3.41 (m, 1H), 3.31 (s, 3H), 3.21-3.10 (m, 1H), 1.70-1.59 (m, 4H), 1.59-1.47 (m, 7H), 0.85 (t, J=6.4 Hz, 3H).

Compound 223. 2-amino-1'-[4-[[(1R)-1-(2-amino-3-pyridyl)ethyl]-ethyl-amino]-6-[(2-methyl-1,3,4,6,7,8-hexahydropyrrolo[1,2-a]pyrazin-8a-yl)methoxy]-1,3,5-triazin-2-yl]spiro[6H-thieno[3,4-b]thiophene-4,3'-azetidine]-3-carbonitrile

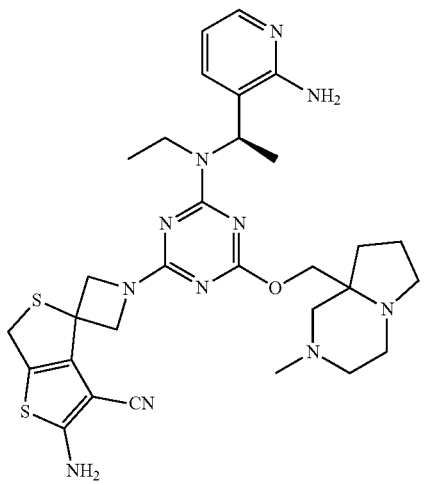 [SMILES: CCN(c1nc(OCC23CCCN2CCN(C)C3)nc(N2CC3(C2)SCc2sc(N)c(C#N)c23)n1)[C@H](C)c1cccnc1N]

Compound 223 was prepared similarly to that of Ex. 4. LCMS calculated for $C_{30}H_{40}N_{11}OS_2$ (M+H)+ m/z=634.2, found: 634.1. $^1$H NMR (400 MHz, CD$_3$OD) δ 7.86 (s, 1H), 7.68 (d, J=7.4 Hz, 1H), 6.74-6.60 (m, 1H), 6.05 (d, J=9.6 Hz, 1H), 4.82 (s, 2H), 4.66 (dd, J=15.2, 8.4 Hz, 1H), 4.58 (d, J=10.0 Hz, 1H), 4.44-4.34 (m, 2H), 4.22 (d, J=10.5 Hz, 1H), 4.05 (s, 2H), 3.48 (s, 1H), 3.11 (d, J=15.6 Hz, 3H), 2.96-2.76 (m, 3H), 2.32 (d, J=13.6 Hz, 2H), 2.25 (s, 3H), 2.06 (d, J=11.2 Hz, 1H), 1.89 (s, 3H), 1.73 (s, 1H), 1.54 (d, J=7.2 Hz, 3H), 0.87 (dd, J=14.6, 8.4 Hz, 3H).

Compound 224. 3-(1-((4-(2'-amino-3'-cyano-6'H-spiro[azetidine-3,4'-thieno[3,4-b]thiophen]-1-yl)-6-(((2R,7aS)-2-fluorotetrahydro-1H-pyrrolizin-7a(5H)-yl)methoxy)-1,3,5-triazin-2-yl)(methyl)amino)ethyl) pyridine 1-oxide

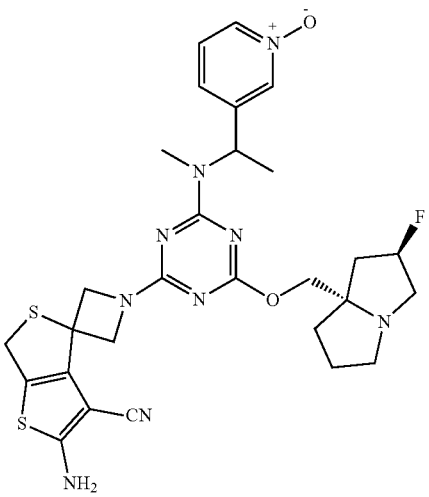

Compound 224 was prepared similarly to that of Ex. 4. LCMS calculated for $C_{28}H_{33}FN_9O_2S_2$ (M+H)+ m/z=610.22; found: 610.3. $^1$H NMR (400 MHz, CD$_3$OD) δ 8.34-8.20 (m, 2H), 7.68-7.46 (m, 2H), 6.19-5.95 (m, 1H), 5.26 (d, J=54.4 Hz, 1H), 4.92-4.89 (m, 1H), 4.64 (d, J=9.2 Hz, 2H), 4.35 (d, J=9.6 Hz, 2H), 4.25-3.97 (m, 4H), 3.24-3.10 (m, 3H), 2.97 (m, 4H), 2.26-1.78 (m, 6H), 1.63 (d, J=7.2 Hz, 3H).

Compound 225. 2-amino-1'-[4-[[(1R)-1-(2-amino-3-pyridyl)ethyl]-ethyl-amino]-6-[[2-[(dimethylamino)methyl]pyrrolidin-2-yl]methoxy]-1,3,5-triazin-2-yl]spiro[6H-thieno[3,4-b]thiophene-4,3'-azetidine]-3-carbonitrile

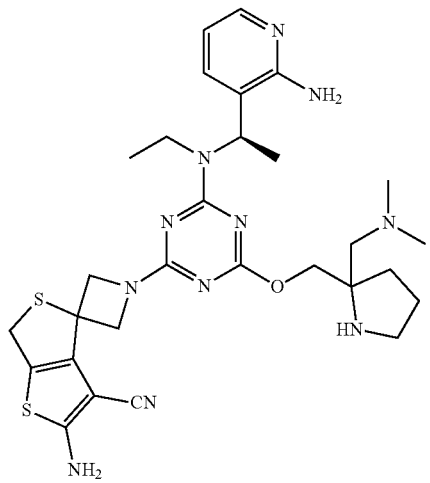 [SMILES: CCN(c1nc(OCC2(CN(C)C)CCCN2)nc(N2CC3(C2)SCc2sc(N)c(C#N)c23)n1)[C@H](C)c1cccnc1N]

Compound 225 was prepared similarly to that of Ex. 4. LCMS calculated for $C_{29}H_{40}N_{11}OS_2$ (M+H)$^+$ m/z=622.29; found: 622.3. $^1$H NMR (400 MHz, CD$_3$OD) δ 7.92-7.79 (m, 1H), 7.72-7.59 (m, 1H), 6.78-6.60 (m, 1H), 6.15-5.95 (m, 1H), 4.78-4.52 (m, 2H), 4.49-4.22 (m, 2H), 4.05 (s, 2H), 3.92-3.39 (m, 5H), 3.21-2.82 (m, 3H), 2.48-1.68 (m, 10H), 1.51 (d, J=6.9 Hz, 3H), 0.95-0.74 (m, 3H).

Example 11. Exemplary synthesis of 2-amino-1'-[4-[[(1R)-1-(2-amino-3-pyridyl)ethyl]-ethyl-amino]-6-[[(2R,8S)-2-fluoro-1,2,3,5,6,7-hexahydropyrrolizin-8-yl]methoxy]-1,3,5-triazin-2-yl]-5-methyl-spiro[6H-thieno[2,3-c]pyrrole-4,3'-azetidine]-3-carbonitrile Compound 226

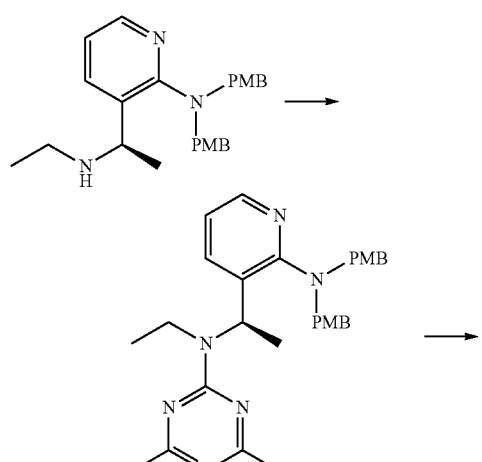

226a

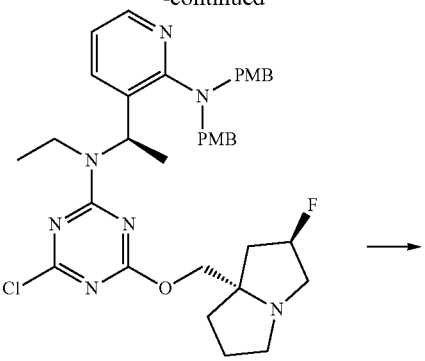

226b

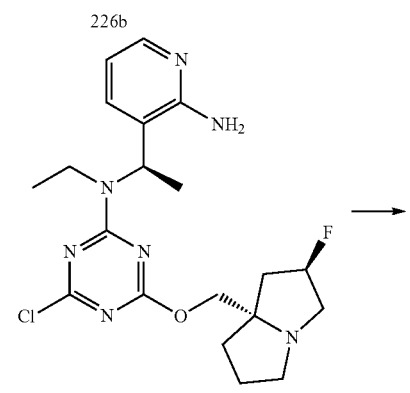

226c

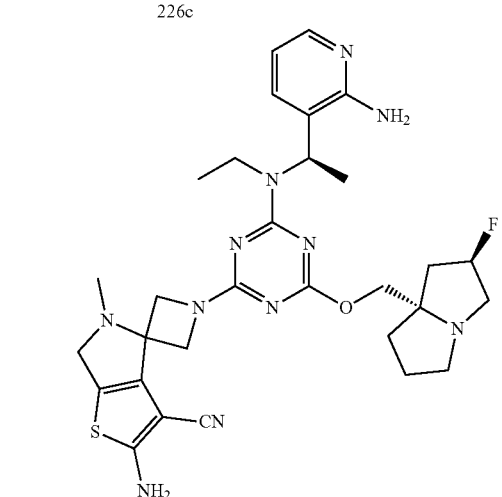

Compound 226

Step 1. Synthesis of N-[(1R)-1-[2-[bis[(4-methoxyphenyl)methyl]amino]-3-pyridyl]ethyl]-4,6-dichloro-N-ethyl-1,3,5-triazin-2-amine (226a). To a solution of 2,4,6-trichloro-1,3,5-triazine (2.73 g, 14.8 mmol) in THF (30 mL) were added 3-[(1R)-1-(ethylamino)ethyl]-N,N-bis[(4-methoxyphenyl)methyl]pyridin-2-amine (3.00 g, 7.40 mmol) and N,N-Diisopropylethylamine (3.87 mL, 22.2 mmol) at −70° C. under N$_2$. The mixture was stirred at −70° C. for 30 min, then the mixture was allowed to warm to 0° C. and stirred for 2 h. The reaction was quenched with ice water, and then extracted with EtOAc (100 mL×2). The combined extracts were washed with water followed by saturated brine, dried over Na$_2$SO$_4$ and concentrated in vacuo to give the crude product. The crude product was purified by flash chromatography to afford N-[(1R)-1-[2-[bis[(4-methoxyphenyl)methyl]amino]-3-pyridyl]ethyl]-4,6-dichloro-N-ethyl-1,3,5-triazin-2-amine (3.15 g, 4.84 mmol, 65.4% yield) as a yellow oil. LCMS calculated for $C_{28}H_{31}C_{12}N_6O_2$ (M+H)$^+$ m/z=553.2; found: 553.2

Step 2. Synthesis of N-[(1R)-1-[2-[bis[(4-methoxyphenyl)methyl]amino]-3-pyridyl]ethyl]-4-chloro-N-ethyl-6-[[(2R,8S)-2-fluoro-1,2,3,5,6,7-hexahydropyrrolizin-8-yl]methoxy]-1,3,5-triazin-2-amine (226b). The mixture of N-[(1R)-1-[2-[bis[(4-methoxyphenyl)methyl]amino]-3-pyridyl]ethyl]-4,6-dichloro-N-ethyl-1,3,5-triazin-2-amine (400 mg, 0.723 mmol), [(2R,8S)-2-fluoro-1,2,3,5,6,7-hexahydropyrrolizin-8-yl]methanol (230 mg, 1.45 mmol) and N,N-Diisopropylethylamine (0.38 mL, 2.17 mmol) in THF (6 mL) was stirred at 30° C. overnight under $N_2$. The mixture was diluted with water, extracted with EtOAc (50 mL×3). The combined extracts were washed with brine, dried over $Na_2SO_4$ and concentrated in vacuo to give the crude product N-[(1R)-1-[2-[bis[(4-methoxyphenyl)methyl]amino]-3-pyridyl]ethyl]-4-chloro-N-ethyl-6-[[(2R,8S)-2-fluoro-1,2,3,5,6,7-hexahydropyrrolizin-8-yl]methoxy]-1,3,5-triazin-2-amine (440 mg, 0.553 mmol, 76.5% yield) as a colorless oil. LCMS calculated for $C_{36}H_{44}ClFN_7O_3$(M+H)$^+$ m/z=676.3; found: 676.3.

Step 3. Synthesis of N-[(1R)-1-(2-amino-3-pyridyl)ethyl]-4-chloro-N-ethyl-6-[[(2R,8S)-2-fluoro-1,2,3,5,6,7-hexahydropyrrolizin-8-yl]methoxy]-1,3,5-triazin-2-amine (226c)

To a solution of N-[(1R)-1-[2-[bis[(4-methoxyphenyl)methyl]amino]-3-pyridyl]ethyl]-4-chloro-N-ethyl-6-[[(2R,8S)-2-fluoro-1,2,3,5,6,7-hexahydropyrrolizin-8-yl]methoxy]-1,3,5-triazin-2-amine (440 mg, 0.553 mmol) in Trifluoroacetic Acid (4.0 mL) was added Methanesulfonic Acid (0.50 mL) dropwise at 0° C. The mixture was stirred at 0° C. for 30 min. The reaction mixture was diluted with EtOAc (20 mL), quenched with aqueous $NaHCO_3$, and then extracted with EtOAc (20 mL×3). The combined extracts were washed with brine, dried over $Na_2SO_4$ and concentrated in vacuo to give the crude product. The crude product was purified by Flash Chromatography to afford N-[(1R)-1-(2-amino-3-pyridyl)ethyl]-4-chloro-N-ethyl-6-[[(2R,8S)-2-fluoro-1,2,3,5,6,7-hexahydropyrrolizin-8-yl]methoxy]-1,3,5-triazin-2-amine (270 mg, 0.619 mmol, 91.3% yield) as a white solid. LCMS calculated for $C_{20}H_{28}ClFN_7O$ (M+H)$^+$ m/z=436.2; found: 436.3.

Step 4. Synthesis of 2-amino-1'-[4-[[(1R)-1-(2-amino-3-pyridyl)ethyl]-ethyl-amino]-6-[[(2R,8S)-2-fluoro-1,2,3,5,6,7-hexahydropyrrolizin-8-yl]methoxy]-1,3,5-triazin-2-yl]-5-methyl-spiro[6H-thieno[2,3-c]pyrrole-4,3'-azetidine]-3-carbonitrile (Compound 226)

The mixture of N-[(1R)-1-(2-amino-3-pyridyl)ethyl]-4-chloro-N-ethyl-6-[[(2R,8S)-2-fluoro-1,2,3,5,6,7-hexahydropyrrolizin-8-yl]methoxy]-1,3,5-triazin-2-amine (70.0 mg, 0.161 mmol), 2-amino-5-methyl-spiro[6H-thieno[2,3-c]pyrrole-4,3'-azetidine]-3-carbonitrile; methanesulfonic acid (79.5 mg, 0.193 mmol) and N,N-Diisopropylethylamine (0.140 mL, 0.803 mmol) in DMSO (2 mL) was stirred at 25° C. overnight under $N_2$. The mixture was purified by Prep-HPLC (mobile phase: $H_2O$ (0.1% $NH_4HCO_3$)/ACN) to afford 2-amino-1'-[4-[[(1R)-1-(2-amino-3-pyridyl)ethyl]-ethyl-amino]-6-[[(2R,8S)-2-fluoro-1,2,3,5,6,7-hexahydropyrrolizin-8-yl]methoxy]-1,3,5-triazin-2-yl]-5-methyl-spiro[6H-thieno[2,3-c]pyrrole-4,3'-azetidine]-3-carbonitrile (51.1 mg, 0.078 mmol, 48.4% yield) as a light yellow solid. LCMS calculated for $C_{30}H_{39}FN_{11}OS$ (M+H)$^+$ m/z=620.3; found: 620.3.

$^1$H NMR (400 MHz, $CD_3OD$) δ=7.87-7.85 (m, 1H), 7.68 (d, J=6.8 Hz, 1H), 6.70-6.67 (m, 1H), 6.15-5.93 (m, 1H), 5.25 (d, J=54.0 Hz, 1H), 4.56-4.02 (m, 6H), 3.96-3.79 (m, 2H), 3.56-3.40 (m, 1H), 3.26-3.08 (m, 4H), 3.03-2.92 (m, 1H), 2.81-2.66 (m, 3H), 2.34-2.04 (m, 3H), 2.01-1.74 (m, 3H), 1.54 (d, J=6.8 Hz, 3H), 0.84 (t, J=5.6 Hz, 3H).

Compound 227. 2-amino-1'-[4-[[(1R)-1-(2-amino-3-pyridyl)ethyl]-ethyl-amino]-6-[[(2R,8S)-2-fluoro-1,2,3,5,6,7-hexahydropyrrolizin-8-yl]methoxy]-1,3,5-triazin-2-yl]-5-(2,2-difluoroethyl)spiro[6H-thieno[2,3-c]pyrrole-4,3'-azetidine]-3-carbonitrile

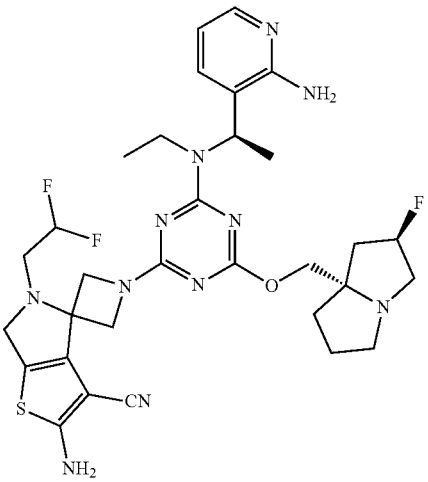 [SMILES: CCN(c1nc(OC[C@@]23CCCN2C[C@H](F)C3)nc(N2CC3(C2)c2c(sc(N)c2C#N)CN3CC(F)F)n1)[C@H](C)c1cccnc1N]

Compound 227 was prepared similarly to that of Ex. 4. LCMS calculated for $C_{31}H_{39}F_3N_{11}OS$ (M+H)$^+$ m/z=670.30; found: 670.3. $^1$H NMR (400 MHz, $CD_3OD$) δ 8.00-7.80 (m, 1H), 7.68 (d, J=6.8 Hz, 1H), 6.70-6.67 (m, 1H), 6.23-5.81 (m, 2H), 5.26 (d, J=54.4 Hz, 1H), 4.54-3.92 (m, 8H), 3.56-3.36 (m, 3H), 3.24-3.07 (m, 4H), 3.04-2.89 (m, 1H), 2.33-2.02 (m, 3H), 2.02-1.74 (m, 3H), 1.54 (d, J=6.8 Hz, 3H), 0.84 (t, J=6.4 Hz, 3H).

Compound 228. 2-amino-1'-[4-[[(1R)-1-(2-amino-3-pyridyl)ethyl]-ethyl-amino]-6-[[(2R,8S)-2-fluoro-1,2,3,5,6,7-hexahydropyrrolizin-8-yl]methoxy]-1,3,5-triazin-2-yl]-5-(cyanomethyl)spiro[6H-thieno[2,3-c]pyrrole-4,3'-azetidine]-3-carbonitrile

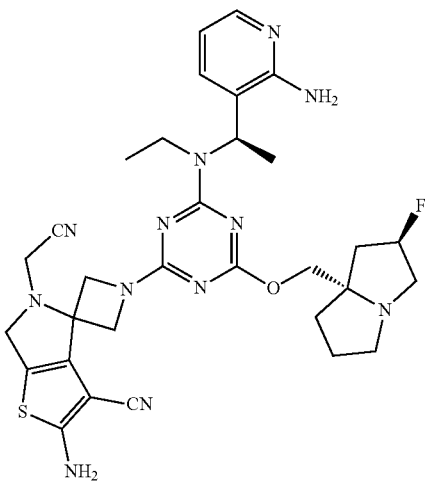 [SMILES: CCN(c1nc(OC[C@@]23CCCN2C[C@H](F)C3)nc(N2CC3(C2)c2c(sc(N)c2C#N)CN3CC#N)n1)[C@H](C)c1cccnc1N]

Compound 228 was prepared similarly to that of Ex. 4. LCMS calculated for $C_{31}H_{38}FN_{12}OS$ (M+H)$^+$ m/z=645.30; found: 645.4. $^1$H NMR (400 MHz, CD$_3$OD) δ 7.92-7.80 (m, 1H), 7.68 (d, J=7.2 Hz, 1H), 6.70-6.67 (t, J=6.0 Hz, 1H), 6.17-5.89 (m, 1H), 5.26 (d, J=54.0 Hz, 1H), 4.63-3.99 (m, 10H), 3.55-3.40 (m, 1H), 3.24-3.08 (m, 4H), 3.04-2.89 (m, 1H), 2.34-2.02 (m, 3H), 2.02-1.73 (m, 3H), 1.54 (d, J=6.8 Hz, 3H), 0.84 (t, J=6.8 Hz, 3H).

Compound 229. 2'-amino-1-(4-(((R)-1-(4-(dimethylphosphoryl)phenyl)ethyl)(methyl)amino)-6-(((2R,7aS)-2-fluorotetrahydro-1H-pyrrolizin-7a(5H)-yl)methoxy)-1,3,5-triazin-2-yl)-6'H-spiro[azetidine-3,4'-thieno[3,4-b]thiophene]-3'-carbonitrile

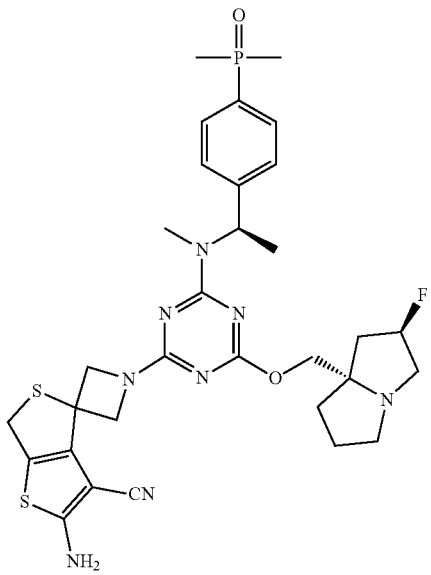 [SMILES: C[C@H](c1ccc(P(C)(C)=O)cc1)N(C)c1nc(OC[C@@]23CCCN2C[C@H](F)C3)nc(N2CC3(C2)SCc2sc(N)c(C#N)c23)n1]

Compound 229 was prepared similarly to that of Ex. 4. LCMS calculated for $C_{31}H_{39}FN_8O_2PS_2$ (M+H)+ m/z=669.23; found: 669.3. $^1$H NMR (400 MHz, CD$_3$OD) δ 7.78-7.73 (m, 2H), 7.61-7.45 (m, 2H), 6.26-6.14 (m, 1H), 5.36-5.15 (m, 1H), 4.73-4.58 (m, 2H), 4.40-4.28 (m, 2H), 4.21-3.99 (m, 4H), 3.25-3.10 (m, 3H), 3.03-2.90 (m, 1H), 2.87 (s, 3H), 2.30-1.82 (m, 6H), 1.77 (d, J=13.4 Hz, 6H), 1.61 (d, J=7.1 Hz, 3H).

Compound 230. 2'-amino-1-(4-(((1-(2-amino-6-methylpyridin-3-yl)ethyl)(methyl)amino)-6-(((2R,7aS)-2-fluorotetrahydro-1H-pyrrolizin-7a(5H)-yl)methoxy)-1,3,5-triazin-2-yl)-6'H-spiro[azetidine-3,4'-thieno[3,4-b]thiophene]-3'-carbonitrile

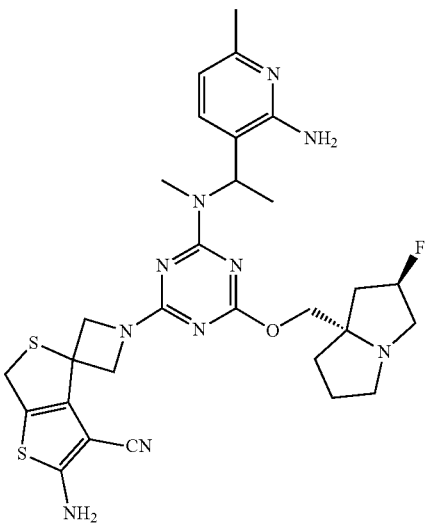 [SMILES: Cc1ccc(C(C)N(C)c2nc(OC[C@@]34CCCN3C[C@H](F)C4)nc(N3CC4(C3)SCc3sc(N)c(C#N)c34)n2)c(N)n1]

Compound 230 was prepared similarly to that of Ex. 4. LCMS calculated for $C_{29}H_{36}FN_{10}OS_2$ (M+H)$^+$ m/z=623.5; found: 623.1. $^1$H NMR (400 MHz, CD$_3$OD) (7.53 (d, J=7.6 Hz, 1H), 6.55 (d, J=7.6 Hz, 1H), 6.09-5.93 (m, 1H), 5.26 (d, J=53.6 Hz, 1H), 4.80-4.59 (m, 2H), 4.45-4.33 (m, 2H), 4.23-4.14 (m, 1H), 4.10-3.99 (m, 3H), 3.24-3.10 (m, 3H), 3.02-2.93 (m, 1H), 2.74 (s, 3H), 2.31 (s, 3H), 2.26-2.04 (m, 3H), 2.00-1.79 (m, 3H), 1.51 (d, J=6.8 Hz, 3H)

Compound 231. 2'-amino-1-(4-((1-(2-amino-4-(dimethylphosphoryl)phenyl)ethyl)(methyl)amino)-6-(((2R,7aS)-2-fluorotetrahydro-1H-pyrrolizin-7a(5H)-yl)methoxy)-1,3,5-triazin-2-yl)-6'H-spiro[azetidine-3,4'-thieno[3,4-b]thiophene]-3'-carbonitrile

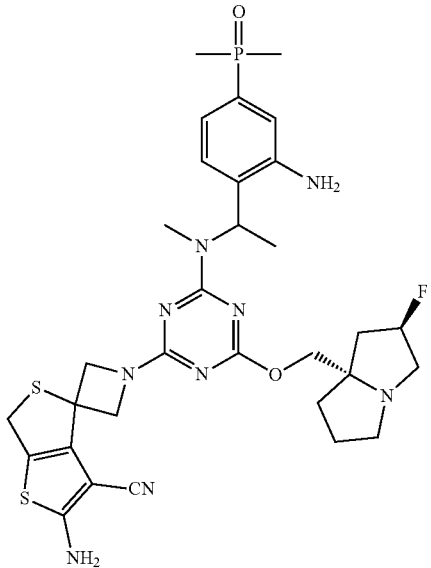 [SMILES: CC(c1ccc(P(C)(C)=O)cc1N)N(C)c1nc(OC[C@@]23CCCN2C[C@H](F)C3)nc(N2CC3(C2)SCc2sc(N)c(C#N)c23)n1]

Compound 231 was prepared similarly to that of Ex. 4. LCMS calculated for $C_{31}H_{40}FN_9O_2PS_2$ (M+H)+ m/z=684.25; found: 684.2. $^1$H NMR (400 MHz, CD$_3$OD) δ 7.45 (dd, J=7.6, 3.2 Hz, 1H), 7.10-7.00 (m, 2H), 6.18-6.04 (m, 1H), 5.26 (d, J=53.6 Hz, 1H), 4.80-4.61 (m, 2H), 4.44-4.31 (m, 2H), 4.25-4.01 (m, 4H), 3.27-3.11 (m, 3H), 3.03-2.92 (m, 1H), 2.74 (s, 3H), 2.30-2.04 (m, 3H), 1.99-1.80 (m, 3H), 1.73 (d, J=13.2 Hz, 6H), 1.55 (d, J=7.2 Hz, 3H).

Compound 232. 2-amino-1'-[4-[1-(2-amino-6-dimethylphosphoryl-3-pyridyl)ethyl-methyl-amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

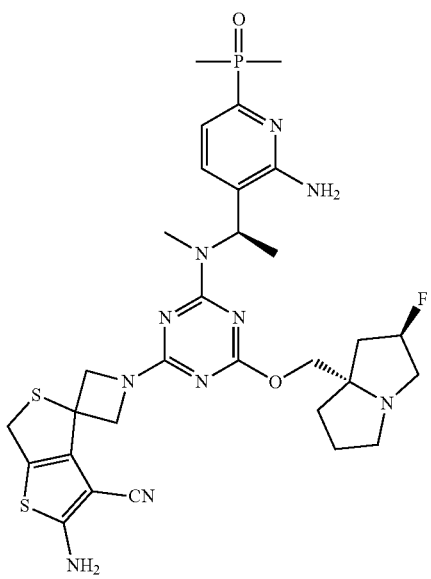 [SMILES: C[C@H](c1ccc(P(C)(C)=O)nc1N)N(C)c1nc(OC[C@@]23CCCN2C[C@H](F)C3)nc(N2CC3(C2)SCc2sc(N)c(C#N)c23)n1]

Compound 232 was prepared similarly to that of Ex. 4. LCMS calculated for $C_{30}H_{39}FN_{10}O_2PS_2$ (M+H)+ m/z=685.24; found: 685.3. $^1$H NMR (400 MHz, CD$_3$OD) δ 7.74 (dd, J=7.4, 3.9 Hz, 1H), 7.30-7.22 (m, 1H), 6.12-5.95 (m, 1H), 5.28 (d, J=52.2 Hz, 1H), 4.73-4.60 (m, 2H), 4.47-4.00 (m, 6H), 3.28-3.14 (m, 3H), 3.05-2.95 (m, 1H), 2.77 (d, J=4.0 Hz, 3H), 2.37-1.78 (m, 6H), 1.72 (d, J=13.6 Hz, 6H), 1.55 (d, J=6.9 Hz, 3H).

Compound 233. 2'-amino-1-(4-((1-(2-amino-6-methoxypyridin-3-yl)ethyl)(methyl)amino)-6-(((2R,7aS)-2-fluorotetrahydro-1H-pyrrolizin-7a(5H)-yl)methoxy)-1,3,5-triazin-2-yl)-6'H-spiro[azetidine-3,4'-thieno[3,4-b]thiophene]-3'-carbonitrile

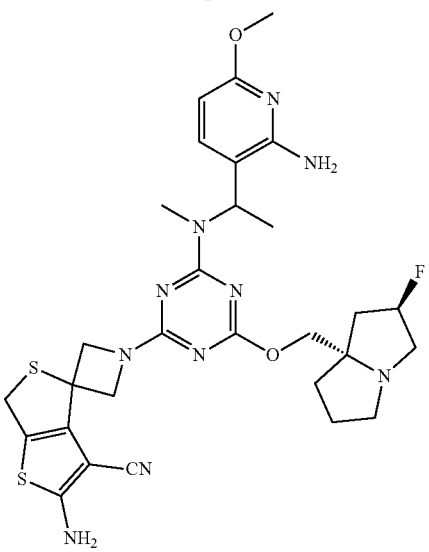 [SMILES: COc1ccc(C(C)N(C)c2nc(OC[C@@]34CCCN3C[C@H](F)C4)nc(N3CC4(C3)SCc3sc(N)c(C#N)c34)n2)c(N)n1]

Compound 233 was prepared similarly to that of Ex. 4. LCMS calculated for $C_{29}H_{36}FN_{10}O_2S_2$ (M+H)+ m/z=639.24; found: 639.3. $^1$H NMR (400 MHz, CD$_3$OD) δ 7.53 (d, J=8.2 Hz, 1H), 6.07 (d, J=8.2 Hz, 1H), 6.03-5.88 (m, 1H), 5.36-5.17 (m, 1H), 4.78-4.58 (m, 2H), 4.46-4.31 (m, 2H), 4.24-4.00 (m, 4H), 3.79 (s, 3H), 3.27-3.14 (m, 3H), 3.04-2.92 (m, 1H), 2.74 (s, 3H), 2.33-1.78 (m, 6H), 1.49 (d, J=6.9 Hz, 3H).

Compound 234. 1-[[4-(2-amino-3-cyano-spiro[6H-thieno[3,4-b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-ethyl-amino]cyclopropanecarboxamide

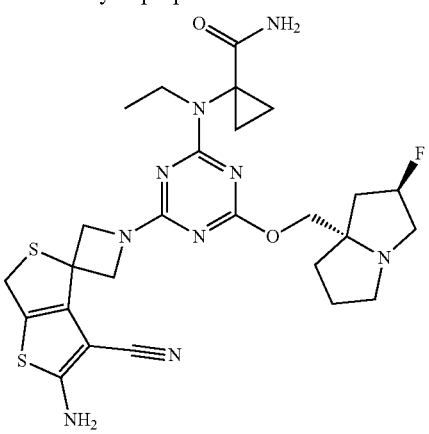

Compound 234 was prepared similarly to that of Ex. 12. LCMS calculated for $C_{26}H_{33}FN_9O_2S_2$ (M+H)$^+$ m/z=586.2, found: 586.2. $^1$H NMR (400 MHz, CD$_3$OD) δ 5.26 (d, J=55.6 Hz, 1H), 4.62 (d, J=10.0 Hz, 2H), 4.35 (d, J=9.6 Hz, 2H), 4.11 (m, 4H), 3.62 (m, 2H), 3.23-3.07 (m, 3H), 2.97 (d, J=5.2 Hz, 1H), 2.17 (m, 3H), 1.88 (m, 3H), 1.59 (m, 2H), 1.26 (m, 5H).

Compound 235. (2R)-2-[[4-(2-amino-3-cyano-spiro[6H-thieno[3,4-b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-ethyl-amino]propanamide

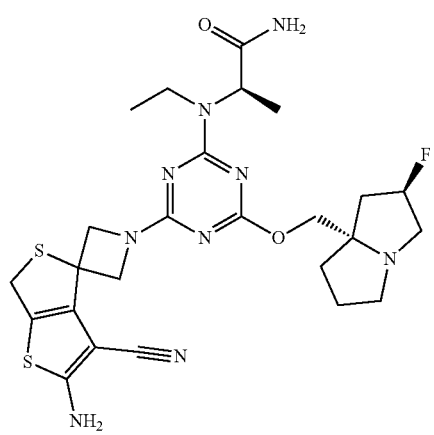 [SMILES: CCN(c1nc(OC[C@@]23CCCN2C[C@H](F)C3)nc(N2CC3(C2)SCc2sc(N)c(C#N)c23)n1)[C@H](C)C(N)=O]

Compound 235 was prepared similarly to that of Ex. 12. LCMS calculated for $C_{25}H_{33}FN_9O_2S_2$ (M+H)+ m/z=574.2, found: 574.1. 1H NMR (400 MHz, CD$_3$OD) δ 5.27 (d, J=54.0 Hz, 1H), 5.01 (s, 1H), 4.65 (s, 2H), 4.34 (m, 2H), 4.11 (m, 4H), 3.71 (s, 1H), 3.49 (m, 1H), 3.17 (m, 3H), 2.98 (m, 1H), 2.38-2.03 (m, 3H), 2.02-1.72 (m, 3H), 1.46 (d, J=7.2 Hz, 3H), 1.24 (t, J=7.0 Hz, 3H).

Example 12. Exemplary synthesis of 2-amino-1'-[4-[[(1R)-1-cyanoethyl]-ethyl-amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile; formic acid Compound 236

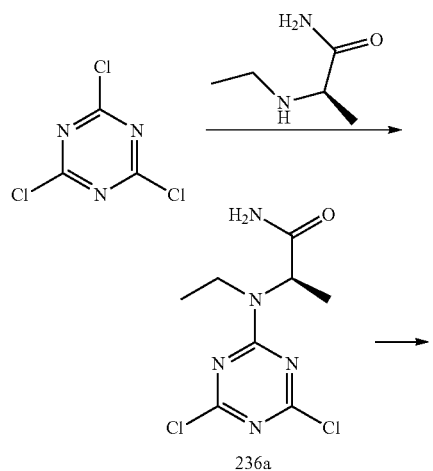

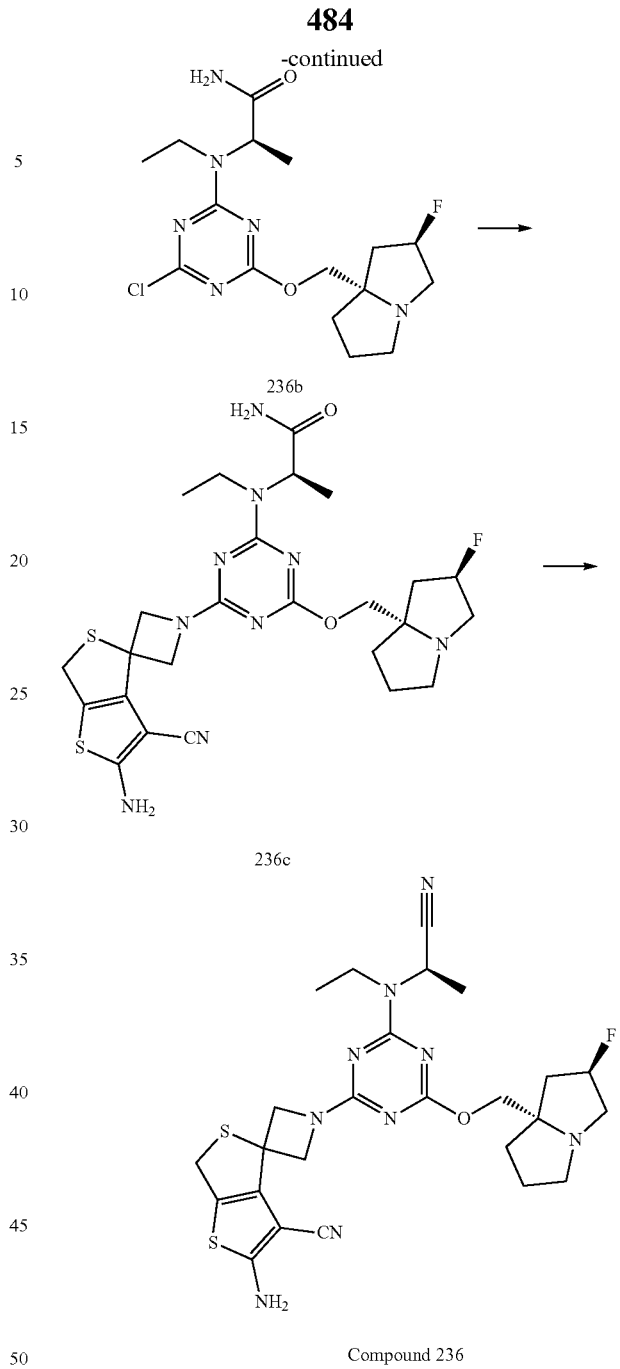

Compound 236

Step 1. Synthesis of (2R)-2-[(4,6-dichloro-1,3,5-triazin-2-yl)-ethyl-amino]propanamide (236a)

To a solution of (2R)-2-(ethylamino)propanamide (50.39 mg, 0.43 mmol) and cyanuric chloride (80 mg, 0.43 mmol) in DCM (10 mL) was added DIEA (0.3 mL, 1.74 mmol) at 0° C. The reaction was stirred at 0° C. for 1 h. The mixture was quenched with water (30 mL) at 0° C., extracted with EtOAc (40 mL×3). The combined organic layers were washed with brine (20 mL), dried over Na$_2$SO$_4$, filtered, and concentrated to afford the crude product. The crude product was purified by flash chromatography to give the desired product (2R)-2-[(4,6-dichloro-1,3,5-triazin-2-yl)-ethylamino]propanamide (56 mg, 0.2120 mmol, 48.874% yield) as white solid. LCMS calculated for $CH_{12}Cl_2N_5O$ $(M+H)^+$ m/z=264.2, found: 264.2

Step 2. Synthesis of (2R)-2-[[4-chloro-6-[[(2R,8S)-2-fluoro-1,2,3,5,6,7-hexahydropyrrolizin-8-yl]methoxy]-1,3,5-triazin-2-yl]-ethyl-amino]propanamide (236b)

To a solution of [(2R,8S)-2-fluoro-1,2,3,5,6,7-hexahydropyrrolizin-8-yl]methanol (45.21 mg, 0.28 mmol) and (2R)-2-[(4,6-dichloro-1,3,5-triazin-2-yl)-ethyl-amino]propanamide (50 mg, 0.19 mmol) in THF (5 mL) was added $Cs_2CO_3$ (123.37 mg, 0.38 mmol). The mixture was stirred at 50° C. for 5 h. (2R)-2-[[4-chloro-6-[[(2R,8S)-2-fluoro-1,2,3,5,6,7-hexahydropyrrolizin-8-yl]methoxy]-1,3,5-triazin-2-yl]-ethyl-amino]propanamide was obtained as THF solution. The reaction mixture was used directly for the next step. LCMS calculated for $C_{16}H_{25}ClFN_6O_2$ $(M+H)^+$ m/z=387.2, found: 387.1.

Step 3. Synthesis of (2R)-2-[[4-(2-amino-3-cyano-spiro[6H-thieno[3,4-b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-ethyl-amino]propanamide (236c)

To a solution of 2-aminospiro[6H-thieno[3,4-b]thiophene-4,3'-azetidine]-3-carbonitrile; methanesulfonic acid (90.41 mg, 0.28 mmol) and (2R)-2-[[4-chloro-6-[[(2R,8S)-2-fluoro-1,2,3,5,6,7-hexahydropyrrolizin-8-yl]methoxy]-1,3,5-triazin-2-yl]-ethyl-amino]propanamide (73 mg, 0.19 mmol) in THF (5 mL) was added DIEA (73.16 mg, 0.57 mmol). The mixture was heated at 70° C. for 5 h. Upon cooled down to RT, the mixture was quenched with $H_2O$ (20 mL) and extracted with EtOAc (20 mL×3), The combined organic layers were washed with brine (10 mL), dried over $Na_2SO_4$, filtered, and concentrated. The crude product was purified by flash chromatography (mobile phase A was 0.10% $NH_4HCO_3$ in $H_2O$, mobile phase B was ACN; Gradient from 5% to 95%) to give the desired product (2R)-2-[[4-(2-amino-3-cyano-spiro[6H-thieno[3,4-b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-ethyl-amino]propanamide (60 mg, 0.1046 mmol, 55.423% yield) as white solid. LCMS calculated for $C_{25}H_{33}FN_9O_2S_2$ $(M+H)^+$ m/z=574.2, found: 574.2.

Step 4. Synthesis of 2-amino-1'-[4-[[(1R)-1-cyano-ethyl]-ethyl-amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile (Compound 236)

To a solution of (2R)-2-[[4-(2-amino-3-cyano-spiro[6H-thieno[3,4-b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-ethyl-amino]propanamide (30 mg, 0.05 mmol) and Pyridine (0.02 mL, 0.21 mmol) in THF (5 mL) was added Trifluoroacetic Anhydride (0.01 mL, 0.1 mmol) at 0° C. The mixture was stirred at 0° C. for 2 h. The mixture was quenched with $H_2O$ (20 mL) and extracted with EtOAc (20 mL×3), The combined organic layers were washed with brine (10 mL), dried over $Na_2SO_4$, filtered and concentrated. The crude product was purified by Prep-HPLC (mobile phase A was 0.1% FA in $H_2O$, mobile phase B was ACN; Gradient from 5% to 95%) to give the desired product 2-amino-1'-[4-[[(1R)-1-cyanoethyl]-ethyl-amino]-6-[[(2R,8S)-2-fluoro-1,2,3,5,6,7-hexahydropyrrolizin-8-yl] methoxy]-1,3,5-triazin-2-yl]spiro[6H-thieno[3,4-b]thiophene-4,3'-azetidine]-3-carbonitrile; formic acid (3.8 mg, 0.0062 mmol, 11.804% yield) as white solid. LCMS calculated for $C_{25}H_{31}FN_9OS_2$ $(M+H)^+$ m/z=556.2, found: 556.0. $^1H$ NMR (400 MHz, $CD_3OD$) δ 5.65 (s, 1H), 5.34 (d, J=54.0 Hz, 1H), 4.66 (d, J=10.4 Hz, 2H), 4.38 (d, J=10.4 Hz, 2H), 4.34-4.13 (m, 2H), 4.06 (s, 2H), 3.68 (s, 2H), 3.50-3.34 (m, 3H), 3.11 (d, J=5.6 Hz, 1H), 2.28 (m, 3H), 1.99 (m, 3H), 1.61 (d, J=7.2 Hz, 3H), 1.28 (t, J=6.8 Hz, 3H).

Compound 237. 2-amino-1'-[4-[cyanomethyl(ethyl)amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

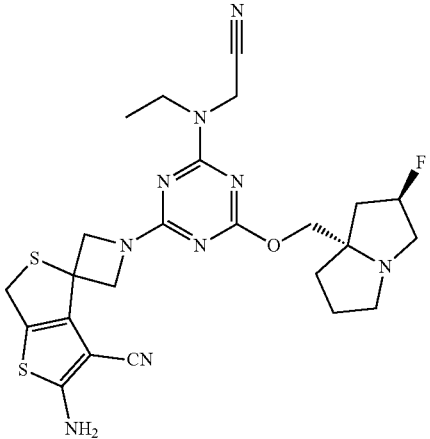 [SMILES: CCN(CC#N)c1nc(OC[C@@]23CCCN2C[C@H](F)C3)nc(N2CC3(C2)SCc2sc(N)c(C#N)c23)n1]

Compound 237 was prepared similarly to that of Ex. 12. LCMS calculated for $C_{24}H_{29}FN_9OS_2$ $(M+H)^+$ m/z=542.1, found: 542.1. $^1H$ NMR (400 MHz, $CD_3OD$) δ: 5.30 (d, J=53.6 Hz, 1H), 4.70-4.50 (m, 4H), 4.38-4.33 (m, 2H), 4.27-4.12 (m, 2H), 4.06-4.02 (m, 2H), 3.75-3.70 (m, 2H), 3.27-3.22 (m, 3H), 3.12-3.01 (m, 1H), 2.32-2.05 (m, 3H), 2.01-1.85 (m, 3H), 1.24-1.21 (m, 3H).

Compound 238. 2-amino-1'-[4-[(1-cyanocyclopropyl)-ethyl-amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

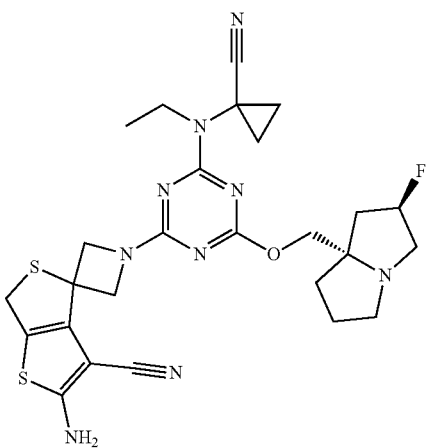 [SMILES: CCN(c1nc(OC[C@@]23CCCN2C[C@H](F)C3)nc(N2CC3(C2)SCc2sc(N)c(C#N)c23)n1)C1(C#N)CC1]

Compound 238 was prepared similarly to that of Ex. 12. LCMS calculated for $C_{26}H_{31}FN_9OS_2$ (M+H)+ m/z=568.2, found: 568.2. ¹H NMR (400 MHz, CD₃OD) δ 5.26 (d, J=53.2 Hz, 1H), 4.69 (dd, J=21.2, 10.4 Hz, 2H), 4.38 (d, J=10.0 Hz, 2H), 4.20 (dd, J=22.0, 15.2 Hz, 2H), 4.06 (s, 2H), 3.69 (s, 2H), 3.21 (d, J=6.0 Hz, 2H), 3.14 (s, 1H), 3.04-2.93 (m, 1H), 2.33-2.06 (m, 3H), 2.00-1.77 (m, 3H), 1.64 (s, 2H), 1.44 (s, 2H), 1.28 (t, J=7.2 Hz, 3H).

Compound 239. 2-amino-1'-[4-[(1-cyanocyclopropyl)methyl-(2-hydroxyethyl)amino]-6-[[(2R,8S)-2-fluoro-1,2,3,5,6,7-hexahydropyrrolizin-8-yl]methoxy]-1,3,5-triazin-2-yl]spiro[6H-thieno[2,3-c]thiophene-4,3'-azetidine]-3-carbonitrile

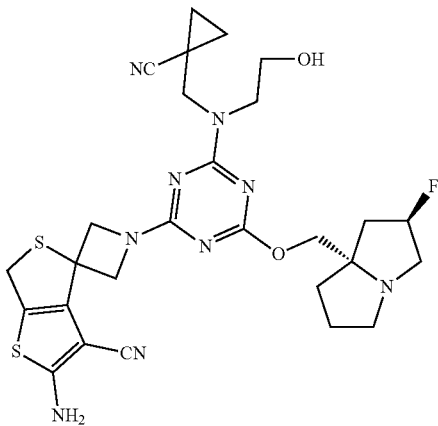 [SMILES: N#Cc1c(N)sc2c1C1(CN(c3nc(OC[C@@]45CCCN4C[C@H](F)C5)nc(N(CCO)CC4(C#N)CC4)n3)C1)SC2]

Compound 239 was prepared similarly to that of Ex. 12 as a formate salt. LCMS calculated for $C_{27}H_{33}FN_9O_2S_2$ (M+H)+ m/z=598.2, found: 598.3. ¹H NMR (400 MHz, CD₃OD) δ 5.51-5.26 (m, 1H), 4.74-4.59 (m, 2H), 4.44-4.32 (m, 3H), 4.31-4.21 (m, 1H), 4.16-3.97 (m, 3H), 3.94-3.67 (m, 5H), 3.61-3.42 (m, 3H), 3.25-3.17 (m, 1H), 2.44-1.89 (m, 6H), 1.32-1.18 (m, 4H).

Compound 240. 2-amino-1'-[4-[(1-cyanocyclopropyl)-(2-hydroxyethyl)amino]-6-[[rac-(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

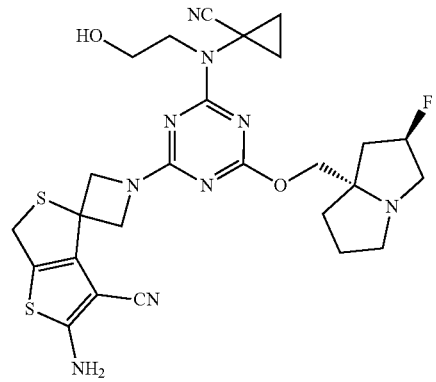 [SMILES: N#Cc1c(N)sc2c1C1(CN(c3nc(OC[C@@]45CCCN4C[C@H](F)C5)nc(N(CCO)C4(C#N)CC4)n3)C1)SC2]

Compound 240 was prepared similarly to that of Ex. 12. LCMS calculated for $C_{26}H_{31}FN_9O_2S_2$ (M+H)+ m/z=584.2, found: 584.2. ¹H NMR (400 MHz, CD₃OD) δ 5.33 (d, J=52.0 Hz, 1H), 4.72-4.65 (m, 2H), 4.40-4.23 (m, 4H), 4.06 (s, 2H), 3.81-3.72 (m, 4H), 3.39-3.37 (m, 3H), 3.13-3.06 (m, 1H), 2.36-1.90 (m, 6H), 1.65-1.54 (m, 4H).

Compound 241. 2-amino-1'-[4-[(1-cyanocyclopropyl)methyl-ethyl-amino]-6-[[(2R,8S)-2-fluoro-1,2,3,5,6,7-hexahydropyrrolizin-8-yl]methoxy]-1,3,5-triazin-2-yl]spiro[6H-thieno[2,3-c]thiophene-4,3'-azetidine]-3-carbonitrile

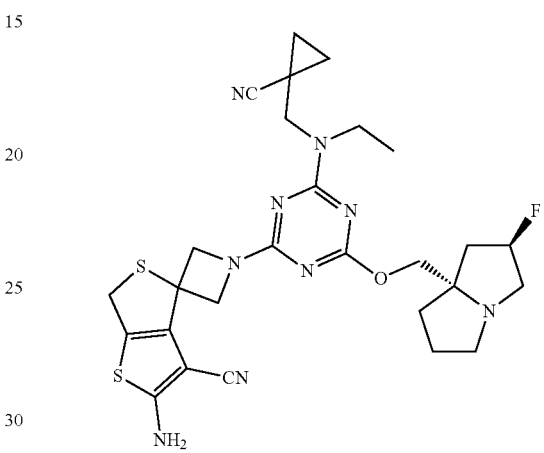

Compound 241 was prepared similarly to that of Ex. 12 as a hydrochloride salt.
LCMS calculated for $C_{27}H_{33}FN_9OS_2$ (M+H)+ m/z=582.2, found: 582.2. ¹H NMR (400 MHz, CD₃OD) δ 5.73-5.39 (m, 1H), 4.82-4.60 (m, 4H), 4.60-4.49 (m, 2H), 4.08 (s, 2H), 4.05-3.98 (m, 1H), 3.99-3.60 (m, 6H), 3.53-3.39 (m, 1H), 2.76-2.50 (m, 2H), 2.48-2.26 (m, 3H), 2.24-2.07 (m, 1H), 1.38-1.20 (m, 7H).

Compound 242. 2-amino-1'-[4-[cyanomethyl(2,2-difluoroethyl)amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

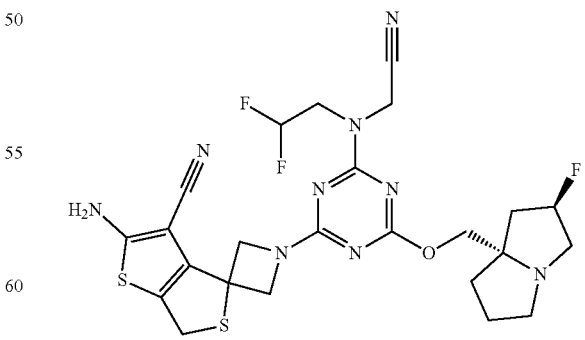

Compound 242 was prepared similarly to that of Ex. 12 as a formate salt. LCMS calculated for $C_{24}H_{27}F_3N_9OS_2$ (M+H)+ m/z=578.7, found: 578.1. ¹H NMR (400 MHz, CD₃OD) δ 6.11 (t, J=56.0 Hz, 1H), 5.33 (d, J=53.6 Hz, 1H), 4.79-4.51 (m, 4H), 4.50-4.36 (m, 2H), 4.37-4.13 (m, 2H), 4.11-3.95 (m, 4H), 3.56-3.33 (m, 3H), 3.18-3.03 (m, 1H), 2.45-2.23 (m, 2H), 2.22-2.11 (m, 1H), 2.06-2.01 (m, 2H), 1.97-1.70 (m, 1H).

Compound 243. 2-amino-1'-[4-[cyanomethyl(prop-2-ynyl)amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

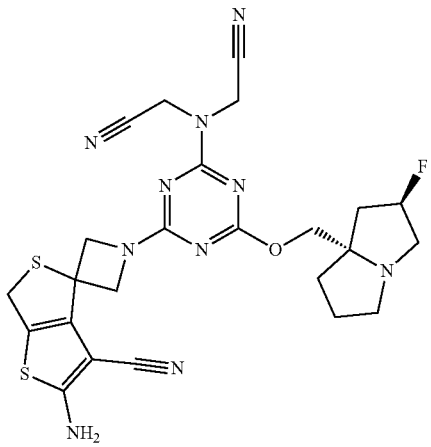 [SMILES: N#CCN(CC#N)c1nc(OC[C@@]23CCCN2C[C@H](F)C3)nc(N2CC3(C2)SCc2sc(N)c(C#N)c23)n1]

Compound 243 was prepared similarly to that of Ex. 12. LCMS calculated for $C_{25}H_{27}FN_9OS_2$ (M+H)$^+$ m/z=552.1, found: 552.0. $^1$H NMR (400 MHz, CD$_3$OD) δ 5.26 (d, J=52.8 Hz, 1H), 4.65 (m, 6H), 4.40 (t, J=12.0 Hz, 2H), 4.25-4.17 (m, 1H), 4.12 (s, 1H), 4.06 (s, 2H), 3.20 (dd, J=16.4, 8.4 Hz, 2H), 3.14 (s, 1H), 2.97 (dd, J=14.8, 9.2 Hz, 1H), 2.75 (t, J=2.4 Hz, 1H), 2.16 (m, 3H), 2.01-1.75 (m, 3H).

Compound 244. 2-amino-1'-[4-[cyanomethyl(1-methylprop-2-ynyl)amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

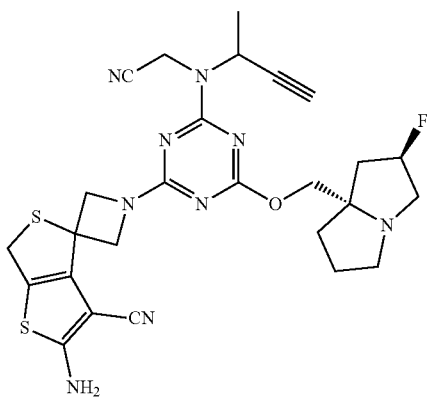 [SMILES: C#CC(C)N(CC#N)c1nc(OC[C@@]23CCCN2C[C@H](F)C3)nc(N2CC3(C2)SCc2sc(N)c(C#N)c23)n1]

Compound 244 was prepared similarly to that of Ex. 12. LCMS calculated for $C_{26}H_{29}FN_9OS_2$ (M+H)$^+$ m/z=566.2, found: 566.1. $^1$H NMR (400 MHz, CD$_3$OD) δ 5.82-5.68 (m, 1H), 5.41-5.15 (m, 1H), 4.77-4.63 (m, 2H), 4.62-4.46 (m, 2H), 4.48-4.35 (m, 2H), 4.32-4.01 (m, 4H), 3.28-3.10 (m, 3H), 3.07-2.83 (m, 2H), 2.35-2.05 (m, 3H), 2.04-1.80 (m, 3H), 1.58-1.38 (m, 3H).

Compound 245. 2-amino-1'-[4-[cyanomethyl(1H-triazol-4-ylmethyl)amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

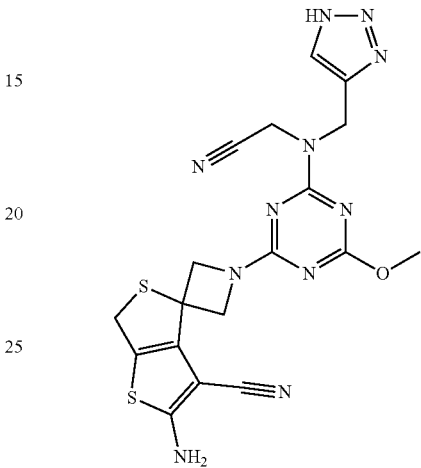

Compound 245 was prepared similarly to that of Ex. 12 as a formate salt. LCMS calculated for $C_{25}H_{28}FN_{12}OS_2$ (M+H)$^+$ m/z=595.2, found: 595.1. $^1$H NMR (400 MHz, CD$_3$OD) δ 7.80 (s, 1H), 5.45 (d, J=53.2 Hz, 1H), 5.03 (s, 3H), 4.68 (m, 4H), 4.52-4.29 (m, 4H), 4.06 (s, 2H), 3.64 (m, 3H), 2.60-2.34 (m, 2H), 2.19 (m, 4H).

Compound 246. 2'-amino-1-(4-(((R)-1-(2-amino-pyridin-3-yl)ethyl)(cyanomethyl)amino)-6-(((2R,7aS)-2-fluorotetrahydro-TH-pyrrolizin-7a(5H)-yl)methoxy)-1,3,5-triazin-2-yl)-6'H-spiro[azetidine-3,4'-thieno[3,4-b]thiophene]-3'-carbonitrile

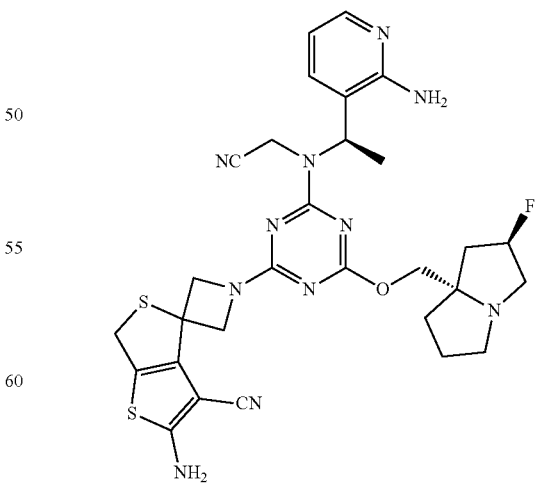

Compound 246 was prepared similarly to that of Ex. 4. LCMS calculated for $C_{29}H_{33}FN_{11}OS_2$ (M+H)$^+$ m/z=634.7;

found: 634.6. ¹H NMR (400 MHz, CD₃OD) δ 7.90 (d, J=5.0 Hz, 1H), 7.73 (dd, J=7.4, 1.0 Hz, 1H), 6.72 (dd, J=7.5, 5.1 Hz, 1H), 6.16-5.96 (m, 1H), 5.25 (d, J=53.8 Hz, 1H), 4.81-4.55 (m, 2H), 4.51-4.37 (m, 2H), 4.29-4.00 (m, 6H), 3.25-3.10 (m, 3H), 3.04-2.92 (m, 1H), 2.35-1.78 (m, 6H), 1.62 (d, J=6.8 Hz, 3H).

Compound 247. 2-amino-1'-[4-[(1-cyanocyclopropyl)-prop-2-ynyl-amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

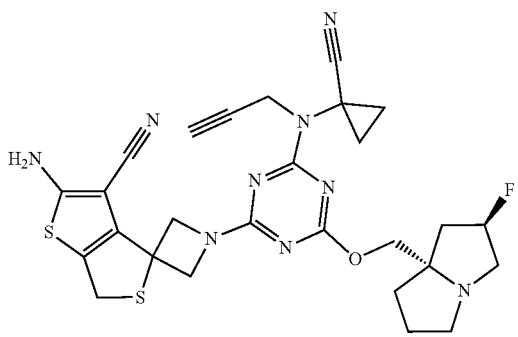 [SMILES: C#CCN(c1nc(OC[C@@]23CCCN2C[C@H](F)C3)nc(N2CC3(C2)SCc2sc(N)c(C#N)c23)n1)C1(C#N)CC1]

Compound 247 was prepared similarly to that of Ex. 12 as a formate salt. LCMS calculated for C₂₇H₂₉FN₉OS₂ (M+H)⁺ m/z=578.7, found: 578.1. ¹H NMR (400 MHz, CD₃OD) δ 5.33 (d, J=54.4 Hz, 1H), 4.79-4.60 (m, 2H), 4.58-4.38 (m, 4H), 4.38-4.16 (m, 2H), 4.06 (s, 2H), 3.44-3.32 (m, 3H), 3.18-2.97 (m, 1H), 2.78-2.60 (m, 1H), 2.49-2.22 (m, 2H), 2.21-2.11 (m, 1H), 2.10-1.98 (m, 2H), 1.97-1.81 (m, 1H), 1.77-1.63 (m, 2H), 1.59-1.48 (m, 2H)

Compound 248. 2-amino-1'-[4-[[(2R,8S)-2-fluoro-1,2,3,5,6,7-hexahydropyrrolizin-8-yl]methoxy]-6-[1-(1,2,4-triazole-1-carbonyl)-1,7-diazaspiro[3.4]octan-7-yl]-1,3,5-triazin-2-yl]spiro[6H-thieno[2,3-c]thiophene-4,3'-azetidine]-3-carbonitrile

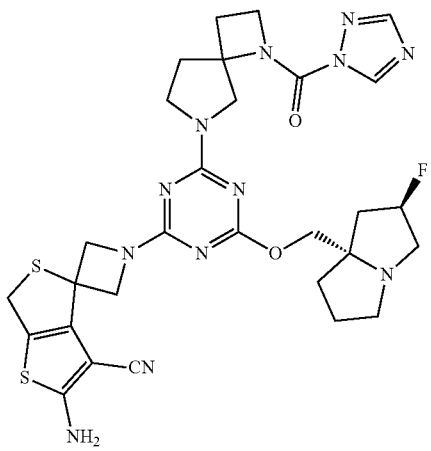 [SMILES: N#Cc1c(N)sc2c1C1(CN(c3nc(OC[C@@]45CCCN4C[C@H](F)C5)nc(N4CCC5(CCN5C(=O)n5cncn5)C4)n3)C1)SC2]

Compound 248 was prepared similarly to that of Ex. 12 as a formate salt. LCMS calculated for C₂₉H₃₄FN₁₂O₂S₂ (M+H)⁺ m/z=665.2, found: 665.2. ¹H NMR (400 MHz, CD³OD) δ 9.04-8.95 (m, 1H), 8.13-8.03 (m, 1H), 5.51-5.27 (m, 1H), 4.73-4.57 (m, 4H), 4.42-4.28 (m, 4H), 4.11-4.03 (m, 2H), 3.99-3.77 (m, 2H), 3.69-3.45 (m, 4H), 3.25-3.14 (m, 1H), 2.93-2.78 (m, 1H), 2.59-1.88 (m, 10H).

Compound 249. 2-amino-1'-[4-[(2-cyano-1-methyl-ethyl)-methyl-amino]-6-[[(2R,8S)-2-fluoro-1,2,3,5,6,7-hexahydropyrrolizin-8-yl]methoxy]-1,3,5-triazin-2-yl]spiro[6H-thieno[2,3-c]thiophene-4,3'-azetidine]-3-carbonitrile

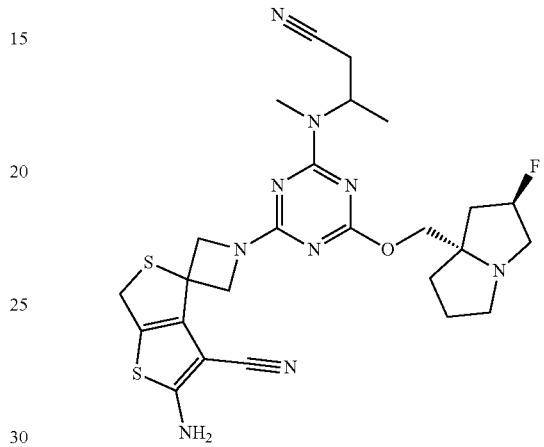

Compound 249 was prepared similarly to that of Ex. 12 as a formate salt. LCMS calculated for C₂₅H₃₁FN₉OS₂ (M+H)⁺ m/z=556.2, found: 556.3. ¹H NMR (400 MHz, CD₃OD) δ 5.72-5.41 (m, 1H), 5.41-5.15 (m, 1H), 4.84-4.51 (m, 6H), 4.13-4.04 (m, 2H), 4.04-3.74 (m, 3H), 3.52-3.40 (m, 1H), 3.23-3.08 (m, 3H), 2.96-2.76 (m, 1H), 2.78-2.27 (m, 6H), 2.26-2.08 (m, 1H), 1.45-1.25 (m, 3H).

Compound 250. 2-amino-1'-[4-[cyanomethyl-[1-(1H-triazol-4-yl)ethyl]amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

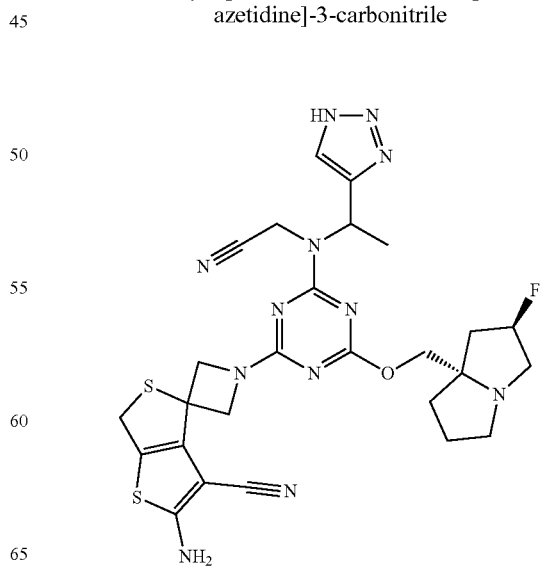

Compound 250 was prepared similarly to that of Ex. 12 as a formate salt. LCMS calculated for $C_{26}H_{30}FN_{12}OS_2$ (M+H)$^+$ m/z=609.2, found: 609.1. $^1$H NMR (400 MHz, CD$_3$OD) δ 7.80 (s, 1H), 6.29 (s, 1H), 5.38 (d, J=51.6 Hz, 1H), 4.69 (m, 2H), 4.38 (m, 6H), 4.06 (s, 2H), 3.45 (m, 3H), 3.22-3.06 (m, 1H), 2.49-2.16 (m, 3H), 2.03 (m, 3H), 1.70 (d, J=7.2 Hz, 3H).

Compound 251. 2-amino-1'-[4-[(1-cyanocyclopropyl)-(cyanomethyl)amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

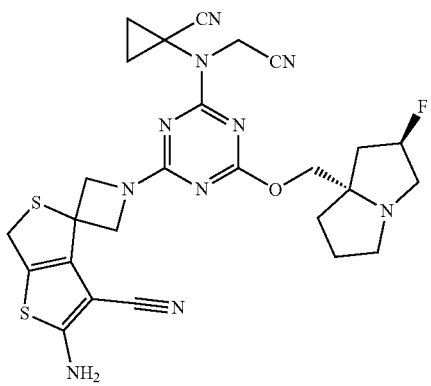 [SMILES: N#CCN(c1nc(OC[C@@]23CCCN2C[C@H](F)C3)nc(N2CC3(C2)SCc2sc(N)c(C#N)c23)n1)C1(C#N)CC1]

Compound 251 was prepared similarly to that of Ex. 12. LCMS calculated for $C_{26}H_{28}FN_{10}OS_2$ (M+H)$^+$ m/z=579.2, found: 579.1. $^1$H NMR (400 MHz, CD$_3$OD) δ 5.26 (d, J=56.0 Hz, 1H), 4.78-4.60 (m, 4H), 4.50-4.36 (m, 2H), 4.32-4.12 (m, 2H), 4.06 (s, 2H), 3.25-3.17 (m, 2H), 3.17-3.08 (m, 1H), 2.99 (dd, J=14.8, 9.6 Hz, 1H), 2.35-2.05 (m, 3H), 2.01-1.76 (m, 3H), 1.72 (s, 2H), 1.57 (s, 2H).

Example 13. Exemplary synthesis of 2-amino-1'-[4-[(3R)-3-hydroxy-3-methyl-1-piperidyl]-6-[[(3SR,8RS)-3-[[6-(trifluoromethyl)pyrimidin-4-yl]oxymethyl]-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile (Compound 252)

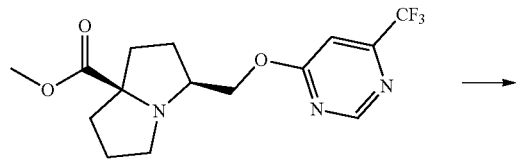

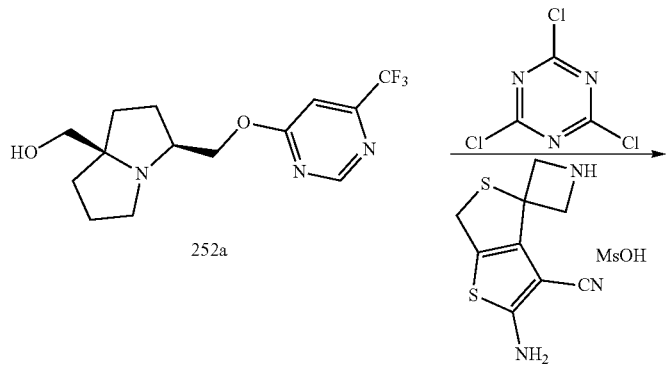

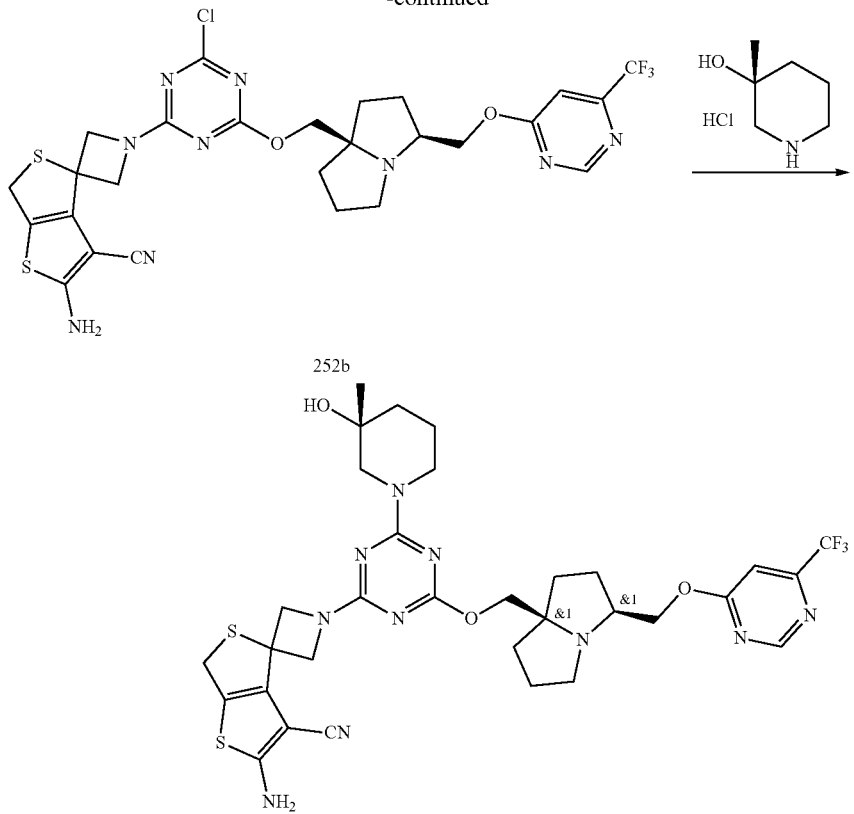

Compound 252

Step 1. Synthesis of [(3S,8R)-3-[[6-(trifluoromethyl)pyrimidin-4-yl]oxymethyl]-1,2,3,5,6,7-hexahydropyrrolizin-8-yl]methanol (252a). To a solution of methyl (3S,8R)-3-[[6-(trifluoromethyl)pyrimidin-4-yl]oxymethyl]-1,2,3,5,6,7-hexahydropyrrolizine-8-carboxylate (308 mg, 0.892 mmol) in THF (2 mL) was added LiAlH$_4$ (50.8 mg, 1.34 mmol) at −20° C. The reaction was stirred at −20° C. for 20 min. Then the mixture was quenched with Na$_2$SO$_4$·10H$_2$O, and was stirred at RT for 15 min. The mixture was filtered through celite. The filtrate was concentrated and purified by flash chromatography to afford [(3S,8R)-3-[[6-(trifluoromethyl)pyrimidin-4-yl]oxymethyl]-1,2,3,5,6,7-hexahydropyrrolizin-8-yl]methanol (157 mg, 0.495 mmol, 55.5% yield) as an oil. LCMS calculated for C$_{14}$H$_{19}$F$_3$N$_3$O$_2$ (M+H)$^+$ m/z=318.1; found: 318.4.

Step 2. Synthesis of 2-amino-1'-[4-chloro-6-[[(3S,8R)-3-[[6-(trifluoromethyl)pyrimidin-4-yl]oxymethyl]-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile (252b). To the solution of [(3S,8R)-3-[[6-(trifluoromethyl)pyrimidin-4-yl]oxymethyl]-1,2,3,5,6,7-hexahydropyrrolizin-8-yl]methanol (50.0 mg, 0.160 mmol) in THF (2 mL) was added LiHMDS (0.160 mL, 0.160 mmol, 1M in THF) at −70° C. under N$_2$. The mixture was stirred at −70° C. for 0.5 h, followed by the addition of cyanuric chloride (29.0 mg, 0.160 mmol). The reaction was stirred for another 2 h before the addition of 2-aminospiro[6H-thieno[3,4-b]thiophene-4,3'-azetidine]-3-carbonitrile; methanesulfonic acid (45.2 mg, 0.140 mmol) and DIEA (61.0 mg, 0.470 mmol). The mixture was allowed to warm to room temperature and stirred overnight. The solvent was removed in vacuo and the residue was purified by flash column chromatography to afford 2-amino-1'-[4-chloro-6-[[(3S,8R)-3-[[6-(trifluoromethyl)pyrimidin-4-yl]oxymethyl]-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile (45.0 mg, 0.0690 mmol, 43.9% yield) as a brown oil. LCMS calculated for C$_{26}$H$_{26}$ClF$_3$N$_9$O$_2$S$_2$ (M+H)$^+$ m/z=652.1; found: 652.2/654.2.

Step 3. Synthesis of 2-amino-1'-[4-[(3R)-3-hydroxy-3-methyl-1-piperidyl]-6-[[(3SR,8RS)-3-[[6-(trifluoromethyl)pyrimidin-4-yl]oxymethyl]-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile (Compound 252). The mixture of 2-amino-1'-[4-chloro-6-[[(3S,8R)-3-[[6-(trifluoromethyl)pyrimidin-4-yl]oxymethyl]-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile (45.0 mg, 0.0700 mmol), (3R)-3-methylpiperidin-3-ol; hydrochloride (15.7 mg, 0.100 mmol) and DIEA (26.8 mg, 0.210 mmol) in DMSO (2 mL) was stirred at 25° C. for 2 h under N$_2$. Then the mixture was filtered and the filtrate was purified by Prep-HPLC (5 uM, 50×150 mm) with mobile phase (MeCN in 0.1% NH$_4$HCO$_3$ H$_2$O) to afford 2-amino-1'-[4-[(3R)-3-hydroxy-3-methyl-1-piperidyl]-6-[[(3SR,8RS)-3-[[6-(trifluoromethyl)pyrimidin-4-yl]oxymethyl]-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile (34.9 mg, 0.0477 mmol, 69.2% yield) as a white solid. LCMS calculated for C$_{32}$H$_{38}$F$_3$N$_{10}$O$_3$S$_2$ (M+H)$^+$ m/z=731.3; found: 731.7

$^1$H NMR (400 MHz, CD$_3$OD) δ 8.86 (s, 1H), 7.27 (s, 1H), 4.69-4.61 (m, 2H), 4.48-4.38 (m, 2H), 4.37-4.30 (m, 2H), 4.17-3.99 (m, 4H), 3.90-3.78 (m, 1H), 3.78-3.69 (m, 1H), 3.68-3.53 (m, 2H), 3.25-3.15 (m, 1H), 3.10-3.00 (m, 1H), 2.91-2.81 (m, 1H), 2.23-2.04 (m, 2H), 1.96-1.76 (m, 5H), 1.73-1.60 (m, 4H), 1.58-1.47 (m, 1H), 1.18 (s, 3H).
Example 14. Synthesis of 2-amino-1'-[4-[(3R)-3-hydroxy-3-methyl-1-piperidyl]-6-[[(3SR,8SR)-3-[[6-(trifluoromethyl)pyrimidin-4-yl]oxymethyl]-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile (Compound 253)
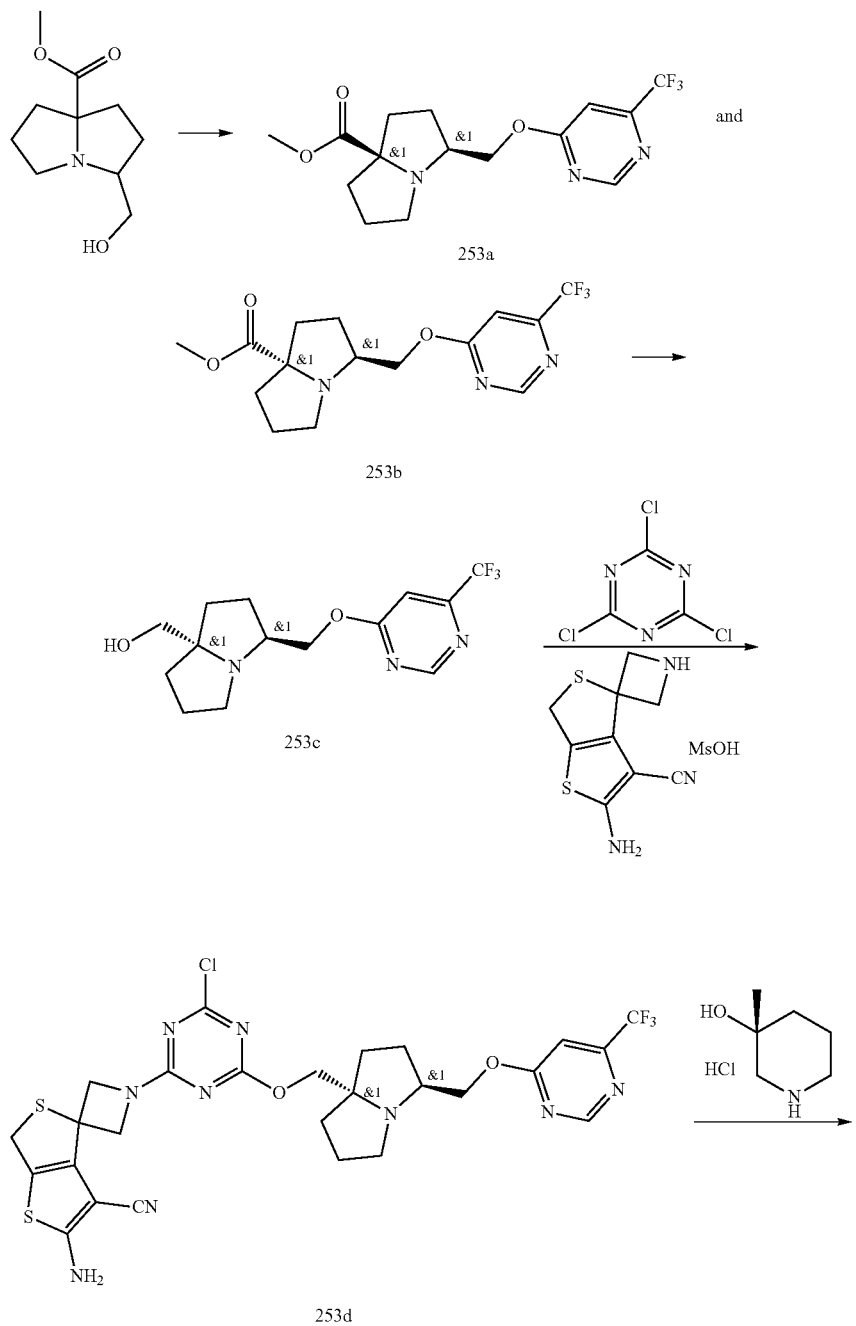

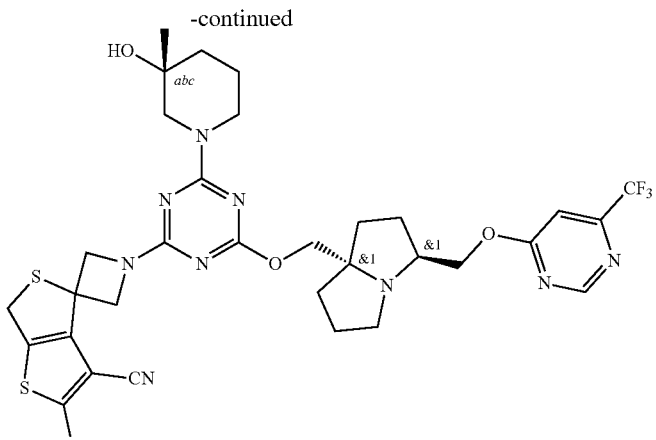

Compound 253

Step 1. Synthesis of methyl (3S,8R)-3-[[6-(trifluoromethyl)pyrimidin-4-yl]oxymethyl]-1,2,3,5,6,7-hexahydropyrrolizine-8-carboxylate (253a) & methyl (3S,8S)-3-[[6-(trifluoromethyl)pyrimidin-4-yl]oxymethyl]-1,2,3,5,6,7-hexahydropyrrolizine-8-carboxylate (253b). To a solution of methyl 3-(hydroxymethyl)-1,2,3,5,6,7-hexahydropyrrolizine-8-carboxylate (330 mg, 1.66 mmol) in THF (6 mL) was added sodium hydride (99.4 mg, 2.48 mmol) slowly at 0° C. and then was stirred at room temperature for 30 min. The mixture was cooled to 0° C. and 4-chloro-6-(trifluoromethyl)pyrimidine (454 mg, 2.48 mmol) was added. The reaction was allowed to warm to RT and was stirred for 3 h. The mixture was quenched with saturated aq. NH$_4$Cl and extracted with EtOAc (30 mL×3). The combined extracts were washed with brine, dried over Na$_2$SO$_4$ and concentrated in vacuo. The residue was purified by flash chromatography to afford methyl (3S,8R)-3-[[6-(trifluoromethyl)pyrimidin-4-yl]oxymethyl]-1,2,3,5,6,7-hexahydropyrrolizine-8-carboxylate (90.0 mg, 0.261 mmol, 15.7% yield) and methyl (3S,8S)-3-[[6-(trifluoromethyl)pyrimidin-4-yl]oxymethyl]-1,2,3,5,6,7-hexahydropyrrolizine-8-carboxylate (120 mg, 0.347 mmol, 21.0% yield) as white solid. LCMS calculated for C$_{15}$H$_{19}$F$_3$N$_3$O$_3$(M+H)$^+$ m/z=346.1; found: 346.2.

Step 2. Synthesis of [(3S,8S)-3-[[6-(trifluoromethyl)pyrimidin-4-yl]oxymethyl]-1,2,3,5,6,7-hexahydropyrrolizin-8-yl]methanol (253c). To a solution of methyl (3S,8S)-3-[[6-(trifluoromethyl)pyrimidin-4-yl]oxymethyl]-1,2,3,5,6,7-hexahydropyrrolizine-8-carboxylate (194 mg, 0.562 mmol) in THF (2 mL) was added LiAlH$_4$ (32.0 mg, 0.843 mmol) at −20° C. and the mixture was stirred at −20° C. for 20 min. The reaction was quenched with Na$_2$SO$_4$ 10H$_2$O and stirred for 15 min. The mixture was filtered through celite. The filtrate was concentrated in vacuo and the residue was purified by Prep-HPLC (5 uM, 50×150 mm, eluted with MeCN in 0.1% NH$_4$HCO$_3$ H$_2$O) to afford the product [(3S,8S)-3-[[6-(trifluoromethyl)pyrimidin-4-yl]oxymethyl]-1,2,3,5,6,7-hexahydropyrrolizin-8-yl]methanol (108 mg, 0.303 mmol, 53.9% yield) as an white solid. LCMS calculated for C$_{14}$H$_{19}$F$_3$N$_3$O$_2$ (M+H)$^+$ m/z=318.1; found: 318.6.

Step 3. Synthesis of 2-amino-1'-[4-chloro-6-[[(3S,8S)-3-[[6-(trifluoromethyl)pyrimidin-4-yl]oxymethyl]-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile (253d). To the solution of [(3S,8S)-3-[[6-(trifluoromethyl)pyrimidin-4-yl]oxymethyl]-1,2,3,5,6,7-hexahydropyrrolizin-8-yl]methanol (99.8 mg, 0.310 mmol) in THF (2 mL) was added LiHMDS (0.310 mL, 0.31 mmol, 1M in THF) at −70° C. The mixture was stirred at −70° C. for 0.5 h followed by the addition of cyanuric chloride (58.0 mg, 0.310 mmol). The reaction was stirred at −70° C. for 2 h. 2-aminospiro[6H-thieno[3,4-b]thiophene-4,3'-azetidine]-3-carbonitrile; methanesulfonic acid (90.4 mg, 0.280 mmol) and DIEA (122 mg, 0.940 mmol) were added. The reaction was warmed to room temperature and stirred overnight. The solvent was removed in vacuo and the residue was purified by flash chromatography (MeOH in DCM, 0 to 10%) to afford 2-amino-1'-[4-chloro-6-[[(3S,8S)-3-[[6-(trifluoromethyl)pyrimidin-4-yl]oxymethyl]-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile (110 mg, 0.169 mmol, 53.6% yield) as a pink solid. LCMS calculated for C$_{26}$H$_{26}$ClF$_3$N$_9$O$_2$S$_2$ (M+H)$^+$ m/z=652.1; found: 651.9/653.9.

Step 4. Synthesis of 2-amino-1'-[4-[(3R)-3-hydroxy-3-methyl-1-piperidyl]-6-[[(3SR,8SR)-3-[[6-(trifluoromethyl)pyrimidin-4-yl]oxymethyl]-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile (Compound 253). The mixture of 2-amino-1'-[4-chloro-6-[[(3S,8S)-3-[[6-(trifluoromethyl)pyrimidin-4-yl]oxymethyl]-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile (50.0 mg, 0.0800 mmol), (3R)-3-methylpiperidin-3-ol; hydrochloride (17.4 mg, 0.120 mmol) and DIEA (29.7 mg, 0.230 mmol) in DMSO (2 mL) was stirred at 25° C. for 2 h under N$_2$. Then the mixture was filtered and the filtrate was purified by Prep-HPLC (5 uM, 50×150 mm, eluted with MeCN in 0.1% NH$_4$HCO$_3$ H$_2$O) to afford 2-amino-1'-[4-[(3R)-3-hydroxy-3-methyl-1-piperidyl]-6-[[(3SR,8SR)-3-[[6-(trifluoromethyl)pyrimidin-4-yl]oxymethyl]-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile (35.0 mg, 0.0474 mmol, 61.8% yield) as a white solid. LCMS calculated for C$_{32}$H$_{38}$F$_3$N$_{10}$O$_3$S$_2$ (M+H)$^+$ m/z=731.3; found: 731.3. $^1$H NMR (400 MHz, CD$_3$OD) δ 8.89 (s, 1H), 7.30 (s, 1H), 4.72-4.70 (m, 2H), 4.66-4.64 (m, 2H), 4.34-4.31 (m, 2H), 4.25-4.04 (m, 2H), 4.04 (s, 2H), 3.90-3.50 (m, 5H), 2.91-2.83 (m, 2H), 2.15-1.64 (m, 12H), 1.18 (s, 3H).

Compound 254. 2-amino-1'-[4-[(2-cyano-1-methyl-ethyl)-ethyl-amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile; formic acid

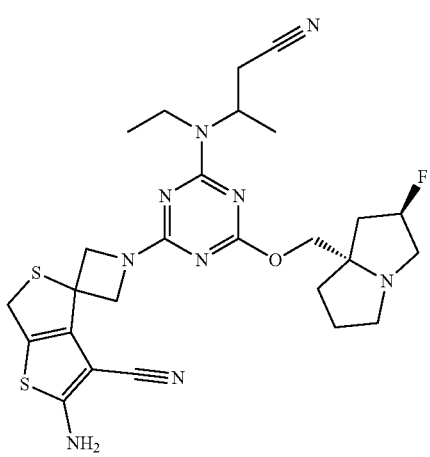 [SMILES: CCN(c1nc(OC[C@@]23CCCN2C[C@H](F)C3)nc(N2CC3(C2)SCc2sc(N)c(C#N)c23)n1)C(C)CC#N]

Compound 254 was prepared similarly to that of Ex. 12. LCMS calculated for $C_{26}H_{33}FN_9OS_2$ (M+H)+ m/z=570.2, found: 570.2. $^1$H NMR (400 MHz, CD$_3$OD) δ 5.53-5.24 (m, 1H), 5.13-4.86 (m, 2H), 4.77-4.57 (m, 2H), 4.43-4.30 (m, 3H), 4.28-4.18 (m, 1H), 4.06 (s, 2H), 3.69-3.42 (m, 5H), 3.25-3.10 (m, 1H), 2.86-2.68 (m, 1H), 2.53-1.88 (m, 6H), 1.54-1.33 (m, 3H), 1.28-1.18 (m, 3H).

Example 15. Exemplary synthesis of 2-amino-1'-[4-[[(2R,8S)-2-fluoro-1,2,3,5,6,7-hexahydropyrrolizin-8-yl]methoxy]-6-(6-hydroxy-8-oxo-4,7-diazaspiro[2.5]octan-4-yl)-1,3,5-triazin-2-yl]spiro[6H-thieno[3,4-b]thiophene-4,3'-azetidine]-3-carbonitrile (Compound 255)

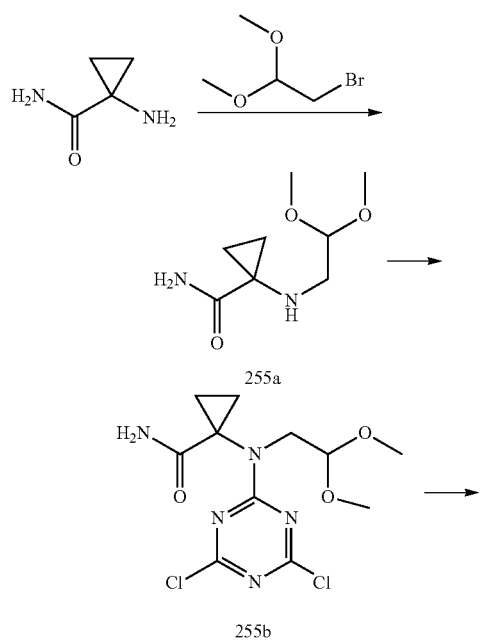

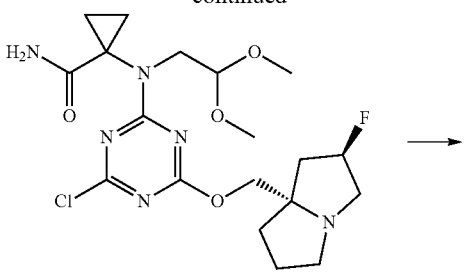

255c

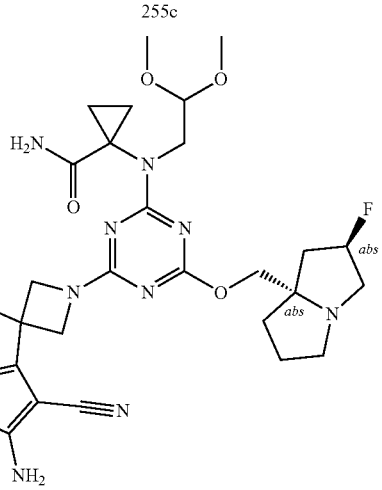

255d

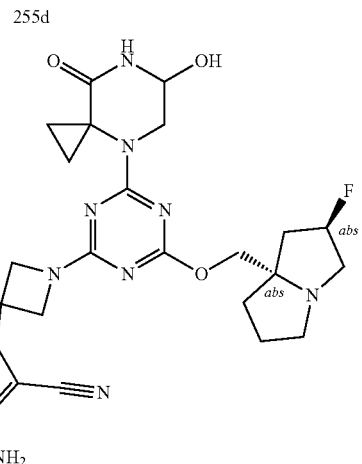

Compound 255

Step 1. Synthesis of 1-(2,2-dimethoxyethylamino)cyclopropanecarboxamide (255a). To a solution of 1-aminocyclopropanecarboxamide (50 mg, 0.5 mmol), 2-bromo-1,1-dimethoxy-ethane (126.61 mg, 0.75 mmol) and NaI (149.71 mg, 1 mmol) in DMSO (1 mL) was added K$_2$CO$_3$ (207.07 mg, 1.5 mmol) at 25° C. under Ar. The mixture was heated at 90° C. for 16 h. The mixture was quenched with water (10 mL) at 0° C., extracted with EtOAc (10 mL×3). The combined organic layers were washed with brine (10 mL), dried over Na$_2$SO$_4$, filtered, and concentrated to afford the crude product. The crude product was purified by flash chromatography (eluted with MeOH in DCM from 0% to 10%) to give the desired product 1-(2,2-dimethoxyethylamino)cyclopropanecarboxamide (30 mg, 0.159 mmol, 31.91% yield) as yellow oil. $^1$H NMR (400 MHz, CDCl$_3$) δ

7.61 (s, 1H), 5.93 (s, 1H), 4.38 (t, J=5.2 Hz, 1H), 3.40 (s, 6H), 2.77 (d, J=5.2 Hz, 2H), 1.37 (q, J=4.4 Hz, 2H), 0.89 (q, J=4.4 Hz, 2H).

Step 2. Synthesis of 1-[(4,6-dichloro-1,3,5-triazin-2-yl)-(2,2-dimethoxyethyl)amino]cyclopropanecarboxamide (255b). To a solution of 1-(2,2-dimethoxyethylamino)cyclopropanecarboxamide (204.15 mg, 1.08 mmol) and Cyanuric chloride (200 mg, 1.08 mmol) in DCM (3 mL) was added N,N-Diisopropylethylamine (0.76 mL, 4.34 mmol) at 15° C. The mixture was stirred at 15° C. for 2 h. (2R)-2-[[4-chloro-6-[[(2R,8S)-2-fluoro-1,2,3,5,6,7-hexahydropyrrolizin-8-yl]methoxy]-1,3,5-triazin-2-yl]-ethyl-amino]propanamide (73 mg, 0.1887 mmol, 99.674% yield) was obtained as THF solution (The reaction mixture was used directly for the next step.). LCMS calculated for $C_{10}H_{12}Cl_2N_5O_2+$ (M-CH$_3$O)$^+$ m/z=304.0, found: 303.9. $^1$H NMR (400 MHz, CDCl$_3$) δ 7.24-7.02 (s, 1H), 5.58 (s, 1H), 4.87 (t, J=5.2 Hz, 1H), 4.33 (s, 1H), 3.46 (s, 6H), 3.29 (s, 1H), 2.50 (s, 1H), 2.09 (s, 1H), 1.36 (s, 1H), 1.01 (s, 1H).

Step 3. Synthesis of 1-[[4-chloro-6-[[(2R,8S)-2-fluoro-1,2,3,5,6,7-hexahydropyrrolizin-8-yl]methoxy]-1,3,5-triazin-2-yl]-(2,2-dimethoxyethyl)amino]cyclopropanecarboxamide (255c). To a solution of [(2R,8S)-2-fluoro-1,2,3,5,6,7-hexahydropyrrolizin-8-yl]methanol (156.28 mg, 0.98 mmol) and 1-[(4,6-dichloro-1,3,5-triazin-2-yl)-(2,2-dimethoxyethyl) amino]cyclopropanecar boxamide (220 mg, 0.65 mmol) in THF (5 mL) was added Cs$_2$CO$_3$ (426.45 mg, 1.31 mmol) at RT. The mixture was heated at 50° C. for 2 h. The reaction was cooled down to RT. 1-[[4-chloro-6-[[(2R,8S)-2-fluoro-1,2,3,5,6,7-hexahydropyrrolizin-8-yl]methoxy]-1,3,5-triazin-2-yl]-(2,2-dimethoxyethyl)amino]cyclopropanecarboxamide (300 mg, 0.3007 mmol, 45.949% yield) was obtained as THF solution (The reaction mixture was used directly for the next step). LCMS calculated for $C_{19}H_{29}ClFN_6O_4$ (M+H)$^+$ m/z=459.2, found: 459.0.

Step 4. Synthesis of 1-[[4-(2-amino-3-cyano-spiro[6H-thieno[3,4-b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-(2,2-dimethoxyethyl)amino] cyclopropanecarboxamide (255d). To a solution of 2-aminospiro[6H-thieno[3,4-b]thiophene-4,3'-azetidine]-3-carbonitrile; methanesulfonic acid (96.05 mg, 0.3 mmol) and 1-[[4-chloro-6-[[(2R,8S)-2-fluoro-1,2,3,5,6,7-hexahydropyrrolizin-8-yl]methoxy]-1,3,5-triazin-2-yl]-(2,2-dimethoxyethyl)amino]cyclopropanecarboxamide (300 mg, 0.3 mmol) in THF (5 mL) was added DIEA (0.1 mL, 0.6 mmol) at rt. The mixture was stirred at 65° C. for 3 h. The reaction was cooled down to RT. The mixture was quenched with H$_2$O (20 mL) and extracted with EtOAc (20 mL×3), The combined organic layers were washed with brine (10 mL), dried over Na$_2$SO$_4$, filtered, and concentrated to offer the crude product. The crude product was purified by flash chromatography (mobile phase A was 0.1% NH$_4$HCO$_3$ in H$_2$O, mobile phase B was ACN; Gradient from 5 to 95%) to give the desired product 1-[[4-(2-amino-3-cyano-spiro[6-thieno[3,4-b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-(2,2-dimethoxyethyl) amino] cyclopropanecarboxamide (120 mg, 0.1858 mmol, 61.796% yield) as yellow solid. LCMS calculated for $C_{28}H_{37}FN_9O_4S_2$ (M+H)$^+$ m/z=646.2, found: 646.2.

Step 5. Synthesis of 2-amino-1'-[4-[[(2R,8S)-2-fluoro-1,2,3,5,6,7-hexahydropyrrolizin-8-yl]methoxy]-6-(6-hydroxy-8-oxo-4,7-diazaspiro[2.5]octan-4-yl)-1,3,5-triazin-2-yl]spiro[6H-thieno[3,4-b]thiophene-4,3'-azetidine]-3-carbonitrile (Compound 255)

To a solution of 1-[[4-(2-amino-3-cyano-spiro[6H-thieno[3,4-b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-(2,2-dimethoxyethyl)amino] cyclopropanecarboxamide (50 mg, 0.08 mmol) in THF (1 mL) was added Hydrochloric Acid (1.29 mL, 3.87 mmol) and stirred at 25° C. for 6 h. The mixture was basified with saturated aqueous NaHCO$_3$ to pH=9, extracted with EtOAc (3×30 mL), dried over Na$_2$SO$_4$, filtered, and concentrated to afford the crude product. The crude product was purified by flash chromatography (mobile phase A was 0.1% NH$_4$HCO$_3$ in H$_2$O, mobile phase B was ACN; Gradient from 5% to 40%) to give the desired product 2-amino-1'-[4-[[(2R,8S)-2-fluoro-1,2,3,5,6,7-hexahydropyrrolizin-8-yl]methoxy]-6-(6-hydroxy-8-oxo-4,7-diazaspiro[2.5]octan-4-yl)-1,3,5-triazin-2-yl]spiro[6H-thieno[3,4-b]thiophene-4,3'-azetidine]-3-carbonitrile (6.76 mg, 0.0112 mmol, 14.439% yield) as white solid. LCMS calculated for $C_{26}H_{31}FN_9O_3S_2$ (M+H)$^+$ m/z=600.2, found: 600.0. $^1$H NMR (400 MHz, CD$_3$OD) δ 5.26 (d, J=54.0 Hz, 1H), 5.14 (m, 1H), 4.75-4.57 (m, 2H), 4.36 (m, 2H), 4.13 (m, 3H), 4.05 (s, 2H), 3.82 (m, 1H), 3.25-3.07 (m, 3H), 3.04-2.91 (m, 1H), 2.33-1.77 (m, 6H), 1.54 (m, 4H).

Compound 256A&B. 2-amino-1'-[4-[(3R)-3-hydroxy-3-methyl-1-piperidyl]-6-[[(3RS,8RS)-3-[[6-(trifluoromethyl)pyrimidin-4-yl]oxymethyl]-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

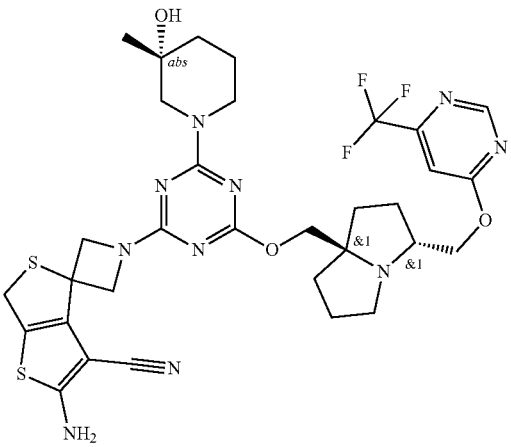 [SMILES: C[C@@]1(O)CCCN(c2nc(OC[C@]34CCCN3[C@@H](COc3cc(C(F)(F)F)ncn3)CC4)nc(N3CC4(C3)SCc3sc(N)c(C#N)c34)n2)C1]

Compound 253 was purified on a DAICELCHIRALCEL®IG (250*25 mm 10 um) column on a Waters SFC 150 system (Mobile Phase A: Supercritical CO$_2$, Mobile Phase B: EtOH[0.2% NH$_3$ (7M in MeOH)]; A:B: 60/40; Flow: 100 ml/min) to give faster eluting P1 (compound 256A), and slower eluting P2 (compound 256B).

Compound 257. 2-amino-1'-[4-[[(1R,4R,5S)-2-azabicyclo[2.1.1]hexan-5-yl]-methyl-amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

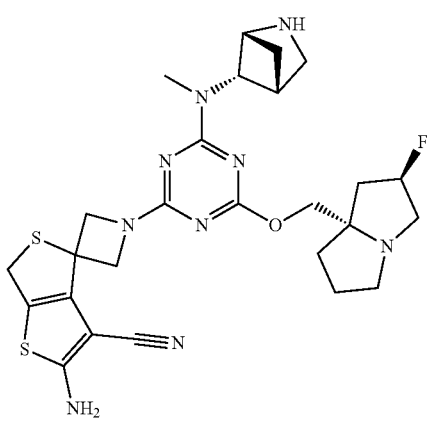 [SMILES: CN(c1nc(OC[C@@]23CCCN2C[C@H](F)C3)nc(N2CC3(C2)SCc2sc(N)c(C#N)c23)n1)[C@H]1[C@H]2CN[C@@H]1C2]

Compound 257 was prepared similarly to that of Ex. 1 as a formate salt. LCMS calculated for $C_{26}H_{33}FN_9OS_2$ (M+H)$^+$ m/z=570.2, found: 570.2. $^1$H NMR (400 MHz, CD$_3$OD) δ 5.44 (d, J=52.9 Hz, 1H), 4.76-4.60 (m, 3H), 4.45-4.24 (m, 4H), 4.12-4.00 (m, 2H), 3.75-3.52 (m, 4H), 3.36 (d, J=9.8 Hz, 1H), 3.24 (m, 3H), 2.95 (s, 3H), 2.46 (m, 2H), 2.31-2.11 (m, 3H), 2.10-1.83 (m, 2H), 1.49 (d, J=9.8 Hz, 1H).

Compound 258. 2-amino-1'-[4-[1-cyanoethyl(2,2-difluoroethyl)amino]-6-[[(2R,8S)-2-fluoro-1,2,3,5,6,7-hexahydropyrrolizin-8-yl]methoxy]-1,3,5-triazin-2-yl]spiro[6H-thieno[2,3-c]thiophene-4,3'-azetidine]-3-carbonitrile

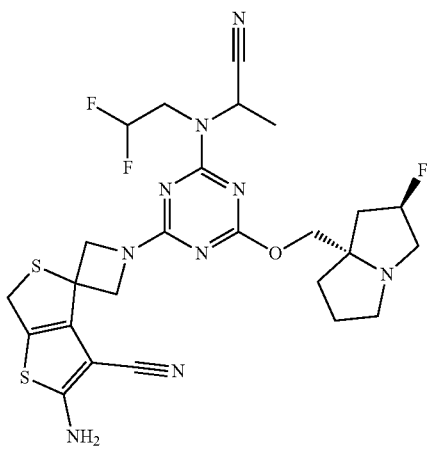 [SMILES: CC(C#N)N(CC(F)F)c1nc(OC[C@@]23CCCN2C[C@H](F)C3)nc(N2CC3(C2)SCc2sc(N)c(C#N)c23)n1]

Compound 258 was prepared similarly to that of Ex. 12 as a formate salt. LCMS calculated for $C_{25}H_{29}F_3N_9OS_2$ (M+H)$^+$ m/z=592.1, found: 592.2. $^1$H NMR (400 MHz, CD$_3$OD) δ 6.18 (t, J=56.0 Hz, 1H), 5.58-5.28 (m, 2H), 4.77-4.62 (m, 2H), 4.48-4.22 (m, 4H), 4.11-3.87 (m, 4H), 3.55-3.43 (m, 3H), 3.21-3.11 (m, 1H), 2.52-2.29 (m, 2H), 2.25-2.16 (m, 1H), 2.16-2.04 (m, 2H), 2.04-1.90 (m, 1H), 1.65 (d, J=6.4 Hz, 3H).

Compound 259. 2-[[4-(2-amino-3-cyano-spiro[6H-thieno[3,4-b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-(1-cyanocyclopropyl)amino]acetic acid

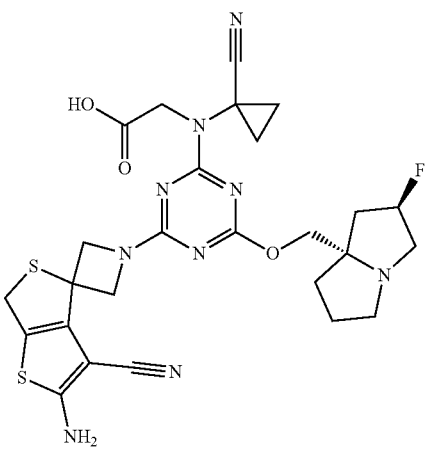 [SMILES: N#Cc1c(N)sc2c1C1(CN(c3nc(OC[C@@]45CCCN4C[C@H](F)C5)nc(N(CC(=O)O)C4(C#N)CC4)n3)C1)SC2]

Compound 259 was prepared similarly to that of Ex. 12 as a TFA salt. LCMS calculated for $C_{26}H_{29}FN_9O_3S_2$ (M+H)$^+$ m/z=598.1, found: 598.1. $^1$H NMR (400 MHz, d6-DMSO) δ 12.78 (s, 1H), 7.41 (s, 2H), 5.52 (d, J=51.2 Hz, 1H), 4.78-4.45 (m, 3H), 4.44-4.27 (m, 3H), 4.27-4.15 (m, 2H), 4.15-3.97 (m, 2H), 3.95-3.52 (m, 3H), 3.50-3.36 (m, 1H), 2.48-2.36 (m, 2H), 2.31-2.04 (m, 3H), 2.05-1.84 (m, 1H), 1.75-1.54 (m, 2H), 1.52-1.30 (m, 2H).

Compound 260. 1'-[4-[(1-acetyl-2-methyl-pyrrolidin-3-yl)-methyl-amino]-6-[[(2R,8S)-2-fluoro-1,2,3,5,6,7-hexahydropyrrolizin-8-yl]methoxy]-1,3,5-triazin-2-yl]-2-amino-spiro[6H-thieno[3,4-b]thiophene-4,3'-azetidine]-3-carbonitrile

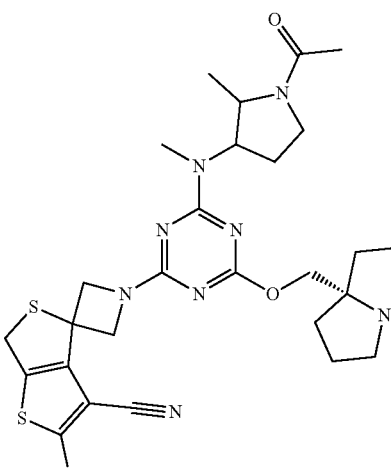

Compound 260 was prepared similarly to that of Ex. 12 as a formate salt. LCMS calculated for $C_{28}H_{37}FN_9O_2S_2$ (M+H)$^+$ m/z=614.2, found: 614.2. $^1$H NMR (400 MHz, CD$_3$OD) δ 5.36 (d, J=53.5 Hz, 1H), 4.78-4.52 (m, 4H), 4.43-4.33 (m, 2H), 4.29-4.21 (m, 1H), 4.21-4.11 (m, 1H), 4.05 (s, 2H), 3.79-3.56 (m, 1H), 3.56-3.47 (m, 1H), 3.46-3.35 (m, 3H), 3.21 (d, J=2.7 Hz, 3H), 3.18-3.00 (m, 1H), 2.61-2.25 (m, 3H), 2.24-2.12 (m, 2H), 2.11-1.99 (m, 5H), 1.98-1.85 (m, 1H), 1.01 (dd, J=23.0, 6.4 Hz, 3H).

Compound 261. 2-amino-1'-[4-[(1-cyanocyclopropyl)-(2-hydroxypropyl)amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

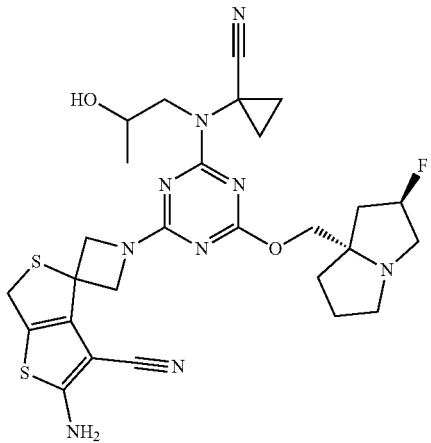 [SMILES: CC(O)CN(c1nc(OC[C@@]23CCCN2C[C@H](F)C3)nc(N2CC3(C2)SCc2sc(N)c(C#N)c23)n1)C1(C#N)CC1]

Compound 261 was prepared similarly to that of Ex. 12 as a hydrofluoride salt. LCMS calculated for $C_{27}H_{33}FN_9O_2S_2$ (M+H)$^+$ m/z=598.73, found: 598.3. $^1$H NMR (400 MHz, CD$_3$OD) δ 5.46 (d, J=52.0 Hz, 1H), 4.91-4.86 (m, 1H), 4.75-4.63 (m, 2H), 4.53-4.34 (m, 4H), 4.17-3.97 (m, 4H), 3.85-3.59 (m, 4H), 2.62-2.38 (m, 2H), 2.35-2.01 (m, 4H), 1.77-1.50 (m, 4H), 1.46 (d, J=6.7 Hz, 3H).

Compound 262. 2-amino-1'-[4-[(1-cyanocyclopropyl)-(2-hydroxy-1-methyl-ethyl)amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

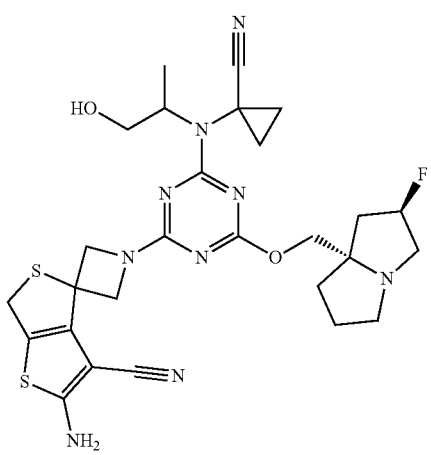 [SMILES: CC(CO)N(c1nc(OC[C@@]23CCCN2C[C@H](F)C3)nc(N2CC3(C2)SCc2sc(N)c(C#N)c23)n1)C1(C#N)CC1]

Compound 262 was prepared similarly to that of Ex. 12 as a hydrofluoride salt. LCMS calculated for $C_{27}H_{33}FN_9O_2S_2$ (M+H)$^+$ m/z=598.1, found: 598.1. $^1$H NMR (400 MHz, CD$_3$OD) δ 5.47 (d, J=52.4 Hz, 1H), 5.01-4.86 (m, 1H), 4.77-4.61 (m, 2H), 4.59-4.44 (m, 2H), 4.44-4.31 (m, 2H), 4.22-4.07 (m, 1H), 4.06 (s, 3H), 3.86-3.58 (m, 4H), 2.64-2.37 (m, 2H), 2.36-2.27 (m, 1H), 2.27-2.14 (m, 2H), 2.13-1.97 (m, 1H), 1.79-1.49 (m, 4H), 1.46 (d, J=6.8 Hz, 3H).

Compound 263. 2-amino-1'-[4-[(1-cyanocyclopropyl)-[(1-hydroxycyclopropyl)methyl]amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

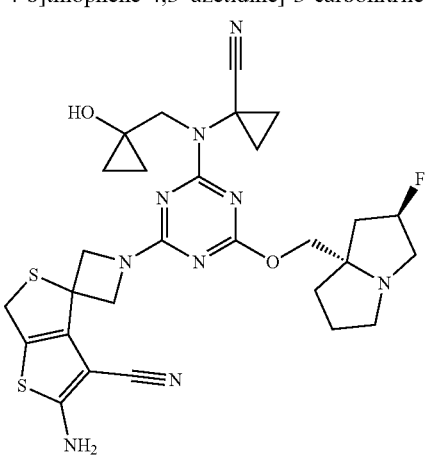

Compound 263 was prepared similarly to that of Ex. 12 as a HCl salt. LCMS calculated for $C_{28}H_{33}FN_9O_2S_2$ (M+H)$^+$ m/z=610.1, found: 610.3. $^1$H NMR (400 MHz, CD$_3$OD) δ 5.74-5.41 (m, 1H), 4.87-4.41 (m, 6H), 4.29-3.69 (m, 7H), 3.53-3.40 (m, 1H), 2.82-2.51 (m, 2H), 2.48-2.27 (m, 3H), 2.26-2.07 (m, 1H), 1.86-1.41 (m, 4H), 0.93-0.62 (m, 4H).

Compound 264. 2-amino-1'-[4-[[(1R)-1-(2-amino-3-pyridyl)ethyl]-cyclopropyl-amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

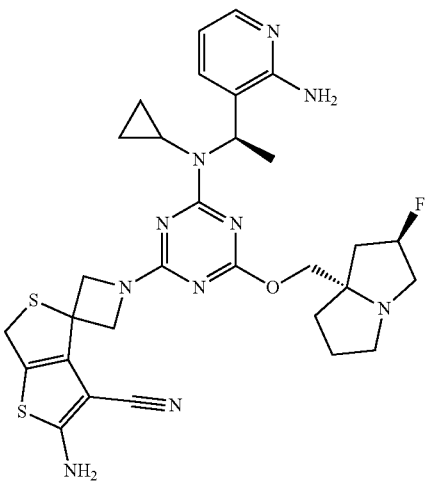 [SMILES: C[C@H](c1cccnc1N)N(c1nc(OC[C@@]23CCCN2C[C@H](F)C3)nc(N2CC3(C2)SCc2sc(N)c(C#N)c23)n1)C1CC1]

Compound 264 was prepared similarly to that of Ex. 5. LCMS calculated for $C_{30}H_{36}FN_{10}OS_2$ (M+H)$^+$=635.2, found 635.3. $^1$H NMR (400 MHz, CD$_3$OD) δ: 7.85-7.84 (m, 1H), 7.66-7.64 (m, 1H), 6.68-6.65 (m, 1H), 6.11-5.99 (m, 1H), 5.68-5.55 (m, 1H), 5.24 (d, J=54.8 Hz, 1H), 4.81-4.71 (m, 3H), 4.70-4.57 (m, 1H), 4.42-4.36 (m, 2H), 4.16-3.95 (m, 5H), 3.82-3.77 (m, 1H), 3.19-3.12 (m, 3H), 2.97-2.92 (m, 1H), 2.30-1.75 (m, 6H), 1.54 (d, J=6.8 Hz, 3H).

Compound 265. 2-amino-1'-[4-[[(2R,8S)-2-fluoro-1,2,3,5,6,7-hexahydropyrrolizin-8-yl]methoxy]-6-(3-oxa-6-azabicyclo[3.1.1]heptan-6-yl)-1,3,5-triazin-2-yl]spiro[6H-thieno[3,4-b]thiophene-4,3'-azetidine]-3-carbonitrile

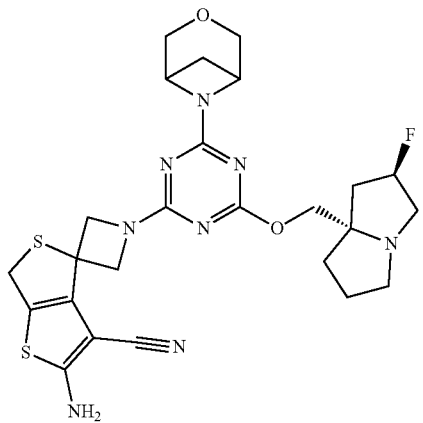 [SMILES: N#Cc1c(N)sc2c1C1(CN(c3nc(OC[C@@]45CCCN4C[C@H](F)C5)nc(N4C5COCC4C5)n3)C1)SC2]

Compound 265 was prepared similarly to that of Ex. 4. LCMS calculated for $C_{25}H_{30}FN_8O_2S_2$ (M+H)$^+$ m/z=557.18; found: 557.2. $^1$H NMR (400 MHz, CD$_3$OD) δ 5.35-5.15 (m, 1H), 4.65 (d, J=10.0 Hz, 2H), 4.45-3.89 (m, 10H), 3.75 (d, J=10.1 Hz, 2H), 3.24-3.09 (m, 3H), 3.03-2.92 (m, 1H), 2.78-2.64 (m, 1H), 2.01 (m, 7H).

Compound 266. 2-[[4-(2-amino-3-cyano-spiro[6H-thieno[3,4-b]thiophene-4,3'-azetidine]-1'-yl)-6-[[(2R,8S)-2-fluoro-1,2,3,5,6,7-hexahydropyrrolizin-8-yl]methoxy]-1,3,5-triazin-2-yl]-(1-cyanocyclopropyl)amino]acetamide

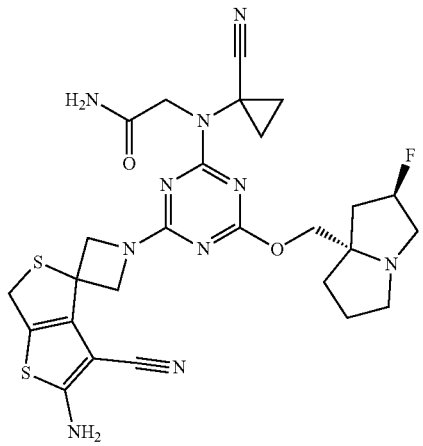 [SMILES: N#Cc1c(N)sc2c1C1(CN(c3nc(OC[C@@]45CCCN4C[C@H](F)C5)nc(N(CC(N)=O)C4(C#N)CC4)n3)C1)SC2]

Compound 266 was prepared similarly to that of Ex. 12. as a TFA salt. LCMS calculated for $C_{26}H_{29}FN_{10}O_2S_2$ (M+H)$^+$ m/z=597.2, found: 597.2. $^1$H NMR (400 MHz, CD$_3$OD) δ 5.55 (d, J=51.2 Hz, 1H), 4.78-4.35 (m, 6H), 4.34-4.13 (m, 2H), 4.06 (s, 2H), 4.00-3.79 (m, 3H), 3.50-3.39 (m, 1H), 2.75-2.48 (m, 2H), 2.41-2.26 (m, 3H), 2.22-2.06 (m, 1H), 1.75-1.57 (m, 4H).

Compound 267. 2-amino-1'-[4-[[(2R,8S)-2-fluoro-1,2,3,5,6,7-hexahydropyrrolizin-8-yl]methoxy]-6-(2-oxo-3,6-diazabicyclo[3.1.1]heptan-6-yl)-1,3,5-triazin-2-yl]spiro[6H-thieno[3,4-b]thiophene-4,3'-azetidine]-3-carbonitrile

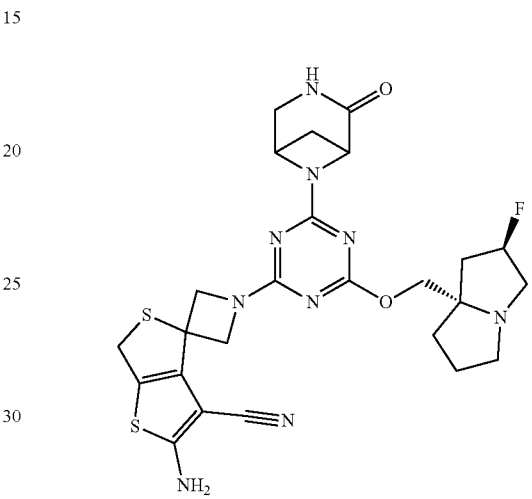

Compound 267 was prepared similarly to that of Ex. 4. LCMS calculated for $C_{25}H_{29}FN_9O_2S_2$ (M+H)$^+$ m/z=570.18; found: 570.4. $^1$H NMR (400 MHz, CD$_3$OD) δ=5.25 (d, J=52.8 Hz, 1H), 4.70-4.57 (m, 2H), 4.36-4.34 (m, 2H), 4.27-4.11 (m, 2H), 4.11-3.79 (m, 4H), 3.40-3.33 (m, 1H), 3.25-3.11 (m, 4H), 3.02-2.85 (m, 2H), 2.29-1.76 (m, 7H).

Compound 268. 2-amino-1'-[4-[[(2R,8S)-2-fluoro-1,2,3,5,6,7-hexahydropyrrolizin-8-yl]methoxy]-6-(6-hydroxy-6-methyl-1,4-oxazepan-4-yl)-1,3,5-triazin-2-yl]spiro[6H-thieno[3,4-b]thiophene-4,3'-azetidine]-3-carbonitrile

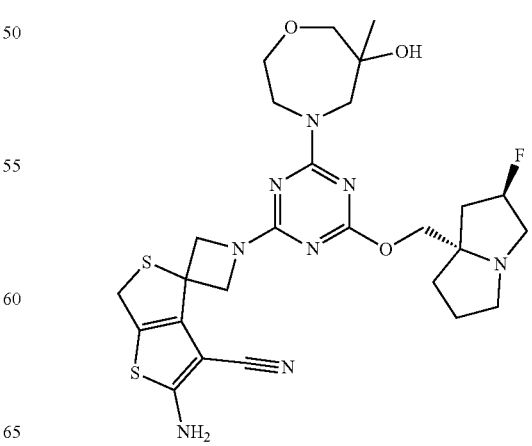

Compound 268 was prepared similarly to that of Ex. 4. LCMS calculated for $C_{26}H_{34}FN_8O_3S_2$ (M+H)$^+$ m/z=609.23; found: 609.2. $^1$H NMR (400 MHz, CD$_3$OD) δ 5.26 (d, J=54.2 Hz, 1H), 4.65-4.54 (m, 2H), 4.40-4.31 (m, 2H), 4.20-3.88 (m, 6H), 3.82-3.63 (m, 4H), 3.60-3.40 (m, 2H), 3.29-3.11 (m, 5H), 3.05-2.91 (m, 1H), 2.31-1.78 (m, 6H), 1.22 (d, J=12.4 Hz, 3H).

Compound 269. 2-amino-1'-[4-[[(2R,8S)-2-fluoro-1,2,3,5,6,7-hexahydropyrrolizin-8-yl]methoxy]-6-(3-thia-6-azabicyclo[3.1.1]heptan-6-yl)-1,3,5-triazin-2-yl]spiro[6H-thieno[3,4-b]thiophene-4,3'-azetidine]-3-carbonitrile

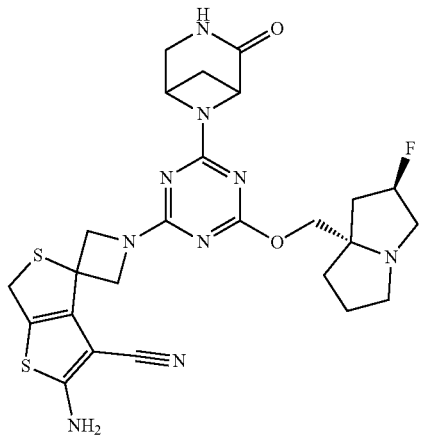 [SMILES: N#Cc1c(N)sc2c1C1(CN(c3nc(OC[C@@]45CCCN4C[C@H](F)C5)nc(N4C5CNC(=O)C4C5)n3)C1)SC2]

Compound 269 was prepared similarly to that of Ex. 4. LCMS calculated for $C_{25}H_{30}FN_8OS_3$ (M+H)$^+$ m/z=573.16; found: 573.2. 1H NMR (400 MHz, CD$_3$OD) δ 5.28 (d, J=54.6 Hz, 1H), 4.66 (d, J=10.2 Hz, 2H), 4.58 (d, J=6.0 Hz, 2H), 4.41-4.35 (m, 2H), 4.21-4.03 (m, 4H), 3.80-3.59 (m, 2H), 3.25-3.18 (m, 3H), 3.06-2.95 (m, 1H), 2.86-2.70 (m, 3H), 2.33-1.78 (m, 7H).

Compound 270. 2-amino-1'-[4-(6-hydroxy-6-methyl-1,4-oxazepan-4-yl)-6-[[1-(morpholinomethyl)cyclopropyl]methoxy]-1,3,5-triazin-2-yl]spiro[6H-thieno[3,4-b]thiophene-4,3'-azetidine]-3-carbonitrile

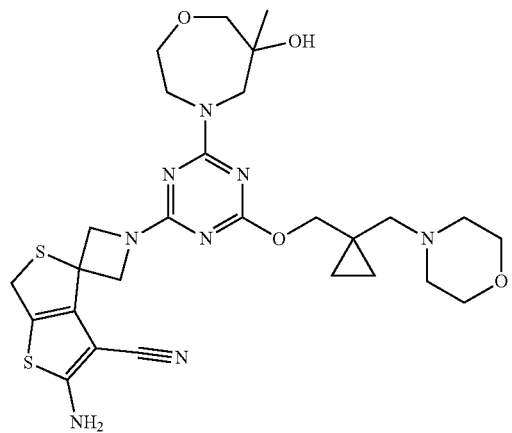 [SMILES: CC1(O)COCCN(c2nc(OCC3(CN4CCOCC4)CC3)nc(N3CC4(C3)SCc3sc(N)c(C#N)c34)n2)C1]

Compound 270 was prepared similarly to that of Ex. 4. LCMS calculated for $C_{27}H_{37}N_8O_4S_2$ (M+H)$^+$ m/z=601.76; found: 601.2. $^1$H NMR (400 MHz, CD$_3$OD) δ 4.70-4.57 (m, 2H), 4.44-3.94 (m, 8H), 3.89-3.39 (m, 11H), 2.56-2.29 (m, 6H), 1.26-1.16 (m, 3H), 0.64 (t, J=4.8 Hz, 2H), 0.44 (t, J=4.9 Hz, 2H).

Compound 271. 2-amino-1'-[4-[[(2R,8S)-2-fluoro-1,2,3,5,6,7-hexahydropyrrolizin-8-yl]methoxy]-6-(4-oxo-3,9-diazabicyclo[4.2.1]nonan-9-yl)-1,3,5-triazin-2-yl]spiro[6H-thieno[3,4-b]thiophene-4,3'-azetidine]-3-carbonitrile

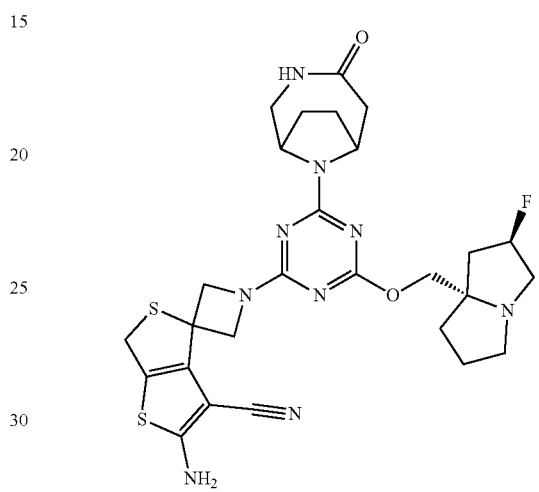

Compound 271 was prepared similarly to that of Ex. 4. LCMS calculated for $C_{27}H_{33}FN_9O_2S_2$ (M+H)$^+$ m/z=598.2; found 598.2. $^1$H NMR (400 MHz, CD$_3$OD) δ 5.33-5.19 (m, 1H), 4.68-4.58 (m, 4H), 4.35-4.32 (m, 2H), 4.20-4.02 (m, 4H), 3.79-3.59 (m, 1H), 3.26-2.90 (m, 6H), 2.53 (d, J=15.2 Hz, 1H), 2.29-1.83 (m, 10H).

Compound 272. 2-amino-1'-[4-[2-aminoethyl-(1-cyanocyclopropyl)amino]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile; formic acid

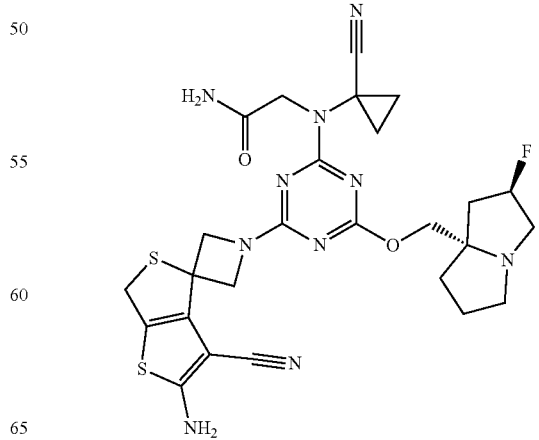

Compound 272 was prepared similarly to that of Ex. 12 as a TFA salt. LCMS calculated for $C_{26}H_{32}FN_{10}OS_2$ (M+H)⁺ m/z=583.3, found: 583.3. ¹H NMR (400 MHz, CD₃OD) δ 5.36 (d, J=53.2 Hz, 1H), 4.76 (d, J=10.4 Hz, 1H), 4.67 (d, J=10.4 Hz, 1H), 4.44 (t, J=10.0 Hz, 2H), 4.39-4.24 (m, 2H), 4.11-4.02 (m, 2H), 4.00-3.80 (m, 2H), 3.52-3.40 (m, 2H), 3.38 (s, 1H), 3.29-3.20 (m, 2H), 3.19-3.08 (m, 1H), 2.45-2.33 (m, 1H), 2.32-2.26 (m, 1H), 2.23-2.15 (m, 1H), 2.14-2.02 (m, 2H), 2.01-1.87 (m, 1H), 1.77-1.62 (m, 2H), 1.60-1.44 (m, 2H).

Compound 273. 2-amino-1'-[4-[[(2R,8S)-2-fluoro-1,2,3,5,6,7-hexahydropyrrolizin-8-yl]methoxy]-6-(3-oxo-8-azabicyclo[3.2.1]octan-8-yl)-1,3,5-triazin-2-yl]spiro[6H-thieno[3,4-b]thiophene-4,3'-azetidine]-3-carbonitrile

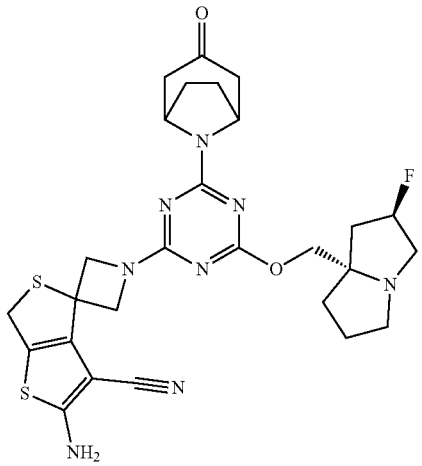 [SMILES: N#Cc1c(N)sc2c1C1(CN(c3nc(OC[C@@]45CCCN4C[C@H](F)C5)nc(N4C5CCC4CC(=O)C5)n3)C1)SC2]

Compound 273 was prepared similarly to that of Ex. 4. LCMS calculated for $C_{27}H_{32}FN_8O_2S_2$ (M+H)⁺ m/z=583.2, found: 583.3. ¹H NMR (400 MHz, CD₃OD) δ 5.26 (d, J=52.8 Hz, 1H), 5.04-4.88 (m, 2H), 4.75-4.59 (m, 2H), 4.42-4.29 (m, 2H), 4.26-4.13 (m, 1H), 4.11-3.95 (m, 3H), 3.26-3.07 (m, 3H), 3.00-2.66 (m, 3H), 2.34-2.19 (m, 3H), 2.16-2.01 (m, 4H), 1.97-1.80 (m, 3H), 1.80-1.69 (m, 2H).

Compound 274. 2-amino-1'-[4-(3-oxa-8-azabicyclo[3.2.1]octan-8-yl)-6-[[rac-(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

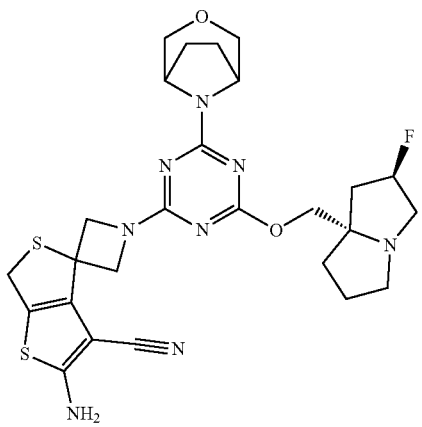 [SMILES: N#Cc1c(N)sc2c1C1(CN(c3nc(OC[C@@]45CCCN4C[C@H](F)C5)nc(N4C5CCC4COC5)n3)C1)SC2]

Compound 274 was prepared similarly to that of Ex. 4. LCMS calculated for $C_{26}H_{32}FN_8O_2S_2$ (M+H)⁺ m/z=571.2, found: 571.2. ¹H NMR (400 MHz, CDCl₃) δ 5.28 (d, J=53.6 Hz, 1H), 5.12-4.93 (m, 2H), 4.75-4.57 (m, 4H), 4.46-4.34 (m, 2H), 4.26-4.13 (m, 1H), 4.05 (s, 2H), 3.80-3.66 (m, 2H), 3.61-3.52 (m, 2H), 3.38-3.16 (m, 2H), 3.05-2.90 (m, 1H), 2.38-2.15 (m, 3H), 2.05-1.87 (m, 7H), 1.75-1.48 (m, 2H).

Compound 25. 2-amino-1'-[4-[[(2R,8S)-2-fluoro-1,2,3,5,6,7-hexahydropyrrolizin-8-yl]methoxy]-6-[(1S,5R)-3-hydroxy-8-azabicyclo[3.2.1]octan-8-yl]-1,3,5-triazin-2-yl]spiro[6H-thieno[3,4-b]thiophene-4,3'-azetidine]-3-carbonitrile

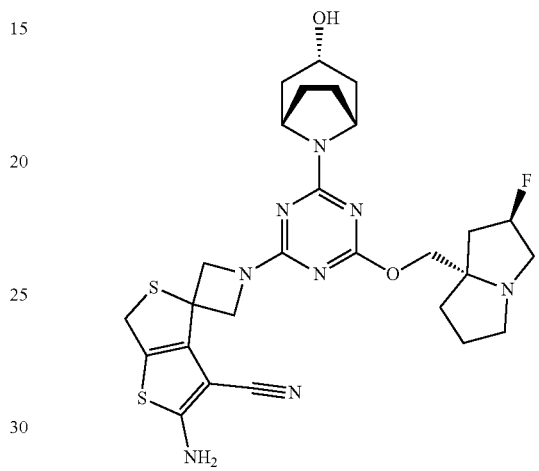

Compound 275 was prepared similarly to that of Ex. 4 as a formate salt. LCMS calculated for $C_{27}H_{34}FN_8O_2S_2$ (M+H)⁺ m/z=585.2, found: 585.3. ¹H NMR (400 MHz, CD₃OD) δ 5.49-5.25 (m, 1H), 4.79-4.57 (m, 4H), 4.43-4.28 (m, 3H), 4.30-4.09 (m, 2H), 4.06 (s, 2H), 3.65-3.38 (m, 3H), 3.23-3.10 (m, 1H), 2.51-2.26 (m, 2H), 2.30-2.04 (m, 3H), 2.05-1.83 (m, 5H), 1.87-1.45 (m, 4H).

Compound 276. 2-amino-1'-[4-[[(2R,8S)-2-fluoro-1,2,3,5,6,7-hexahydropyrrolizin-8-yl]methoxy]-6-(7-oxo-3,9-diazabicyclo[3.3.1]nonan-9-yl)-1,3,5-triazin-2-yl]spiro[6H-thieno[3,4-b]thiophene-4,3'-azetidine]-3-carbonitrile

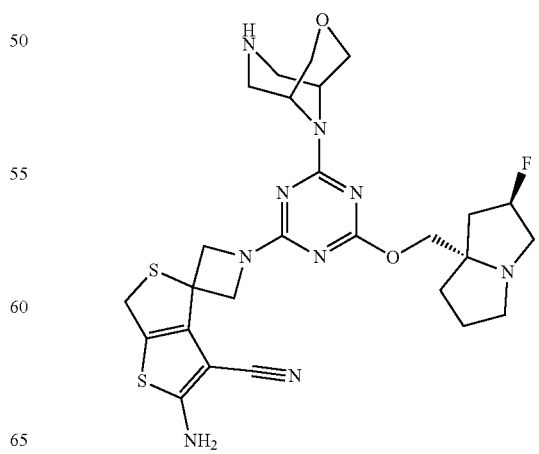

Compound 276 was prepared similarly to that of Ex. 4. LCMS calculated for $C_{27}H_{33}FN_9O_2S_2$ (M+H)$^+$ m/z=598.21; found: 598.3. $^1$H NMR (400 MHz, CD$_3$OD) δ 5.26 (d, J=54.2 Hz, 1H), 5.21-5.07 (m, 2H), 4.72-4.60 (m, 2H), 4.41-3.97 (m, 6H), 3.27-3.10 (m, 4H), 3.00-2.84 (m, 4H), 2.70-2.46 (m, 2H), 2.45-2.31 (m, 2H), 2.28-1.79 (m, 6H).

Compound 277. 2-amino-1'-[4-[[(2R,8S)-2-fluoro-1,2,3,5,6,7-hexahydropyrrolizin-8-yl]methoxy]-6-(7-oxo-3,9-diazabicyclo[3.3.1]nonan-3-yl)-1,3,5-triazin-2-yl]spiro[6H-thieno[3,4-b]thiophene-4,3'-azetidine]-3-carbonitrile

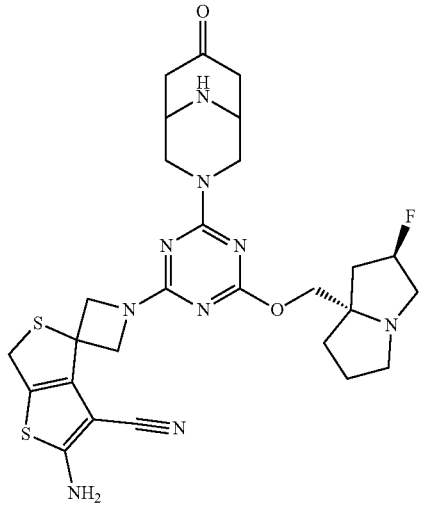 [SMILES: N#Cc1c(N)sc2c1C1(CN(c3nc(OC[C@@]45CCCN4C[C@H](F)C5)nc(N4CC5CC(=O)CC(C4)N5)n3)C1)SC2]

Compound 277 was prepared similarly to that of Ex. 4. LCMS calculated for $C_{27}H_{33}FN_9O_2S_2$ (M+H)$^+$ m/z=598.2; found: 598.2. $^1$H NMR (400 MHz, CD$_3$OD) δ 5.26 (d, J=52.8 Hz, 1H), 4.73-4.54 (m, 4H), 4.43-4.29 (m, 2H), 4.23-3.94 (m, 4H), 3.65-3.54 (m, 2H), 3.25-3.16 (m, 2H), 3.15-3.06 (m, 3H), 3.02-2.92 (m, 1H), 2.70-2.53 (m, 2H), 2.39-2.04 (m, 5H), 2.03-1.77 (m, 3H).

Compound 278. N-[(1R)-1-(2-amino-3-pyridyl)ethyl]-4-[[(2R,8S)-2-fluoro-1,2,3,5,6,7-hexahydropyrrolizin-8-yl]methoxy]-N-methyl-6-(1-methylspiro[4,5-dihydrocyclopenta[d]pyrazole-6,3'-azetidine]-1'-yl)-1,3,5-triazin-2-amine

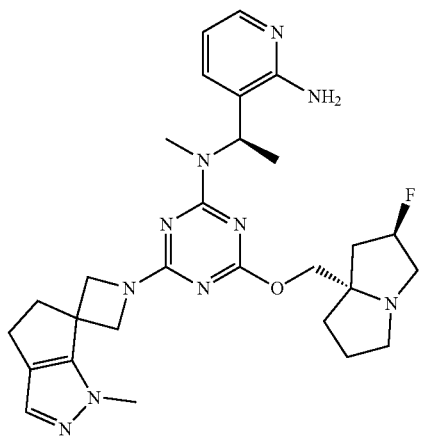 [SMILES: C[C@H](c1cccnc1N)N(C)c1nc(OC[C@@]23CCCN2C[C@H](F)C3)nc(N2CC3(CCc4cnn(C)c43)C2)n1]

Compound 278 was prepared similarly to that of Ex. 1. LCMS calculated for $C_{28}H_{38}FN_{10}O$ (M+H)$^+$ m/z=549.3; found 549.2. $^1$H NMR (400 MHz, CD$_3$OD) δ 7.87-7.86 (m, 1H), 7.67-7.64 (m, 1H), 7.11 (s, 1H), 6.69 (dd, J=7.2, 5.2 Hz, 1H), 6.02 (s, 1H), 5.26 (d, J=54.0 Hz, 1H), 4.39-4.05 (m, 6H), 3.90 (s, 3H), 3.20-3.13 (m, 3H), 2.98-2.95 (m, 1H), 2.87 (s, 2H), 2.78 (s, 3H), 2.62 (t, J=6.0 Hz, 2H), 2.21-1.83 (m, 6H), 1.53 (d, J=6.8 Hz, 3H).

Compound 279. 2-amino-1'-[4-[(1RS,2RS,4SR)-2-cyano-7-azabicyclo[2.2.1]heptan-7-yl]-6-[[(2R,8S)-2-fluoro-1,2,3,5,6,7-hexahydropyrrolizin-8-yl]methoxy]-1,3,5-triazin-2-yl]spiro[6H-thieno[3,4-b]thiophene-4,3'-azetidine]-3-carbonitrile

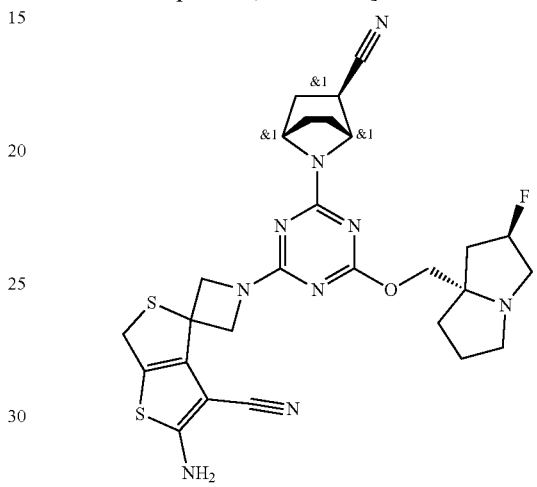

Compound 279 was prepared similarly to that of Ex. 4 as a formate salt. LCMS calculated for $C_{27}H_{31}FN_9OS_2$ (M+H)$^+$ m/z=580.2, found: 579.8. $^1$H NMR (400 MHz, CD$_3$OD) δ 5.29 (d, J=52.7 Hz, 1H), 4.80-4.51 (m, 4H), 4.45-4.29 (m, 2H), 4.26-3.96 (m, 4H), 3.29-3.18 (m, 2H), 3.15-2.94 (m, 2H), 2.42-2.18 (m, 3H), 2.16-1.77 (m, 8H), 1.76-1.58 (m, 2H).

Compound 280. 2-amino-1'-[4-[[(2R,8S)-2-fluoro-1,2,3,5,6,7-hexahydropyrrolizin-8-yl]methoxy]-6-(2-oxo-7-azabicyclo[2.2.1]heptan-7-yl)-1,3,5-triazin-2-yl]spiro[6H-thieno[3,4-b]thiophene-4,3'-azetidine]-3-carbonitrile

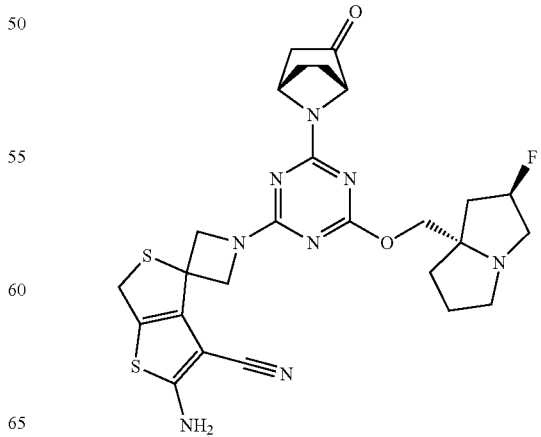

Compound 280 was prepared similarly to that of Ex. 4 as a formate salt. LCMS calculated for $C_{26}H_{30}FN_8O_2S_2$ (M+H)$^+$ m/z=569.1, found: 569.2. $^1$H NMR (400 MHz, CD$_3$OD) δ: 5.29 (d, J=55.2 Hz, 1H), 4.99-4.96 (m, 1H), 4.84-4.63 (m, 3H), 4.38-4.36 (m, 2H), 4.21-4.17 (m, 1H), 4.11-4.05 (m, 3H), 3.26-3.21 (m, 3H), 3.05-3.00 (m, 1H), 2.51-2.42 (m, 1H), 2.33-2.11 (m, 4H), 2.01-1.84 (m, 5H), 1.75-1.61 (m, 2H).

Compound 281. 2-amino-1'-[4-[[1-[(dimethylamino)methyl]-2,2-difluoro-cyclopropyl]methoxy]-6-(6-hydroxy-6-methyl-1,4-oxazepan-4-yl)-1,3,5-triazin-2-yl]spiro[6H-thieno[3,4-b]thiophene-4,3'-azetidine]-3-carbonitrile

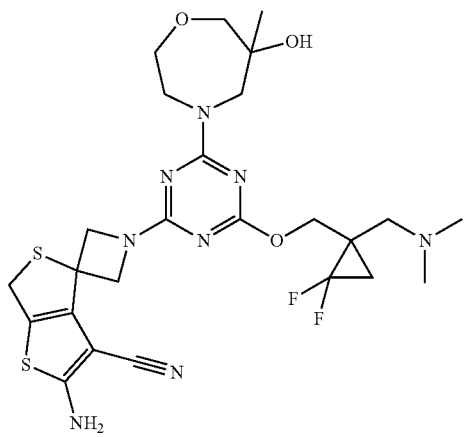 [SMILES: CN(C)CC1(COc2nc(N3CCOCC(C)(O)C3)nc(N3CC4(C3)SCc3sc(N)c(C#N)c34)n2)CC1(F)F]

Compound 281 was prepared similarly to that of Ex. 4. LCMS calculated for $C_{25}H_{33}F_2N_8O_3S_2$ (M+H)$^+$ m/z=595.20; found: 595.1. $^1$H NMR (400 MHz, CD$_3$OD) δ 4.68-4.30 (m, 6H), 4.21-3.42 (m, 10H), 2.79 (d, J=13.2 Hz, 1H), 2.38 (d, J=13.2 Hz, 1H), 2.25 (s, 6H), 1.68-1.53 (s, 1H), 1.43-1.10 (m, 4H).

Compound 282. 2-amino-1'-[4-[[(2R,8S)-2-fluoro-1,2,3,5,6,7-hexahydropyrrolizin-8-yl]methoxy]-6-[(1RS,2SR,4SR)-2-hydroxy-7-azabicyclo[2.2.1]heptan-7-yl]-1,3,5-triazin-2-yl]spiro[6H-thieno[3,4-b]thiophene-4,3'-azetidine]-3-carbonitrile

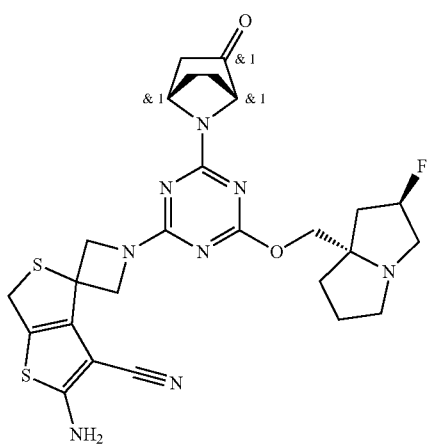 [SMILES: N#Cc1c(N)sc2c1C1(CN(c3nc(OC[C@@]45CCCN4C[C@H](F)C5)nc(N4[C@H]5CC[C@@H]4C(=O)C5)n3)C1)SC2]

Compound 282 was prepared similarly to that of Ex. 4. LCMS calculated for $C_{26}H_{32}FN_8O_2S_2$ (M+H)$^+$ m/z=571.2, found: 571.3. $^1$H NMR (400 MHz, CD$_3$OD) δ: 5.26 (d, J=52.8 Hz, 1H), 4.71-4.63 (m, 2H), 4.57-4.50 (m, 2H), 4.36-4.32 (m, 2H), 4.26-4.14 (m, 2H), 4.06-3.99 (m, 3H), 3.23-3.12 (m, 3H), 3.00-2.94 (m, 1H), 2.28-2.14 (m, 4H), 2.09-2.05 (m, 1H), 1.99-1.71 (m, 4H), 1.67-1.52 (m, 2H), 1.13-1.09 (m, 1H).

Compound 283. 2-amino-1'-[4-[[(2R,8S)-2-fluoro-1,2,3,5,6,7-hexahydropyrrolizin-8-yl]methoxy]-6-(3-oxo-2-oxa-7-azaspiro[3.5]nonan-7-yl)-1,3,5-triazin-2-yl]spiro[6H-thieno[3,4-b]thiophene-4,3'-azetidine]-3-carbonitrile

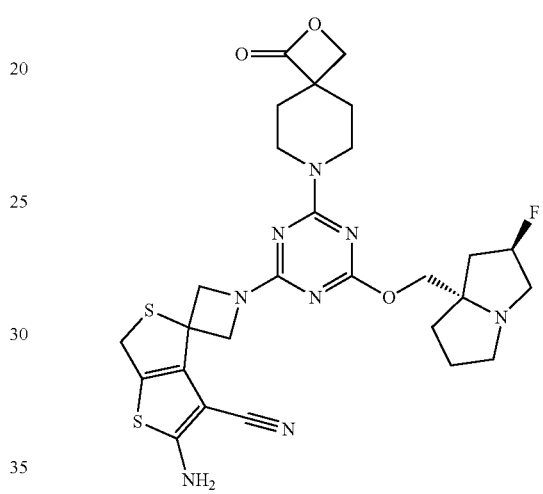

Compound 283 was prepared similarly to that of Ex. 4. LCMS calculated for $C_{27}H_{32}FN_8O_3S_2$ (M+H)$^+$ m/z=598.2; found: 599.3.

Example 16: Nucleotide Exchange Assay

Ras proteins cycle between an active, GTP bound state, and an inactive GDP-bound state. This activity is tightly regulated by GTPase activating proteins (GAPs) and guanine nucleotide exchange factors (GEFs). GEFs, such as SOS1/2, activate Ras proteins by exchanging GDP for GTP, thus returning Ras to its active conformation (Simanshu, Nissley, & McCormick, 2017). Therefore, a small molecule that binds K-Ras in a manner that prevents SOS-mediated nucleotide exchange locks KRas in its inactive state. Homogenous time resolved fluorescence (HTRF) was used to detect SOS-mediated binding of a fluorescent GTP analog, GTP-DY-647P1 (Jena Biosciences NU-820-647P1) to GST-tagged KRAS-G12D (2-169) or to GST-tagged KRAS-G12V (2-169, Reaction Biology, MSC-11-540).

GST-tagged KRAS-G12D (2-169) and anti-GST MAb Tb Cryptate Gold (CisBio 61GSTTLB) were diluted into assay buffer (20 mM HEPES, pH 7.3, 150 mM NaCl, 5 mM MgCl2, 0.05% BSA 0.0025% NP40, 1 mM DTT) to prepare a 2.5× donor solution. 5× compound was added to the protein mixture and incubated for 1 h at RT. 2.5× acceptor solution containing SOS1cat (564-1049, Reaction Biology MSC-11-502) and GTP-DY-647P1 were then added to the donor KRAS mixture such that the final concentration of the reaction contained 0.25 nM GST-tagged KRAS-G12D (2-169), 20 nM SOScat, and 150 nM GTP-DY-647P1. The reaction was monitored using at RT with the Envision multimode plate reader (Ex/Em 337/665, 620 nM) up to 90 minutes at 5 minute intervals. To monitor KRAS-G12V SOS-mediated nucleotide exchange, 80 nM SOS was added to reaction instead of 20 nM. All other components were the same as previously described. Data was blanked to reactions without SOS1 and % inhibition was calculated such that DMSO only =0% and blank=100%. Curve fitting was done using a 4 parameter fit. Reported IC50 values were extracted at 30 min and 90 min for the KRAS-G12D and KRAS-G12V assays, respectively.

NEA KRAS G12D IC50 (uM) values of selected compounds are depicted in Table 2 with compounds having a value <0.01 uM as ++++; ≥0.01 uM to 0.1 uM as +++; ≥0.1 uM to 1 uM as ++; ≥1 uM to 20 uM as +; and ≥20 uM as NA.

Example 17: Protein Constructs for Protein-Protein Interaction

TABLE 1

Assay, Protein construct, and protein construct sequences

| Assay | Protein Construct | Protein Construct Sequence |
|---|---|---|
| NEA | GST-KRAS-G12D (2-169) | MSPILGYWKIKGLVQPTRLLLEYLEEKYEEHLYERDEGDKW RNKKFELGLEFPNLPYYIDGDVKLTQSMAIIRYIADKHNML GGCPKERAEISMLEGAVLDIRYGVSRIAYSKDFETLKVDFLS KLPEMLKMFEDRLCHKTYLNGDHVTHPDFMLYDALDVVLY MDPMCLDAFPKLVCFKKRIEAIPQIDKYLKSSKYIAWPLQG WQATFGGGDHPPKSDENLYFQGGSTSTEYKLVVVGADG VGKSALTIQLIQNHFVDEYDPTIEDSYRKQVVIDGETCLLDIL DTAGQEEYSAMRDQYMRTGEGFLCVFAINNTKSFEDIHH YREQIKRVKDSEDVPMVLVGNKCDLPSRTVDTKQAQDLAR SYGIPFIETSAKTRQGVDDAFYTLVREIRKHKEK |
| NEA | GST-KRAS-G12V (2-169) | MSPILGYWKIKGLVQPTRLLLEYLEEKYEEHLYERDEGDKW RNKKFELGLEFPNLPYYIDGDVKLTQSMAIIRYIADKHNML GGCPKERAEISMLEGAVLDIRYGVSRIAYSKDFETLKVDFLS KLPEMLKMFEDRLCHKTYLNGDHVTHPDFMLYDALDVVLY MDPMCLDAFPKLVCFKKRIEAIPQIDKYLKSSKYIAWPLQG WQATFGGGDHPPKSDENLYFQGGSTSTEYKLVVVGAVG VGKSALTIQLIQNHFVDEYDPTIEDSYRKQVVIDGETCLLDIL DTAGQEEYSAMRDQYMRTGEGFLCVFAINNTKSFEDIHH YREQIKRVKDSEDVPMVLVGNKCDLPSRTVDTKQAQDLAR SYGIPFIETSAKTRQGVDDAFYTLVREIRKHKEK |
| PPI | Biotinylated Avi-KRAS-G12D (1-169) | SGLNDIFEAQKIEWHEMTEYKLVVVGADGVGKSALTIQLIQ NHFVDEYDPTIEDSYRKQVVIDGETCLLDILDTAGQEEYSA MRDQYMRTGEGFLCVFAINNTKSFEDIHHYREQIKRVKDS EDVPMVLVGNKCDLPSRTVDTKQAQDLARSYGIPFIETSAK TRQGVDDAFYTLVREIRKHKEK |
| PPI | Biotinylated Avi-KRAS-G12V (1-169) | SGLNDIFEAQKIEWHEMTEYKLVVVGAVGVGKSALTIQLIQ NHFVDEYDPTIEDSYRKQVVIDGETCLLDILDTAGQEEYSA MRDQYMRTGEGFLCVFAINNTKSFEDIHHYREQIKRVKDS EDVPMVLVGNKCDLPSRTVDTKQAQDLARSYGIPFIETSAK TRQGVDDAFYTLVREIRKHKEK |
| PPI | Biotinylated Avi-KRAS wt (1-169) | SGLNDIFEAQKIEWHEMTEYKLVVVGAGGVGKSALTIQLI QNHFVDEYDPTIEDSYRKQVVIDGETCLLDILDTAGQEEYSA MRDQYMRTGEGFLCVFAINNTKSFEDIHHYREQIKRVKDS EDVPMVLVGNKCDLPSRTVDTKQAQDLARSYGIPFIETSAK TRQGVDDAFYTLVREIRKHKEK |
| PPI | Biotinylated Avi-NRAS (1-169) | SGLNDIFEAQKIEWHEMTEYKLVVVGAGGVGKSALTIQLI QNHFVDEYDPTIEDSYRKQVVIDGETCLLDILDTAGQEEYSA MRDQYMRTGEGFLCVFAINNSKSFADINLYREQIKRVKDS DDVPMVLVGNKCDLPTRTVDTKQAHELAKSYGIPFIETSAK TRQGVEDAFYTLVREIRQYRMK |
| PPI | His8-RAF1 RBD (52-131) | SHHHHHHHHSKTSNTIRVFLPNKQRTVVNVRNGMSLHDC LMKALKVRGLQPECCAVFRLLHEHKGKKARLDWNTDAASL IGEELQVDFL |

Example 18. Recombinant Protein Production

GST-tagged KRAS G12D (2-169) was expressed in BL21 (DE3)-CodonPlus *E. coli* at 18° C. The GST-tagged protein was purified over a GST column followed by size exclusion on a HiLoad™ 16/600 Superdex™ column in 20 mM HEPES, pH7.5, 300 mM NaCl, 5 mM MgCl2, 1 mM TCEP. Fractions containing the protein of interest were pooled, concentrated, and confirmed by mass spectrometry.

Biotinylated KRAS wt and KRAS G12D/V proteins were expressed and purified in conditions similar to those previously reported (Tran, et al., 2021) (Zhang, et al., 2020). Briefly, KRAS (1-169) proteins were expressed in BL21 (DE3)-CodonPlus *E. coli* at 18° C. with an upstream TEV cleavage site (ENLFYQS (SEQ ID NO: 8)) followed an Avi tag sequence (GLNDIFEAQKIEWHE (SEQ ID NO: 9)). KRAS expression constructs contained both a His6 (SEQ ID NO: 10) and maltose-binding protein (MBP) tags at the N-terminus for Ni-NTA column purification prior to overnight TEV cleavage and MBP column purification. The avi-tagged NRAS expression construct contained both a His6 tag (SEQ ID NO: 10) and SUMO cleavage sige at the N-terminus for Ni-NTA column purification followed by His-ULP1 digestion overnight. All avi-tagged RAS proteins were dialyzed into buffer containing ATP, biotin, and BirA followed by purification over a second Ni-NTA column and then run over a size exclusion HiLoad™ 26/600 Superdex™ column in 20 mM HEPES, pH 7.5, 300 mM NaCl, 5 mM MgCl2, and 1 mM TCEP. Fractions containing the protein of interest were pooled, concentrated, and confirmed by intact mass spectrometry.

To prepare 'GTP' loaded KRAS and NRAS, biotinylated KRAS or NRAS was nucleotide exchanged from GDP-bound protein to GppNHp-bound (Jena Biosciences, NU-401-50) protein in the presence of alkaline phosphatase and excess GppNHp as previously described, and the resulting nucleotide content was confirmed by HPLC reverse phase analytical chromatography (Donohue, et al., 2019) (Tran, et al., 2021).

His-tagged RAF1 (52-131) was similarly expressed in *E. coli* at 18° C. overnight with an upstream TEV cleavage site. His-tagged RAF1 expression construct contained both a His6 and MBP tags at the N-terminus for Ni-NTA column purification followed by MBP-tagged TEV digestion overnight. RAF1 protein samples were further purified over a MBP column followed by a Ni-NTA column and a second MBP column. The fractions containing the protein of interest were pooled, concentrated, and further purified over a HiLoad™ 16/600 Superdex™ 75 pg size exclusion column into 20 mM HEPES, pH8.0, 200 mM NaCl, 5 mM TCEP.

Example 19: Protein-Protein Interaction (PPI) Assay

When RAS proteins are in the active GTP-bound conformation, they bind the effector protein RAF1 at the N-terminus Ras-binding domain (RBD, residues 52-131) (Tran, et al., 2021). Homogenous time resolved fluorescence (HTRF) was used to monitor the interaction between wt or mutant KRAS and RAF1 or wt NRAS and RAF1. Compounds were assayed in the presence of KRAS G12D/V and RAF1 versus wt KRAS to assess activity against mutant and w.t. KRAS. Similarly, compounds were then assayed in the presence of w.t. NRAS and RAF1 to assess RAS isoform selectivity. In all assay formats, His-tagged RAF1 protein was incubated with the HTRF donor, anti-6His Tb Cryptate gold (Cisbio 61DB10RDF), and biotinylated RAS proteins were incubated with the HTRF acceptor, streptavidin-d2 (CisBio 610SADLA). The intensity of the fluorescence signal emitted is proportional to binding between the two proteins. The donor solution was prepared by mixing 16 nM His-tagged RAF1 in protein dilution buffer with 1:100 anti-6His Tb cryptate in PPI-Terbium detection buffer. 16 nM biotinylated RAS protein was diluted into protein dilution buffer (50 mM Tris-HCl pH 7.5, 150 mM NaCl, 0.1 mM MgCl2, 1 mM TCEP, 0.005% Tween20) and mixed with 1:2000 Streptavidin-d2 diluted in PPI-Terbium detection buffer (CisBio 61DB10RDF). 50× compound in DMSO was mixed with 16 nM KRAS-acceptor solution and incubated for 30 minutes at room temperature. After compound pre-incubation with KRAS, the RAF1 donor solution was added to the KRAS-acceptor solution and incubated for 1 hour at room temperature. The fluorescence signal emitted was monitored at 665 nm and 615 nm using an Envision multimode plate reader. The HTRF ratio (665/615) was calculated and normalized to 0% inhibition in the absence of compound and 100% inhibition in the presence of untagged RAF1 protein. PPI KRAS G12D/RAF1, KRAS G12V/RAF1, w.t. KRAS/RAF1 and NRAS/RAF1 IC50 (uM) values of selected compounds are depicted in Table 3 and Table 4 with compounds having a value <0.1 uM as ++++; ≥0.1 uM to 1 uM as +++; ≥1 uM to 10 uM as ++; ≥10 uM to 100 uM as +; and ≥100 uM as NA.

Compounds described herein are active against KRAS G12 mutant and other alleles representative by PPI-G12D, PPI-G12V and PPI-w.t. KRAS potency for broad activity against mutant KRAS and wt KRAS amplification driven malignancies. Compounds described herein are selective for the KRAS isoform representative by lack of activity in the PPI-NRAS assay.

Example 20. pERK Inhibition cellular HTRF assay in AGS Cell Lines (Method A)

The Phospho-ERK cellular HTRF assay measures ERK protein phosphorylated at Thr202/Tyr204 as a readout of MAPK pathway inhibition (Cisbio 64ERKPEH). AGS cells (ATCC CRL-1739) are cultured in the complete medium containing 10% fetal bovine serum (AGS cells: RPMI 1640 medium) and 1× Penicillin/Streptomycin in a 37° C. humid incubator supplied with 5% CO2.

On day 1, the cells are plated in tissue-culture treated 96-well plates at the specified densities and allowed to attach for overnight (AGS: 30,000 cells/well). On day 2, the cells are treated with the serially diluted compound solutions. Final concentration of DMSO is 0.5%. After the treatment for the specified time (AGS cells: 3 hours), the supernatant is removed, and the cells are lysed by the lysis buffer supplied with the kit. Then, the cell lysates are treated with the detection reagents overnight at 4° C. in darkness. On day 3, the fluorescence intensities at the wavelengths of 665 and 620 nm are measured by the Envision plate reader (Perkin Elmer). The data are processed and fitted to a 4-parameter logistic model for IC50 calculations (GraphPad Prism 9). AGS pERK HTRF (Method A) $IC_{50}$ (uM) values (<0.01 uM as ++++; ≥0.01 uM to 0.1 uM as +++; ≥0.1 uM to 1 uM as ++; ≥1 uM to 20 uM as + and ≥20 uM as NA).

Example 11. pERK In Cell Western (ICW) Assay (Method B)

pERK ICW is a high throughput screening assay to evaluate the cellular potency of mutant KRAS small molecule inhibitors. KRAS mutant cell lines AGS, GP2D (KRAS-G12D) as well as SW620 (KRAS-G12V) were purchased from ATCC and maintained respectively in RPMI/DMEM/RPMI medium supplemented with 10% fetal bovine serum.

Cells grown in exponential phase were trypsinized, resuspended in fresh media, and viable cells were counted using a cell counter with Trypan Blue (BioRad TC20). Cells were seeded into 384-well plate (Greiner 781091) at density of 5,000 cells/well for AGS and 10,000 cells/well for GP2D/SW620 and allowed to grow overnight in a 37° C. $CO_2$ incubator. The next day, compounds were dispensed into wells with a ½ log, 9-point serial dilution using a Tecan D300e dispenser and incubated for 3 hours in a 37° C. CO2 incubator. Cells were then fixed with paraformaldehyde (Electron Microscopy Sciences, 15710, 4% final concentration) for 30 min, permeabilized with wash buffer (1×PBS+0.1% Triton X-100) for 30 min and blocked with Odyssey blocking buffer (Li—COR 927-70001) for 1 hour, all at room temperature (RT). Phospho-ERK antibody (CST 4370L) was diluted 1:500 in Odyssey T20 (PBS) antibody diluent (Li—COR 927-75001) and incubated with cells overnight at 4° C. The next day, plates were washed 5× with wash buffer, incubated with IRDye 800 CW, Goat anti-Rabbit secondary antibody (Li—COR 926-32211, 1:800) and DRAQ5 (CST 4084L, 1:5,000) diluted in in Odyssey T20 (PBS) antibody diluent for 1 hour, washed 5×, and imaged on an Odyssey CLx imaging system.

For data analysis, signal intensities from 800 (phosphor-ERK) and 700 (DRAQ5) channels were extracted, and phospho-ERK signals were normalized to DRAQ5 signals for each well and percent of blank control values were computed. Data were then imported into Graphpad Prism to compute half-maximal inhibitory concentrations ($IC_{50}$) using a 4-parameter variable slope model. Z-factor for each plate was computed from signals derived from wells treated with either DMSO or 5 μM of control compound. AGS pERK ICW (Method B) $IC_{50}$ (uM) values of selected compounds are depicted in Table 2 with compounds having a value ≥0.001 uM to 0.01 uM as ++++; ≥0.01 uM to 0.1 uM as +++; ≥0.1 uM to 1 uM as ++; ≥1 uM to 10 uM as + and ≥10 uM as NA.

Table 2 includes NEA KRAS G12D $IC_{50}$ (uM) values (<0.01 uM as ++++; ≥0.01 uM to 0.1 uM as +++; ≥0.1 uM to 1 uM as ++; ≥1 uM to 20 uM as +; and ≥20 uM as NA), PPI KRAS G12D/RAF1 $IC_{50}$ (uM) values (<0.1 uM as ++++; ≥0.1 uM to 1 uM as +++; ≥1 uM to 10 uM as ++; ≥10 uM to 100 uM as +; and ≥100 uM as NA), and AGS pERK ICW (Method B) $IC_{50}$ (uM) values (≥0.001 uM to 0.01 uM as ++++; ≥0.01 uM to 0.1 uM as +++; ≥0.1 uM to 1 uM as ++; ≥1 uM to 10 uM as + and ≥10 uM as NA) of selected compounds. ND indicates not determined.

TABLE 2

| | $IC_{50}$ (uM) values for various assays | | |
|---|---|---|---|
| cpd# | NEA-G12D (uM) | PPI-G12D (uM) | pERK-AGS (uM) Method B |
| 1 | ++++ | +++ | ++ |
| 2 | ++++ | ++ | ++ |
| 3 | ++++ | ++ | ++ |
| 4 | ++++ | ++ | + |
| 5 | ++++ | + | ++ |
| 6 | +++ | ND | ND |
| 7 | ++++ | +++ | ND |
| 8 | +++ | ++ | ND |
| 9 | ++++ | ++ | ++ |
| 10 | ++++ | ++ | ++ |

TABLE 2-continued

| | $IC_{50}$ (uM) values for various assays | | |
|---|---|---|---|
| cpd# | NEA-G12D (uM) | PPI-G12D (uM) | pERK-AGS (uM) Method B |
| 11 | ++ | ND | ND |
| 12 | ++ | + | ND |
| 13 | +++ | ++ | + |
| 14 | + | ND | ND |
| 15 | ++ | ++ | ND |
| 16 | +++ | ++ | + |
| 17 | ++ | + | ND |
| 18 | +++ | ++ | + |
| 19 | +++ | ++ | ++ |
| 20 | +++ | + | + |
| 21 | +++ | +++ | ++ |
| 22 | +++ | ++ | + |

Table 3 includes KRAS-G12V/RAFT, wt KRAS/RAF1 and wt NRAS/RAF1 PPI IC₅₀ (uM) values of selected compounds; with compounds having a value <0.1 uM as ++++; ≥0.1 uM to 1 uM as +++; ≥1 uM to 10 uM as ++; ≥10 uM to 100 uM as +; and 100 uM as NA.

TABLE 3

| | $IC_{50}$ (uM) values for KRASG12V/RAF1, wtKRAS/RAF1 and wtNRAS/RAF1 PPI | | |
|---|---|---|---|
| cpd# | PPI-G12V (uM) | PPI-w.t. KRAS (uM) | PPI-w.t. NRAS (uM) |
| 1 | +++ | ++ | NA |
| 2 | ++ | ++ | NA |
| 3 | + | ++ | NA |
| 4 | ND | ND | NA |
| 5 | ND | ND | NA |
| 6 | ND | ND | ND |
| 7 | +++ | +++ | NA |
| 8 | ++ | ++ | ND |
| 9 | + | ND | ND |
| 10 | ++ | ++ | NA |
| 11 | ND | ND | ND |
| 12 | + | ND | ND |
| 13 | ++ | ++ | ND |
| 14 | ND | ND | ND |
| 15 | ++ | ++ | ND |
| 16 | ++ | + | ND |
| 17 | + | ND | ND |
| 18 | ++ | ++ | ND |
| 19 | ++ | ++ | ND |
| 20 | + | ND | ND |
| 21 | ++ | +++ | ND |
| 22 | + | ++ | ND |

Table 4 includes NEA KRAS G12D/V $IC_{50}$ (uM) values (<0.01 uM as ++++; ≥0.01 uM to 0.1 uM as +++; ≥0.1 uM to 1 uM as ++; ≥1 uM to 20 uM as +; and ≥20 uM as NA), GP2D and SW620 pERK ICW (Method B) $IC_{50}$ (uM) values (<0.01 uM as ++++; ≥0.01 uM to 0.1 uM as +++; ≥0.1 uM to 1 uM as ++; ≥1 uM to 20 uM as + and ≥20 uM as NA) of selected compounds. ND indicates not determined.

TABLE 4

| $IC_{50}$ (uM) NEA G12D, G12V, ICW GP2D and SW620. | | | | |
|---|---|---|---|---|
| EXAMPLE | NEA G12D | NEA G12V | ICW GP2D | ICW SW620 |
| 1 | ++++ | +++ | +++ | ND |
| 2 | ++++ | ++ | +++ | ND |
| 3 | ++++ | ++ | +++ | ND |
| 4 | ++++ | + | ND | ND |

TABLE 4-continued

IC$_{50}$ (uM) NEA G12D, G12V, ICW GP2D and SW620.

| EXAMPLE | NEA G12D | NEA G12V | ICW GP2D | ICW SW620 |
|---|---|---|---|---|
| 5 | ++++ | ++++ | ND | ND |
| 6 | +++ | ND | ND | ND |
| 7 | ++++ | ++++ | + | + |
| 8 | +++ | ++++ | ++ | ++ |
| 9 | ++++ | + | +++ | ND |
| 10 | ++++ | ++++ | +++ | ++ |
| 11 | ++ | ++ | ND | ND |
| 12 | ++ | ++ | ND | ND |
| 13 | +++ | +++ | ++ | ++ |
| 14 | + | + | ND | ND |
| 15 | ++ | +++ | ND | ND |
| 16 | +++ | +++ | + | ND |
| 17 | ++ | +++ | ND | ND |
| 18 | +++ | +++ | + | ND |
| 19 | +++ | +++ | ++ | ND |
| 20 | +++ | +++ | + | ND |
| 21 | +++ | +++ | ++ | ND |
| 22 | +++ | +++ | + | ND |
| 23 | ++ | ++ | ND | ND |
| 24 | ++ | ++ | + | ND |
| 25 | +++ | +++ | ++ | ND |
| 26 | +++ | +++ | NA | ND |
| 28 | + | ++ | ND | ND |
| 29 | ++ | ++ | ND | ND |
| 30 | +++ | +++ | ++ | ND |
| 31 | +++ | ++ | ++ | ND |
| 33 | +++ | ++++ | ++ | ND |
| 34 | ++++ | ++++ | +++ | ND |
| 35 | ++ | + | + | NA |
| 36 | ++ | ++ | ND | ND |
| 37 | ++++ | ++++ | +++ | ++ |
| 38 | +++ | ++++ | + | ++ |
| 39 | +++ | +++ | + | + |
| 40 | ++ | + | + | NA |
| 41 | + | ++ | ND | ND |
| 42 | + | ++ | ND | ND |
| 43 | +++ | +++ | + | + |
| 44 | +++ | +++ | ++ | + |
| 45 | ++++ | ++++ | ++ | + |
| 46 | ++ | +++ | ND | ND |
| 47 | ++++ | ++++ | ++ | NA |
| 48 | +++ | ++++ | ++ | ++ |
| 49 | ++++ | ++++ | ++++ | ++ |
| 50 | +++ | +++ | ++ | ++ |
| 51 | +++ | +++ | ++ | + |
| 52 | +++ | +++ | ++ | + |
| 53 | + | ++ | ND | ND |
| 54 | ++ | +++ | ND | ND |
| 55 | ++++ | ++++ | +++ | ++ |
| 56 | ++ | +++ | ++ | + |
| 57 | ++ | +++ | + | + |
| 58 | +++ | +++ | + | + |
| 59 | ++ | ++ | NA | NA |
| 60 | + | + | ND | ND |
| 61 | ++++ | +++ | +++ | ++ |
| 62 | ++ | ++ | NA | NA |
| 63 | ++ | ++ | ND | ND |
| 64 | + | + | ND | ND |
| 65 | ++ | +++ | + | + |
| 66 | ++ | +++ | ND | ND |
| 67 | +++ | +++ | ++ | NA |
| 68 | ++++ | +++ | ++ | ++ |
| 69 | +++ | +++ | + | + |
| 70 | ++++ | ++++ | ++ | ++ |
| 71 | ++++ | +++ | ++ | ++ |
| 72 | ++ | ++ | ND | ND |
| 73 | ++++ | ++++ | +++ | +++ |
| 74 | +++ | ++++ | ++ | ++ |
| 75 | + | ++ | ND | ND |
| 76 | + | ++ | ND | ND |
| 77 | + | ++ | ND | ND |
| 78 | + | ++ | ND | ND |
| 79 | +++ | ++++ | ++ | + |
| 80 | ND | + | ND | ND |
| 81 | ++++ | ++++ | ++ | + |
| 82 | ++++ | ++++ | +++ | ++ |
| 83 | ++++ | ++++ | ND | ND |
| 84 | ++ | ++ | + | NA |
| 85 | ++ | +++ | + | + |
| 86 | +++ | +++ | ++ | + |
| 87 | +++ | +++ | ++ | + |
| 88 | ++ | ++++ | ND | ND |
| 89 | +++ | ++++ | ++ | ++ |
| 90 | ++ | ++ | ND | ND |
| 91A | ++++ | ++++ | ++ | ++ |
| 91B | ++++ | ++++ | ++ | +++ |
| 92 | ++ | ++ | ND | ND |
| 93 | ++++ | ++++ | +++ | +++ |
| 94 | + | ++ | ND | ND |
| 95 | +++ | +++ | ND | ND |
| 96 | ++ | +++ | ND | ND |
| 97 | +++ | ++++ | + | ++ |
| 98 | ++++ | ++++ | +++ | ++ |
| 99 | + | ++ | ND | ND |
| 100A | ++++ | ++++ | +++ | ++++ |
| 100B | +++ | ++++ | ++ | +++ |
| 101 | +++ | ++++ | ++ | + |
| 102 | +++ | ++++ | ND | ND |
| 103 | + | ++ | ND | ND |
| 104 | ++++ | ++++ | ++++ | +++ |
| 105 | + | ++ | ND | ND |
| 106 | +++ | +++ | ++ | + |
| 107 | ++++ | ++++ | +++ | +++ |
| 108 | ++++ | ++++ | +++ | +++ |
| 109 | ++++ | ++++ | ++ | +++ |
| 110 | ++++ | ++++ | ND | ND |
| 111 | ++++ | ++++ | ++ | ++ |
| 112 | + | ++ | ND | ND |
| 113 | ++ | ++ | ND | ND |
| 114 | ++++ | ++++ | +++ | ++ |
| 115 | ++++ | ++++ | ND | ND |
| 116A | ++++ | ++++ | +++ | +++ |
| 116B | ++ | +++ | ND | ND |
| 117 | ++ | +++ | ++ | ++ |
| 118 | ++++ | ++++ | ++++ | ++++ |
| 119 | + | + | ND | ND |
| 120A | ++++ | ++++ | ++++ | ++++ |
| 120B | ++++ | ++++ | +++ | +++ |
| 121 | NA | NA | ND | ND |
| 122A | ++++ | ++++ | ++++ | ++++ |
| 122B | ++++ | ++++ | +++ | +++ |
| 123 | ++++ | ++++ | +++ | ++ |
| 124 | ++++ | ++++ | ++ | +++ |
| 125 | + | +++ | ND | ND |
| 126 | +++ | + | ND | ND |
| 127 | + | ++ | ND | ND |
| 128 | +++ | ++++ | ++ | +++ |
| 129 | ++ | ++++ | + | + |
| 130 | ++++ | ++++ | ++ | + |
| 131 | ++ | +++ | ND | ND |
| 132 | +++ | ++++ | + | ++ |
| 133 | ++++ | ++++ | ++ | +++ |
| 134 | ++++ | ++++ | +++ | ++++ |
| 135 | ++ | ++ | ND | ND |
| 136 | ++ | ++ | + | + |
| 137 | ++ | +++ | + | + |
| 138 | ++ | + | + | + |
| 139A | ++++ | ++++ | ++++ | ++++ |
| 139B | ++++ | ++++ | +++ | +++ |
| 140 | + | ++ | ND | ND |
| 141 | +++ | ++++ | + | ++ |
| 142 | ++++ | ++++ | +++ | +++ |
| 143 | ++++ | ++++ | ++++ | +++ |
| 144 | ++++ | ++++ | ND | ND |
| 145 | + | ++ | ND | ND |
| 146 | +++ | ++++ | ++ | ++ |
| 147 | ++ | +++ | ND | ND |
| 148 | ++++ | ++++ | +++ | ++++ |
| 149 | ++++ | ++++ | + | ++ |
| 150 | + | ++ | ND | ND |

TABLE 4-continued

IC$_{50}$ (uM) NEA G12D, G12V, ICW GP2D and SW620.

| EXAMPLE | NEA G12D | NEA G12V | ICW GP2D | ICW SW620 |
|---|---|---|---|---|
| 151 | + | ++ | ND | ND |
| 152 | + | ++ | + | + |
| 153 | ++++ | ++++ | ++++ | +++ |
| 154 | +++ | ++++ | ND | ND |
| 155 | + | + | ND | ND |
| 156 | ++ | ++++ | + | +++ |
| 157 | ++ | +++ | + | + |
| 158 | ++ | ++++ | + | ++ |
| 159 | +++ | ++ | ++ | + |
| 160 | +++ | +++ | ++ | ++ |
| 161 | + | ++ | ND | ND |
| 162 | +++ | ++++ | ++ | +++ |
| 163 | ++++ | ++++ | ++++ | ++++ |
| 164 | ++ | +++ | ND | ND |
| 165 | + | ++ | ND | ND |
| 166 | +++ | ++++ | ++ | +++ |
| 167 | ++++ | +++ | ++++ | + |
| 168A | ++++ | ++++ | ++++ | ++++ |
| 168B | +++ | ++++ | ++ | +++ |
| 169 | + | ++ | + | + |
| 170 | +++ | ++++ | ++ | +++ |
| 171 | +++ | ++++ | +++ | ++++ |
| 172 | ++++ | ++++ | ++ | +++ |
| 173 | ++++ | ++++ | ++++ | ++++ |
| 174 | ++++ | ++++ | +++ | ++++ |
| 175A | +++ | ++++ | ND | ND |
| 175B | ++ | ++++ | ND | ND |
| 176 | ++ | ++++ | + | +++ |
| 177 | +++ | ++++ | ++ | ++ |
| 178 | +++ | ++++ | ++ | +++ |
| 179 | +++ | ++++ | ++ | +++ |
| 180 | ++++ | ++++ | ++++ | ++++ |
| 181 | ++ | +++ | ND | ND |
| 182 | +++ | +++ | ND | ND |
| 183 | ++++ | ++++ | ++++ | ++++ |
| 184A | ++++ | ++++ | +++ | ++++ |
| 184B | ++ | +++ | ND | ND |
| 185 | ++++ | ++ | ND | ND |
| 186 | ++++ | +++ | ND | ND |
| 187 | +++ | ++++ | ND | ND |
| 188 | ++++ | +++ | ++++ | ND |
| 189 | ++ | +++ | + | + |
| 190 | ++++ | +++ | ++ | + |
| 191 | +++ | ++++ | ND | +++ |
| 192 | ++ | +++ | ND | ND |
| 193 | ++++ | +++ | ND | ND |
| 194 | ++++ | ++++ | + | + |
| 195 | +++ | ++++ | ND | ND |
| 196 | ++++ | ++++ | +++ | ++++ |
| 197 | ++++ | ++++ | ND | ND |
| 198 | ++++ | ++++ | ND | ND |
| 199 | ++++ | ++++ | ND | ND |
| 200 | +++ | ++++ | ND | ++ |
| 201 | ++++ | ++++ | +++ | +++ |
| 202 | ++++ | ++++ | +++ | +++ |
| 203 | ++++ | ++++ | +++ | +++ |
| 204 | +++ | ++++ | ++ | +++ |
| 205 | + | ++ | ND | ND |
| 206 | ++++ | ++++ | ++++ | +++ |
| 207 | ++++ | ++++ | +++ | +++ |
| 208 | ++++ | ++++ | ND | ND |
| 209 | ++++ | ++++ | ++++ | +++ |
| 210 | ++++ | ++++ | ++ | +++ |
| 211 | ++++ | ++++ | ND | ND |
| 212 | ++++ | ++++ | ND | ND |
| 213 | ++++ | ++++ | +++ | +++ |
| 214 | ++++ | ++++ | ND | ND |
| 215 | ++ | ++ | ND | ND |
| 216 | ++ | ++++ | ND | ND |
| 217 | + | ++ | ND | ND |
| 218 | +++ | ++++ | ND | ND |
| 219 | ++++ | ++++ | ++ | +++ |
| 220 | ++++ | ++++ | ND | ND |
| 221 | ++++ | ++++ | ND | ND |
| 222 | + | ++ | ND | ND |
| 223 | ++++ | ++++ | +++ | +++ |
| 224 | +++ | +++ | ND | ND |
| 225 | +++ | ++++ | ND | ND |
| 226 | ++++ | ++++ | +++ | +++ |
| 227 | ++ | +++ | ND | ND |
| 228 | + | ++ | ND | ND |
| 229 | + | + | ND | ND |
| 230 | + | + | ND | ND |
| 231 | NA | NA | ND | ND |
| 232 | + | ++ | ND | ND |
| 233 | + | ++ | ND | ND |
| 234 | ++ | +++ | ND | ND |
| 235 | ++++ | ++++ | ND | ++ |
| 236 | ++++ | ++++ | ND | +++ |
| 237 | ++++ | ++++ | ND | +++ |
| 238 | ++++ | ++++ | ND | +++ |
| 239 | ++++ | ++++ | ND | ++ |
| 240 | ++++ | ++++ | ND | +++ |
| 241 | ++++ | ++++ | ND | ++ |
| 242 | ++++ | ++++ | ND | +++ |
| 243 | ++++ | ++++ | ND | ++ |
| 244 | ++++ | ++++ | ND | ++ |
| 245 | ++++ | ++++ | ND | + |
| 246 | ++++ | ++++ | ND | ++++ |
| 247 | ++++ | ++++ | ND | ++ |
| 248 | ND | + | ND | ND |
| 249 | ++++ | ++++ | ND | + |
| 250 | ++++ | ++++ | ND | ++ |
| 251 | ++++ | ++++ | ND | +++ |
| 252 | ++++ | ++++ | ND | ND |
| 253 | ND | ++++ | ND | ND |
| 254 | ++++ | ++++ | ND | ++ |
| 255 | ++++ | ++++ | ND | + |
| 256A | ++++ | ++++ | ND | ++ |
| 256B | ++++ | ++++ | ND | ND |
| 257 | ++++ | +++ | ND | ND |
| 258 | ++++ | ++++ | +++ | +++ |
| 259 | ND | ND | ND | + |
| 260 | ++ | +++ | ND | ND |
| 261 | ++++ | ++++ | ND | ND |
| 262 | ++++ | ++++ | +++ | +++ |
| 263 | +++ | +++ | ND | ND |
| 264 | ++++ | ++++ | +++ | ++++ |
| 265 | ++ | +++ | ND | ND |
| 266 | ++++ | ++++ | ND | ND |
| 267 | +++ | ++++ | ND | ND |
| 268 | ++++ | ++++ | ND | ND |
| 269 | ++ | +++ | ND | ND |
| 270 | ++++ | ++++ | ND | ND |
| 271 | + | ++ | ND | ND |
| 272 | ++++ | +++ | ND | ND |
| 273 | ++ | +++ | ND | ND |
| 274 | ++ | +++ | ND | ND |
| 275 | ++ | ++ | ND | ND |
| 276 | ++ | +++ | ND | ND |
| 277 | +++ | ++++ | ND | ND |
| 278 | + | + | ND | ND |
| 279 | ++ | ND | ND | ND |
| 280 | +++ | ND | ND | ND |
| 281 | ++++ | ++++ | ND | ND |
| 282 | ++ | +++ | ND | ND |
| 283 | ++ | ++ | ND | ND |

SEQUENCE LISTING

```
Sequence total quantity: 10
SEQ ID NO: 1                   moltype = AA  length = 399
FEATURE                        Location/Qualifiers
source                         1..399
                               mol_type = protein
                               organism = synthetic construct
SEQUENCE: 1
MSPILGYWKI KGLVQPTRLL LEYLEEKYEE HLYERDEGDK WRNKKFELGL EFPNLPYYID   60
GDVKLTQSMA IIRYIADKHN MLGGCPKERA EISMLEGAVL DIRYGVSRIA YSKDFETLKV  120
DFLSKLPEML KMFEDRLCHK TYLNGDHVTH PDFMLYDALD VVLYMDPMCL DAFPKLVCFK  180
KRIEAIPQID KYLKSSKYIA WPLQGWQATF GGGDHPPKSD ENLYFQGGST STEYKLVVVG  240
ADGVGKSALT IQLIQNHFVD EYDPTIEDSY RKQVVIDGET CLLDILDTAG QEEYSAMRDQ  300
YMRTGEGFLC VFAINNTKSF EDIHHYREQI KRVKDSEDVP MVLVGNKCDL PSRTVDTKQA  360
QDLARSYGIP FIETSAKTRQ GVDDAFYTLV REIRKHKEK                         399

SEQ ID NO: 2                   moltype = AA  length = 399
FEATURE                        Location/Qualifiers
source                         1..399
                               mol_type = protein
                               organism = synthetic construct
SEQUENCE: 2
MSPILGYWKI KGLVQPTRLL LEYLEEKYEE HLYERDEGDK WRNKKFELGL EFPNLPYYID   60
GDVKLTQSMA IIRYIADKHN MLGGCPKERA EISMLEGAVL DIRYGVSRIA YSKDFETLKV  120
DFLSKLPEML KMFEDRLCHK TYLNGDHVTH PDFMLYDALD VVLYMDPMCL DAFPKLVCFK  180
KRIEAIPQID KYLKSSKYIA WPLQGWQATF GGGDHPPKSD ENLYFQGGST STEYKLVVVG  240
AVGVGKSALT IQLIQNHFVD EYDPTIEDSY RKQVVIDGET CLLDILDTAG QEEYSAMRDQ  300
YMRTGEGFLC VFAINNTKSF EDIHHYREQI KRVKDSEDVP MVLVGNKCDL PSRTVDTKQA  360
QDLARSYGIP FIETSAKTRQ GVDDAFYTLV REIRKHKEK                         399

SEQ ID NO: 3                   moltype = AA  length = 185
FEATURE                        Location/Qualifiers
source                         1..185
                               mol_type = protein
                               organism = synthetic construct
SEQUENCE: 3
SGLNDIFEAQ KIEWHEMTEY KLVVVGADGV GKSALTIQLI QNHFVDEYDP TIEDSYRKQV   60
VIDGETCLLD ILDTAGQEEY SAMRDQYMRT GEGFLCVFAI NNTKSFEDIH HYREQIKRVK  120
DSEDVPMVLV GNKCDLPSRT VDTKQAQDLA RSYGIPFIET SAKTRQGVDD AFYTLVREIR  180
KHKEK                                                              185

SEQ ID NO: 4                   moltype = AA  length = 185
FEATURE                        Location/Qualifiers
source                         1..185
                               mol_type = protein
                               organism = synthetic construct
SEQUENCE: 4
SGLNDIFEAQ KIEWHEMTEY KLVVVGAVGV GKSALTIQLI QNHFVDEYDP TIEDSYRKQV   60
VIDGETCLLD ILDTAGQEEY SAMRDQYMRT GEGFLCVFAI NNTKSFEDIH HYREQIKRVK  120
DSEDVPMVLV GNKCDLPSRT VDTKQAQDLA RSYGIPFIET SAKTRQGVDD AFYTLVREIR  180
KHKEK                                                              185

SEQ ID NO: 5                   moltype = AA  length = 185
FEATURE                        Location/Qualifiers
source                         1..185
                               mol_type = protein
                               organism = synthetic construct
SEQUENCE: 5
SGLNDIFEAQ KIEWHEMTEY KLVVVGAGGV GKSALTIQLI QNHFVDEYDP TIEDSYRKQV   60
VIDGETCLLD ILDTAGQEEY SAMRDQYMRT GEGFLCVFAI NNTKSFEDIH HYREQIKRVK  120
DSEDVPMVLV GNKCDLPSRT VDTKQAQDLA RSYGIPFIET SAKTRQGVDD AFYTLVREIR  180
KHKEK                                                              185

SEQ ID NO: 6                   moltype = AA  length = 185
FEATURE                        Location/Qualifiers
source                         1..185
                               mol_type = protein
                               organism = synthetic construct
SEQUENCE: 6
SGLNDIFEAQ KIEWHEMTEY KLVVVGAGGV GKSALTIQLI QNHFVDEYDP TIEDSYRKQV   60
VIDGETCLLD ILDTAGQEEY SAMRDQYMRT GEGFLCVFAI NNSKSFADIN LYREQIKRVK  120
DSDDVPMVLV GNKCDLPTRT VDTKQAHELA KSYGIPFIET SAKTRQGVED AFYTLVREIR  180
QYRMK                                                              185

SEQ ID NO: 7                   moltype = AA  length = 89
FEATURE                        Location/Qualifiers
source                         1..89
                               mol_type = protein
                               organism = synthetic construct
```

```
SEQUENCE: 7
SHHHHHHHHS KTSNTIRVFL PNKQRTVVNV RNGMSLHDCL MKALKVRGLQ PECCAVFRLL    60
HEHKGKKARL DWNTDAASLI GEELQVDFL                                     89

SEQ ID NO: 8            moltype = AA   length = 7
FEATURE                 Location/Qualifiers
source                  1..7
                        mol_type = protein
                        organism = synthetic construct
SEQUENCE: 8
ENLFYQS                                                              7

SEQ ID NO: 9            moltype = AA   length = 15
FEATURE                 Location/Qualifiers
source                  1..15
                        mol_type = protein
                        organism = synthetic construct
SEQUENCE: 9
GLNDIFEAQK IEWHE                                                    15

SEQ ID NO: 10           moltype = AA   length = 6
FEATURE                 Location/Qualifiers
source                  1..6
                        mol_type = protein
                        organism = synthetic construct
SEQUENCE: 10
HHHHHH                                                               6
```

What is claimed is:

1. A compound selected from

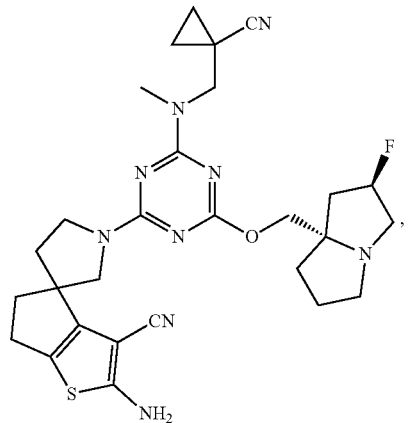

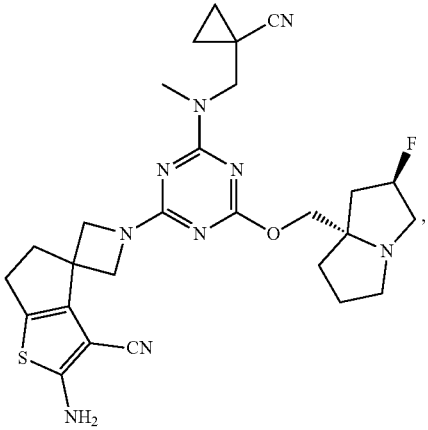

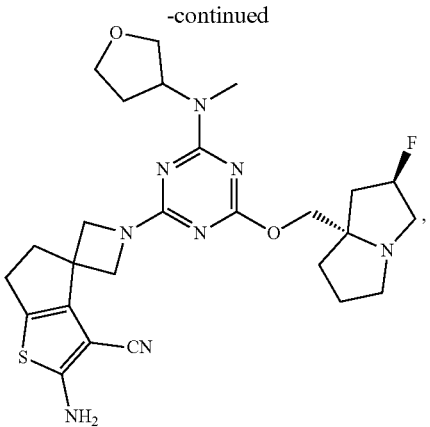

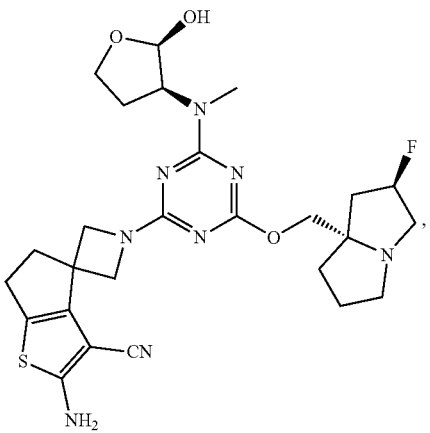

533
-continued
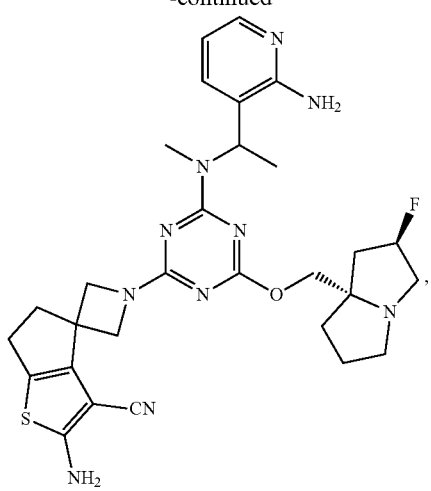
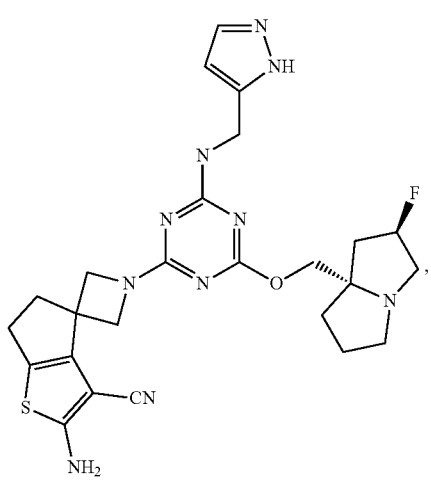
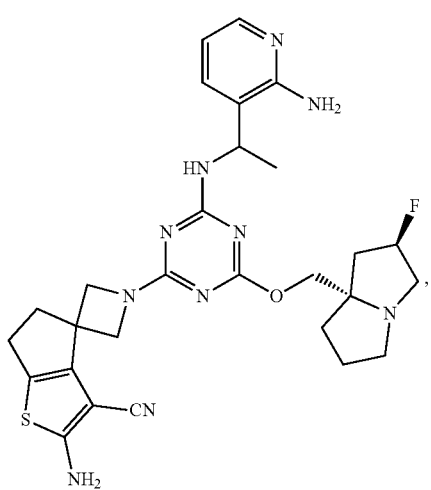
534
-continued
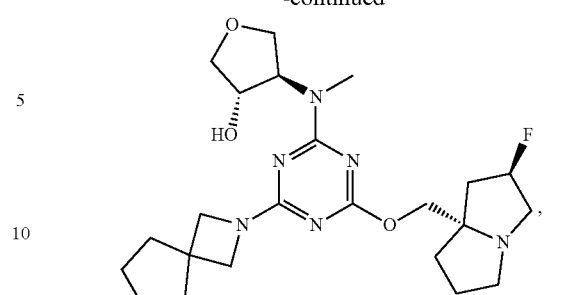
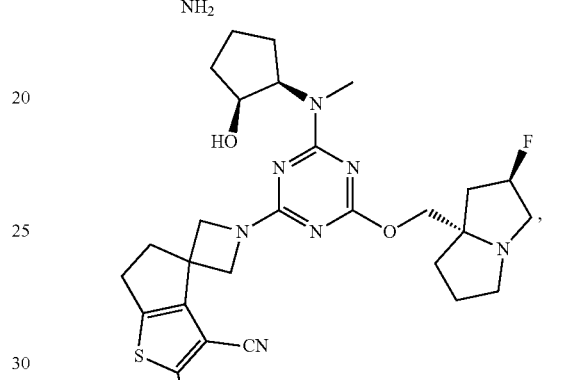
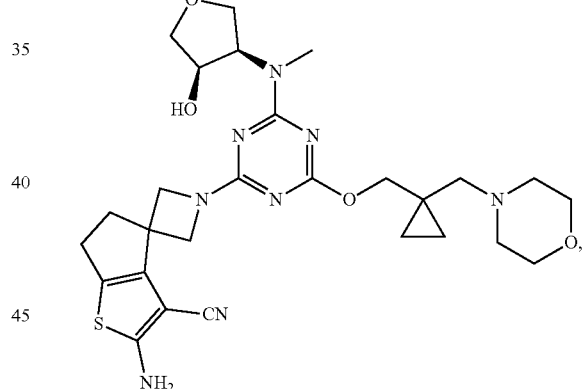
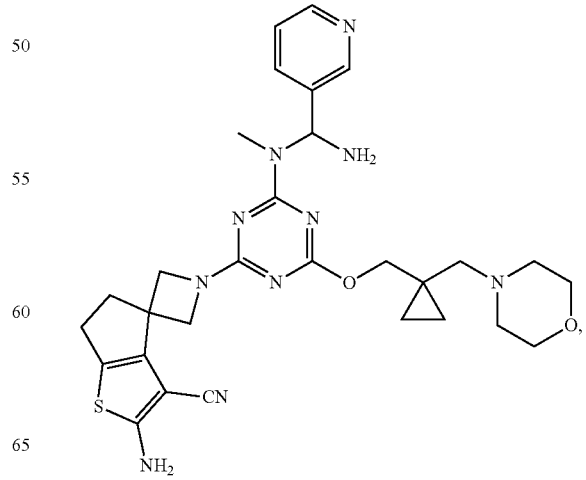

535
-continued
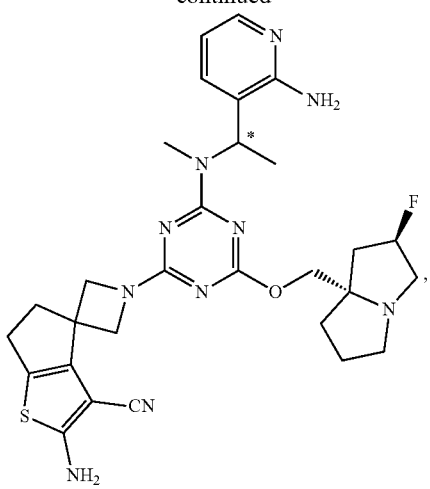
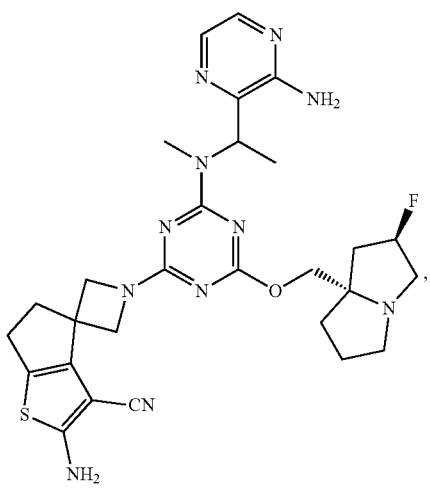
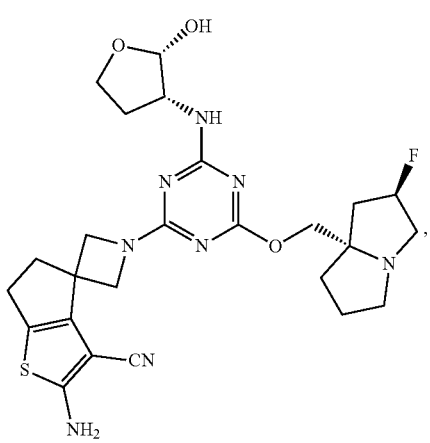
536
-continued
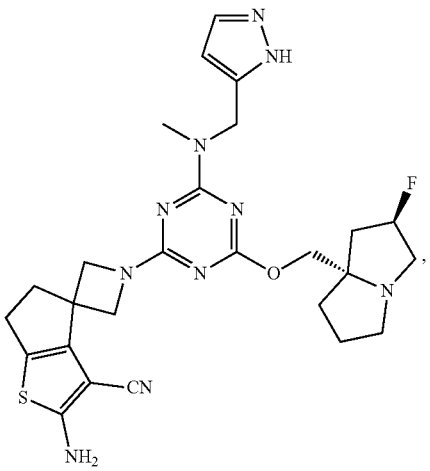
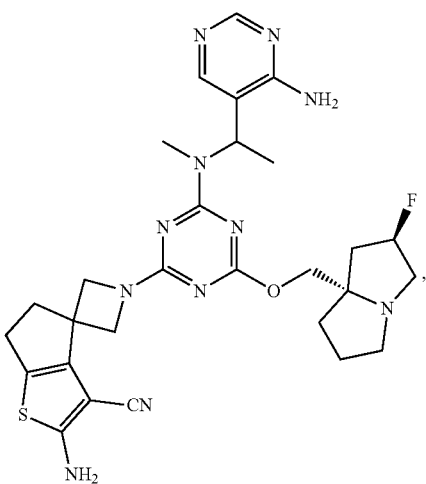

537
-continued
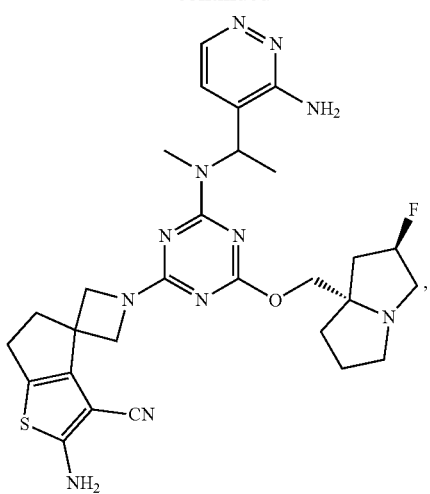
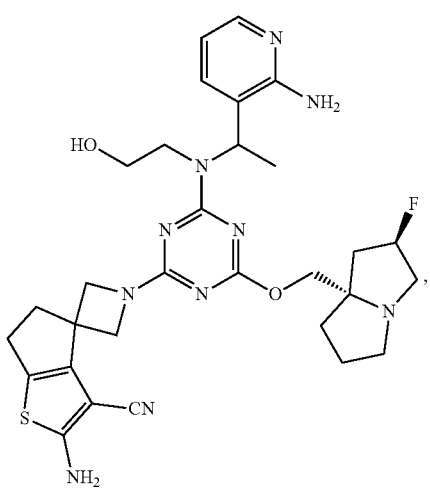
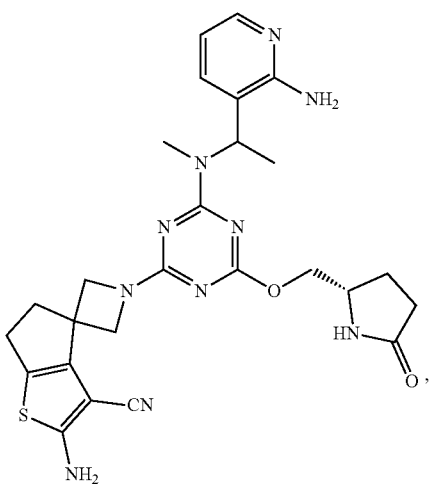
538
-continued
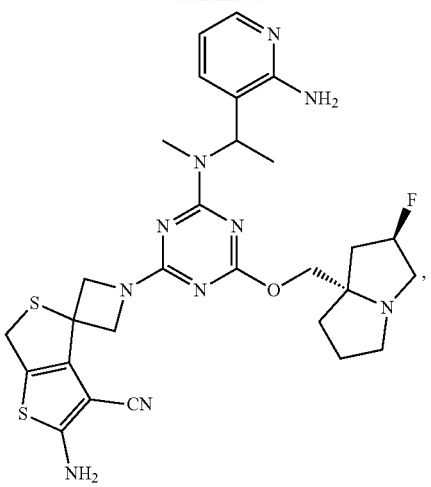
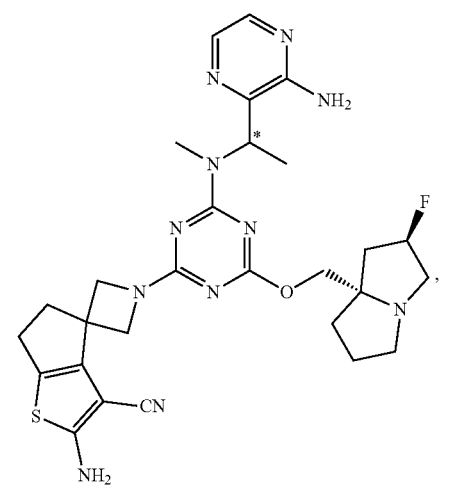
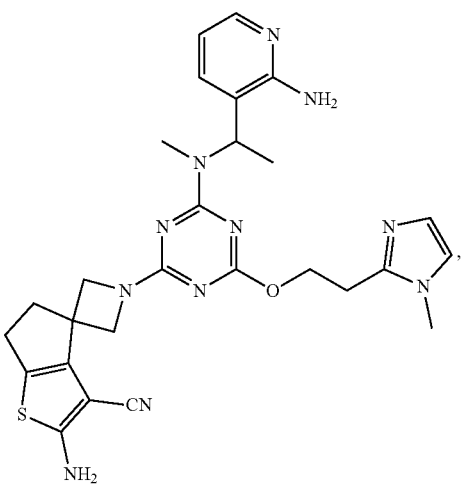

539
-continued
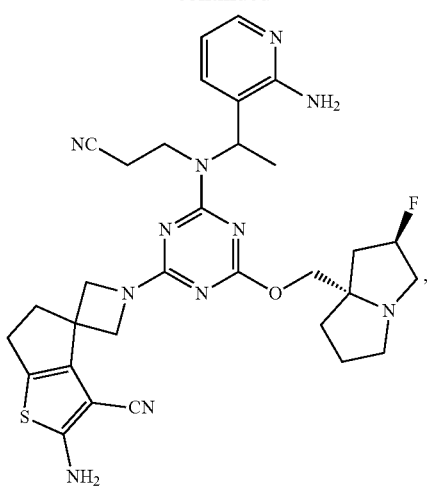
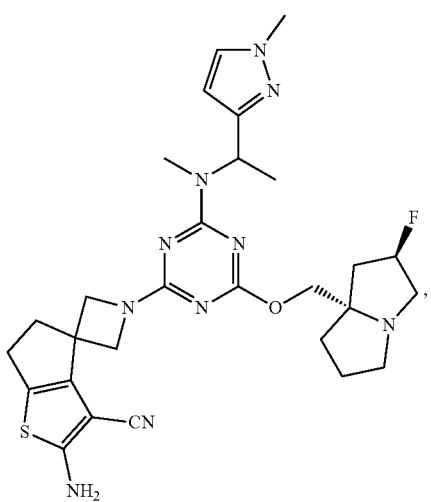
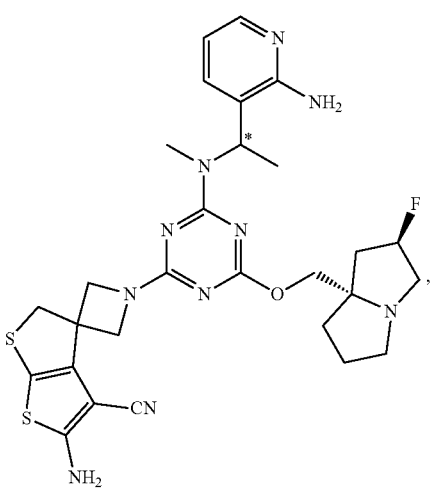
540
-continued
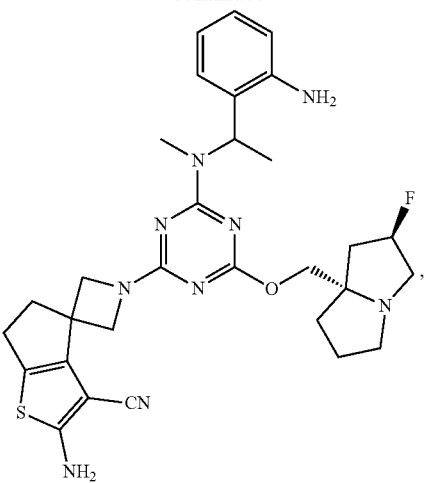
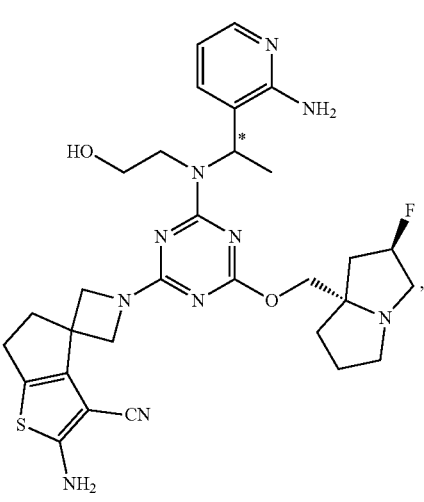
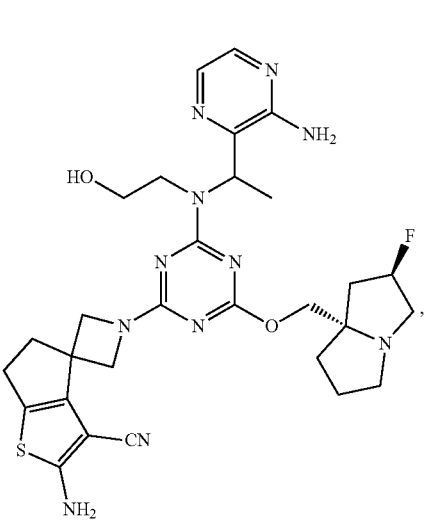

541
-continued
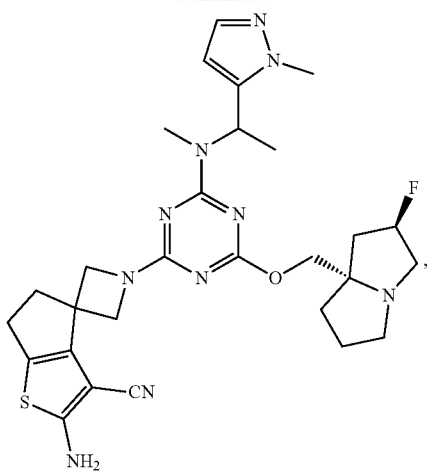
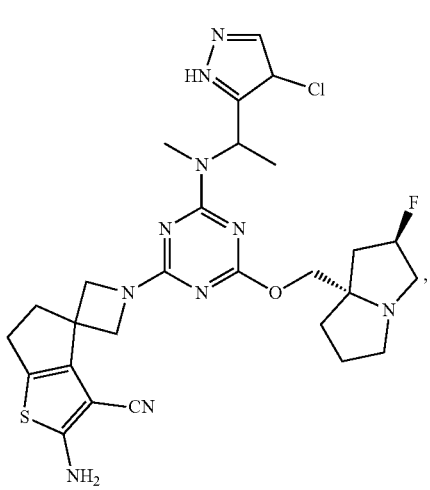
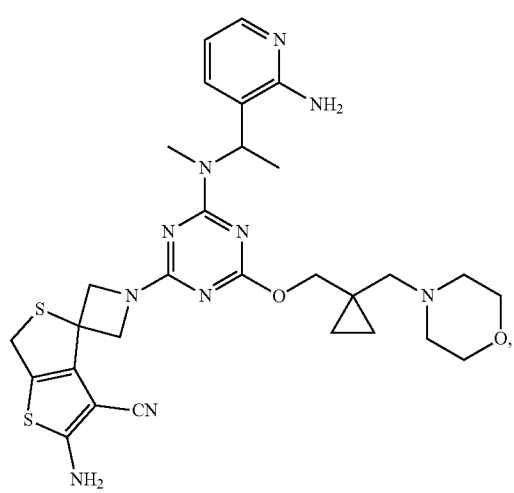
542
-continued
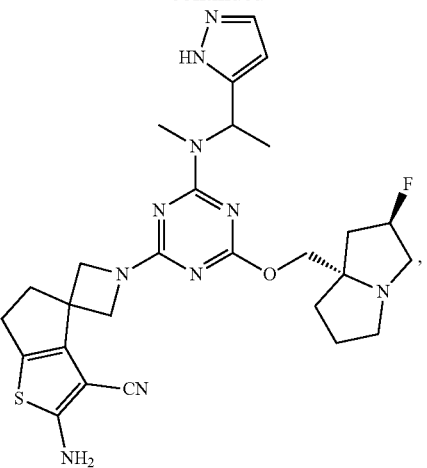
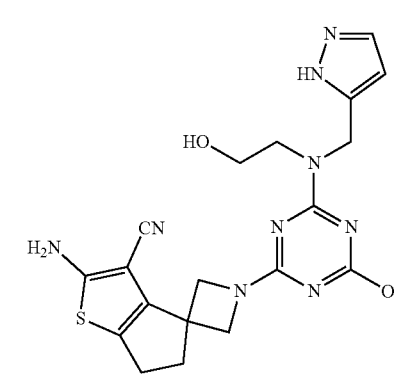
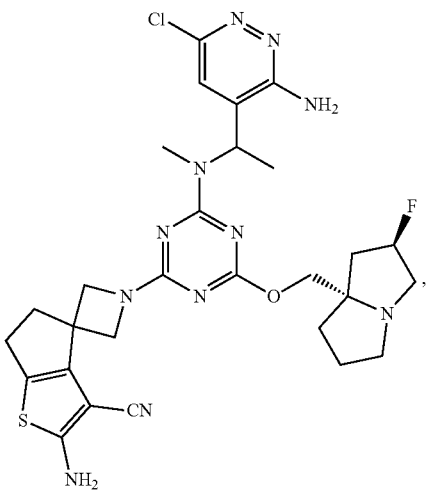

543
-continued
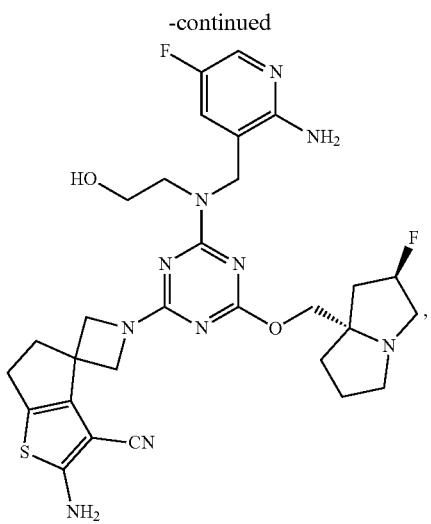
544
-continued
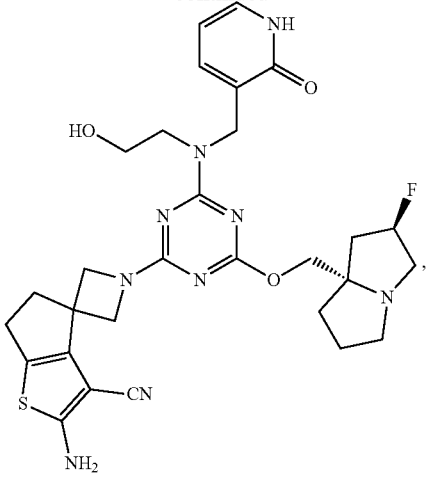
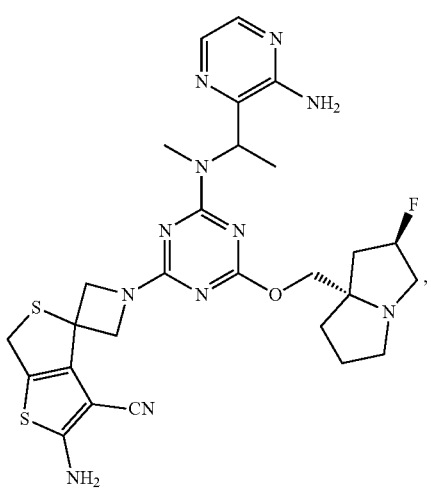
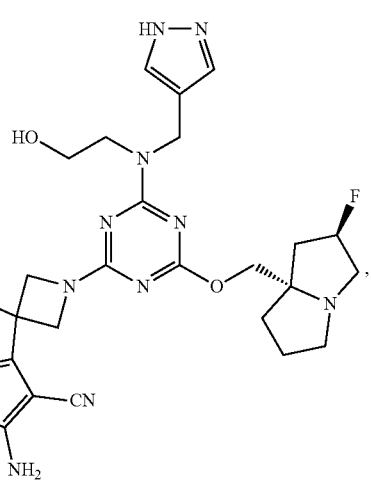
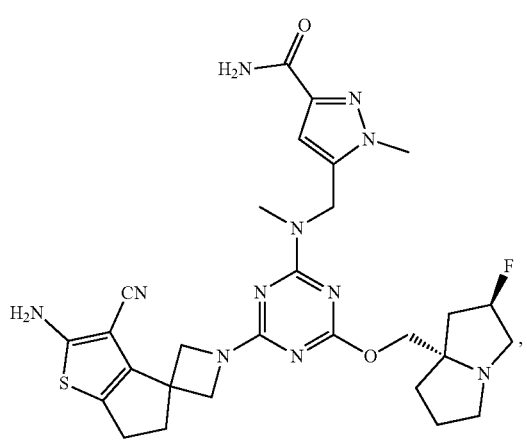
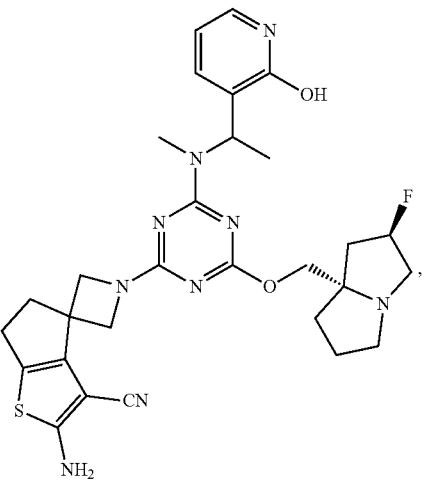

545
-continued
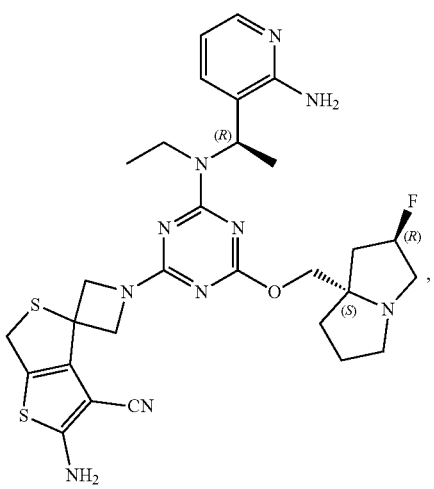
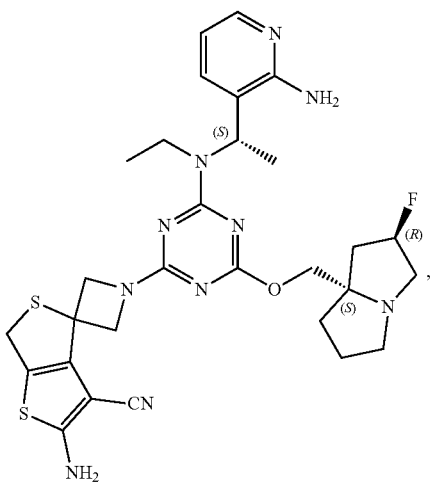
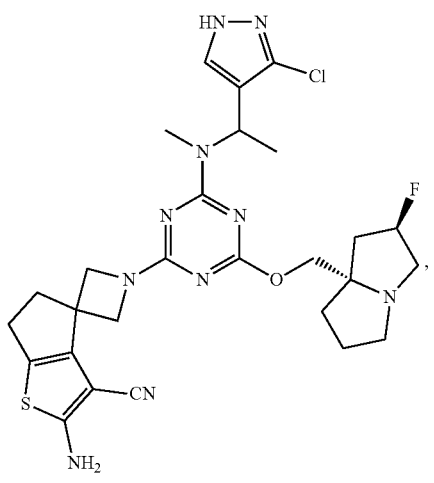
546
-continued
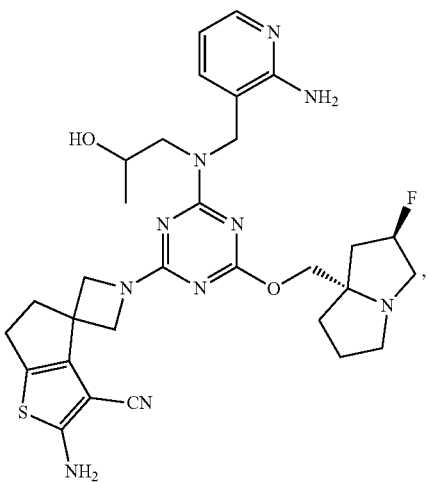
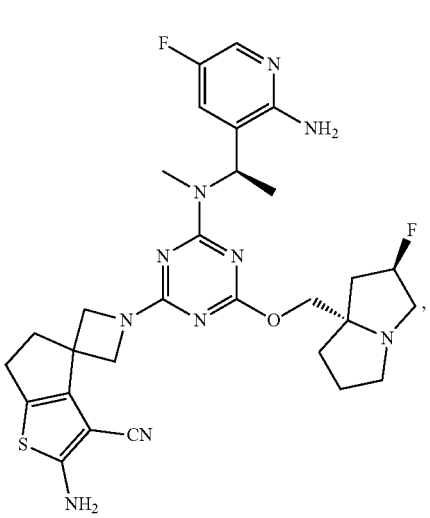

547
-continued
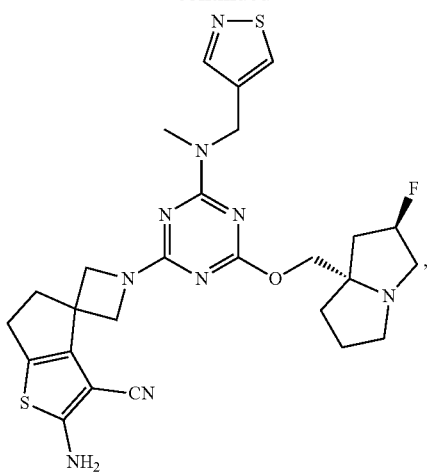
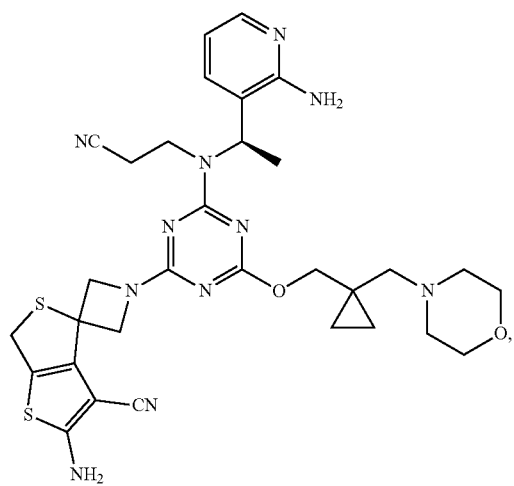
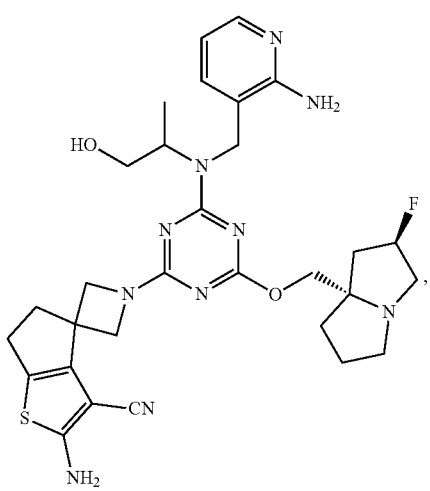
548
-continued
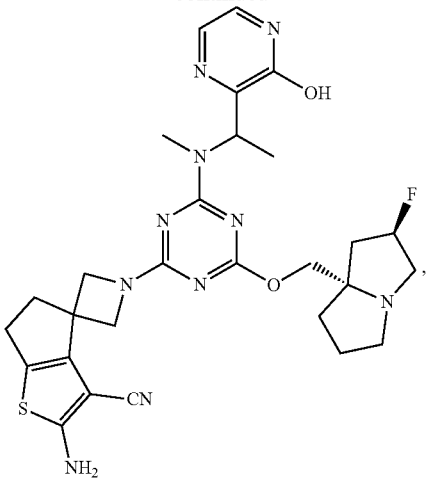
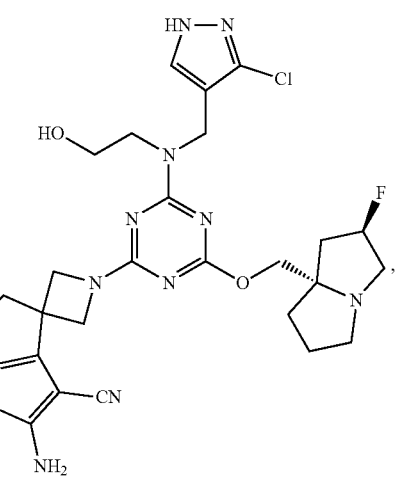
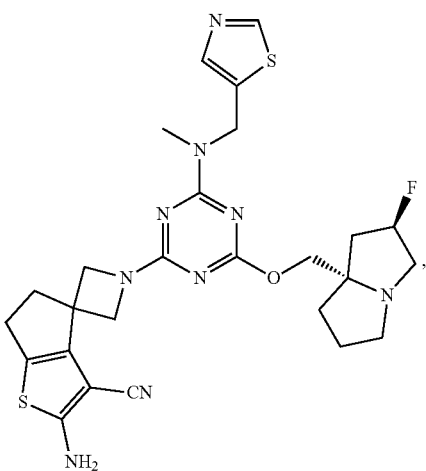

549
-continued
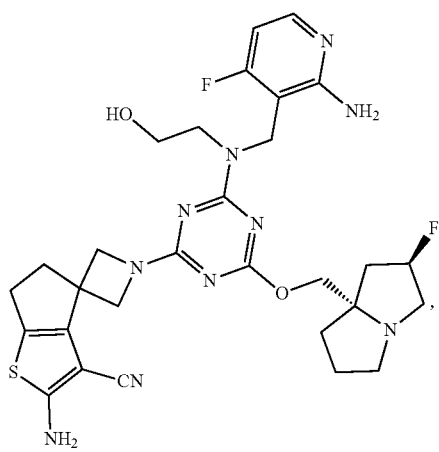
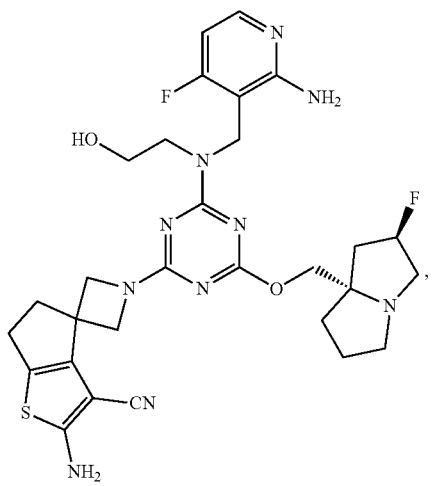
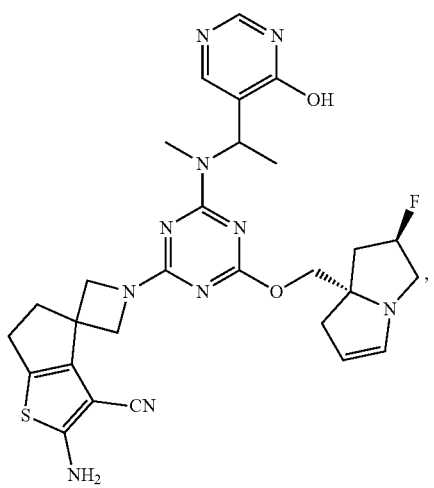
550
-continued
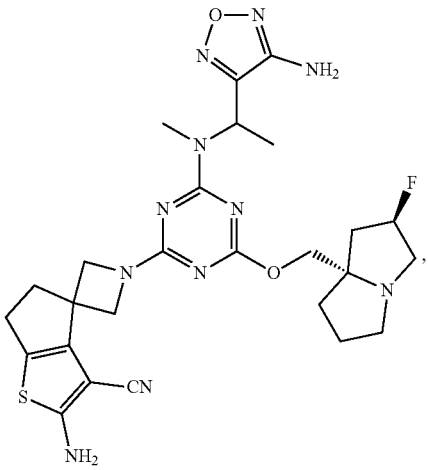
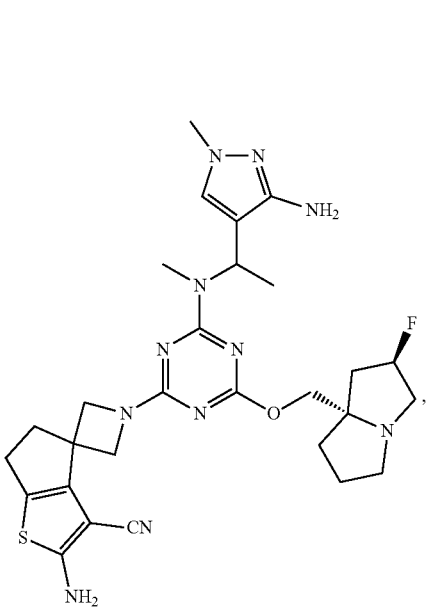
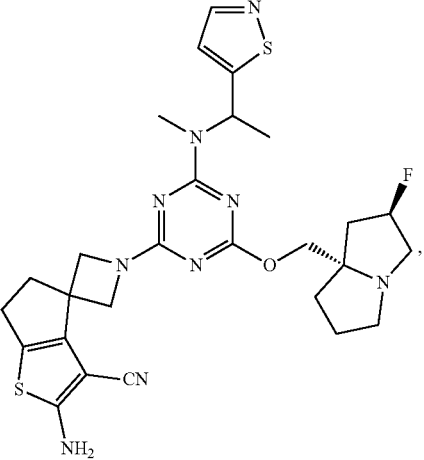

551
-continued
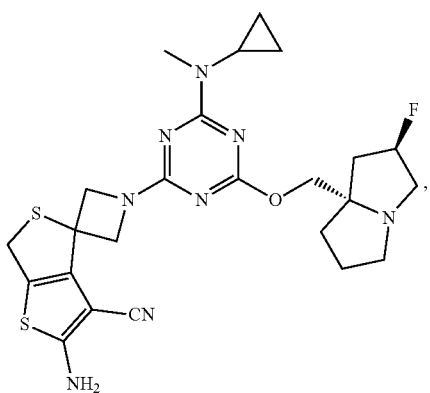
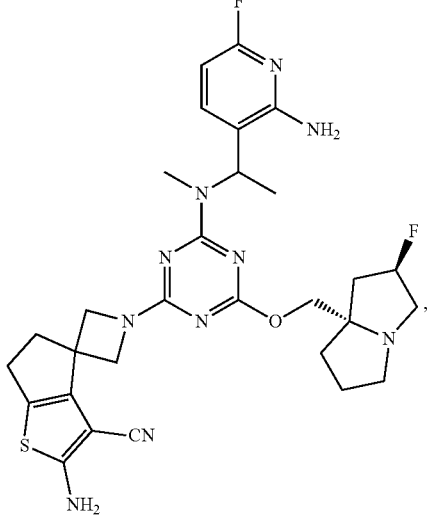
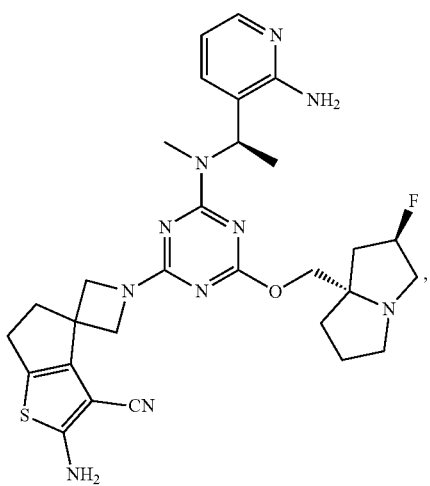
552
-continued
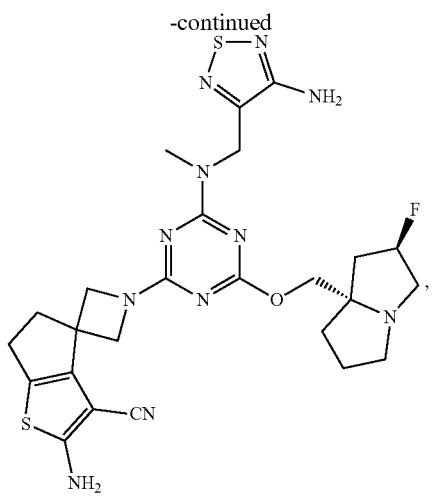
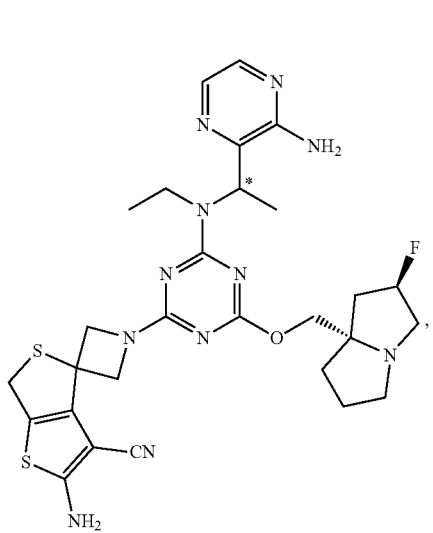
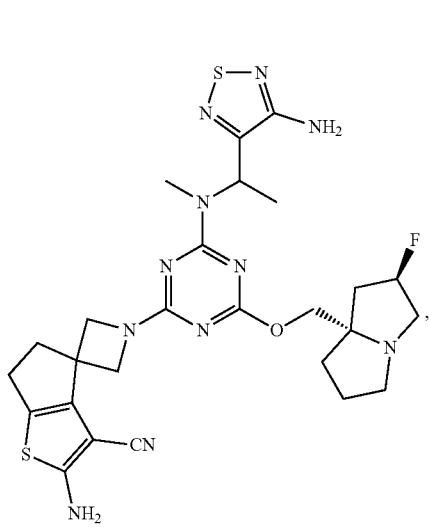

553
-continued
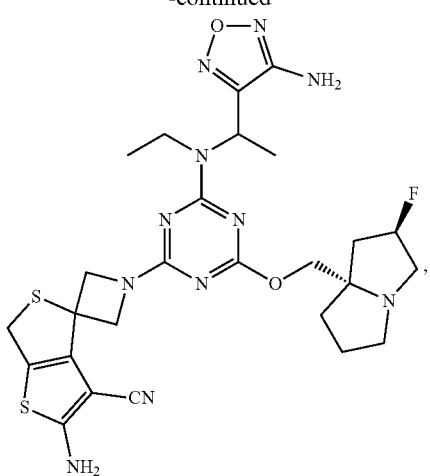
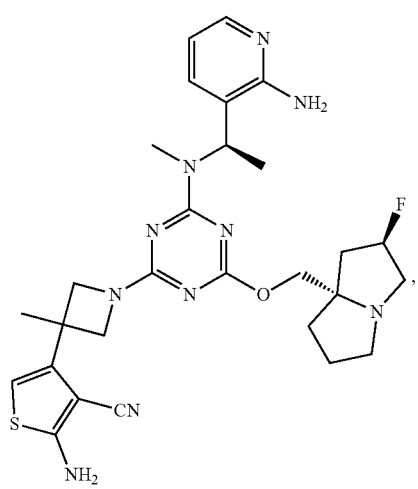
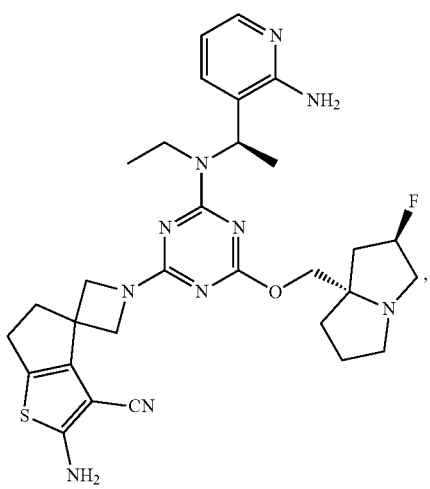
554
-continued
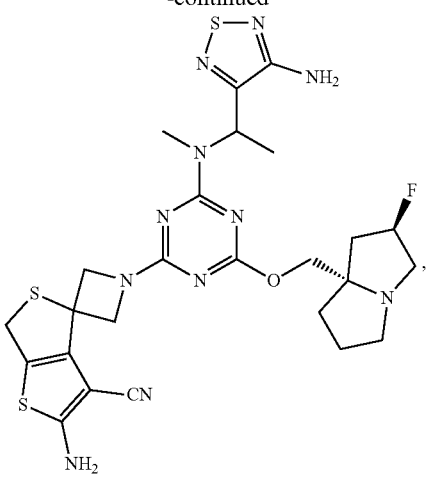
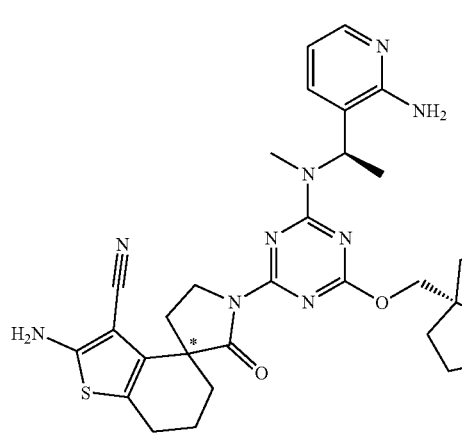
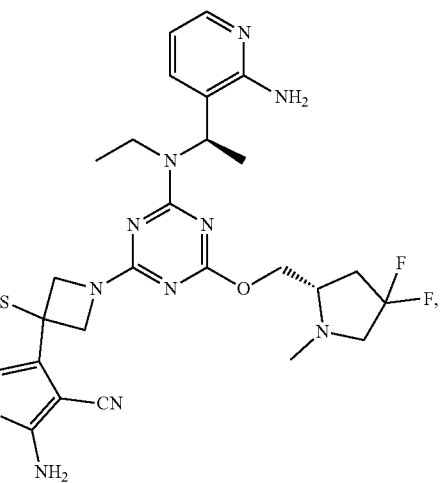

555
-continued
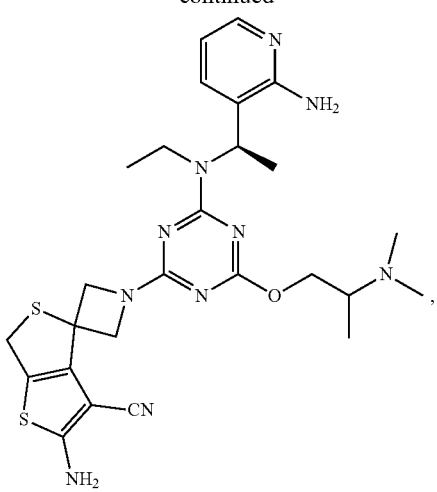
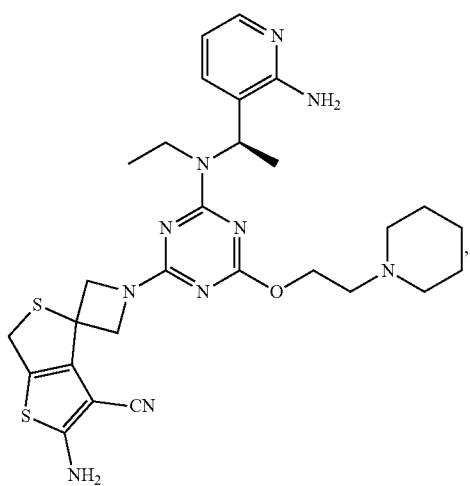
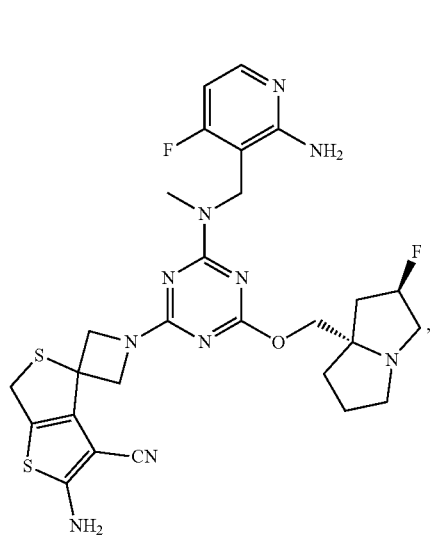
556
-continued
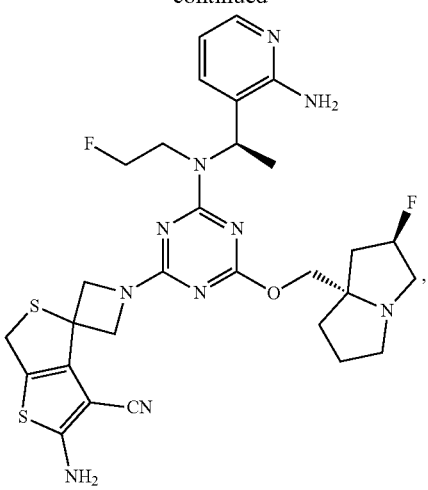
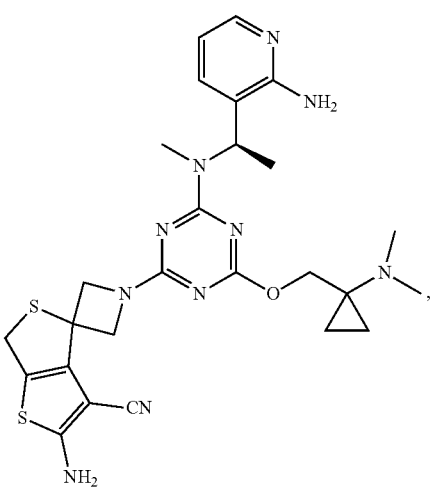
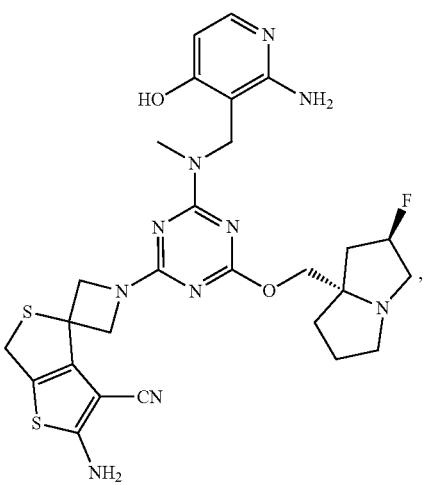

557
-continued
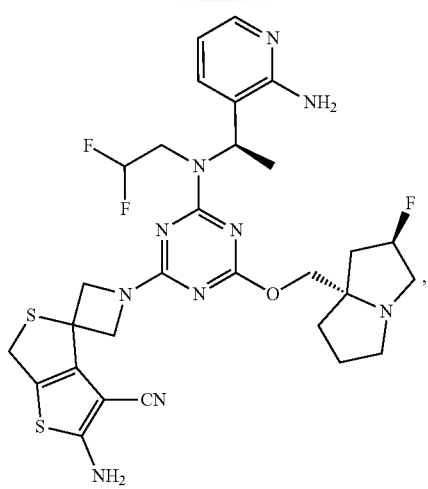
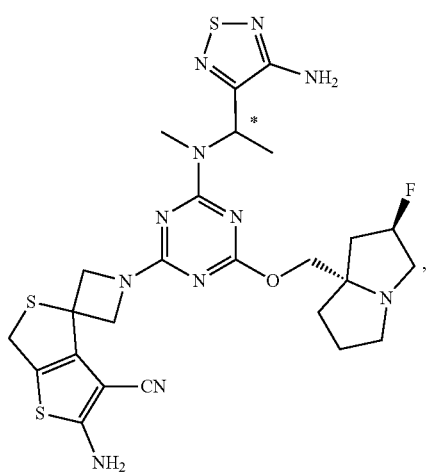
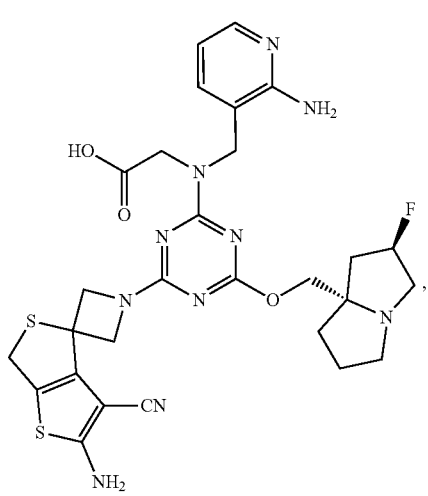
558
-continued
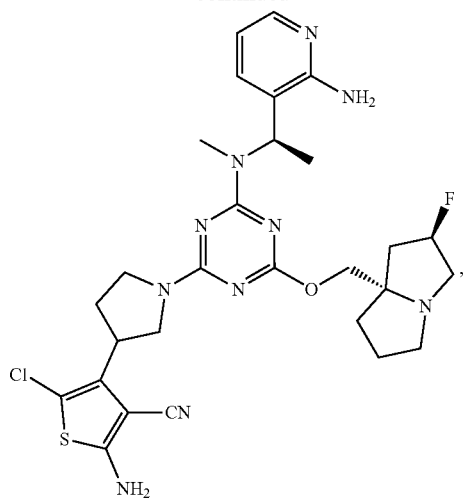
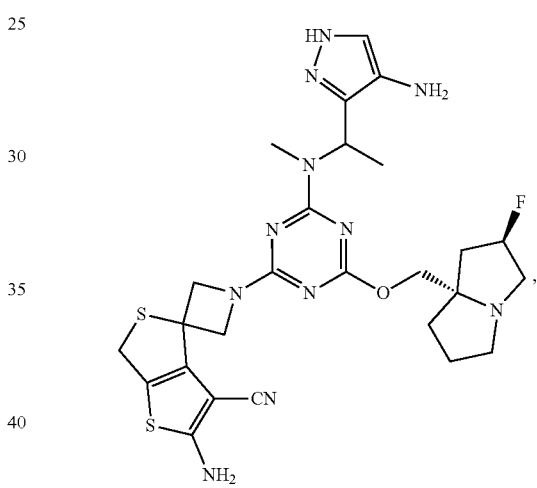
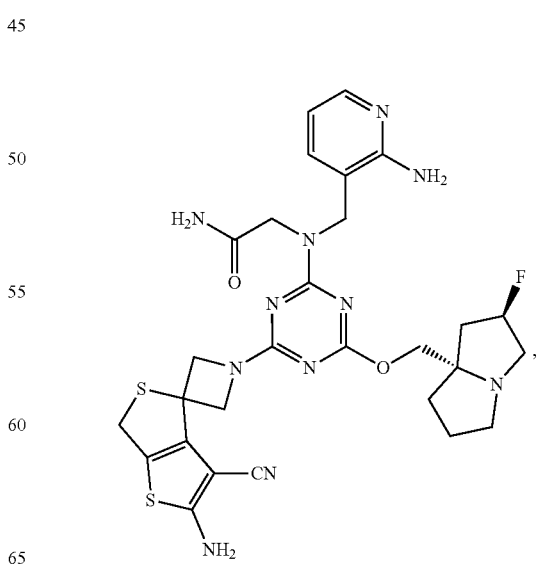

| 559 | 560 |
|---|---|
| 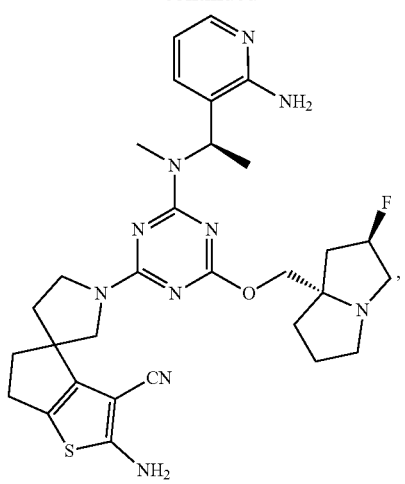 | 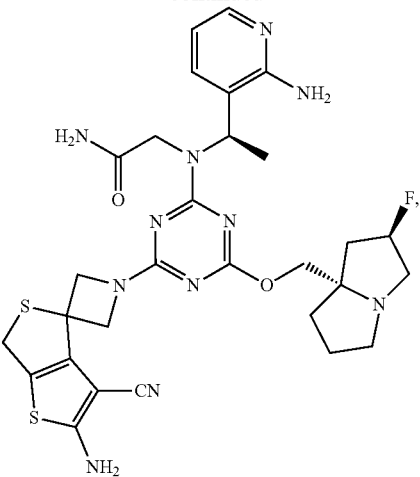 |
| 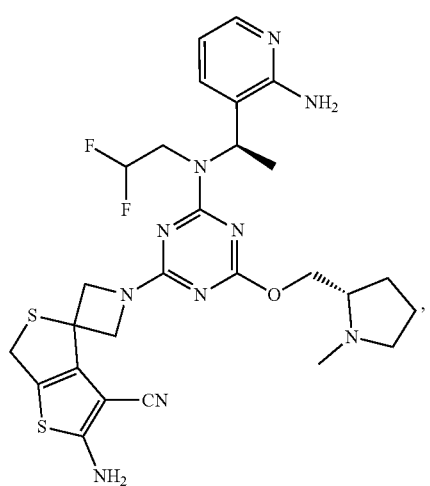 | 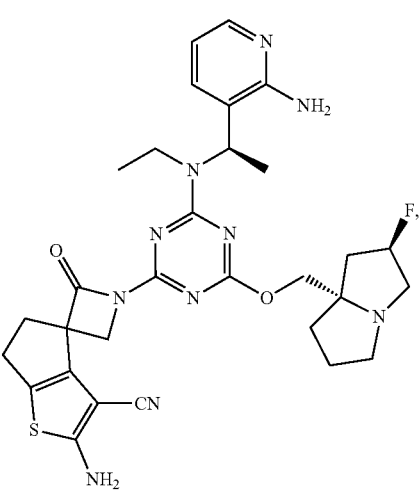 |
| 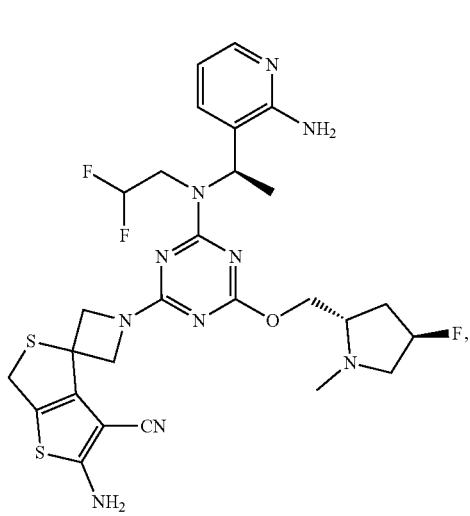 | 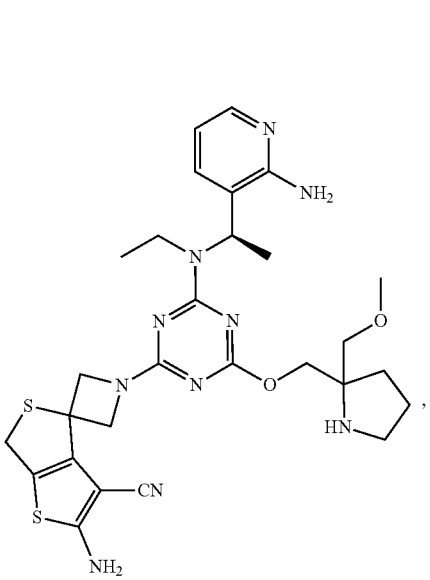 |

561
-continued
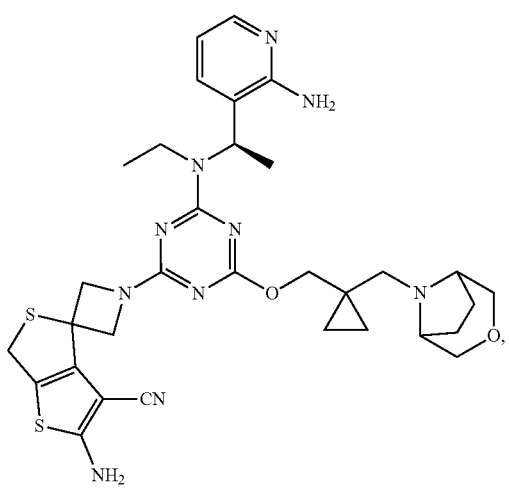
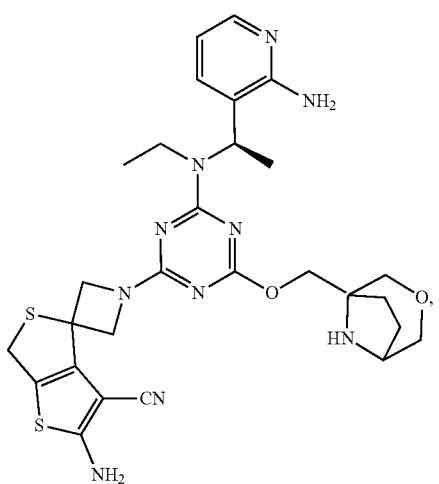
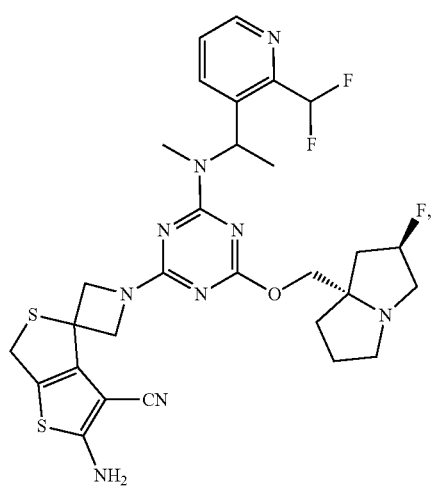
562
-continued
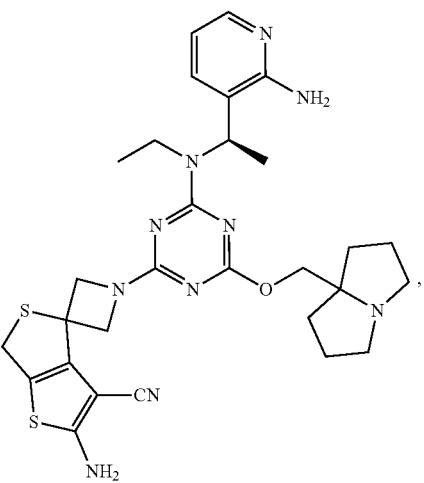
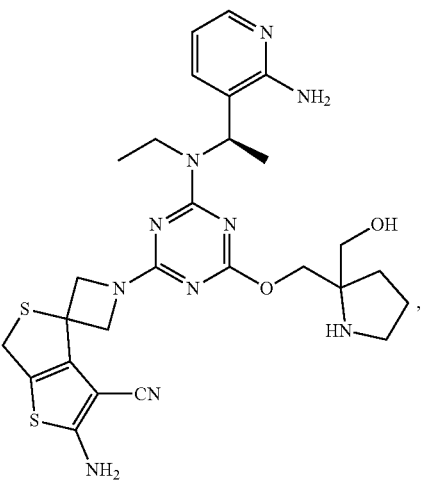

563
-continued
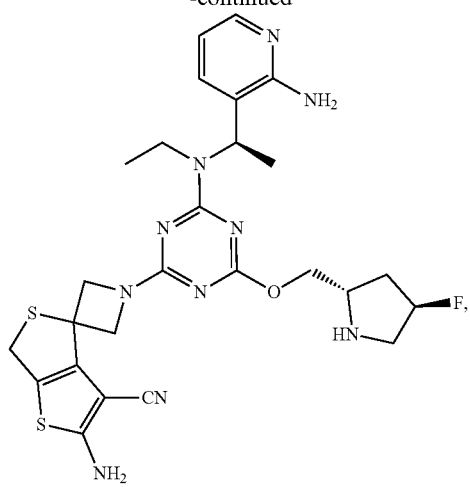
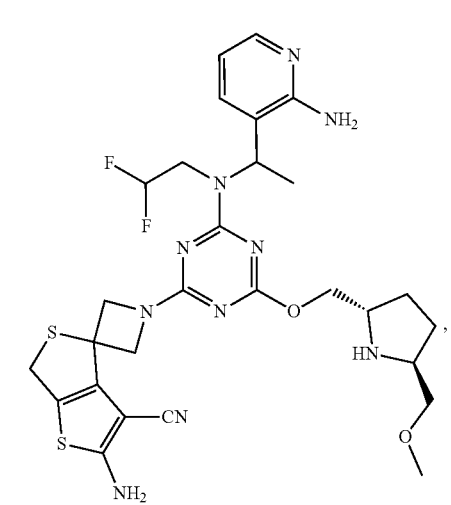
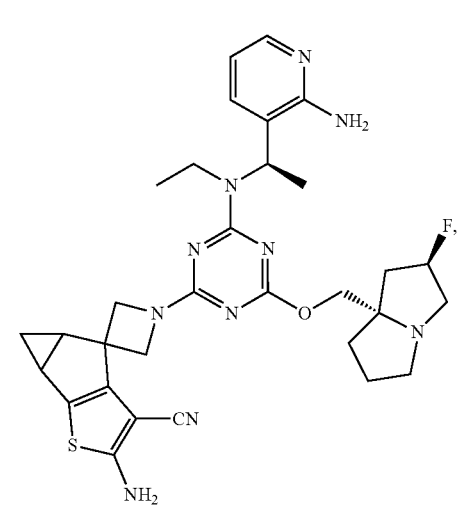
564
-continued
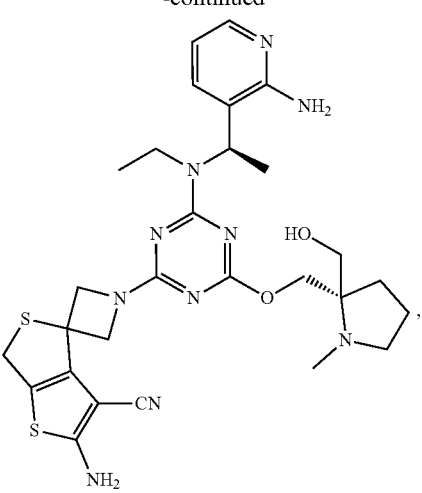
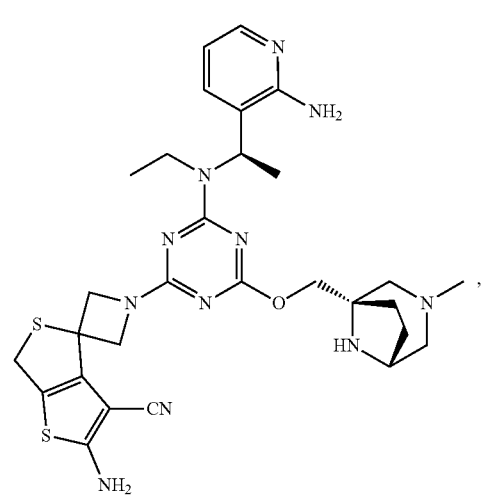
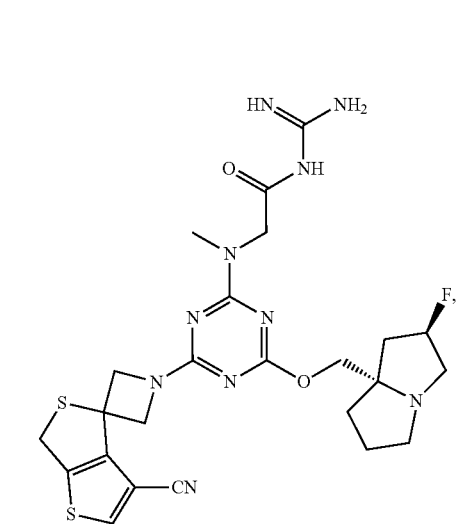

565
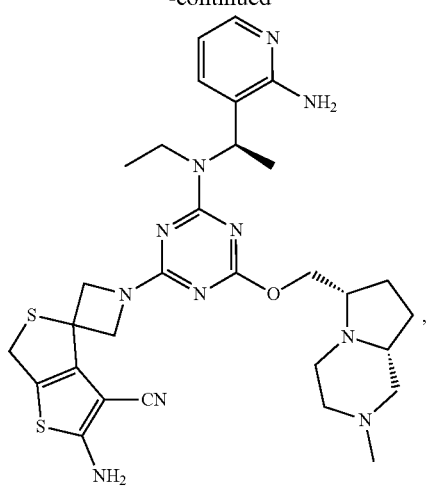,
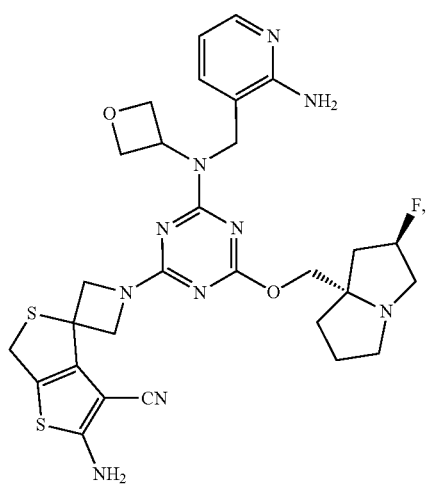,
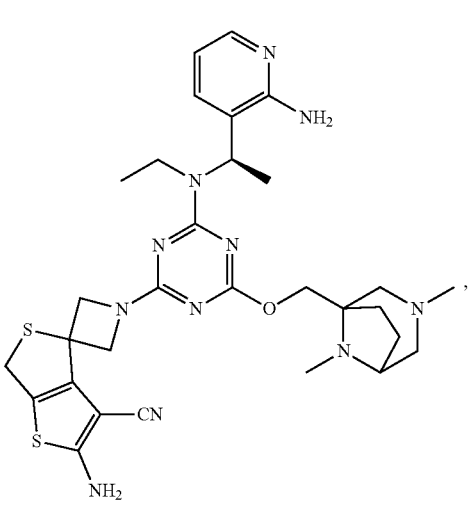,
566
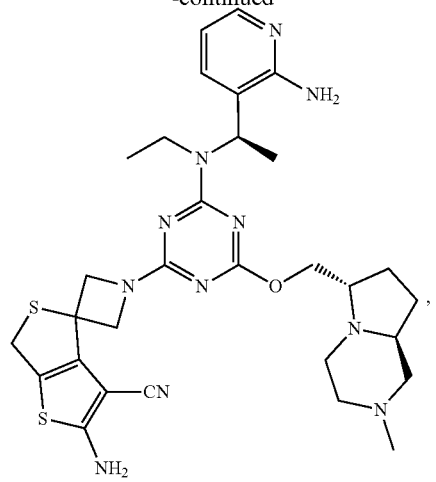,
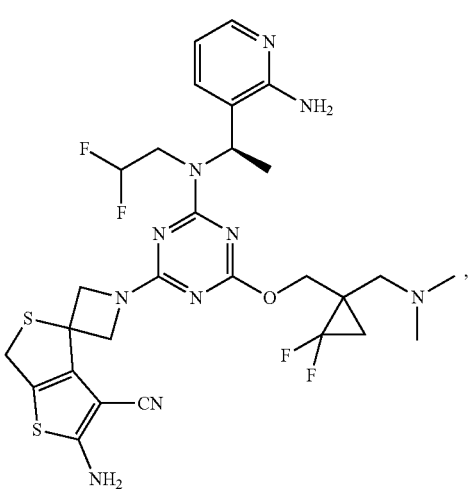,
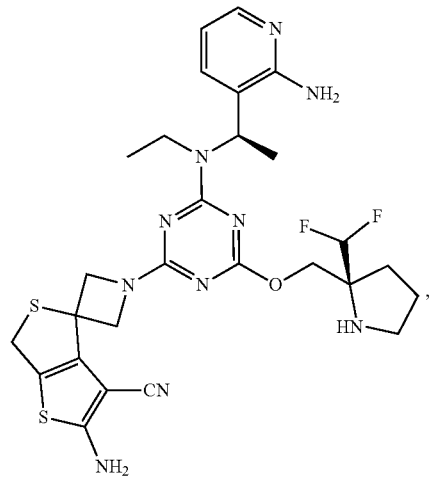, 567
-continued
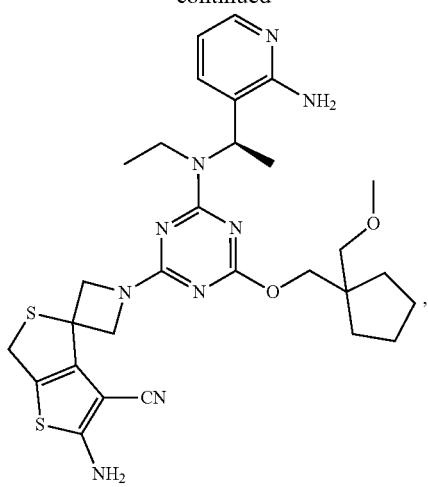
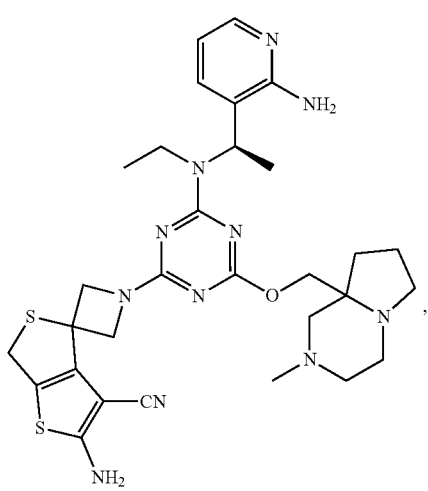
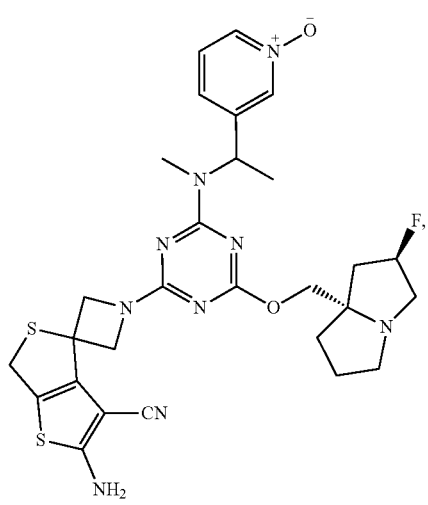
568
-continued
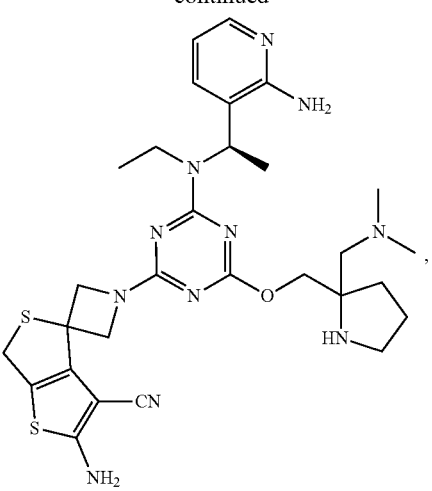
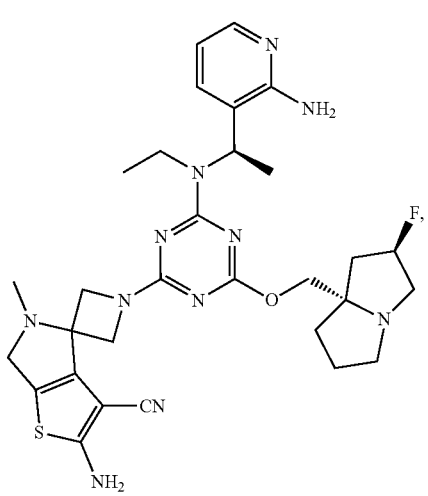
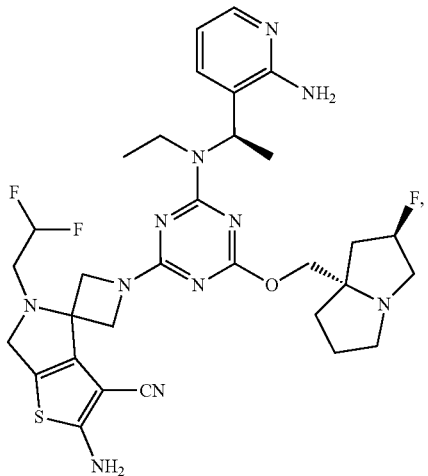

569
-continued
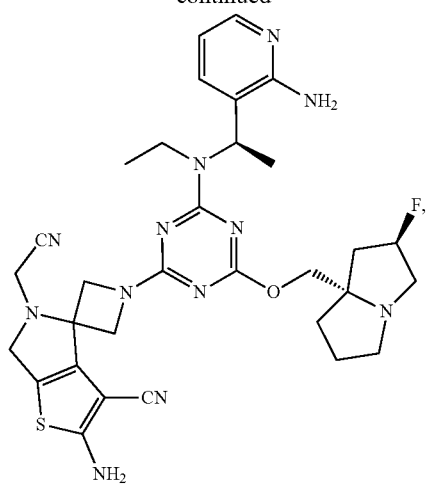
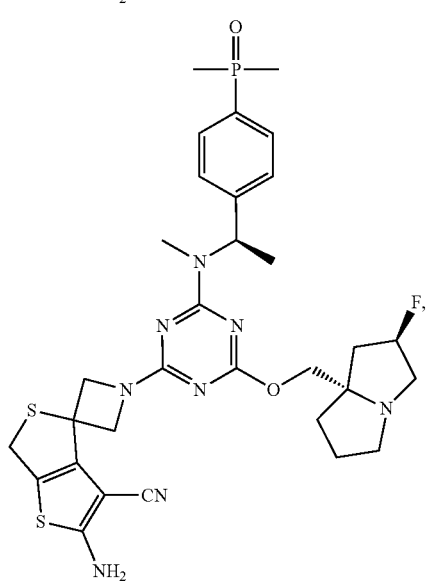
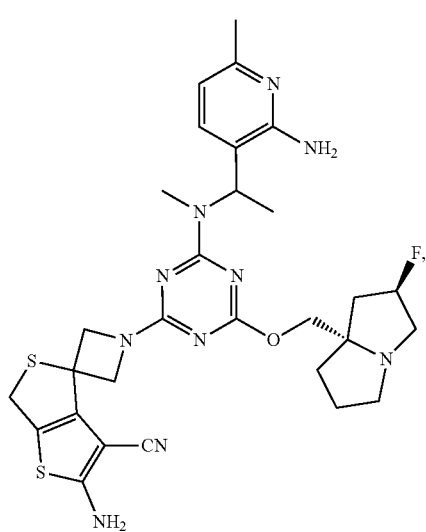
570
-continued
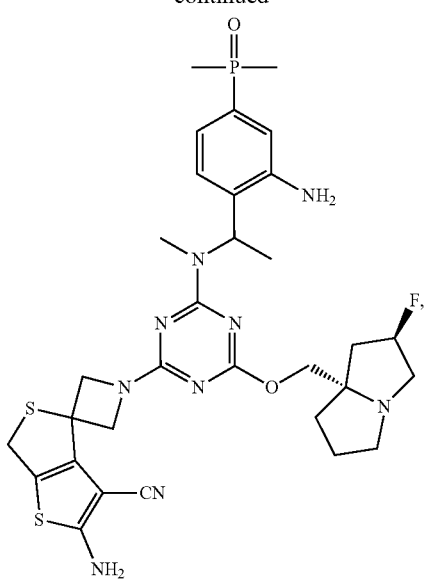
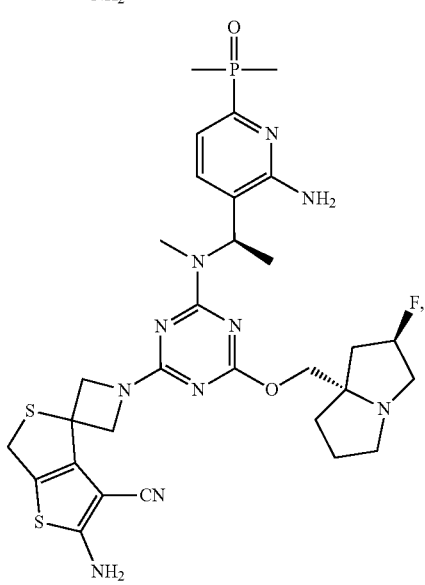
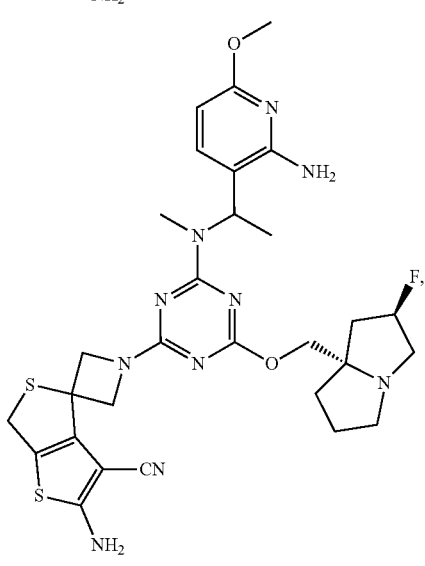 [SMILES: CC(c1ccc(P(C)(C)=O)cc1N)N(C)c1nc(OC[C@@]23CCCN2C[C@H](F)C3)nc(N2CC3(C2)SCc2sc(N)c(C#N)c23)n1]

571
-continued
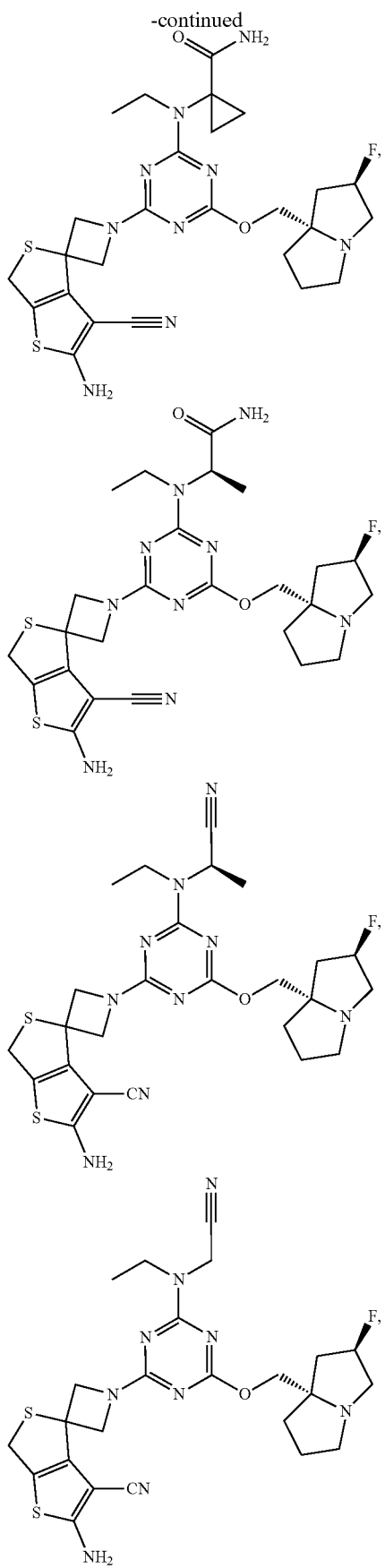
572
-continued
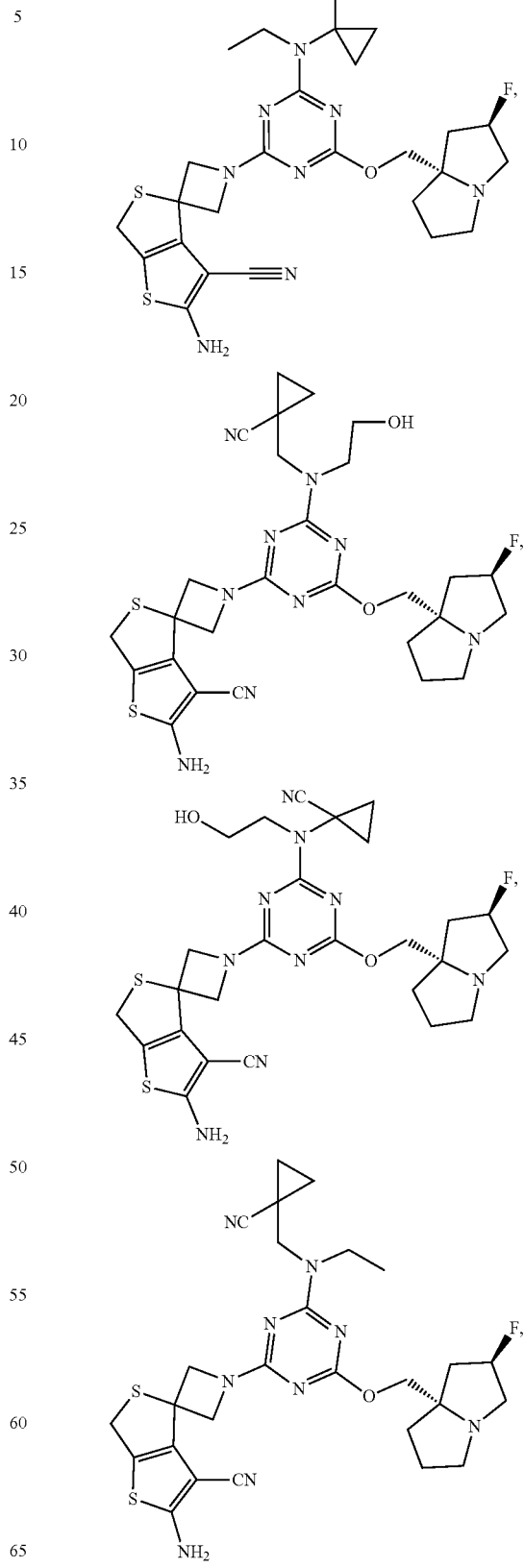

573
-continued
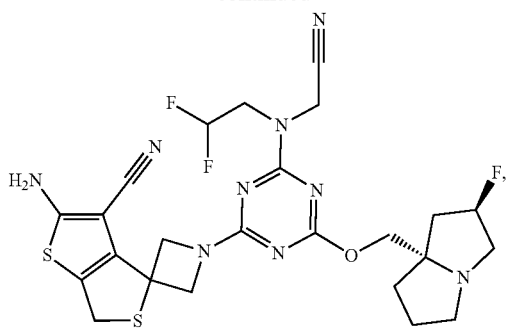
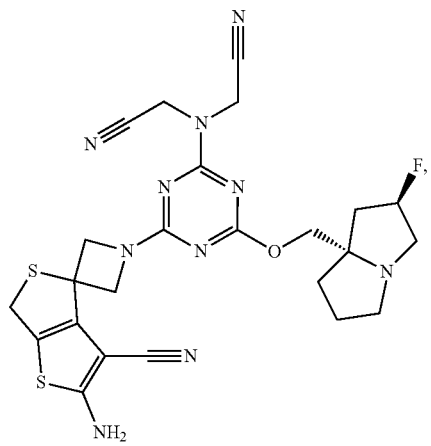
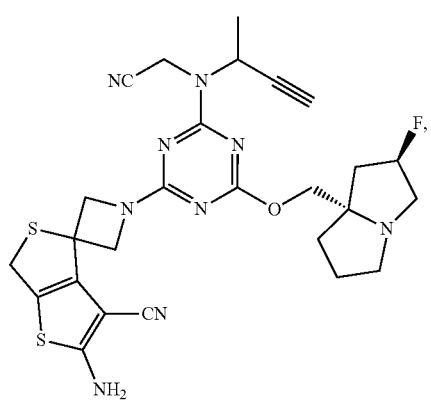
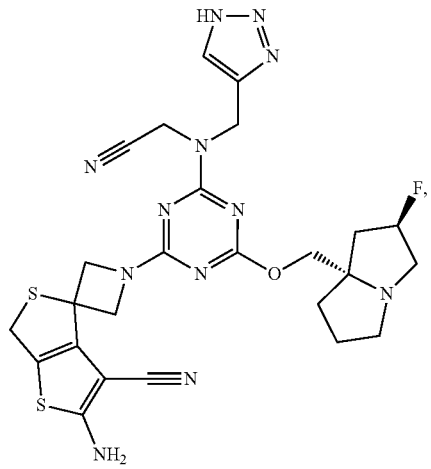
574
-continued
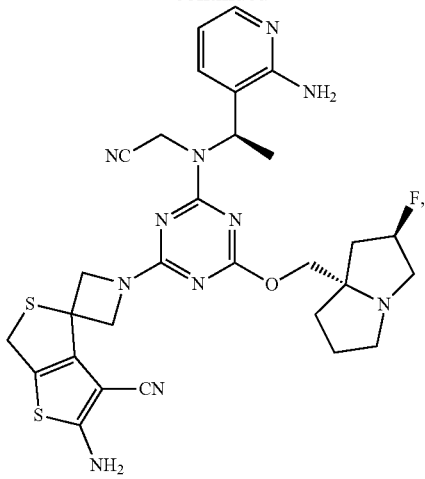
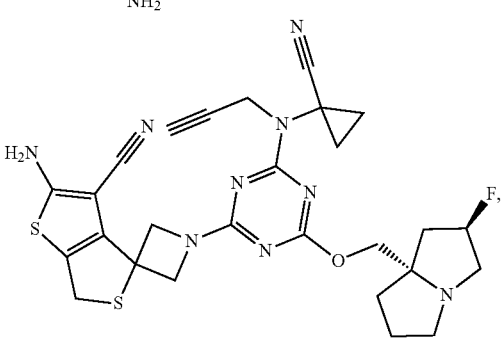
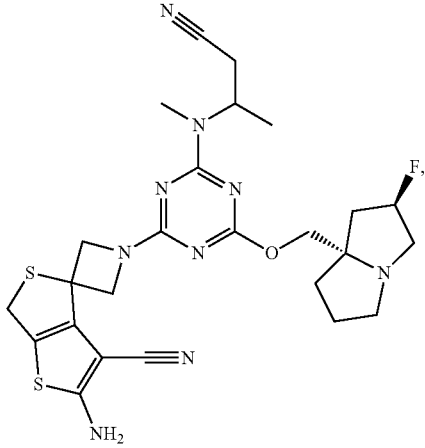
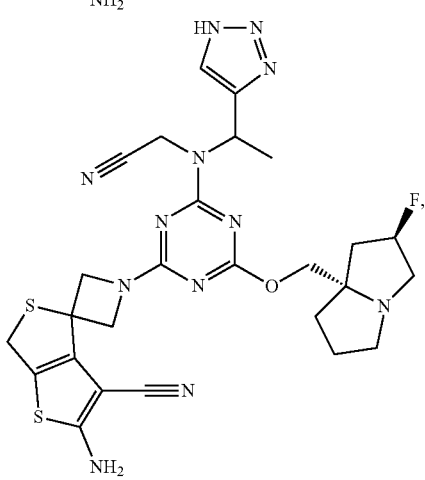

575
-continued
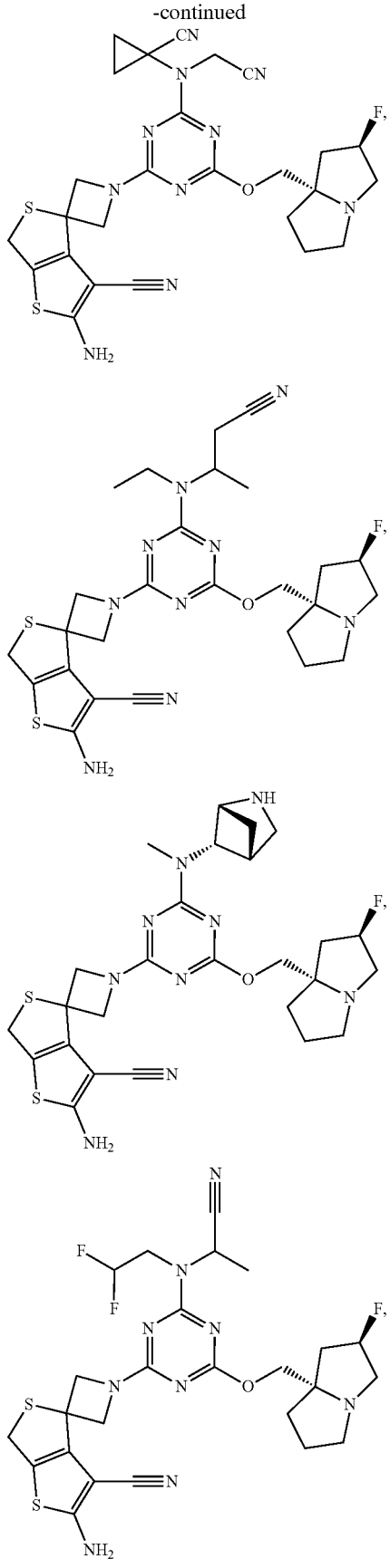
576
-continued
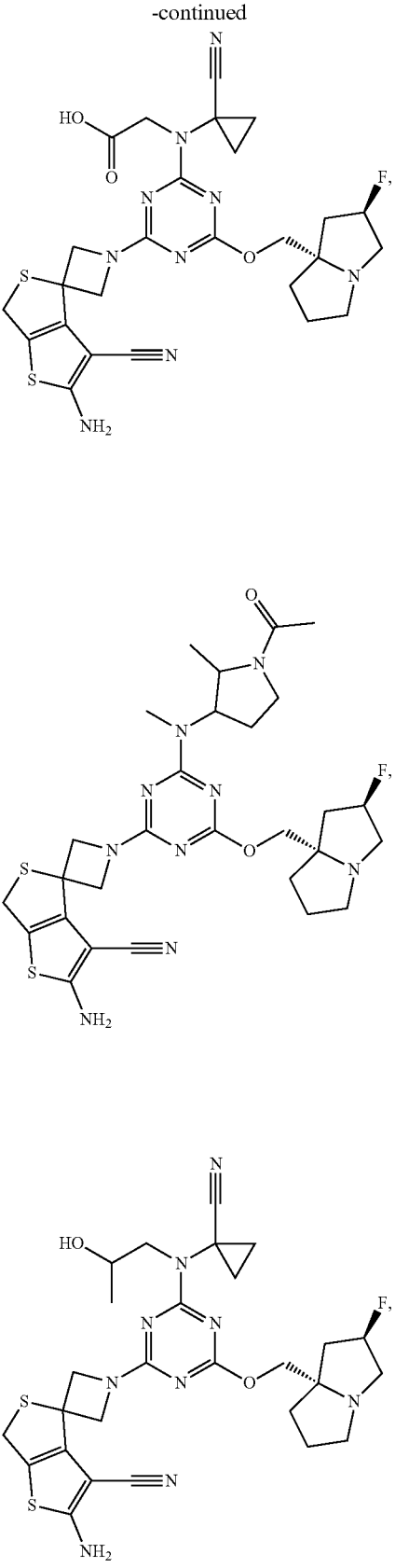

577
-continued
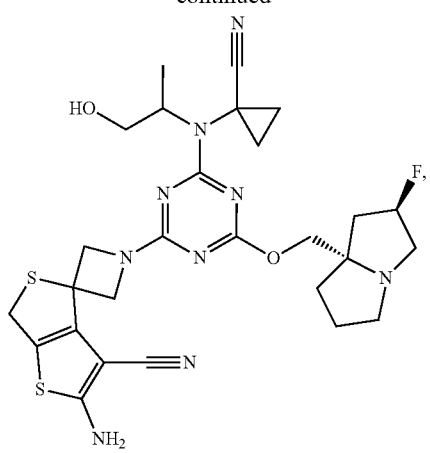
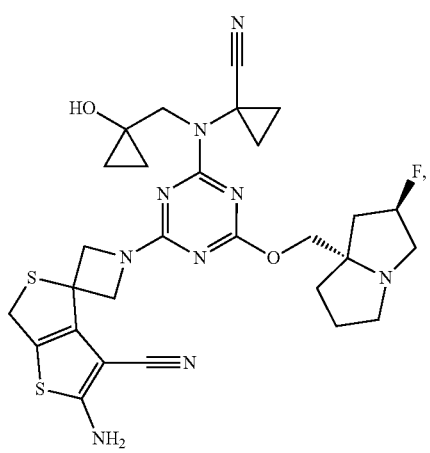
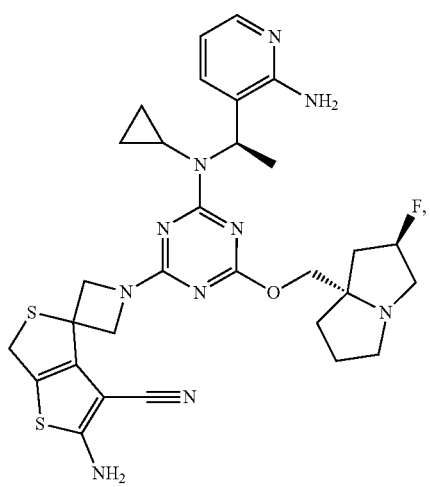
578
-continued
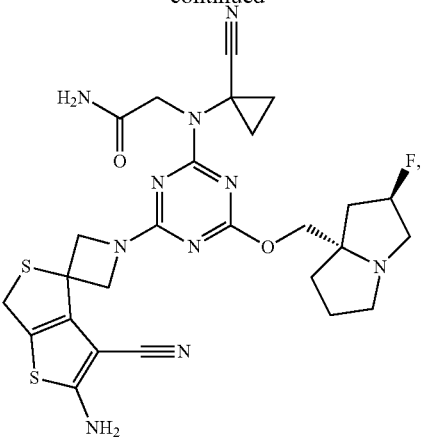
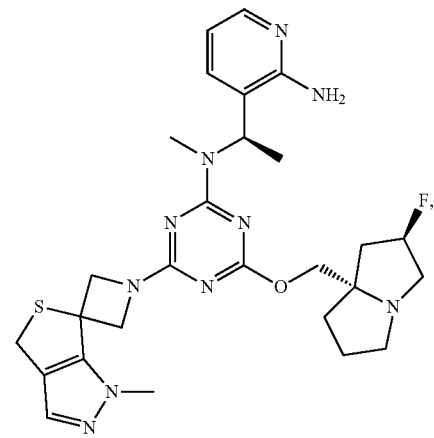
and
or a pharmaceutically acceptable salt of any one thereof.

2. A compound selected from
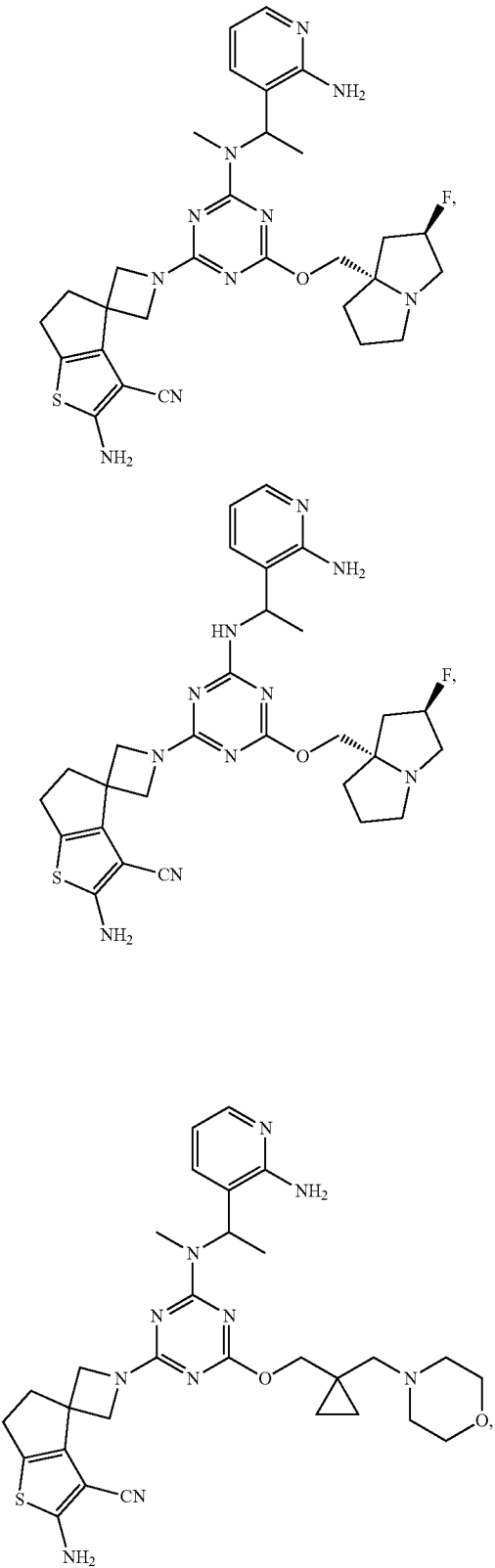
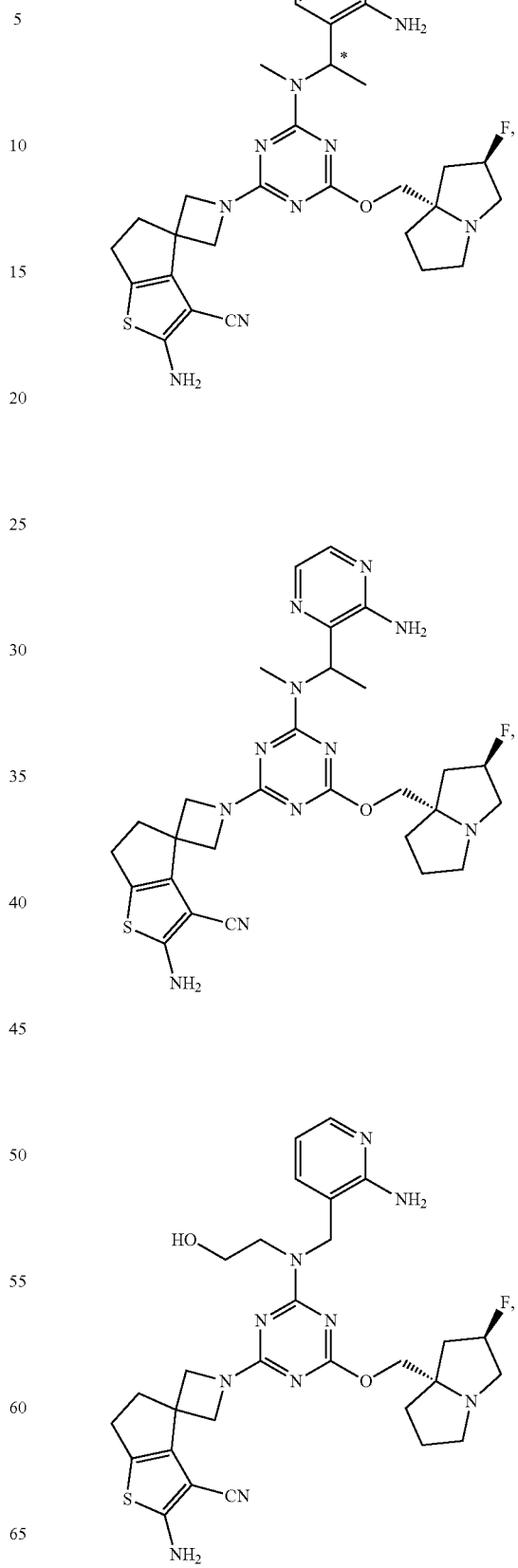

581
-continued
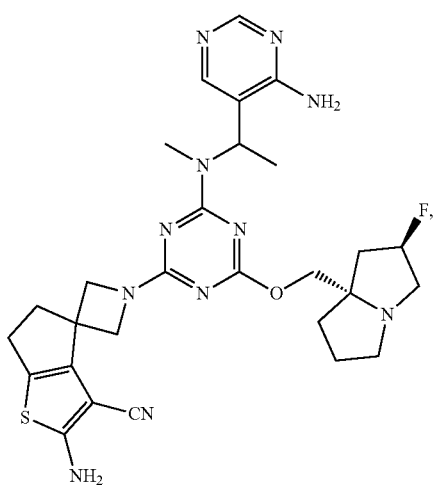
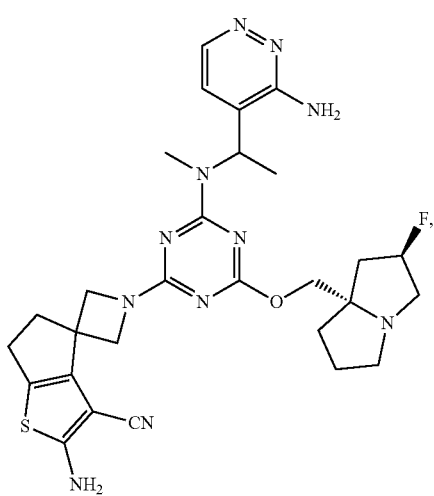
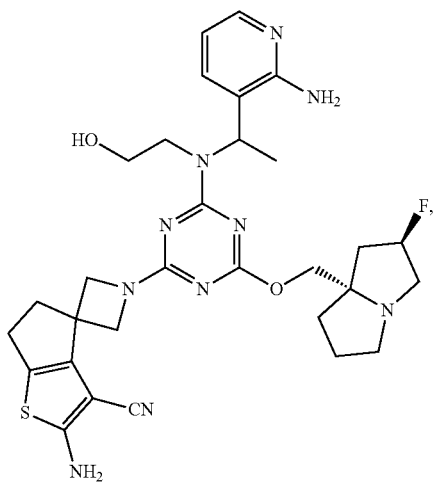
582
-continued
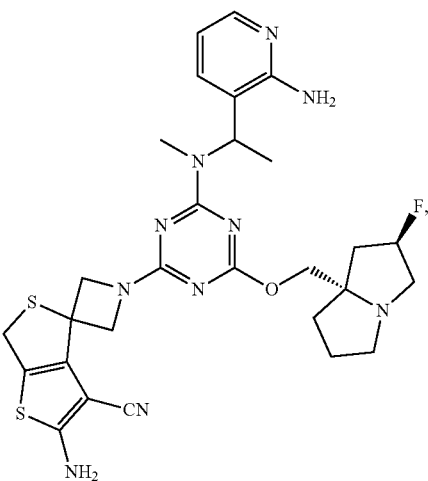
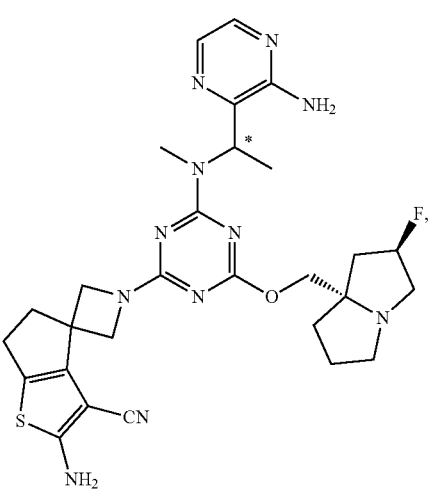
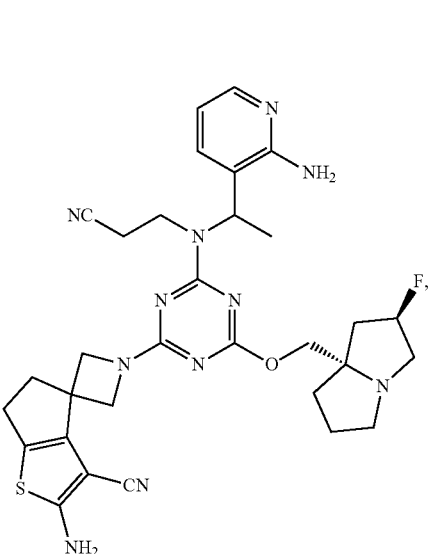

583
-continued
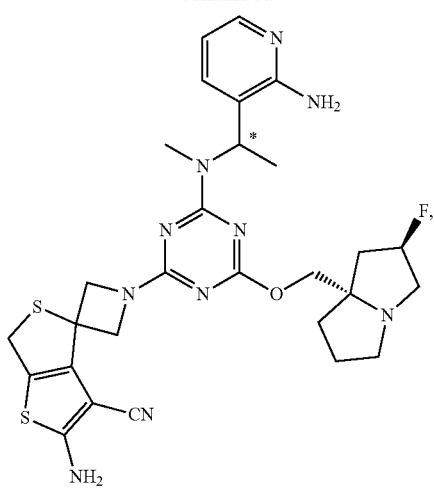
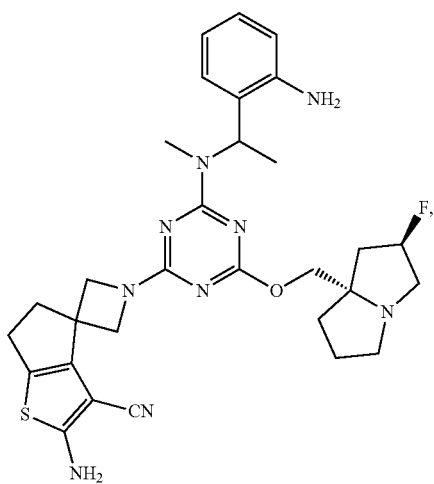
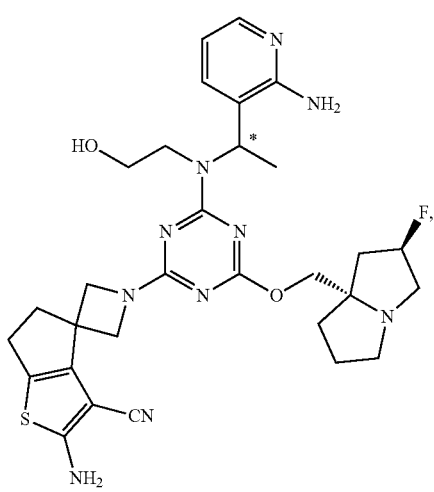
584
-continued
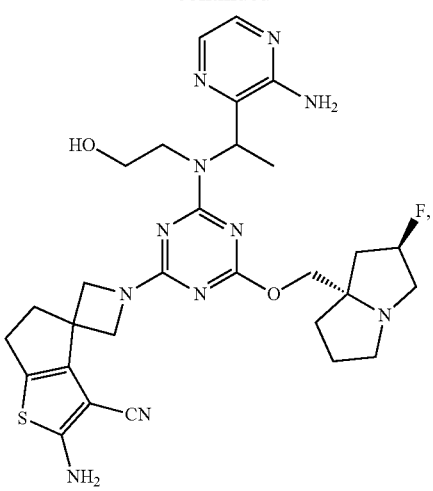
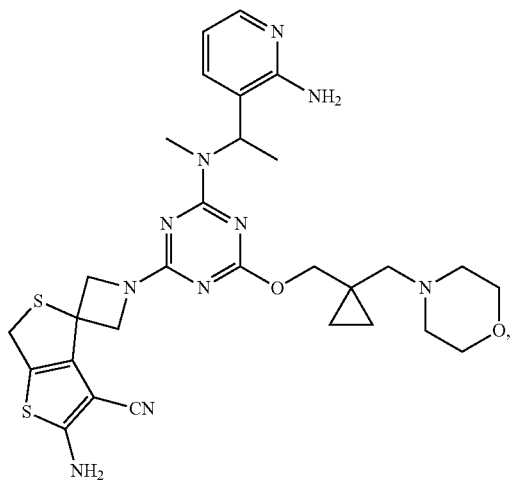
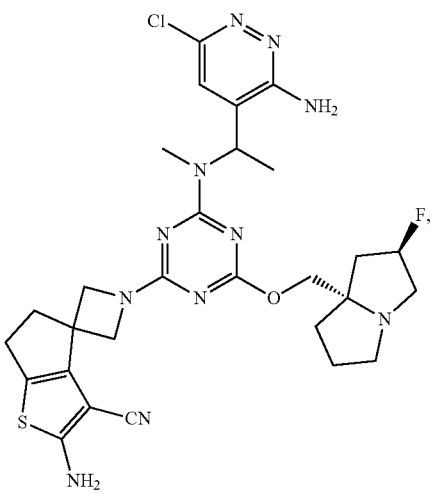

585
-continued
586
-continued
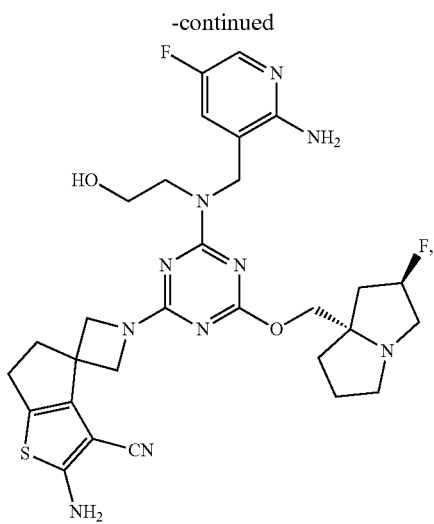
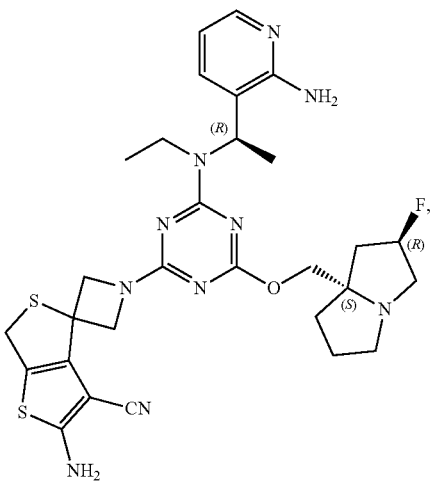
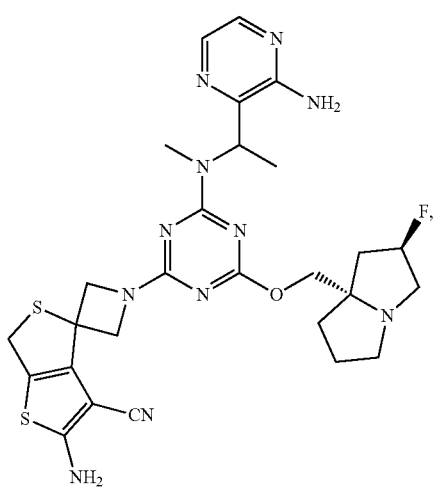
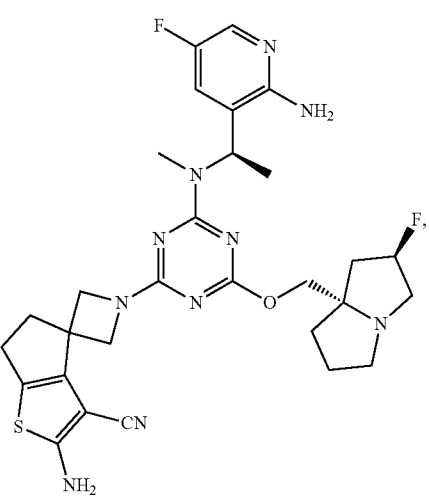
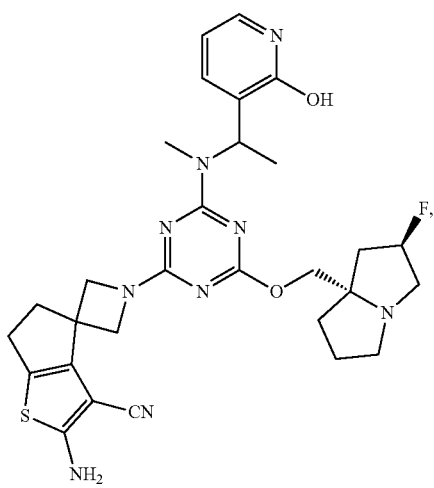

| 587 -continued | 588 -continued |
|---|---|
| 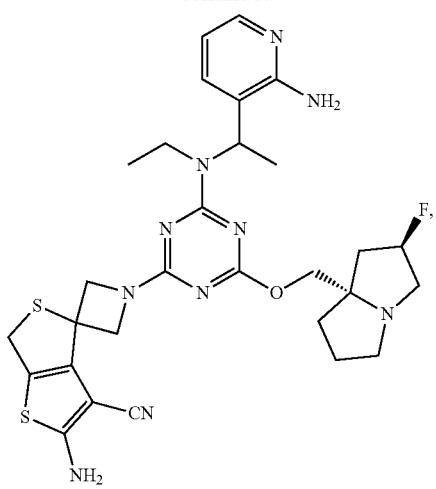 | 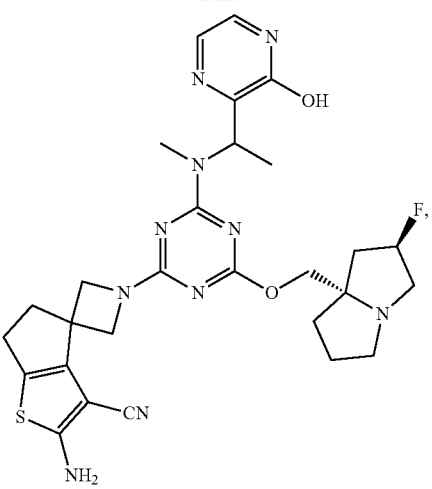 |
| 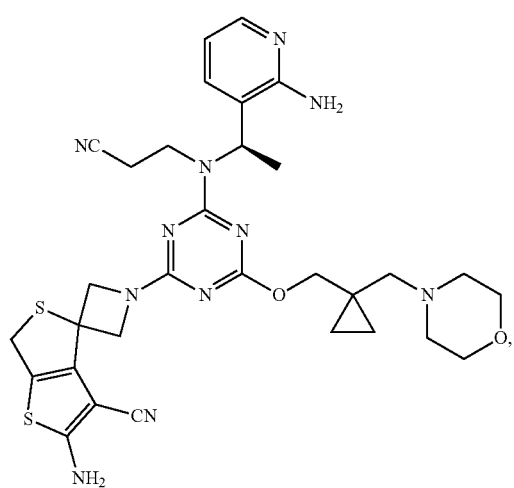 | 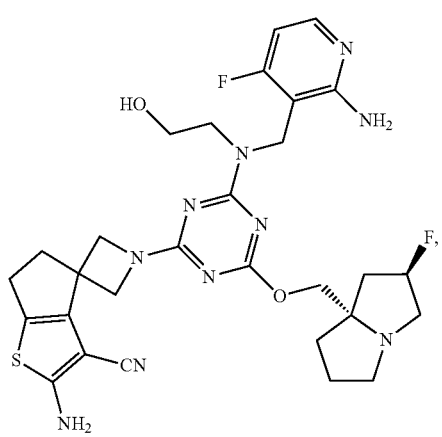 |
| 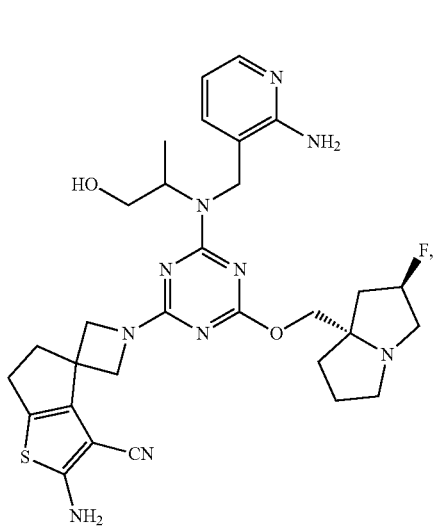 | 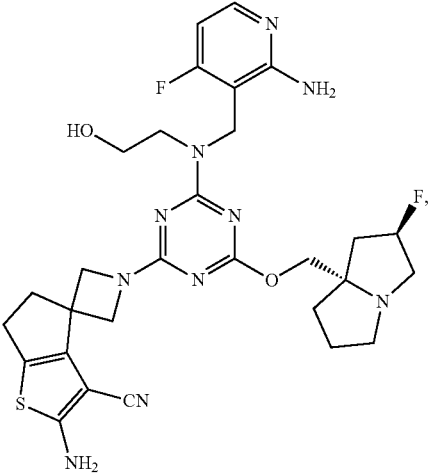 |

589
-continued
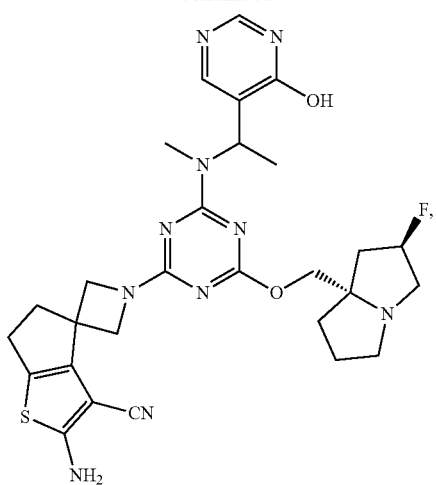
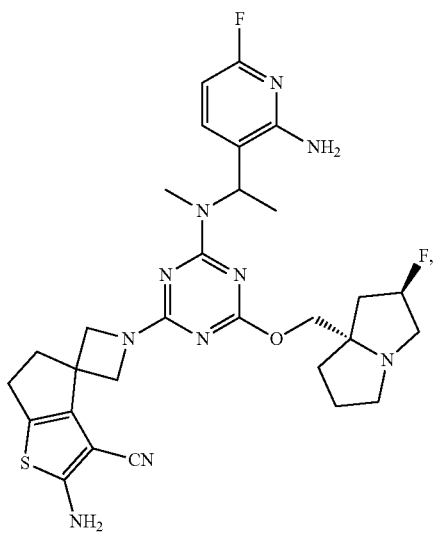
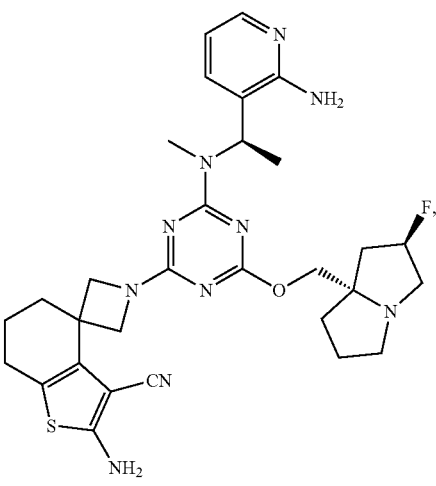
590
-continued
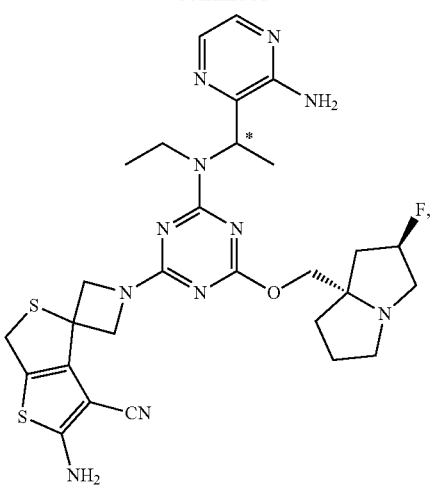
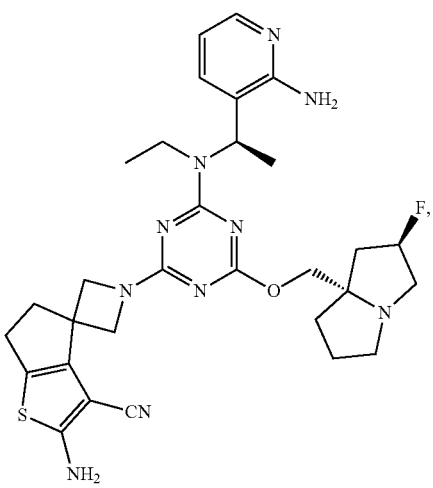
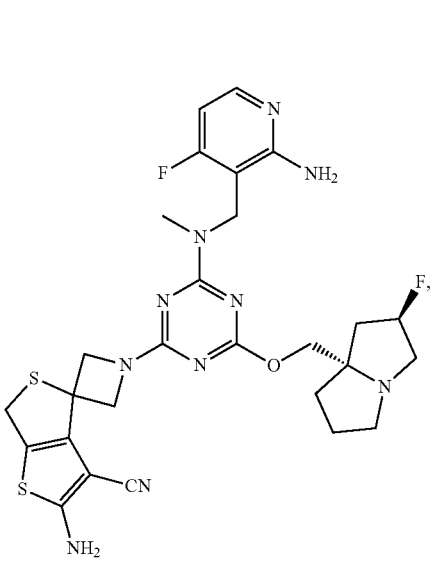

591
-continued
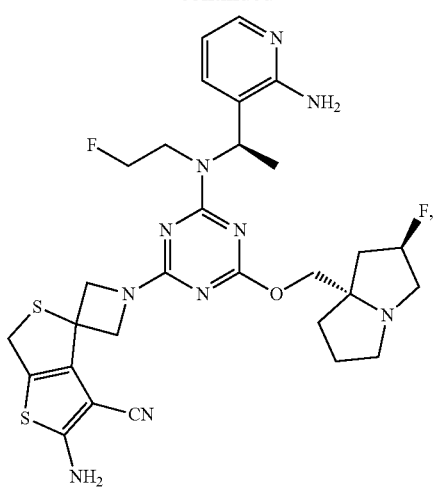
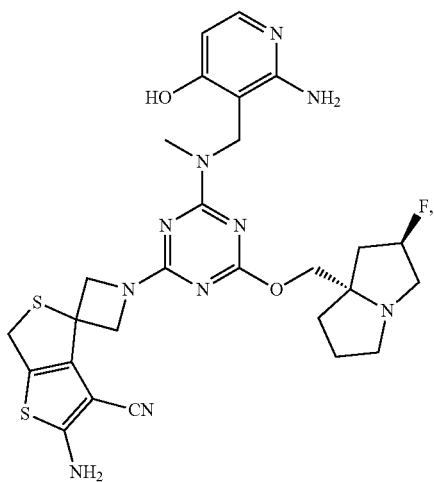
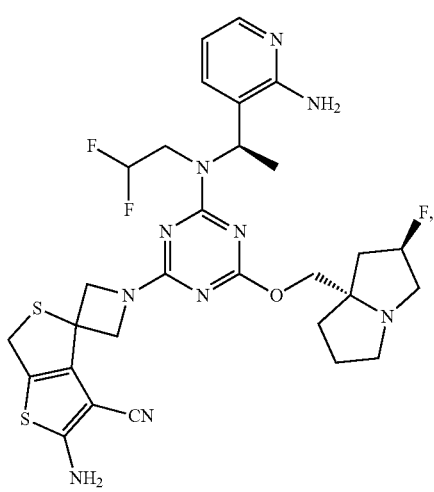
592
-continued
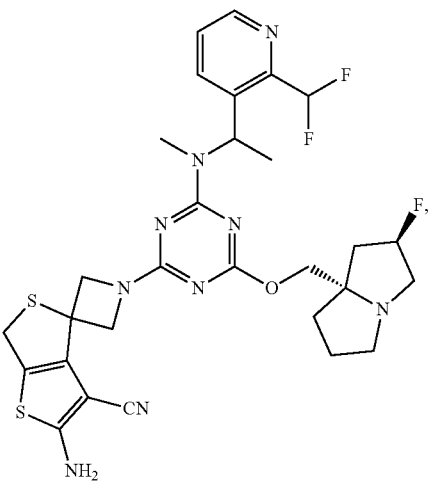
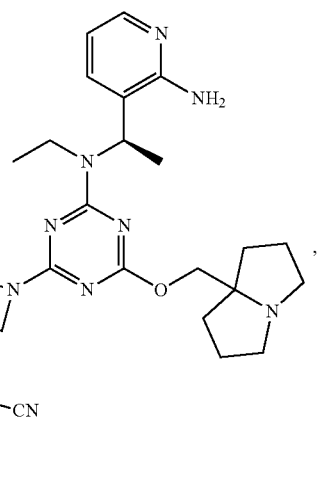
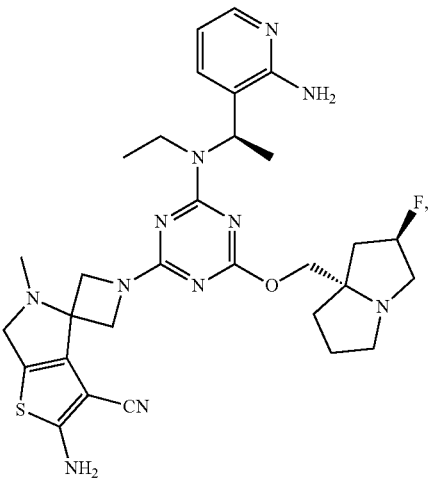

-continued

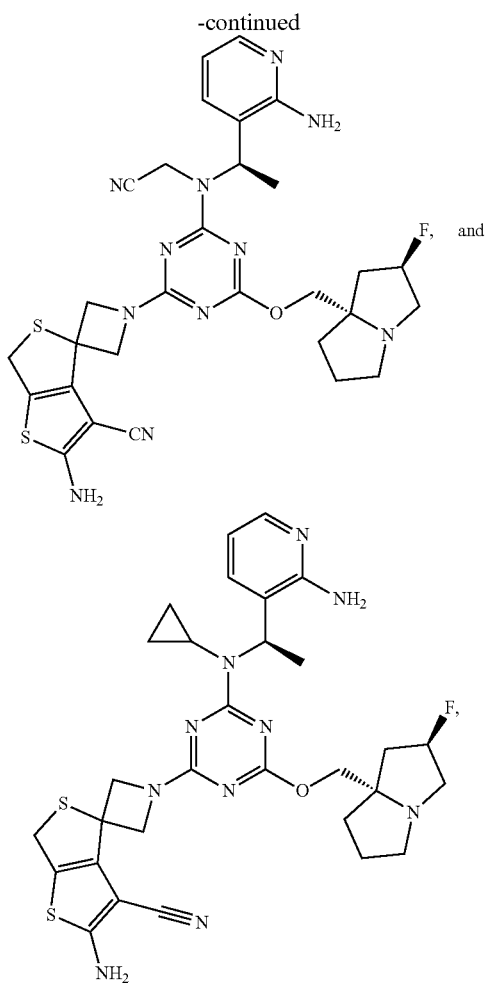

and or a pharmaceutically acceptable salt of any one thereof.

3. A pharmaceutical composition comprising the compound or salt of claim 1 and a pharmaceutically acceptable excipient.

4. The compound or salt of claim 1, wherein the compound is

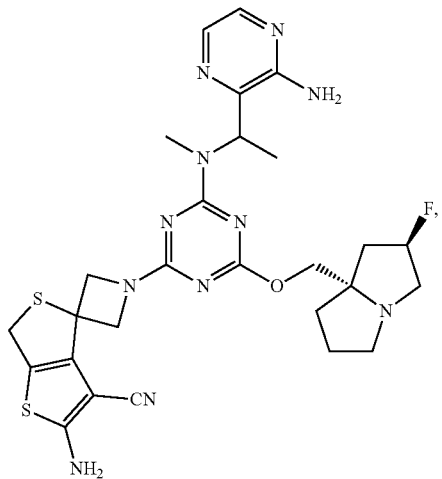 [SMILES: CC(c1nccnc1N)N(C)c1nc(OC[C@@]23CCCN2C[C@H](F)C3)nc(N2CC3(C2)SCc2sc(N)c(C#N)c23)n1]

or a pharmaceutically acceptable salt thereof.

5. The compound or salt of claim 1, wherein the compound is

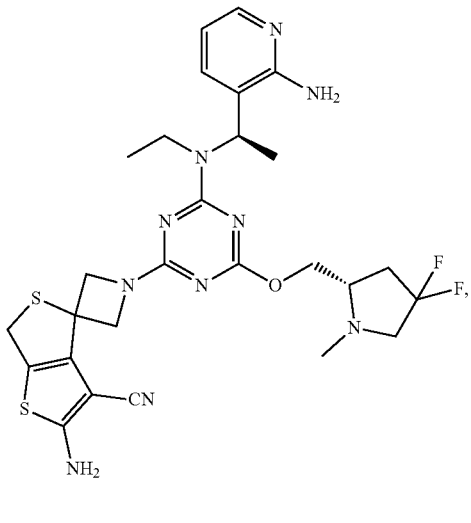 [SMILES: CCN(c1nc(OC[C@@H]2CC(F)(F)CN2C)nc(N2CC3(C2)SCc2sc(N)c(C#N)c23)n1)[C@H](C)c1cccnc1N]

or a pharmaceutically acceptable salt thereof.

6. The compound or salt of claim 1, wherein the compound is

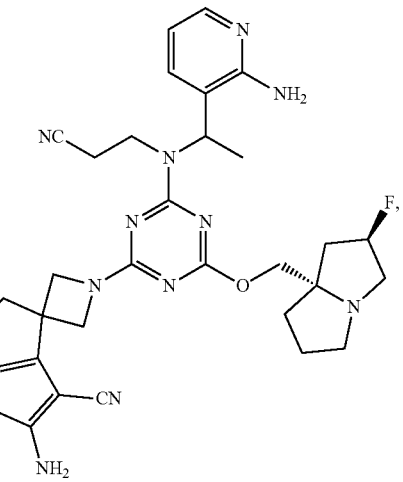

or a pharmaceutically acceptable salt thereof.

7. The compound or salt of claim 1, wherein the compound is

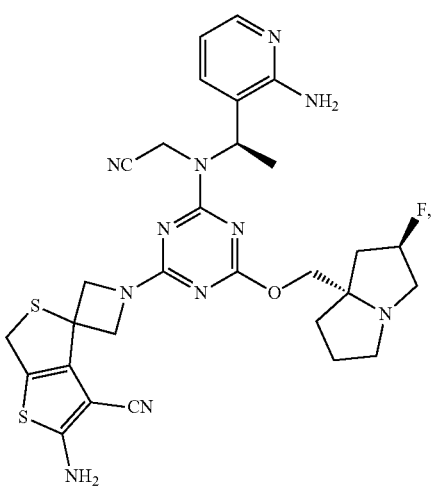 [SMILES: C[C@H](c1cccnc1N)N(CC#N)c1nc(OC[C@@]23CCCN2C[C@H](F)C3)nc(N2CC3(C2)SCc2sc(N)c(C#N)c23)n1]

or a pharmaceutically acceptable salt thereof.

8. The compound or salt of claim 1, wherein the compound is

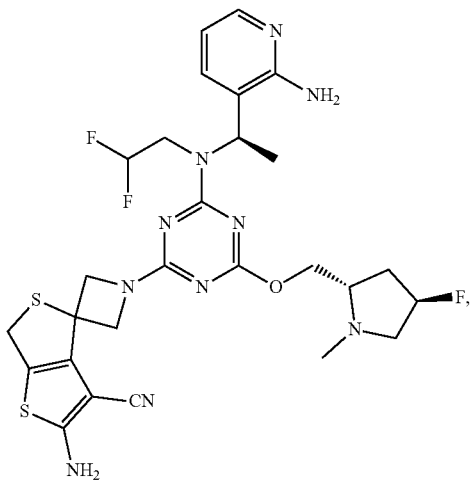 [SMILES: C[C@H](c1cccnc1N)N(CC(F)F)c1nc(OC[C@@H]2C[C@@H](F)CN2C)nc(N2CC3(C2)SCc2sc(N)c(C#N)c23)n1]

or a pharmaceutically acceptable salt thereof.

9. The compound or salt of claim 1, wherein the compound is

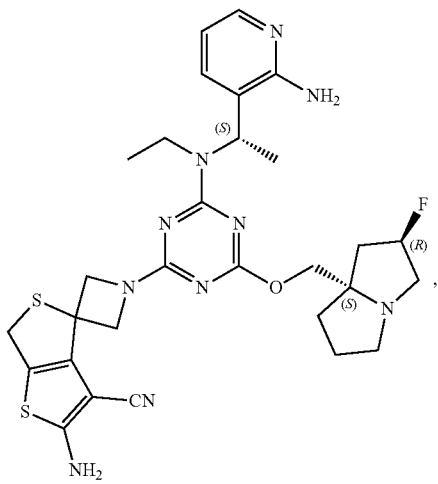

or a pharmaceutically acceptable salt thereof.

10. The compound or salt of claim 1, wherein the compound is

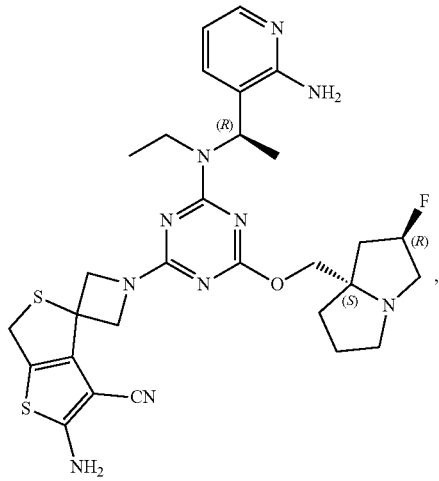

or a pharmaceutically acceptable salt thereof.

11. The compound or salt of claim 1, wherein the compound is

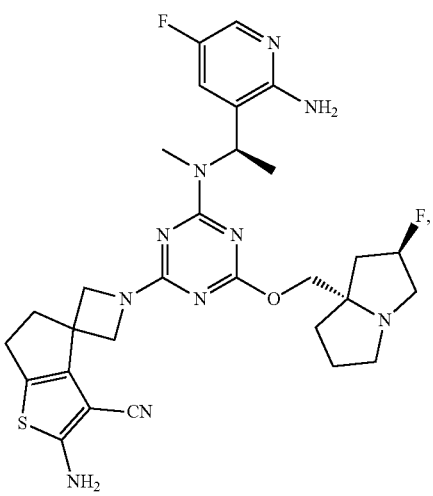 [SMILES: C[C@H](c1cc(F)cnc1N)N(C)c1nc(OC[C@@]23CCCN2C[C@H](F)C3)nc(N2CC3(CCc4sc(N)c(C#N)c43)C2)n1]

or a pharmaceutically acceptable salt thereof.

12. The compound or salt of claim 1, wherein the compound is

13. The compound or salt of claim 1, wherein the compound is

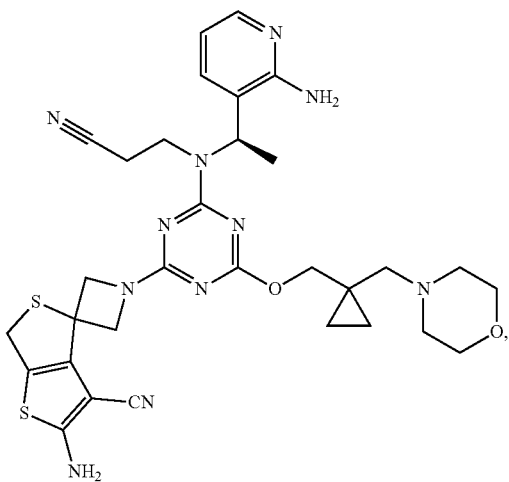 [SMILES: C[C@H](c1cccnc1N)N(CCC#N)c1nc(OCC2(CN3CCOCC3)CC2)nc(N2CC3(C2)SCc2sc(N)c(C#N)c23)n1]

or a pharmaceutically acceptable salt thereof.

14. The compound or salt of claim 1, wherein the compound is

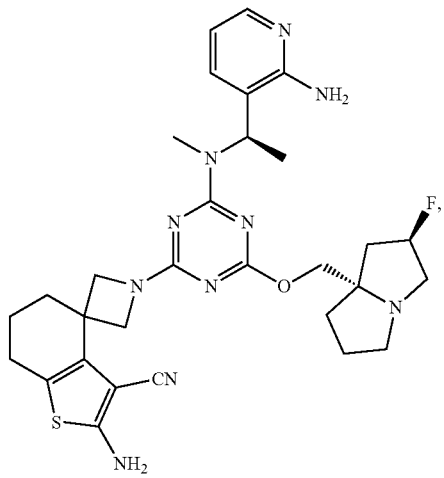 [SMILES: C[C@H](c1cccnc1N)N(C)c1nc(OC[C@@]23CCCN2C[C@H](F)C3)nc(N2CC3(CCCc4sc(N)c(C#N)c43)C2)n1]

or a pharmaceutically acceptable salt thereof.

15. The compound or salt of claim 1, wherein the compound is

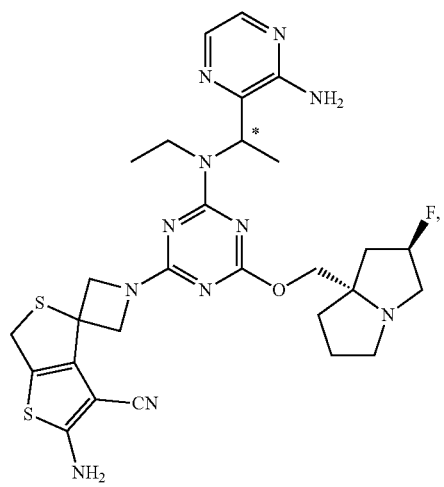 [SMILES: CCN(c1nc(OC[C@@]23CCCN2C[C@H](F)C3)nc(N2CC3(C2)SCc2sc(N)c(C#N)c23)n1)C(C)c1nccnc1N]

or a pharmaceutically acceptable salt thereof.

16. The compound or salt of claim 1, wherein the compound is

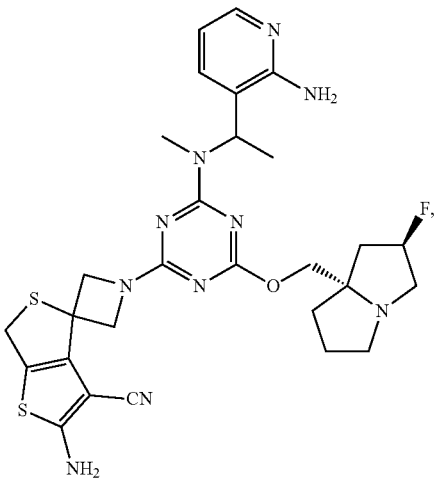 [SMILES: CC(c1cccnc1N)N(C)c1nc(OC[C@@]23CCCN2C[C@H](F)C3)nc(N2CC3(C2)SCc2sc(N)c(C#N)c23)n1]

or a pharmaceutically acceptable salt thereof.

17. The compound or salt of claim 1, wherein the compound is

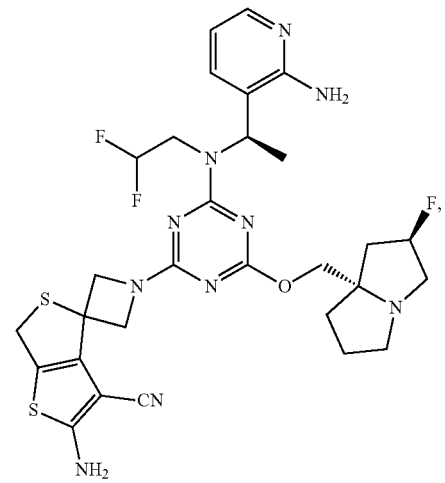 [SMILES: C[C@H](c1cccnc1N)N(CC(F)F)c1nc(OC[C@@]23CCCN2C[C@H](F)C3)nc(N2CC3(C2)SCc2sc(N)c(C#N)c23)n1]

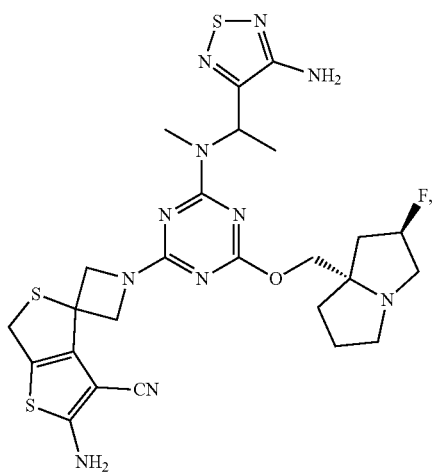 [SMILES: CC(c1nsnc1N)N(C)c1nc(OC[C@@]23CCCN2C[C@H](F)C3)nc(N2CC3(C2)SCc2sc(N)c(C#N)c23)n1]
or a pharmaceutically acceptable salt thereof.
* * * * *